(12) United States Patent
Shelton, IV et al.

(10) Patent No.: US 11,291,510 B2
(45) Date of Patent: Apr. 5, 2022

(54) METHOD OF HUB COMMUNICATION WITH SURGICAL INSTRUMENT SYSTEMS

(71) Applicant: Ethicon LLC, Guaynabo, PR (US)

(72) Inventors: Frederick E. Shelton, IV, Hillsboro, OH (US); Jason L. Harris, Lebanon, OH (US)

(73) Assignee: Cilag GmbH International, Zug (CH)

(*) Notice: Subject to any disclaimer, the term of this patent is extended or adjusted under 35 U.S.C. 154(b) by 438 days.

(21) Appl. No.: 16/172,219

(22) Filed: Oct. 26, 2018

(65) Prior Publication Data
US 2019/0125456 A1 May 2, 2019

Related U.S. Application Data

(60) Provisional application No. 62/665,129, filed on May 1, 2018, provisional application No. 62/665,128, filed (Continued)

(51) Int. Cl.
*A61B 34/00* (2016.01)
*A61B 17/02* (2006.01)
(Continued)

(52) U.S. Cl.
CPC ............. *A61B 34/25* (2016.02); *A61B 5/00* (2013.01); *A61B 17/0206* (2013.01);
(Continued)

(58) Field of Classification Search
CPC ............. A61B 17/0206; A61B 17/062; A61B 17/0644; A61B 17/072; A61B 17/07207; A61B 17/083; A61B 17/105; A61B 17/1155; A61B 17/1222; A61B 17/1285; A61B 17/29; A61B 17/320068; A61B 17/3421; A61B 18/1206;
(Continued)

(56) References Cited

U.S. PATENT DOCUMENTS

| 1,853,416 A | 4/1932 | Hall |
|---|---|---|
| 2,222,125 A | 11/1940 | Stehlik |

(Continued)

FOREIGN PATENT DOCUMENTS

| AU | 2015201140 A1 | 3/2015 |
|---|---|---|
| CA | 2795323 A1 | 5/2014 |

(Continued)

OTHER PUBLICATIONS

US 10,504,709 B2, 12/2019, Karancsi et al. (withdrawn)
(Continued)

*Primary Examiner* — Ryan J. Severson

(57) ABSTRACT

A method for downloading data from a surgical hub to a surgical instrument is disclosed. The method comprises assembling a first shaft assembly to a handle and downloading a first set of operational data from the surgical hub to the handle once the first shaft assembly is attached to the handle. The method further comprises assembling a second shaft assembly to the handle and downloading a second set of operational data from the surgical hub to the handle once the second shaft assembly is attached to the handle, wherein the second set of operational data is different than the first set of operational data.

21 Claims, 373 Drawing Sheets

Related U.S. Application Data on May 1, 2018, provisional application No. 62/665,139, filed on May 1, 2018, provisional application No. 62/665,177, filed on May 1, 2018, provisional application No. 62/665,192, filed on May 1, 2018, provisional application No. 62/665,134, filed on May 1, 2018, provisional application No. 62/659,900, filed on Apr. 19, 2018, provisional application No. 62/649,294, filed on Mar. 28, 2018, provisional application No. 62/649,313, filed on Mar. 28, 2018, provisional application No. 62/649,310, filed on Mar. 28, 2018, provisional application No. 62/649,307, filed on Mar. 28, 2018, provisional application No. 62/649,300, filed on Mar. 28, 2018, provisional application No. 62/649,327, filed on Mar. 28, 2018, provisional application No. 62/649,320, filed on Mar. 28, 2018, provisional application No. 62/649,333, filed on Mar. 28, 2018, provisional application No. 62/649,302, filed on Mar. 28, 2018, provisional application No. 62/649,323, filed on Mar. 28, 2018, provisional application No. 62/649,296, filed on Mar. 28, 2018, provisional application No. 62/649,315, filed on Mar. 28, 2018, provisional application No. 62/649,291, filed on Mar. 28, 2018, provisional application No. 62/649,309, filed on Mar. 28, 2018, provisional application No. 62/611,339, filed on Dec. 28, 2017, provisional application No. 62/611,340, filed on Dec. 28, 2017, provisional application No. 62/611,341, filed on Dec. 28, 2017, provisional application No. 62/578,835, filed on Oct. 30, 2017, provisional application No. 62/578,844, filed on Oct. 30, 2017, provisional application No. 62/578,855, filed on Oct. 30, 2017, provisional application No. 62/578,817, filed on Oct. 30, 2017, provisional application No. 62/578,804, filed on Oct. 30, 2017, provisional application No. 62/578,793, filed on Oct. 30, 2017.

(51) Int. Cl.

| | | |
|---|---|---|
| *A61B 90/98* | (2016.01) | |
| *G16H 40/00* | (2018.01) | |
| *A61B 17/115* | (2006.01) | |
| *A61B 17/072* | (2006.01) | |
| *A61B 34/37* | (2016.01) | |
| *A61B 5/00* | (2006.01) | |
| *A61B 90/30* | (2016.01) | |
| *A61B 34/10* | (2016.01) | |
| *A61B 34/30* | (2016.01) | |
| *A61B 17/10* | (2006.01) | |
| *A61B 17/128* | (2006.01) | |
| *A61B 18/12* | (2006.01) | |
| *A61B 17/00* | (2006.01) | |
| *A61B 34/20* | (2016.01) | |
| *A61B 90/96* | (2016.01) | |
| *A61B 90/00* | (2016.01) | |
| *A61B 17/064* | (2006.01) | |
| *A61B 17/32* | (2006.01) | |
| *A61B 17/28* | (2006.01) | |
| *A61B 17/29* | (2006.01) | |
| *A61B 90/90* | (2016.01) | |
| *A61B 17/062* | (2006.01) | |
| *A61B 17/08* | (2006.01) | |
| *A61B 17/122* | (2006.01) | |
| *A61B 17/34* | (2006.01) | |

(52) U.S. Cl.
CPC ...... *A61B 17/072* (2013.01); *A61B 17/07207* (2013.01); *A61B 17/105* (2013.01); *A61B 17/1155* (2013.01); *A61B 17/1285* (2013.01); *A61B 18/1206* (2013.01); *A61B 34/10* (2016.02); *A61B 34/30* (2016.02); *A61B 34/37* (2016.02); *A61B 34/76* (2016.02); *A61B 90/30* (2016.02); *A61B 90/98* (2016.02); *G16H 40/00* (2018.01); *A61B 17/062* (2013.01); *A61B 17/0644* (2013.01); *A61B 17/083* (2013.01); *A61B 17/1222* (2013.01); *A61B 17/29* (2013.01); *A61B 17/320068* (2013.01); *A61B 17/3421* (2013.01); *A61B 34/20* (2016.02); *A61B 90/90* (2016.02); *A61B 90/96* (2016.02); *A61B 2017/0003* (2013.01); *A61B 2017/00017* (2013.01); *A61B 2017/00022* (2013.01); *A61B 2017/00026* (2013.01); *A61B 2017/00039* (2013.01); *A61B 2017/0046* (2013.01); *A61B 2017/00057* (2013.01); *A61B 2017/00061* (2013.01); *A61B 2017/00084* (2013.01); *A61B 2017/00115* (2013.01); *A61B 2017/00119* (2013.01); *A61B 2017/00199* (2013.01); *A61B 2017/00221* (2013.01); *A61B 2017/00398* (2013.01); *A61B 2017/00464* (2013.01); *A61B 2017/00473* (2013.01); *A61B 2017/00477* (2013.01); *A61B 2017/00725* (2013.01); *A61B 2017/00734* (2013.01); *A61B 2017/00809* (2013.01); *A61B 2017/07214* (2013.01); *A61B 2017/07271* (2013.01); *A61B 2017/2825* (2013.01); *A61B 2017/2926* (2013.01); *A61B 2017/2927* (2013.01); *A61B 2017/2941* (2013.01); *A61B 2017/2943* (2013.01); *A61B 2017/2945* (2013.01); *A61B 2017/320074* (2017.08); *A61B 2017/320094* (2017.08); *A61B 2018/126* (2013.01); *A61B 2018/1253* (2013.01); *A61B 2034/107* (2016.02); *A61B 2034/2051* (2016.02); *A61B 2034/2055* (2016.02); *A61B 2090/061* (2016.02); *A61B 2090/065* (2016.02); *A61B 2090/066* (2016.02); *A61B 2090/0803* (2016.02); *A61B 2090/0808* (2016.02); *A61B 2090/0811* (2016.02); *A61B 2090/365* (2016.02); *A61B 2090/366* (2016.02); *A61B 2217/005* (2013.01); *A61B 2217/007* (2013.01); *A61B 2218/008* (2013.01)

(58) Field of Classification Search
CPC ........... A61B 2017/00017; A61B 2017/00022; A61B 2017/00026; A61B 2017/0003; A61B 2017/00039; A61B 2017/00057; A61B 2017/00061; A61B 2017/00084; A61B 2017/00115; A61B 2017/00119; A61B 2017/00199; A61B 2017/00221; A61B 2017/00398; A61B 2017/0046; A61B 2017/0464; A61B 2017/00473; A61B 2017/00477; A61B 2017/00725; A61B 2017/00734; A61B 2017/00809; A61B 2017/07214; A61B 2017/07271; A61B 2017/2825; A61B 2017/2926; A61B 2017/2927; A61B 2017/2941; A61B 2017/2943; A61B 2017/2945; A61B 2017/320074; A61B 2017/320094; A61B 2018/1253; A61B 2018/126; A61B 2034/107; A61B 2034/2051; A61B 2034/2055; A61B 2090/061; A61B 2090/065; A61B 2090/066; A61B 2090/0803; A61B 2090/0808; A61B 2090/0811; A61B 2090/365; A61B 2090/366; A61B 2217/005; A61B 2217/007; A61B 2218/008; A61B 34/10; A61B 34/20; A61B 34/25; A61B 34/30; A61B 34/37; A61B 34/76; A61B 5/00; A61B 90/30; A61B 90/90; A61B 90/96; A61B 90/98; G16H 40/00; H04L 67/12

See application file for complete search history.

(56) References Cited

U.S. PATENT DOCUMENTS

| | | | |
|---|---|---|---|
| 3,082,426 A | 3/1963 | Miles | |
| 3,503,396 A | 3/1970 | Pierie et al. | |
| 3,584,628 A | 6/1971 | Green | |
| 3,626,457 A | 12/1971 | Duerr et al. | |
| 3,633,584 A | 1/1972 | Farrell | |
| 3,759,017 A | 9/1973 | Young | |
| 3,863,118 A | 1/1975 | Lander et al. | |
| 3,898,545 A | 8/1975 | Coppa et al. | |
| 3,912,121 A | 10/1975 | Steffen | |
| 3,915,271 A | 10/1975 | Harper | |
| 3,932,812 A | 1/1976 | Milligan | |
| 4,041,362 A | 8/1977 | Ichiyanagi | |
| 4,052,649 A | 10/1977 | Greenwell et al. | |
| 4,087,730 A | 5/1978 | Goles | |
| 4,157,859 A | 6/1979 | Terry | |
| 4,171,700 A | 10/1979 | Farin | |
| 4,202,722 A | 5/1980 | Paquin | |
| 4,412,539 A | 11/1983 | Jarvik | |
| 4,448,193 A | 5/1984 | Ivanov | |
| 4,523,695 A | 6/1985 | Braun et al. | |
| 4,608,160 A | 8/1986 | Zoch | |
| 4,614,366 A | 9/1986 | North et al. | |
| 4,633,874 A | 1/1987 | Chow et al. | |
| 4,701,193 A | 10/1987 | Robertson et al. | |
| 4,735,603 A | 4/1988 | Goodson et al. | |
| 4,788,977 A | 12/1988 | Farin et al. | |
| 4,849,752 A | 7/1989 | Bryant | |
| D303,787 S | 10/1989 | Messenger et al. | |
| 4,892,244 A | 1/1990 | Fox et al. | |
| 5,010,341 A | 4/1991 | Huntley et al. | |
| 5,026,387 A | 6/1991 | Thomas | |
| 5,035,692 A | 7/1991 | Lyon et al. | |
| 5,042,460 A | 8/1991 | Sakurai et al. | |
| 5,047,043 A | 9/1991 | Kubota et al. | |
| 5,084,057 A | 1/1992 | Green et al. | |
| 5,100,402 A | 3/1992 | Fan | |
| D327,061 S | 6/1992 | Soren et al. | |
| 5,129,570 A | 7/1992 | Schulze et al. | |
| 5,151,102 A | 9/1992 | Kamiyama et al. | |
| 5,156,315 A | 10/1992 | Green et al. | |
| 5,158,585 A | 10/1992 | Saho et al. | |
| 5,171,247 A | 12/1992 | Hughett et al. | |
| 5,189,277 A | 2/1993 | Boisvert et al. | |
| 5,197,962 A | 3/1993 | Sansom et al. | |
| 5,204,669 A | 4/1993 | Dorfe et al. | |
| 5,242,474 A | 9/1993 | Herbst et al. | |
| 5,253,793 A | 10/1993 | Green et al. | |
| 5,271,543 A | 12/1993 | Grant et al. | |
| RE34,519 E | 1/1994 | Fox et al. | |
| 5,275,323 A | 1/1994 | Schulze et al. | |
| 5,318,516 A | 6/1994 | Cosmescu | |
| 5,318,563 A | 6/1994 | Malis et al. | |
| 5,322,055 A | 6/1994 | Davison et al. | |
| 5,342,349 A | 8/1994 | Kaufman | |
| 5,364,003 A | 11/1994 | Williamson, IV | |
| 5,383,880 A | 1/1995 | Hooven | |
| 5,396,900 A | 3/1995 | Slater et al. | |
| 5,397,046 A | 3/1995 | Savage et al. | |
| 5,403,312 A | 4/1995 | Yates et al. | |
| 5,403,327 A | 4/1995 | Thornton et al. | |
| 5,413,267 A | 5/1995 | Solyntjes et al. | |
| 5,415,335 A | 5/1995 | Knodell, Jr. | |
| 5,417,699 A | 5/1995 | Klein et al. | |
| 5,439,468 A | 8/1995 | Schulze et al. | |
| 5,445,304 A | 8/1995 | Plyley et al. | |
| 5,462,545 A | 10/1995 | Wang et al. | |
| 5,465,895 A | 11/1995 | Knodel et al. | |
| 5,467,911 A | 11/1995 | Tsuruta et al. | |
| 5,474,566 A | 12/1995 | Alesi et al. | |
| 5,485,947 A | 1/1996 | Olson et al. | |
| 5,496,315 A | 3/1996 | Weaver et al. | |
| 5,503,320 A | 4/1996 | Webster et al. | |
| 5,529,235 A | 6/1996 | Boiarski et al. | |
| 5,531,743 A | 7/1996 | Nettekoven et al. | |
| 5,545,148 A | 8/1996 | Wurster | |
| 5,552,685 A | 9/1996 | Young et al. | |
| 5,560,372 A | 10/1996 | Cory | |
| 5,584,425 A | 12/1996 | Savage et al. | |
| 5,610,379 A | 3/1997 | Muz et al. | |
| 5,610,811 A | 3/1997 | Honda | |
| 5,613,966 A | 3/1997 | Makower et al. | |
| 5,624,452 A | 4/1997 | Yates | |
| D379,346 S | 5/1997 | Mieki | |
| 5,626,587 A | 5/1997 | Bishop et al. | |
| 5,643,291 A | 7/1997 | Pier et al. | |
| 5,654,750 A | 8/1997 | Weil et al. | |
| 5,673,841 A | 10/1997 | Schulze et al. | |
| 5,673,842 A | 10/1997 | Bittner et al. | |
| 5,675,227 A | 10/1997 | Roos et al. | |
| 5,693,042 A | 12/1997 | Boiarski et al. | |
| 5,693,052 A | 12/1997 | Weaver | |
| 5,695,502 A | 12/1997 | Pier et al. | |
| 5,697,926 A | 12/1997 | Weaver | |
| 5,706,998 A | 1/1998 | Plyley et al. | |
| 5,718,359 A | 2/1998 | Palmer et al. | |
| 5,724,468 A | 3/1998 | Leone et al. | |
| 5,725,536 A | 3/1998 | Oberlin et al. | |
| 5,725,542 A | 3/1998 | Yoon | |
| 5,735,445 A | 4/1998 | Vidal et al. | |
| 5,735,848 A | 4/1998 | Yates et al. | |
| 5,746,209 A | 5/1998 | Yost et al. | |
| 5,749,362 A | 5/1998 | Funda et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,766,186 A | 6/1998 | Faraz et al. | |
| 5,769,791 A | 6/1998 | Benaron et al. | |
| 5,775,331 A | 7/1998 | Raymond et al. | |
| 5,797,537 A | 8/1998 | Oberlin et al. | |
| 5,800,350 A | 9/1998 | Coppleson et al. | |
| D399,561 S | 10/1998 | Ellingson | |
| 5,817,093 A | 10/1998 | Williamson, IV et al. | |
| 5,820,009 A | 10/1998 | Melling et al. | |
| 5,833,690 A | 11/1998 | Yates et al. | |
| 5,836,849 A | 11/1998 | Mathiak et al. | |
| 5,836,869 A | 11/1998 | Kudo et al. | |
| 5,836,909 A | 11/1998 | Cosmescu | |
| 5,843,080 A | 12/1998 | Fleenor et al. | |
| 5,846,237 A | 12/1998 | Nettekoven | |
| 5,849,022 A | 12/1998 | Sakashita et al. | |
| 5,873,873 A | 2/1999 | Smith et al. | |
| 5,878,938 A | 3/1999 | Bittner et al. | |
| 5,893,849 A | 4/1999 | Weaver | |
| 5,906,625 A | 5/1999 | Bito et al. | |
| 5,942,333 A | 8/1999 | Arnett et al. | |
| 5,947,996 A | 9/1999 | Logeman | |
| 5,968,032 A | 10/1999 | Sleister | |
| 5,980,510 A | 11/1999 | Tsonton et al. | |
| 5,987,346 A | 11/1999 | Benaron et al. | |
| 5,997,528 A | 12/1999 | Bisch et al. | |
| 6,010,054 A | 1/2000 | Johnson et al. | |
| 6,030,437 A | 2/2000 | Gourrier et al. | |
| 6,036,637 A | 3/2000 | Kudo | |
| 6,039,734 A | 3/2000 | Goble | |
| 6,039,735 A | 3/2000 | Greep | |
| 6,059,799 A | 5/2000 | Aranyi et al. | |
| 6,066,137 A | 5/2000 | Greep | |
| 6,079,606 A | 6/2000 | Milliman et al. | |
| 6,090,107 A | 7/2000 | Borgmeier et al. | |
| 6,099,537 A | 8/2000 | Sugai et al. | |
| 6,102,907 A | 8/2000 | Smethers et al. | |
| 6,109,500 A | 8/2000 | Alli et al. | |

(56) References Cited

U.S. PATENT DOCUMENTS

| | | |
|---|---|---|
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |

(56) References Cited

U.S. PATENT DOCUMENTS

| | | |
|---|---|---|
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| D687,146 S | 7/2013 | Juzkiw et al. |
| 8,476,227 B2 | 7/2013 | Kaplan et al. |

(56) References Cited

U.S. PATENT DOCUMENTS

| | | |
|---|---|---|
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 * | 2/2014 | Quick .................... A61B 10/02 606/1 |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |

(56) References Cited

U.S. PATENT DOCUMENTS

| | | |
|---|---|---|
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |

(56) References Cited

U.S. PATENT DOCUMENTS

| | | |
|---|---|---|
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Res et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |

(56) References Cited

U.S. PATENT DOCUMENTS

| | | |
|---|---|---|
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondon et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |

(56) References Cited

U.S. PATENT DOCUMENTS

| | | |
|---|---|---|
| 10,137,245 B2 | 11/2018 | Melker et al. |
| 10,143,526 B2 | 12/2018 | Walker et al. |
| 10,143,948 B2 | 12/2018 | Bonitas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |

(56) References Cited

U.S. PATENT DOCUMENTS

| | | |
|---|---|---|
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savaii et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |

(56) References Cited

U.S. PATENT DOCUMENTS

| | | |
|---|---|---|
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,580 B2 | 2/2021 | Green et al. |
| 10,912,619 B2 | 2/2021 | Jarc et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,954,935 B2 | 3/2021 | O'Shea et al. |
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 10,966,791 B2 | 4/2021 | Harris et al. |
| 10,966,798 B2 | 4/2021 | Tesar et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,973,682 B2 | 4/2021 | Vezzu et al. |
| 10,980,536 B2 | 4/2021 | Weaner et al. |
| 10,980,537 B2 | 4/2021 | Shelton, IV et al. |
| 10,980,560 B2 | 4/2021 | Shelton, IV et al. |
| 10,980,610 B2 | 4/2021 | Rosenberg et al. |

(56) References Cited

U.S. PATENT DOCUMENTS

| | | |
|---|---|---|
| 10,987,102 B2 | 4/2021 | Gonzalez et al. |
| 10,987,178 B2 | 4/2021 | Shelton, IV et al. |
| 10,992,698 B2 | 4/2021 | Patel et al. |
| 10,993,715 B2 | 5/2021 | Shelton, IV et al. |
| 10,998,098 B2 | 5/2021 | Greene et al. |
| 11,000,276 B2 | 5/2021 | Shelton, IV et al. |
| 11,051,817 B2 | 7/2021 | Shelton, IV et al. |
| 11,058,501 B2 | 7/2021 | Tokarchuk et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2003/0009111 A1 | 1/2003 | Cory et al. |
| 2003/0018329 A1 | 1/2003 | Hooven |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0179223 A1* | 9/2003 | Ying .................... G06F 3/0488 715/702 |
| 2003/0210812 A1 | 11/2003 | Khamene et al. |
| 2003/0223877 A1 | 12/2003 | Anstine et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0192633 A1 | 9/2005 | Montpetit |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0084896 A1 | 4/2007 | Doll et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1* | 6/2010 | Ramstein ............... A61B 17/29 606/1 |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0292535 A1 | 11/2010 | Paskar |
| 2010/0292684 A1 | 11/2010 | Cybulski et al. |
| 2011/0022032 A1 | 1/2011 | Zemlok et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0264000 A1 | 10/2011 | Paul et al. |
| 2011/0273465 A1 | 11/2011 | Konishi et al. |
| 2011/0278343 A1 | 11/2011 | Knodel et al. |

(56) References Cited

U.S. PATENT DOCUMENTS

| | | |
|---|---|---|
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203785 A1 | 8/2012 | Awada |
| 2012/0211542 A1 | 8/2012 | Racenet |
| 2012/0245958 A1 | 9/2012 | Lawrence et al. |
| 2012/0253329 A1 | 10/2012 | Zemlok et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0209980 A1* | 8/2013 | Kuchenbecker ..... G09B 23/285 434/262 |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R et al. |
| 2014/0148729 A1 | 5/2014 | Schmitz et al. |
| 2014/0166724 A1 | 6/2014 | Schellin et al. |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0276749 A1 | 9/2014 | Johnson |
| 2014/0303660 A1 | 10/2014 | Boyden et al. |
| 2014/0303990 A1 | 10/2014 | Schoenefeld et al. |
| 2014/0305987 A1* | 10/2014 | Parihar ................ A61B 17/282 227/175.2 |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051617 A1 | 2/2015 | Takemura et al. |
| 2015/0053737 A1 | 2/2015 | Leimbach et al. |
| 2015/0057675 A1 | 2/2015 | Akeel et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0173673 A1 | 6/2015 | Toth et al. |
| 2015/0173756 A1 | 6/2015 | Baxter, III et al. |
| 2015/0196295 A1 | 7/2015 | Shelton, IV et al. |
| 2015/0199109 A1 | 7/2015 | Lee |
| 2015/0208934 A1 | 7/2015 | Sztrubel et al. |
| 2015/0237502 A1 | 8/2015 | Schmidt et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0066909 A1* | 3/2016 | Baber ................ A61B 17/072 227/176.1 |
| 2016/0066913 A1 | 3/2016 | Swayze et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0158468 A1 | 6/2016 | Tang et al. |
| 2016/0174998 A1 | 6/2016 | Lal et al. |
| 2016/0180045 A1 | 6/2016 | Syed |
| 2016/0184054 A1 | 6/2016 | Lowe |
| 2016/0192960 A1 | 7/2016 | Bueno et al. |
| 2016/0206202 A1 | 7/2016 | Frangioni |
| 2016/0224760 A1 | 8/2016 | Petak et al. |
| 2016/0225551 A1 | 8/2016 | Shedletsky |
| 2016/0228204 A1 | 8/2016 | Quaid et al. |
| 2016/0235303 A1 | 8/2016 | Fleming et al. |
| 2016/0249910 A1 | 9/2016 | Shelton, IV et al. |
| 2016/0278841 A1 | 9/2016 | Panescu et al. |

(56) References Cited

U.S. PATENT DOCUMENTS

| | | |
|---|---|---|
| 2016/0287312 A1 | 10/2016 | Tegg et al. |
| 2016/0287912 A1 | 10/2016 | Warnking |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0361070 A1 | 12/2016 | Ardel et al. |
| 2016/0367305 A1 | 12/2016 | Hareland |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0042659 A1 | 2/2018 | Rupp et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0177383 A1 | 6/2018 | Noonan et al. |
| 2018/0206884 A1 | 7/2018 | Beaupre |
| 2018/0206905 A1 | 7/2018 | Batchelor et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0333207 A1 | 11/2018 | Moctezuma De la Barrera |
| 2018/0360456 A1 | 12/2018 | Shelton, IV et al. |
| 2018/0368930 A1 | 12/2018 | Esterberg et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0046198 A1 | 2/2019 | Stokes et al. |
| 2019/0053801 A1 | 2/2019 | Wixey et al. |
| 2019/0053866 A1 | 2/2019 | Seow et al. |

(56) References Cited

U.S. PATENT DOCUMENTS

| | | |
|---|---|---|
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0167296 A1 | 6/2019 | Tsubuku et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |

(56) References Cited

U.S. PATENT DOCUMENTS

| | | |
|---|---|---|
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0214699 A1 | 7/2020 | Shelton, IV et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |

(56) References Cited

U.S. PATENT DOCUMENTS

| | | |
|---|---|---|
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5373315 A | 6/1978 |
| JP | 2001029353 A | 2/2001 |
| JP | 2007123394 A | 5/2007 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015129395 A1 | 9/2015 |
| WO | WO-2016100719 A1 | 6/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trendbased methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

(56) References Cited

OTHER PUBLICATIONS

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Phumzile Malindi, "5. QoS in Telemedicine," "Telemedicine," Jun. 20, 2011, IntechOpen, pp. 119-138.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Octobers, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from Internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

\* cited by examiner

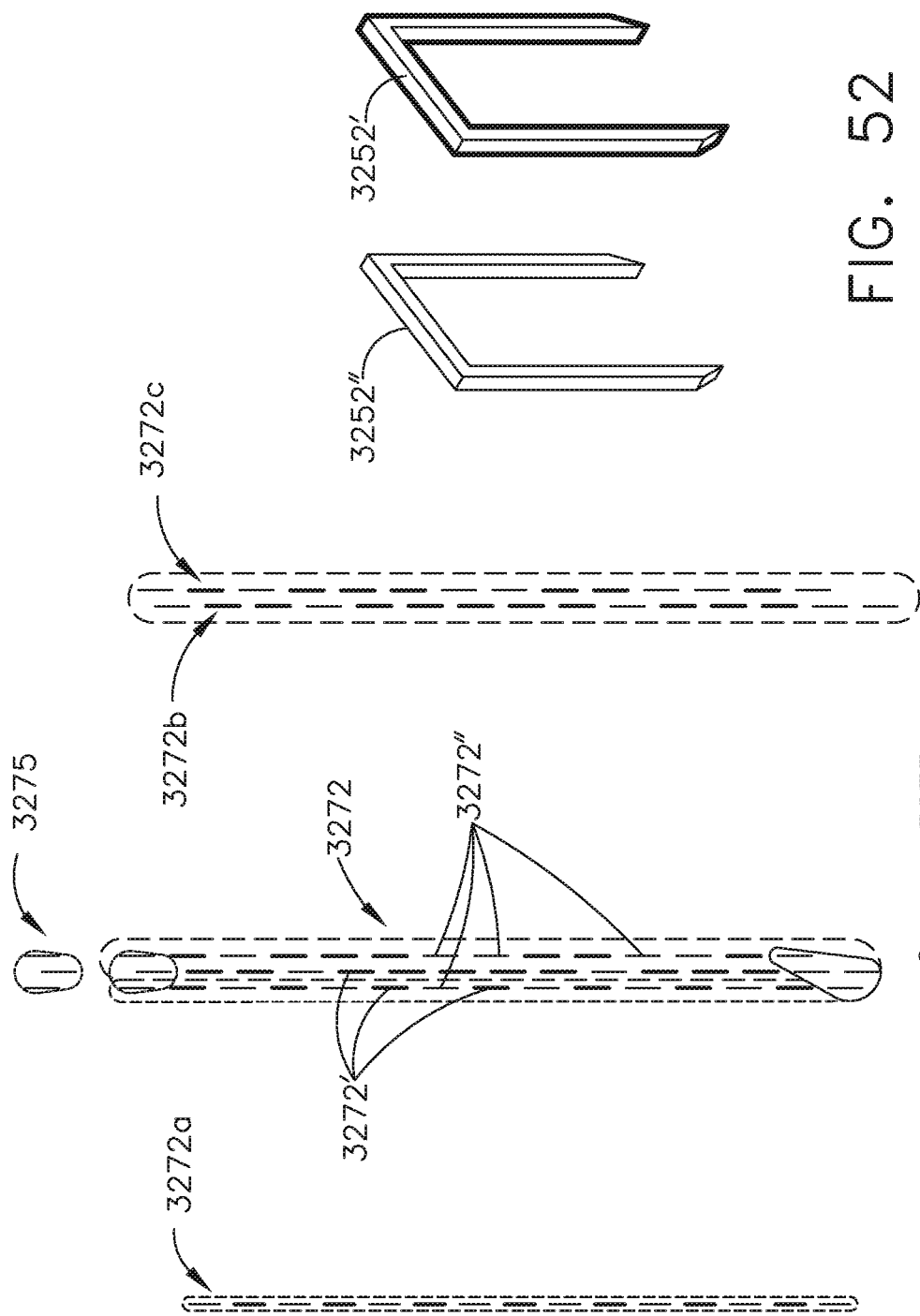

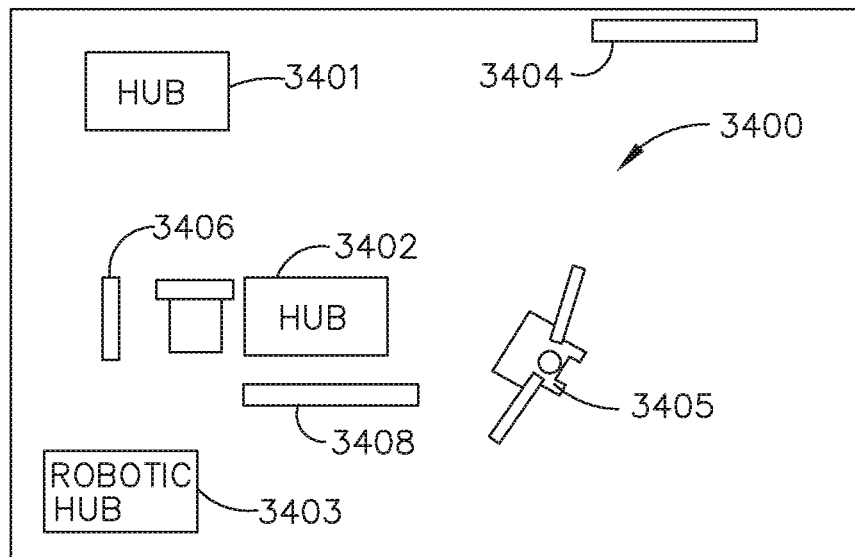
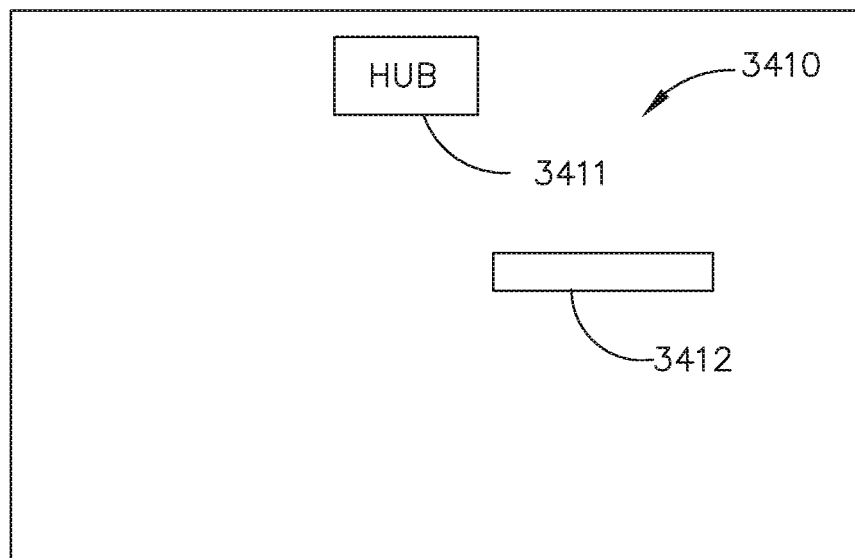
FIG. 56

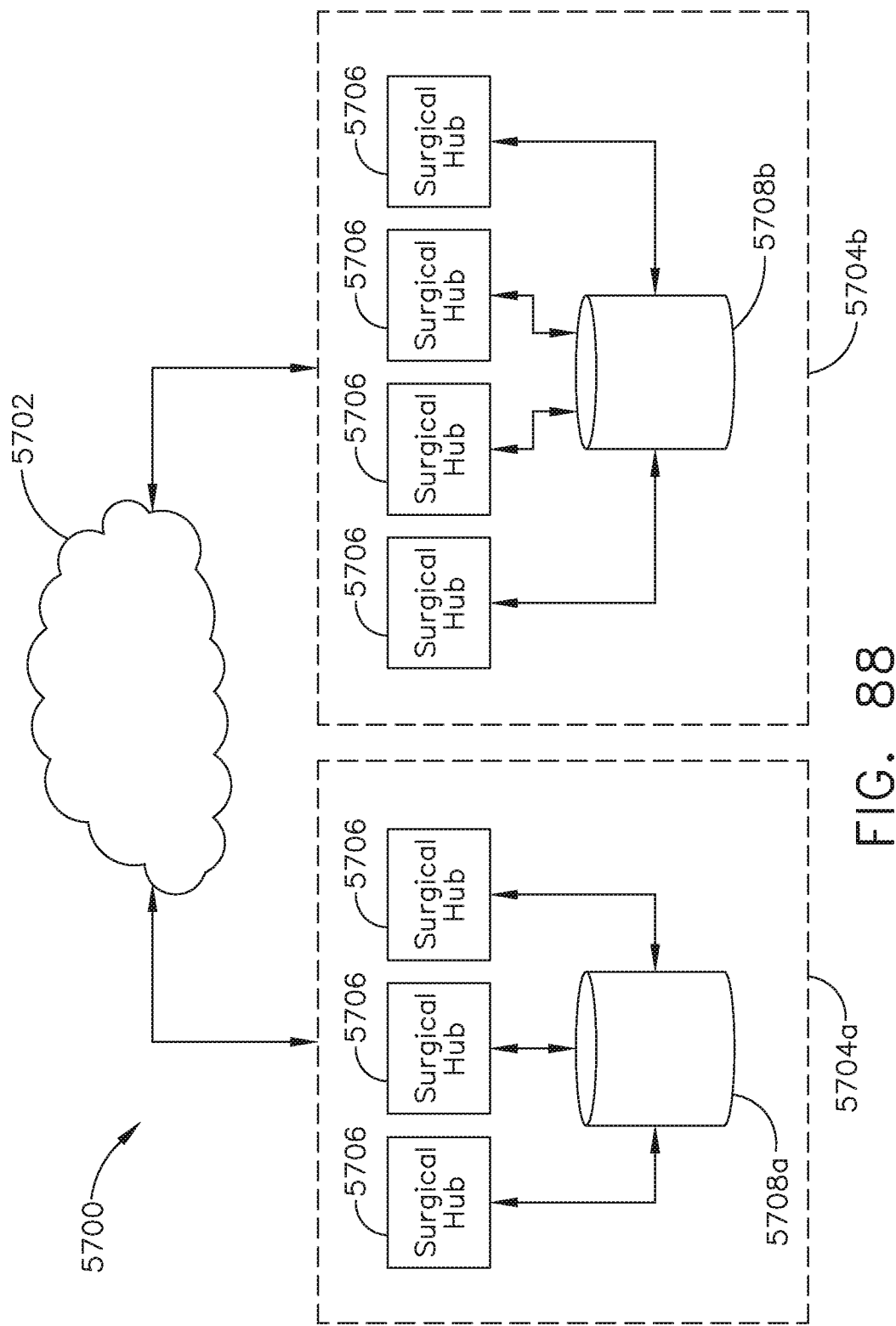

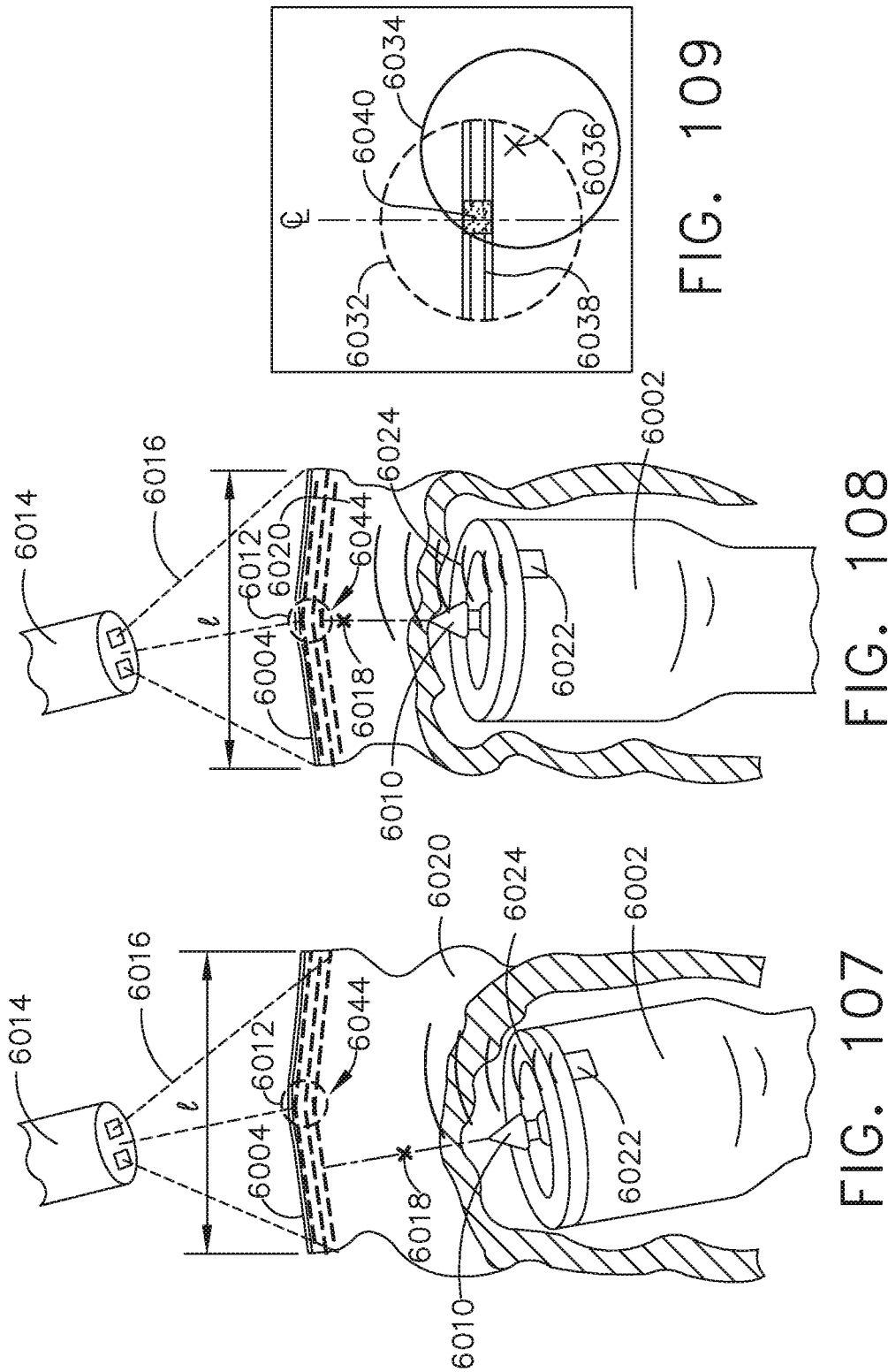

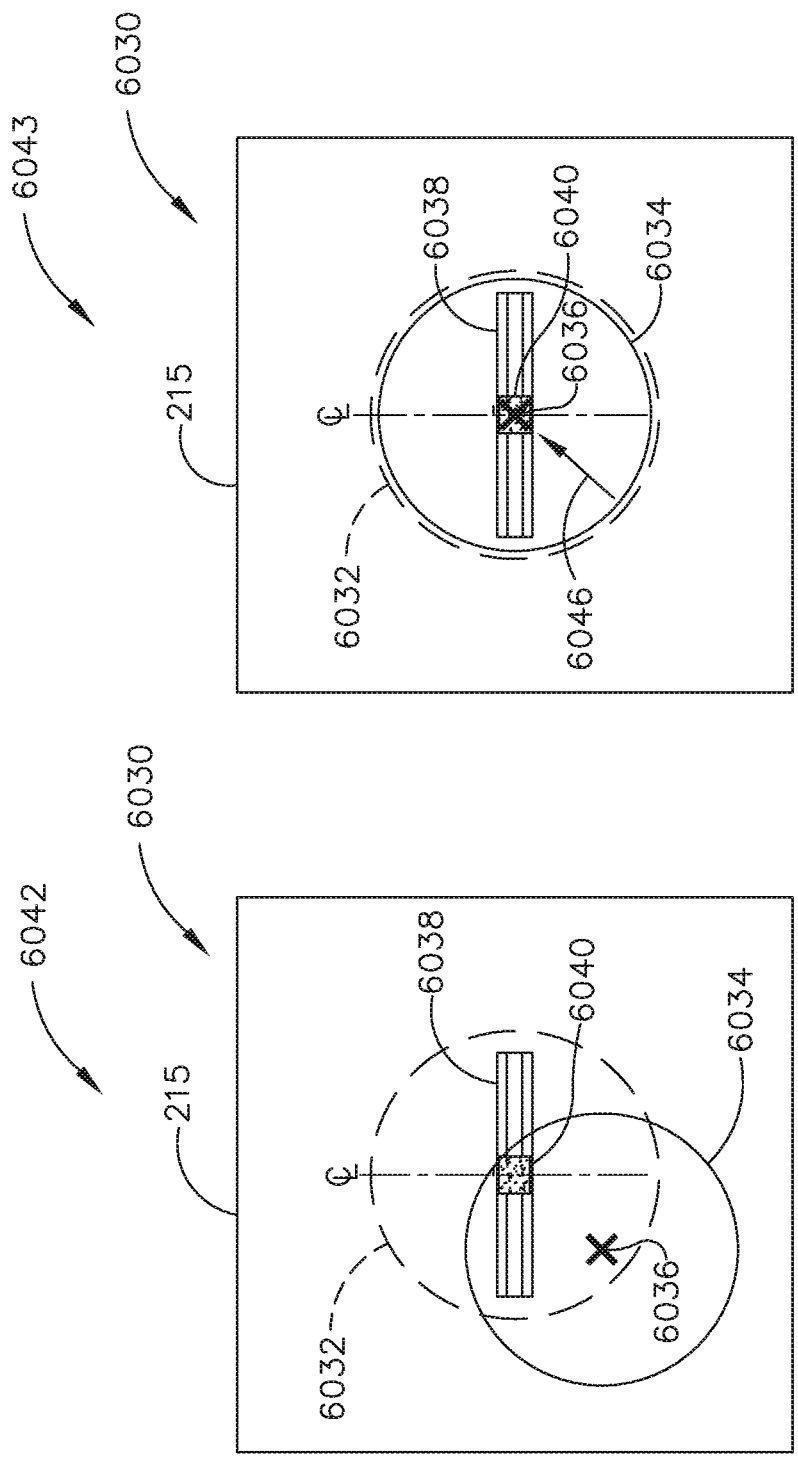

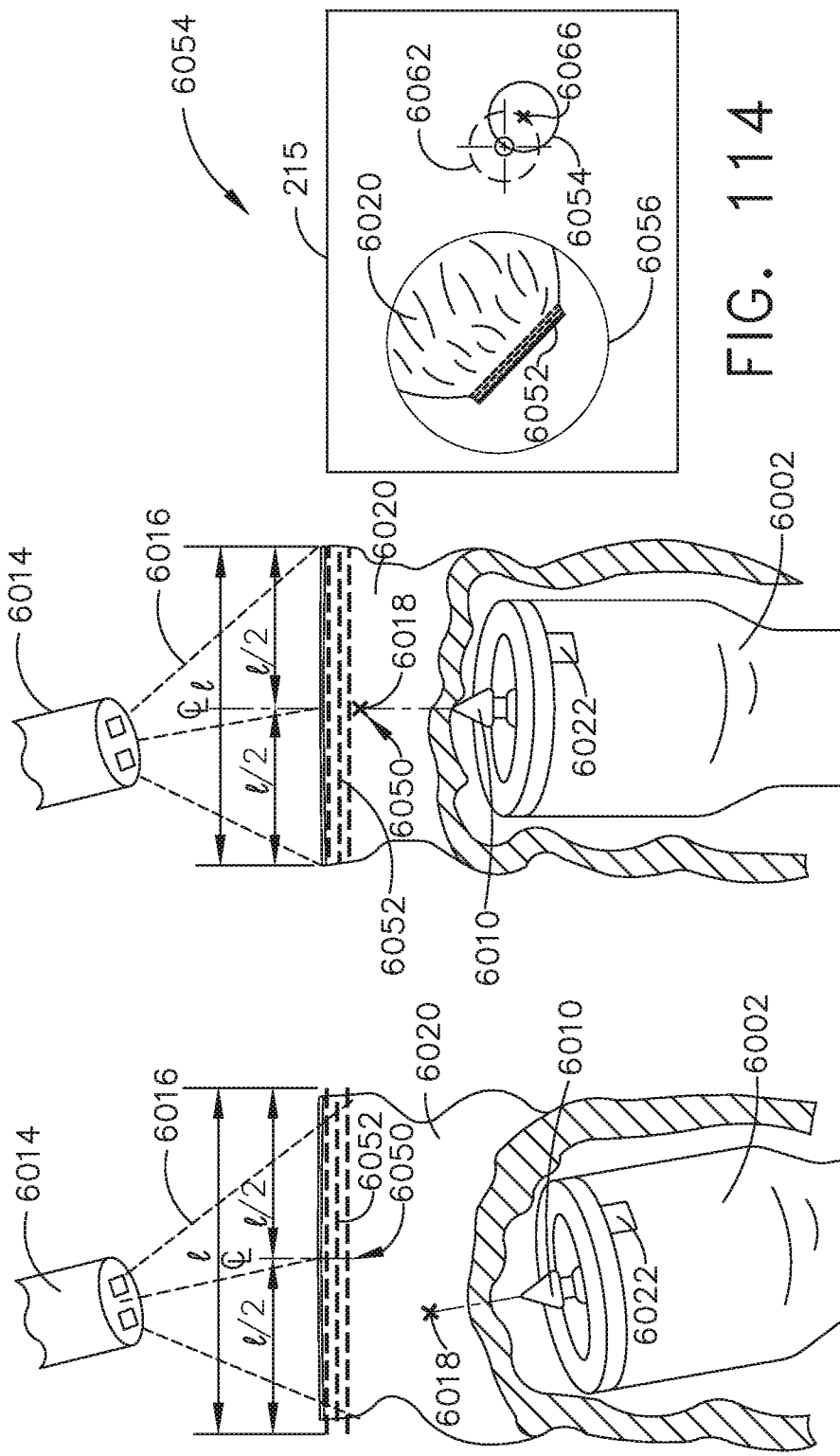

THRESHOLD TO 100%
COMPLETE CREEP
STABILITY METER

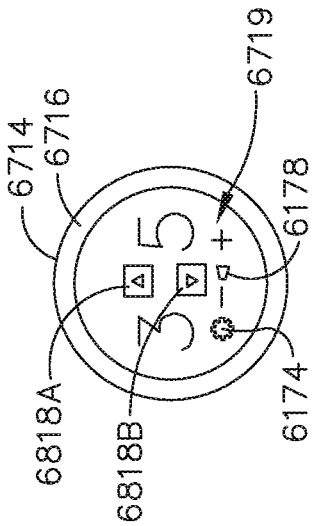
FIG. 138E
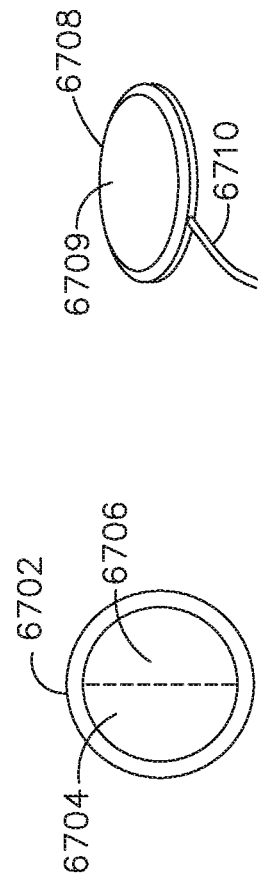
FIG. 138C
FIG. 138B
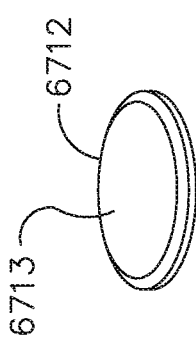
FIG. 138D
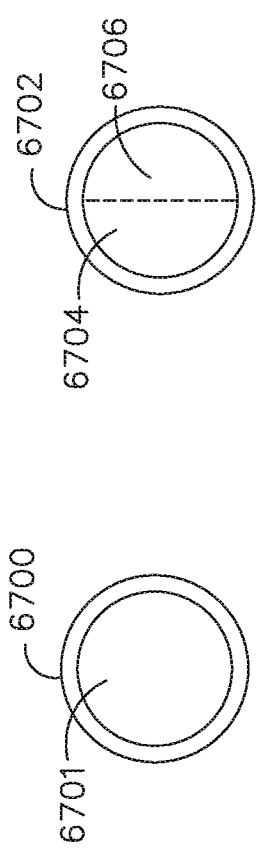
FIG. 138A

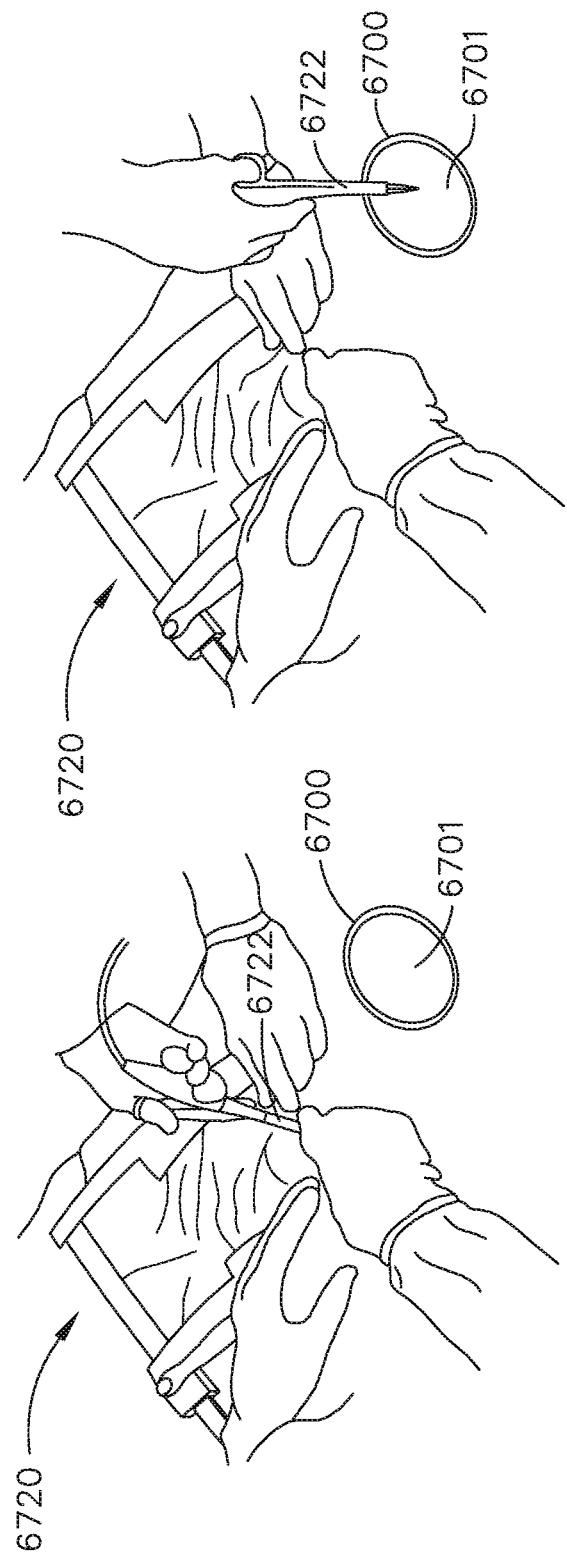

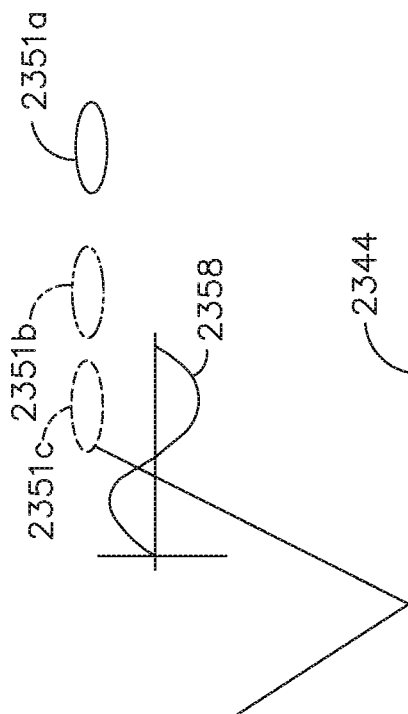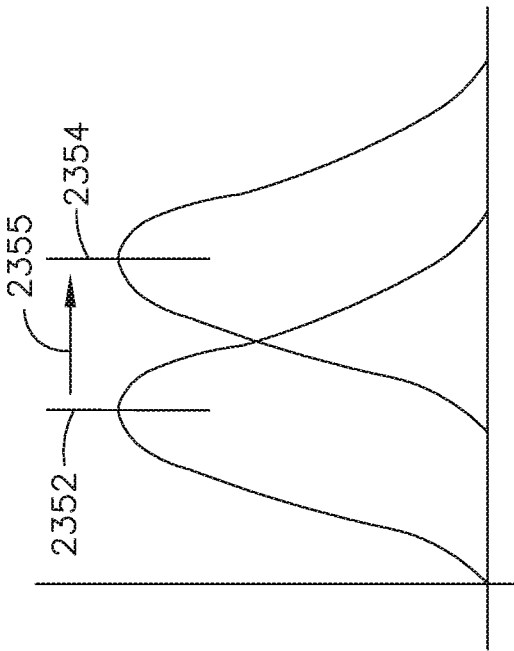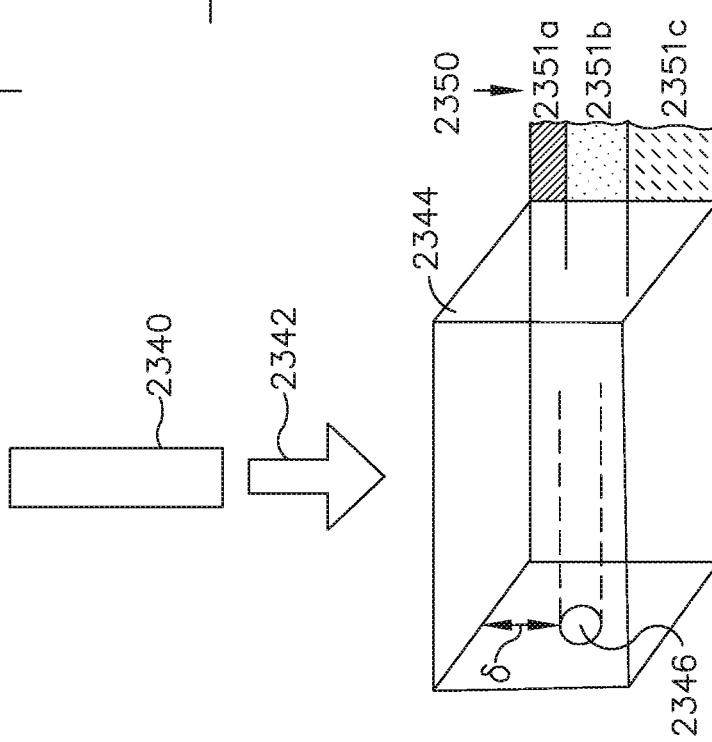
FIG. 160C
FIG. 160B
FIG. 160A

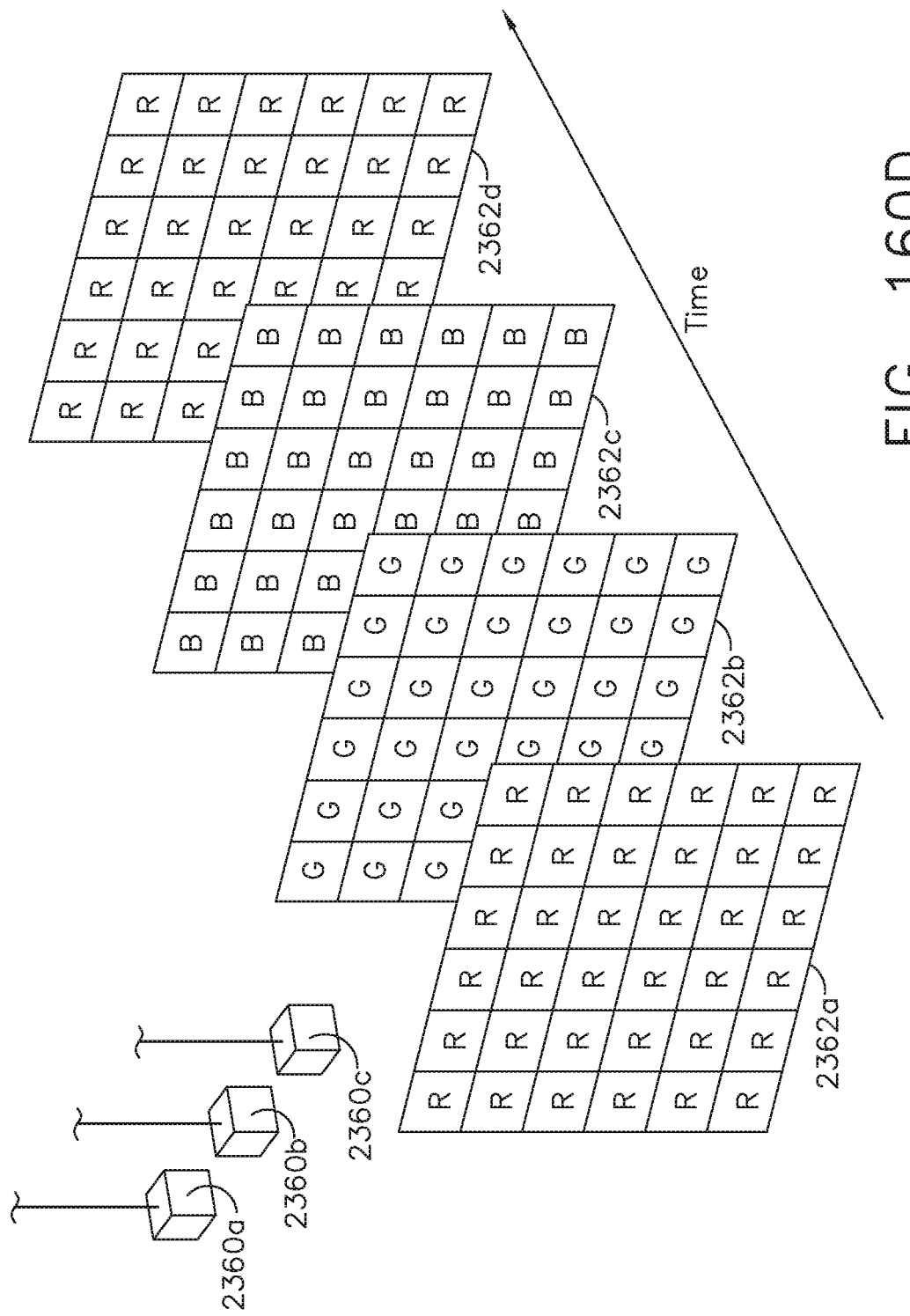

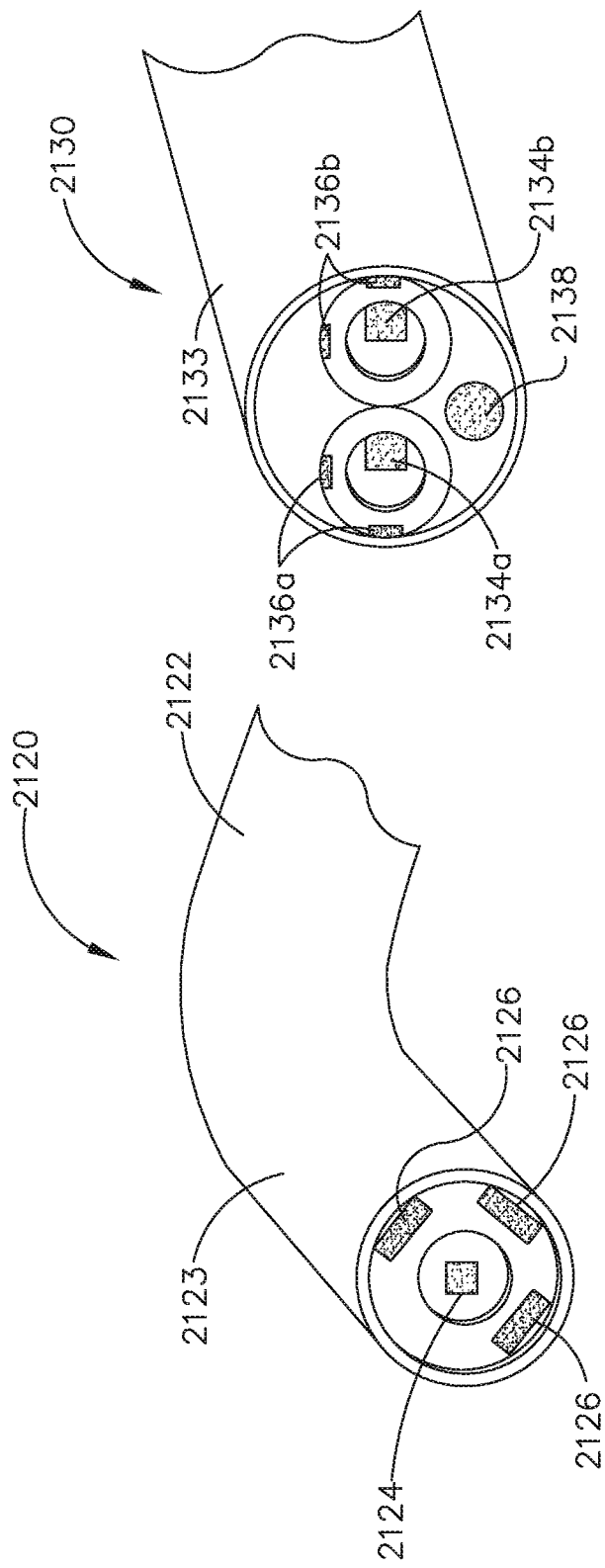

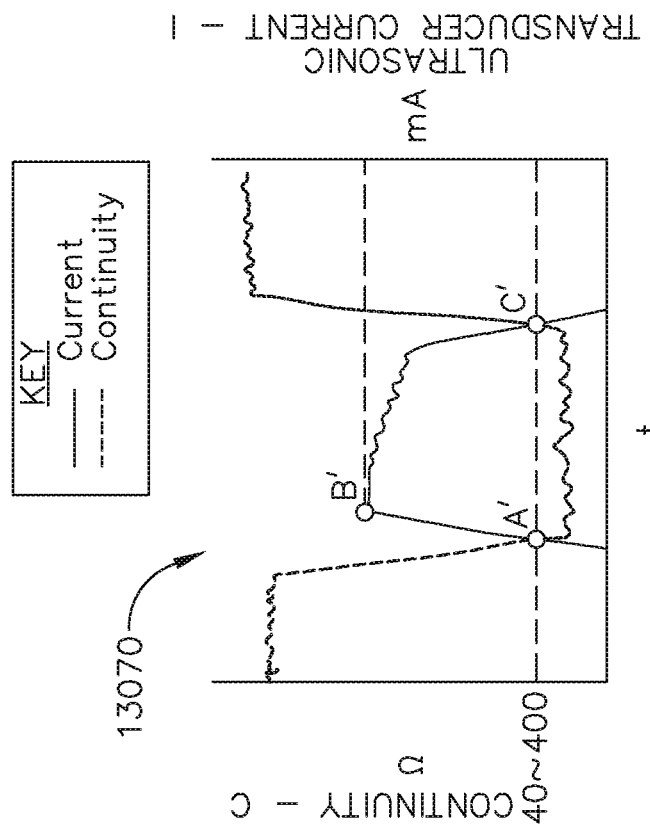
FIG. 243
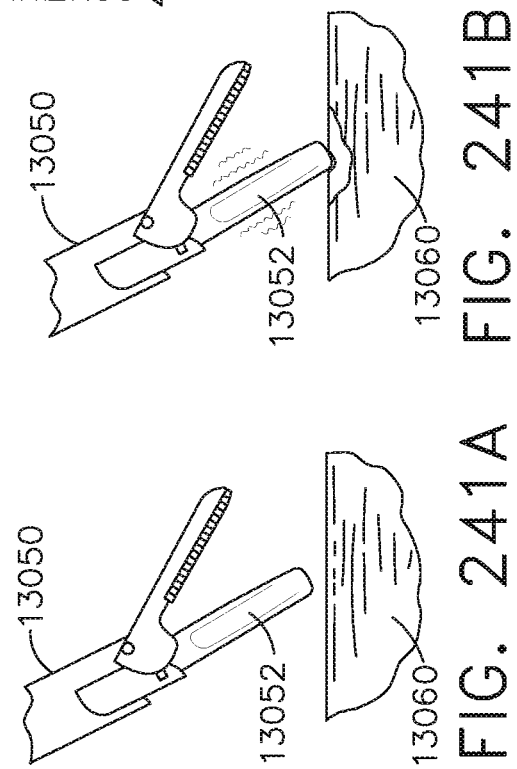
FIG. 241B
FIG. 241A

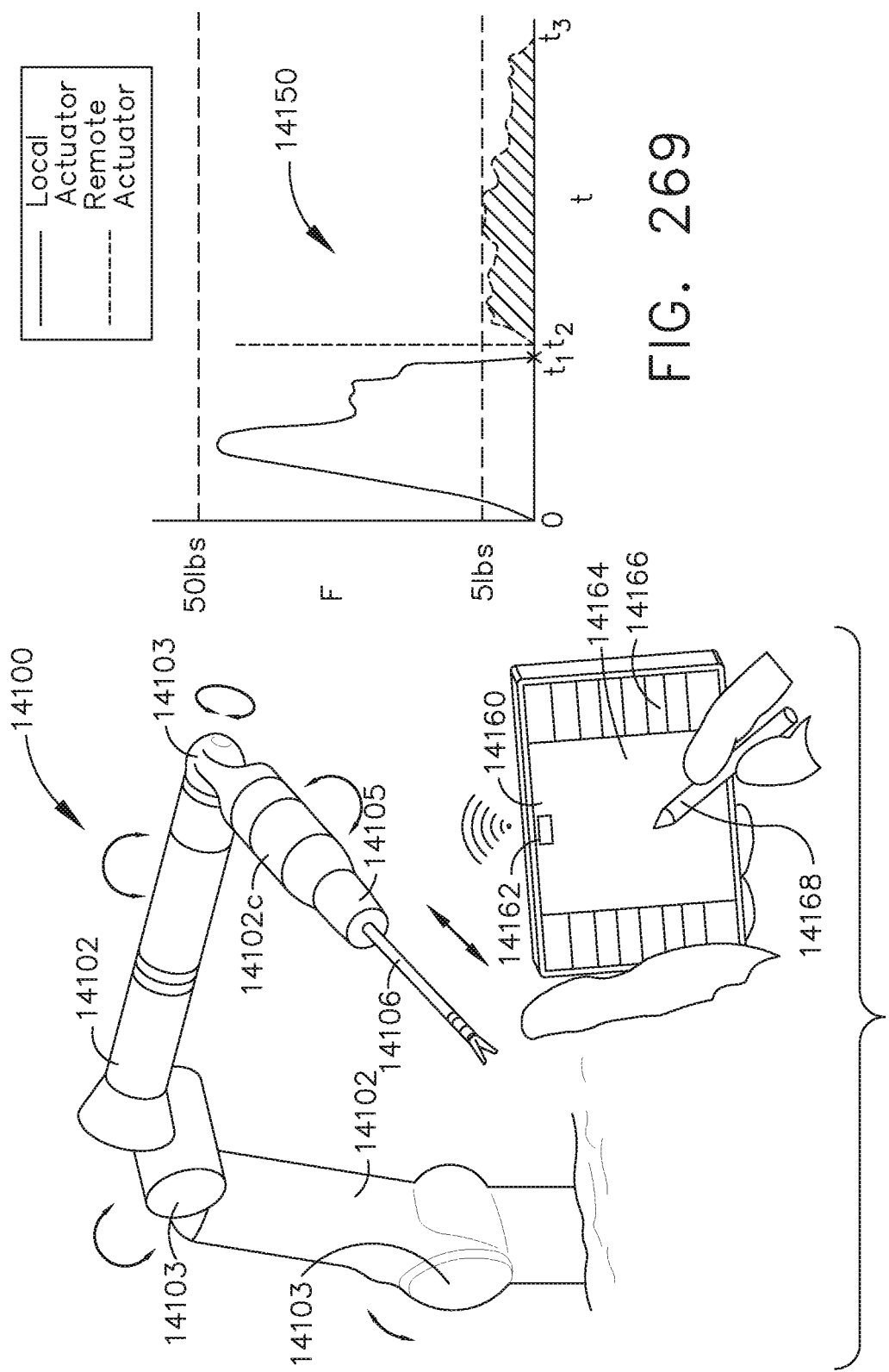

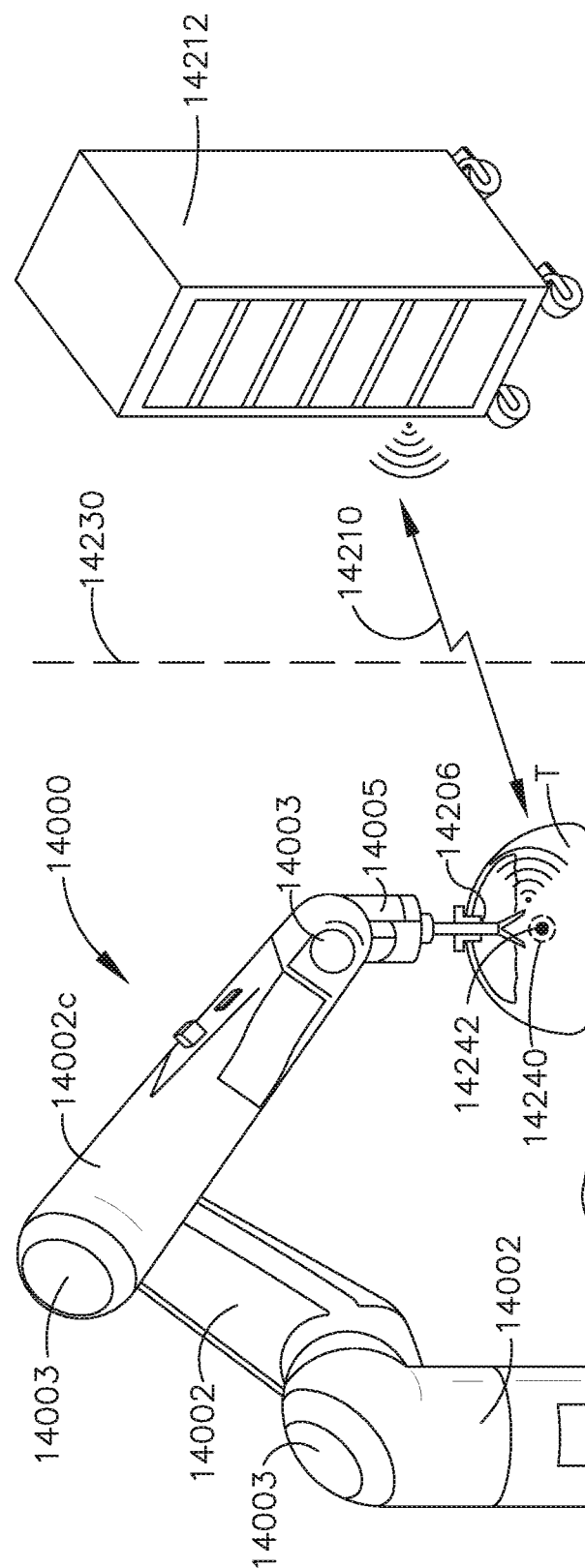

FIG. 2777

| | RT/LE SHAFT ARTICULATION | DISTAL HEAD ROTATION | END-EFFECTOR ACTUATION #1 | END-EFFECTOR ACTUATION #2 | SHAFT ROTATION |
|---|---|---|---|---|---|
| 1 PENCIL HANDLE (8) | 8mm MOTOR/ +30° | MANUAL/ >360° | LOCKED OUT | LOCKED OUT | LOCKED OUT |
| 2 SCISSOR HANDLE (12) | 12mm MOTOR 1/ +45° | MANUAL/ >360° | MOTOR 2 | LOCKED OUT | LOCKED OUT |
| 3 PISTOL HANDLE (12) | 12mm MOTOR1/ 5mm ±45° 10mm ±90° | 12mm MOTOR 3/ >360° | MOTOR 2 | MOTOR 2 WITH SHIFT | MANUAL/ >360° |

FIG. 356

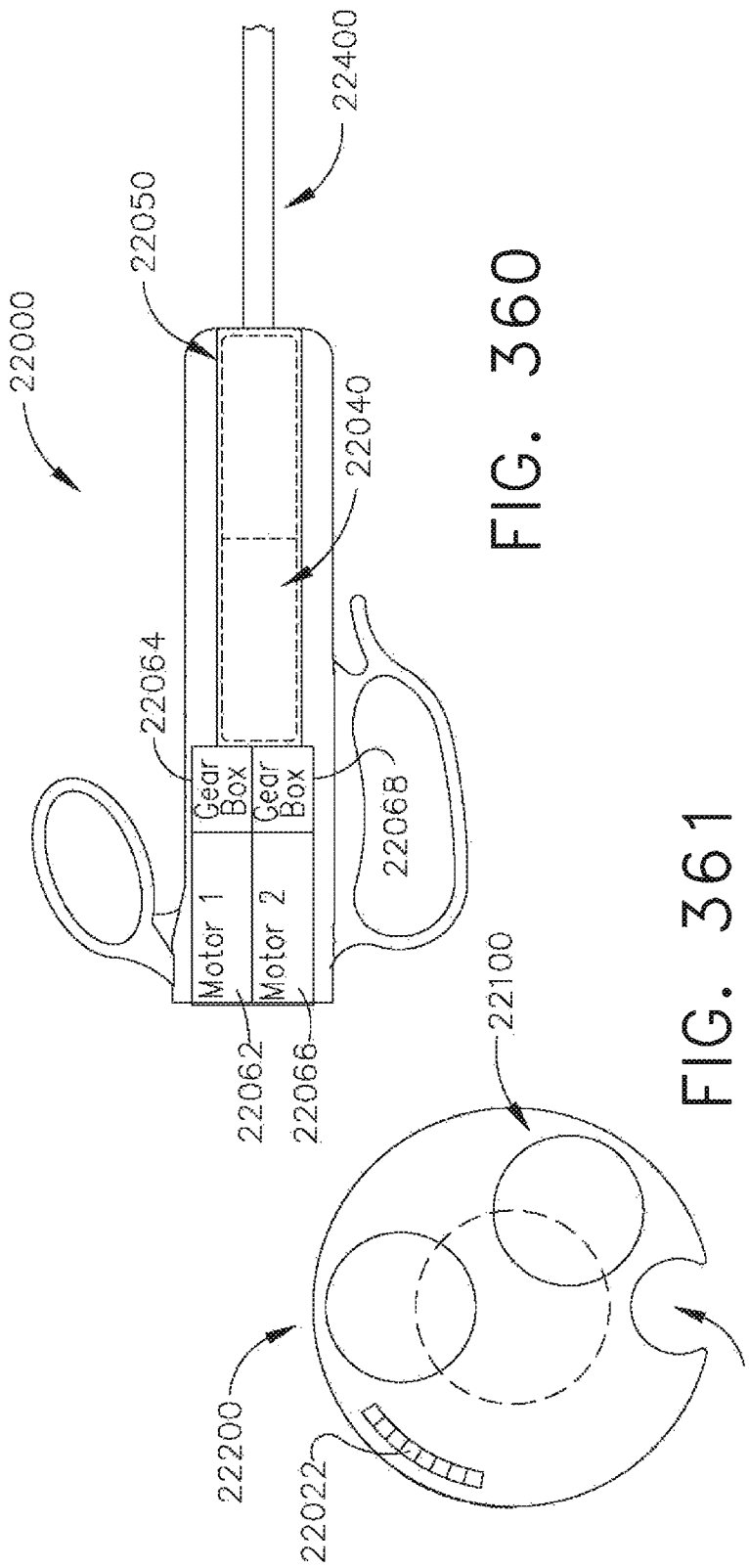

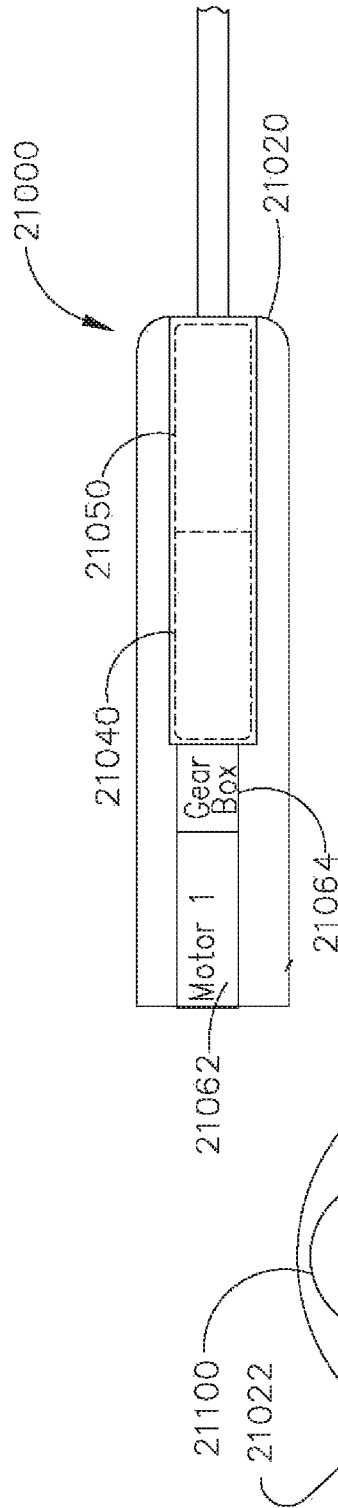
FIG. 364
FIG. 365
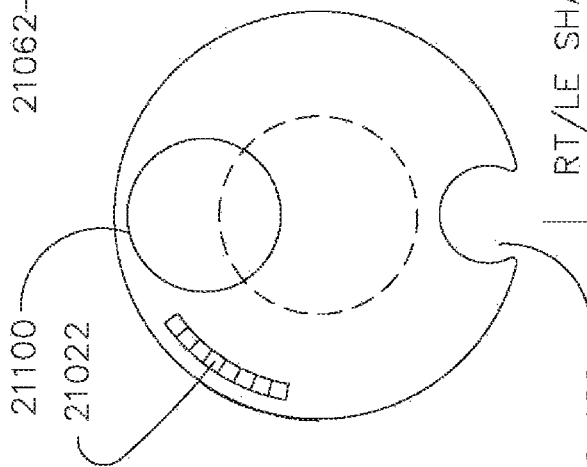
FIG. 366

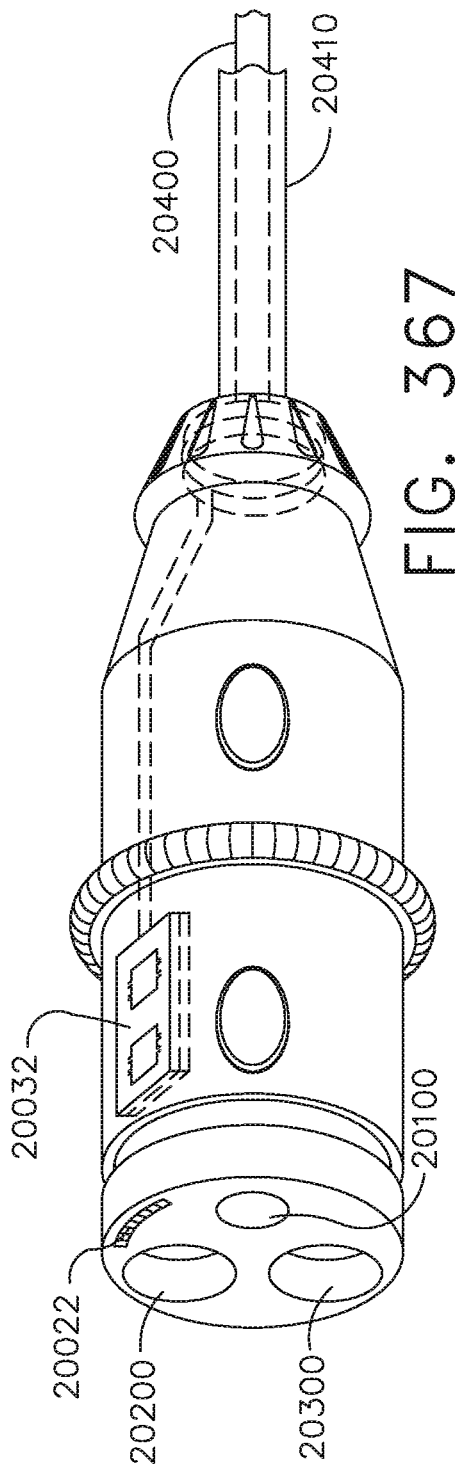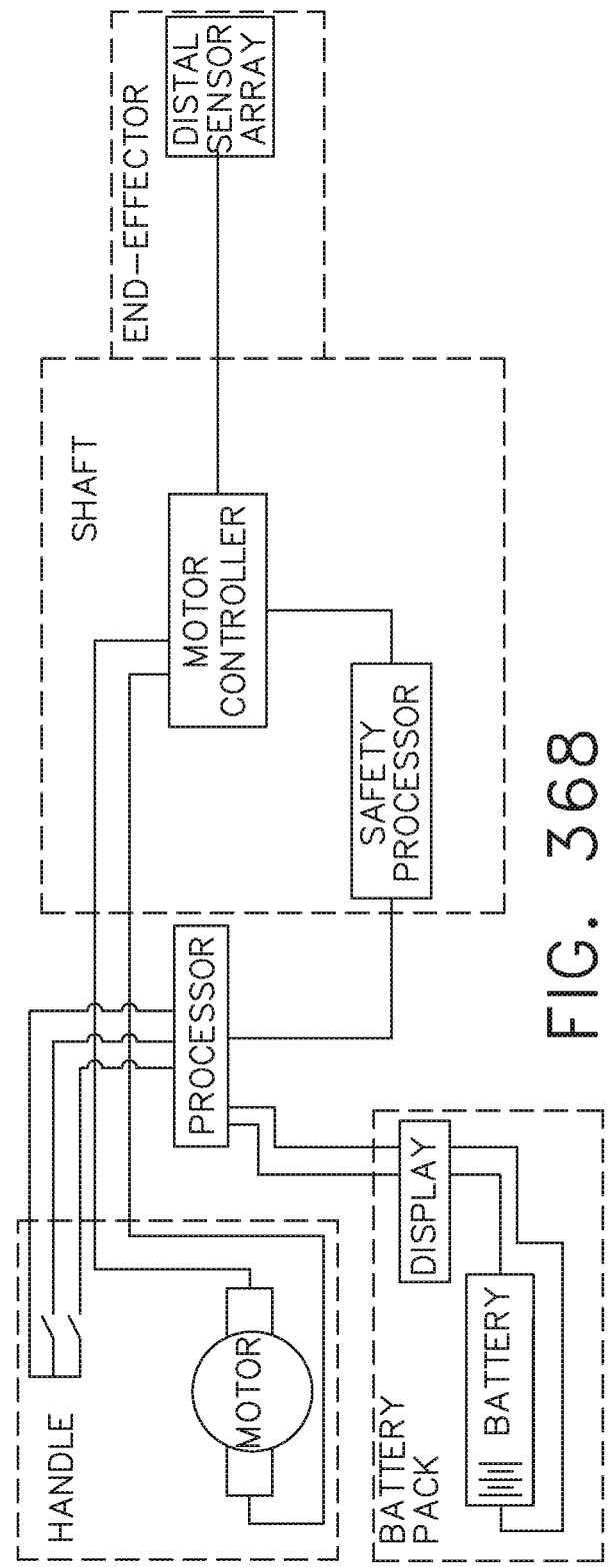

ODø_T < IDø_EAP
Non-energized

ODø_T = IDø_EAP
Energized

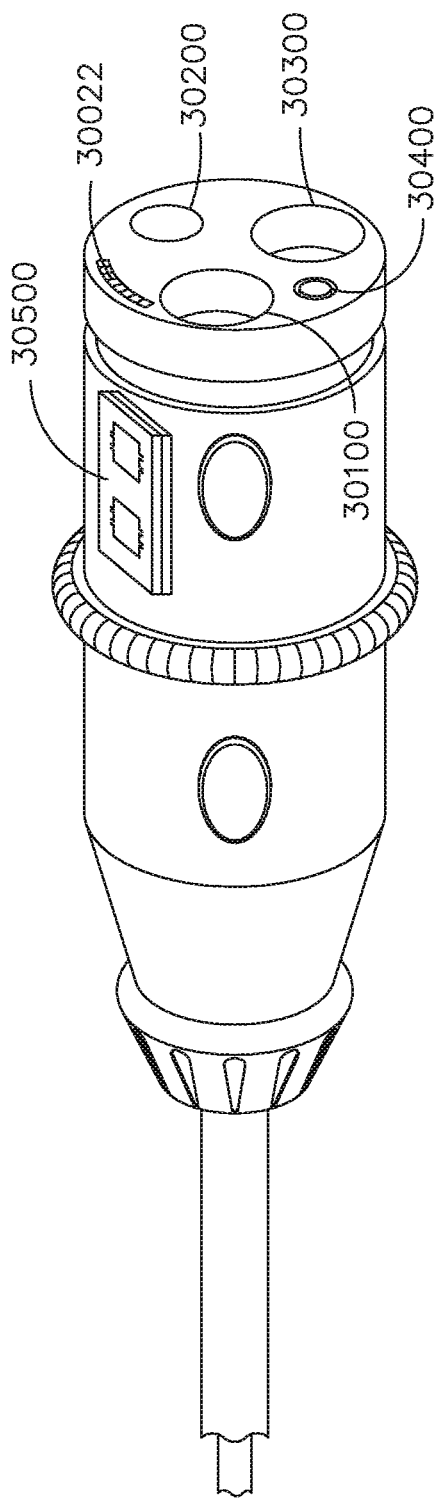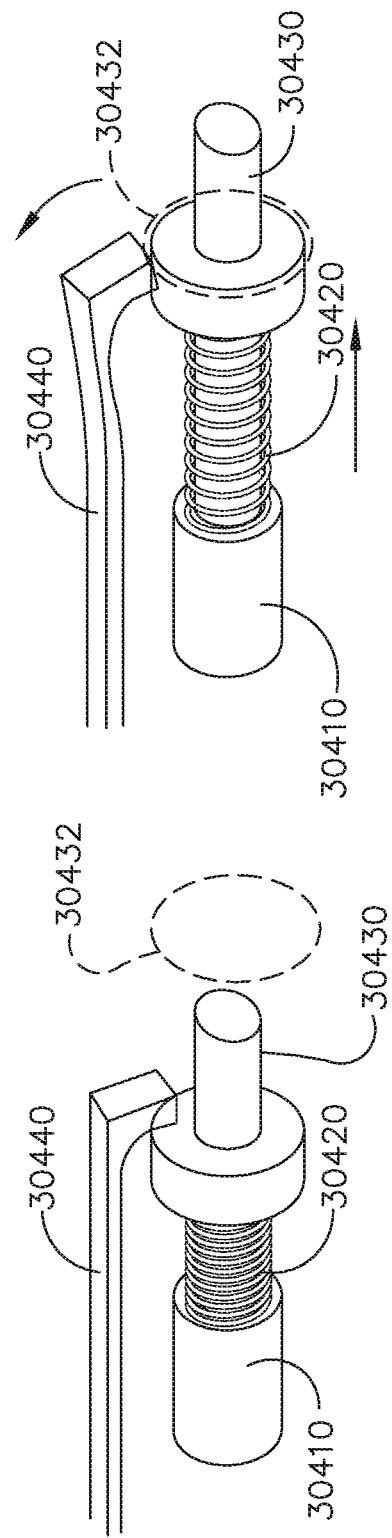
FIG. 378
FIG. 379
FIG. 380

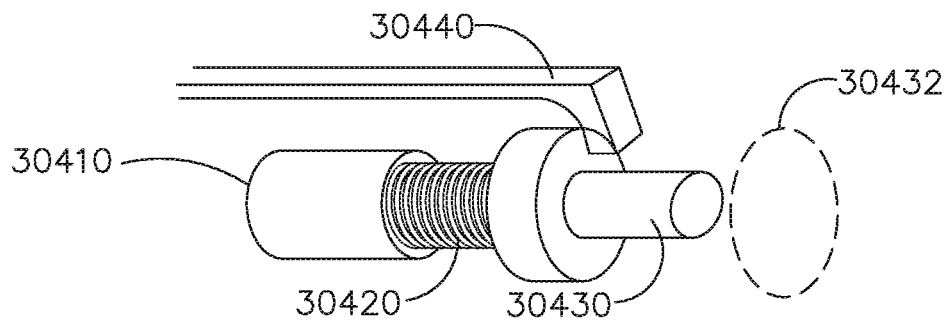
FIG. 381 Unfired, Attached/Detached
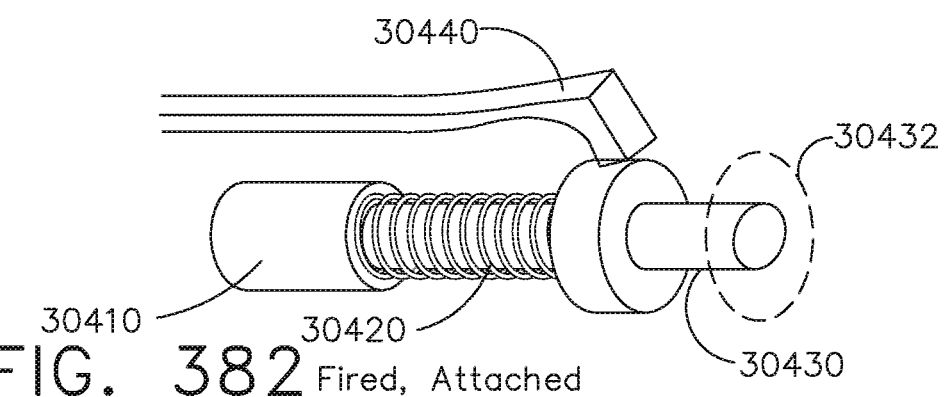
FIG. 382 Fired, Attached
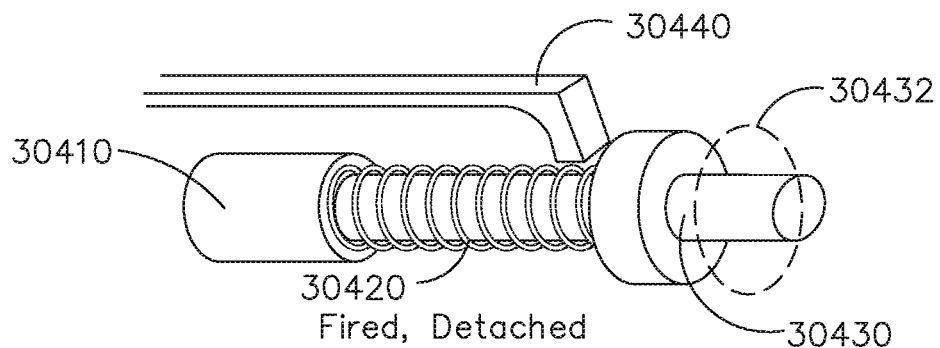
FIG. 383

METHOD OF HUB COMMUNICATION WITH SURGICAL INSTRUMENT SYSTEMS

CROSS-REFERENCE TO RELATED APPLICATIONS

This application claims the benefit of U.S. Provisional Patent Application Ser. No. 62/659,900, entitled METHOD OF HUB COMMUNICATION, filed Apr. 19, 2018, the disclosure of which is incorporated by reference herein in its entirety. This application claims the benefit of U.S. Provisional Patent Application Ser. No. 62/665,128, entitled MODULAR SURGICAL INSTRUMENTS, filed May 1, 2018, of U.S. Provisional Patent Application Ser. No. 62/665,129, entitled SURGICAL SUTURING SYSTEMS, filed May 1, 2018, of U.S. Provisional Patent Application Ser. No. 62/665,134, entitled SURGICAL CLIP APPLIER, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, and of U.S. Provisional Patent Application Ser. No. 62/665,192, entitled SURGICAL DISSECTORS, filed May 1, 2018, the disclosures of which are incorporated by reference herein in their entireties. This application claims the benefit of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,307, entitled AUTOMATIC TOOL ADJUSTMENTS FOR ROBOT-ASSISTED SURGICAL PLATFORMS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional Patent Application Ser. No. 62/649,323, entitled SENSING ARRANGEMENTS FOR ROBOT-ASSISTED SURGICAL PLATFORMS, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, and of U.S. Provisional Patent Application Ser. No. 62/649,333, entitled CLOUD-BASED MEDICAL ANALYTICS FOR CUSTOMIZATION AND RECOMMENDATIONS TO A USER, filed Mar. 28, 2018, the disclosures of which are incorporated by reference herein in their entireties. This application claims the benefit of U.S. Provisional Patent Application Ser. No. 62/611,339, entitled ROBOT ASSISTED SURGICAL PLATFORM, filed Dec. 28, 2017, of U.S. Provisional Patent Application Ser. No. 62/611,340, entitled CLOUD-BASED MEDICAL ANALYTICS, filed Dec. 28, 2017, and of U.S. Provisional Patent Application Ser. No. 62/611,341, entitled INTERACTIVE SURGICAL PLATFORM, filed Dec. 28, 2017, the disclosures of which are incorporated by reference herein in their entireties. This application claims the benefit of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entireties.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

Furthermore, in the Digital and Information Age, medical systems and facilities are often slower to implement systems or procedures utilizing newer and improved technologies due to patient safety and a general desire for maintaining traditional practices. However, often times medical systems and facilities may lack communication and shared knowledge with other neighboring or similarly situated facilities as a result. To improve patient practices, it would be desirable to find ways to help interconnect medical systems and facilities better.

The present disclosure also relates to robotic surgical systems. Robotic surgical systems can include a central control unit, a surgeon's command console, and a robot having one or more robotic arms. Robotic surgical tools can be releasably mounted to the robotic arm(s). The number and type of robotic surgical tools can depend on the type of surgical procedure. Robotic surgical systems can be used in connection with one or more displays and/or one or more handheld surgical instruments during a surgical procedure.

The present invention also relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 51 illustrates three rows of staples deployed on one side of a tissue stapled and cut by a surgical stapler, in accordance with at least one aspect of the present disclosure;

FIG. 52 illustrates a non-anodized staple and an anodized staple, in accordance with at least one aspect of the present disclosure;

FIG. 56 illustrates an interaction between two surgical hubs in different operating rooms ("OR1" and "OR3"), in accordance with at least one aspect of the present disclosure;

FIG. 84I illustrates a logic flow diagram of a process for determining a patient status according to pulse oximeter, blood pressure monitor, and/or EKG monitor perioperative data, in accordance with at least one aspect of the present disclosure;

FIG. 88 illustrates a block diagram of a computer-implemented interactive surgical system, in accordance with at least one aspect of the present disclosure;

FIG. 104 illustrates a logic flow diagram of a process for shifting distributed computing resources, in accordance with at least one aspect of the present disclosure;

FIG. 105 illustrates a diagram of an imaging system and a surgical instrument bearing a calibration scale, in accordance with at least one aspect of the present disclosure;

FIG. 106 illustrates a diagram of a surgical instrument centered on a linear staple transection line using the benefit of centering tools and techniques described in connection with FIGS. 107-119, in accordance with at least one aspect of the present disclosure;

FIGS. 107-109 illustrate a process of aligning an anvil trocar of a circular stapler to a staple overlap portion of a linear staple line created by a double-stapling technique, in accordance with at least one aspect of the present disclosure, where:

FIG. 107 illustrates an anvil trocar of a circular stapler that is not aligned with a staple overlap portion of a linear staple line created by a double-stapling technique;

Figures 115, 116, 117:
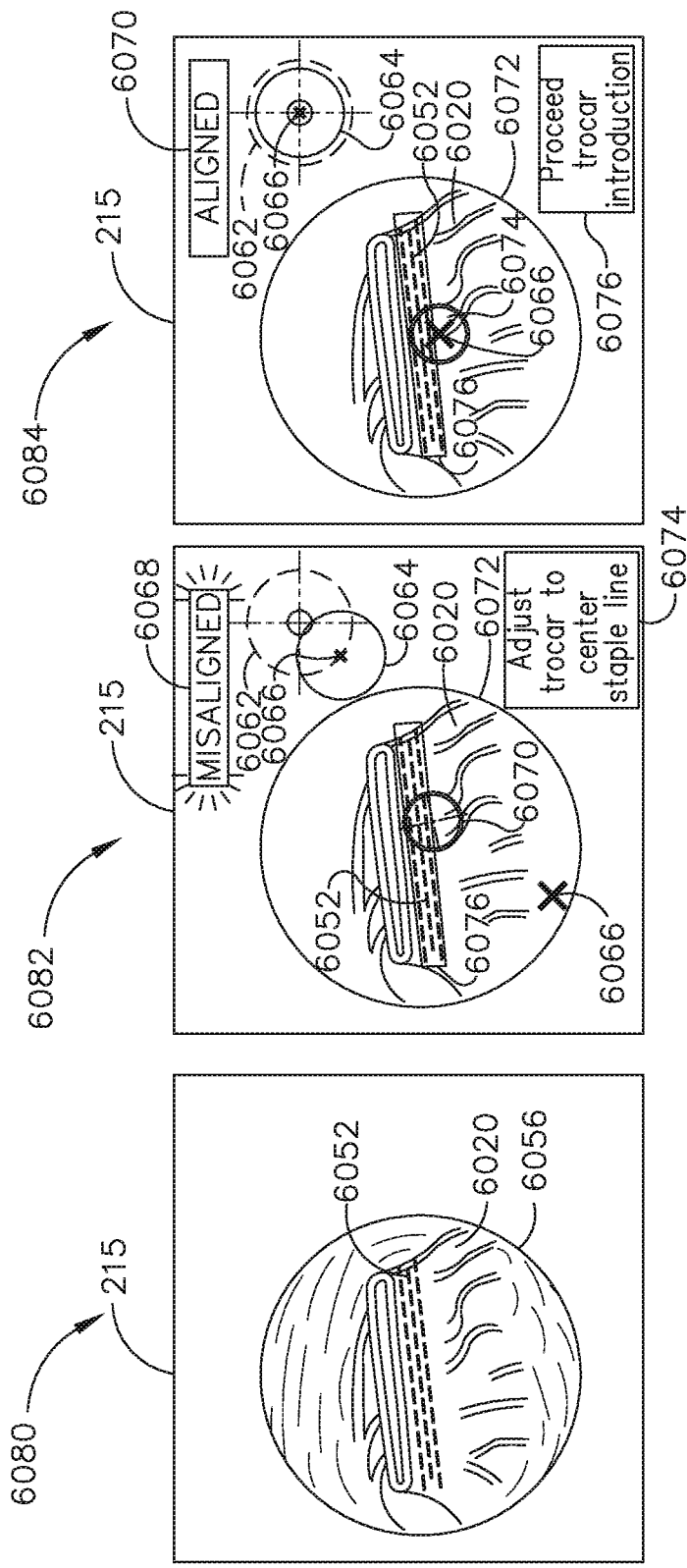
Figure 118:
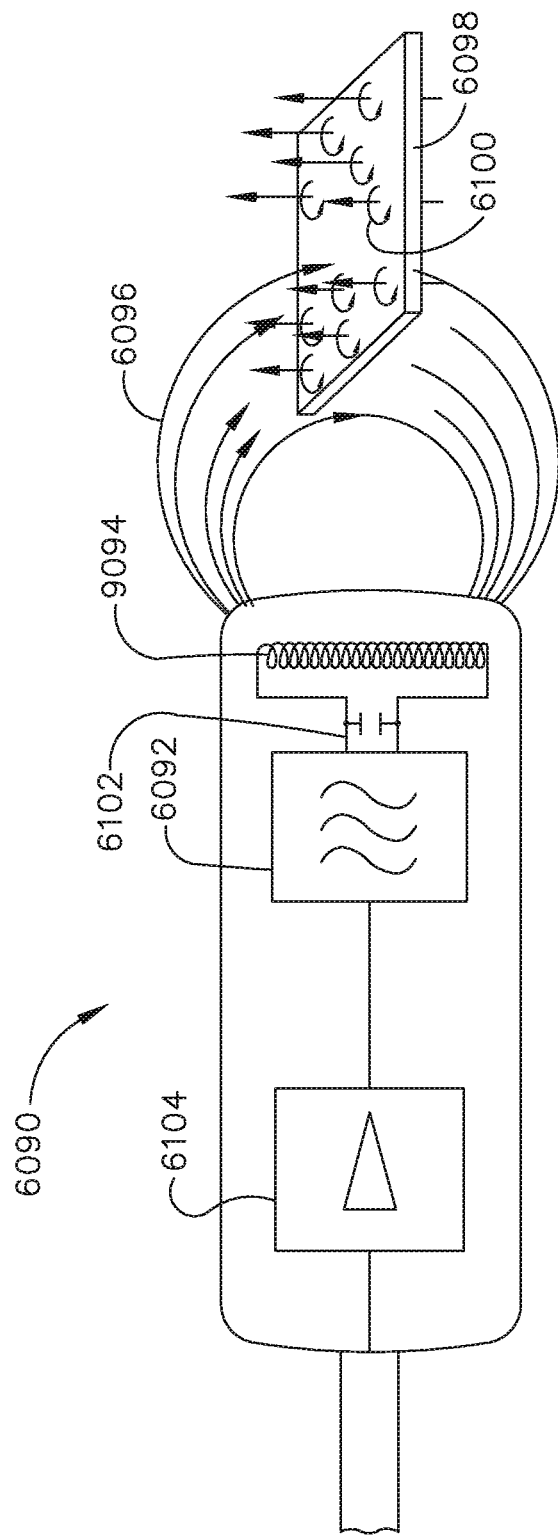
Figure 119:
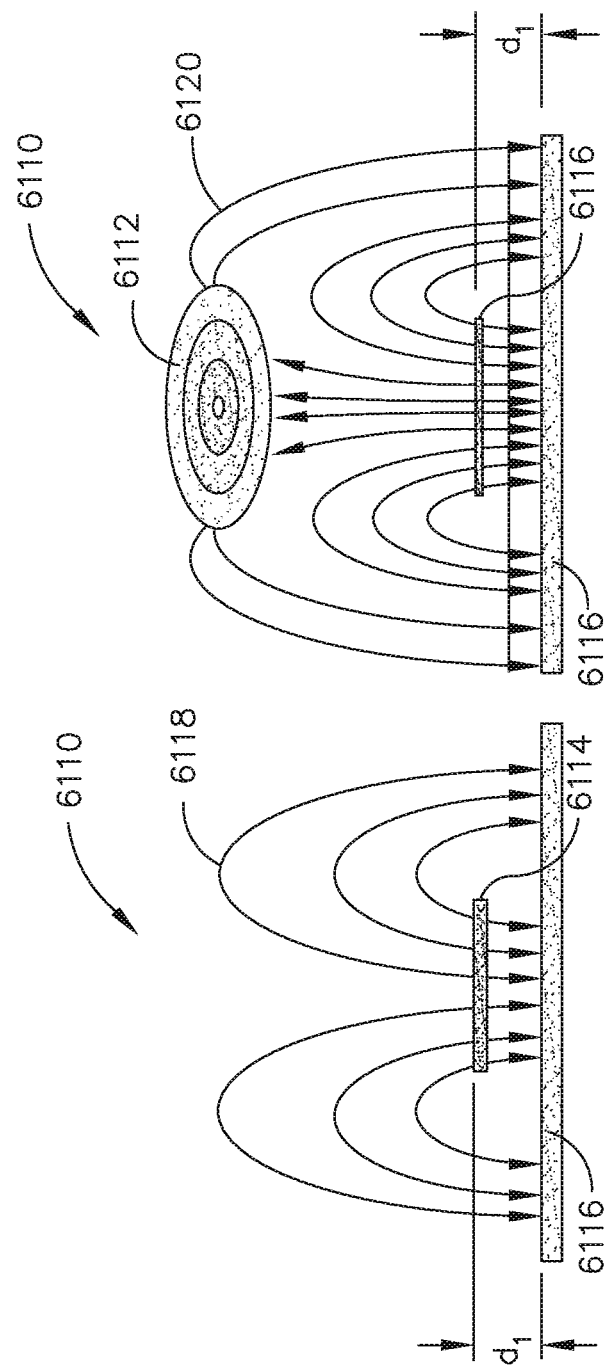
Figure 120:
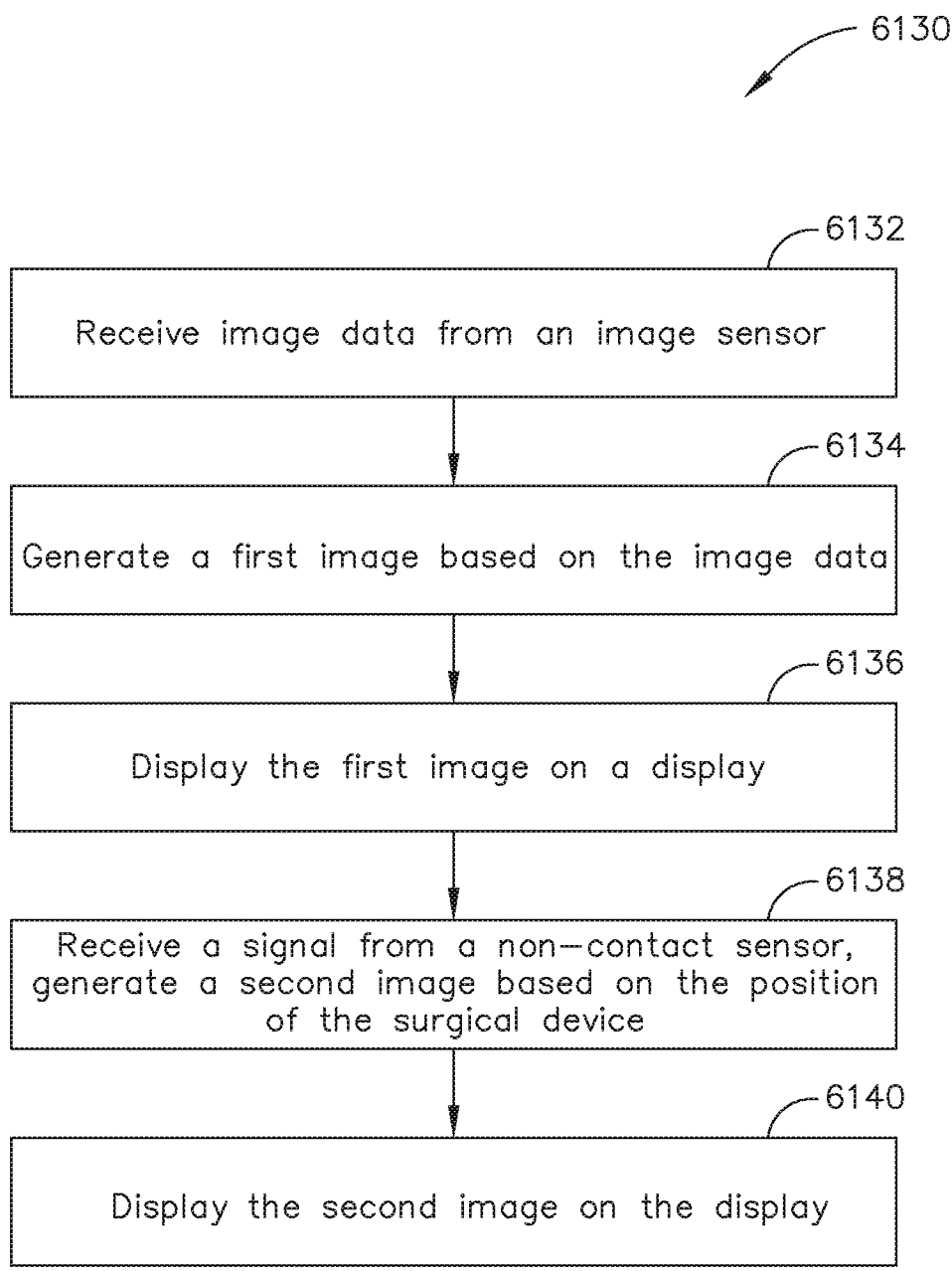
Figure 121:
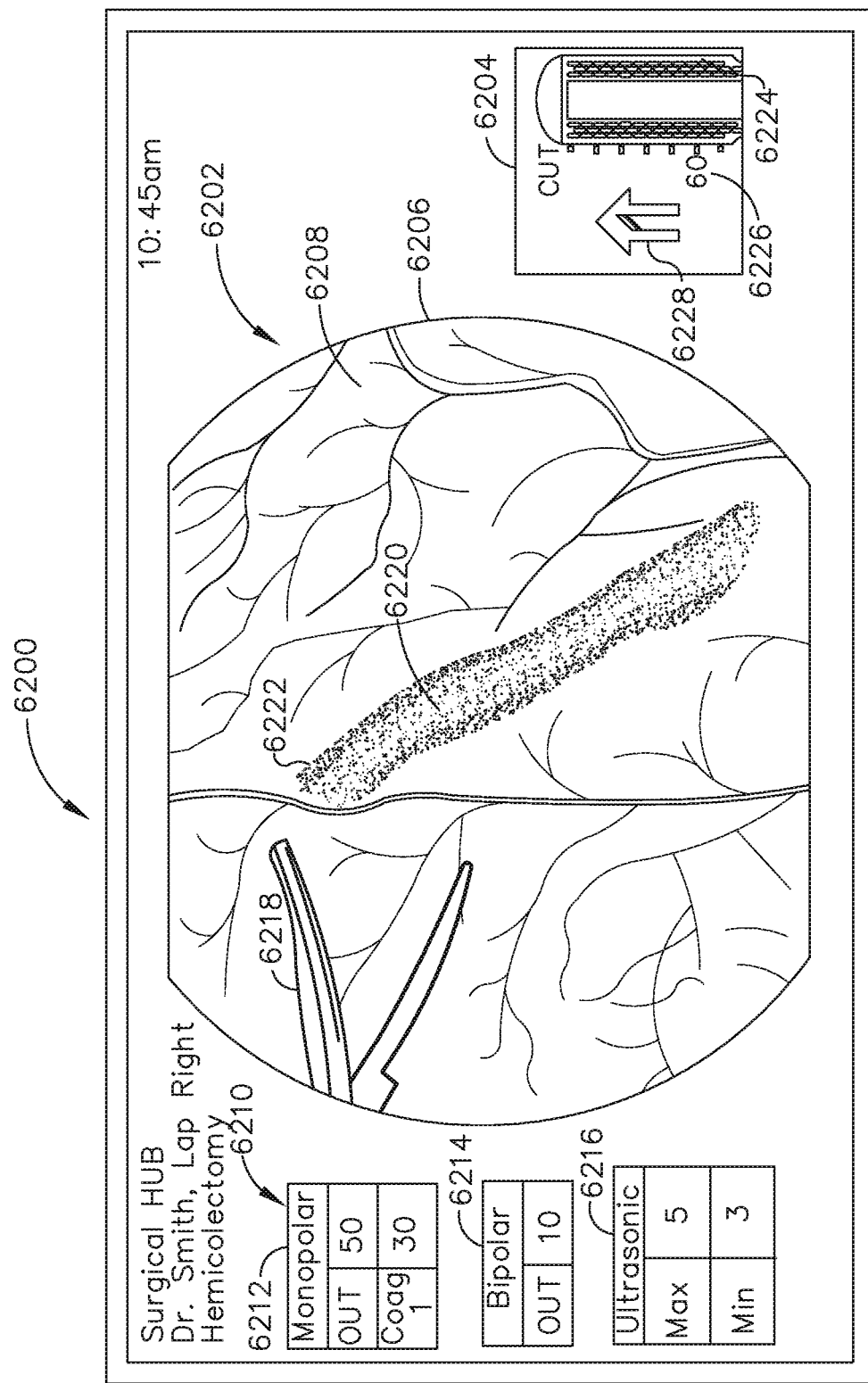
Figure 122:
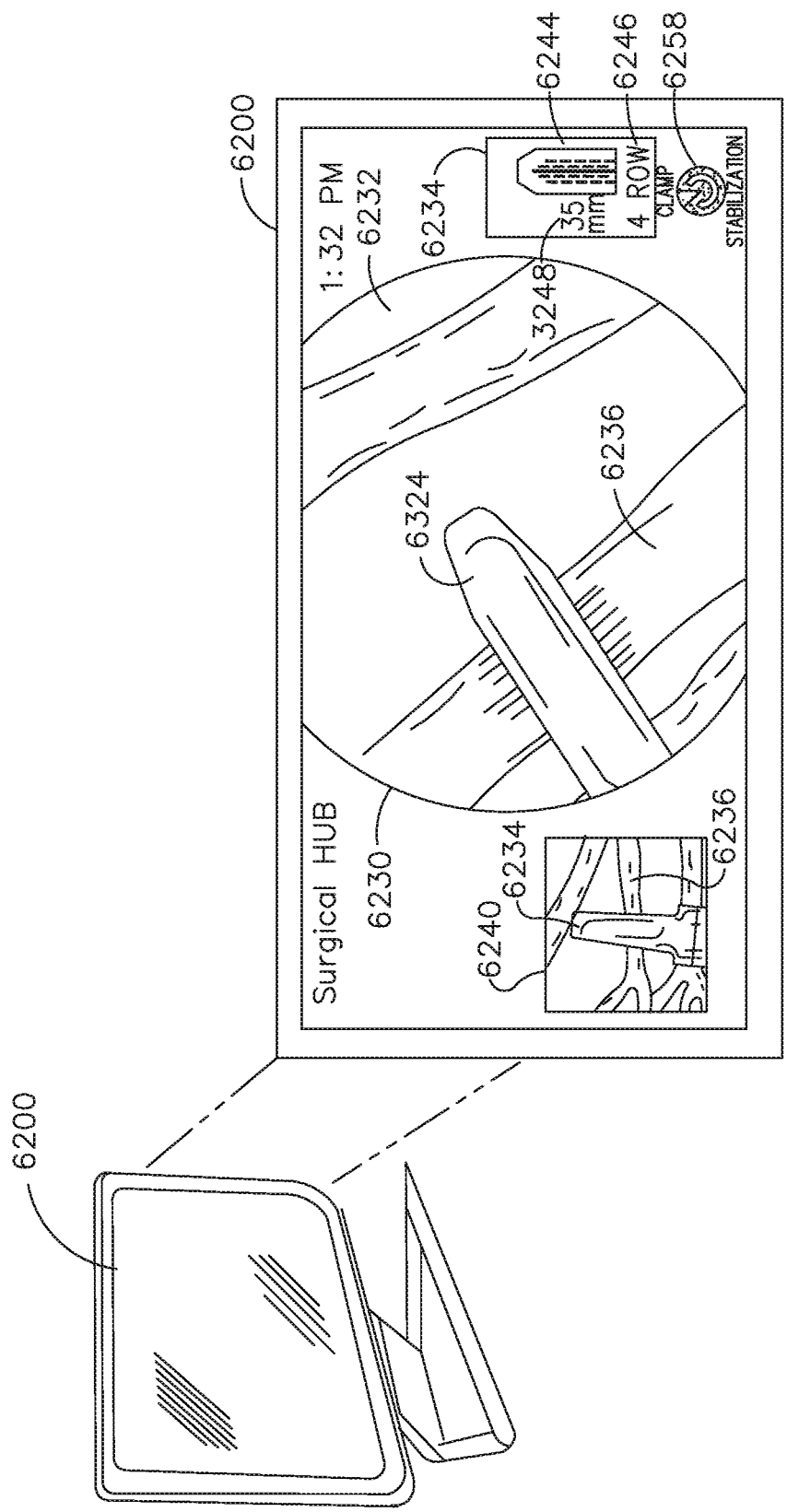
Figure 123:
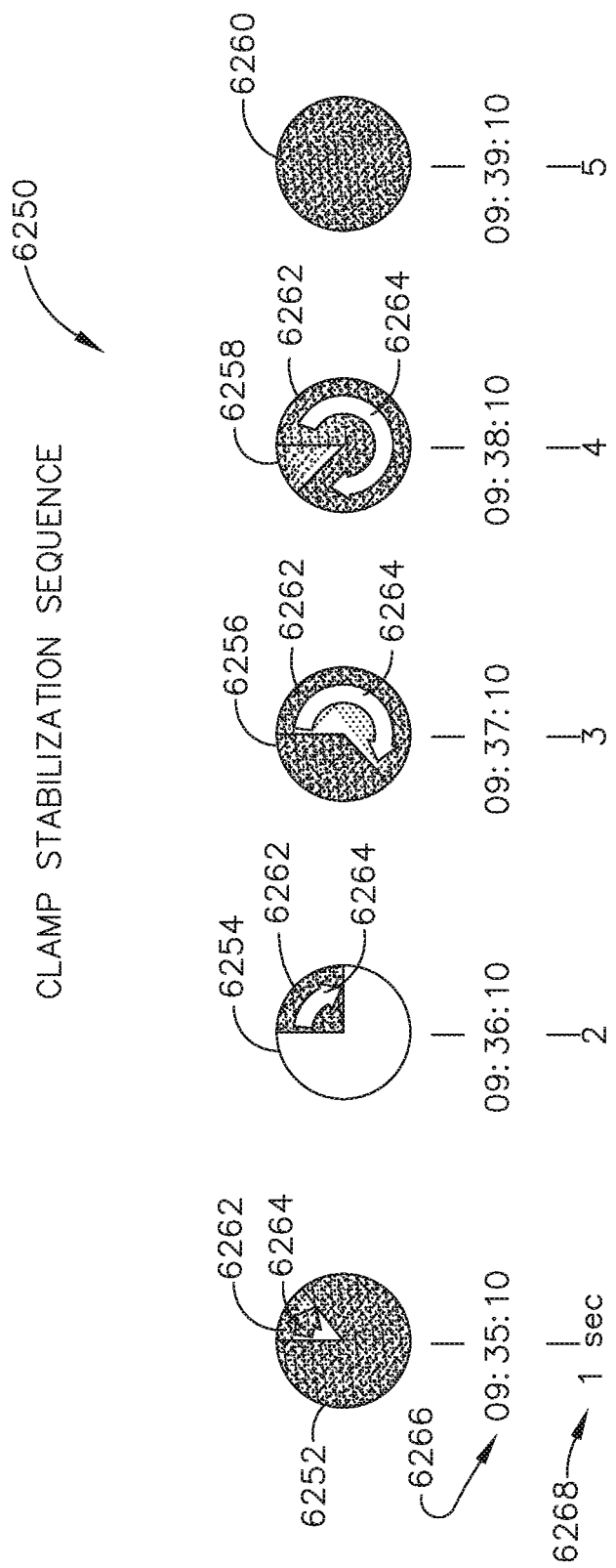
Figure 124:
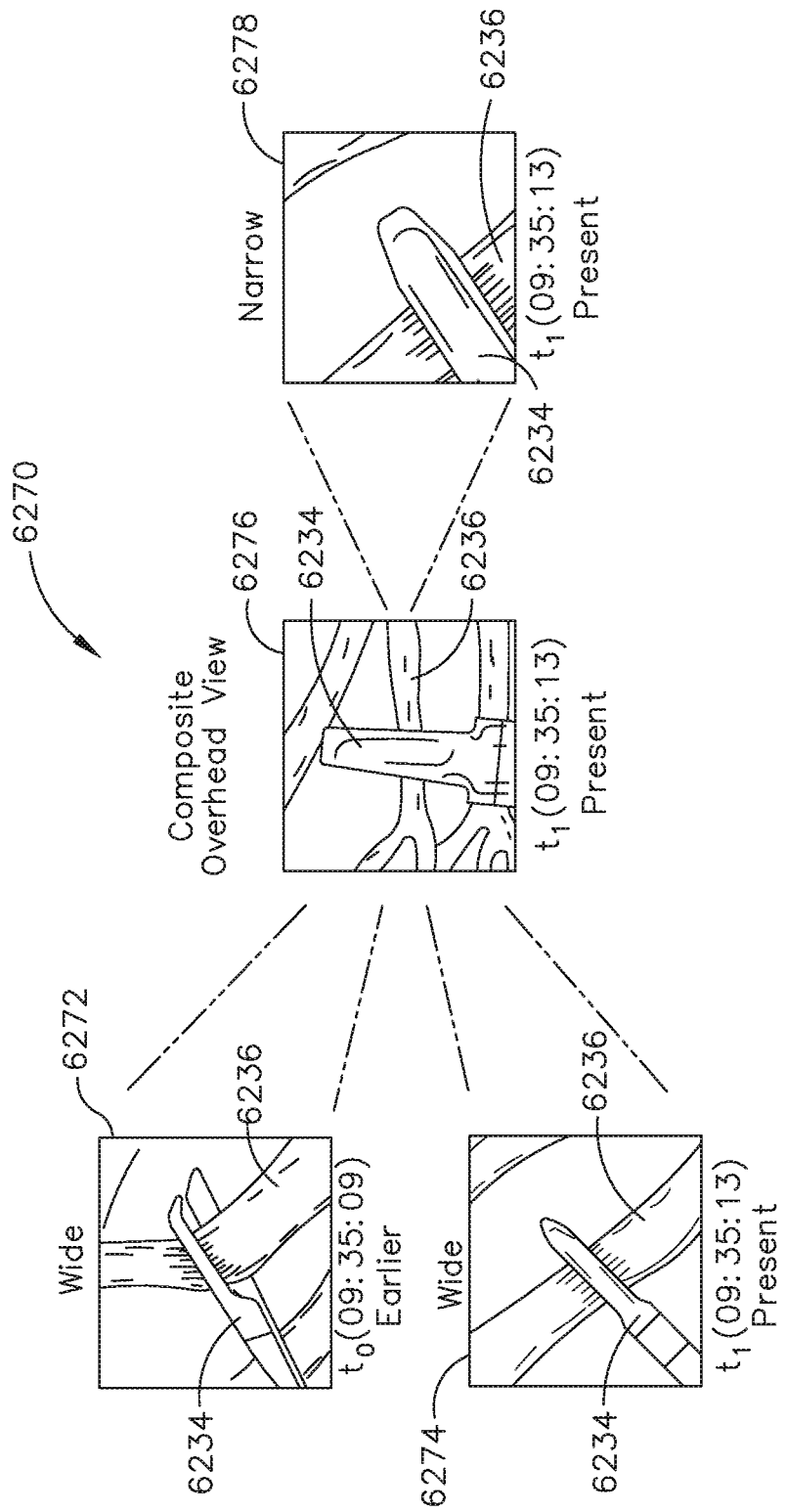
Figure 125:
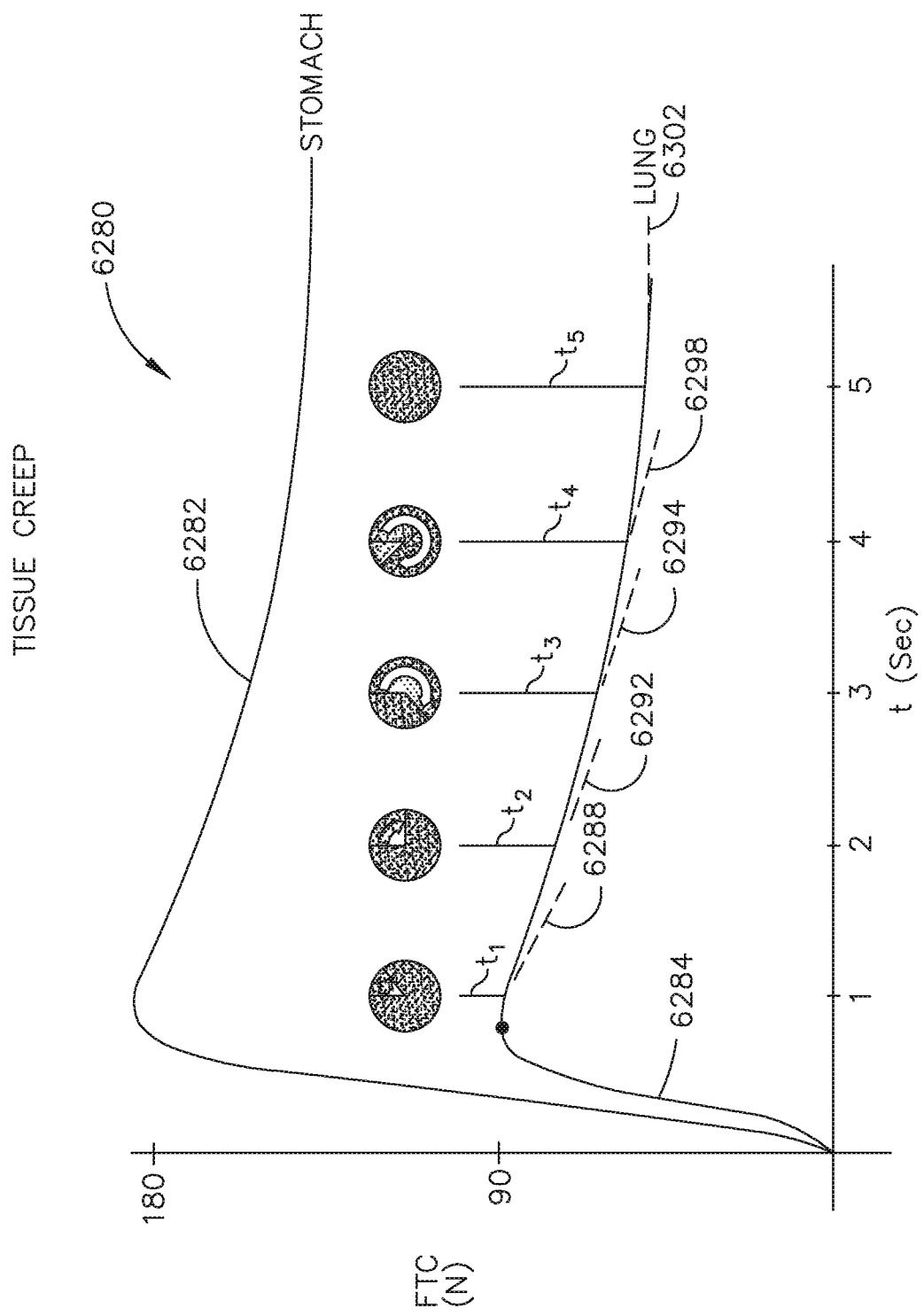
Figure 126:
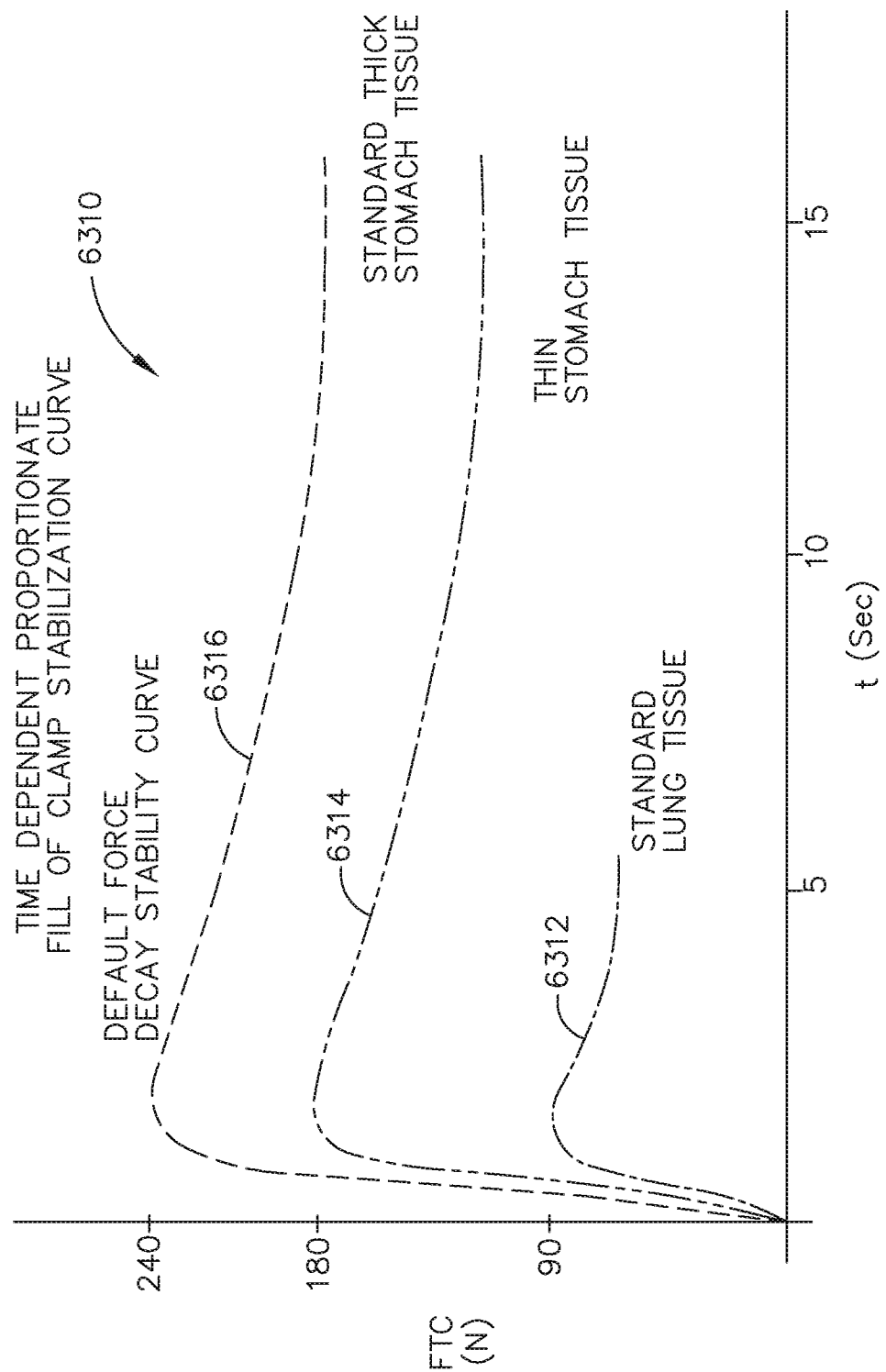
Figure 127:
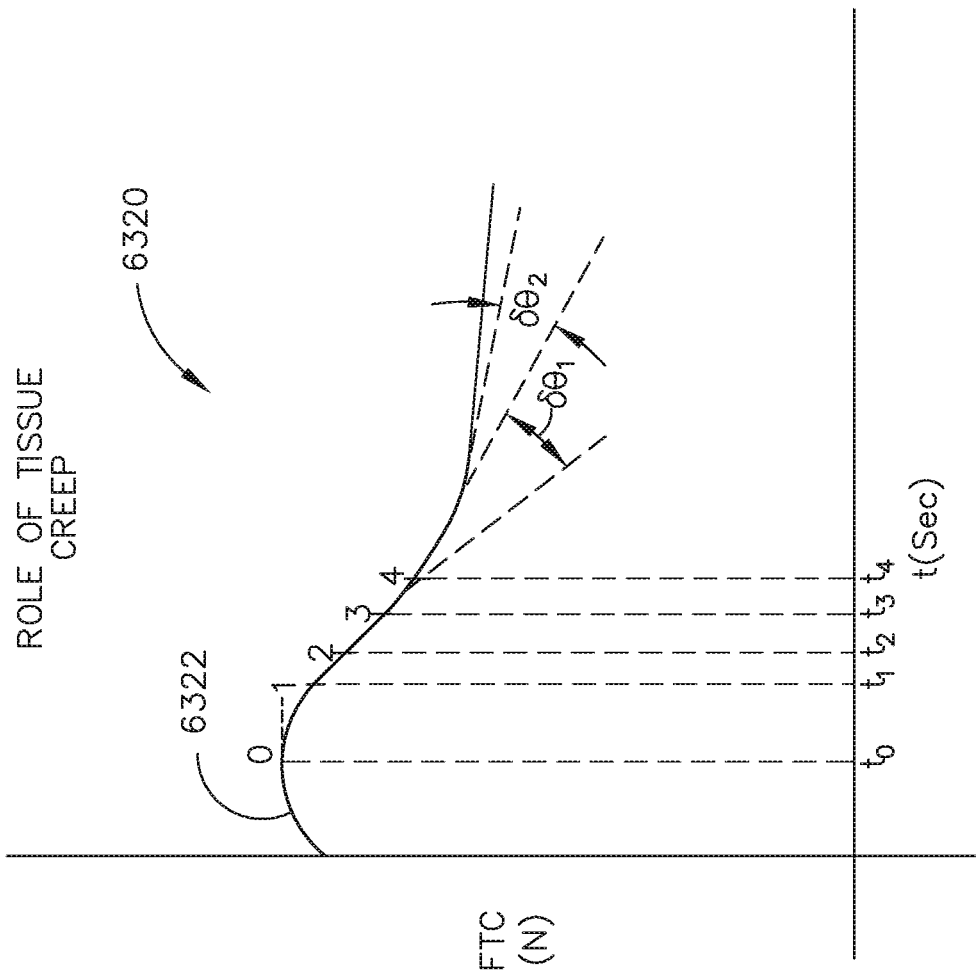
Figure 128A:
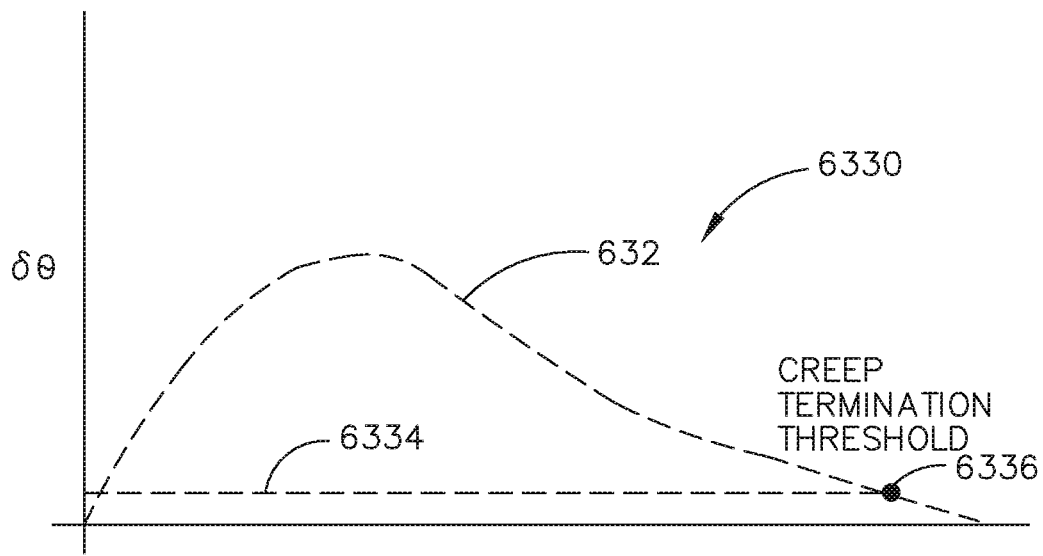
Figure 128B:
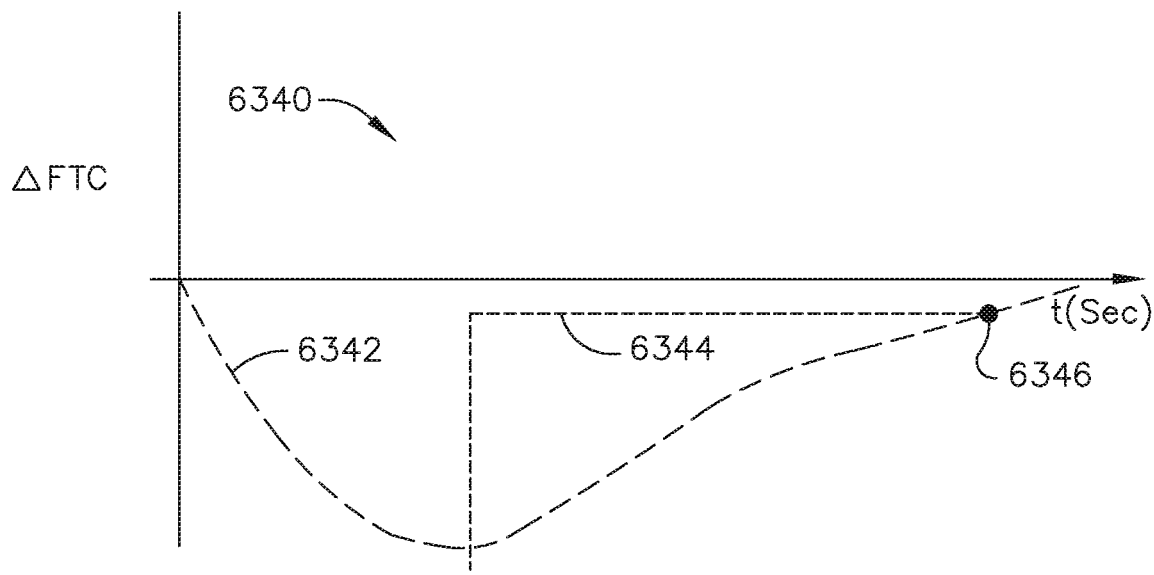
Figure 129:
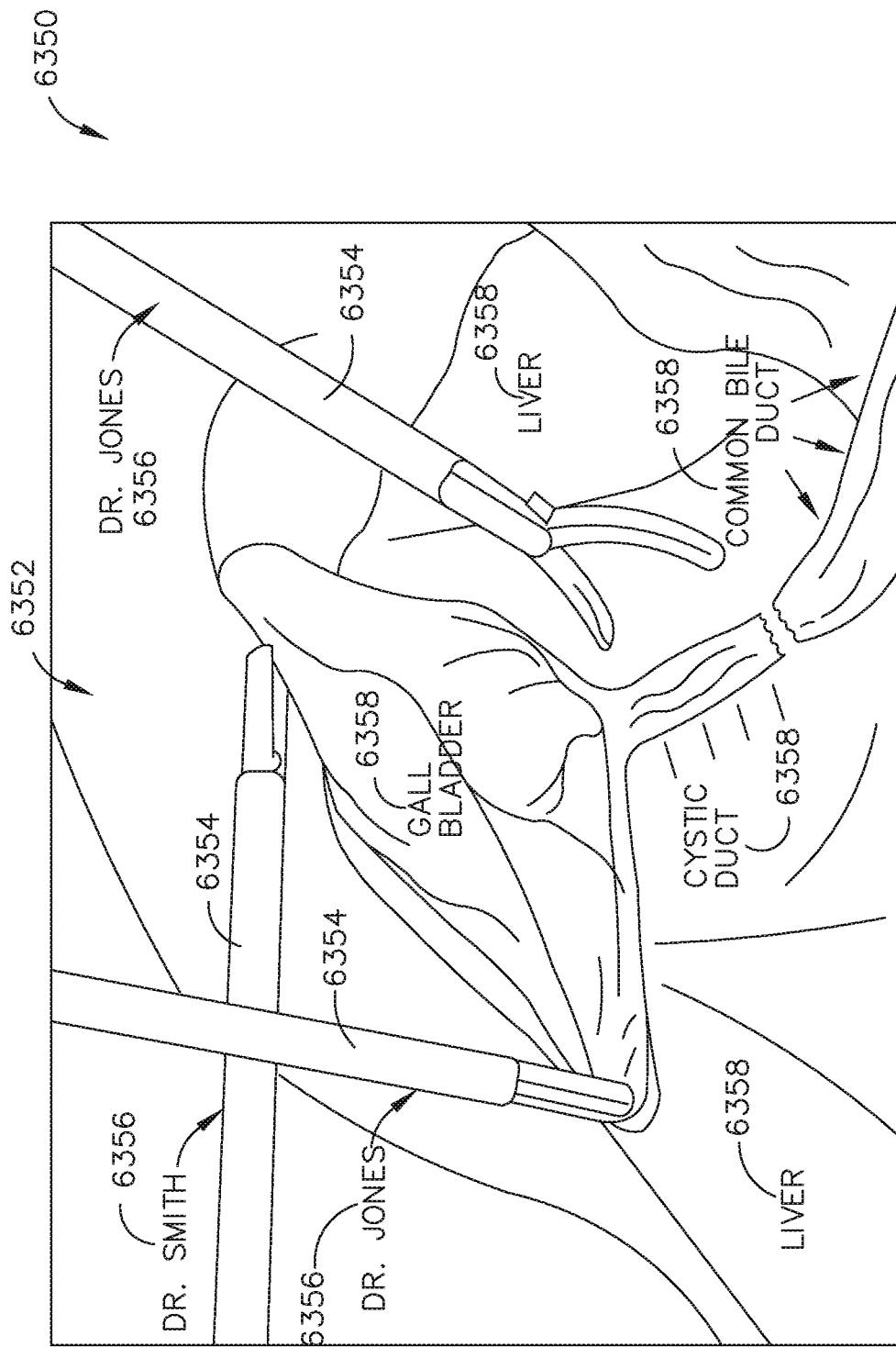
Figure 130:
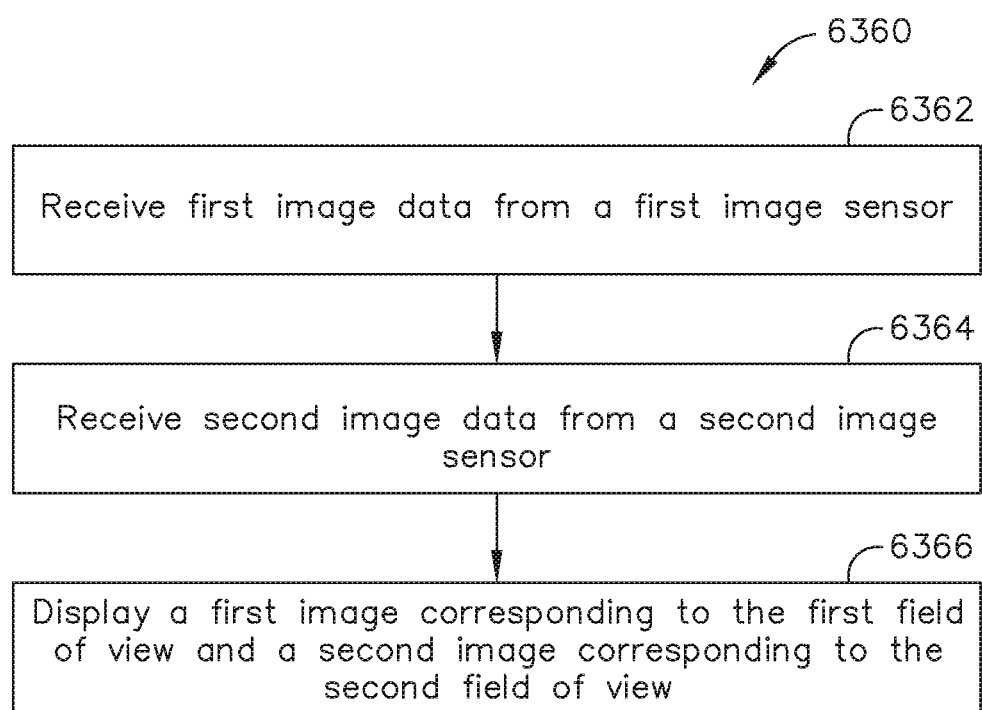
Figure 131:
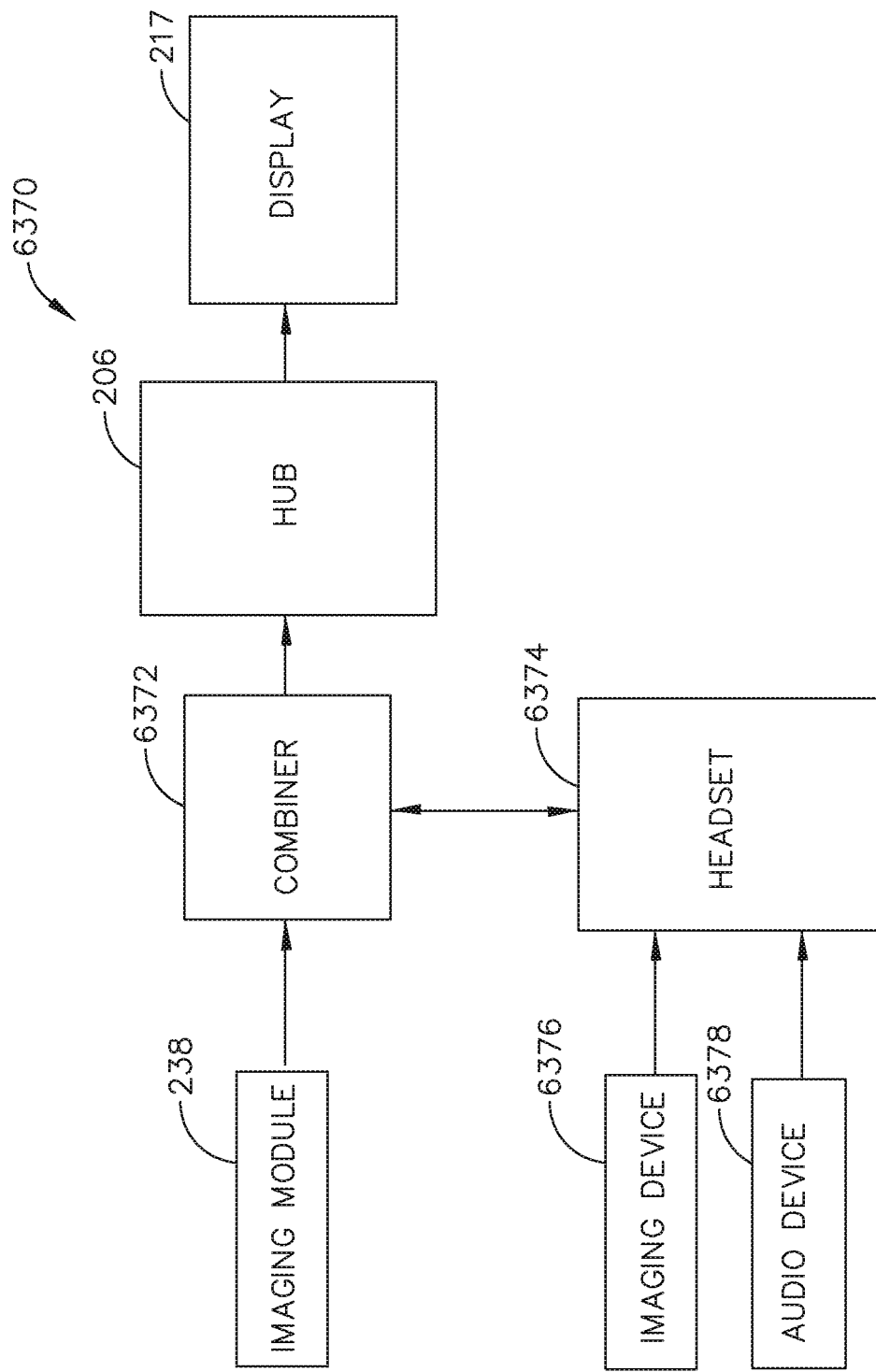
Figure 132:
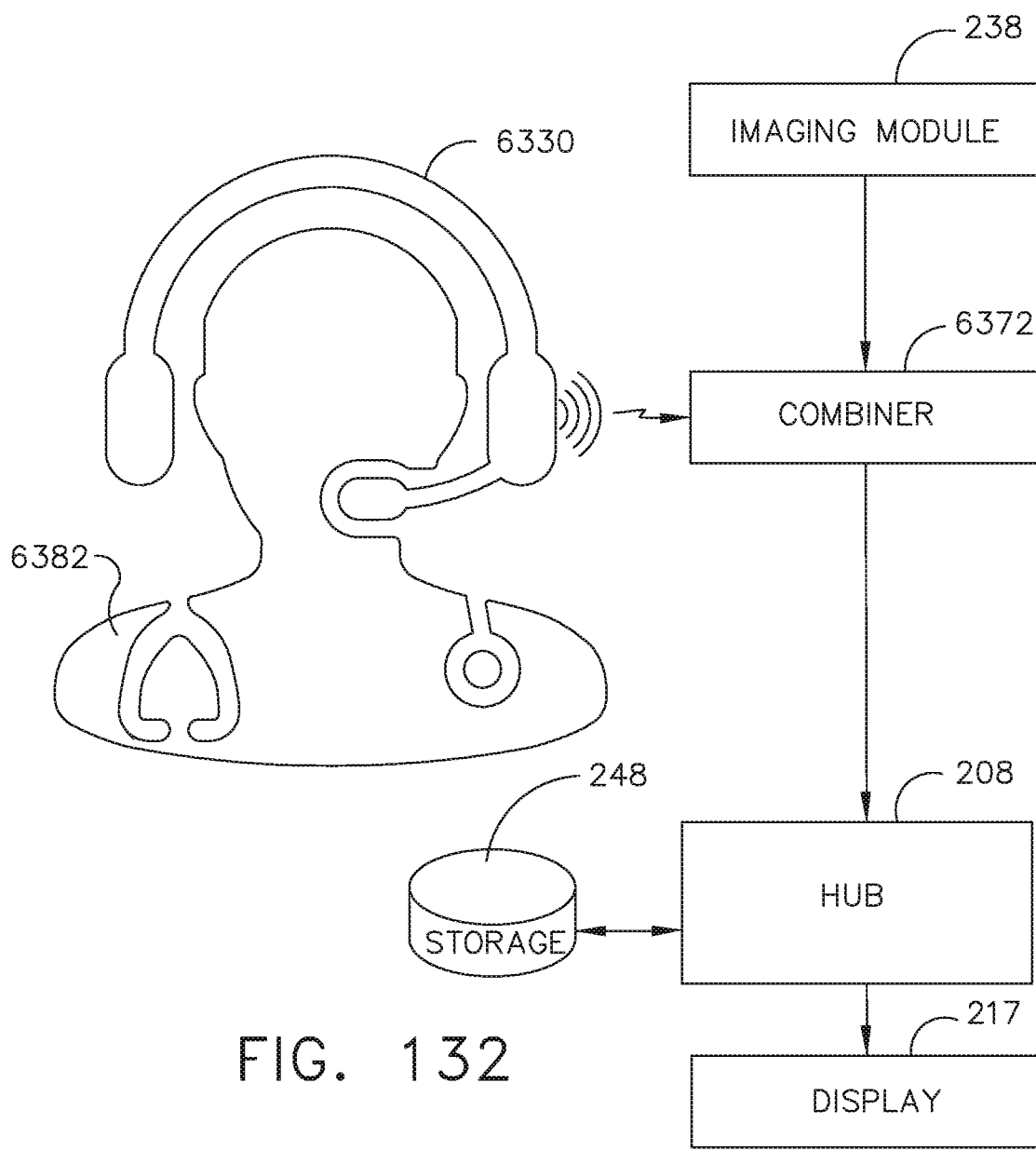
Figure 133:
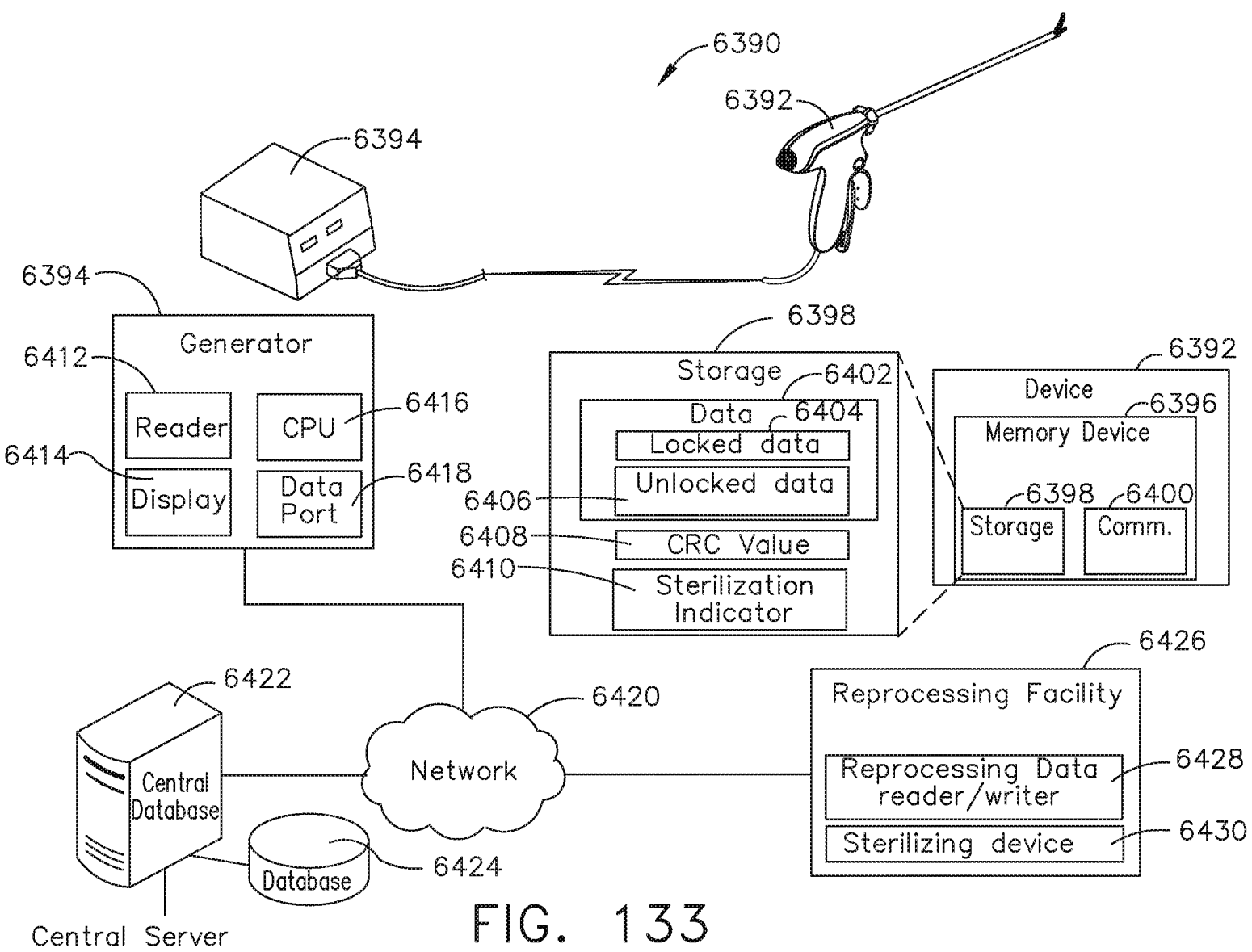
Figure 134:
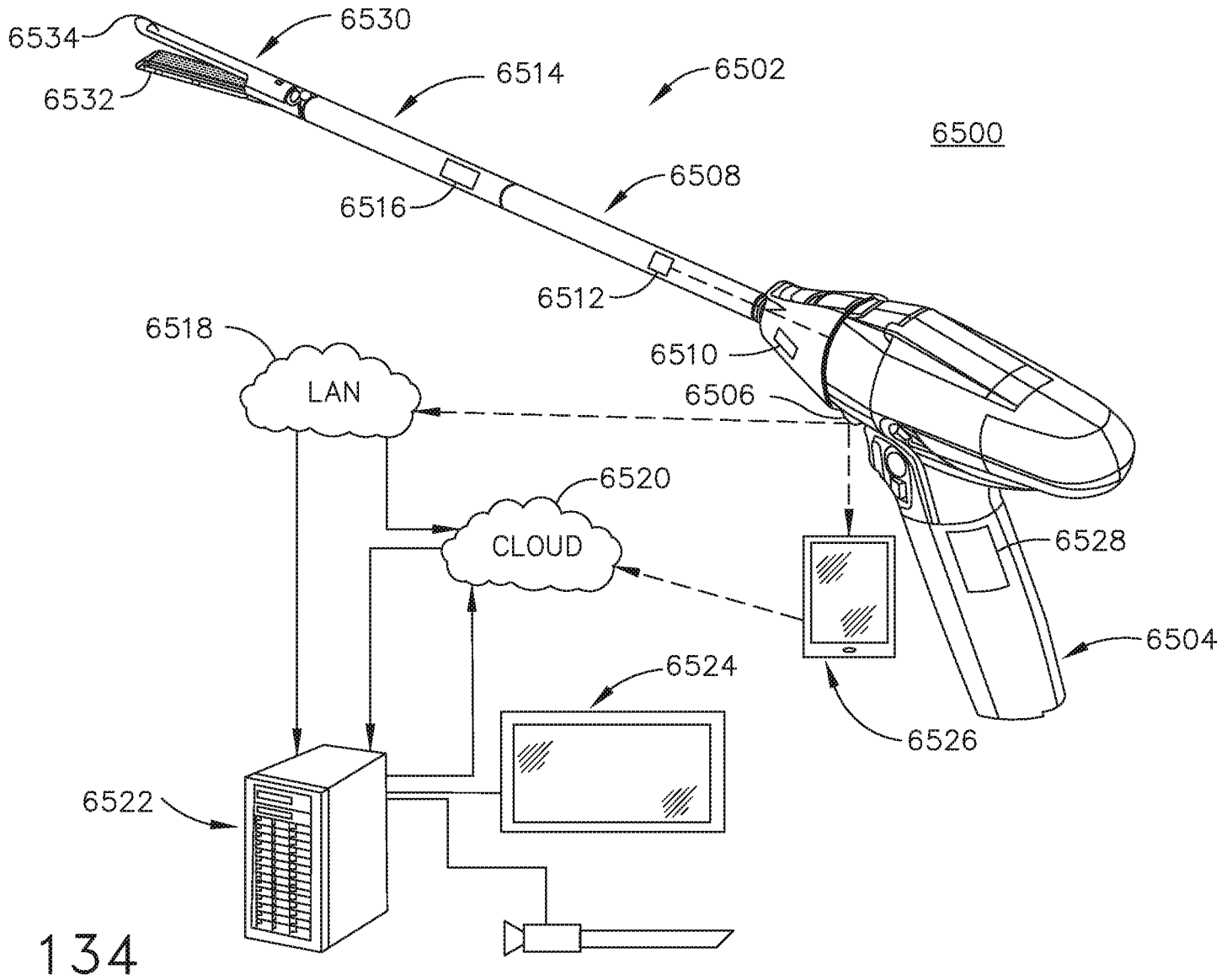
Figure 135:
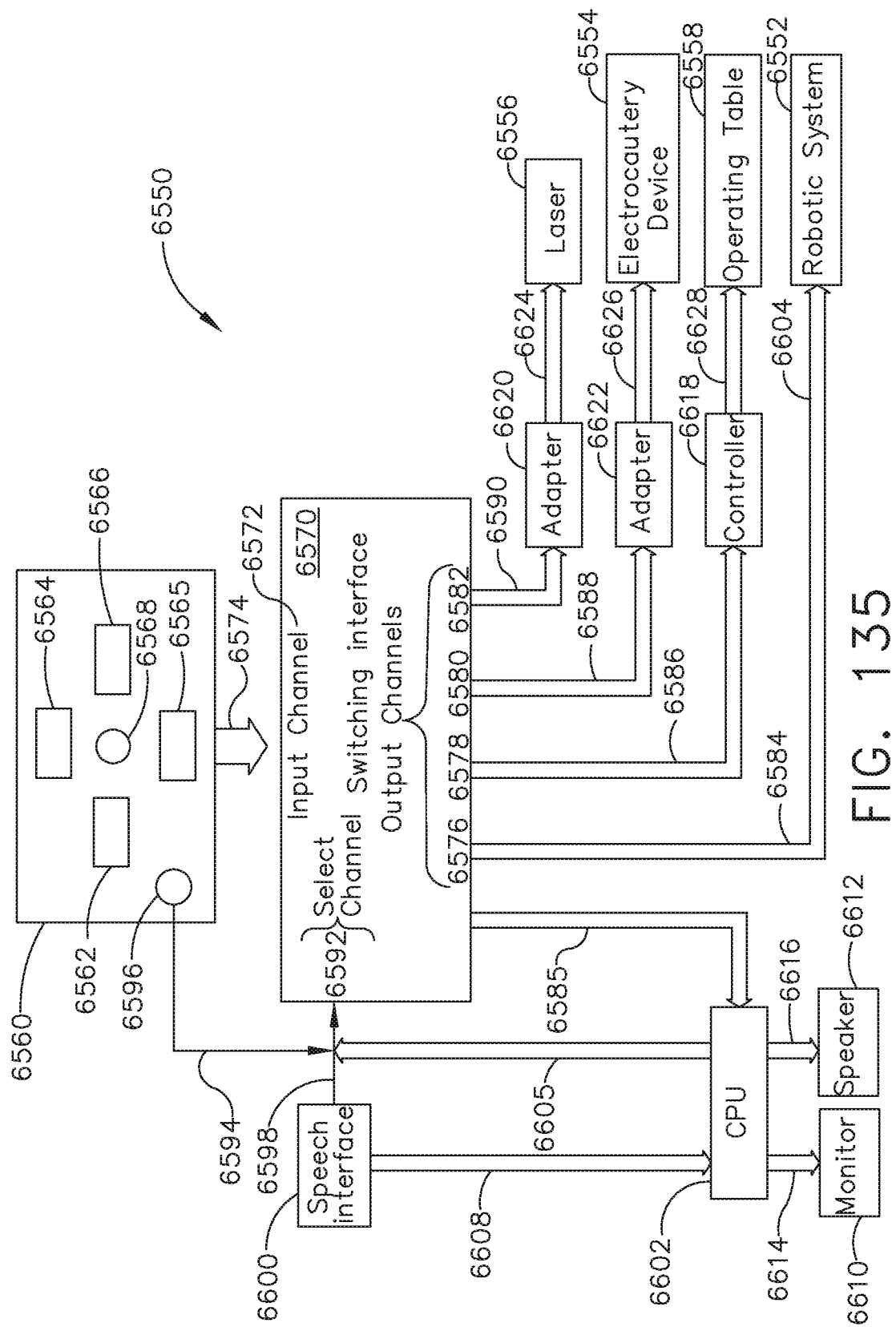
Figure 136:
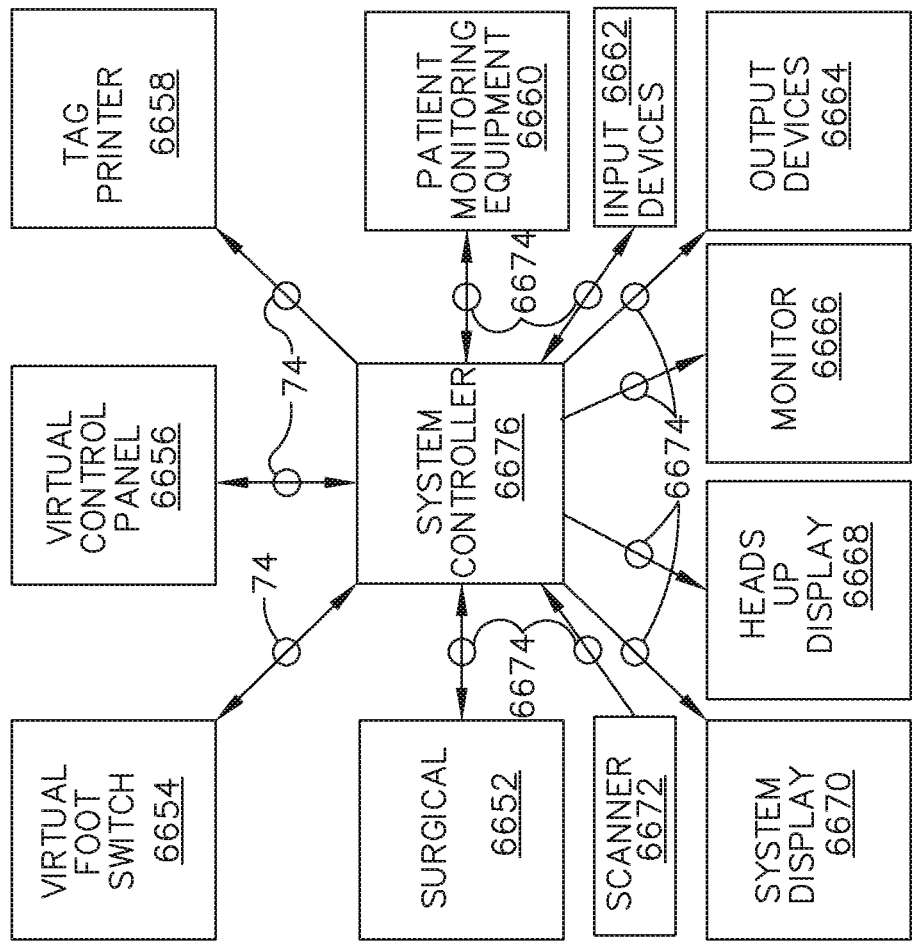
Figure 137:
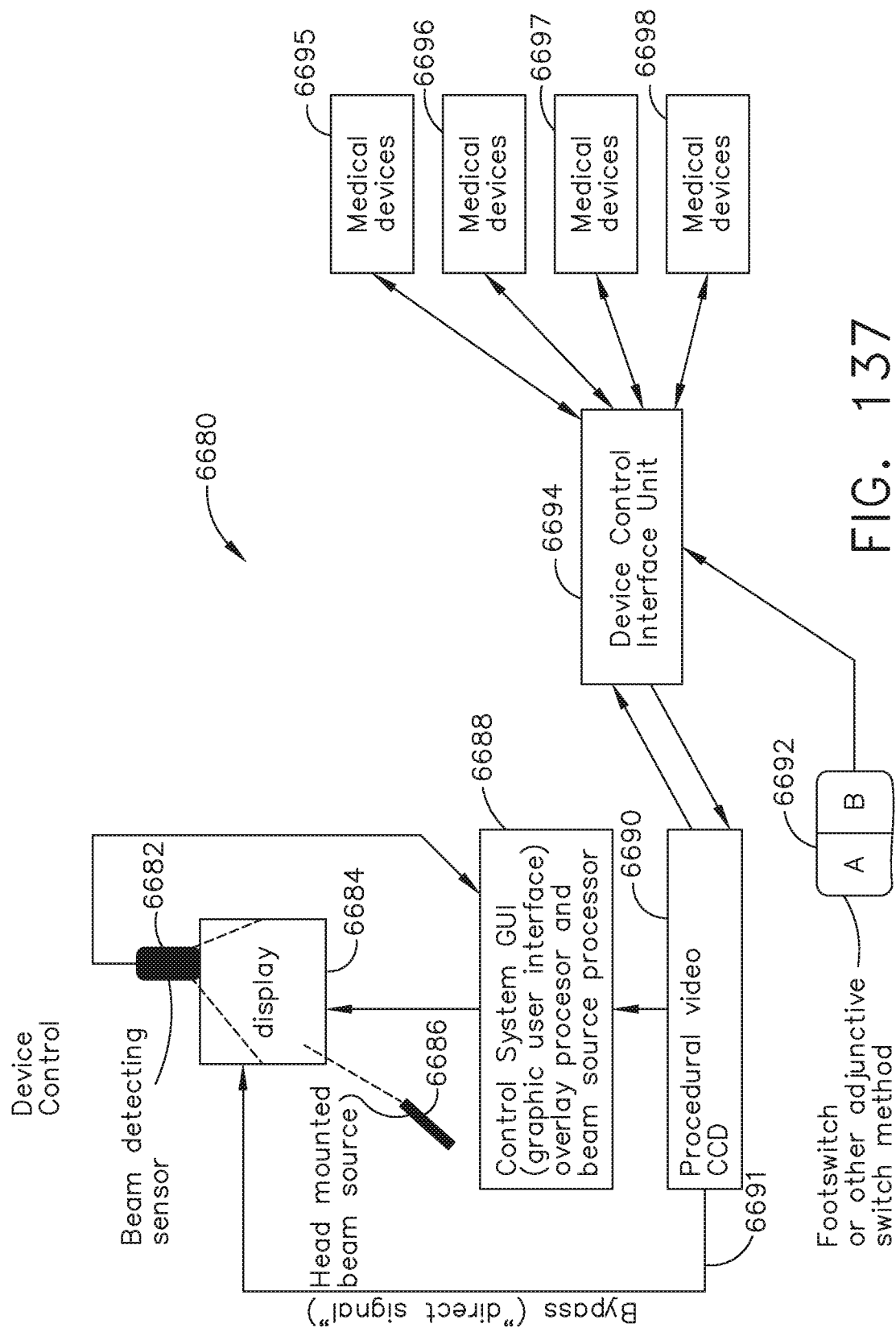
Figure 140:
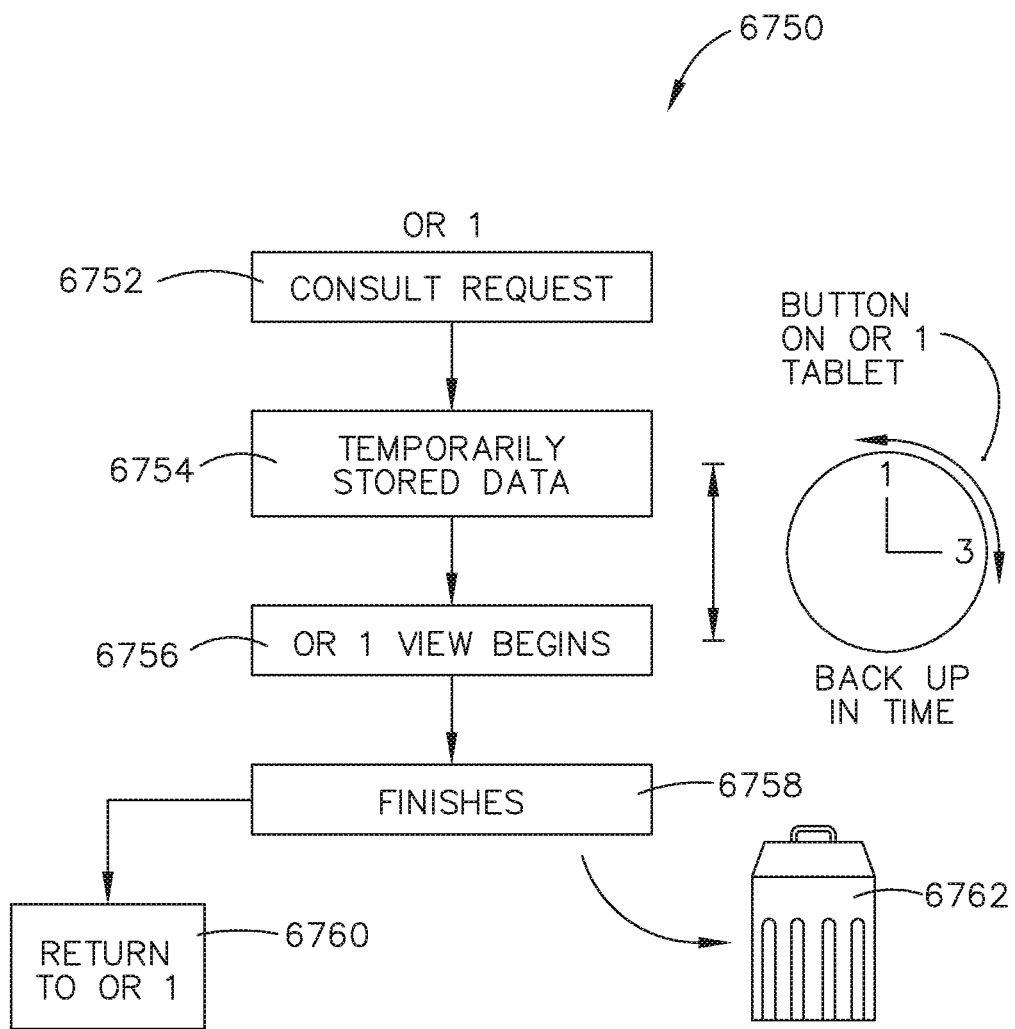
Figure 141:
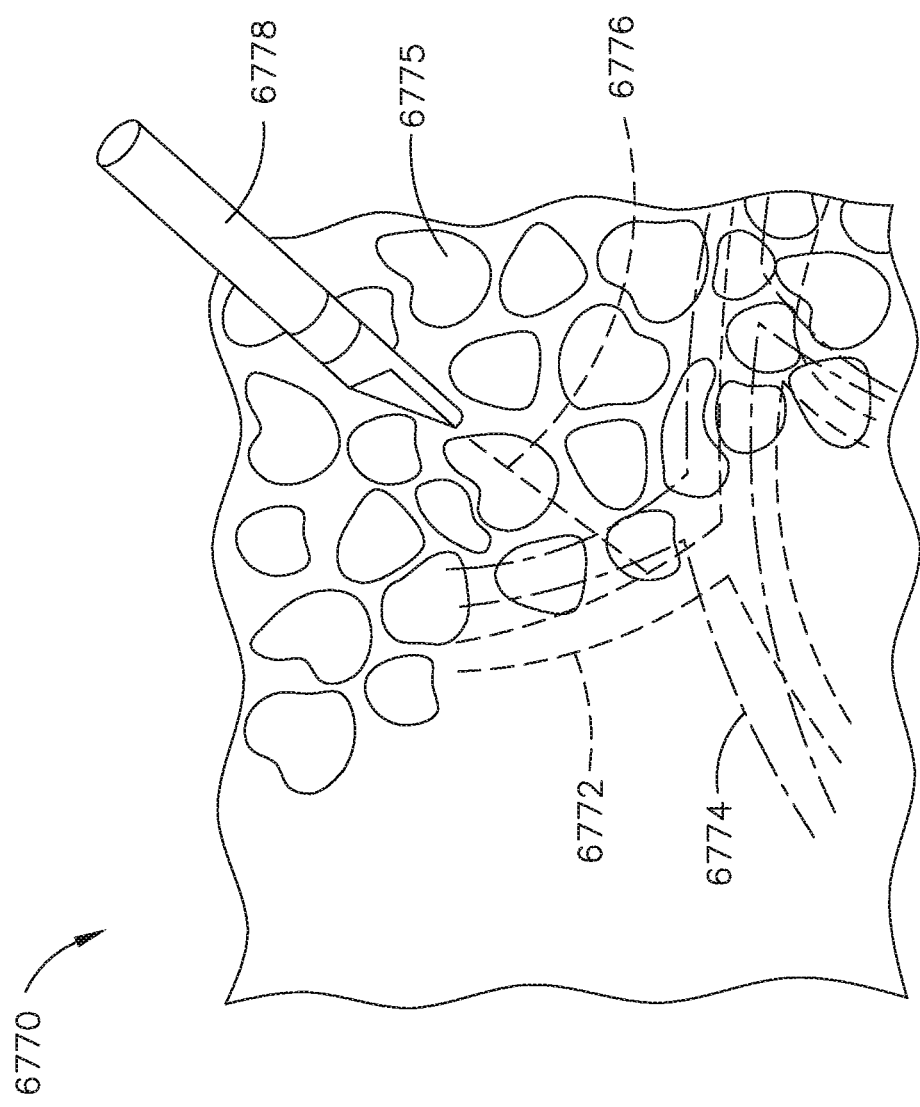
Figure 142A:
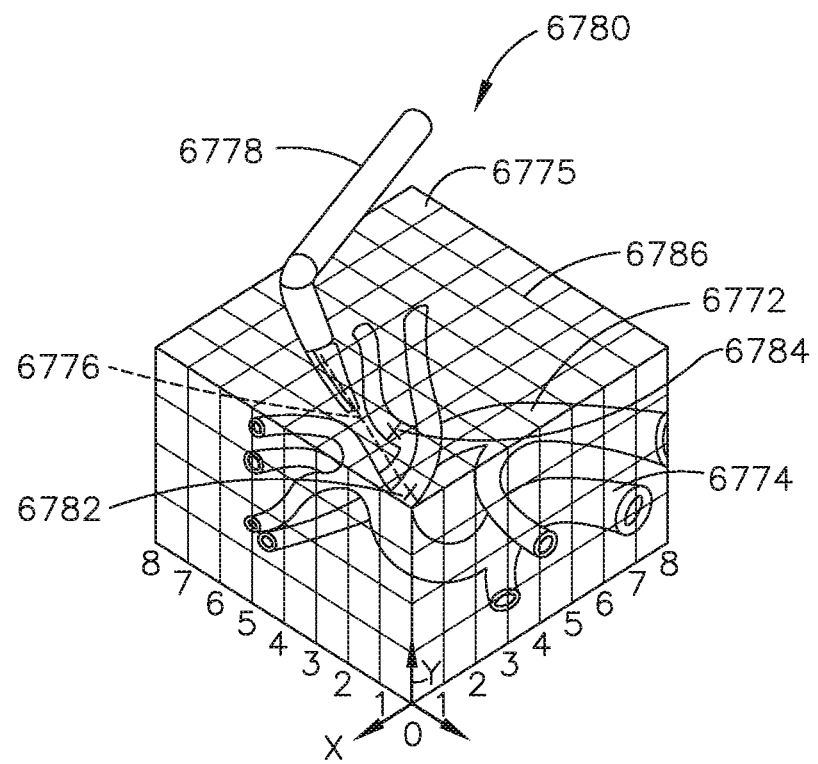
Figure 142B:
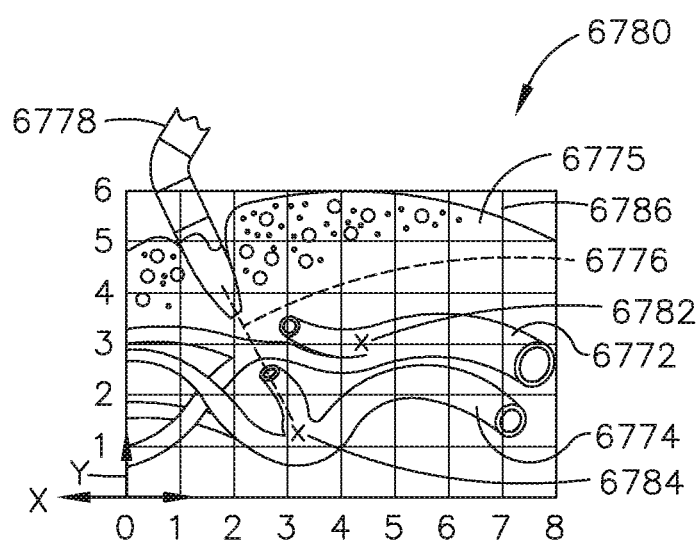
Figure 142C:
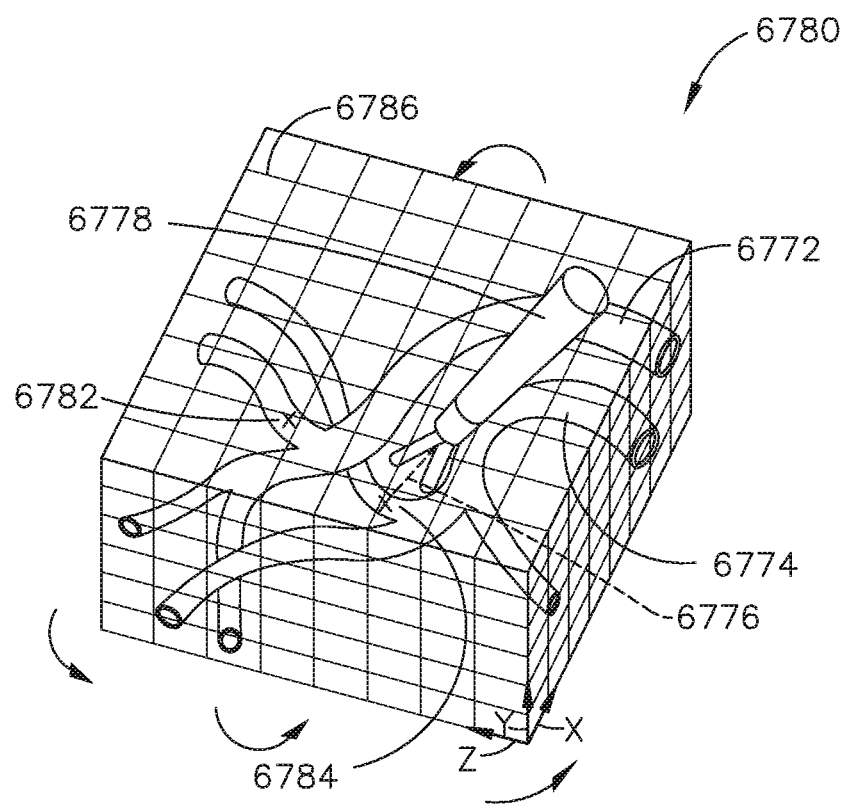

FIG. 108 illustrates an anvil trocar of a circular stapler that is aligned with the center of the staple overlap portion of the linear staple line created by a double-stapling technique; and FIG. 109 illustrates a centering tool displayed on a surgical hub display showing a staple overlap portion of a linear staple line created by a double-stapling technique to be cut out by a circular stapler, where the anvil trocar is not aligned with the staple overlap portion of the double staple line as shown in FIG. 107;

FIGS. 110 and 111 illustrate a before image and an after image of a centering tool, in accordance with at least one aspect of the present disclosure, where:

FIG. 110 illustrates an image of a projected cut path of an anvil trocar and circular knife before alignment with the target alignment ring circumscribing the image of the linear staple line over the image of the staple overlap portion presented on a surgical hub display; and FIG. 111 illustrates an image of a projected cut path of an anvil trocar and circular knife after alignment with the target alignment ring circumscribing the image of the linear staple line over the image of the staple overlap portion presented on a surgical hub display;

FIGS. 112-114 illustrate a process of aligning an anvil trocar of a circular stapler to a center of a linear staple line, in accordance with at least one aspect of the present disclosure, where:

FIG. 112 illustrates the anvil trocar out of alignment with the center of the linear staple line;

FIG. 113 illustrates the anvil trocar in alignment with the center of the linear staple line; and FIG. 114 illustrates a centering tool displayed on a surgical hub display of a linear staple line, where the anvil trocar is not aligned with the staple overlap portion of the double staple line as shown in FIG. 112;

FIG. 115 is an image of a standard reticle field view of a linear staple line transection of a surgical as viewed through a laparoscope displayed on the surgical hub display, in accordance with at least one aspect of the present disclosure;

FIG. 116 is an image of a laser-assisted reticle field of view of the surgical site shown in FIG. 115 before the anvil trocar and circular knife of the circular stapler are aligned to the center of the linear staple line, in accordance with at least one aspect of the present disclosure;

FIG. 117 is an image of a laser-assisted reticle field of view of the surgical site shown in FIG. 116 after the anvil trocar and circular knife of the circular stapler are aligned to the center of the linear staple line, in accordance with at least one aspect of the present disclosure;

FIG. 118 illustrates a non-contact inductive sensor implementation of a non-contact sensor to determine an anvil trocar location relative to the center of a staple line transection, in accordance with at least one aspect of the present disclosure;

FIGS. 119A and 119B illustrate one aspect of a non-contact capacitive sensor implementation of the non-contact sensor to determine an anvil trocar location relative to the center of a staple line transection, in accordance with at least one aspect of the present disclosure, where:

FIG. 119A shows the non-contact capacitive sensor without a nearby metal target; and FIG. 119B shows the non-contact capacitive sensor near a metal target;

FIG. 120 is a logic flow diagram of a process depicting a control program or a logic configuration for aligning a surgical instrument, in accordance with at least one aspect of the present disclosure;

FIG. 121 illustrates a primary display of the surgical hub comprising a global and local display, in accordance with at least one aspect of the present disclosure;

FIG. 122 illustrates a primary display of the surgical hub, in accordance with at least one aspect of the present disclosure;

FIG. 123 illustrates a clamp stabilization sequence over a five second period, in accordance with at least one aspect of the present disclosure;

FIG. 124 illustrates a diagram of four separate wide angle view images of a surgical site at four separate times during the procedure, in accordance with at least one aspect of the present disclosure;

FIG. 125 is a graph of tissue creep clamp stabilization curves for two tissue types, in accordance with at least one aspect of the present disclosure;

FIG. 126 is a graph of time dependent proportionate fill of a clamp force stabilization curve, in accordance with at least one aspect of the present disclosure;

FIG. 127 is a graph of the role of tissue creep in the clamp force stabilization curve, in accordance with at least one aspect of the present disclosure;

FIGS. 128A and 128B illustrate two graphs for determining when the clamped tissue has reached creep stability, in accordance with at least one aspect of the present disclosure, where:

FIG. 128A illustrates a curve that represents a vector tangent angle $d\theta$ as a function of time; and FIG. 128B illustrates a curve that represents change in force-to-close ($\Delta FTC$) as a function of time;

FIG. 129 illustrates an example of an augmented video image of a pre-operative video image augmented with data identifying displayed elements, in accordance with at least one aspect of the present disclosure;

FIG. 130 is a logic flow diagram of a process depicting a control program or a logic configuration to display images, in accordance with at least one aspect of the present disclosure;

FIG. 131 illustrates a communication system comprising an intermediate signal combiner positioned in the communication path between an imaging module and a surgical hub display, in accordance with at least one aspect of the present disclosure;

FIG. 132 illustrates an independent interactive headset worn by a surgeon to communicate data to the surgical hub, according to one aspect of the present disclosure;

FIG. 133 illustrates a method for controlling the usage of a device, in accordance with at least one aspect of the present disclosure, in accordance with at least one aspect of the present disclosure;

FIG. 134 illustrates a surgical system that includes a handle having a controller and a motor, an adapter releasably coupled to the handle, and a loading unit releasably coupled to the adapter, in accordance with at least one aspect of the present disclosure;

FIG. 135 illustrates a verbal Automated Endoscopic System for Optimal Positioning (AESOP) camera positioning system, in accordance with at least one aspect of the present disclosure;

FIG. 136 illustrates a multi-functional surgical control system and switching interface for virtual operating room integration, in accordance with at least one aspect of the present disclosure;

FIG. 137 illustrates a diagram of a beam source and combined beam detector system utilized as a device control mechanism in an operating theater, in accordance with at least one aspect of the present disclosure;

FIGS. 138A-E illustrate various types of sterile field control and data input consoles, in accordance with at least one aspect of the present disclosure, where:

FIG. 138A illustrates a single zone sterile field control and data input console;

FIG. 138B illustrates a multi zone sterile field control and data input console;

FIG. 138C illustrates a tethered sterile field control and data input console;

FIG. 138D illustrates a battery operated sterile field control and data input console; and FIG. 138E illustrates a battery operated sterile field control and data input console;

FIGS. 139A-139B illustrate a sterile field console in use in a sterile field during a surgical procedure, in accordance with at least one aspect of the present disclosure, where:

FIG. 139A shows the sterile field console positioned in the sterile field near two surgeons engaged in an operation; and FIG. 139B shows one of the surgeons tapping the touchscreen of the sterile field console;

FIG. 140 illustrates a process for accepting consult feeds from another operating room, in accordance with at least one aspect of the present disclosure;

FIG. 141 illustrates a standard technique for estimating vessel path and depth and device trajectory, in accordance with at least one aspect of the present disclosure;

FIGS. 142A-142D illustrate multiple real time views of images of a virtual anatomical detail for dissection, in accordance with at least one aspect of the present disclosure, where:

FIG. 142A is a perspective view of the virtual anatomical detail;

FIG. 142B is a side view of the virtual anatomical detail;

FIG. 142C is a perspective view of the virtual anatomical detail; and

Figure 142D:
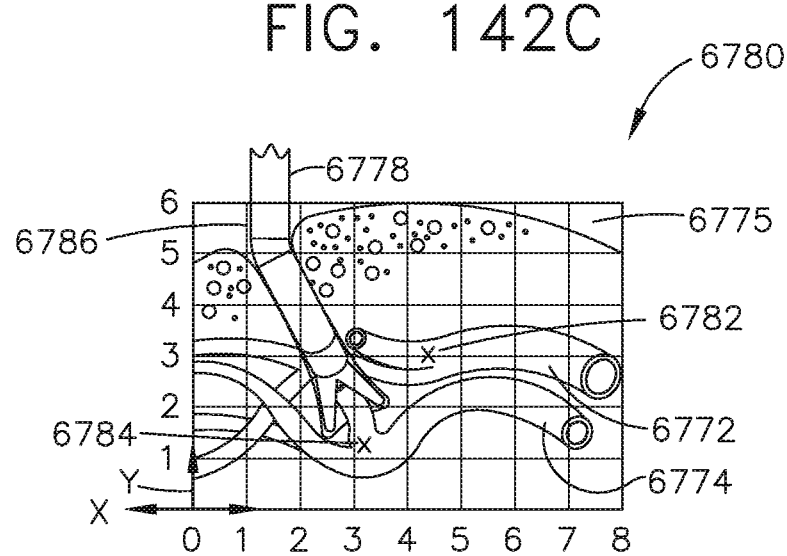
Figures 143A, 143B, 143C, 143D, 143E:
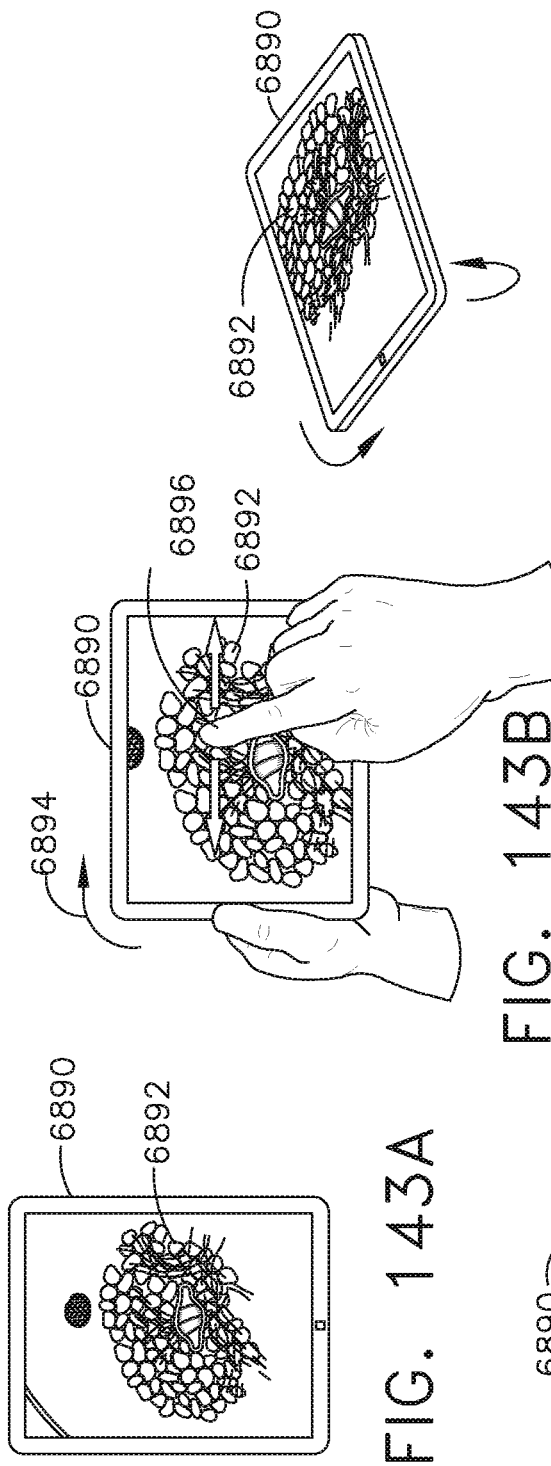
Figure 144:
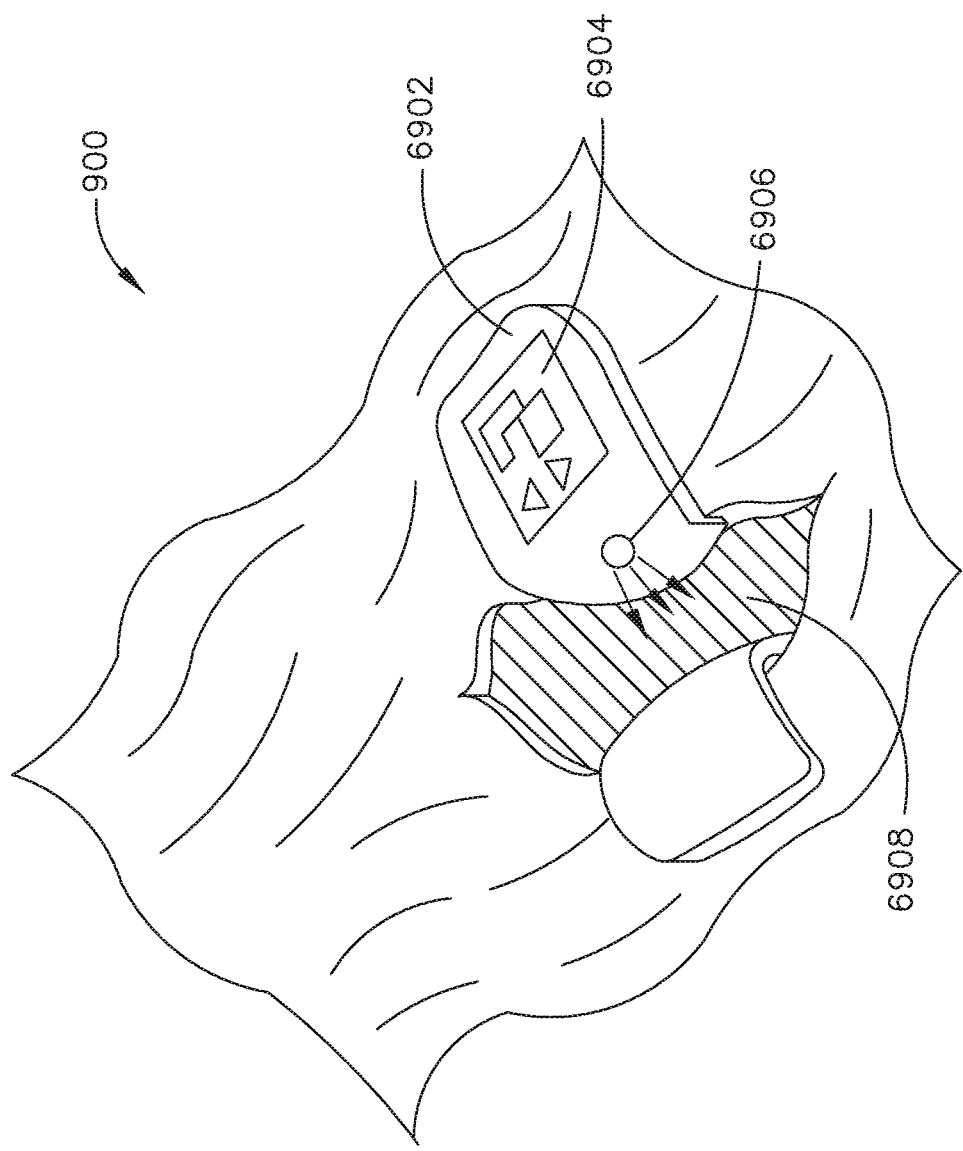
Figure 145:
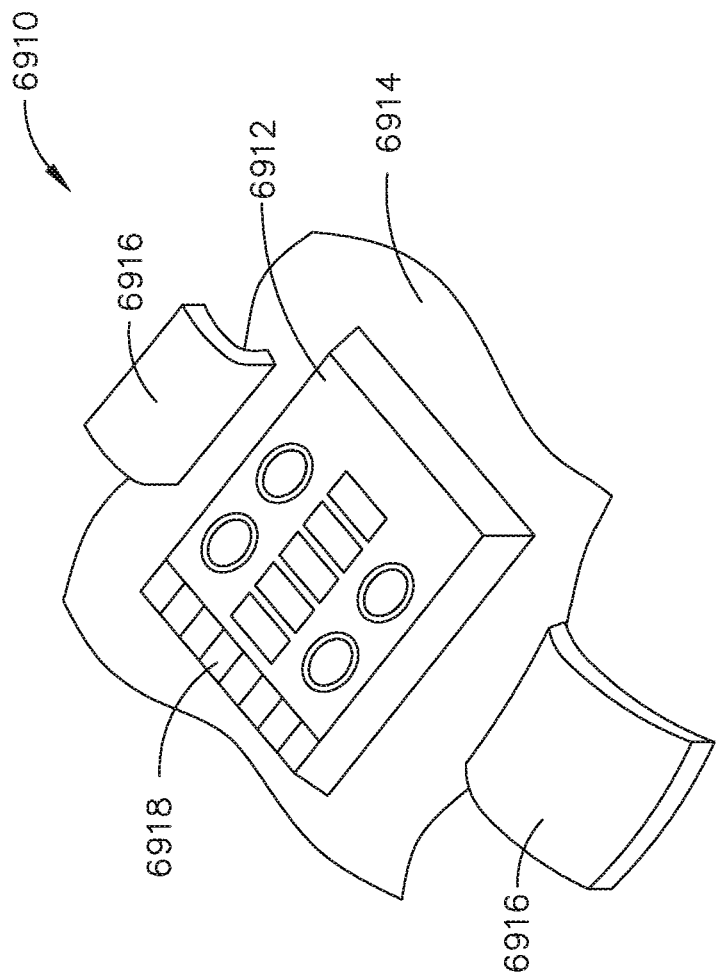
Figure 146:
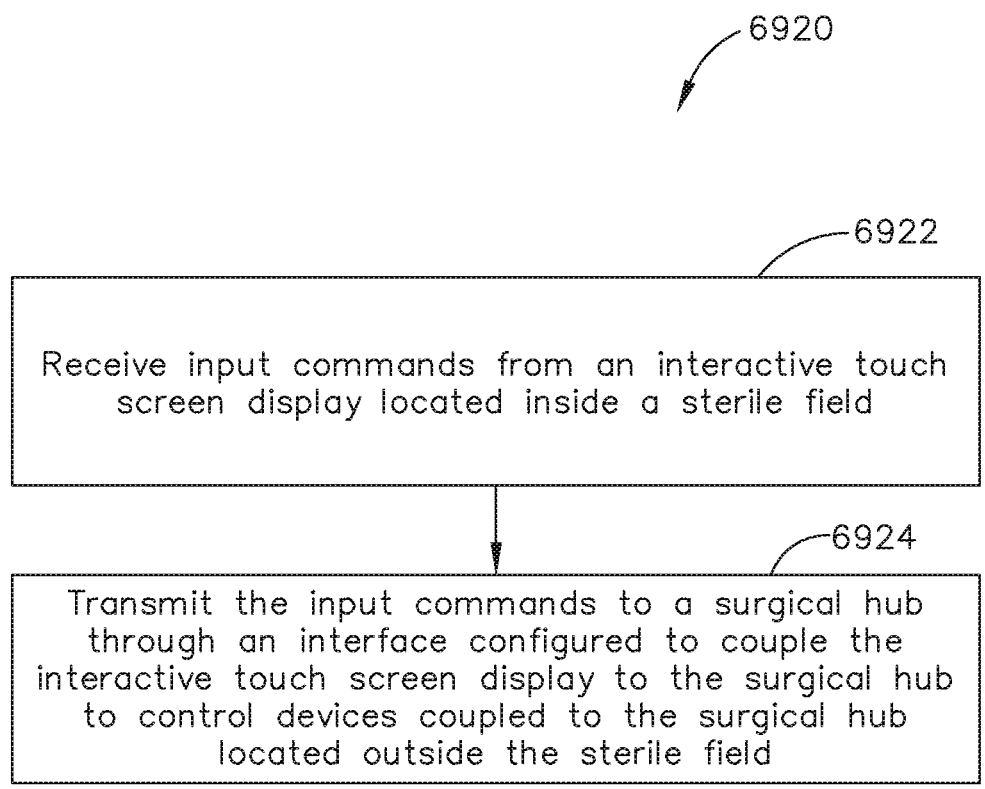
Figure 147:
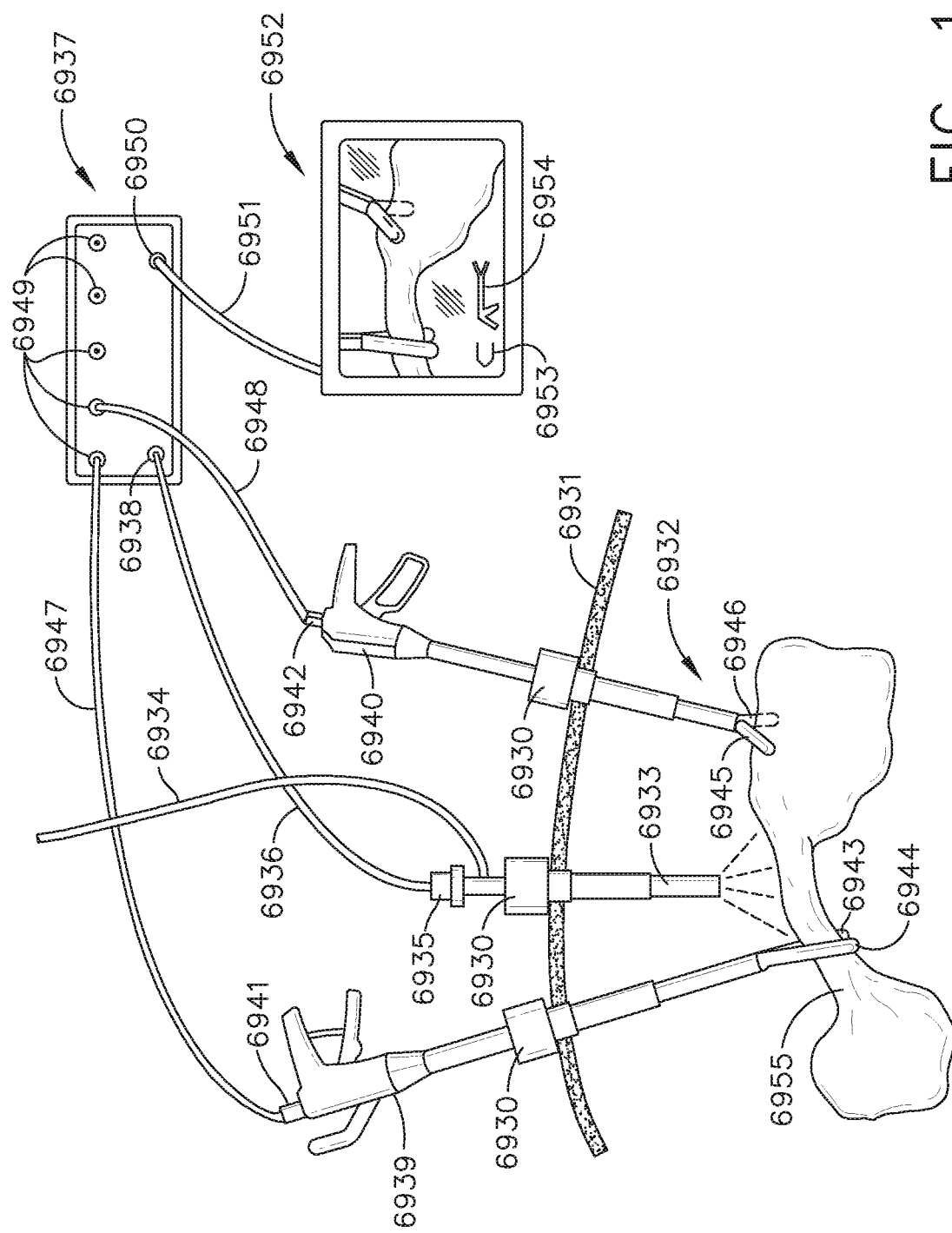
Figure 148:
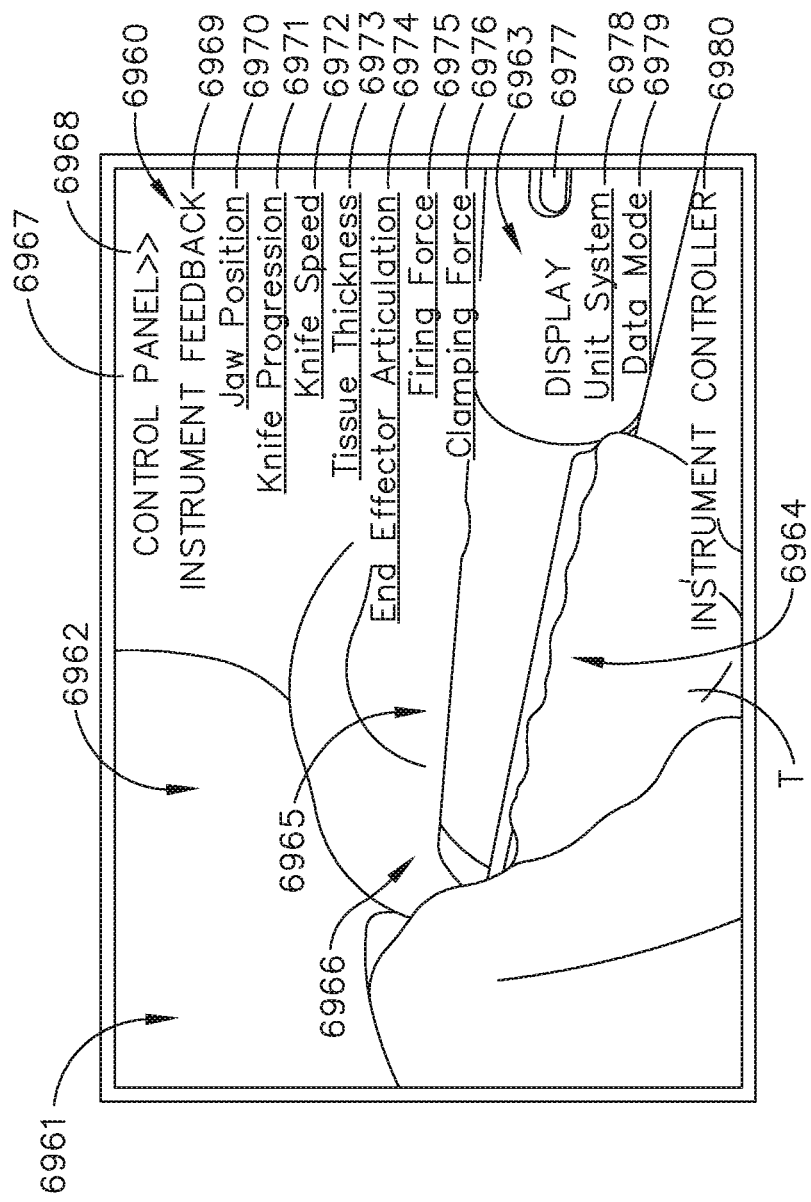
Figure 149:
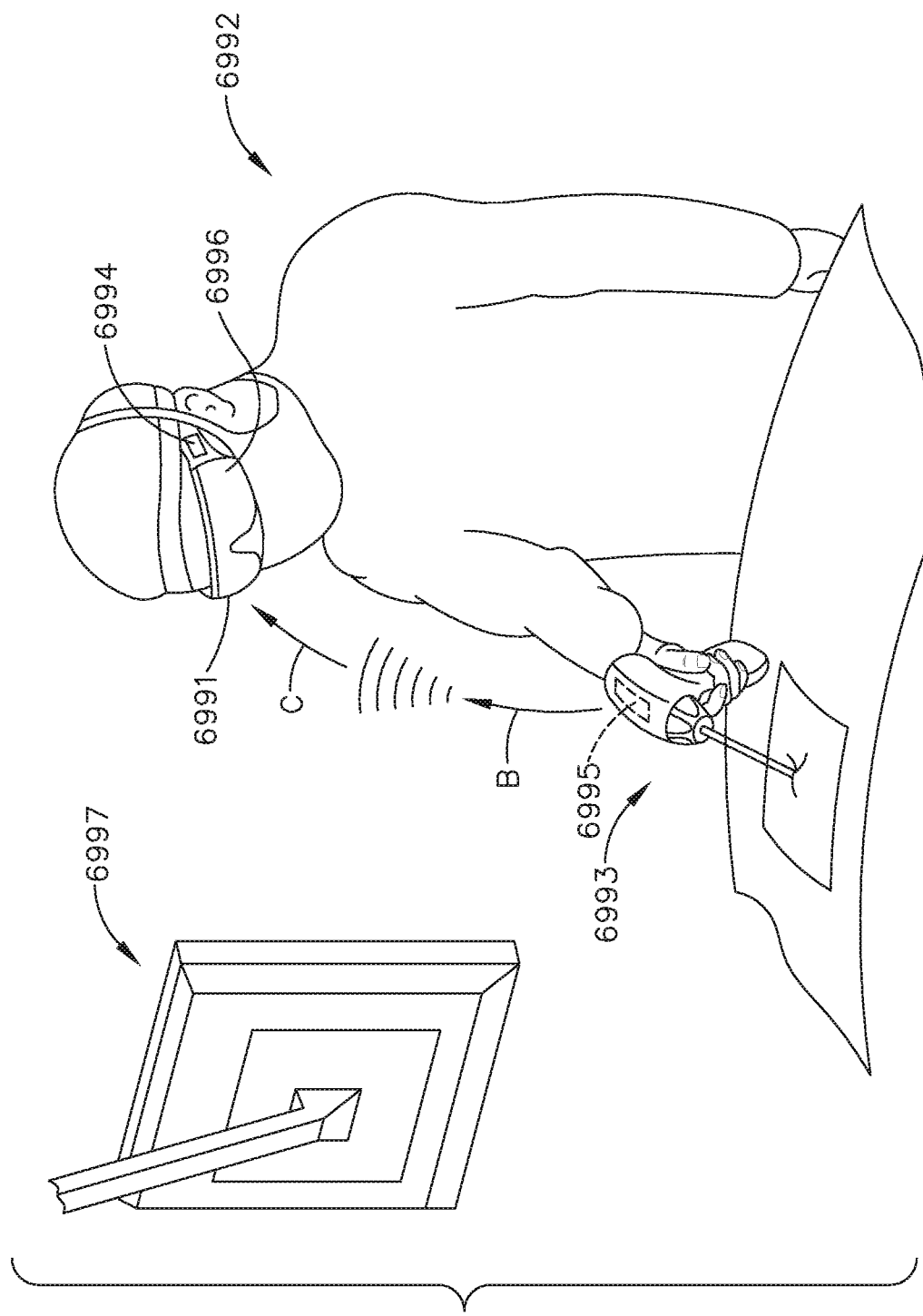
Figure 150:
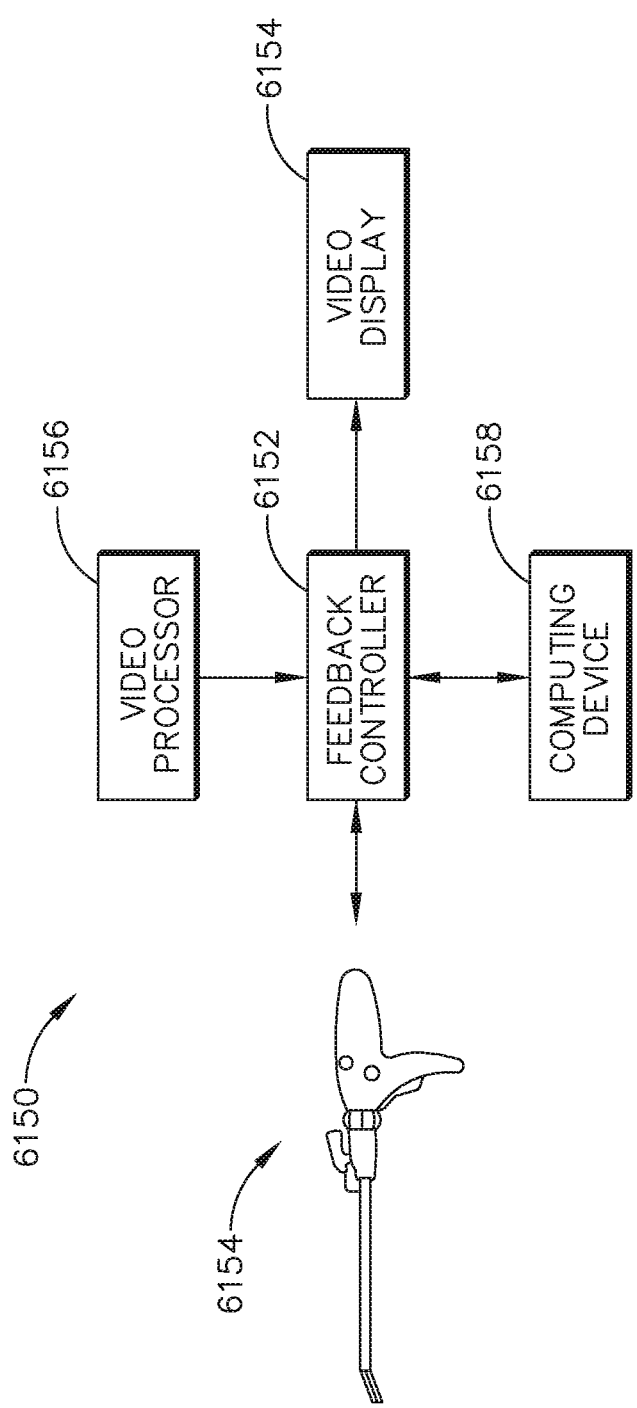
Figure 151:
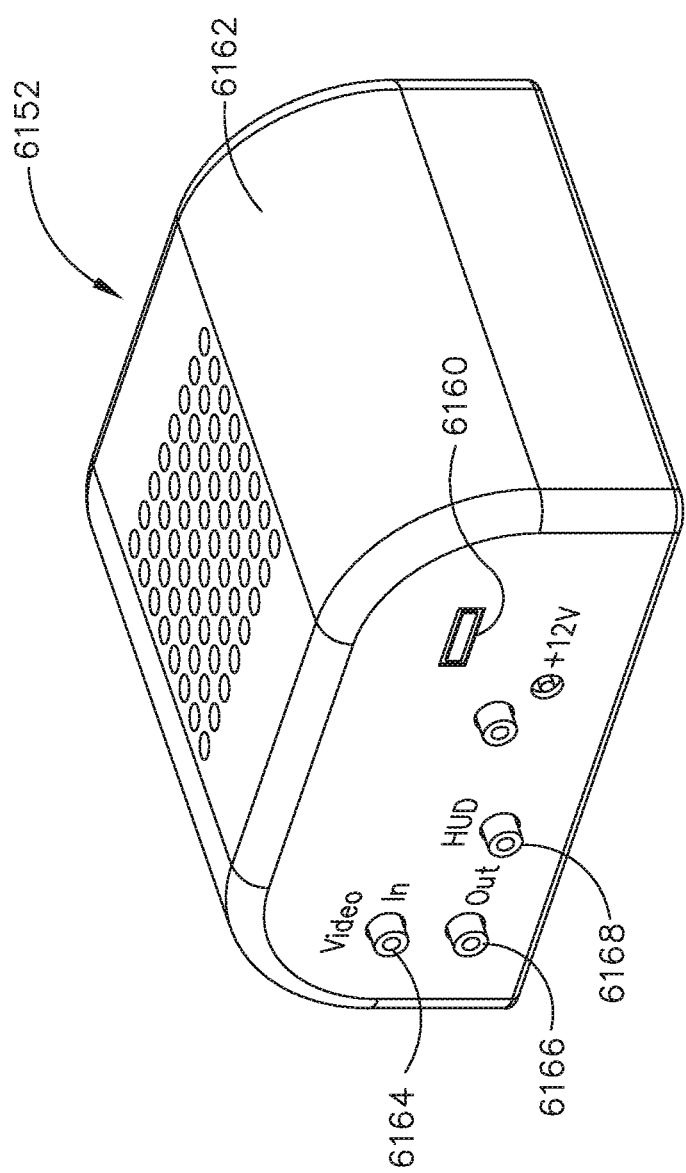
Figure 152A:
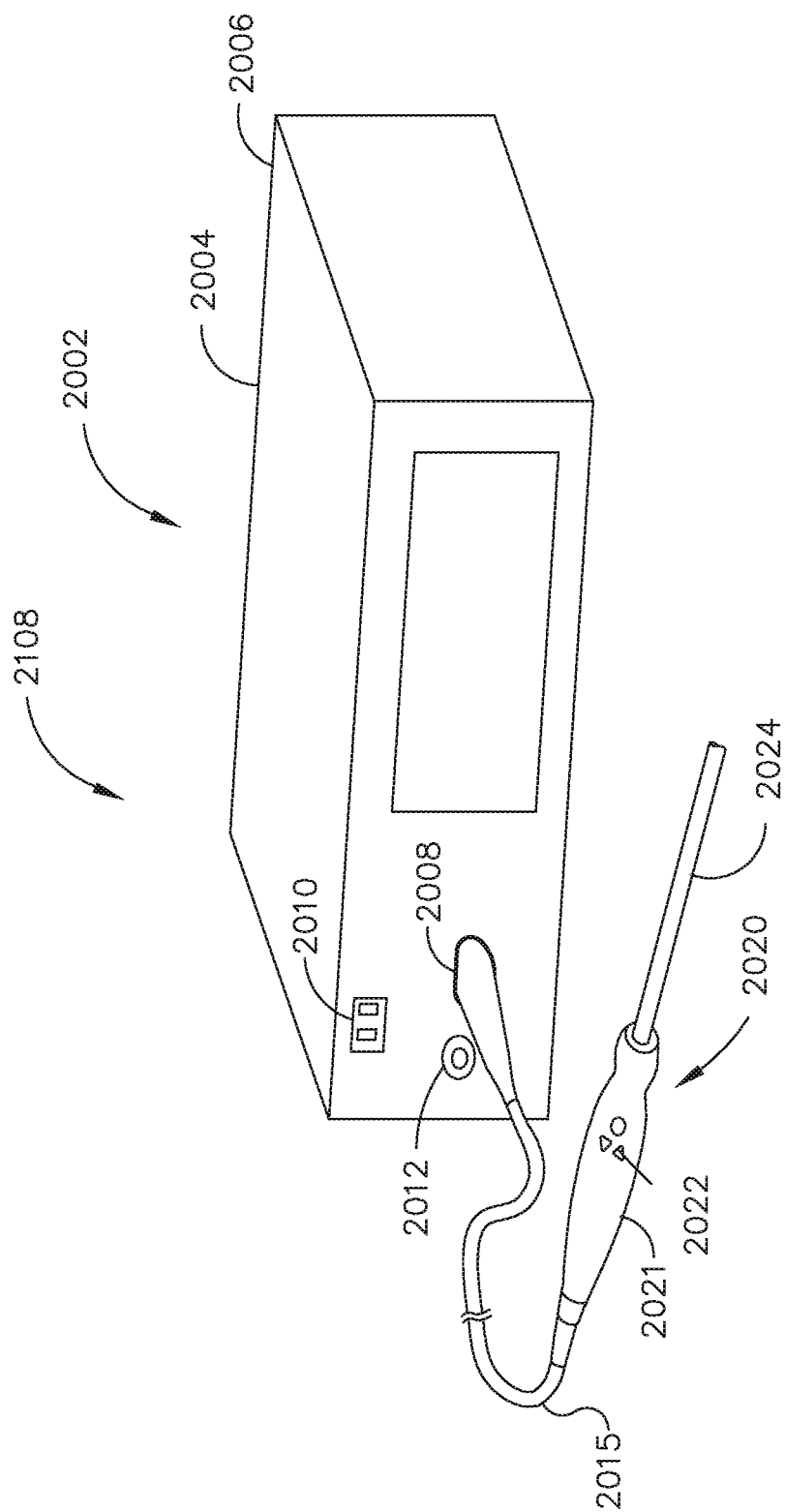
Figure 152B:
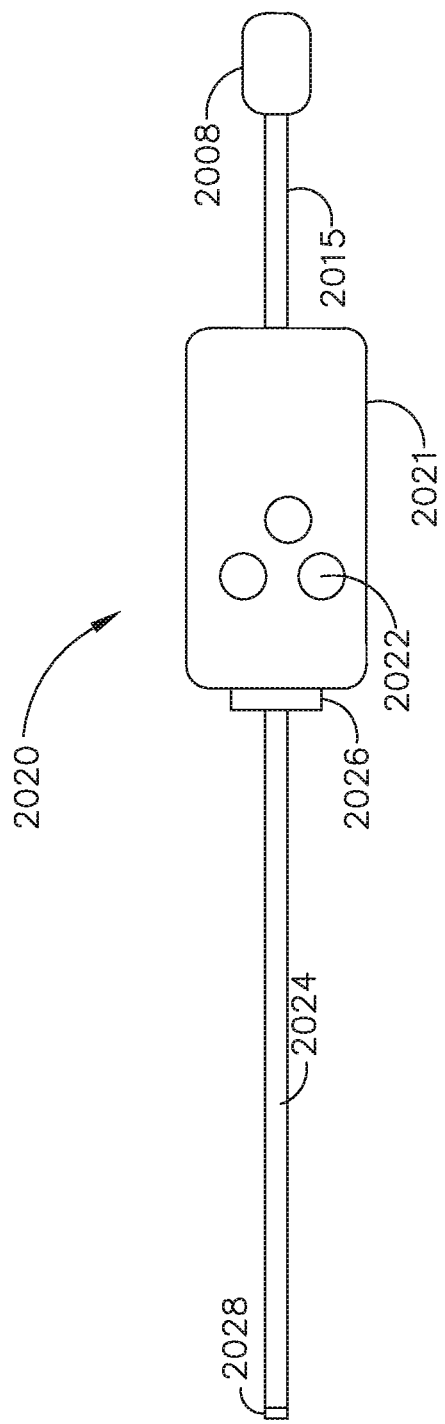
Figure 152C:
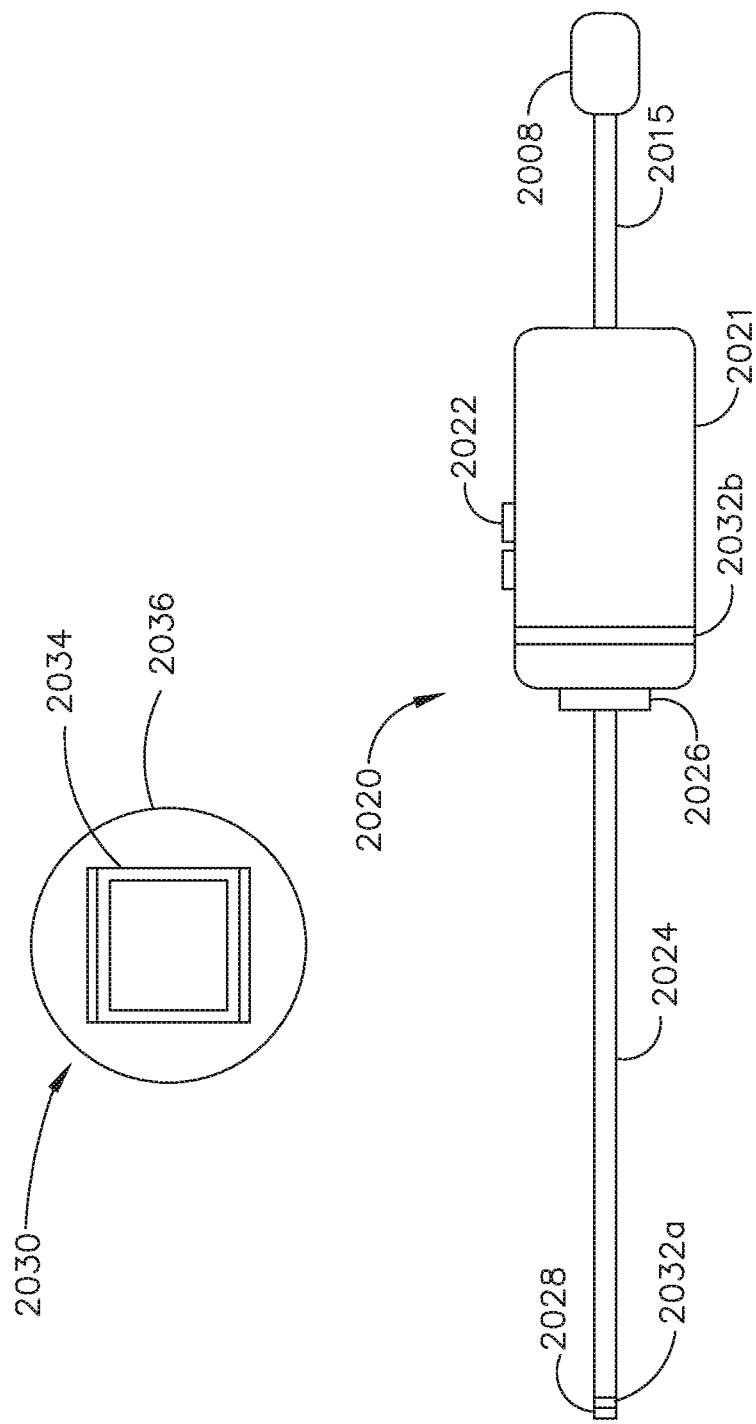
Figure 152D:
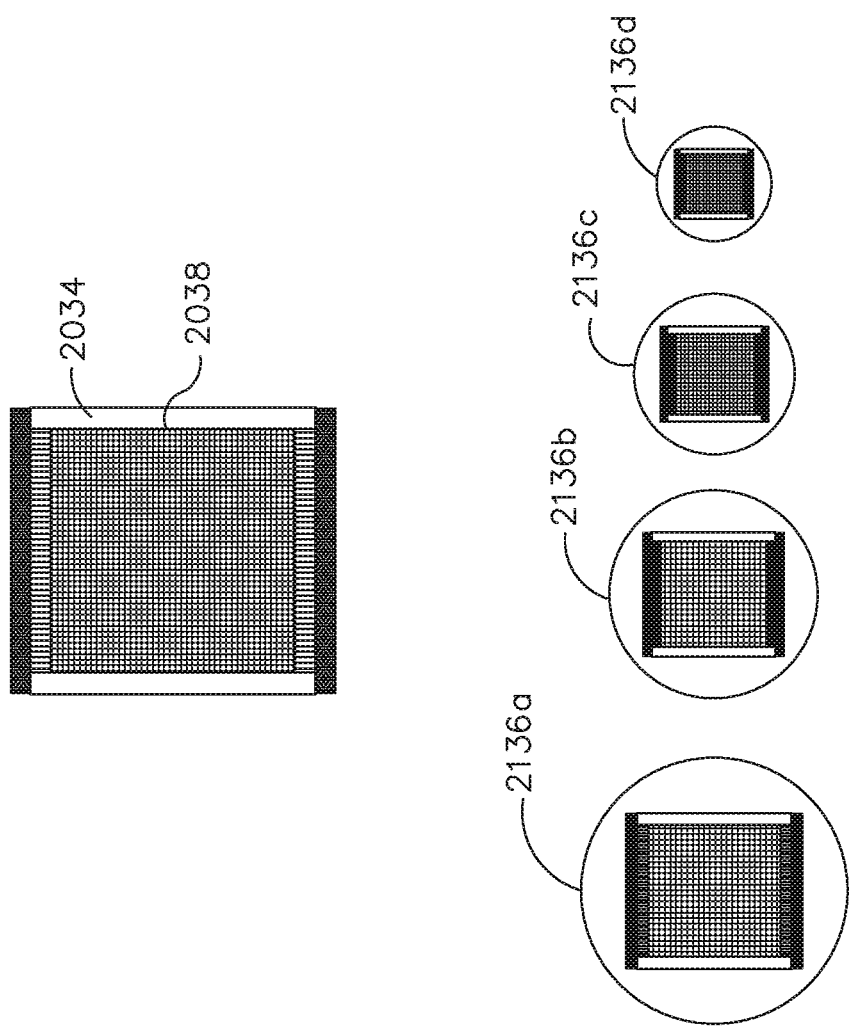
Figure 153A:
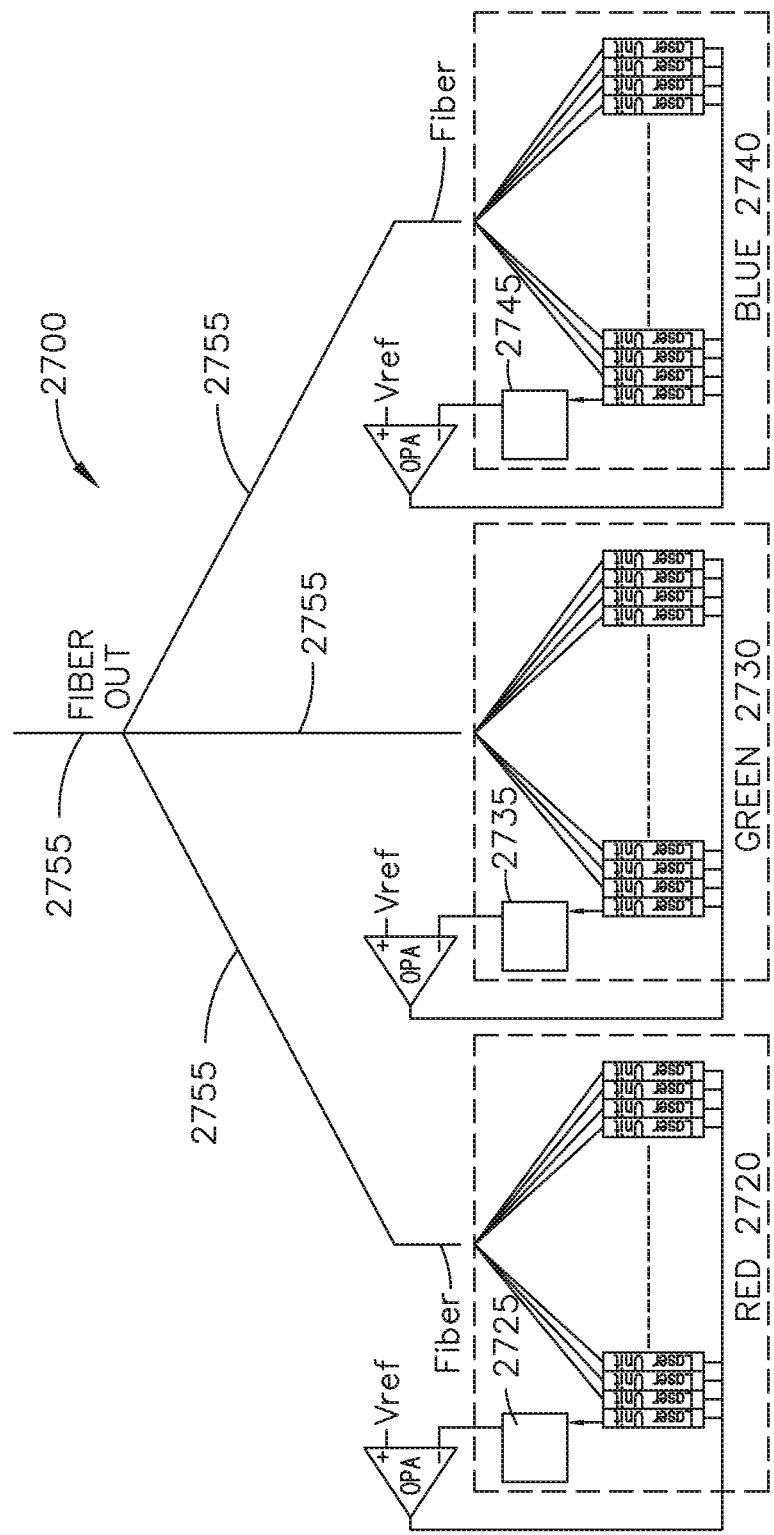
Figure 153B:
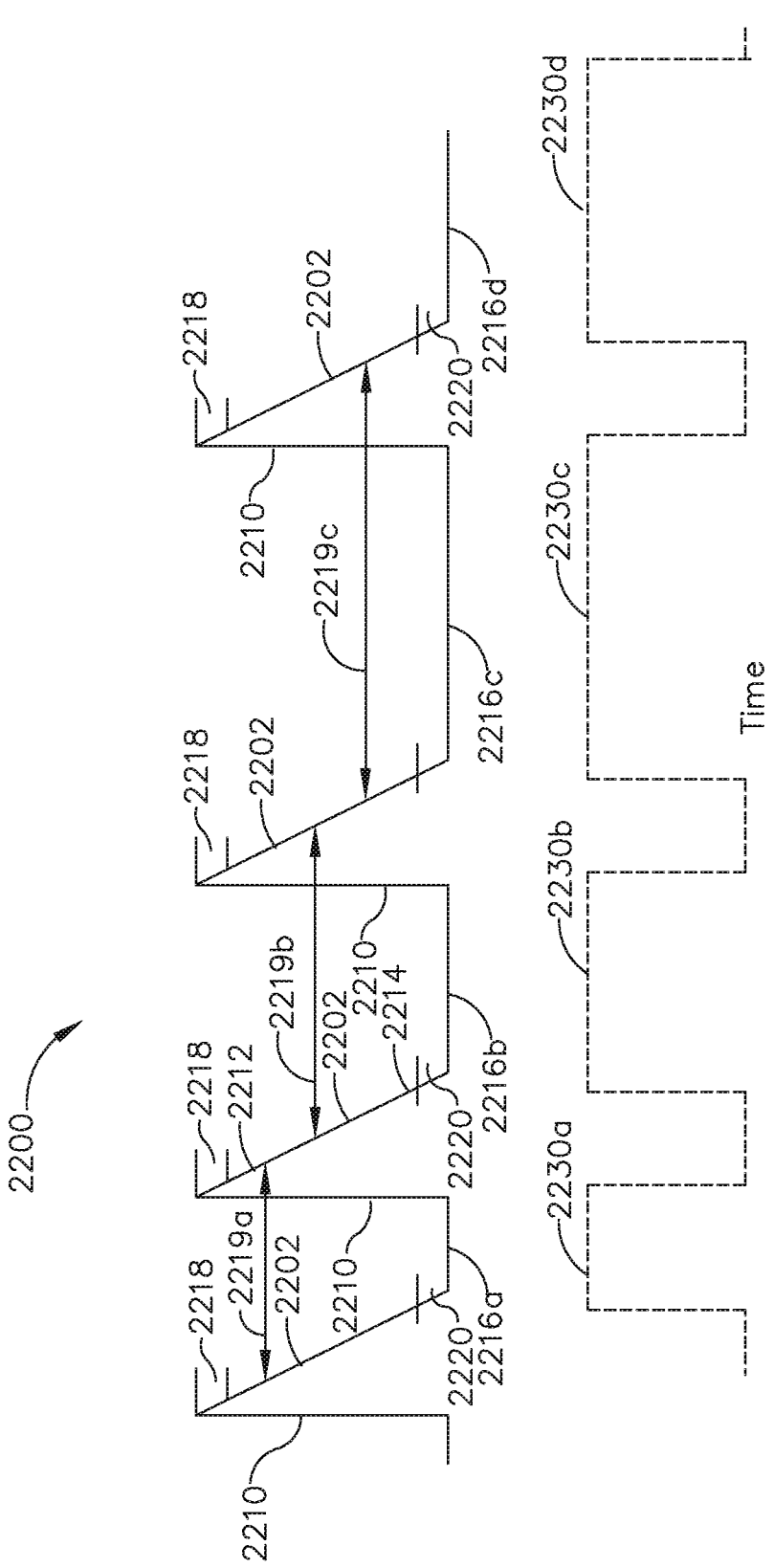
Figure 153C:
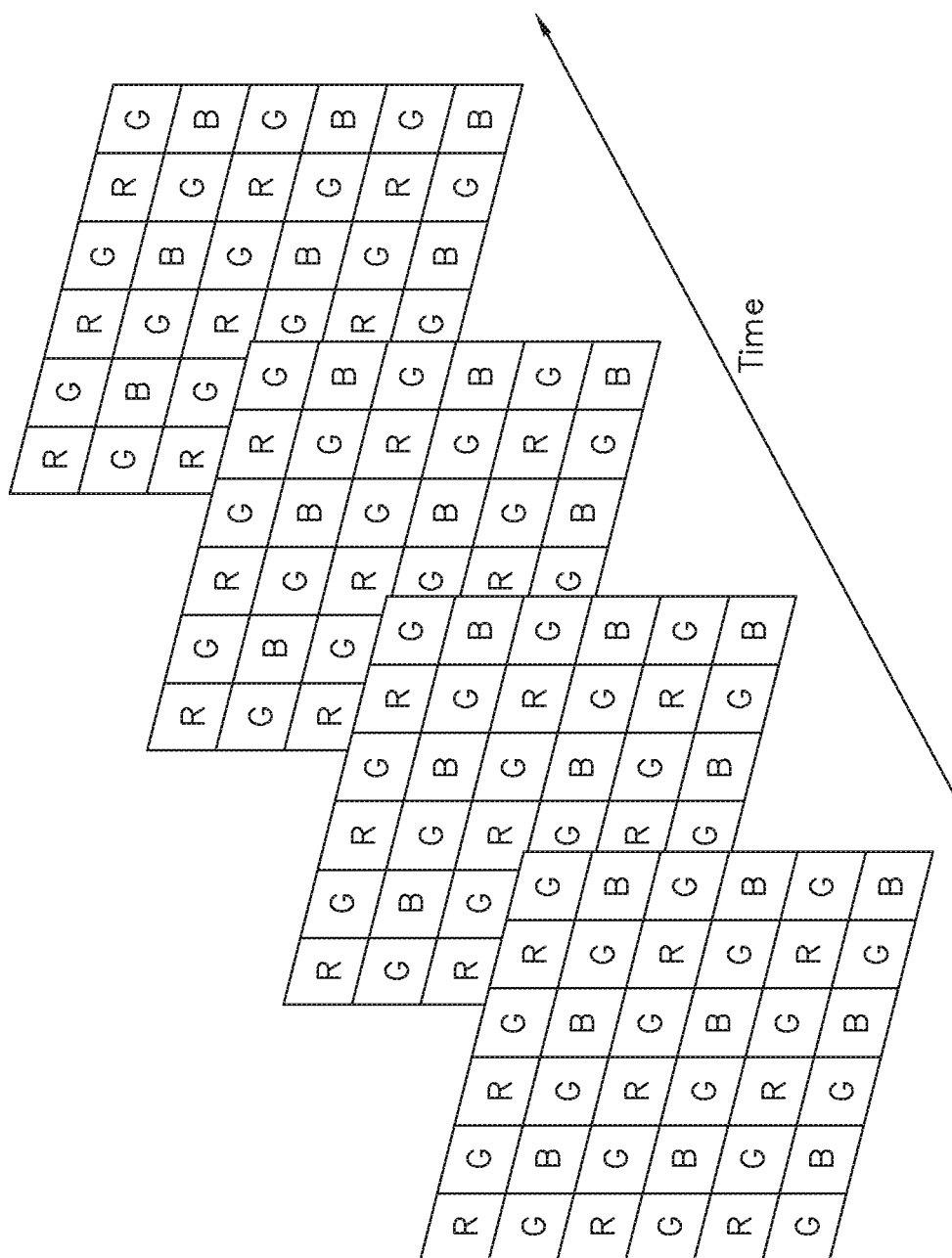
Figure 153D:
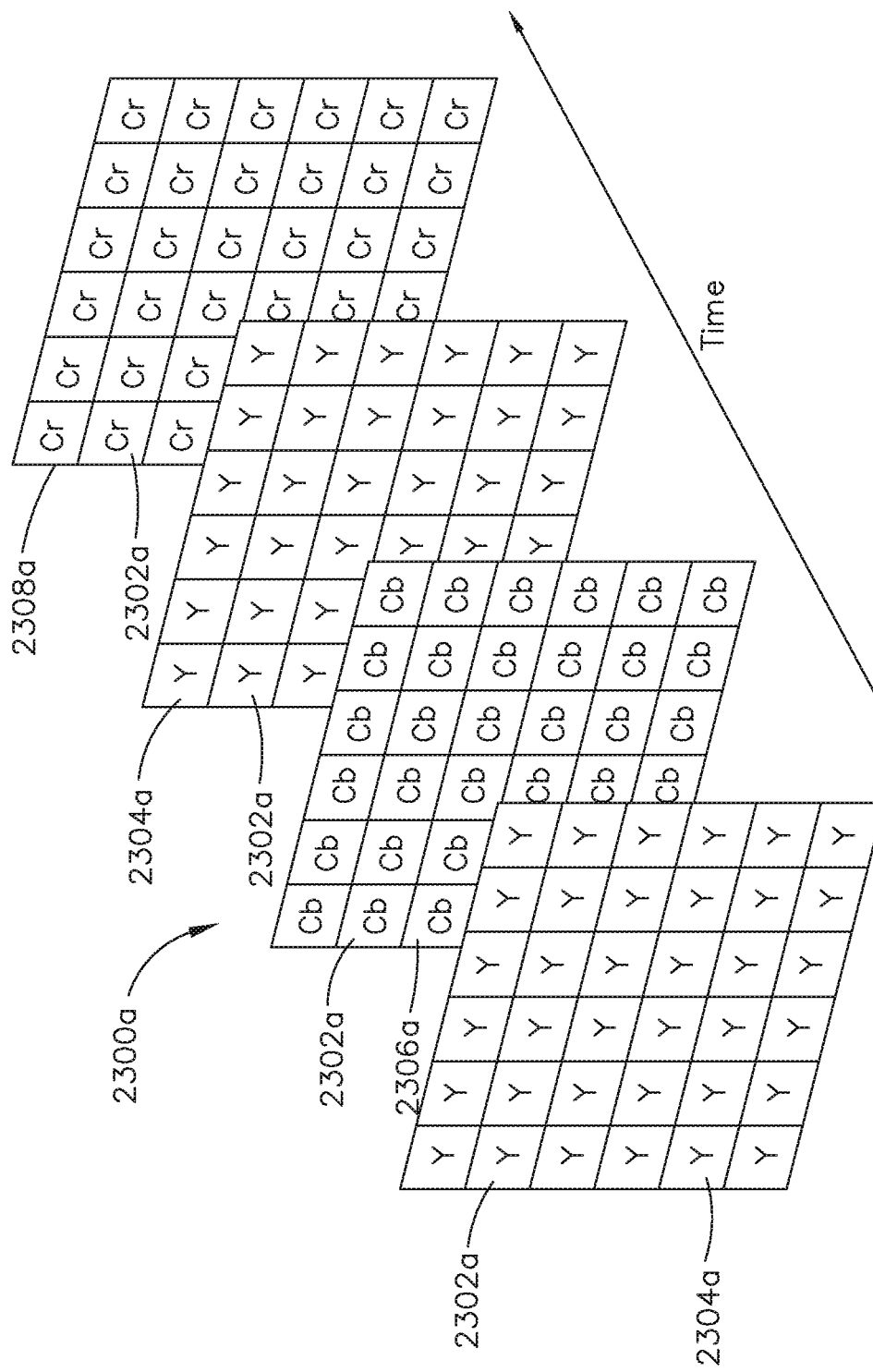
Figure 153E:
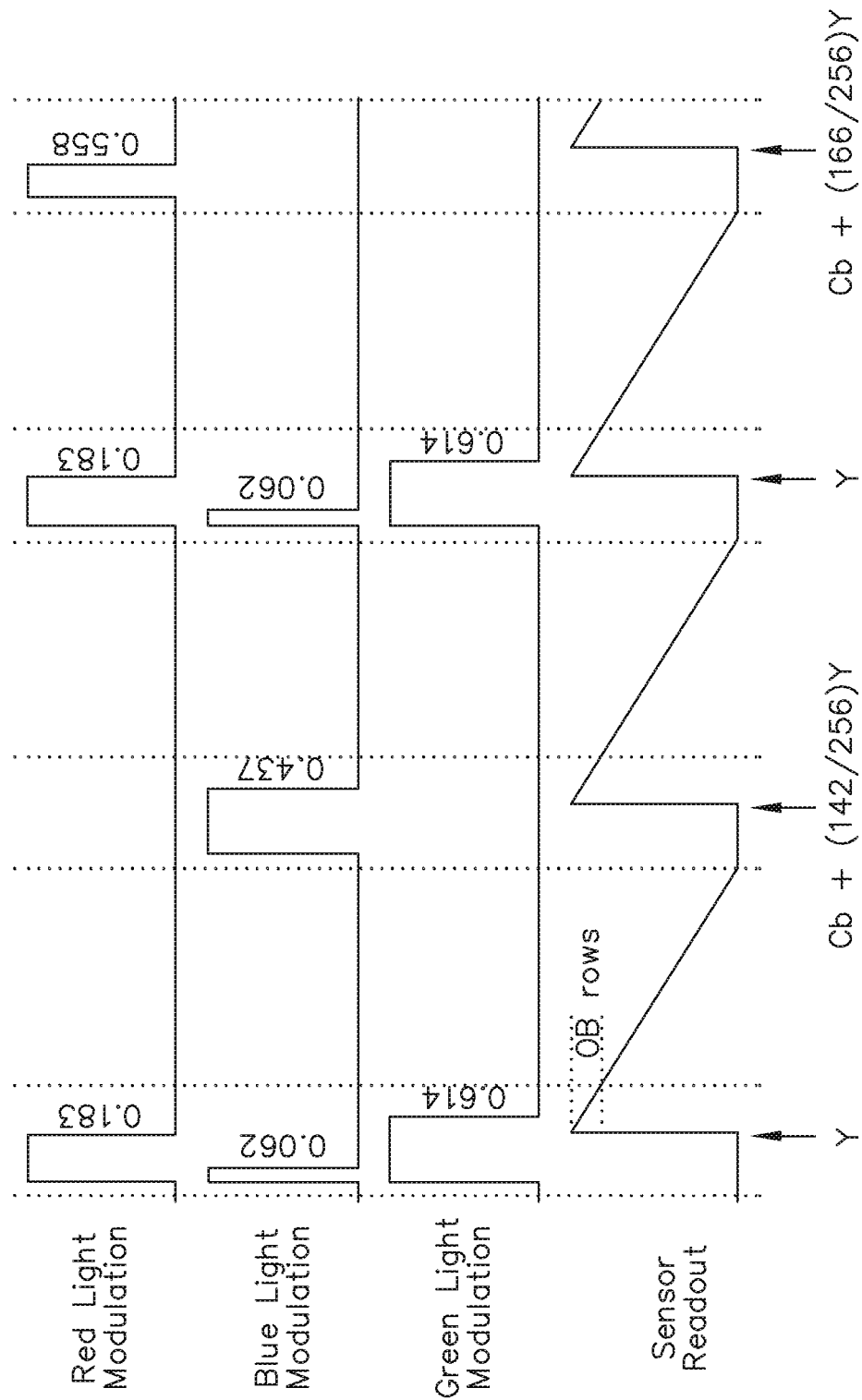
Figure 153F:
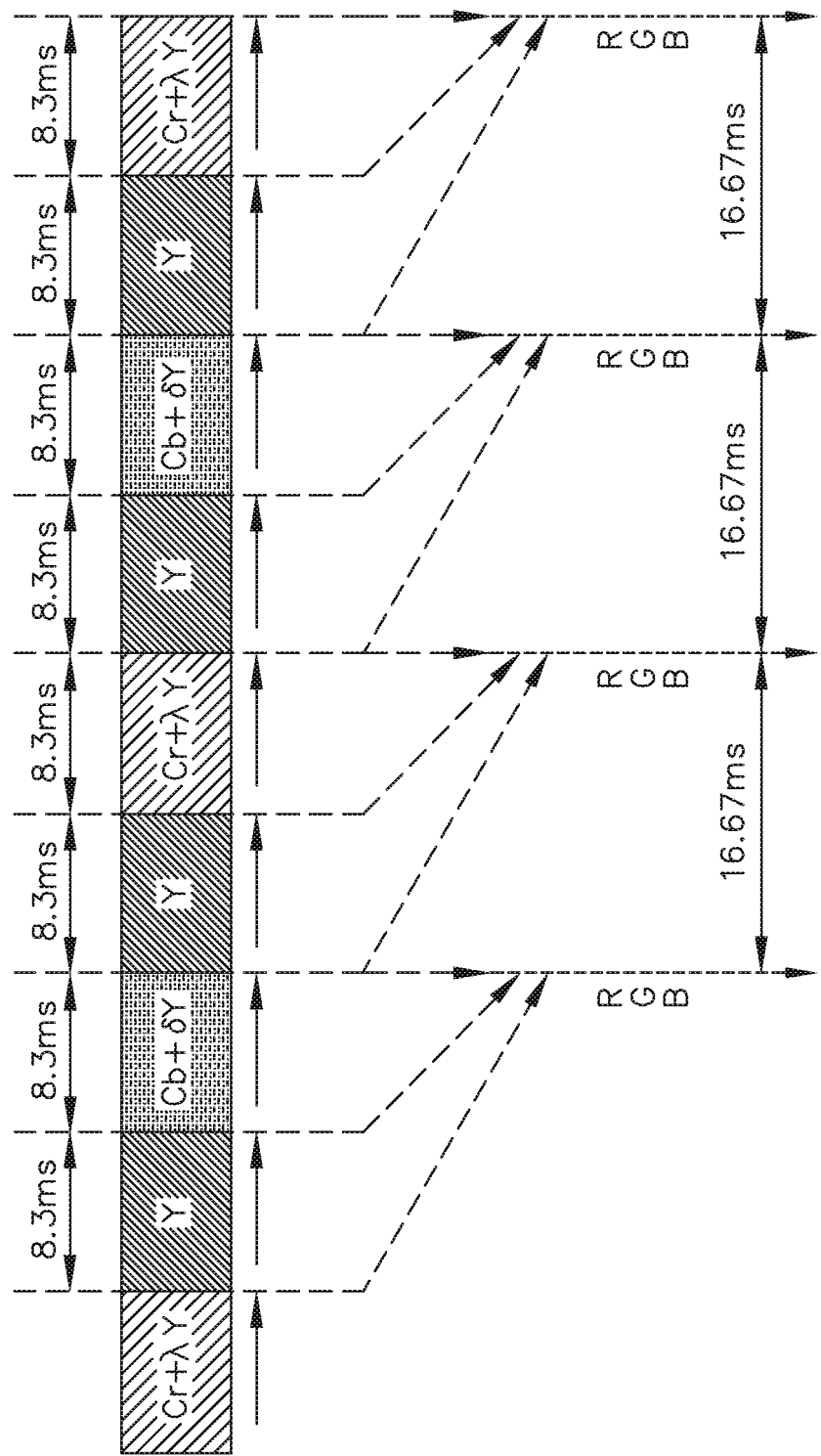
Figure 154:
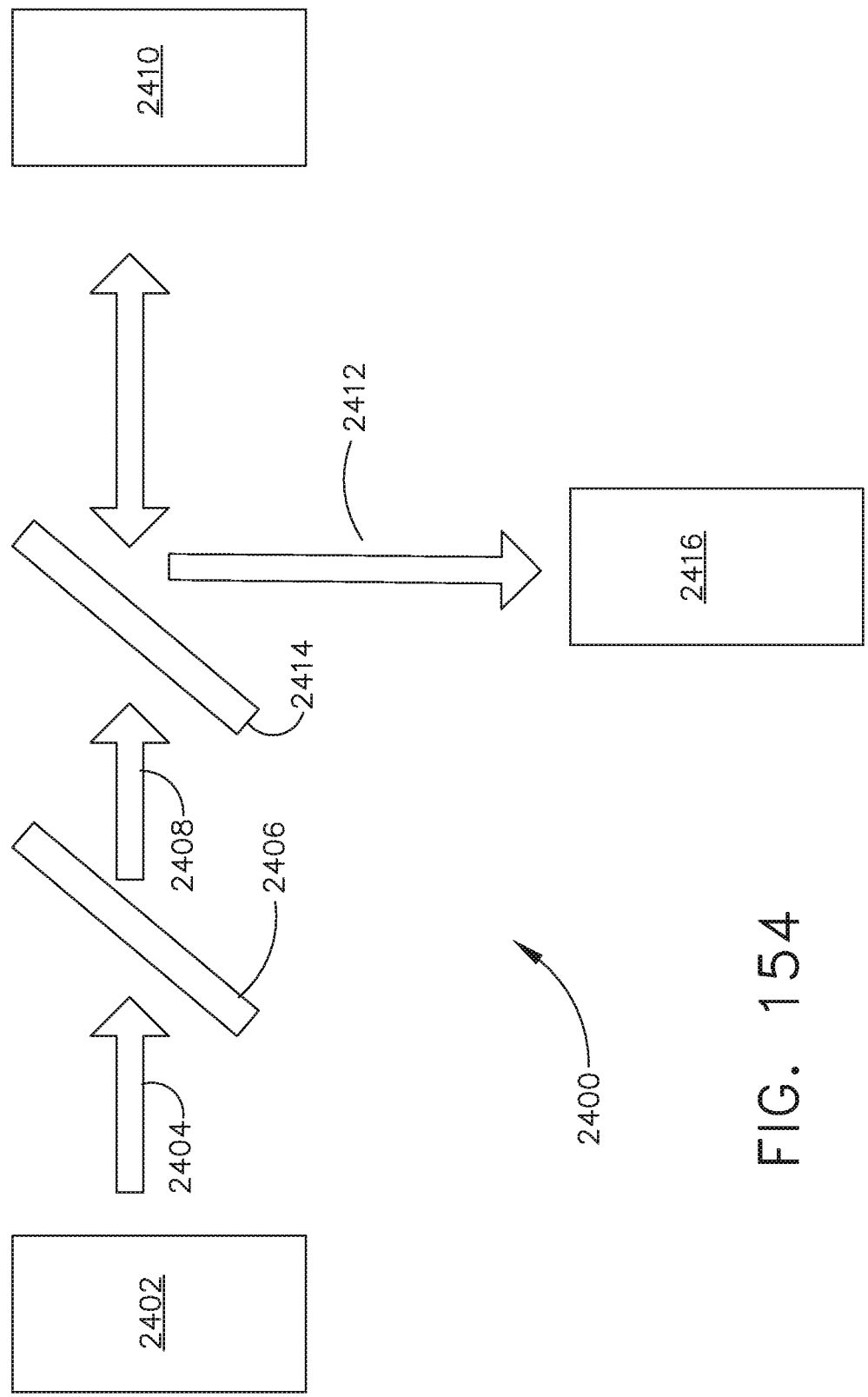
Figure 155:
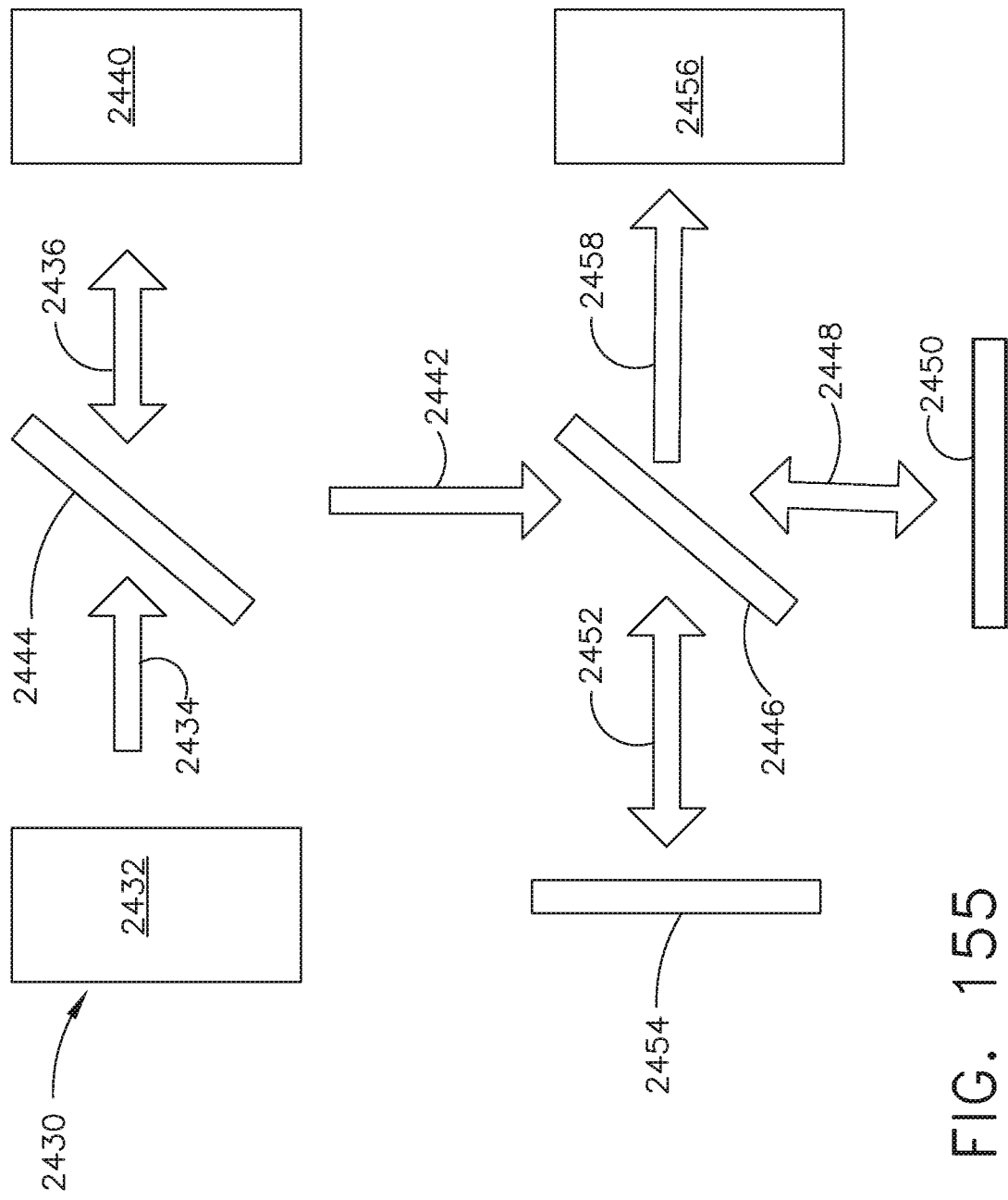
Figure 156C:
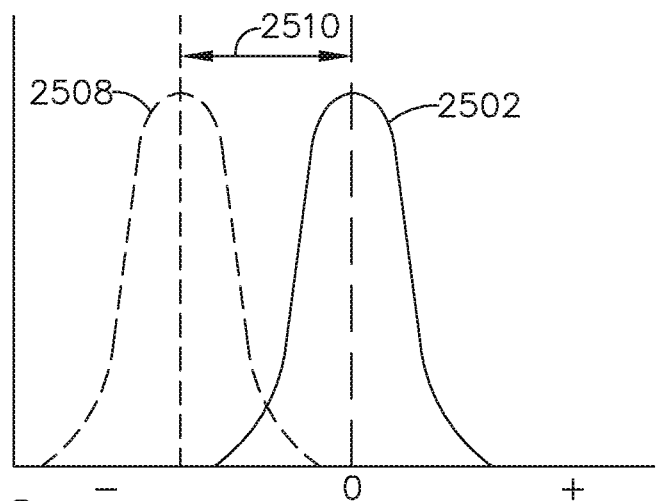
Figure 156B:
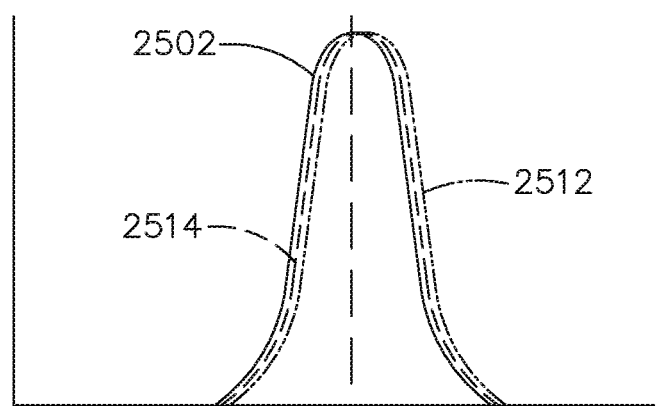
Figure 156A:
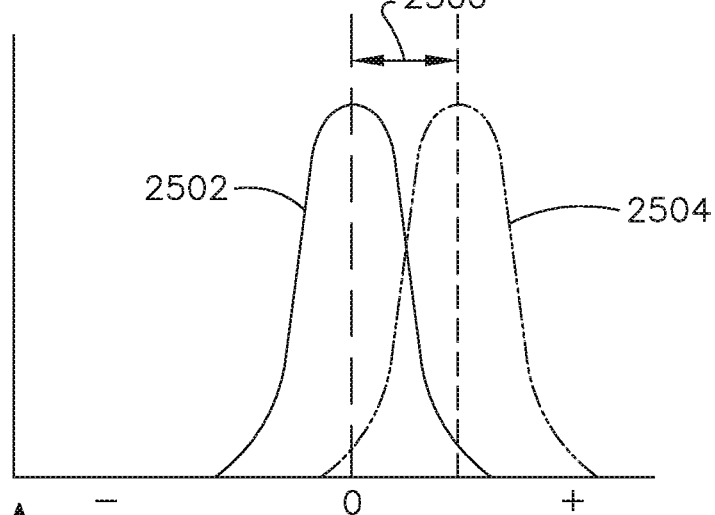
Figure 157:
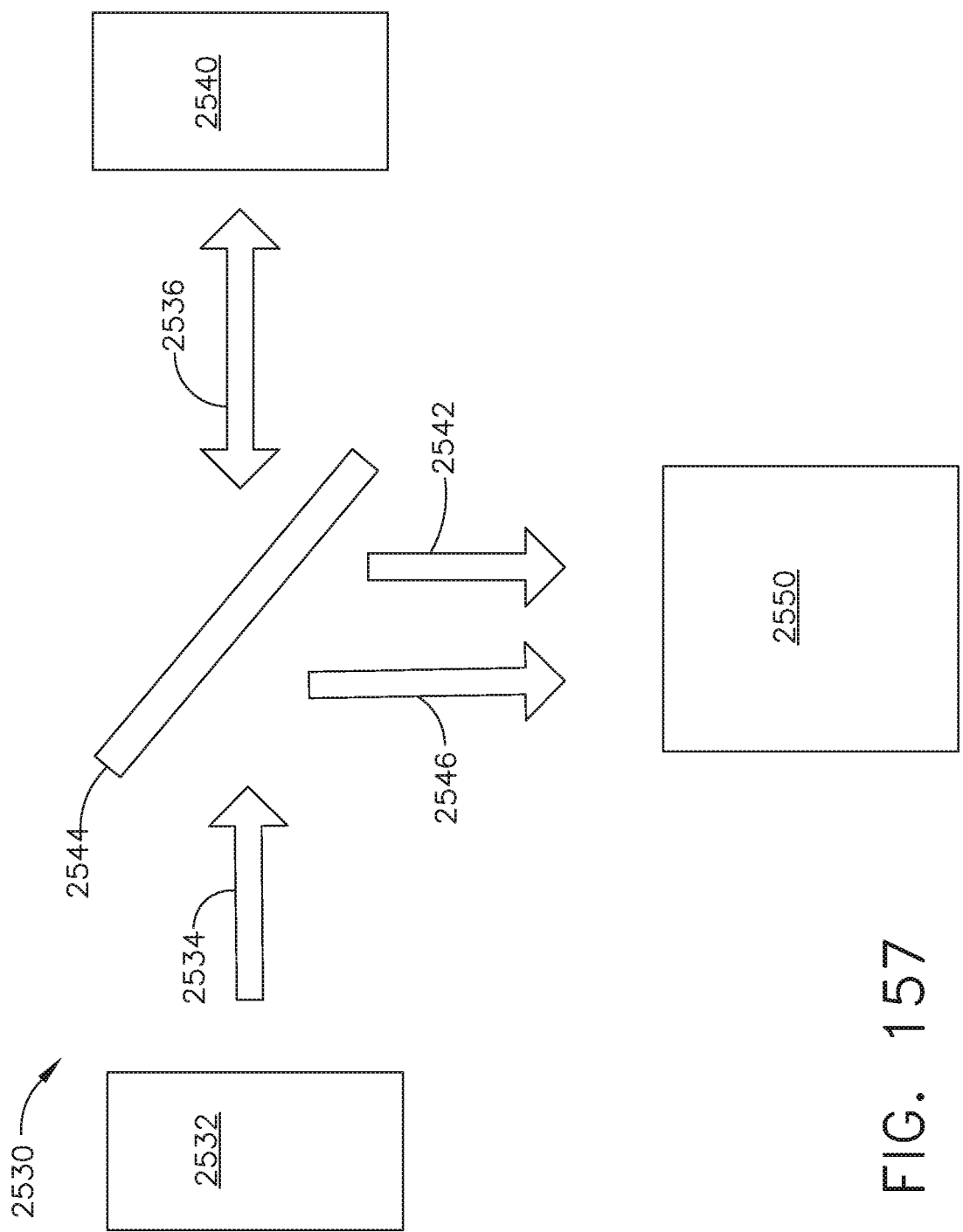
Figure 158:
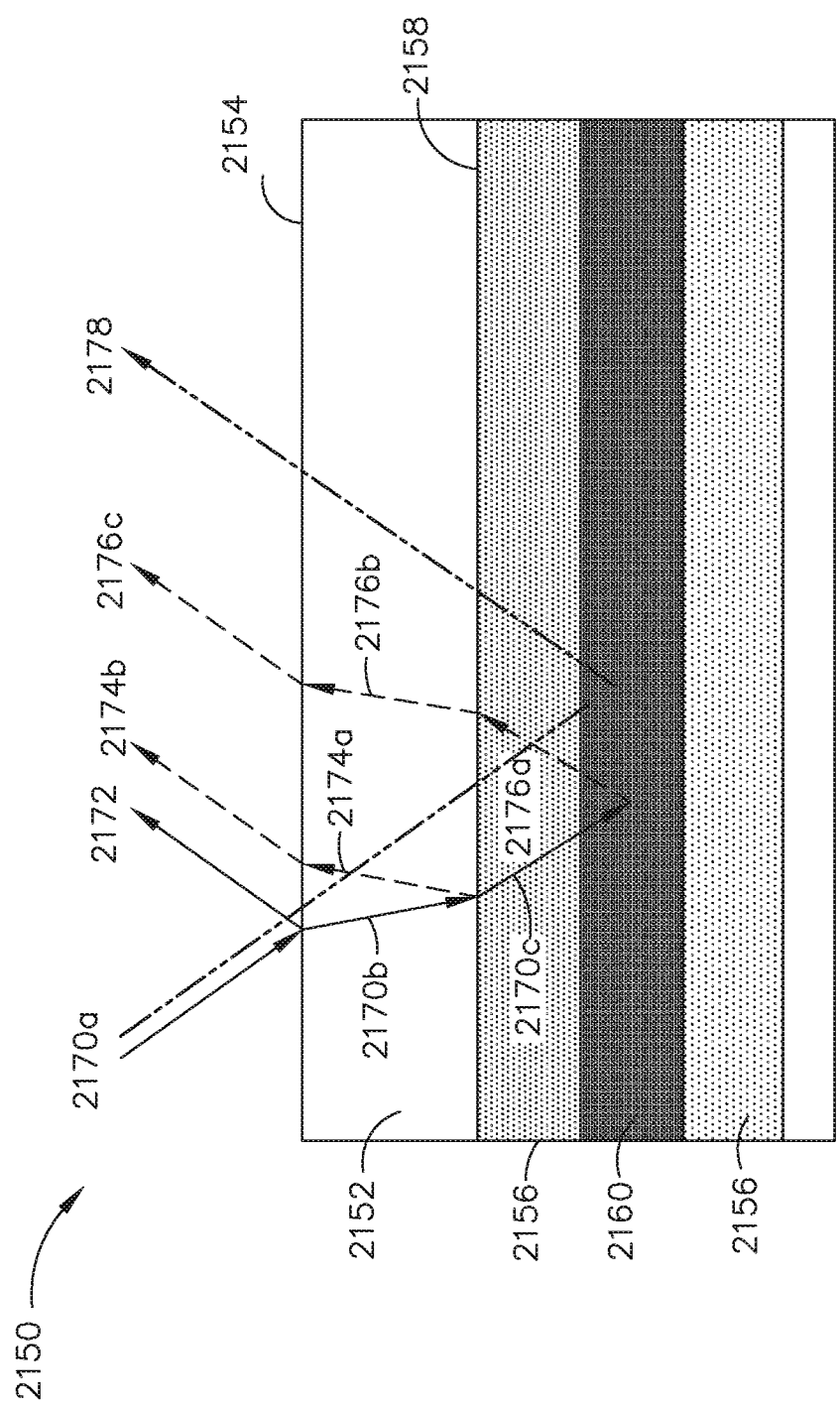
Figure 159:
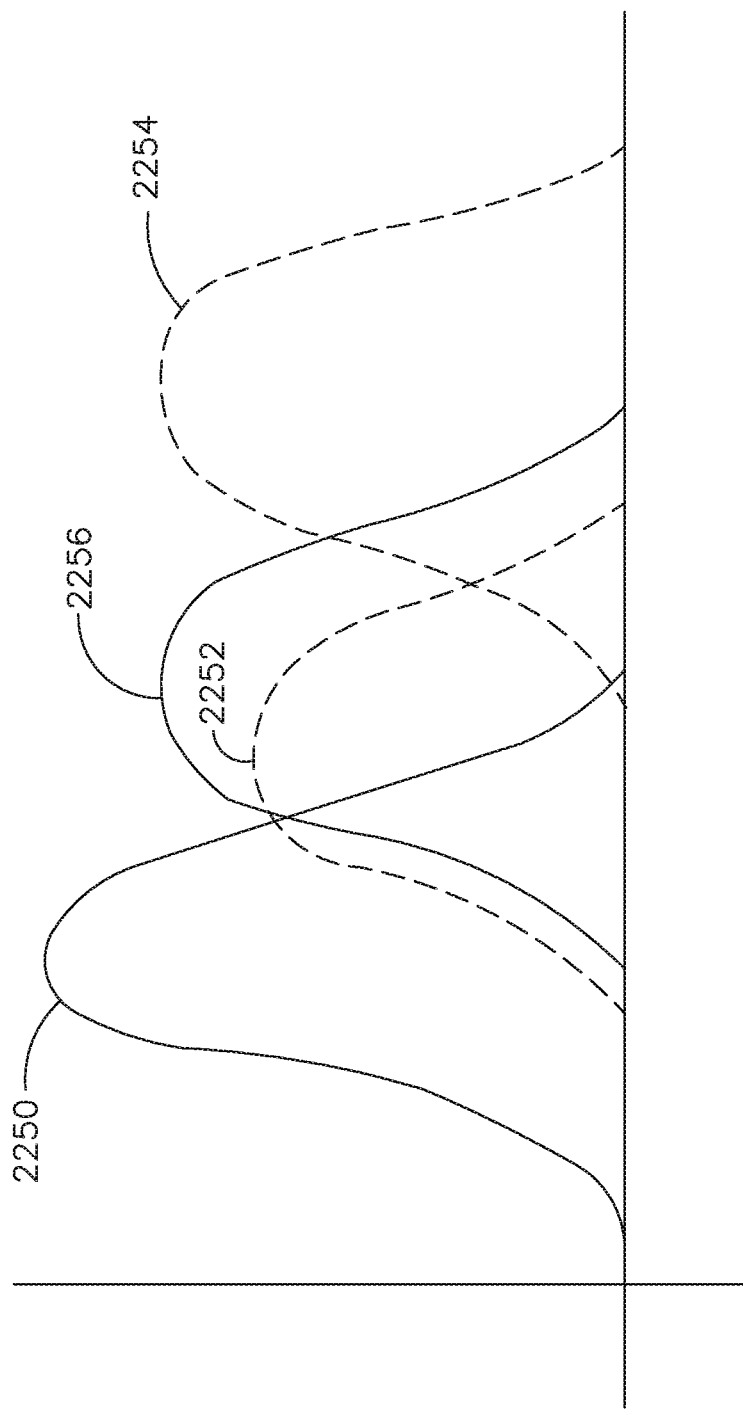
Figure 161:
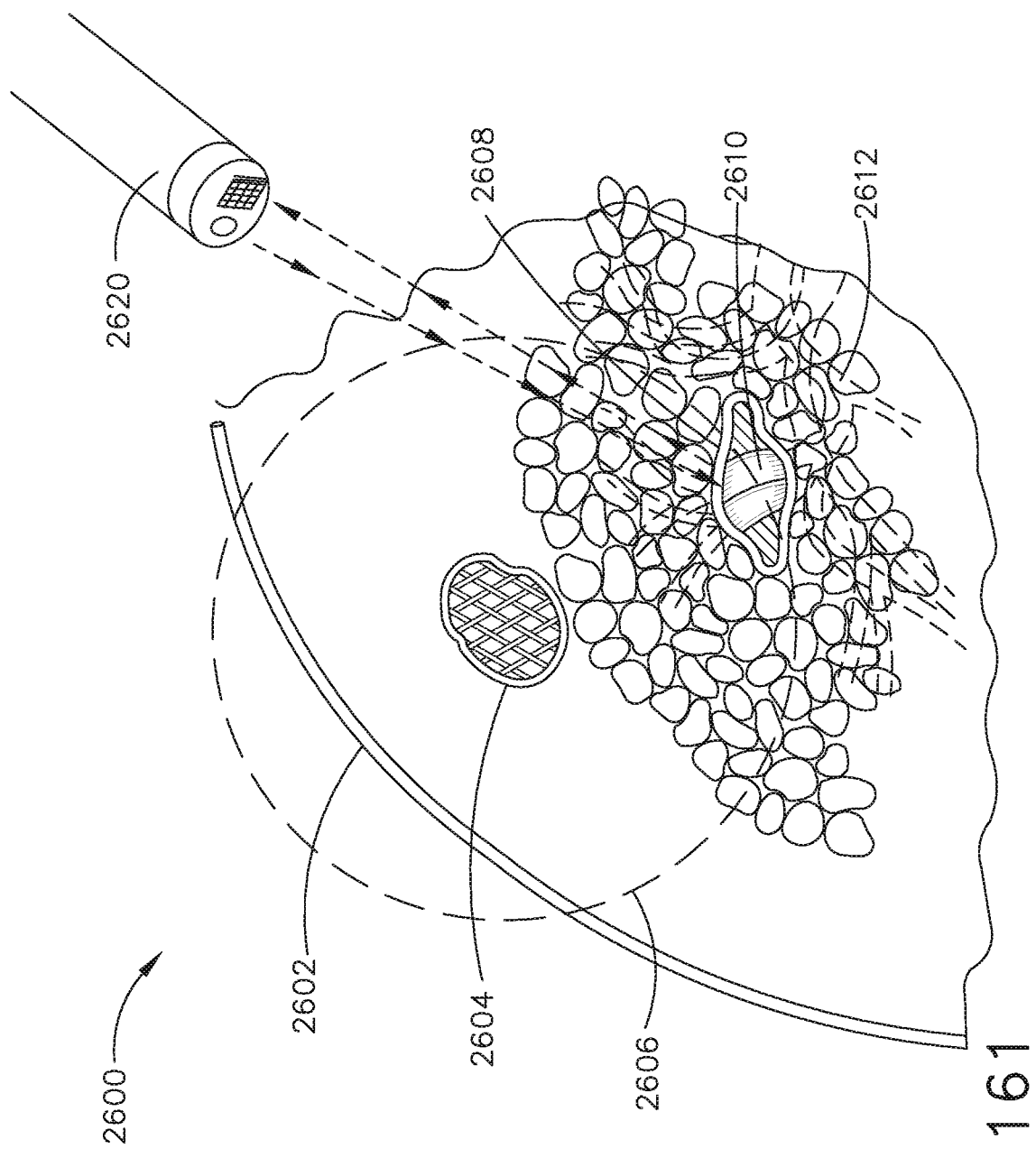
Figure 162:
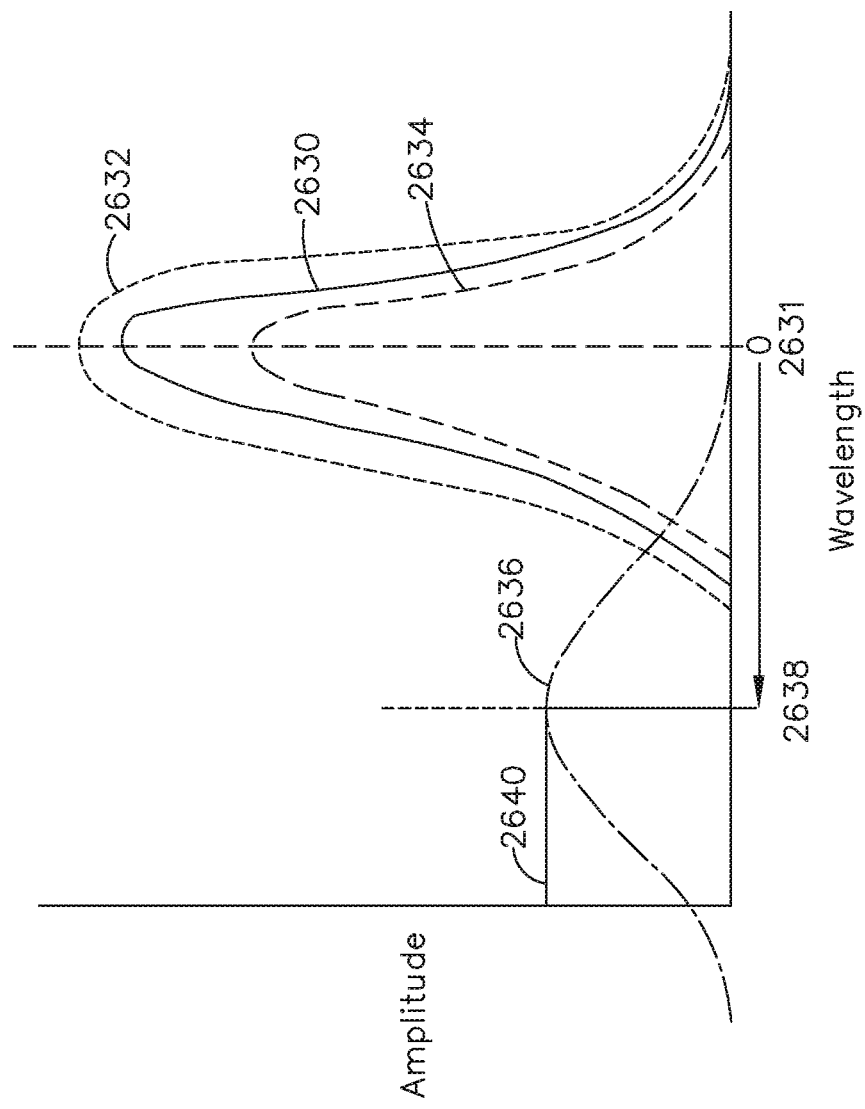
Figure 163:
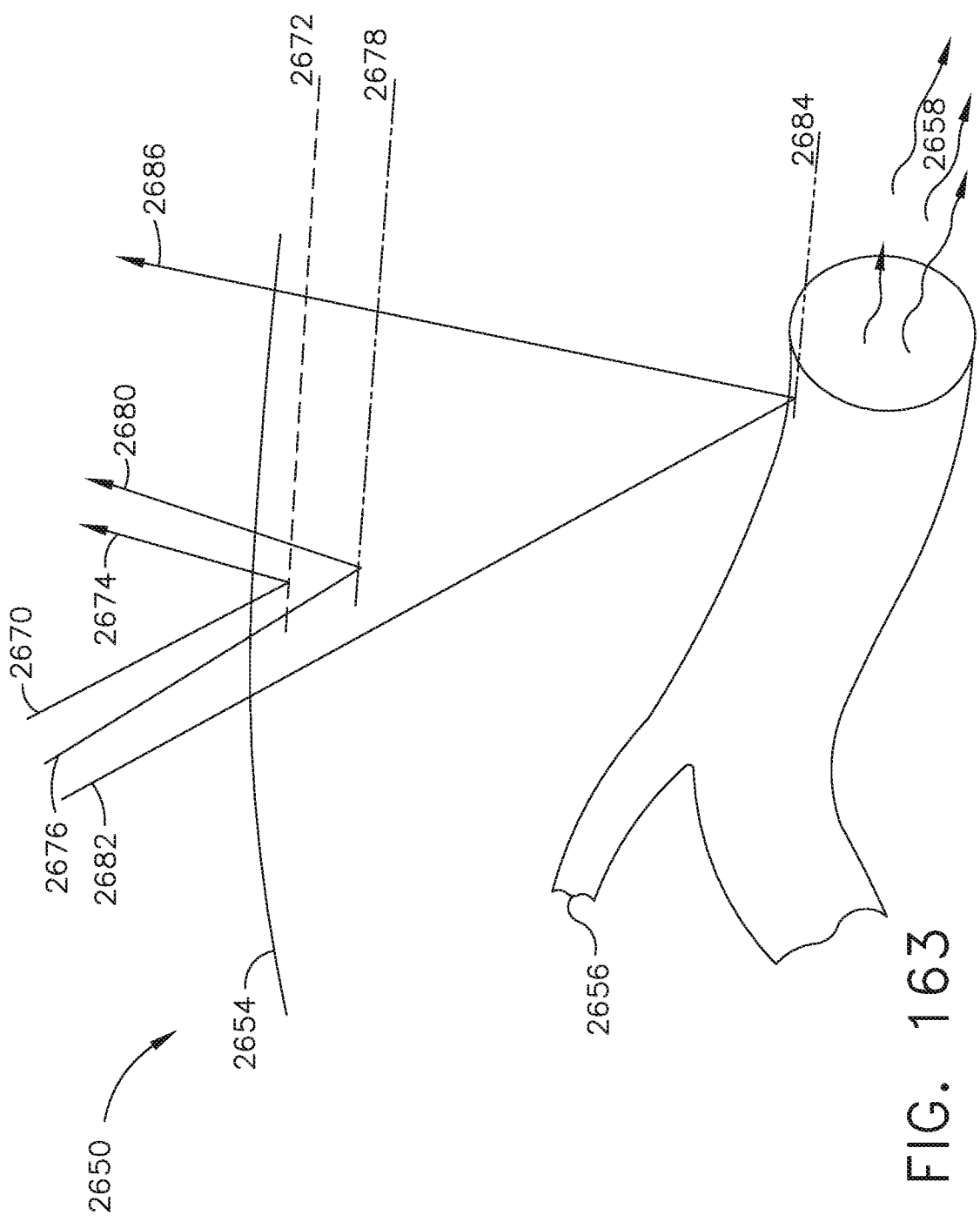
Figure 164:
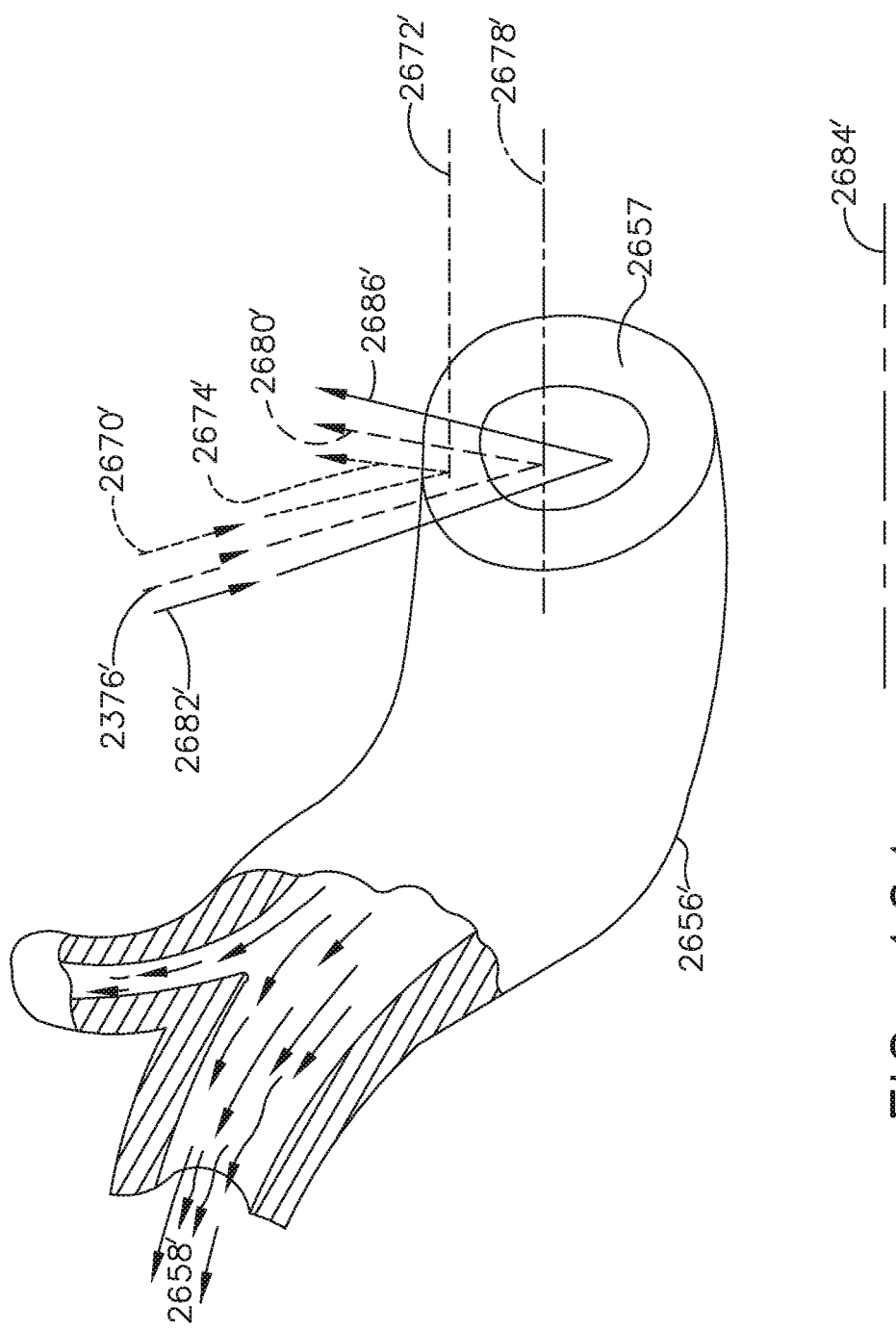
Figure 165:
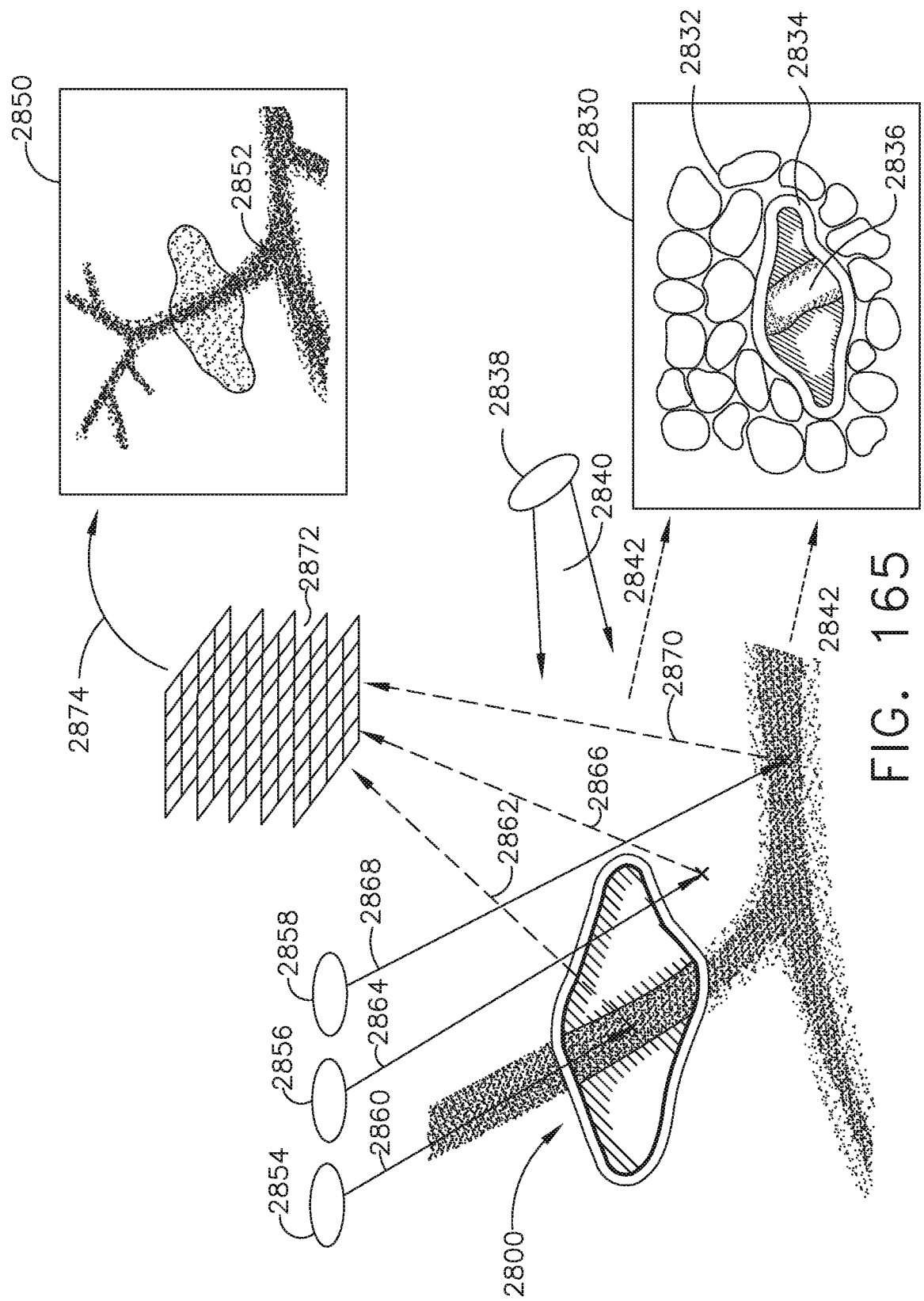
Figure 166:
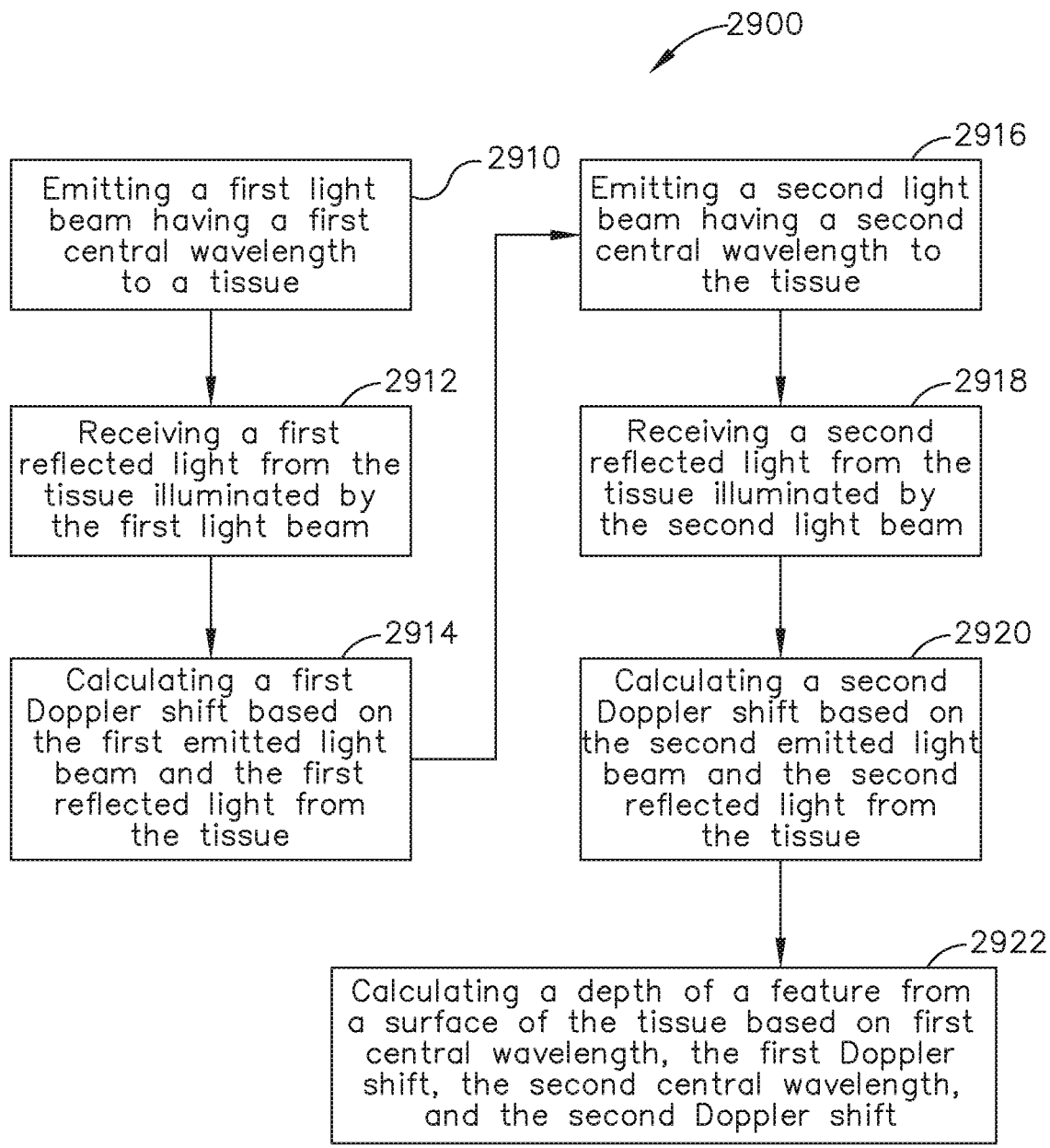
Figure 167:
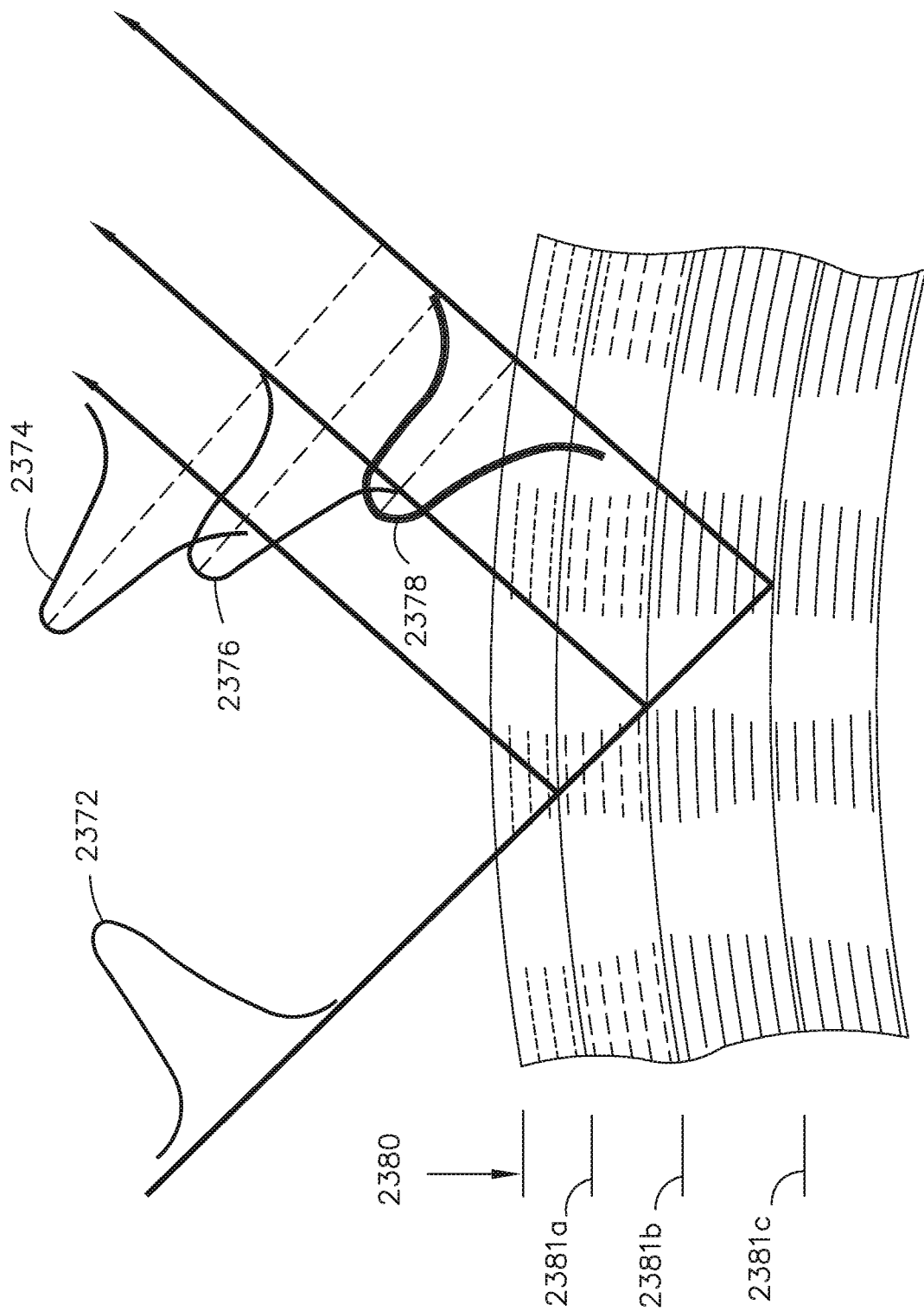
Figure 168:
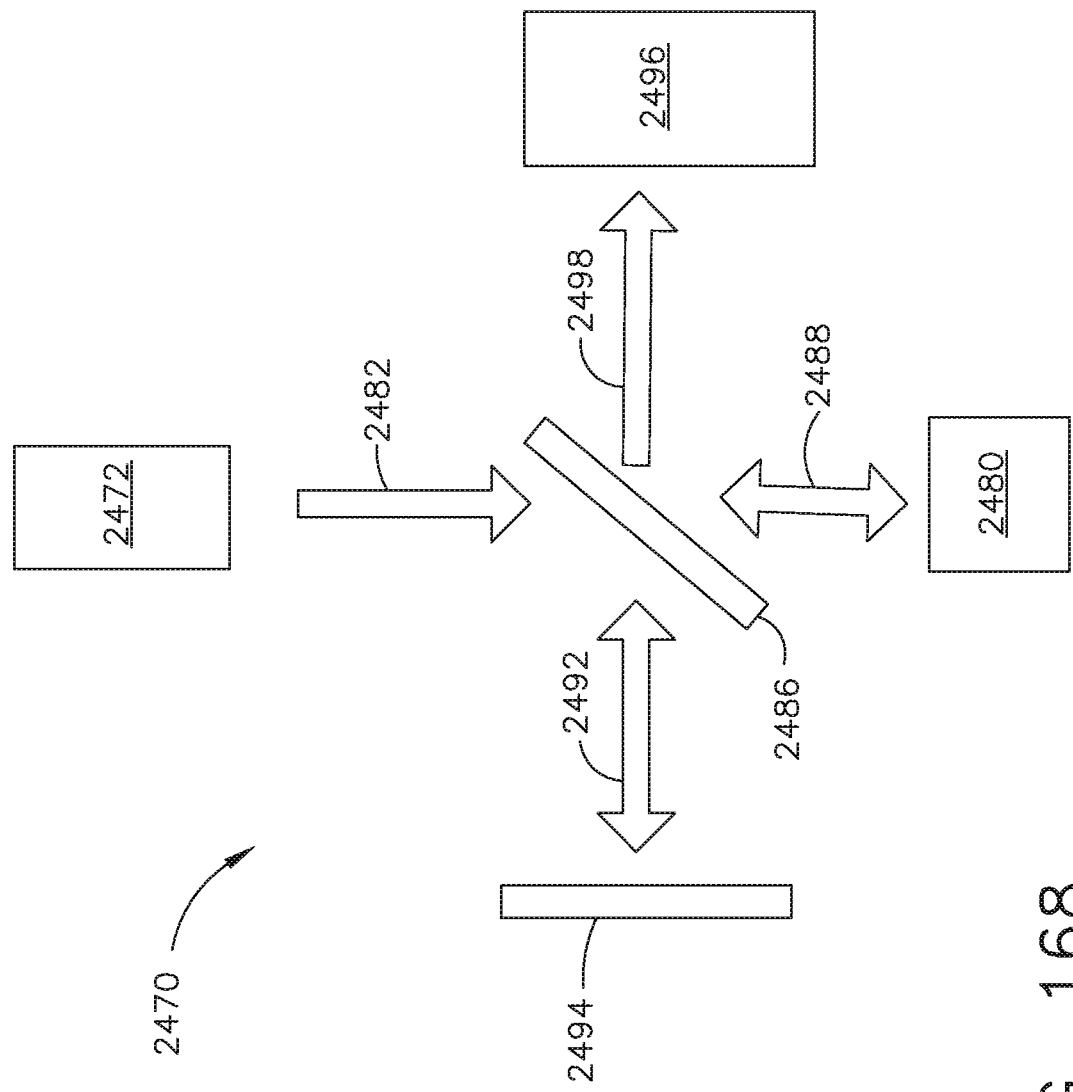
Figure 169:
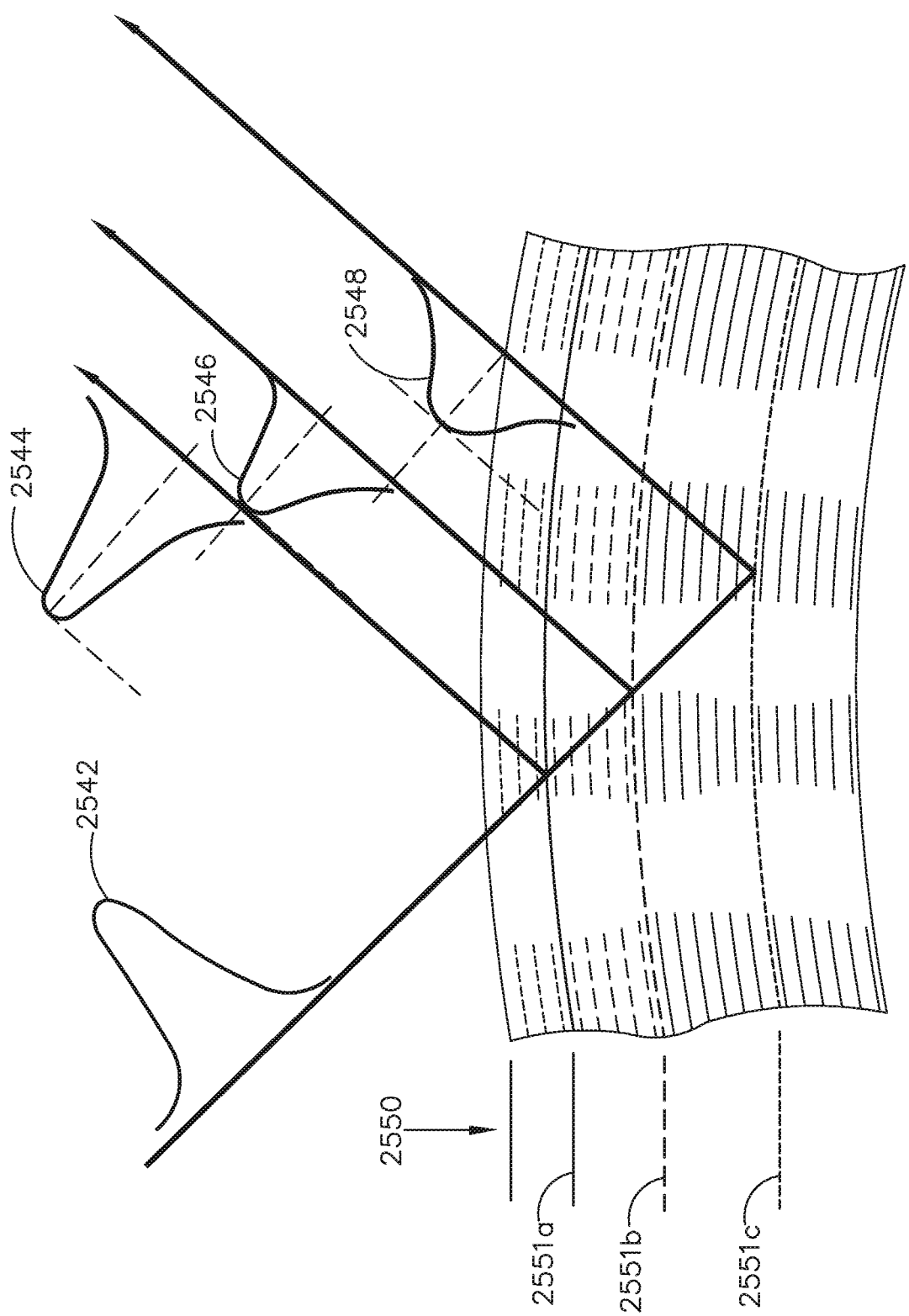
Figure 170:
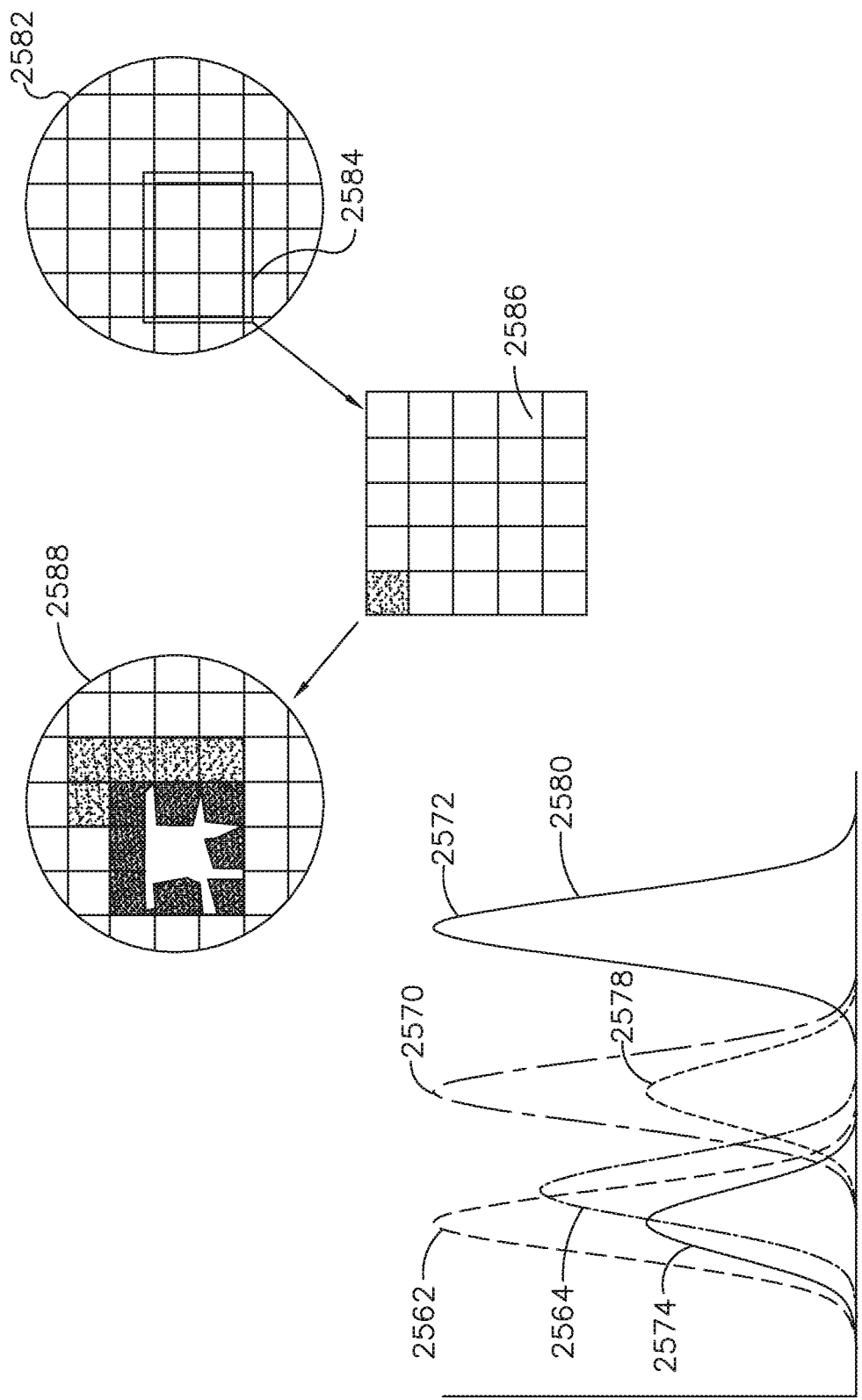
Figure 171A:
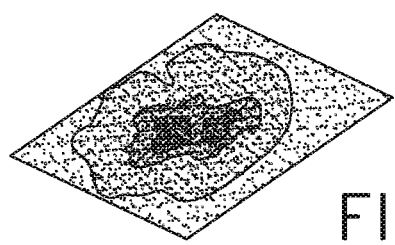
Figure 171B:
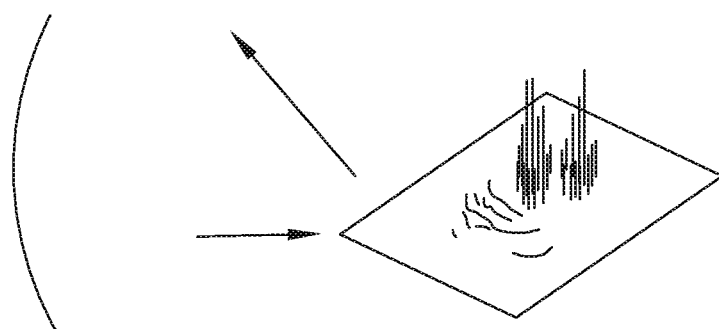
Figure 171C:
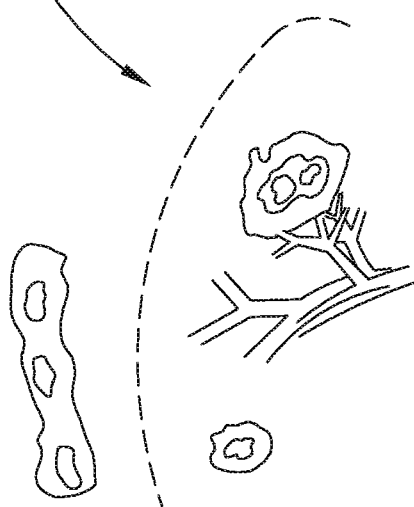
Figure 172:
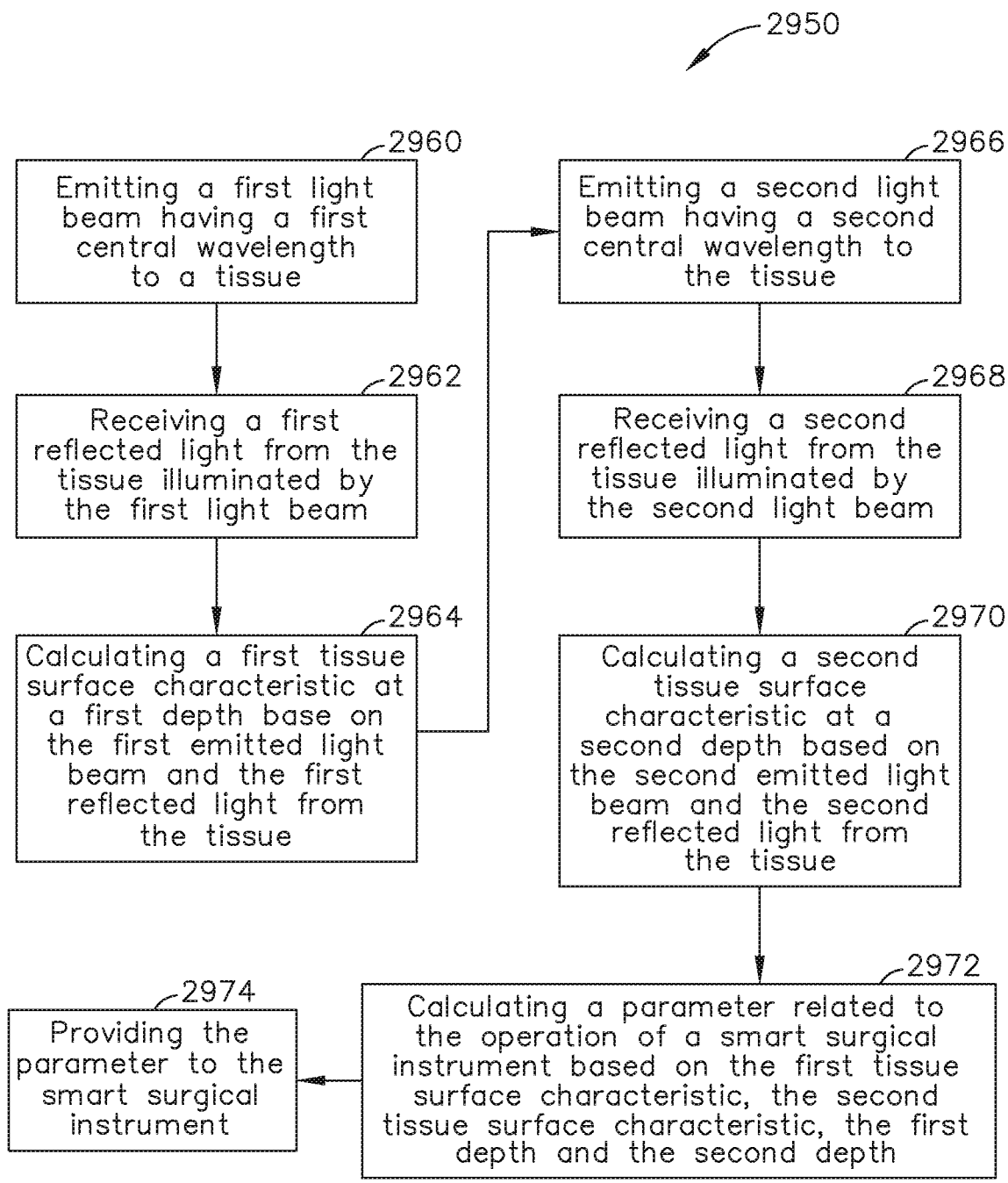
Figure 173A:
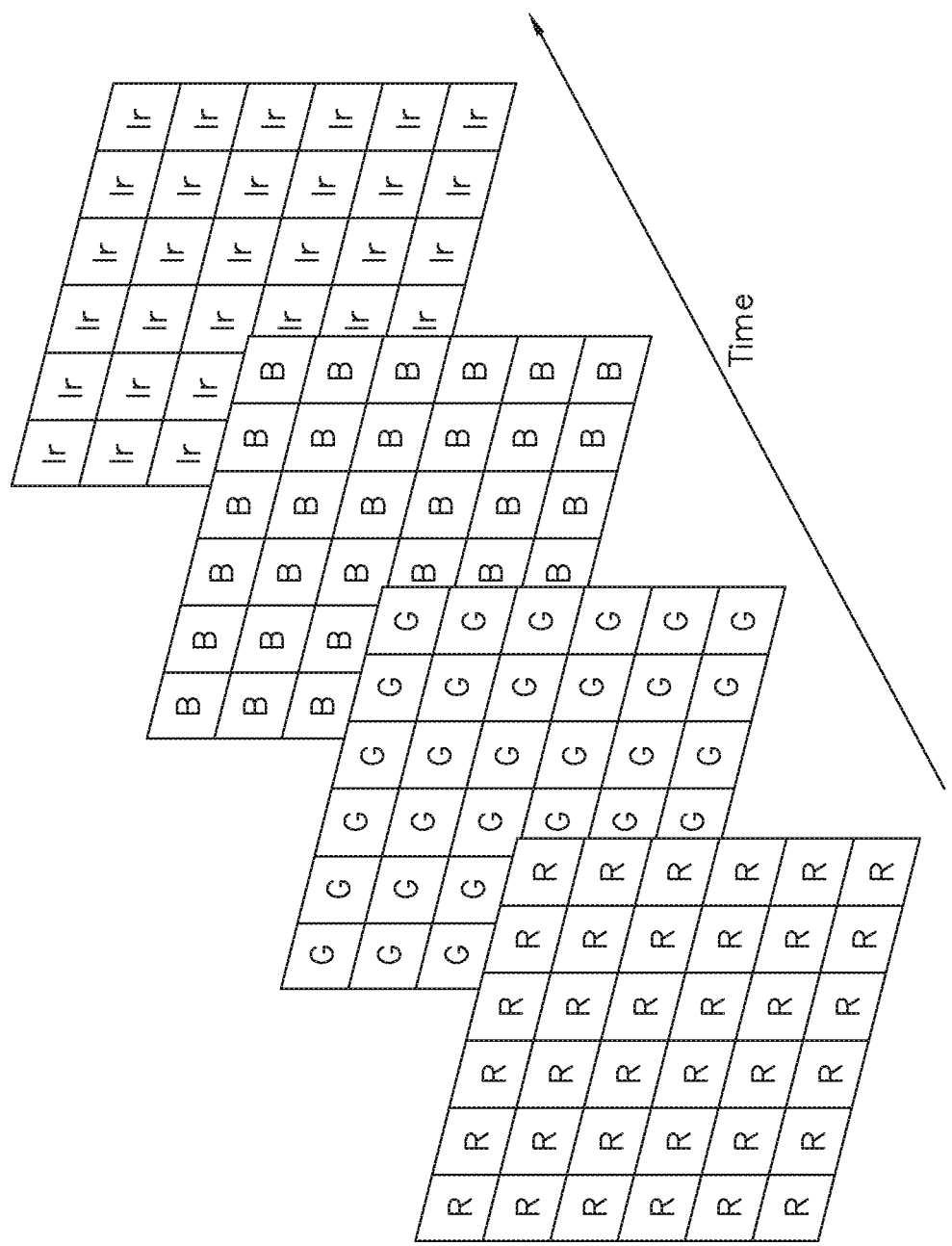
Figure 173B:
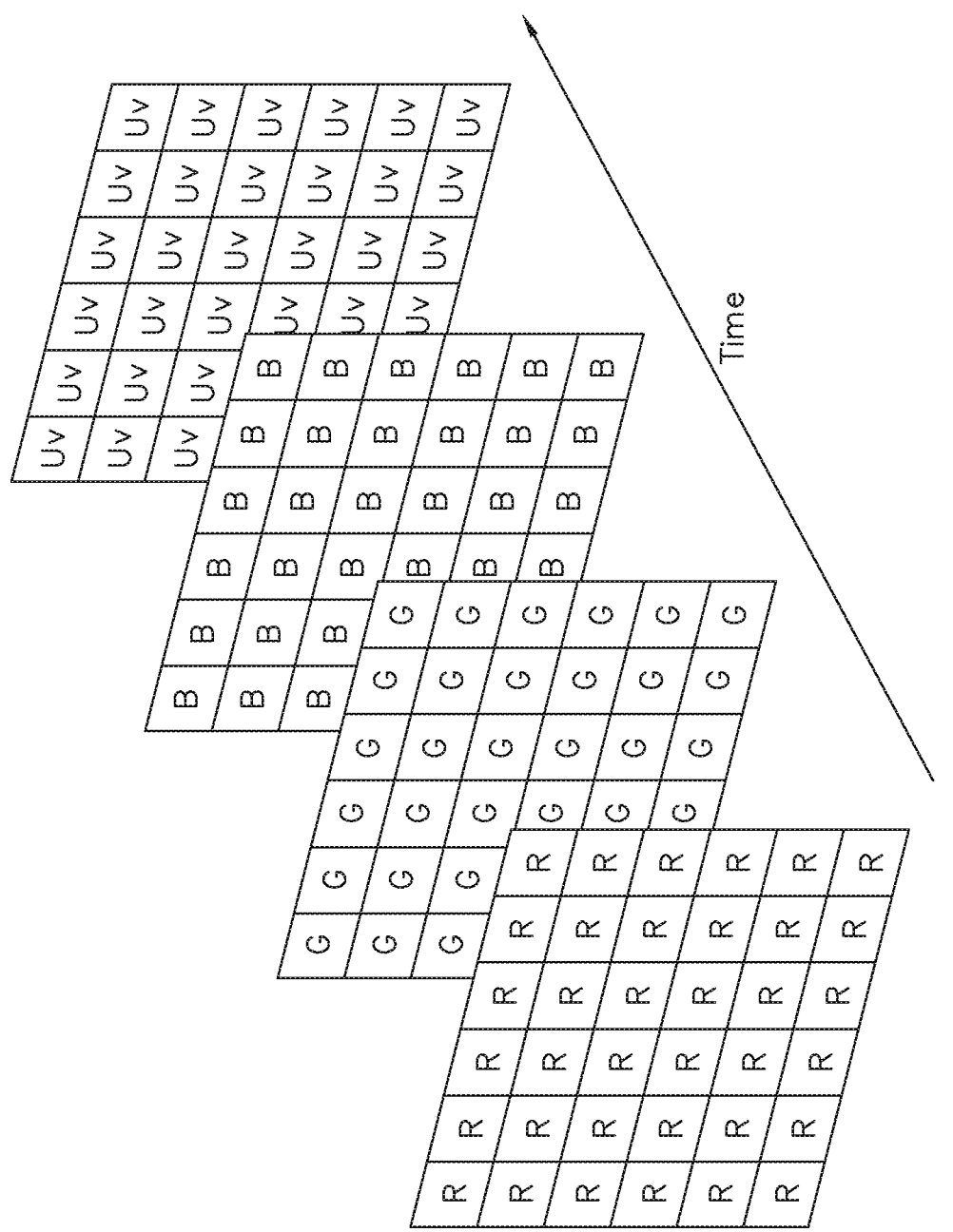
Figure 174C:
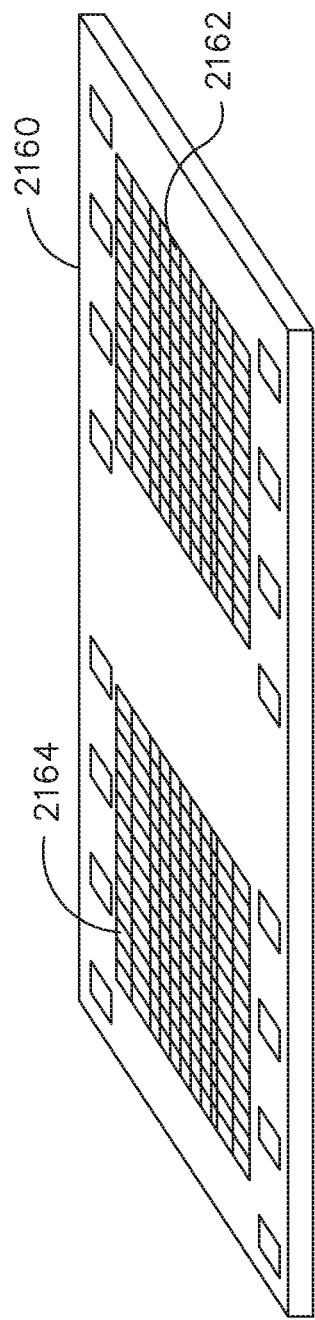
Figure 175:
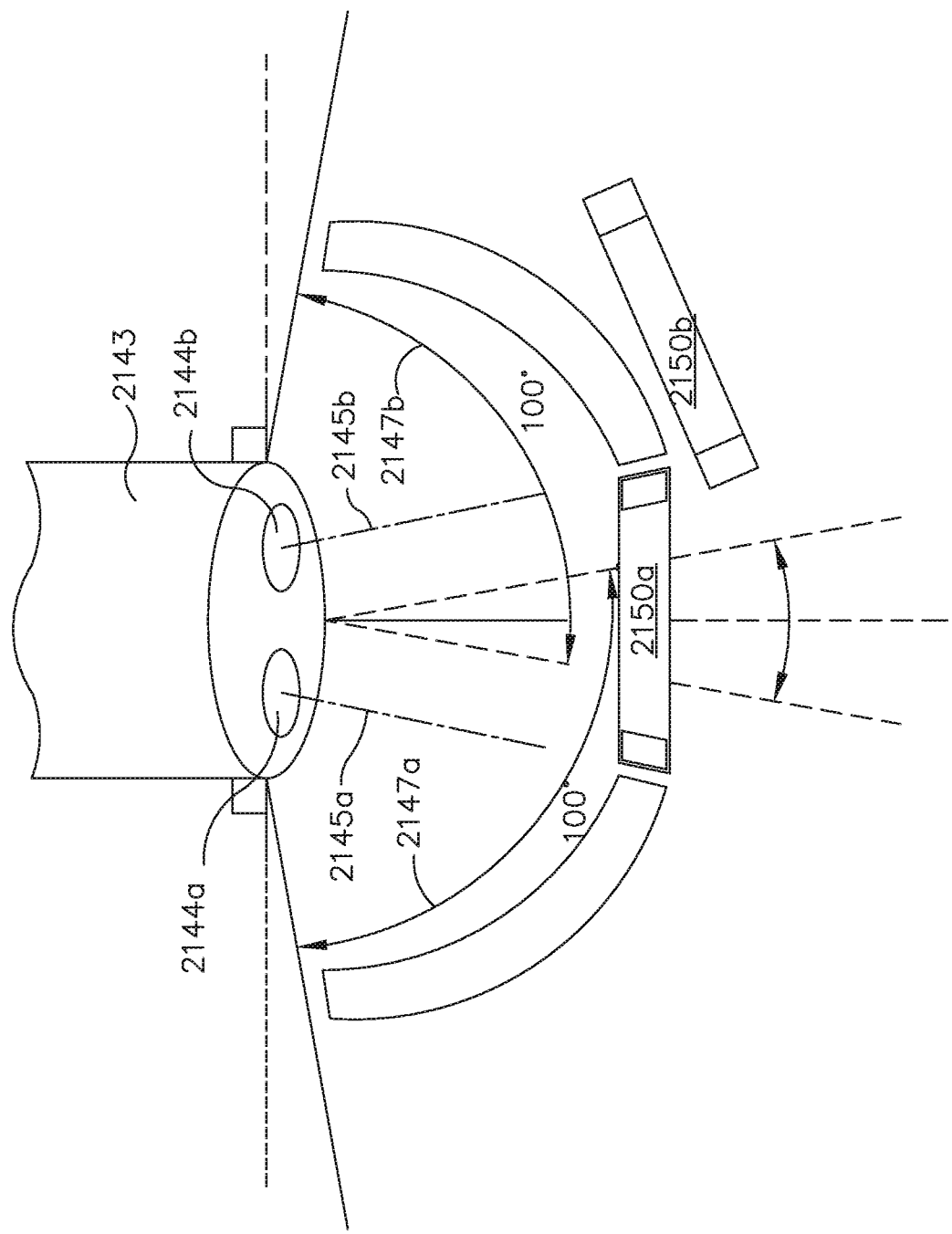
Figure 176A:
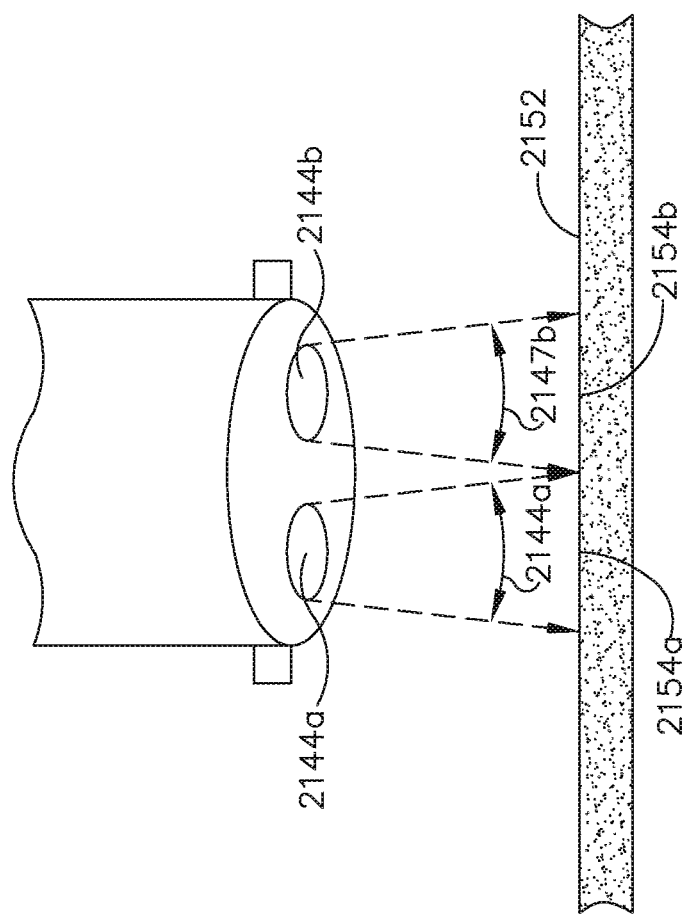
Figure 176B:
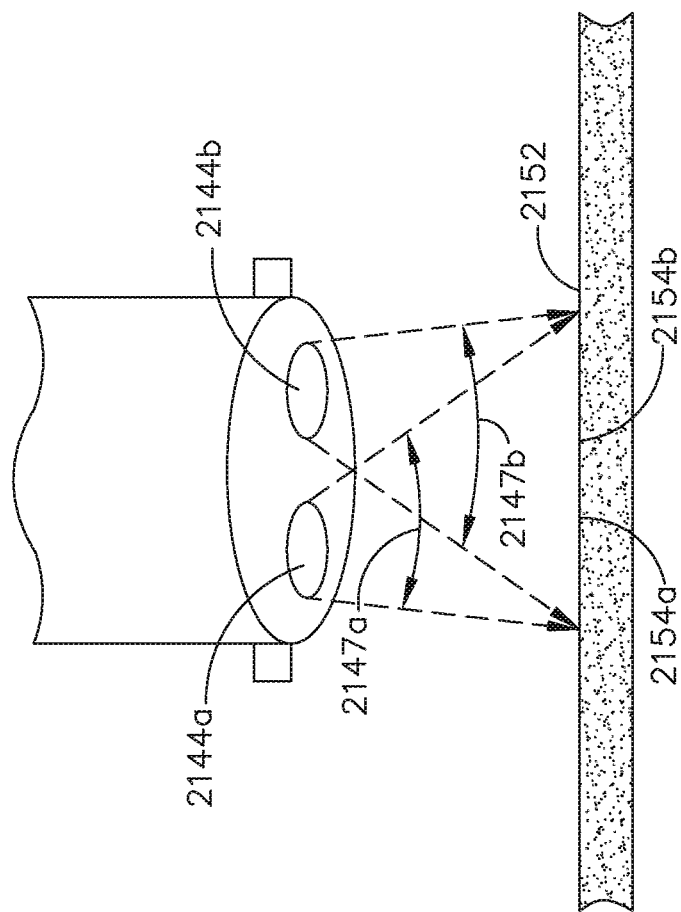
Figure 176C:
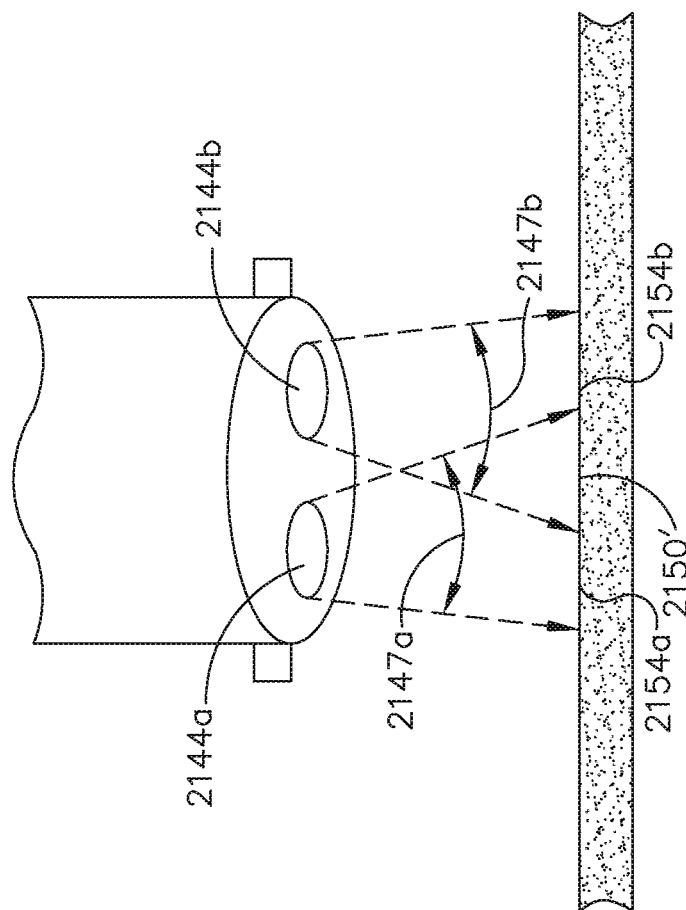
Figure 176D:
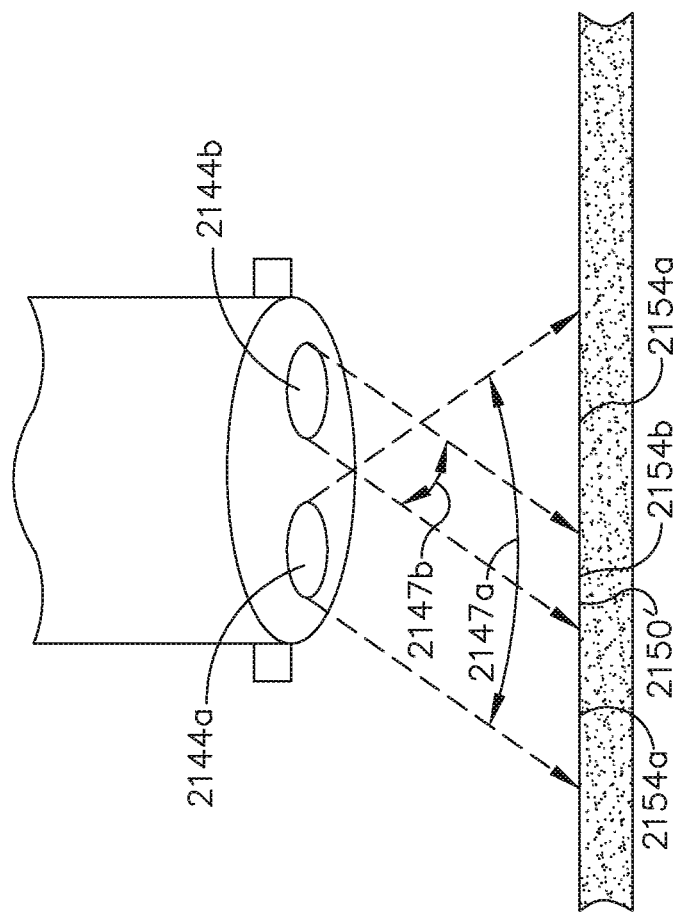
Figures 177A, 177B, 177C:
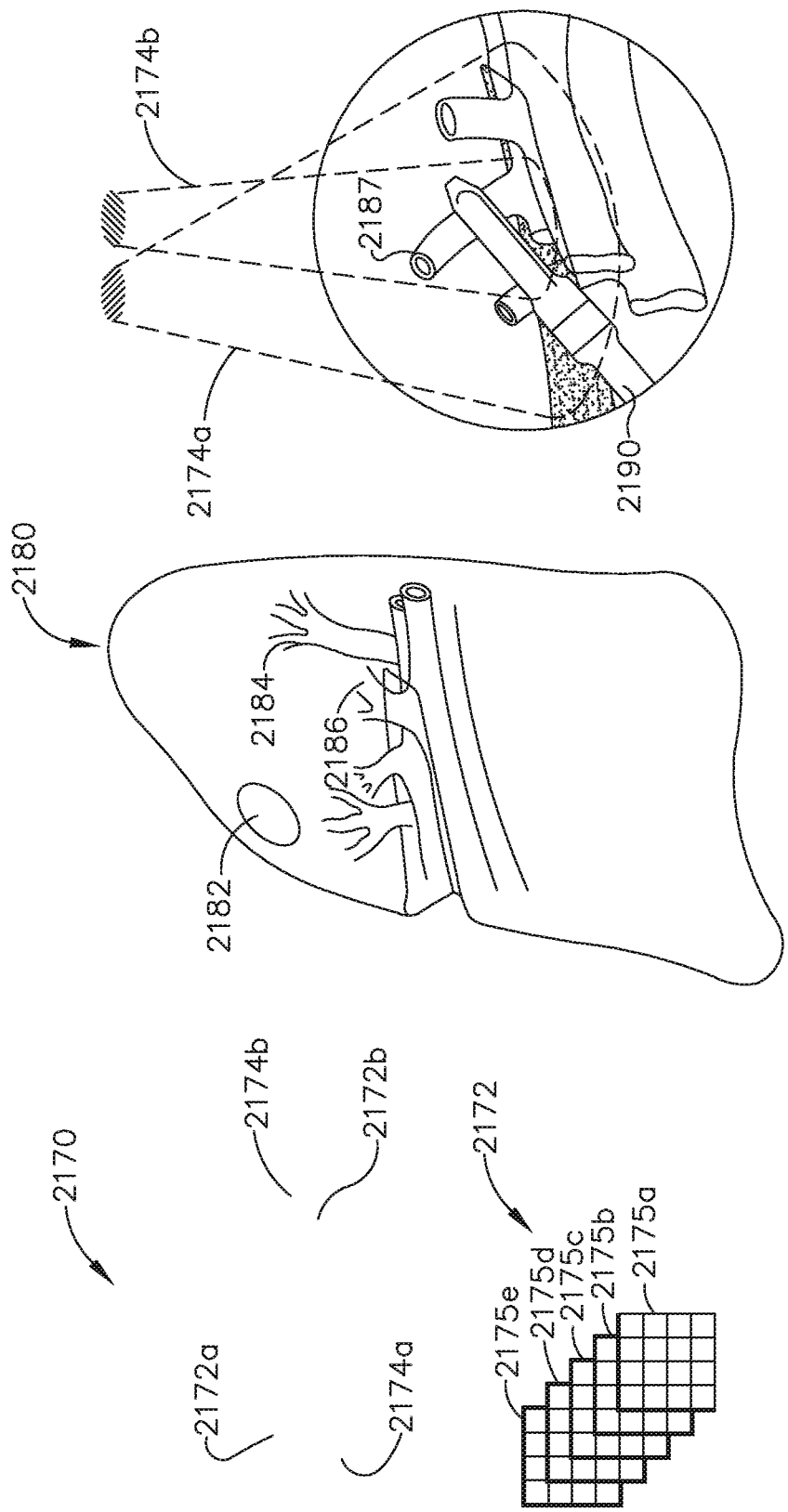
Figure 178B:
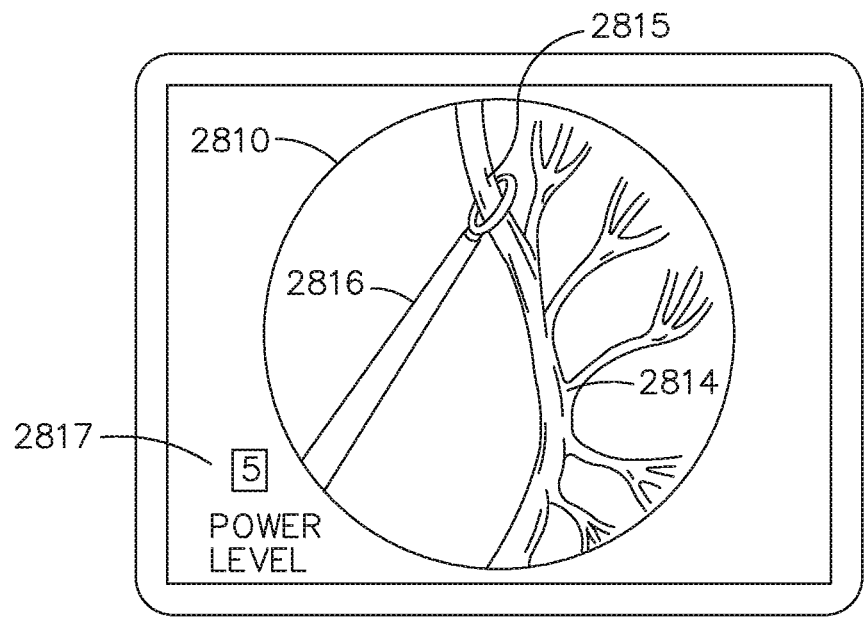
Figure 178A:
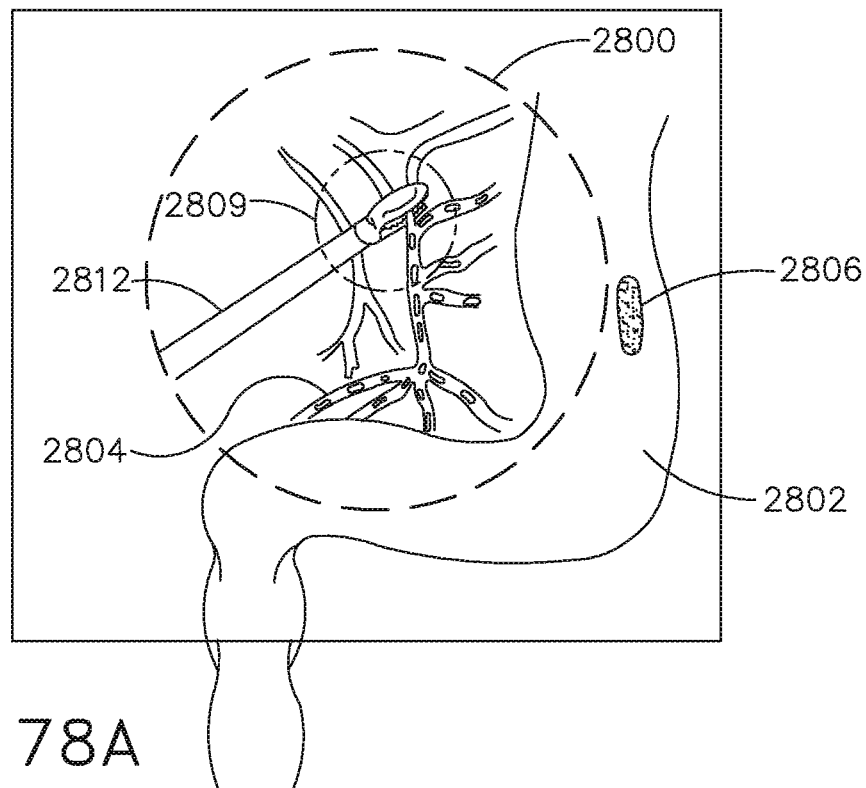
Figure 179A:
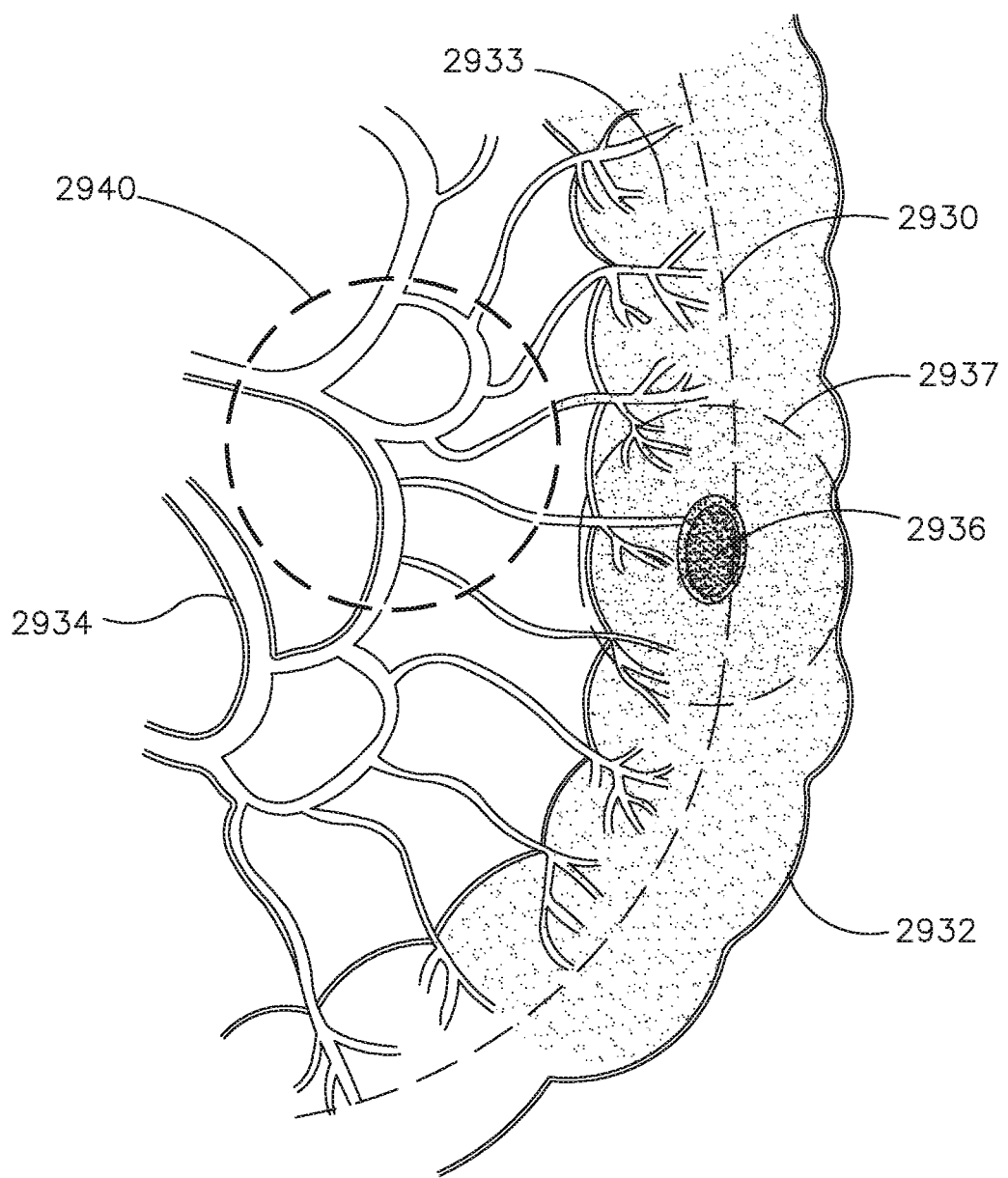
Figure 179B:
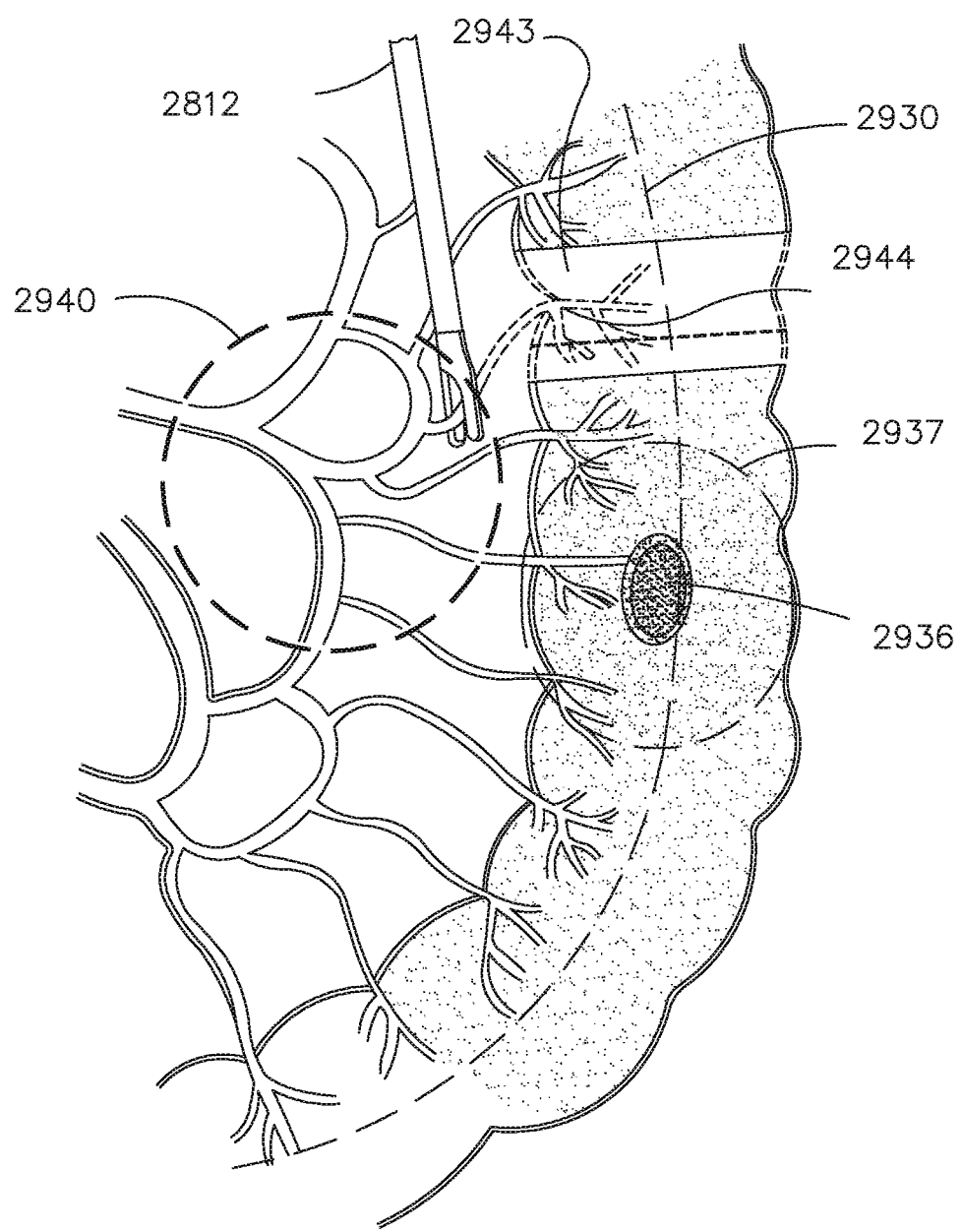
Figure 179C:
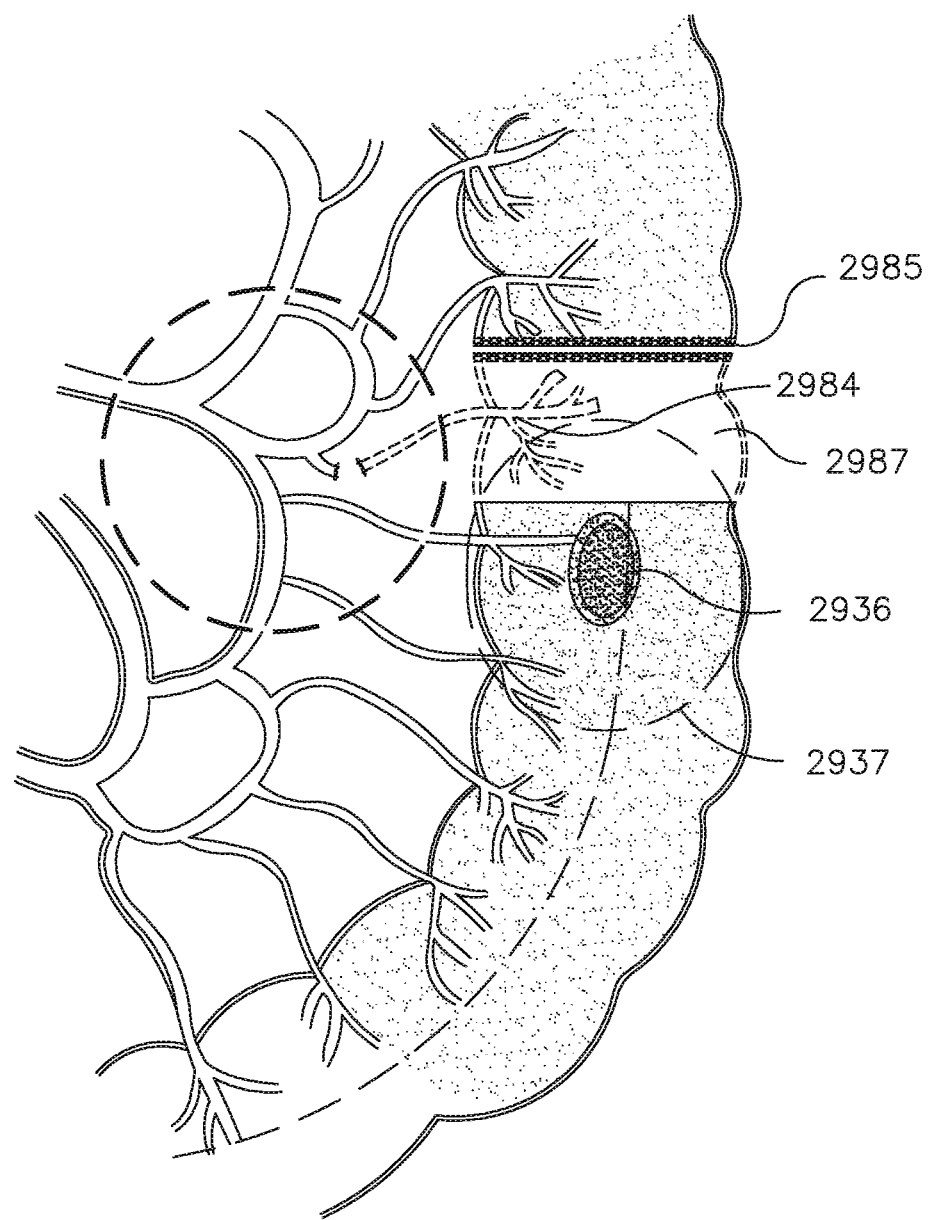
Figure 180:
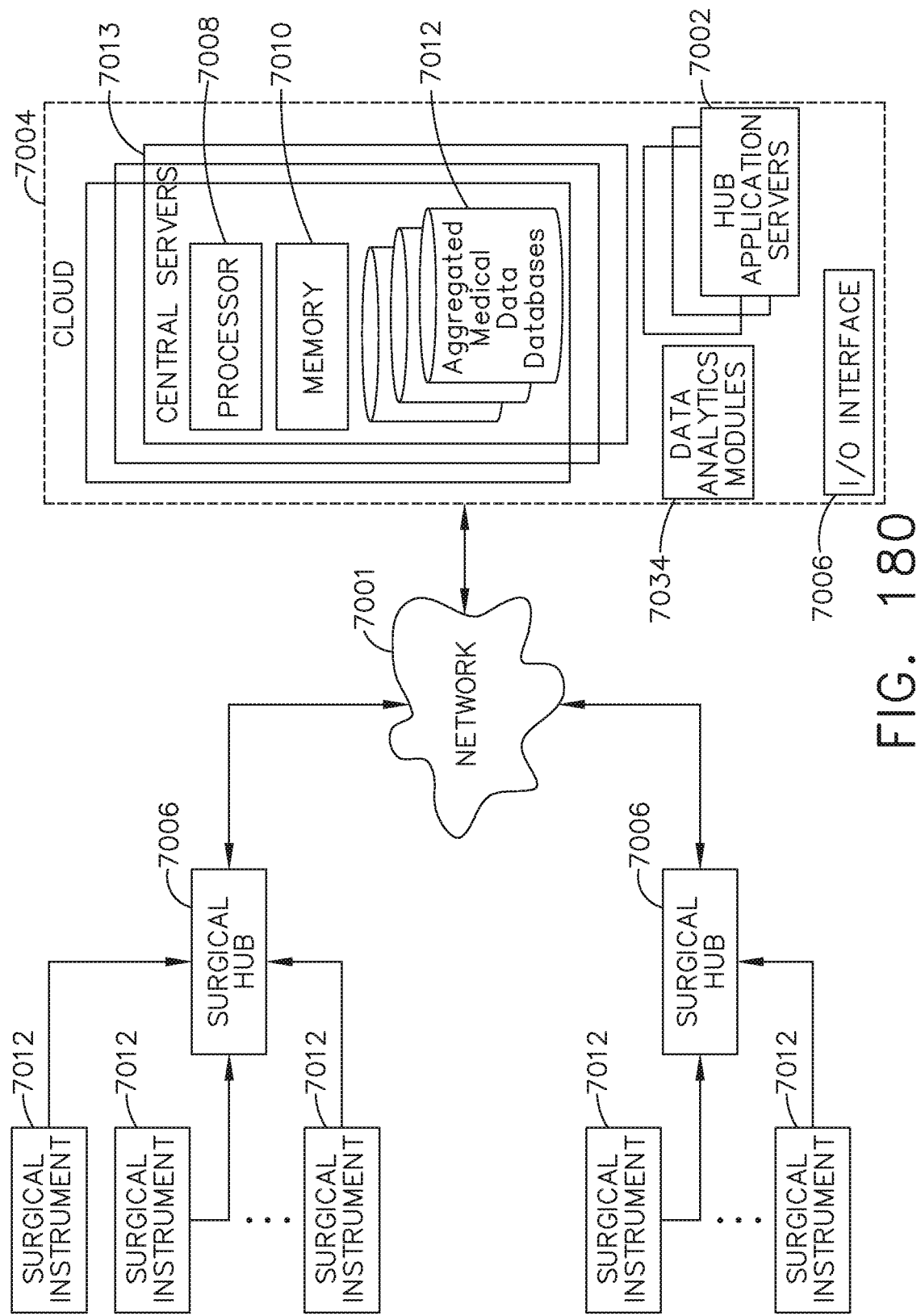
Figure 181:
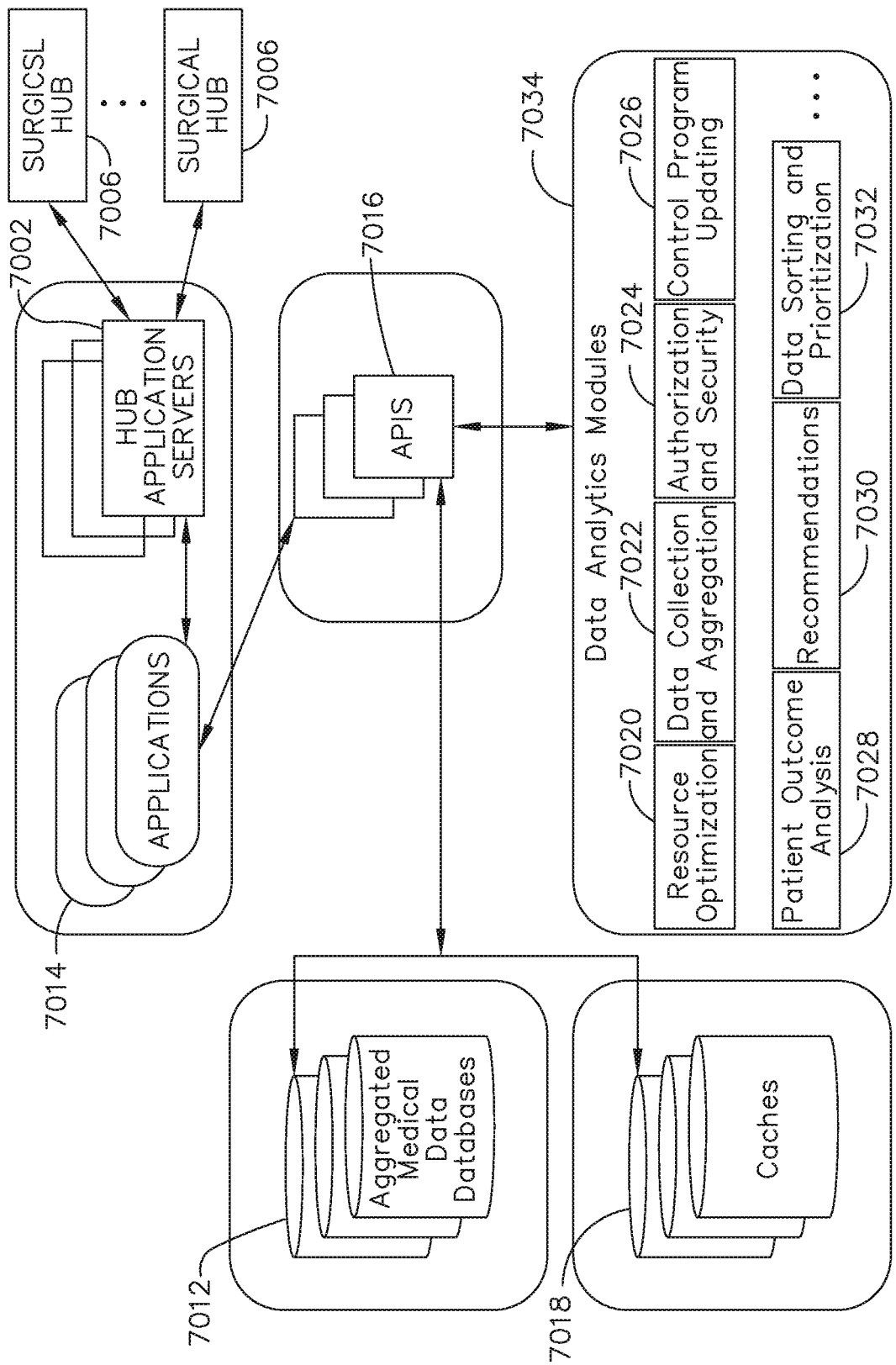
Figure 182:
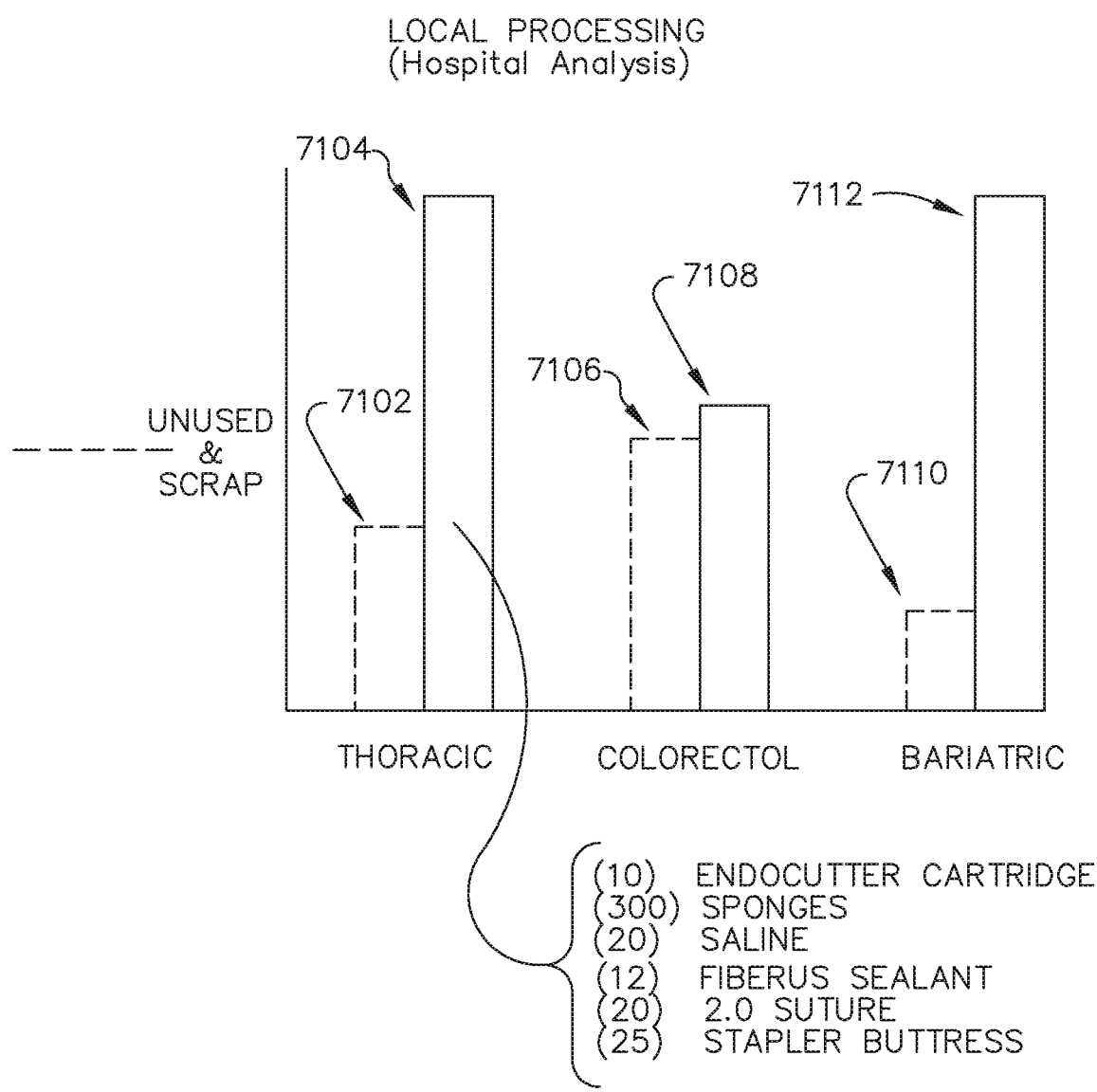
Figure 183:
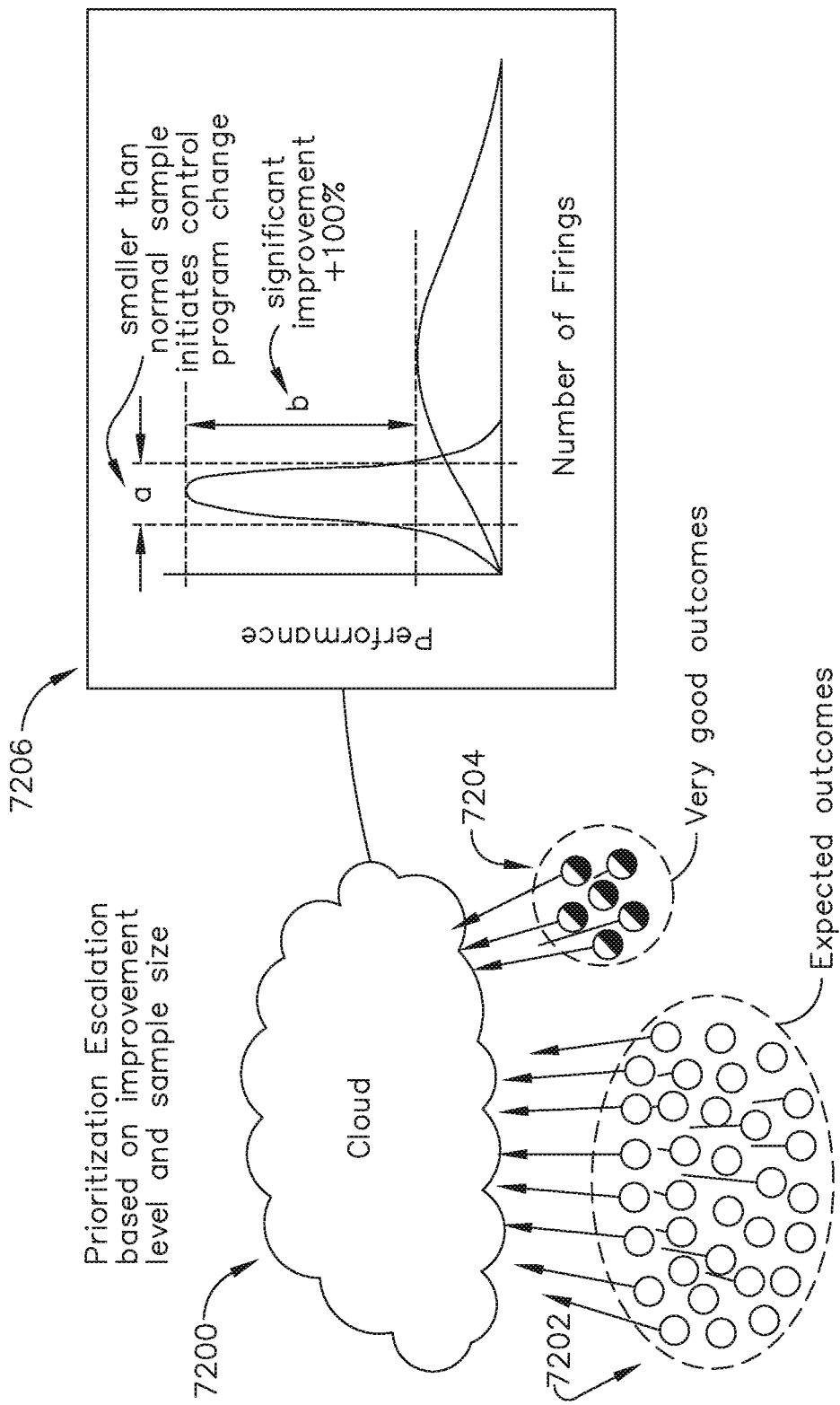
Figure 184:
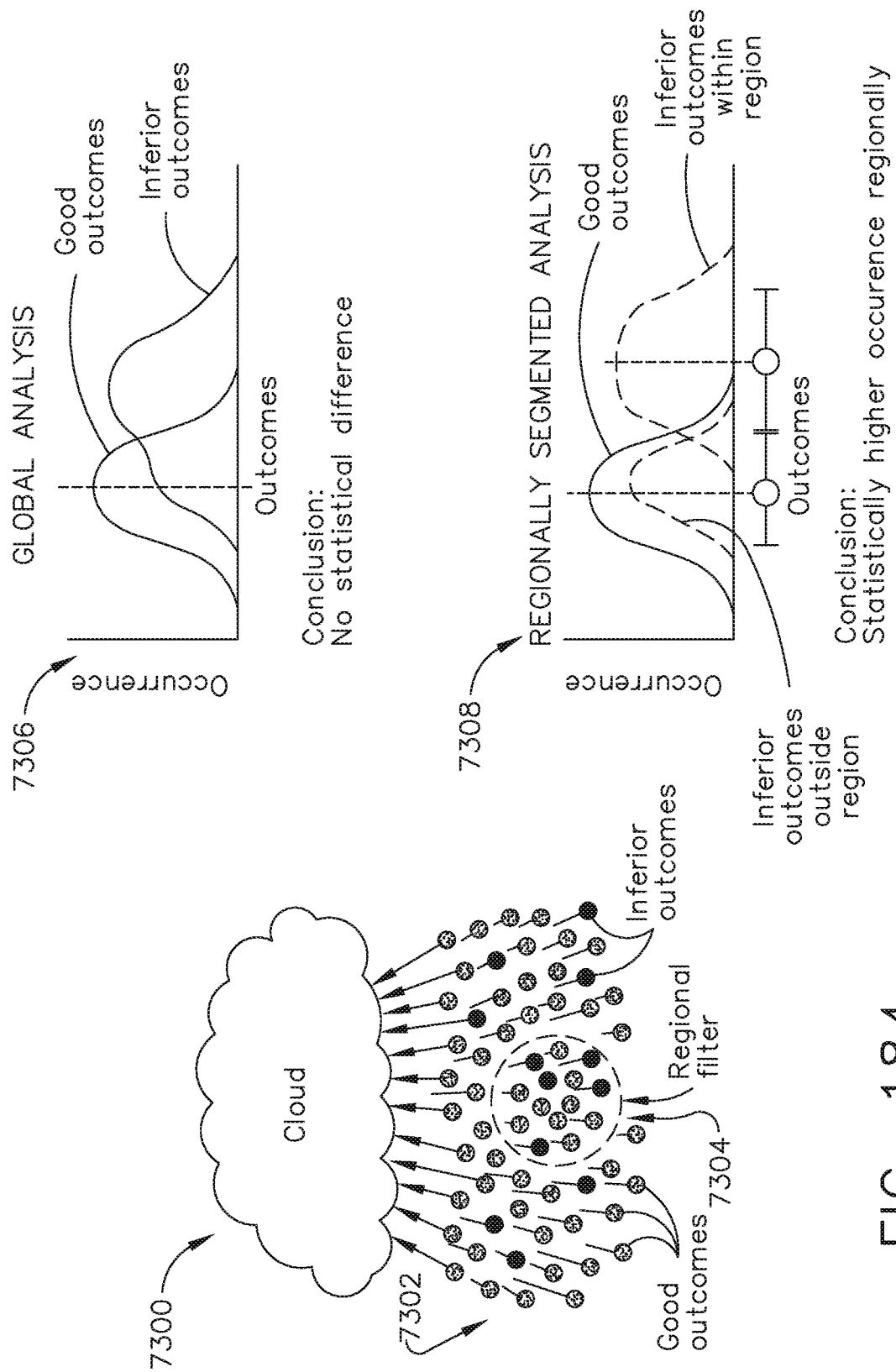
Figure 185:
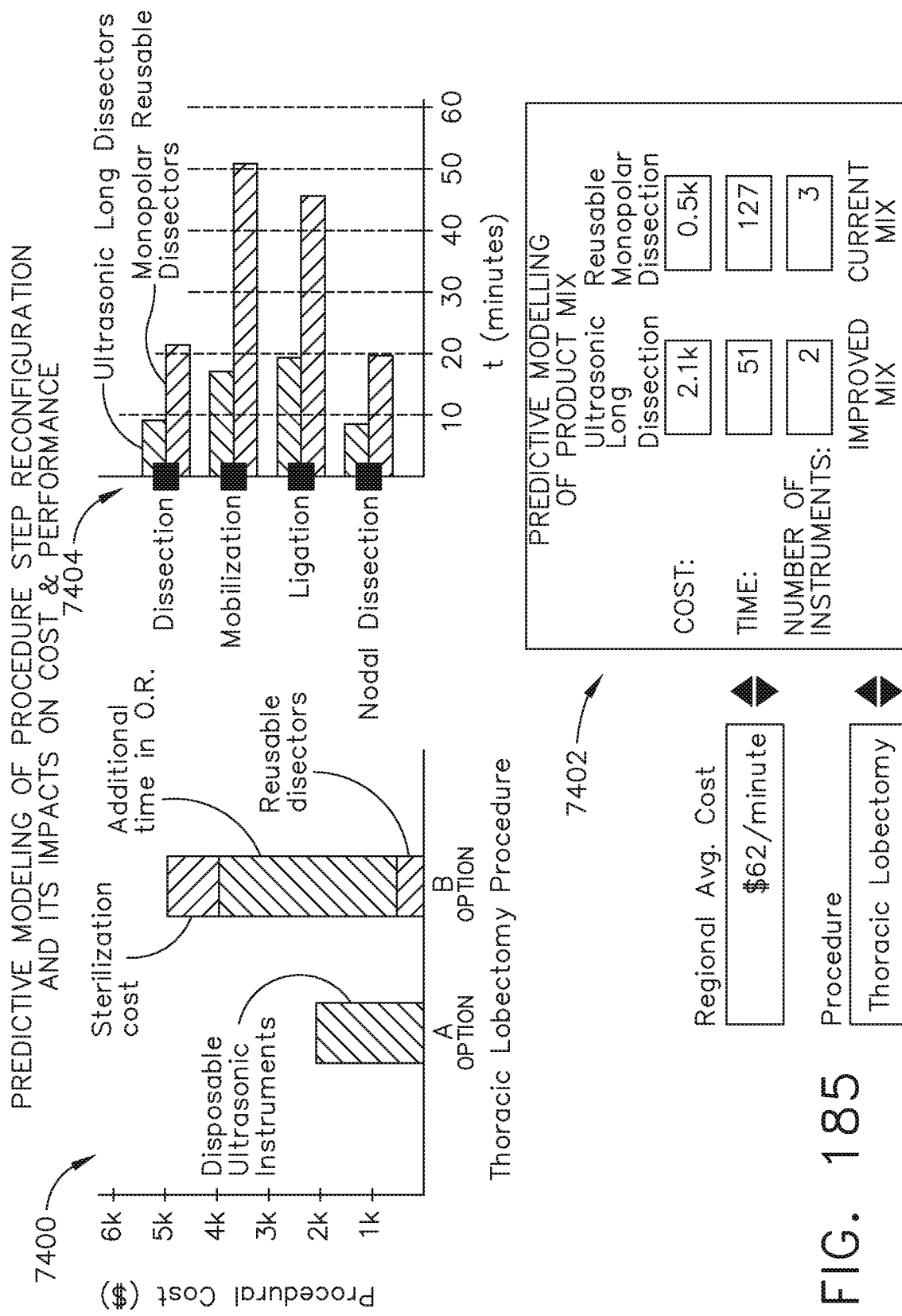
Figure 186:
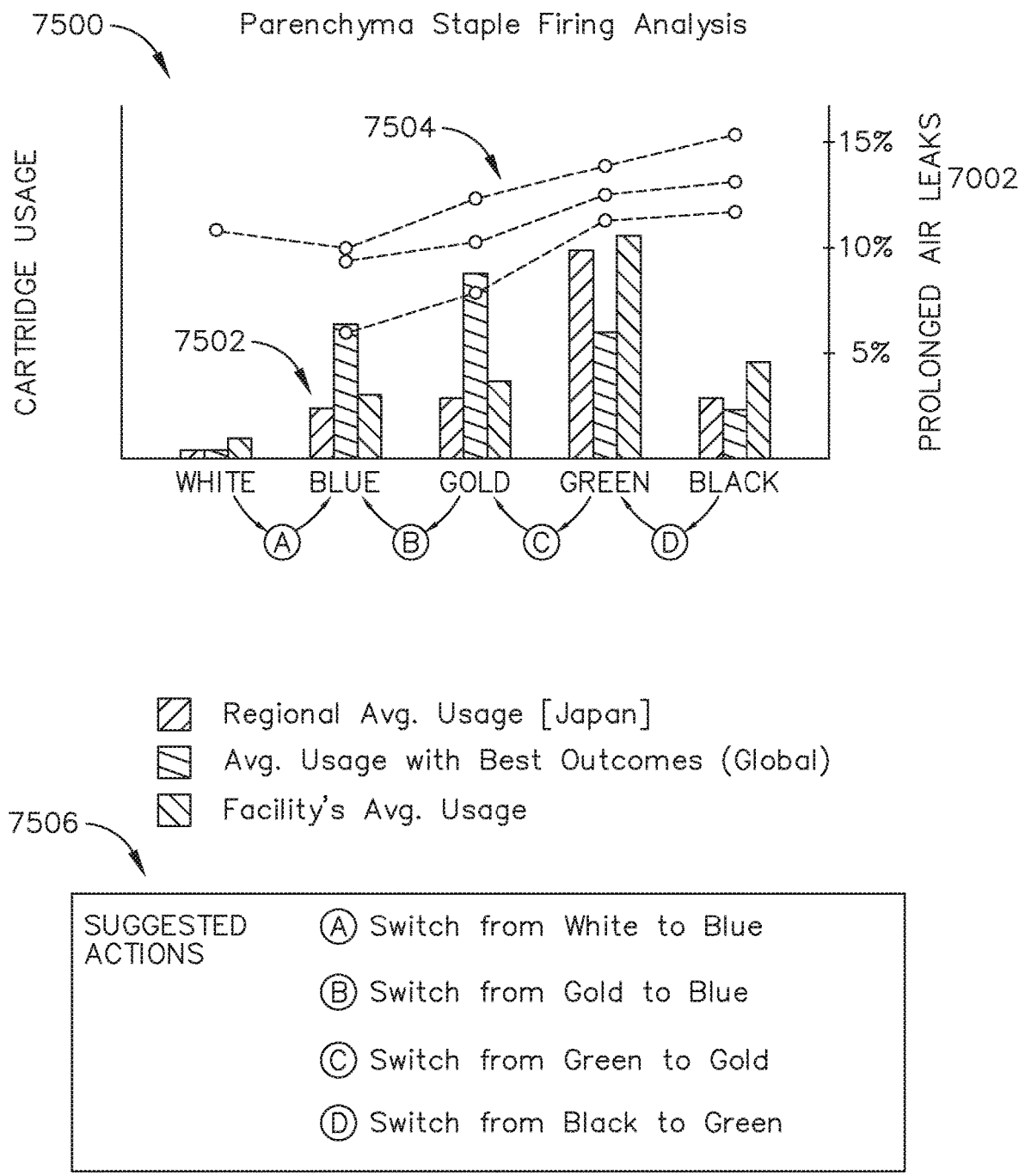
Figure 187:
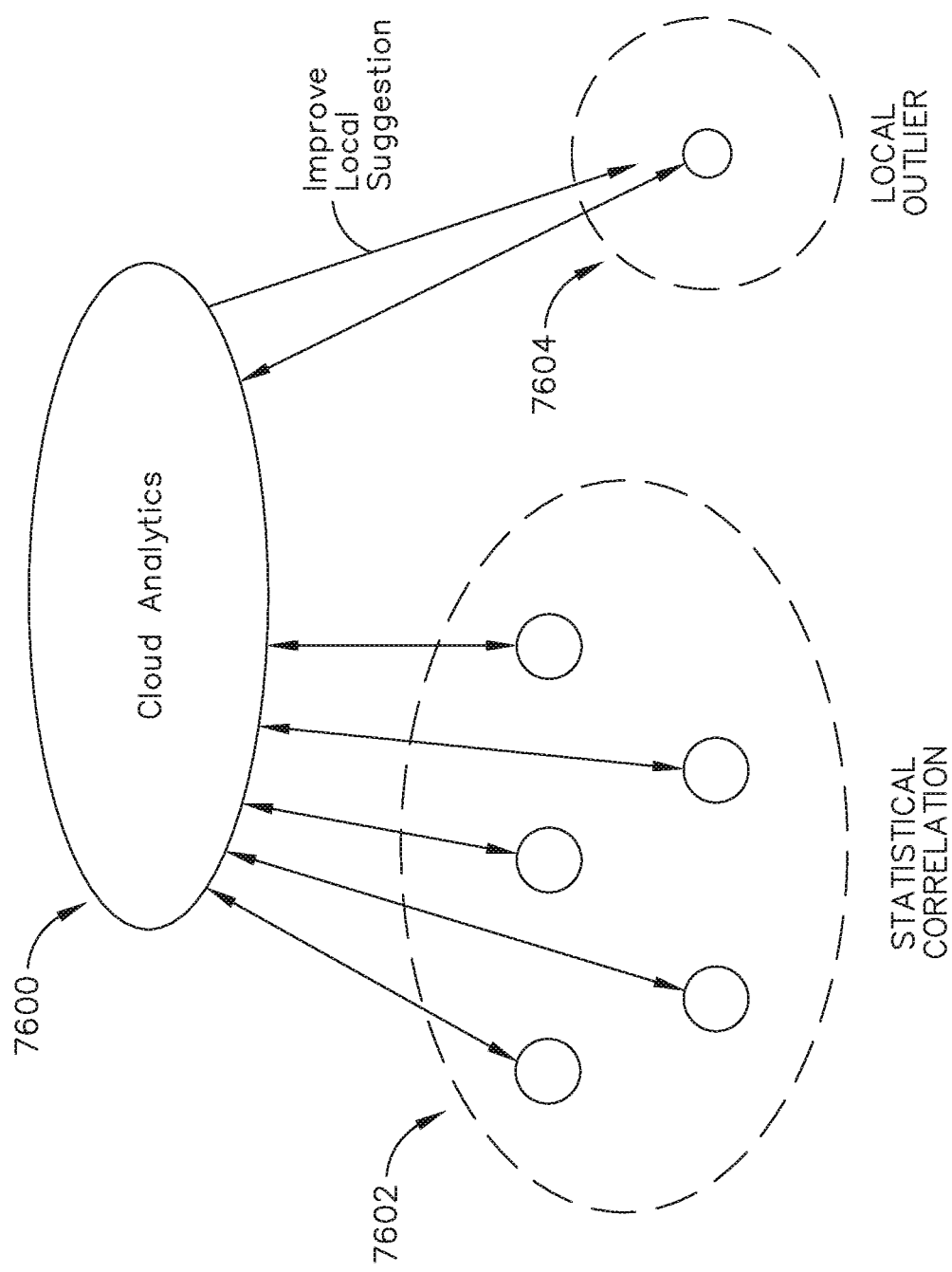
Figure 188:
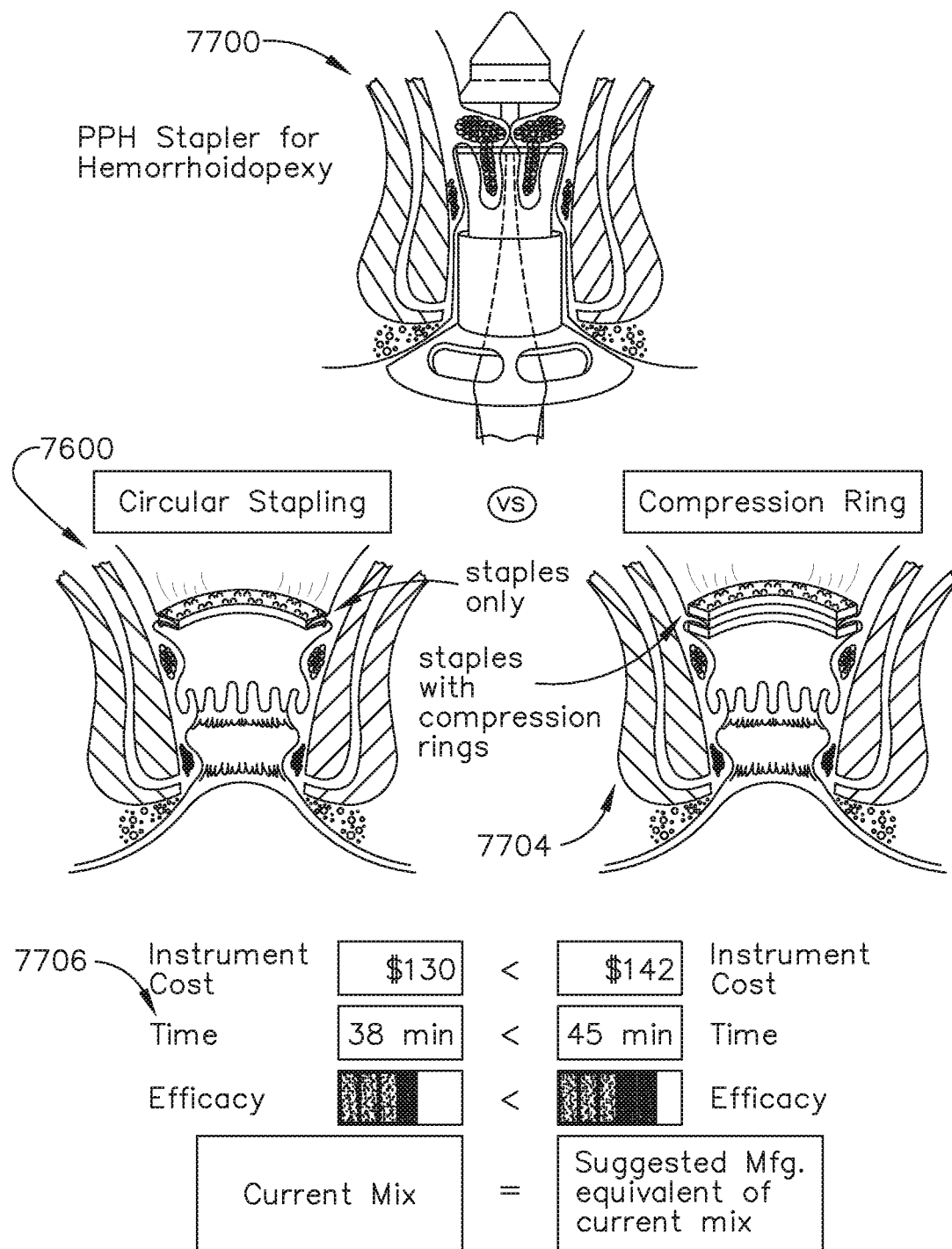
Figure 189:
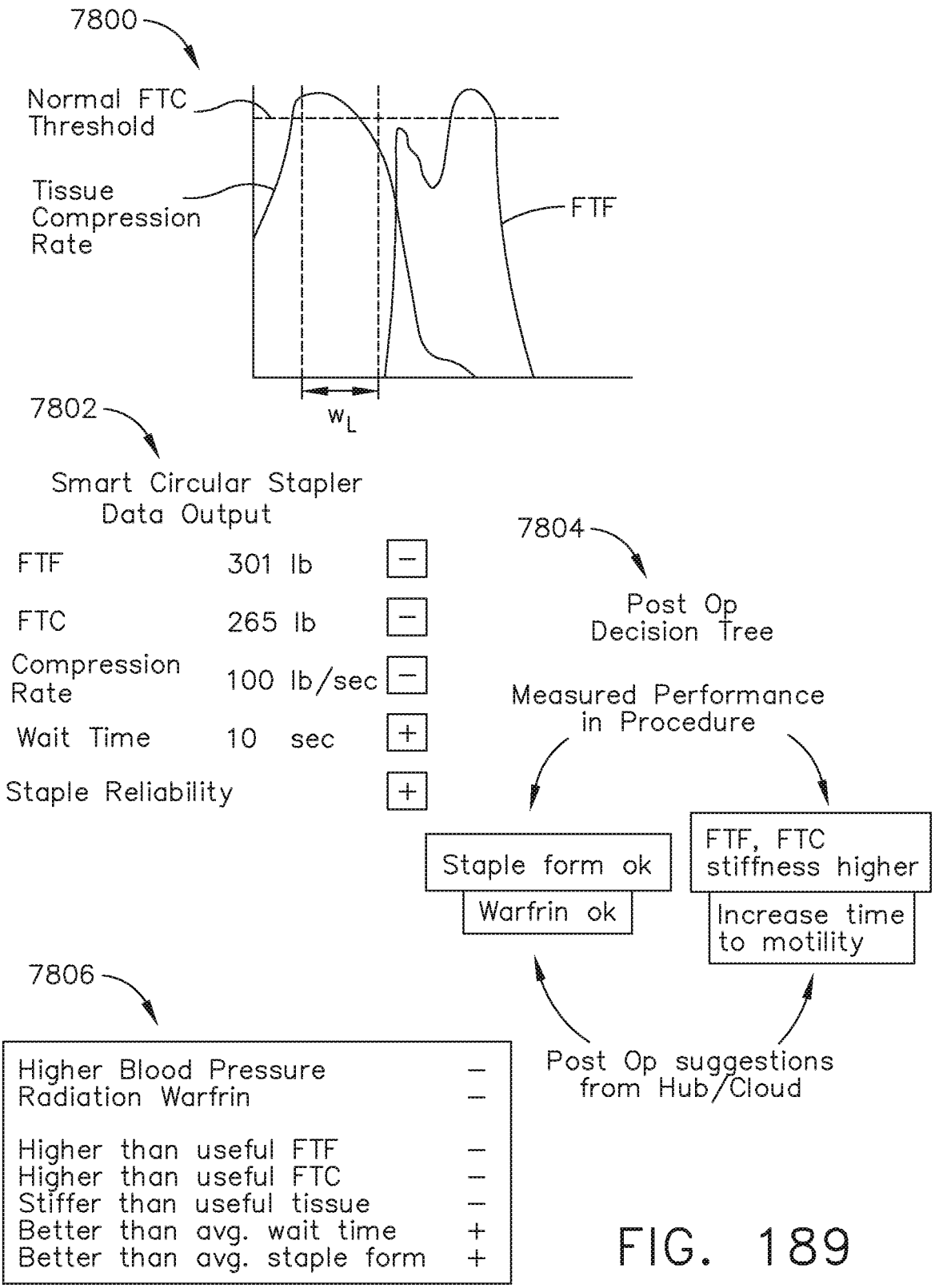
Figure 190:
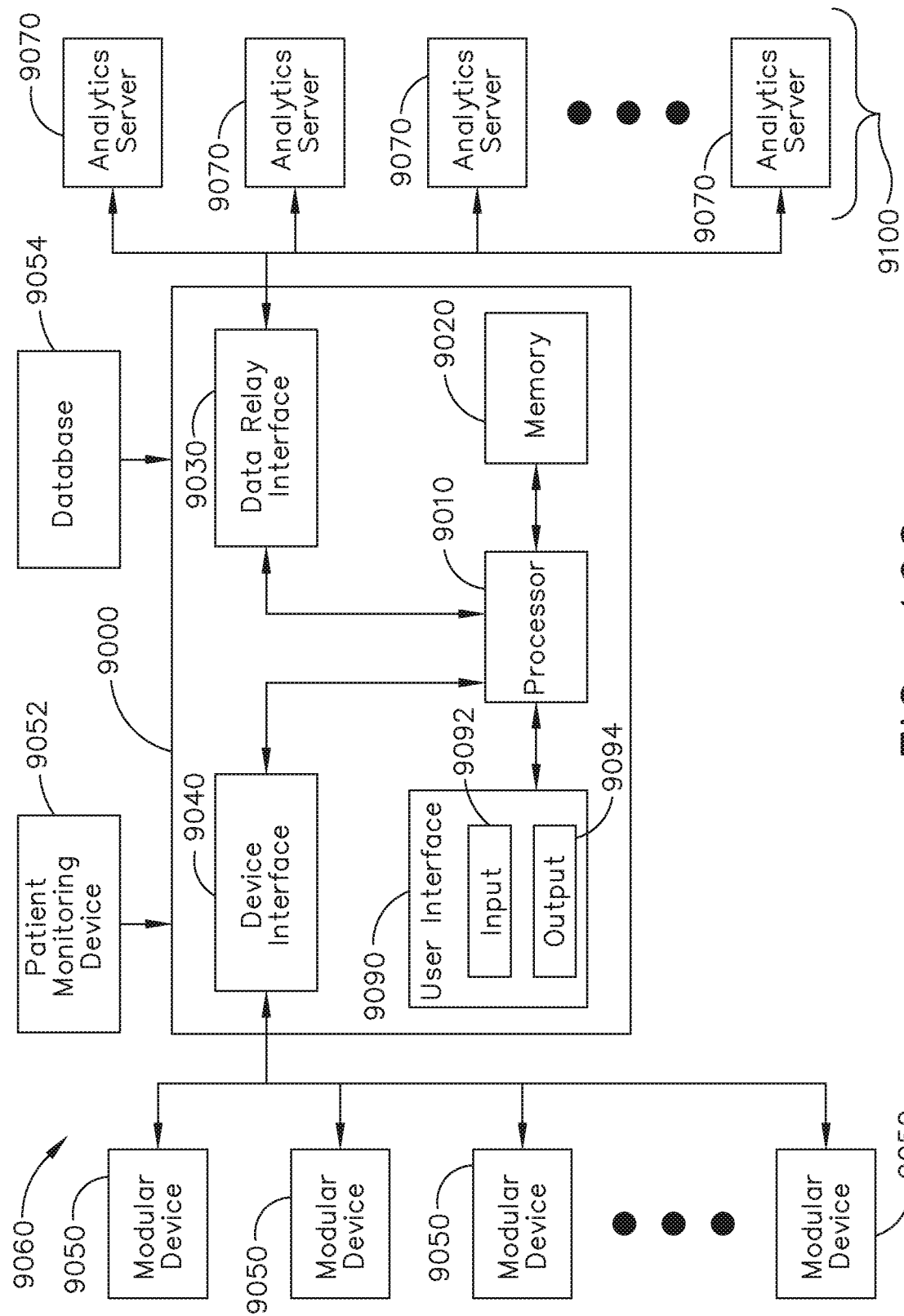
Figure 191:
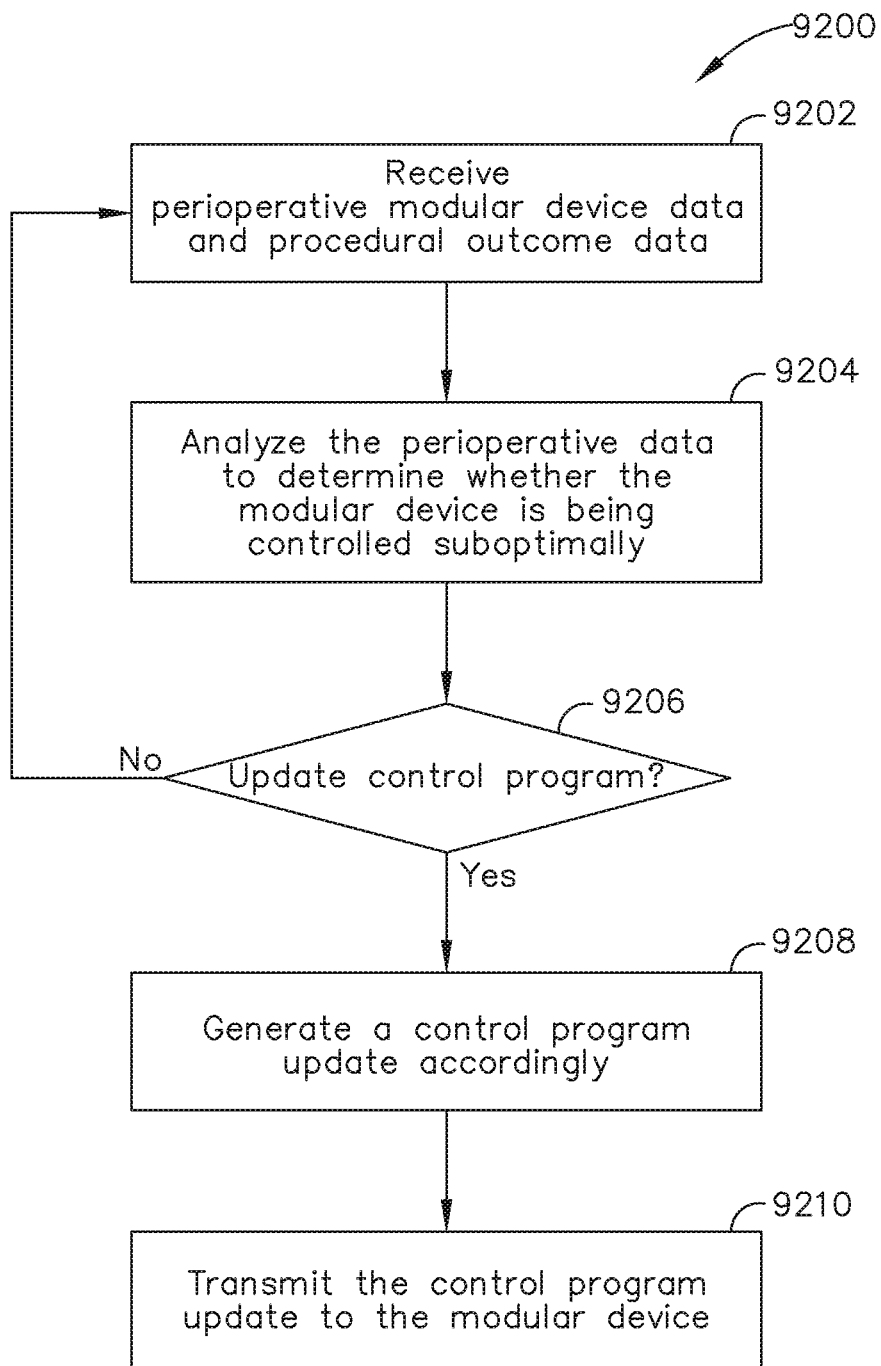
Figure 192:
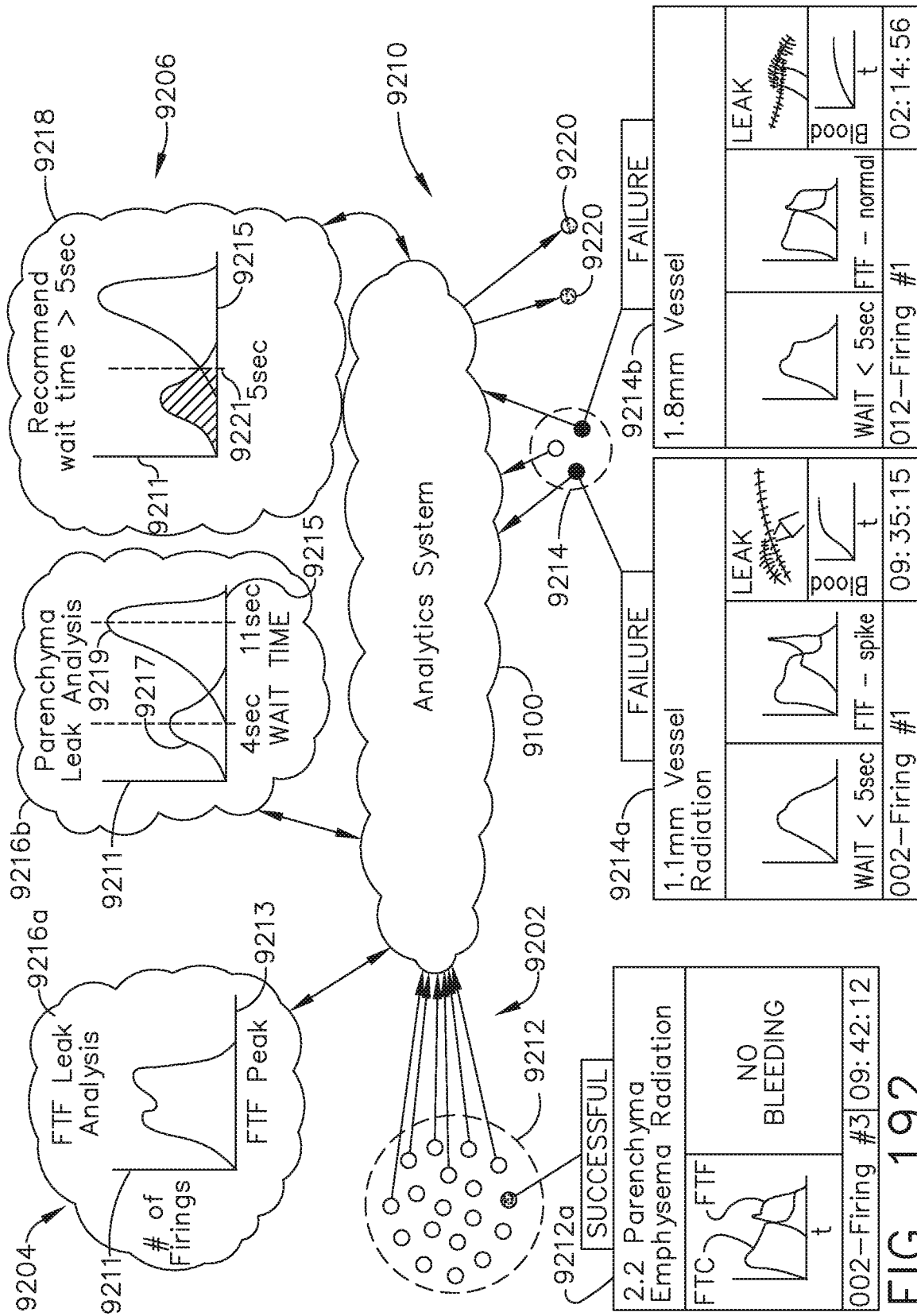
Figure 193:
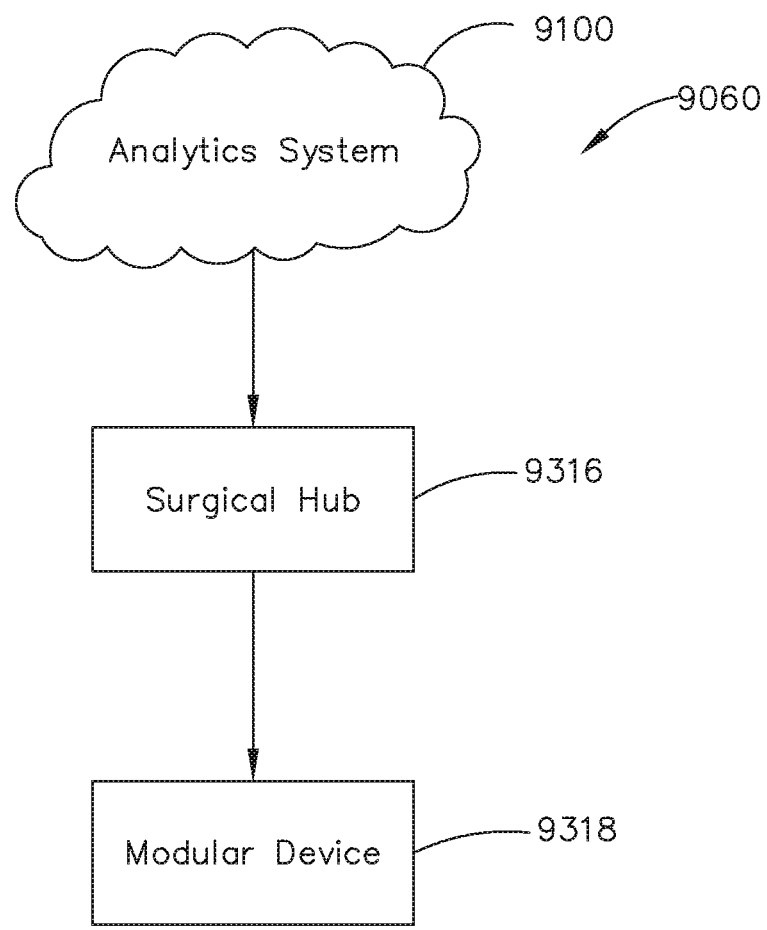
Figure 194:
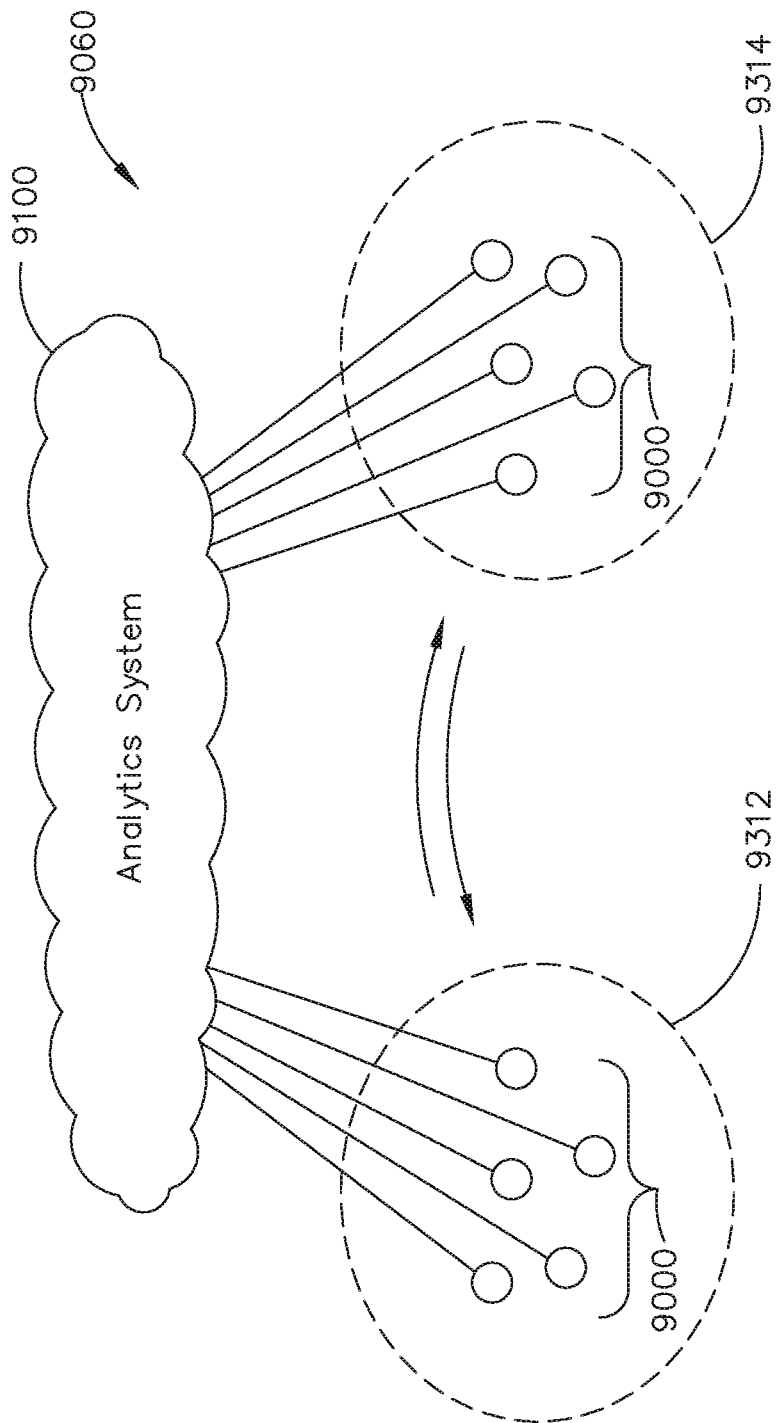
Figure 195:
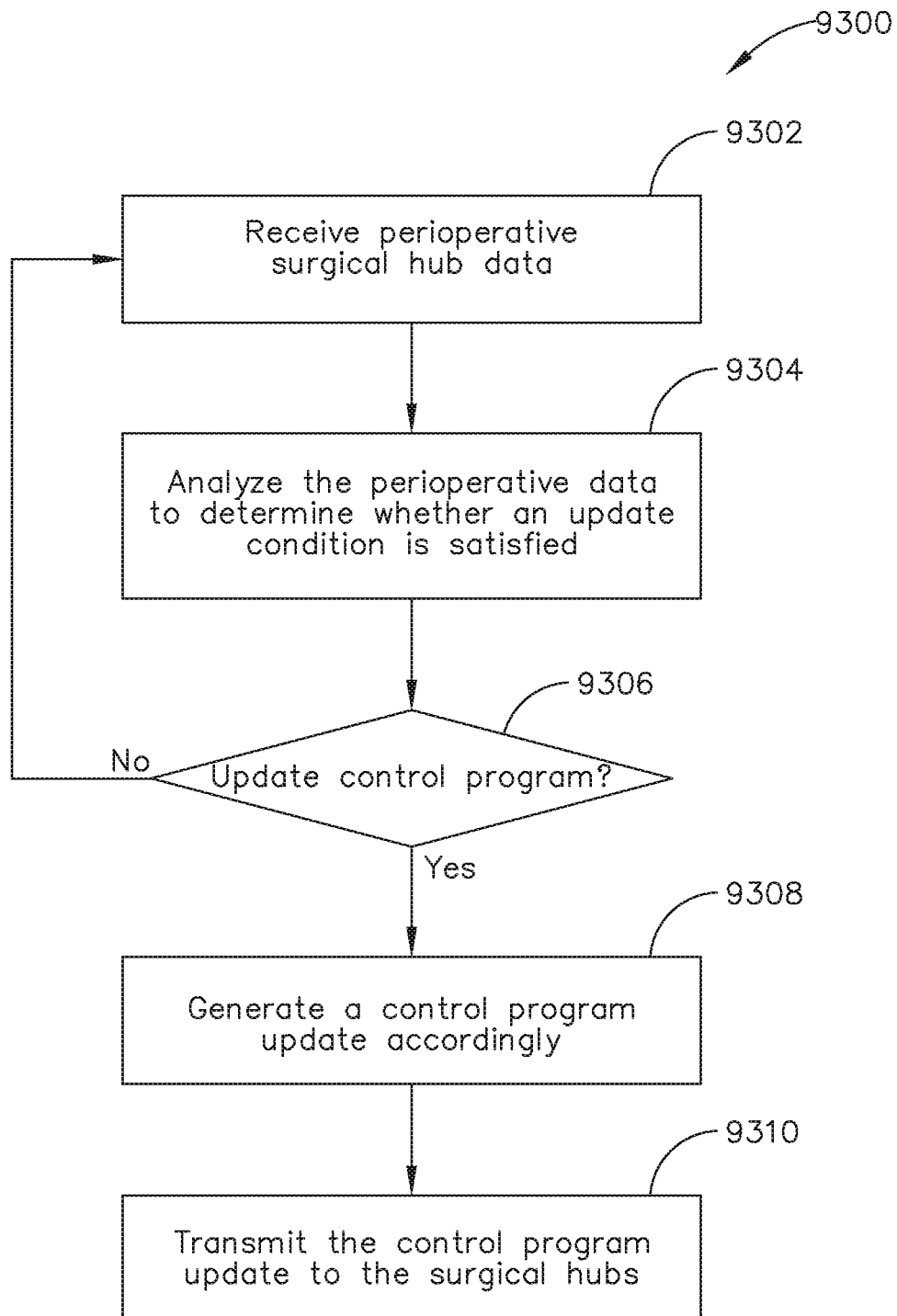
Figure 196:
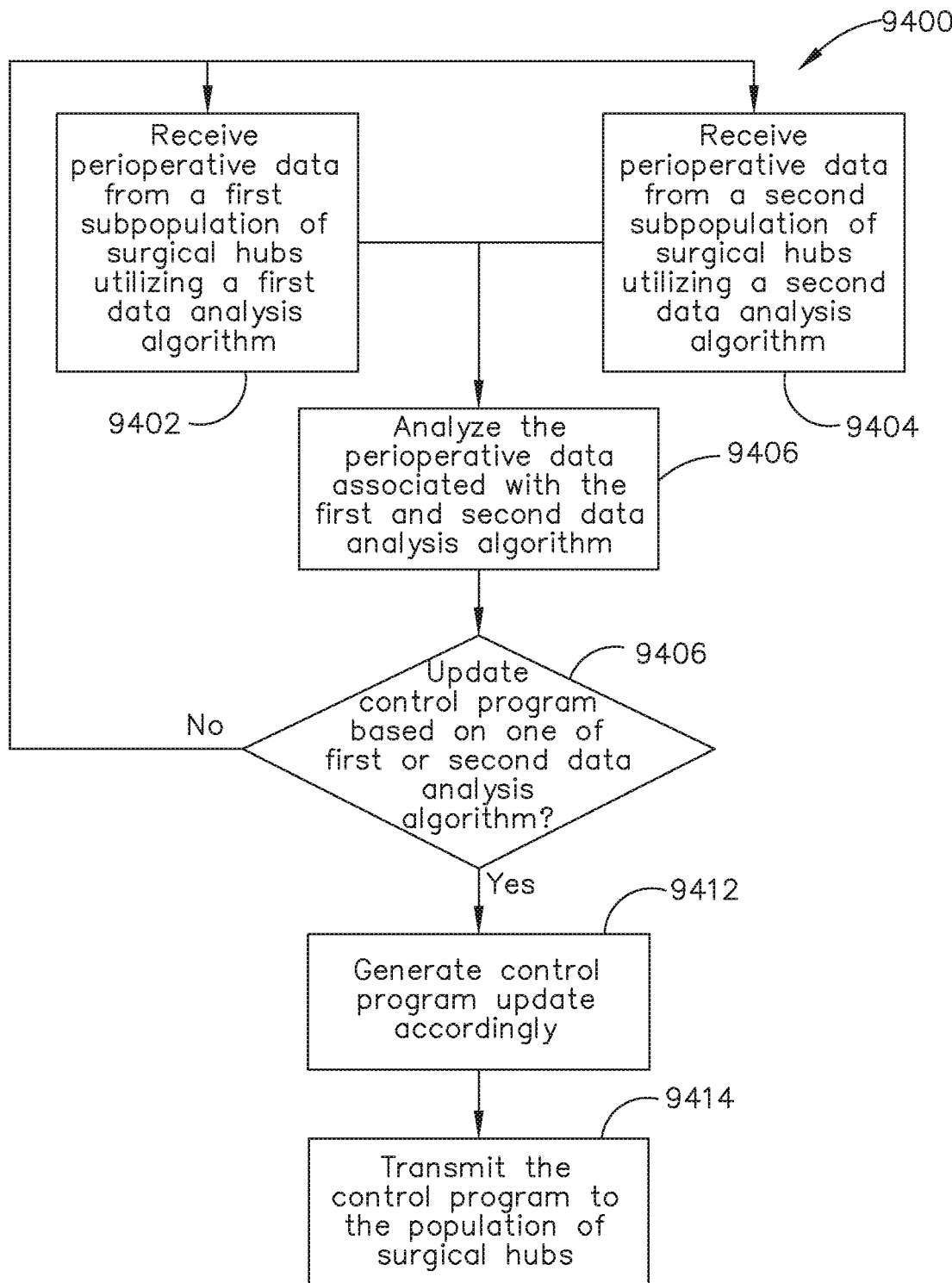
Figure 197:
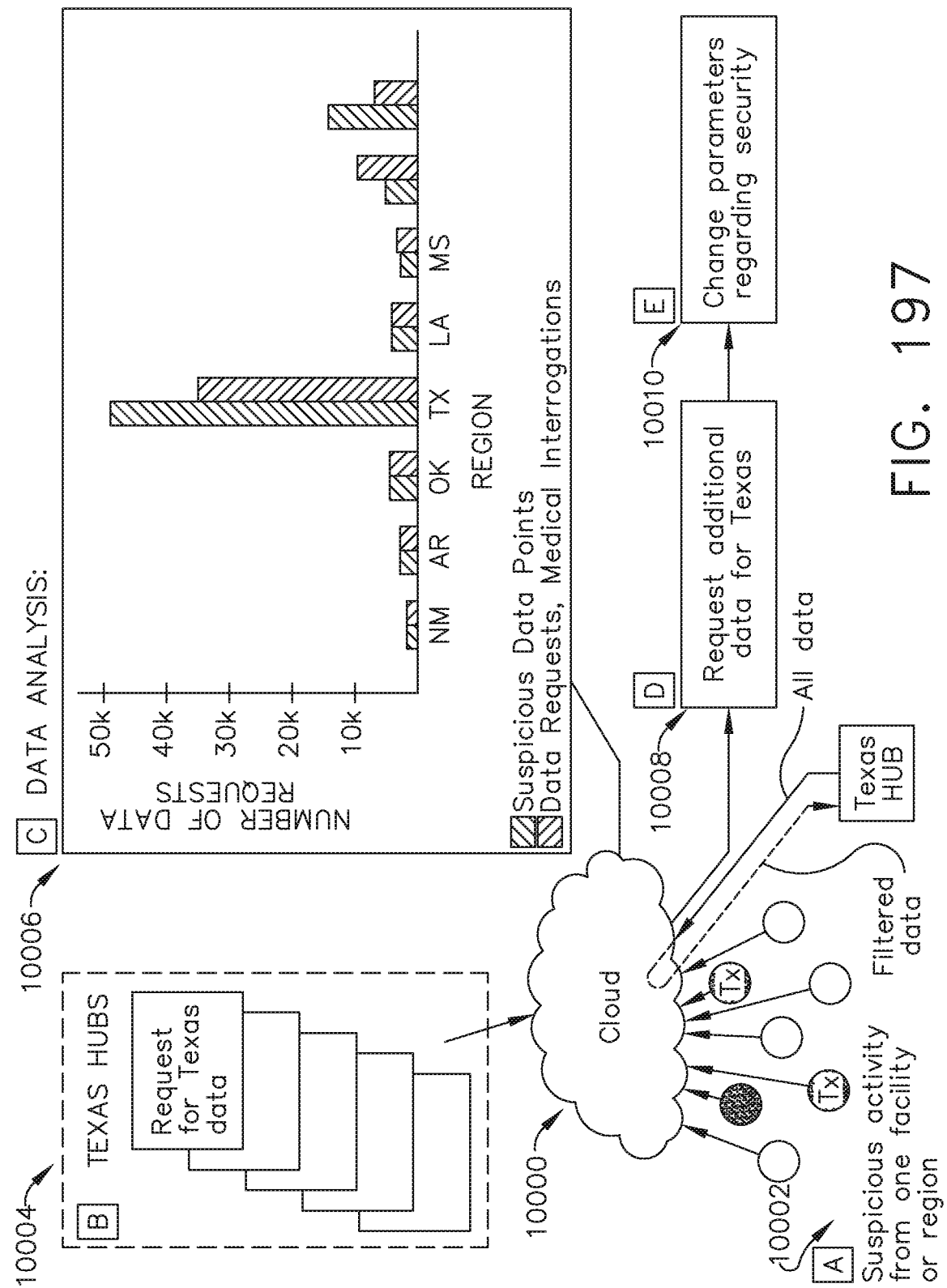
Figure 198:
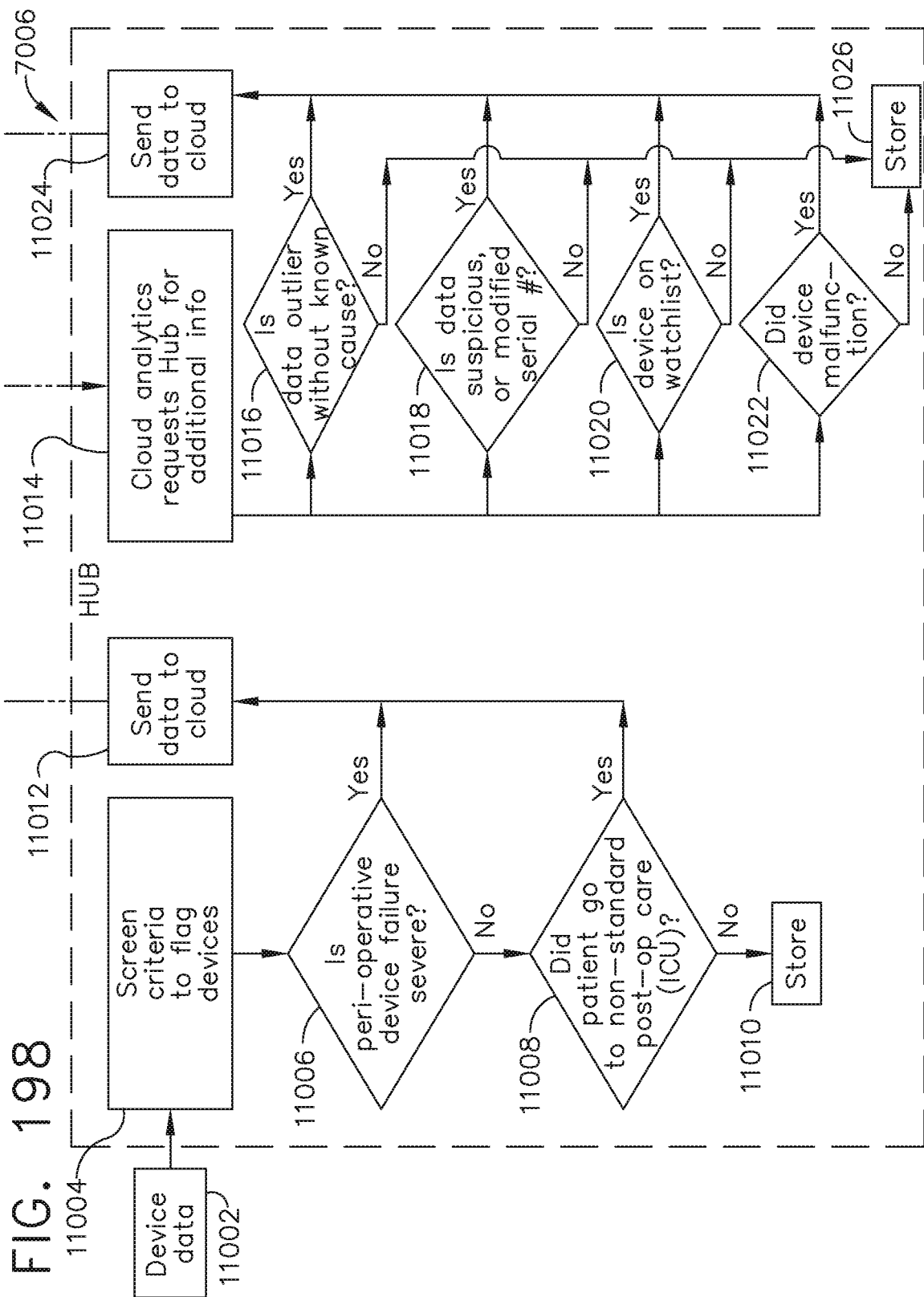
Figure 199:
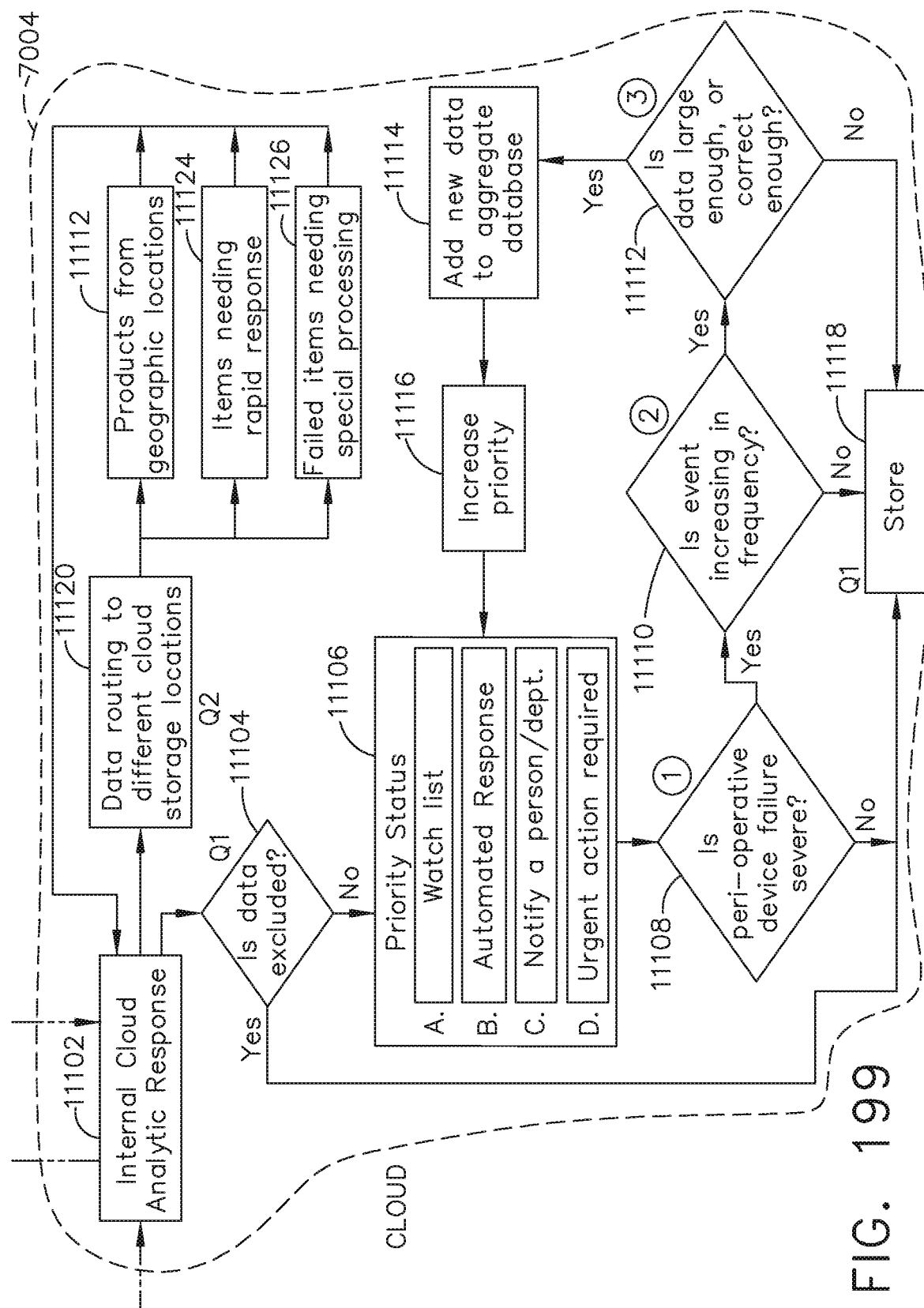
Figure 200:
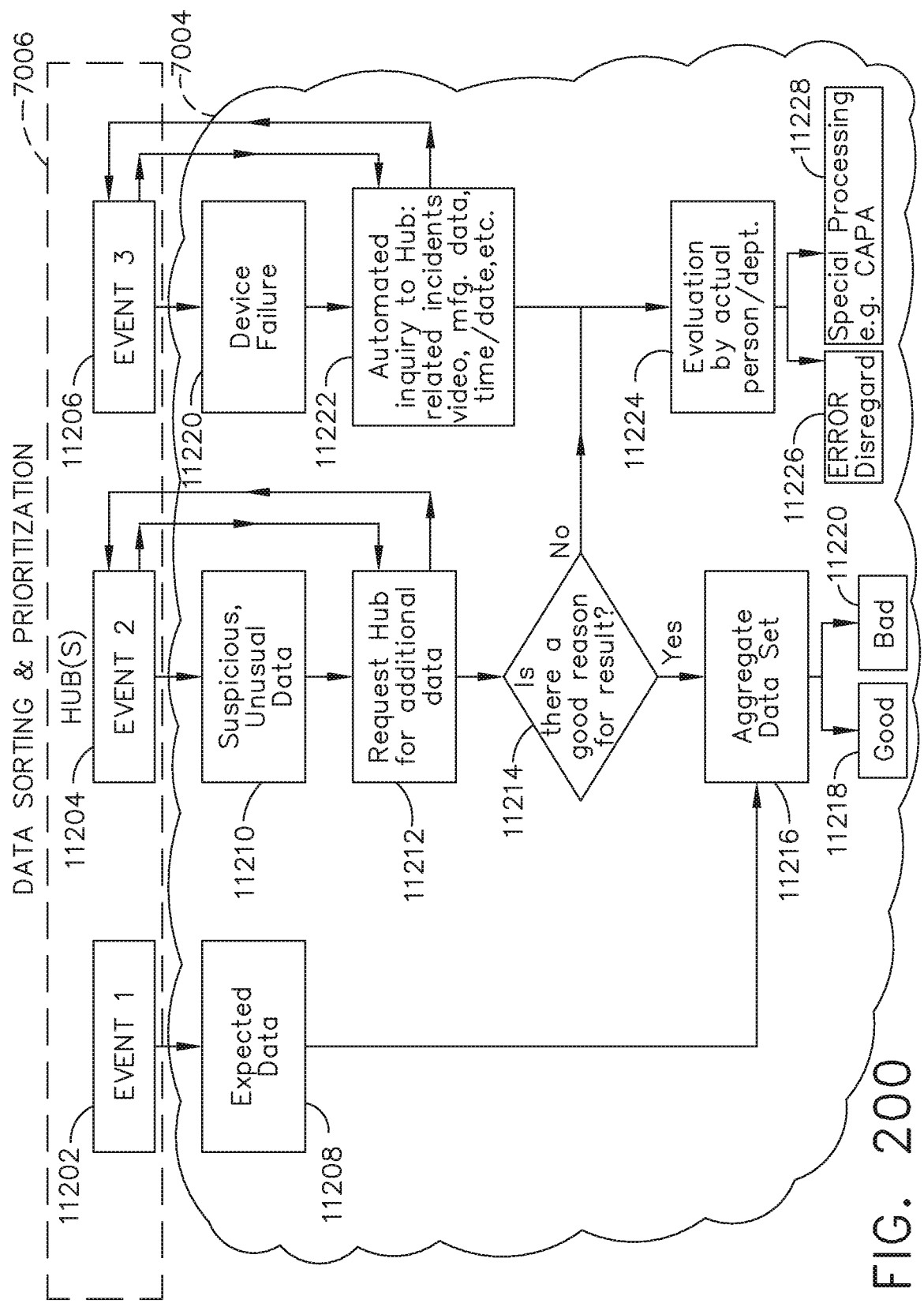
Figure 201:
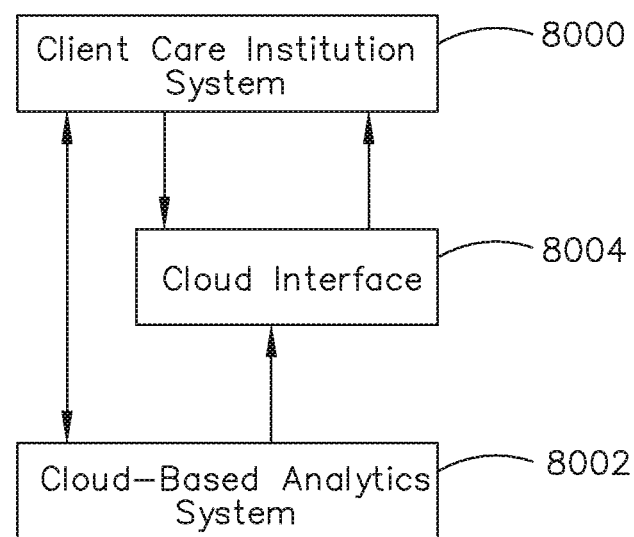
Figures 202, 203:
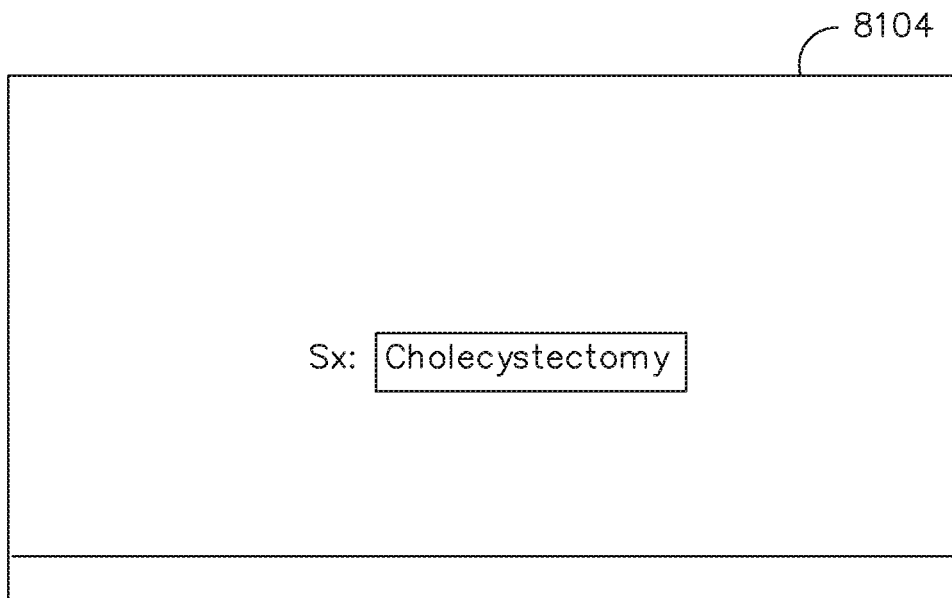
Figure 204:
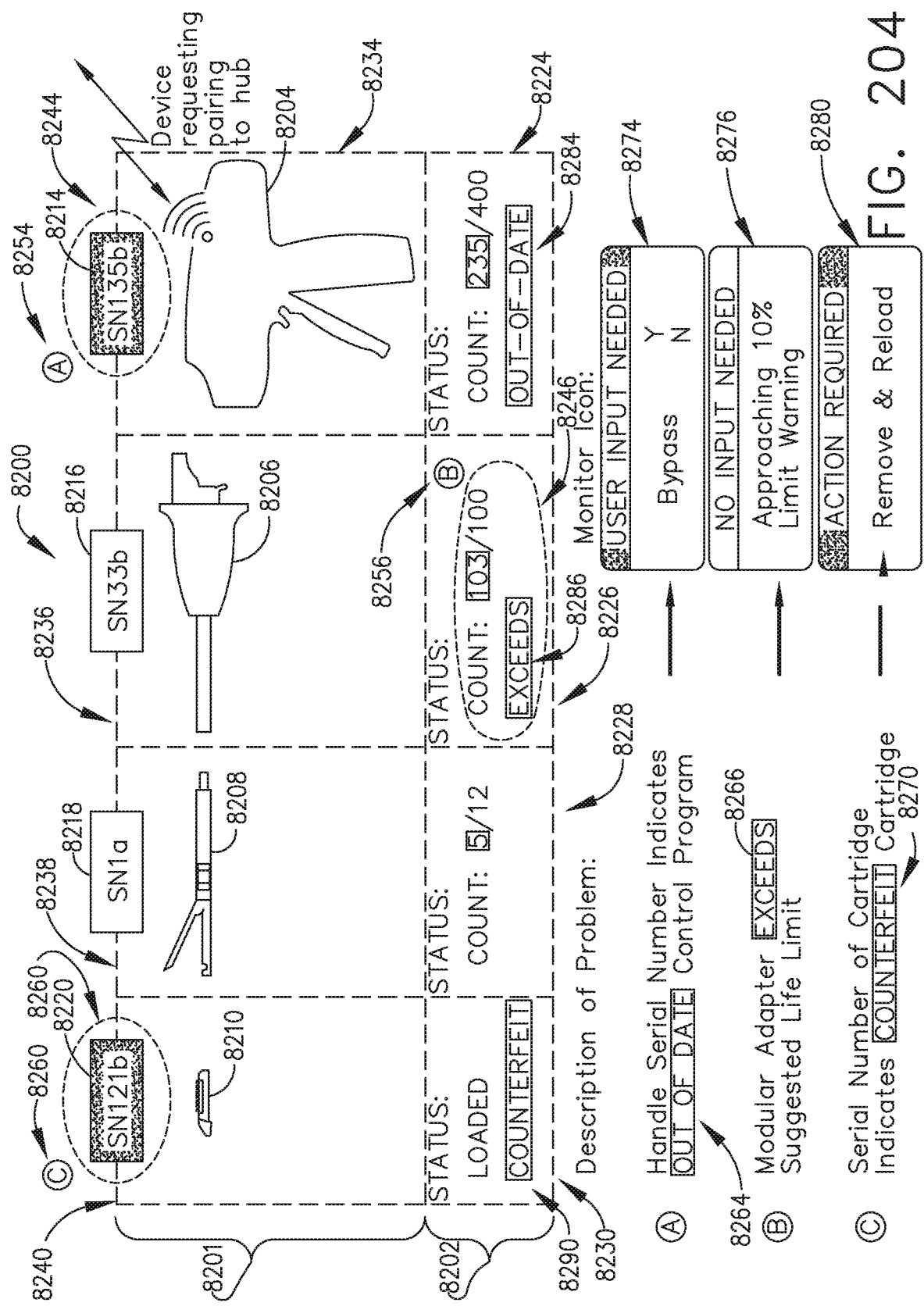
Figure 205:
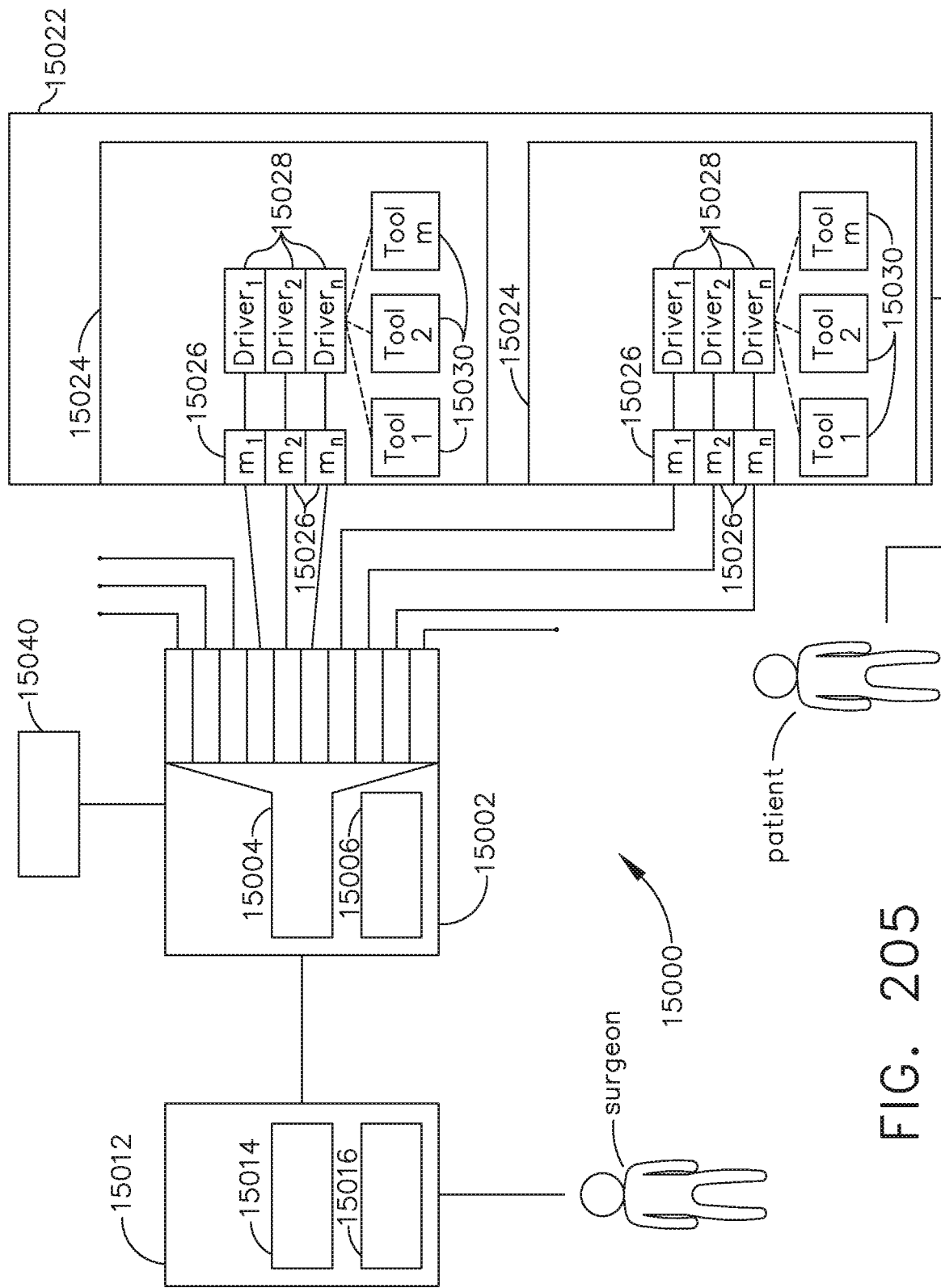
Figure 206:
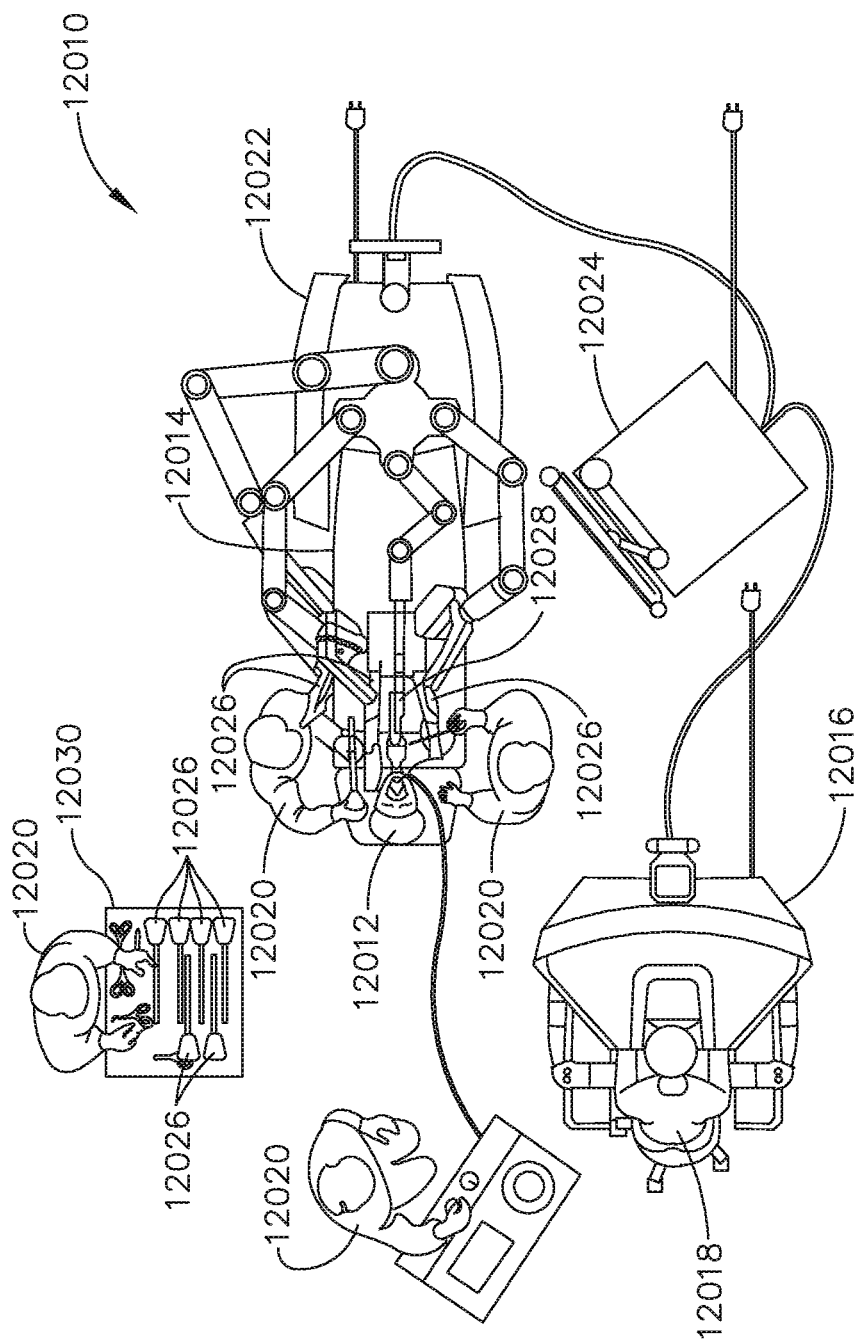
Figure 207:
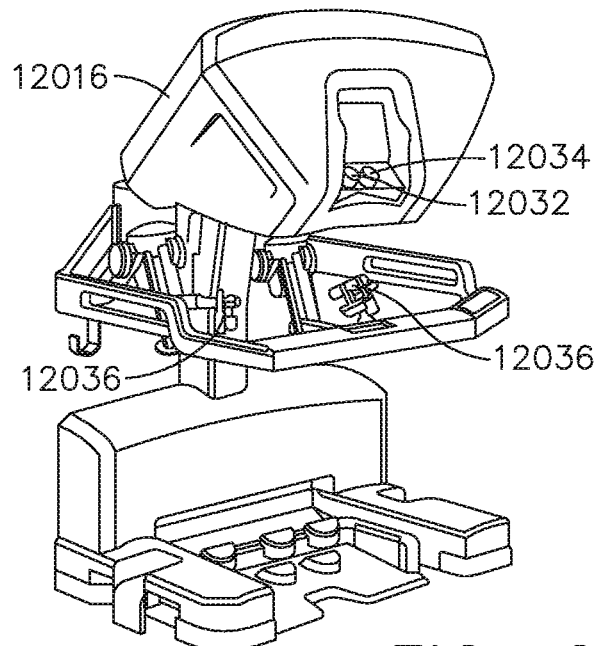
Figure 208:
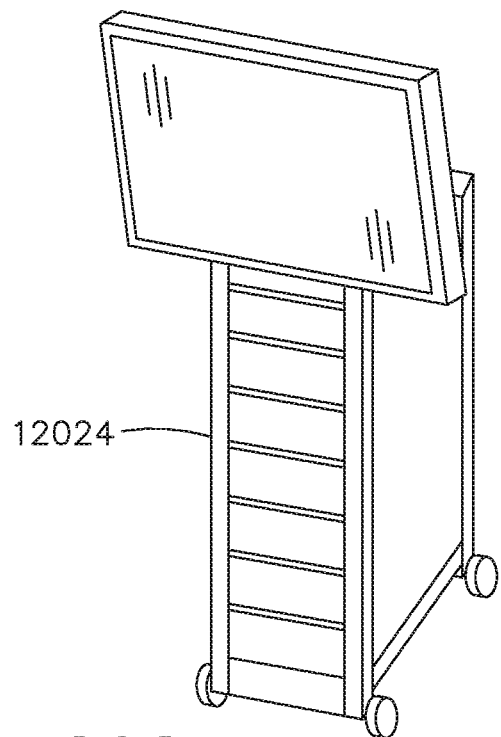
Figure 209:
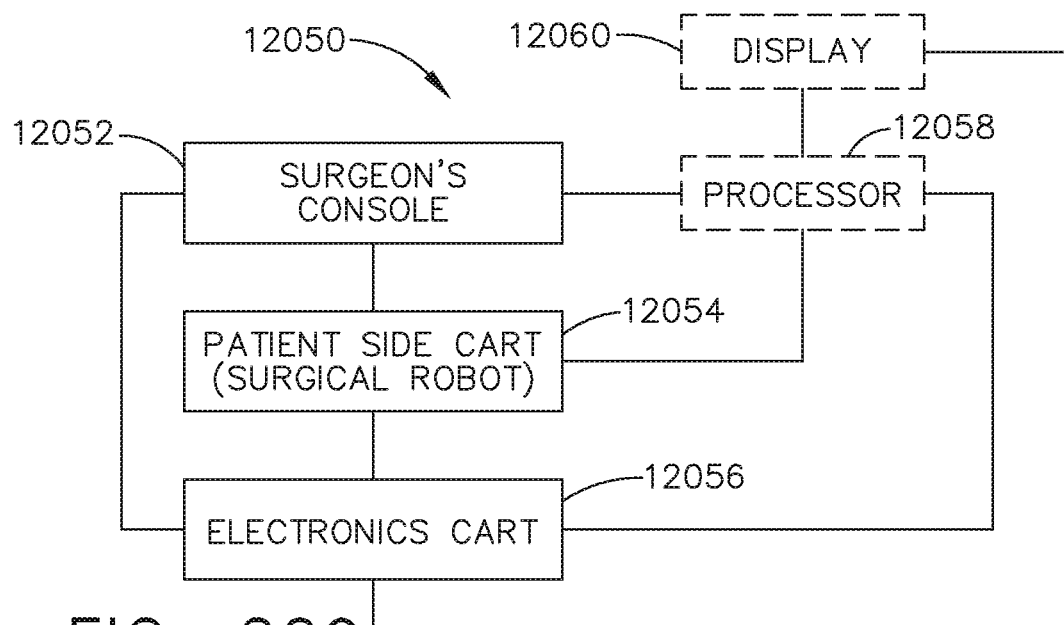
Figure 210:
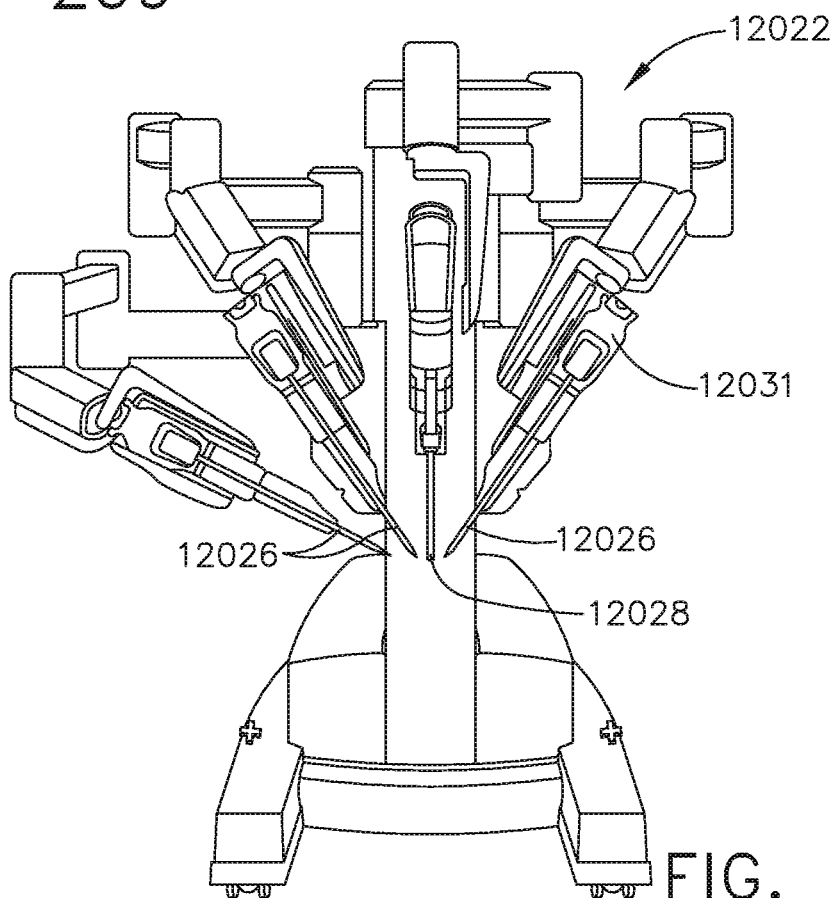
Figure 211:
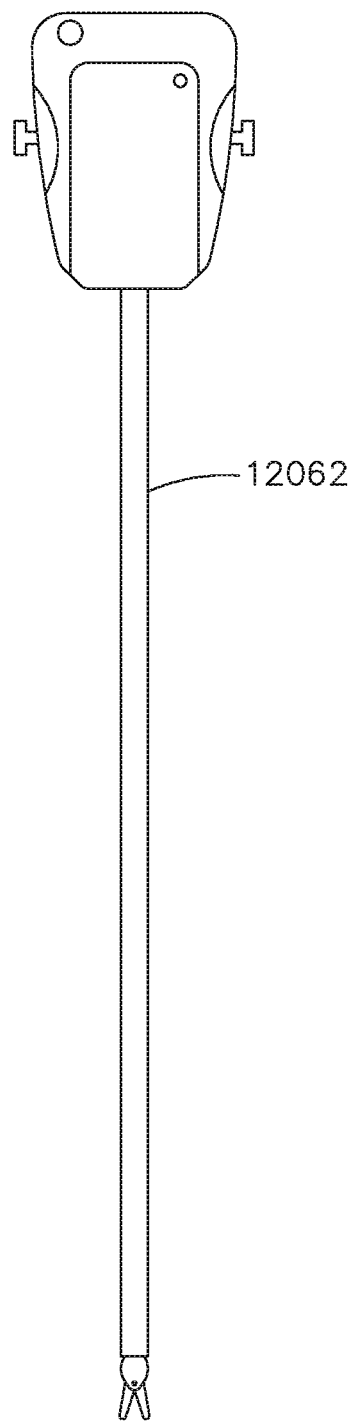
Figure 212:
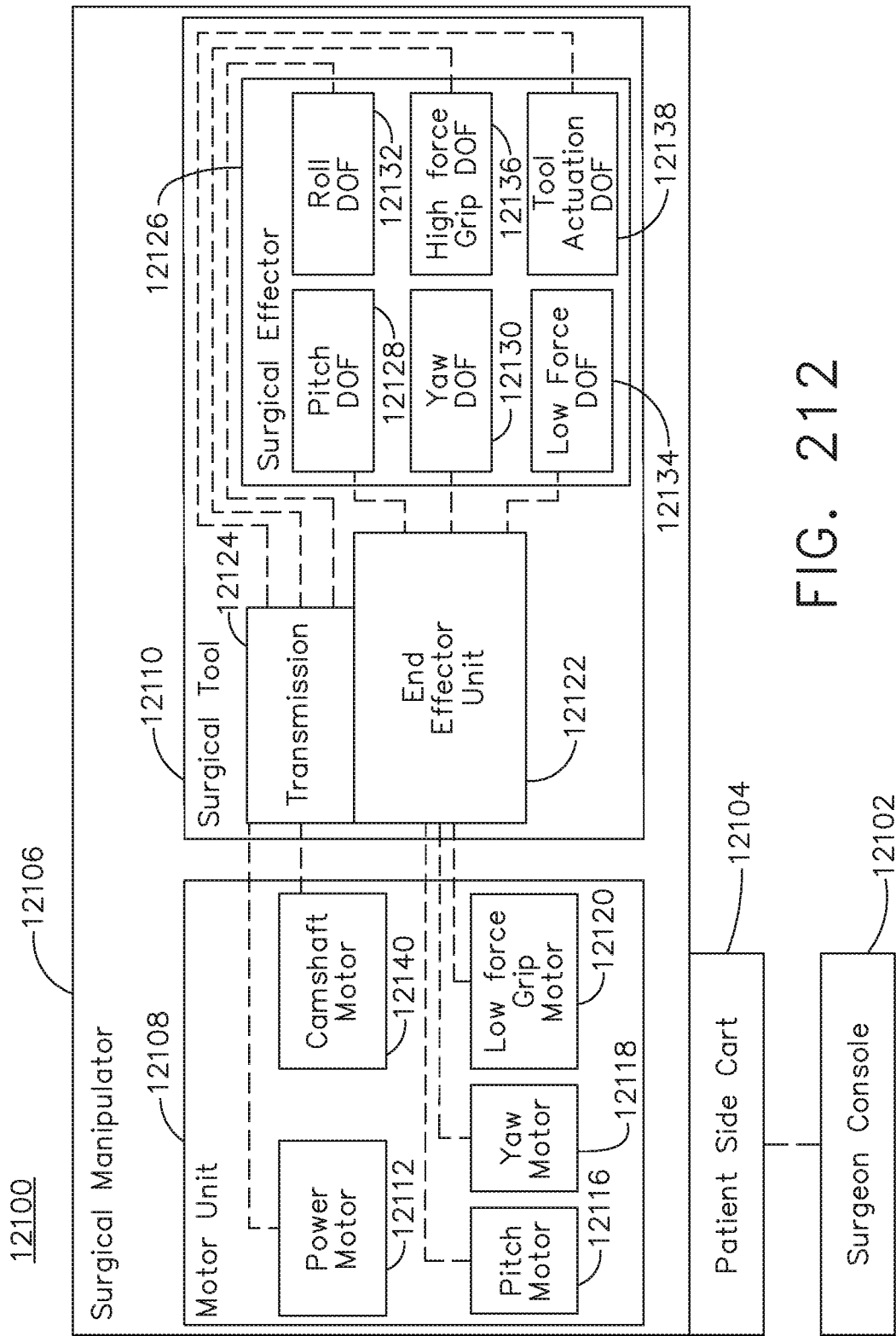
Figure 213:
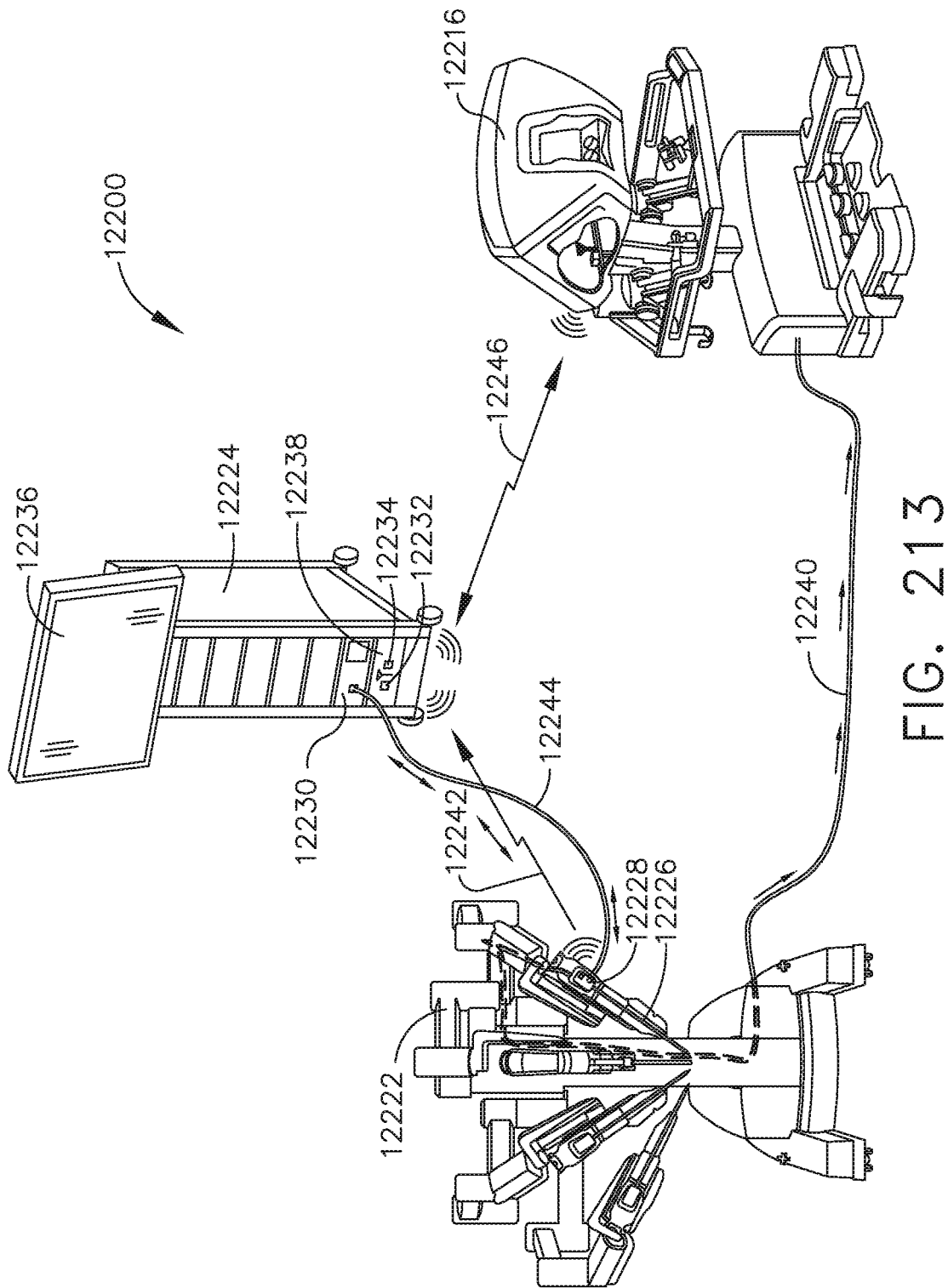
Figure 214:
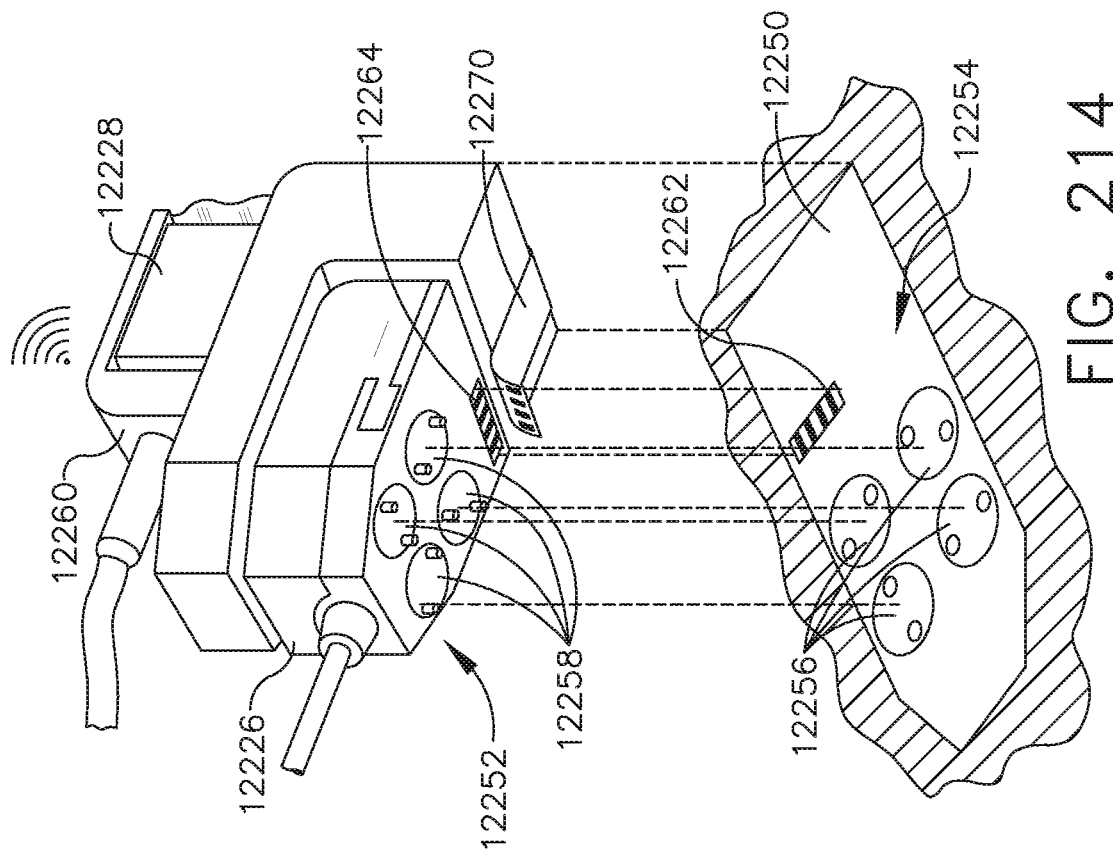
Figure 215:
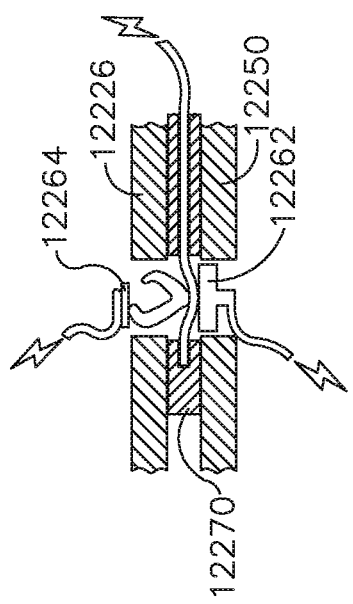
Figure 216:
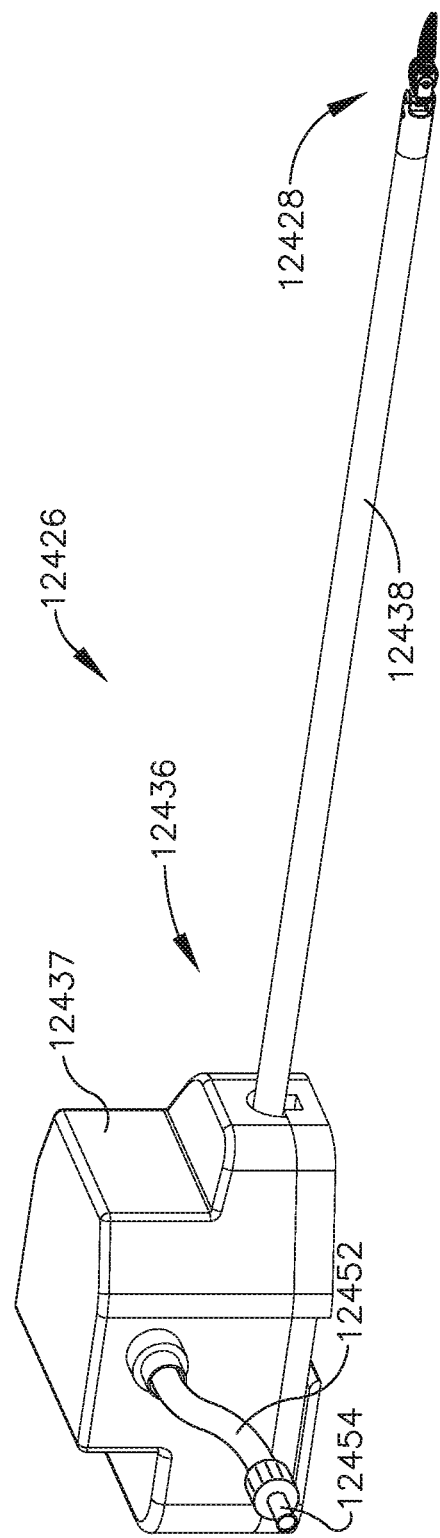
Figure 217:
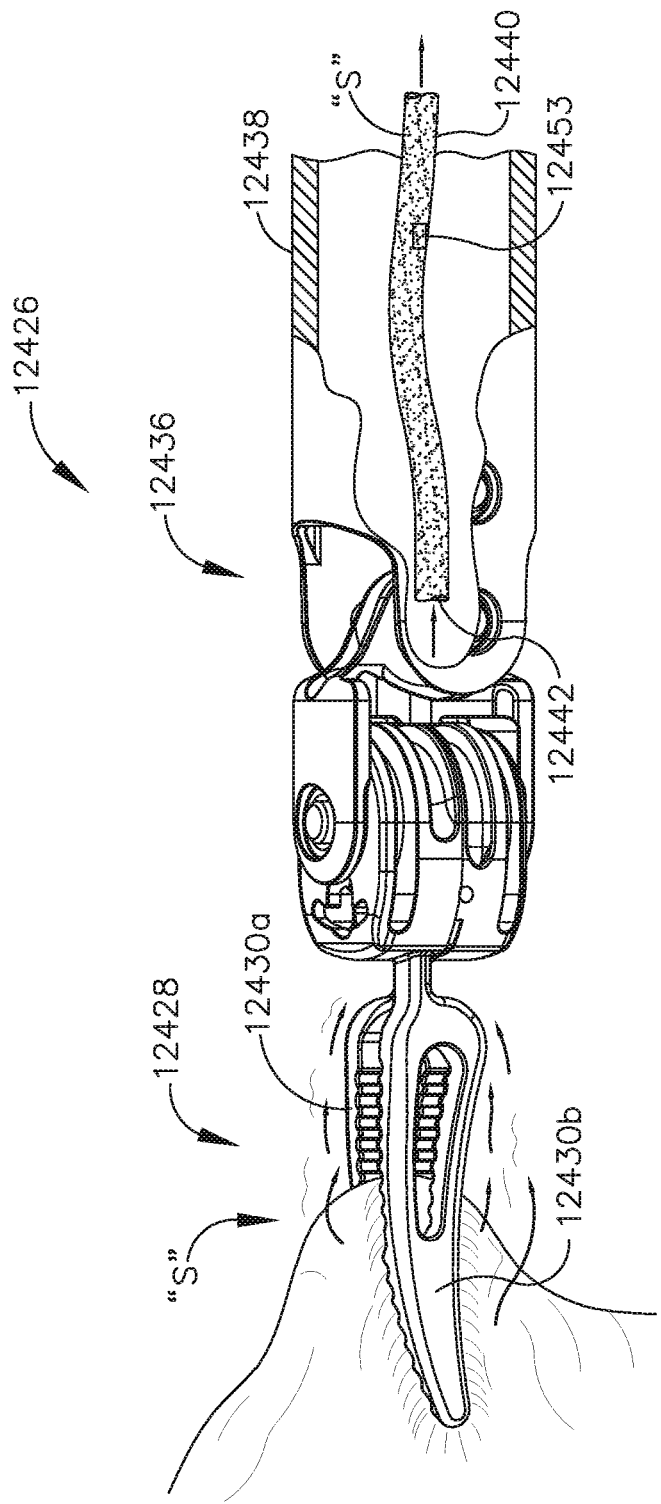
Figure 218:
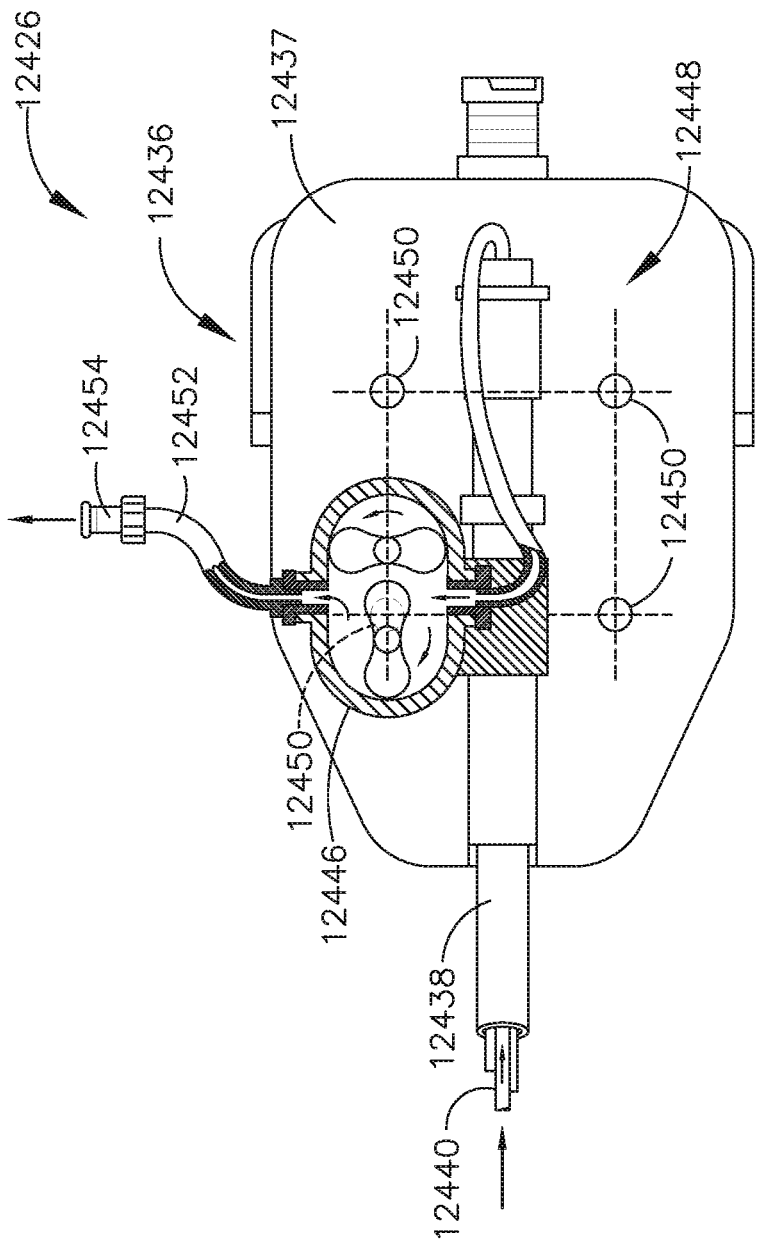
Figure 219:
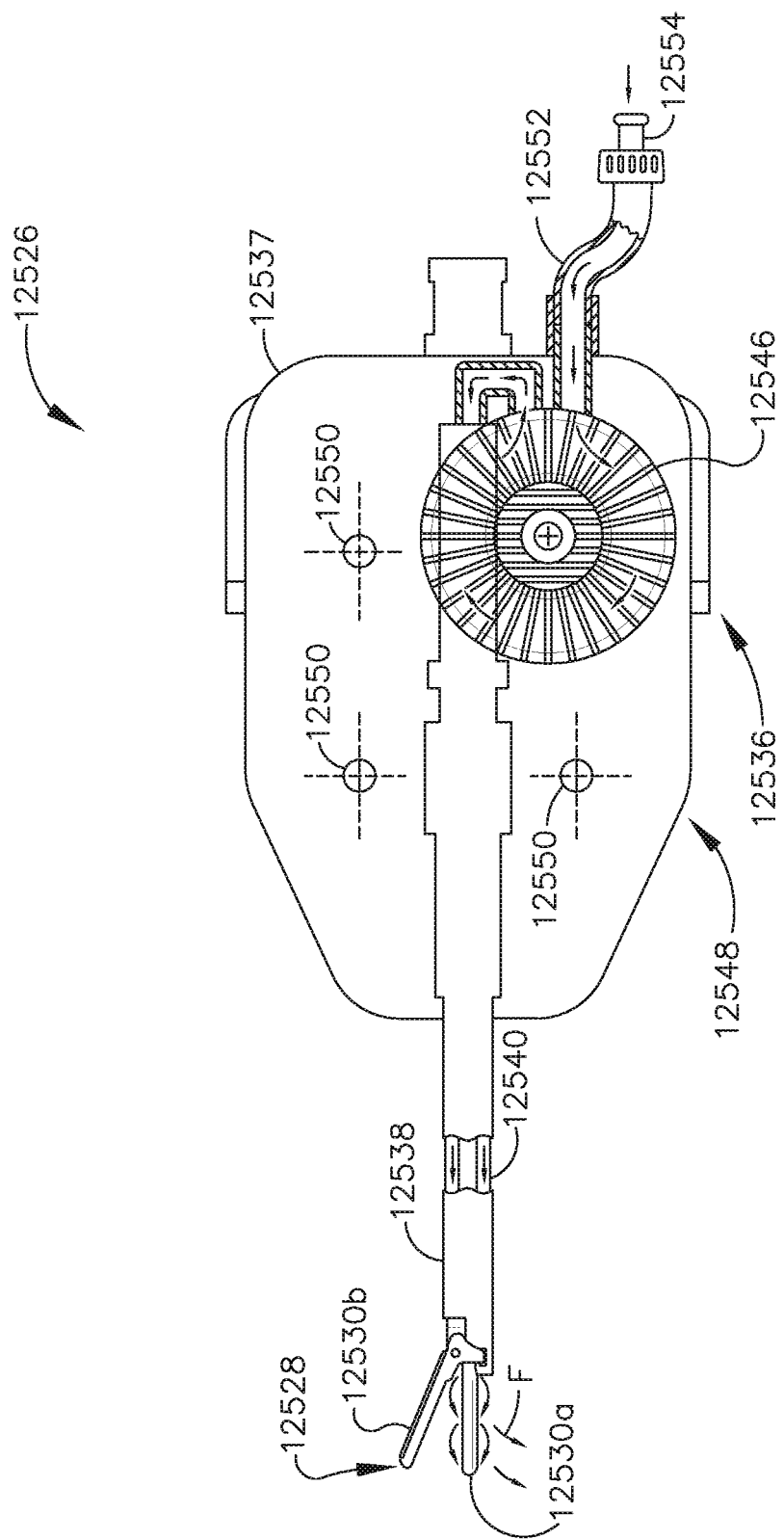
Figure 220:
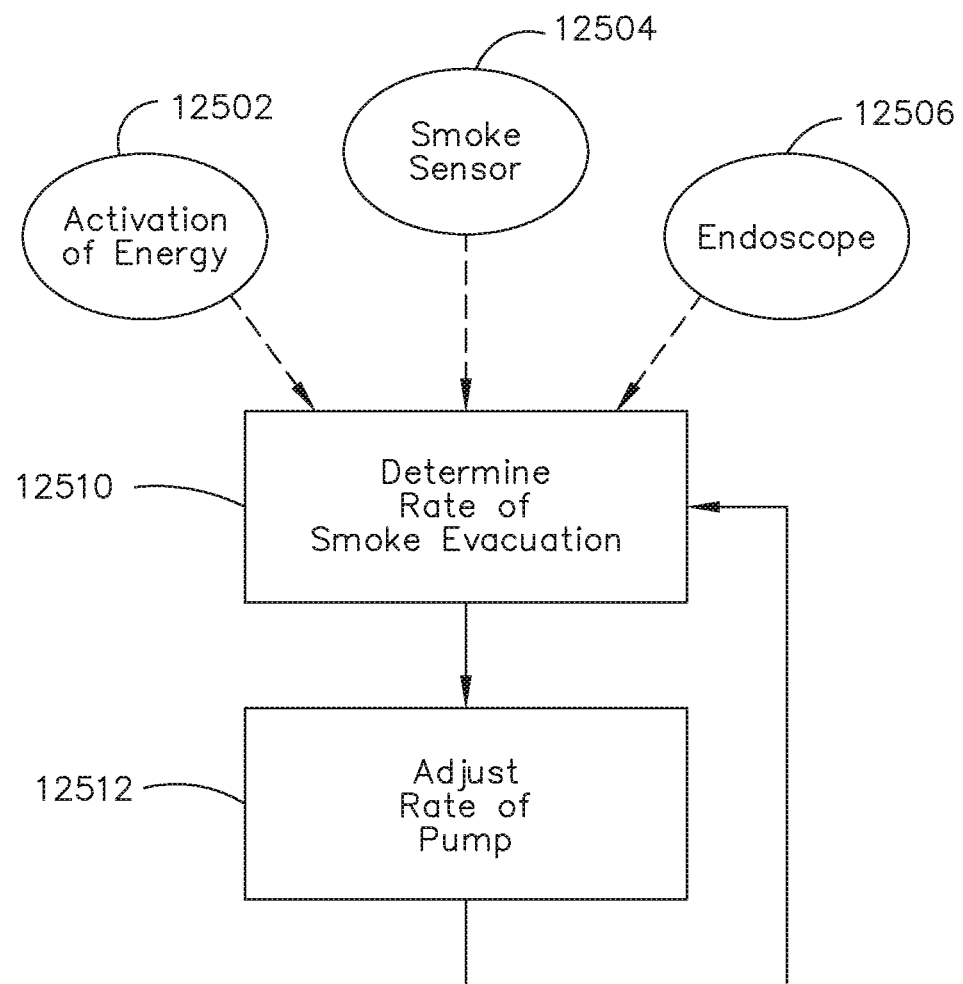
Figure 221:
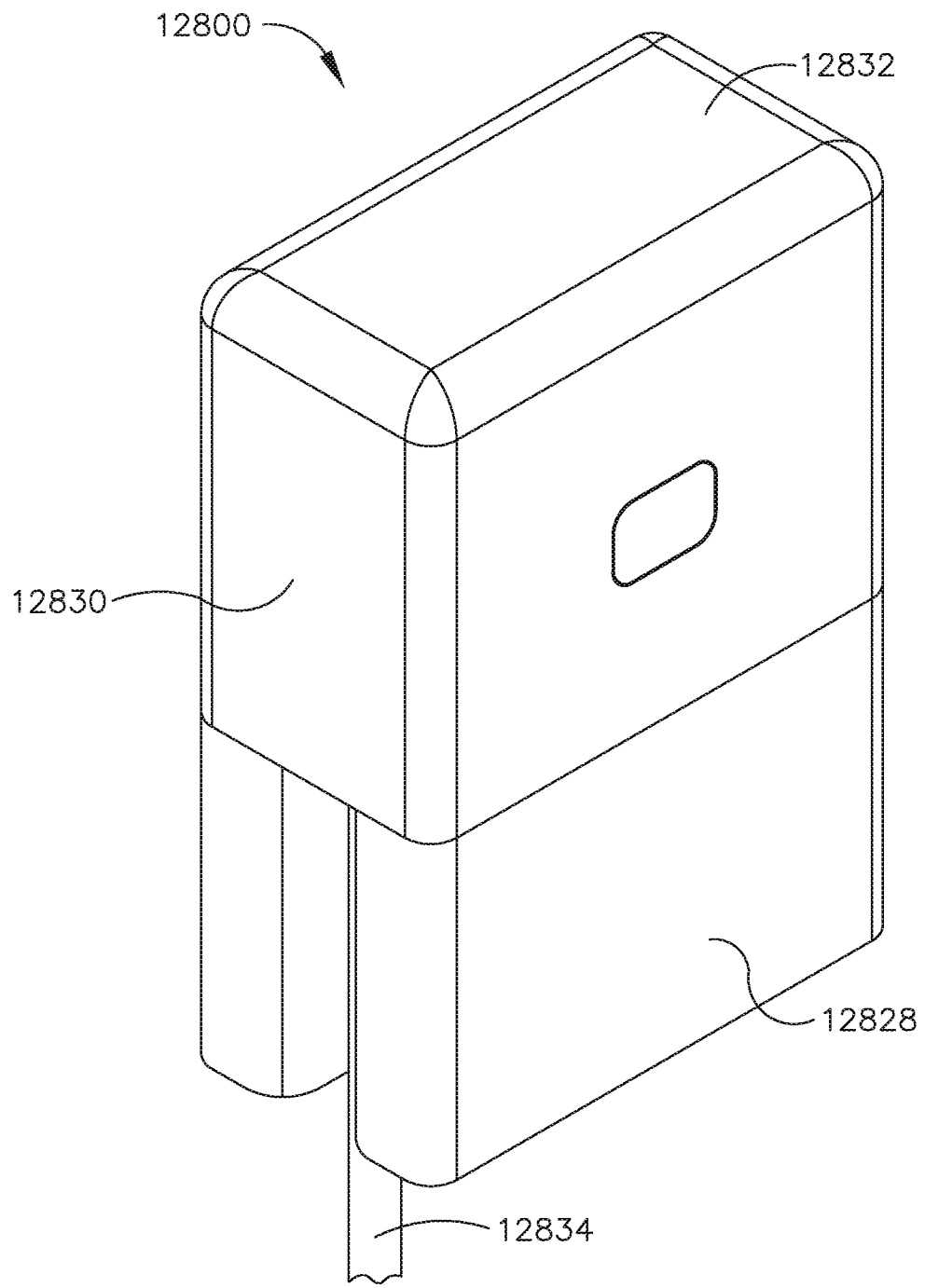
Figure 222:
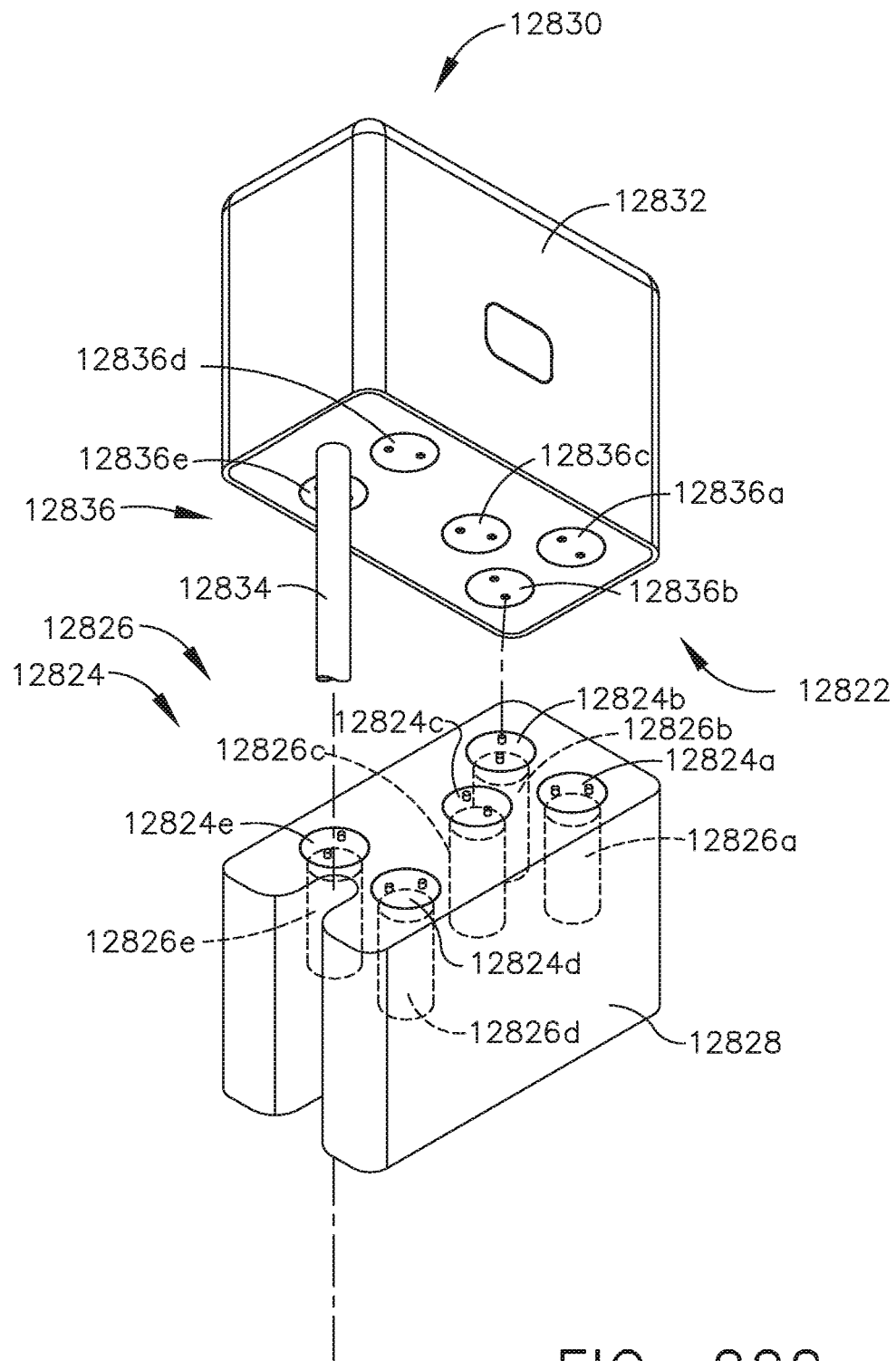
Figure 223:
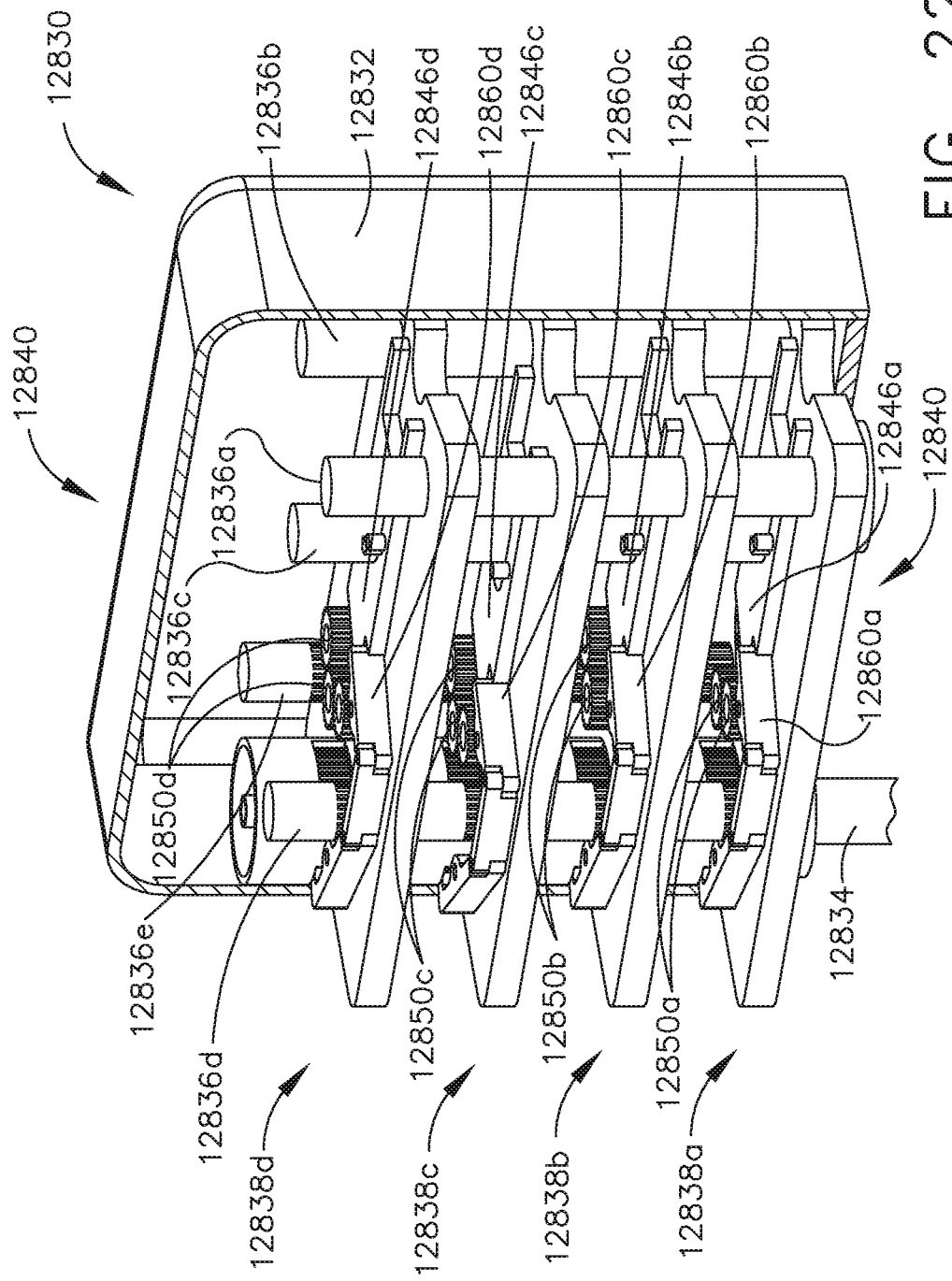
Figure 224:
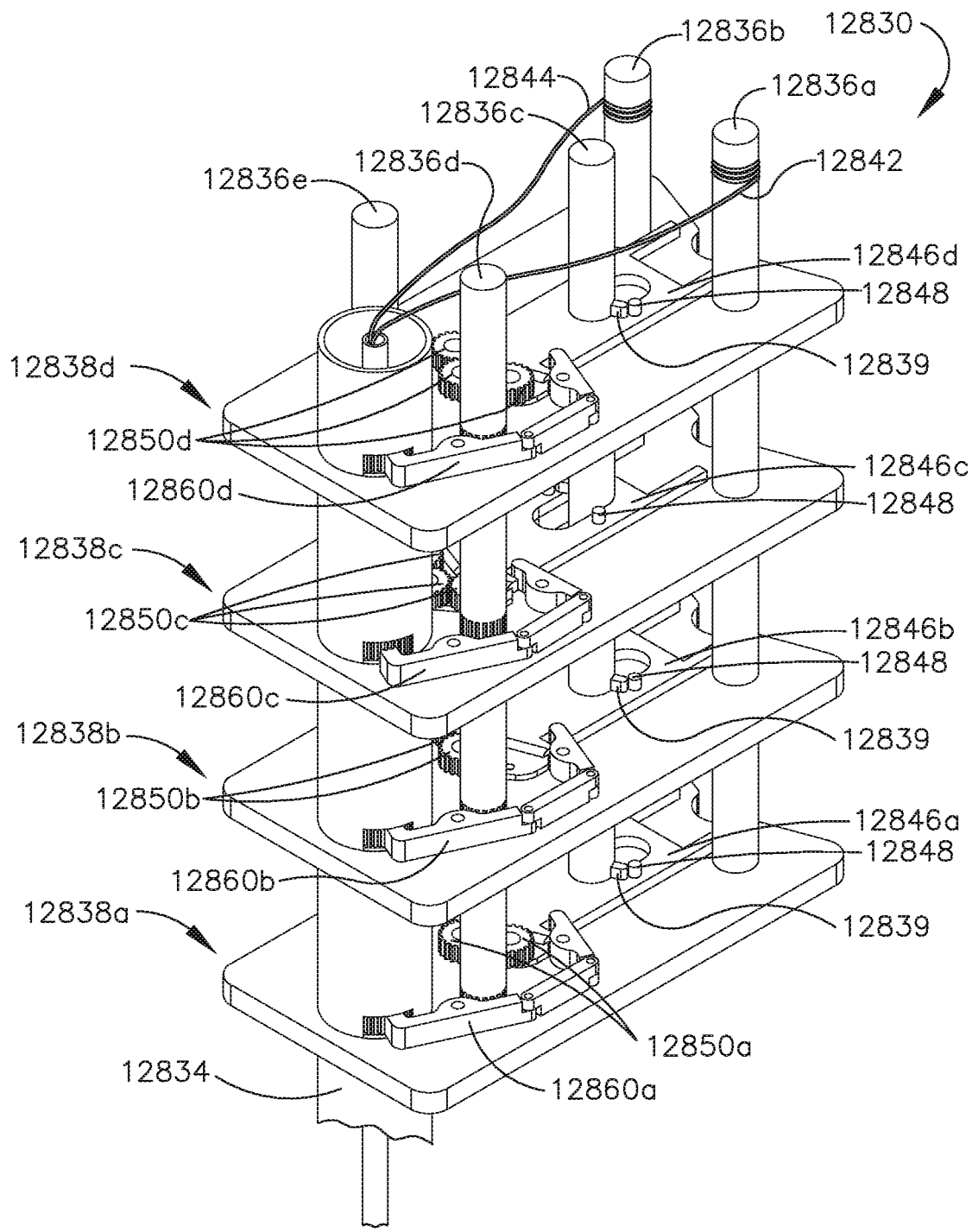
Figure 225:
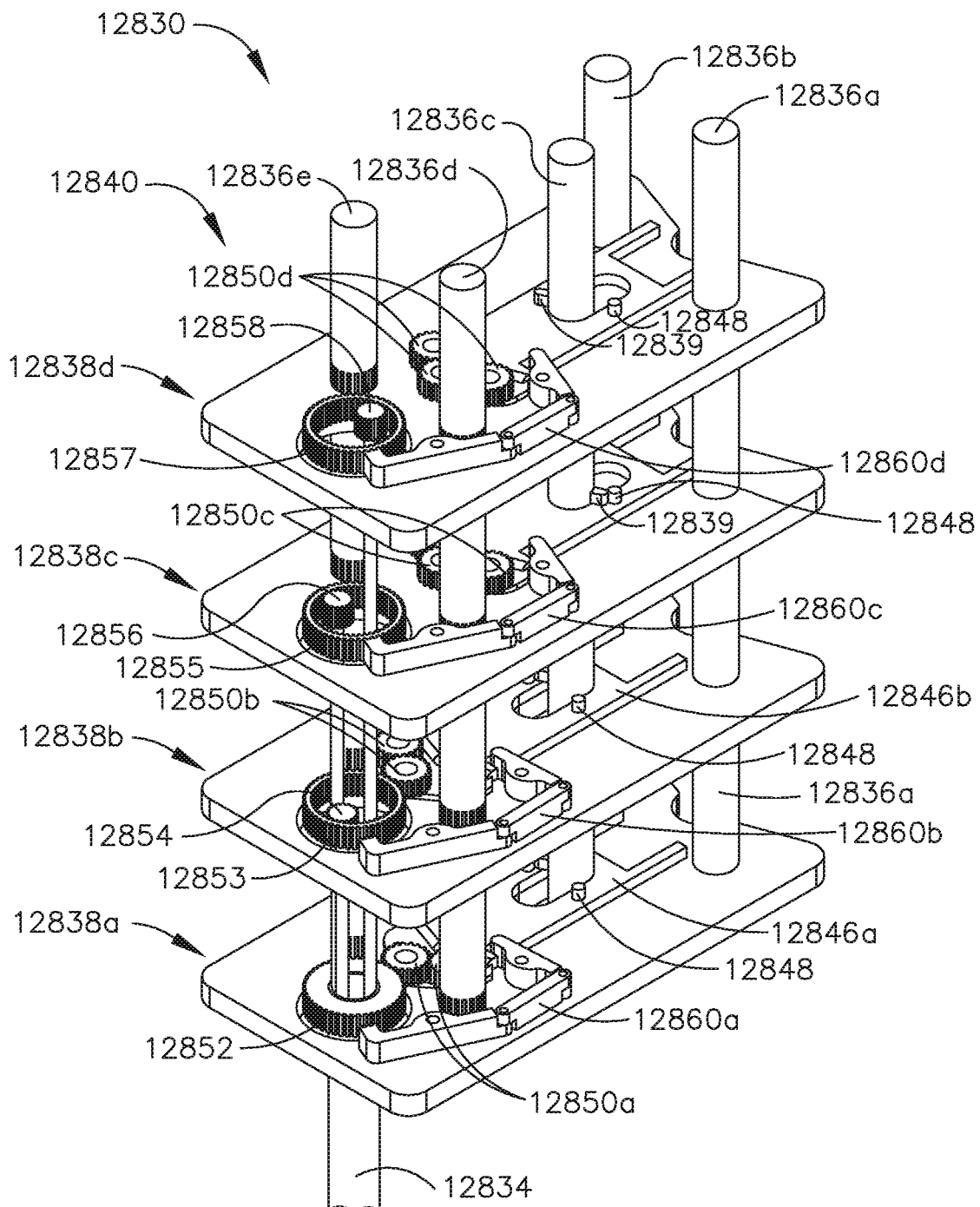
Figure 226:
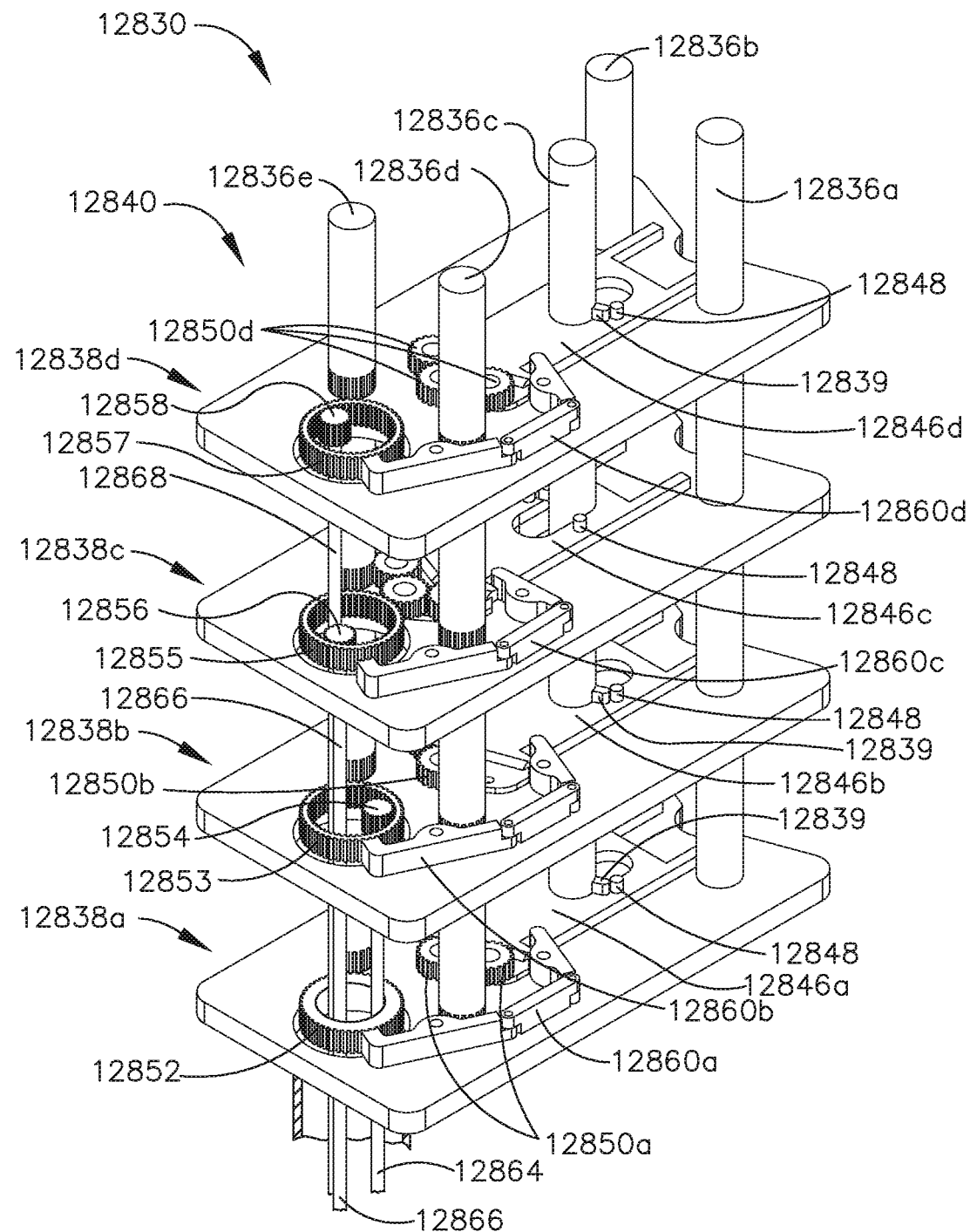
Figure 227:
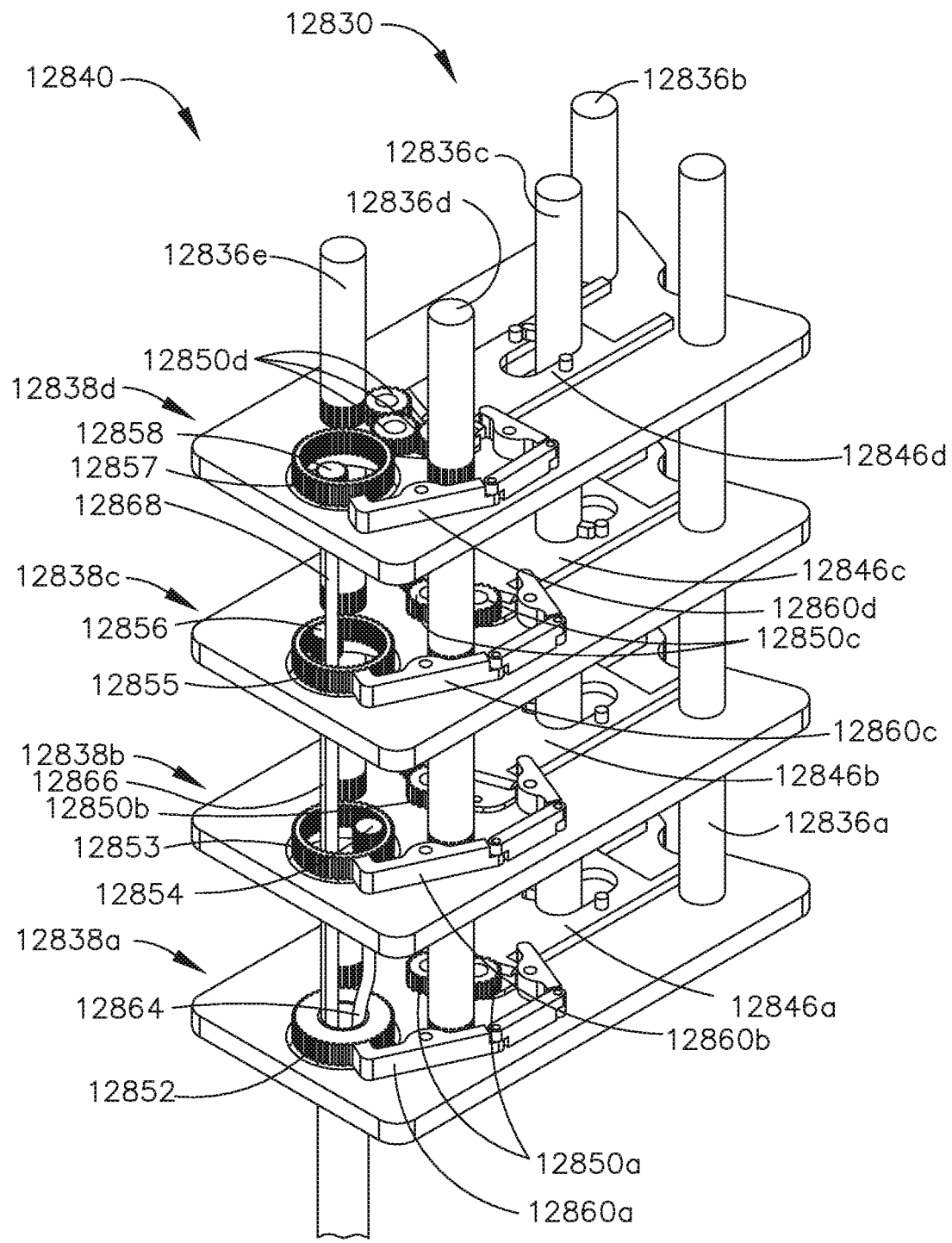
Figure 228:
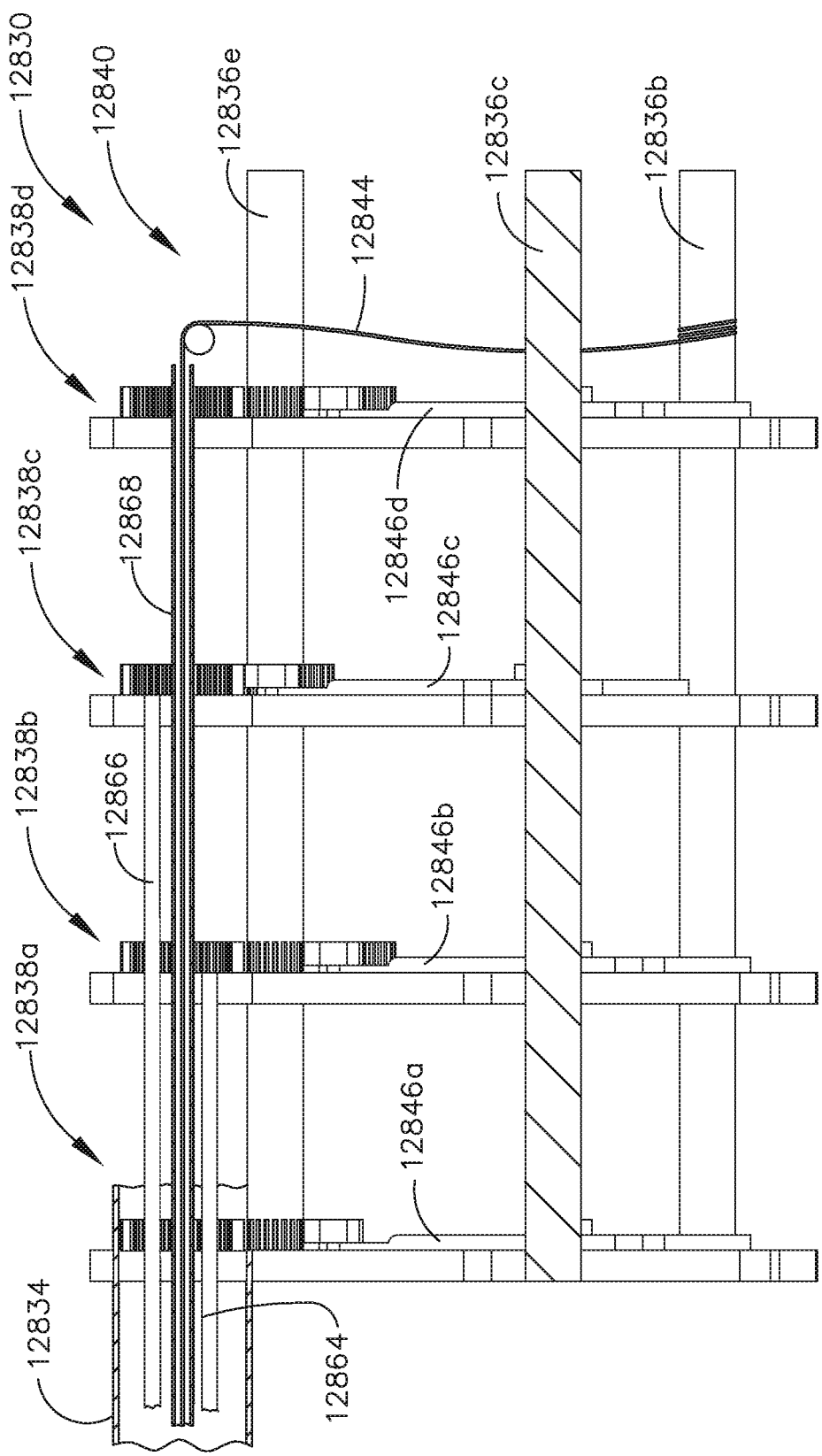
Figure 229:
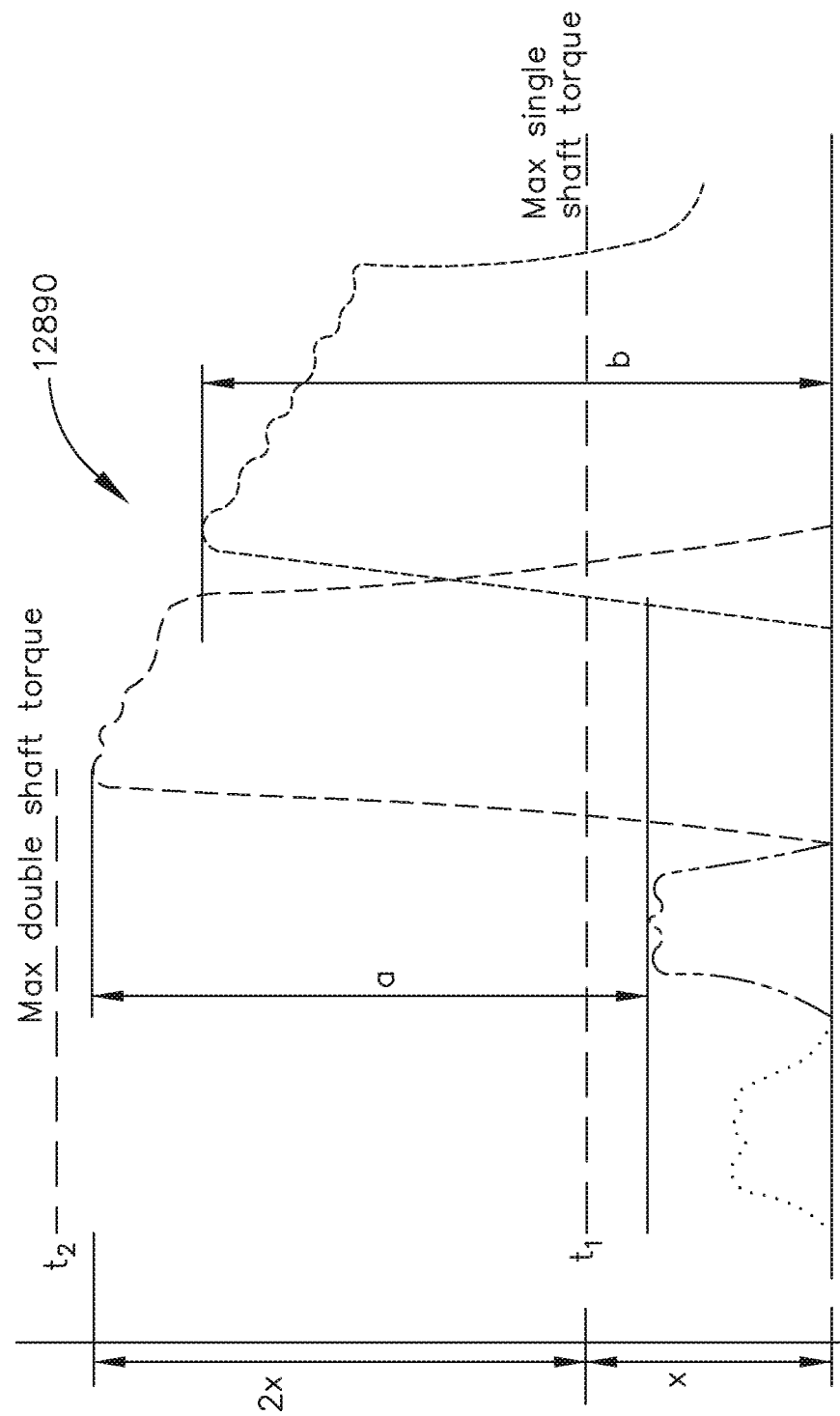
Figure 230:
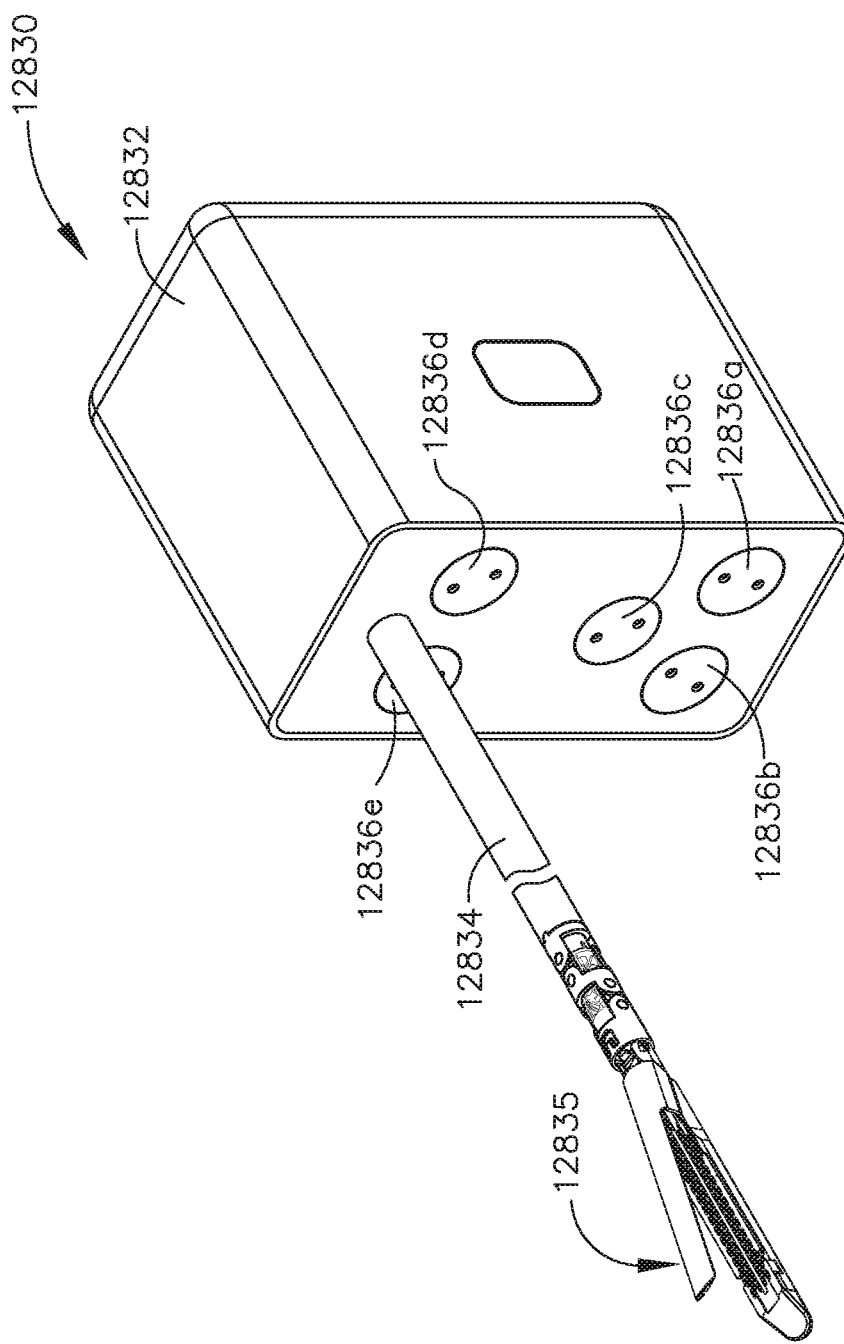
Figure 231:
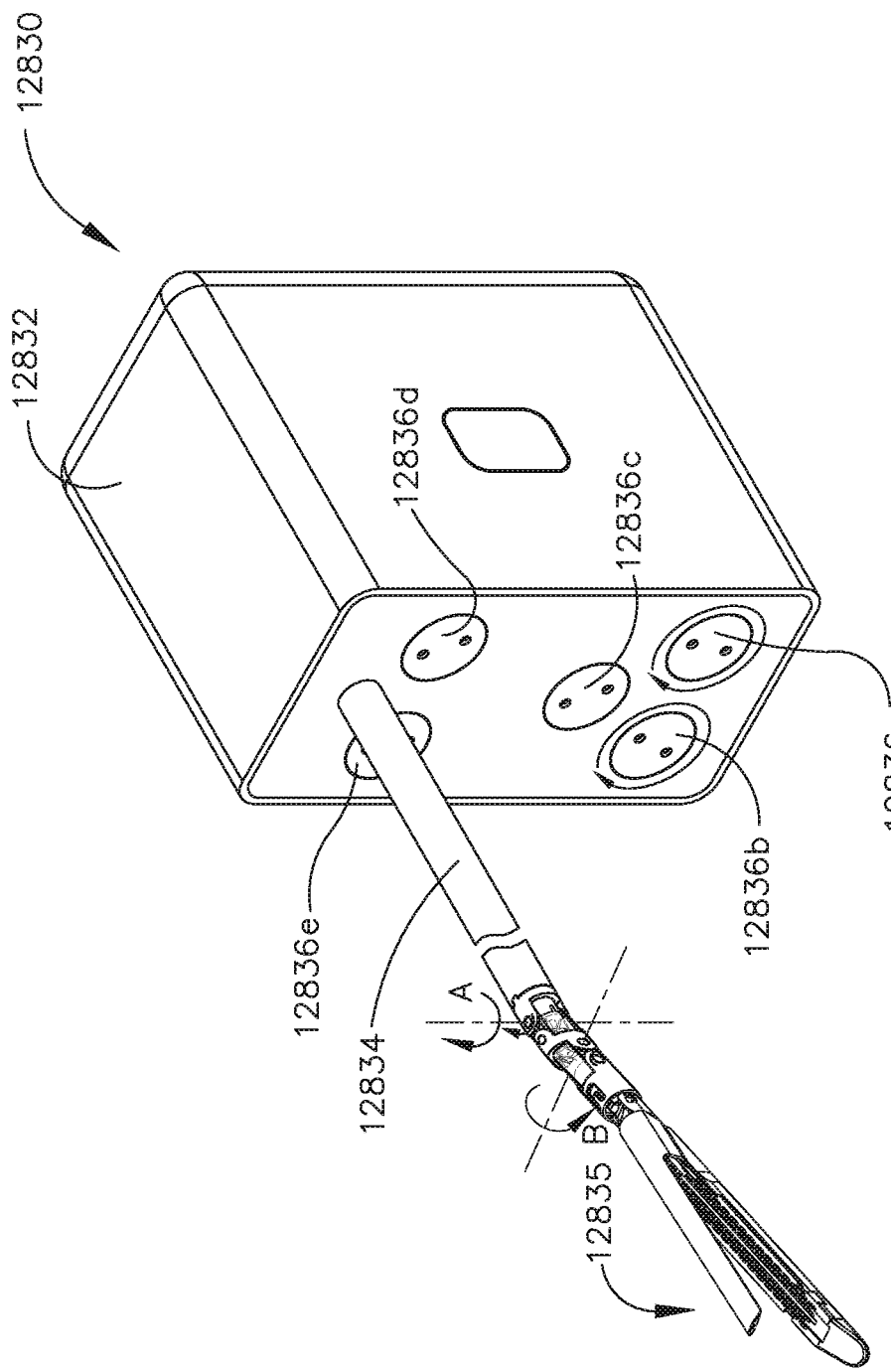
Figure 232:
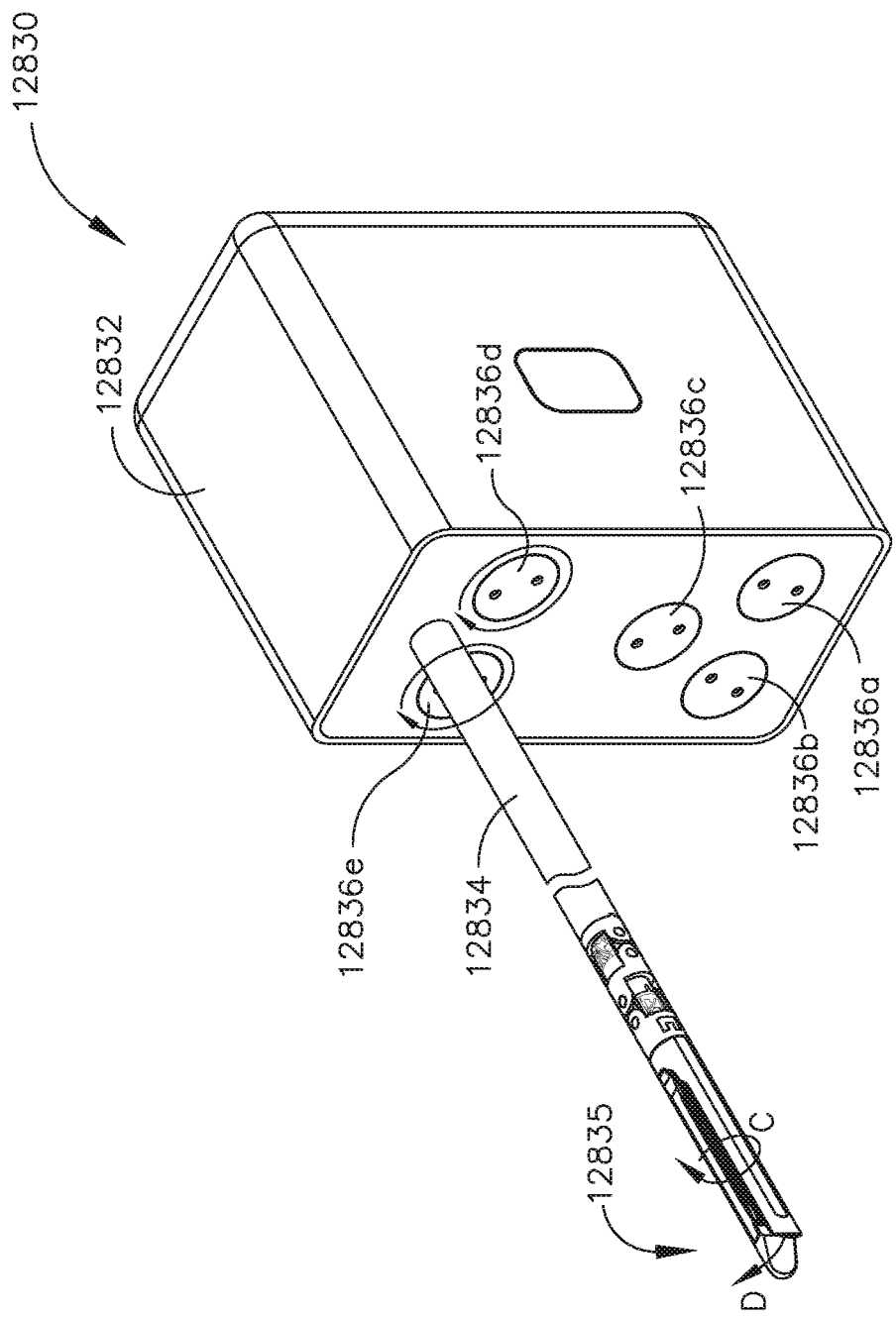
Figure 233:
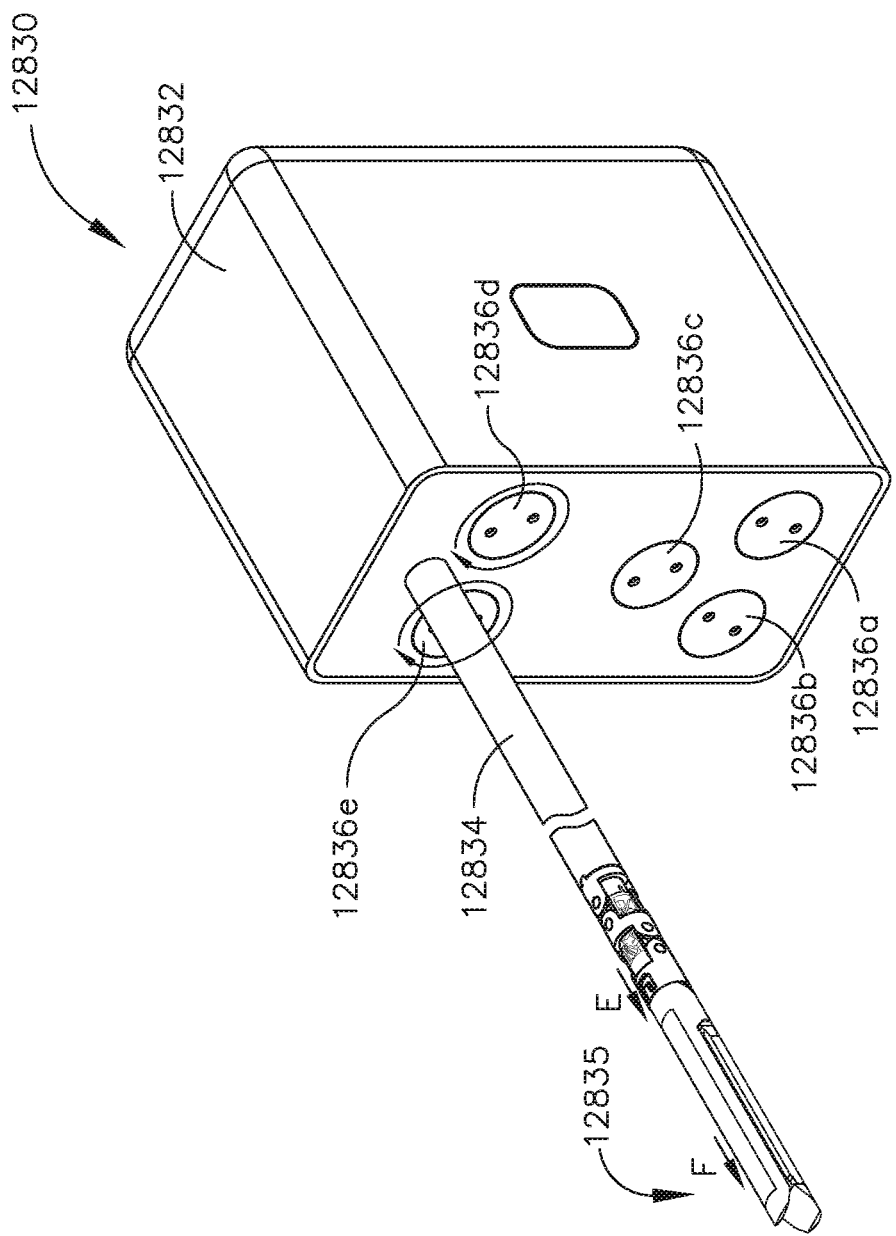
Figure 234:
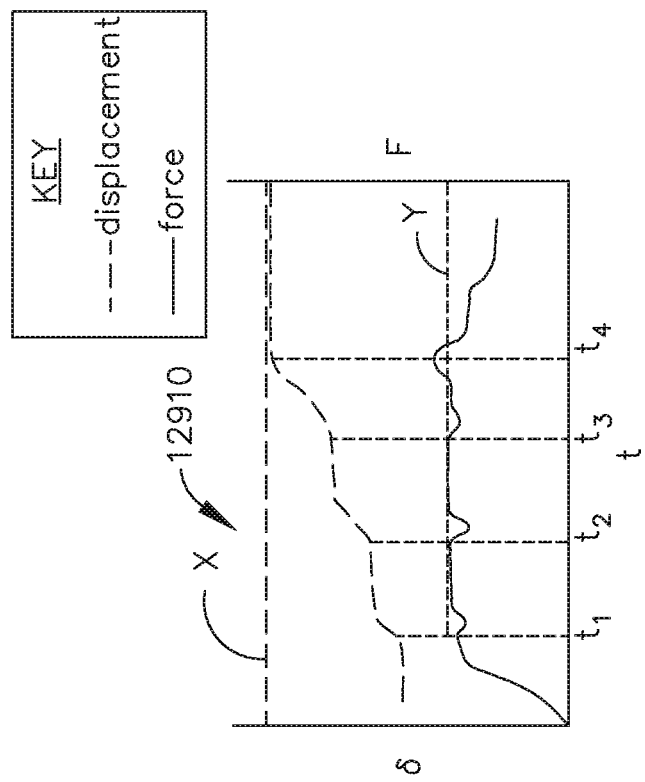
Figure 236:
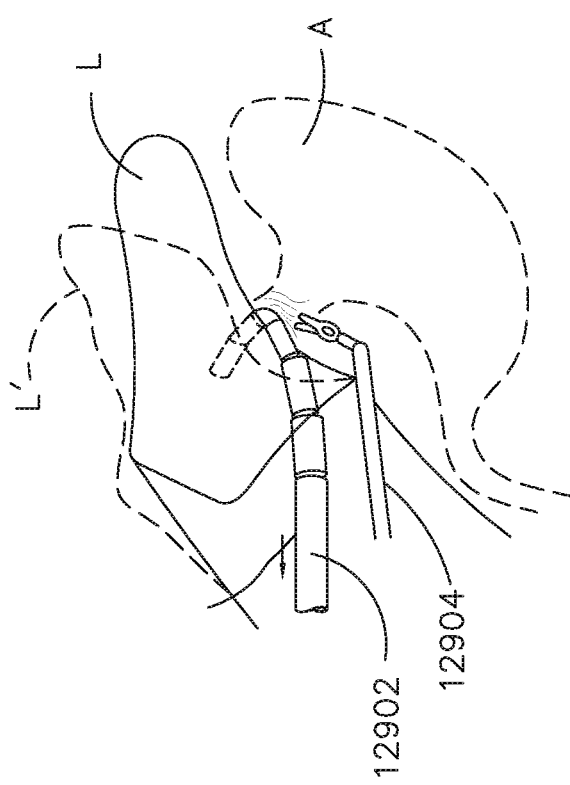
Figure 235:
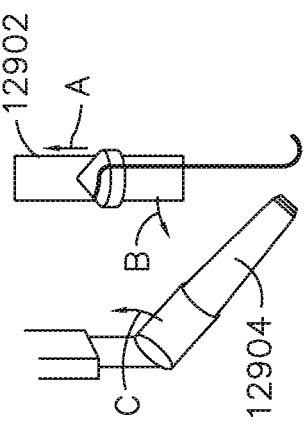
Figure 237:
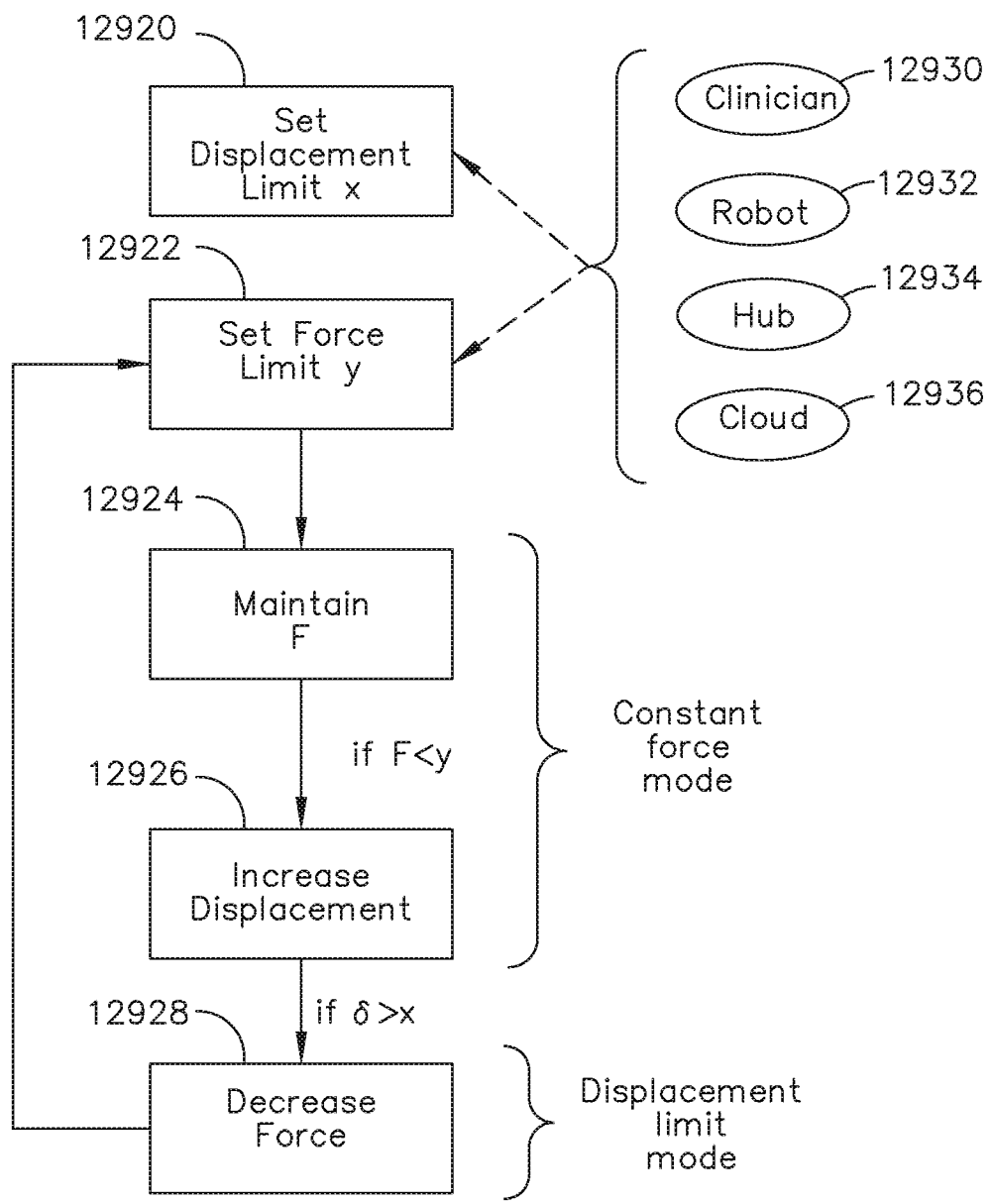
Figure 238:
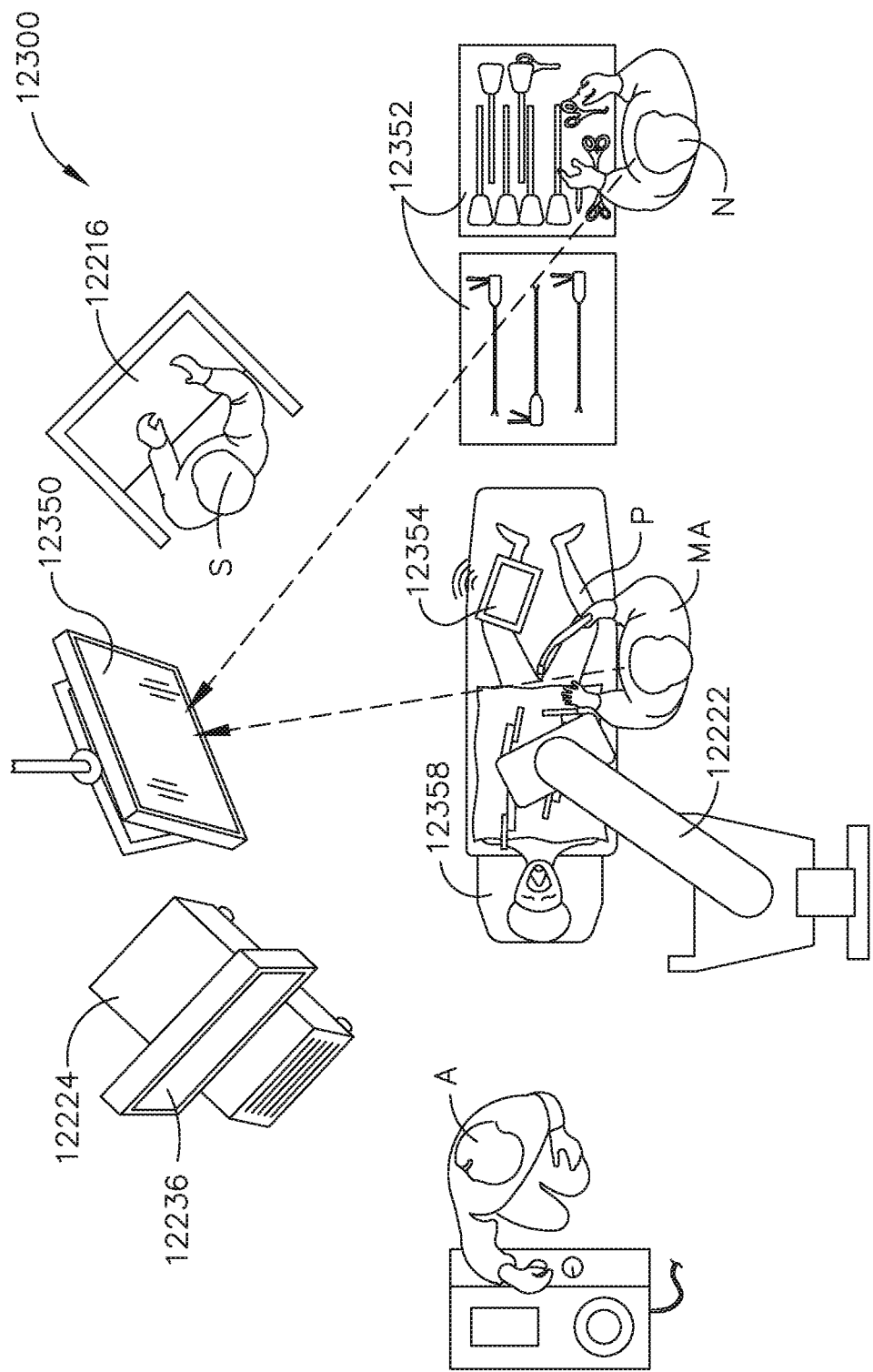
Figure 239:
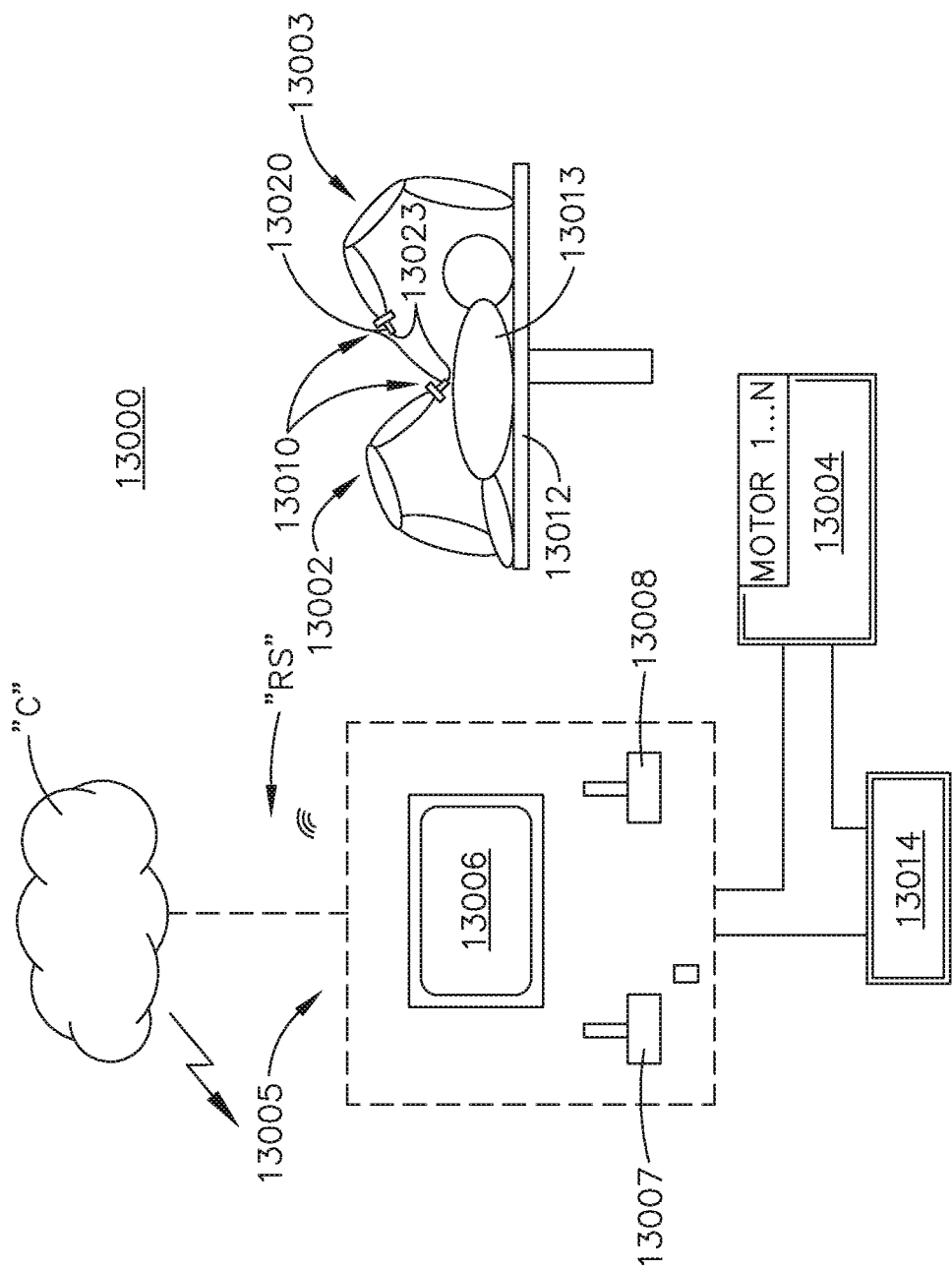
Figure 240:
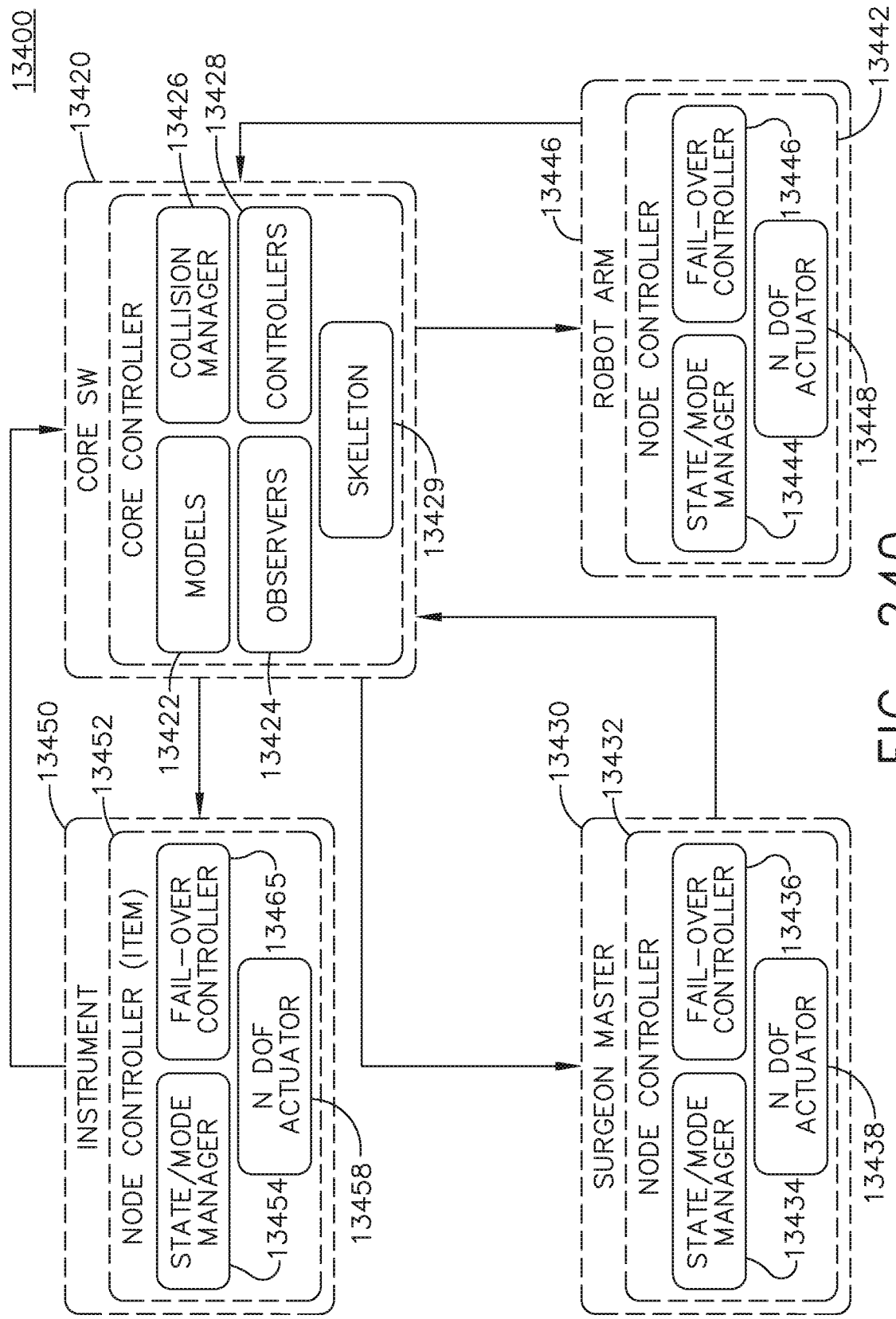
Figure 242B:
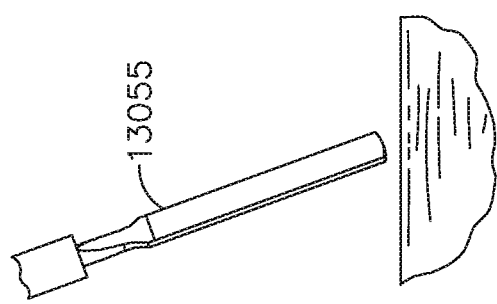
Figure 242A:
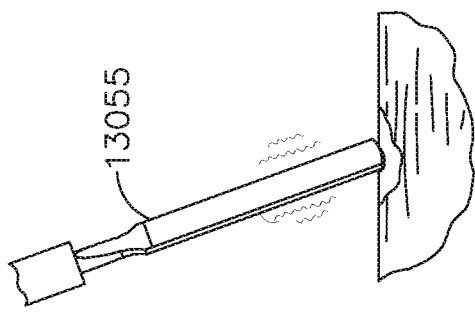
Figure 244:
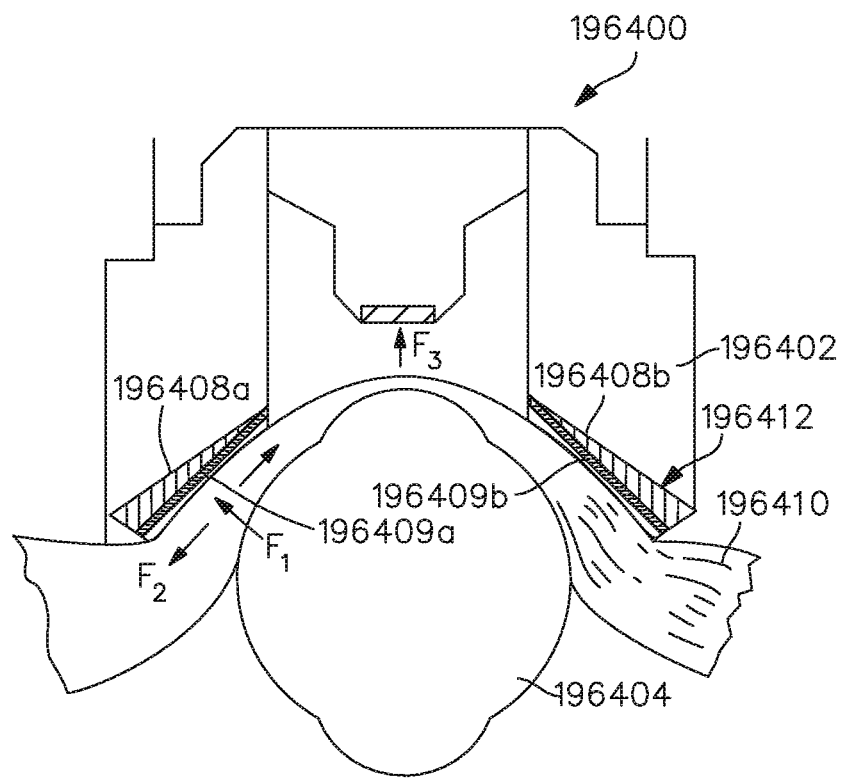
Figure 245:
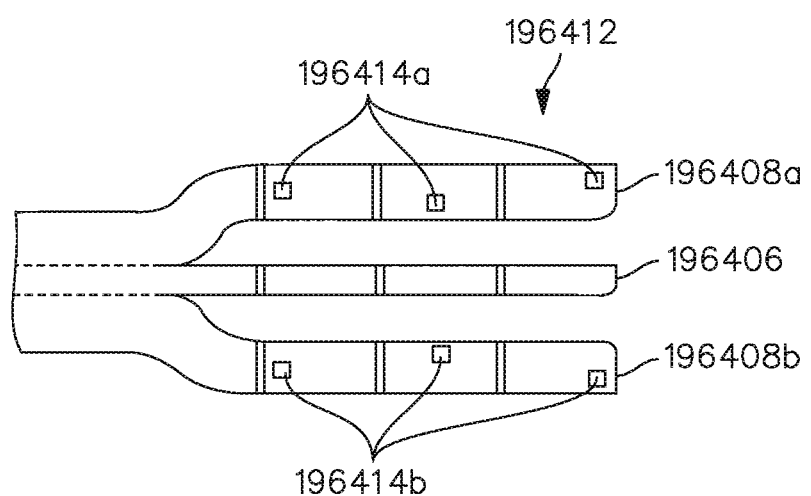
Figure 246:
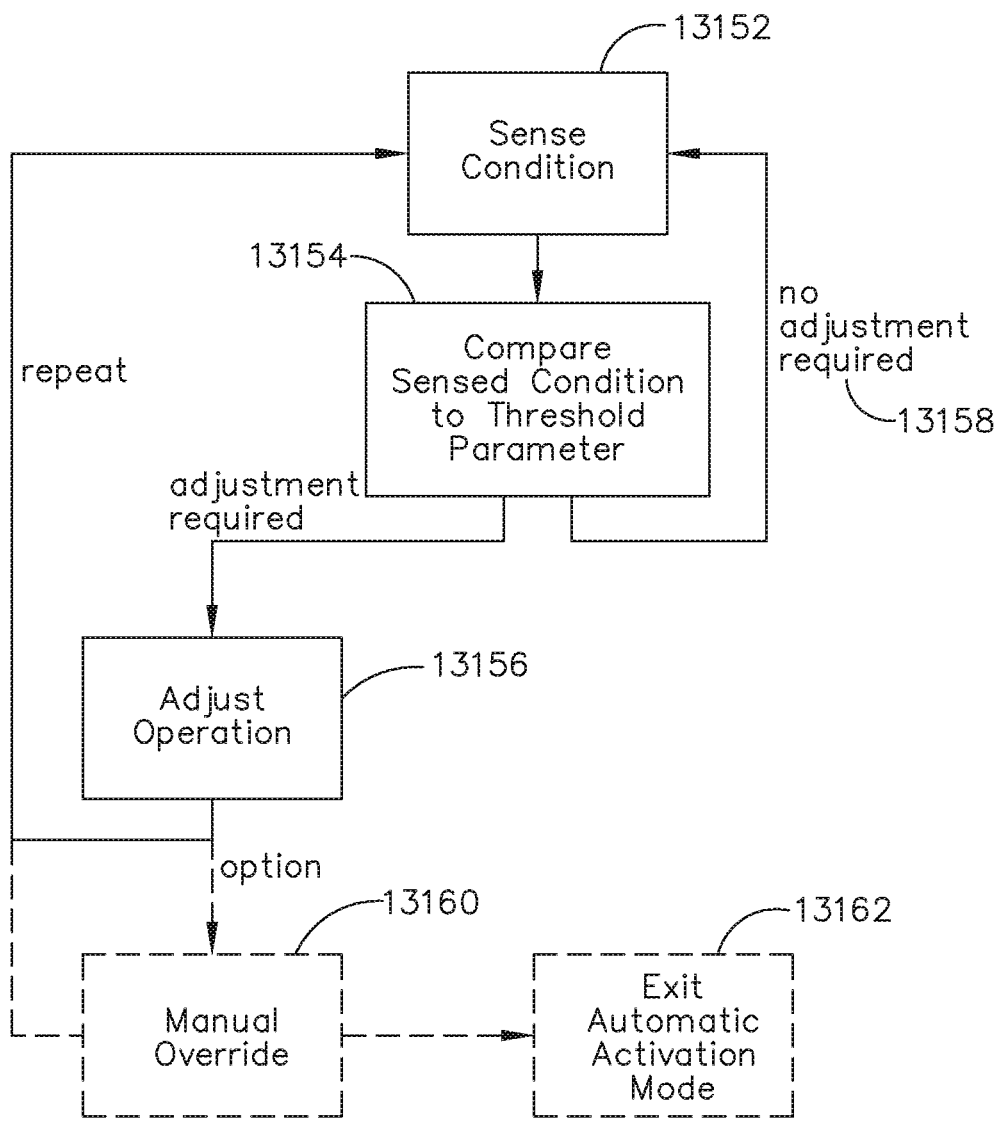
Figure 247:
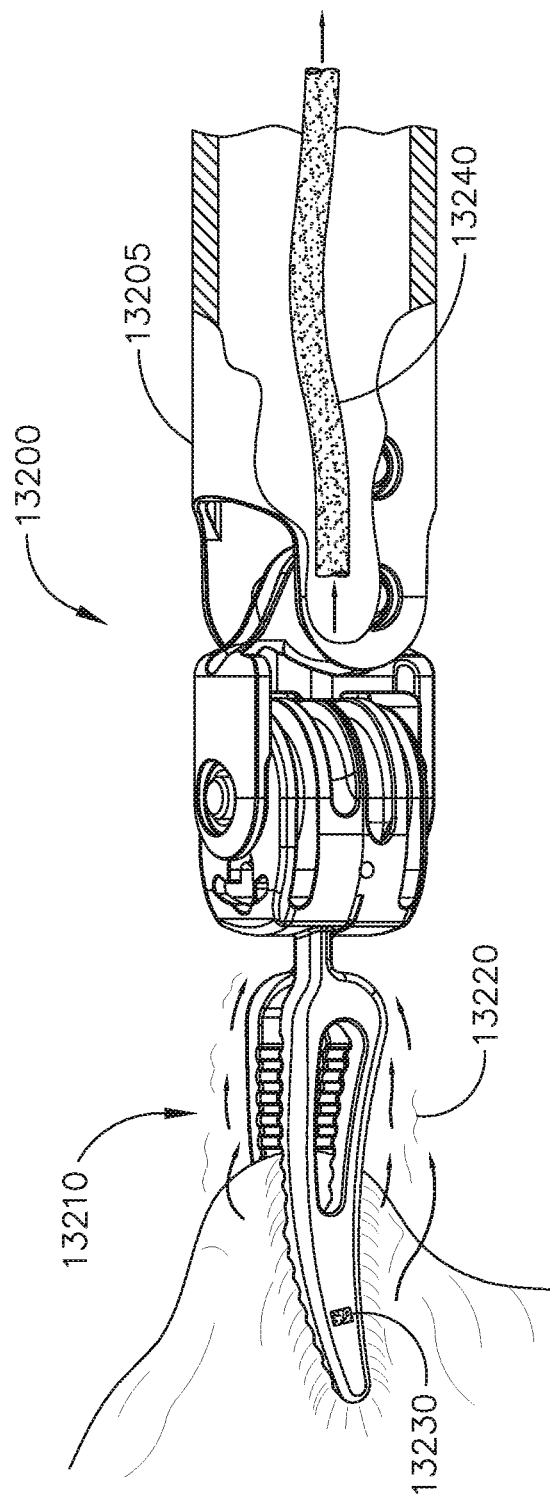
Figure 248:
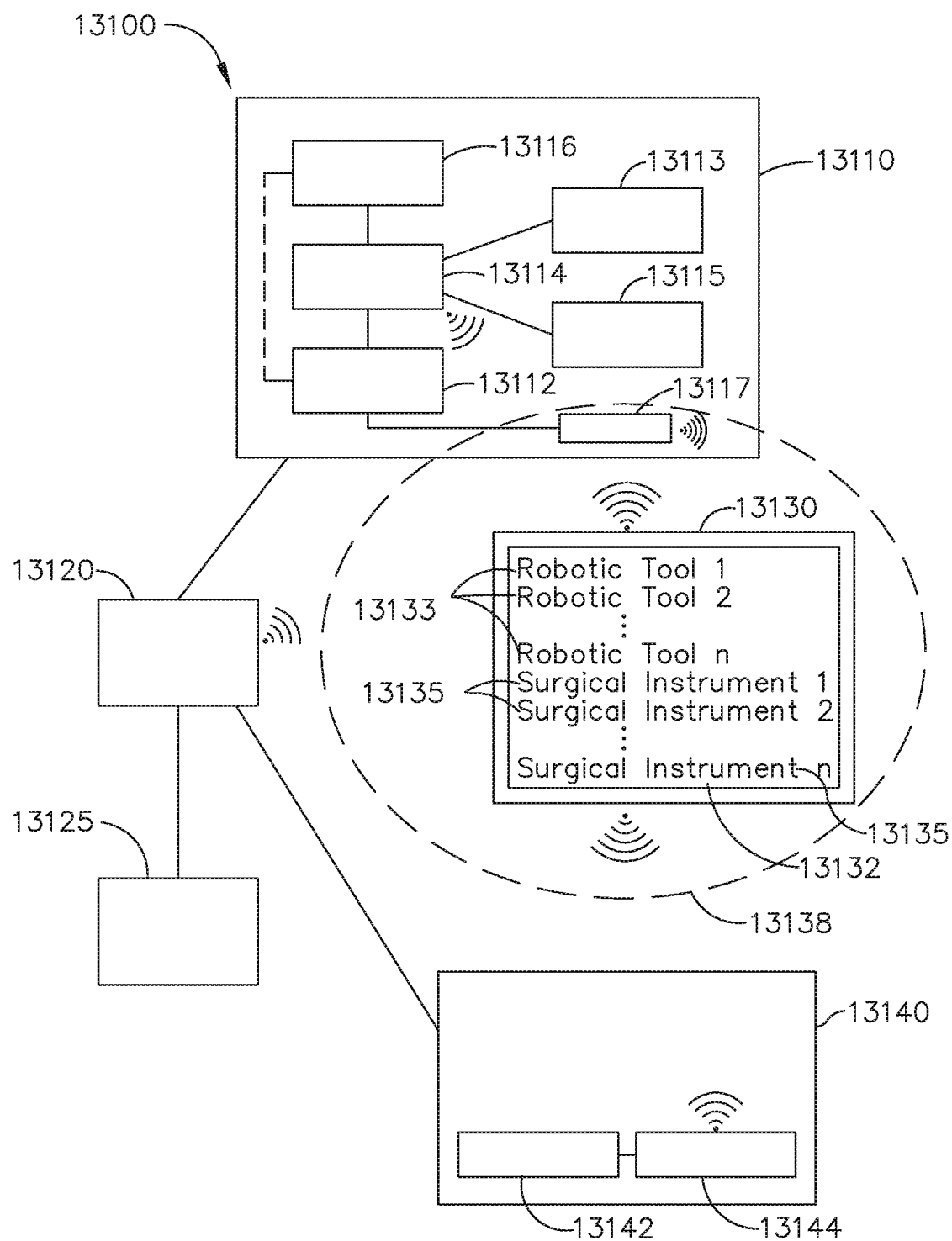
Figure 249:
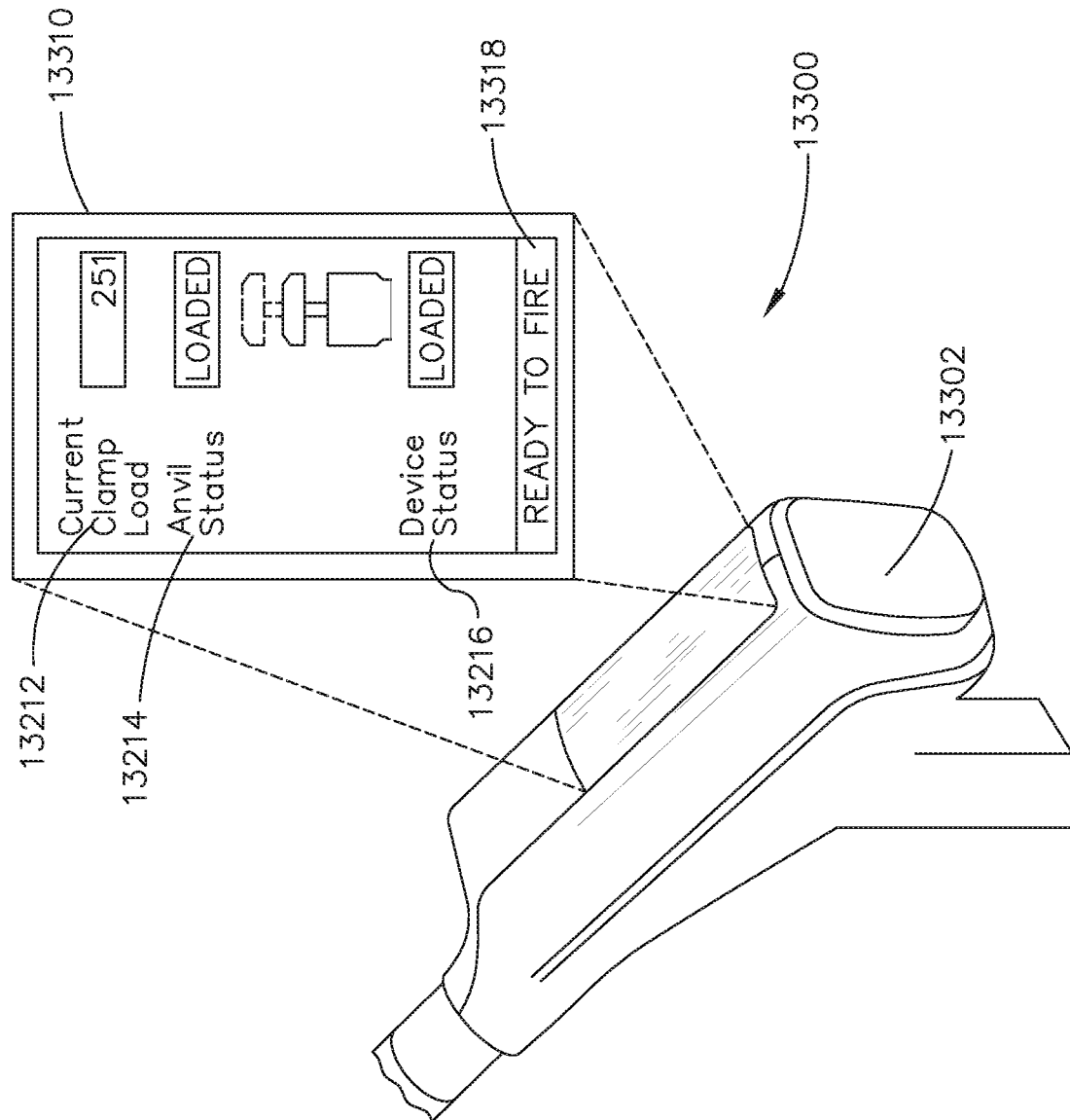
Figure 250:
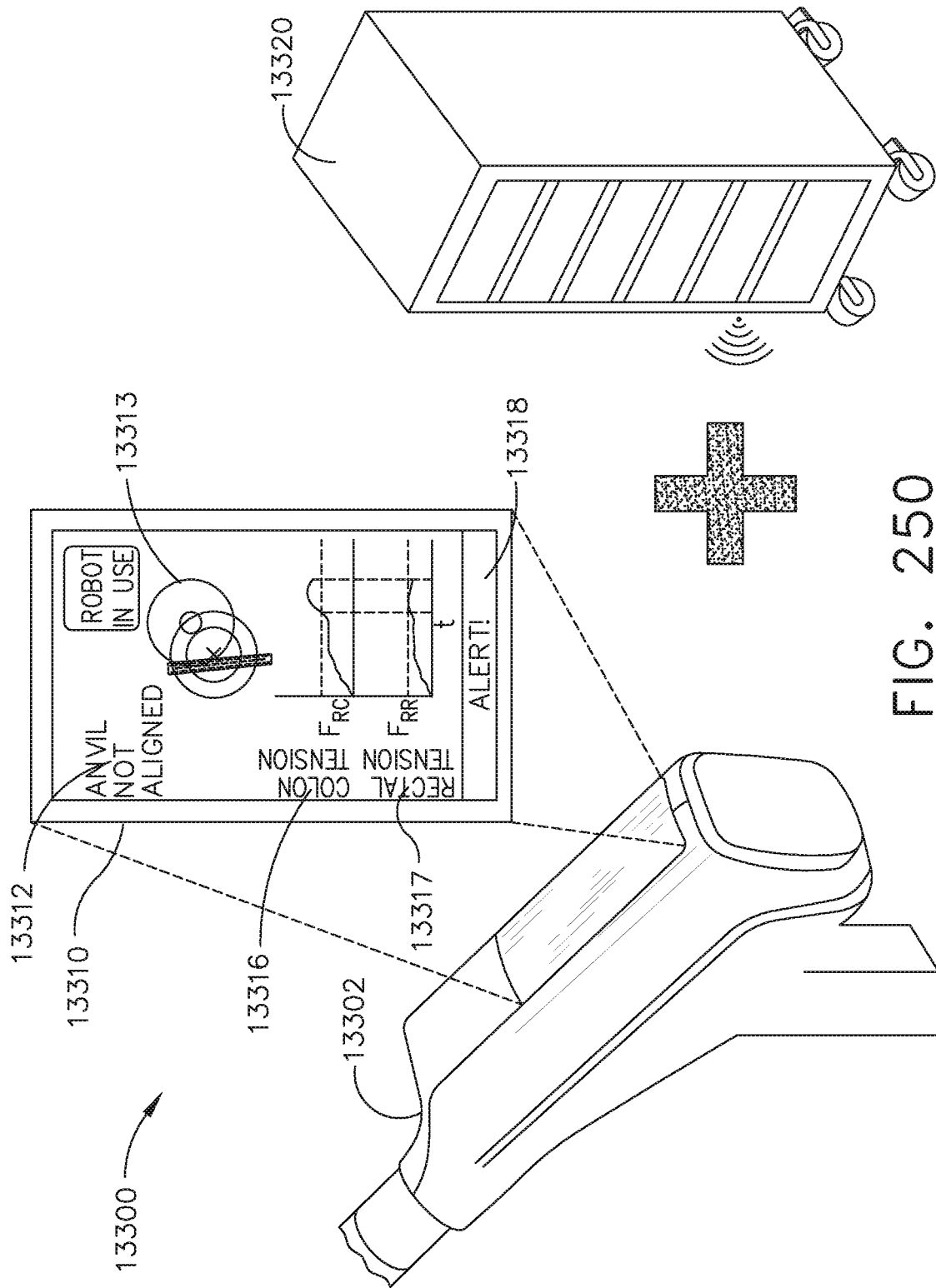
Figure 251:
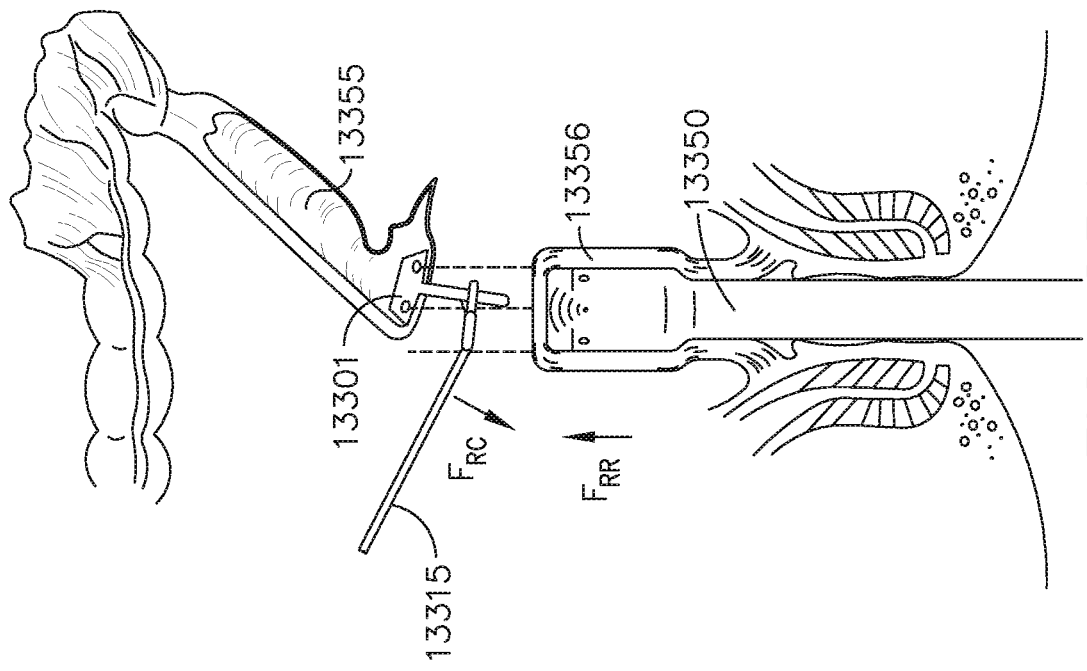
Figure 252:
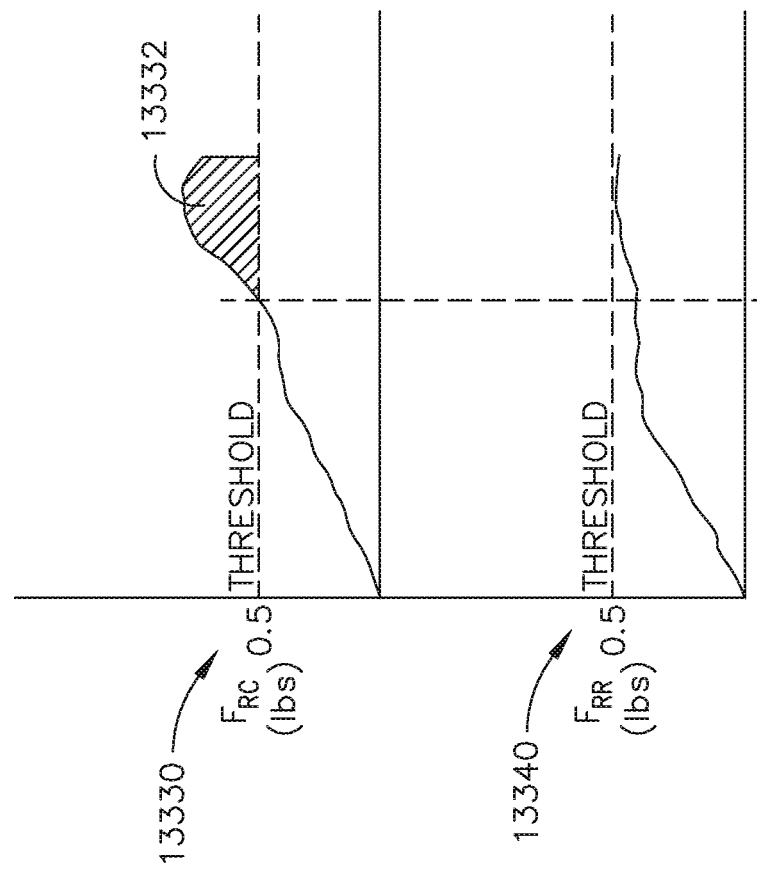
Figure 253:
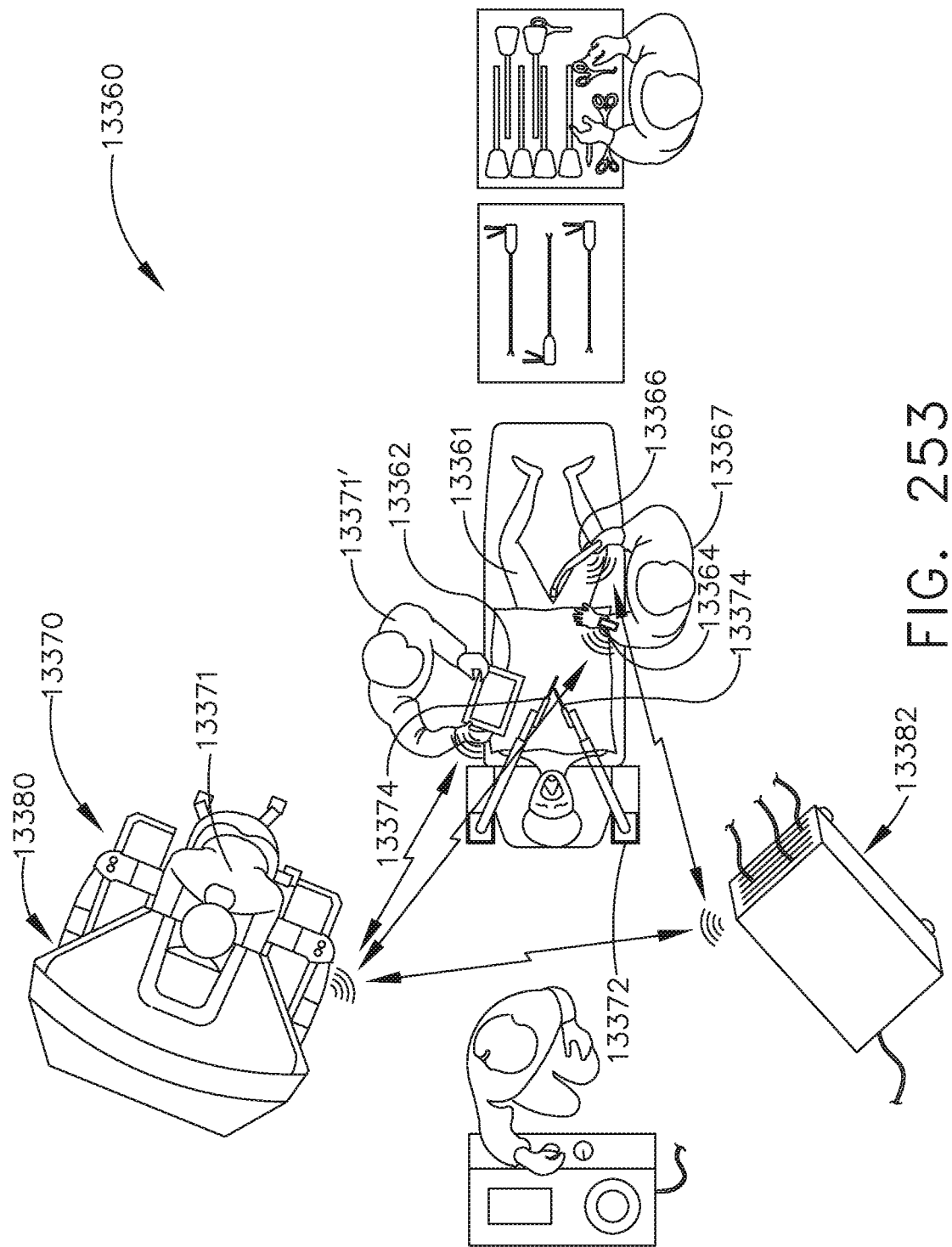
Figure 254:
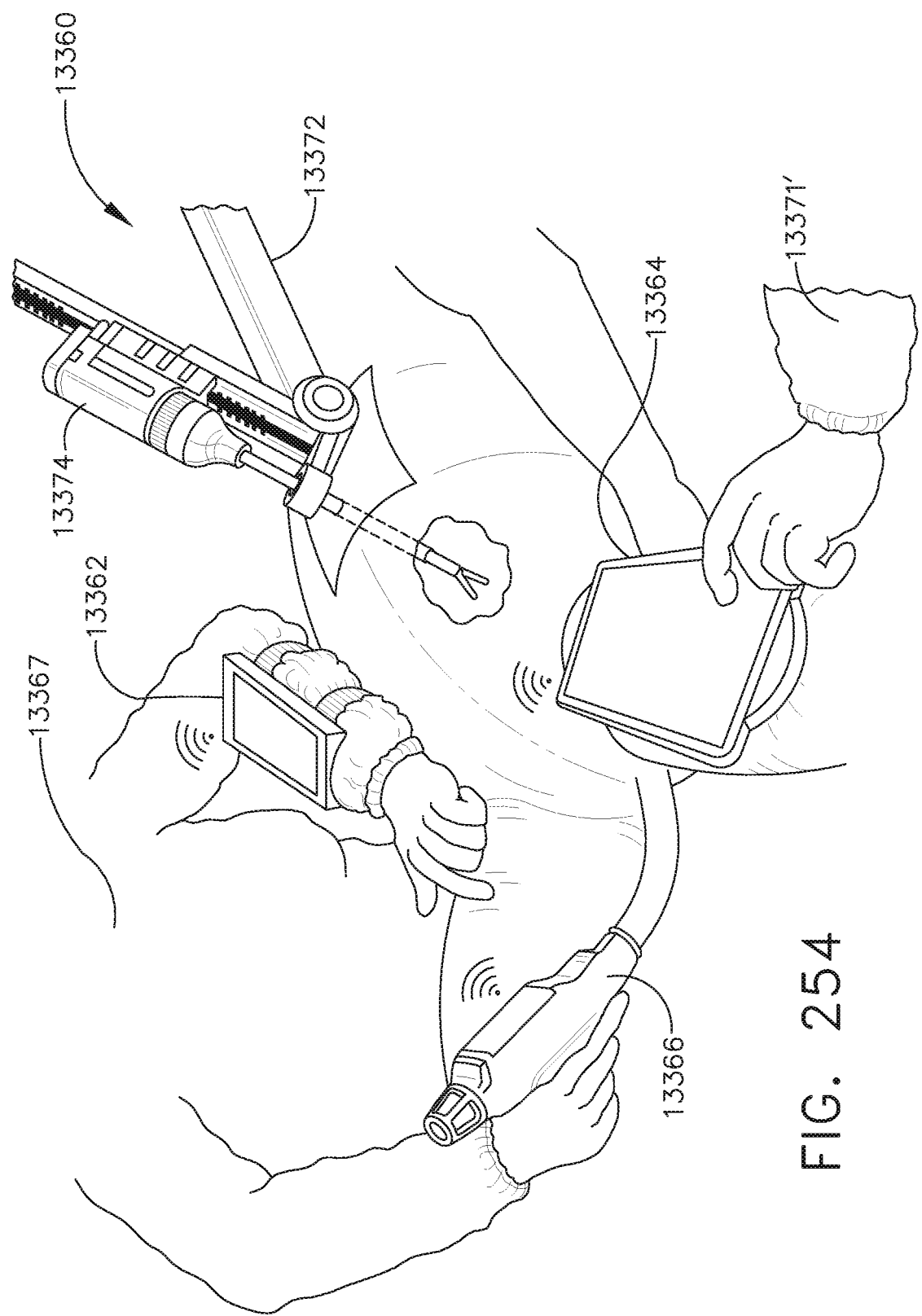
Figure 255:
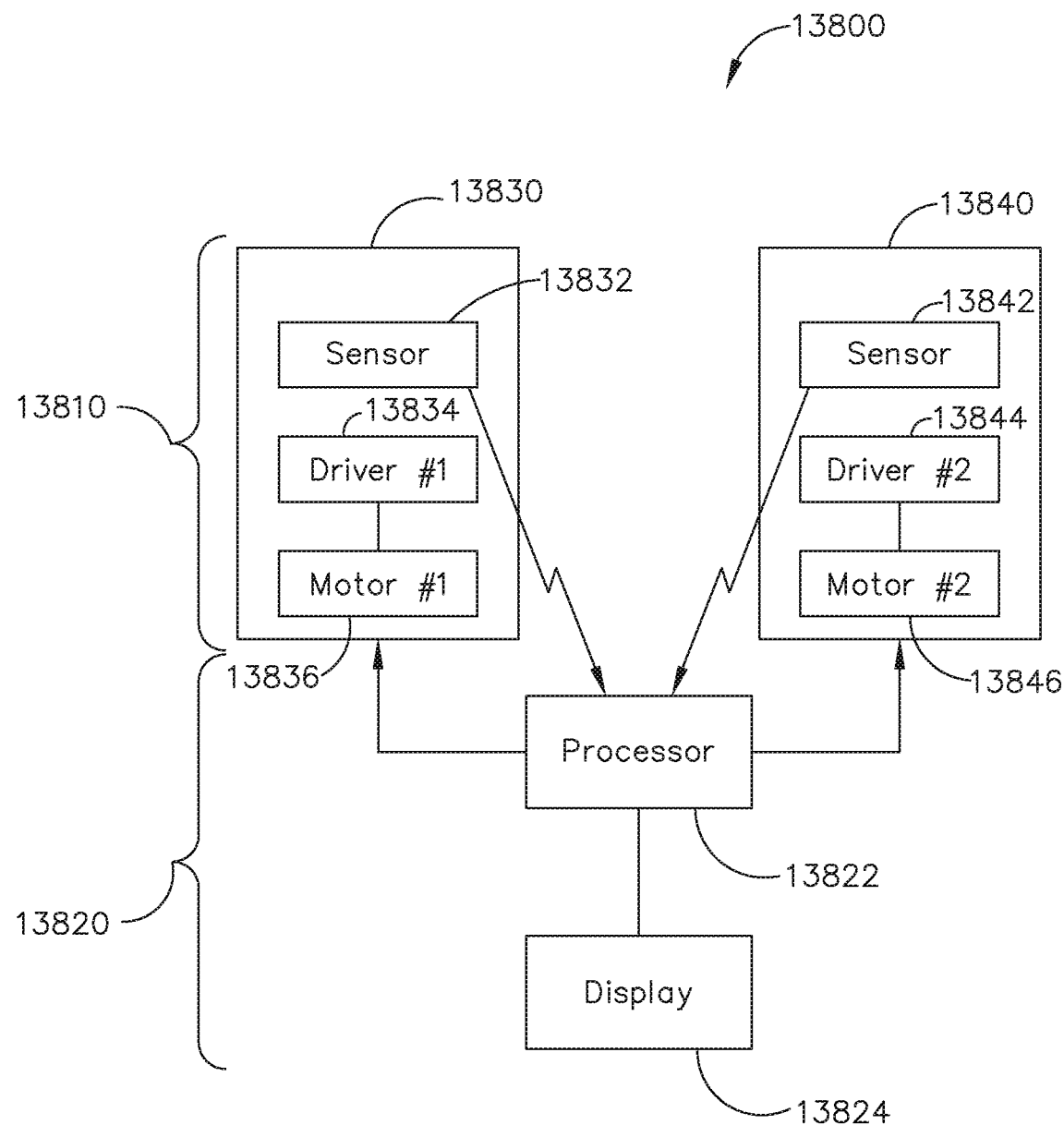
Figure 257:
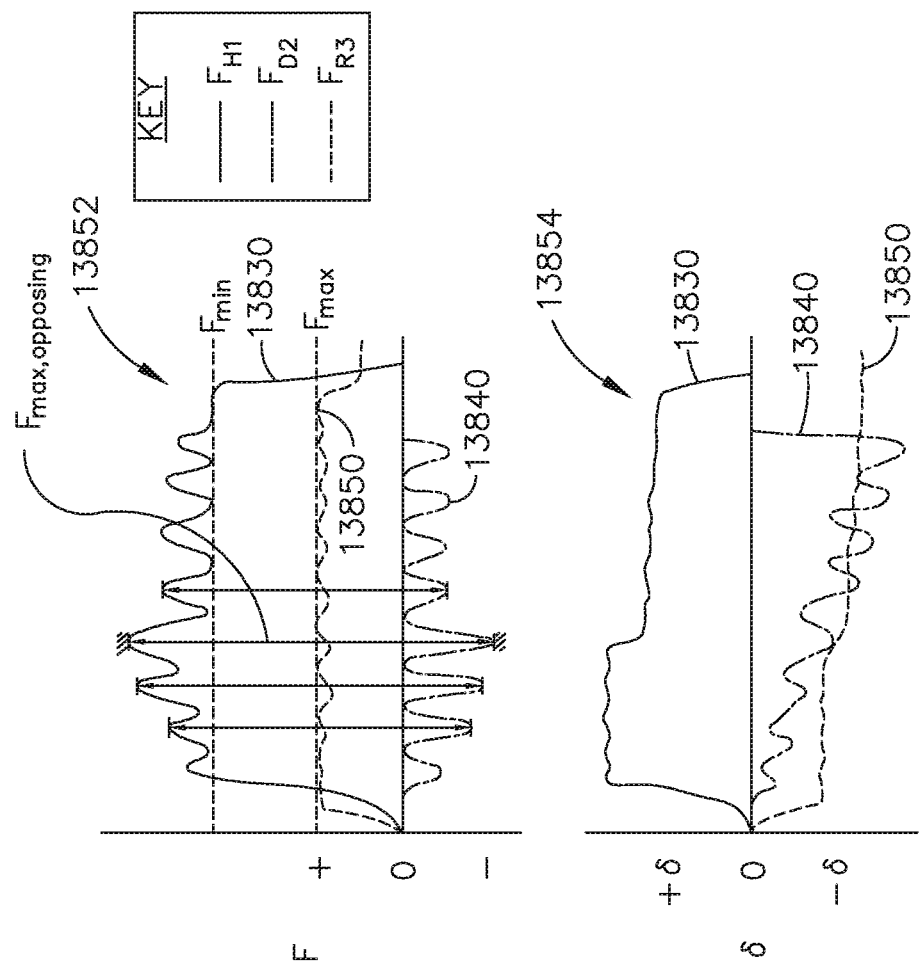
Figure 256:
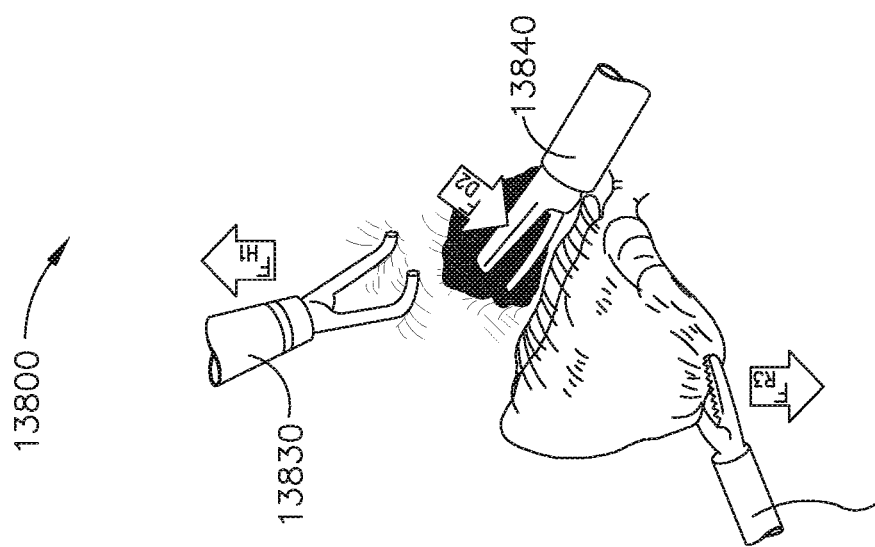
Figure 258:
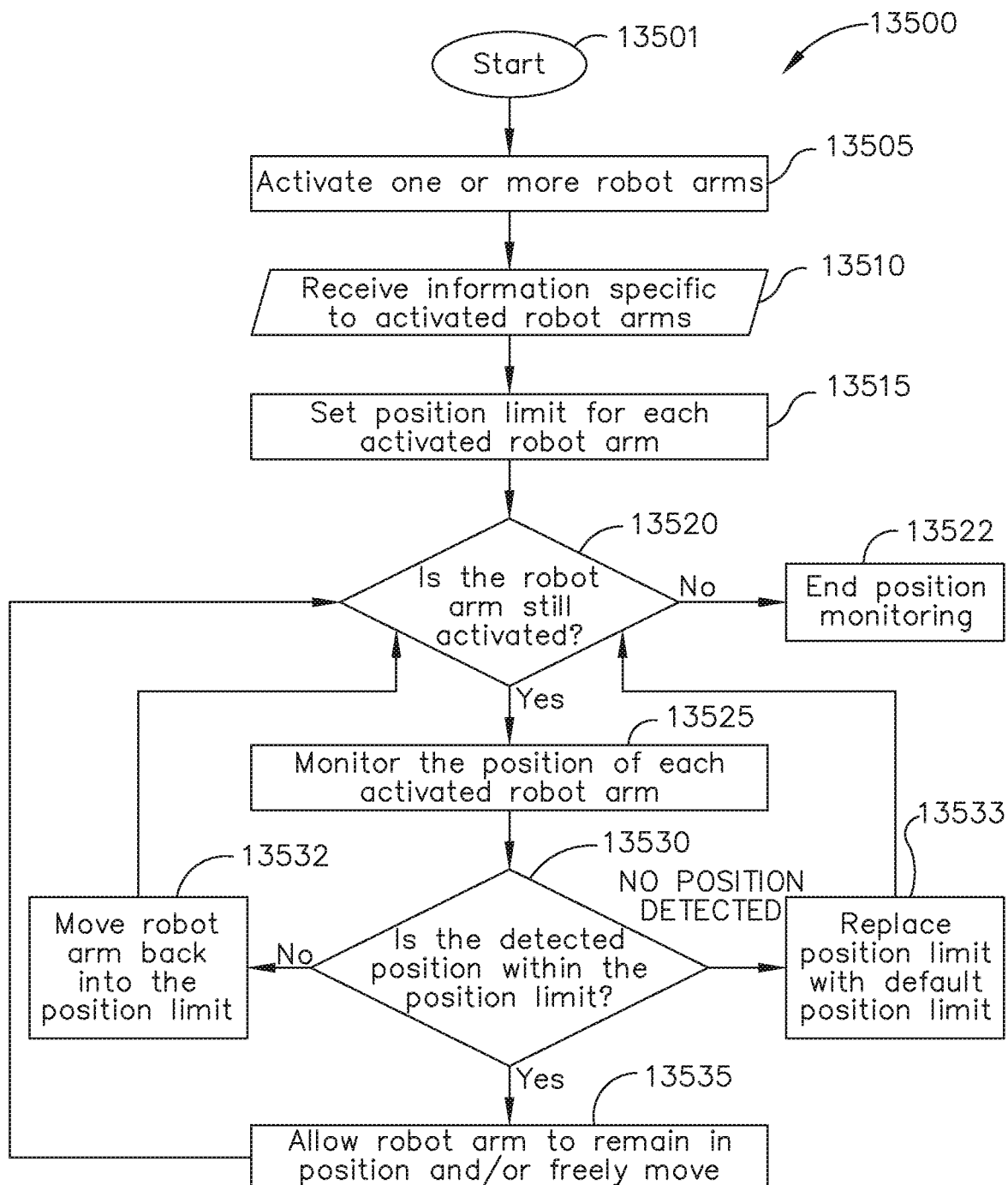
Figure 259:
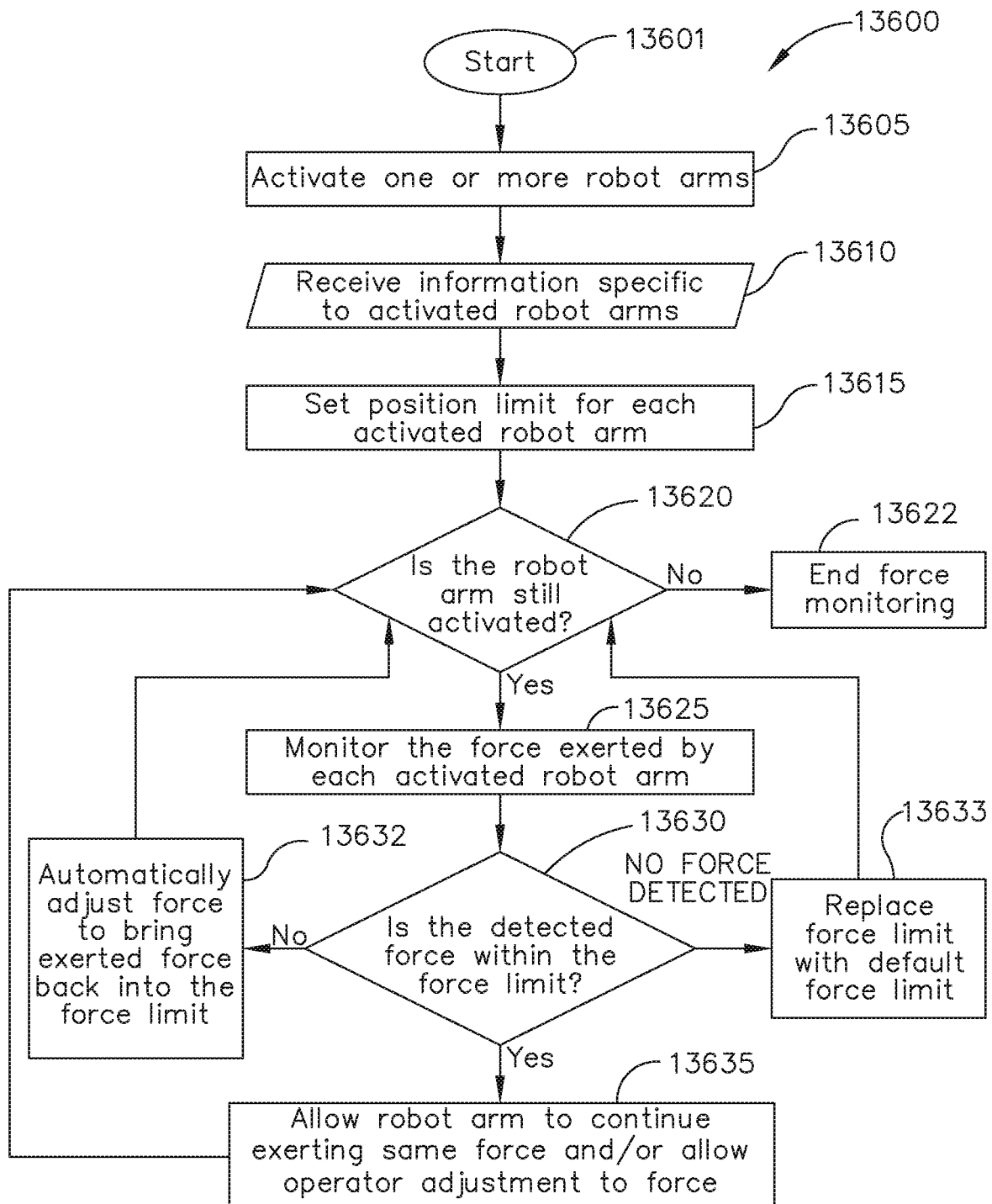
Figure 260:
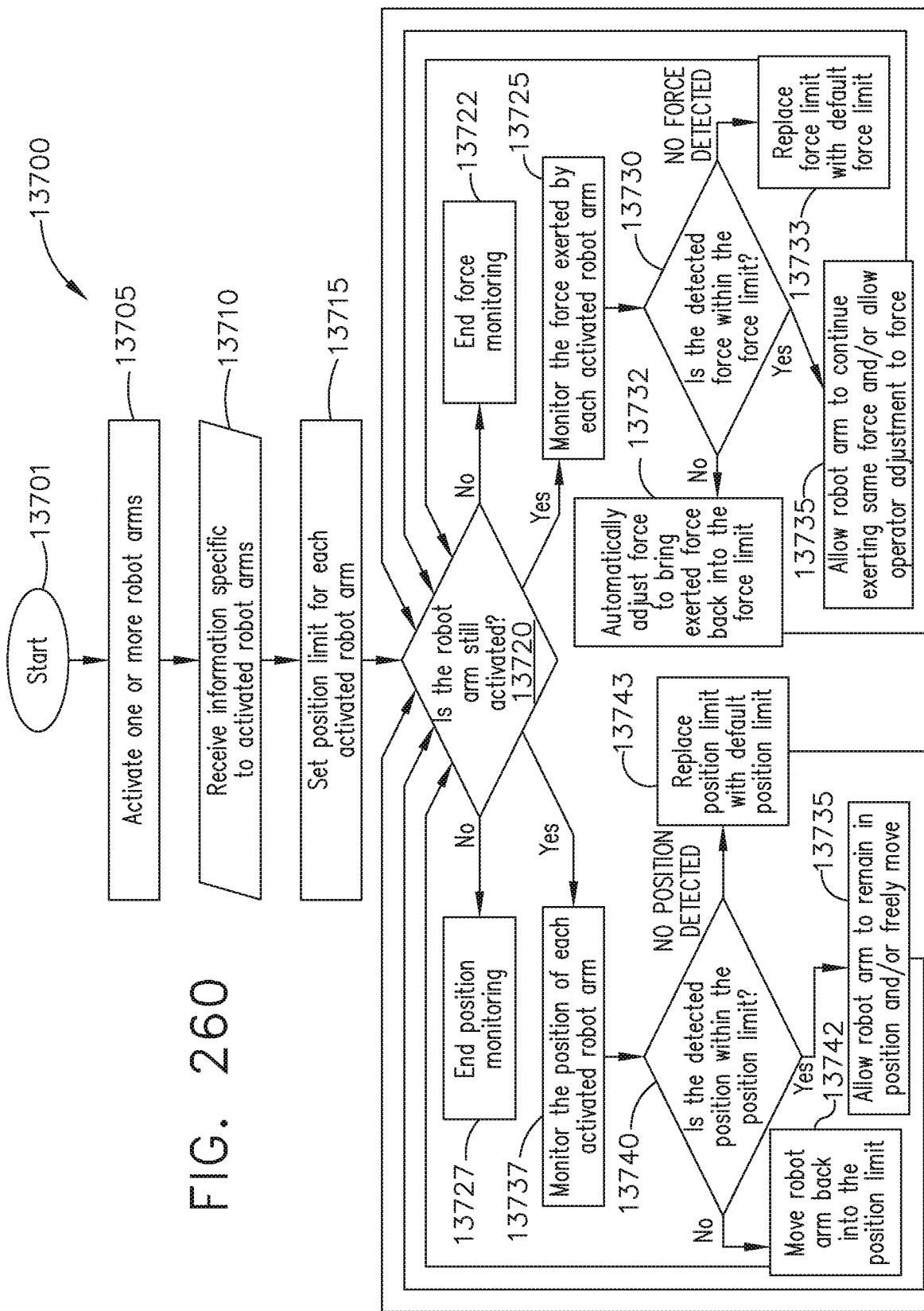
Figure 261:
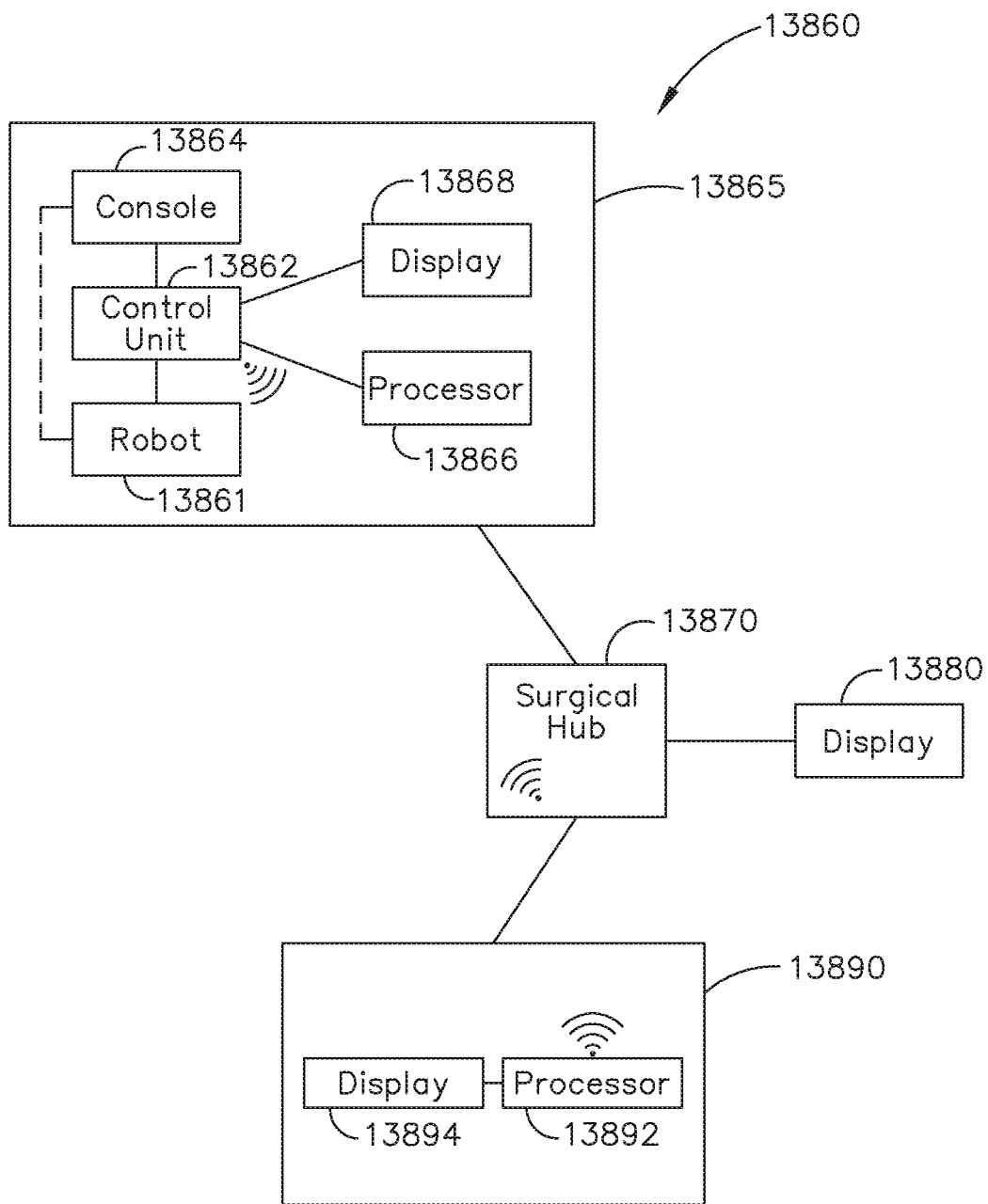
Figure 262:
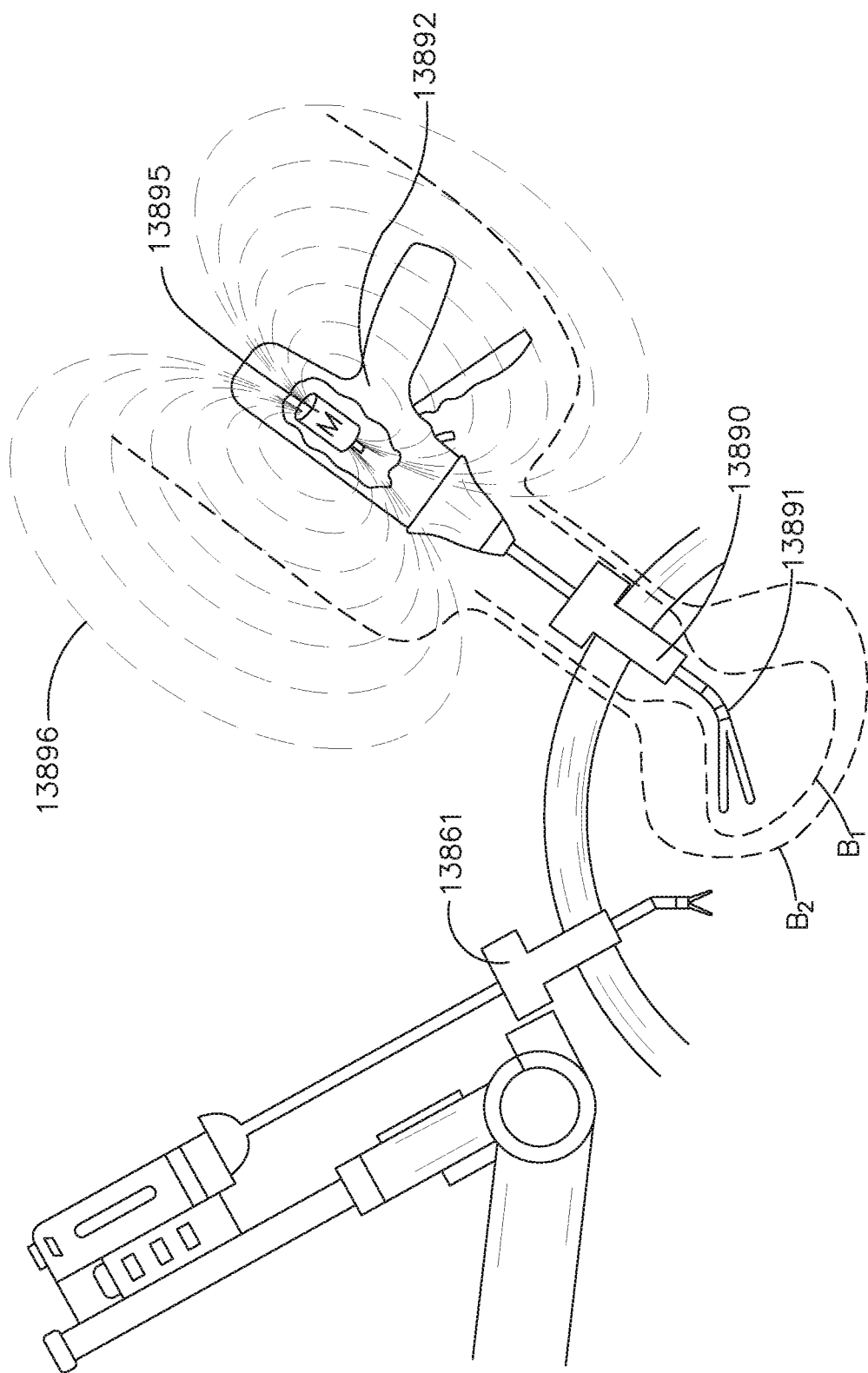
Figure 263:
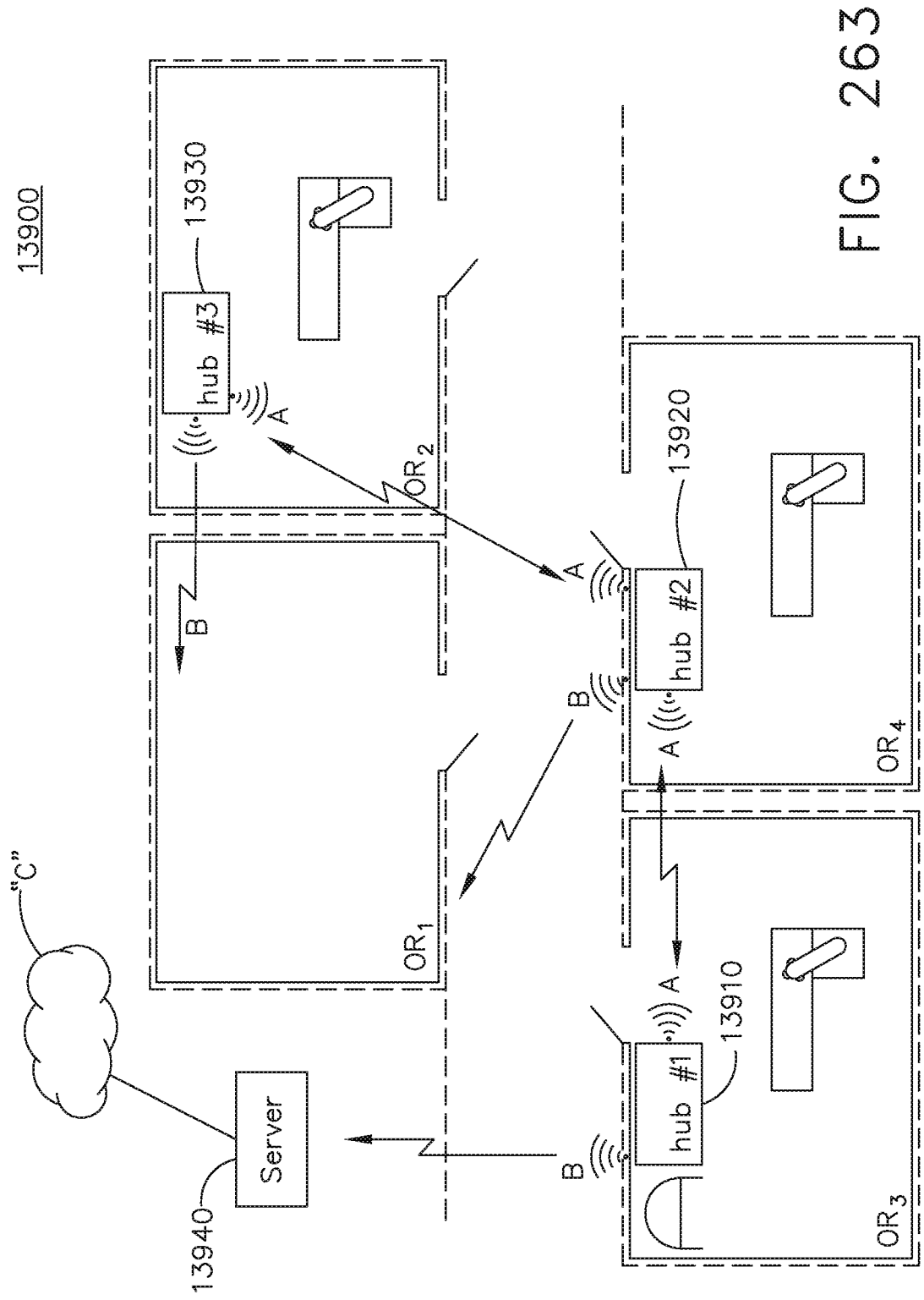
Figure 264:
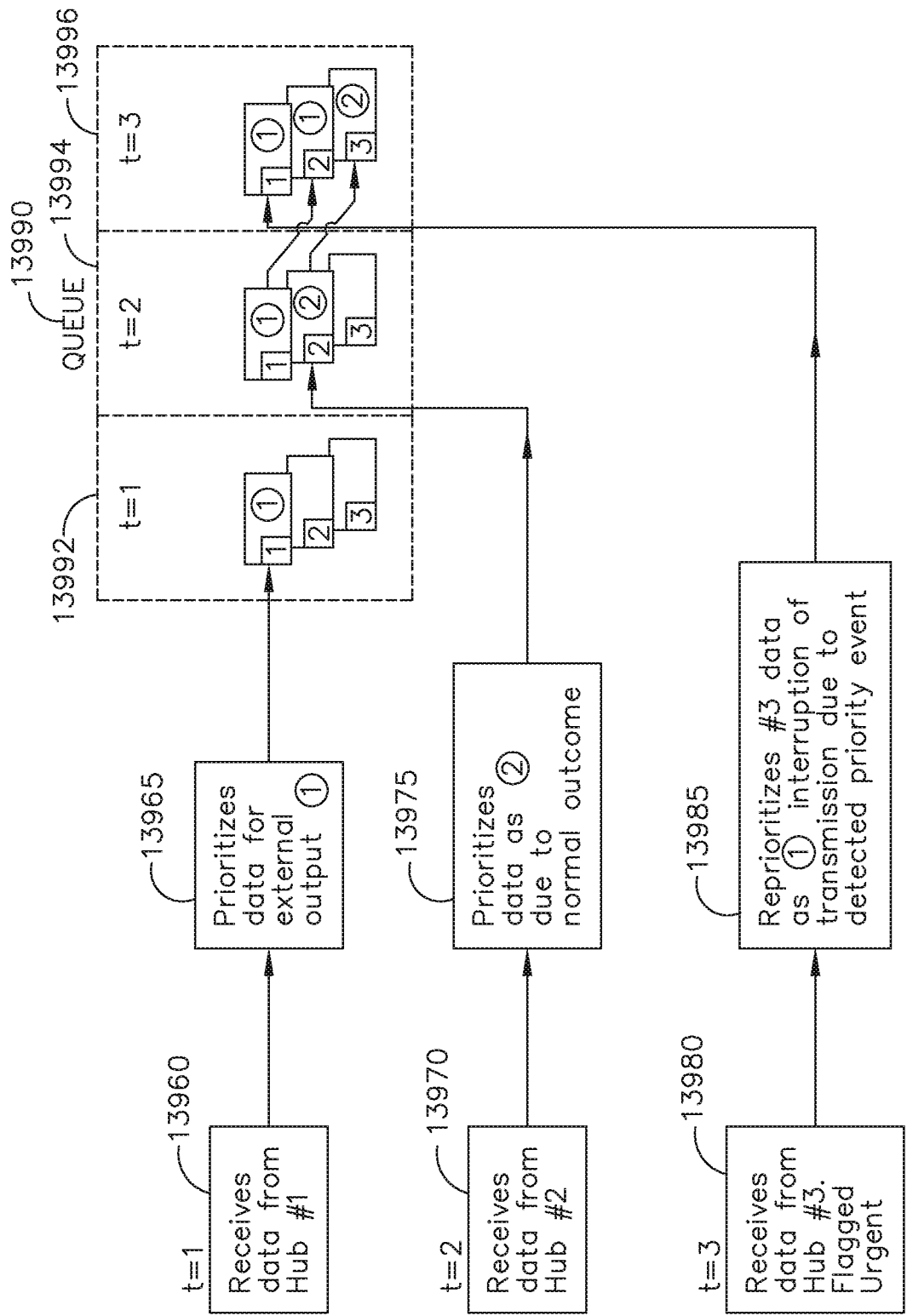
Figure 265:
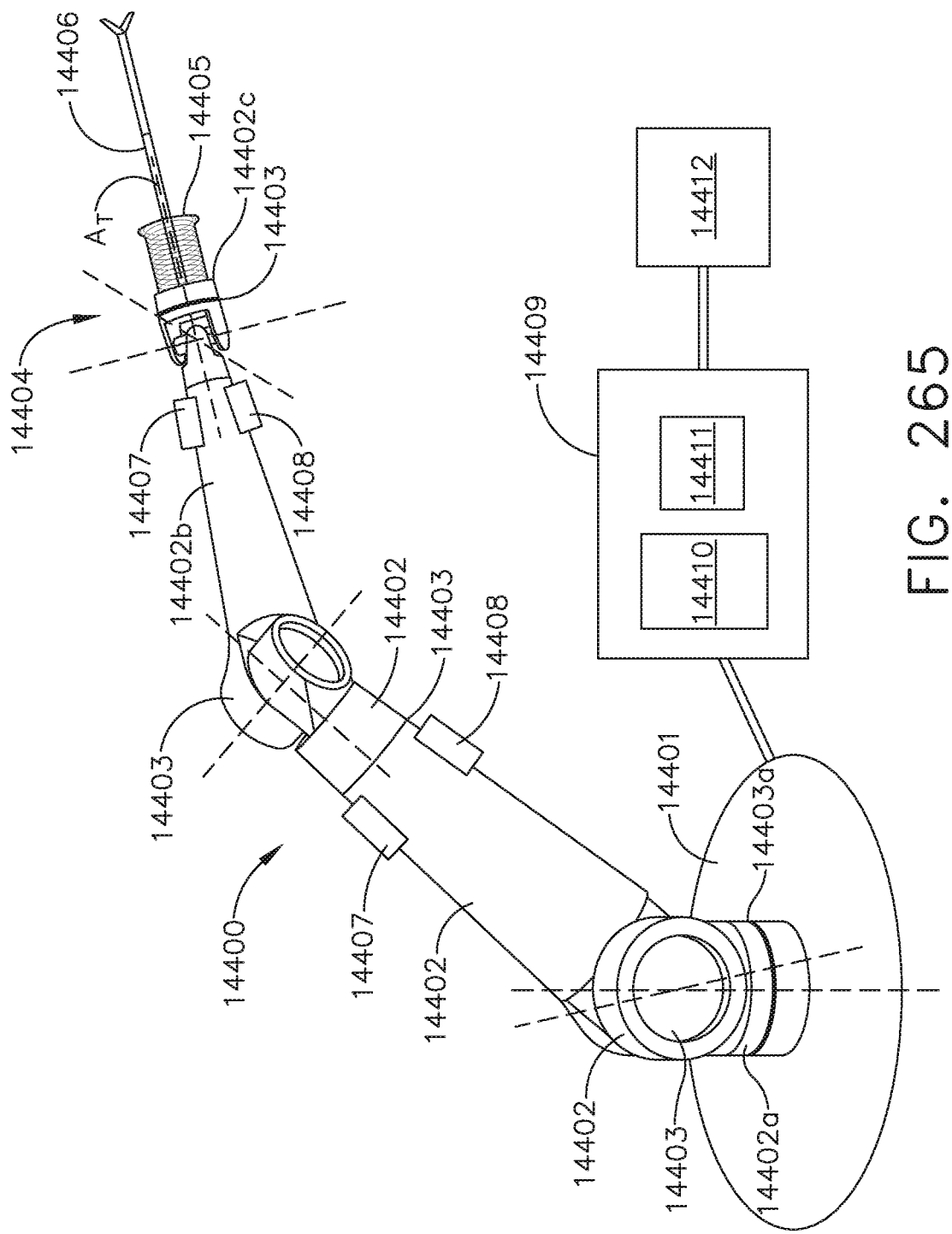
Figure 266:
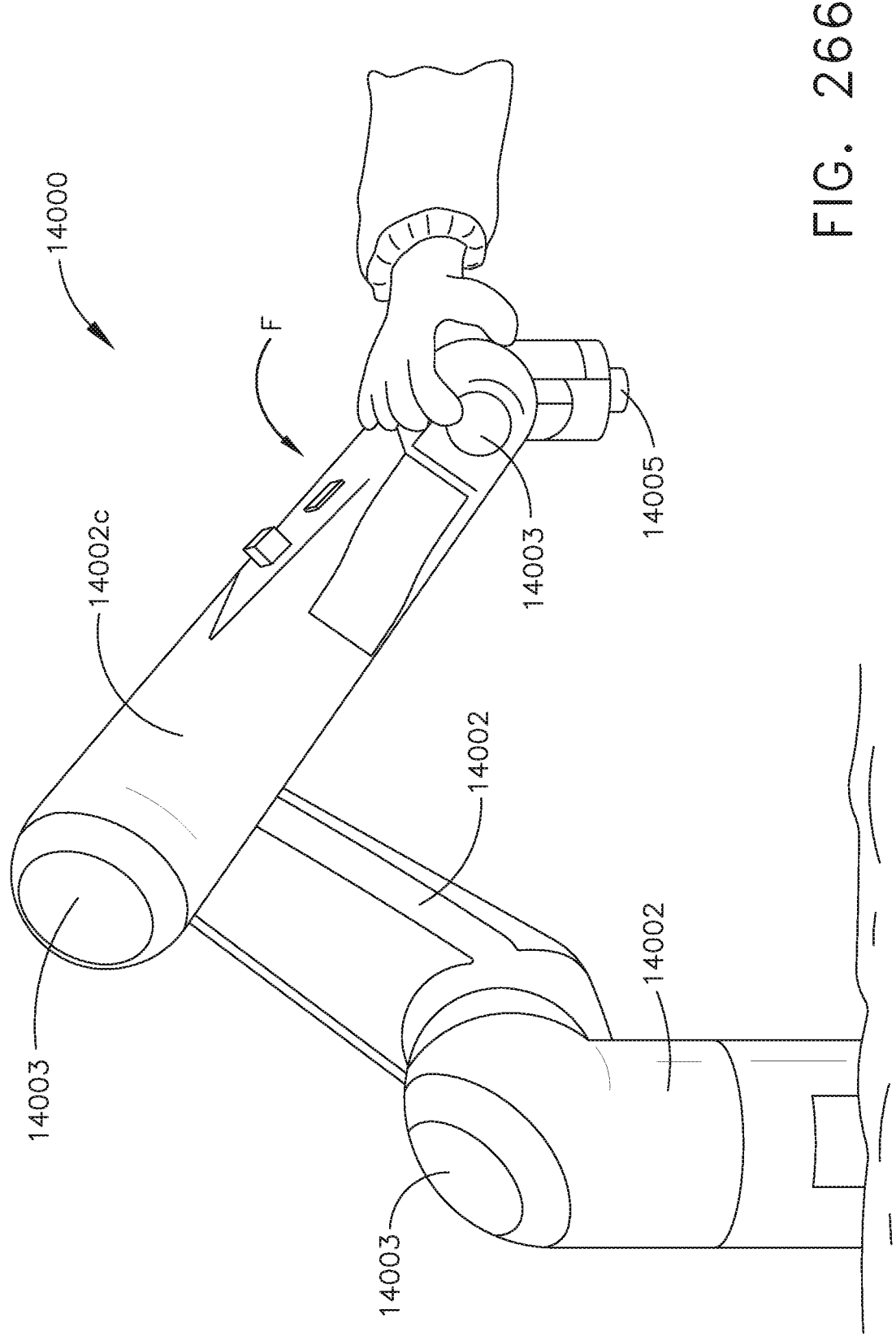
Figure 267:
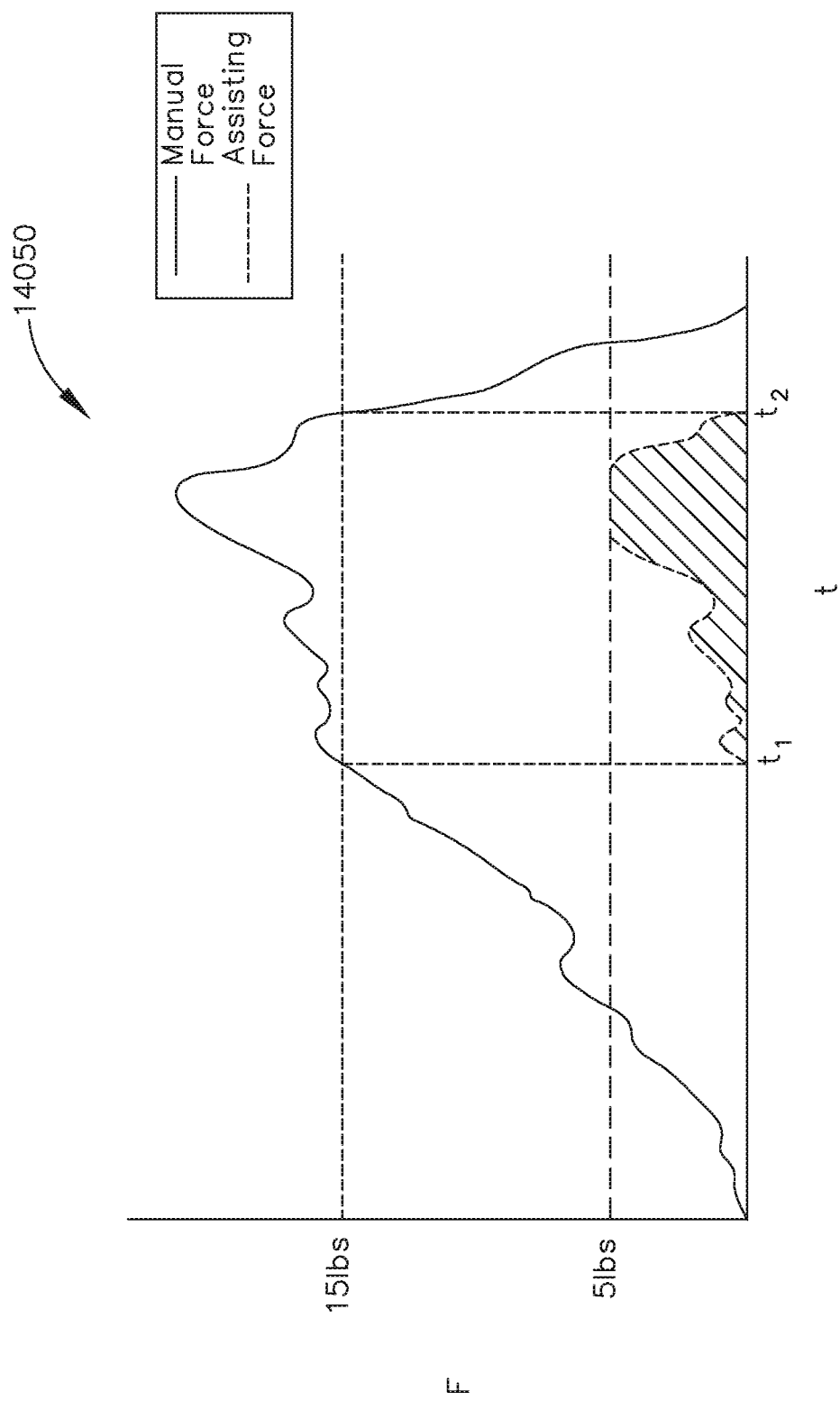

FIG. 142D is a side view of the virtual anatomical detail;

FIGS. 143A-143B illustrate a touchscreen display that may be used within the sterile field, in accordance with at least one aspect of the present disclosure, where:

FIG. 143A illustrates an image of a surgical site displayed on a touchscreen display in portrait mode;

FIG. 143B shows the touchscreen display rotated in landscape mode and the surgeon uses his index finger to scroll the image in the direction of the arrows;

FIG. 143C shows the surgeon using his index finger and thumb to pinch open the image in the direction of the arrows to zoom in;

FIG. 143D shows the surgeon using his index finger and thumb to pinch close the image in the direction of the arrows to zoom out; and FIG. 143E shows the touchscreen display rotated in two directions indicated by arrows to enable the surgeon to view the image in different orientations;

FIG. 144 illustrates a surgical site employing a smart retractor comprising a direct interface control to a surgical hub, in accordance with at least one aspect of the present disclosure;

FIG. 145 illustrates a surgical site with a smart flexible sticker display attached to the body of a patient, in accordance with at least one aspect of the present disclosure;

FIG. 146 is a logic flow diagram of a process depicting a control program or a logic configuration to communicate from inside a sterile field to a device located outside the sterile field, in accordance with at least one aspect of the present disclosure;

FIG. 147 illustrates a system for performing surgery, in accordance with at least one aspect of the present disclosure;

FIG. 148 illustrates a second layer of information overlaying a first layer of information, in accordance with at least one aspect of the present disclosure;

FIG. 149 depicts a perspective view of a surgeon using a surgical instrument that includes a handle assembly housing and a wireless circuit board during a surgical procedure, with the surgeon wearing a set of safety glasses, in accordance with at least one aspect of the present disclosure;

FIG. 150 is a schematic diagram of a feedback control system for controlling a surgical instrument, in accordance with at least one aspect of the present disclosure;

FIG. 151 illustrates a feedback controller that includes an on-screen display module and a heads up display (HUD) module, in accordance with at least one aspect of the present disclosure;

FIG. 152A illustrates a visualization system that may be incorporated into a surgical system, in accordance with at least one aspect of the present disclosure;

FIG. 152B illustrates a top plan view of a hand unit of the visualization system of FIG. 152A, in accordance with at least one aspect of the present disclosure;

FIG. 152C illustrates a side plan view of the hand unit depicted in FIG. 152A along with an imaging sensor disposed therein, in accordance with at least one aspect of the present disclosure;

FIG. 152D illustrates a plurality of an imaging sensors a depicted in FIG. 152C, in accordance with at least one aspect of the present disclosure;

FIG. 153A illustrates a plurality of laser emitters that may be incorporated in the visualization system of FIG. 152A, in accordance with at least one aspect of the present disclosure;

FIG. 153B illustrates illumination of an image sensor having a Bayer pattern of color filters, in accordance with at least one aspect of the present disclosure;

FIG. 153C illustrates a graphical representation of the operation of a pixel array for a plurality of frames, in accordance with at least one aspect of the present disclosure;

FIG. 153D illustrates a schematic of an example of an operation sequence of chrominance and luminance frames, in accordance with at least one aspect of the present disclosure;

FIG. 153E illustrates an example of sensor and emitter patterns, in accordance with at least one aspect of the present disclosure;

FIG. 153F illustrates a graphical representation of the operation of a pixel array, in accordance with at least one aspect of the present disclosure;

FIG. 154 illustrates a schematic of one example of instrumentation for NIR spectroscopy, according to one aspect of the present disclosure;

FIG. 155 illustrates schematically one example of instrumentation for determining NIRS based on Fourier transform infrared imaging, in accordance with at least one aspect of the present disclosure;

FIGS. 156A-C illustrate a change in wavelength of light scattered from moving blood cells, in accordance with at least one aspect of the present disclosure;

FIG. 157 illustrates an aspect of instrumentation that may be used to detect a Doppler shift in laser light scattered from portions of a tissue, in accordance with at least one aspect of the present disclosure;

FIG. 158 illustrates schematically some optical effects on light impinging on a tissue having subsurface structures, in accordance with at least one aspect of the present disclosure;

FIG. 159 illustrates an example of the effects on a Doppler analysis of light impinging on a tissue sample having subsurface structures, in accordance with at least one aspect of the present disclosure;

FIGS. 160A-C illustrate schematically the detection of moving blood cells at a tissue depth based on a laser Doppler analysis at a variety of laser wavelengths, in accordance with at least one aspect of the present disclosure;

FIG. 160D illustrates the effect of illuminating a CMOS imaging sensor with a plurality of light wavelengths over time, in accordance with at least one aspect of the present disclosure;

FIG. 161 illustrates an example of a use of Doppler imaging to detect the present of subsurface blood vessels, in accordance with at least one aspect of the present disclosure;

FIG. 162 illustrates a method to identify a subsurface blood vessel based on a Doppler shift of blue light due to blood cells flowing therethrough, in accordance with at least one aspect of the present disclosure;

FIG. 163 illustrates schematically localization of a deep subsurface blood vessel, in accordance with at least one aspect of the present disclosure;

FIG. 164 illustrates schematically localization of a shallow subsurface blood vessel, in accordance with at least one aspect of the present disclosure;

FIG. 165 illustrates a composite image comprising a surface image and an image of a subsurface blood vessel, in accordance with at least one aspect of the present disclosure;

FIG. 166 is a flow chart of a method for determining a depth of a surface feature in a piece of tissue, in accordance with at least one aspect of the present disclosure;

FIG. 167 illustrates the effect of the location and characteristics of non-vascular structures on light impinging on a tissue sample, in accordance with at least one aspect of the present disclosure;

FIG. 168 schematically depicts one example of components used in a full field OCT device, in accordance with at least one aspect of the present disclosure;

FIG. 169 illustrates schematically the effect of tissue anomalies on light reflected from a tissue sample, in accordance with at least one aspect of the present disclosure;

FIG. 170 illustrates an image display derived from a combination of tissue visualization modalities, in accordance with at least one aspect of the present disclosure;

FIGS. 171A-C illustrate several aspects of displays that may be provided to a surgeon for a visual identification of a combination of surface and sub-surface structures of a tissue in a surgical site, in accordance with at least one aspect of the present disclosure;

FIG. 172 is a flow chart of a method for providing information related to a characteristic of a tissue to a smart surgical instrument, in accordance with at least one aspect of the present disclosure;

FIGS. 173A and 173B illustrate a multi-pixel light sensor receiving by light reflected by a tissue illuminated by sequential exposure to red, green, blue, and infrared light, and red, green, blue, and ultraviolet laser light sources, respectively, in accordance with at least one aspect of the present disclosure;

FIGS. 174A and 174B illustrate the distal end of an elongated camera probe having a single light sensor and two light sensors, respectively, in accordance with at least one aspect of the present disclosure;

FIG. 174C illustrates a perspective view of an example of a monolithic sensor having a plurality of pixel arrays, in accordance with at least one aspect of the present disclosure;

FIG. 175 illustrates one example of a pair of fields of view available to two image sensors of an elongated camera probe, in accordance with at least one aspect of the present disclosure;

FIGS. 176A-D illustrate additional examples of a pair of fields of view available to two image sensors of an elongated camera probe, in accordance with at least one aspect of the present disclosure;

FIGS. 177A-C illustrate an example of the use of an imaging system incorporating the features disclosed in FIG. 176D, in accordance with at least one aspect of the present disclosure;

FIGS. 178A and 178B depict another example of the use of a dual imaging system, in accordance with at least one aspect of the present disclosure;

FIGS. 179A-C illustrate examples of a sequence of surgical steps which may benefit from the use of multi-image analysis at the surgical site, in accordance with at least one aspect of the present disclosure;

FIG. 180 is a block diagram of the computer-implemented interactive surgical system, in accordance with at least one aspect of the present disclosure;

FIG. 181 is a block diagram which illustrates the functional architecture of the computer-implemented interactive surgical system, in accordance with at least one aspect of the present disclosure;

FIG. 182 is an example illustration of a tabulation of various resources correlated to particular types of surgical categories, in accordance with at least one aspect of the present disclosure;

FIG. 183 provides an example illustration of how data is analyzed by the cloud system to provide a comparison between multiple facilities to compare use of resources, in accordance with at least one aspect of the present disclosure;

FIG. 184 illustrates one example of how the cloud system may determine efficacy trends from an aggregated set of data across whole regions, in accordance with at least one aspect of the present disclosure;

FIG. 185 provides an example illustration of some types of analysis the cloud system may be configured to perform to provide the predicting modeling, in accordance with at least one aspect of the present disclosure;

FIG. 186 provides a graphical illustration of a type of example analysis the cloud system may perform to provide these recommendations, in accordance with at least one aspect of the present disclosure;

FIG. 187 provides an illustration of how the cloud system may conduct analysis to identify a statistical correlation to a local issue that is tied to how a device is used in the localized setting, in accordance with at least one aspect of the present disclosure;

FIG. 188 provides a graphical illustration of an example of how some devices may satisfy an equivalent use compared to an intended device, and that the cloud system may determine such equivalent use, in accordance with at least one aspect of the present disclosure;

FIG. 189 provides various examples of how some data may be used as variables in deciding how a post-operative decision tree may branch out, in accordance with at least one aspect of the present disclosure;

FIG. 190 illustrates a block diagram of a computer-implemented interactive surgical system that is configured to adaptively generate control program updates for modular devices, in accordance with at least one aspect of the present disclosure;

FIG. 191 illustrates a logic flow diagram of a process for updating the control program of a modular device, in accordance with at least one aspect of the present disclosure;

FIG. 192 illustrates a diagram of an illustrative analytics system updating a surgical instrument control program, in accordance with at least one aspect of the present disclosure;

FIG. 193 illustrates a diagram of an analytics system pushing an update to a modular device through a surgical hub, in accordance with at least one aspect of the present disclosure;

FIG. 194 illustrates a diagram of a computer-implemented interactive surgical system that is configured to adaptively generate control program updates for surgical hubs, in accordance with at least one aspect of the present disclosure;

FIG. 195 illustrates a logic flow diagram of a process for updating the control program of a surgical hub, in accordance with at least one aspect of the present disclosure;

FIG. 196 illustrates a logic flow diagram of a process for updating the data analysis algorithm of a control program of a surgical hub, in accordance with at least one aspect of the present disclosure;

FIG. 197 provides an illustration of example functionality by a cloud medical analytics system for providing improved security and authentication to multiple medical facilities that are interconnected, in accordance with at least one aspect of the present disclosure;

FIG. 198 is a flow diagram of the computer-implemented interactive surgical system programmed to use screening criteria to determine critical data and to push requests to a surgical hub to obtain additional data, in accordance with at least one aspect of the present disclosure;

FIG. 199 is a flow diagram of an aspect of responding to critical data by the computer-implemented interactive surgical system, in accordance with at least one aspect of the present disclosure;

FIG. 200 is a flow diagram of an aspect of data sorting and prioritization by the computer-implemented interactive surgical system, in accordance with at least one aspect of the present disclosure;

FIG. 201 illustrates an example system for implementing automated inventory control, in accordance with at least one aspect of the present disclosure;

FIG. 202 illustrates one example of an institution's cloud interface through which a proposed surgical procedure may be entered, in accordance with at least one aspect of the present disclosure;

FIG. 203 illustrates one example of an institution's cloud interface through which a cloud-based system provides knowledge regarding the availability and/or usability of inventory items associated with an entered surgical procedure based on system-defined constraints, in accordance with at least one aspect of the present disclosure;

FIG. 204 illustrates a surgical tool including modular components wherein the status of each modular component is evaluated based on system-defined constraints, in accordance with at least one aspect of the present disclosure;

FIG. 205 is a schematic of a robotic surgical system, in accordance with one aspect of the present disclosure;

FIG. 206 is a plan view of a minimally invasive telesurgically-controlled robotic surgical system being used to perform a surgery, in accordance with one aspect of the present disclosure;

FIG. 207 is a perspective view of a surgeon's control console of the surgical system of FIG. 206, in accordance with one aspect of the present disclosure;

FIG. 208 is a perspective view of an electronics cart of the surgical system of FIG. 206, in accordance with one aspect of the present disclosure;

FIG. 209 is a diagram of a telesurgically-controlled surgical system, in accordance with one aspect of the present disclosure;

FIG. 210 is a partial view of a patient side cart of the surgical system of FIG. 206, in accordance with one aspect of the present disclosure;

FIG. 211 is a front view of a telesurgically-operated surgery tool for the surgical system of FIG. 206, in accordance with one aspect of the present disclosure;

FIG. 212 is a control schematic diagram of a telesurgically-controlled surgical system, in accordance with one aspect of the present disclosure;

FIG. 213 is an elevation view of a robotic surgical system and various communication paths thereof, in accordance with one aspect of the present disclosure;

FIG. 214 is a perspective, exploded view of an interface between a robotic tool and a tool mounting portion of the robotic surgical system of FIG. 213;

FIG. 215 is a detail view of the interface of FIG. 214, in accordance with one aspect of the present disclosure;

FIG. 216 is a perspective view of a bipolar radio frequency (RF) robotic tool having a smoke evacuation pump for use with a robotic surgical system, in accordance with one aspect of the present disclosure;

FIG. 217 is a perspective view of the end effector of the bipolar radio frequency robotic tool of FIG. 216 depicting the end effector clamping and treating tissue, in accordance with one aspect of the present disclosure;

FIG. 218 is a plan view of the tool drive interface of the bipolar radio frequency robotic tool of FIG. 216 with components removed for clarity, in accordance with one aspect of the present disclosure;

FIG. 219 is a plan view of an ultrasonic robotic tool having cooling and insufflation features for use with a robotic surgical system, in accordance with one aspect of the present disclosure;

FIG. 220 is a flow chart of a control algorithm for a robotic tool for use with a robotic surgical system, in accordance with one aspect of the present disclosure;

FIG. 221 is a perspective view of a drive system for a robotic surgical tool, in accordance with one aspect of the present disclosure;

FIG. 222 is an exploded perspective view of the drive system of FIG. 221, in accordance with at least one aspect of the present disclosure;

FIG. 223 is a perspective, partial cross-section view of a proximal housing of the robotic surgical tool of FIG. 221, depicting a transmission arrangement within the proximal housing, in accordance with at least one aspect of the present disclosure;

FIG. 224 is an exploded perspective view of the transmission arrangement of FIG. 223, in accordance with one aspect of the present disclosure;

FIG. 225 is an exploded perspective view of the transmission arrangement of FIG. 223 with various parts removed for clarity, depicting the transmission arrangement in a first configuration in which a first cooperative drive is drivingly coupled to a first output shaft and a second cooperative drive is drivingly coupled to a second output shaft, in accordance with one aspect of the present disclosure;

FIG. 226 is an exploded perspective view of the transmission arrangement of FIG. 223 with various parts removed for clarity, depicting the transmission arrangement in a second configuration in which the first cooperative drive and the second cooperative drive are drivingly coupled to a third output shaft, in accordance with one aspect of the present disclosure;

FIG. 227 is an exploded perspective view of the transmission arrangement of FIG. 223 with various parts removed for clarity, depicting the transmission arrangement in a third configuration in which the first cooperative drive and the second cooperative drive are drivingly coupled to a fourth output shaft, in accordance with one aspect of the present disclosure;

FIG. 228 is an exploded, cross-section elevation view of the transmission arrangement of FIG. 223, in accordance with at least one aspect of the present disclosure;

FIG. 229 is a graphical display of output torque for different surgical functions of the robotic surgical tool of FIG. 221, in accordance with at least one aspect of the present disclosure;

FIG. 230 is a perspective view of the robotic surgical tool of FIG. 221 in an unactuated configuration, in accordance with one aspect of the present disclosure;

FIG. 231 is a perspective view of the robotic surgical tool of FIG. 221 in an articulated configuration, in accordance with one aspect of the present disclosure;

FIG. 232 is a perspective view of the robotic surgical tool of FIG. 221 in a rotated configuration, in accordance with one aspect of the present disclosure;

FIG. 233 is a perspective view of the robotic surgical tool of FIG. 221 in a clamped and fired configuration, in accordance with one aspect of the present disclosure;

FIG. 234 is a view of robotically-controlled end effectors at a surgical site, in accordance with one aspect of the present disclosure;

FIG. 235 is a view of the robotically-controlled end effectors of FIG. 234, in accordance with one aspect of the present disclosure;

FIG. 236 is a graphical display of force and displacement over time for one of the robotically-controlled end effectors of FIG. 234, in accordance with one aspect of the present disclosure;

FIG. 237 is a flow chart of a control algorithm for one a surgical tool for use with a robotic surgical system, in accordance with one aspect of the present disclosure;

FIG. 238 is an elevation view of a surgical procedure involving a robotic surgical system and a handheld surgical instrument and depicting multiple displays in the surgical theater, in accordance with one aspect of the present disclosure;

FIG. 239 is a schematic of a robotic surgical system, in accordance with at least one aspect of the present disclosure;

FIG. 240 is a block diagram of control components for the robotic surgical system of FIG. 239, in accordance with at least one aspect of the present disclosure;

FIG. 241A is an elevation view of an ultrasonic surgical tool positioned out of contact with tissue, in accordance with at least one aspect of the present disclosure;

FIG. 241B is an elevation view of the ultrasonic surgical tool of FIG. 241A positioned in abutting contact with tissue, in accordance with at least one aspect of the present disclosure;

FIG. 242A is an elevation view of a monopolar cautery pencil positioned out of contact with tissue, in accordance with at least one aspect of the present disclosure;

FIG. 242B is an elevation view of the monopolar cautery pencil of FIG. 242A positioned in abutting contact with tissue, in accordance with at least one aspect of the present disclosure;

FIG. 243 is a graphical display of continuity and current over time for the ultrasonic surgical tool of FIGS. 241A and 241B, in accordance with at least one aspect of the present disclosure;

FIG. 244 illustrates an end effector comprising radio frequency (RF) data sensors located on a jaw member, in accordance with at least one aspect of the present disclosure;

FIG. 245 illustrates the sensors shown in FIG. 244 mounted to or formed integrally with a flexible circuit, in accordance with at least one aspect of the present disclosure;

FIG. 246 is a flow chart depicting an automatic activation mode of a surgical instrument, in accordance with at least one aspect of the present disclosure;

FIG. 247 is a perspective view of an end effector of a bipolar radio frequency (RF) surgical tool having a smoke evacuation pump for use with a robotic surgical system, depicting the surgical tool clamping and treating tissue, in accordance with at least one aspect of the present disclosure;

FIG. 248 is a block diagram of a surgical system comprising a robotic surgical system, a handheld surgical instrument, and a surgical hub, in accordance with at least one aspect of the present disclosure;

FIG. 249 is a perspective view of a handle portion of a handheld surgical instrument including a display and further depicting a detail view of the display depicting information from the instrument itself, in accordance with at least one aspect of the present disclosure;

FIG. 250 is a perspective view of the handle portion of the handheld surgical instrument of FIG. 249 depicting the instrument paired with a surgical hub and further including a detail view of the display depicting information from the surgical hub, in accordance with at least one aspect of the present disclosure;

FIG. 251 is a schematic of a colon resection procedure, in accordance with at least one aspect of the present disclosure;

FIG. 252 is a graphical display of force over time for the colon resection procedure displayed on the instrument display in FIG. 251, in accordance with at least one aspect of the present disclosure;

FIG. 253 is a schematic of a robotic surgical system during a surgical procedure including a plurality of hubs and interactive secondary displays, in accordance with at least one aspect of the present disclosure;

FIG. 254 is a detail view of the interactive secondary displays of FIG. 253, in accordance with at least one aspect of the present disclosure;

FIG. 255 is a block diagram of a robotic surgical system comprising more than one robotic arm, in accordance with at least one aspect of the present disclosure;

FIG. 256 is a schematic of a surgical procedure utilizing the robotic surgical system of FIG. 255, in accordance with at least one aspect of the present disclosure;

FIG. 257 shows graphical representations of forces and positional displacements experienced by the robotic arms of FIG. 255, in accordance with at least one aspect of the present disclosure;

FIG. 258 is a flow chart depicting an algorithm for controlling the position of the robotic arms of a robotic surgical system, in accordance with at least one aspect of the present disclosure;

FIG. 259 is a flow chart depicting an algorithm for controlling the forces exerted by robotic arms of a robotic surgical system, in accordance with at least one aspect of the present disclosure;

FIG. 260 is a flow chart depicting an algorithm for monitoring the position and forces exerted by robotic arms of a robotic surgical system, in accordance with at least one aspect of the present disclosure;

FIG. 261 is a block diagram of a surgical system comprising a robotic surgical system, a powered handheld surgical instrument, and a surgical hub, in accordance with at least one aspect of the present disclosure;

FIG. 262 is a perspective view of a robotic tool and a handheld surgical instrument during a surgical procedure, in accordance with at least one aspect of the present disclosure;

FIG. 263 is a schematic depicting communication links between surgical hubs and a primary server, in accordance with at least one aspect of the present disclosure;

FIG. 264 is a flow chart depicting a queue for external output of data received from the various surgical hubs of FIG. 263, in accordance with at least one aspect of the present disclosure;

FIG. 265 is a perspective view of a robot arm of a robotic surgical system and schematically depicts additional components of the robotic surgical system, in accordance with one aspect of the present disclosure;

FIG. 266 is a perspective view of a robotic arm of a robotic surgical system, and further depicts an operator manually adjusting the position of the robotic arm, in accordance with one aspect of the present disclosure;

FIG. 267 is a graphical display of force over time of the robotic arm of FIG. 266 in a passive power assist mode, in accordance with one aspect of the present disclosure;

FIG. 268 is a perspective view of a robotic arm and a secondary interactive display within a sterile field, in accordance with at least one aspect of the present disclosure.

Figure 272:
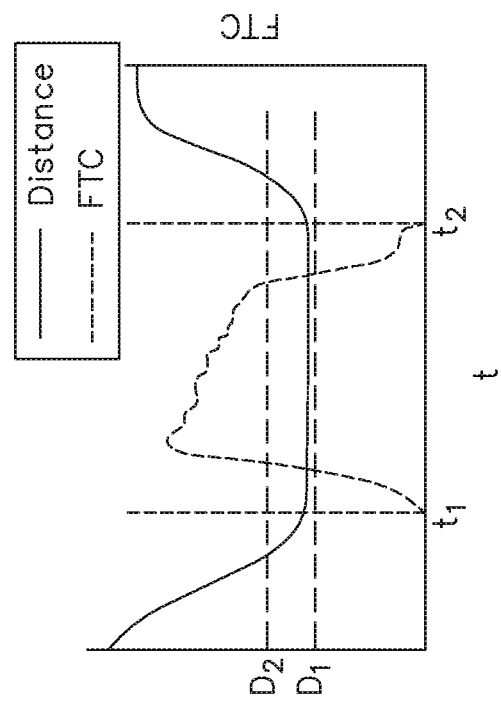
Figure 271:
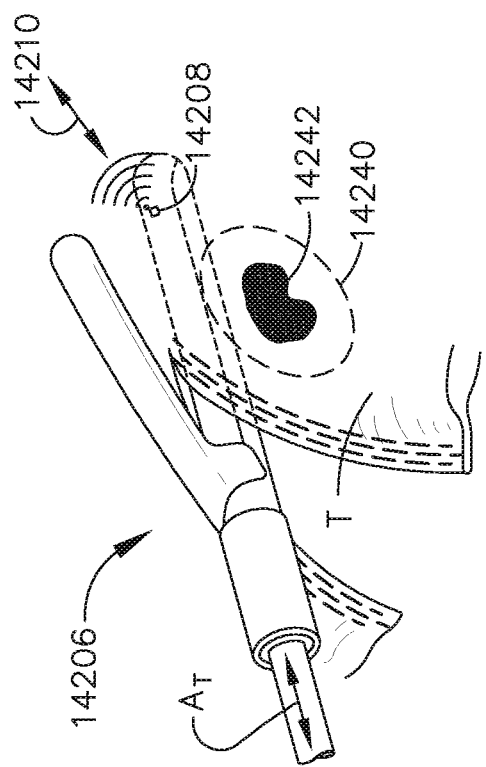
Figures 273, 273A:
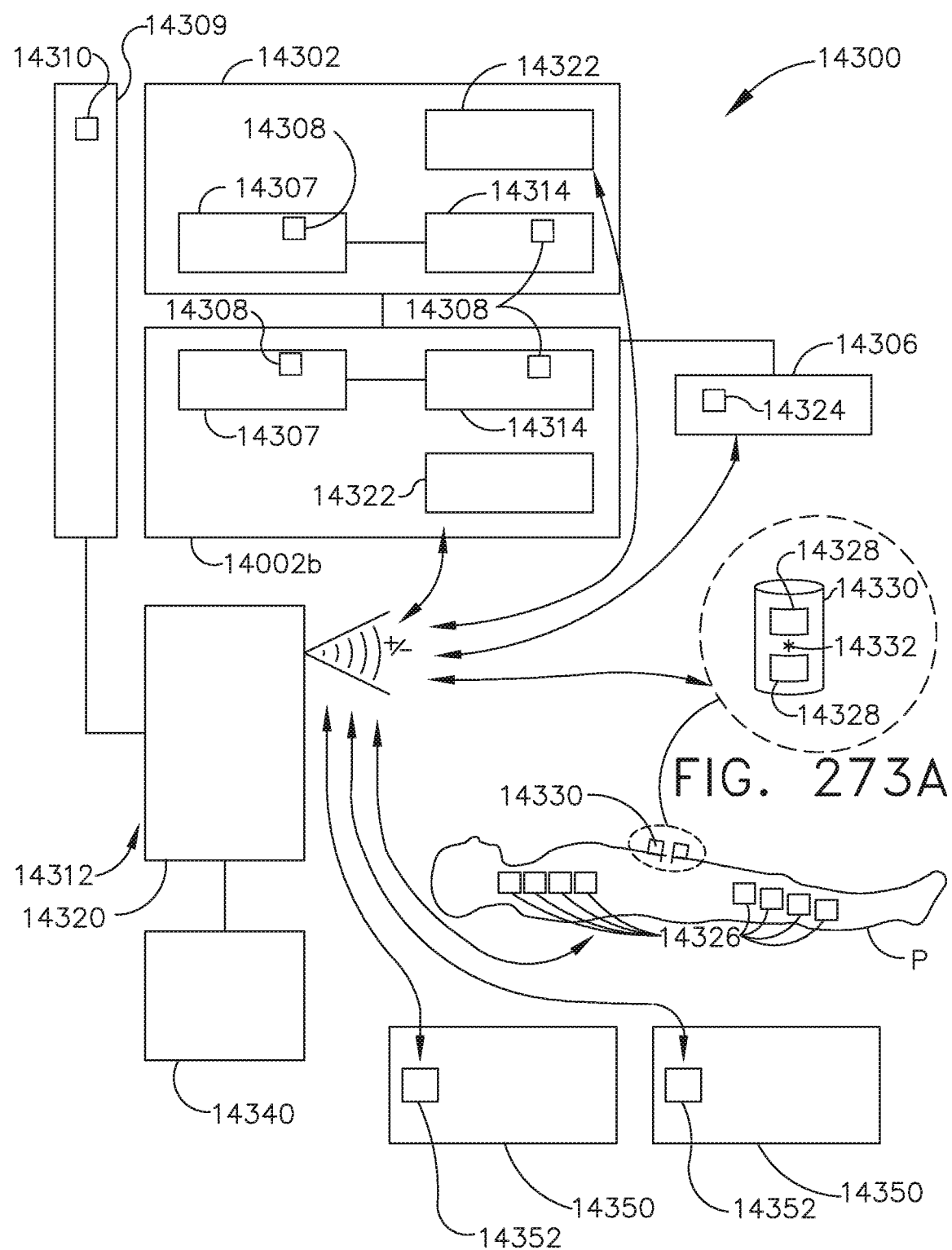
Figure 274:
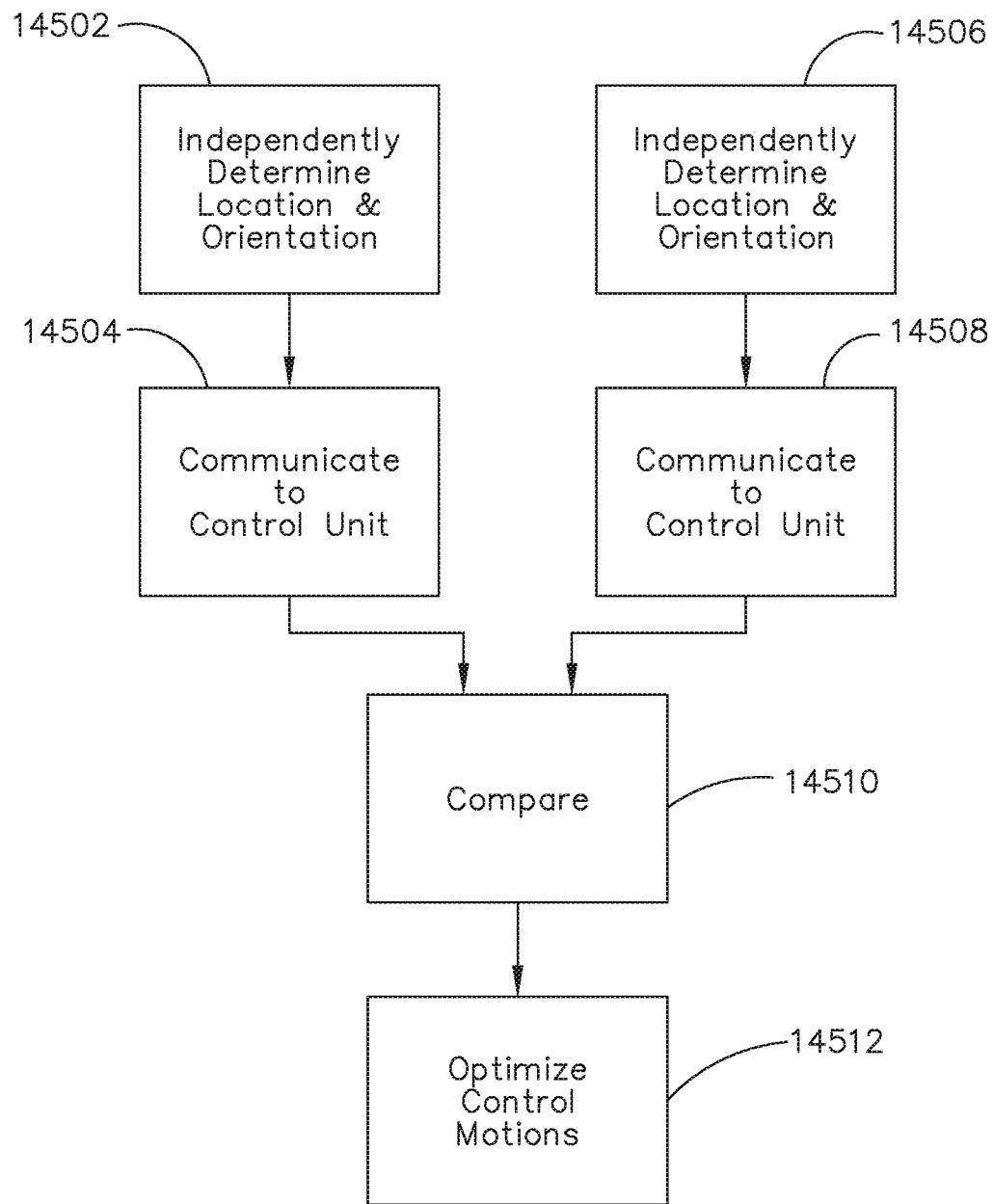
Figure 275:
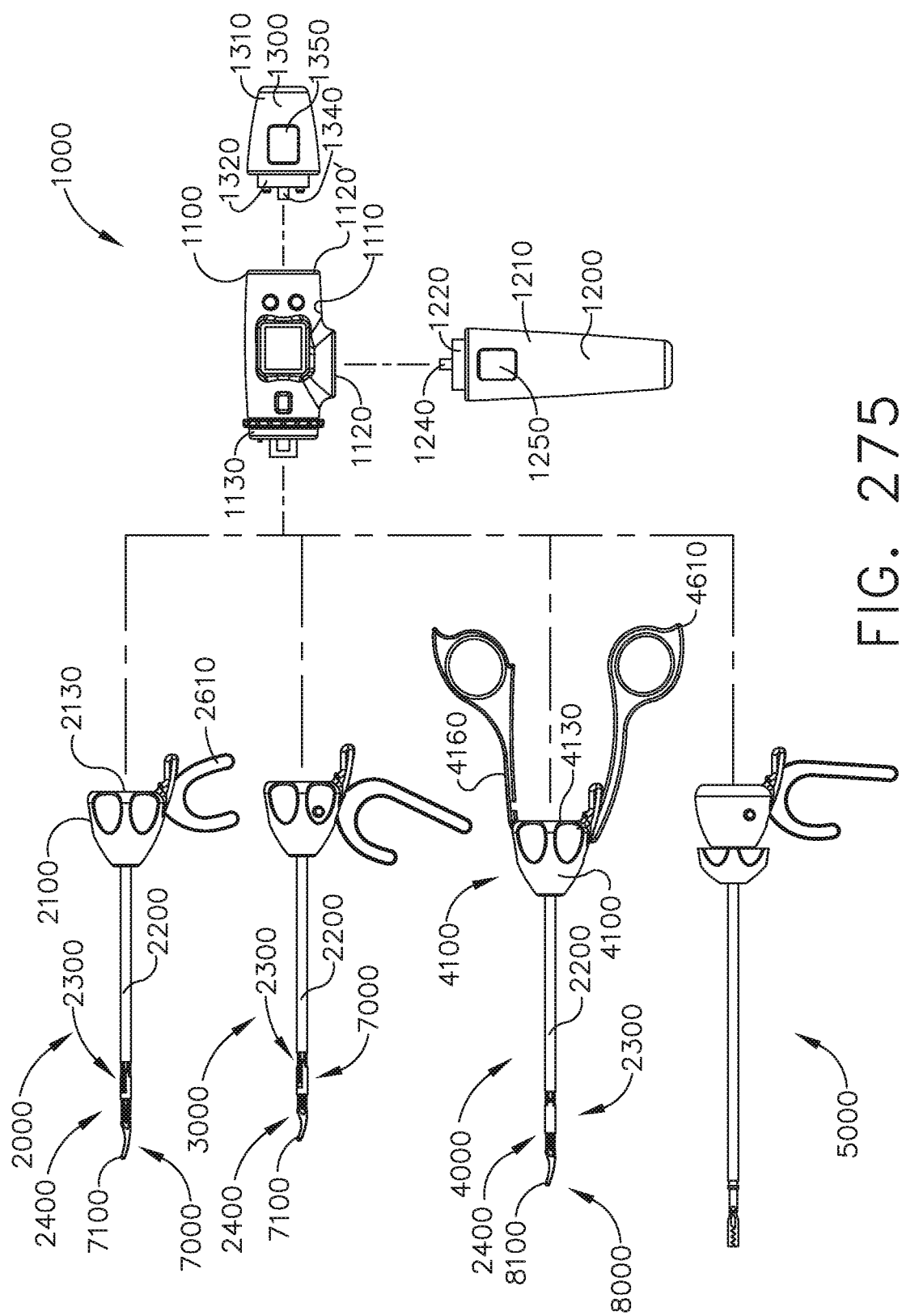
Figure 276:
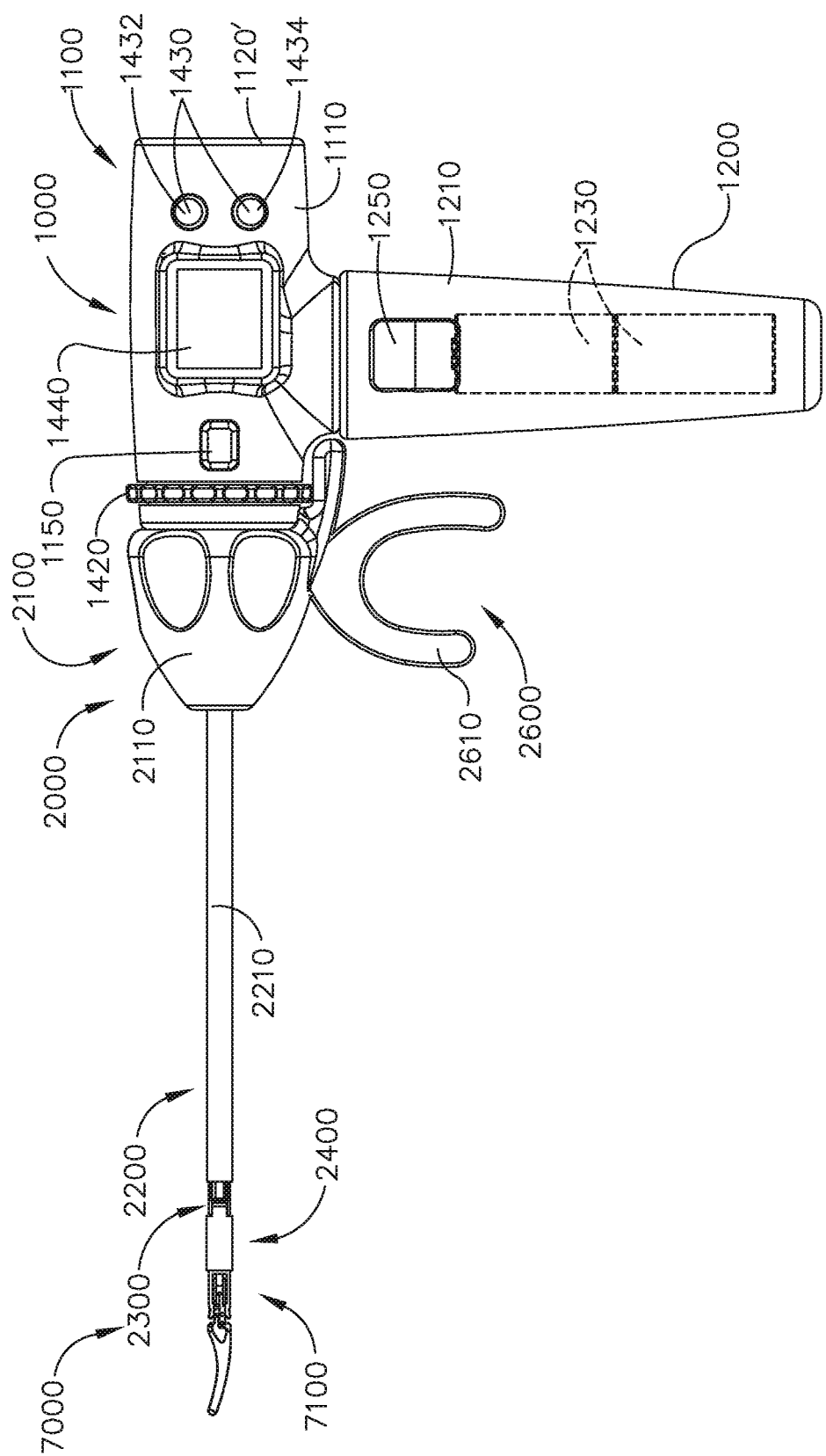
Figure 277:
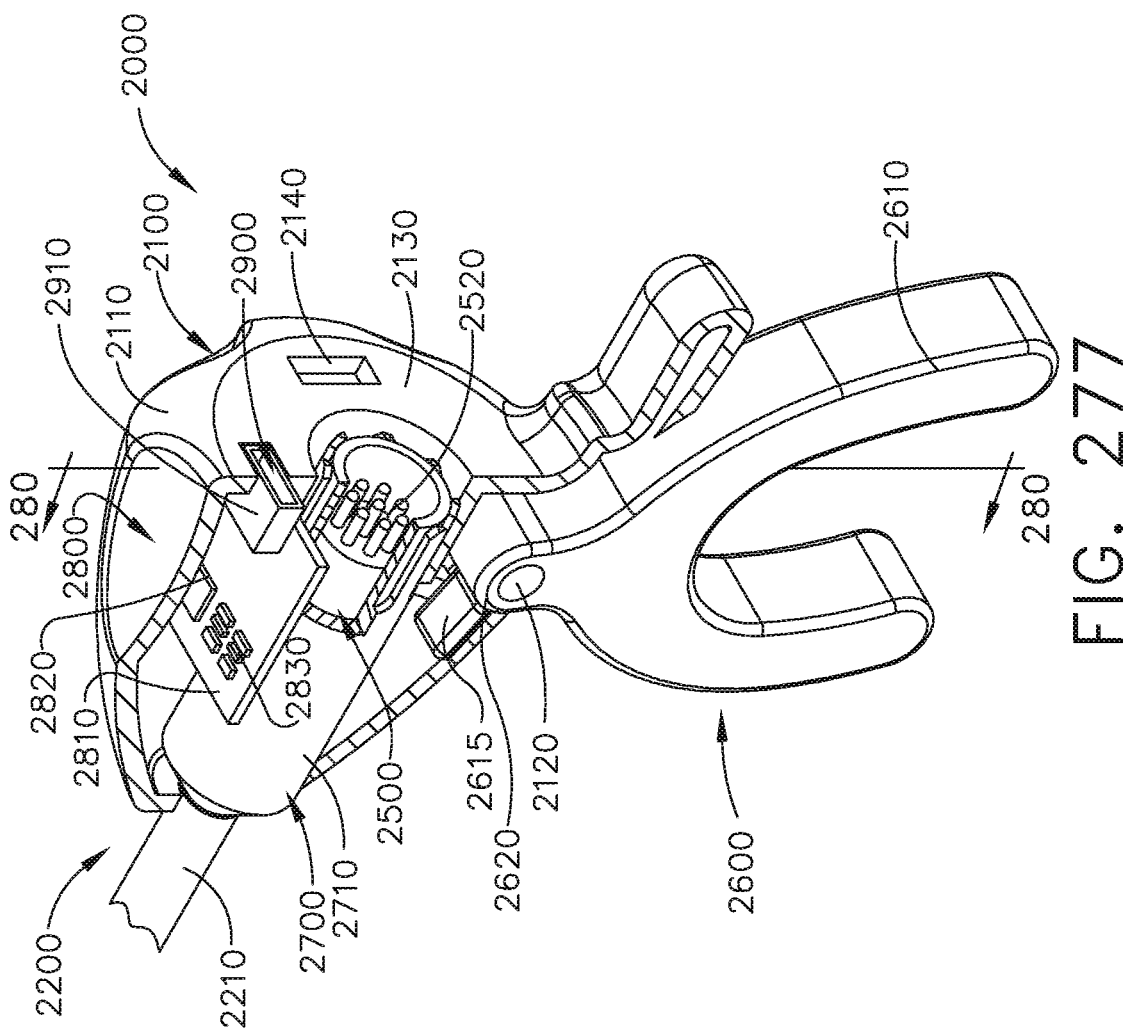
Figure 278:
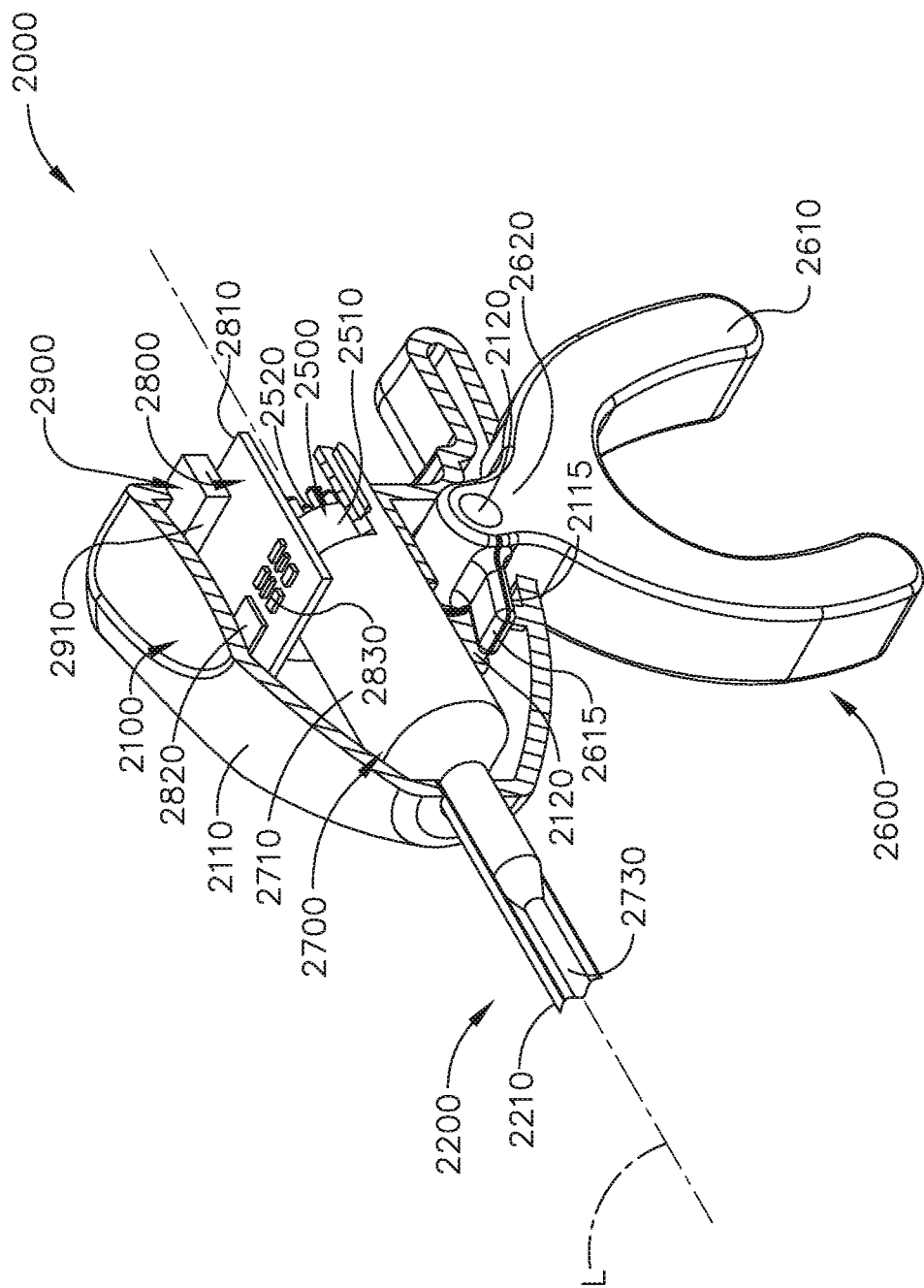
Figure 279:
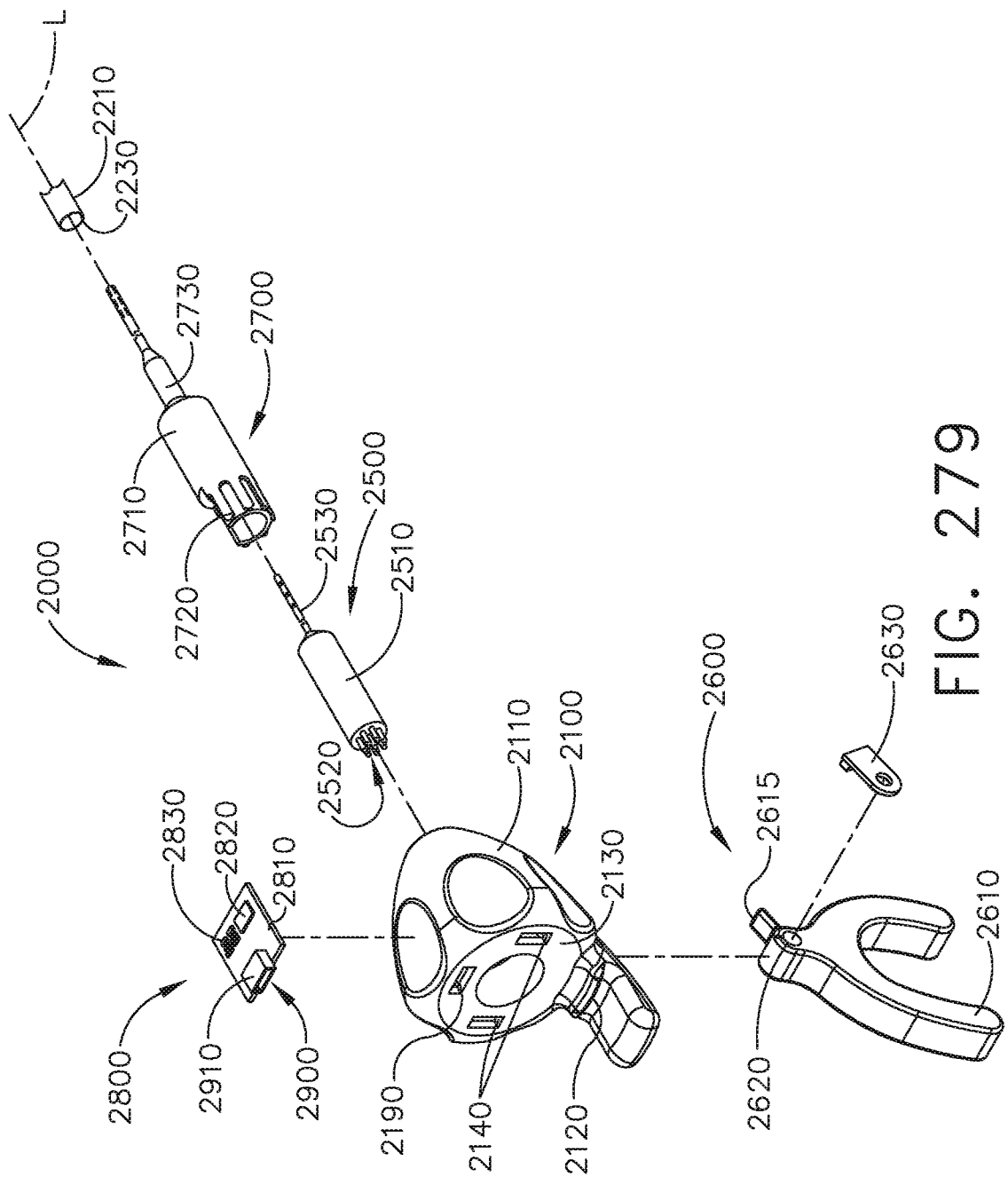
Figure 280:
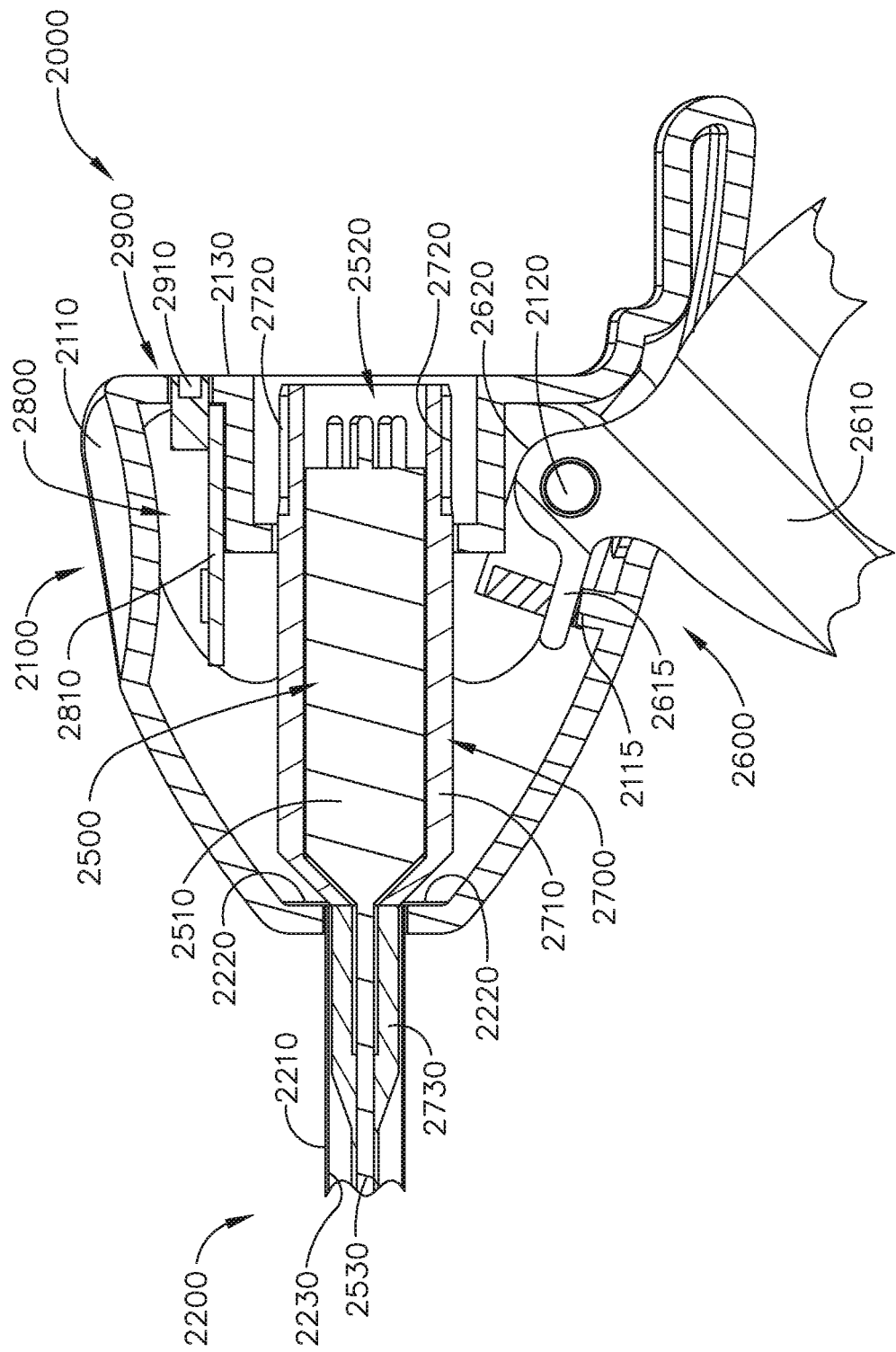
Figure 281:
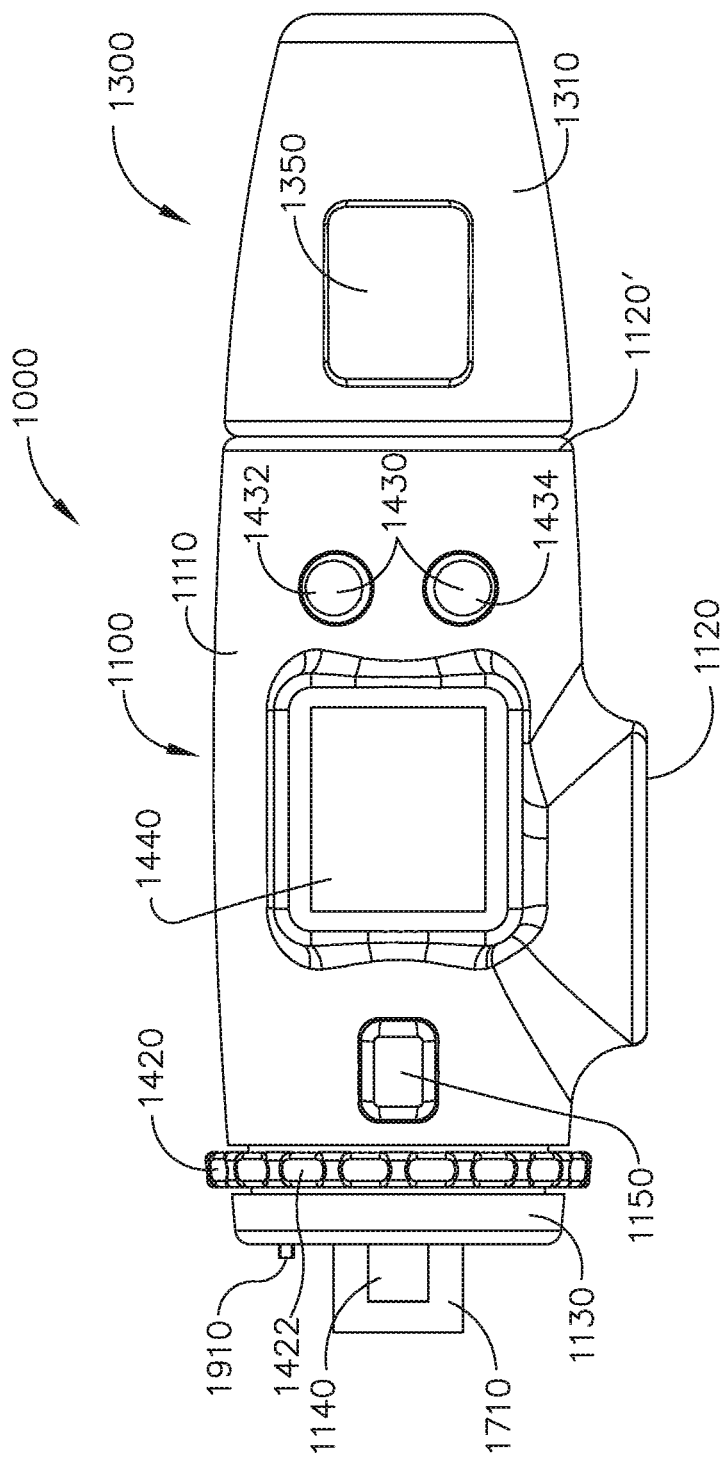
Figure 282:
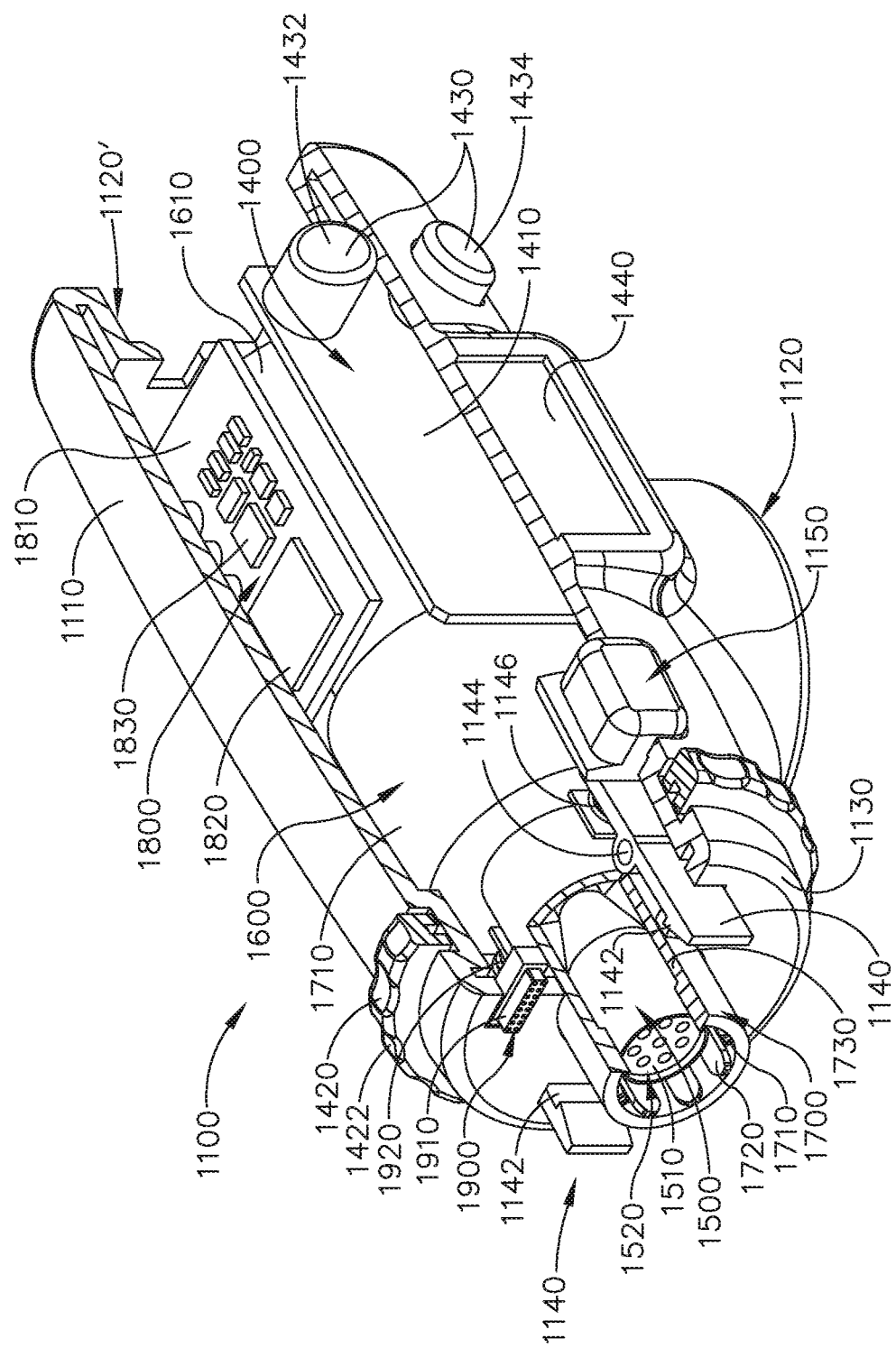
Figure 283:
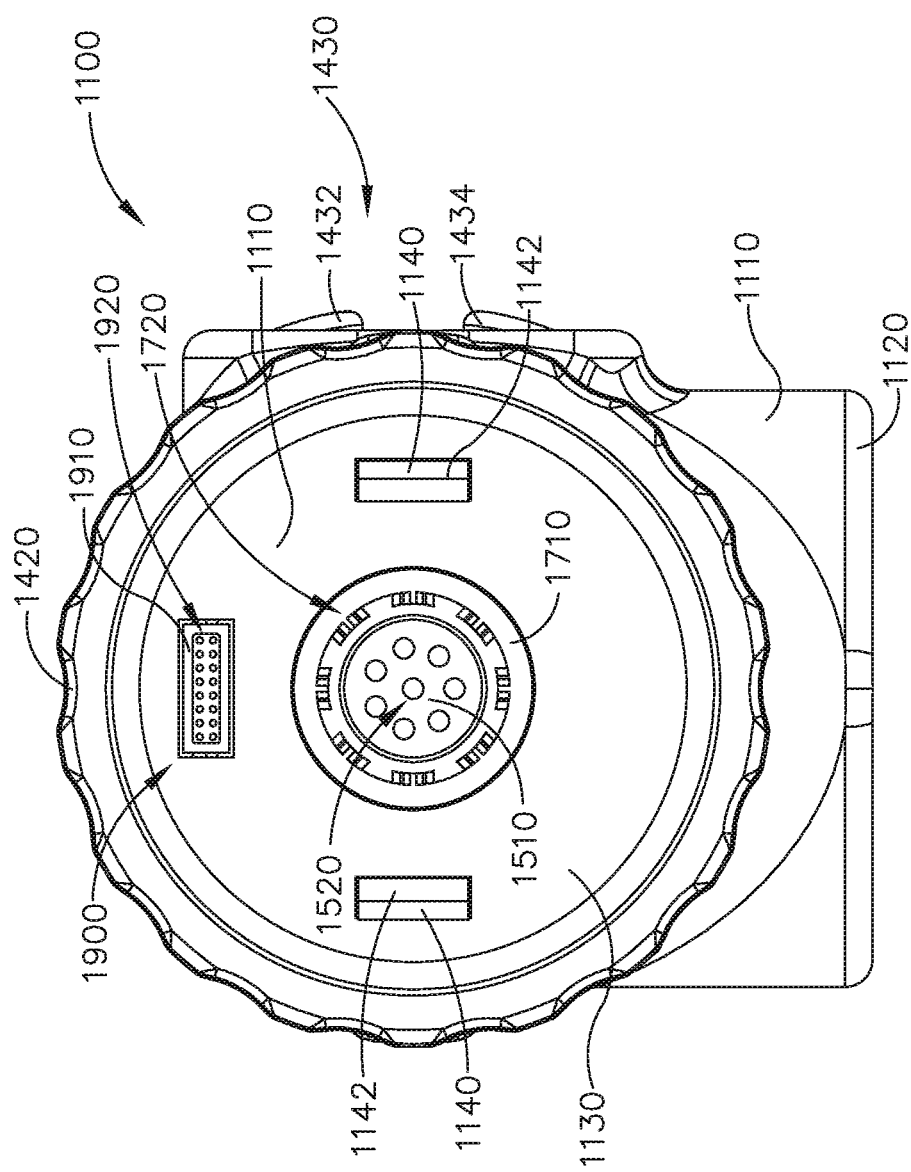
Figure 284:
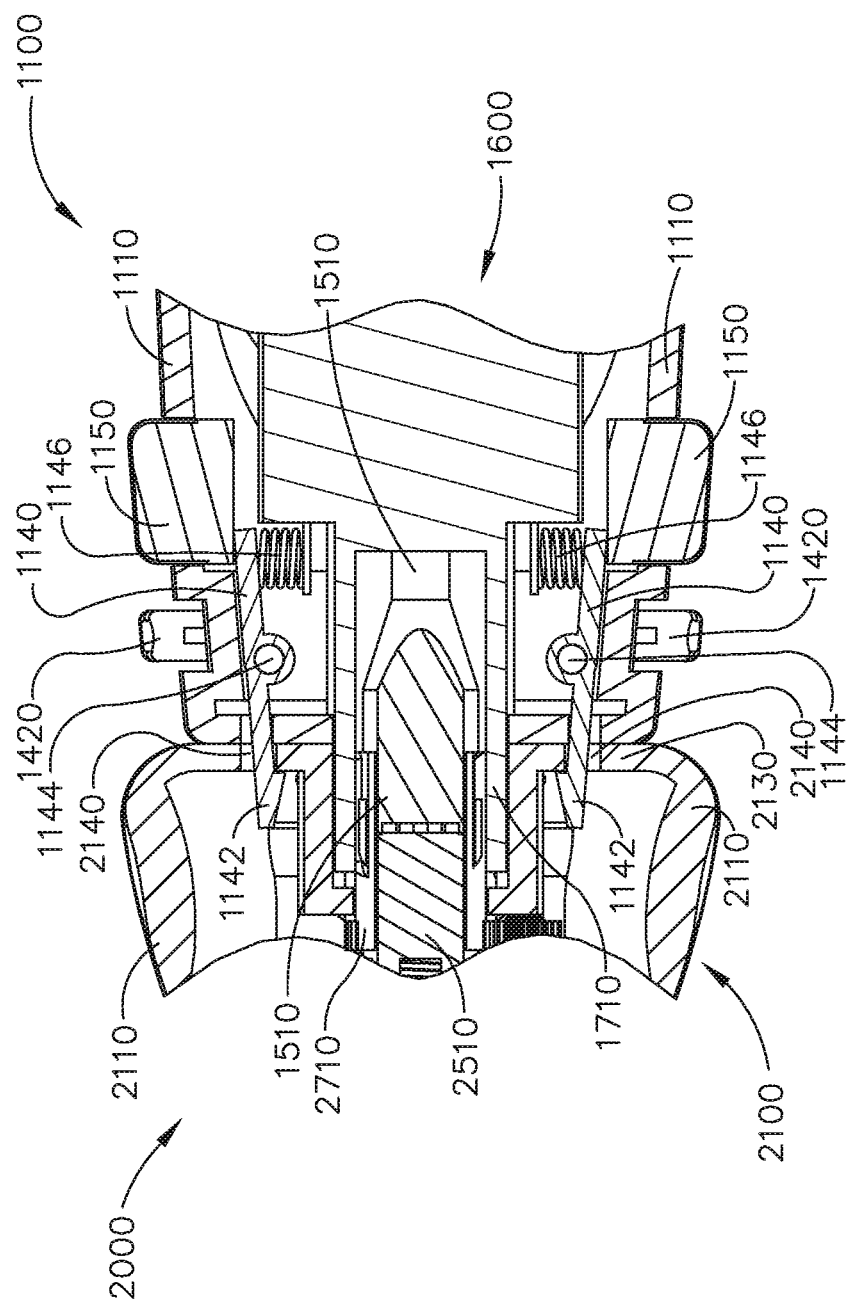
Figure 285:
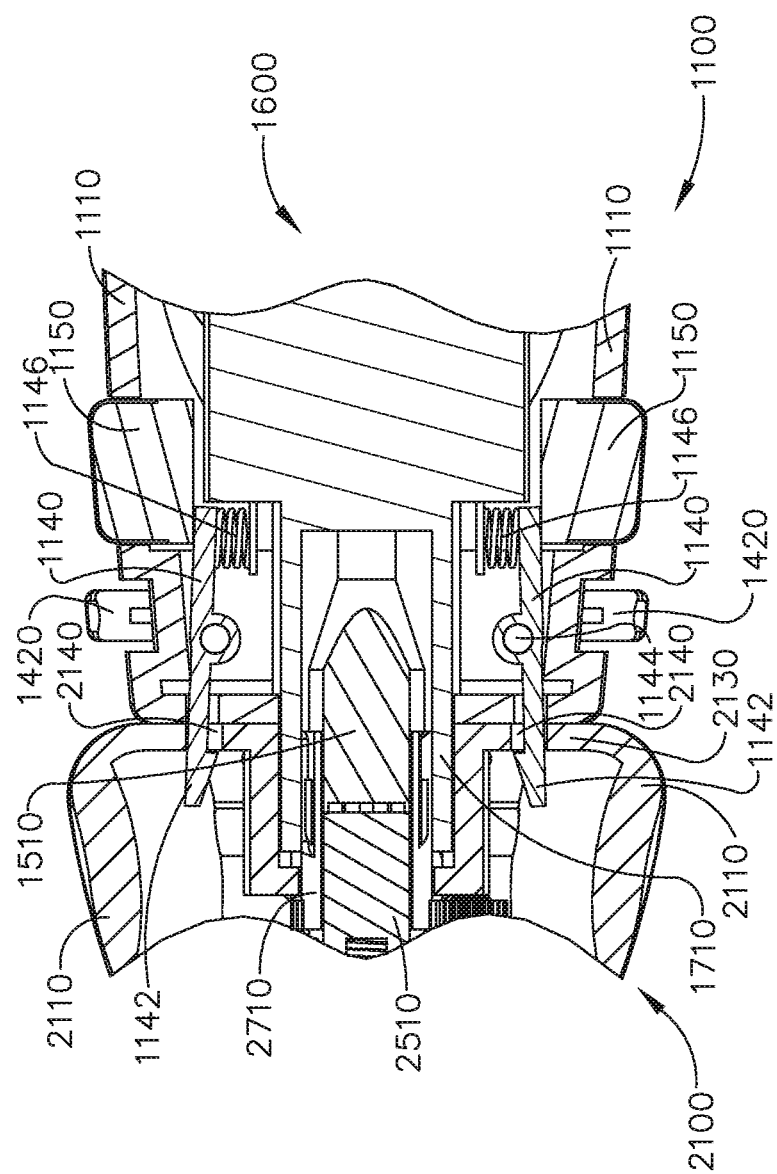
Figure 286:
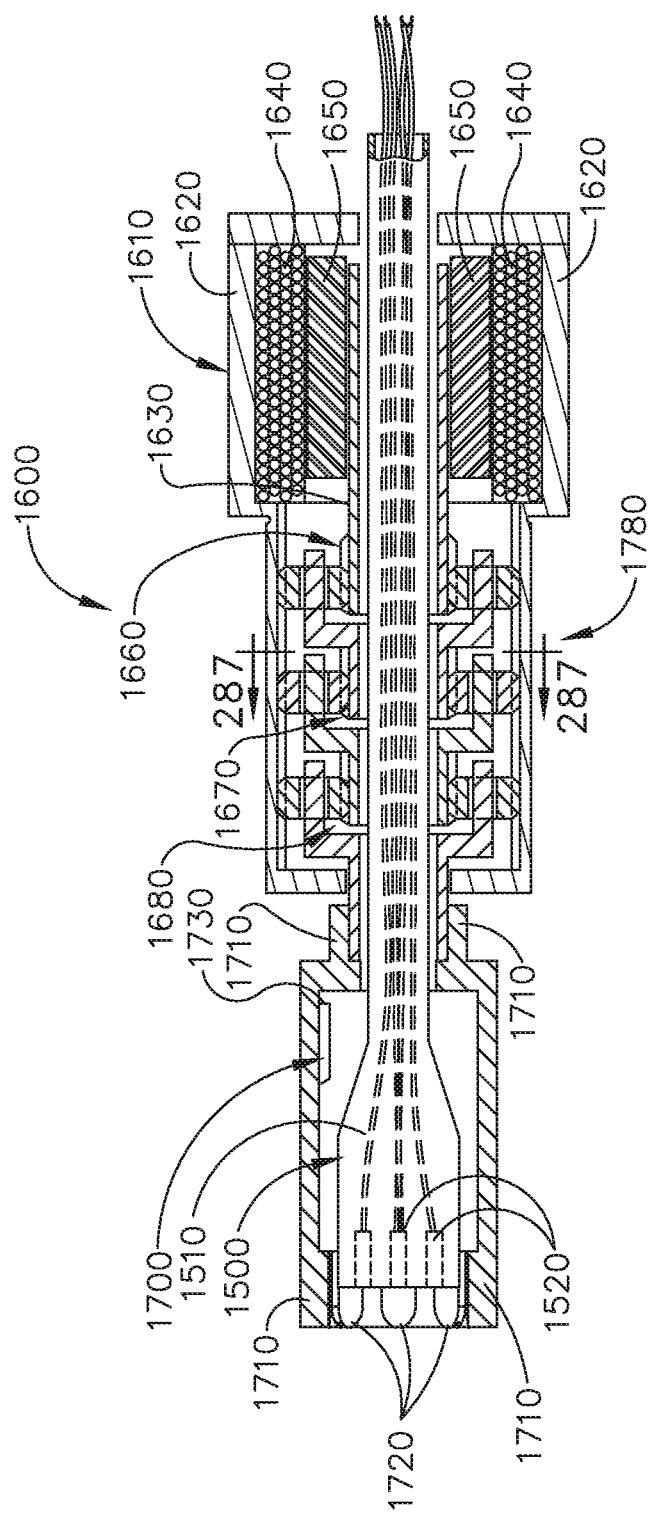
Figure 287:
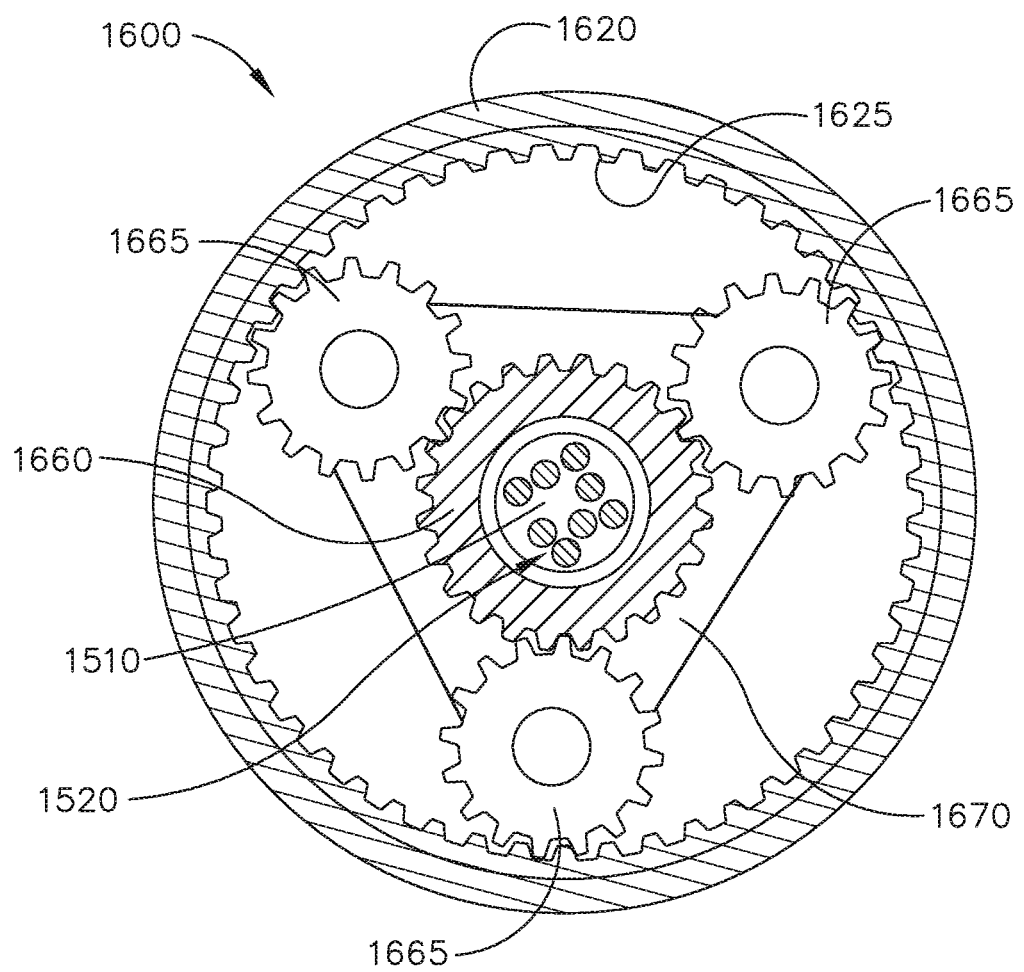
Figure 288:
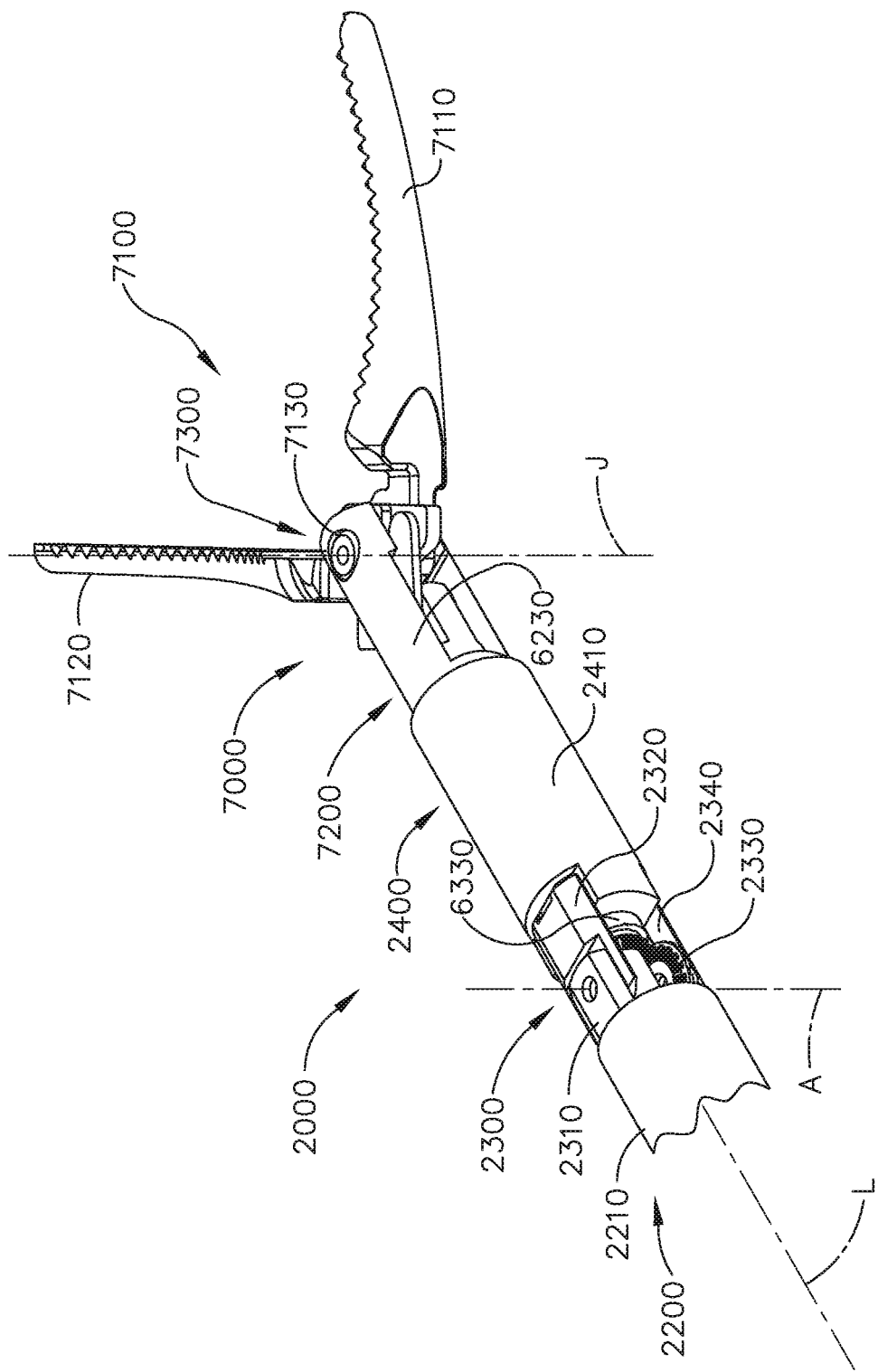
Figure 289:
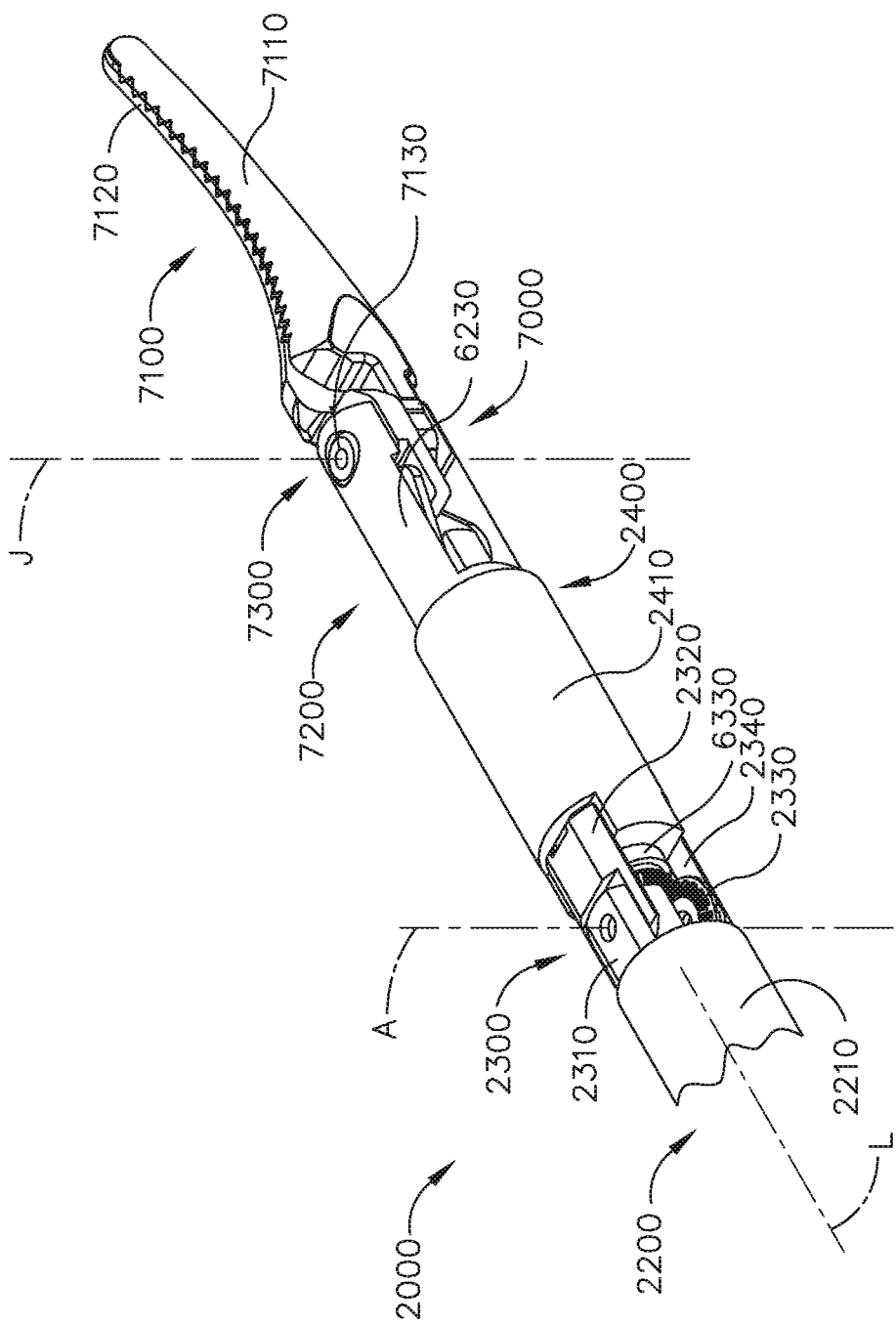
Figure 290:
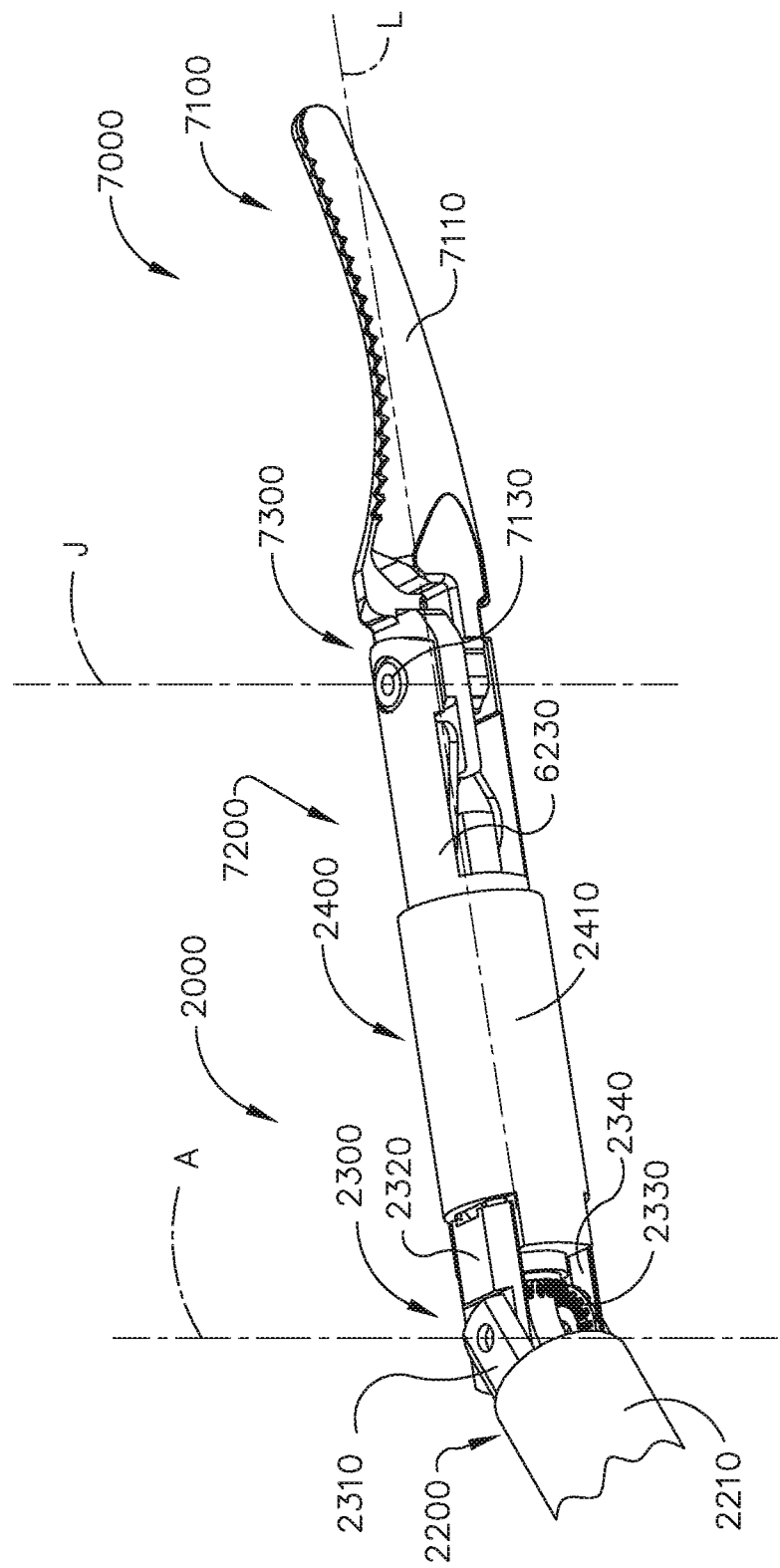
Figure 291:
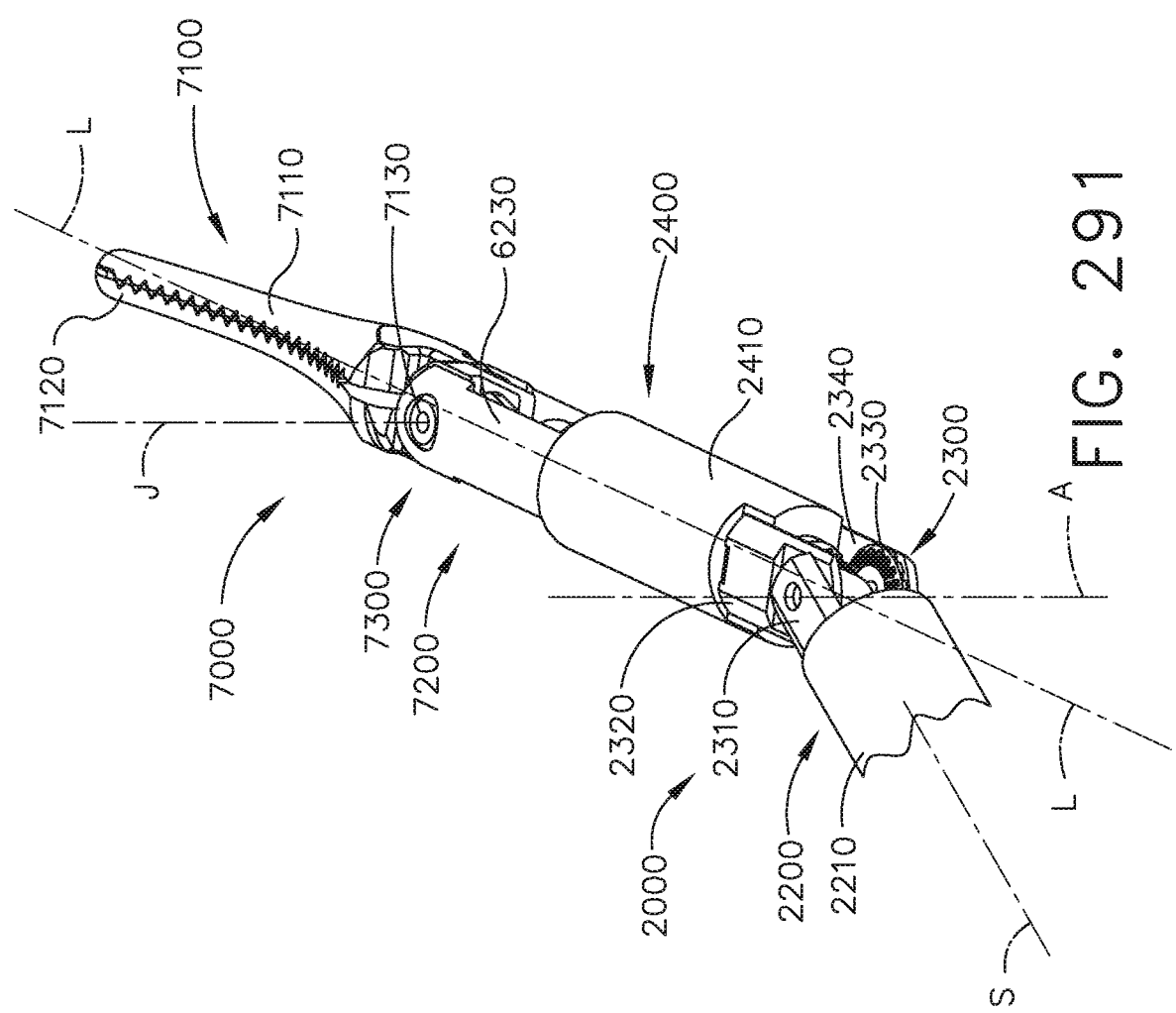
Figure 292:
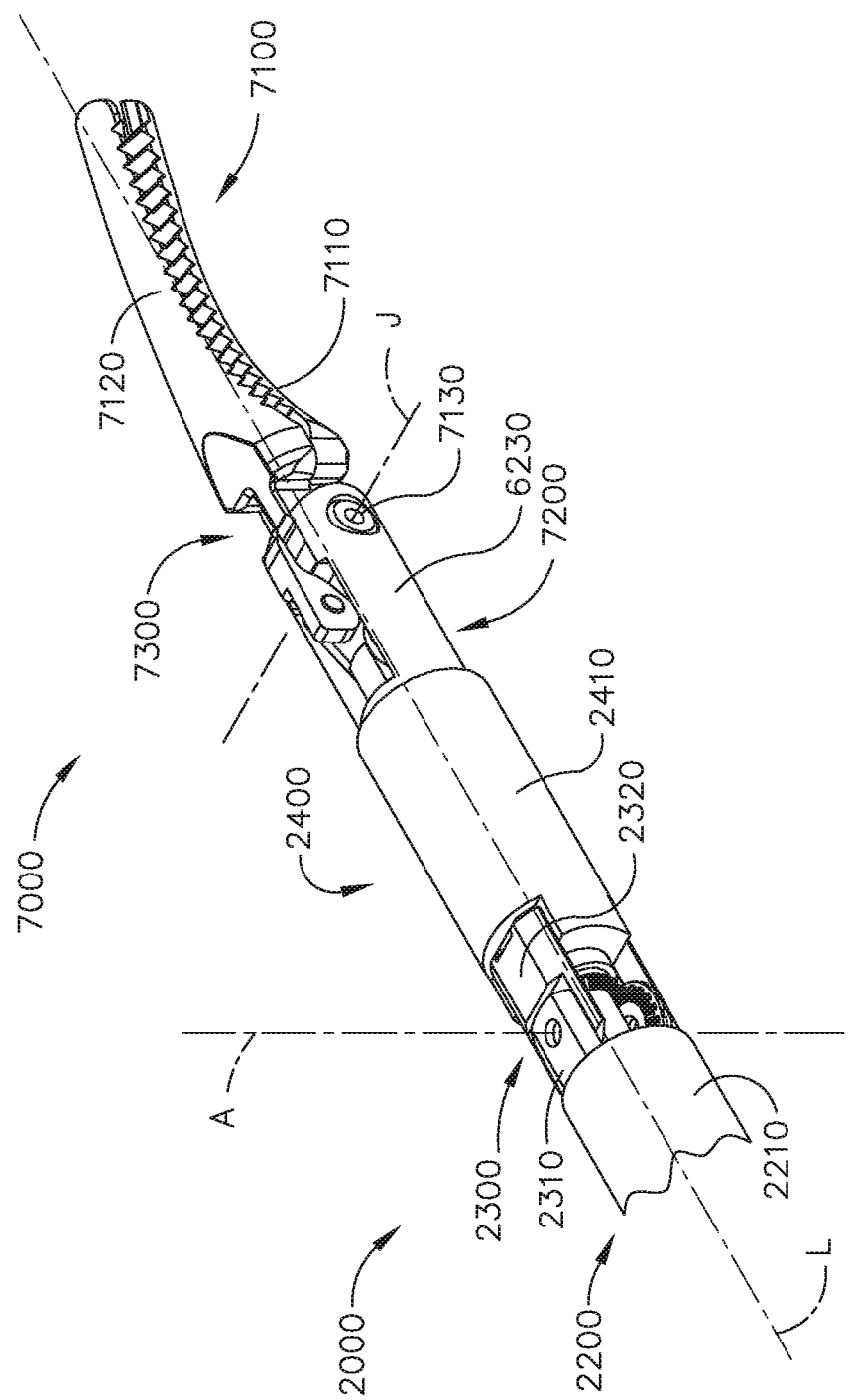
Figure 293:
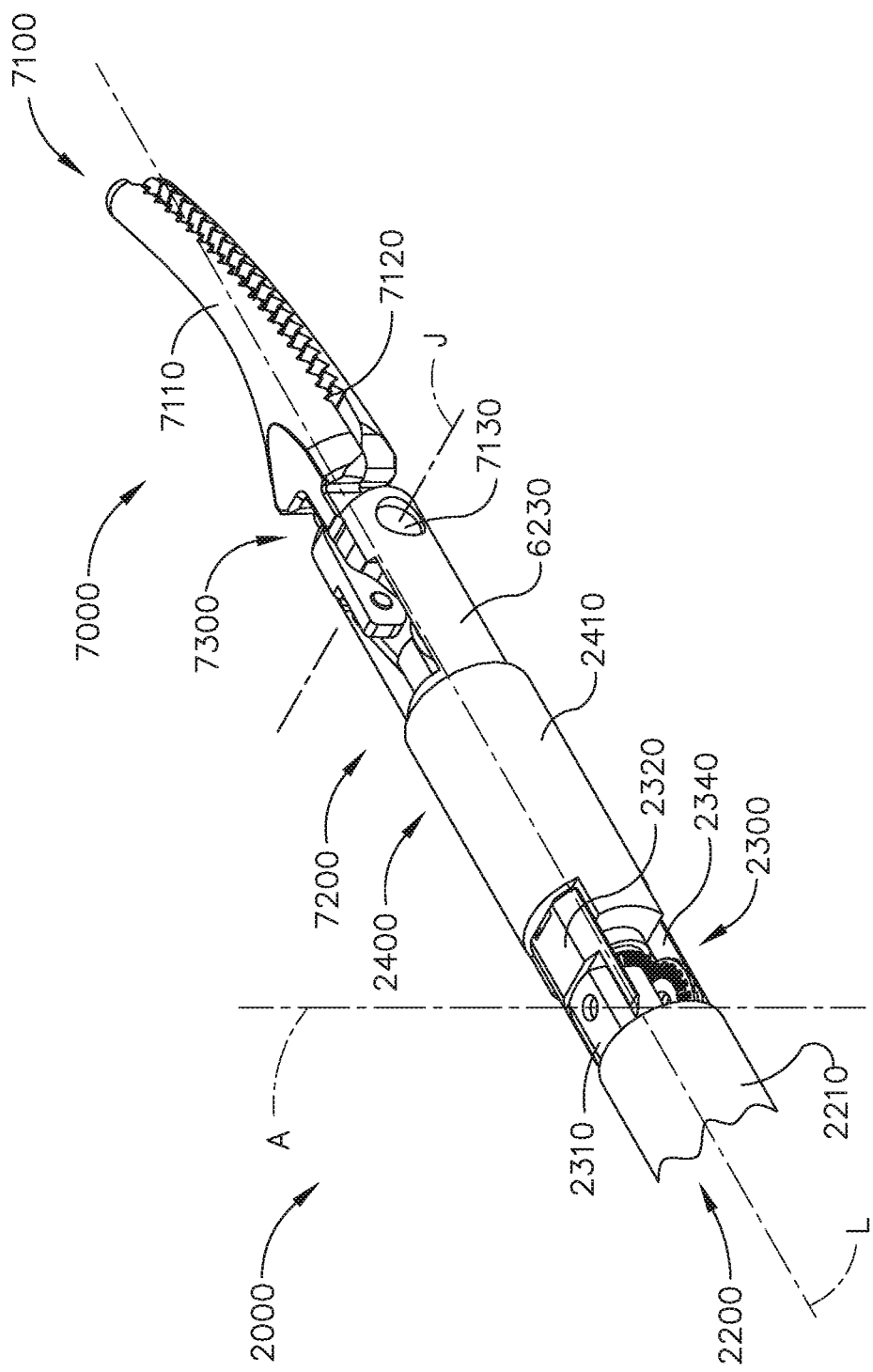
Figure 294:
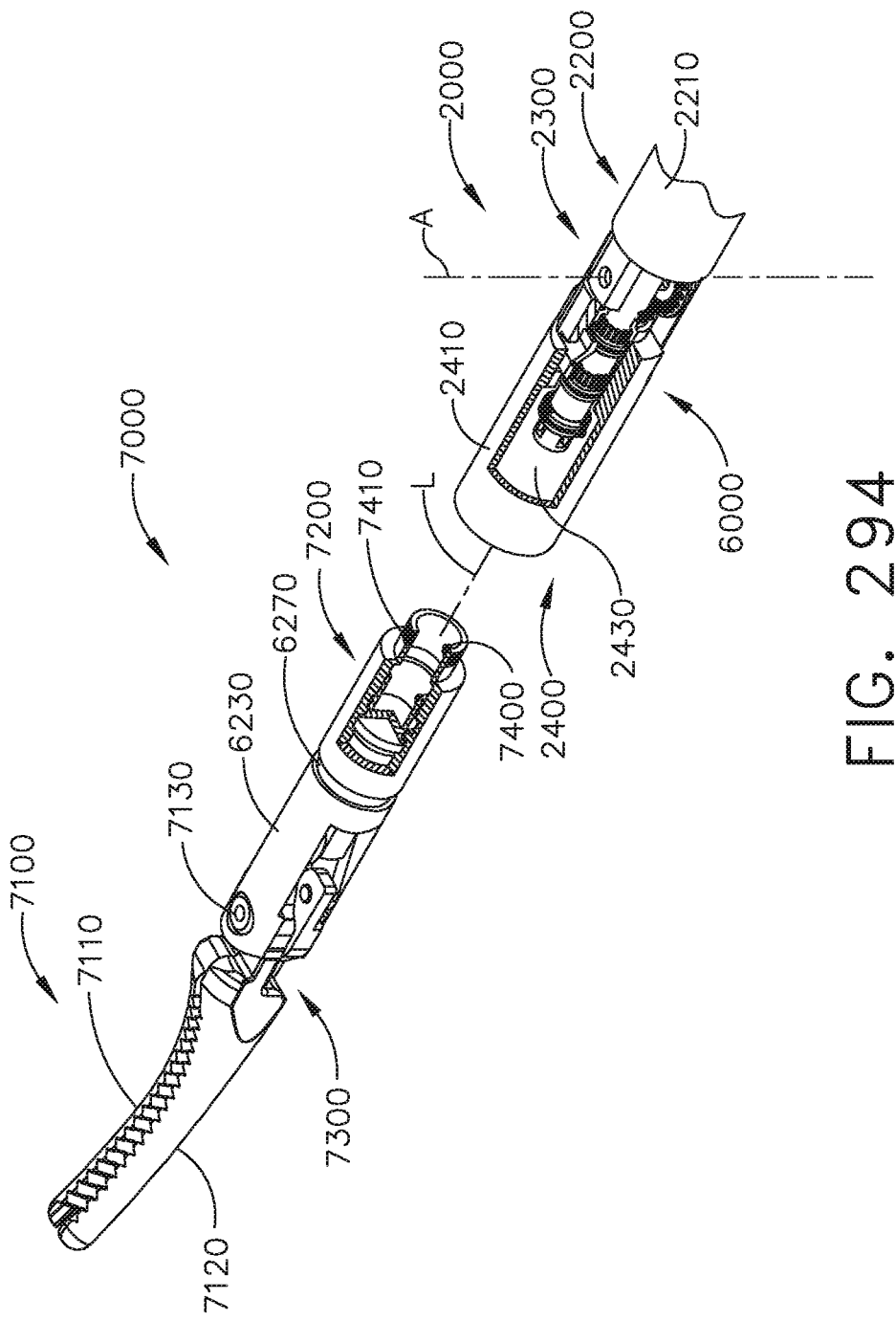
Figure 295:
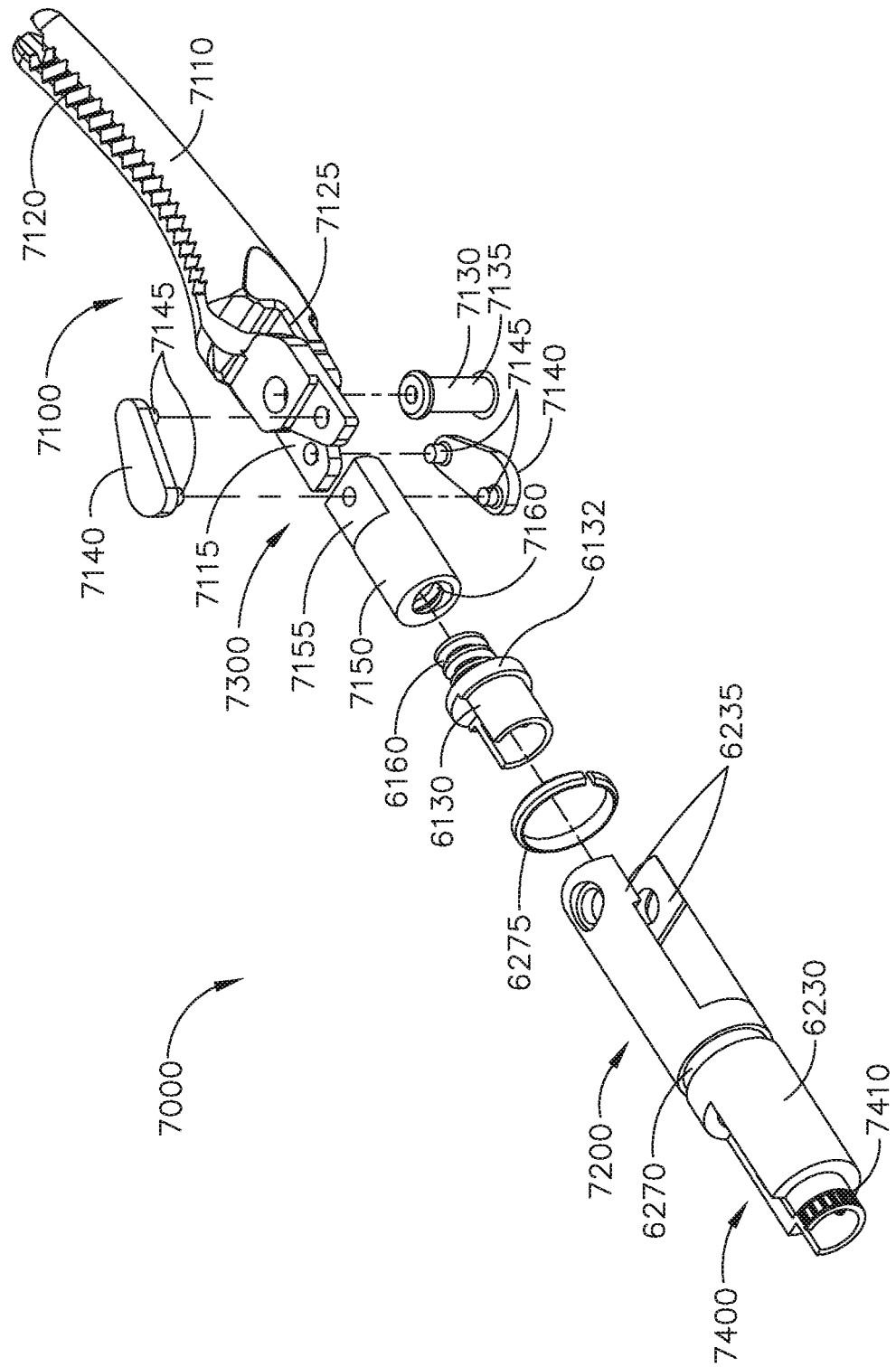
Figure 296:
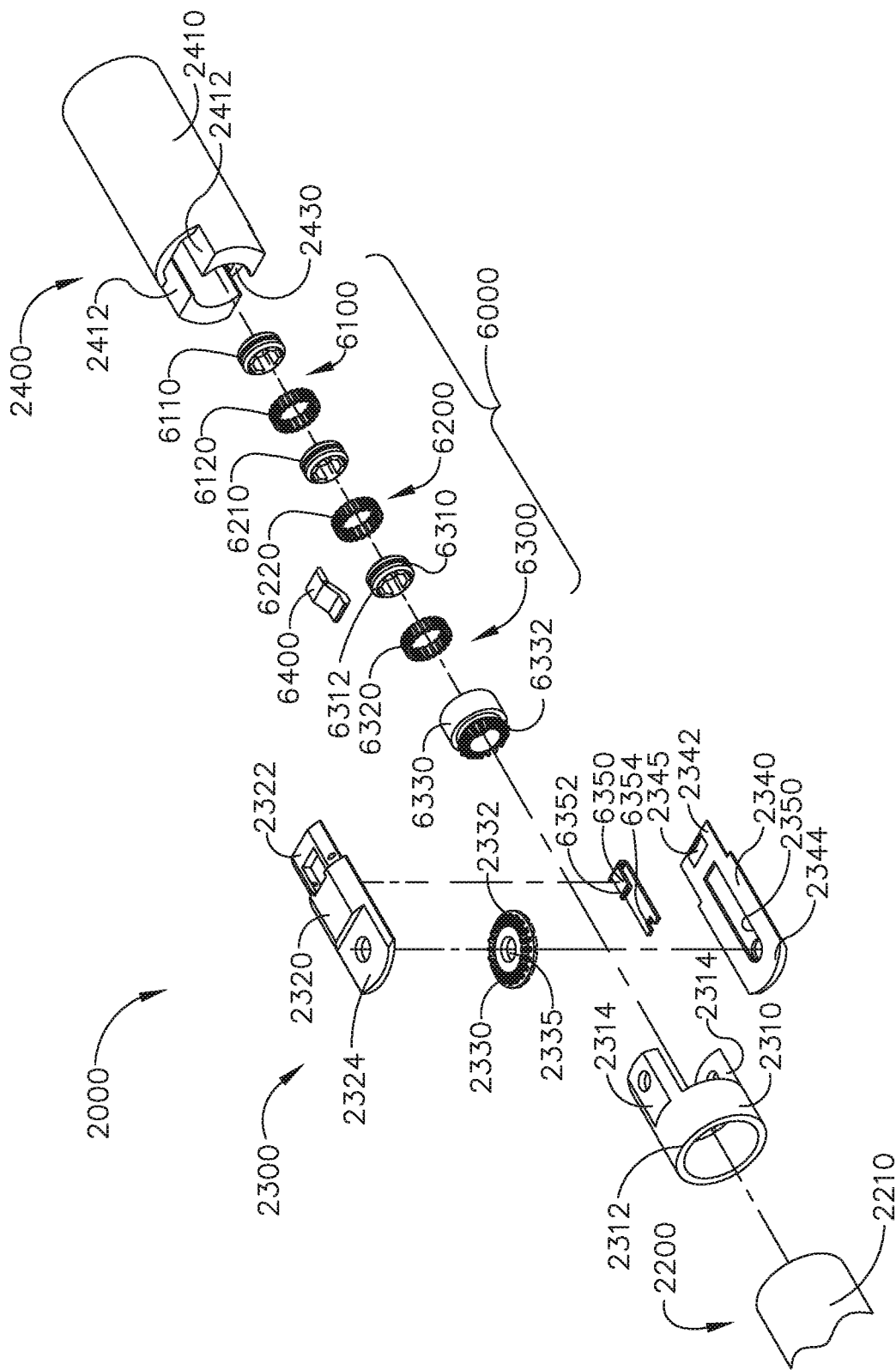
Figure 297:
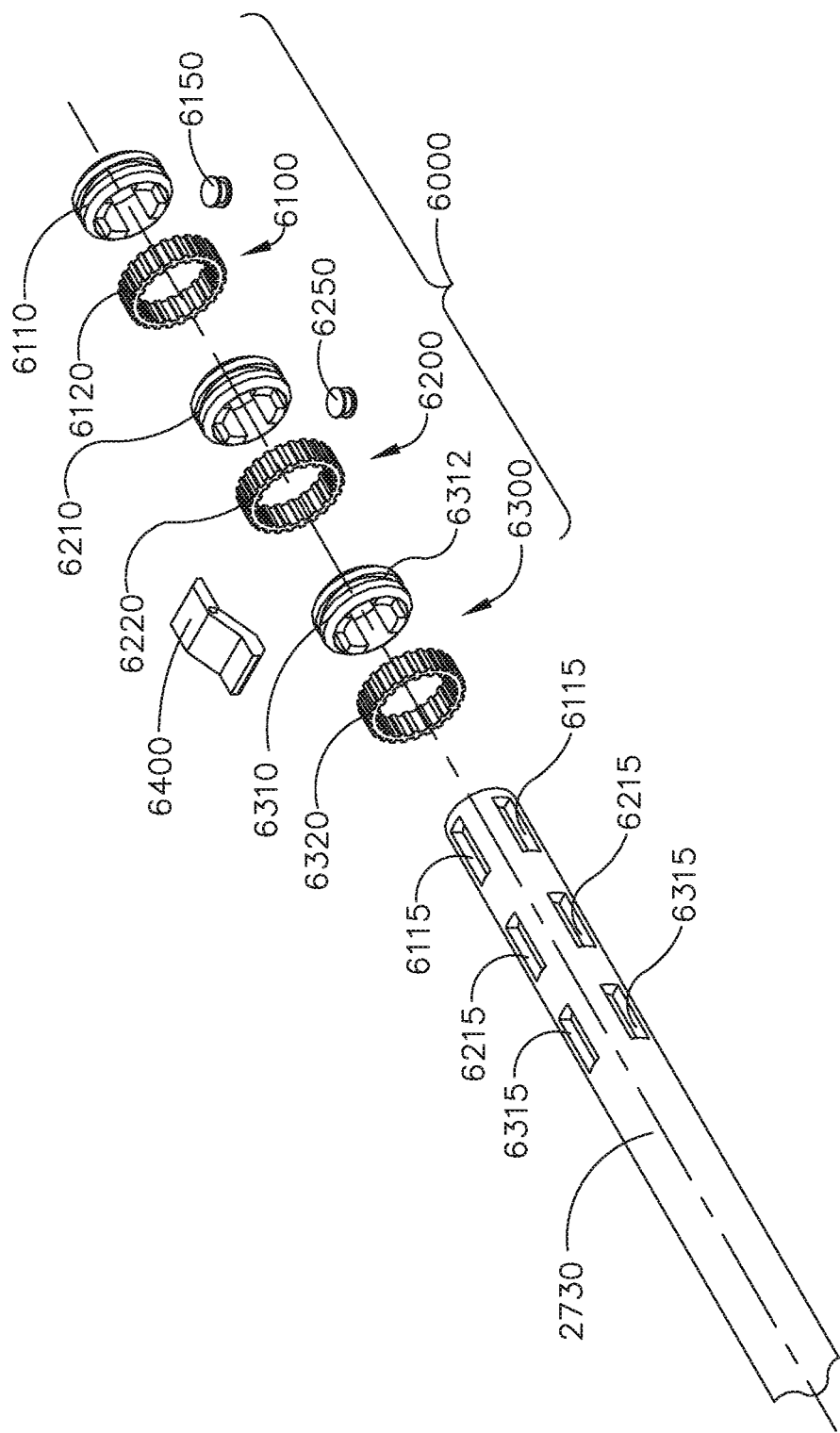
Figure 298:
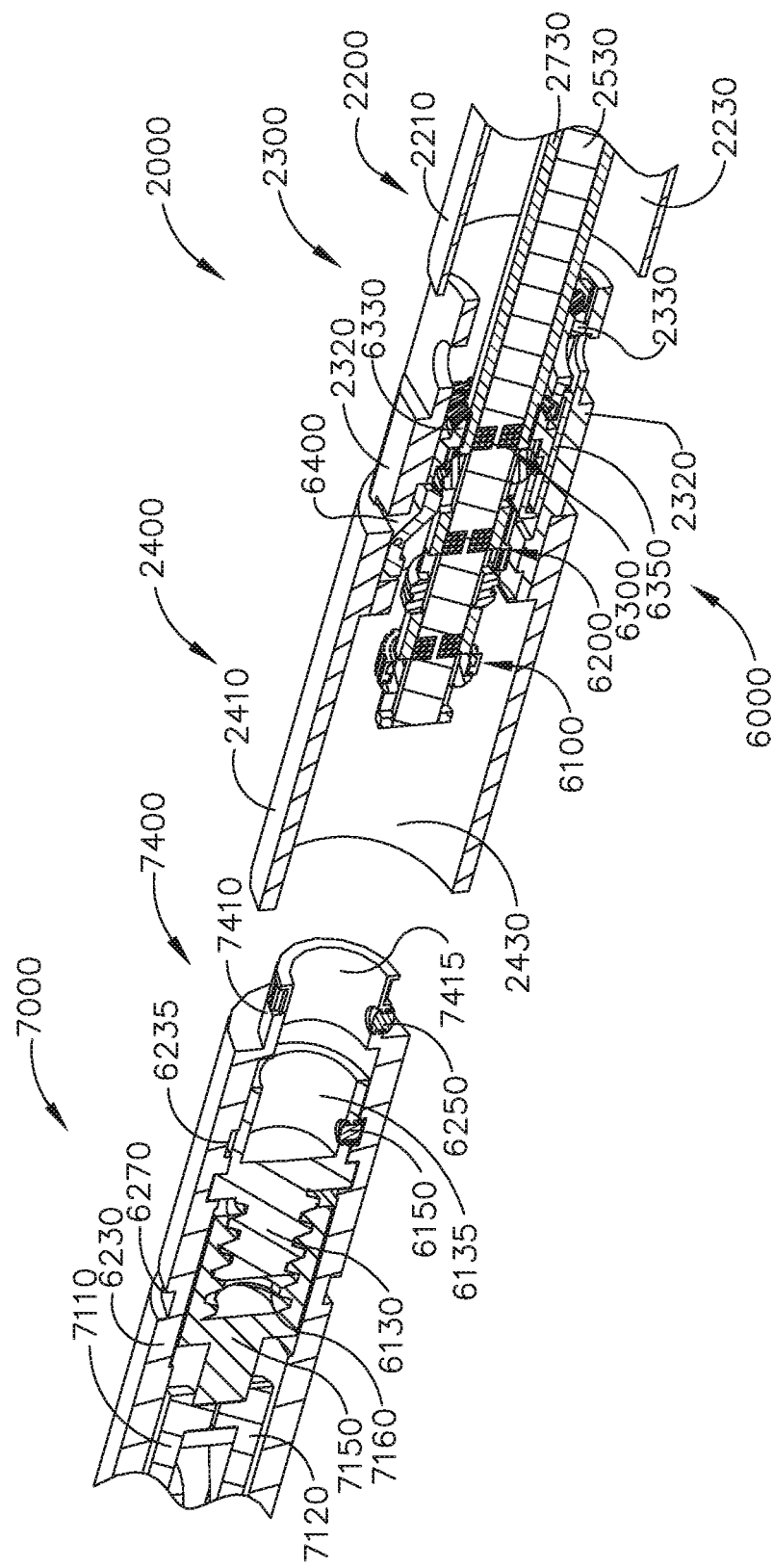
Figure 299:
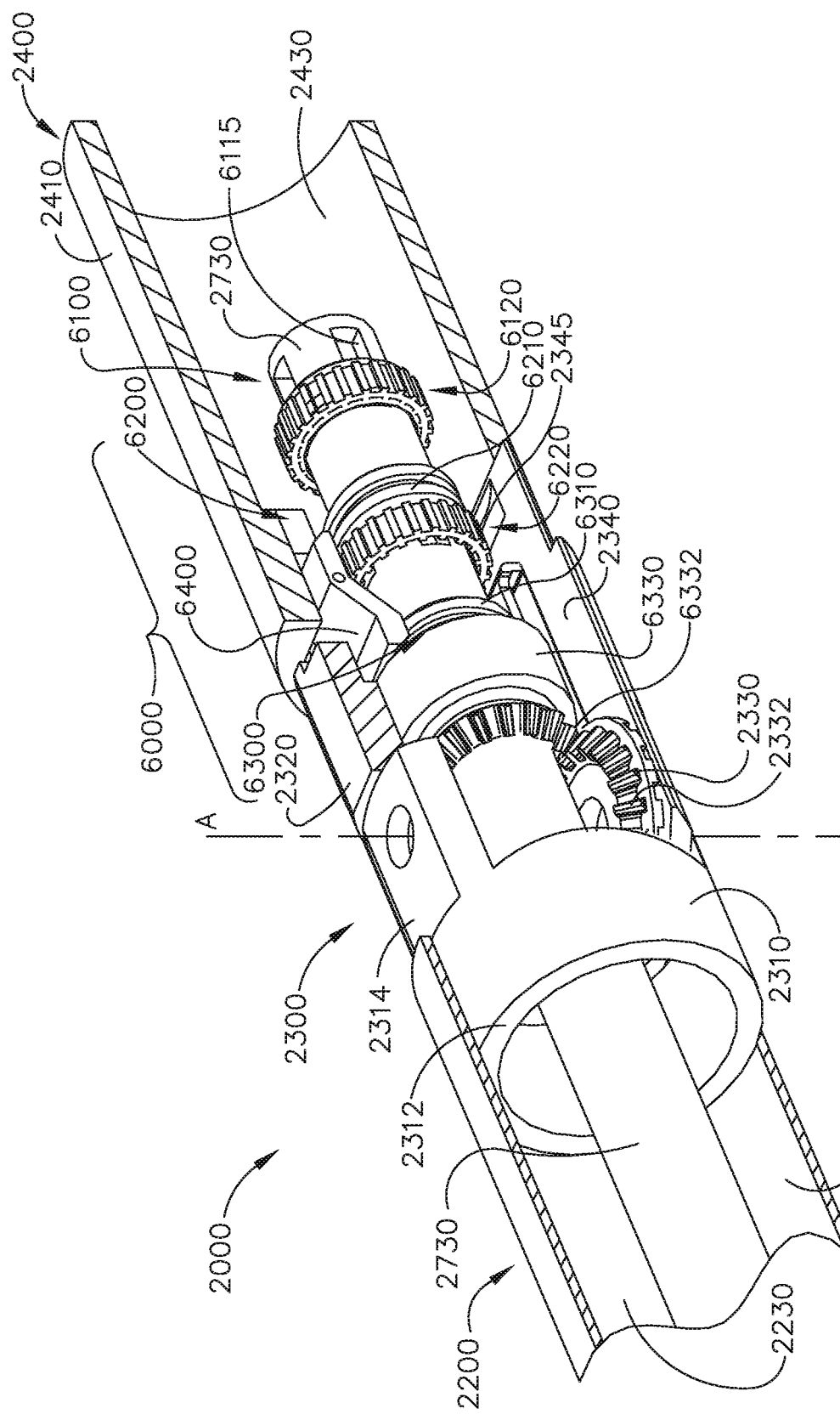
Figure 300:
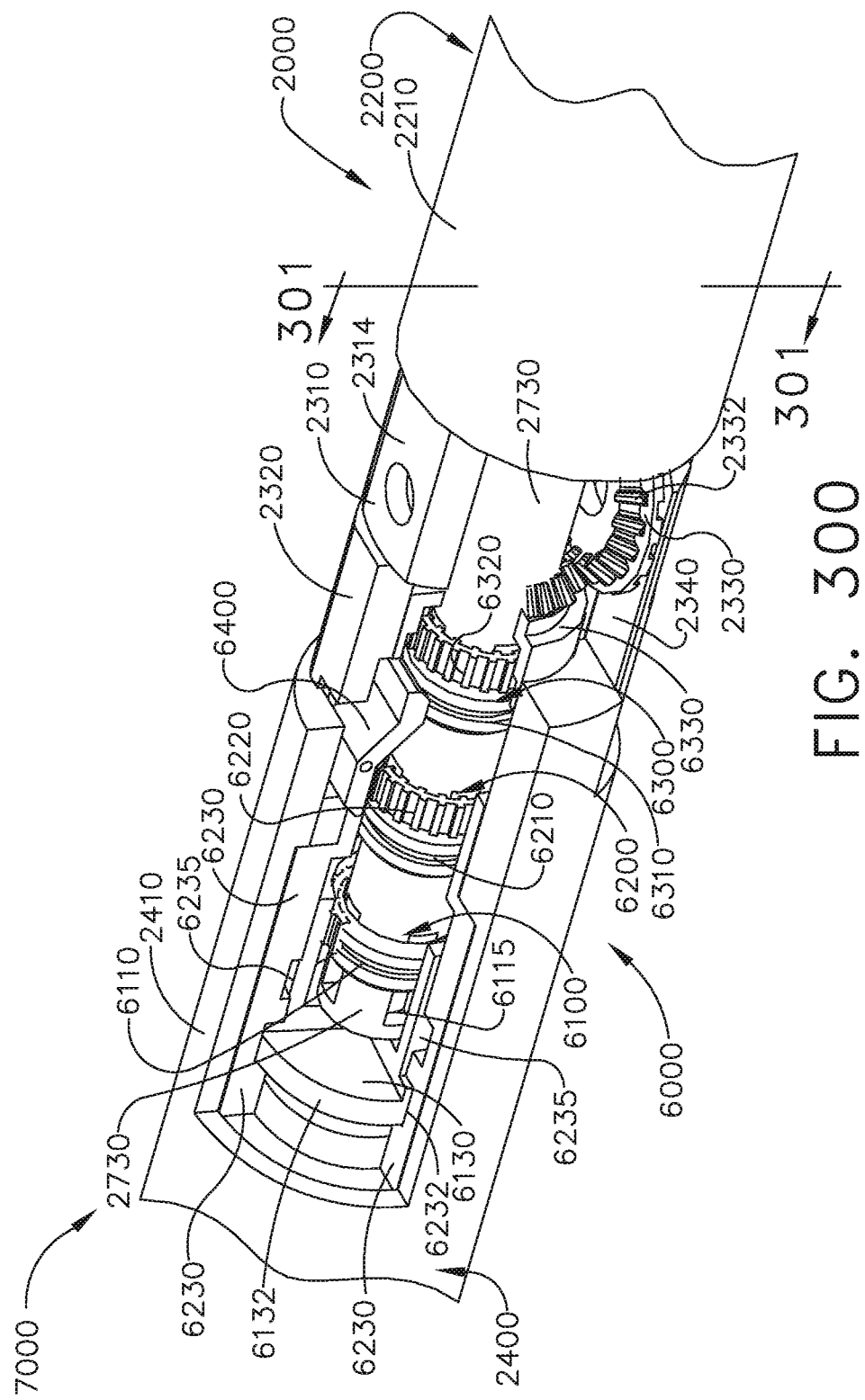
Figure 301:
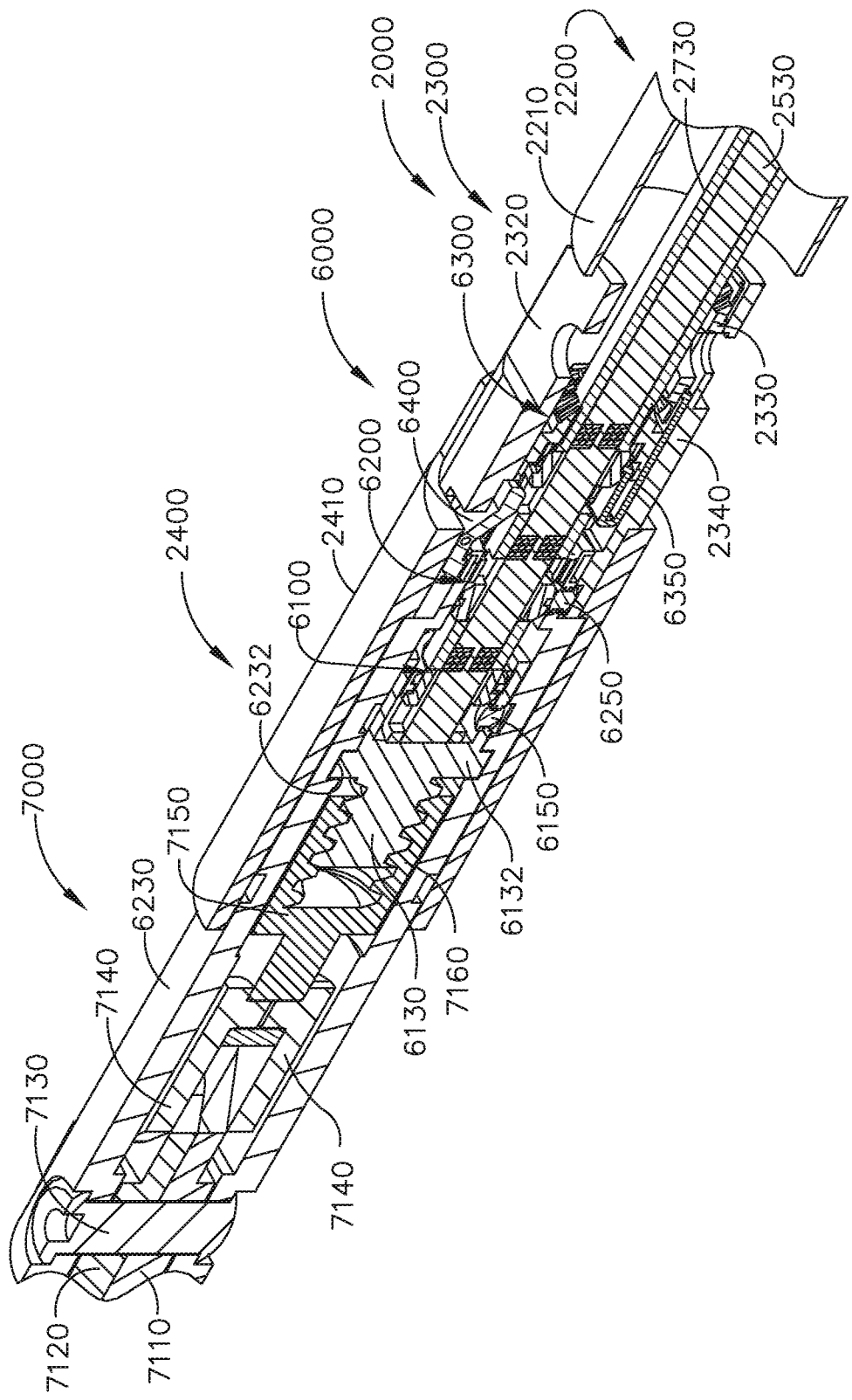
Figure 302:
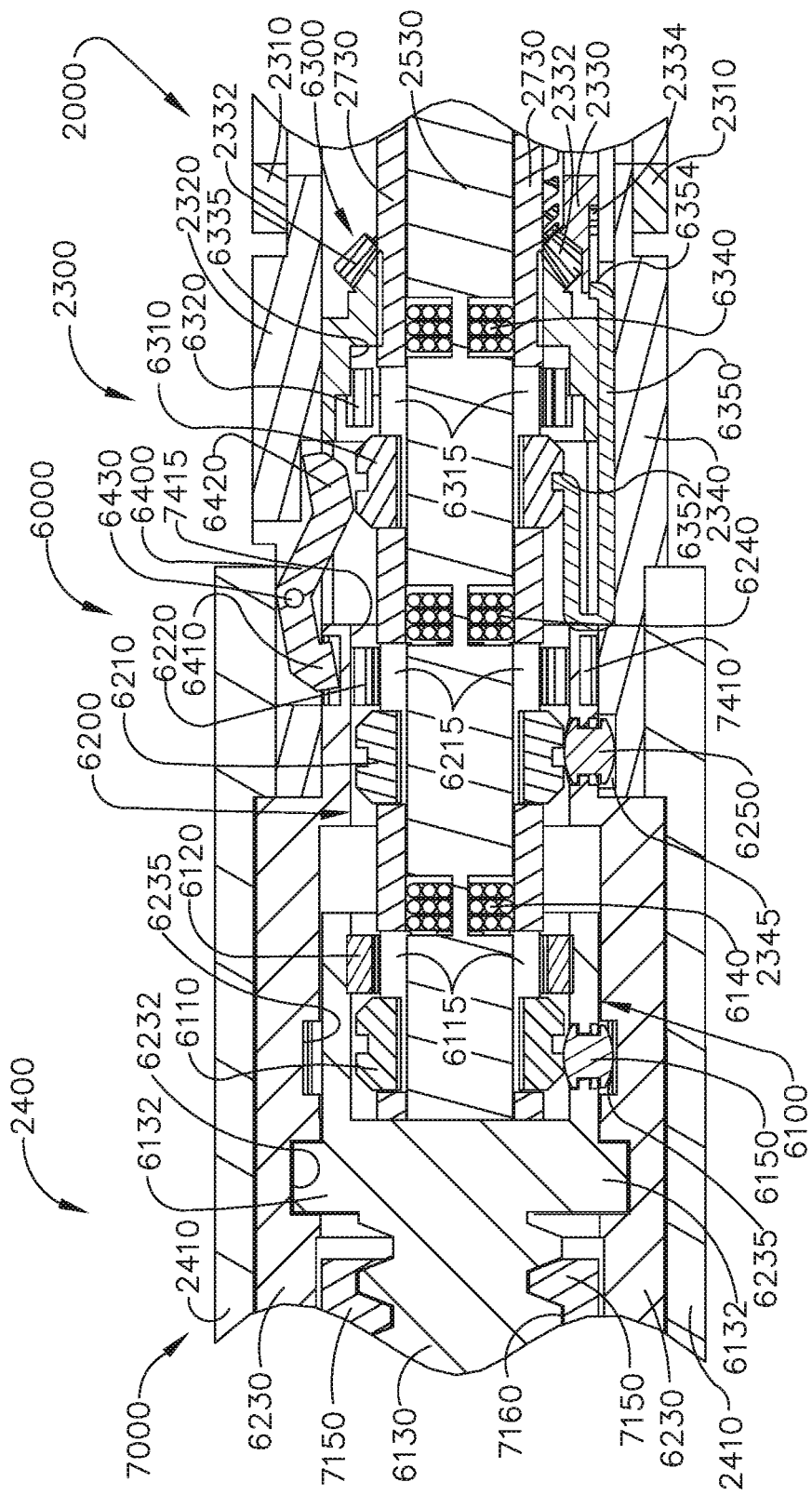
Figure 303:
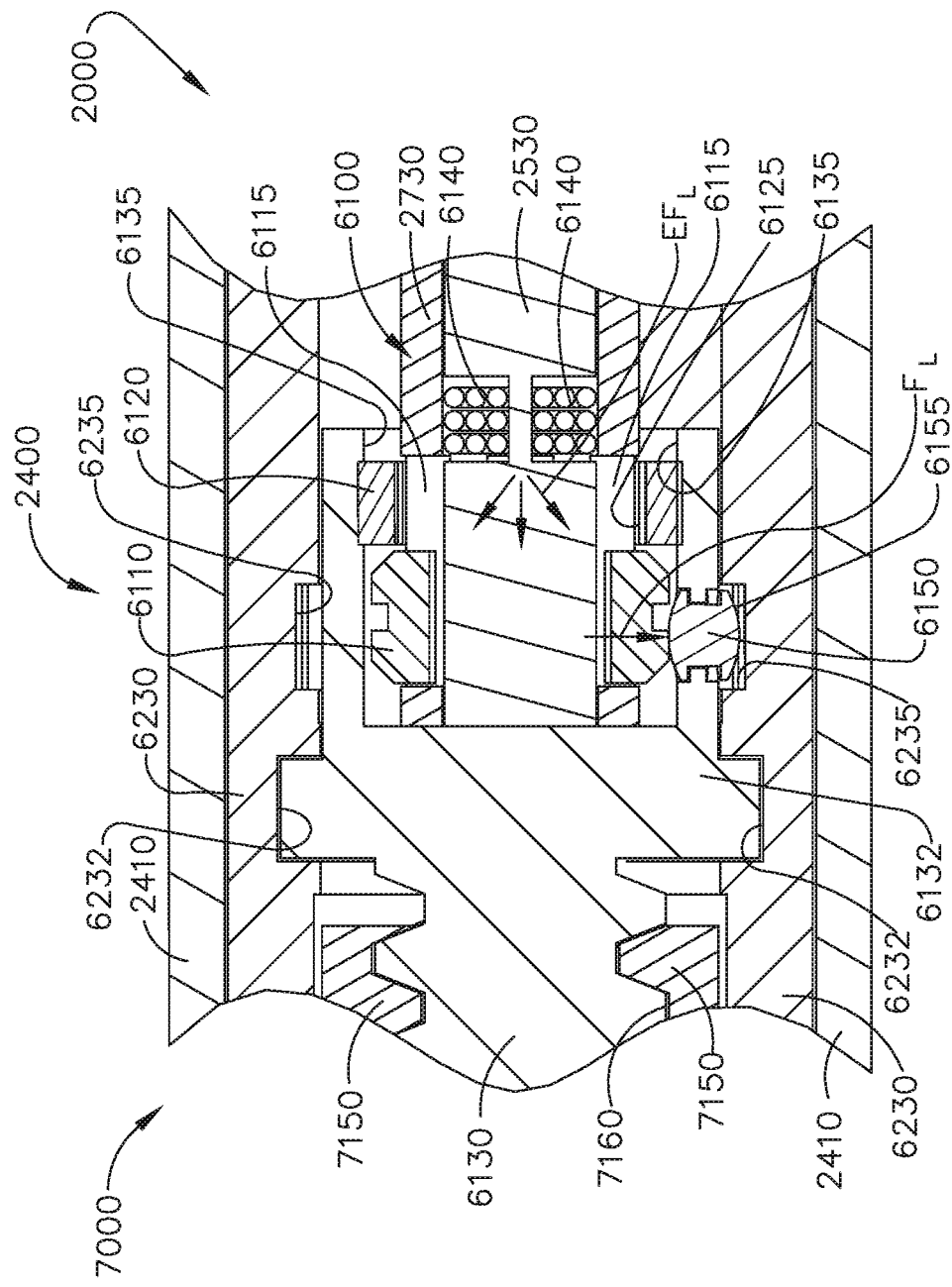
Figure 304:
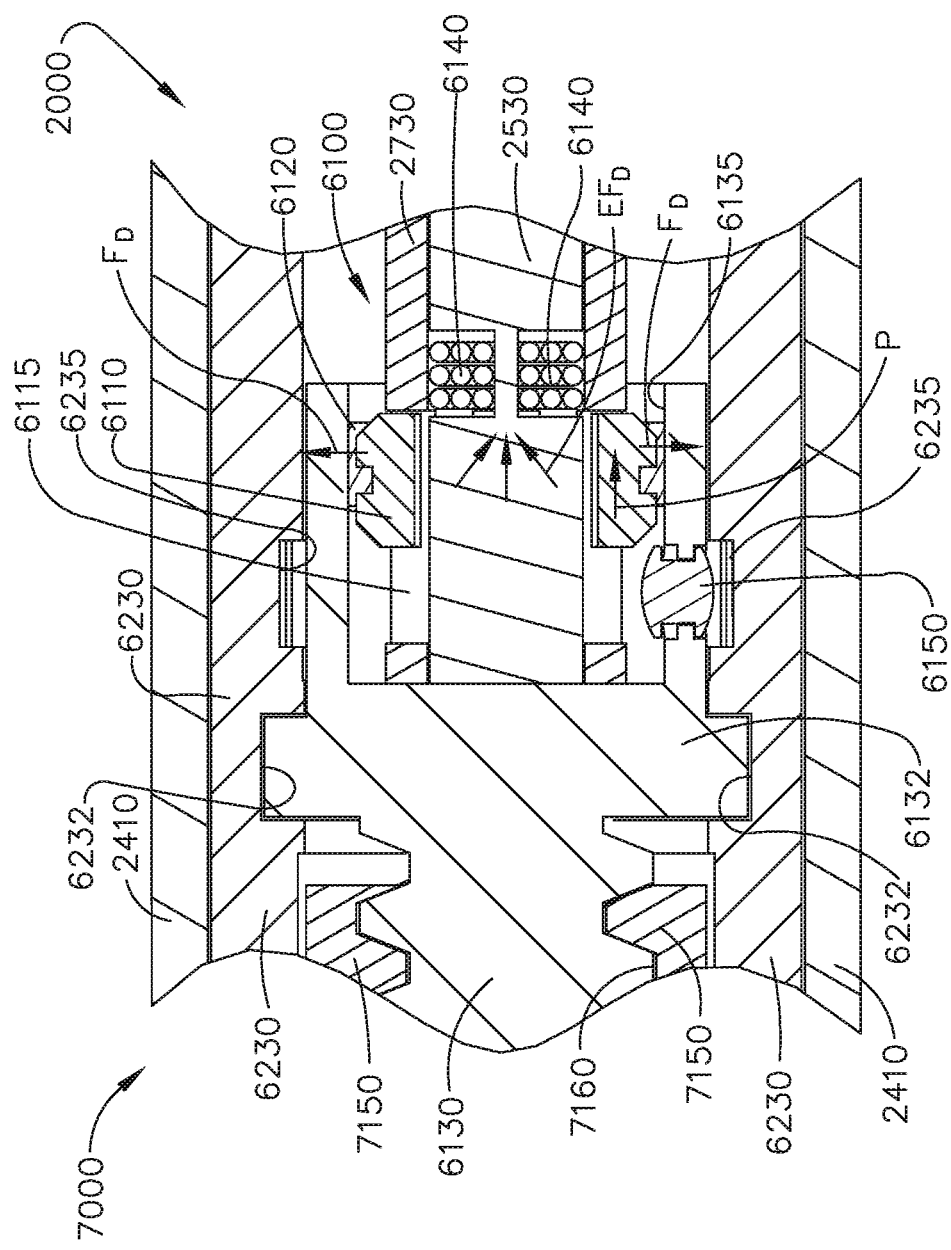
Figure 305:
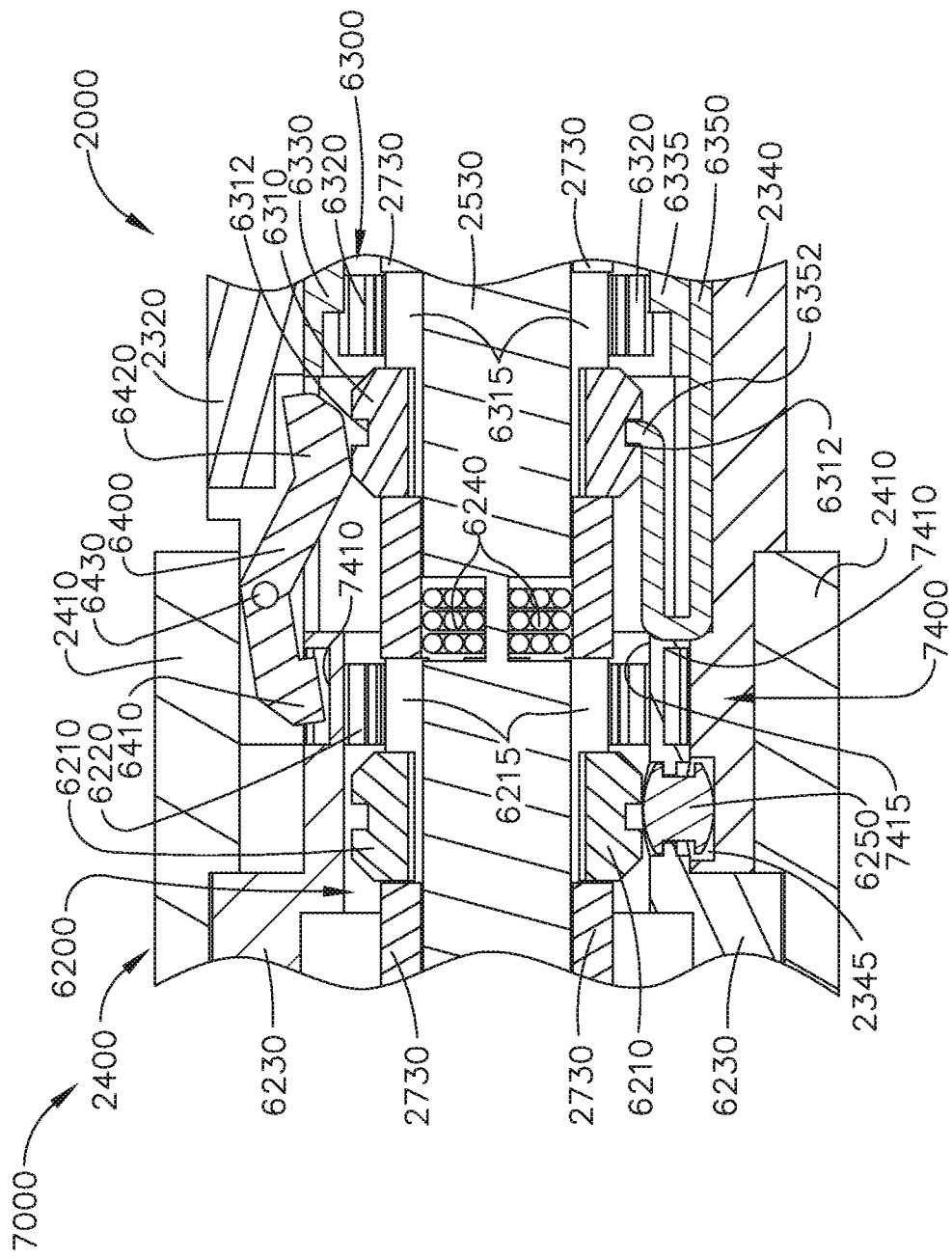
Figure 306:
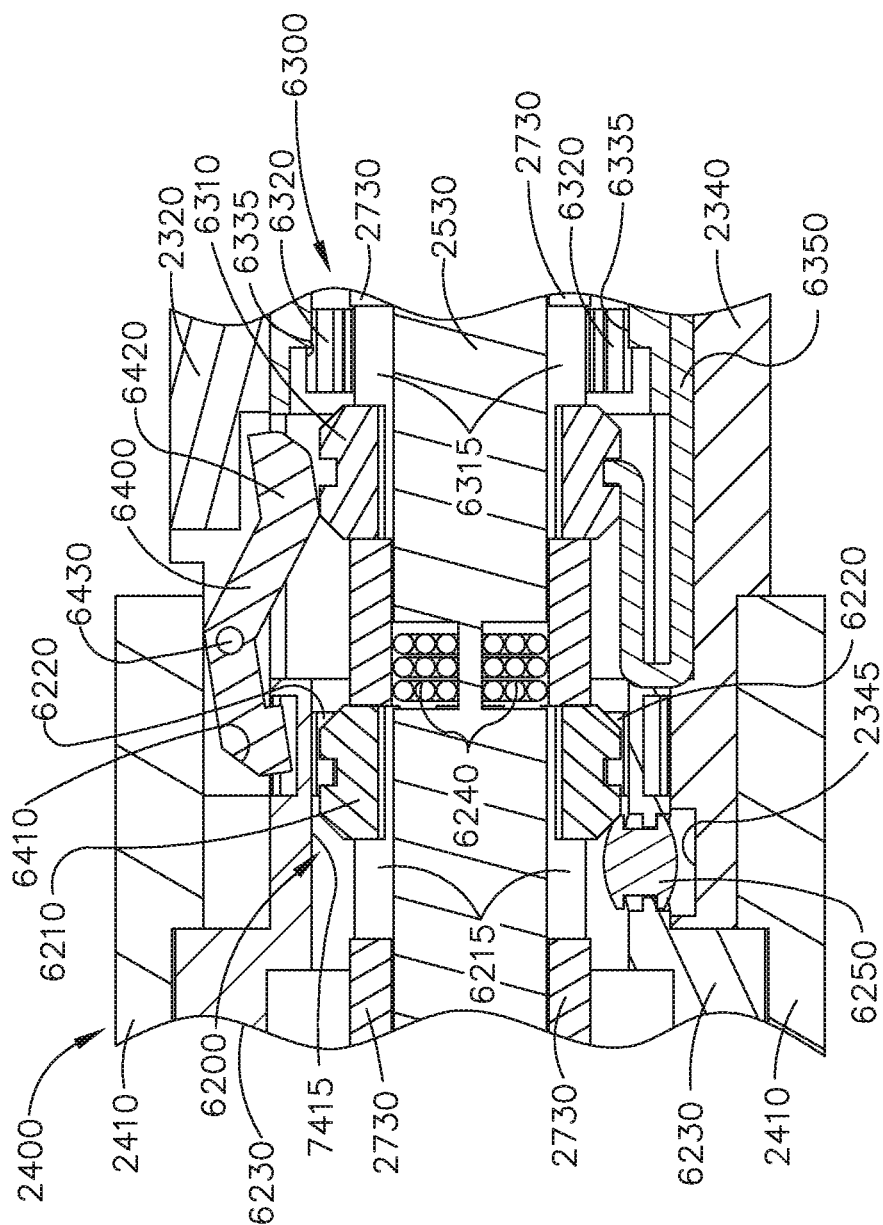
Figure 307:
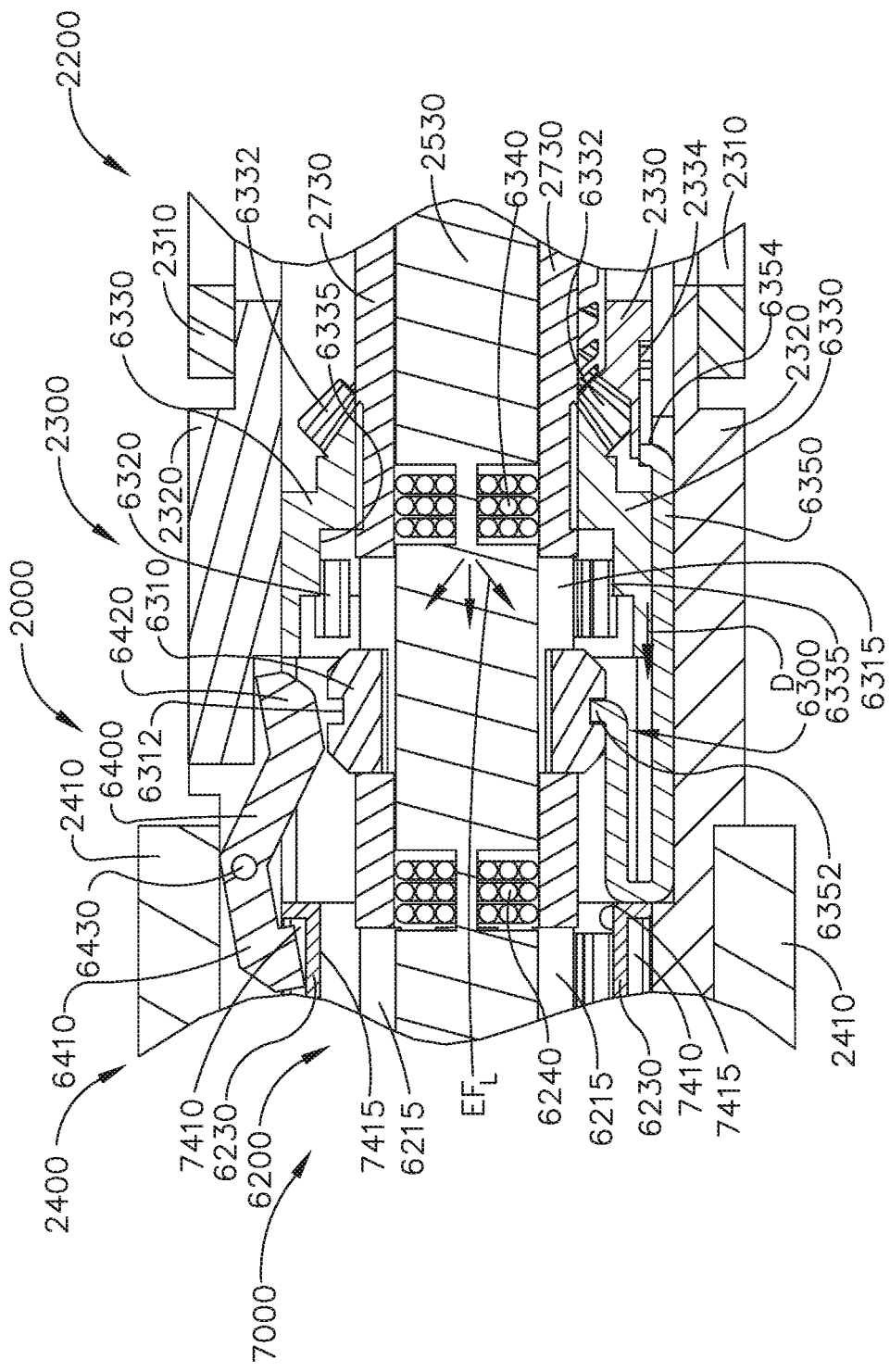
Figure 308:
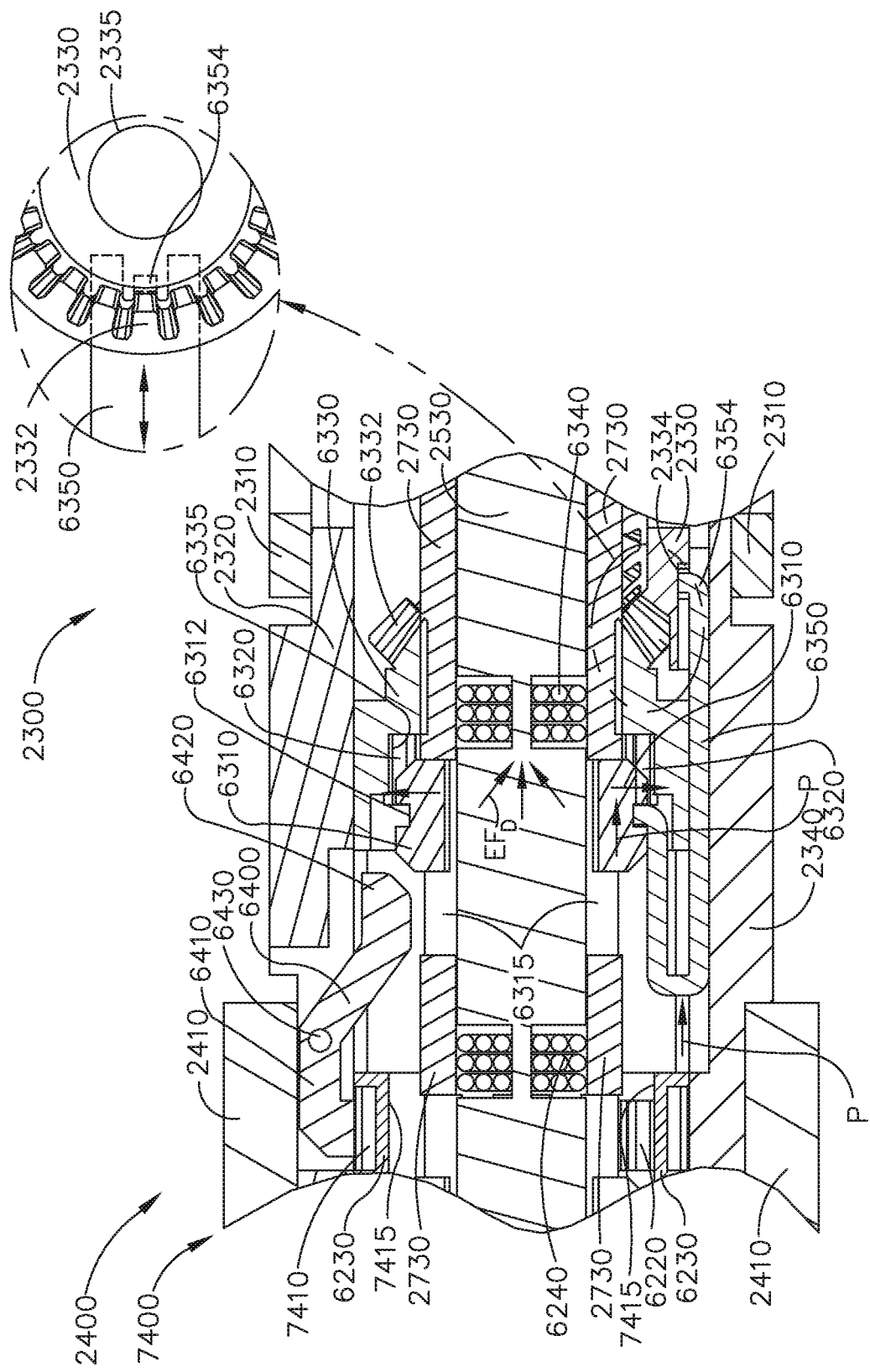
Figure 309:
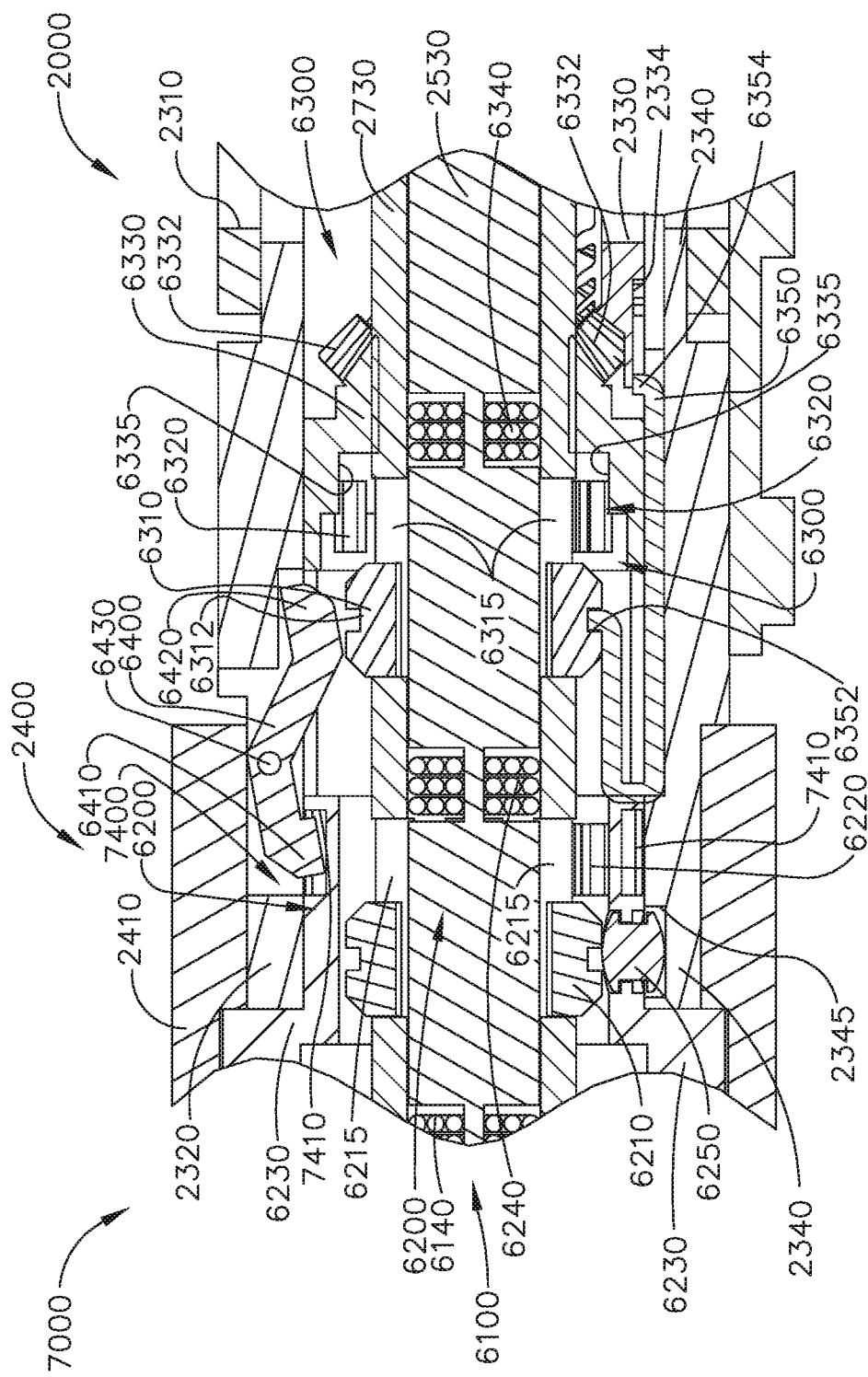
Figure 310:
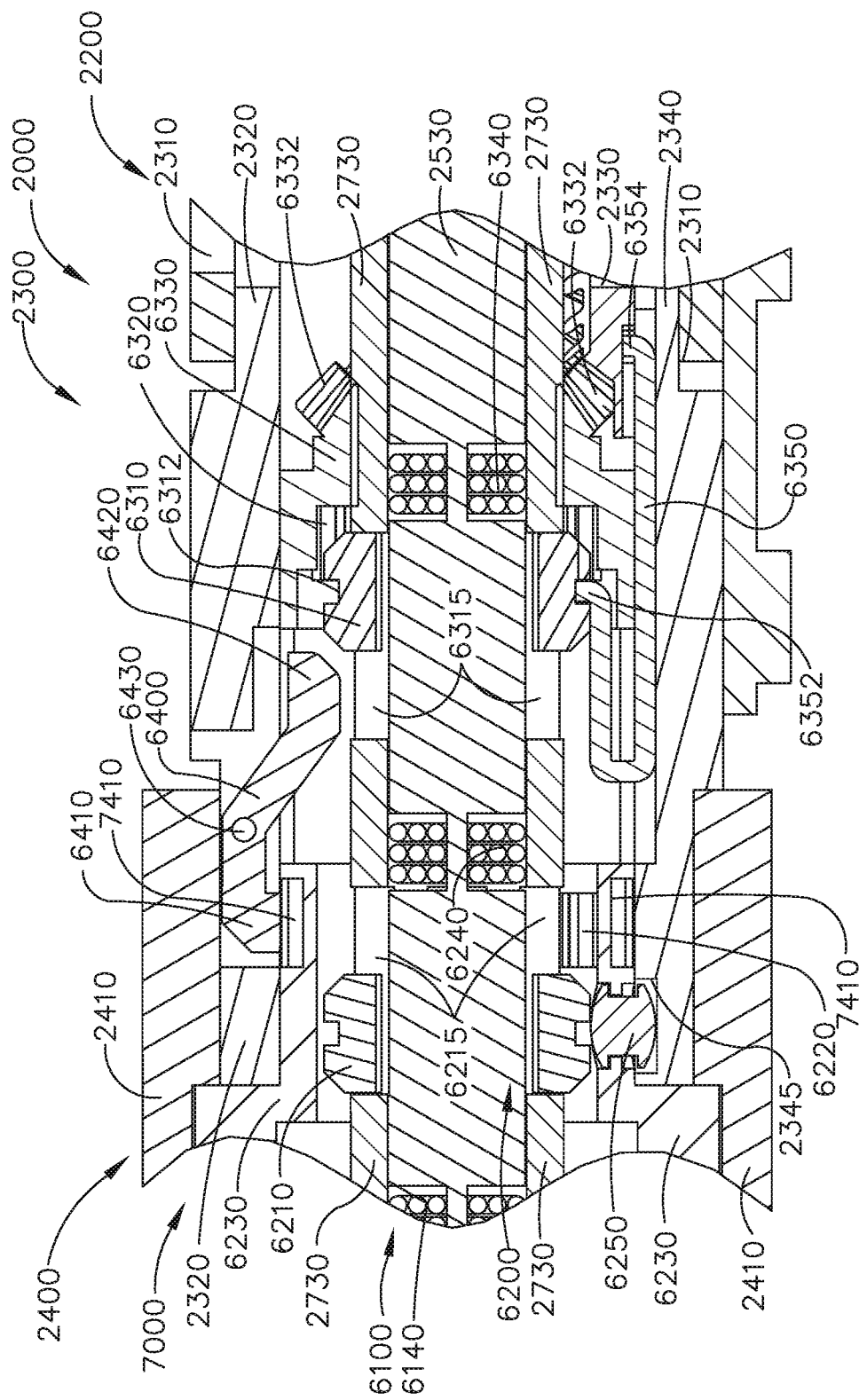
Figure 311:
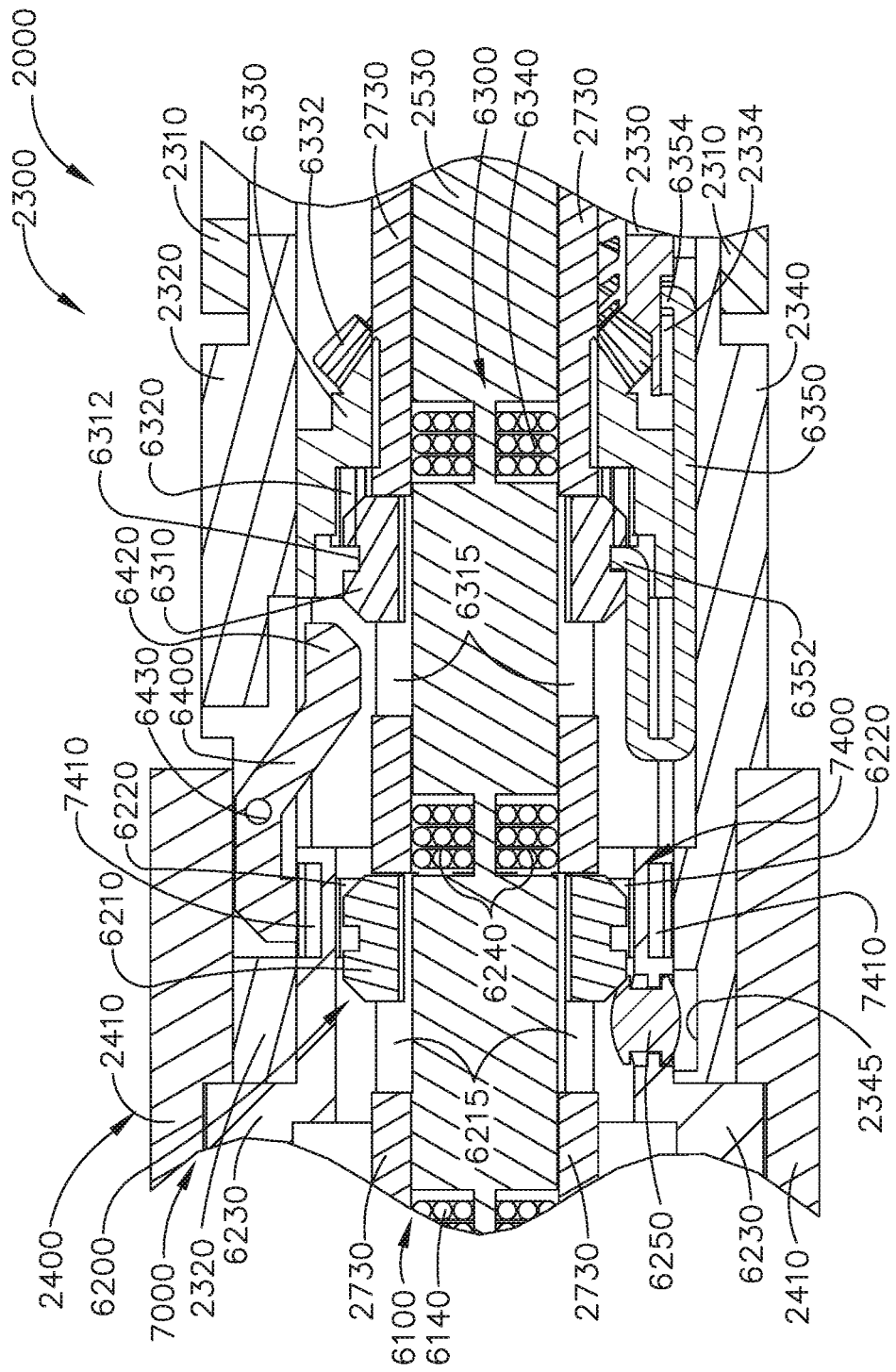
Figure 312:
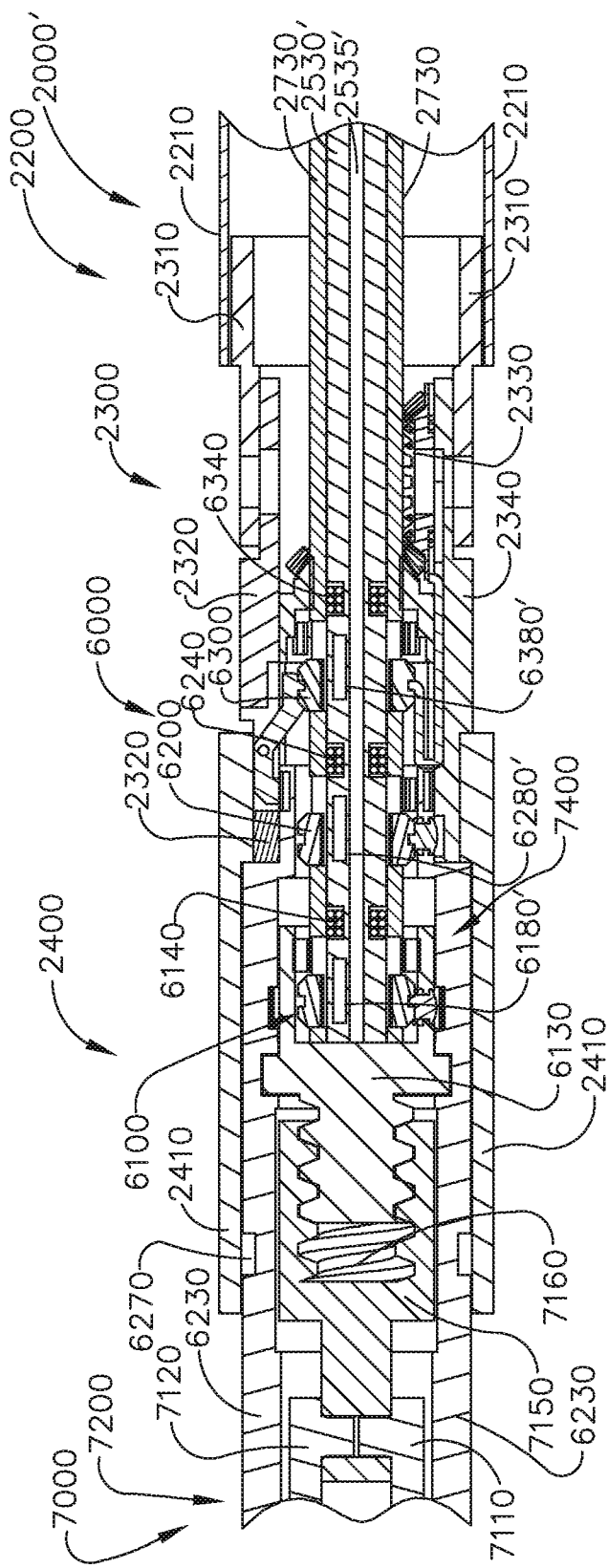
Figure 313:
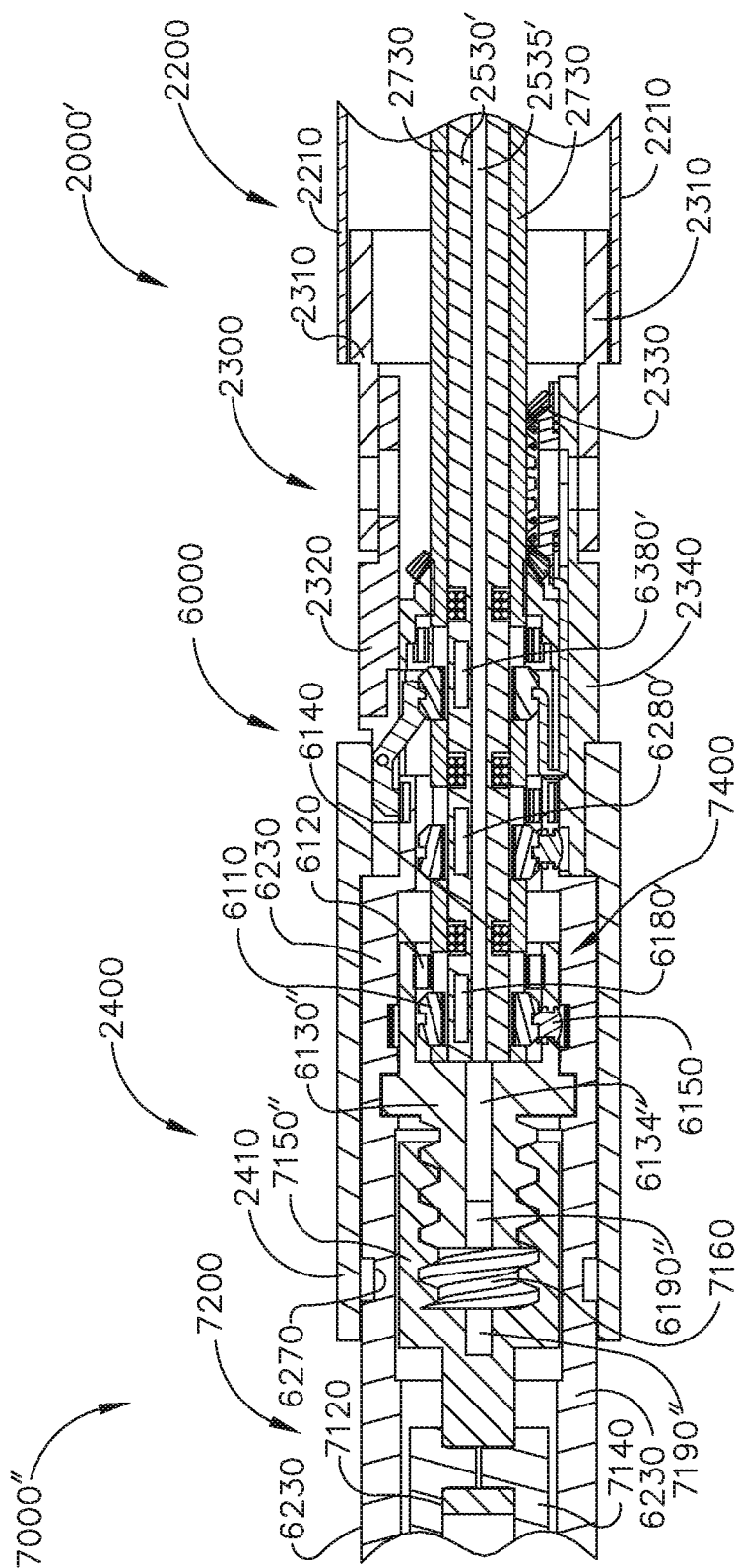
Figure 314:
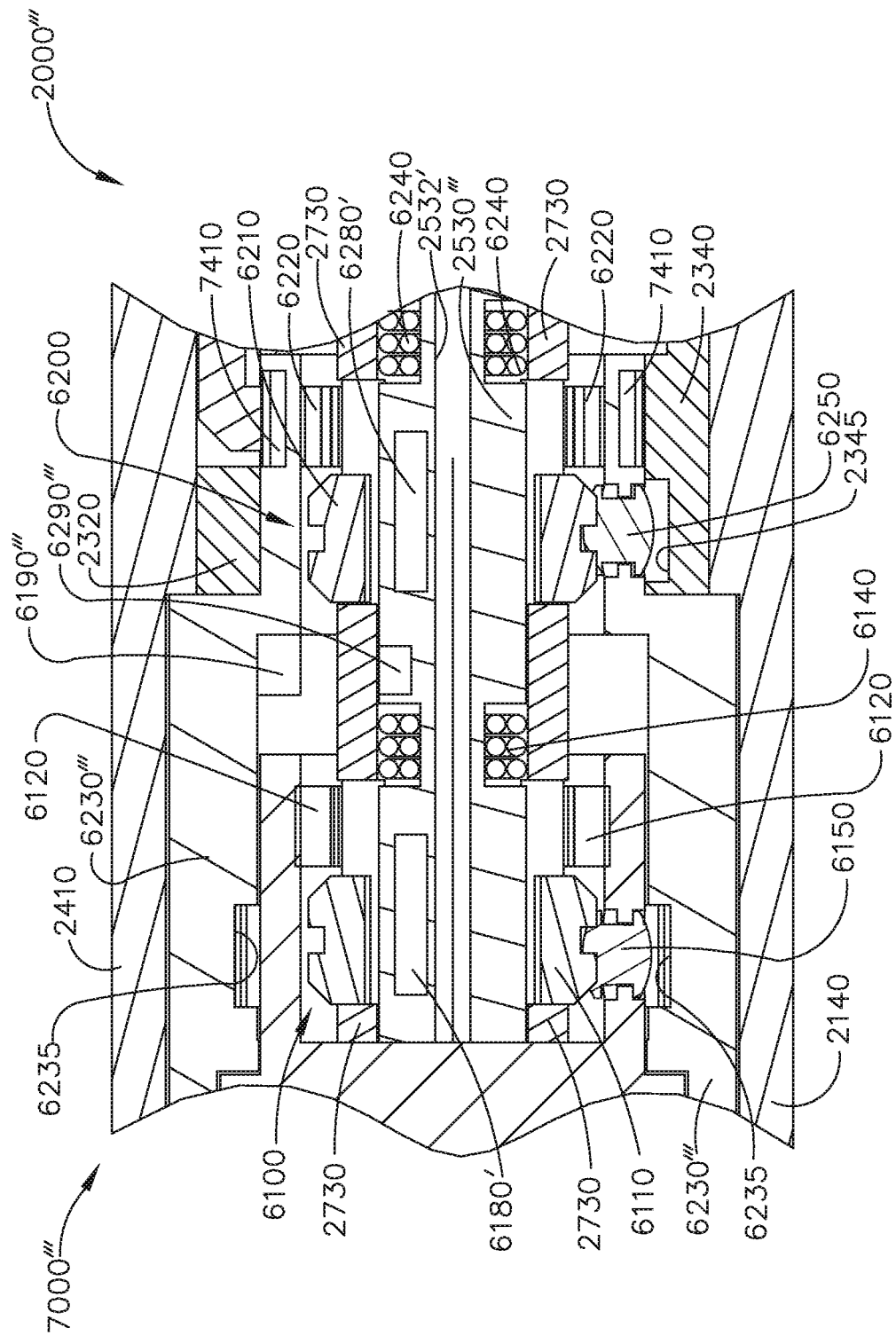
Figure 315:
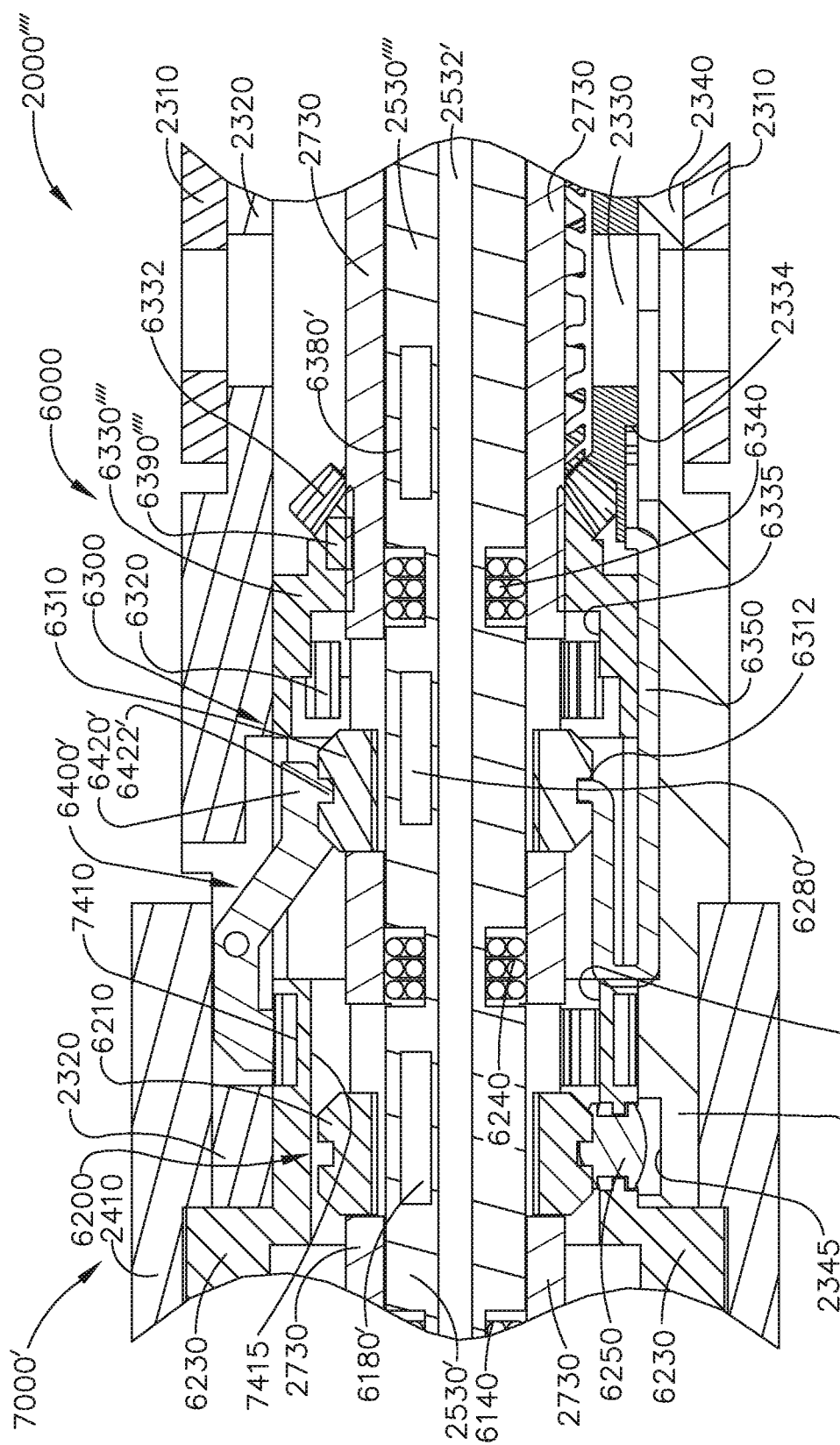
Figure 316:
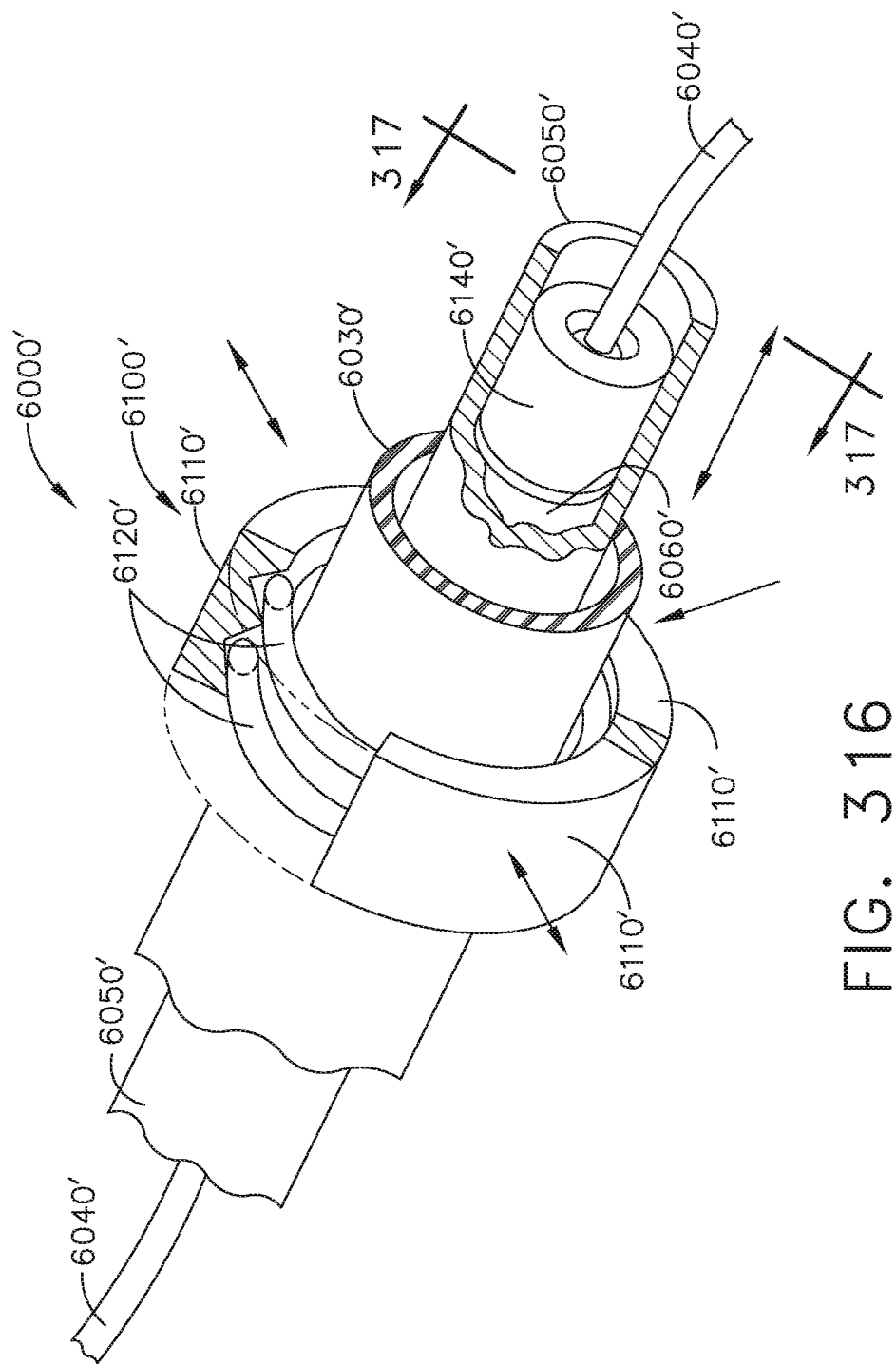
Figure 317:
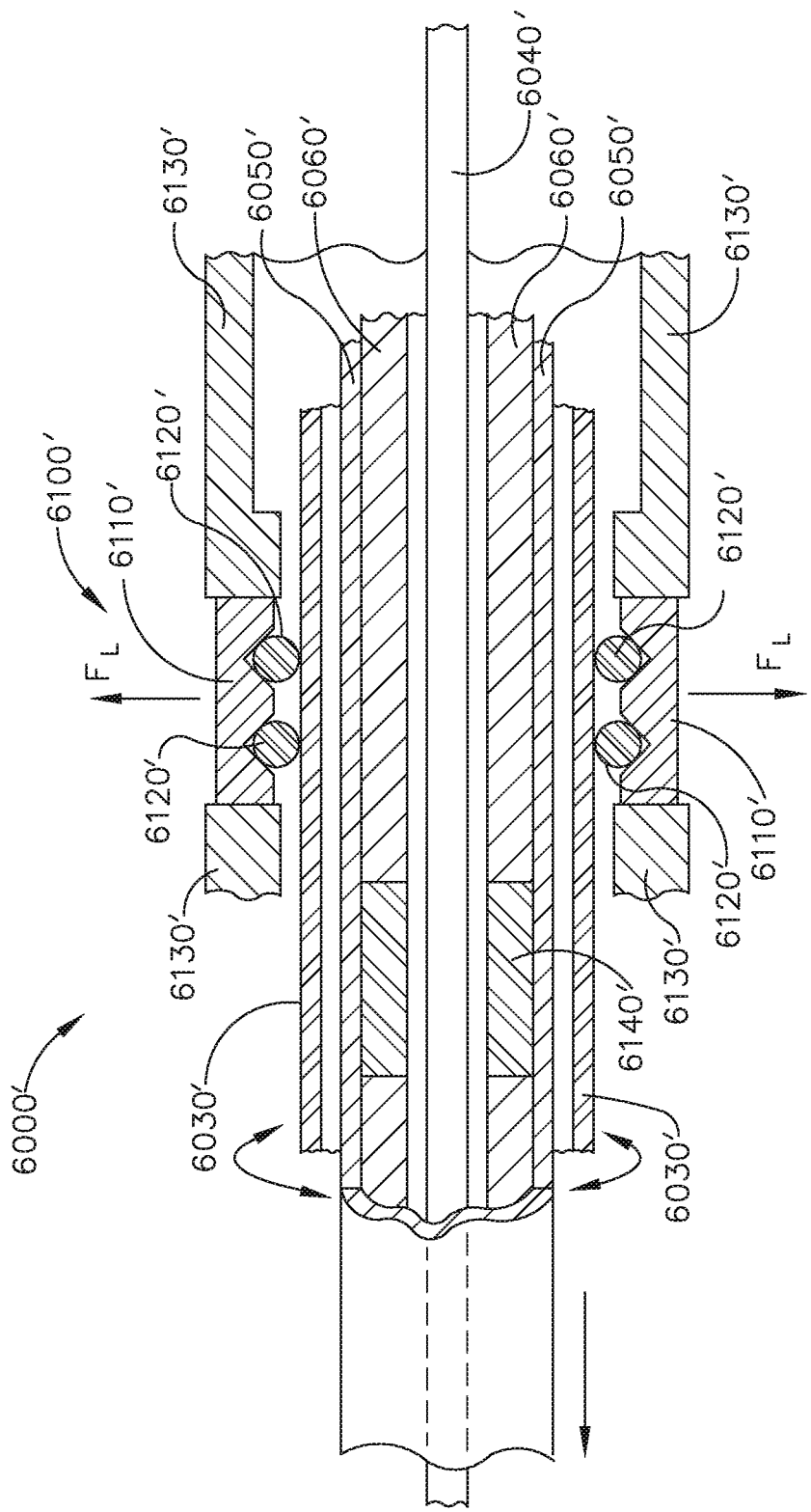
Figure 318:
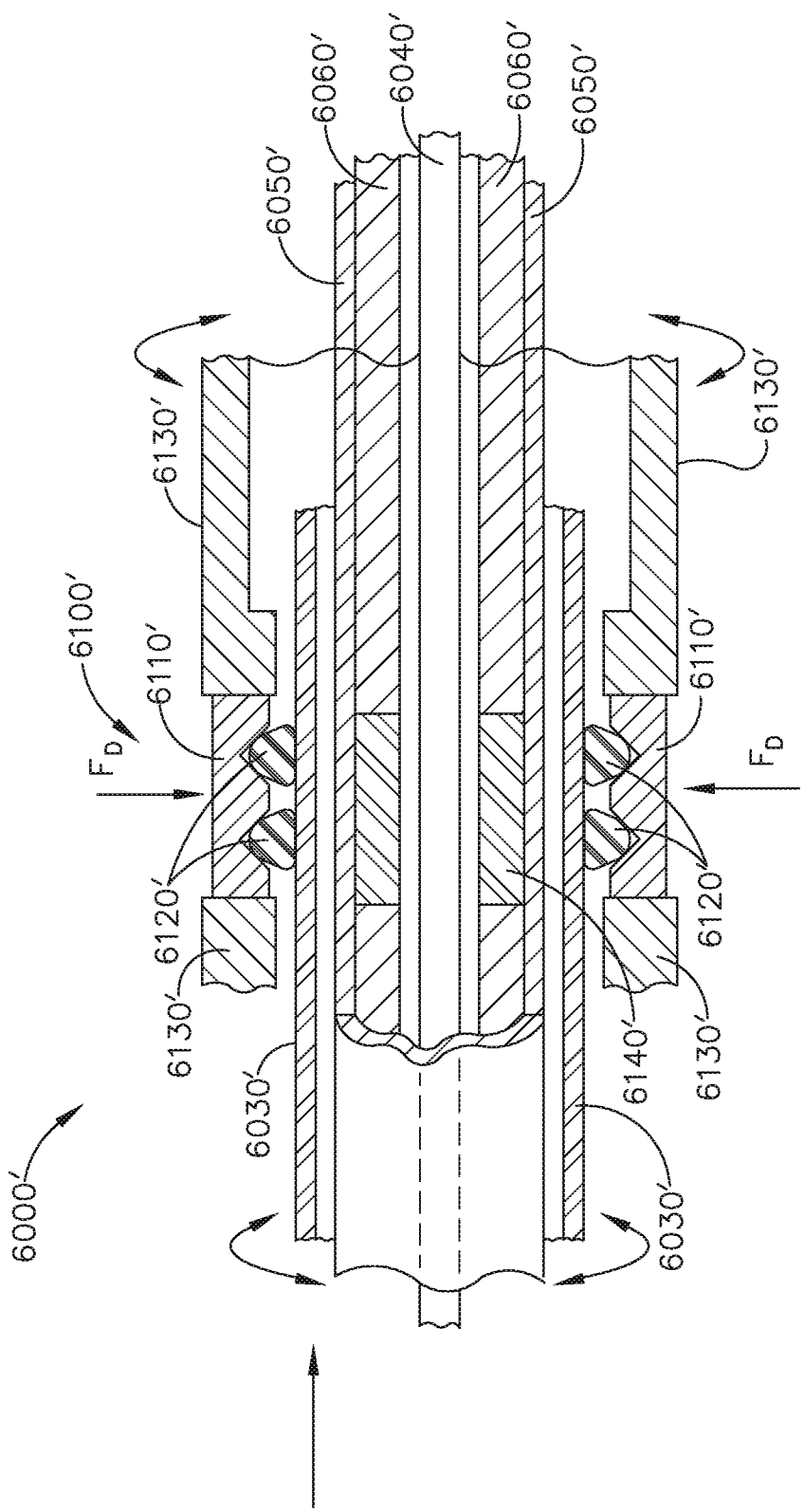
Figure 319:
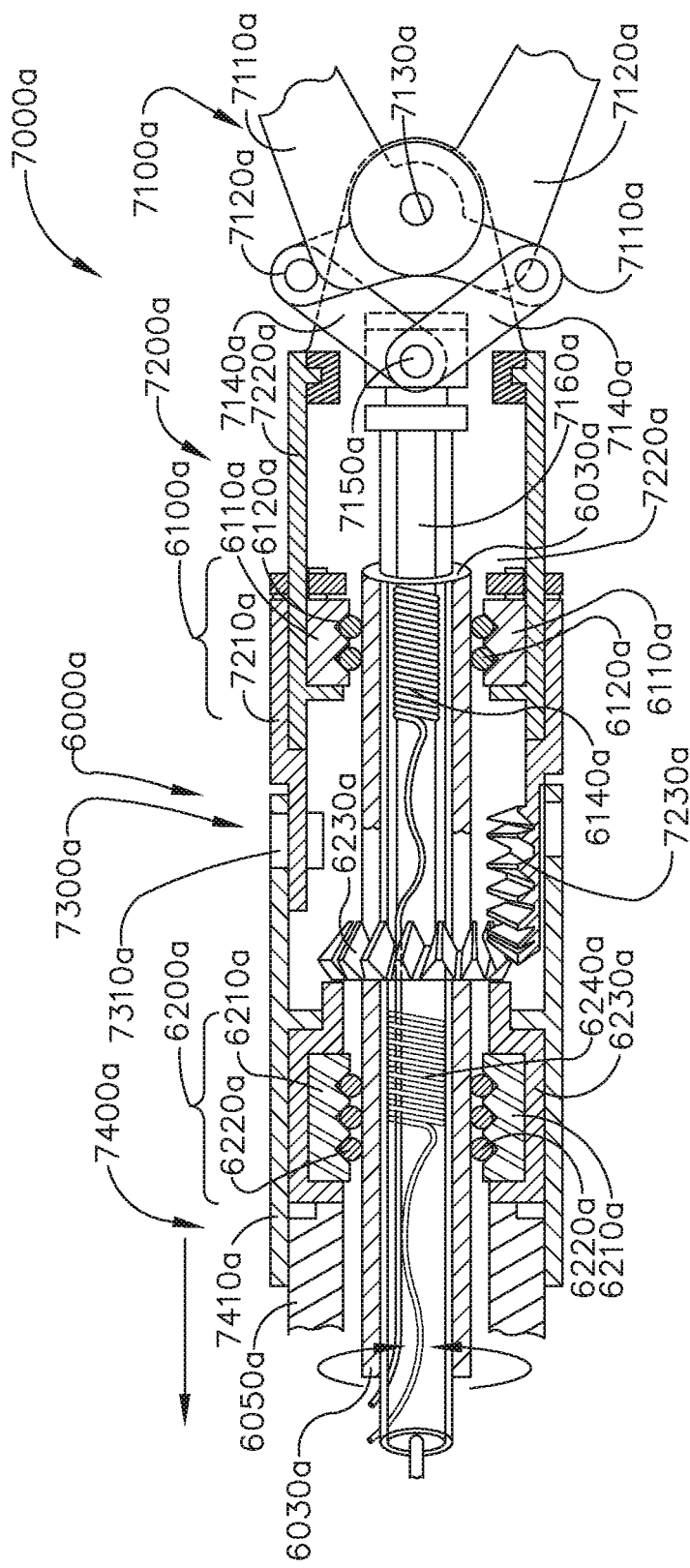
Figure 320:
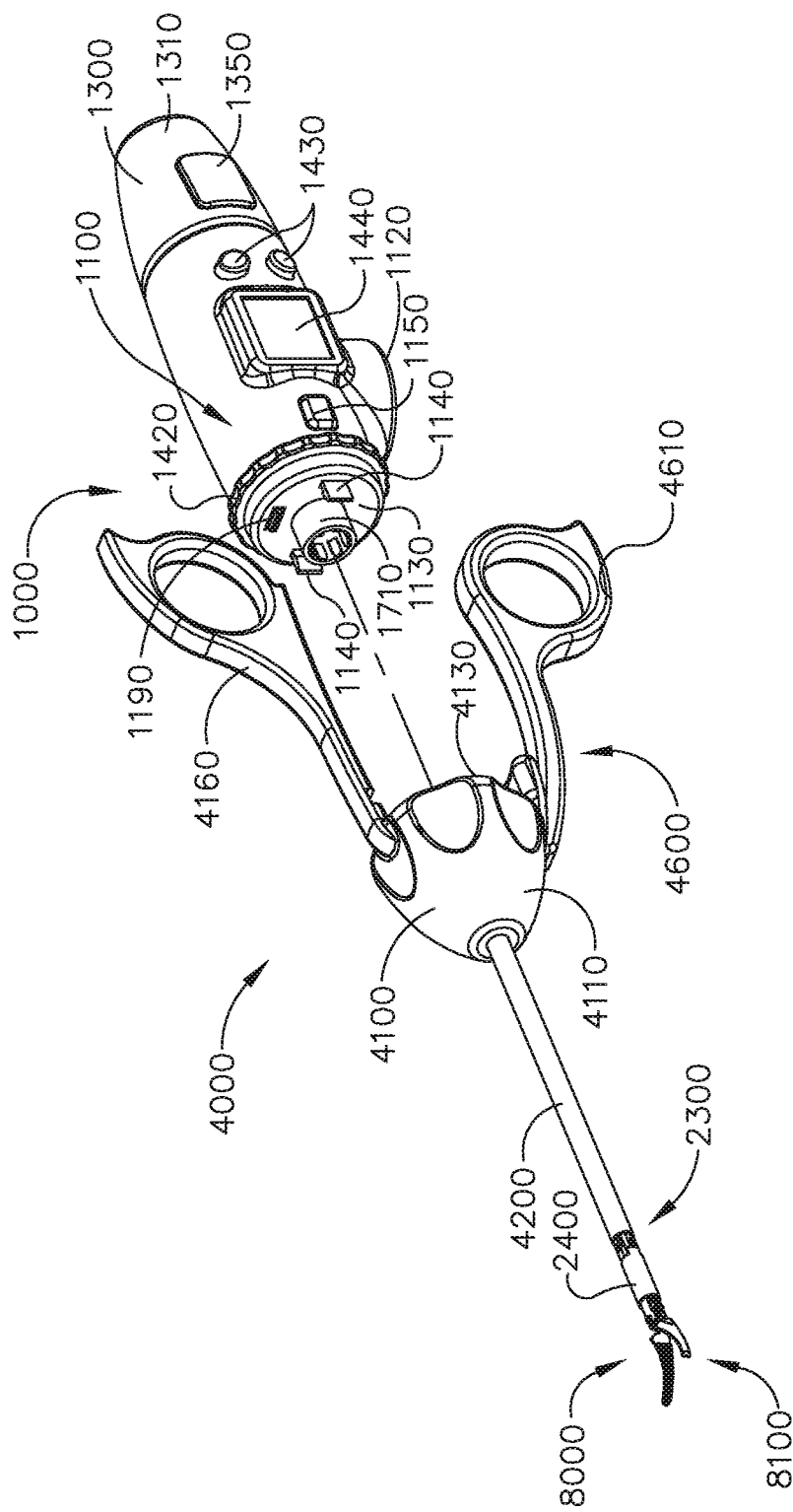
Figure 321:
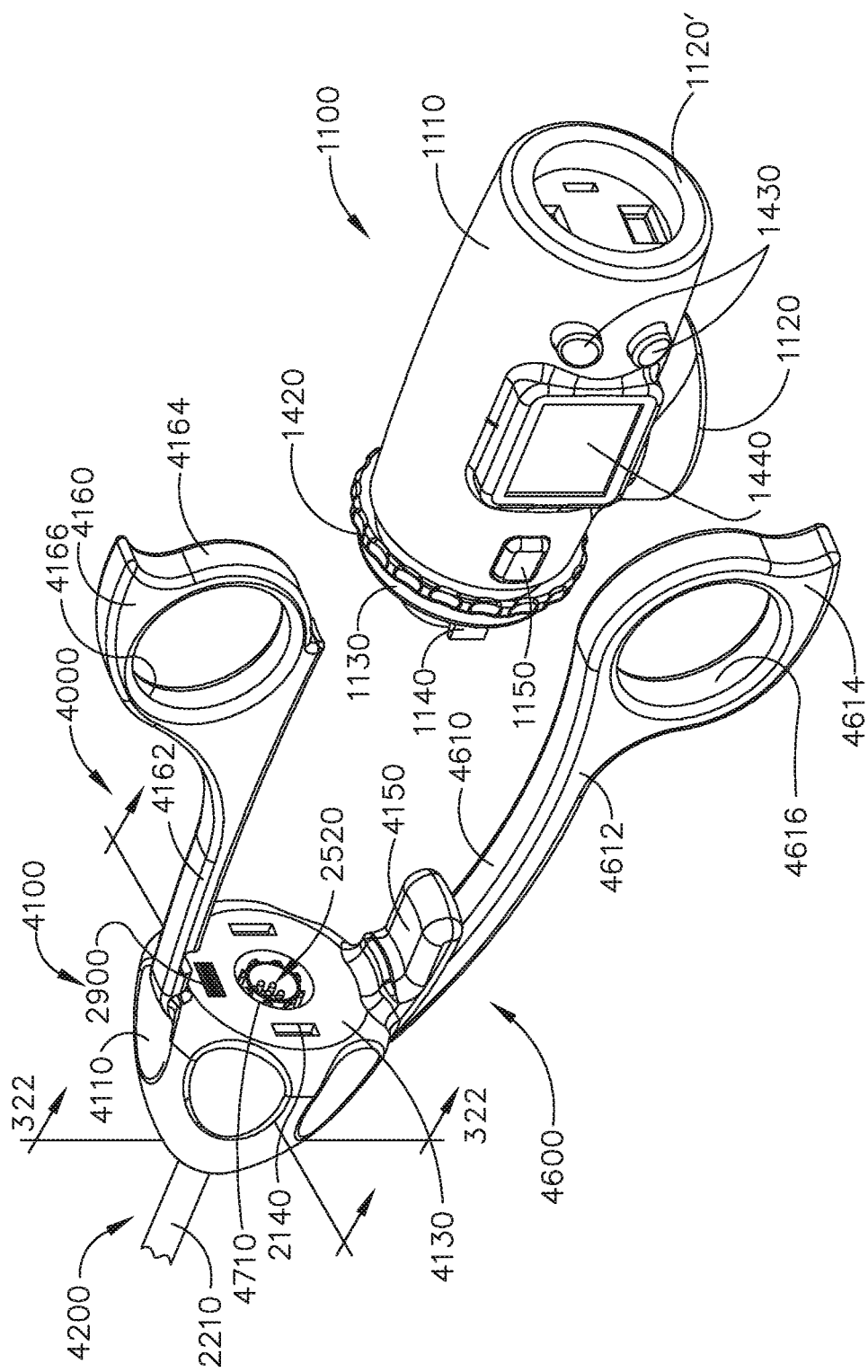
Figure 322:
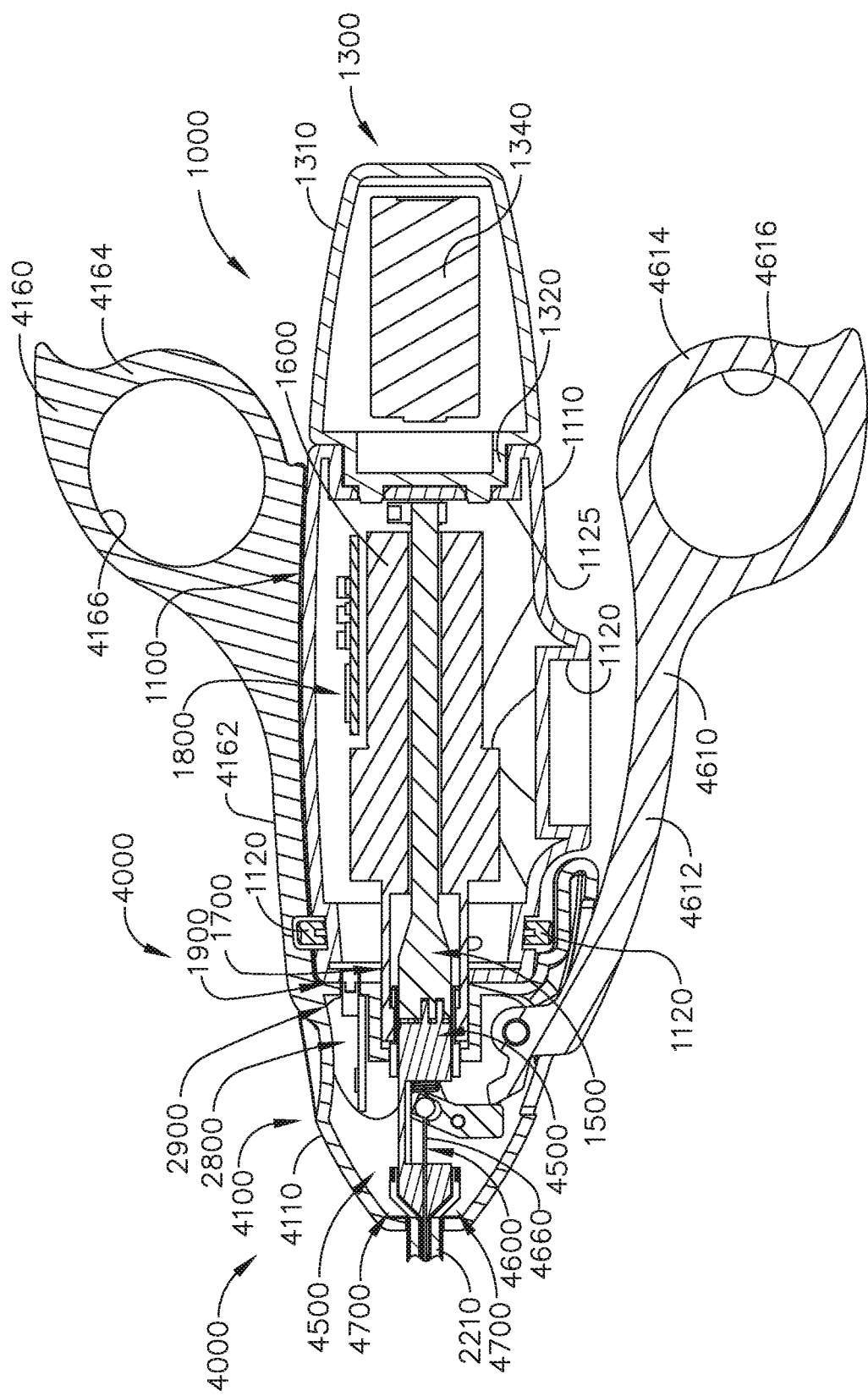
Figure 323:
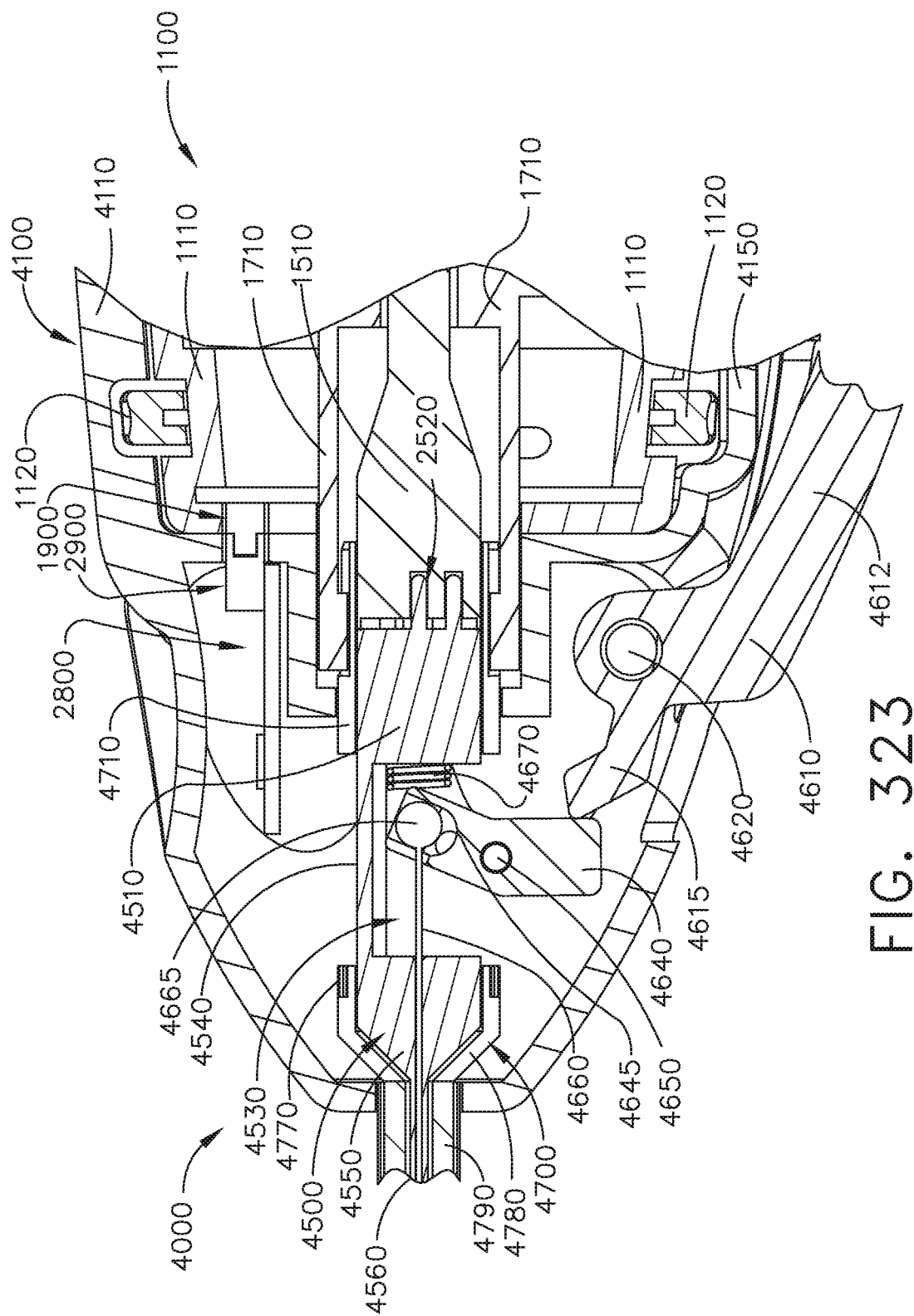
Figure 324:
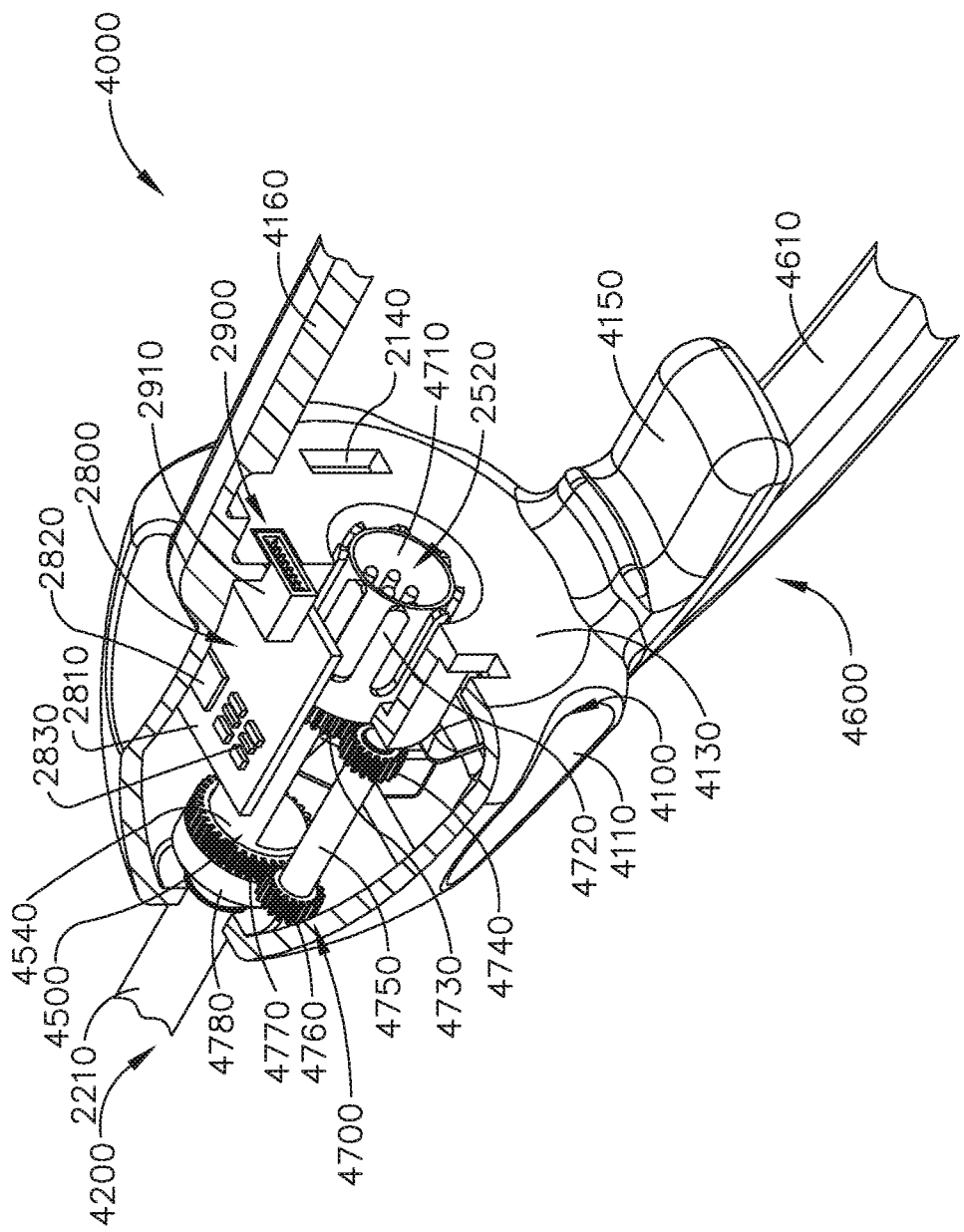
Figure 325:
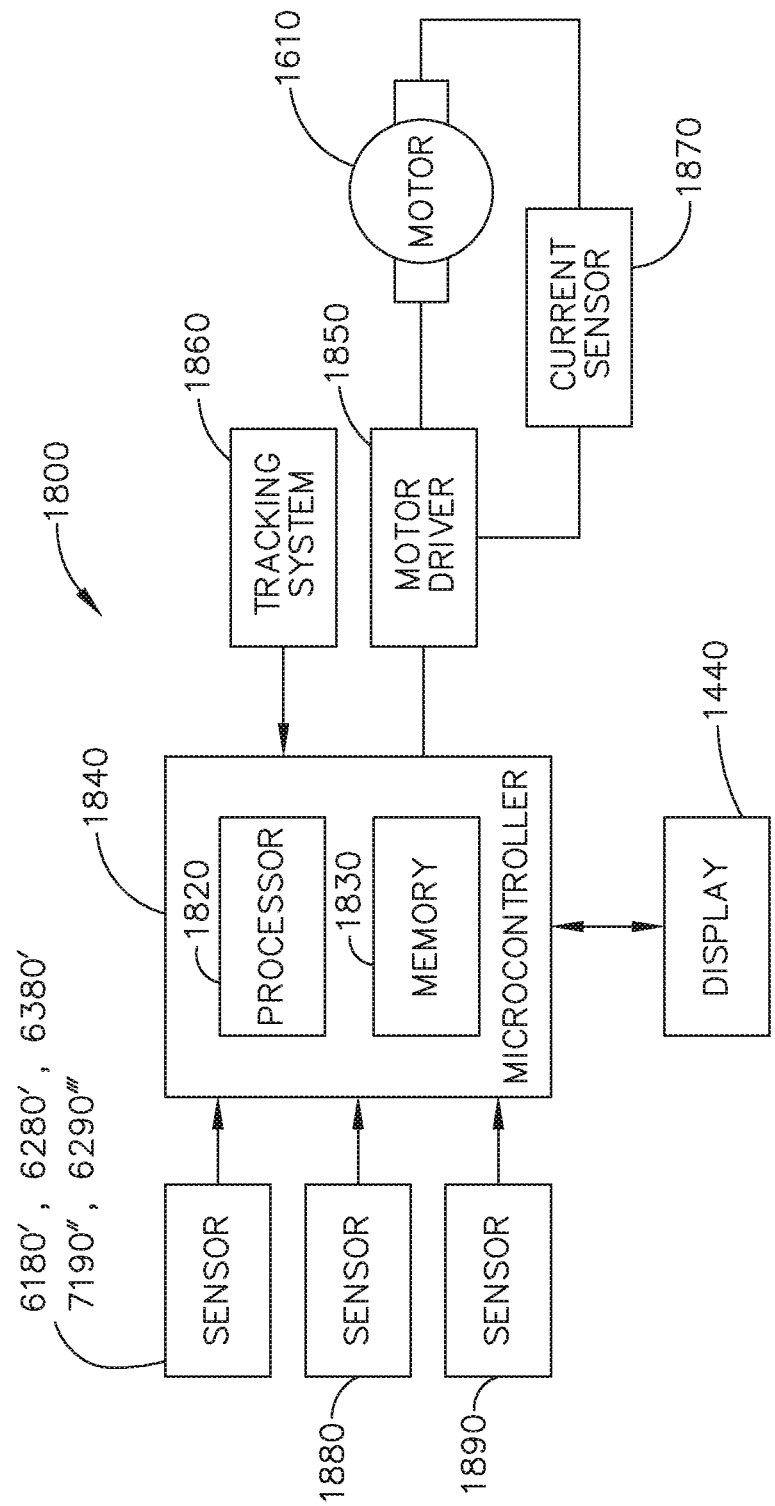

FIG. 269 is a graphical display of force over time of the robotic arm of FIG. 268, in accordance with one aspect of the present disclosure;

FIG. 270 is a perspective view of a robotic arm and a robotic hub of a robotic surgical system, in accordance with at least one aspect of the present disclosure;

FIG. 271 is a detail view of an end effector of a linear stapler attached to the robotic arm of FIG. 270, depicting the end effector positioned relative to a targeted tissue region during a surgical procedure, in accordance with at least one aspect of the present disclosure;

FIG. 272 is a graphical display of distance and force-to-close over time for the linear stapler of FIG. 271, in accordance with one aspect of the present disclosure;

FIG. 273 is a schematic depicting a robotic surgical system having a plurality of sensing systems, in accordance with one aspect of the present disclosure;

FIG. 273A is a detail view of a trocar of FIG. 273, in accordance with at least one aspect of the present disclosure;

FIG. 274 is a flowchart depicting a robotic surgical system utilizing a plurality of independent sensing systems, in accordance with one aspect of the present disclosure;

FIG. 275 illustrates a surgical system comprising a handle and several shaft assemblies—each of which are selectively attachable to the handle in accordance with at least one embodiment;

FIG. 276 is an elevational view of the handle and one of the shaft assemblies of the surgical system of FIG. 275;

FIG. 277 is a partial cross-sectional perspective view of the shaft assembly of FIG. 276;

FIG. 278 is another partial cross-sectional perspective view of the shaft assembly of FIG. 276;

FIG. 279 is a partial exploded view of the shaft assembly of FIG. 276;

FIG. 280 is a partial cross-sectional elevational view of the shaft assembly of FIG. 276;

FIG. 281 is an elevational view of a drive module of the handle of FIG. 275;

FIG. 282 is a cross-sectional perspective view of the drive module of FIG. 281;

FIG. 283 is an end view of the drive module of FIG. 281;

FIG. 284 is a partial cross-sectional view of the interconnection between the handle and shaft assembly of FIG. 276 in a locked configuration;

FIG. 285 is a partial cross-sectional view of the interconnection between the handle and shaft assembly of FIG. 276 in an unlocked configuration;

FIG. 286 is a cross-sectional perspective view of a motor and a speed reduction gear assembly of the drive module of FIG. 281;

FIG. 287 is an end view of the speed reduction gear assembly of FIG. 286;

FIG. 288 is a partial perspective view of an end effector of the shaft assembly of FIG. 276 in an open configuration;

FIG. 289 is a partial perspective view of the end effector of FIG. 288 in a closed configuration;

FIG. 290 is a partial perspective view of the end effector of FIG. 288 articulated in a first direction;

FIG. 291 is a partial perspective view of the end effector of FIG. 288 articulated in a second direction;

FIG. 292 is a partial perspective view of the end effector of FIG. 288 rotated in a first direction;

FIG. 293 is a partial perspective view of the end effector of FIG. 288 rotated in a second direction;

FIG. 294 is a partial cross-sectional perspective view of the end effector of FIG. 288 detached from the shaft assembly of FIG. 276;

FIG. 295 is an exploded view of the end effector of FIG. 288 illustrated with some components removed;

FIG. 296 is an exploded view of a distal attachment portion of the shaft assembly of FIG. 276;

FIG. 297 is an exploded view of the distal portion of the shaft assembly of FIG. 276 illustrated with some components removed;

FIG. 298 is another partial cross-sectional perspective view of the end effector of FIG. 288 detached from the shaft assembly of FIG. 276;

FIG. 299 is a partial cross-sectional perspective view of the end effector of FIG. 288 attached to the shaft assembly of FIG. 276;

FIG. 300 is a partial cross-sectional perspective view of the end effector of FIG. 288 attached to the shaft assembly of FIG. 276;

FIG. 301 is another partial cross-sectional perspective view of the end effector of FIG. 288 attached to the shaft assembly of FIG. 276;

FIG. 302 is a partial cross-sectional view of the end effector of FIG. 288 attached to the shaft assembly of FIG. 276 depicting a first, second, and third clutch of the end effector;

FIG. 303 depicts the first clutch of FIG. 302 in an unactuated condition;

FIG. 304 depicts the first clutch of FIG. 302 in an actuated condition;

FIG. 305 depicts the second clutch of FIG. 302 in an unactuated condition;

FIG. 306 depicts the second clutch of FIG. 302 in an actuated condition;

FIG. 307 depicts the third clutch of FIG. 302 in an unactuated condition;

FIG. 308 depicts the third clutch of FIG. 302 in an actuated condition;

FIG. 309 depicts the second and third clutches of FIG. 302 in their unactuated conditions and the end effector of FIG. 288 locked to the shaft assembly of FIG. 276;

FIG. 310 depicts the second clutch of FIG. 302 in its unactuated condition and the third clutch of FIG. 302 in its actuated condition;

FIG. 311 depicts the second and third clutches of FIG. 302 in their actuated conditions and the end effector of FIG. 288 unlocked from the shaft assembly of FIG. 276;

FIG. 312 is a partial cross-sectional view of a shaft assembly in accordance with at least one alternative embodiment comprising sensors configured to detect the conditions of the first, second, and third clutches of FIG. 302;

FIG. 313 is a partial cross-sectional view of a shaft assembly in accordance with at least one alternative embodiment comprising sensors configured to detect the conditions of the first, second, and third clutches of FIG. 302;

FIG. 314 depicts the first and second clutches of FIG. 313 in their unactuated conditions and a sensor in accordance with at least one alternative embodiment;

FIG. 315 depicts the second and third clutches of FIG. 313 in their unactuated conditions and a sensor in accordance with at least one alternative embodiment;

FIG. 316 is a partial cross-sectional view of a shaft assembly in accordance with at least one embodiment;

FIG. 317 is a partial cross-sectional view of the shaft assembly of FIG. 316 comprising a clutch illustrated in an unactuated condition;

FIG. 318 is a partial cross-sectional view of the shaft assembly of FIG. 316 illustrating the clutch in an actuated condition;

FIG. 319 is a partial cross-sectional view of a shaft assembly in accordance with at least one embodiment comprising first and second clutches illustrated in an unactuated condition;

FIG. 320 is a perspective view of the handle drive module of FIG. 281 and one of the shaft assemblies of the surgical system of FIG. 275;

FIG. 321 is another perspective view of the handle drive module of FIG. 281 and the shaft assembly of FIG. 320;

FIG. 322 is a partial cross-sectional view of the shaft assembly of FIG. 320 attached to the handle of FIG. 275;

FIG. 323 is another partial cross-sectional view of the shaft assembly of FIG. 320 attached to the handle of FIG. 275;

FIG. 324 is a partial cross-sectional perspective view of the shaft assembly of FIG. 320;

FIG. 325 is a schematic of the control system of the surgical system of FIG. 275.

Figure 326:
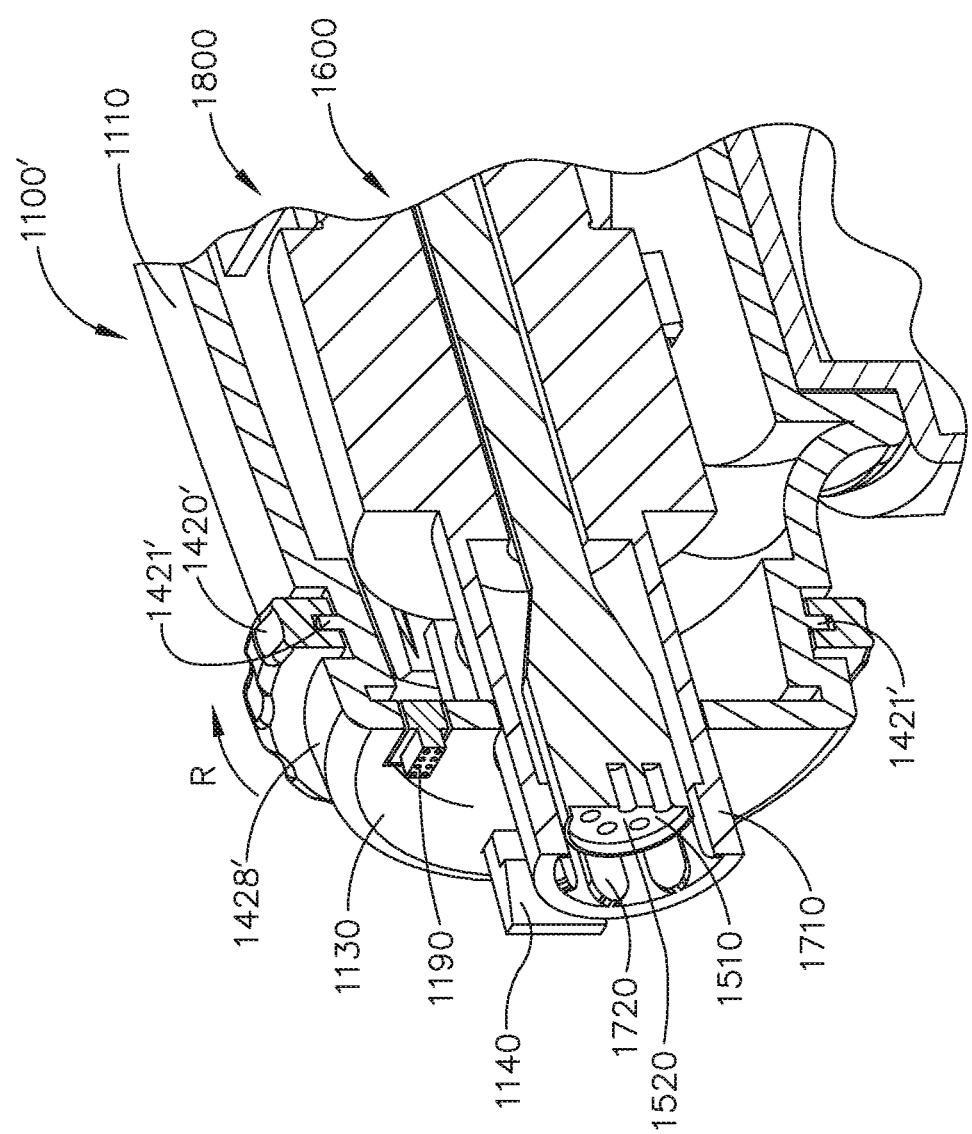
Figure 327:
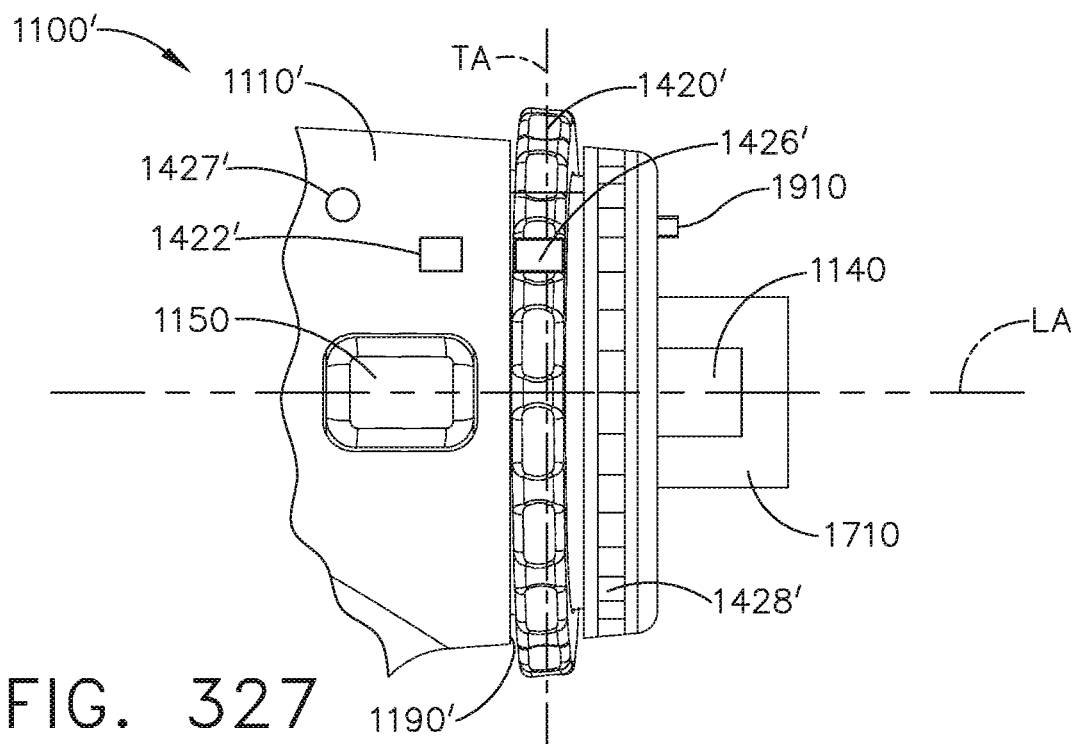
Figure 328:
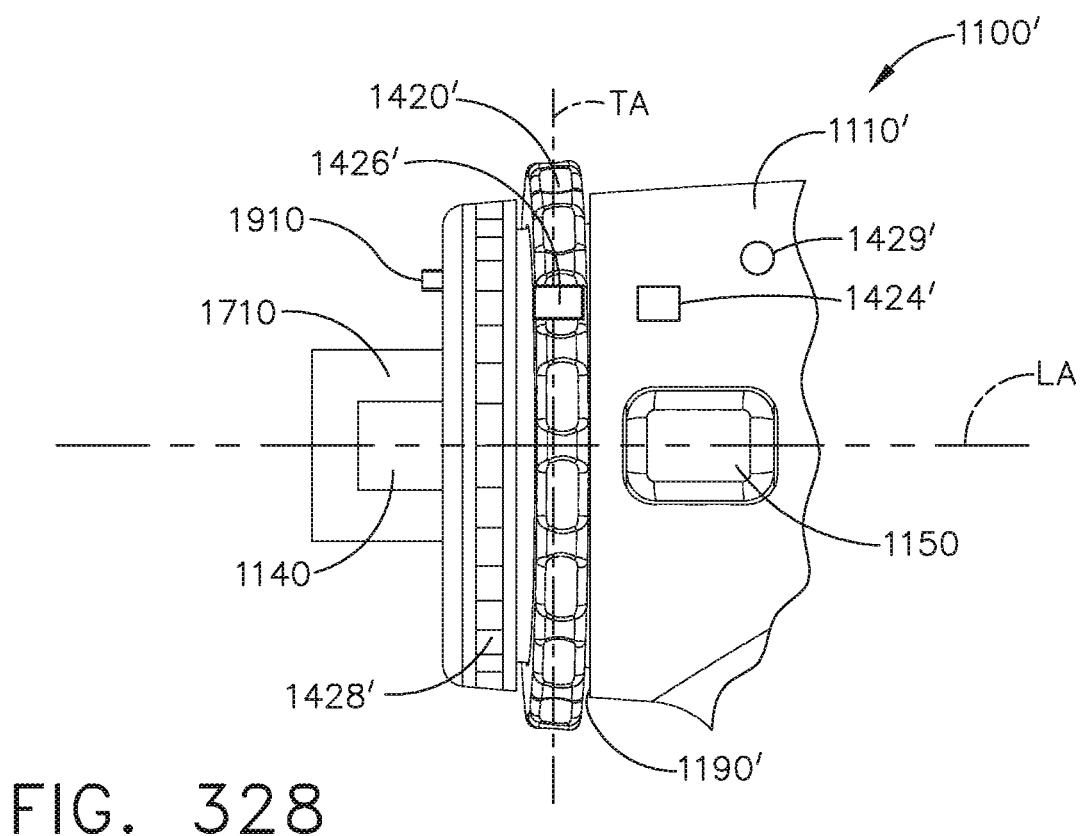
Figure 329:
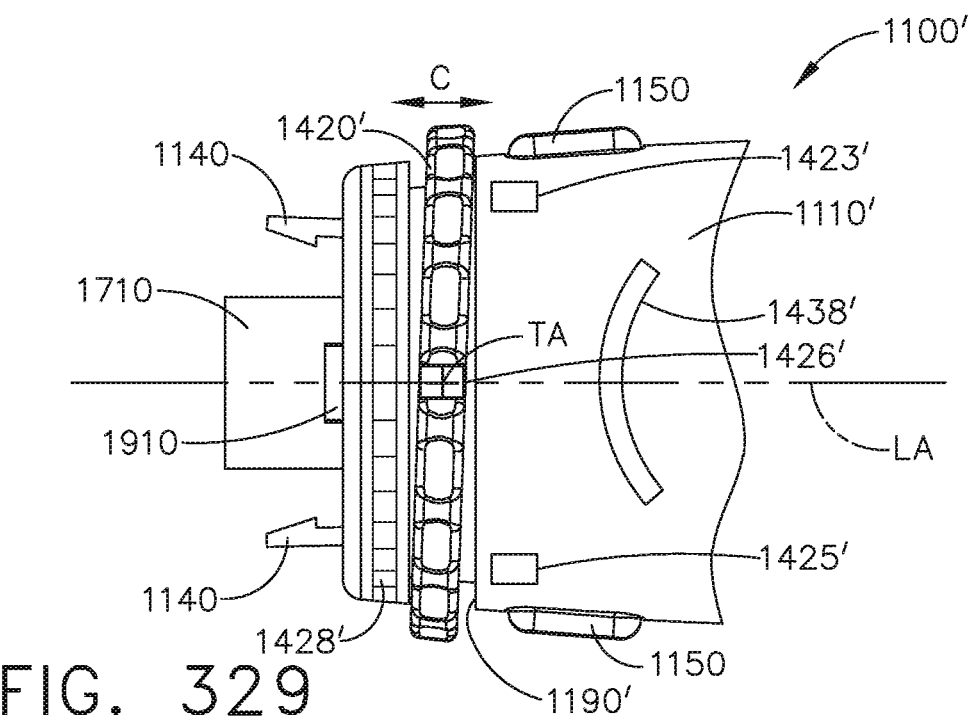
Figure 330:
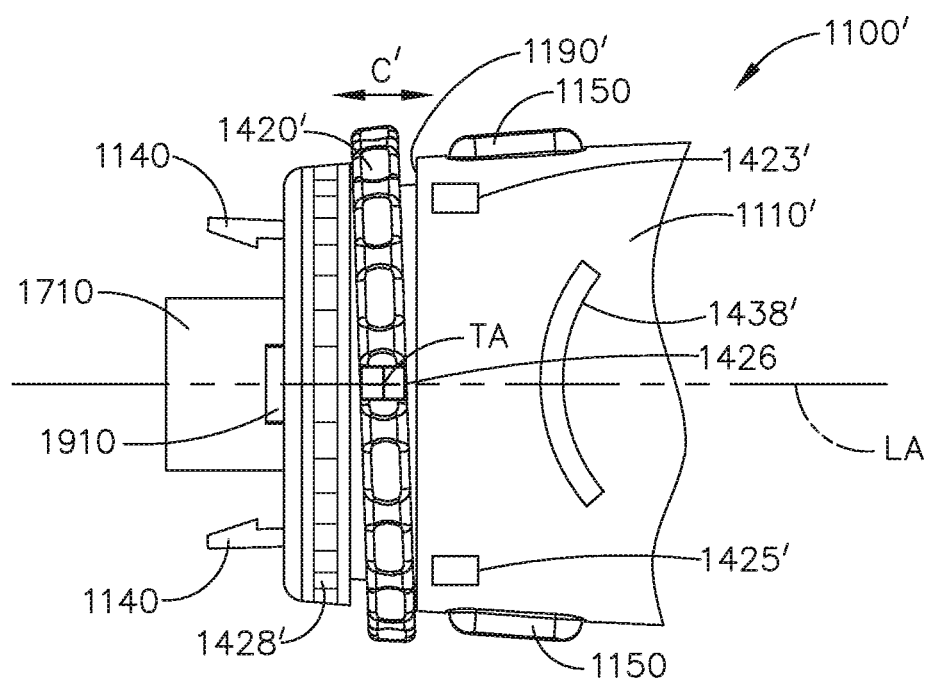
Figure 331:
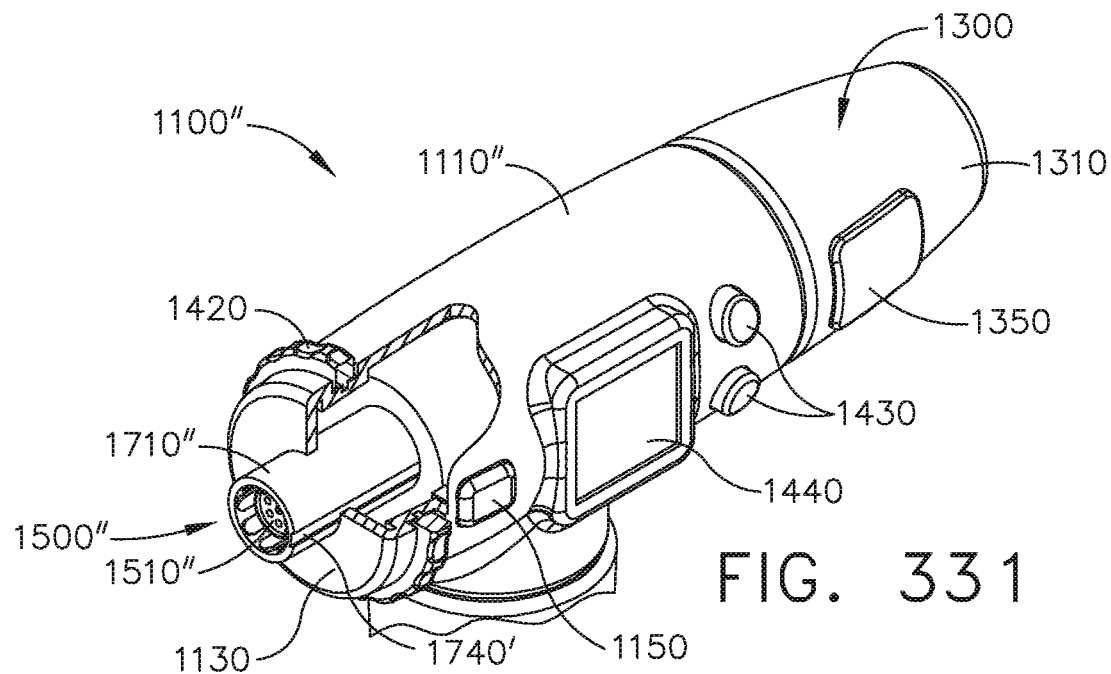
Figure 332:
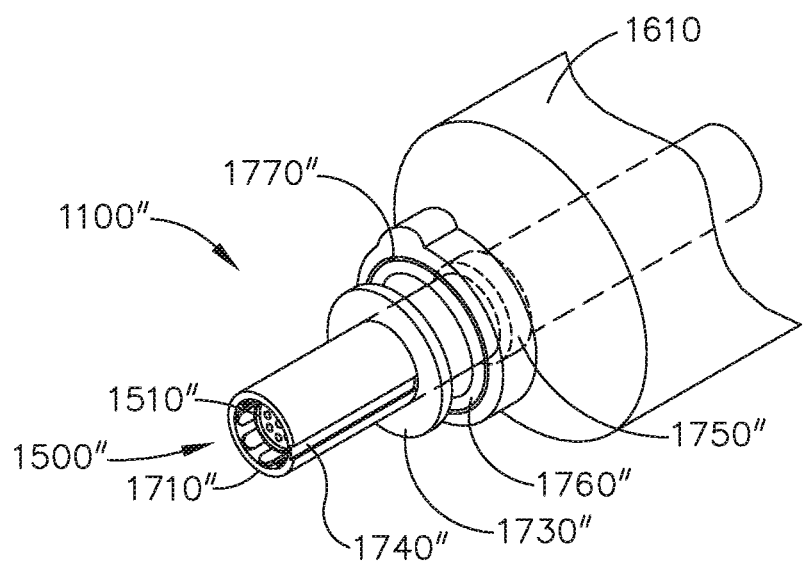
Figure 333:
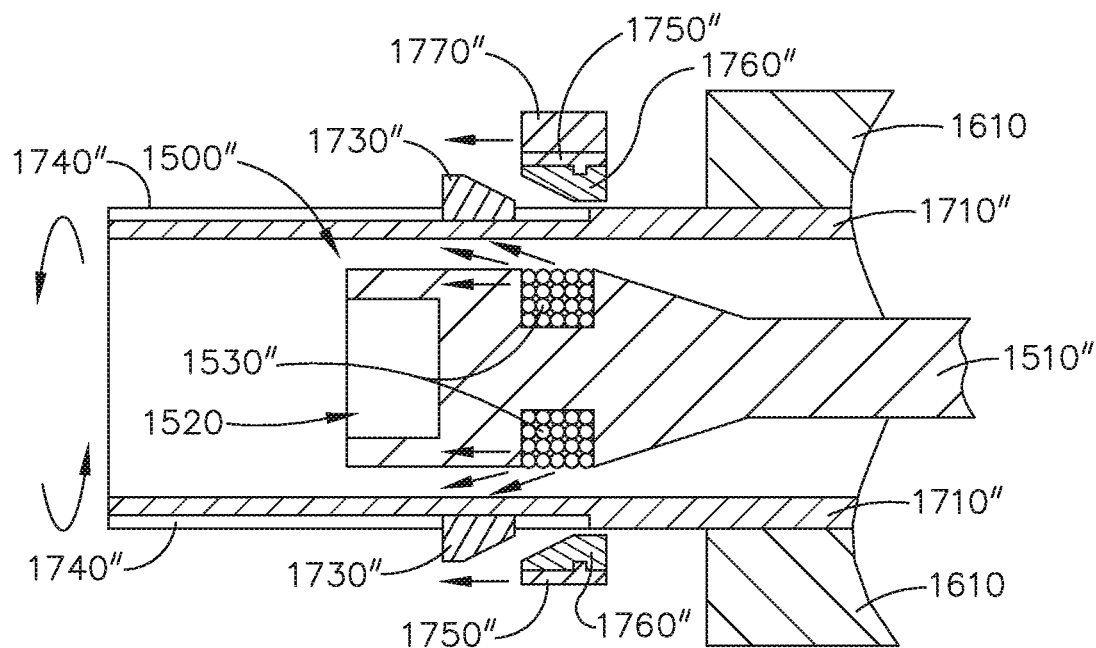
Figure 334:
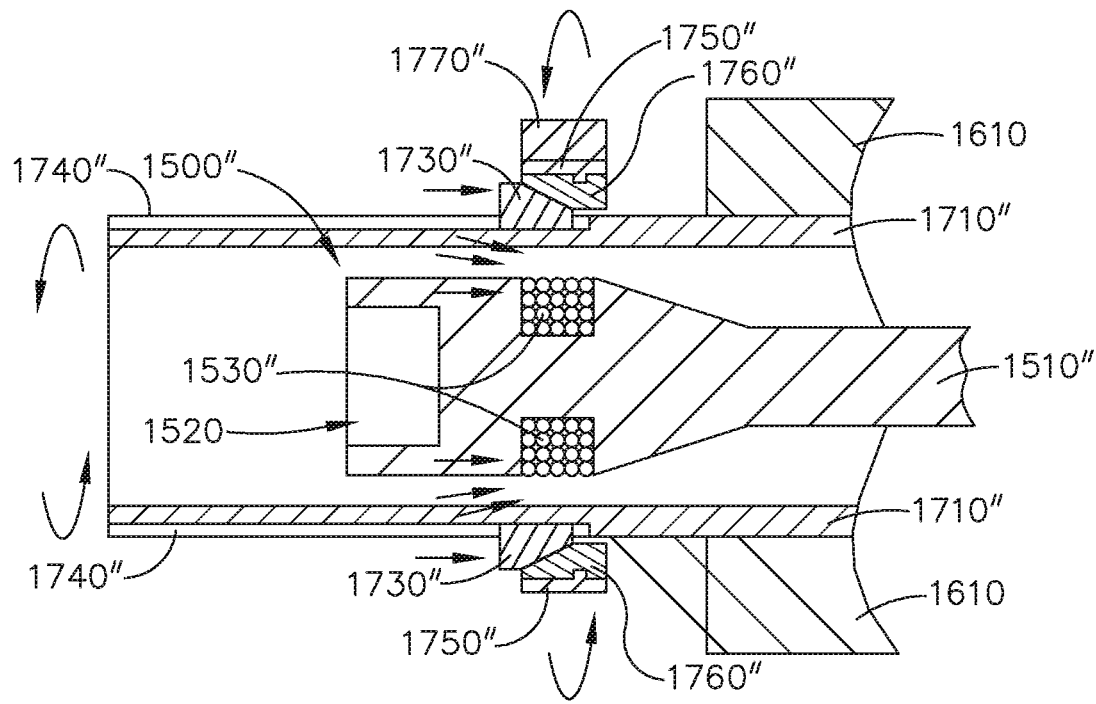

FIG. 326 is an elevational view of a handle in accordance with at least one embodiment and one of the shaft assemblies of the surgical system of FIG. 275;

FIG. 327 is a partial top view of a drive module of the handle of FIG. 326 illustrated in a first rotation configuration;

FIG. 328 is a partial top view of the drive module of FIG. 327 illustrated in a second rotation configuration;

FIG. 329 is a partial top view of the drive module of FIG. 327 illustrated in a first articulation configuration;

FIG. 330 is a partial top view of the drive module of FIG. 327 illustrated in a second articulation configuration;

FIG. 331 is a partial cross-sectional perspective view of a drive module in accordance with at least one embodiment;

FIG. 332 is a partial perspective view of the drive module of FIG. 331 illustrated with some components removed;

FIG. 333 is a partial cross-sectional view of the drive module of FIG. 331 illustrating an eccentric drive in a disengaged condition; and FIG. 334 is a partial cross-sectional view of the drive module of FIG. 331 illustrating the eccentric drive of FIG. 333 in an engaged condition.

Figure 335:
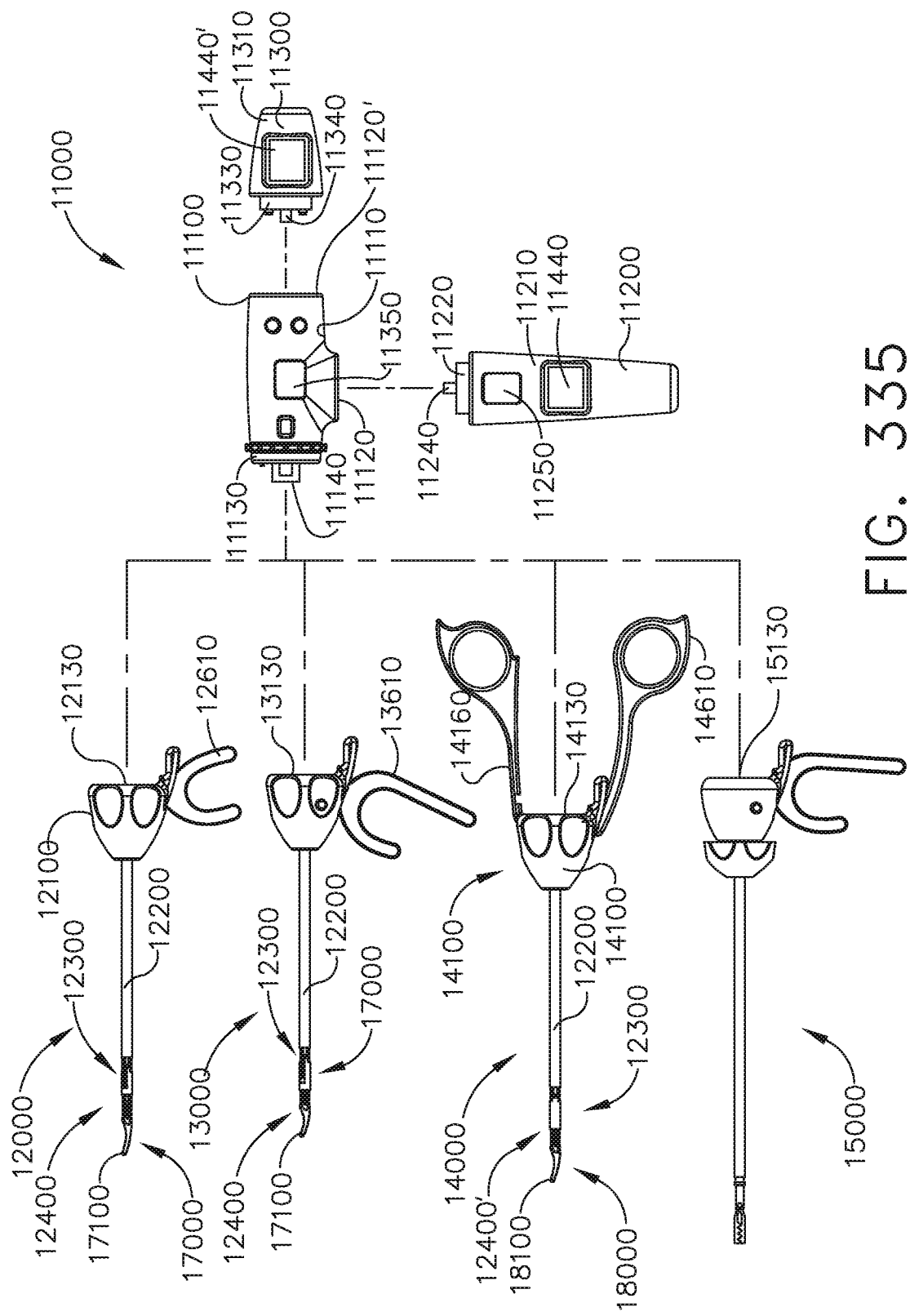
Figure 336:
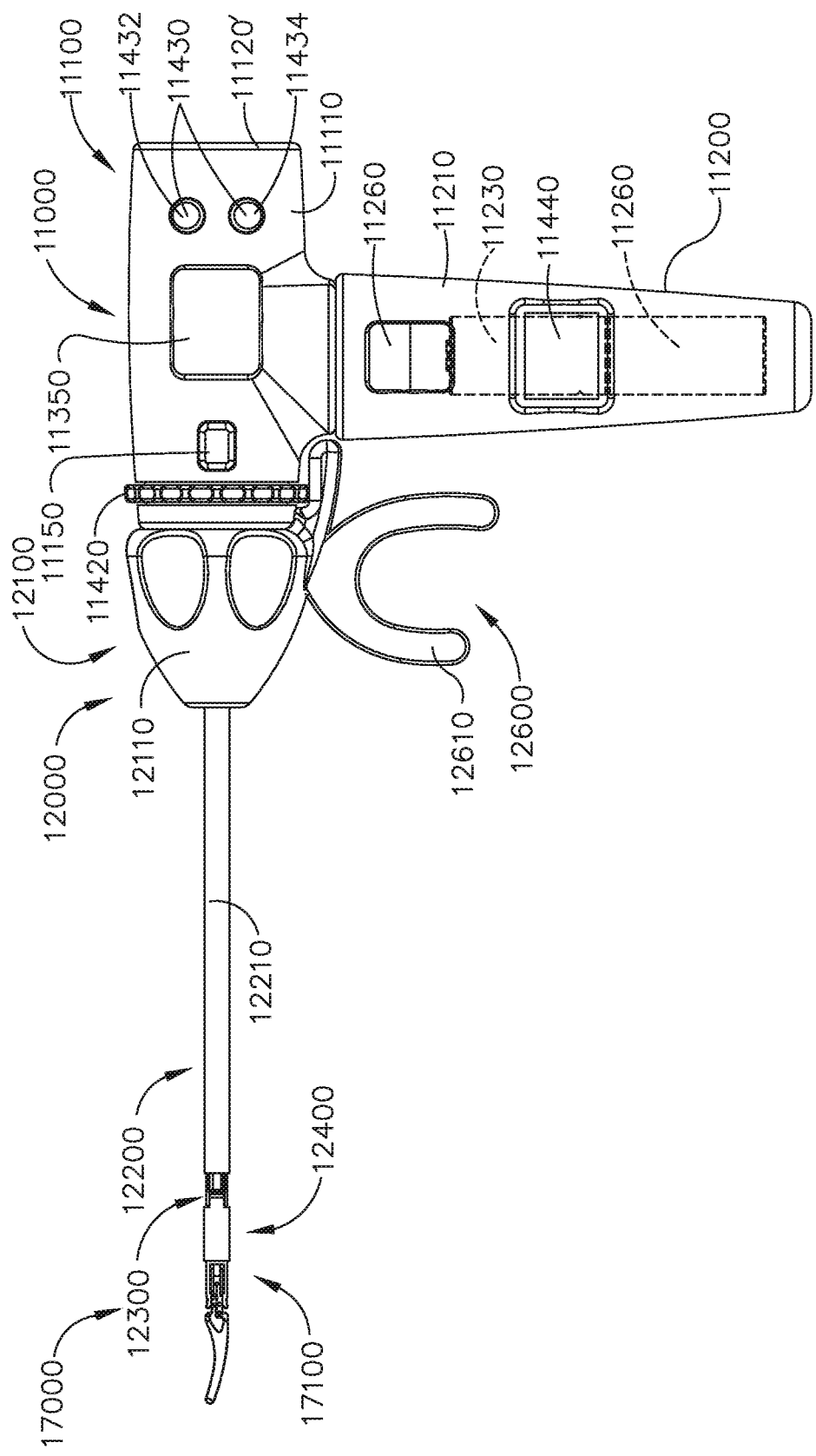
Figure 337:
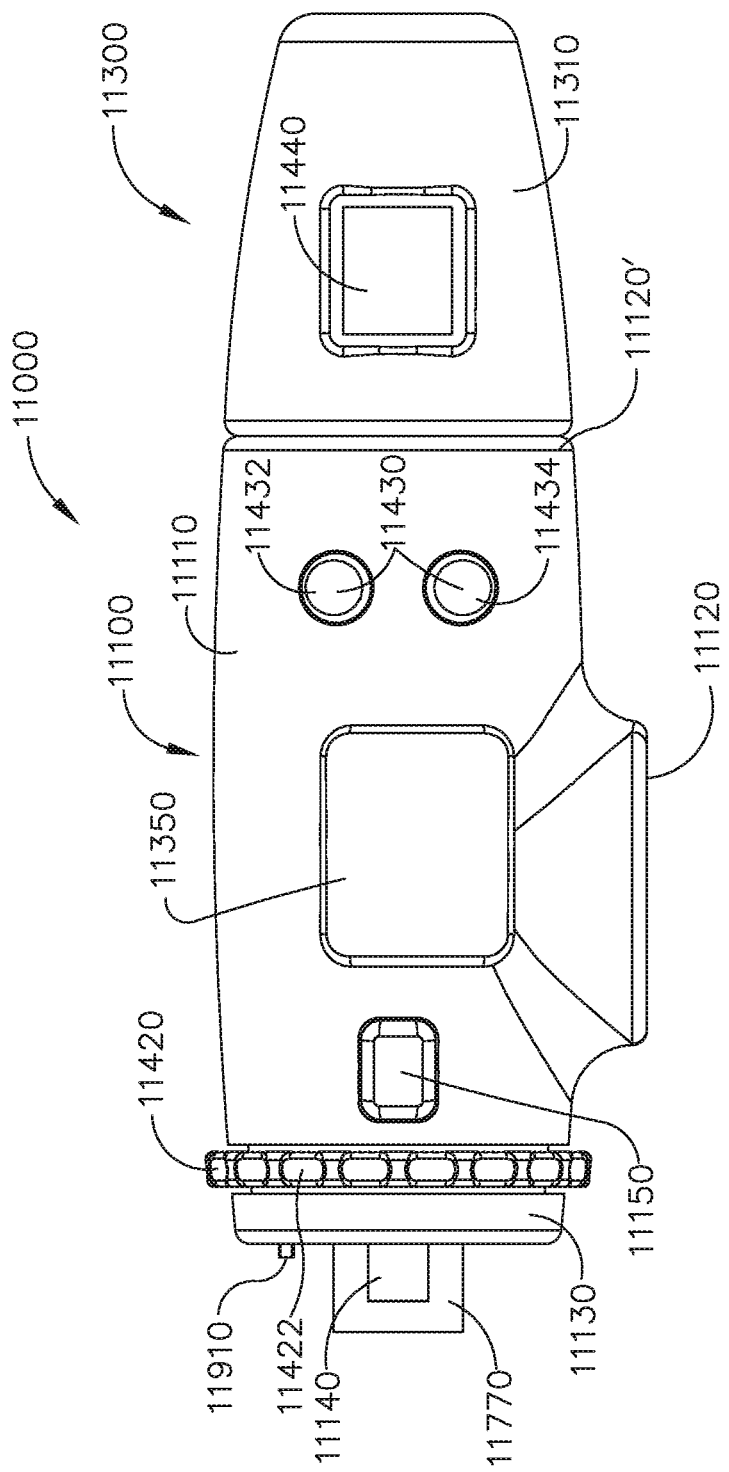
Figure 338:
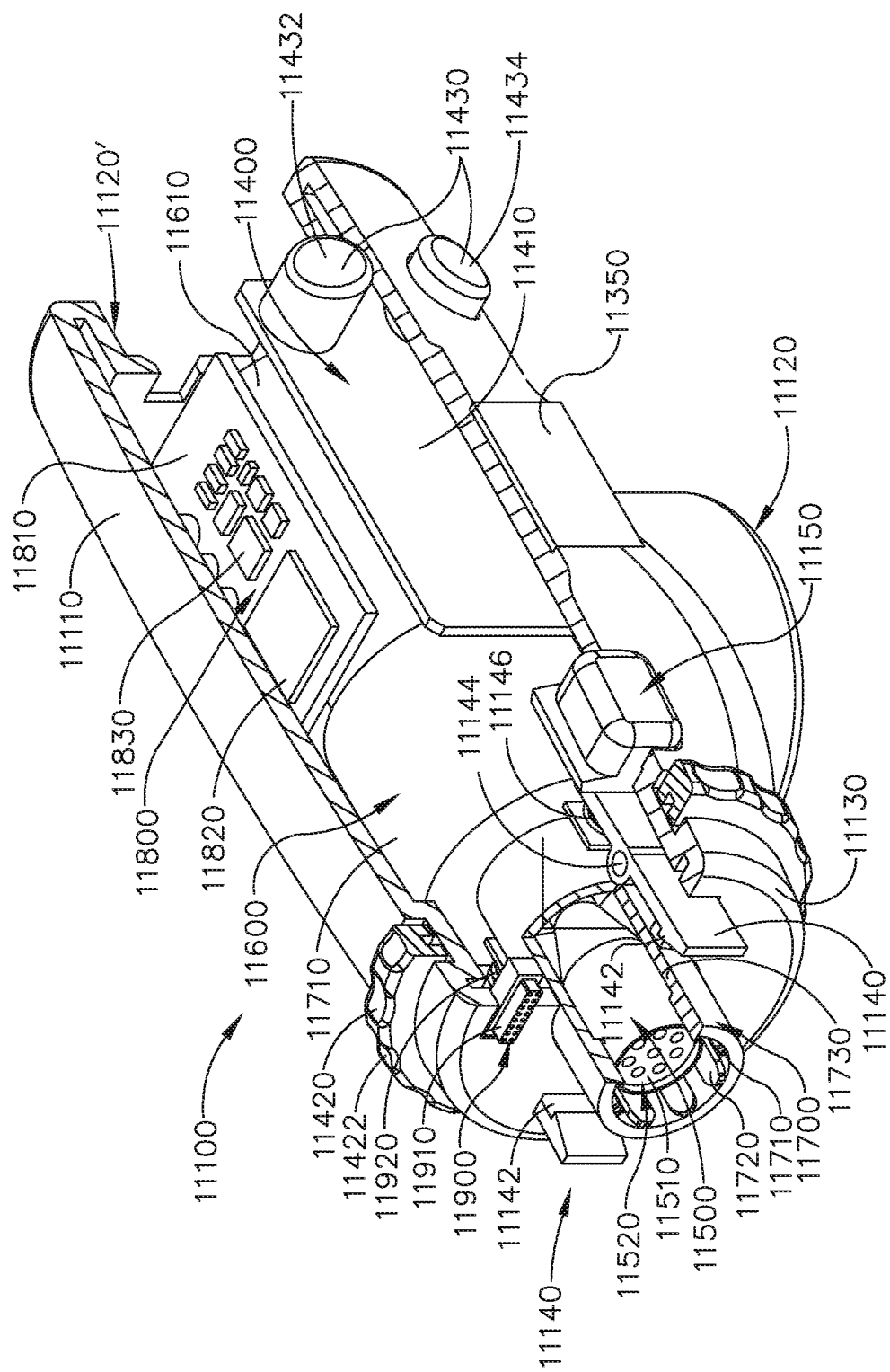
Figure 339:
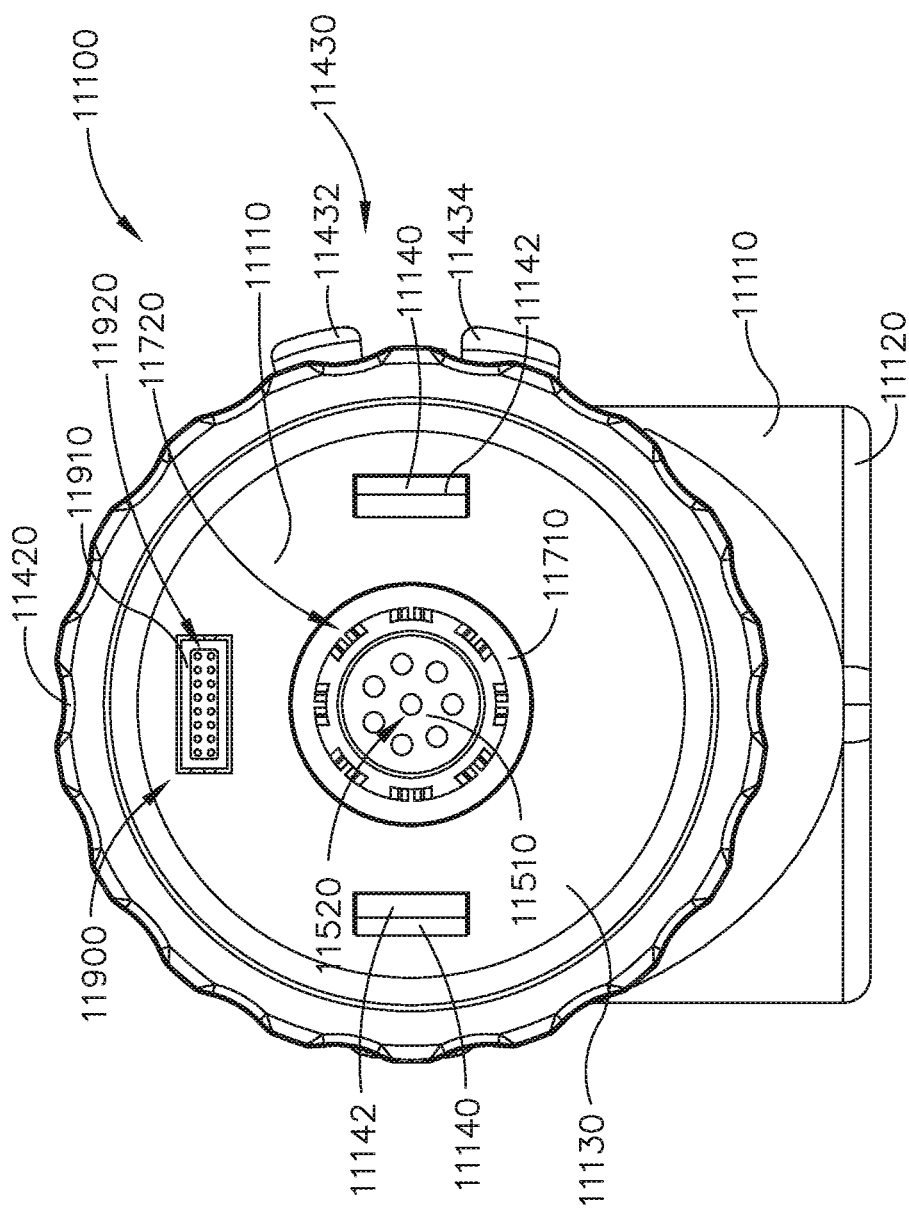
Figure 340:
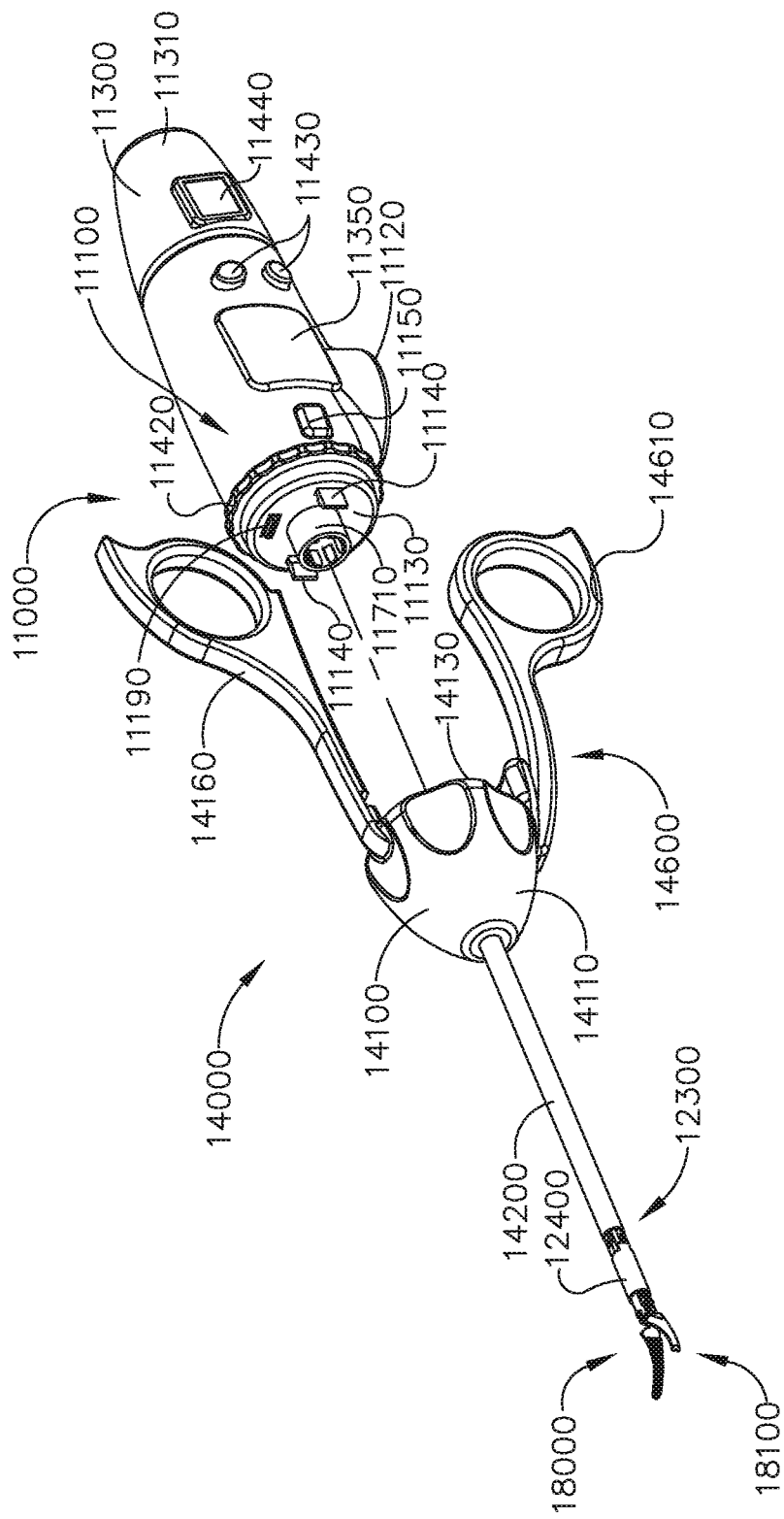
Figure 341:
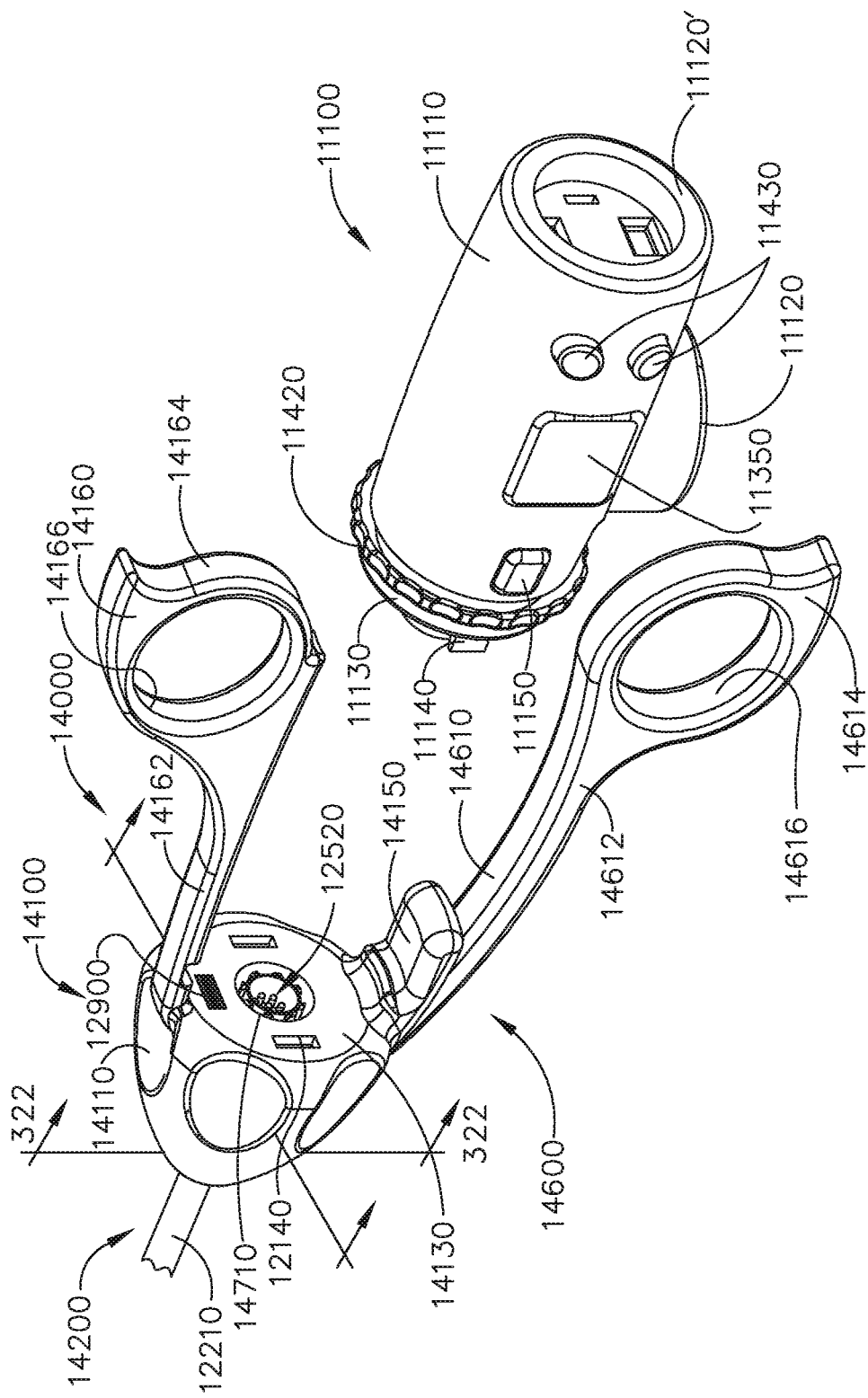
Figure 342:
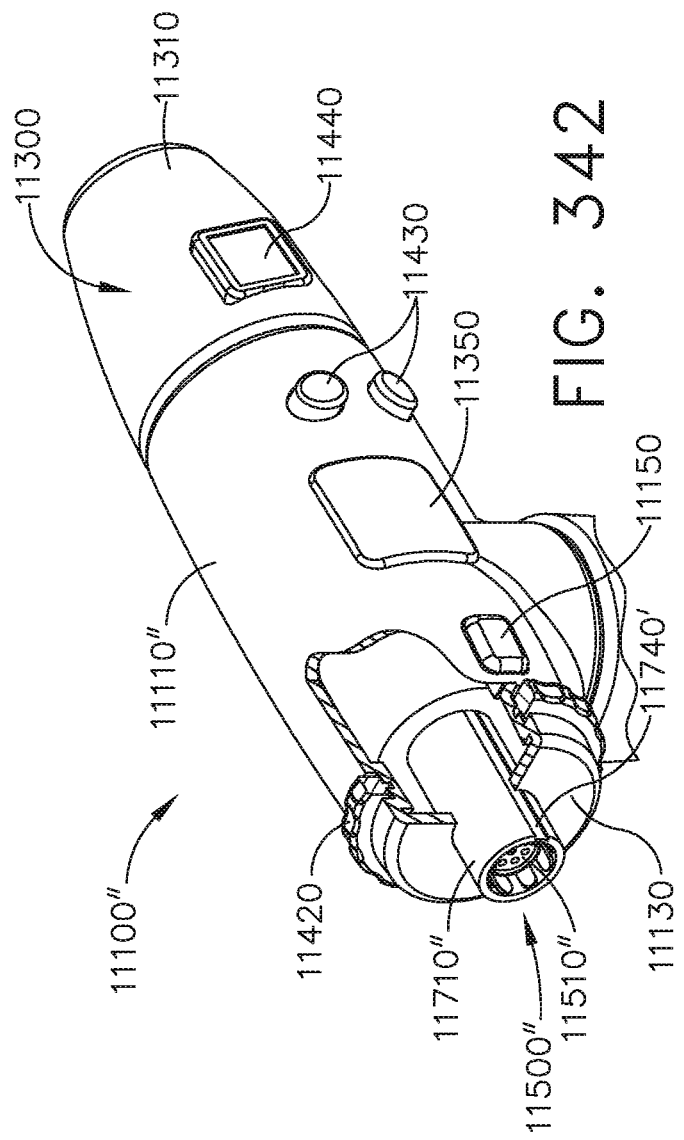
Figure 343:
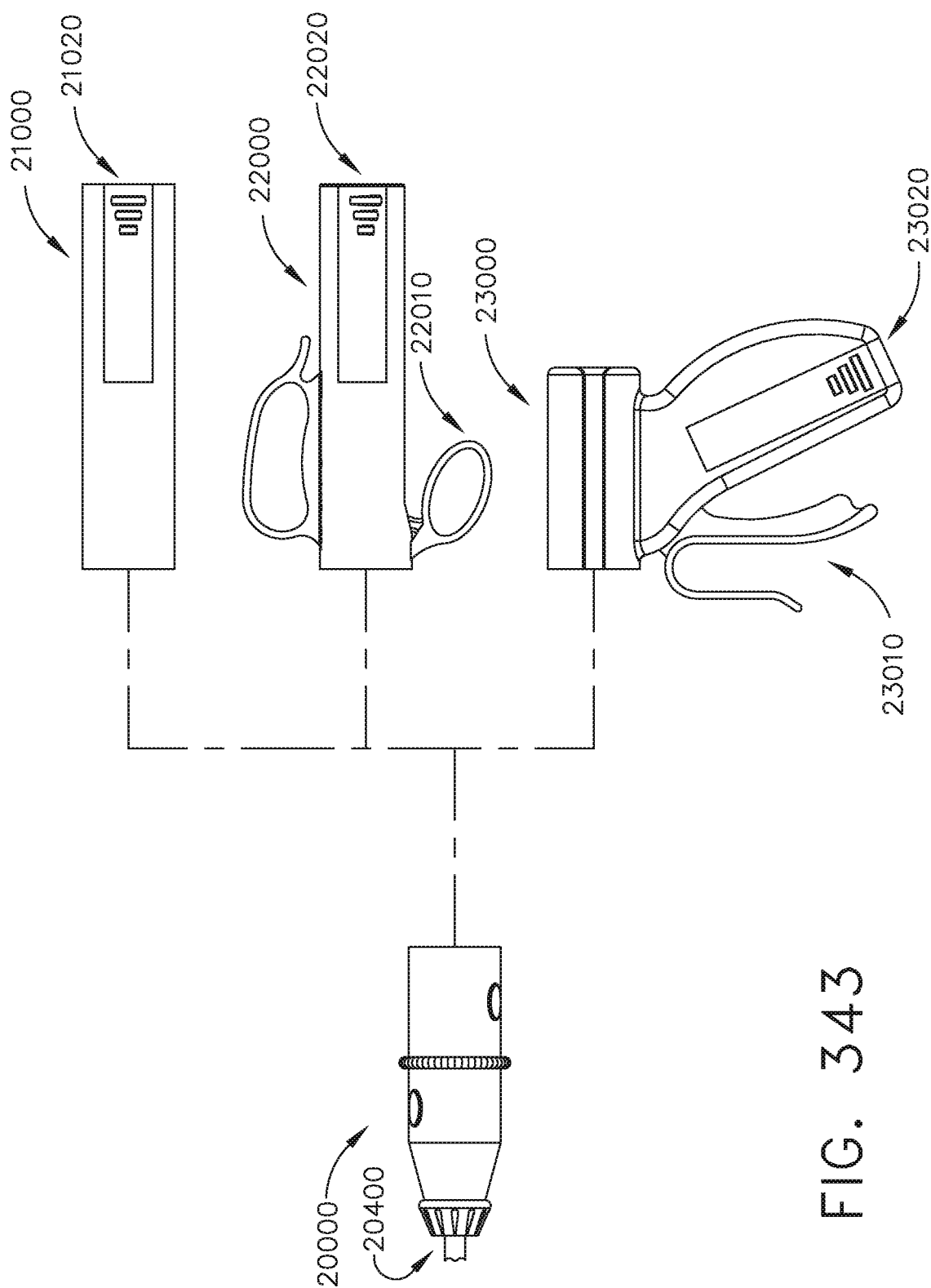
Figure 344:
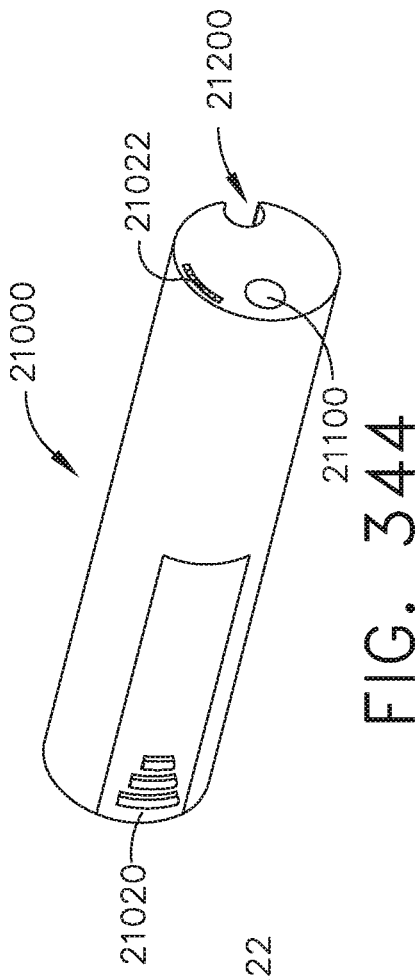
Figure 345:
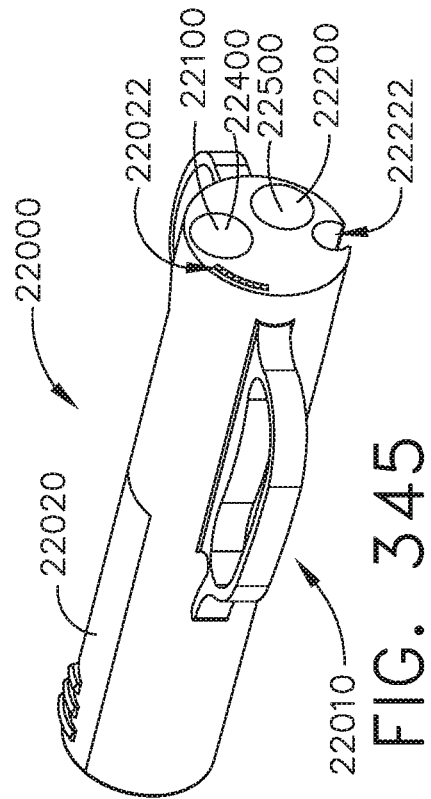
Figure 346:
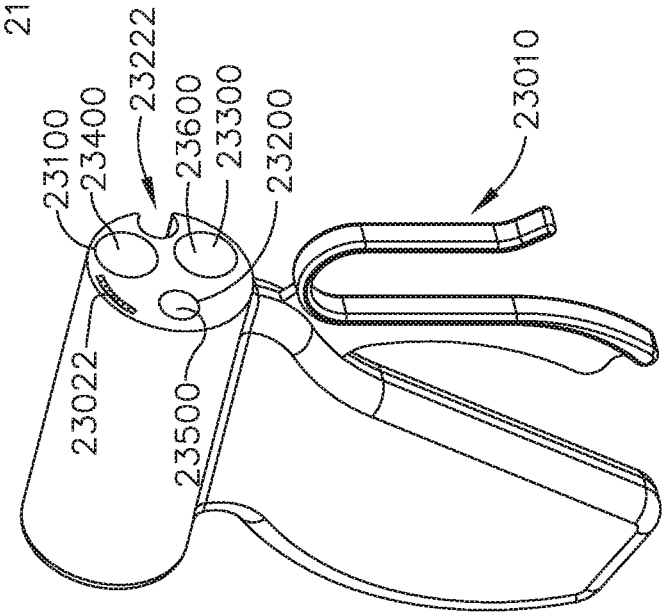
Figure 347:
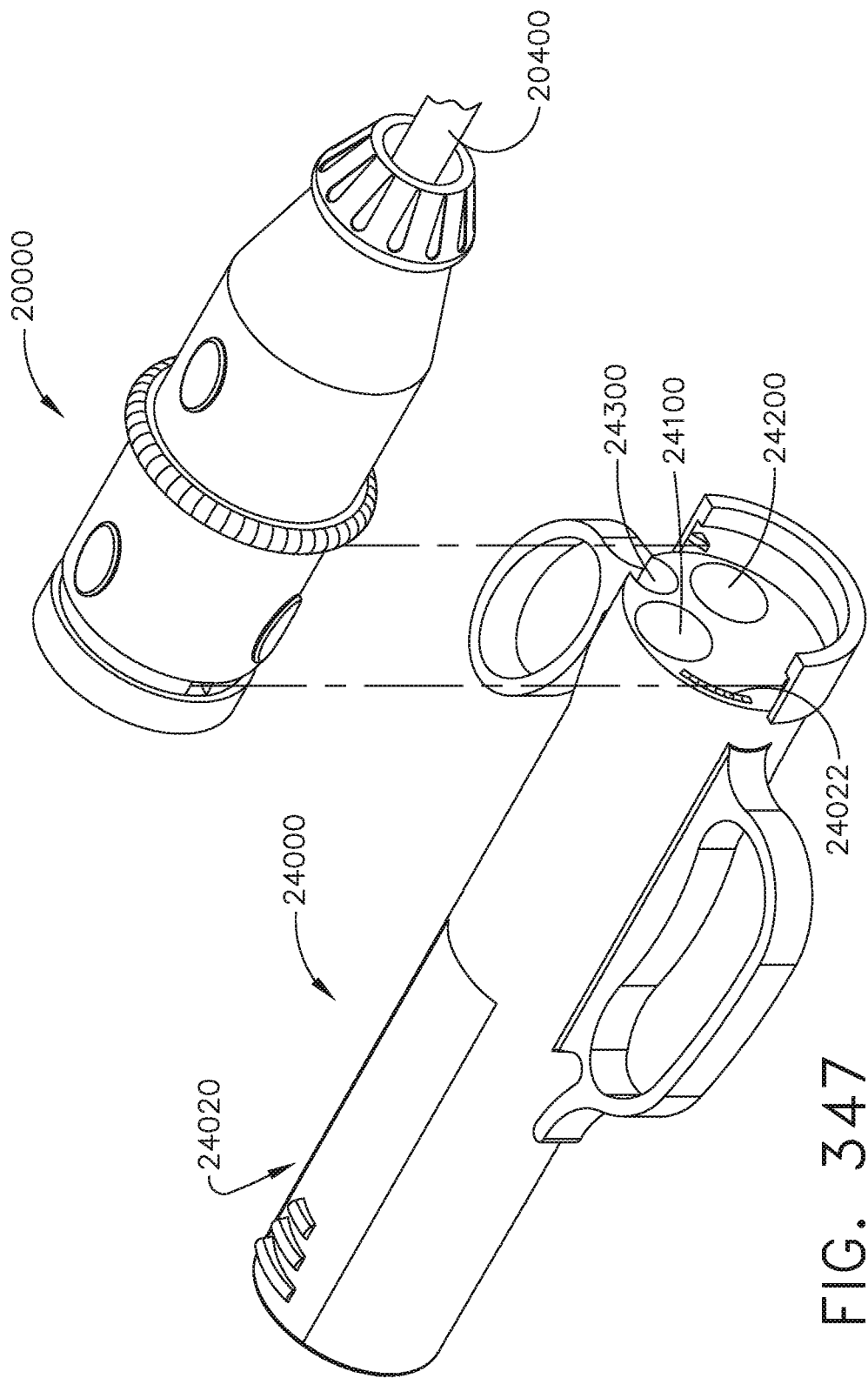
Figure 348:
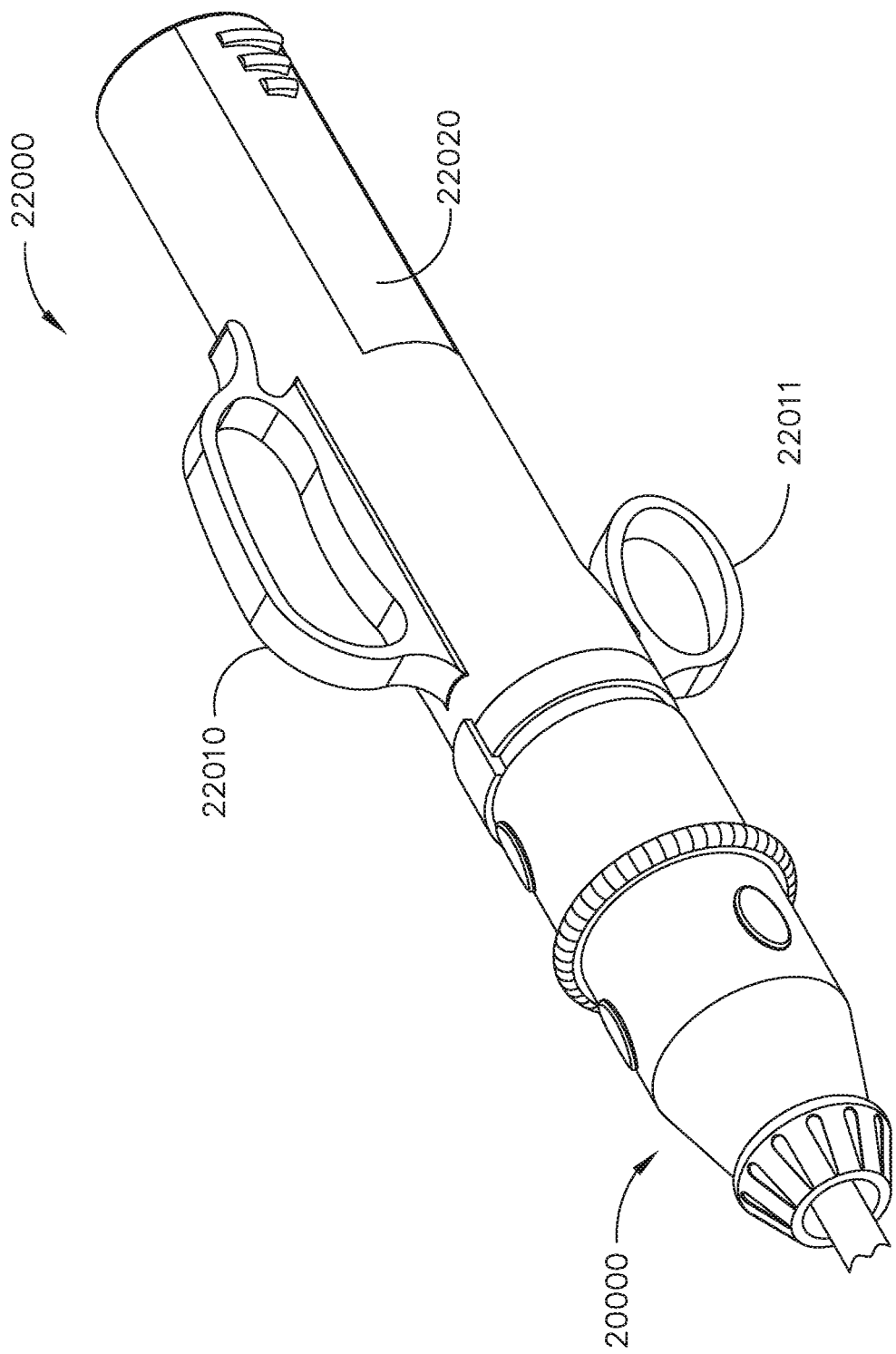
Figure 349:
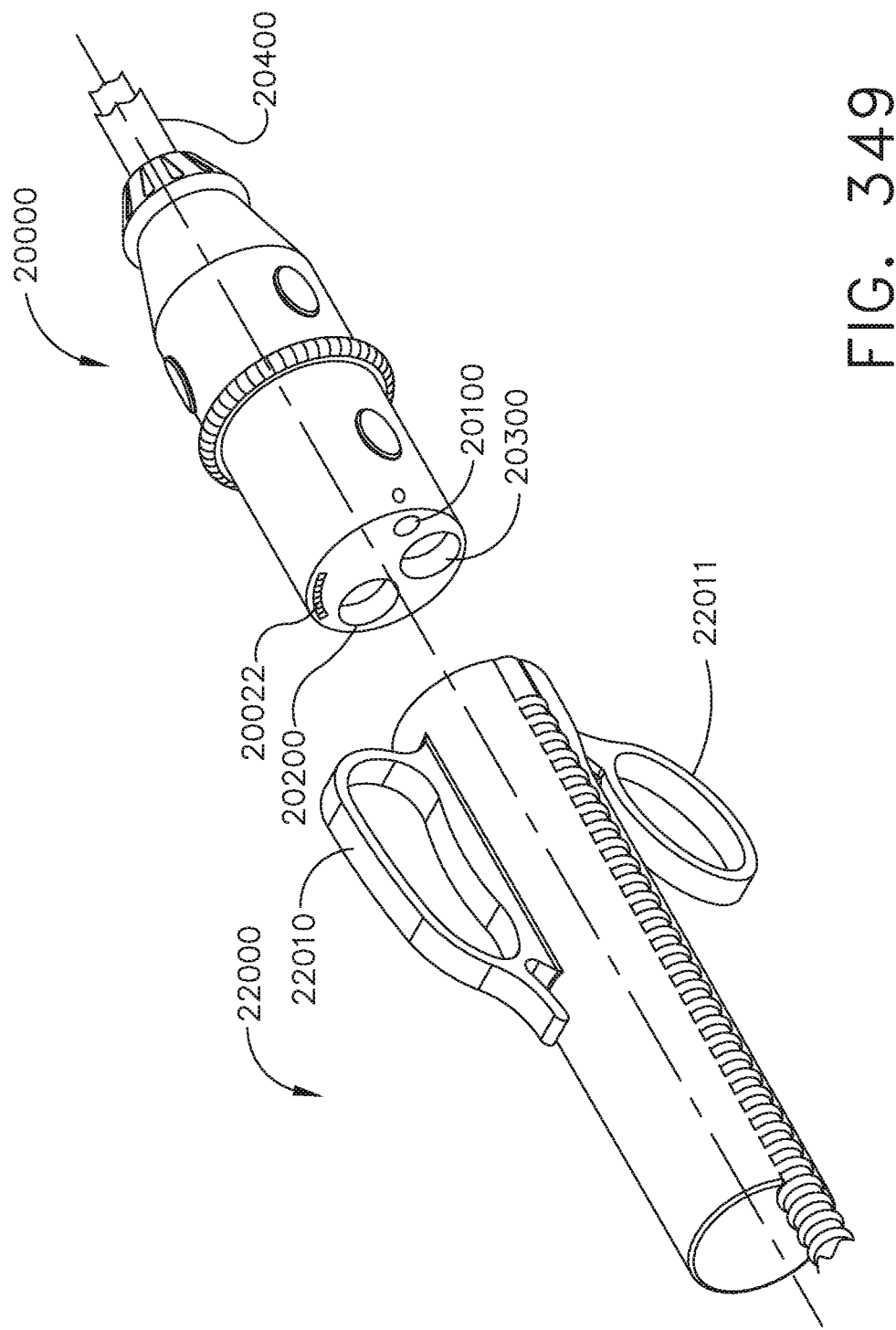
Figure 350:
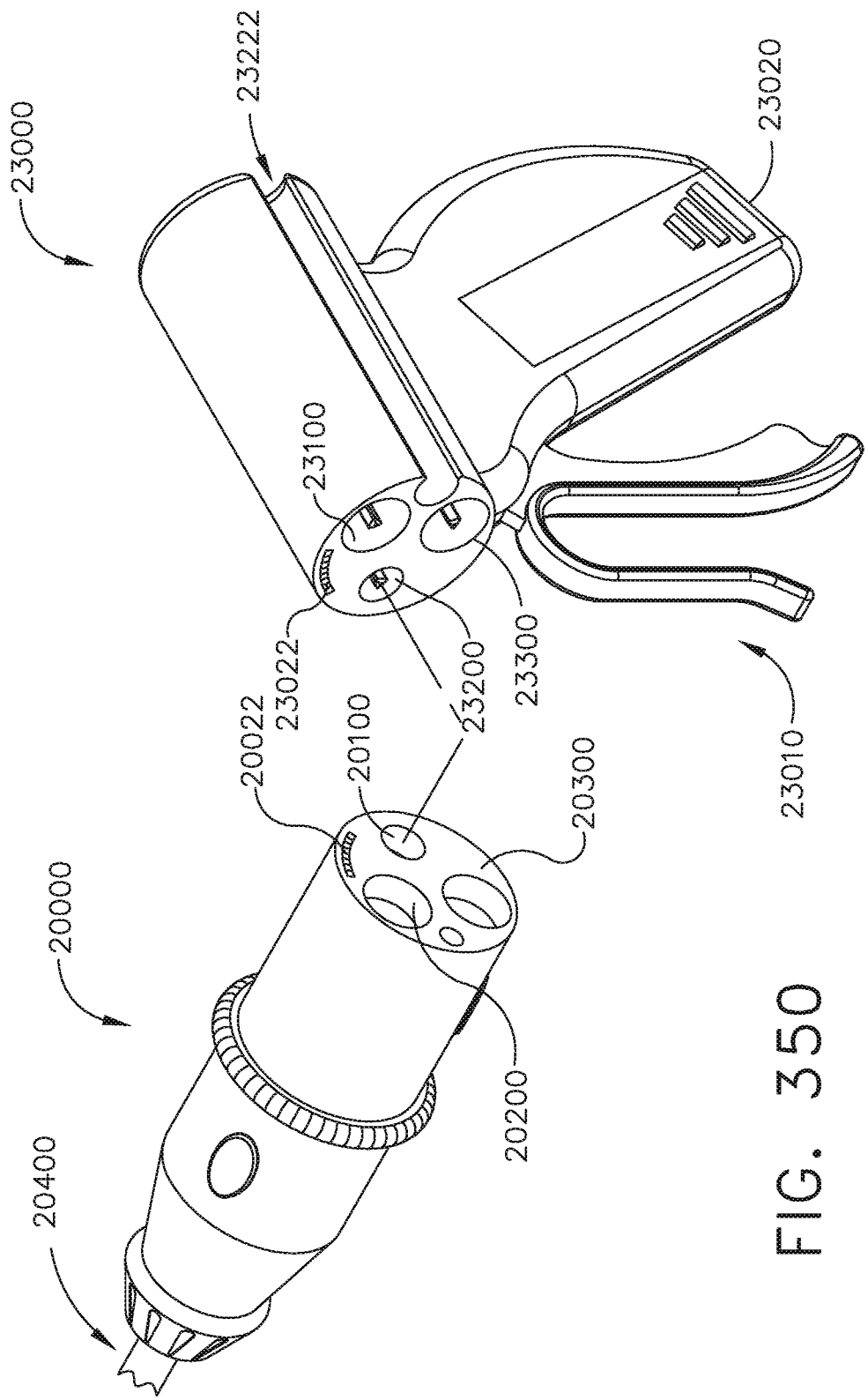
Figure 351:
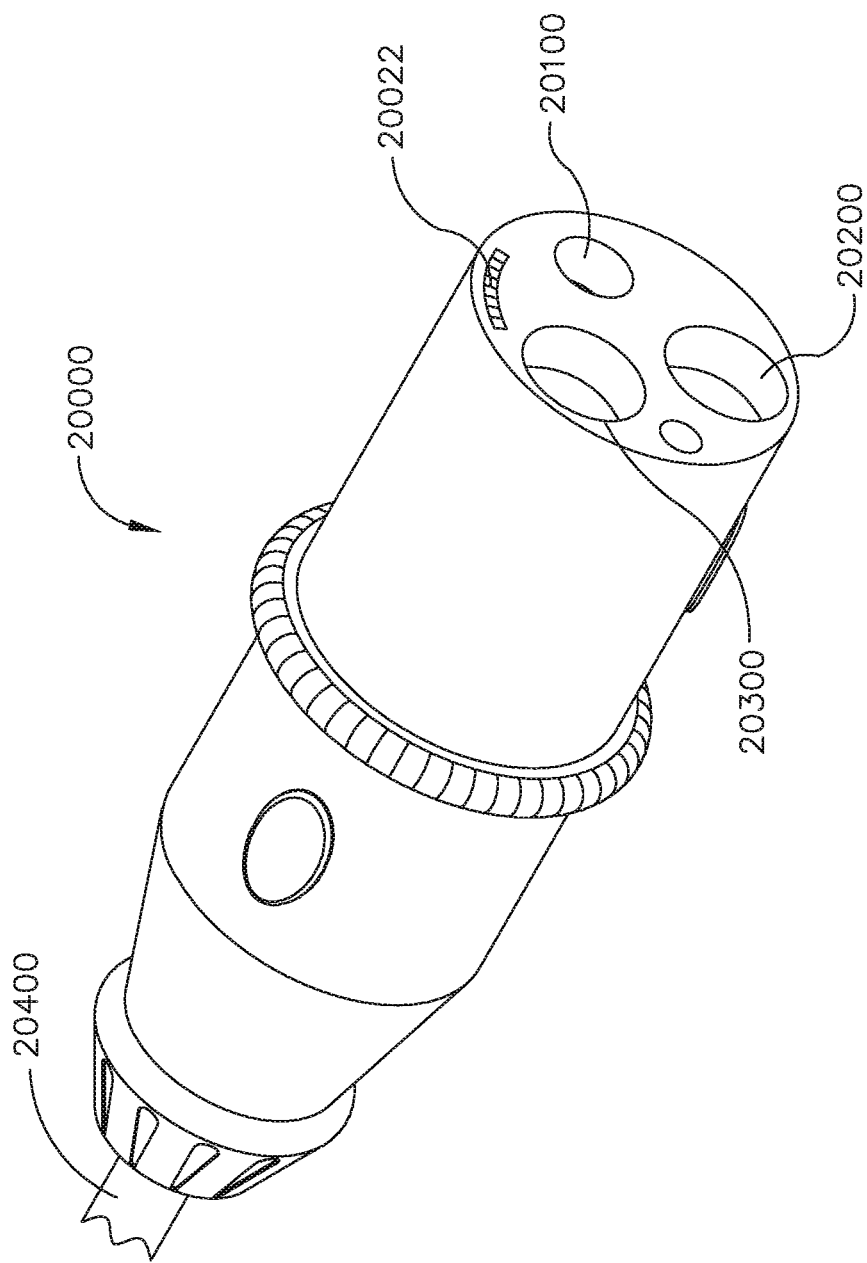
Figure 354:
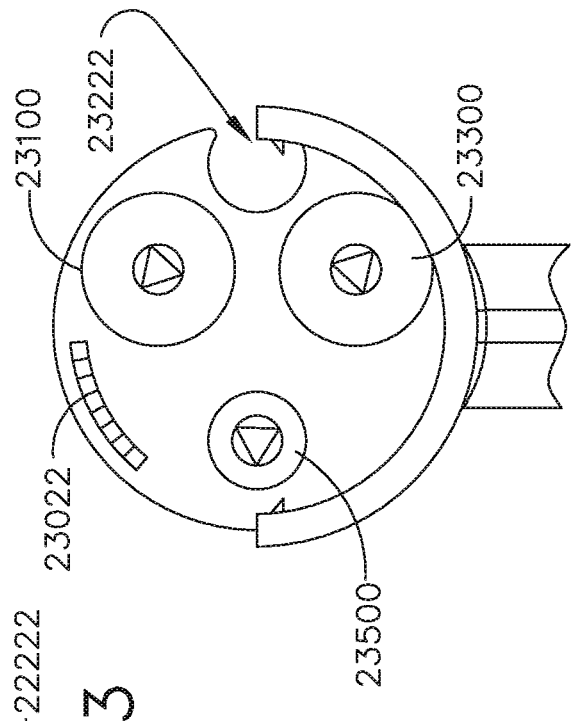
Figure 353:
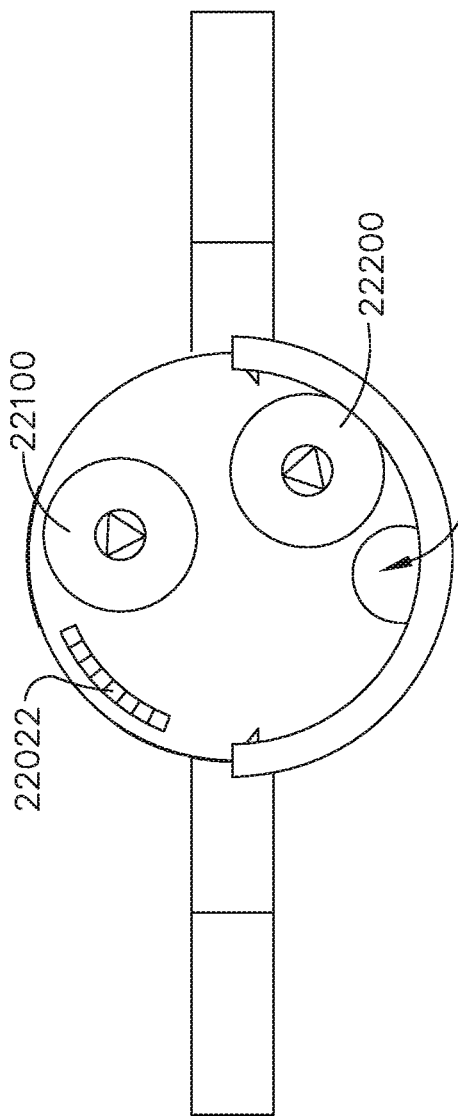
Figure 352:
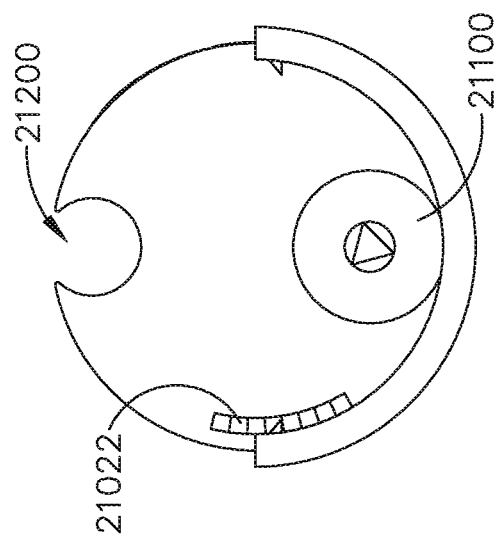
Figure 355:
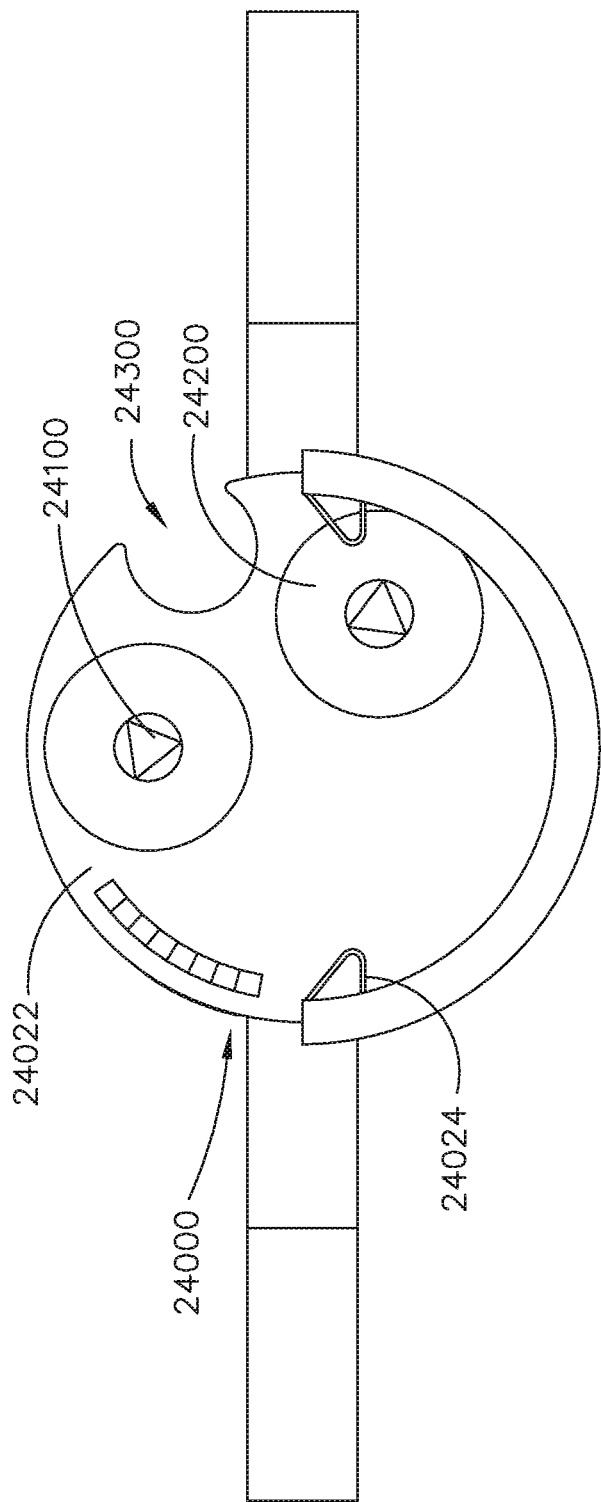
Figure 357:
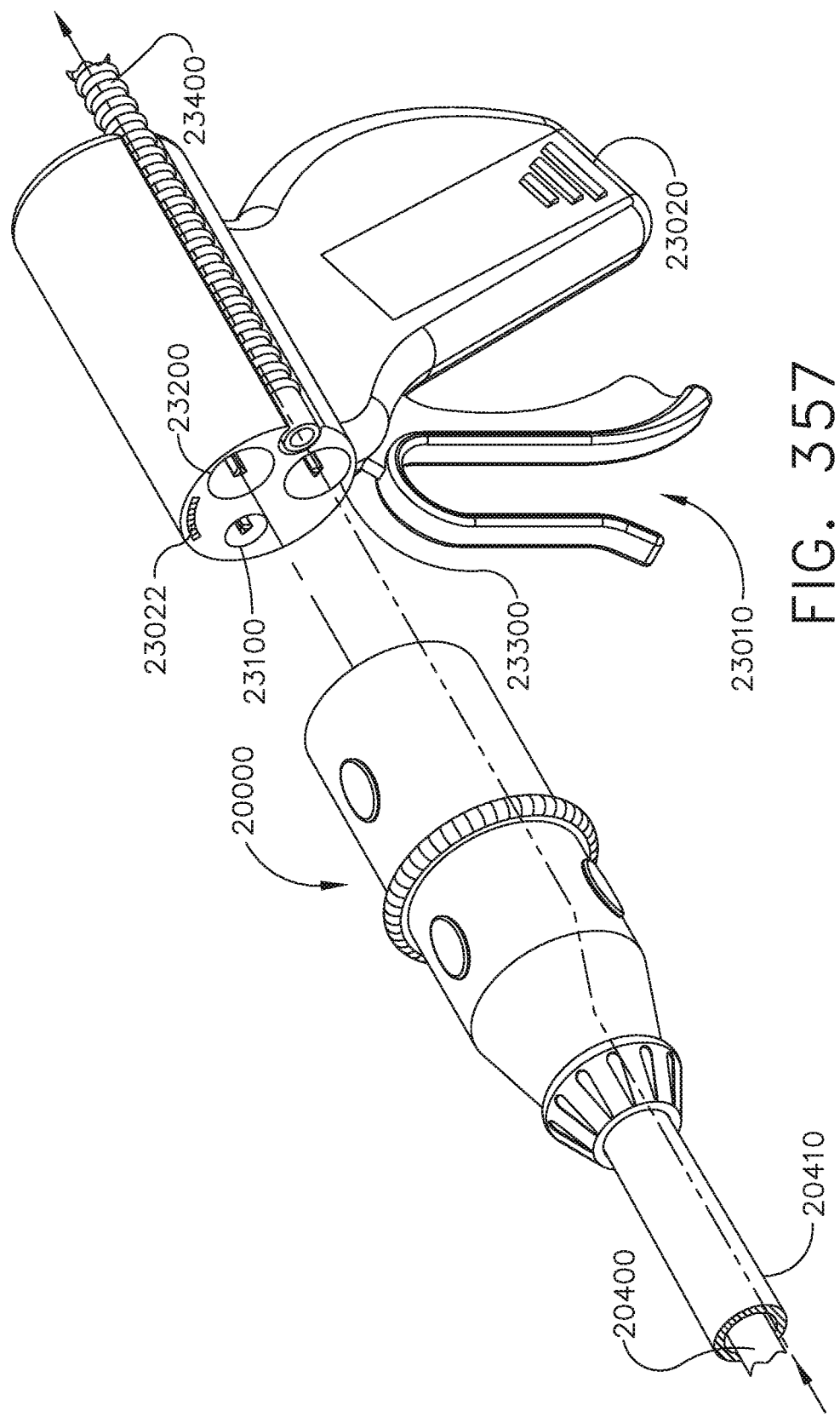
Figure 358:
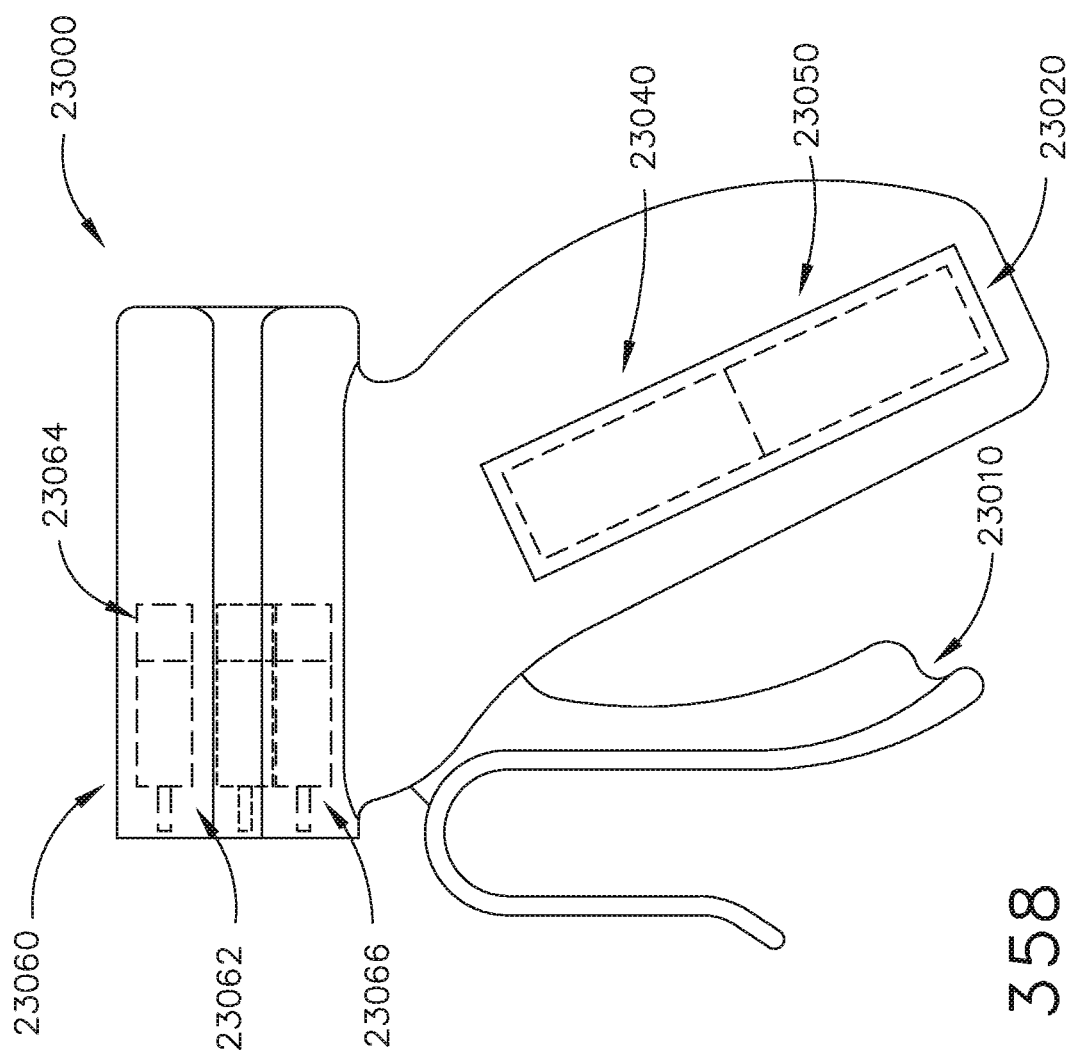
Figure 359:
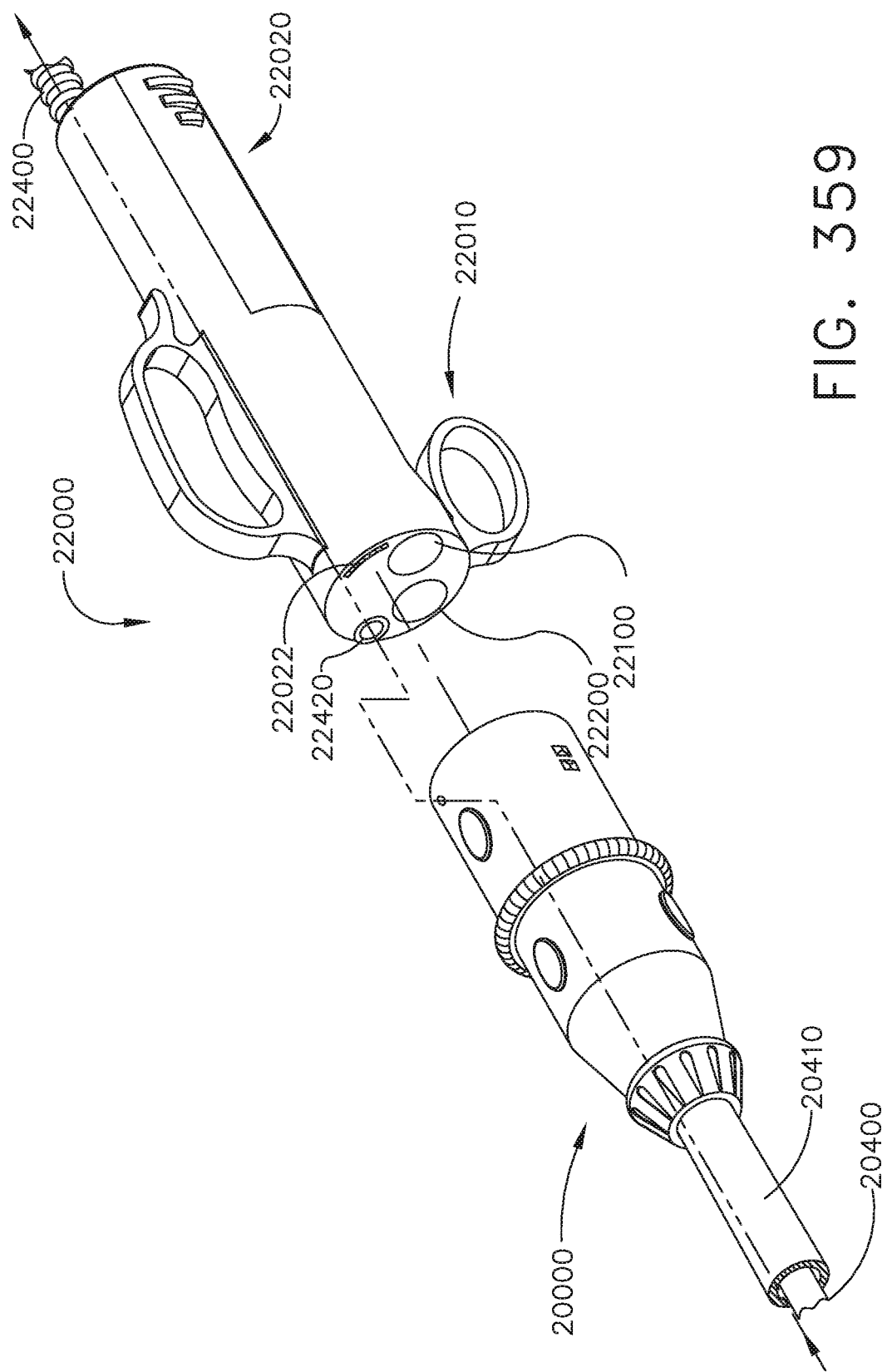
Figure 363:
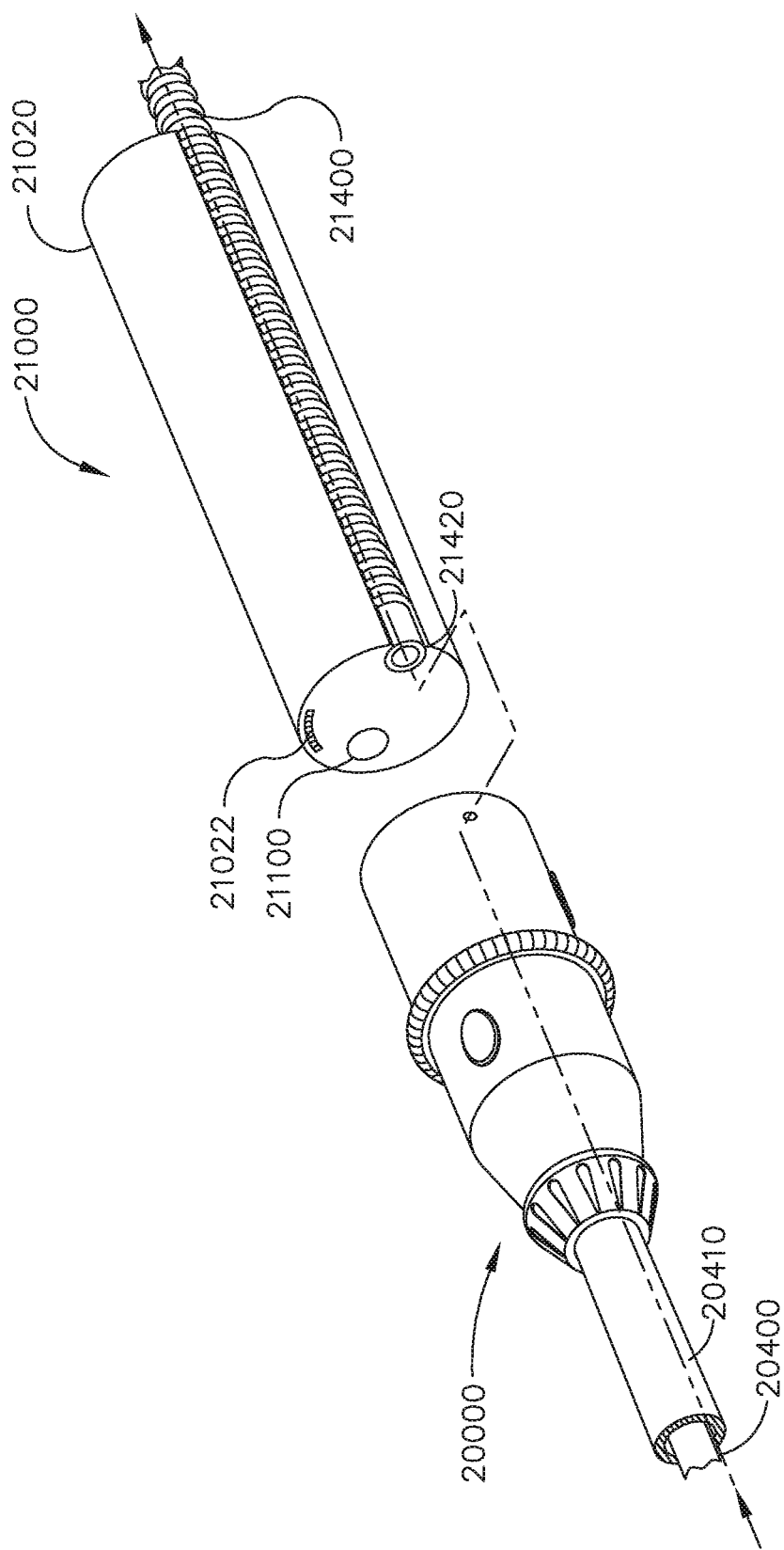
Figure 369:
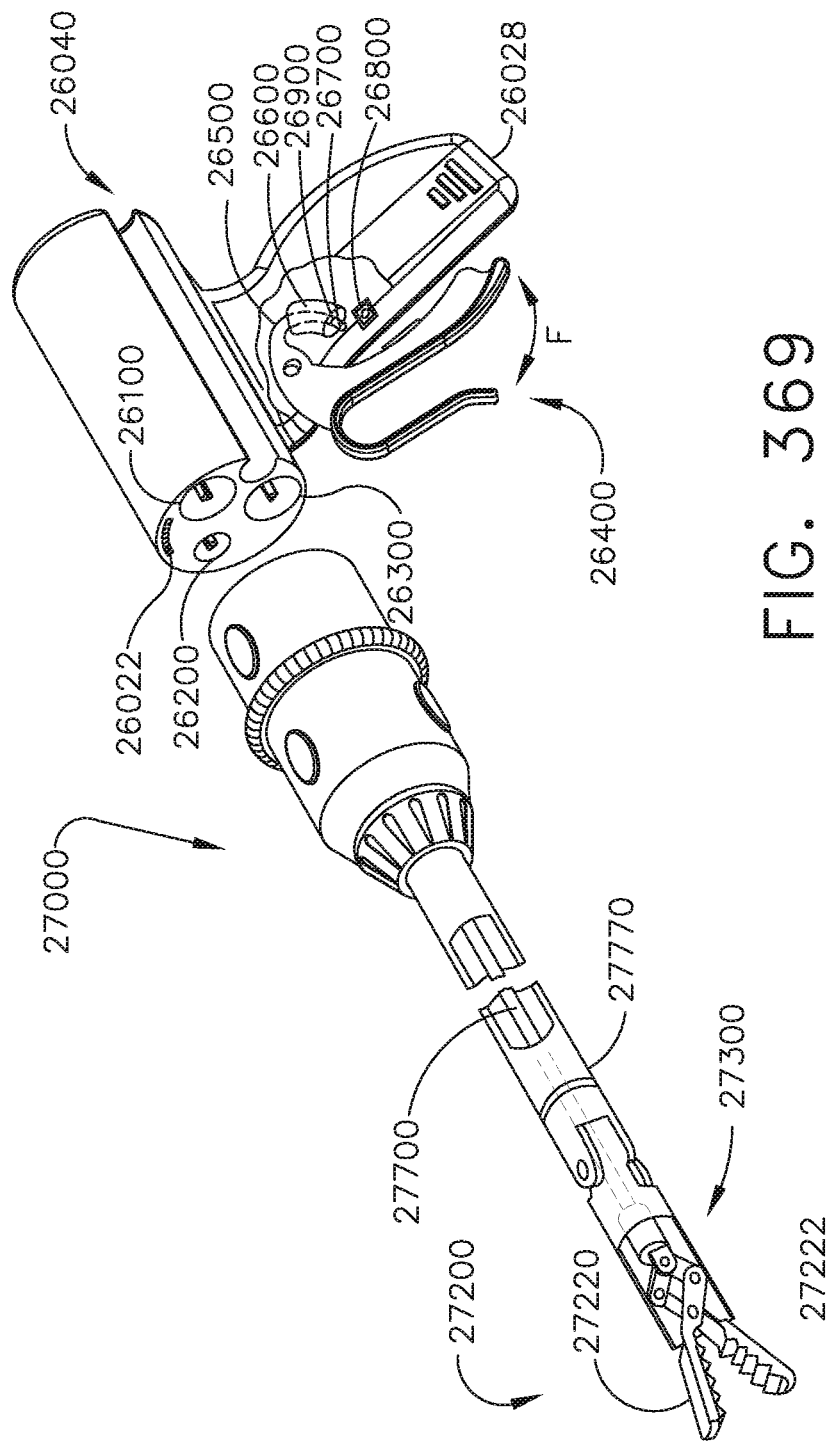
Figure 370:
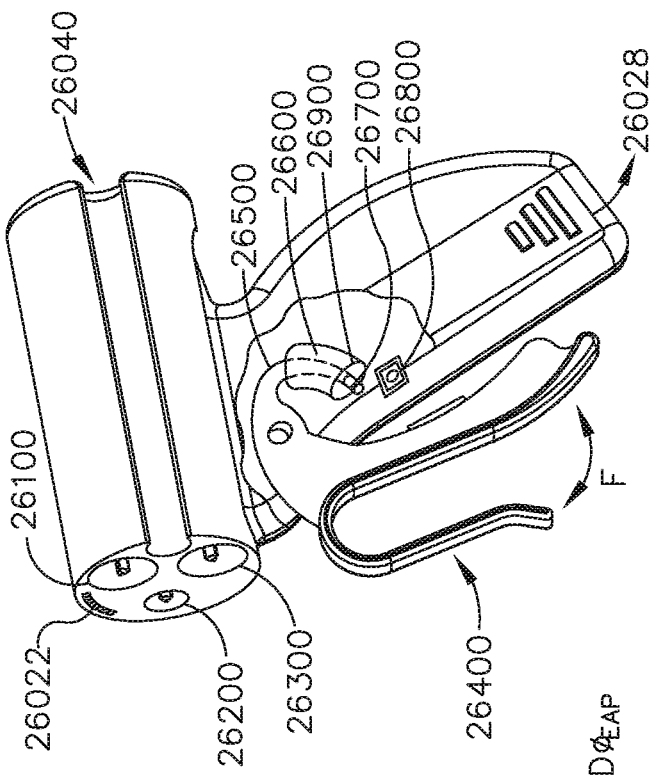
Figure 371:
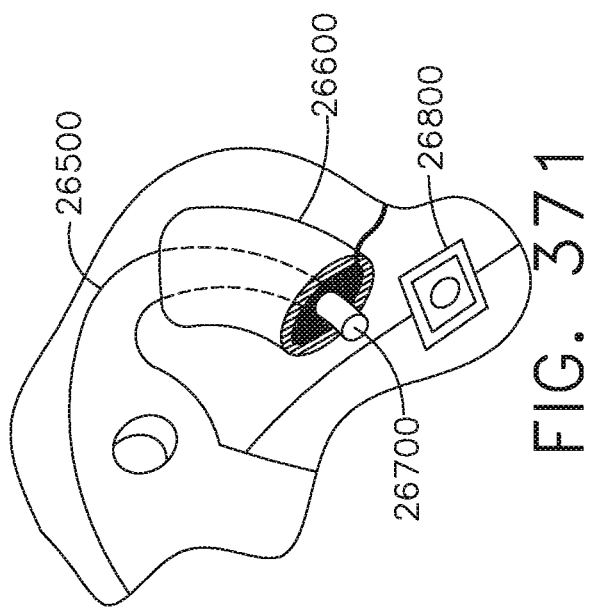
Figure 372:
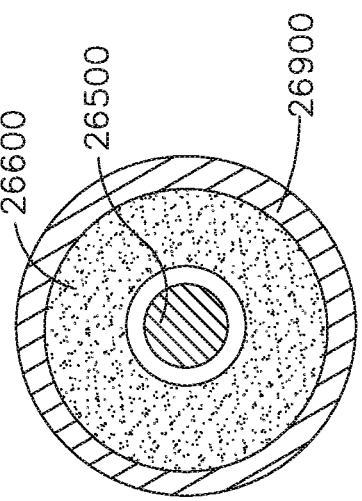
Figure 373:
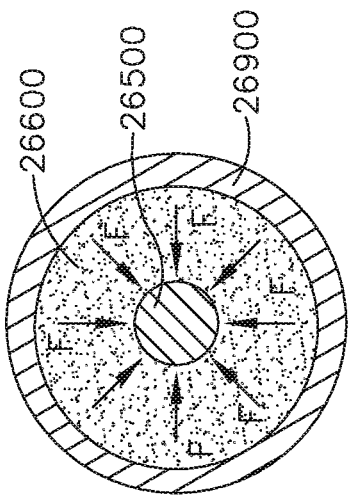
Figure 374:
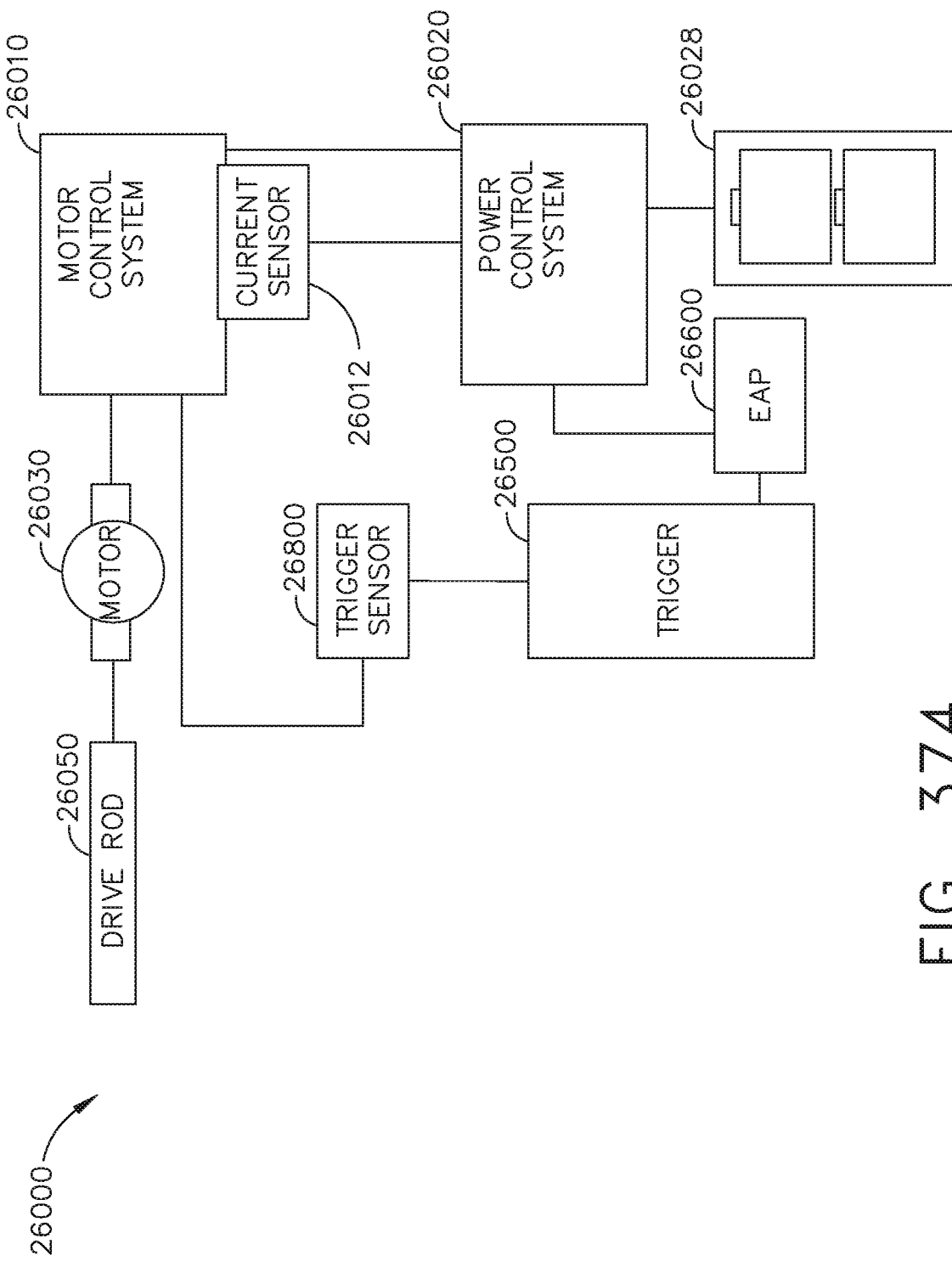
Figure 375:
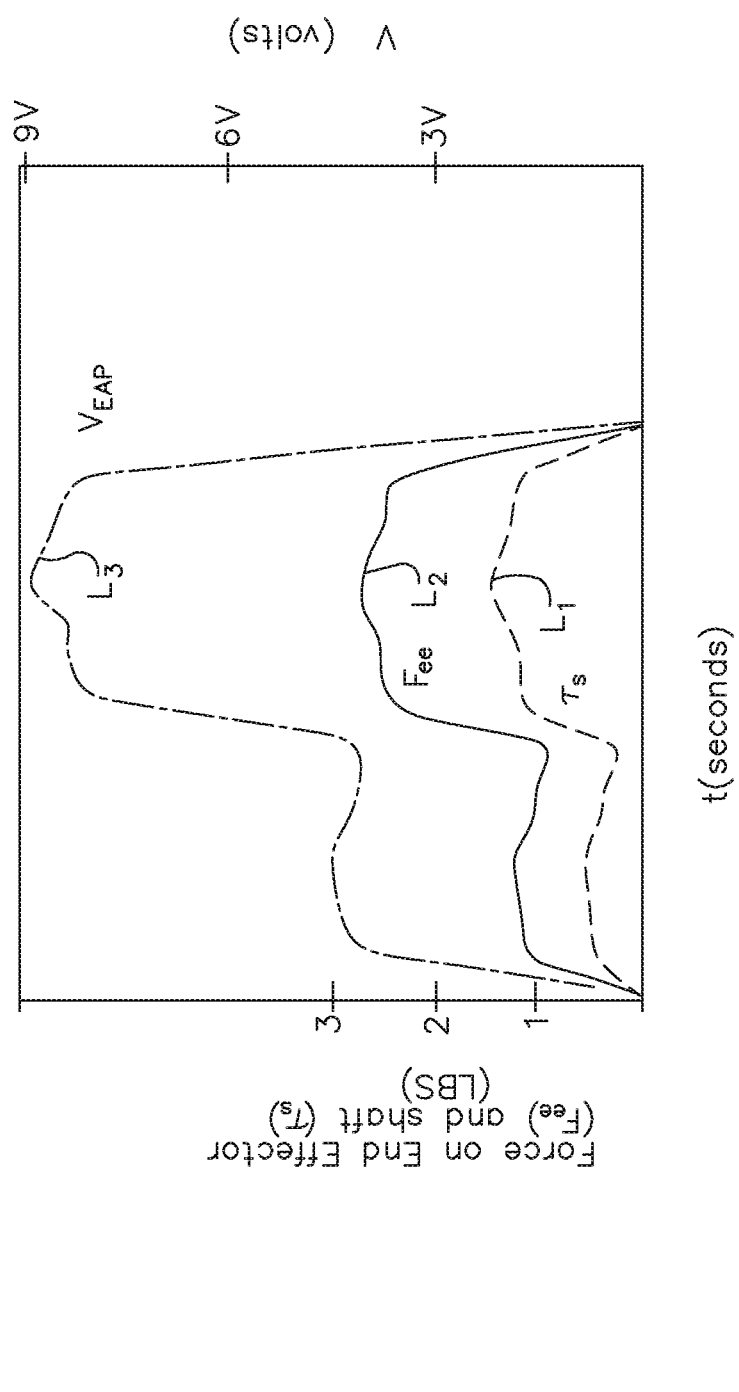
Figure 376:
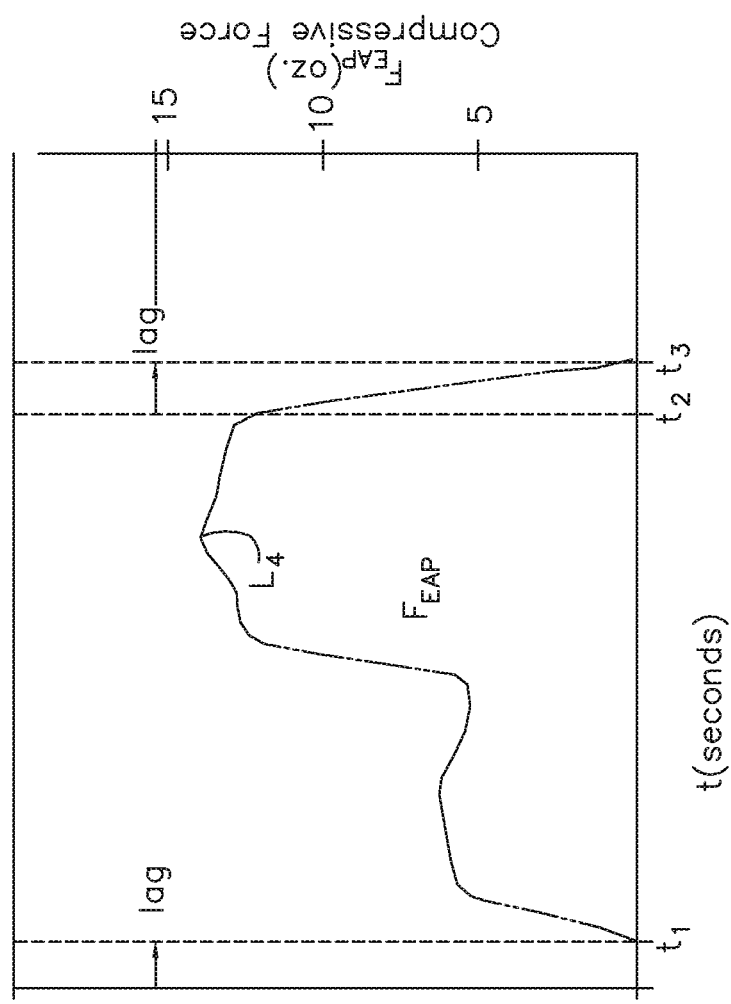
Figure 377:
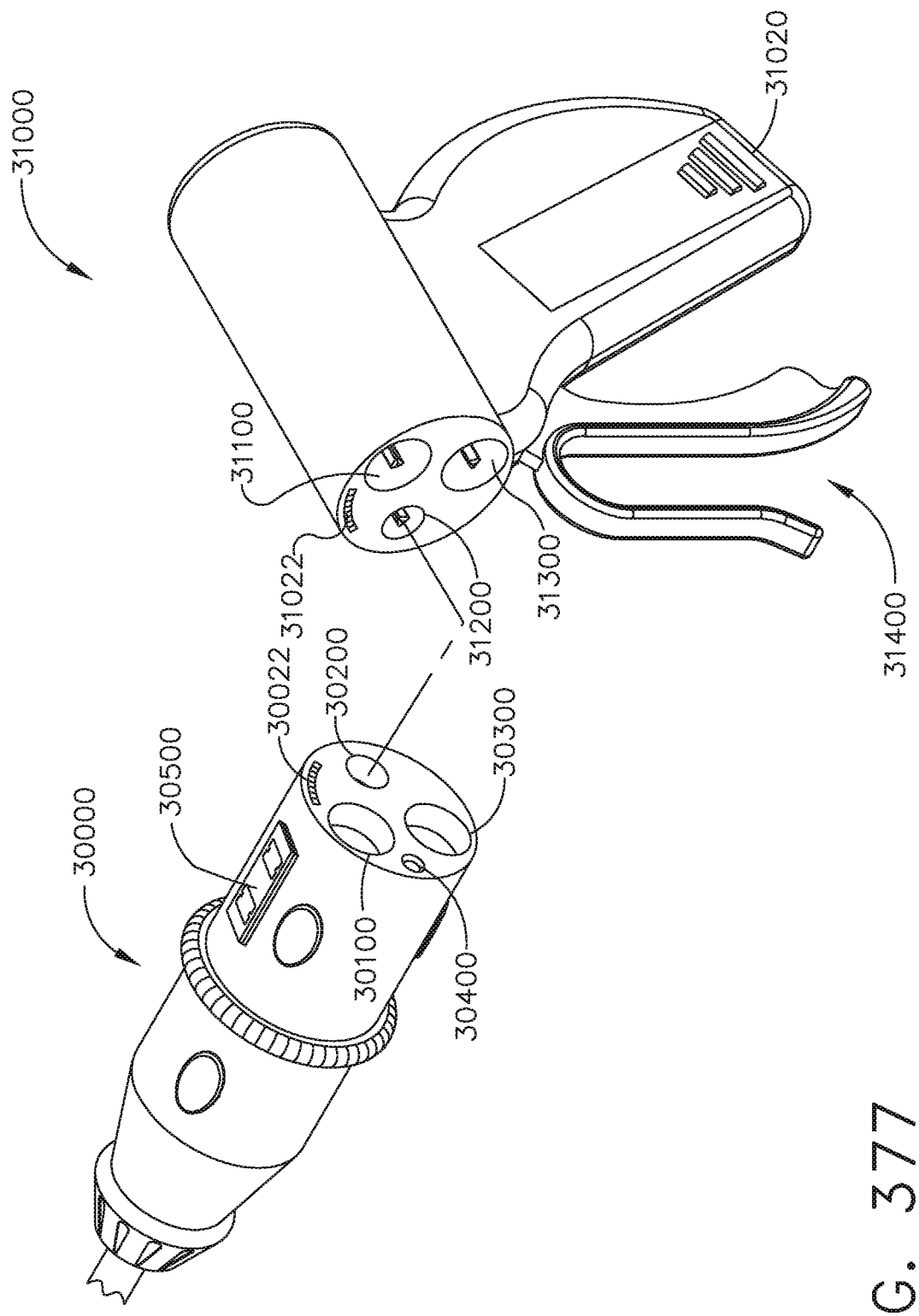
Figure 384:
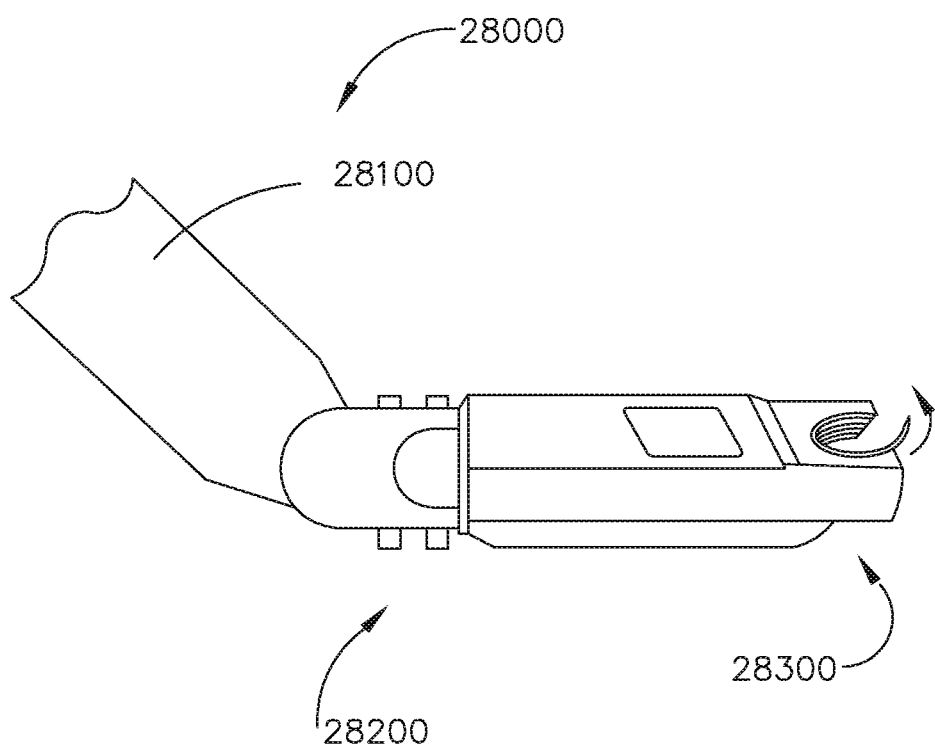
Figure 385:
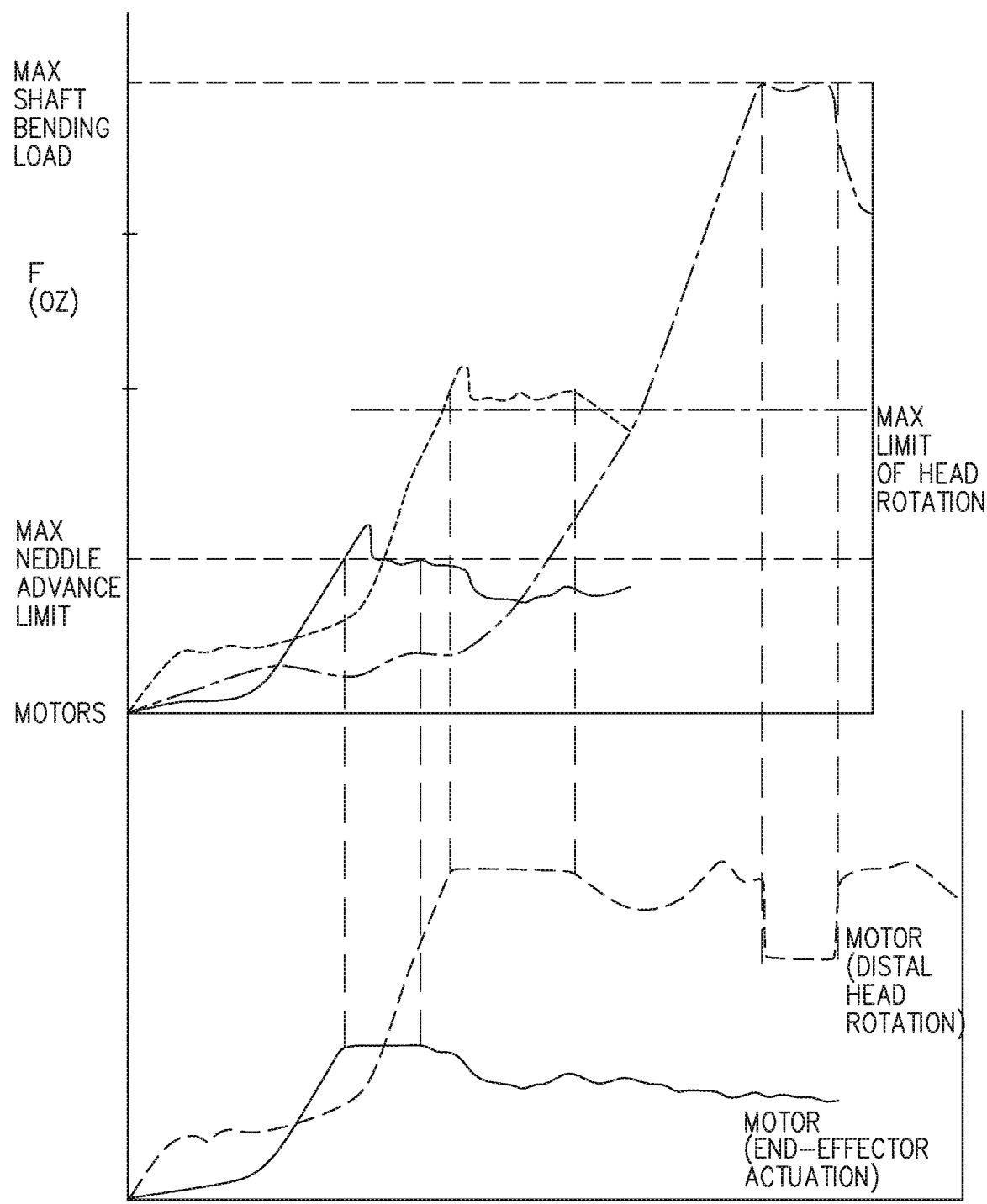
Figure 386:
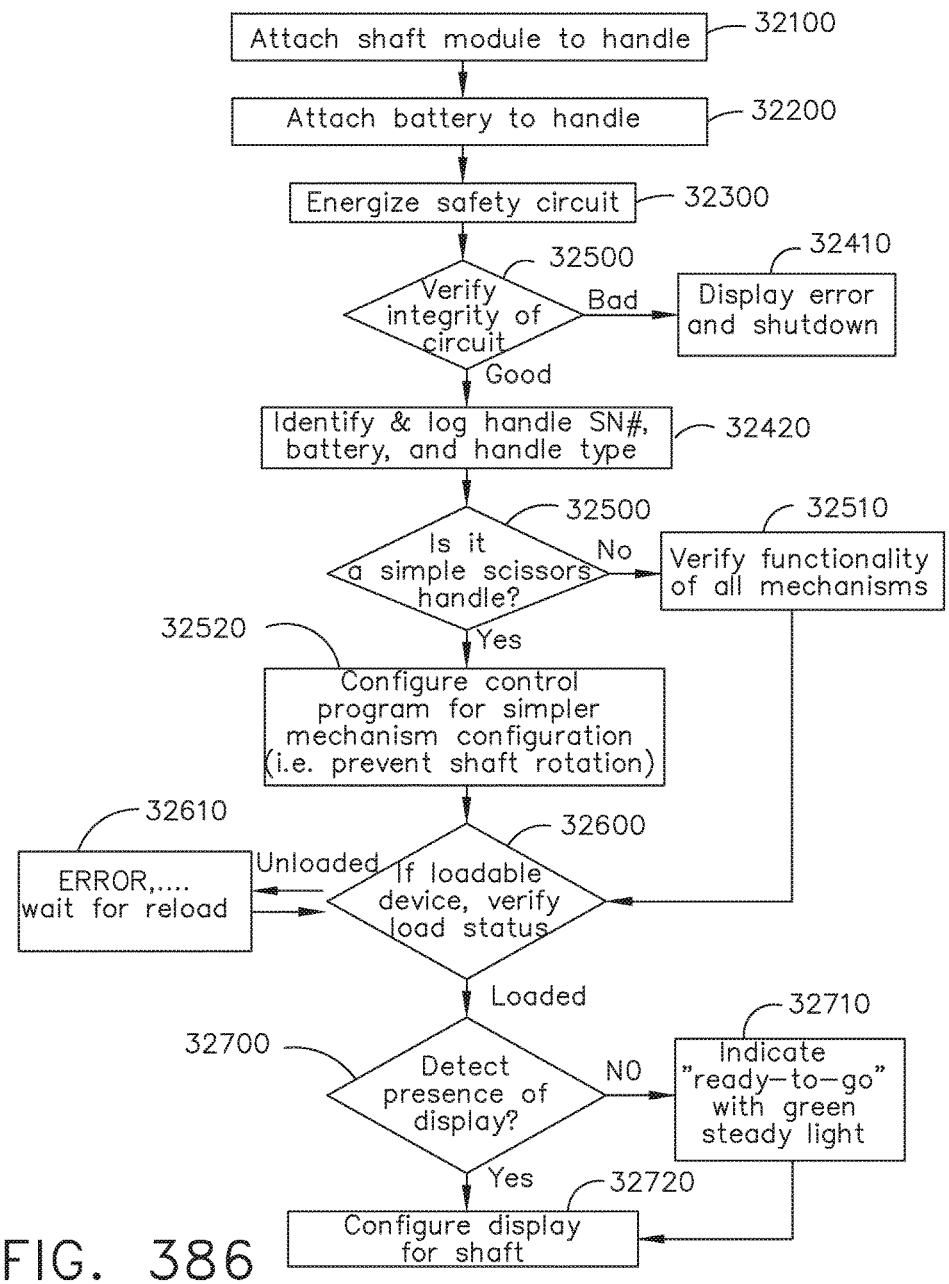

FIG. 335 illustrates a surgical instrument system comprising a handle and several shaft assemblies—each of which are selectively attachable to the handle in accordance with at least one embodiment;

FIG. 336 is an elevational view of the handle and one of the shaft assemblies of the surgical instrument system of FIG. 335;

FIG. 337 is an elevational view of a drive module of the handle of FIG. 335;

FIG. 338 is a cross-sectional perspective view of the drive module of FIG. 337;

FIG. 339 is an end view of the drive module of FIG. 337;

FIG. 340 is a perspective view of the handle drive module of FIG. 337 and one of the shaft assemblies of the surgical instrument system of FIG. 335;

FIG. 341 is another perspective view of the handle drive module of FIG. 335 and the shaft assembly of FIG. 340;

FIG. 342 is a partial cross-sectional perspective view of a handle drive module in accordance with at least one embodiment;

FIG. 343 illustrates a surgical instrument system comprising several handle assemblies and a shaft assembly selectively attachable to the handle assemblies in accordance with at least one embodiment;

FIG. 344 is an elevational view of a handle assembly of FIG. 343 in accordance with at least one embodiment;

FIG. 345 is an elevational view of a handle assembly of FIG. 343 in accordance with at least one embodiment;

FIG. 346 is an elevational view of a handle assembly of FIG. 343 in accordance with at least one embodiment;

FIG. 347 is an elevational view of a handle assembly and the shaft assembly of FIG. 343 in accordance with at least one embodiment;

FIG. 348 is an elevational view of the handle assembly of FIG. 345 attached to the shaft assembly of FIG. 343 in accordance with at least one embodiment;

FIG. 349 is an elevational view of the handle assembly of FIG. 345 and the shaft assembly of FIG. 343 in accordance with at least one embodiment;

FIG. 350 is an elevational view of the handle assembly of FIG. 346 and the shaft assembly of FIG. 343 in accordance FIG. 351 is a perspective view of the shaft assembly of FIG. 343;

FIG. 352 is a proximal end view of the handle assembly of FIG. 344;

FIG. 353 is a proximal end view of the handle assembly of FIG. 345;

FIG. 354 is a proximal end view of the handle assembly of FIG. 346;

FIG. 355 is a proximal end view of the shaft assembly of FIG. 347;

FIG. 356 illustrates a chart depicting various functions of the surgical instrument system of FIG. 343;

FIG. 357 is an exploded view of one of the handle assemblies and the shaft assembly of FIG. 343;

FIG. 358 depicts various aspects of the handle assembly of FIG. 357;

FIG. 359 is an exploded view of the handle assembly of FIG. 345 and the shaft assembly of FIG. 343;

FIG. 360 depicts various aspects of the handle assembly of FIG. 359;

FIG. 361 is a proximal end view of the handle assembly of FIG. 359;

FIG. 362 illustrates a chart depicting various functions of the handle assembly of FIG. 359;

FIG. 363 is a partial exploded view the handle assembly of FIG. 344 and the shaft assembly of FIG. 343;

FIG. 364 depicts various aspects of the handle assembly of FIG. 363;

FIG. 365 is a proximal end view of the handle assembly of FIG. 363;

FIG. 366 illustrates a chart depicting various functions of the handle assembly of FIG. 363;

FIG. 367 illustrates a shaft assembly in accordance with at least one embodiment;

FIG. 368 is a block diagram illustrating the electrical connections of a surgical instrument system in accordance with at least one embodiment;

FIG. 369 illustrates a surgical system comprising a handle and a shaft assembly in accordance with at least one embodiment;

FIG. 370 is a perspective view of the handle assembly of FIG. 369;

FIG. 371 is a cut-away view of a curved cylinder of the handle assembly of FIG. 369;

FIG. 372 is a partial cross-sectional view of the curved cylinder of FIG. 370 illustrating an electroactive polymer located in the cylinder in a non-energized state;

FIG. 373 is a partial cross-sectional view of the curved cylinder of FIG. 370 illustrating the electroactive polymer located in the cylinder in an energized state;

FIG. 374 is a block diagram illustrating various aspects of the handle and shaft assembly of FIG. 369 in accordance with at least one embodiment;

FIG. 375 is a graph illustrating the relationship between the forces experienced by an end effector and shaft of the surgical system of FIG. 369 and the voltage applied to the electroactive polymer over time;

FIG. 376 is a graph illustrating the compressive force applied by the electroactive polymer over time;

FIG. 377 illustrates a surgical system comprising a handle and a shaft assembly in accordance with at least one embodiment;

FIG. 378 is a partial perspective view of the shaft assembly of FIG. 377 comprising a locking mechanism;

FIG. 379 is a perspective view of the locking mechanism of FIG. 378 in an unlocked configuration;

FIG. 380 is a perspective view of the locking mechanism of FIG. 378 in a locked configuration;

FIGS. 381-383 illustrate the locking mechanism of FIG. 378 in three different states during the operation of the surgical instrument system;

FIG. 384 is a partial perspective view of a distal attachment portion selectively attachable to the surgical system of FIG. 377;

FIG. 385 is a graph illustrating possible drive force curves of the distal attachment portion of FIG. 384; and FIG. 386 is a flow chart illustrating a start-up process of a surgical instrument system in accordance with at least one embodiment.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. Patent Applications that were filed on Aug. 24, 2018 which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER;

U.S. patent application Ser. No. 16/112,155, entitled SURGICAL SUTURING INSTRUMENT COMPRISING A CAPTURE WIDTH WHICH IS LARGER THAN TROCAR DIAMETER;

U.S. patent application Ser. No. 16/112,168, entitled SURGICAL SUTURING INSTRUMENT COMPRISING A NON-CIRCULAR NEEDLE;

U.S. patent application Ser. No. 16/112,180, entitled ELECTRICAL POWER OUTPUT CONTROL BASED ON MECHANICAL FORCES;

U.S. patent application Ser. No. 16/112,193, entitled REACTIVE ALGORITHM FOR SURGICAL SYSTEM;

U.S. patent application Ser. No. 16/112,099, entitled SURGICAL INSTRUMENT COMPRISING AN ADAPTIVE ELECTRICAL SYSTEM;

U.S. patent application Ser. No. 16/112,112, entitled CONTROL SYSTEM ARRANGEMENTS FOR A MODULAR SURGICAL INSTRUMENT;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE;

U.S. patent application Ser. No. 16/112,097, entitled SURGICAL INSTRUMENT SYSTEMS COMPRISING BATTERY ARRANGEMENTS;

U.S. patent application Ser. No. 16/112,109, entitled SURGICAL INSTRUMENT SYSTEMS COMPRISING HANDLE ARRANGEMENTS;

U.S. patent application Ser. No. 16/112,114, entitled SURGICAL INSTRUMENT SYSTEMS COMPRISING FEEDBACK MECHANISMS;

U.S. patent application Ser. No. 16/112,117, entitled SURGICAL INSTRUMENT SYSTEMS COMPRISING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. patent application Ser. No. 16/112,151, entitled SURGICAL INSTRUMENTS COMPRISING A SYSTEM FOR ARTICULATION AND ROTATION COMPENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTURING TECHNIQUES;

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. Patent Applications that were filed on May 1, 2018 and which are each herein incorporated by reference in their respective entireties:

U.S. Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Patent Application Ser. No. 62/665,177, entitled SURGICAL INSTRUMENTS COMPRISING HANDLE ARRANGEMENTS;

U.S. Patent Application Ser. No. 62/665,128, entitled MODULAR SURGICAL INSTRUMENTS;

U.S. Patent Application Ser. No. 62/665,192, entitled SURGICAL DISSECTORS; and

U.S. Patent Application Ser. No. 62/665,134, entitled SURGICAL CLIP APPLIER.

Applicant of the present application owns the following U.S. Patent Applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL

ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. Patent Applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Aspects of the present disclosure are presented for a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more surgical devices that are used to conduct medical procedures on patients. The surgical hubs provide a wide array of functionality to improve the outcomes of medical procedures. The data generated by the various surgical devices and medical hubs about the patient and the medical procedure may be transmitted to the cloud-based medical analytics system. This data may then be aggregated with similar data gathered from many other surgical hubs and surgical devices located at other medical facilities. Various patterns and correlations may be found through the cloud-based analytics system analyzing the collected data. Improvements in the techniques used to generate the data may be generated as a result, and these improvements may then be disseminated to the various surgical hubs and surgical devices. Due to the interconnectedness of all of the aforementioned components, improvements in medical procedures and practices may be found that otherwise may not be found if the many components were not so interconnected. Various examples of structures and functions of these various components will be described in more detail in the following description.

Figure 1:
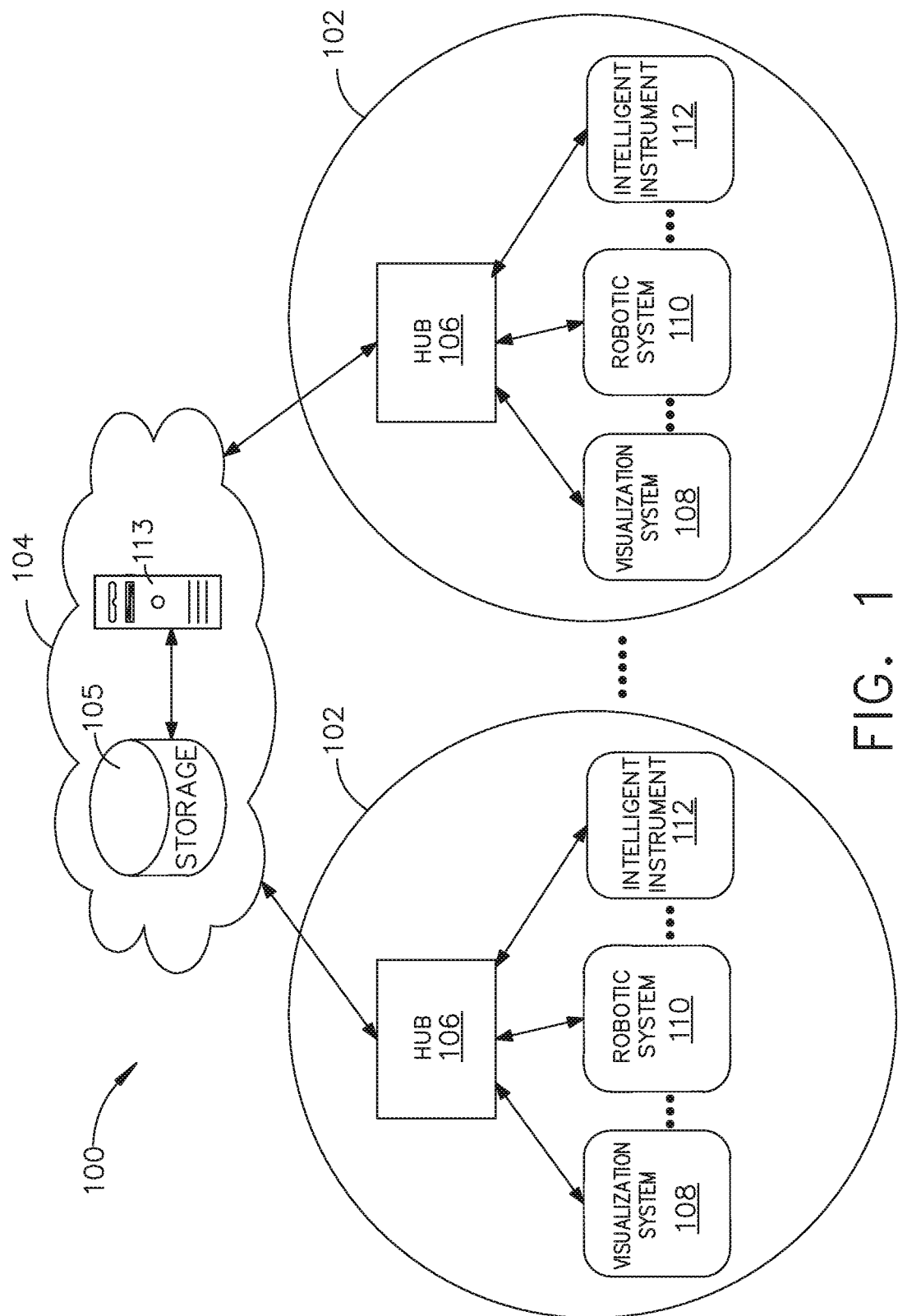
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
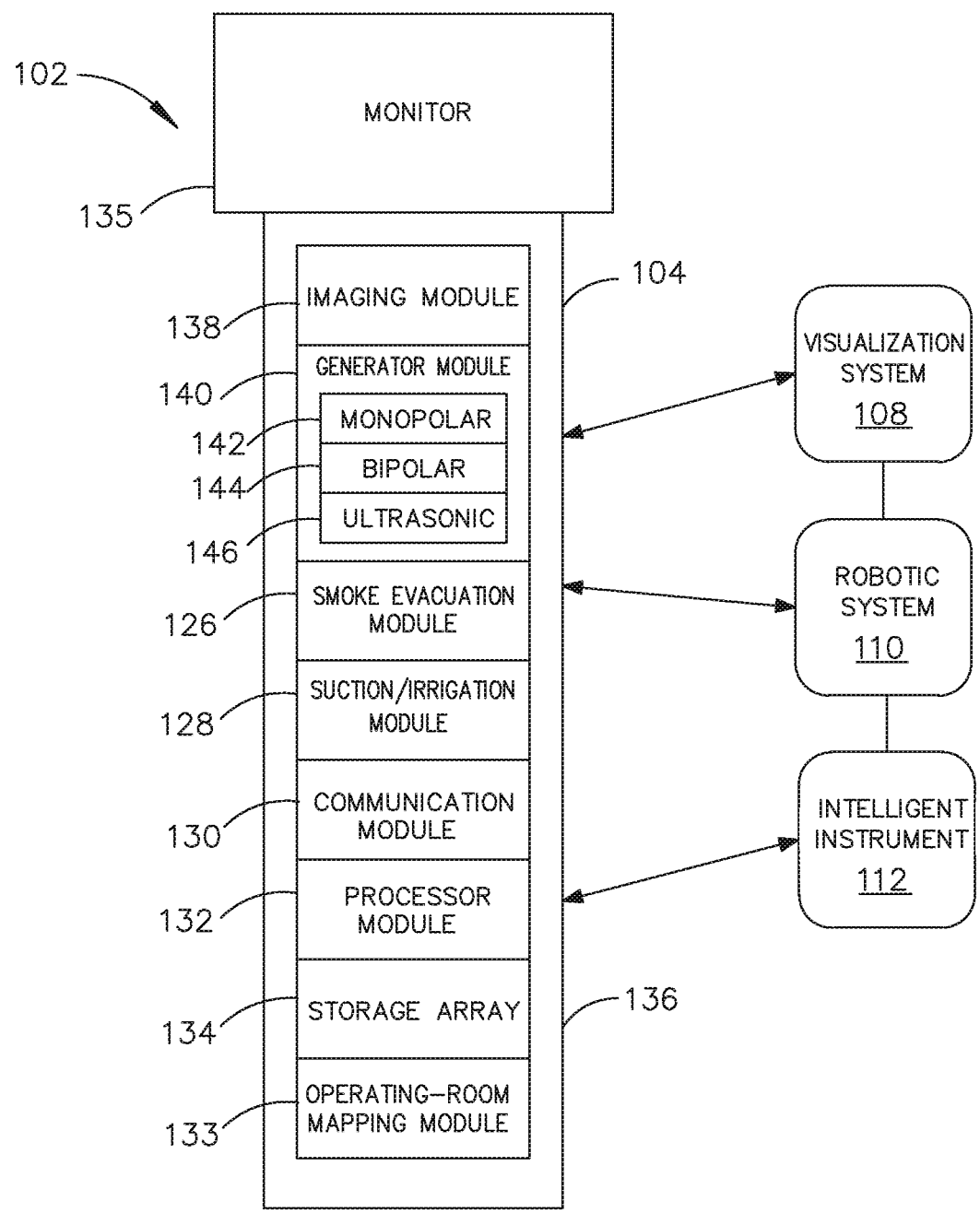
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
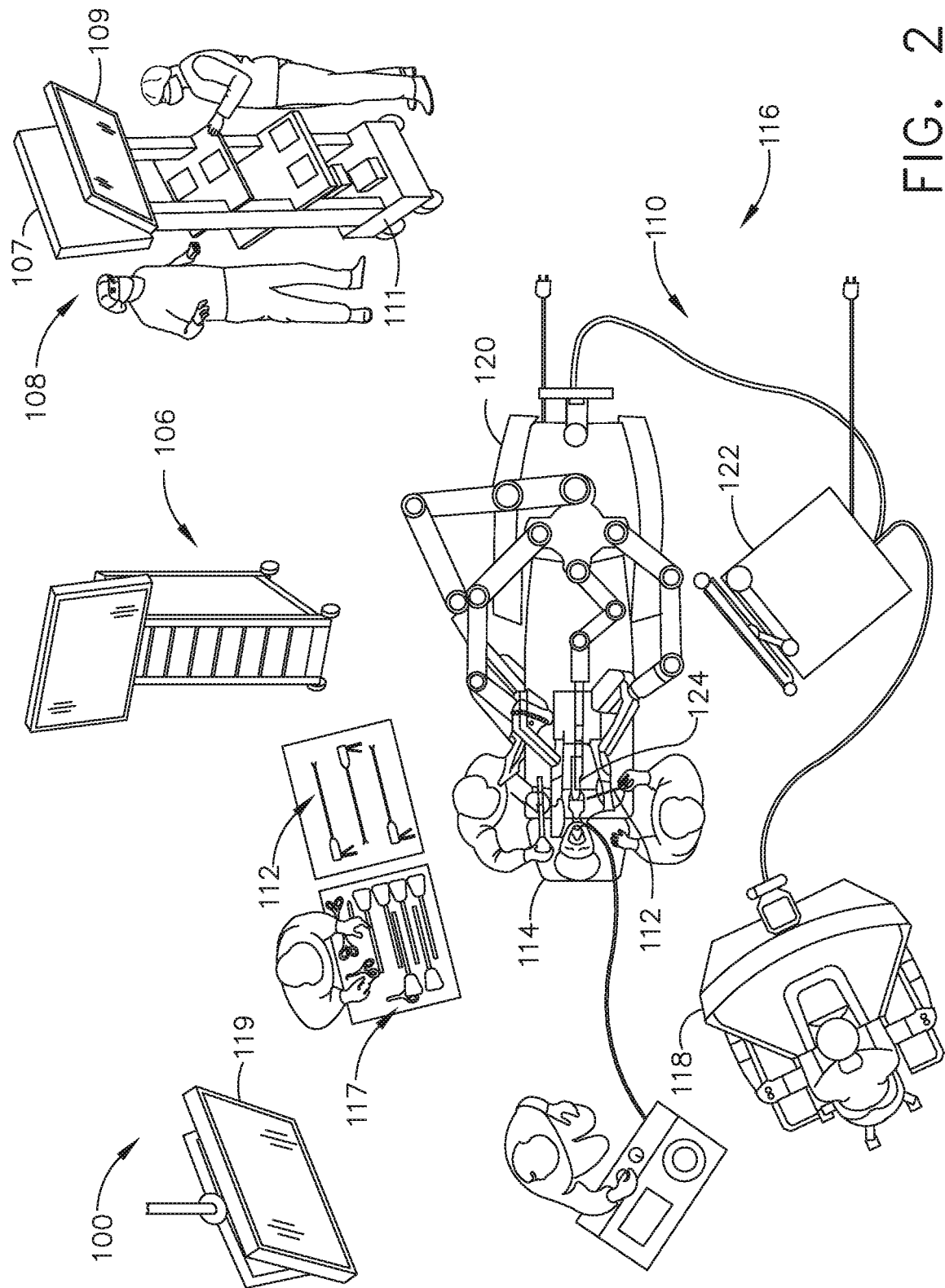
FIG. 2 is a surgical system being used to perform a surgical procedure in an operating room, in accordance with at least one aspect of the present disclosure.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
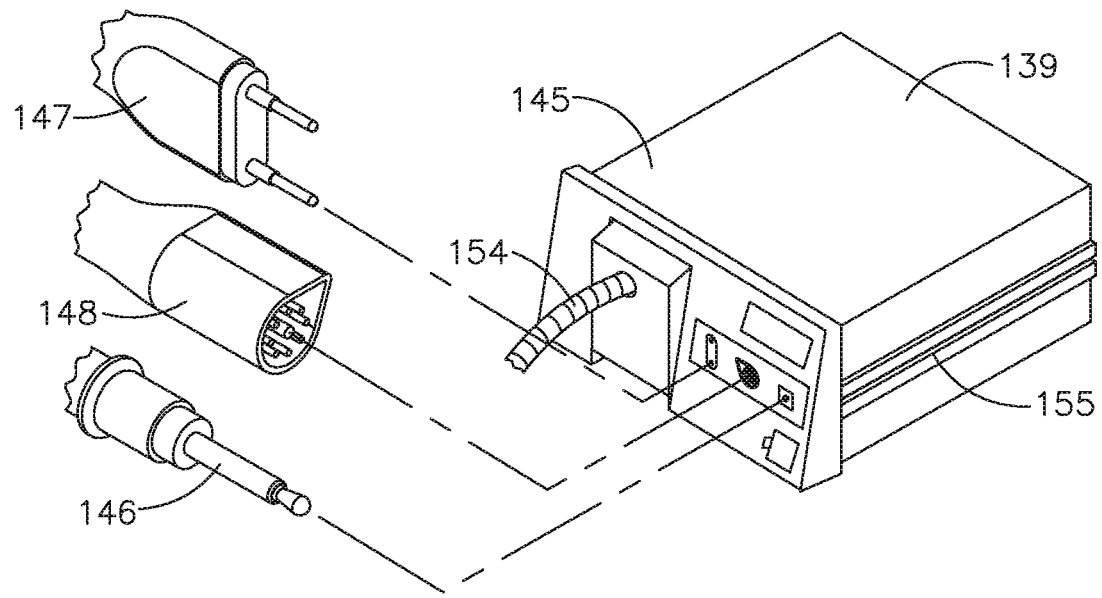
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
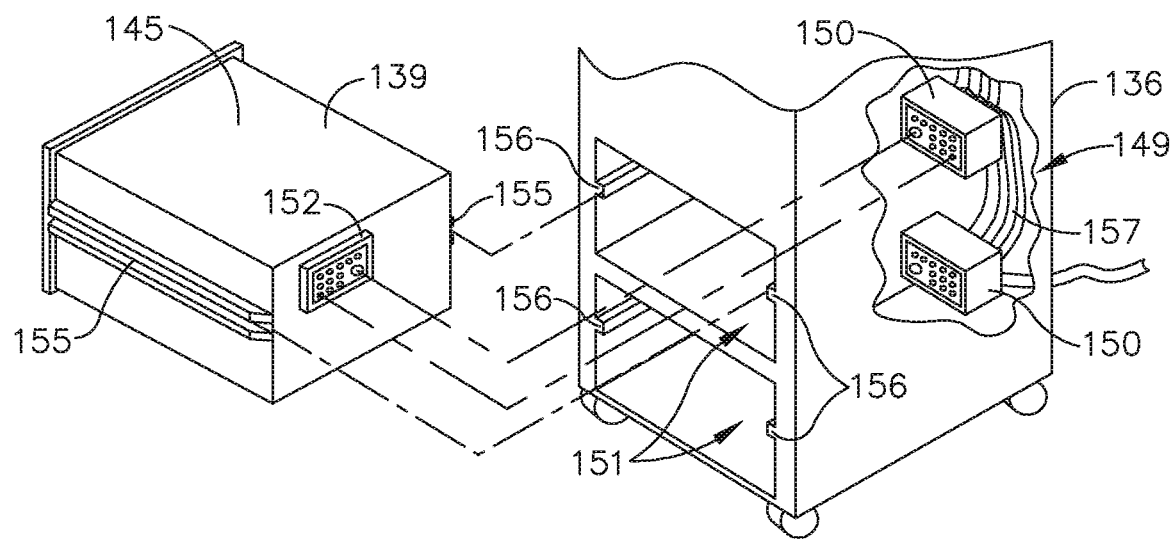
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
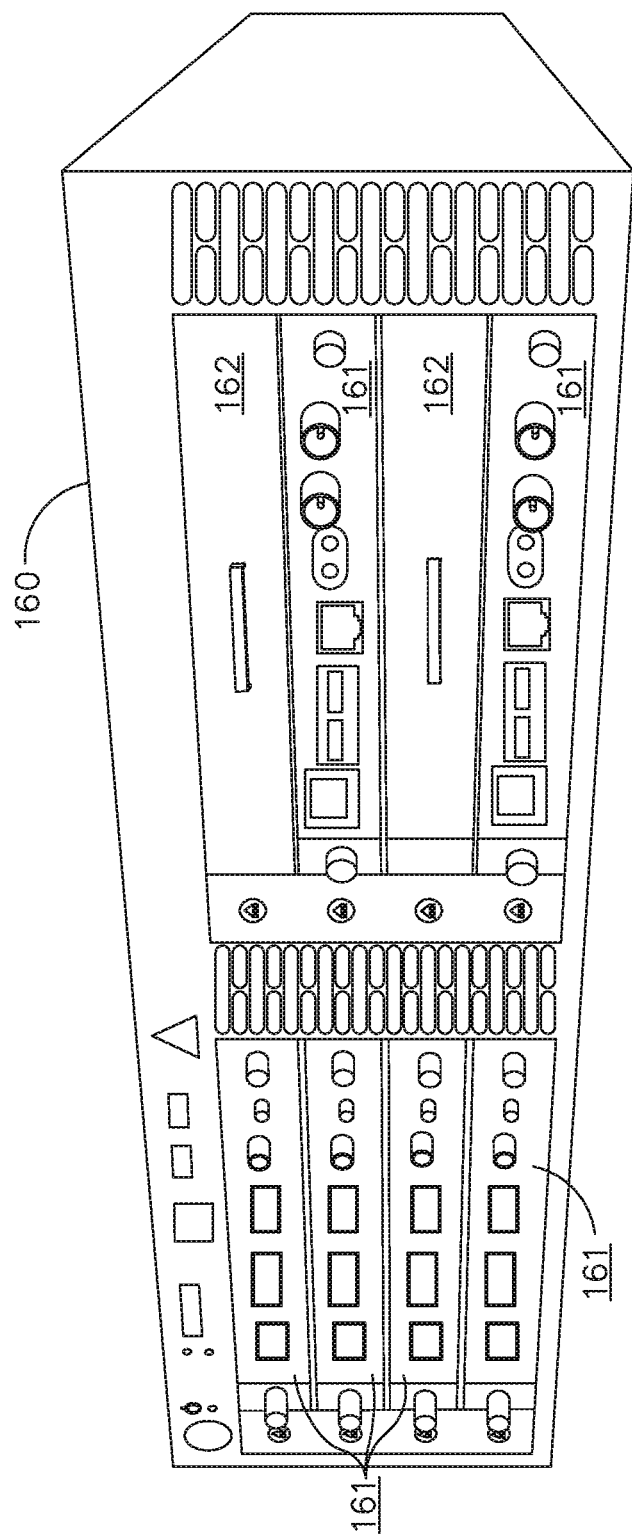
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
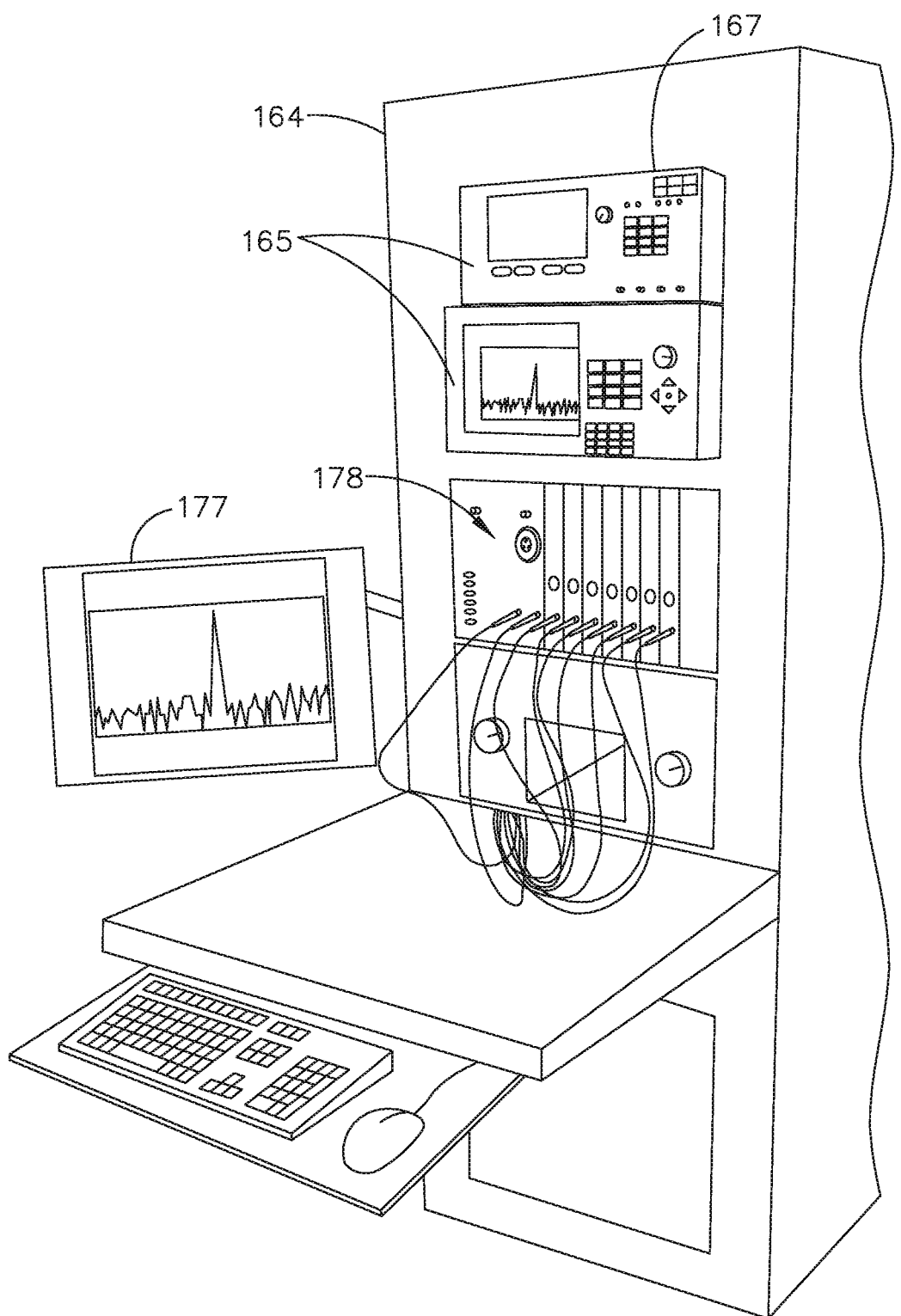
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
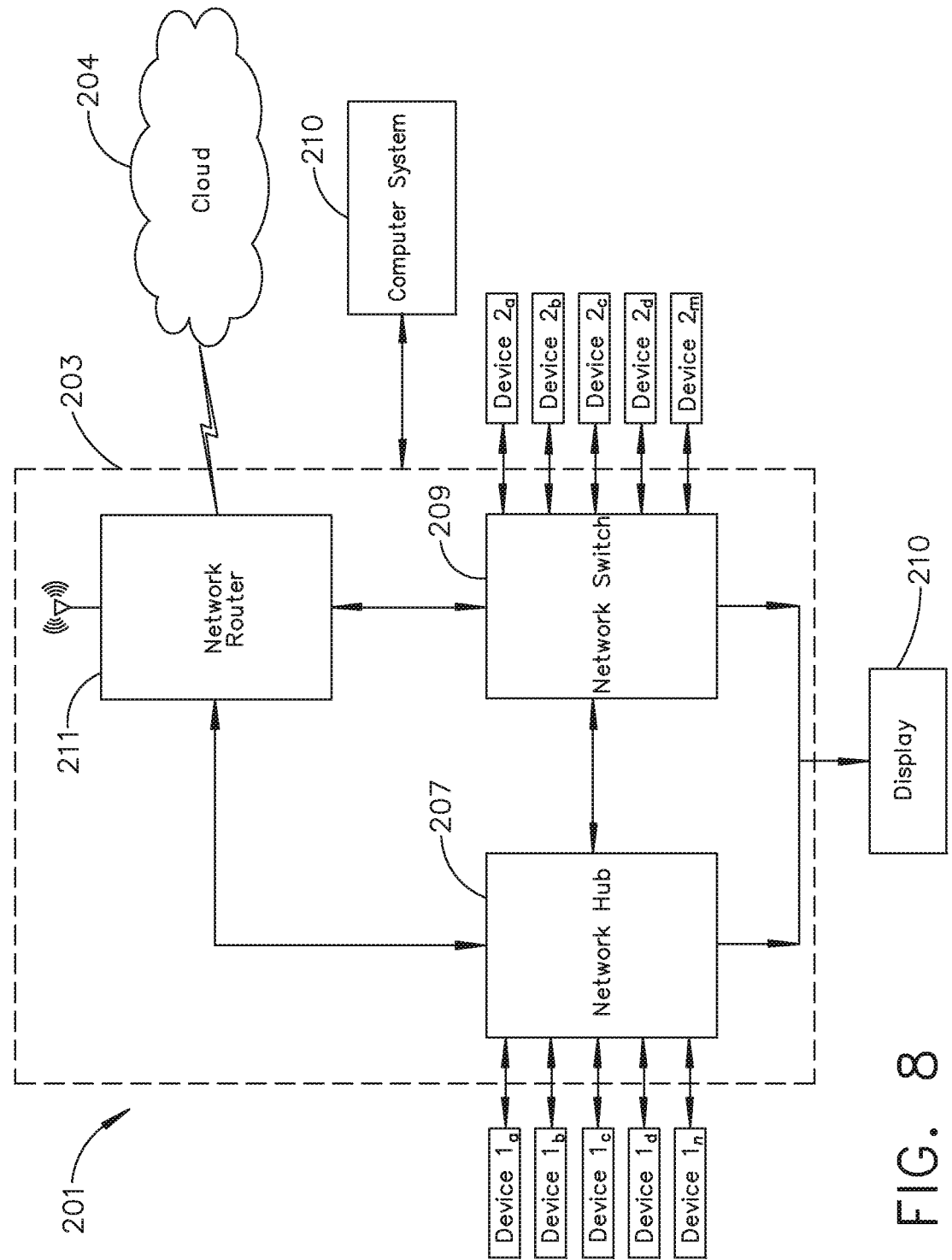
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
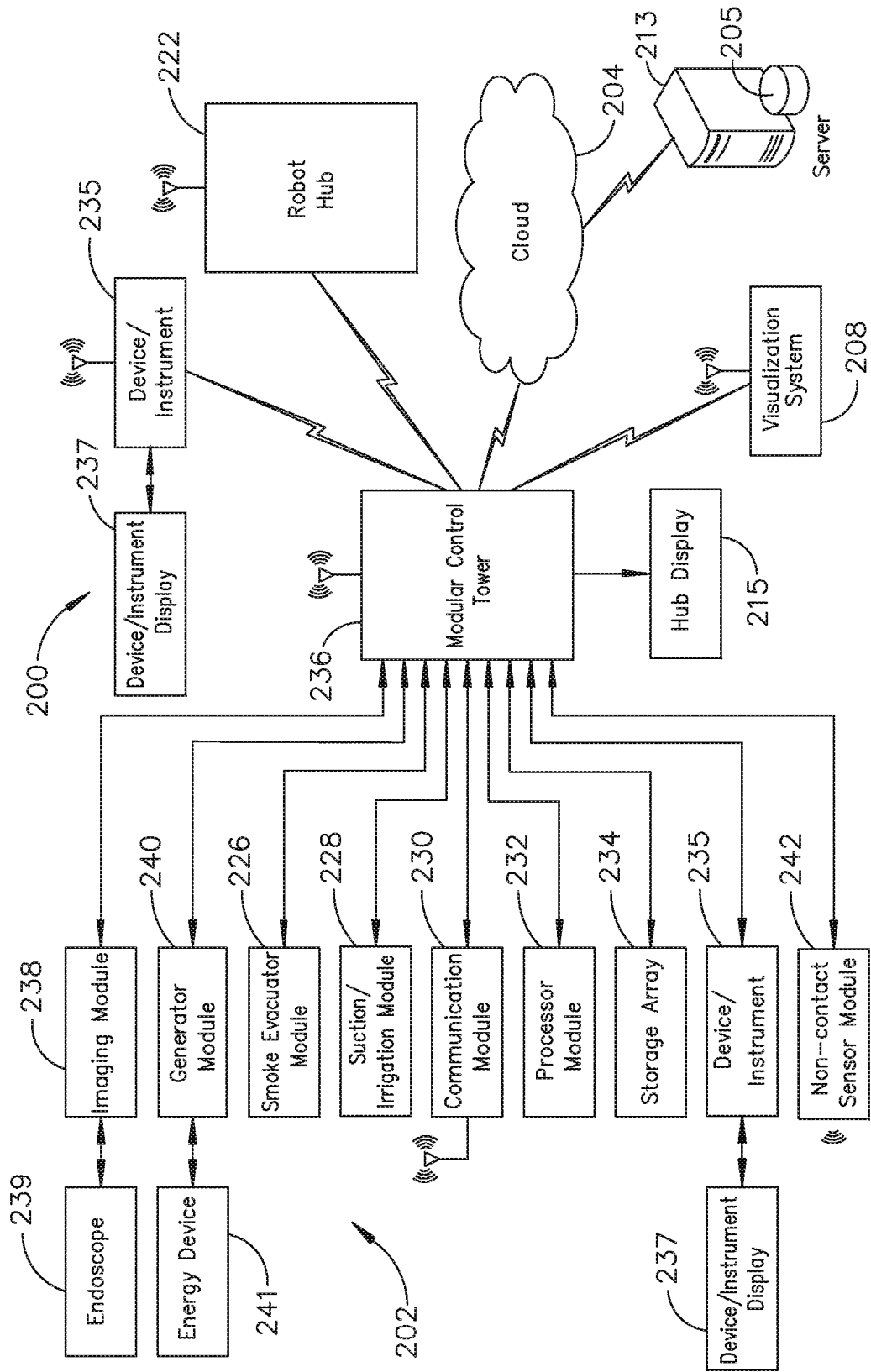
FIG. 9 illustrates a computer-implemented interactive surgical system, in accordance with at least one aspect of the present disclosure.
Figure 10:
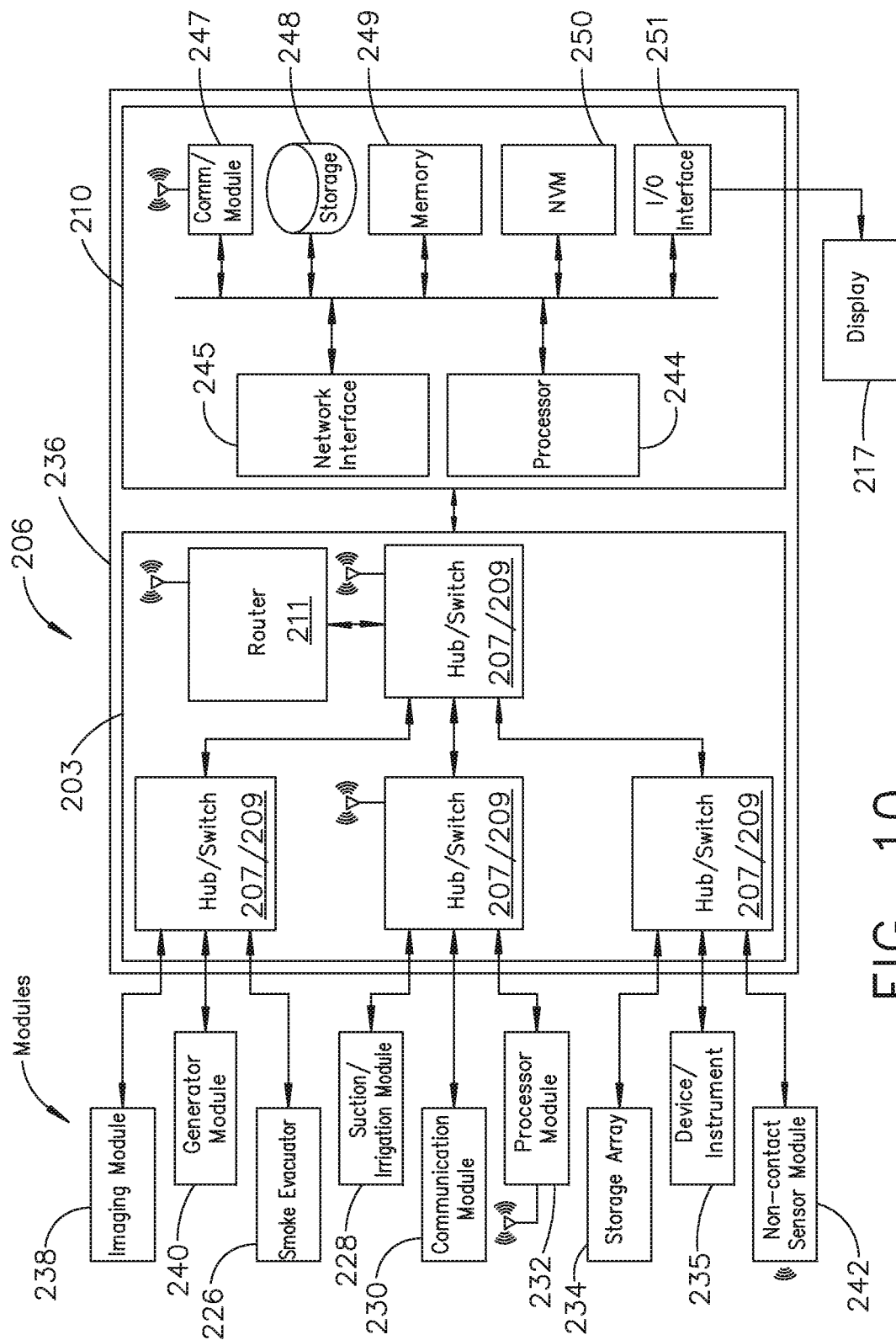
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
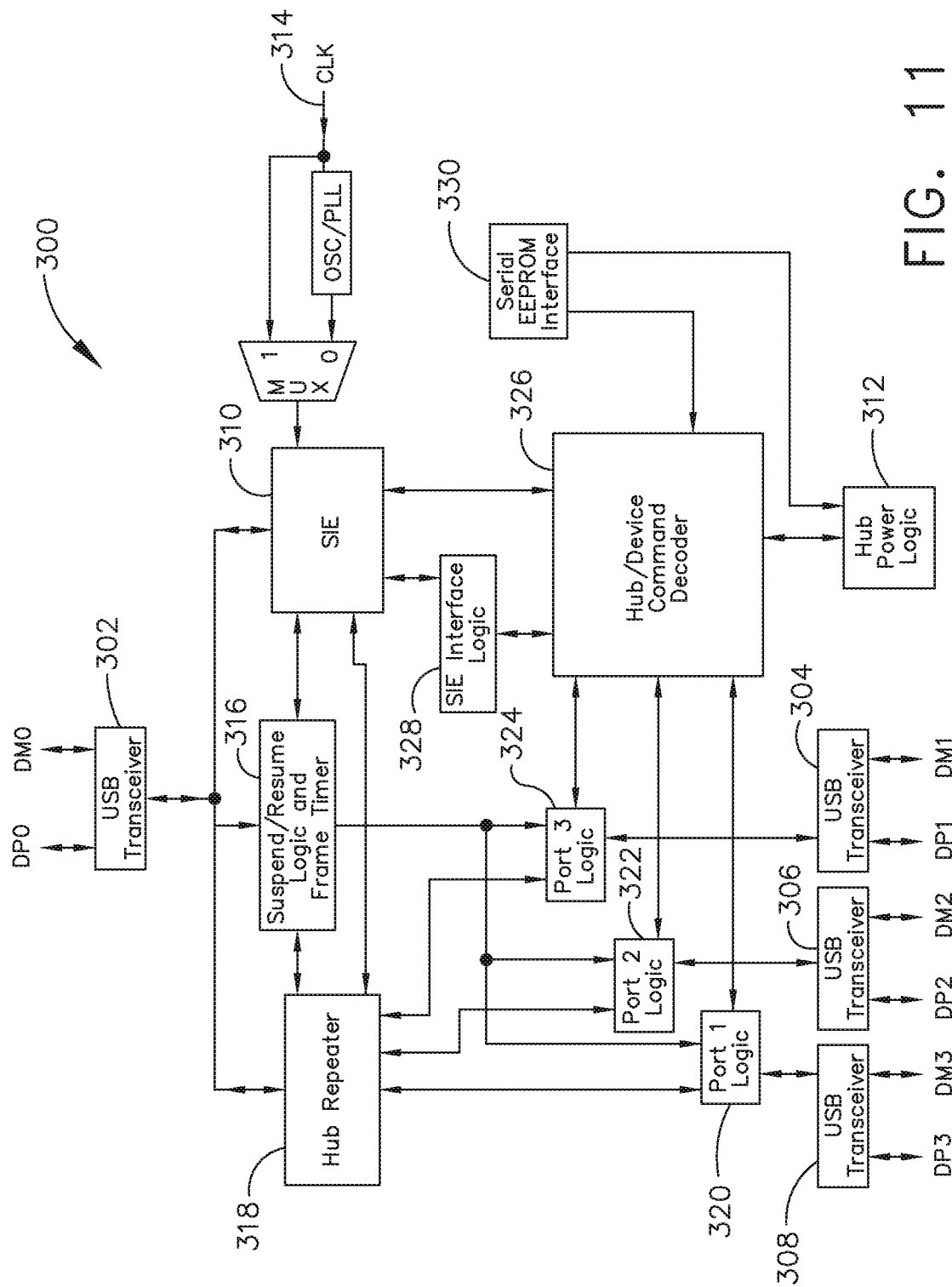
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
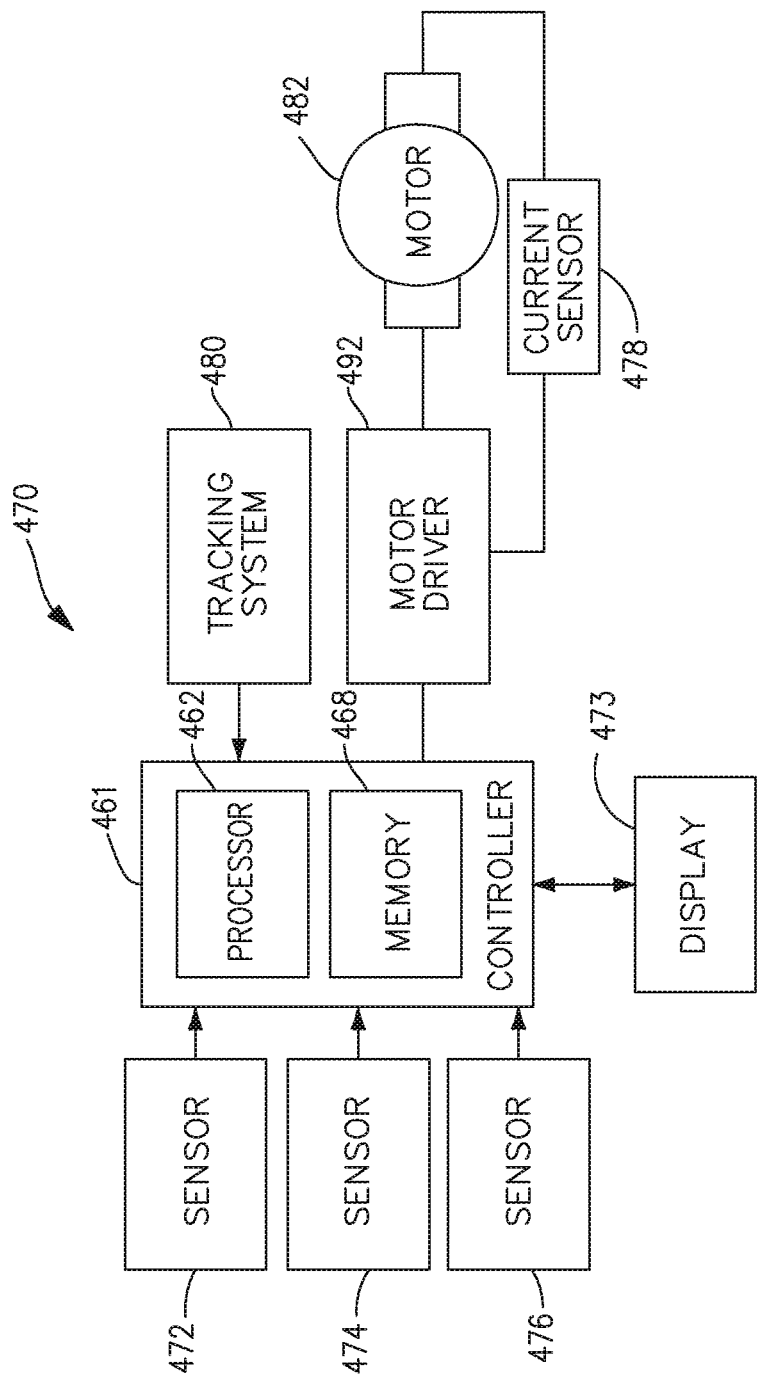
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICK- NESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
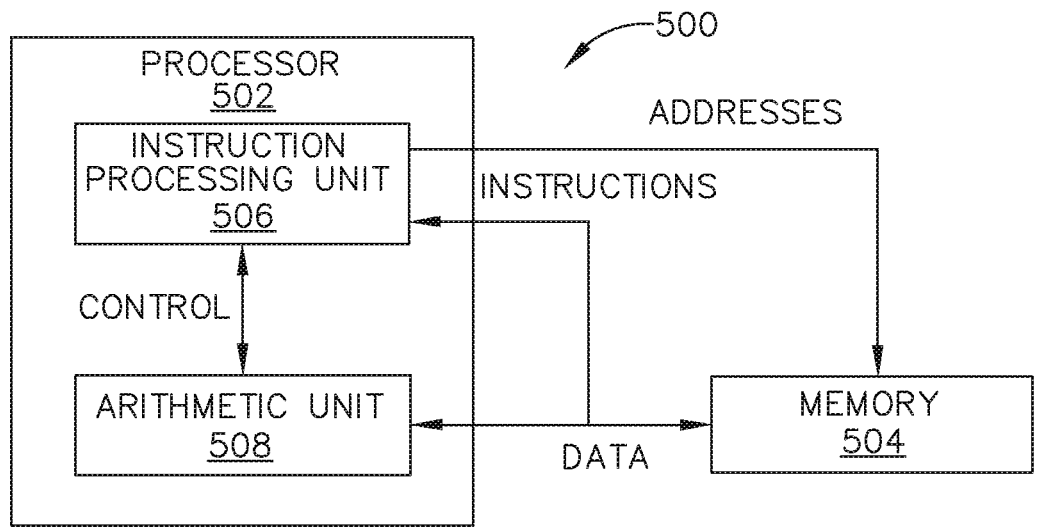
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
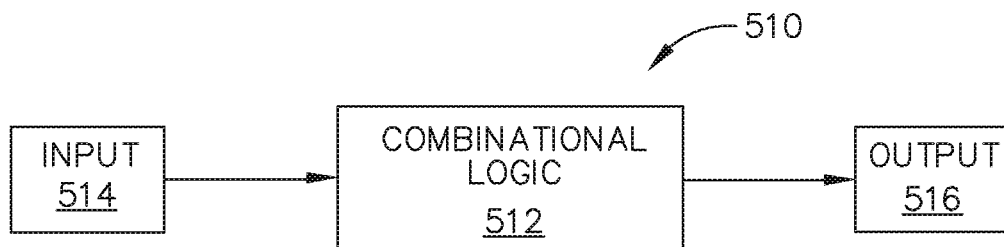
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
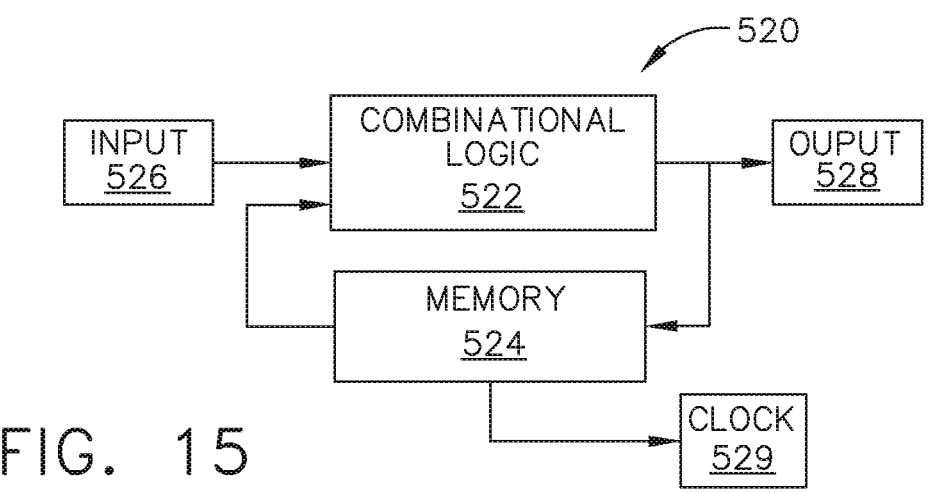
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
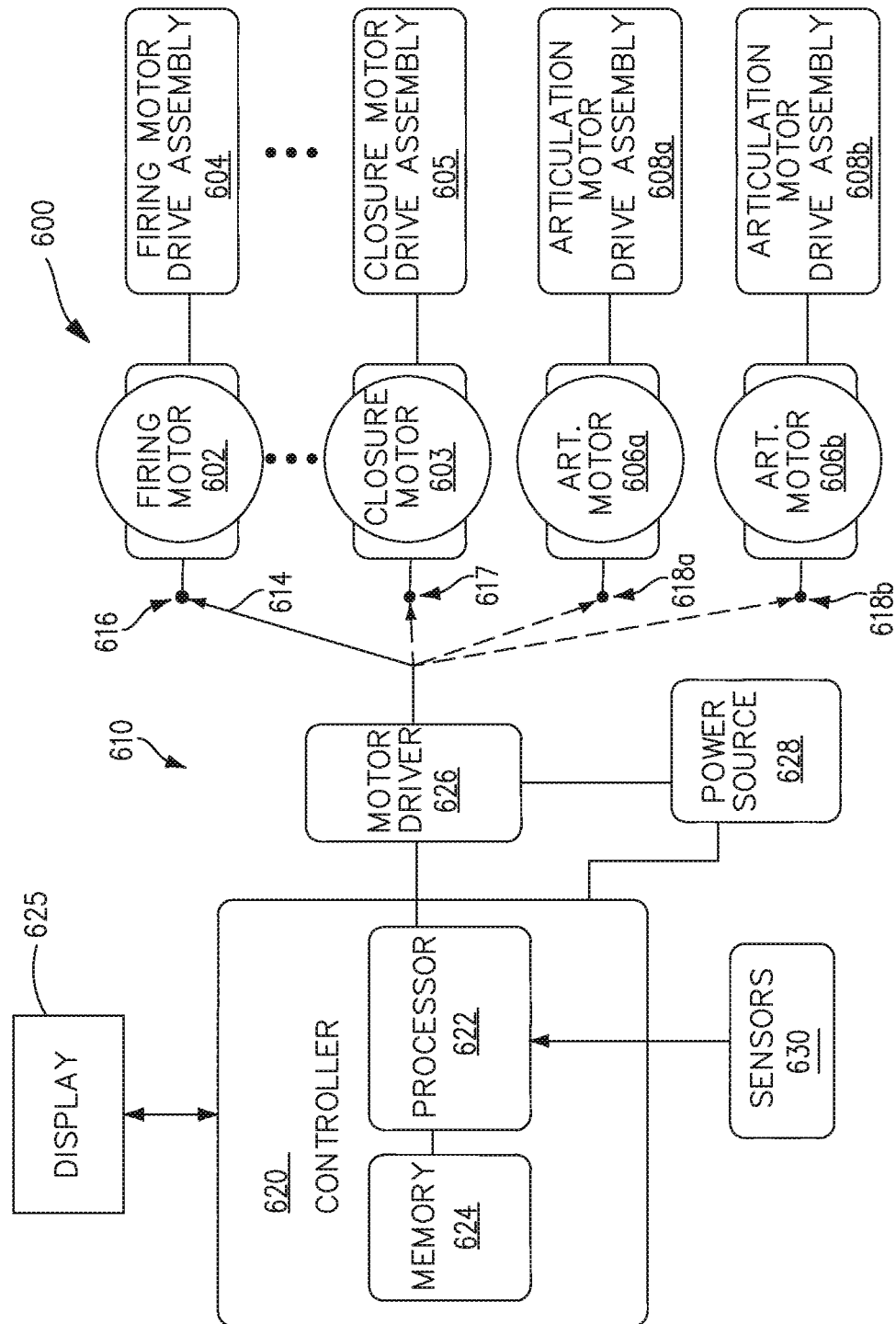
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be coupleable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
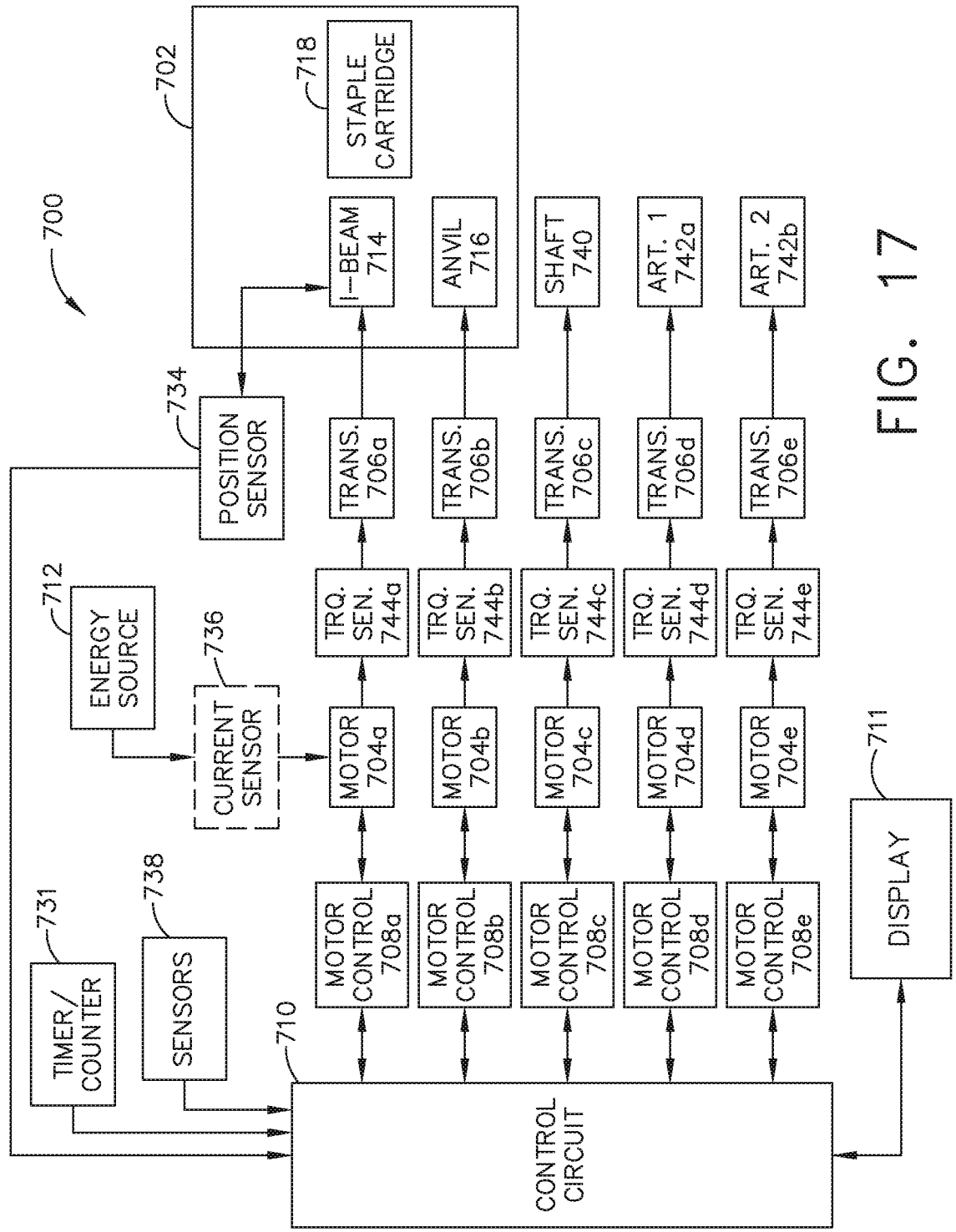
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
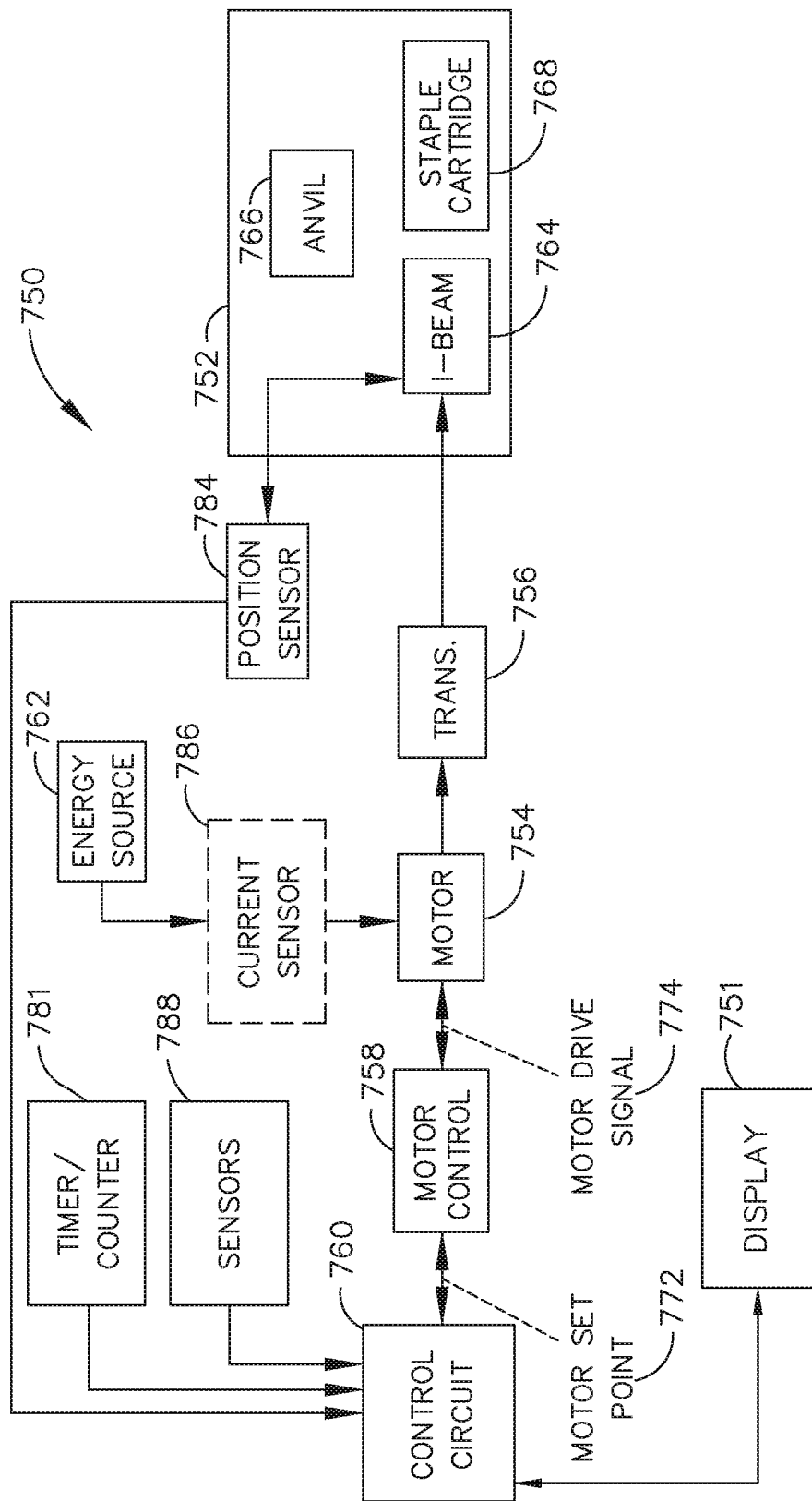
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
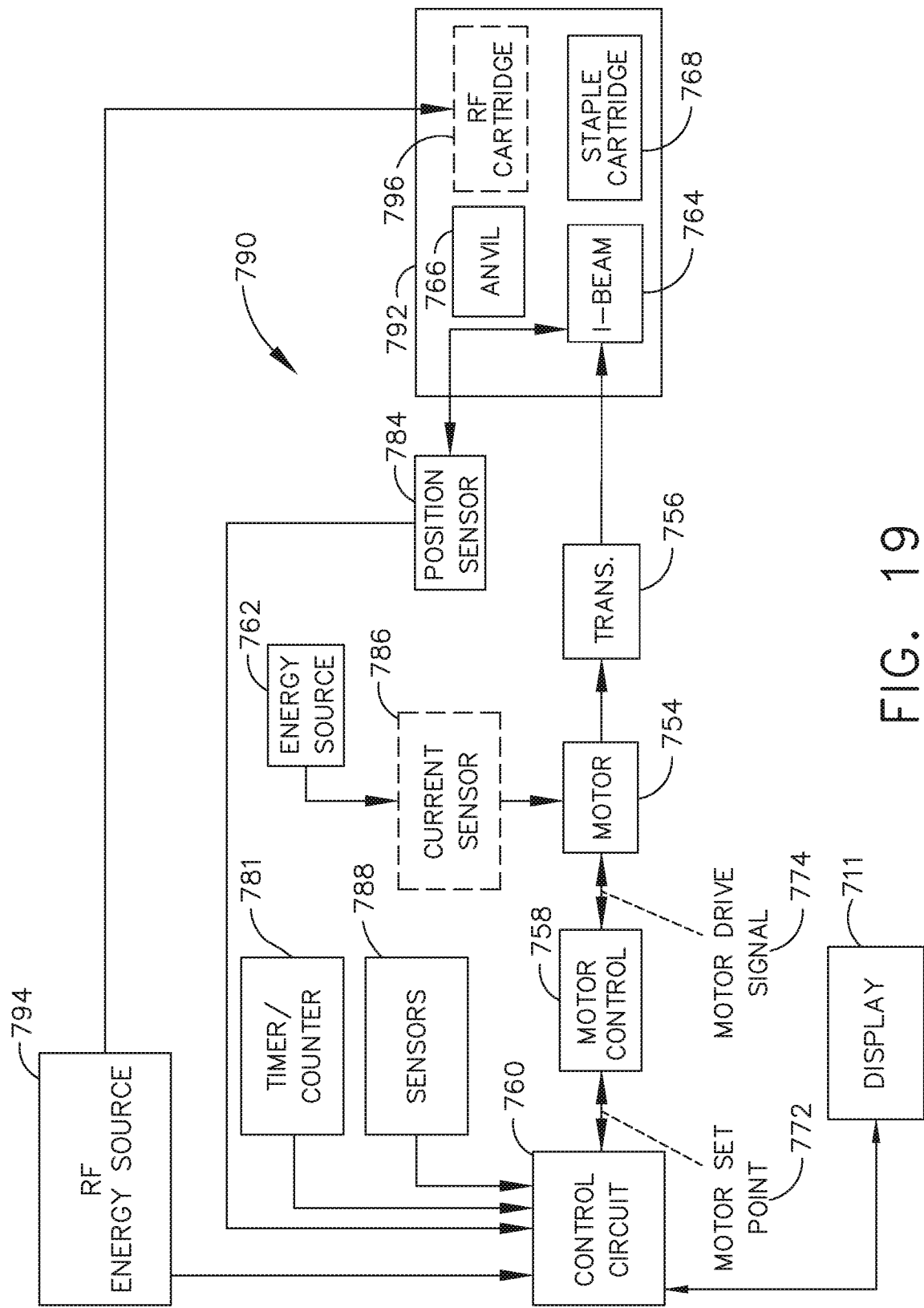
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly-owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

Figure 20:
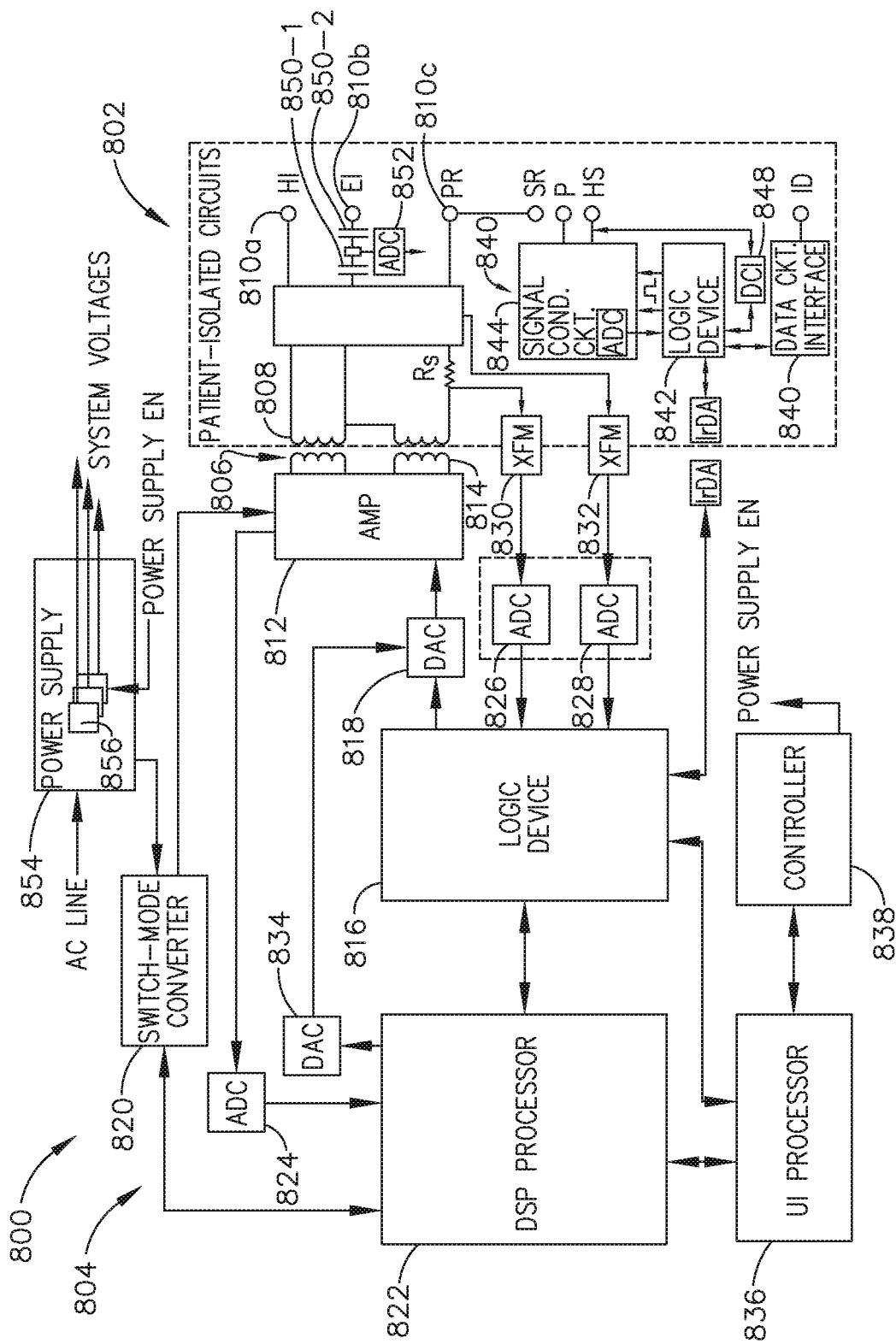
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy.

The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
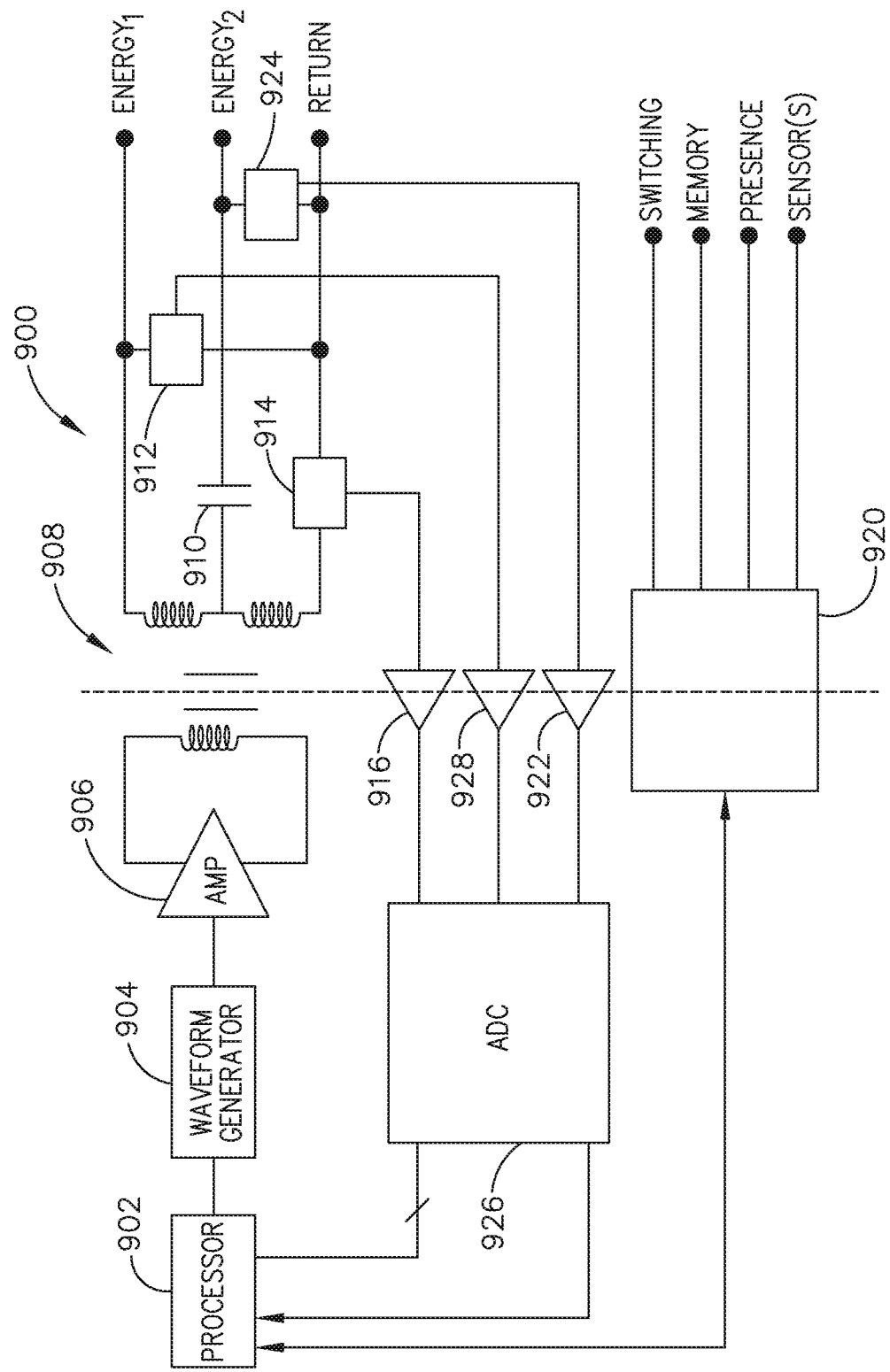
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 20). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Long Distance Communication and Condition Handling of Devices and Data

Surgical procedures are performed by different surgeons at different locations, some with much less experience than others. For a given surgical procedure, there are many parameters that can be varied to attempt to realize a desired outcome. For example, for a given surgical procedure which utilizes energy supplied by a generator, the surgeon often relies on experience alone for determining which mode of energy to utilize, which level of output power to utilize, the duration of the application of the energy, etc., in order to attempt to realize the desired outcome. To increase the likelihood of realizing desired outcomes for a plurality of different surgical procedures, each surgeon should be provided with best practice recommendations which are based on important relationships identified within large, accurate data sets of information associated with multiple surgical procedures performed in multiple locations over time. However, there are many ways that such data sets can be rendered compromised, inaccurate, and/or unsecure, thereby calling into question the applicability of the best practice recommendations derived therefrom. For example, for data sent from a source to a cloud-based system, the data can be lost while in transit to the cloud-based system, the data can be corrupted while in transit to the cloud-based system, the confidentiality of the data can be comprised while in transit to the cloud-based system, and/or the content of the data can be altered while in transit to the cloud-based system.

A plurality of operating rooms located in multiple locations can each be equipped with a surgical hub. When a given surgical procedure is performed in a given operating room, the surgical hub can receive data associated with the surgical procedure and communicate the data to a cloud-based system. Over time, the cloud-based system will receive large data sets of information associated with the surgeries. The data can be communicated from the surgical hubs to the cloud-based system in a manner which allows for the cloud-based system to (1) verify the authenticity of the communicated data, (2) authenticate each of the respective surgical hubs which communicated the data, and (3) trace the paths the data followed from the respective surgical hubs to the cloud-based system.

Accordingly, in one aspect, the present disclosure provides a surgical hub for transmitting generator data associated with a surgical procedure to a cloud-based system communicatively coupled to a plurality of surgical hubs. The surgical hub comprises a processor and a memory coupled to the processor. The memory stores instructions executable by the processor to receive data from a generator, encrypt the data, generate a message authentication code (MAC) based on the data, generate a datagram comprising the encrypted data, the generated MAC, a source identifier, and a destination identifier, and transmit the datagram to a cloud-based system. The data is structured into a data packet comprising at least two of the following fields: a field that indicates the source of the data, a unique time stamp, a field indicating an energy mode of the generator, a field indicating the power output of the generator, and a field indicating a duration of the power output of the generator. The datagram allows for the cloud-based system to decrypt the encrypted data of the transmitted datagram, verify integrity of the data based on the MAC, authenticate the surgical hub as the source of the datagram, and validate a transmission path followed by the datagram between the surgical hub and the cloud-based system. In various aspects, the present disclosure provides a control circuit to transmit generator data associated with a surgical procedure to a cloud-based system communicatively coupled to a plurality of surgical hubs, as described above. In various aspects, the present disclosure provides a non-transitory computer-readable medium storing computer-readable instructions which, when executed, causes a machine to transmit generator data associated with a surgical procedure to a cloud-based system communicatively coupled to a plurality of surgical hubs, as described above.

In another aspect, the present disclosure provides a cloud-based system communicatively coupled to a plurality of surgical hubs. Each surgical hub is configured to transmit generator data associated with a surgical procedure to the cloud-based system. The cloud-based system comprises a processor and a memory coupled to the processor. The memory stores instructions executable by the processor to receive a datagram generated by a surgical hub, decrypt the encrypted generator data of the received datagram, verify integrity of the generator data based on the MAC, authenticate the surgical hub as the source of the datagram, and validate a transmission path followed by the datagram between the surgical hub and the cloud-based system. The datagram comprises generator data captured from a generator associated with the surgical hub, a MAC generated by the surgical hub based on the generator data, a source identifier, and a destination identifier. The generator data has been encrypted by the surgical hub. The encrypted generator data has been structured into a data packet comprising at least two of the following fields: a field that indicates the source of the data, a unique time stamp, a field indicating an energy mode, a field indicating power output, and a field indicating a duration of applied power.

In various aspects, the present disclosure provides a control circuit to transmit generator data associated with a surgical procedure to the cloud-based system. In various aspects, the present disclosure provides a non-transitory computer-readable medium storing computer-readable instructions which, when executed, causes a machine to transmit generator data associated with a surgical procedure to the cloud-based system.

In another aspect, the present disclosure provides a method, comprising capturing data from a combination generator of a surgical hub during a surgical procedure, wherein the combination generator is configured to supply two or more different modes of energy. Encrypting the captured generator data, generating a MAC based on the captured generator data, generating a datagram comprising the encrypted generator data, the MAC, a source identifier, and a destination identifier, and communicating the datagram from the surgical hub to a cloud-based system. The datagram allows for the cloud-based system to authenticate integrity of the communicated generator data, authenticate the surgical hub as a source of the datagram, and determine a communication path followed by the datagram between the surgical hub and the cloud-based system.

By sending captured generator data from a plurality of different surgical hubs to a cloud-based system, the cloud-based system is able to quickly build large data sets of information associated with multiple surgical procedures performed in multiple locations over time. Furthermore, due to the composition of the respective datagrams, for a given datagram, the cloud-based system is able to determine whether the datagram was originally sent by one of the surgical hubs (source validation), thereby providing an indication that the generator data received at the cloud-based system is legitimate data. For the given datagram, the cloud-based system is also able to determine whether the generator data received at the cloud-based system is identical to the generator data sent by the given surgical hub (data integrity), thereby allowing for the authenticity of the received generator data to be verified. Additionally, for the given datagram, the cloud-based system is also able to re-trace the communication path followed by the datagram, thereby allowing for enhanced troubleshooting if a datagram received by the cloud-based system was originally sent from a device other than the surgical hubs and/or if the content of the datagram was altered while in transit to the cloud-based system. Notably, the present disclosure references generator data in particular. Here, the present disclosure should not be limited as being able to process only generator data. For example, the surgical hub 206 and/or the cloud-based system 205 may process data received from any component (e.g., imaging module 238, generator module 240, smoke evacuator module 226, suction/irrigation module 228, communication module 230, processor module 232, storage array 234, smart device/instrument 235, non-contact sensor module 242, robot hub 222, a non-robotic surgical hub 206, wireless smart device/instrument 235, visualization system 208) of the surgical system 202 that is coupled to the surgical hub 206 and/or data from any devices (e.g., endoscope 239, energy device 241) coupled to/through such components (e.g., see FIGS. 9-10), in a similar manner as discussed herein.

Unfortunately, the outcome of a surgical procedure is not always optimal. For example, a failure event such as a surgical device failure, an unwanted tissue perforation, an unwanted post-operative bleeding, or the like can occur. The occurrence of a failure event can be attributed to any of a variety of different people and devices, including one or more surgeons, one or more devices associated with the surgery, a condition of the patient, and combinations thereof. When a given failure event occurs, it is not always clear regarding who or what caused the failure event or how the occurrence of the failure event can be mitigated in connection with a future surgery.

During a given surgical procedure, a large amount of data associated with the surgical procedure can be generated and captured. All of the captured data can be communicated to a surgical hub, and the captured data can be time-stamped either before or after being received at the surgical hub. When a failure event associated with the surgical procedure is detected and/or identified, it can be determined which of the captured data is associated with the failure event and/or which of the captured data is not associated with the failure event. In making this determination, the failure event can be defined to include a period of time prior to the detection/identification of the failure event. Once the determination is made regarding the captured data associated with the failure event, the surgical hub can separate the captured data associated with the failure event from all other captured data, and the captured data can be separated based on tagging, flagging, or the like. The captured data associated with the failure event can then be chronologized based on the time-stamping and the defined time period applicable to the failure event. The chronologized captured data can then be communicated to a cloud-based system on a prioritized basis for analysis, where the prioritized basis is relative to the captured data which is not associated with the failure event. Whether or not the analysis identifies a device associated with the surgical procedure as the causation of the failure event, the surgical hub can tag the device for removal of the device from future use, further analysis of the device, and/or to return the device to the manufacturer.

When a given surgical procedure is performed, a large amount of data associated with the surgical procedure can be generated and captured. All of the captured data can be communicated to a surgical hub, where the information can be stripped of all "personal" associations. The captured data can be time-stamped before being received at the surgical hub, after being received at the surgical hub, before being stripped of the "personal" associations, or after being stripped of the "personal" associations. The surgical hub can communicate the stripped data to the cloud-based system for subsequent analysis. Over time, the cloud-based system will receive large data sets of information associated with the surgeries.

Accordingly, in one aspect, the present disclosure provides a surgical hub for prioritizing surgical data associated with a surgical procedure to a cloud-based system communicatively coupled to a plurality of surgical hubs. The surgical hub comprises a processor and a memory coupled to the processor. The memory stores instructions executable by the processor to capture surgical data, wherein the surgical data comprises data associated with a surgical device, time-stamp the captured surgical data, identify a failure event, identify a time period associated with the failure event, isolate failure event surgical data from surgical data not associated with the failure event based on the identified time period, chronologize the failure event surgical data by time-stamp, encrypt the chronologized failure event surgical data, generate a datagram comprising the encrypted failure event surgical data, and transmit the datagram to a cloud-based system. The datagram is structured to include a field which includes a flag that prioritizes the encrypted failure event surgical data over other encrypted data of the datagram. The datagram allows for the cloud-based system to decrypt the encrypted failure event surgical data, focus analysis on the failure event surgical data rather than surgical data not associated with the failure event, and flag the surgical device associated with the failure event for at least one of the following: removal from an operating room, return to a manufacturer, or future inoperability in the cloud-based system.

In various aspects, the present disclosure provides a control circuit to prioritize surgical data associated with a surgical procedure to a cloud-based system communicatively coupled to a plurality of surgical hubs. In various aspects, the present disclosure provides a non-transitory computer-readable medium storing computer-readable instructions which, when executed, causes a machine to prioritize surgical data associated with a surgical procedure to a cloud-based system communicatively coupled to a plurality of surgical hubs.

In another aspect, the present disclosure provides a method, comprising capturing data during a surgical procedure, communicating the captured data to a surgical hub, time-stamping the captured data, identifying a failure event associated with the surgical procedure, determining which of the captured data is associated with the failure event, separating the captured data associated with the failure event from all other captured data, chronologizing the captured data associated with the failure event, and communicating the chronologized captured data to a cloud-based system on a prioritized basis.

By capturing the large amount of data associated with the surgical procedure, and with having the captured data time-stamped, the portion of the captured data which is relevant to the detected/identified failure event can be more easily isolated from all of the other captured data, thereby allowing for a more focused subsequent analysis on just the relevant captured data. The data associated with the failure event can then be chronologized (this requires less processing power than chronologizing all of the captured data), thereby allowing for the events leading up to the detection/identification of the failure event to be more easily considered during the subsequent analysis of the failure event. The chronologized data can then be communicated to the cloud-based system (this requires less communication resources than communicating all of the captured data at the same time) on a prioritized basis, thereby allowing for the focused subsequent analysis of the fault event to be performed by the cloud-based system in a more time-sensitive manner.

To help ensure that the best practice recommendations are developed based on accurate data, it would be desirable to ensure that the generator data received at the cloud-based system is the same as the generator data communicated to the cloud-based system. Also, to help to be able to determine the cause of a failure event as quickly as possible, it would be desirable to ensure that surgical data associated with the failure event is communicated to the cloud-based system in a prioritized manner (relative to surgical data not associated with the failure event) so that analysis of the surgical data can be performed in an expedited manner.

Aspects of a system and method for communicating data associated with a surgical procedure are described herein. As shown in FIG. 9, various aspects of the computer implemented interactive surgical system 200 includes a device/instrument 235, a generator module 240, a modular control tower 236, and a cloud-based system 205. As shown in FIG. 10, the device/instrument 235, the generator module 240, and the modular control tower 236 are components/portions of a surgical hub 206.

Figure 22:
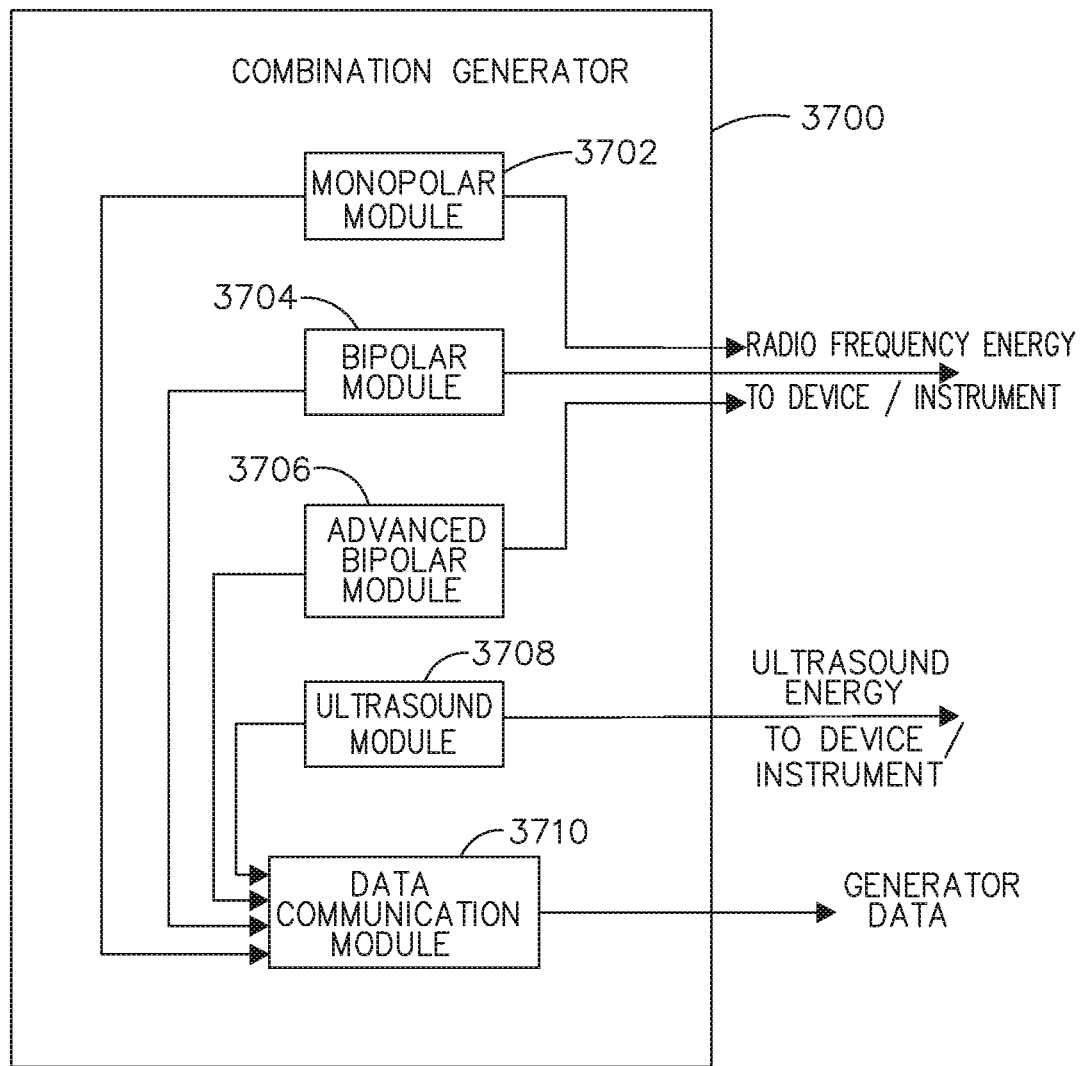
FIG. 22 illustrates a combination generator, in accordance with at least one aspect of the present disclosure.

In various aspects, the generator module 240 of the surgical hub 206 can supply radio-frequency energy such as monopolar radio-frequency energy, bipolar radio-frequency energy, and advanced bipolar energy and/or ultrasonic energy to a device/instrument 235 for use in a surgical procedure. Thus, the generator module 240 may be referred to as a combination generator. An example of such a combination generator is shown in FIG. 22, where the combination generator 3700 is shown as including a monopolar module 3702, a bipolar module 3704, an advanced bipolar module 3706, and an ultrasound module 3708. When utilized during a surgical procedure, the respective energy modules (e.g., 3702, 3704, 3706, and/or 3708) of the combination generator 3700 can provide generator data such as type of energy supplied to the device instrument (e.g., radio-frequency energy, ultrasound energy, radio-frequency energy and ultrasound energy), type of radio-frequency energy (e.g., monoplar, bipolar, advanced bipolar), frequency, power output, duration, etc., to the data communication module 3710 of the combination generator 3700.

Figure 23:
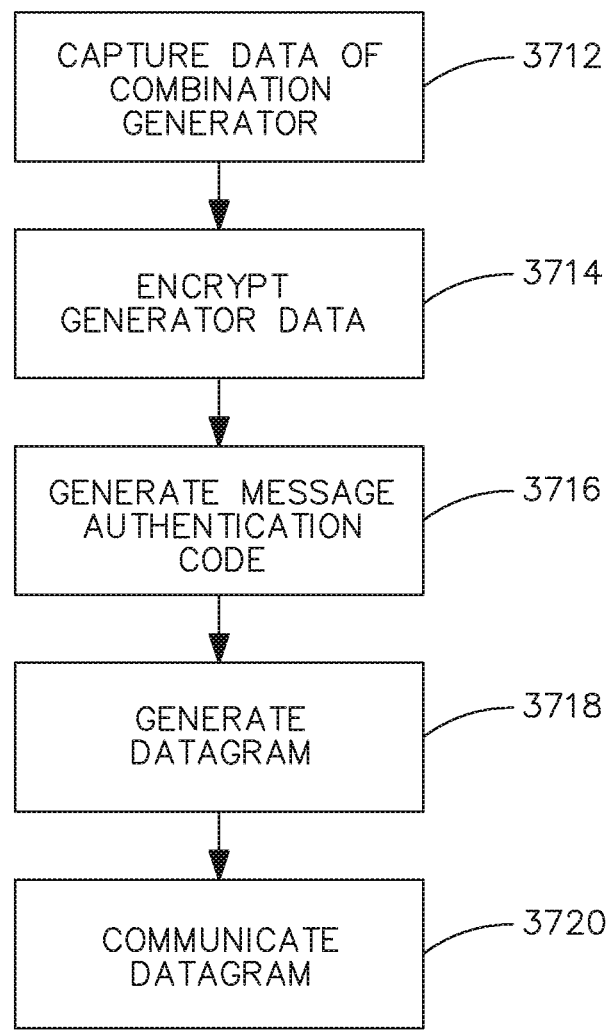
FIG. 23 illustrates a method of capturing data from a combination generator and communicating the captured generator data to a cloud-based system, in accordance with at least one aspect of the present disclosure.

FIG. 23 illustrates various aspects of a method of capturing data from a combination generator 3700 and communicating the captured generator data to a cloud-based system 205. Notably, as discussed herein, the present disclosure should not be limited to processing generator data. As such, the method of FIG. 23 similarly extends to other types of data received from other components coupled to the surgical hub 206 (e.g., imaging module data, smoke evacuator data, suction/irrigation data, device/instrument data). The method comprises (1) capturing 3712 data from a combination generator 3700 of a surgical hub 206 during a surgical procedure, wherein the combination generator 3700 is configured to supply two or more different modes of energy; (2) encrypting 3714 the captured generator data; (3) generating 3716 a MAC based on the captured generator data; (4) generating 3718 a datagram comprising the encrypted generator data, the MAC, a source identifier, and a destination identifier; and (5) communicating 3720 the datagram from the surgical hub 206 to a cloud-based system 205, wherein the datagram allows for the cloud-based system 205 to (i) authenticate integrity of the communicated generator data, (ii) authenticate the surgical hub as a source of the datagram, and (iii) determine a communication path followed by the datagram between the surgical hub 206 and the cloud-based system 205.

More specifically, once the generator data is received at the data communication module 3710 of the combination generator 3700, the generator data can be communicated to the modular communication hub 203 of the surgical hub 206 for subsequent communication to the cloud-based system 205. The data communication module 3710 can communicate the generator data to the modular communication hub 203 serially over a single communication line or in parallel over a plurality of communication lines, and such communication can be performed in real time or near real time. Alternatively, such communication can be performed in batches.

Figure 24:
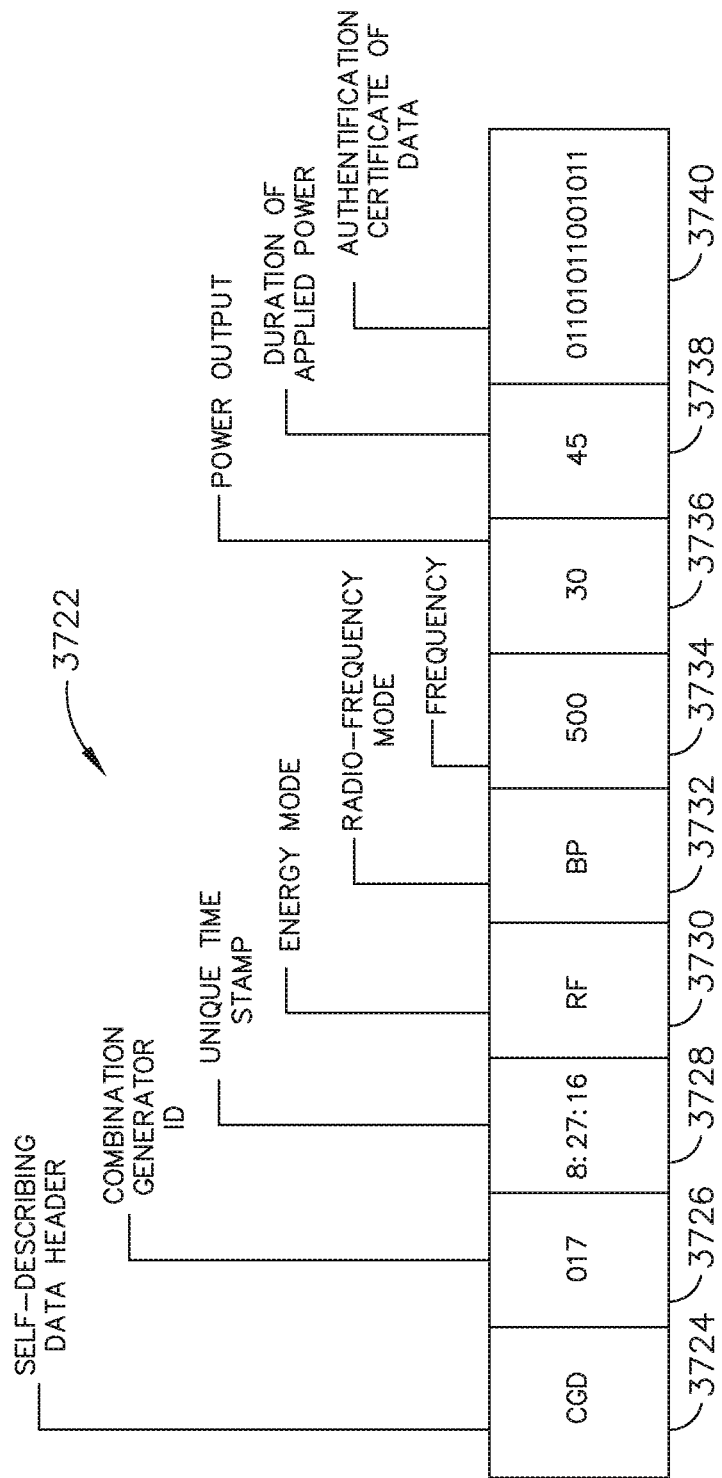
FIG. 24 illustrates a data packet of combination generator data, in accordance with at least one aspect of the present disclosure.

According to various aspects, prior to communicating the generator data to the modular communication hub 203, a component of the combination generator 3700 (e.g., the data communication module 3710) can organize the generator data into data packets. An example of such a data packet is shown in FIG. 24, where the data packet 3722 includes a preamble 3724 or self-describing data header which defines what the data is (e.g., combination generator data—CGD) and fields which indicate where the generator data came from [e.g., combination generator ID number 3726—(e.g., 017), a unique time stamp 3728 (e.g., 08:27:16), the energy mode utilized 3730 (e.g., RF, U, RF+U), the type of radio-frequency energy or radio frequency mode 3732 (e.g., MP, BP, ABP), the frequency 3734 (e.g., 500 Khz), the power output 3736 (e.g., 30 watts), the duration of applied power 3738 (e.g., 45 milliseconds), and an authentication/identification certificate of the data point 3740 (e.g., 01101011001011). The example data packet 3722 may be considered a self-describing data packet, and the combination generator 3700 and other intelligent devices (e.g., the surgical hub 206) can use the self-describing data packets to minimize data size and data-handling resources. Again, as discussed herein, the present disclosure should not be limited to processing generator data received from a combination generator 3700. As such, the data packet 3722 of FIG. 24 similarly extends to other types of data received from other components coupled to the surgical hub 206. In one aspect, the data packet 3722 may comprise data associated with endoscope 239 (e.g., image data) received from a component of the imaging module 238. In another aspect, the data packet 3722 may comprises data associated with an evacuation system (e.g., pressures, particle counts, flow rates, motor speeds) received from a component of the smoke evacuator module 226. In yet another aspect, the data packet 3722 may comprise data associated with a device/instrument (e.g., temperature sensor data, firing data, sealing data) received from a component of the device/instrument 235. In various other aspects, the data packet 3722 may similarly comprise data received from other components coupled to the surgical hub 206 (e.g., suction/irrigation module 228, non-contact sensor module 242)

Additionally, the data communication module 3710 can compress the generator data and/or encrypt the generator data prior to communicating the generator data to the modular communication hub 203. The specific method of compressing and/or encrypting can be the same as or different from the compressing and/or encrypting which may be performed by the surgical hub 206 as described in more detail below.

The modular communication hub 203 can receive the generator data communicated from the combination generator 3700 (e.g., via the data communication module 3710), and the generator data can be subsequently communicated to the cloud-based system 205 (e.g., through the Internet). According to various aspects, the modular communication hub 203 can receive the generator data through a hub/switch 207/209 of the modular communication hub 203 (See FIG. 10), and the generator data can be communicated to the cloud-based system 205 by a router 211 of the modular communication hub 203 (See FIG. 10). The generator data may be communicated in real time, near real time, or in batches to the cloud-based system 205 or may be stored at the surgical hub 206 prior to being communicated to the cloud-based system 205. The generator data can be stored, for example, at the storage array 234 or at the memory 249 of the computer system 210 of the surgical hub 206.

In various aspects, for instances where the generator data received at the modular communication hub 203 is not encrypted, prior to the received generator data being communicated to the cloud-based system 205, the generator data is encrypted to help ensure the confidentiality of the generator data, either while it is being stored at the surgical hub 206 or while it is being transmitted to the cloud 204 using the Internet or other computer networks. According to various aspects, a component of the surgical hub 206 utilizes an encryption algorithm to convert the generator data from a readable version to an encoded version, thereby forming the encrypted generator data. The component of the surgical hub 206 which utilizes/executes the encryption algorithm can be, for example, the processor module 232, the processor 244 of the computer system 210, and/or combinations thereof. The utilized/executed encryption algorithm can be a symmetric encryption algorithm and/or an asymmetric encryption algorithm.

Using a symmetric encryption algorithm, the surgical hub 206 would encrypt the generator data using a shared secret (e.g., private key, passphrase, password). In such an aspect, a recipient of the encrypted generator data (e.g., cloud-based system 205) would then decrypt the encrypted generator data using the same shared secret. In such an aspect, the surgical hub 206 and the recipient would need access to and/or knowledge of the same shared secret. In one aspect, a shared secret can be generated/chosen by the surgical hub 206 and securely delivered (e.g., physically) to the recipient before encrypted communications to the recipient.

Alternatively, using an asymmetric encryption algorithm, the surgical hub 206 would encrypt the generator data using a public key associated with a recipient (e.g., cloud-based system 205). This public key could be received by the surgical hub 206 from a certificate authority that issues a digital certificate certifying the public key as owned by the recipient. The certificate authority can be any entity trusted by the surgical hub 206 and the recipient. In such an aspect, the recipient of the encrypted generator data would then decrypt the encrypted generator data using a private key (i.e., known only by the recipient) paired to the public key used by the surgical hub 206 to encrypt the generator data.

Notably, in such an aspect, the encrypted generator data can only be decrypted using the recipient's private key.

According to aspects of the present disclosure, components (e.g., surgical device/instrument 235, energy device 241, endoscope 239) of the surgical system 202 are associated with unique identifiers, which can be in the form of serial numbers. As such, according to various aspects of the present disclosure, when a component is coupled to a surgical hub 206, the component may establish a shared secret with the surgical hub 206 using the unique identifier of the coupled component as the shared secret. Further, in such an aspect, the component may derive a checksum value by applying a checksum function/algorithm to the unique identifier and/or other data being communicated to the surgical hub 206. Here, the checksum function/algorithm is configured to output a significantly different checksum value if there is a modification to the underlying data.

In one aspect, the component may initially encrypt the unique identifier of a coupled component using a public key associated with the surgical hub (e.g., received by the component from the surgical hub 206 upon/after connection) and communicate the encrypted unique identifier to the surgical hub 206. In other aspects, the component may encrypt the unique identifier and the derived checksum value of a coupled component using a public key associated with the surgical hub 206 and communicate the encrypted unique identifier and linked/associated checksum value to the surgical hub 206.

In yet other aspects, the component may encrypt the unique identifier and a checksum function/algorithm using a public key associated with the surgical hub 206 and communicate the encrypted unique identifier and the checksum function/algorithm to the surgical hub 206. In such aspects, the surgical hub 206 would then decrypt the encrypted unique identifier or the encrypted unique identifier and the linked/associated checksum value or the encrypted unique identifier and the checksum function/algorithm using a private key (i.e., known only by the surgical hub 206) paired to the public key used by the component to encrypt the unique identifier.

Since the encrypted unique identifier can only be decrypted using the surgical hub's 206 private key and the private key is only known by the surgical hub, this is a secure way to communicate a shared secret (e.g., the unique identifier of the coupled component) to the surgical hub 206. Further, in aspects where a checksum value is linked to/associated with the unique identifier, the surgical hub 206 may apply the same checksum function/algorithm to the decrypted unique identifier to generate a validating checksum value. If the validating checksum value matches the decrypted checksum value, the integrity of the decrypted unique identifier is further verified. Further, in such aspects, with a shared secret established, the component can encrypt future communications to the surgical hub 206, and the surgical hub 206 can decrypt the future communications from the component using the shared secret (e.g., the unique identifier of the coupled component). Here, according to various aspects, a checksum value may be derived for and communicated with each communication between the component and the surgical hub 206 (e.g., the checksum value based on the communicated data or at least a designated portion thereof). Here, a checksum function/algorithm (e.g., known by the surgical hub 206 and/or component or communicated when establishing the shared secret between the surgical hub 206 and the component as described above) may be used to generate validating checksum values for comparison with communicated checksum values to further verify the integrity of communicated data in each communication.

Notably, asymmetric encryption algorithms may be complex and may require significant computational resources to execute each communication. As such, establishing the unique identifier of the coupled component as the shared secret is not only quicker (e.g., no need to generate a shared secret using a pseudorandom key generator) but also increases computational efficiency (e.g., enables the execution of faster, less complex symmetric encryption algorithms) for all subsequent communications. In various aspects, this established shared secret may be utilized by the component and surgical hub 206 until the component is decoupled from the surgical hub (e.g., surgical procedure ended).

According to other aspects of the present disclosure, components (e.g., surgical device/instrument 235, energy device 241, endoscope 239) of the surgical system 202 may comprise sub-components (e.g., handle, shaft, end effector, cartridge) each associated with its own unique identifier. As such, according to various aspects of the present disclosure, when a component is coupled to the surgical hub 206, the component may establish a shared secret with the surgical hub 206 using a unique compilation/string (e.g., ordered or random) of the unique identifiers associated with the sub-components that combine to form the coupled component. In one aspect, the component may initially encrypt the unique compilation/string of the coupled component using a public key associated with the surgical hub 206 and communicate the encrypted unique compilation/string to the surgical hub 206. In such an aspect, the surgical hub 206 would then decrypt the encrypted unique compilation/string using a private key (i.e., known only by the surgical hub 206) paired to the public key used by the component to encrypt the unique compilation/string. Since the encrypted unique compilation/string can only be decrypted using the surgical hub's 206 private key and the private key is only known by the surgical hub 206, this is a secure way to communicate a shared secret (e.g., the unique compilation/string of the coupled component) to the surgical hub 206. Further, in such an aspect, with a shared secret established, the component can encrypt future communications to the surgical hub 206, and the surgical hub 206 can decrypt the future communications from the component using the shared secret (e.g., the unique compilation/string of the coupled component).

Again, asymmetric encryption algorithms may be complex and may require significant computational resources to execute each communication. As such, establishing the unique compilation/string of the coupled component (i.e., readily combinable by the component) as the shared secret is not only quicker (e.g., no need to generate a shared secret using a pseudorandom key generator) but also increases computational efficiency (e.g., enables the execution of faster, less complex symmetric encryption algorithms) for all subsequent communications. In various aspects, this established shared secret may be utilized by the component and surgical hub 206 until the component is decoupled from the surgical hub 206 (e.g., surgical procedure ended). Furthermore, in such an aspect, since various sub-components may be reusable (e.g., handle, shaft, end effector) while other sub-components may not be reusable (e.g., end effector, cartridge) each new combination of sub-components that combine to form the coupled component provide a unique compilation/string usable as a shared secret for component communications to the surgical hub 206.

According to further aspects of the present disclosure, components (e.g., surgical device/instrument 235, energy device 241, endoscope 239) of the surgical system 202 are associated with unique identifiers. As such, according to various aspects of the present disclosure, when a component is coupled to the surgical hub 206, the surgical hub 206 may establish a shared secret with a recipient (e.g., cloud-based system 205) using the unique identifier of the coupled component. In one aspect, the surgical hub 206 may initially encrypt the unique identifier of a coupled component using a public key associated with the recipient and communicate the encrypted unique identifier to the recipient. In such an aspect, the recipient would then decrypt the encrypted unique identifier using a private key (i.e., known only by the recipient) paired to the public key used by the surgical hub 206 to encrypt the unique identifier. Since the encrypted unique identifier can only be decrypted using the recipient's private key and the private key is only known by the recipient, this is a secure way to communicate a shared secret (e.g., the unique identifier of the coupled component) to the recipient (e.g., cloud-based system). Further in such an aspect, with a shared secret established, the surgical hub 206 can encrypt future communications to the recipient (e.g., cloud-based system 205), and the recipient can decrypt the future communications from the surgical hub 206 using the shared secret (e.g., the unique identifier of the coupled component).

Notably, asymmetric encryption algorithms may be complex and may require significant computational resources to execute each communication. As such, establishing the unique identifier of the coupled component (i.e., already available to the surgical hub 206) as the shared secret is not only quicker (e.g., no need to generate a shared secret using a pseudorandom key generator) but also increases computational efficiency by, for example, enabling the execution of faster, less complex symmetric encryption algorithms for all subsequent communications. In various aspects, this established shared secret may be utilized by the surgical hub 206 until the component is decoupled from the surgical hub (e.g., surgical procedure ended).

According to yet further aspects of the present disclosure, components (e.g., surgical device/instrument 235, energy device 241, endoscope 239) of the surgical system 202 may comprise sub-components (e.g., handle, shaft, end effector, cartridge) each associated with its own unique identifier. As such, according to various aspects of the present disclosure, when a component is coupled to the surgical hub 206, the surgical hub 206 may establish a shared secret with a recipient (e.g., cloud-based system 205) using a unique compilation/string (e.g., ordered or random) of the unique identifiers associated with the sub-components that combine to form the coupled component.

In one aspect, the surgical hub 206 may initially encrypt the unique compilation/string of the coupled component using a public key associated with the recipient and communicate the encrypted unique compilation/string to the recipient. In such an aspect, the recipient would then decrypt the encrypted unique compilation/string using a private key (i.e., known only by the recipient) paired to the public key used by the surgical hub 206 to encrypt the unique compilation/string. Since the encrypted unique compilation/string can only be decrypted using the recipient's private key and the private key is only known by the recipient, this is a secure way to communicate a shared secret (e.g., the unique compilation/string of the coupled component) to the recipient. With a shared secret established, the surgical hub 206 can encrypt future communications to the recipient (e.g., cloud-based system 205), and the recipient can decrypt the future communications from the surgical hub 206 using the shared secret (e.g., the unique compilation/string of the coupled component). Again, asymmetric encryption algorithms may be complex and may require significant computational resources to execute each communication. As such, establishing the unique compilation/string of the coupled component (i.e., readily combinable by the surgical hub 206) as the shared secret is not only quicker (e.g., no need to generate a shared secret using a pseudorandom key generator) but also increases computational efficiency (e.g., enables the execution of faster, less complex symmetric encryption algorithms) for all subsequent communications.

In various aspects, this established shared secret may be utilized by the surgical hub 206 until the component is decoupled from the surgical hub (e.g., surgical procedure ended). Furthermore, in such an aspect, since various sub-components may be reusable (e.g., handle, shaft, end effector) while other sub-components may not be reusable (e.g., end effector, cartridge) each new combination of sub-components that combine to form the coupled component provide a unique compilation/string usable as a shared secret for surgical hub 206 communications to the recipient.

Figure 25:
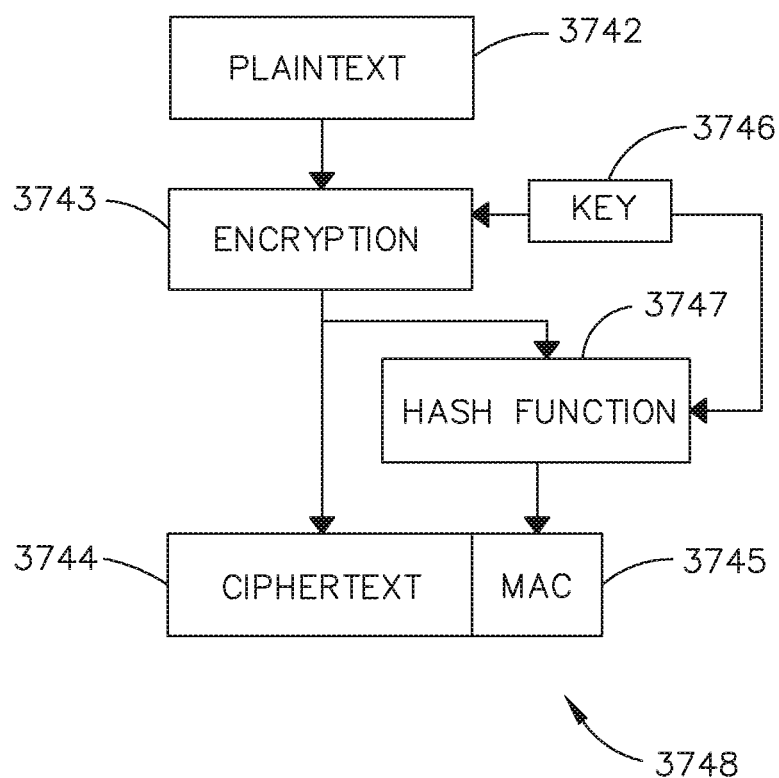
FIG. 25 illustrates an encryption algorithm, in accordance with at least one aspect of the present disclosure.

In some aspects, an encrypt-then-MAC (EtM) approach may be utilized to produce the encrypted generator data. An example of this approach is shown in FIG. 25, where the non-encrypted generator data (i.e., the plaintext 3742, e.g., data packet 3722) is first encrypted 3743 (e.g., via key 3746) to produce a ciphertext 3744 (i.e., the encrypted generator data), then a MAC 3745 is produced based on the resulting ciphertext 3744, the key 3746, and a MAC algorithm (e.g., a hash function 3747). More specifically, the ciphertext 3744 is processed through the MAC algorithm using the key 3746. In one aspect similar to symmetric encryption discussed herein, the key 3746 is a secret key accessible/known by the surgical hub 206 and the recipient (e.g., cloud-based system 205). In such an aspect, the secret key is a shared secret associated with/chosen by the surgical hub 206, a shared secret associated with/chosen by the recipient, or a key selected via a pseudorandom key generator. For this approach, as shown generally at 3748, the encrypted generator data (i.e., the ciphertext 3744) and the MAC 3745 would be communicated together to the cloud-based system 205.

Figure 26:
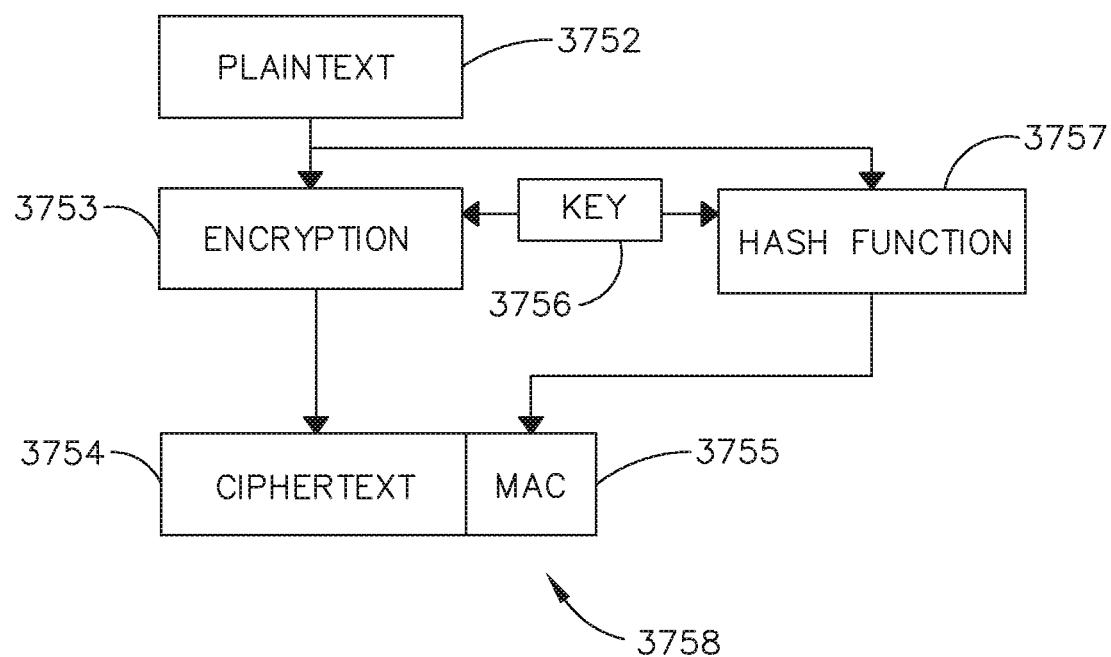
FIG. 26 illustrates another encryption algorithm, in accordance with at least one aspect of the present disclosure.

In other aspects, an encrypt-and-MAC (E&M) approach may be utilized to produce the encrypted generator data. An example of this approach is shown in FIG. 26, where the MAC 3755 is produced based on the non-encrypted generator data (i.e., the plaintext 3752, e.g., data packet 3722), a key 3756, and a MAC algorithm (e.g., a hash function 3757). More specifically, the plaintext 3752 is processed through the MAC algorithm using the key 3756. In one aspect similar to symmetric encryption discussed herein, the key 3756 is a secret key accessible/known by the surgical hub 206 and the recipient (e.g., cloud-based system 205). In such an aspect, the secret key is a shared secret associated with/chosen by the surgical hub 206, a shared secret associated with/chosen by the recipient, or a key selected via a pseudorandom key generator. Further, in such an aspect, the non-encrypted generator data (i.e., the plaintext 3752, e.g., data packet 3722) is encrypted 3753 (e.g., via key 3756) to produce a ciphertext 3754. For this approach, as shown generally at 3758, the MAC 3755 (i.e., produced based on the non-encrypted generator data) and the encrypted generator data (i.e., the ciphertext 3754) would be communicated together to the cloud-based system 205.

Figure 27:
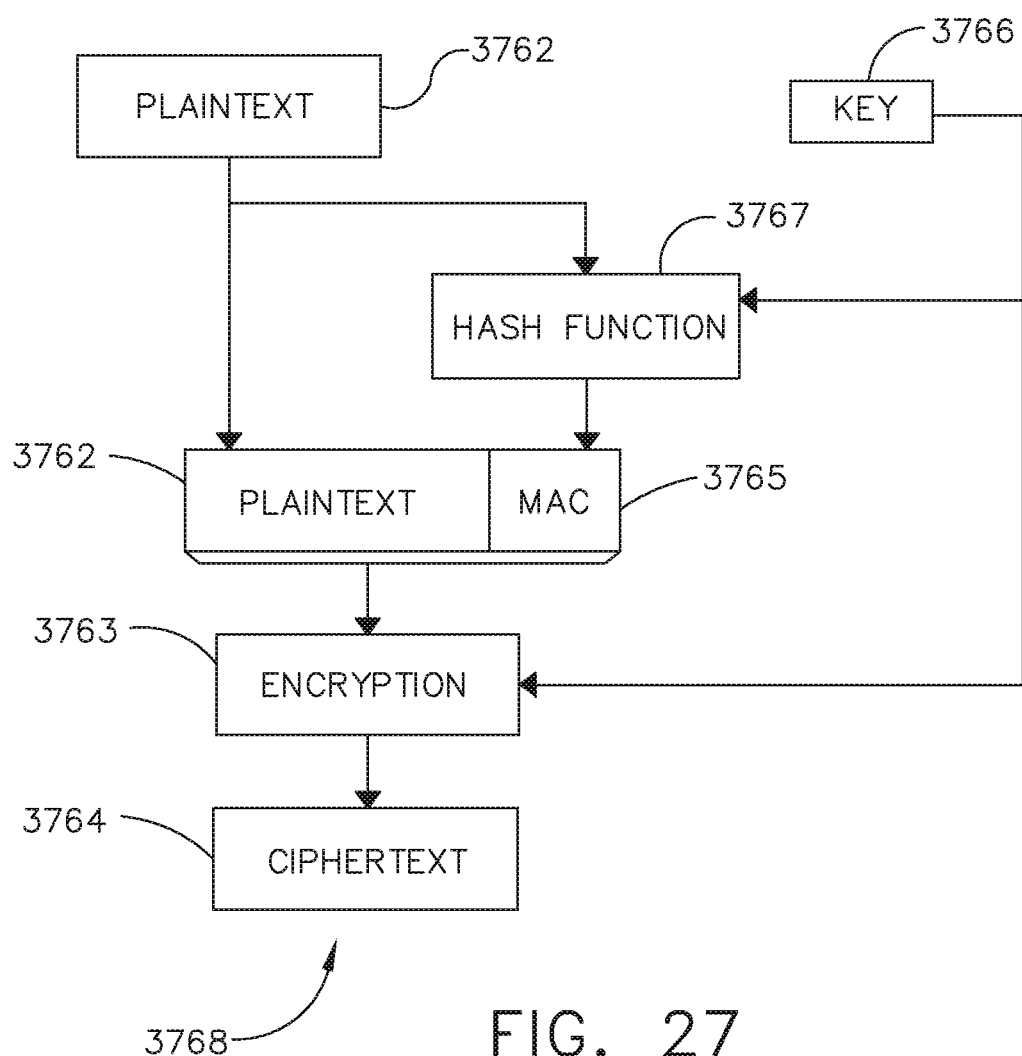
FIG. 27 illustrates yet another encryption algorithm, in accordance with at least one aspect of the present disclosure.

In yet other aspects, a MAC-then-encrypt (MtE) approach may be utilized to produce the encrypted generator data. An example of this approach is shown in FIG. 27, where the MAC 3765 is produced based on the non-encrypted generator data (i.e., the plaintext 3762), a key 3766, and a MAC algorithm (e.g., a hash function 3767). More specifically, the plaintext 3762 is processed through the MAC algorithm using the key 3766. In one aspect similar to symmetric encryption discussed herein, the key 3766 is a secret key accessible/known by the surgical hub 206 and the recipient (e.g., cloud-based system 205). In such an aspect, the secret key is a shared secret associated with/chosen by the surgical hub 206, a shared secret associated with/chosen by the recipient, or a key selected via a pseudorandom key generator. Next, the non-encrypted generator data (i.e., the plaintext 3762) and the MAC 3765 are together encrypted 3763 (e.g., via key 3766) to produce a ciphertext 3764 based on both. For this approach, as shown generally at 3768, the ciphertext 3764 (i.e., which includes the encrypted generator data and the encrypted MAC 3765) would be communicated to the cloud-based system 205.

In alternative aspects, the key used to encrypt the non-encrypted generator data (e.g., FIG. 25 and FIG. 26) or the non-encrypted generator data and the MAC (e.g., FIG. 27) may be different from the key (e.g., keys 3746, 3756, 3766) used to produce the MAC. For example, the key used to encrypt the non-encrypted generator data (e.g., FIG. 25 and FIG. 26) or the non-encrypted generator data and the MAC (e.g., FIG. 27) may be a different shared secret or a public key associated with the recipient.

In lieu of utilizing the MAC to provide for a subsequent assurance of data integrity to the cloud-based system 205, according to other aspects, the surgical hub 206 can utilize a digital signature to allow the cloud-based system 205 to subsequently authenticate integrity of the communicated generator data. For example, the processor module 232 and/or the processor 244 of the computer system 210 can utilize one or more algorithms to generate a digital signature associated with the generator data, and the cloud-based system 205 can utilize an algorithm to determine the authenticity of the received generator data. The algorithms utilized by the processor module 232 and/or the processor 244 of the computer system 210 can include: (1) a key generation algorithm that selects a private key uniformly at random from a set of possible private keys, where the key generation algorithm outputs the private key and a corresponding public key; and (2) a signing algorithm that, given the generator data and a private key, produces a digital signature associated with the generator data. The cloud-based system 205 can utilize a signature verifying algorithm that, given the received generator data, public key, and digital signature, can accept the received generator data as authentic if the digital signature is determined to be authentic or consider the generator data to be compromised or altered if the digital signature is not determined to be authentic.

According to other aspects of the present disclosure, the surgical hub 206 can utilize a commercial authentication program (e.g., Secure Hash Algorithm, SHA-2 comprising SHA-256) to provide for a subsequent assurance of data integrity of the communicated generator data to the cloud-based system 205.

After the generator data has been encrypted (e.g., via EtM, E&M, MtE), a component of the surgical hub 206 can communicate the encrypted generator data to the cloud-based system 205. The component of the surgical hub 206 which communicates the encrypted generator data to the cloud-based system 205 can be, for example, the processor module 232, a hub/switch 207/209 of the modular communication hub 203, the router 211 of the modular communication hub 203, the communication module 247 of the computer system 210, etc.

Figure 28:
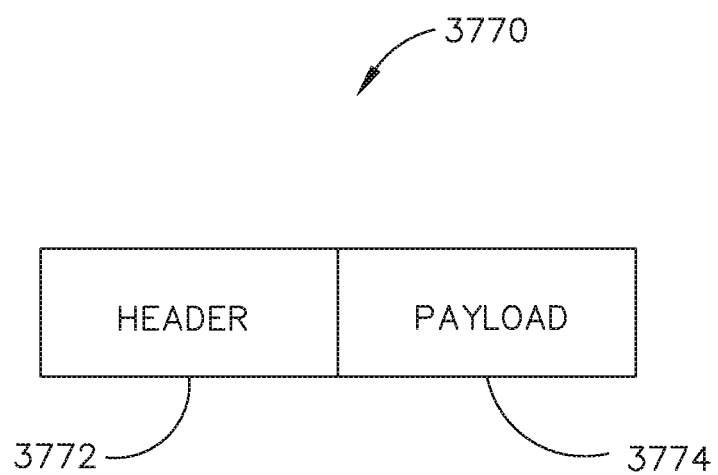
FIG. 28 illustrates a high-level representation of a datagram, in accordance with at least one aspect of the present disclosure.
Figure 29:
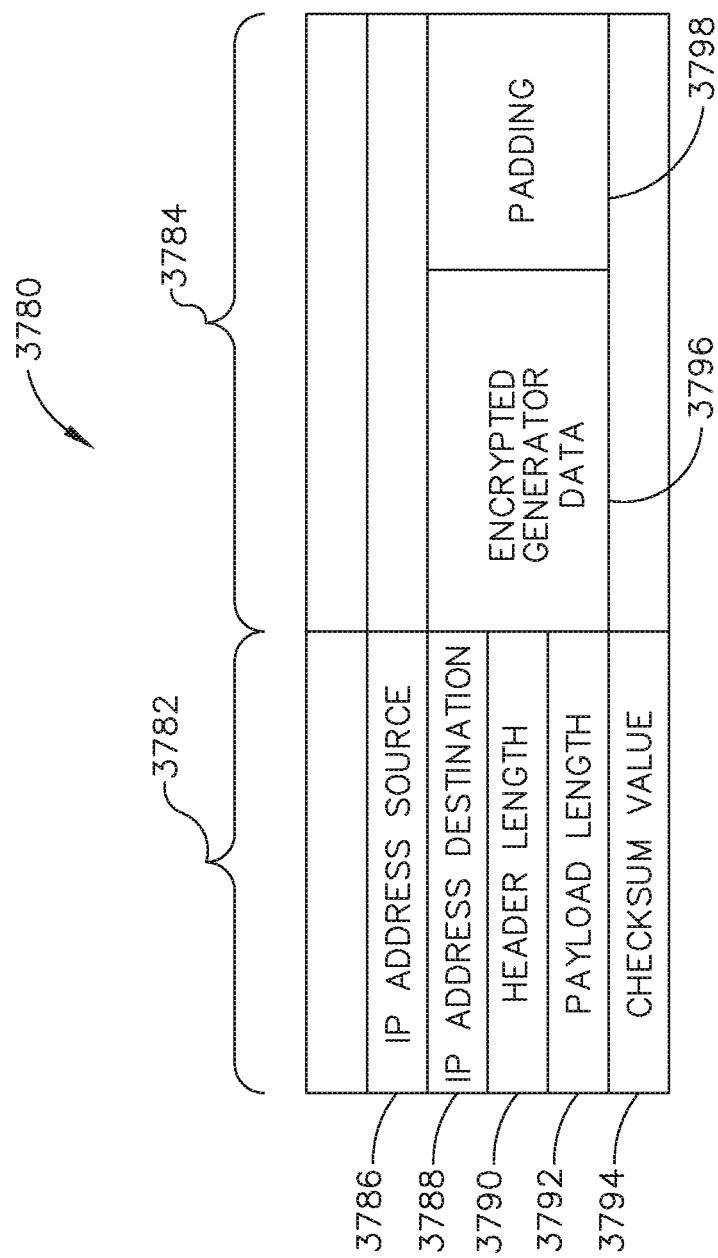
FIG. 29 illustrates a more detailed representation of the datagram of FIG. 28, in accordance with at least one aspect of the present disclosure.

According to various aspects, the communication of the encrypted generator data through the Internet can follow an IP which: (1) defines datagrams that encapsulate the encrypted generator data to be delivered and/or (2) defines addressing methods that are used to label the datagram with source and destination information. A high-level representation of an example datagram 3770 is shown in FIG. 28, where the datagram 3770 includes a header 3772 and a payload 3774, and in other aspects also may include a trailer (not shown). A more detailed representation of an example datagram 3780 is shown in FIG. 29, where the header 3782 can include fields for information such as, for example, the IP address of the source 3786 which is sending the datagram (e.g., the router 211 of the modular communication hub 203), the IP address of the destination 3788 which is to receive the datagram (e.g., the cloud 204 and/or the remote server 213 associated with the cloud-based system 205), a type of service designation (not shown), a header length 3790, a payload length 3792, and a checksum value 3794. In such an aspect, the surgical hub 206 may further apply a checksum function/algorithm to the non-encrypted generator data (i.e., the plaintext 3742, e.g., data packet 3722) or at least a portion of the non-encrypted generator data (e.g., combination generator ID 3726) to derive the checksum value 3794. Here, the checksum function/algorithm is configured to output a significantly different checksum value if there is any modification (e.g., even a slight change) to the underlying data (e.g., generator data). After decryption of the encrypted generator data by its recipient (e.g., cloud-based system 205), the recipient may apply the same checksum function/algorithm to the decrypted generator data to generate a validating checksum value. If the validating checksum value matches the checksum value 3794 (i.e., stored in the header 3782 of the received datagram 3780), the integrity of the received generator data is further verified. The payload 3784 may include the encrypted generator data 3796 and can also include padding 3798 if the encrypted generator data 3796 is less than a specified payload length. Notably, the communicated encrypted generator data 3796 may comprise a MAC as discussed in FIGS. 25, 26, and 27 above (e.g., references 3748, 3758, and 3768, respectively). In some aspects, the header 3782 can further include a specific path the datagram is to follow when the datagram is communicated from the surgical hub 206 to the cloud-based system 205 (e.g., from IP address of the source, to IP address of at least one intermediate network component (e.g., specified routers, specified servers), to IP address of the destination).

According to various aspects, prior to the generator data being encrypted, the generator data can be time-stamped (if not already time-stamped by the combination generator 3700) and/or the generator data can be compressed (if not already compressed by the combination generator 3700). Time-stamping allows for the cloud-based system 205 to correlate the generator data with other data (e.g., stripped patient data) which may be communicated to the cloud-based system 205. The compression allows for a smaller representation of the generator data to be subsequently encrypted and communicated to the cloud-based system 205. For the compression, a component of the surgical hub 206 can utilize a compression algorithm to convert a representation of the generator data to a smaller representation of the generator data, thereby allowing for a more efficient and economical encryption of the generator data (e.g., less data to encrypt utilizes less processing resources) and a more efficient and economical communication of the encrypted generator data (e.g., smaller representations of the generator data within the payload of the datagrams (e.g., FIGS. 28 and 29) allow for more generator data to be included in a given datagram, for more generator data to be communicated within a given time period, and/or for generator data to be communicated with fewer communication resources). The component of the surgical hub 206 which utilizes/executes the compression algorithm can be, for example, the processor module 232, the processor 244 of the computer system, and/or combinations thereof. The utilized/executed compression algorithm can be a lossless compression algorithm or a lossy compression algorithm.

Once the generator data and the MAC for a given datagram has been received at the cloud-based system 205 (e.g., FIG. 25, reference 3748; FIG. 26, reference 3758; and FIG. 27, reference 3768), the cloud-based system 205 can decrypt the encrypted generator data from the payload of the communicated datagram to realize the communicated generator data.

In one aspect, referring back to FIG. 25, the recipient (e.g., cloud-based system 205) may, similar to the surgical hub 206, process the ciphertext 3744 through the same MAC algorithm using the same known/accessible secret key to produce an authenticating MAC. If the received MAC 3745 matches this authenticating MAC, the recipient (e.g., cloud-based system 205) may safely assume that the ciphertext 3744 has not been altered and is from the surgical hub 206. The recipient (e.g., cloud-based system 205) may then decrypt the ciphertext 3744 (e.g., via key 3746) to realize the plaintext 3742 (e.g., data packet comprising generator data).

In another aspect, referring back to FIG. 26, the recipient (e.g., cloud-based system 205) may decrypt the ciphertext 3754 (e.g., via key 3756) to realize the plaintext 3752 (e.g., data packet comprising generator data). Next, similar to the surgical hub 206, the recipient (e.g., cloud-based system 205) may process the plaintext 3752 through the same MAC algorithm using the same known/accessible secret key to produce an authenticating MAC. If the received MAC 3755 matches this authenticating MAC, the recipient (e.g., cloud-based system 205) may safely assume that the plaintext 3752 has not been altered and is from the surgical hub 206.

In yet another aspect, referring back to FIG. 27, the recipient (e.g., cloud-based system 205) may decrypt the ciphertext 3764 (e.g., via key 3766) to realize the plaintext 3762 (e.g., data packet comprising generator data) and the MAC 3765. Next, similar to the surgical hub 206, the recipient (e.g., cloud-based system 205) may process the plaintext 3762 through the same MAC algorithm using the same known/accessible secret key to produce an authenticating MAC. If the received MAC 3765 matches this authenticating MAC, the recipient (e.g., cloud-based system 205) may safely assume that the plaintext 3762 has not been altered and is from the surgical hub 206.

In alternative aspects, the key used to encrypt the non-encrypted generator data (e.g., FIG. 25 and FIG. 26) or the non-encrypted generator data and the MAC (e.g., FIG. 27) may be different from the key (e.g., keys 3746, 3756, 3766) used to produce the MAC. For example, the key used to encrypt the non-encrypted generator data (e.g., FIG. 25 and FIG. 26) or the non-encrypted generator data and the MAC (e.g., FIG. 27) may be a different shared secret or a public key associated with the recipient. In such aspects, referring to FIG. 25, the recipient (e.g., cloud-based system 205) may, after verifying the authenticating MAC via key 3746 (described above), then decrypt the ciphertext 3744 (e.g., via the different shared secret or private key associated with the recipient) to realize the plaintext 3742 (e.g., data packet comprising generator data). In such aspects, referring to FIG. 26, the recipient may decrypt the ciphertext 3754 (e.g., via the different shared secret or private key associated with the recipient) to realize the plaintext 3752 (e.g., data packet comprising generator data), then verify the authenticating MAC via key 3756 (described above). In such aspects, referring to FIG. 27, the recipient may decrypt the ciphertext 3764 (e.g., via the different shared secret or private key associated with the recipient) to realize the plaintext 3762 (e.g., data packet comprising generator data) and the MAC 3765, then verify the authenticating MAC via key 3766 (described above).

In sum, referring to FIGS. 25-27, if an authenticating MAC, as determined/calculated by the cloud-based system 205, is the same as the MAC which was received with the datagram, the cloud-based system 205 can have confidence that the received generator data is authentic (i.e., it is the same as the generator data which was communicated by the surgical hub 206) and that the data integrity of the communicated generator data has not been compromised or altered. As described above, the recipient may further apply the plaintext 3742, 3752, 3762, or at least a portion thereof to the same checksum function/algorithm (i.e., used by the surgical hub 206) to generate a validating checksum value to further verify the integrity of the generator data based on the checksum value stored in the header of the communicated datagram.

Additionally, based on the decrypted datagram, the IP address of the source (e.g., FIG. 29, reference 3786) which originally communicated the datagram to the cloud-based system 205 can be determined from the header of the communicated datagram. If the determined source is a recognized source, the cloud-based system 205 can have confidence that the generator data originated from a trusted source, thereby providing source authentication and even more assurance of the data integrity of the generator data. Furthermore, since each router the datagram passed through in route to the cloud-based system 205 includes its IP address with its forwarded communication, the cloud-based system 205 is able to trace back the path followed by the datagram and identify each router which handled the datagram. The ability to identify the respective routers can be helpful in instances where the content of the datagram received at the cloud-based system 205 is not the same as the content of the datagram as originally communicated by the surgical hub 206. For aspects where the communication path was pre-specified and included in the header of the communicated datagram, the ability to identify the respective routers can allow for path validation and provide additional confidence of the authenticity of the received generator data.

Furthermore, according to various aspects, after authenticating the received generator data, the cloud-based system 205 can communicate a message (e.g., a handshake or similar message) to the surgical hub 206 via the Internet or another communication network, confirming/guaranteeing that the datagram communicated from the surgical hub 206 was received intact by the cloud-based system 205, thereby effectively closing the loop for that particular datagram.

Aspects of the above-described communication method, and/or variations thereof, can also be employed to communicate data other than generator data to the cloud-based system 205 and/or to communicate generator data and/or other data from the surgical hub 206 to systems and/or devices other than the cloud-based system 205. For example, according to various aspects, the generator data and/or other data can be communicated from the surgical hub 206 to a hand-held surgical device/instrument (e.g., wireless device/instrument 235), to a robotic interface of a surgical device/instrument (e.g., robot hub 222) and/or to other servers, including servers (e.g., similar to server 213) associated with other cloud-based systems (e.g., similar to cloud-based system 205) in accordance with the above-described communication method. For example, in certain instances, an EEPROM chip of a given surgical instrument can initially be provided with merely an electronic chip device ID. Upon connection of the given surgical instrument to the combination generator 3700, data can be downloaded from the cloud-based system 205 to the surgical hub 206 and subsequently to the EEPROM of the surgical instrument in accordance with the above-described communication method.

In addition to communicating generator data to the cloud-based system 205, the surgical hub 206 can also utilize the above-described method of communication, and/or variations thereof, to communicate data other than generator data to the cloud-based system 205. For example, the surgical hub 206 can also communicate other information associated with the surgical procedure to the cloud-based system 205. Such other information can include, for example, the type of surgical procedure being performed, the name of the facility where the surgical procedure is being performed, the location of the facility where the surgical procedure is being performed, an identification of the operating room within the facility where the surgical procedure is being performed, the name of the surgeon performing the surgical procedure, the age of the patient, and data associated with the condition of the patient (e.g., blood pressure, heart rate, current medications). According to various aspects, such other information may be stripped of all information which could identify the specific surgery, the patient, or the surgeon, so that the information is essentially anonymized for further processing and analysis by the cloud-based system 205. In other words, the stripped data is not correlated to a specific surgery, patient, or surgeon. The stripped information can be communicated to the cloud-based system 205 either together with or distinct from the communicated generator data.

For instances where the stripped/other data is to be communicated apart from the generator data, the stripped/other data can be time-stamped, compressed, and/or encrypted in a manner identical to or different from that described above regarding the generator data, and the surgical hub 206 may be programmed/configured to generate a datagram which includes the encrypted stripped/other information in lieu of the encrypted generator data. The datagram can then be communicated from the surgical hub 206 through the Internet to the cloud-based system 205 following an IP which: (1) defines datagrams that encapsulate the encrypted stripped/other data to be delivered, and (2) defines addressing methods that are used to label the datagram with source and destination information.

Figure 30:
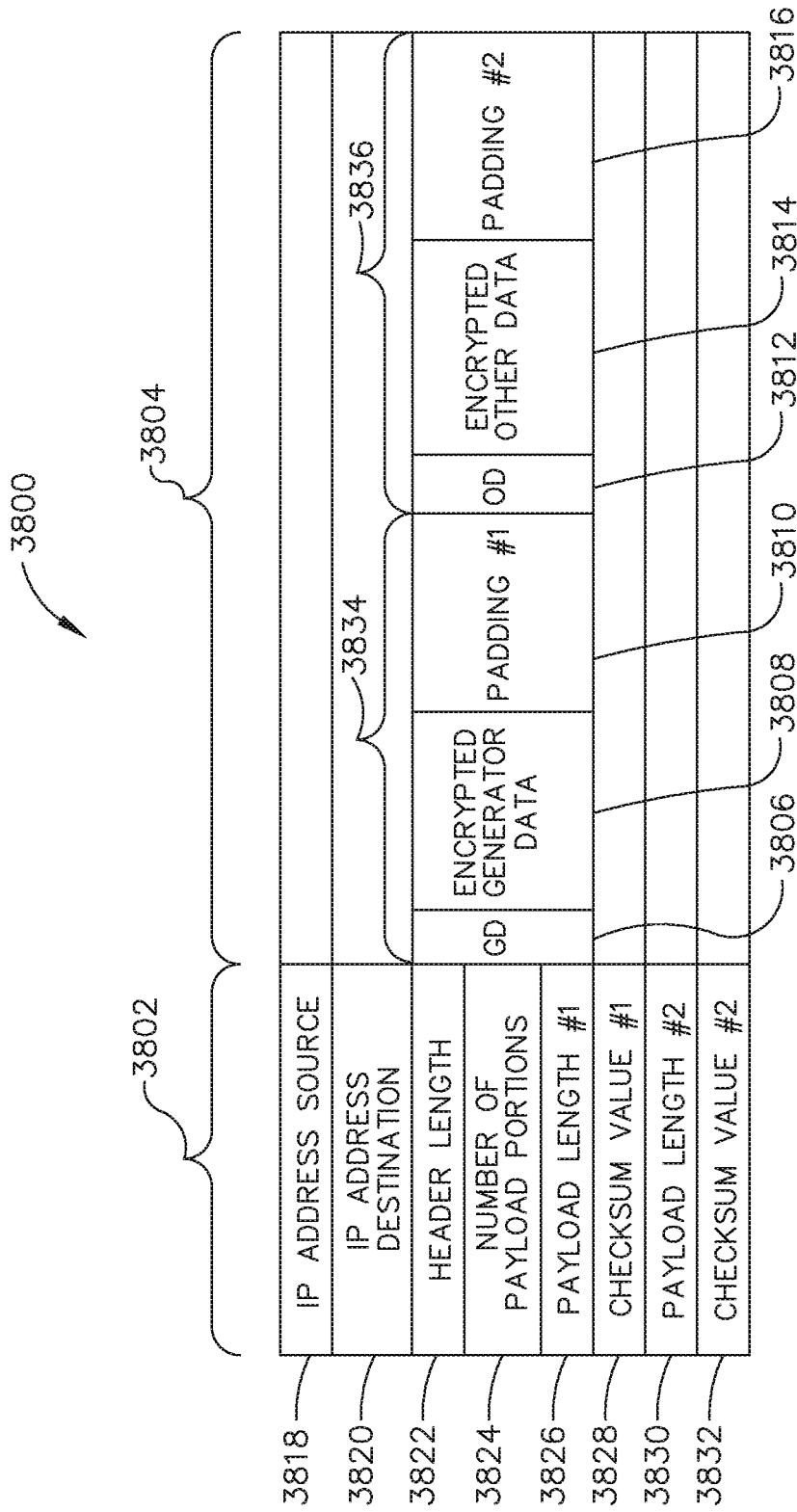
FIG. 30 illustrates another representation of the datagram of FIG. 28, in accordance with at least one aspect of the present disclosure.

For instances where the stripped/other information is to be communicated with the generator data, the stripped/other data can be time-stamped, compressed, and/or encrypted in a manner identical to or different from that described above regarding the generator data, and the surgical hub 206 may be programmed/configured to generate a datagram which includes both the encrypted generator data and the encrypted stripped/other information. An example of such a datagram in shown in FIG. 30, where the payload 3804 of the datagram 3800 is divided into two or more distinct payload data portions (e.g., one for the encrypted generator data 3834, one for the encrypted stripped/other information 3836), with each portion having an identifying bit (e.g., generator data (GD) 3806, other data (OD) 3812), the associated encrypted data 3808, 3814, and the associated padding 3810, 3816, if needed, respectively. Further, as shown in FIG. 30, the header 3802 may be the same as (e.g., IP address source 3818, IP address destination 3820, header length 3822) or different from the header 3782 described with reference to the datagram 3780 shown in FIG. 29. For example, the header 3802 may be different in that the header 3802 further includes a field designating the number of payload data portions 3824 (e.g., 2) included in the payload 3804 of the datagram 3800. The header 3802 can also be different in that it can include fields designating the payload length 3826, 3830 and the checksum value 3828, 2832 for each payload data portion 3834, 3836, respectively. Although only two payload data portions are shown in FIG. 30, it will be appreciated that the payload 3804 of the datagram 3800 may include any quantity/number of payload data portions (e.g., 1, 2, 3, 4, 5), where each payload data portion includes data associated with a different aspect of the surgical procedure. The datagram 3800 can then be communicated from the surgical hub 206 through the Internet to the cloud-based system 205 following an IP which: (1) defines datagrams that encapsulate the encrypted generator data and the encrypted stripped/other data to be delivered, and (2) defines addressing methods that are used to label the datagram with source and destination information.

As set forth above, it is an unfortunate reality that the outcomes of all surgical procedures are not always optimal and/or successful. For instances where a failure event is detected and/or identified, a variation of the above-described communication methods can be utilized to isolate surgical data which is associated with the failure event (e.g., failure event surgical data) from surgical data which is not associated with the failure event (e.g., non-failure event surgical data) and communicate the surgical data which is associated with the failure event (e.g., failure event data) from the surgical hub 206 to the cloud-based system 205 on a prioritized basis for analysis. According to one aspect of the present disclosure, failure event surgical data is communicated from the surgical hub 206 to the cloud-based system 205 on a prioritized basis relative to non-failure event surgical data.

Figure 31:
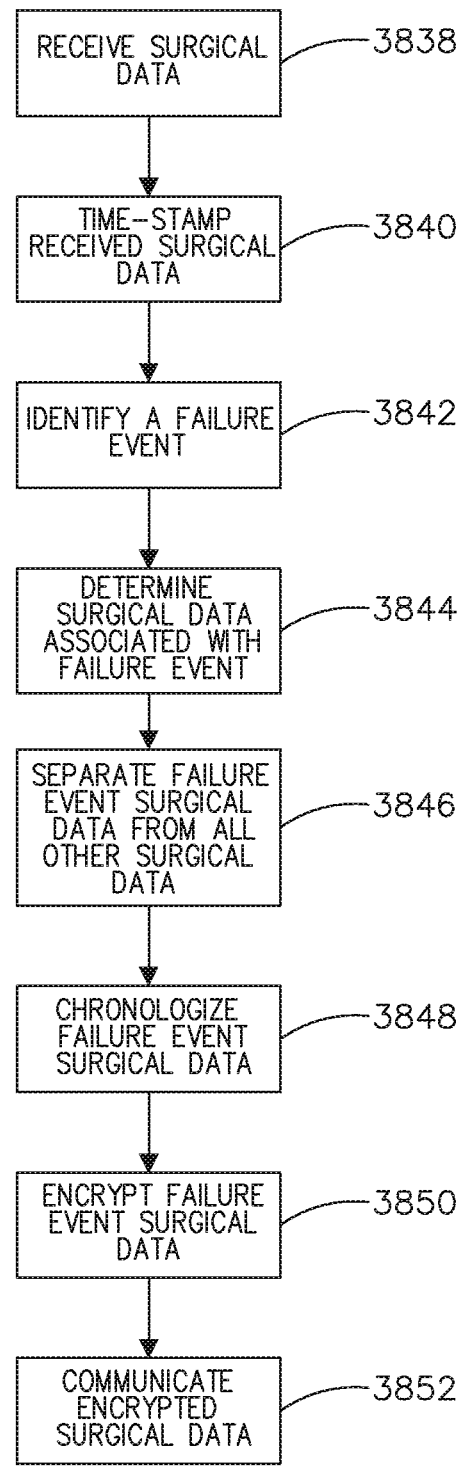
FIG. 31 illustrates a method of identifying surgical data associated with a failure event and communicating the identified surgical data to a cloud-based system on a prioritized basis, in accordance with at least one aspect of the present disclosure.

FIG. 31 illustrates various aspects of a system-implemented method of identifying surgical data associated with a failure event (e.g., failure event surgical data) and communicating the identified surgical data to a cloud-based system 205 on a prioritized basis. The method comprises (1) receiving 3838 surgical data at a surgical hub 206, wherein the surgical data is associated with a surgical procedure; (2) time-stamping 3840 the surgical data; (3) identifying 3842 a failure event associated with the surgical procedure; (4) determining 3844 which of the surgical data is associated with the failure event (e.g., failure event surgical data); (5) separating 3846 the surgical data associated with the failure event from all other surgical data (e.g., non-failure event surgical data) received at the surgical hub 206; (6) chronologizing 3848 the surgical data associated with the failure event; (7) encrypting 3850 the surgical data associated with the failure event; and (8) communicating 3852 the encrypted surgical data to a cloud-based system 205 on a prioritized basis.

More specifically, various surgical data can be captured during a surgical procedure and the captured surgical data, as well as other surgical data associated with the surgical procedure, can be communicated to the surgical hub 206.

The surgical data can include, for example, data associated with a surgical device/instrument (e.g., FIG. 9, surgical device/instrument 235) utilized during the surgery, data associated with the patient, data associated with the facility where the surgical procedure was performed, and data associated with the surgeon. Either prior to or subsequent to the surgical data being communicated to and received by the surgical hub 206, the surgical data can be time-stamped and/or stripped of all information which could identify the specific surgery, the patient, or the surgeon, so that the information is essentially anonymized for further processing and analysis by the cloud-based system 205.

Once a failure event has been detected and/or identified (e.g., which can be either during or after the surgical procedure), the surgical hub 206 can determine which of the surgical data is associated with the failure event (e.g., failure event surgical data) and which of the surgical data is not associated with the surgical event (e.g., non-failure event surgical data). According to one aspect of the present disclosure, a failure event can include, for example, a detection of one or more misfired staples during a stapling portion of a surgical procedure. For example, in one aspect, referring to FIG. 9, an endoscope 239 may take snapshots while a surgical device/instrument 235 comprising an end effector including a staple cartridge performs a stapling portion of a surgical procedure. In such an aspect, an imaging module 238 may compare the snapshots to stored images and/or images downloaded from the cloud-based system 205 that convey correctly fired staples to detect a misfired staple and/or evidence of a misfired staple (e.g., a leak). In another aspect, the imaging module 238 may analyze the snapshots themselves to detect a misfired staple and/or evidence of a misfired staple. In one alternative aspect, the surgical hub 206 may communicate the snapshots to the cloud-based system 205, and a component of the cloud-based system 205 may perform the various imaging module functions described above to detect a misfired staple and/or evidence of a misfired staple and to report the detection to the surgical hub 206. According to another aspect of the present disclosure, a failure event can include a detection of a tissue temperature which is below the expected temperature during a tissue-sealing portion of a surgical procedure and/or a visual indication of excessive bleeding or oozing following a surgical procedure (e.g., FIG. 9, via endoscope 239). For example, in one aspect, referring to FIG. 9, the surgical device/instrument 235 may comprise an end effector, including a temperature sensor and the surgical hub 206, and/or the cloud-based system may compare at least one temperature detected by the temperature sensor (e.g., during a tissue-sealing portion of a surgical procedure) to a stored temperature and/or a range of temperatures expected and/or associated with that surgical procedure to detect an inadequate/low sealing temperature. In another aspect, an endoscope 239 may take snapshots during a surgical procedure. In such an aspect, an imaging module 238 may compare the snapshots to stored images and/or images downloaded from the cloud-based system 205 that convey tissue correctly sealed at expected temperatures to detect evidence of an improper/insufficient sealing temperature (e.g., charring, oozing/bleeding). Further, in such an aspect, the imaging module 238 may analyze the snapshots themselves to detect evidence of an improper/insufficient sealing temperature (e.g., charring, oozing/bleeding). In one alternative aspect, the surgical hub 206 may communicate the snapshots to the cloud-based system 205, and a component of the cloud-based system 205 may perform the various imaging module functions described above to detect evidence of an improper/insufficient sealing temperature and to report the detection to the surgical hub 206. According to the various aspects described above, in response to the detected and/or identified failure event, the surgical hub 206 may download a program from the cloud-based system 205 for execution by the surgical device/instrument 235 that corrects the detected issue (i.e., program that alters surgical device/instrument parameters to prevent misfired staples, program that alters surgical device/instrument parameters to ensure correct sealing temperature).

In some aspects, a failure event is deemed to cover a certain time period, and all surgical data associated with that certain time period can be deemed to be associated with the failure event.

After the surgical data associated with the failure event has been identified, the identified surgical data (e.g., failure event surgical data) can be separated or isolated from all of the other surgical data associated with the surgical procedure (e.g., non-failure event surgical data). The separation can be realized, for example, by tagging or flagging the identified surgical data, by storing the identified surgical data apart from all of the other surgical data associated with the surgical procedure, or by storing only the other surgical data while continuing to process the identified surgical data for subsequent prioritized communication to the cloud-based system 205. According to various aspects, the tagging or flagging of the identified surgical data can occur during the communication process when the datagram is generated as described in more detail below.

The time-stamping of all of the surgical data (e.g., either before or after the surgical data is received at the surgical hub) can be utilized by a component of the surgical hub 206 to chronologize the identified surgical data associated with the failure event. The component of the surgical hub 206 which utilizes the time-stamping to chronologize the identified surgical data can be, for example, the processor module 232, the processor 244 of the computer system 210, and/or combinations thereof. By chronologizing the identified surgical data, the cloud-based system 205 and/or other interested parties can subsequently better understand the conditions which were present leading up to the occurrence of the failure event and possibly pinpoint the exact cause of the failure event, thereby providing the knowledge to potentially mitigate a similar failure event from occurring during a similar surgical procedure performed at a future date.

Once the identified surgical data has been chronologized, the chronologized surgical data may be encrypted in a manner similar to that described above with respect to the encryption of the generator data. Thus, the identified surgical data can be encrypted to help ensure the confidentiality of the identified surgical data, either while it is being stored at the surgical hub 206 or while it is being transmitted to the cloud-based system 205 using the Internet or other computer networks. According to various aspects, a component of the surgical hub 206 utilizes an encryption algorithm to convert the identified surgical data from a readable version to an encoded version, thereby forming the encrypted surgical data associated with the failure event (e.g., FIGS. 25-27). The component of the surgical hub which utilizes the encryption algorithm can be, for example, the processor module 232, the processor 244 of the computer system 210, and/or combinations thereof. The utilized encryption algorithm can be a symmetric encryption algorithm or an asymmetric encryption algorithm.

Figure 32:
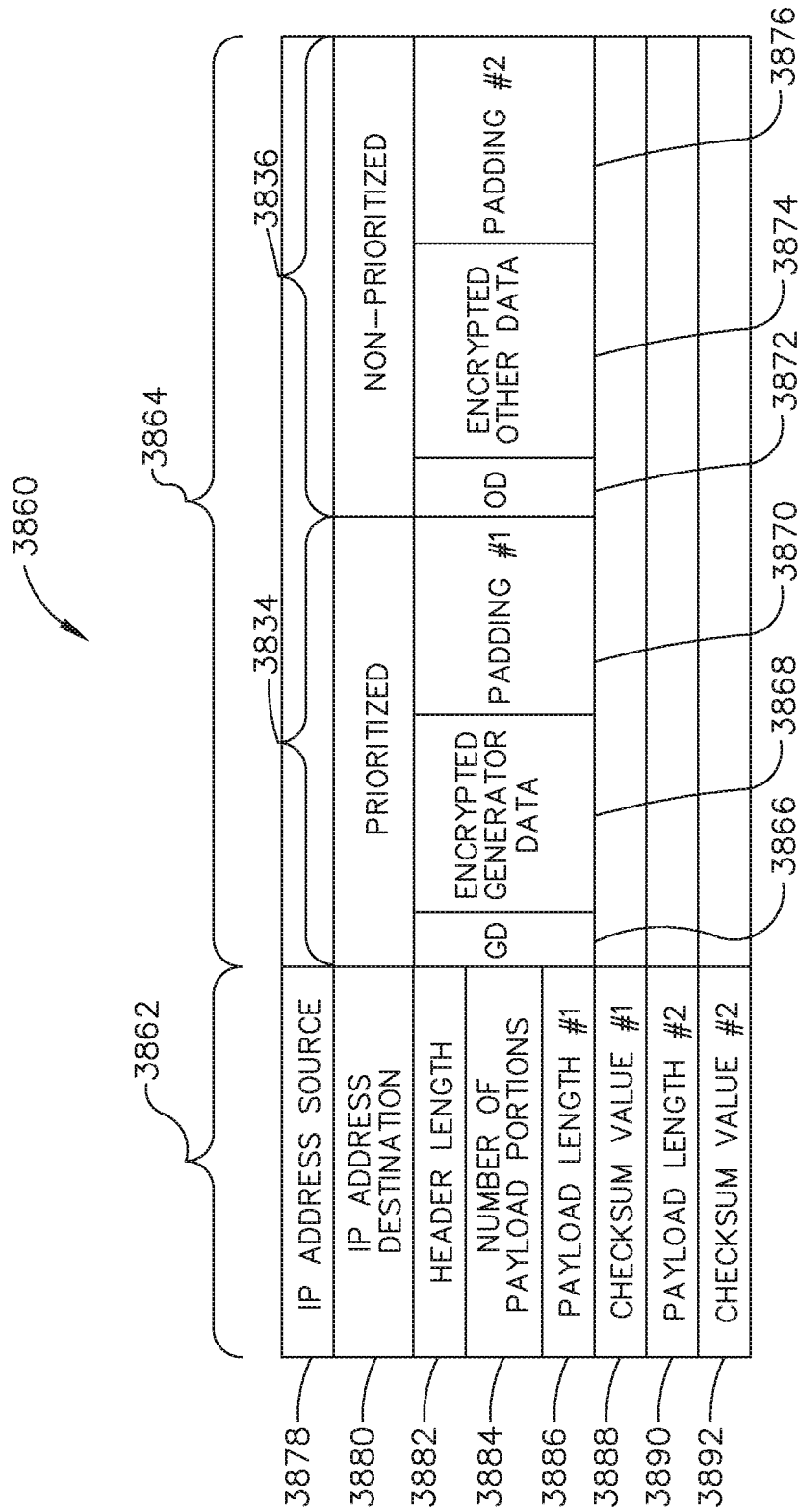
FIG. 32 illustrates yet another representation of the datagram of FIG. 28, in accordance with at least one aspect of the present disclosure.

After the identified surgical data has been encrypted, a component of the surgical hub can communicate the encrypted surgical data associated with the failure event (e.g., encrypted failure event surgical data) to the cloud-based system 205. The component of the surgical hub which communicates the encrypted surgical data to the cloud-based system 205 can be, for example, the processor module 232, a hub/switch 207/209 of the modular communication hub 203, the router 211 of the modular communication hub 203, or the communication module 247 of the computer system 210. According to various aspects, the communication of the encrypted surgical data (e.g., encrypted failure event surgical data) through the Internet can follow an IP which: (1) defines datagrams that encapsulate the encrypted surgical data to be delivered, and (2) defines addressing methods that are used to label the datagram with source and destination information. The datagram can be similar to the datagram shown in FIG. 29 or the datagram shown in FIG. 30, but can be different in that either the header or the payload of the datagram can include a field which includes a flag or a tag which identifies the encrypted surgical data (e.g., encrypted failure event surgical data) as being prioritized relative to other non-prioritized surgical data (e.g., encrypted non-failure event surgical data). An example of such a datagram is shown in FIG. 32, where the payload 3864 of the datagram 3860 includes a field which indicates (e.g., a prioritized designation 3834) that the payload 3864 includes prioritized surgical data (e.g., combination generator data 3868). According to various aspects, the payload 3864 of the datagram 3860 can also include non-flagged/non-tagged/non-prioritized surgical data 3836 (e.g., other surgical data 3874) as shown in FIG. 32.

According to various aspects, prior to the identified surgical data (e.g., failure event surgical data) being encrypted, the identified surgical data can be compressed (if not already compressed by the source(s) of the relevant surgical data). The compression allows for a smaller representation of the surgical data associated with the failure event to be subsequently encrypted and communicated to the cloud-based system 205. For the compression, a component of the surgical hub 206 can utilize a compression algorithm to convert a representation of the identified surgical data to a smaller representation of the identified surgical data, thereby allowing for a more efficient and economical encryption of the identified surgical data (less data to encrypt utilizes less processing resources) and a more efficient and economical communication of the encrypted surgical data (smaller representations of the surgical data within the payload of the datagrams allow for more identified surgical data to be included in a given datagram, for more identified surgical data to be communicated within a given time period, and/or for identified surgical data to be communicated with fewer communication resources). The component of the surgical hub 206 which utilizes the compression algorithm can be, for example, the processor module 232, the processor 244 of the computer system 210, and/or combinations thereof. The utilized compression algorithm can be a lossless compression algorithm or a lossy compression algorithm.

In instances where other non-prioritized surgical data (e.g., non-failure event surgical data) is to be communicated with prioritized surgical data (e.g., failure event surgical data), the other non-prioritized surgical data can be time-stamped, compressed, and/or encrypted in a manner identical to or different from that described above regarding the surgical data identified as associated with a failure event (e.g., failure event surgical data), and the surgical hub 206 may be programmed/configured to generate a datagram which includes both the encrypted prioritized surgical data (e.g., encrypted failure event surgical data) and the encrypted other non-prioritized surgical data (e.g., encrypted non-failure event surgical data). For example, in light of FIG. 32, the payload 3864 of the datagram 3860 may be divided into two or more distinct payload data portions (e.g., one for the prioritized surgical data 3834, one for the non-prioritized surgical data 3836), with each portion having an identifying bit (e.g., generator data (GD) 3866, other data (OD) 3872), the associated encrypted data (e.g., encrypted prioritized surgical data 3868, encrypted non-prioritized surgical data 3874), and the associated padding 3870, 3876, if needed, respectively. Further, similar to FIG. 30, the header 3862 may be the same as (e.g., IP address source 3878, IP address destination 3880, header length 3882) or different from the header 3782 described with reference to the datagram 3780 shown in FIG. 29. For example, the header 3862 may be different in that the header 3862 further includes a field designating the number of payload data portions 3884 (e.g., 2) included in the payload 3864 of the datagram 3860. The header 3862 can also be different in that it can include fields designating the payload length 3886, 3890 and the checksum value 3888, 2892 for each payload data portion 3834, 3836, respectively. Although only two payload data portions are shown in FIG. 32, it will be appreciated that the payload 3864 of the datagram 3860 may include any quantity/number of payload data portions (e.g., 1, 2, 3, 4, 5), where each payload data portion includes data associated with a different aspect of the surgical procedure. The datagram 3860 can then be communicated from the surgical hub 206 through the Internet to the cloud-based system 205 following an IP which: (1) defines datagrams that encapsulate the encrypted generator data and the encrypted stripped/other data to be delivered, and (2) defines addressing methods that are used to label the datagram with source and destination information.

In some aspects, once a failure event associated with a surgical procedure has been identified, the surgical hub 206 and/or the cloud-based system 205 can subsequently flag or tag a surgical device/instrument 235 which was utilized during the surgical procedure for inoperability and/or removal. For example, in one aspect, information (e.g., serial number, ID) associated with the surgical device/instrument 235 and stored at the surgical hub 206 and/or the cloud-based system 205 can be utilized to effectively block the surgical device/instrument 235 from being used again (e.g., blacklisted). In another aspect, information (e.g., serial number, ID) associated with the surgical device/instrument can initiate the printing of a shipping slip and shipping instructions for returning the surgical device/instrument 235 back to a manufacturer or other designated party so that a thorough analysis/inspection of the surgical device/instrument 235 can be performed (e.g., to determine the cause of the failure). According to various aspects described herein, once the cause of a failure is determined (e.g., via the surgical hub 206 and/or the cloud-based system 205), the surgical hub 206 may download a program from the cloud-based system 205 for execution by the surgical device/instrument 235 that corrects the determined cause of the failure (i.e., program that alters surgical device/instrument parameters to prevent the failure from occurring again).

According to some aspects, the surgical hub 206 and/or the cloud-based system 205 can also provide/display a reminder (e.g., via hub display 215 and/or surgical device/instrument display 237) to administrators, staff, and/or other personnel to physically remove the surgical device/instrument 235 from the operating room (e.g., if detected as still present in the operating room) and/or to send the surgical device/instrument 235 to the manufacturer or the other designated party. In one aspect, the reminder may be set up to be provided/displayed periodically until an administrator can remove the flag or tag of the surgical device/instrument 235 from the surgical hub 206 and/or the cloud-based system 205. According to various aspects, an administrator may remove the flag or tag once the administrator can confirm (e.g., system tracking of the surgical device/instrument 235 via its serial number/ID) that the surgical device/instrument 235 has been received by the manufacturer or the other designated party. By using the above-described method to flag and/or track surgical data associated with a failure event, a closed loop control of the surgical data associated with the failure event and/or with a surgical device/instrument 235 can be realized. Additionally, in view of the above, it will be appreciated that the surgical hub 206 can be utilized to effectively manage the utilization (or non-utilization) of surgical devices/instruments 235 which have or potentially could be utilized during a surgical procedure.

In various aspects of the present disclosure, the surgical hub 206 and/or cloud-based system 205 may want to control which components (e.g., surgical device/instrument 235, energy device 241) are being utilized in its interactive surgical system 100/200 to perform surgical procedures (e.g., to minimize future failure events, to avoid the use of unauthorized or knock-off components).

As such, in various aspects of the present disclosure, since an interactive surgical system 100 may comprise a plurality of surgical hubs 106, a cloud-based system 105 and/or each surgical hub 106 of the interactive surgical system 100 may want to track component-surgical hub combinations utilized over time. In one aspect, upon/after a component (See FIG. 9, e.g., surgical device/instrument 235, energy device 241) is connected to/used with a particular surgical hub 106 (e.g., surgical device/instrument 235 wired/wirelessly connected to the particular surgical hub 106, energy device 241 connected to the particular surgical hub 106 via generator module 240), the particular surgical hub 106 may communicate a record/block of that connection/use (e.g., linking respective unique identifiers of the connected devices) to the cloud-based system 105 and/or to the other surgical hubs 106 in the interactive surgical system 100. For example, upon/after the connection/use of an energy device 241, a particular surgical hub 106 may communicate a record/block (e.g., linking a unique identifier of the energy device 241 to a unique identifier of a generator module 240 to a unique identifier of the particular surgical hub 106) to the cloud-based system 105 and/or other surgical hubs 106 in the interactive surgical system 100. In such an aspect, if this is the first time the component (e.g., energy device) is connected to/used with a surgical hub 106 in the interactive surgical system 100, the cloud-based system 105 and/or each surgical hub 106 of the interactive surgical system 100 may store the record/block as a genesis record/block. In such an aspect, the genesis record/block stored at the cloud-based system 105 and/or each surgical hub 106 may comprise a time stamp. However, in such an aspect, if this is not the first time the component (e.g., energy device 241) has been connected to/used with a surgical hub 106 in the interactive surgical system 100, the cloud-based system 105 and/or each surgical hub 106 of the interactive surgical system may store the record/block as a new record/block in a chain of record/blocks associated with the component. In such an aspect, the new record/block may comprise a cryptographic hash of the most recently communicated record/block stored at the cloud-based system 105 and/or each surgical hub 106, the communicated linkage data, and a time stamp. In such an aspect, each cryptographic hash links each new record/block (e.g., each use of the component) to its prior record/block to form a chain confirming the integrity of each prior record/block(s) back to an original genesis record/block (e.g., first use of the component). According to such an aspect, this blockchain of records/blocks may be developed at the cloud-based system 105 and/or each surgical hub 106 of the interactive surgical system 100 to permanently and verifiably tie usage of a particular component to one or more than one surgical hub 106 in the interactive surgical system 100 over time. Here, according to another aspect, this approach may be similarly applied to sub-components (e.g., handle, shaft, end effector, cartridge) of a component when/after the component is connected to/used with a particular surgical hub 106 of an interactive surgical system 100.

According to various aspects of the present disclosure, the cloud-based system 105 and/or each surgical hub 106 may utilize such records/blocks to trace usage of a particular component and/or a sub-component back to its initial usage in the interactive surgical system 100. For example, if a particular component (e.g., surgical device/instrument 235) is flagged/tagged as related to a failure event, the cloud-based system 105 and/or a surgical hub 106 may analyze such records/blocks to determine whether past usage of that component and/or a sub-component of that component contributed to or caused the failure event (e.g., overused). In one example, the cloud-based system 105 may determine that a sub-component (e.g., end effector) of that component may actually be contributing/causing the failure event and then tag/flag that component for inoperability and/or removal based on the determination.

According to another aspect, the cloud-based system 205 and/or surgical hub 206 may control which components (e.g., surgical device/instrument 235, energy device 241) are being utilized in an interactive surgical system 200 to perform surgical procedures by authenticating the component and/or its supplier/manufacturer. In one aspect, the supplier/manufacturer of a component may associate a serial number and a source ID with the component. In such an aspect, the supplier/manufacturer may create/generate a private key for the serial number, encrypt the serial number with the private key, and store the encrypted serial number and the source ID on an electronic chip (e.g., memory) in the component prior to shipment to a surgical site. Here, upon/after connection of the component to a surgical hub 206, the surgical hub 206 may read the encrypted serial number and the source ID from the electronic chip. In response, the surgical hub 206 may send a message (i.e., comprising the encrypted serial number) to a server of the supplier/manufacturer associated with the source ID (e.g., directly or via the cloud-based system 205). In such an aspect, the surgical hub 206 may encrypt the message using a public key associated with that supplier/manufacturer. In response, the surgical hub 206 may receive a message (i.e., comprising the private key the supplier/manufacturer generated for/associated with that encrypted serial number) from the supplier/manufacturer server (e.g., directly or via the cloud-based system 205). In such an aspect, the supplier/manufacturer server may encrypt the message using a public key associated with the surgical hub 206. Further, in such an aspect, the surgical hub 206 may then decrypt the message (e.g., using a private key paired to the public key used to encrypt the message) to reveal the private key associated with the encrypted serial number. The surgical hub 206 may then decrypt the encrypted serial number, using that private key, to reveal the serial number. Further, in such an aspect, the surgical hub 206 may then compare the decrypted serial number to a comprehensive list of authorized serial numbers (e.g., stored at the surgical hub 206 and/or the cloud-based system and/or downloaded from the cloud-based system, e.g., received separately from the supplier/manufacturer) and permit use of the connected component if the decrypted serial number matches an authorized serial number. Initially, such a process permits the surgical hub 206 to authenticate the supplier/manufacturer. In particular, the surgical hub 206 encrypted the message comprising the encrypted serial number using a public key associated with the supplier/manufacturer. As such, receiving a response message (i.e., comprising the private key) authenticates the supplier/manufacturer to the surgical hub 206 (i.e., otherwise the supplier/manufacturer would not have access to the private key paired to the public key used by the surgical hub 206 to encrypt the message, and the supplier/manufacturer would not have been able to associate the encrypted serial number received in the message to its already generated private key). Furthermore, such a process permits the surgical hub 206 to authenticate the connected component/device itself. In particular, the supplier/manufacturer (e.g., just authenticated) encrypted the serial number of the component using the delivered private key. Upon secure receipt of the private key, the surgical hub 206 is able to decrypt the encrypted serial number (i.e., read from the connected component), which authenticates the component and/or its association with the supplier/manufacturer (i.e., only that private key as received from that supplier/manufacturer would decrypt the encrypted serial number). Nonetheless, the surgical hub 206 further verifies the component as authentic (e.g., compares the decrypted serial number to a comprehensive list of authorized serial numbers received separately from the supplier/manufacturer). Notably, such aspects as described above can alternatively be performed by the cloud-based system 205 and/or a combination of the cloud-based system 205 and the surgical hub 206 to control which components (e.g., surgical device/instrument 235, energy device 241) are being utilized in an interactive surgical system 200 (e.g., to perform surgical procedures) by authenticating the component and/or its supplier/manufacturer. In one aspect, such described approaches may prevent the use of knock-off component(s) within the interactive surgical system 200 and ensure the safety and well-being of surgical patients.

According to another aspect, the electronic chip of a component (e.g., surgical device/instrument 235, energy device 241) may store (e.g., in memory) data associated with usage of that component (i.e., usage data, e.g., number of uses with a limited use device, number of uses remaining, firing algorithms executed, designation as a single-use component). In such an aspect, the surgical hub 206 and/or the cloud-based system 205, upon/after connection of the component to the interactive surgical system, may read such usage data from the memory of a component and write back at least a portion of that usage data for storage (e.g., in memory 249) at the surgical hub 206 and/or for storage at the cloud-based system 205 (e.g., individually and/or under a blockchain approach discussed herein). According to such an aspect, the surgical hub 206 and/or the cloud-based system 205, upon/after a subsequent connection of that component to the interactive surgical system, may again read such usage data and compare that usage to previously stored usage data. Here, if a discrepancy exists or if a predetermined/authorized usage has been met, the surgical hub 206 and/or the cloud-based system 205 may prevent use of that component (e.g., blacklisted, rendered inoperable, flagged for removal) on the interactive surgical system 200. In various aspects, such an approach prevents bypass of the encryption chip systems. If the component's electronic chip/memory has been tampered with (e.g., memory reset, number of uses altered, firing algorithms altered, single-use device designated as a multi-use device), a discrepancy will exist, and the component's use will be controlled/prevented.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is incorporated herein by reference in its entirety.

Surgical Hub Coordination of Device Pairing in an Operating Room

One of the functions of the surgical hub 106 is to pair (also referred to herein as "connect" or "couple") with other components of the surgical system 102 to control, gather information from, or coordinate interactions between the components of the surgical system 102. Since the operating rooms of a hospital are likely in close physical proximity to one another, a surgical hub 106 of a surgical system 102 may unknowingly pair with components of a surgical system 102 in a neighboring operating room, which would significantly interfere with the functions of the surgical hub 106. For example, the surgical hub 106 may unintentionally activate a surgical instrument in a different operating room or record information from a different ongoing surgical procedure in a neighboring operating room.

Aspects of the present disclosure present a solution, wherein a surgical hub 106 only pairs with detected devices of the surgical system 102 that are located within the bounds of its operating room.

Furthermore, the surgical hub 106 relies on its knowledge of the location of other components of the surgical system 102 within its operating room in making decisions about, for example, which surgical instruments should be paired with one another or activated. A change in the position of the surgical hub 106 or another component of the surgical system 102 can be problematic.

Aspects of the present disclosure further present a solution wherein the surgical hub 106 is configured to reevaluate or redetermine the bounds of its operating room upon detecting that the surgical hub 106 has been moved. Aspects of the present disclosure further present a solution wherein the surgical hub 106 is configured to redetermine the bounds of its operating room upon detection of a potential device of the surgical system 102, which can be an indication that the surgical hub 106 has been moved.

In various aspects, a surgical hub 106 is used with a surgical system 102 in a surgical procedure performed in an operating room. The surgical hub 106 comprises a control circuit configured to determine the bounds of the operating room, determine devices of the surgical system 102 located within the bounds of the operating room, and pair the surgical hub 106 with the devices of the surgical system 102 located within the bounds of the operating room.

In one aspect, the control circuit is configured to determine the bounds of the operating room after activation of the surgical hub 106. In one aspect, the surgical hub 106 includes a communication circuit configured to detect and pair with the devices of the surgical system located within the bounds of the operating room. In one aspect, the control circuit is configured to redetermine the bounds of the operating room after a potential device of the surgical system 102 is detected. In one aspect, the control circuit is configured to periodically determine the bounds of the operating room.

In one aspect, the surgical hub 106 comprises an operating room mapping circuit that includes a plurality of non-contact sensors configured to measure the bounds of the operating room.

In various aspects, the surgical hub 106 includes a processor and a memory coupled to the processor. The memory stores instructions executable by the processor to pair the surgical hub with devices of the surgical system 102 located within the bounds of the operating room, as described above. In various aspects, the present disclosure provides a non-transitory computer-readable medium storing computer-readable instructions which, when executed, cause a machine to pair the surgical hub 106 with devices of the surgical system 102 located within the bounds of the operating room, as described above.

Figure 35:
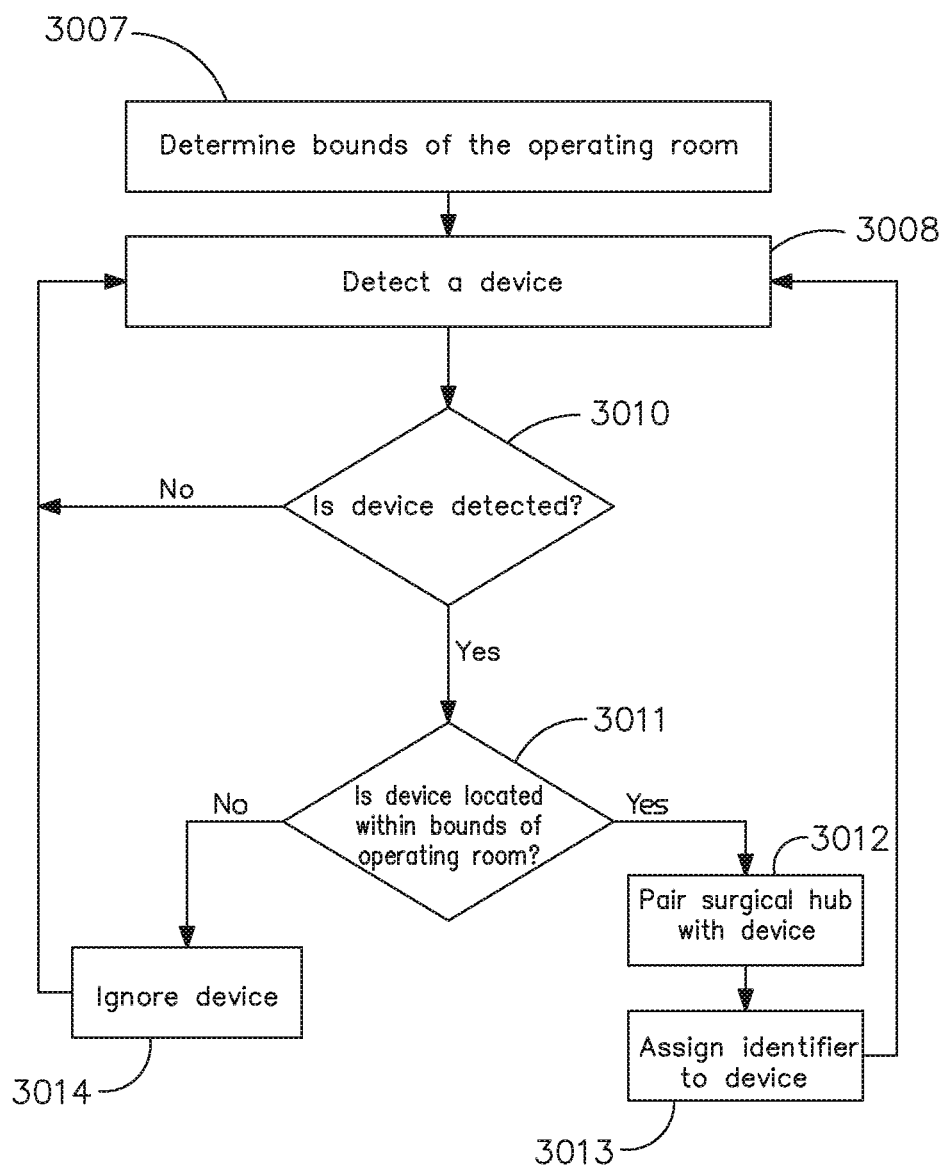
FIG. 35 is a logic flow diagram of a process depicting a control program or a logic configuration for surgical hub pairing with surgical devices of a surgical system that are located within the bounds of an operating room, in accordance with at least one aspect of the present disclosure.
Figure 36:
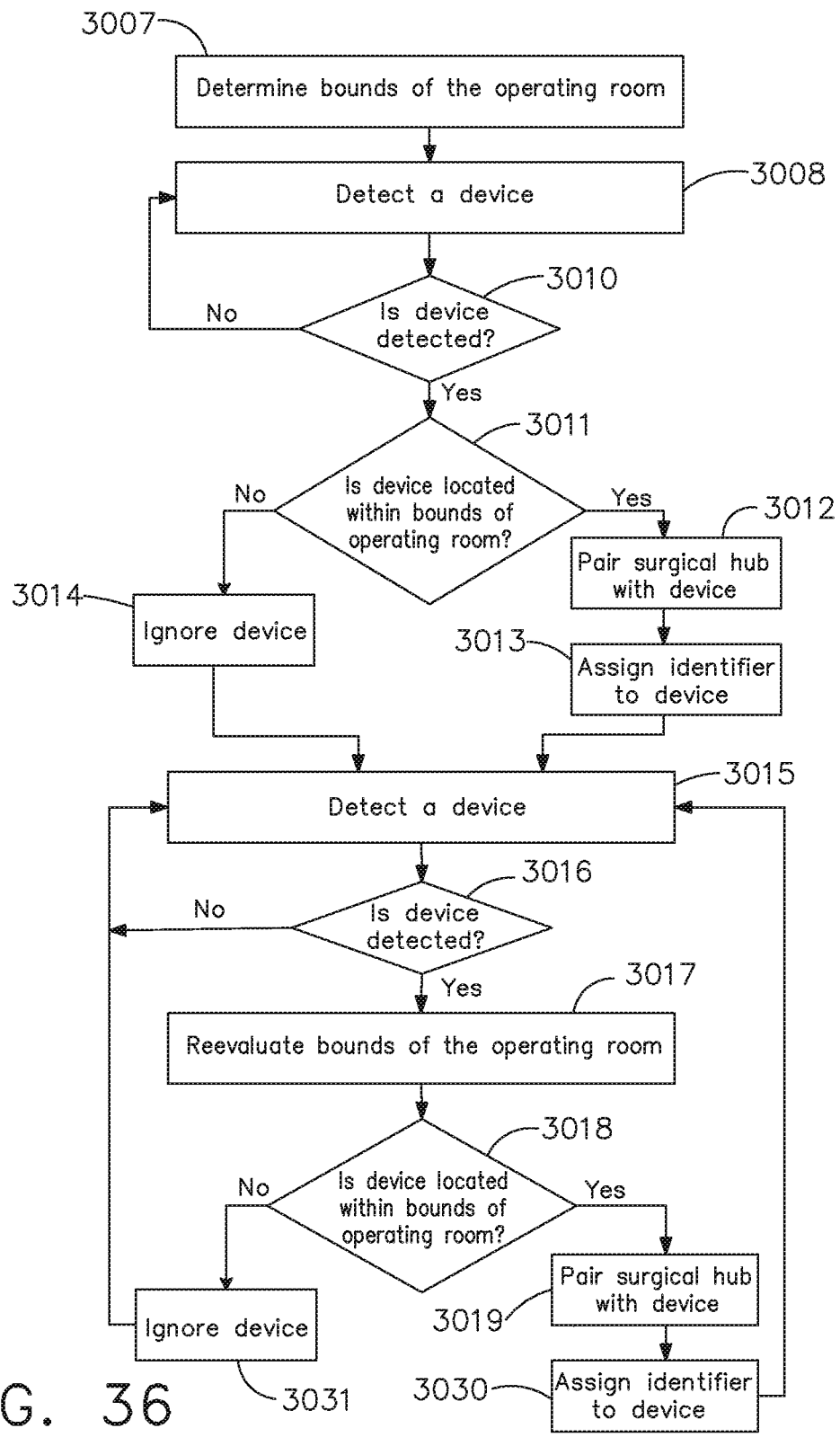
FIG. 36 is a logic flow diagram of a process depicting a control program or a logic configuration for selectively forming and severing connections between devices of a surgical system, in accordance with at least one aspect of the present disclosure.

FIGS. 35 and 36 are logic flow diagrams of processes depicting control programs or logic configurations for pairing the surgical hub 106 with devices of the surgical system 102 located within the bounds of the operating room, as described above.

The surgical hub 106 performs a wide range of functions that requires short- and long-range communication, such as assisting in a surgical procedure, coordinating between devices of the surgical system 102, and gathering and transmitting data to the cloud 104. To properly perform its functions, the surgical hub 106 is equipped with a communication module 130 capable of short-range communication with other devices of the surgical system 102. The communication module 130 is also capable of long-range communication with the cloud 104.

The surgical hub 106 is also equipped with an operating-room mapping module 133 which is capable of identifying the bounds of an operating room, and identifying devices of the surgical system 102 within the operating room. The surgical hub 106 is configured to identify the bounds of an operating room, and only pair with or connect to potential devices of the surgical system 102 that are detected within the operating room.

In one aspect, the pairing comprises establishing a communication link or pathway. In another aspect, the pairing comprises establishing a control link or pathway.

Figure 37:
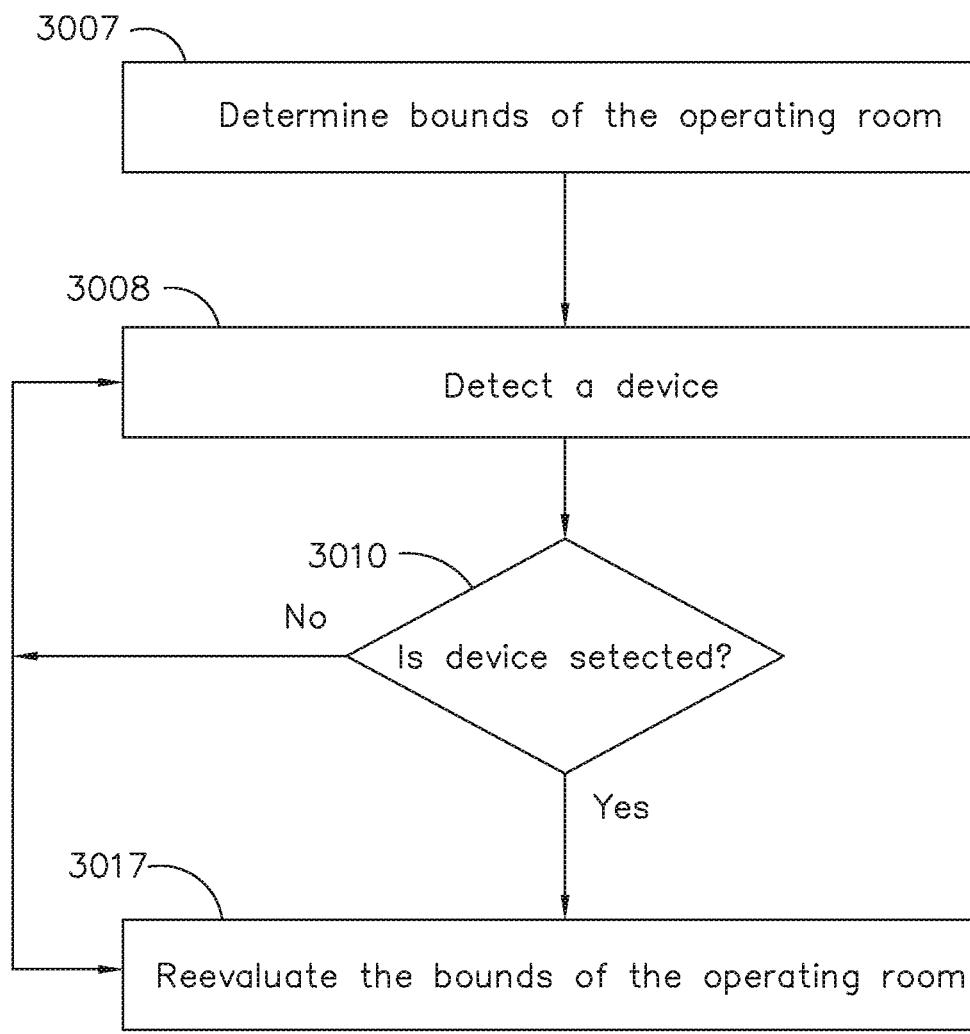
FIG. 37 is a logic flow diagram of a process depicting a control program or a logic configuration for selectively reevaluating the bounds of an operating room after detecting a new device, in accordance with at least one aspect of the present disclosure.
Figure 38:
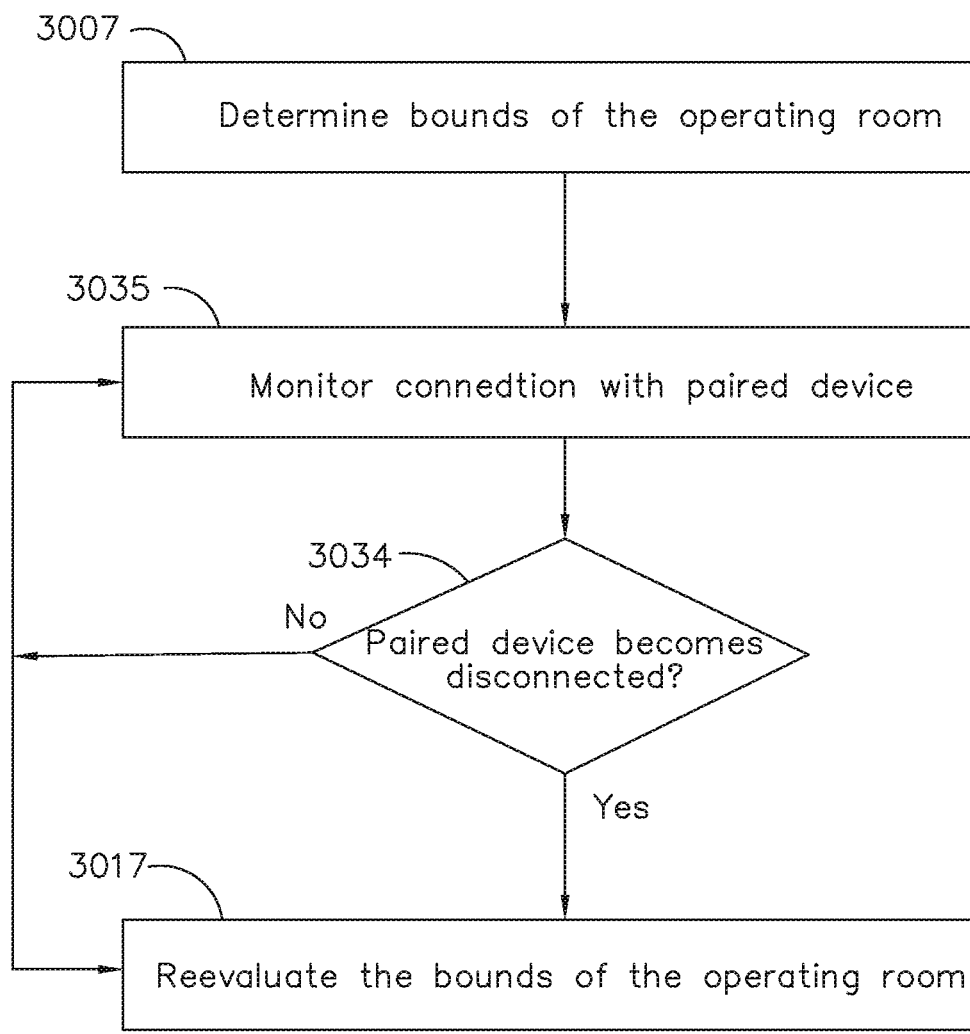
FIG. 38 is a logic flow diagram of a process depicting a control program or a logic configuration for selectively reevaluating the bounds of an operating room after disconnection of a paired device, in accordance with at least one aspect of the present disclosure.
Figure 39:
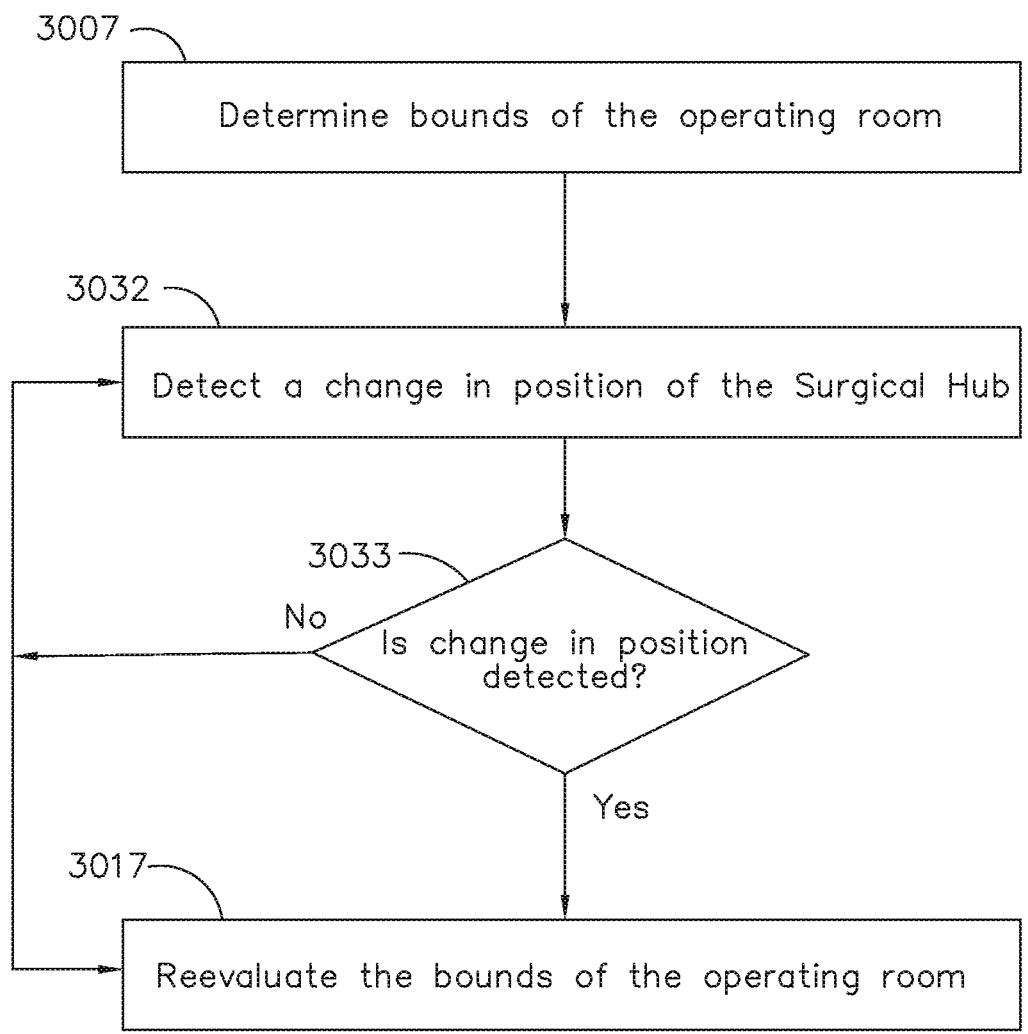
FIG. 39 is a logic flow diagram of a process depicting a control program or a logic configuration for reevaluating the bounds of an operating room by a surgical hub after detecting a change in the position of the surgical hub, in accordance with at least one aspect of the present disclosure.

An initial mapping or evaluation of the bounds of the operating room takes place during an initial activation of the surgical hub 106. Furthermore, the surgical hub 106 is configured to maintain spatial awareness during operation by periodically mapping its operating room, which can be helpful in determining if the surgical hub 106 has been moved. The reevaluation 3017 can be performed periodically or it can be triggered by an event such as observing a change in the devices of the surgical system 102 that are deemed within the operating room. In one aspect, the change is detection 3010 of a new device that was not previously deemed as within the bounds of the operating room, as illustrated in FIG. 37. In another aspect, the change is a disappearance, disconnection, or un-pairing of a paired device that was previously deemed as residing within the operating room, as illustrated in FIG. 38. The surgical hub 106 may continuously monitor 3035 the connection with paired devices to detect 3034 the disappearance, disconnection, or un-pairing of a paired device.

In other aspects, reevaluation triggering events can be, for example, changes in surgeons' positions, instrument exchanges, or sensing of a new set of tasks being performed by the surgical hub 106.

In one aspect, the evaluation of the bounds of the room by the surgical hub 106 is accomplished by activation of a sensor array of the operating-room mapping module 133 within the surgical hub 106 which enables it to detect the walls of the operating room.

Other components of the surgical system 102 can be made to be spatially aware in the same, or a similar, manner as the surgical hub 106. For example, a robotic hub 122 may also be equipped with an operating-room mapping module 133.

The spatial awareness of the surgical hub 106 and its ability to map an operating room for potential components of the surgical system 102 allows the surgical hub 106 to make autonomous decisions about whether to include or exclude such potential components as part of the surgical system 102, which relieves the surgical staff from dealing with such tasks. Furthermore, the surgical hub 106 is configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation.

In one aspect, the surgical hub 106 employs the operating-room mapping module 133 to determine the bounds of the surgical theater (e.g., a fixed, mobile, or temporary operating room or space) using either ultrasonic or laser non-contact measurement devices.

Figure 34:
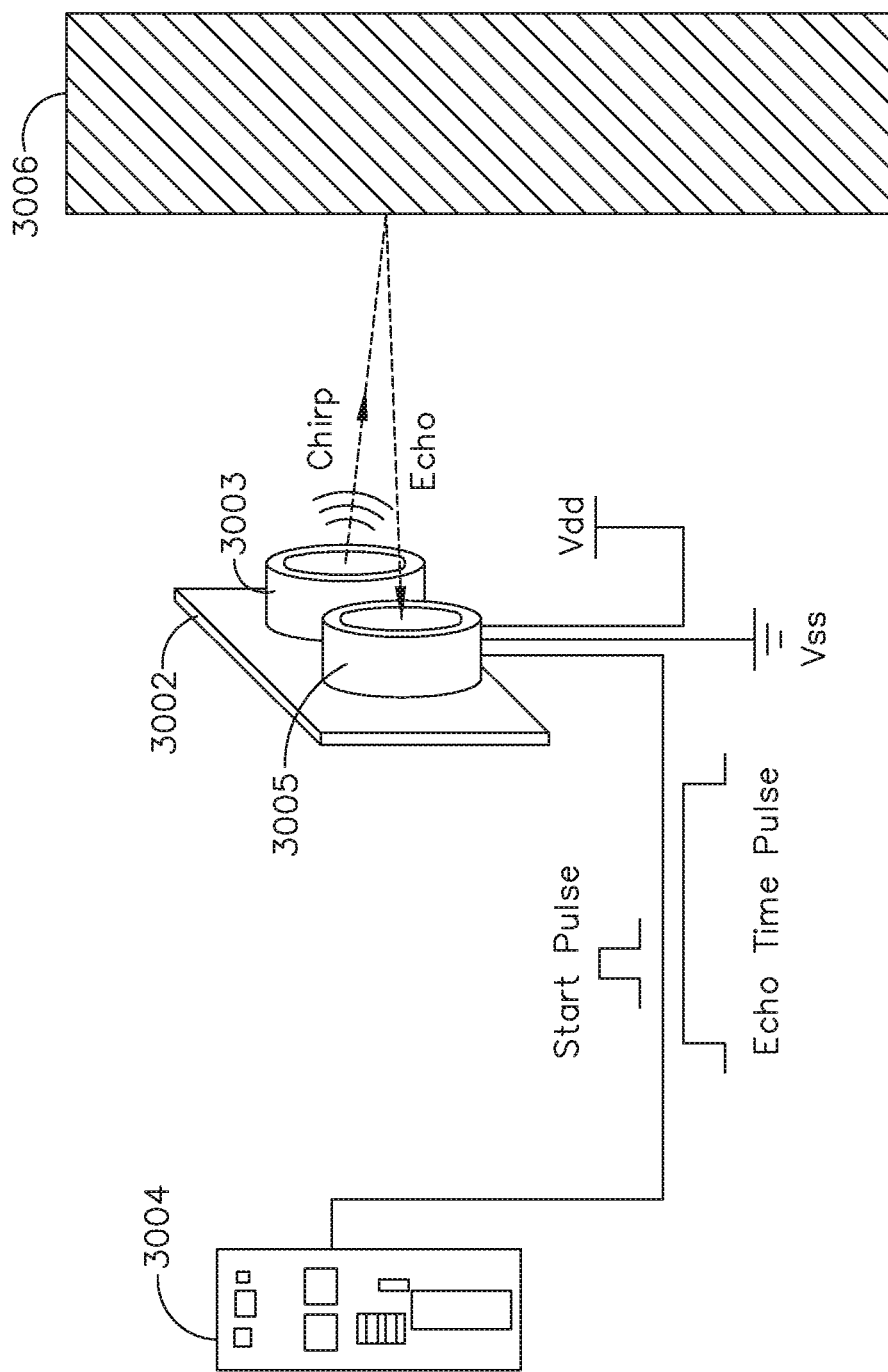
FIG. 34 illustrates ultrasonic pinging of an operating room wall to determine a distance between a surgical hub and the operating room wall, in accordance with at least one aspect of the present disclosure.

Referring to FIG. 34, ultrasound based non-contact sensors 3002 can be employed to scan the operating theater by transmitting a burst of ultrasound and receiving the echo when it bounces off a perimeter wall 3006 of an operating theater to determine the size of the operating theater and to adjust Bluetooth pairing distance limits. In one example, the non-contact sensors 3002 can be Ping ultrasonic distance sensors, as illustrated in FIG. 34.

FIG. 34 shows how an ultrasonic sensor 3002 sends a brief chirp with its ultrasonic speaker 3003 and makes it possible for a micro-controller 3004 of the operating-room mapping module 133 to measure how long the echo takes to return to the ultrasonic sensor's ultrasonic microphone 3005. The micro-controller 3004 has to send the ultrasonic sensor 3002 a pulse to begin the measurement. The ultrasonic sensor 3002 then waits long enough for the micro-controller program to start a pulse input command. Then, at about the same time the ultrasonic sensor 3002 chirps a 40 kHz tone, it sends a high signal to the micro-controller 3004. When the ultrasonic sensor 3002 detects the echo with its ultrasonic microphone 3005, it changes that high signal back to low. The micro-controller's pulse input command measures the time between the high and low changes and stores its measurement in a variable. This value can be used along with the speed of sound in air to calculate the distance between the surgical hub 106 and the operating-room wall 3006.

Figure 33:
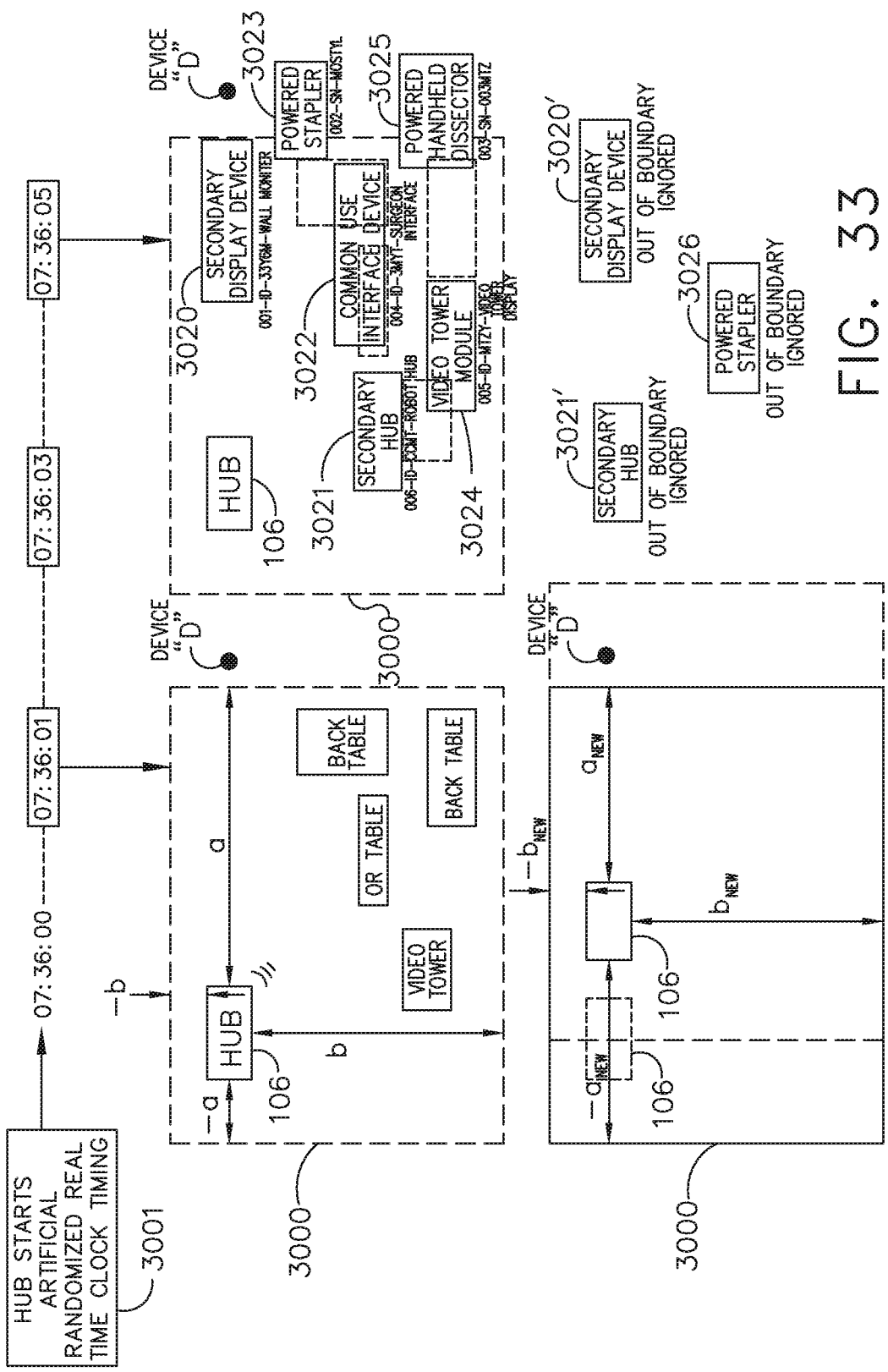
FIG. 33 illustrates a partial artificial timeline of a surgical procedure performed in an operating room via a surgical system, in accordance with at least one aspect of the present disclosure.

In one example, as illustrated in FIG. 33, a surgical hub 106 can be equipped with four ultrasonic sensors 3002, wherein each of the four ultrasonic sensors is configured to assess the distance between the surgical hub 106 and a wall of the operating room 3000. A surgical hub 106 can be equipped with more or less than four ultrasonic sensors 3002 to determine the bounds of an operating room.

Other distance sensors can be employed by the operating-room mapping module 133 to determine the bounds of an operating room. In one example, the operating-room mapping module 133 can be equipped with one or more photo-electric sensors that can be employed to assess the bounds of an operating room. In one example, suitable laser distance sensors can also be employed to assess the bounds of an operating room. Laser-based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits.

Referring to the top left corner of FIG. 33, a surgical hub 106 is brought into an operating room 3000. The surgical hub 106 is activated at the beginning of the set-up that occurs prior to the surgical procedure. In the example of FIG. 33, the set-up starts at an actual time of 11:31:14 (EST) based on a real-time clock. However, at the stated procedure set-up start time, the surgical hub 106 starts 3001 an artificial randomized real-time clock timing scheme at artificial real time 07:36:00 to protect private patient information.

At artificial real time 07:36:01, the operating-room mapping module 133 employs the ultrasonic distance sensors to ultrasonically ping the room (e.g., sends out a burst of ultrasound and listens for the echo when it bounces off the perimeter walls of the operating room as described above) to verify the size of the operating room and to adjust pairing distance limits.

At artificial real time 07:36:03, the data is stripped and time-stamped. At artificial real time 07:36:05, the surgical hub 106 begins pairing devices located only within the operating room 3000 as verified using ultrasonic distance sensors 3002 of the operating-room mapping module 133. The top right corner of FIG. 33 illustrates several example devices that are within the bounds of the operating room 3000 and are paired with the surgical hub 106, including a secondary display device 3020, a secondary hub 3021, a common interface device 3022, a powered stapler 3023, a video tower module 3024, and a powered handheld dissector 3025. On the other hand, secondary hub 3021', secondary display device 3020', and powered stapler 3026 are all outside the bounds of the operating room 3000 and, accordingly, are not paired with the surgical hub 106.

In addition to establishing a communication link with the devices of the surgical system 102 that are within the operating room, the surgical hub 106 also assigns a unique identification and communication sequence or number to each of the devices. The unique sequence may include the device's name and a time stamp of when the communication was first established. Other suitable device information may also be incorporated into the unique sequence of the device.

As illustrated in the top left corner of FIG. 33, the surgical hub 106 has determined that the operating room 3000 bounds are at distances a, −a, b, and −b from the surgical hub 106. Since Device "D" is outside the determined bounds of its operating room 3000, the surgical hub 106 will not pair with the Device "D." FIG. 35 is an example algorithm illustrating how the surgical hub 106 only pairs with devices within the bounds of its operating room. After activation, the surgical hub 106 determines 3007 bounds of the operating room using the operating-room mapping module 133, as described above. After the initial determination, the surgical hub 106 continuously searches for or detects 3008 devices within a pairing range. If a device is detected 3010, the surgical hub 106 then determines 3011 whether the detected device is within the bounds of the operating room. The surgical hub 106 pairs 3012 with the device if it is determined that the device is within the bounds of the operating room. In certain instances, the surgical hub 106 will also assign 3013 an identifier to the device. If, however, the surgical hub 106 determines that the detected device is outside the bounds of the operating room, the surgical hub 106 will ignore 3014 the device.

Referring to FIG. 36, after an initial determination of the bounds of the room, and after an initial pairing of devices located within such bounds, the surgical hub 106 continues to detect 3015 new devices that become available for pairing. If a new device is detected 3016, the surgical hub 106 is configured to reevaluate 3017 the bounds of the operating room prior to pairing with the new device. If the new device is determined 3018 to be within the newly determined bounds of the operating room, then the surgical hub 106 pairs with the device 3019 and assigns 3030 a unique identifier to the new device. If, however, the surgical hub 106 determines that the new device is outside the newly determined bounds of the operating room, the surgical hub 106 will ignore 3031 the device.

For pairing, the operating-room mapping module 133 contains a compass and integrated Bluetooth transceiver. Other communication mechanisms, which are not significantly affected by the hospital environment or geographical location, can be employed. Bluetooth Low Energy (BLE) beacon technology can currently achieve indoor distance measurements with accuracy of about 1-2 meters, with improved accuracy in closer proximities (within 0-6 meters). To improve the accuracy of the distance measurements, a compass is used with the BLE. The operating-room mapping module 133 utilizes the BLE and the compass to determine where modules are located in relation to the patient. For example, two modules facing each other (detected by compass) with greater than one meter distance between them may clearly indicate that the modules are on opposite sides of the patient. The more "Hub"-enabled modules that reside in the operating room, the greater the achievable accuracy becomes due to triangulation techniques.

In the situations where multiple surgical hubs 106, modules, and/or other peripherals are present in the same operating room, as illustrated in the top right corner of FIG. 33, the operating-room mapping module 133 is configured to map the physical location of each module that resides within the operating room. This information could be used by the user interface to display a virtual map of the room, enabling the user to more easily identify which modules are present and enabled, as well as their current status. In one aspect, the mapping data collected by surgical hubs 106 are uploaded to the cloud 104, where the data are analyzed for identifying how an operating room is physically setup, for example.

The surgical hub 106 is configured to determine a device's location by assessing transmission radio signal strength and direction. For Bluetooth protocols, the Received Signal Strength Indication (RSSI) is a measurement of the received radio signal strength. In one aspect, the devices of the surgical system 102 can be equipped with USB Bluetooth dongles. The surgical hub 106 may scan the USB Bluetooth beacons to get distance information. In another aspect, multiple high-gain antennas on a Bluetooth access point with variable attenuators can produce more accurate results than RSSI measurements. In one aspect, the hub is configured to determine the location of a device by measuring the signal strength from multiple antennas. Alternatively, in some examples, the surgical hub 106 can be equipped with one or more motion sensor devices configured to detect a change in the position of the surgical hub 106.

Referring to the bottom left corner of FIG. 33, the surgical hub 106 has been moved from its original position, which is depicted in dashed lines, to a new position closer to the device "D," which is still outside the bounds of the operating room 3000. The surgical hub 106 in its new position, and based on the previously determined bounds of the operating room, would naturally conclude that the device "D" is a potential component of the surgical system 102. However, the introduction of a new device is a triggering event for reevaluation 3017 of the bounds of the operating room, as illustrated in the example algorithm of FIGS. 35, 37. After performing the reevaluation, the surgical hub 106 determines that the operating room bounds have changed. Based on the new bounds, at distances $a_{new}$, $-a_{new}$, $b_{new}$, and $-b_{new}$, the surgical hub 106 concludes that it has been moved and that the Device "D" is outside the newly determined bounds of its operating room. Accordingly, the surgical hub 106 will still not pair with the Device "D."

In one aspect, one or more of the processes depicted in FIGS. 35-39 can be executed by a control circuit of a surgical hub 106, as depicted in FIG. 10 (processor 244). In another aspect, one or more of the processes depicted in FIGS. 35-39 can be executed by a cloud computing system 104, as depicted in FIG. 1. In yet another aspect, one or more of the processes depicted in FIGS. 35-39 can be executed by at least one of the aforementioned cloud computing systems 104 and/or a control circuit of a surgical hub 106 in combination with a control circuit of a modular device, such as the microcontroller 461 of the surgical instrument depicted in FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18-19, or the controller 838 of the generator 800 depicted in FIG. 20.

Spatial Awareness of Surgical Hubs in Operating Rooms

During a surgical procedure, a surgical instrument such as an ultrasonic or an RF surgical instrument can be coupled to a generator module 140 of the surgical hub 106. In addition, a separate surgical instrument controller such as a foot, or hand, switch or activation device can be used by an operator of the surgical instrument to activate the energy flow from the generator to the surgical instrument. Multiple surgical instrument controllers and multiple surgical instruments can be used concurrently in an operating room. Pressing or activating the wrong surgical instrument controller can lead to undesirable consequences. Aspects of the present disclosure present a solution in which the surgical hub 106 coordinates the pairing of surgical instrument controllers and surgical instruments to ensure patient and operator safety.

Aspects of the present disclosure are presented for a surgical hub 106 configured to establish and sever pairings between components of the surgical system 102 within the bounds of the operating room to coordinate flow of information and control actions between such components. The surgical hub 106 can be configured to establish a pairing between a surgical instrument controller and a surgical instrument that reside within the bounds of an operating room of surgical hub 106.

In various aspects, the surgical hub 106 can be configured to establish and sever pairings between components of the surgical system 102 based on operator request or situational and/or spatial awareness. The hub situational awareness is described in greater detail below in connection with FIG. 86.

Aspects of the present disclosure are presented for a surgical hub for use with a surgical system in a surgical procedure performed in an operating room. The surgical hub includes a control circuit that selectively forms and severs pairings between devices of the surgical system. In one aspect, the hub includes a control circuit is configured to pair the hub with a first device of the surgical system, assign a first identifier to the first device, pair the hub with a second device of the surgical system, assign a second identifier to the second device, and selectively pair the first device with the second device. In one aspect, the surgical hub includes a storage medium, wherein the control circuit is configured to store a record indicative of the pairing between the first device and the second device in the storage medium. In one aspect, the pairing between the first device and the second device defines a communication pathway therebetween. In one aspect, the pairing between the first device and the second device defines a control pathway for transmitting control actions from the second device to the first device.

Further to the above, in one aspect, the control circuit is further configured to pair the hub with a third device of the surgical system, assign a third identifier to the third device, sever the pairing between the first device and the second device, and selectively pair the first device with the third device. In one aspect, the control circuit is further configured to store a record indicative of the pairing between the first device and the third device in the storage medium. In one aspect, the pairing between the first device and the third device defines a communication pathway therebetween. In one aspect, the pairing between the first device and the third device defines a control pathway for transmitting control actions from the third device to the first device.

Figure 40:
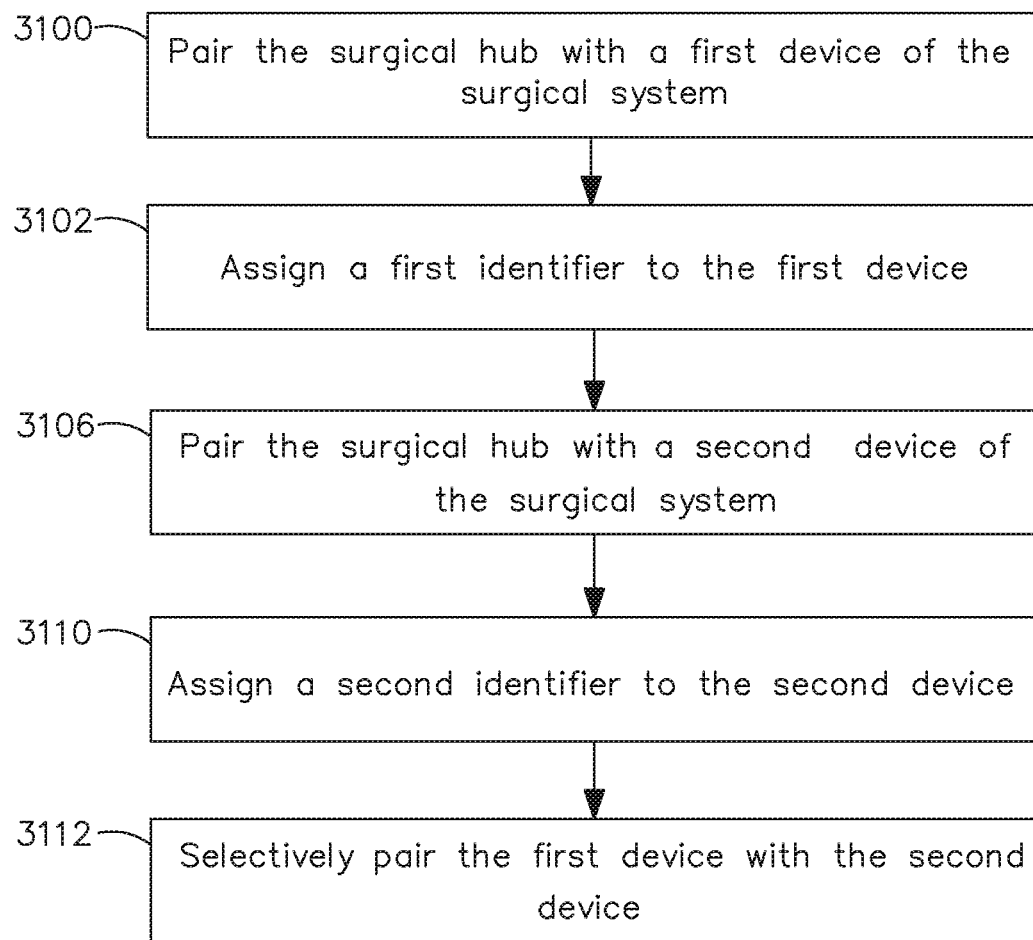
FIG. 40 is a logic flow diagram of a process depicting a control program or a logic configuration for selectively forming connections between devices of a surgical system, in accordance with at least one aspect of the present disclosure.
Figure 41:
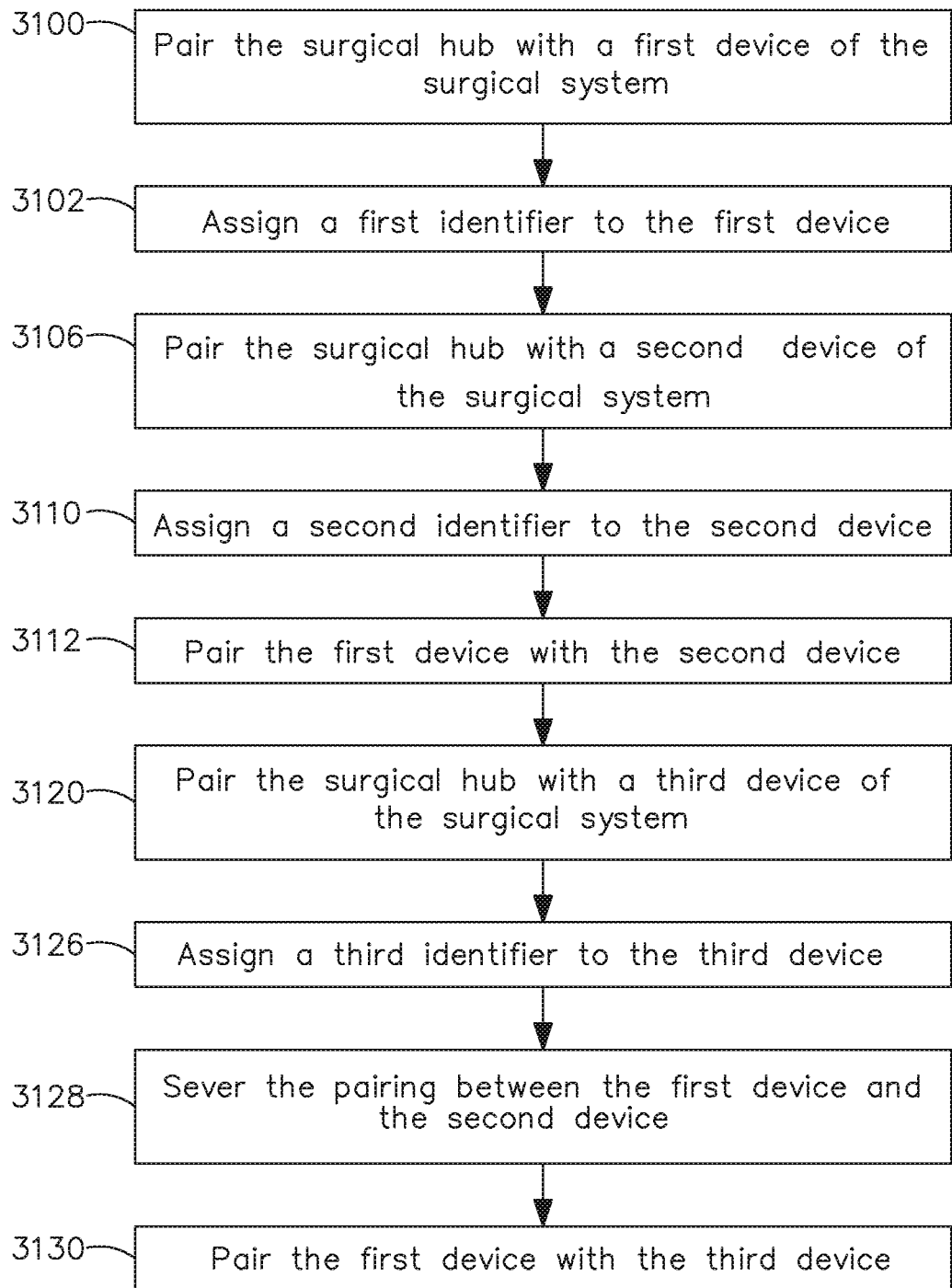
FIG. 41 is a logic flow diagram of a process depicting a control program or a logic configuration for selectively forming and severing connections between devices of a surgical system, in accordance with at least one aspect of the present disclosure.

In various aspects, the surgical hub includes a processor and a memory coupled to the processor. The memory stores instructions executable by the processor to selectively form and sever pairings between the devices of the surgical system, as described above. In various aspects, the present disclosure provides a non-transitory computer-readable medium storing computer-readable instructions which, when executed, cause a machine to selectively form and sever pairings between the devices of the surgical system, as described above. FIGS. 40 and 41 are logic flow diagrams of processes depicting control programs or logic configurations for selectively forming and severing pairings between the devices of the surgical system, as described above.

In one aspect, the surgical hub 106 establishes a first pairing with a surgical instrument and a second pairing with the surgical instrument controller. The surgical hub 106 then links the pairings together allowing the surgical instrument and the surgical instrument controller to operate with one another. In another aspect, the surgical hub 106 may sever an existing communication link between a surgical instrument and a surgical instrument controller, then link the surgical instrument to another surgical instrument controller that is linked to the surgical hub 106.

In one aspect, the surgical instrument controller is paired to two sources. First, the surgical instrument controller is paired to the surgical hub 106, which includes the generator module 140, for control of its activation. Second, the surgical instrument controller is also paired to a specific surgical instrument to prevent inadvertent activation of the wrong surgical instrument.

Figure 42:
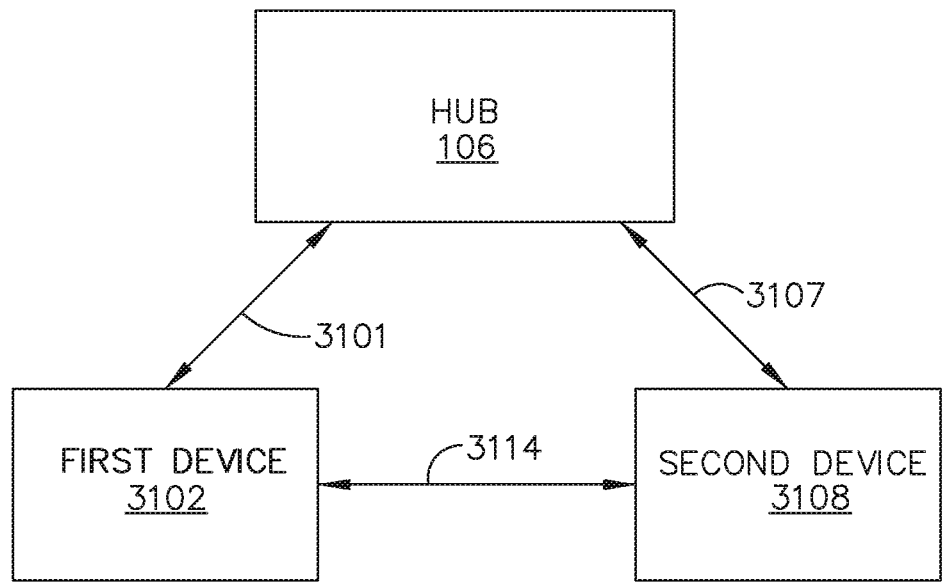
FIG. 42 illustrates a surgical hub pairing a first device and a second device of a surgical system in an operating room, in accordance with at least one aspect of the present disclosure.

Referring to FIGS. 40 and 42, the surgical hub 106 may cause the communication module 130 to pair 3100 or establish a first communication link 3101 with a first device 3102 of the surgical system 102, which can be a first surgical instrument. Then, the hub may assign 3104 a first identification number to the first device 3102. This is a unique identification and communication sequence or number that may include the device's name and a time stamp of when the communication was first established.

In addition, the surgical hub 106 may then cause the communication module 130 to pair 3106 or establish a second communication link 3107 with a second device 3108 of the surgical system 102, which can be a surgical instrument controller. The surgical hub 106 then assigns 3110 a second identification number to the second device 3108.

In various aspects, the steps of pairing a surgical hub 106 with a device may include detecting the presence of a new device, determining that the new device is within bounds of the operating room, as described above in greater detail, and only pairing with the new device if the new device is located within the bounds of the operating room.

The surgical hub 106 may then pair 3112 or authorize a communication link 3114 to be established between the first device 3102 and the second device 3108, as illustrated in FIG. 42. A record indicative of the communication link 3114 is stored by the surgical hub 106 in the storage array 134. In one aspect, the communication link 3114 is established through the surgical hub 106. In another aspect, as illustrated in FIG. 42, the communication link 3114 is a direct link between the first device 3102 and the second device 3108.

Figure 43:
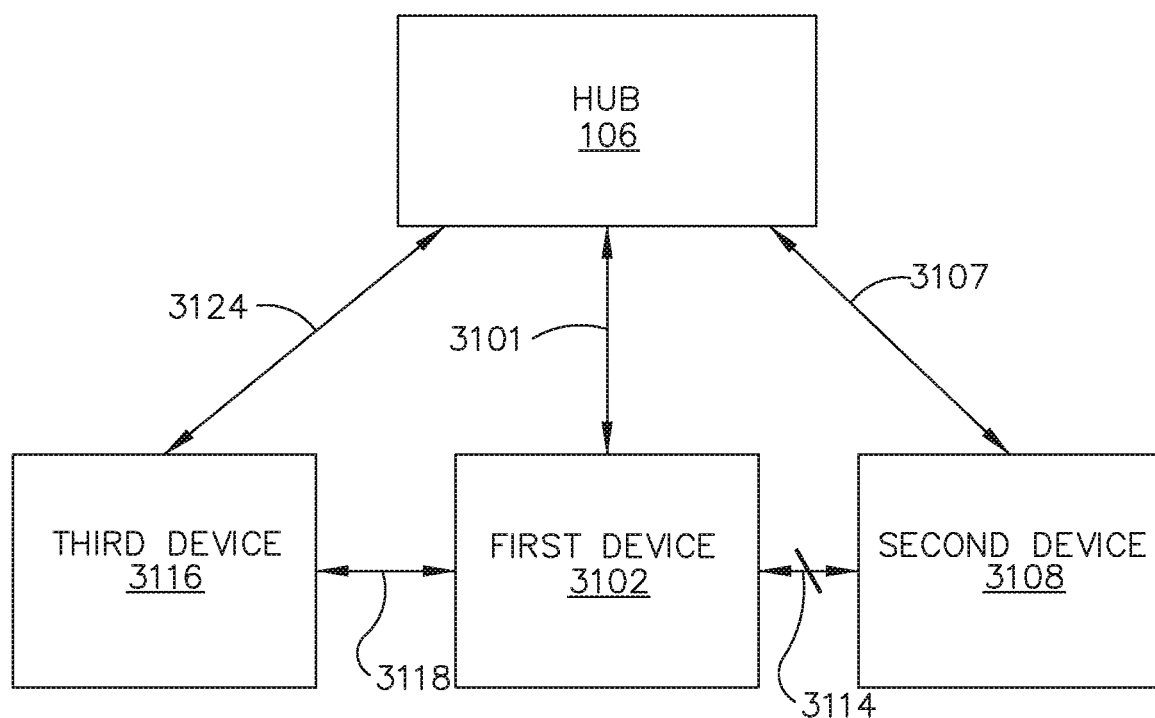
FIG. 43 illustrates a surgical hub unpairing a first device and a second device of a surgical system in an operating room, and pairing the first device with a third device in the operating room, in accordance with at least one aspect of the present disclosure.

Referring to FIGS. 41 and 43, the surgical hub 106 may then detect and pair 3120 or establish a third communication link 3124 with a third device 3116 of the surgical system 102, which can be another surgical instrument controller, for example. The surgical hub 106 may then assign 3126 a third identification number to the third device 3116.

In certain aspects, as illustrated in FIG. 43, the surgical hub 106 may then pair 3130 or authorize a communication link 3118 to be established between the first device 3102 and the third device 3116, while causing the communication link 3114 to be severed 3128, as illustrated in FIG. 43. A record indicative of the formation of the communication link 3118 and severing of the communication link 3114 is stored by the surgical hub 106 in the storage array 134. In one aspect, the communication link 3118 is established through the surgical hub 106. In another aspect, as illustrated in FIG. 43, the communication link 3118 is a direct link between the first device 3102 and the third device 3116.

As described above, the surgical hub 106 can manage an indirect communication between devices of the surgical system 102. For example, in situations where the first device 3102 is a surgical instrument and the second device 3108 is a surgical instrument controller, an output of the surgical instrument controller can be transmitted through the communication link 3107 to the surgical hub 106, which may then transmit the output to the surgical instrument through the communication link 3101.

In making a decision to connect or sever a connection between devices of the surgical system 102, the surgical hub 106 may rely on perioperative data received or generated by the surgical hub 106. Perioperative data includes operator input, hub-situational awareness, hub-spatial awareness, and/or cloud data. For example, a request can be transmitted to the surgical hub 106 from an operator user-interface to assign a surgical instrument controller to a surgical instrument. If the surgical hub 106 determines that the surgical instrument controller is already connected to another surgical instrument, the surgical hub 106 may sever the connection and establish a new connection per the operator's request.

In certain examples, the surgical hub 106 may establish a first communication link between the visualization system 108 and the primary display 119 to transmit an image, or other information, from the visualization system 108, which resides outside the sterile field, to the primary display 119, which is located within the sterile field. The surgical hub 106 may then sever the first communication link and establish a second communication link between a robotic hub 122 and the primary display 119 to transmit another image, or other information, from the robotic hub 122 to the primary display 119, for example. The ability of the surgical hub 106 to assign and reassign the primary display 119 to different components of the surgical system 102 allows the surgical hub 106 to manage the information flow within the operating room, particularly between components inside the sterile field and outside the sterile field, without physically moving these components.

In another example that involves the hub-situational awareness, the surgical hub 106 may selectively connect or disconnect devices of the surgical system 102 within an operating room based on the type of surgical procedure being performed or based on a determination of an upcoming step of the surgical procedure that requires the devices to be connected or disconnected. The hub situational awareness is described in greater detail below in connection with FIG. 86.

Figure 44:
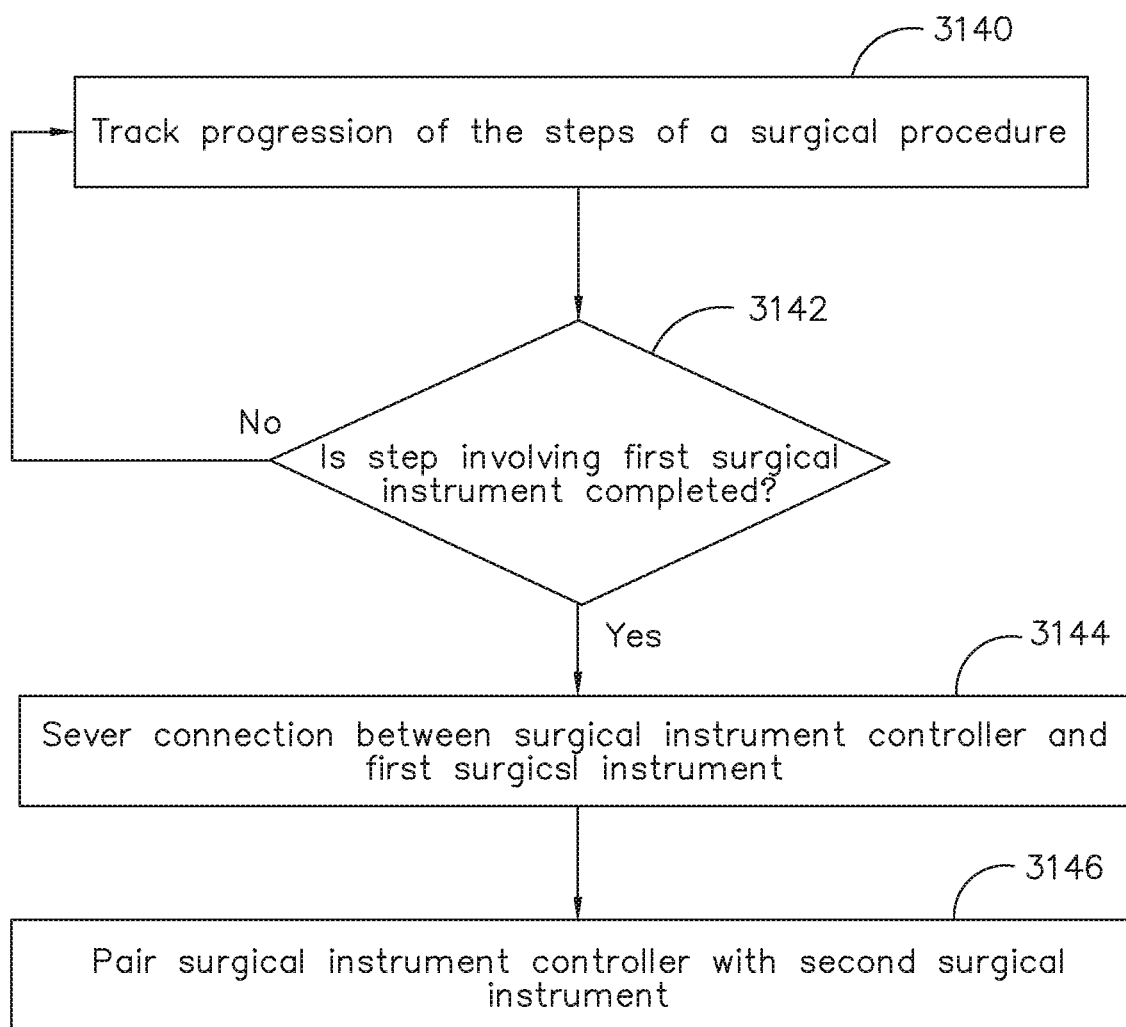
FIG. 44 is a logic flow diagram of a process depicting a control program or a logic configuration for forming an severing connections between devices of a surgical system in an operating room during a surgical procedure based on progression of the steps of the surgical procedure, in accordance with at least one aspect of the present disclosure.

Referring to FIG. 44, the surgical hub 106 may track 3140 the progression of surgical steps in a surgical procedure and may coordinate pairing and unpairing of the devices of the surgical system 102 based upon such progression. For example, the surgical hub 106 may determine that a first surgical step requires use of a first surgical instrument, while a second surgical step, occurring after completion of the first surgical step, requires use of a second surgical instrument. Accordingly, the surgical hub 106 may assign a surgical instrument controller to the first surgical instrument for the duration of the first surgical step. After detecting completion 3142 of the first surgical step, the surgical hub 106 may cause the communication link between the first surgical instrument and the surgical instrument controller to be severed 3144. The surgical hub 106 may then assign the surgical instrument controller to the second surgical instrument by pairing 3146 or authorizing the establishment of a communication link between the surgical instrument controller and the second surgical instrument.

Various other examples of the hub-situational awareness, which can influence the decision to connect or disconnect devices of the surgical system 102, are described in greater detail below in connection with FIG. 86.

In certain aspects, the surgical hub 106 may utilize its spatial awareness capabilities, as described in greater detail elsewhere herein, to track progression of the surgical steps of a surgical procedure and autonomously reassign a surgical instrument controller from one surgical instrument to another surgical instrument within the operating room of the surgical hub 106. In one aspect, the surgical hub 106 uses Bluetooth pairing and compass information to determine the physical position of the components of the surgical system 102.

In the example illustrated in FIG. 2, the surgical hub 106 is paired with a first surgical instrument held by a surgical operator at the operating table and a second surgical instrument positioned on a side tray. A surgical instrument controller can be selectively paired with either the first surgical instrument or the second surgical instrument. Utilizing the Bluetooth pairing and compass information, the surgical hub 106 autonomously assigns the surgical instrument controller to the first surgical instrument because of its proximity to the patient.

After completion of the surgical step that involved using the first surgical instrument, the first surgical instrument may be returned to the side tray or otherwise moved away from the patient. Detecting a change in the position of the first surgical instrument, the surgical hub 106 may sever the communication link between the first surgical instrument and the surgical instrument controller to protect against unintended activation of the first surgical instrument by the surgical instrument controller. The surgical hub 106 may also reassign the surgical instrument controller to another surgical instrument if the surgical hub 106 detects that it has been moved to a new position at the operating table.

In various aspects, devices of the surgical system 102 are equipped with an easy hand-off operation mode that would allow one user to give activation control of a device they currently control to another surgical instrument controller within reach of another operator. In one aspect, the devices are equipped to accomplish the hand-off through a predetermined activation sequence of the devices that causes the devices that are activated in the predetermined activation sequence to pair with one another.

In one aspect, the activation sequence is accomplished by powering on the devices to be paired with one another in a particular order. In another aspect, the activation sequence is accomplished by powering on the devices to be paired with one another within a predetermined time period. In one aspect, the activation sequence is accomplished by activating communication components, such as Bluetooth, of the devices to be paired with one another in a particular order. In another aspect, the activation sequence is accomplished by activating communication components, such as Bluetooth, of the devices to be paired within one another within a predetermined time period.

Alternatively, the hand-off can also be accomplished by a selection of a device through one of the surgical-operator input devices. After the selection is completed, the next activation by another controller would allow the new controller to take control.

In various aspects, the surgical hub 106 can be configured to directly identify components of the surgical system 102 as they are brought into an operating room. In one aspect, the devices of the surgical system 102 can be equipped with an identifier recognizable by the surgical hub 106, such as, for example, a bar code or an RFID tag. NFC can also be employed. The surgical hub 106 can be equipped with a suitable reader or scanner for detecting the devices brought into the operating room.

The surgical hub 106 can also be configured to check and/or update various control programs of the devices of the surgical system 102. Upon detecting and establishing a communication link of a device of the surgical system 102, the surgical hub 106 may check if its control program is up to date. If the surgical hub 106 determines that a later version of the control program is available, the surgical hub 106 may download the latest version from the cloud 104 and may update the device to the latest version. The surgical hub 106 may issue a sequential identification and communication number to each paired or connected device.

Cooperative Utilization of Data Derived from Secondary Sources by Intelligent Surgical Hubs In a surgical procedure, the attention of a surgical operator must be focused on the tasks at hand. Receiving information from multiple sources, such as, for example, multiple displays, although helpful, can also be distracting. The imaging module 138 of the surgical hub 106 is configured to intelligently gather, analyze, organize/package, and disseminate relevant information to the surgical operator in a manner that minimizes distractions.

Aspects of the present disclosure are presented for cooperative utilization of data derived from multiple sources, such as, for example, an imaging module 138 of the surgical hub 106. In one aspect, the imaging module 138 is configured to overlay data derived from one or more sources onto a livestream destined for the primary display 119, for example. In one aspect, the overlaid data can be derived from one or more frames acquired by the imaging module 138. The imaging module 138 may commandeer image frames on their way for display on a local display such as, for example, the primary display 119. The imaging module 138 also comprises an image processor that may preform an array of local image processing on the commandeered images.

Furthermore, a surgical procedure generally includes a number of surgical tasks which can be performed by one or more surgical instruments guided by a surgical operator or a surgical robot, for example. Success or failure of a surgical procedure depends on the success or failure of each of the surgical tasks. Without relevant data on the individual surgical tasks, determining the reason for a failed surgical procedure is a question of probability.

Aspects of the present disclosure are presented for capturing one or more frames of a livestream of a surgical procedure for further processing and/or pairing with other data. The frames may be captured at the completion of a surgical task (also referred to elsewhere herein as "surgical step") to assess whether the surgical task was completed successfully. Furthermore, the frames, and the paired data, can be uploaded to the cloud for further analysis.

In one aspect, one or more captured images are used to identify at least one previously completed surgical task to evaluate the outcome of the surgical task. In one aspect, the surgical task is a tissue-stapling task. In another aspect, the surgical task is an advanced energy transection.

Figure 45:
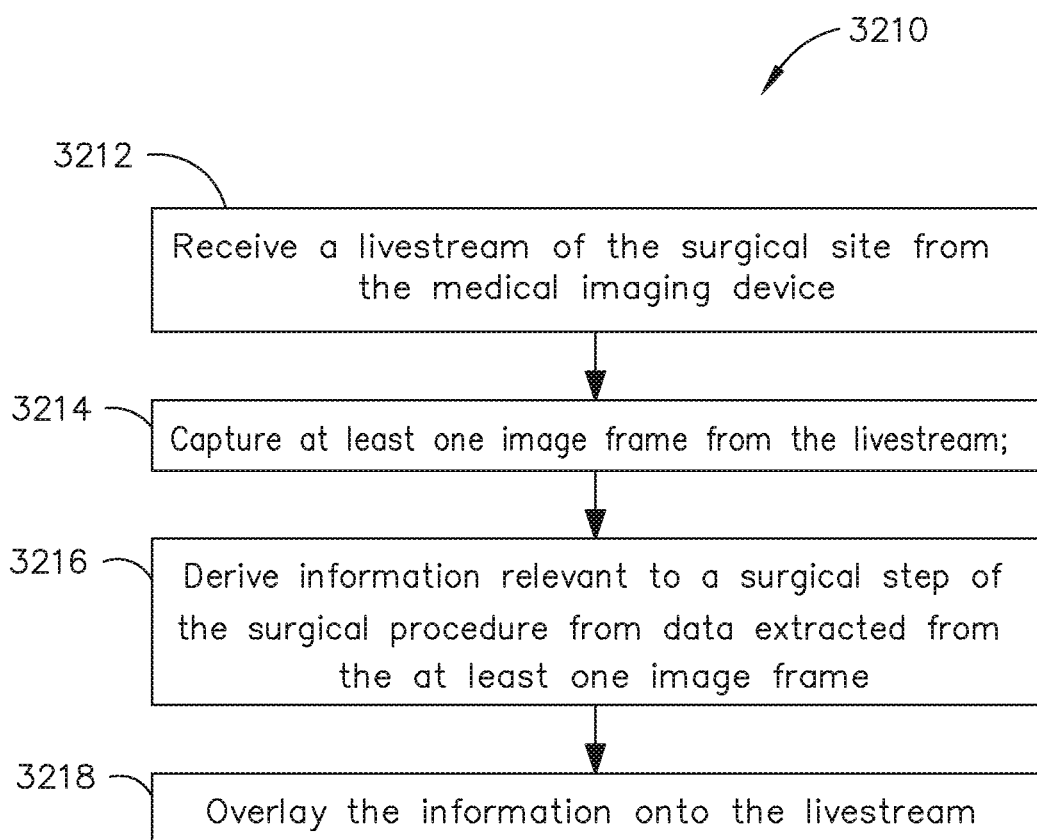
FIG. 45 is a logic flow diagram of a process depicting a control program or a logic configuration for overlaying information derived from one or more still frames of a livestream of a remote surgical site onto the livestream, in accordance with at least one aspect of the present disclosure.

FIG. 45 is a logic flow diagram of a process 3210 depicting a control program or a logic configuration for overlaying information derived from one or more still frames of a livestream of a remote surgical site onto the livestream. The process 3210 includes receiving 3212 a livestream of a remote surgical site from a medical imaging device 124, for example, capturing 3214 at least one image frame of a surgical step of the surgical procedure from the livestream, deriving 3216 information relevant to the surgical step from data extracted from the at least one image frame, and overlaying 3218 the information onto the livestream.

In one aspect, the still frames can be of a surgical step performed at the remote surgical site. The still frames can be analyzed for information regarding completion of the surgical step. In one aspect, the surgical step comprises stapling tissue at the surgical site. In another aspect, the surgical task comprises applying energy to tissue at the surgical site.

Figure 46:
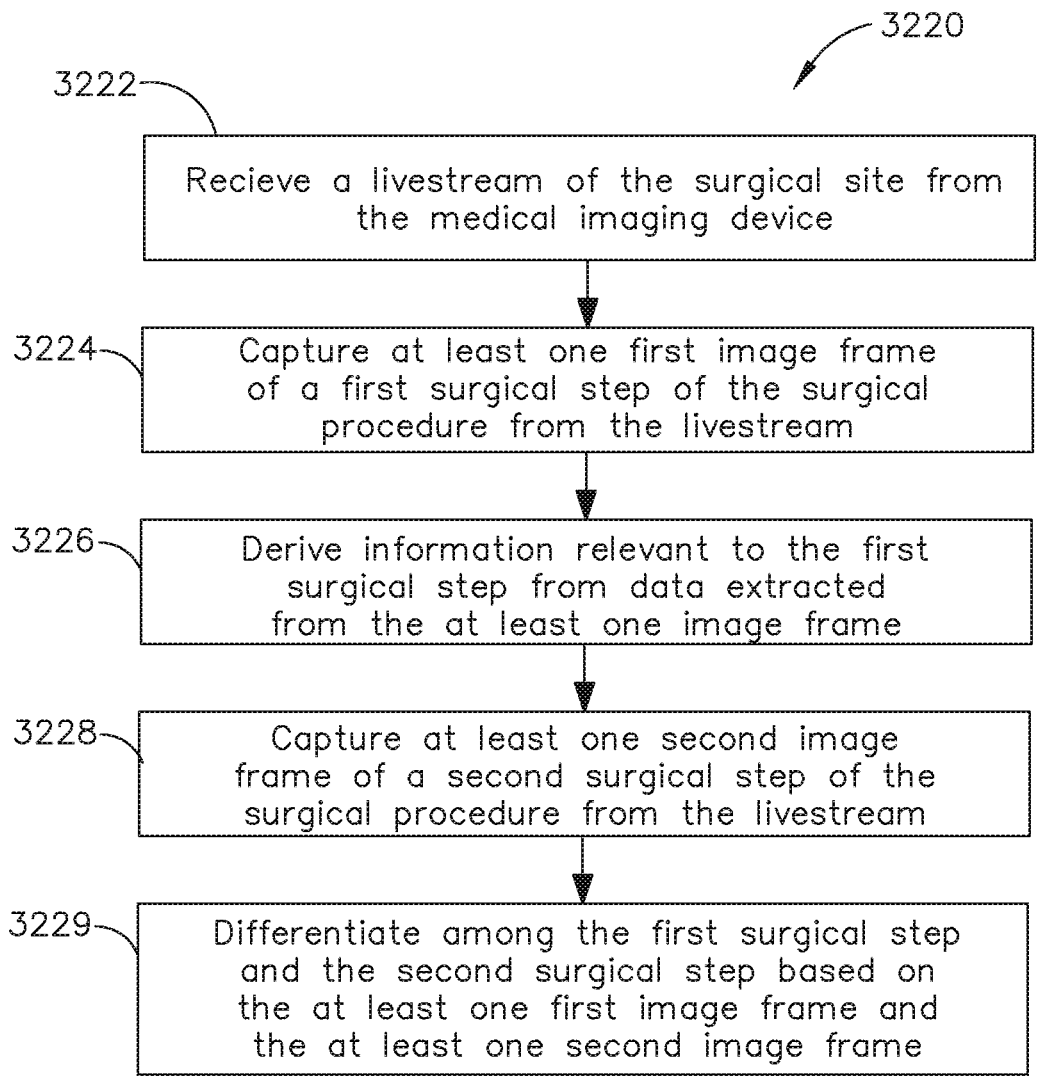
FIG. 46 is a logic flow diagram of a process depicting a control program or a logic configuration for differentiating among surgical steps of a surgical procedure, in accordance with at least one aspect of the present disclosure.

FIG. 46 is a logic flow diagram of a process 3220 depicting a control program or a logic configuration for differentiating among surgical steps of a surgical procedure. The process 3220 includes receiving 3222 a livestream of a surgical site from a medical imaging device 124, for example, capturing 3224 at least one first image frame of a first surgical step of the surgical procedure from the livestream, deriving 3226 information relevant to the first surgical step from data extracted from the at least one image frame, capturing 3228 at least one second image frame of a second surgical step of the surgical procedure from the livestream, and differentiating 3229 among the first surgical step and the second surgical step based on the at least one first image frame and the at least one second image frame.

Figure 47:
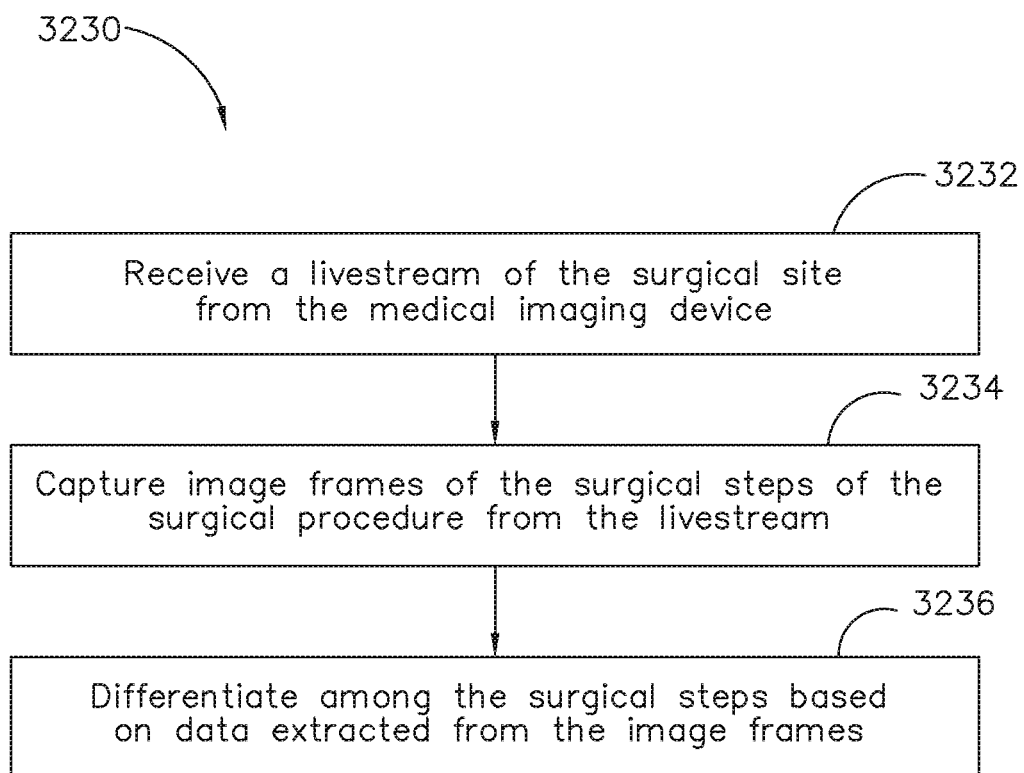
FIG. 47 is a logic flow diagram of a process 3230 depicting a control program or a logic configuration for differentiating among surgical steps of a surgical procedure, in accordance with at least one aspect of the present disclosure.

FIG. 47 is a logic flow diagram of a process 3230 depicting a control program or a logic configuration for differentiating among surgical steps of a surgical procedure. The process 3232 includes receiving 3232 a livestream of the surgical site from a medical imaging device 124, for example, capturing 3234 image frames of the surgical steps of the surgical procedure from the livestream and differentiating 3236 among the surgical steps based on data extracted from the image frames.

Figure 48:
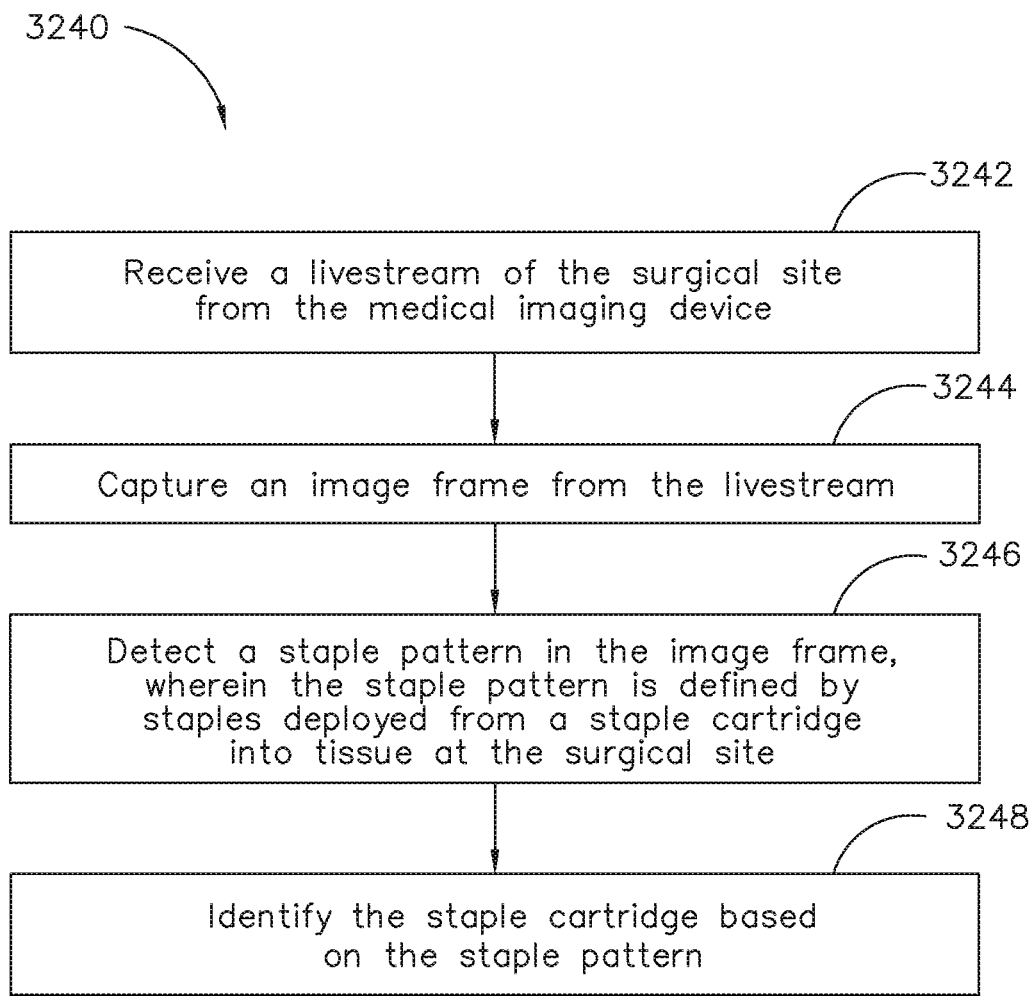
FIG. 48 is a logic flow diagram of a process 3240 depicting a control program or a logic configuration for identifying a staple cartridge from information derived from one or more still frames of staples deployed from the staple cartridge into tissue, in accordance with at least one aspect of the present disclosure.

FIG. 48 is a logic flow diagram of a process 3240 depicting a control program or a logic configuration for identifying a staple cartridge from information derived from one or more still frames of staples deployed from the staple cartridge into tissue. The process 3240 includes receiving 3242 a livestream of the surgical site from medical imaging device 124, for example, capturing 3244 an image frame from the livestream, detecting 3246 a staple pattern in the image frame, wherein the staple pattern is defined by staples deployed from a staple cartridge into tissue at the surgical site. The process 3240 further includes identifying 3248 the staple cartridge based on the staple pattern.

In various aspects, one or more of the steps of the processes 3210, 3220, 3230, 3240 can be executed by a control circuit of an imaging module of a surgical hub, as depicted in FIGS. 3, 9, 10. In certain examples, the control circuit may include a processor and a memory coupled to the processor, wherein the memory stores instructions executable by the processor to perform one or more of the steps of the processes 3210, 3220, 3230, 3240. In certain examples, a non-transitory computer-readable medium stores computer-readable instructions which, when executed, cause a machine to perform one or more of the steps of the processes 3210, 3220, 3230, 3240. For economy, the following description of the processes 3210, 3220, 3230, 3240 will be described as being executed by the control circuit of an imaging module of a surgical hub; however, it should be understood that the execution of the processes 3210, 3220, 3230, 3240 can be accomplished by any of the aforementioned examples.

Figure 49:
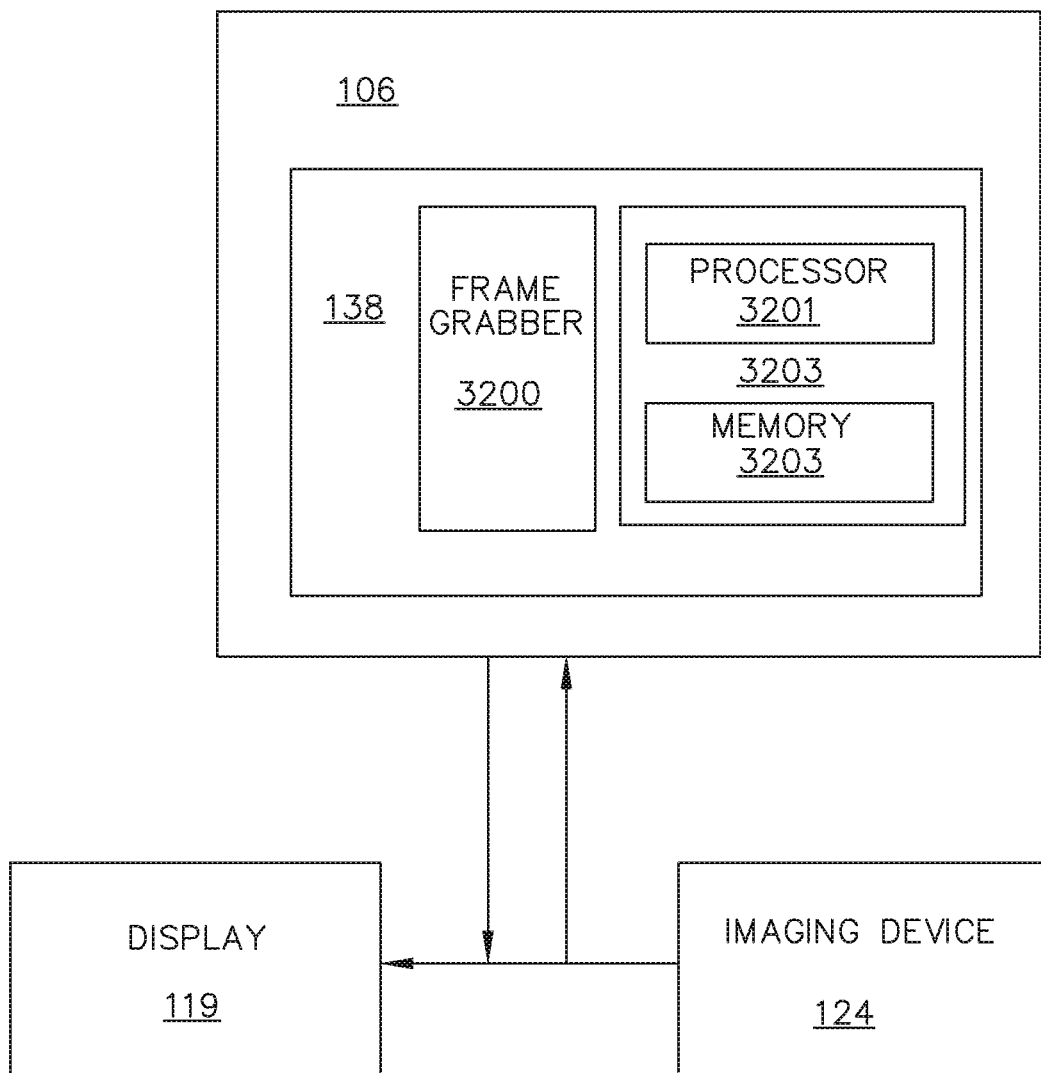
FIG. 49 is a partial view of a surgical system in an operating room, the surgical system including a surgical hub that has an imaging module in communication with an imaging device at a remote surgical site, in accordance with at least one aspect of the present disclosure.

Referring to FIGS. 34 and 49, a surgical hub 106 is in communication with a medical imaging device 124 located at a remote surgical site during a surgical procedure. The imaging module 138 receives a livestream of the remote surgical site transmitted by the imaging device 124 to a primary display 119, for example, in accordance with steps 3212, 3222, 3232, 3242.

Further to the above, the imaging module 138 of the surgical hub 106 includes a frame grabber 3200. The frame grabber 3200 is configured to capture (i.e., "grabs") individual, digital still frames from the livestream transmitted by the imaging device 124, for example, to a primary display 119, for example, during a surgical procedure, in accordance with steps 3214, 3224, 3234, 3244. The captured still frames are stored and processed by a computer platform 3203 (FIG. 49) of the imaging module 138 to derive information about the surgical procedure.

Processing of the captured frames may include performance of simple operations, such as histogram calculations, 2D filtering, and arithmetic operations on arrays of pixels to the performance of more complex tasks, such as object detection, 3D filtering, and the like.

In one aspect, the derived information can be overlaid onto the livestream. In one aspect, the still frames and/or the information resulting from processing the still frames can be communicated to a cloud 104 for data aggregation and further analysis.

In various aspects, the frame grabber 3200 may include a digital video decoder and a memory for storing the acquired still frames, such as, for example, a frame buffer. The frame grabber 3200 may also include a bus interface through which a processor can control the acquisition and access the data and a general purpose I/O for triggering image acquisition or controlling external equipment.

As described above, the imaging device 124 can be in the form of an endoscope, including a camera and a light source positioned at a remote surgical site, and configured to provide a livestream of the remote surgical site at the primary display 119, for example.

In various aspects, image recognition algorithms can be implemented to identify features or objects in still frames of a surgical site that are captured by the frame grabber 3200. Useful information pertaining to the surgical steps associated with the captured frames can be derived from the identified features. For example, identification of staples in the captured frames indicates that a tissue-stapling surgical step has been performed at the surgical site. The type, color, arrangement, and size of the identified staples can also be used to derive useful information regarding the staple cartridge and the surgical instrument employed to deploy the staples. As described above, such information can be overlaid on a livestream directed to a primary display 119 in the operating room.

The image recognition algorithms can be performed at least in part locally by the computer platform 3203 (FIG. 49) of the imaging module 138. In certain instances, the image recognition algorithms can be performed at least in part by the processor module 132 of the surgical hub 106. An image database can be utilized in performance of the image recognition algorithms and can be stored in a memory 3202 of the computer platform 3203. Alternatively, the imaging database can be stored in the storage array 134 (FIG. 3) of the surgical hub 106. The image database can be updated from the cloud 104.

An example image recognition algorithm that can be executed by the computer platform 3203 may include a key points-based comparison and a region-based color comparison. The algorithm includes: receiving an input at a processing device, such as, for example, the computer platform 3203; the input, including data related to a still frame of a remote surgical site; performing a retrieving step, including retrieving an image from an image database and, until the image is either accepted or rejected, designating the image as a candidate image; performing an image recognition step, including using the processing device to perform an image recognition algorithm on the still frame and candidate images in order to obtain an image recognition algorithm output; and performing a comparison step, including: if the image recognition algorithm output is within a pre-selected range, accepting the candidate image as the still frame and if the image recognition algorithm output is not within the pre-selected range, rejecting the candidate image and repeating the retrieving, image recognition, and comparison steps.

Figure 50:
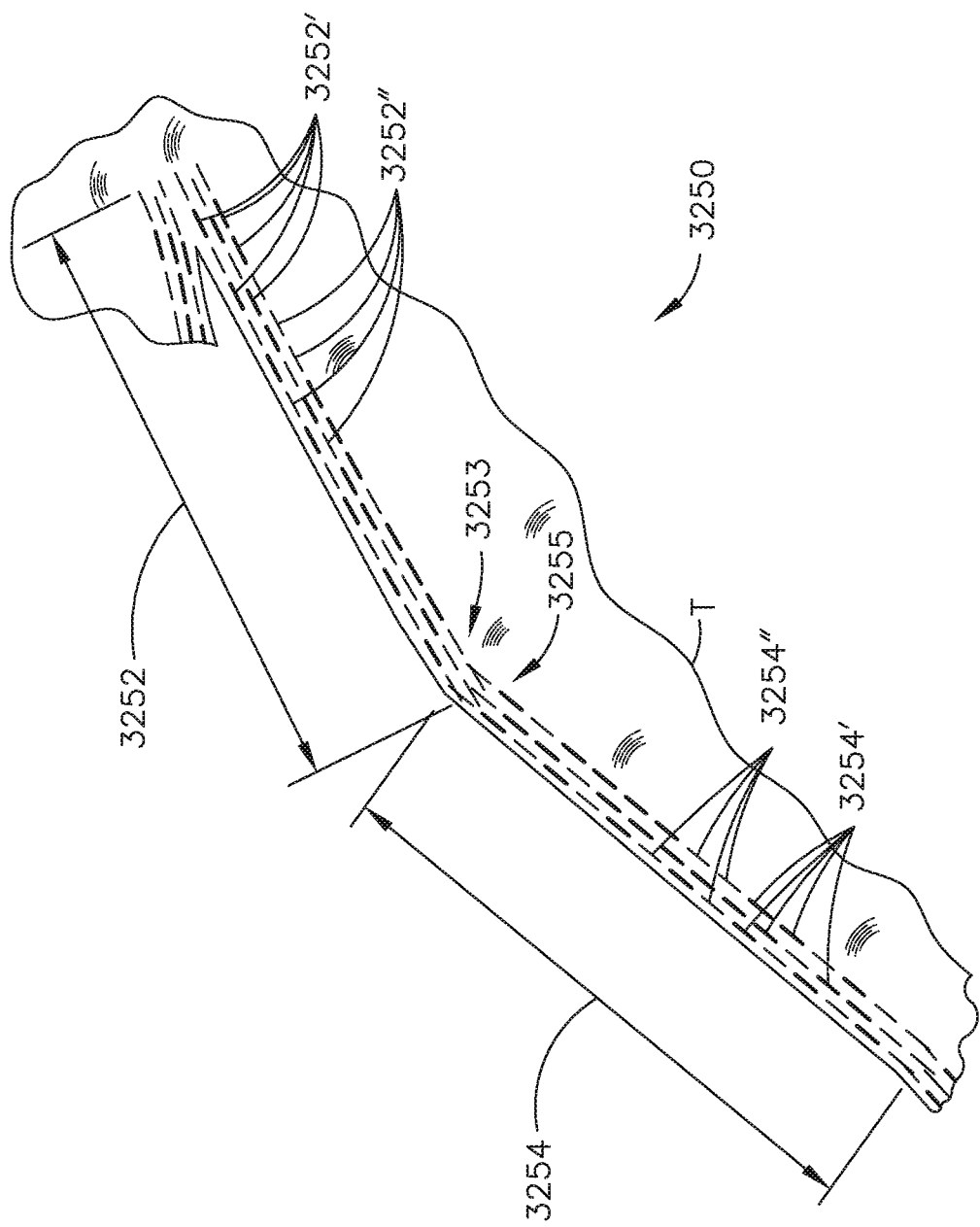
FIG. 50 illustrates a partial view of stapled tissue that received a first staple firing and a second staple firing arranged end-to-end, in accordance with at least one aspect of the present disclosure.

Referring to FIGS. 50-52, in one example, a surgical step involves stapling and cutting tissue. FIG. 50 depicts a still frame 3250 of a stapled and cut tissue T. A staple deployment 3252 includes staples 3252', 3252" from a first staple cartridge. A second staple deployment 3254 includes staples 3254', 3254" from a second staple cartridge. A proximal portion 3253 of the staple deployment 3252 overlaps with a distal portion 3255 of the staple deployment 3254. Six rows of staples were deployed in each deployment. Tissue T was cut between the third and fourth rows of each deployment, but only one side of the stapled tissue T is fully shown.

In various aspects, the imaging module 138 identifies one or more of the staples 3252', 3252", 3254', 3254" in the still frame 3250, which were absent in a previous still frame captured by the frame grabber 3200. The imaging module 138 then concludes that a surgical stapling and cutting instrument has been used at the surgical site.

In the example of FIG. 50, the staple deployment 3252 includes two different staples 3252', 3252". Likewise, the staple deployment 3254 includes two different staples 3254', 3254". For brevity, the following description focuses on the staples 3252', 3252", but is equally applicable to the staples 3254', 3254". The staples 3252', 3252" are arranged in a predetermined pattern or sequence that forms a unique identifier corresponding to the staple cartridge that housed the staples 3252', 3252". The unique pattern can be in a single row or multiple rows of the staples 3250. In one example, the unique pattern can be achieved by alternating the staples 3252', 3252" at a predetermined arrangement.

In one aspect, multiple patterns can be detected in a firing of staples. Each pattern can be associated with a unique characteristic of the staples, the staple cartridge that housed the staples, and/or the surgical instrument that was employed to fire the staple. For example, a firing of staples may include patterns that represent staple form, staple size, and/or location of the firing.

In the example, of FIG. 50, the imaging module 138 may identify a unique pattern of the staples 3252 from the still frame 3250. A database storing staple patterns and corresponding identification numbers of staple cartridges can then be explored to determine an identification number of a staple cartridge that housed the staples 3252.

The patterns of the example of FIG. 50 are based on only two different staples; however, other aspects may include three or more different staples. The different staples can be coated with different coatings, which can be applied to the staples by one or more of the following methods: anodizing, dying, electro-coating, photoluminescent coating, application of nitrides, methyl methacylate, painting, powder coating, coating with paraffins, oil stains or phosphor coatings, the use of hydroxyapatite, polymers, titanium oxinitrides, zinc sulfides, carbides, etc. It should be noted that, while the listed coatings are fairly specific as disclosed herein, other coatings known in the art to distinguish the staple are within the contemplated scope of the present disclosure.

In the example of FIGS. 50-52, the staples 3252' are anodized staples, while the staples 3252" are non-anodized staples. In one aspect, the different staples may comprise two or more different colors. Different metal staples may comprise magnetic or radioactive staple markers that differentiate them from unmarked staples.

FIG. 51 illustrates a staple deployment 3272 deployed into tissue from a staple cartridge via a surgical instrument. Only three staple rows 3272a, 3272b, 3272c are depicted in FIG. 51. The rows 3272a, 3272b, 3272c are arranged between a medial line, where the tissue was cut, and a lateral line at the tissue edge. For clarity, the inner row 3272a of staples is redrawn separately to the left and the outer two rows 3272b, 3272c are redrawn separately to the right. A proximal end 3273 and a distal end portion of the staple deployment 3272 are also redrawn in FIG. 51 for clarity.

The staple deployment 3272 includes two different staples 3272', 3272" that are arranged in predetermined patterns that serve various functions. For example, the inner row 3272a comprises a pattern of alternating staples 3272', 3272", which defines a metric for distance measurements in the surgical field. In other words, the pattern of the inner row 3272a acts as a ruler for measuring distances, which can be helpful in accurately determining the position of a leak, for example. The outer rows 3272b, 3272c define a pattern that represents an identification number of the staple cartridge that housed the staples 3272', 3272".

Furthermore, unique patterns at the ends of the staple deployment 3272 identify the proximal end portion 3273 and distal end portion 3275. In the example of FIG. 51, a unique arrangement of three staples 3272" identifies the distal end 3275, while a unique arrangement of four staples 3272" identifies the proximal end 3273. Identification of the proximal and distal ends of a staple deployment allows the imaging module 128 to distinguish between different staple deployments within a captured frame, which can be useful in pointing the source of a leak, for example.

In various aspects, the imaging module 138 may detect a sealed tissue in a still frame of a remote surgical site captured by the frame grabber 3200. Detection of the sealed tissue can be indicative of a surgical step that involves applying therapeutic energy to tissue.

Sealing tissue can be accomplished by the application of energy, such as electrical energy, for example, to tissue captured or clamped within an end effector of a surgical instrument in order to cause thermal effects within the tissue. Various mono-polar and bi-polar RF surgical instruments and harmonic surgical instruments have been developed for such purposes. In general, the delivery of energy to captured tissue can elevate the temperature of the tissue and, as a result, the energy can at least partially denature proteins within the tissue. Such proteins, like collagen, for example, can be denatured into a proteinaceous amalgam that intermixes and fuses, or seals, together as the proteins renature.

Accordingly, sealed tissue has a distinct color and/or shape that can be detected by the imaging module 138 using image recognition algorithms, for example. In addition, smoke detection at the surgical site can indicate that therapeutic energy application to the tissue is in progress.

Further to the above, the imaging module 138 of the surgical hub 106 is capable of differentiating between surgical steps of a surgical procedure based on the captured frames. As described above, a still frame that comprises fired staples is indicative of a surgical step involving tissue stapling, while a still frame that comprises a sealed tissue is indicative of a surgical step involving energy application to tissue.

In one aspect, the surgical hub 106 may selectively overlay information relevant to a previously completed surgical task onto the livestream. For example, the overlaid information may comprise image data from a still frame of the surgical site captured during the previously completed surgical task. Furthermore, guided by common landmark locations at the surgical site, the imaging module 138 can interlace one image frame to another to establish and detect surgical locations and relationship data of a previously completed surgical task.

In one example, the surgical hub 106 is configured to overlay information regarding a potential leak in a tissue treated by stapling or application of therapeutic energy in a previously completed surgical task. The potential leak can be spotted by the imaging module 138 during the processing of a still frame of the tissue. The surgical operator can be alerted about the leak by overlaying information about the potential leak onto the livestream.

In various aspects, still frames of an end effector of a surgical instrument at a surgical site can be used to identify the surgical instrument. For example, the end effector may include an identification number that can be recognized by the imaging module 138 during image processing of the still frame. Accordingly, the still frames captured by the imaging module 138 may be used to identify a surgical instrument utilized in a surgical step of a surgical procedure. The still frames may also include useful information regarding the performance of the surgical instrument. All such information can be uploaded to the cloud 104 for data aggregation and further analysis.

In various examples, the surgical hub 106 may also selectively overlay information relevant to a current or upcoming surgical task, such as an anatomical location or a surgical instrument suitable for the surgical task.

The imaging module 138 may employ various images and edge detection techniques to track a surgical site where a surgical instrument was used to complete a surgical task. Success or failure of the surgical task can then be assessed. For example, a surgical instrument can be employed to seal and/or cut tissue at the surgical site. A still frame of the surgical site can be stored in the memory 3202 or the storage array 134 of the surgical hub 106, for example, upon completion of the surgical task.

In the following surgical step, the quality of the seal can be tested via different mechanisms. To ensure that the testing is accurately applied to the treated tissue, the stored still frame of the surgical site is overlaid onto the livestream in search of a match. Once a match is found, the testing can take place. One or more additional still frames can be taken during the testing, which can be later analyzed by the imaging module 138 of the surgical hub 106. The testing mechanisms include bubble detection, bleeding detection, dye detection (where a dye is employed at the surgical site), and/or burst stretch detection (where a localized strain is applied adjacent to an anastomosis site), for example.

The imaging module 138 may capture still frames of the response of the treated tissue to these tests, which can be stored in the memory 3202 or the storage array 134 of the surgical hub 106, for example. The still frames can be stored alone or in combination with other data, such as, for example, data from the surgical instrument that performed the tissue treatment. The paired data can also be uploaded to the cloud 104 for additional analysis and/or pairing.

In various aspects, the still frames captured by the frame grabber 3200 can be processed locally, paired with other data, and can also be transmitted to the cloud 104. The size of the processed and/or transmitted data will depend on the number of captured frames. In various aspects, the rate at which the frame grabber 3200 captures the still frames from the livestream can be varied in an effort to reduce the size of the data without sacrificing quality.

In one aspect, the frame-capturing rate may depend on the type of surgical task being performed. Certain surgical tasks may need a higher number of still frames than others for an evaluation of success or failure. The frame-capturing rate can be scalded to accommodate such needs.

In one aspect, the frame-capturing rate is dependent upon the detected motion of the imaging device 124. In use, an imaging device 124 may target one surgical site for a period of time. Observing no or minor changes in the still frames captured while the imaging device 124 is not being moved, the imaging module 138 may reduce the frame-capturing rate of the frame grabber 3200. If the situation changes, however, where frequent motion is detected, the imaging module 138 may respond by increasing the frame-capturing rate of the frame grabber 3200. In other words, the imaging module 138 may be configured to correlate the frame-capturing rate of the frame grabber 3200 with the detected degree of motion of the imaging device 124.

For additional efficiency, only portions of the still frames, where motion is detected, need to be stored, processed, and/or transmitted to the cloud 104. The imaging module 138 can be configured to select the portions of the still frames where motion is detected. In one example, motion detection can be achieved by comparing a still frame to a previously captured still frame. If movement is detected, the imaging module 138 may cause the frame grabber 3200 to increase the frame-capturing rate, but only the portions where motion is detected are stored, processed, and/or transmitted to the cloud 104.

In another aspect, the data size can be managed by scaling the resolution of the captured information based on the area of the screen where the focal point is or where end effectors are located, for example. The remainder of the screen could be captured at a lower resolution.

In one aspect, the corners of the screen and the edges could generally be captured at a lower resolution. The resolution, however, can be scalded up if an event of significance is observed.

During a surgical procedure, the surgical hub 106 can be connected to various operating-room monitoring devices, such as, for example, heart rate monitors and insufflation pumps. Data collected from these devices can improve the situational awareness of the surgical hub 106. The hub situational awareness is described in greater detail below in connection with FIG. 86.

In one example, the surgical hub 106 can be configured to utilize patient data received from a heart rate monitor connected along with data regarding the location of the surgical site to assess proximity of the surgical site to sensory nerves. An increase in the patient's heart rate, when combined with anatomical data indicating that the surgical site is in a region high in sensory nerves, can be construed as an indication of sensory nerve proximity. Anatomical data can be available to the surgical hub 106 through accessing patient records (e.g., an EMR database containing patient records).

The surgical hub 106 may be configured to determine the type of surgical procedure being performed on a patient from data received from one or more of the operating-room monitoring devices, such as, for example, heart rate monitors and insufflation pumps. Abdominal surgical procedures generally require insufflation of the abdomen, while insufflation is not required in theoretic surgery. The surgical hub 106 can be configured to determine whether a surgical procedure is an abdominal or a thoracic surgical procedure by detecting whether the insufflation pump is active. In one aspect, the surgical hub 106 may be configured to monitor insufflation pressure on the output side of the insufflation pump in order to determine whether the surgical procedure being performed is one that requires insufflation.

The surgical hub 106 may also gather information from other secondary devices in the operating room to assess, for example, whether the surgical procedure is a vascular or avascular procedure.

The surgical hub 106 may also monitor AC current supply to one or more of its components to assess whether a component is active. In one example, the surgical hub 106 is configured to monitor AC current supply to the generator module to assess whether the generator is active, which can be an indication that the surgical procedure being performed is one that requires application of energy to seal tissue.

In various aspects, secondary devices in the operating room that are incapable of communication with the surgical hub 106 can be equipped with communication interface devices (communication modules) that can facilitate pairing of these devices with the surgical hub 106. In one aspect, the communication interface devices may be configured to be bridging elements, which would allow them two-way communication between the surgical hub 106 and such devices.

In one aspect, the surgical hub 106 can be configured to control one or more operational parameters of a secondary device through a communication interface device. For example, the surgical hub 106 can be configured to increase or decrease the insufflation pressure through a communication interface device coupled to an insufflation device.

In one aspect, the communication interface device can be configured to engage with an interface port of the device. In another aspect, the communication interface device may comprise an overlay or other interface that directly interacts with a control panel of the secondary device. In other aspects, the secondary devices, such as, for example, the heart rate monitor and/or the insufflation devices, can be equipped with integrated communication modules that allow them to pair with the hub for two-way communication therewith.

In one aspect, the surgical hub 106 can also be connected through a communication interface device, for example, to muscle pads that are connected to the neuro-stim detection devices to improve resolution of a nerve-sensing device.

Furthermore, the surgical hub 106 can also be configured to manage operating room supplies. Different surgical procedures require different supplies. For example, two different surgical procedures may require different sets of surgical instruments. Certain surgical procedures may involve using a robotic system, while others may not. Furthermore, two different surgical procedures may require staple cartridges that are different in number, type, and/or size. Accordingly, the supplies brought into the operating room can provide clues as to the nature of the surgical procedure that will be performed.

In various aspects, the surgical hub 106 can be integrated with an operating room supplies scanner to identify items pulled into the operating room and introduced into the sterile field. The surgical hub 106 may utilize data from the operating room supplies scanner, along with data from the devices of the surgical system 102 that are paired with the surgical hub 106, to autonomously determine the type of surgical procedure that will be performed. In one example, the surgical hub 106 may record a list of serial numbers of the smart cartridge that are going to be used in the surgical procedure. During the surgical procedure, the surgical hub 106 may gradually remove the staples that have been fired, based on information collected from the staple cartridge chips. In one aspect, the surgical hub 106 is configured to make sure that all the items are accounted for at the end of the procedure.

Surgical Hub Control Arrangements

In a surgical procedure, a second surgical hub may be brought into an operating room already under the control of a first surgical hub. The second surgical hub can be, for example, a surgical robotic hub brought into the operating room as a part of a robotic system. Without coordination between the first and second surgical hubs, the robotic surgical hub will attempt to pair with all the other components of the surgical system 102 that are within the operating room. The confusion arising from the competition between two hubs in a single operating room can lead to undesirable consequences. Also, sorting out the instrument distribution between the hubs during the surgical procedure can be time consuming.

Aspects of the present disclosure are presented for a surgical hub for use with a surgical system in a surgical procedure performed in an operating room. A control circuit of the surgical hub is configured to determine the bounds of the operating room and establish a control arrangement with a detected surgical hub located within the bounds of the operating room.

In one aspect, the control arrangement is a peer-to-peer arrangement. In another aspect, the control arrangement is a master-slave arrangement. In one aspect, the control circuit is configured to select one of a master mode of operation or a slave mode of operation in the master-slave arrangement. In one aspect, the control circuit is configured to surrender control of at least one surgical instrument to the detected surgical hub in the slave mode of operation.

In one aspect, the surgical hub includes an operating room mapping circuit that includes a plurality of non-contact sensors configured to measure the bounds of the operating room.

In various aspects, the surgical hub includes a processor and a memory coupled to the processor. The memory stores instructions executable by the processor to coordinate a control arrangement between surgical hubs, as described above. In various aspects, the present disclosure provides a non-transitory computer-readable medium storing computer-readable instructions which, when executed, cause a machine to coordinate a control arrangement between surgical hubs, as described above.

Aspects of the present disclosure are presented for a surgical system comprising two independent surgical hubs that are configured to interact with one another. Each of the hubs has their own linked surgical devices and the control designation of and distribution of where data is recorded and processed. This interaction causes one or both hubs to change how they were behaving before the interaction. In one aspect, the change involves a redistribution of devices previously assigned to each of the hubs. In another aspect, the change involves establishing a master-slave arrangement between the hubs. In yet another aspect, the change can be a change in the location of the processing shared between the hubs.

Figure 53:
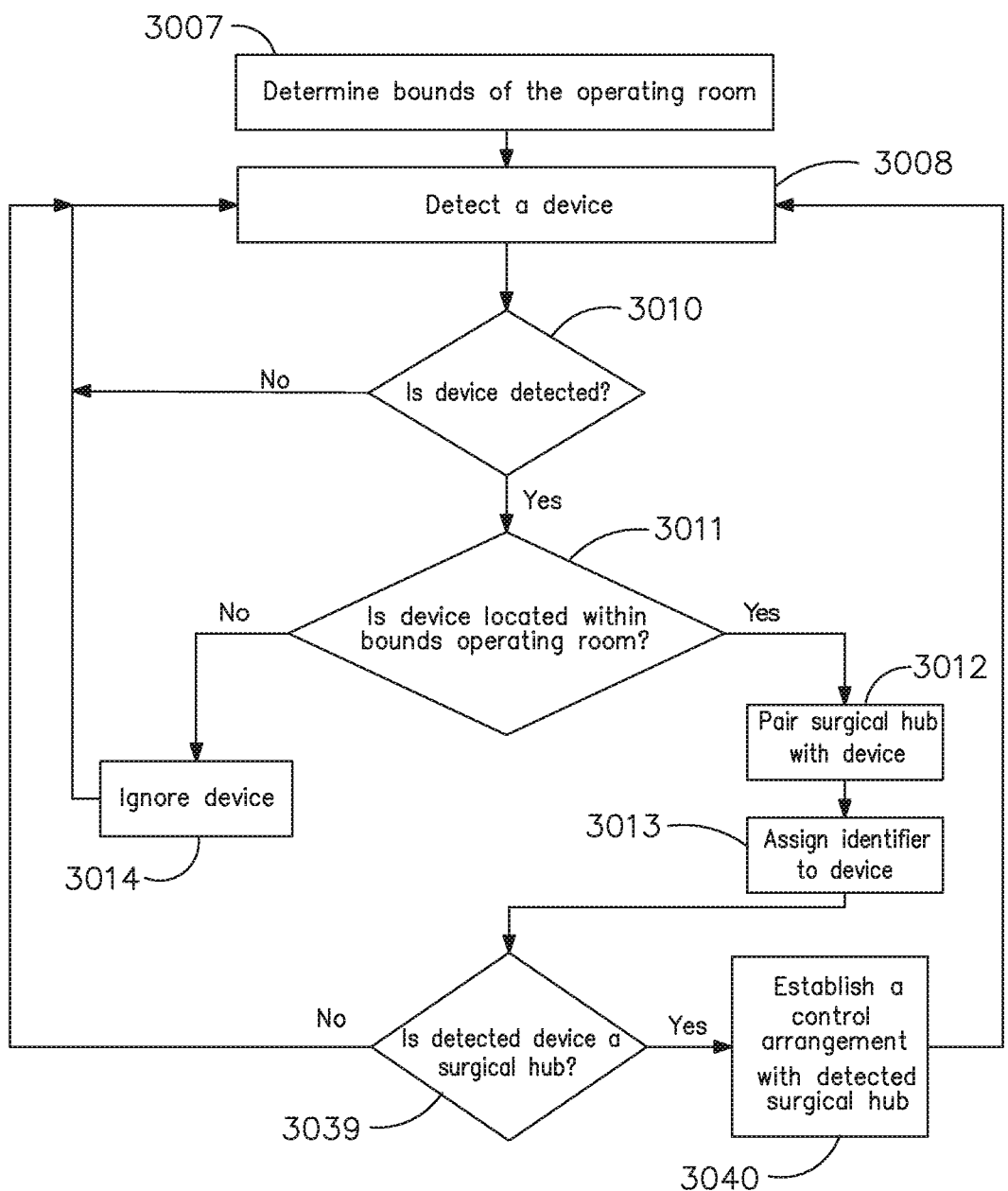
FIG. 53 is a logic flow diagram of a process depicting a control program or a logic configuration for coordinating a control arrangement between surgical hubs, in accordance with at least one aspect of the present disclosure.

FIG. 53 is a logic flow diagram of a process depicting a control program or a logic configuration for coordinating a control arrangement between surgical hubs. The process of FIG. 53 is similar in many respects to the process of FIG. 35 except that the process of FIG. 53 addresses detection of a surgical hub by another surgical hub. As illustrated in FIG. 53, the surgical hub 106 determines 3007 the bounds of the operating room. After the initial determination, the surgical hub 106 continuously searches for or detects 3008 devices within a pairing range. If a device is detected 3010, and if the detected device is located 3011 within the bounds of the operating room, the surgical hub 106 pairs 3012 with the device and assigns 3013 an identifier to the device. If through an initial interaction, as described below in greater detail, the surgical hub 106 determines 3039 that the device is another surgical hub, a control arrangement is established 3040 therebetween.

Figure 54:
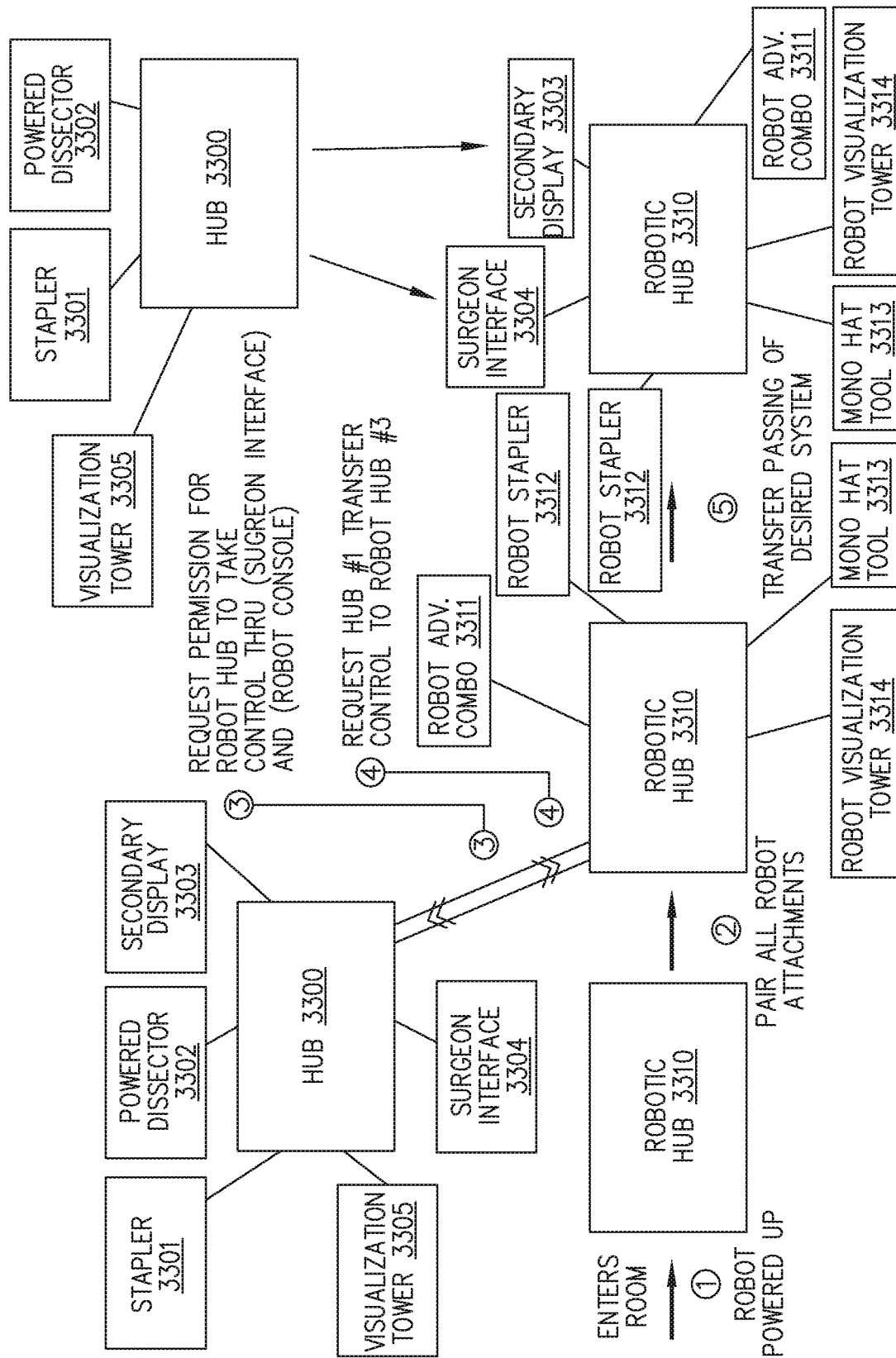
FIG. 54 illustrates an interaction between two surgical hubs in an operating room, in accordance with at least one aspect of the present disclosure.

Referring to FIG. 54, a robotic surgical hub 3300 enters an operating room already occupied by a surgical hub 3300. The robotic surgical hub 3310 and the surgical hub 3300 are similar in many respects to other surgical hubs described in greater detail elsewhere herein, such as, for example, the surgical hubs 106. For example, the robotic surgical hub 3310 includes non-contact sensors configured to measure the bounds of the operating room, as described in greater detail elsewhere herein in connection with FIGS. 33, 34.

As the robotic surgical hub 3310 is powered up, it determines the bounds of the operating room and begins to pair with other components of the surgical system 102 that are located within the bounds of the operating room. The robotic surgical hub 3310 pairs with a robotic advanced energy tool 3311, a robotic stapler 3312, a monopolar energy tool 3313, and a robotic visualization tower 3314, which are all located within the bounds of the operating room. The surgical hub 3300 is already paired with a handheld stapler 3301, a handheld powered dissector 3302, a secondary display 3303, a surgeon interface 3304, and a visualization tower 3305. Since the handheld stapler 3301, the handheld powered dissector 3302, the secondary display 3303, the surgeon interface 3304, and the visualization tower 3305 are already paired with the surgical hub 3300, such devices cannot pair with another surgical hub without permission from the surgical hub 3300.

Further to the above, the robotic surgical hub 3310 detects and/or is detected by the surgical hub 3300. A communication link is established between the communication modules of the surgical hubs 3300, 3310. The surgical hubs 3300, 3310 then determine the nature of their interaction by determining a control arrangement therebetween. In one aspect, the control arrangement can be a master-slave arrangement. In another aspect, the control arrangement can be a peer-to-peer arrangement.

In the example of FIG. 54, a master-slave arrangement is established. The surgical hubs 3300, 3310 request permission from a surgical operator for the robotic surgical hub 3310 to take control of the operating room from the surgical hub 3300. The permission can be requested through a surgeon interface or console 3304. Once permission is granted, the robotic surgical hub 3310 requests the surgical hub 3300 to transfer control to the robotic surgical hub 3310.

Alternatively, the surgical hubs 3300, 3310 can negotiate the nature of their interaction without external input based on previously gathered data. For example, the surgical hubs 3300, 3310 may collectively determine that the next surgical task requires use of a robotic system. Such determination may cause the surgical hub 3300 to autonomously surrender control of the operating room to the robotic surgical hub 3310. Upon completion of the surgical task, the robotic surgical hub 3310 may then autonomously return the control of the operating room to surgical hub 3300.

The outcome of the interaction between the surgical hubs 3300, 3310 is illustrated on the right of FIG. 54. The surgical hub 3300 has transferred control to the robotic surgical hub 3310, which has also taken control of the surgeon interface 3304 and the secondary display 3303 from the surgical hub 3300. The robotic surgical hub 3310 assigns new identification numbers to the newly transferred devices. The surgical hub 3300 retains control the handheld stapler 3301, the handheld powered dissector 3302, and visualization tower 3305. In addition, the surgical hub 3300 performs a supporting role, wherein the processing and storage capabilities of the surgical hub 3300 are now available to the robotic surgical hub 3310.

Figure 55:
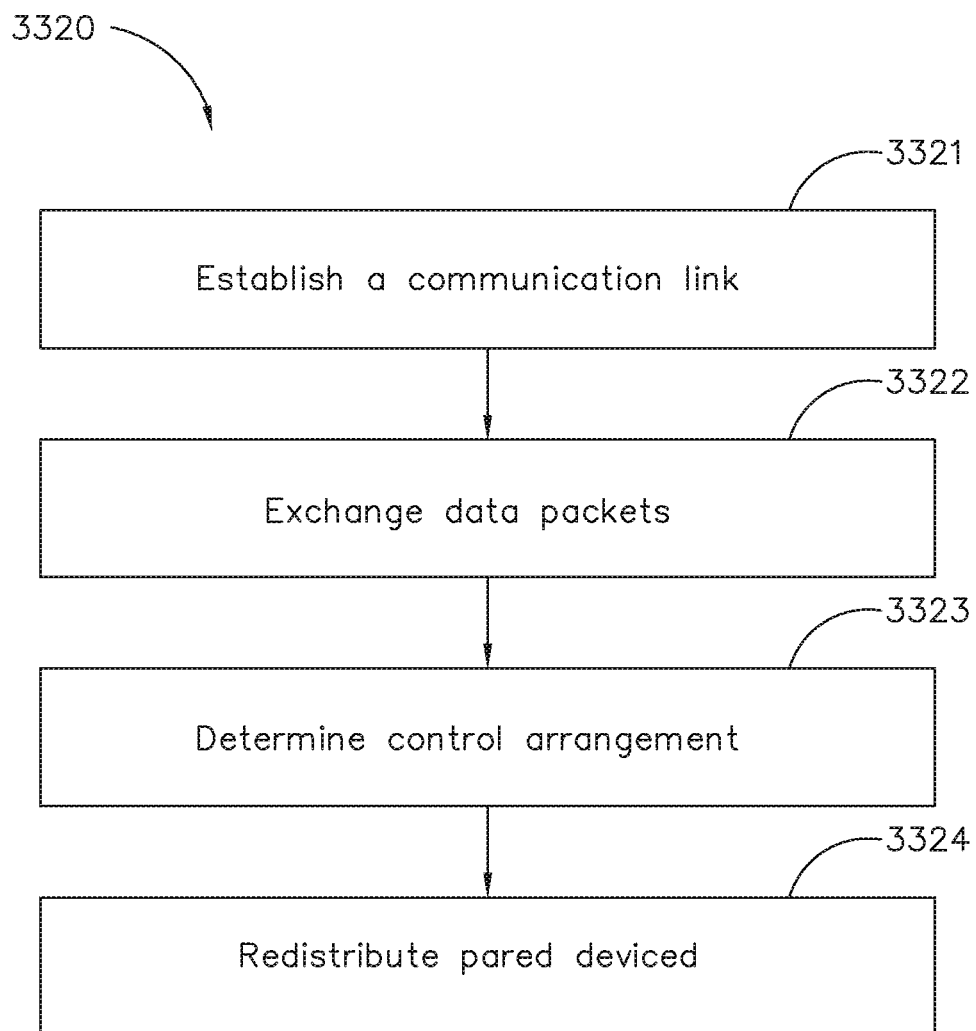
FIG. 55 is a logic flow diagram of a process depicting a control program or a logic configuration for coordinating a control arrangement between surgical hubs, in accordance with at least one aspect of the present disclosure.

FIG. 55 is a logic flow diagram of a process depicting a control program or a logic configuration for coordinating a control arrangement between surgical hubs. In various aspects, two independent surgical hubs will interact with one another in a predetermined manner to assess the nature of their relationship. In one example, after establishing 3321 a communication link, the surgical hubs exchange 3322 data packets. A data packet may include type, identification number, and/or status of a surgical hub. A data packet may further include a record of devices under control of the surgical hub and/or any limited communication connections, such as data ports for other secondary operating room devices.

The control arrangement between the surgical hubs is then determined 3323 based on input from a surgical operator or autonomously between the surgical hubs. The surgical hubs may store instructions as to how to determine a control arrangement therebetween. The control arrangement between two surgical hubs may depend on the type of surgical procedure being performed. The control arrangement between two surgical hubs may depend on their types, identification information, and/or status. The control arrangement between two surgical hubs may depend on the devices paired with the surgical hubs. The surgical hubs then redistribute 3324 the devices of the surgical system 102 therebetween based upon the determined control arrangement.

In the master-slave arrangement, the record communication can be unidirectional from the slave hub to the master hub. The master hub may also require the slave hub to hand-off some of its wireless devices to consolidate communication pathways. In one aspect, the slave hub can be relegated to a relay configuration with the master hub originating all commands and recording all data. The slave hub can remain linked to the master hub for a distributed sub-processing of the master hub commands, records, and/or controls. Such interaction expands the processing capacity of the dual linked hubs beyond the capabilities of the master hub by itself.

In a peer-to-peer arrangement, each surgical hub may retain control of its devices. In one aspect, the surgical hubs may cooperate in controlling a surgical instrument. In one aspect, an operator of the surgical instrument may designate the surgical hub that will control the surgical instrument at the time of its use.

Referring generally to FIGS. 56-61, the interaction between surgical hubs can be extended beyond the bounds of the operating room. In various aspects, surgical hubs in separate operating rooms may interact with one another within predefined limits. Depending on their relative proximity, surgical hubs in separate operating rooms may interact through any suitable wired or wireless data communication network such as Bluetooth and WiFi. As used here, a "data communication network" represents any number of physical, virtual, or logical components, including hardware, software, firmware, and/or processing logic configured to support data communication between an originating component and a destination component, where data communication is carried out in accordance with one or more designated communication protocols over one or more designated communication media.

In various aspects, a first surgical operator in a first operating room may wish to consult a second surgical operator in a second operating room, such as in case of an emergency. A temporary communication link may be established between the surgical hubs of the first and second operating room to facilitate the consult while the first and second surgical operators remain in their respective operating rooms.

The surgical operator being consulted can be presented with a consult request through the surgical hub in his/her operating room. If the surgical operator accepts, he/she will have access to all the data compiled by the surgical hub requesting the consult. The surgical operator may access all previously stored data, including a full history of the procedure. In addition, a livestream of the surgical site at the requesting operating room can be transmitted through the surgical hubs to a display at the receiving operating room.

When a consult request begins, the receiving surgical hub begins to record all received information in a temporarily storage location, which can be a dedicated portion of the storage array of the surgical hub. At the end of the consult, the temporary storage location is purged from all the information. In one aspect, during a consult, the surgical hub records all accessible data, including blood pressure, ventilation data, oxygen stats, generator settings and uses, and all patient electronic data. The recorded data will likely be more than the data stored by the surgical hub during normal operation, which is helpful in providing the surgical operator being consulted with as much information as possible for the consult.

Referring to FIG. 56, a non-limiting example of an interaction between surgical hubs in different operating rooms is depicted. FIG. 56 depicts an operating room OR 1 that includes a surgical system 3400 supporting a thoracic segmentectomy and a second operating room OR 3 that includes a surgical system 3410 supporting a colorectal procedure. The surgical system 3400 includes surgical hub 3401, surgical hub 3402, and robotic surgical hub 3403. The surgical system 3400 further includes a personal interface 3406, a primary display 3408, and secondary displays 3404, 3405. The surgical system 3410 includes a surgical hub 3411 and a secondary display 3412. For clarity, several components of the surgical systems 3400, 3410 are removed.

In the example of FIG. 56, the surgical operator of OR 3 is requesting a consult from the surgical operator of OR 1. A surgical hub 3411 of the OR 3 transmits the consult request to one of the surgical hubs of the OR 1, such as the surgical hub 3401. In OR 1, the surgical hub 3401 presents the request at a personal interface 3406 held by the surgical operator. The consult is regarding selecting an optimal location of a colon transection. The surgical operator of OR 1, through a personal interface 3406, recommends an optimal location for the transection site that avoids a highly vascular section of the colon. The recommendation is transmitted in real time through the surgical hubs 3401, 3411. Accordingly, the surgical operator is able to respond to the consult request in real time without having to leave the sterile field of his own operating room. The surgical operator requesting the consult also did not have to leave the sterile field of OR 3.

If the surgical hub 3401 is not in communication with the personal interface 3406, it may relay the message to another surgical hub such as, for example, the surgical hub 3402 or the robotic surgical hub 3403. Alternatively, the surgical hub 3401 may request control of the personal interface 3406 from another surgical hub.

Figure 57:
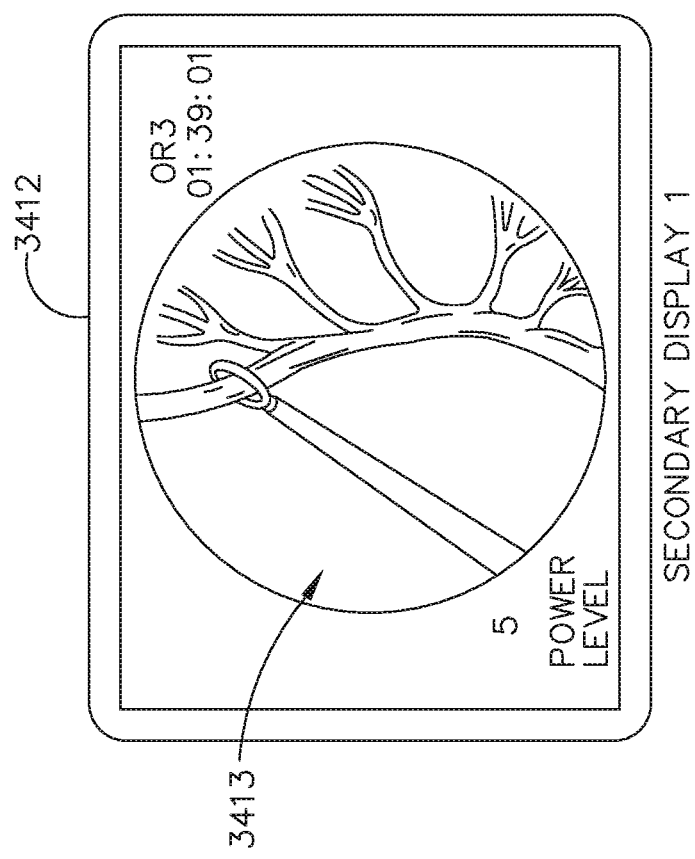
FIG. 57 illustrates a secondary display in an operating room ("OR3") showing a surgical site in a colorectal procedure, in accordance with at least one aspect of the present disclosure.
Figure 58:
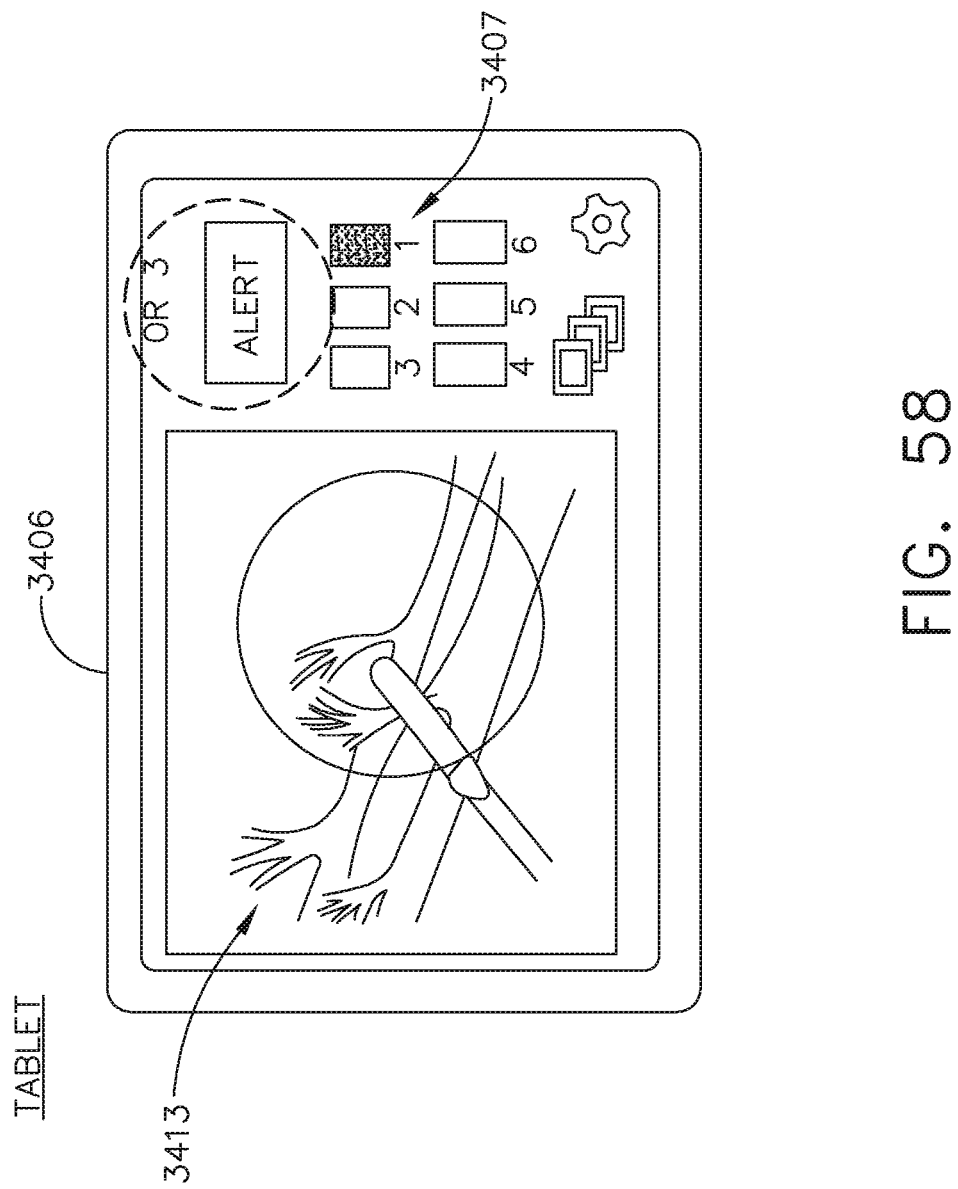
FIG. 58 illustrates a personal interface or tablet in OR1 displaying the surgical site of OR3, in accordance with at least one aspect of the present disclosure.

In any event, if the surgical operator of OR 1 decides to accept the consult request, a livestream, or frames, of a surgical site 3413 of the colorectal procedure of OR 3 is transmitted to OR 1 through a connection established between the surgical hubs 3401, 3411, for example. FIG. 57 illustrates a livestream of the surgical site 3413 displayed on a secondary display of OR 3. The surgical hubs 3401, 3411 cooperate to transmit the livestream of the surgical site of OR 3 to the personal interface 3406 of the OR 1, as illustrated in FIG. 58.

Figure 59:
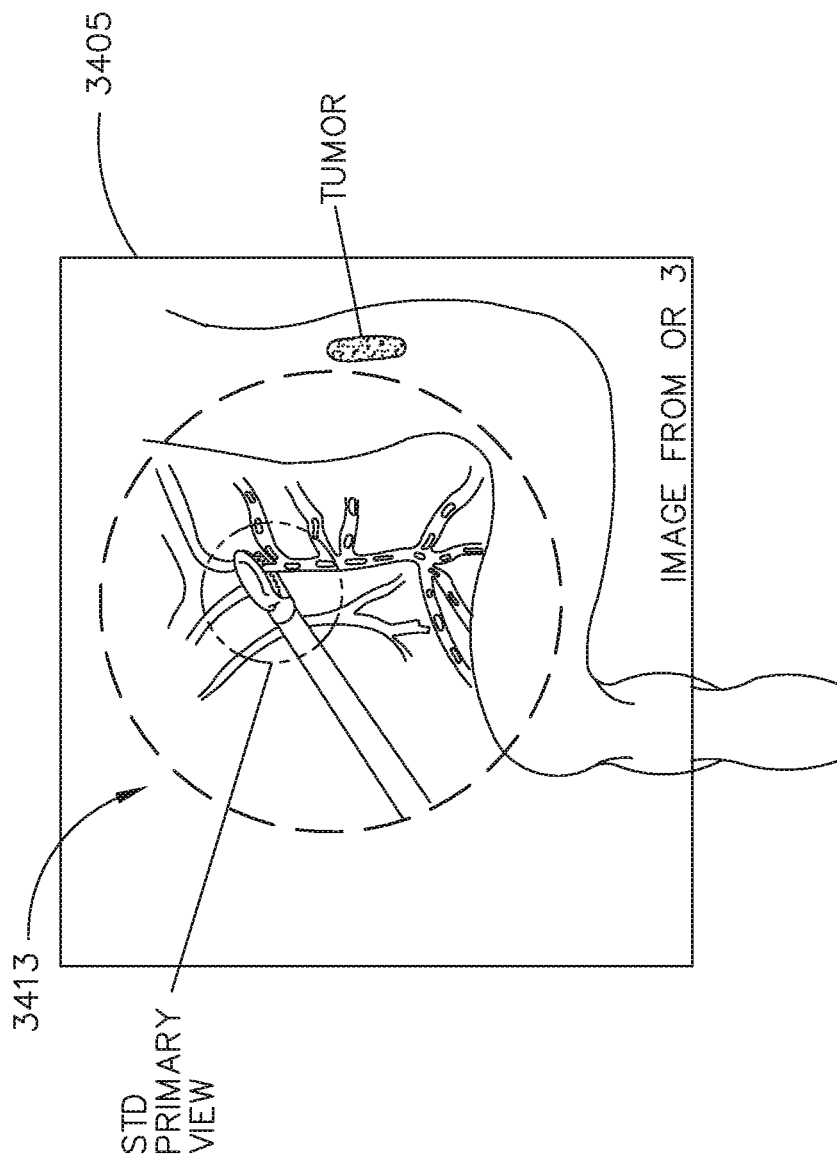
FIG. 59 illustrates an expanded view of the surgical site of OR3 displayed on a primary display of OR1, in accordance with at least one aspect of the present disclosure.
Figure 60:
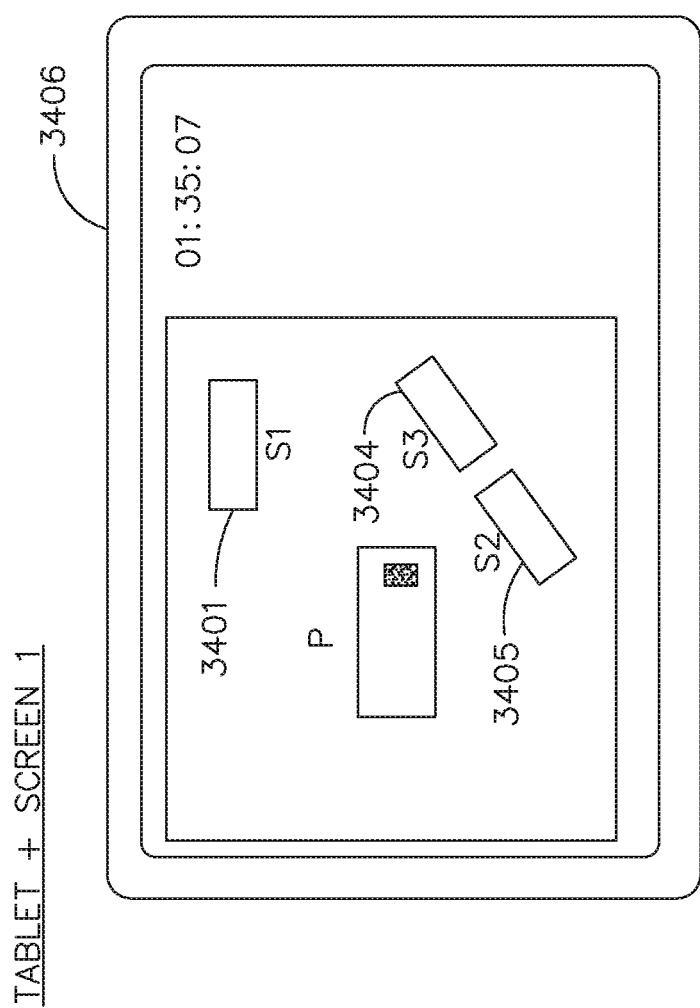
FIG. 60 illustrates a personal interface or tablet displaying a layout of OR1 that shows available displays, in accordance with at least one aspect of the present disclosure.
Figure 61:
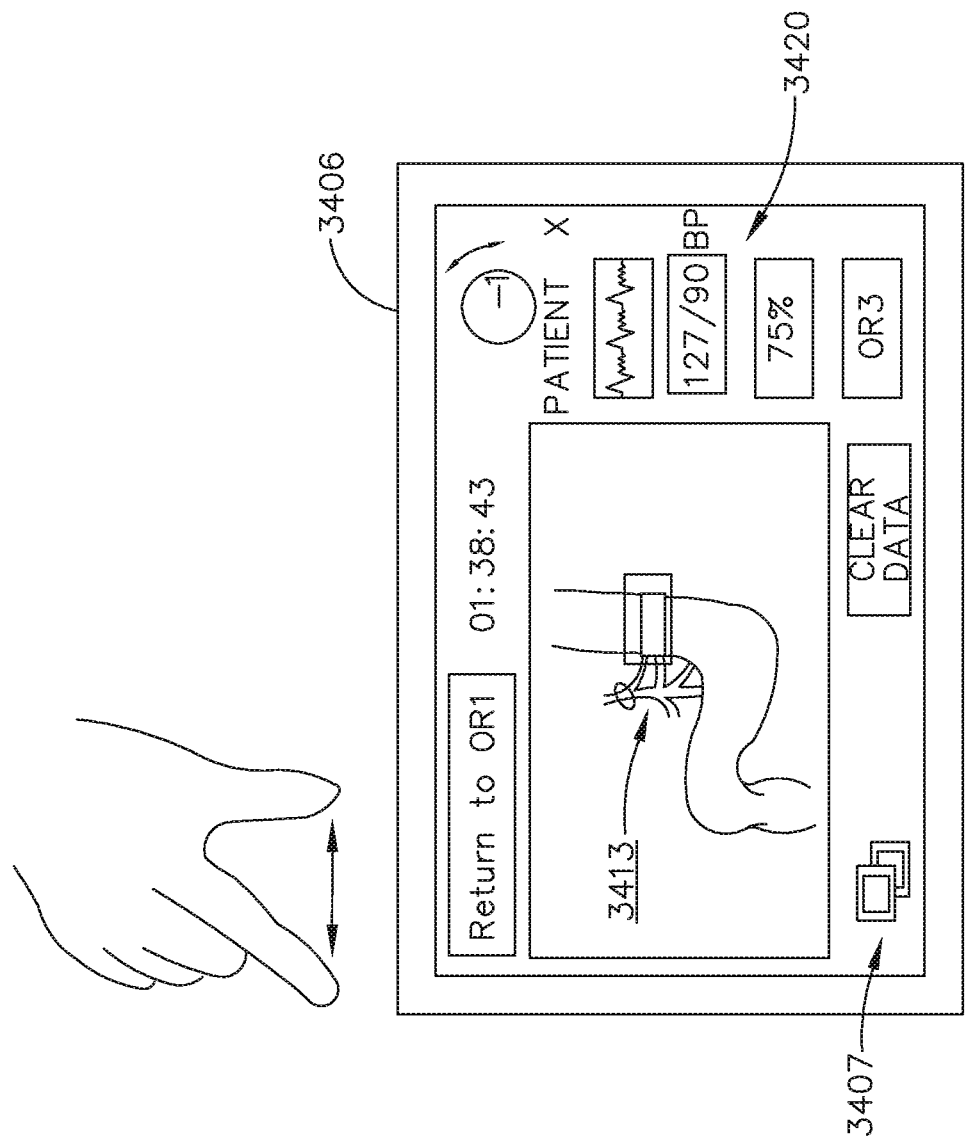
FIG. 61 illustrates a recommendation of a transection location of a surgical site of OR3 made by a surgical operator in OR1 via a personal interface or tablet in OR1, in accordance with at least one aspect of the present disclosure.

Referring to FIGS. 59-61, the surgical operator may expand the laparoscopic livestream from OR 3 onto the primary display 3405 in OR 1, for example, through the controls of the personal interface 3406. The personal interface 3406 allows the surgical operator to select a destination for the livestream by presenting the surgical operator with icons that represent the displays that are available in OR 1, as illustrated in FIG. 60. Other navigation controls 3407 are available to the surgical operator through the personal interface 3406, as illustrated in FIG. 61. For example, the personal interface 3406 includes navigation controls for adjusting the livestream of the surgical site of OR 3 in OR 1 by the surgical operator moving his or her fingers on the livestream displayed on the personal interface 3406. To visualize the high vasculature regions, the consulted surgical operator may change the view of the livestream from OR 3 through the personal interface 3406 to an advanced imaging screen. The surgical operator may then manipulate the image in multiple planes to see the vascularization using a wide-angle multi-spectral view, for example.

As illustrated in FIG. 61, the surgical operator also has access to an array of relevant information 3420, such as, for example, heart rate, blood pressure, ventilation data, oxygen stats, generator settings and uses, and all patient electronic data of the patient in OR 3.

Data Management and Collection

In one aspect the surgical hub provides data storage capabilities. The data storage includes creation and use of self-describing data including identification features, management of redundant data sets, and storage of the data in a manner of paired data sets which can be grouped by surgery but not necessarily keyed to actual surgical dates and surgeons to maintain data anonymity. The following description incorporates by reference all of the "hub" and "cloud" analytics system hardware and software processing techniques to implement the specific data management and collection techniques described hereinbelow, as incorporated by reference herein. FIGS. 62-80 will be described in the context of the interactive surgical system 100 environment including a surgical hub 106, 206 described in connection FIGS. 1-11 and intelligent instruments and generators described in connection with FIGS. 12-21.

Electronic Medical Record (EMR) Interaction

Figure 62:
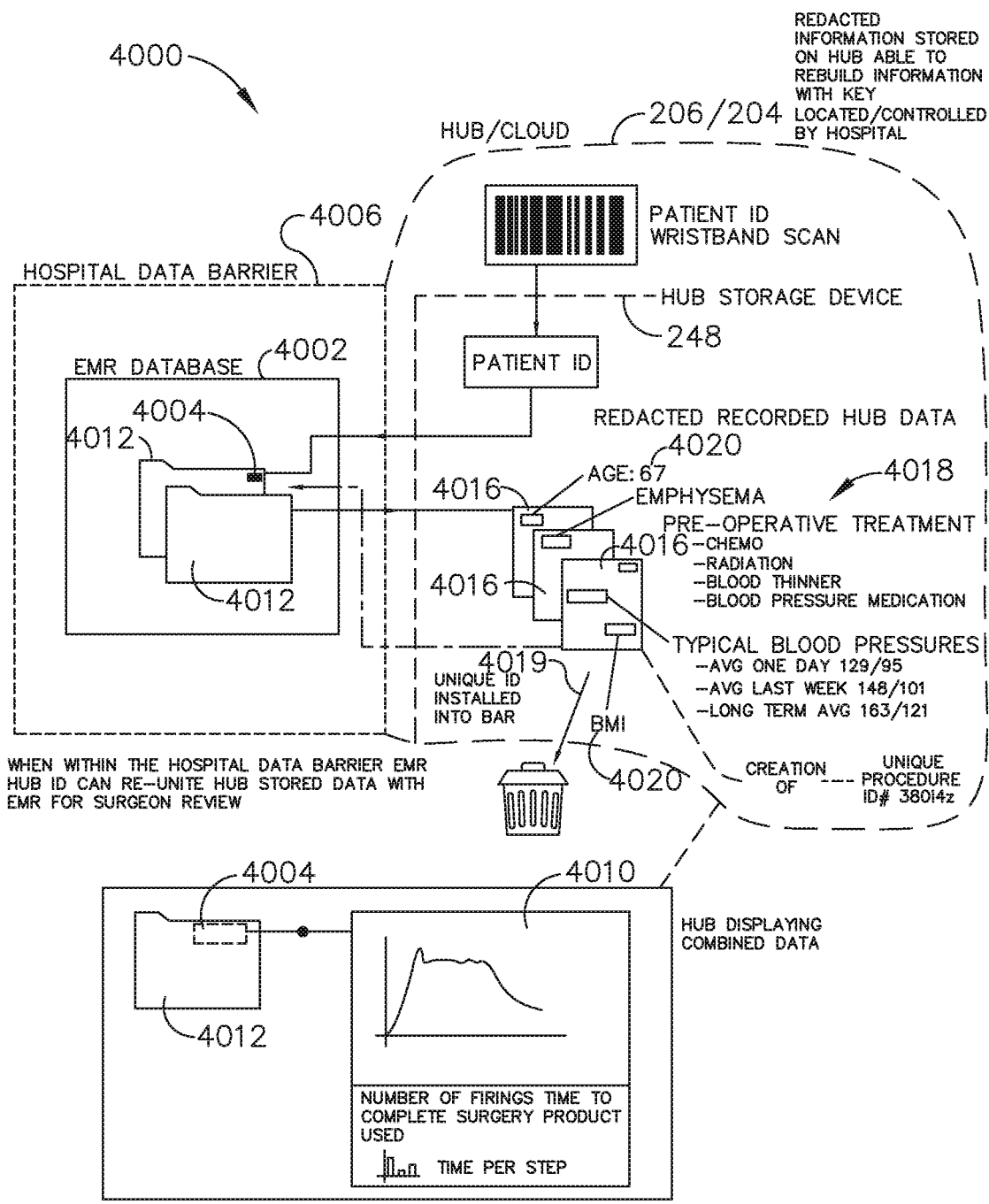
FIG. 62 is a diagram illustrating a technique for interacting with a patient Electronic Medical Record (EMR) database, in accordance with at least one aspect of the present disclosure.

FIG. 62 is a diagram 4000 illustrating a technique for interacting with a patient Electronic Medical Record (EMR) database 4002, according to one aspect of the present disclosure. In one aspect, the present disclosure provides a method of embedding a key 4004 within the EMR database 4002 located within the hospital or medical facility. A data barrier 4006 is provided to preserve patient data privacy and allows the reintegration of stripped and isolated data pairs, as described hereinbelow, from the surgical hub 106, 206 or the cloud 104, 204, to be reassembled. A schematic diagram of the surgical hub 206 is described generally in FIGS. 1-11 and in particular in FIGS. 9-10. Therefore, in the description of FIG. 62, the reader is guided to FIG. 1-11 and in particular FIGS. 9-10 for any implementation details of the surgical hub 206 that may be omitted here for conciseness and clarity of disclosure. Returning to FIG. 62, the method allows the users full access to all the data collected during a surgical procedure and patient information stored in the form of electronic medical records 4012. The reassembled data can be displayed on a monitor 4010 coupled to the surgical hub 206 or secondary monitors but is not permanently stored on any surgical hub storage device 248. The reassembled data is temporarily stored in a storage device 248 located either in the surgical hub 206 or the cloud 204 and is deleted at the end of its use and overwritten to insure it cannot be recovered. The key 4004 in the EMR database 4002 is used to reintegrate anonymized hub data back into full integrated patient electronic medical records 4012 data.

As shown in FIG. 62, the EMR database 4002 is located within the hospital data barrier 4006. The EMR database 4002 may be configured for storing, retrieving, and managing associative arrays, or other data structures known today as a dictionary or hash. Dictionaries contain a collection of objects, or records, which in turn have many different fields within them, each containing data. The patient electronic medical records 4012 may be stored and retrieved using a key 4004 that uniquely identifies the patient electronic medical record 4012, and is used to quickly find the data within the EMR database 4002. The key-value EMR database 4002 system treats the data as a single opaque collection which may have different fields for every record.

Information from the EMR database 4002 may be transmitted to the surgical hub 206 and the patient electronic medical records 4012 data is redacted and stripped before it is sent to an analytics system based either on the hub 206 or the cloud 204. An anonymous data file 4016 is created by redacting personal patient data and stripping relevant patient data 4018 from the patient electronic medical record 4012. As used herein, the redaction process includes deleting or removing personal patient information from the patient electronic medical record 4012 to create a redacted record that includes only anonymous patient data. A redacted record is a record from which sensitive patient information has been expunged. Un-redacted data may be deleted 4019. The relevant patient data 4018 may be referred to herein as stripped/extracted data 4018. The relevant patient data 4018 is used by the surgical hub 206 or cloud 204 processing engines for analytic purposes and may be stored on the storage device 248 of the surgical hub 206 or may be stored on the cloud 204 based analytics system storage device 205. The surgical hub anonymous data file 4016 can be rebuilt using a key 4004 stored in the EMR database 4002 to reintegrate the surgical hub anonymous data file 4016 back into a fully integrated patient electronic medical record 4012. The relevant patient data 4018 that is used in analytic processes may include information such as the patient's diagnoses of emphysema, pre-operative treatment (e.g., chemotherapy, radiation, blood thinner, blood pressure medication, etc.), typical blood pressures, or any data that alone cannot be used to ascertain the identity of the patient. Data 4020 to be redacted includes personal information removed from the patient electronic medical record 4012, may include age, employer, body mass index (BMI), or any data that can be used to ascertain the identify of the patient. The surgical hub 206 creates a unique anonymous procedure ID number (e.g., 380i4z), for example, as described in FIG. 63. Within the EMR database 4002 located in the hospital data barrier 4006, the surgical hub 206 can reunite the data in the anonymous data file 4016 stored on the surgical hub 206 storage device 248 with the data in the patient electronic medical record 4012 stored on the EMR database 4002 for surgeon review. The surgical hub 206 displays the combined patient electronic medical record 4012 on a display or monitor 4010 coupled to the surgical hub 206. Ultimately, un-redacted data is deleted 4019 from the surgical hub 206 storage 248.

Creation of a Hospital Data Barrier, Inside which the Data from Hubs can be Compared Using Non-Anonymized Data and Outside of which the Data has to be Stripped In one aspect, the present disclosure provides a surgical hub 206 as described in FIGS. 9 and 10, for example, where the surgical hub 206 comprises a processor 244; and a memory 249 coupled to the processor 244. The memory 249 stores instructions executable by the processor 244 to interrogate a surgical instrument 235, retrieve a first data set from the surgical instrument 235, interrogate a medical imaging device 238, retrieve a second data set from the medical imaging device 238, associate the first and second data sets by a key, and transmit the associated first and second data sets to a remote network, e.g., the cloud 204, outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

In another aspect, the first and second data sets define first and second data payloads in respective first and second data packets.

In various aspects, the present disclosure provides a control circuit to associate the first and second data sets by a key as described above. In various aspects, the present disclosure provides a non-transitory computer readable medium storing computer readable instructions which, when executed, causes a machine to associate the first and second data sets by a key as described above.

During a surgical procedure it would be desirable to monitor data associated with the surgical procedure to enable configuration and operation of instruments used during the procedure to improve surgical outcomes. The technical challenge is to retrieve the data in a manner that maintains the anonymity of the patient to maintain privacy of the data associated with the patient. The data may be used for conglomeration with other data without individualizing the data.

One solution provides a surgical hub 206 to interrogate an electronic medical records database 4002 for patient electronic medical records 4012 data, strip out desirable or relevant patient data 4018 from the patient electronic medical record 4012, and redact any personal information that could be used to identify the patient. The redaction technique removes any information that could be used to correlate the stripped relevant patient data 4018 to a specific patient, surgery, or time. The surgical hub 206 and the instruments 235 coupled to the surgical hub 206 can then be configured and operated based on the stripped relevant patient data 4018.

As disclosed in connection with FIG. 62, extracting (or stripping) relevant patient data 4018 from a patient electronic medical record 4012 while redacting any information that can be used to correlate the patient with the surgery or a scheduled time of the surgery enables the relevant patient data 4018 to be anonymized. The anonymous data file 4016 can then be sent to the cloud 204 for aggregation, processing, and manipulation. The anonymous data file 4016 can be used to configure the surgical instrument 235, or any of the modules shown in FIGS. 9 and 10 or the surgical hub 206 during the surgery based on the extracted anonymous data file 4016.

In one aspect, a hospital data barrier 4006 is created such that inside the data barrier 4006 data from various surgical hubs 206 can be compared using non-anonymized unredacted data and outside the data barrier 4006 data from various surgical hubs 206 are stripped to maintain anonymity and protect the privacy of the patient and the surgeon. This aspect is discussed further in connection with FIG. 66.

In one aspect, the data from a surgical hub 206 can be exchanged between surgical hubs 206 (e.g., hub-to-hub, switch-to-switch, or router-to-router) to provide in-hospital analysis and display of the data. FIG. 1 shows an example of multiple hubs 106 in communication which each other and with the cloud 104. This aspect also is discussed further in connection with FIG. 66.

In another aspect, an artificial time measure is substituted for a real time clock for all information stored internally within an instrument 235, a robot located in a robot hub 222, a surgical hub 206, and/or hospital computer equipment. The anonymized data, which may include anonymized patient and surgeon data, is transmitted to the server 213 in the cloud 204 and it is stored in the cloud storage device 205 coupled to the server 213. The substitution of an artificial real time clock enables anonymizing the patient data and surgeon data while maintaining data continuity. In one aspect, the instrument 235, robot hub 222, surgical hub 206, and/or the cloud 204 are configured to obscure patient identification (ID) while maintaining data continuity. This aspect is discussed further in connection with FIG. 63.

Within the surgical hub 206, a local decipher key 4004 allows information retrieved from the surgical hub 206 itself to reinstate the real-time information from the anonymized data set located in the anonymous data file 4016. The data stored on the hub 206 or the cloud 204, however, cannot be reinstated to real-time information from the anonymized data set in the anonymous data file 4016. The key 4004 is held locally in the surgical hub 206 computer/storage device 248 in an encrypted format. The surgical hub 206 network processor ID is part of the decryption mechanism such that if the key 4004 and data is removed, the anonymized data set in the anonymous data file 4016 cannot be restored without being on the original surgical hub 206 computer/storage device 248.

Figure 63:
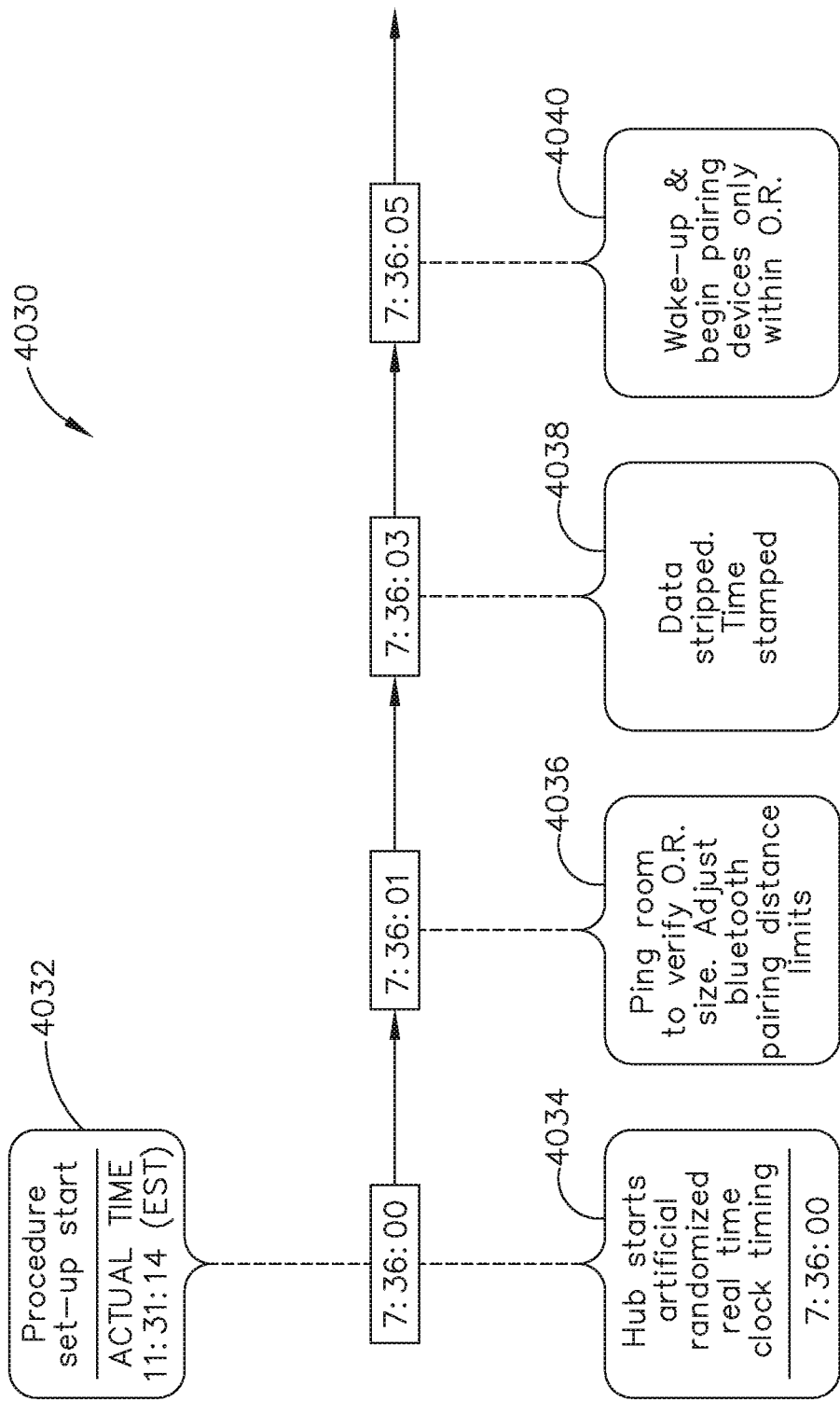
FIG. 63 illustrates a process of anonymizing a surgical procedure by substituting an artificial time measure for a real time clock for all information stored internally within the instrument, robot, surgical hub, and/or hospital computer equipment, in accordance with at least one aspect of the present disclosure.

Substituting Artificial Time Measure for Real Time Clock for all Internally Stored Information and Sent to the Cloud as a Means to Anonymizing the Patient and Surgeon Data FIG. 63 illustrates a process 4030 of anonymizing a surgical procedure by substituting an artificial time measure for a real time clock for all information stored internally within the instrument, robot, surgical hub, and/or hospital computer equipment, according to one aspect of the present disclosure. As shown in FIG. 63, the surgical procedure set-up start time 4032 was scheduled to begin at an actual time of 11:31:14 (EST) based on a real time clock. At the stated procedure set-up start time 4032, the surgical hub 206 starts 4034 an artificial randomized real time clock timing scheme at artificial real time of 07:36:00. The surgical hub 206 then ultrasonically pings 4036 the operating theater (e.g., sends out a burst of ultrasound and listens for the echo when it bounces off the perimeter walls of an operating theater (e.g., a fixed, mobile, temporary, or field the operating room) as described in connection with FIG. 64 to verify the size of the operating theater and to adjust short range wireless, e.g., Bluetooth, pairing distance limits at artificial real time 07:36:01. At artificial real time 07:36:03, the surgical hub 206 strips 4038 the relevant data and applies a time stamp to the stripped data. At artificial real time 07:36:05, the surgical hub 206 wakes up and begins pairing 4040 only devices located within the operating theater as verified using the ultrasonic pinging 4036 process.

Figure 64:
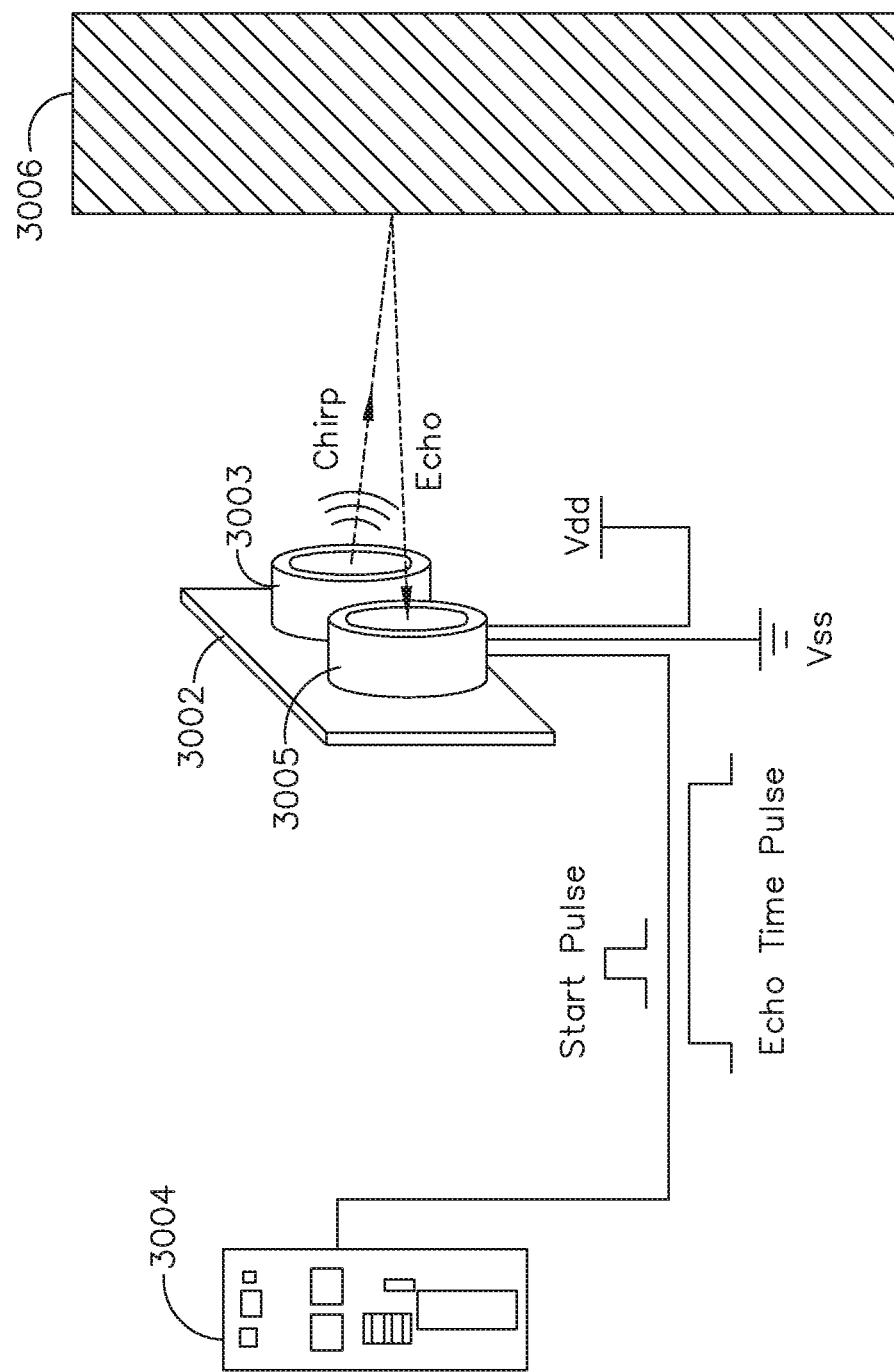
FIG. 64 illustrates ultrasonic pinging of an operating room wall to determine a distance between a surgical hub and the operating room wall, in accordance with at least one aspect of the present disclosure.

FIG. 64 illustrates ultrasonic pinging of an operating room wall to determine a distance between a surgical hub and the operating room wall, in accordance with at least one aspect of the present disclosure. With reference also to FIG. 2, the spatial awareness of the surgical hub 206 and its ability to map an operating room for potential components of the surgical system allows the surgical hub 206 to make autonomous decisions about whether to include or exclude such potential components as part of the surgical system, which relieves the surgical staff from dealing with such tasks. Furthermore, the surgical hub 206 is configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation.

In one aspect, the surgical hub 206 employs the operating-room mapping module, such as, for example, the non-contact sensor module 242 to determine the bounds of the surgical theater (e.g., a fixed, mobile, or temporary operating room or space) using either ultrasonic or laser non-contact measurement devices.

Referring now to FIG. 64, ultrasound based non-contact sensors 3002 can be employed to scan the operating theater by transmitting a burst of ultrasound and receiving the echo when it bounces off a perimeter wall 3006 of an operating theater to determine the size of the operating theater and to adjust short range wireless, e.g., Bluetooth, pairing distance limits. In one example, the non-contact sensors 3002 can be Ping ultrasonic distance sensors, as illustrated in FIG. 64.

FIG. 64 shows how an ultrasonic sensor 3002 sends a brief chirp with its ultrasonic speaker 3003 and makes it possible for a micro-controller 3004 of the operating-room mapping module to measure how long the echo takes to return to the ultrasonic sensor's ultrasonic microphone 3005. The micro-controller 3004 has to send the ultrasonic sensor 3002 a pulse to begin the measurement. The ultrasonic sensor 3002 then waits long enough for the micro-controller program to start a pulse input command. Then, at about the same time the ultrasonic sensor 3002 chirps a 40 kHz tone, it sends a high signal to the micro-controller 3004. When the ultrasonic sensor 3002 detects the echo with its ultrasonic microphone 3005, it changes that high signal back to low. The micro-controller's pulse input command measures the time between the high and low changes, and stores it measurement in a variable. This value can be used along with the speed of sound in air to calculate the distance between the surgical hub 106 and the operating-room wall 3006.

In one example, a surgical hub 206 can be equipped with four ultrasonic sensors 3002, wherein each of the four ultrasonic sensors is configured to assess the distance between the surgical hub 206 and a wall of the operating room 3000. A surgical hub 206 can be equipped with more or less than four ultrasonic sensors 3002 to determine the bounds of an operating room.

Other distance sensors can be employed by the operating-room mapping module to determine the bounds of an operating room. In one example, the operating-room mapping module can be equipped with one or more photoelectric sensors that can be employed to assess the bounds of an operating room. In one example, suitable laser distance sensors can also be employed to assess the bounds of an operating room. Laser based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust short range wireless, e.g., Bluetooth, pairing distance limits.

Stripping Out Data from Images and Connected Smart Instrument Data to Allow Conglomeration but not Individualization In one aspect, the present disclosure provides a data stripping method which interrogates the electronic patient records provided, extracts the relevant portions to configure and operate the surgical hub and instruments coupled to the surgical hub, while anonymizing the surgery, patient, and all identifying parameters to maintain patient privacy.

With reference now back to FIG. 63 and also to FIGS. 1-11 to show interaction with an interactive surgical system 100 environment including a surgical hub 106, 206, once the size of the operating theater has been verified and Bluetooth pairing is complete, based on artificial real time, the computer processor 244 of the surgical hub 206 begins stripping 4038 data received from the modules coupled to the surgical hub 206. In one example, the processor 244 begins stripping 4083 images received from the imaging module 238 and connected smart instruments 235, for example. Stripping 4038 the data allows conglomeration of the data but not individualization of the data. This enables stripping 4038 the data identifier, linking the data, and monitoring an event while maintaining patient privacy by anonymizing the data.

With reference to FIGS. 1-64, in one aspect, a data stripping 4038 method is provided. In accordance with the data stripping 4038 method, the surgical hub 206 processor 244 interrogates the patient records stored in the surgical hub database 238 and extracts the relevant portions of the patient records to configure and operate the surgical hub 206 and its instruments 235, robots, and other modular devices, e.g., modules. The data stripping 4038 method anonymizes the surgical procedure, patient, and all identifying parameters associated with the surgical procedure. Stripping 4038 the data on the fly ensures that at no time the data is correlated to a specific patient, surgical procedure, surgeon, time or other possible identifier that can be used to correlate the data.

The data may be stripped 4038 for compilation of the base information at a remote cloud 204 database storage device 205 coupled to the remote server 213. The data stored in the database storage device 248 can be used in advanced cloud based analytics, as described in U.S. Provisional Patent Application Ser. No. 62/611,340, filed Dec. 28, 2017, titled CLOUD-BASED MEDICAL ANALYTICS, which is incorporated herein by reference in its entirety. A copy of the information with data links intact also can be stored into the patient EMR database 4002 (FIG. 62). For example, the surgical hub 206 may import patient tissue irregularities or co-morbidities to add to an existing data set stored in the database 248. The data may be stripped 4038 before the surgery and/or may be stripped 4038 as the data is transmitted to the cloud 204 database storage device 205 coupled to the remote server 213.

Figure 65:
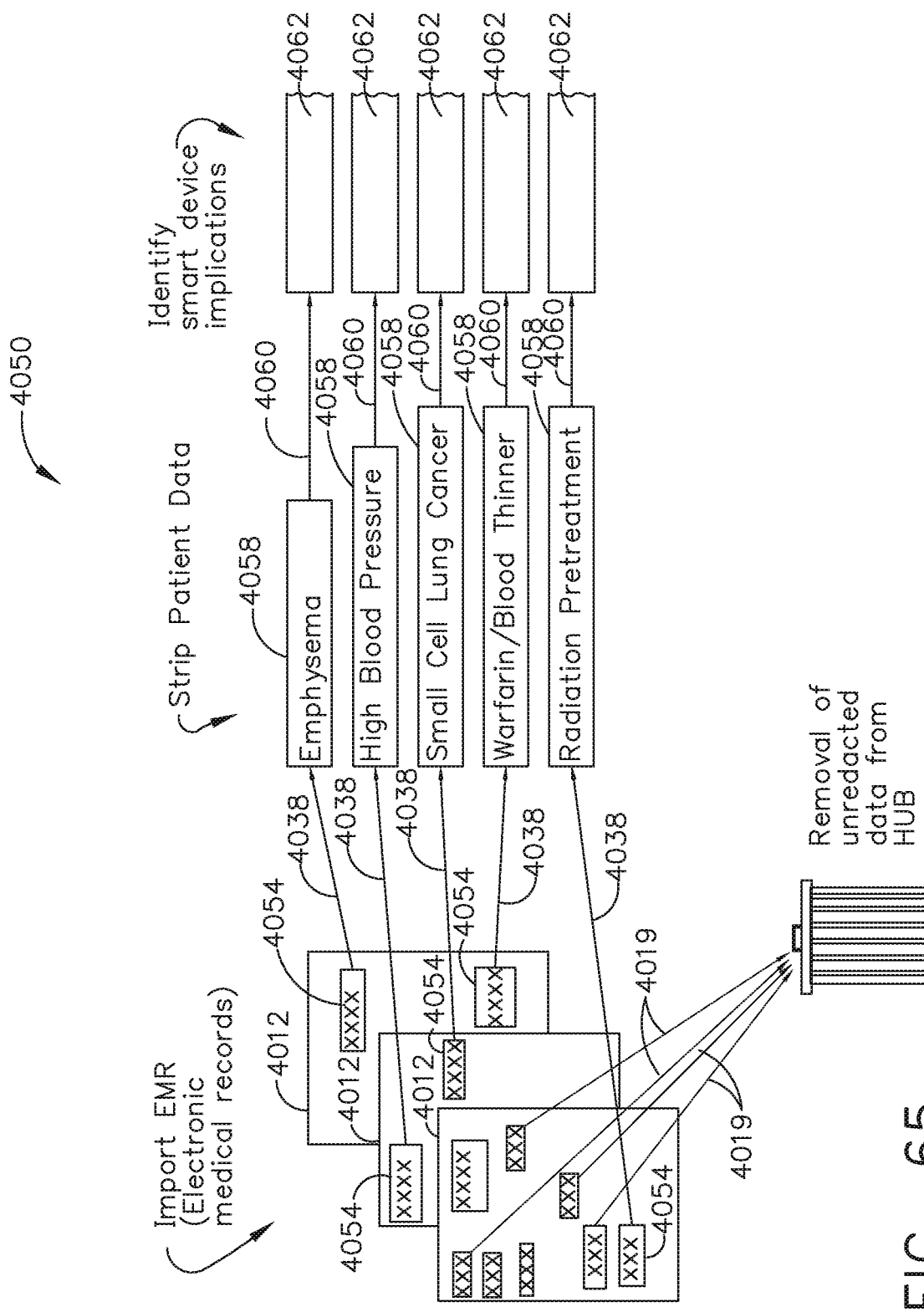
FIG. 65 illustrates a diagram depicting the process of importing patient data stored in an Electronic Medical Record (EMR) database, stripping the patient data, and identifying smart device implications, in accordance with at least one aspect of the present disclosure.

With continued reference to FIGS. 1-11 and 62-64, FIG. 65 is a diagram 4050 depicting the process of importing patient electronic medical records 4012 containing surgical procedure and relevant patient data 4018 stored in the EMR database 4002, stripping 4038 the relevant patient data 4018 from the imported medical records 4012, and identifying 4060 smart device implications 4062, or inferences, according to one aspect of the present disclosure. As shown in FIG. 65, the patient electronic medical records 4012, containing information stored in the patient EMR database 4002, are retrieved from the EMR database 4002, imported into the surgical hub 206, and stored in the surgical hub 206 storage device 248. Un-redacted data is removed or deleted 4019 from the patient electronic medical records 4012 before they are stored in the surgical hub 206 storage device 248 as an anonymous data file 4016 (FIG. 62). The relevant patient data 4018 is then stripped 4038 from the medical records 4012 to remove the desired relevant patient data 4018 and delete 4019 un-redacted data to maintain patient anonymity. In the illustrated example, the stripped data 4058 includes emphysema, high blood pressure, small lung cancer, warfarin/blood thinner, and/or radiation pretreatment. The stripped data 4058 is employed to identify 4060 smart device implications while maintaining patient anonymity as described hereinbelow.

Although the surgical procedure data and relevant patient data 4018 is described as being imported from patient electronic medical records 4012 stored in the EMR database 4002, in various aspects, the surgical procedure data and relevant patient data 4018 may be retrieved from a modular device coupled to the surgical hub 206 before being stored in the EMR database 4002. For example, the surgical hub 206 may interrogate the module to retrieve the surgical procedure data and relevant patient data 4018 from the module. As described herein, a module includes an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242, among other modules as illustrated in FIGS. 3 and 8-10.

For example, the anonymized stripped data 4058 may be employed to identify 4060 catastrophic failures of instruments, and other smart devices, and may initiate an automatic archive process and submission of data for further implications analysis. For example, the implication of detecting a counterfeit component or adapter on an original equipment manufacturer (OEM) device would be to initiate documentation of the component and recording of the results and outcome of its use. For example, the surgical hub 206 may execute situational awareness algorithms as described in connection FIG. 86. In one aspect, the surgical hub 206 may initially receive or identify a variety of implications 4062 that are derived from anonymized stripped data 4058. The surgical hub 206 is configured to control the instruments 235, or other modules, so that they operate correspondingly to the derived implications 4062. In one example, the surgical hub 206 control logic identifies that (i) lung tissue may be more fragile than normal (e.g., due to emphysema), (ii) hemostasis issues are more likely (e.g., due to high blood pressure and/or the patient being on a blood thinner, such as warfarin), (iii) cancer may be more aggressive (e.g., due to the target of the procedure being a small cell lung cancer), and (iv) lung tissue may be stiffer and more prone to fracture (e.g., due to the patient having received a radiation pretreatment). The control logic or processor 244 of the surgical hub 206 then interprets how this data impacts the instruments 235, or other modules, so that the instruments 235 are operated consistently with the data and then communicates the corresponding adjustments to each of the instruments 235.

In one example relating to a stapler type of surgical instrument 235, based on the implications 4062 identified 4060 from the anonymized stripped data 4058, the control logic or processor 244 of the surgical hub 206 may (i) notify the stapler to adjust the compression rate threshold parameter, (ii) adjust the surgical hub 206 visualization threshold value to quantify the bleeding and internal parameters, (iii) notify the combo generator module 240 of the lung tissue and vessel tissue types so that the power and generator module 240 control algorithms are adjusted accordingly, (iv) notify the imaging module 238 of the aggressive cancer tag to adjust the margin ranges accordingly, (v) notify the stapler of the margin parameter adjustment needed (the margin parameter corresponds to the distance or amount of tissue around the cancer that will be excised), and (vi) notify the stapler that the tissue is potentially fragile. Furthermore, the anonymized stripped data 4058, upon which the implications 40602 are based, is identified by the surgical hub 206 and is fed into the situational awareness algorithm (see FIG. 86). Examples include, without limitations, thoracic lung resection, e.g., segmentectomy, among others.

Figure 66:
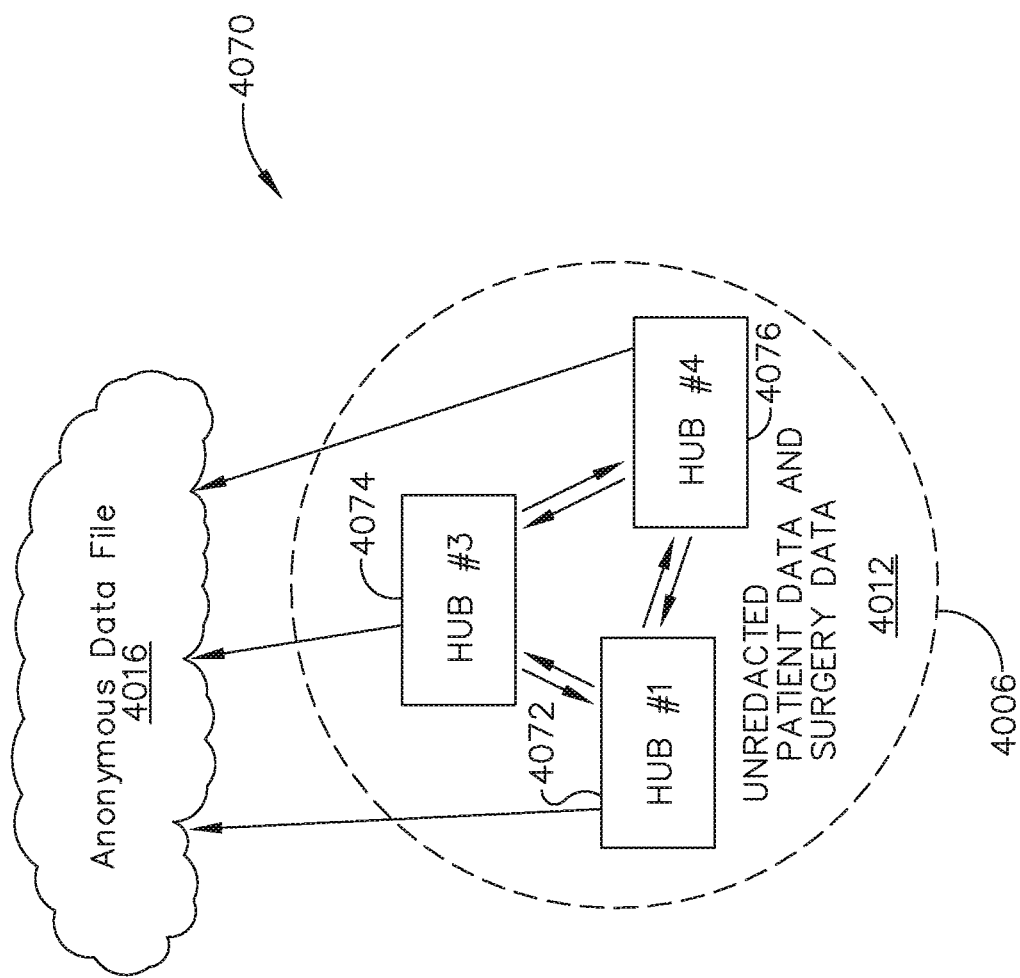
FIG. 66 illustrates the application of cloud based analytics to redacted and stripped patient data and independent data pairs, in accordance with at least one aspect of the present disclosure.

FIG. 66 is a diagram 4070 illustrating the application of cloud based analytics to un-redacted data, stripped relevant patient data 4018, and independent data pairs, according to one aspect of the present disclosure. As shown, multiple surgical hubs Hub #1 4072, Hub #3 4074, and Hub #4 4076 are located within the hospital data barrier 4006 (see also FIG. 62). The un-redacted patient electronic medical record 4012 including patient data and surgery related data may be used and exchanged between the surgical hubs: Hub #1 4072, Hub #3 4074, and Hub #4 4076 located within the hospital data barrier 4006. Prior to transmitting the un-redacted patient electronic medical record 4012 containing patient data and surgery related data outside the hospital data barrier 4006, however, the patient electronic medical record 4012 patient data is redacted and stripped to create an anonymous data file 4016 containing anonymized information for further analysis and processing of the redacted/stripped data by a cloud based analytic processes in the cloud 204.

Figure 67:
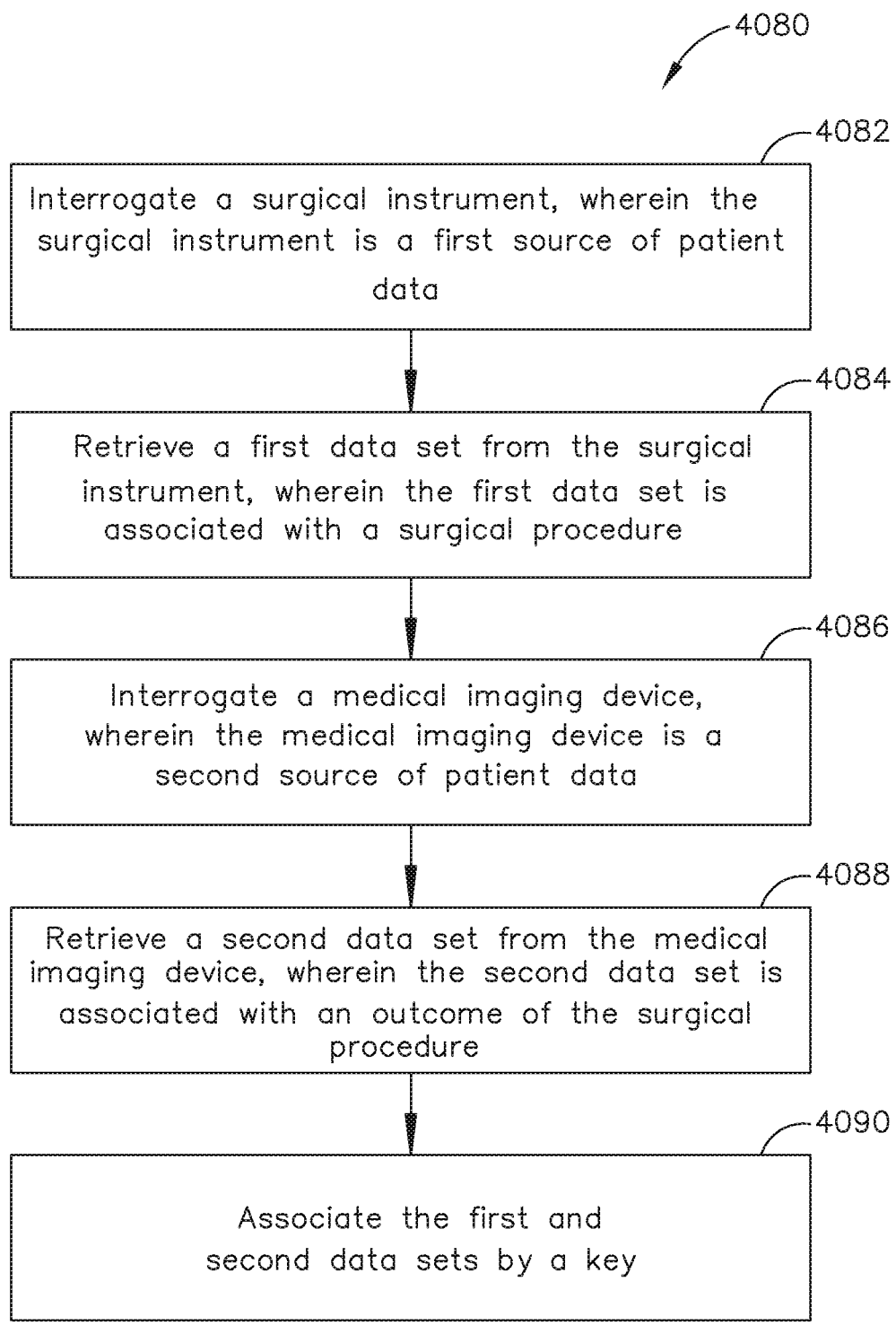
FIG. 67 is a logic flow diagram of a process depicting a control program or a logic configuration for associating patient data sets from first and second sources of data, in accordance with at least one aspect of the present disclosure.

FIG. 67 is a logic flow diagram 4080 of a process depicting a control program or a logic configuration for associating patient data sets from first and second sources of data, according to one aspect of the present disclosure. With reference to FIG. 67 and with reference also to FIGS. 1-11 to show interaction with an interactive surgical system 100 environment including a surgical hub 106, 206, in one aspect, the present disclosure provides a surgical hub 206, comprising a processor 244; and a memory 249 coupled to the processor 244. The memory 249 stores instructions executable by the processor 244 to interrogate 4082 a surgical instrument 235, retrieve 4084 a first data set from the surgical instrument 235, interrogate 4086 a medical imaging device 238, retrieve 4088 a second data set from the medical imaging device 238, associate 4090 the first and second data sets by a key, and transmit the associated first and second data sets to a remote network outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

Figure 68:
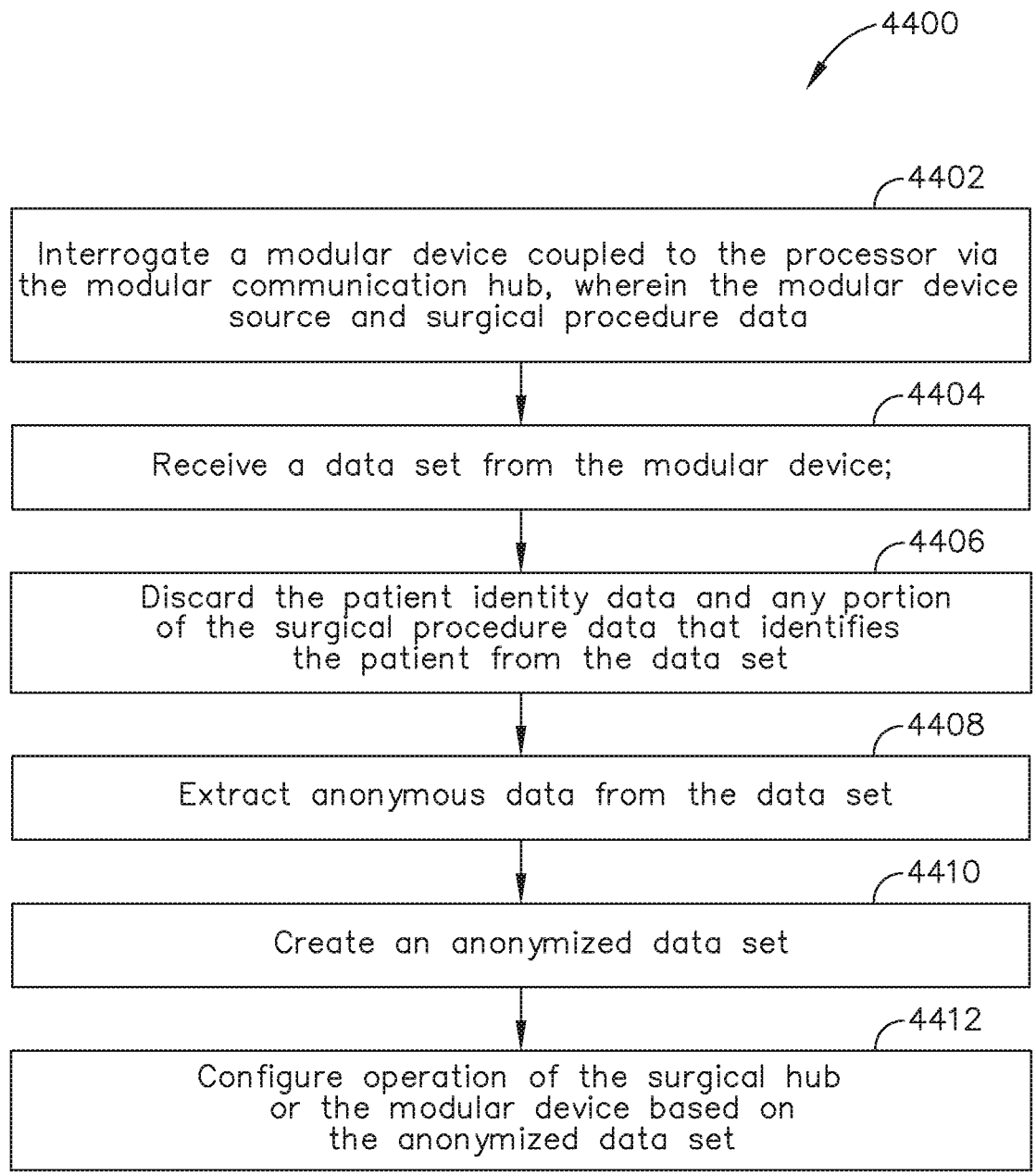
FIG. 68 is a logic flow diagram of a process depicting a control program or a logic configuration for stripping data to extract relevant portions of the data to configure and operate the surgical hub and modules (e.g., instruments) coupled to the surgical hub, in accordance with at least one aspect of the present disclosure.

FIG. 68 is a logic flow diagram of a process 4400 depicting a control program or a logic configuration for stripping data to extract relevant portions of the data to configure and operate the surgical hub 206 and modules (e.g., instruments 235) coupled to the surgical hub 206, according to one aspect of the present disclosure. With reference to FIG. 68 and with reference also to FIGS. 1-11 to show interaction with an interactive surgical system 100 environment including a surgical hub 106, 206, in one aspect, the surgical hub 206 may be configured to interrogate a module coupled to surgical hub 206 for data, and strip the data to extract relevant portions of the data to configure and operate the surgical hub 206 and modules (e.g., instruments 235) coupled to the surgical hub 206 and anonymize the surgery, patient, and other parameters that can be used to identify the patient to maintain patient privacy. According to the process 4400, in one aspect the present disclosure provides a surgical hub 206 including a processor 244, a modular communication hub 203 coupled to the processor 244, where the modular communication hub 203 is configured to connect modular devices located in one or more operating theaters to the surgical hub 206. The processor 244 is coupled to a memory 249, where the memory 249 stores instructions executable by the processor 244 to cause the processor to interrogate 4402 a modular device coupled to the processor 244 via the modular communication hub 203. The modular device is a source of data sets that include patient identity data and surgical procedure data. The processor 244 receives 4404 a data set from the modular device. The processor 244 discards 4406 the patient identity data and any portion of the surgical procedure data that identifies the patient from the data set. The processor 244 extracts 4408 anonymous data from the data set and creates 4410 an anonymized data set. The processor 244 configures 4412 the operation of the surgical hub 206 or the modular device based on the anonymized data set.

In another aspect, where the anonymized data set includes catastrophic failure of a modular device, the memory 249 stores instructions executable by the processor 244 to initiate automatic archiving and submission of data for implications analysis based on the catastrophic failure of the modular device. In another aspect, the memory 249 stores instructions executable by the processor 244 to detect counterfeit component information from the anonymized data set. In another aspect, the memory 249 stores instructions executable by the processor 244 to derive implications of the modular device from the anonymized data set and the memory 249 stores instructions executable by the processor 244 to configure the modular device to operate based on the derived implications or to configure the surgical hub based on the derived implications. In another aspect, the memory 249 stores instructions executable by the processor 244 to conglomerate the anonymized data. In another aspect, the memory 249 stores instructions executable by the processor 244 to extract the anonymized data prior to storing the received data in a storage device coupled to the surgical hub. In another aspect, the memory 249 stores instructions executable by the processor to transmit the anonymized data to a remote network outside of the surgical hub, compile the anonymized data at the remote network, and store a copy of the data set from the modular device in a patient electronic medical records database.

Storage of Data Creation and Use of
Self-Describing Data Including Identification
Features In one aspect, the present disclosure provides self-describing data packets generated at the issuing instrument and including identifiers for all devices that handled the packet. The self description allows the processor to interpret the data in the self-describing packet without knowing the data type in advance prior to receipt of the self-describing packet. The data applies to every data point or data string and includes the type of data, the source of the self-describing packet, the device identification that generated the packet, the units, the time of generation of the packet, and an authentication that the data contained in the packet is unaltered. When the processor (in the device or the surgical hub) receives an unexpected packet and verifies the source of the packet, the processor alters the collection techniques to be ready for any subsequent packets from that source.

With reference also to FIGS. 1-11 to show interaction with an interactive surgical system 100 environment including a surgical hub 106, 206, during a surgical procedure being performed in a surgical hub 206 environment, the size and quantity of data being generated by surgical devices 235 coupled to the surgical hub 206 can become quite large. Also, data exchanged between the surgical devices 235 and/or the surgical hub 206 can become quite large.

One solution provides a techniques for minimizing the size of the data and handling the data within a surgical hub 206 by generating a self-describing packet. The self-describing packet is initially assembled by the instrument 235 that generated it. The packet is then ordered and encrypted b generating an encryption certificate which is unique for each data packet. The data is then communicated from the instrument 235 via encrypted wired or wireless protocols and stored on the surgical hub 206 for processing and transmission to the cloud 204 analytics engine. Each self-describing data packet includes an identifier to identify the specific instrument that generated it and the time it was generated. A surgical hub 206 identifier is added to the packet when the packet is received by the surgical hub 206.

In one aspect, the present disclosure provides a surgical hub 206 comprising a processor 244 and a memory 249 coupled to the processor 244. The memory 249 storing instructions executable by the processor 244 to receive a first data packet from a first source, receive a second data packet from a second source, associate the first and second data packets, and generate a third data packet comprising the first and second data payloads. The first data packet comprises a first preamble, a first data payload, a source of the first data payload, and a first encryption certificate. The first preamble defines the first data payload and the first encryption certificate verifies the authenticity of the first data packet. The second data packet comprises a second preamble, a second data payload, a source of the second data payload, and a second encryption certificate. The second preamble defines the second data payload and the second encryption certificate verifies the authenticity of the second data packet.

In another aspect, the memory 249 stores instructions executable by the processor 244 to determine that a data payload is from a new source, verify the new source of the data payload, and alter a data collection process at the surgical hub to receive subsequent data packets from the new source.

In another aspect, the memory 249 stores instructions executable by the processor 244 to associate the first and second data packets based on a key. In another aspect, the memory 249 stores instructions executable by the processor 244 to anonymize the data payload of the third data packet. In another aspect, the memory 249 stores instructions executable by the processor 244 to receive an anonymized third data packet and reintegrate the anonymized third data packet into the first and second data packets using the key.

In various aspects, the present disclosure provides a control circuit to receive and process data packets as described above. In various aspects, the present disclosure provides a non-transitory computer-readable medium storing computer readable instructions, which when executed, causes a machine to receive and process data packets as described above.

In other aspects, the present disclosure a method of generating a data packet comprising self-describing data. In one aspect, a surgical instrument includes a processor and a memory coupled to the processor, a control circuit, and/or a computer-readable medium configured to generate a data packet comprising a preamble, a data payload, a source of the data payload, and an encryption certificate. The preamble defines the data payload and the encryption certificate verifies the authenticity of the data packet. In various aspects, the data packet may be generated by any module coupled to the surgical hub. Self-describing data packets minimize data size and data handing in the surgical hub.

In one aspect, the present disclosure provides a self-describing data packet generated at an issuing device (e.g., instrument, tool, robot). The self-describing data packet comprises identifiers for all devices that handle the data packet along a communication path; a self description to enable a processor to interpret that data contained in the data packet without having been told in advance of receipt of the data packet along a path; data for every data point or data string; and type of data, source of data, device IDs that generated the data, units of the data, time of generation, and authentication that the data packet is unaltered. In another aspect, when a processor receives a data packet from an unexpected source and verifies the source of the data, the processor alters the data collection technique to prepare for any subsequent data packets from the source.

In the creation and use of a data packet comprising self-describing data, the surgical hub includes identification features. The hub and intelligent devices use self-describing data packets to minimize data size and data handling. In a surgical hub that generates large volumes of data, the self-describing data packets minimize data size and data handling, thus saving time and enabling the operating theater to run more efficiently.

Figure 69:
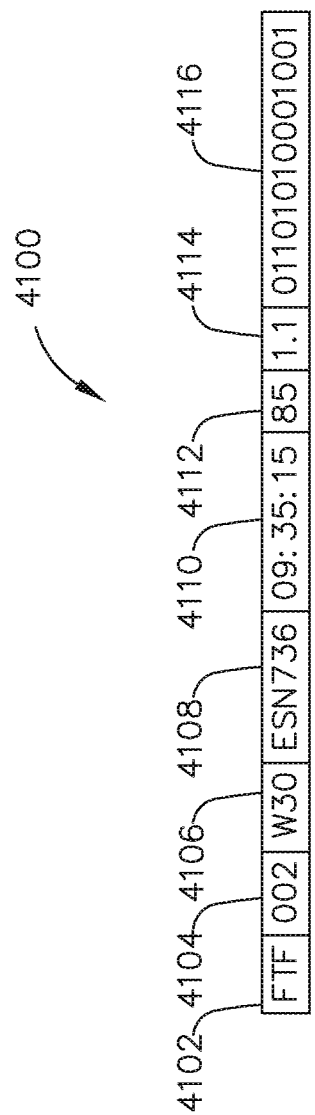
FIG. 69 illustrates a self-describing data packet comprising self-describing data, in accordance with at least one aspect of the present disclosure.

FIG. 69 illustrates a self-describing data packet 4100 comprising self-describing data, according to one aspect of the present disclosure. With reference also to FIGS. 1-11 to show interaction with an interactive surgical system 100 environment including a surgical hub 106, 206, in one aspect, self-describing data packets 4100 as shown in FIG. 69 are generated at an issuing instrument 235, or device or module located in or in communication with the operating theater, and include identifiers for all devices 235 that handle the packet along a communication path. The self description allows a processor 244 to interpret the data payload of the packet 4100 without having advance knowledge of the definition of the data payload prior to receiving the self-describing data packet 4100. The processor 244 can interpret the data payload by parsing an incoming self-describing packet 4100 as it is received and identifying the data payload without being notified in advance that the self-describing packet 4100 was received. The data is for every data point or data string. The data payload includes type of data, source of data, device IDs that generated the data, data units, time when data was generated, and an authentication that the self-describing data packet 4100 is unaltered. Once the processor 244, which may be located either in the device or the surgical hub 206, receives an unexpected self-describing data packet 4100 and verifies the source of the self-describing data packet 4100, the processor 244 alters the data collection means to be ready for any subsequent self-describing data packets 4100 from that source. In one example, the information contained in a self-describing packet 4100 may be recorded during the first firing 4172 in the lung tumor resection surgical procedure described in connection with FIGS. 71-75.

The self-describing data packet 4100 includes not only the data but a preamble which defines what the data is and where the data came from as well as an encryption certificate verifying the authenticity of each data packet 4100. As shown in FIG. 69, the data packet 4100 may comprise a self-describing data header 4102 (e.g., force-to-fire [FTF], force-to-close [FTC], energy amplitude, energy frequency, energy pulse width, speed of firing, and the like), a device ID 4104 (e.g., 002), a shaft ID 4106 (e.g., W30), a cartridge ID 4108 (e.g., ESN736), a unique time stamp 4110 (e.g., 09:35:15), a force-to-fire value 4112 (e.g., 85) when the self-describing data header 4102 includes FTF (force-to-fire), otherwise, this position in the data packet 4100 includes the value of force-to-close, energy amplitude, energy frequency, energy pulse width, speed of firing, and the like. The data packet 4100, further includes tissue thickness value 4114 (e.g., 1.1 mm), and an identification certificate of data value 4116 (e.g., 01101010001001) that is unique for each data packet 4100. Once the self-describing data packet 4100 is received by another instrument 235, surgical hub 206, cloud 204, etc., the receiver parses the self-describing data header 4102 and based on its value knows what data type is contained in the self-describing data packet 4100. TABLE 1 below lists the value of the self-describing data header 4102 and the corresponding data value.

TABLE 1

| Self-Describing Data Header (4102) | Data Type |
| --- | --- |
| FTF | Force To Fire (N) |
| FTC | Force To Close (N) |
| EA | Energy Amplitude (J) |
| EF | Energy Frequency (Hz) |
| EPW | Energy Pulse Width (Sec) |
| SOF | Speed Of Firing (mm/sec) |

Each self-describing data packet 4100 comprising self-describing data is initially assembled by the instrument 235, device, or module that generated the self-describing data packet 4100. Subsequently, the self-describing data packet 4100 comprising self-describing data is ordered and encrypted to generate an encryption certificate. The encryption certificate is unique for each self-describing data packet 4100. That data is then communicated via encrypted wired or wireless protocols and stored on the surgical hub 206 for processing and transmission to the cloud 204 analytics engine.

Each self-describing data packet 4100 comprising self-describing data includes a device ID 4104 to identify the specific instrument 235 that generated the self-describing data packet 4100, a time stamp 4110 to indicate the time that the data packet 4100 was generated, and when the self-describing data packet 4100 is received by the surgical hub 206. The surgical hub 206 ID also may be added to the self-describing data packet 4100.

Each of the self-describing data packets 4100 comprising self-describing data may include a packet wrapper that defines the beginning of the data packet 4100 and the end of the data packet 4100 including any identifiers necessary to forecast the number and order of the bits in the self-describing data packet.

The surgical hub 206 also manages redundant data sets. As the device 235 functions and interconnects with other surgical hubs 206, multiple sets of the same data may be created and stored on various devices 235. Accordingly, the surgical hub 206 manages multiple images of redundant data as well as anonymization and security of data. The surgical hub 206 also provides temporary visualization and communication, incident management, peer-to-peer processing or distributed processing, and storage backup and protection of data.

Figure 70:
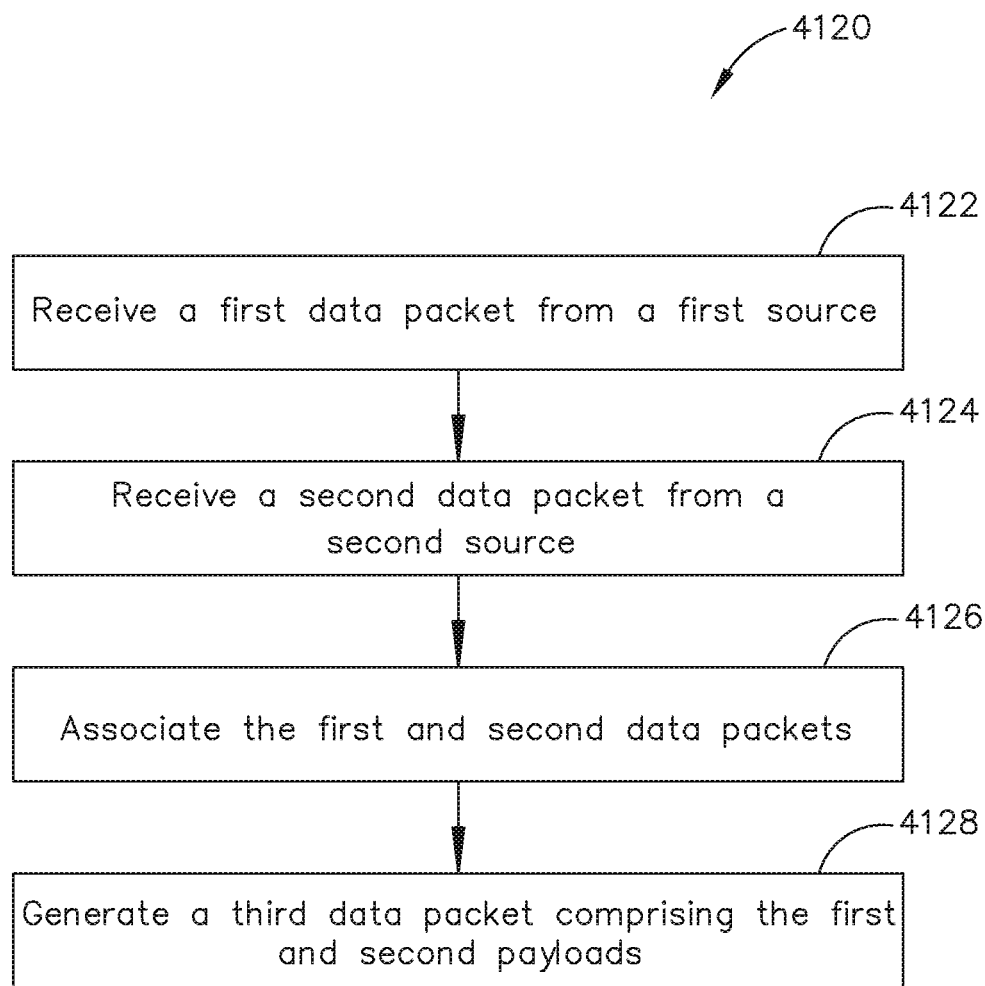
FIG. 70 is a logic flow diagram of a process depicting a control program or a logic configuration for using data packets comprising self-describing data, in accordance with at least one aspect of the present disclosure.

FIG. 70 is a logic flow diagram 4120 of a process depicting a control program or a logic configuration for using data packets comprising self-describing data, according to one aspect of the present disclosure. With reference to FIGS. 1-69, in one aspect, the present disclosure provides a surgical hub 206 comprising a processor 244 and a memory 249 coupled to the processor 244. The memory 249 storing instructions executable by the processor 244 to receive a first data packet from a first source, receive a second data packet from a second source, associate the first and second data packets, and generate a third data packet comprising the first and second data payloads. The first data packet comprises a first preamble, a first data payload, a source of the first data payload, and a first encryption certificate. The first preamble defines the first data payload and the first encryption certificate verifies the authenticity of the first data packet. The second data packet comprises a second preamble, a second data payload, a source of the second data payload, and a second encryption certificate. The second preamble defines the second data payload and the second encryption certificate verifies the authenticity of the second data packet.

In another aspect, the memory 249 stores instructions executable by the processor 244 to determine that a data payload is from a new source, verify the new source of the data payload, and alter a data collection process at the surgical hub to receive subsequent data packets from the new source.

In another aspect, the memory 249 stores instructions executable by the processor 244 to associate the first and second data packets based on a key. In another aspect, the memory 249 stores instructions executable by the processor 244 to anonymize the data payload of the third data packet. In another aspect, the memory 244 stores instructions executable by the processor 244 to receive an anonymized third data packet and reintegrate the anonymized third data packet into the first and second data packets using the key.

Figure 71:
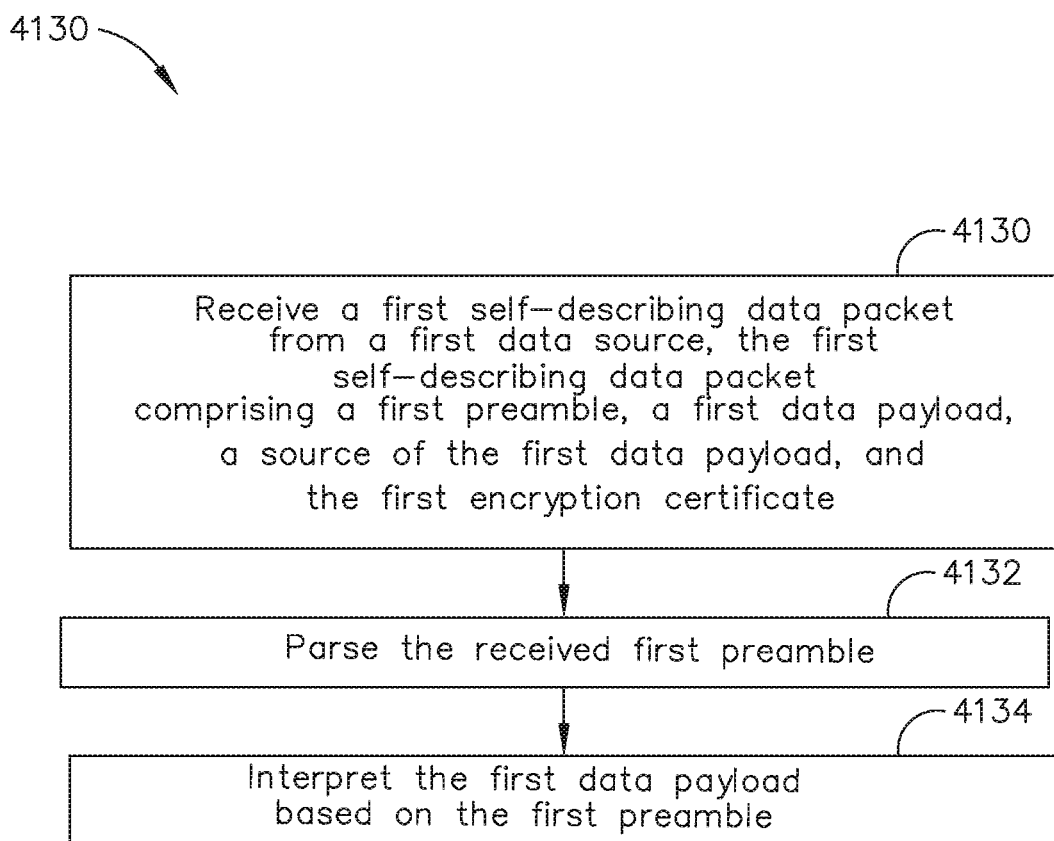
FIG. 71 is a logic flow diagram of a process depicting a control program or a logic configuration for using data packets comprising self-describing data, in accordance with at least one aspect of the present disclosure.

FIG. 71 is a logic flow diagram 4130 of a process depicting a control program or a logic configuration for using data packets comprising self-describing data, according to one aspect of the present disclosure. With reference to FIG. 71 and with reference also to FIGS. 1-11 to show interaction with an interactive surgical system 100 environment including a surgical hub 106, 206, in one aspect, the present disclosure provides a surgical hub 206 comprising a processor 244 and a memory 249 coupled to the processor 244. The memory 249 storing instructions executable by the processor 244 to receive 4132 a first self-describing data packet from a first data source, the first self-describing data packet comprising a first preamble, a first data payload, a source of the first data payload, and a first encryption certificate. The first preamble defines the first data payload and the first encryption certificate verifies the authenticity of the first data packet. The memory 249 storing instructions executable by the processor 244 to parse 4134 the received first preamble and interpret 4136 the first data payload based on the first preamble.

In various aspects, the memory 249 stores instructions executable by the processor 244 to receive a second self-describing data packet from a second data source, the second self-describing data packet comprising a second preamble, a second data payload, a source of the second data payload, and a second encryption certificate. The second preamble defines the second data payload and the second encryption certificate verifies the authenticity of the second data packet. The memory 249 storing instructions executable by the processor 244 to parse the received second preamble, interpret the second data payload based on the second preamble, associate the first and second self-describing data packets, and generate a third self-describing data packet comprising the first and second data payloads. In one aspect, the memory stores instructions executable by the processor to anonymize the data payload of the third self-describing data packet.

In various aspects, the memory stores instructions executable by the processor to determine that a data payload was generated by a new data source, verify the new data source of the data payload, and alter a data collection process at the surgical hub to receive subsequent data packets from the new data source. In one aspect, the memory stores instructions executable by the processor to associate the first and second self-describing data packets based on a key. In another aspect, the memory stores instructions executable by the processor to receive an anonymized third self-describing data packet and reintegrate the anonymized third self-describing data packet into the first and second self-describing data packets using the key.

Storage of the Data in a Manner of Paired Data Sets which can be Grouped by Surgery but not Necessarily Keyed to Actual Surgical Dates and Surgeons In one aspect, the present disclosure provides a data pairing method that allows a surgical hub to interconnect a device measured parameter with a surgical outcome. The data pair includes all the relevant surgical data or patient qualifiers without any patient identifier data. The data pair is generated at two separate and distinct times. The disclosure further provides configuring and storing the data in such a manner as to be able to rebuild a chronological series of events or merely a series of coupled but unconstrained data sets. The disclosure further provides storing data in an encrypted form and having predefined backup and mirroring to the cloud.

To determine the success or failure of a surgical procedure, data stored in a surgical instrument should be correlated with the outcome of the surgical procedure while simultaneously anonymizing the data to protect the privacy of the patient. One solution is to pair data associated with a surgical procedure, as recorded by the surgical instrument during the surgical procedure, with data assessing the efficacy of the procedure. The data is paired without identifiers associated with surgery, patient, or time to preserve anonymity. The paired data is generated at two separate and distinct times.

In one aspect, the present disclosure provides a surgical hub configured to communicate with a surgical instrument. The surgical hub comprises a processor and a memory coupled to the processor. The memory storing instructions executable by the processor to receive a first data set associated with a surgical procedure, receive a second data set associated with the efficacy of the surgical procedure, anonymize the first and second data sets by removing information that identifies a patient, a surgery, or a scheduled time of the surgery, and store the first and second anonymized data sets to generate a data pair grouped by surgery. The first data set is generated at a first time, the second data set is generated at a second time, and the second time is separate and distinct from the first time.

In another aspect, the memory stores instructions executable by the processor to reconstruct a series of chronological events based on the data pair. In another aspect, the memory stores instructions executable by the processor to reconstruct a series of coupled but unconstrained data sets based on the data pair. In another aspect, the memory stores instructions executable by the processor to encrypt the data pair, define a backup format for the data pair, and mirror the data pair to a cloud storage device.

In various aspects, the present disclosure provides a control circuit to receive and process data sets as described above. In various aspects, the present disclosure provides a non-transitory computer-readable medium storing computer readable instructions, which when executed, causes a machine to receive and process data sets as described above.

Storage of paired anonymous data enables the hospital or surgeon to use the data pairs locally to link to specific surgeries or to store the data pairs to analyze overall trends without extracting specific events in chronological manner.

In one aspect, the surgical hub provides user defined storage and configuration of data. Storage of the data may be made in a manner of paired data sets which can be grouped by surgery, but not necessarily keyed to actual surgical dates and surgeons. This technique provides data anonymity with regard to the patient and surgeon.

In one aspect, the present disclosure provides a data pairing method. The data pairing method comprises enabling a surgical hub to interconnect a device measured parameter with an outcome, wherein a data pair includes all the relevant tissue or patient qualifiers without any of the identifiers, wherein the data pair is generated at two distinct and separate times. In another aspect, the present disclosure provides a data configuration that includes whether the data is stored in such a manner as to enable rebuilding a chronological series of events or merely a series of coupled but unconstrained data sets. In another aspect, the data may be stored in an encrypted form. The stored data may comprise a predefined backup and mirroring to the cloud.

The data may be encrypted locally to the device. The data backup may be automatic to an integrated load secondary storage device. The device and/or the surgical hub may be configured to maintain the time of storage of the data and compile and transmit the data to another location for storage, e.g., another surgical hub or a cloud storage device. The data may be grouped together and keyed for transmission to the cloud analytics location. A cloud based analytics system is described in commonly-owned U.S. Provisional Patent Application Ser. No. 62/611,340, filed Dec. 28, 2017, titled CLOUD-BASED MEDICAL ANALYTICS, which is incorporated herein by reference in its entirety.

In another aspect, the hub provides user selectable options for storing the data. In one technique, the hub enables the hospital or the surgeon to select if the data should be stored in such a manner that it could be used locally in a surgical hub to link to specific surgeries. In another technique, the surgical hub enables the data to be stored as data pairs so that overall trends can be analyzed without specific events extracted in a chronological manner.

Figure 72:
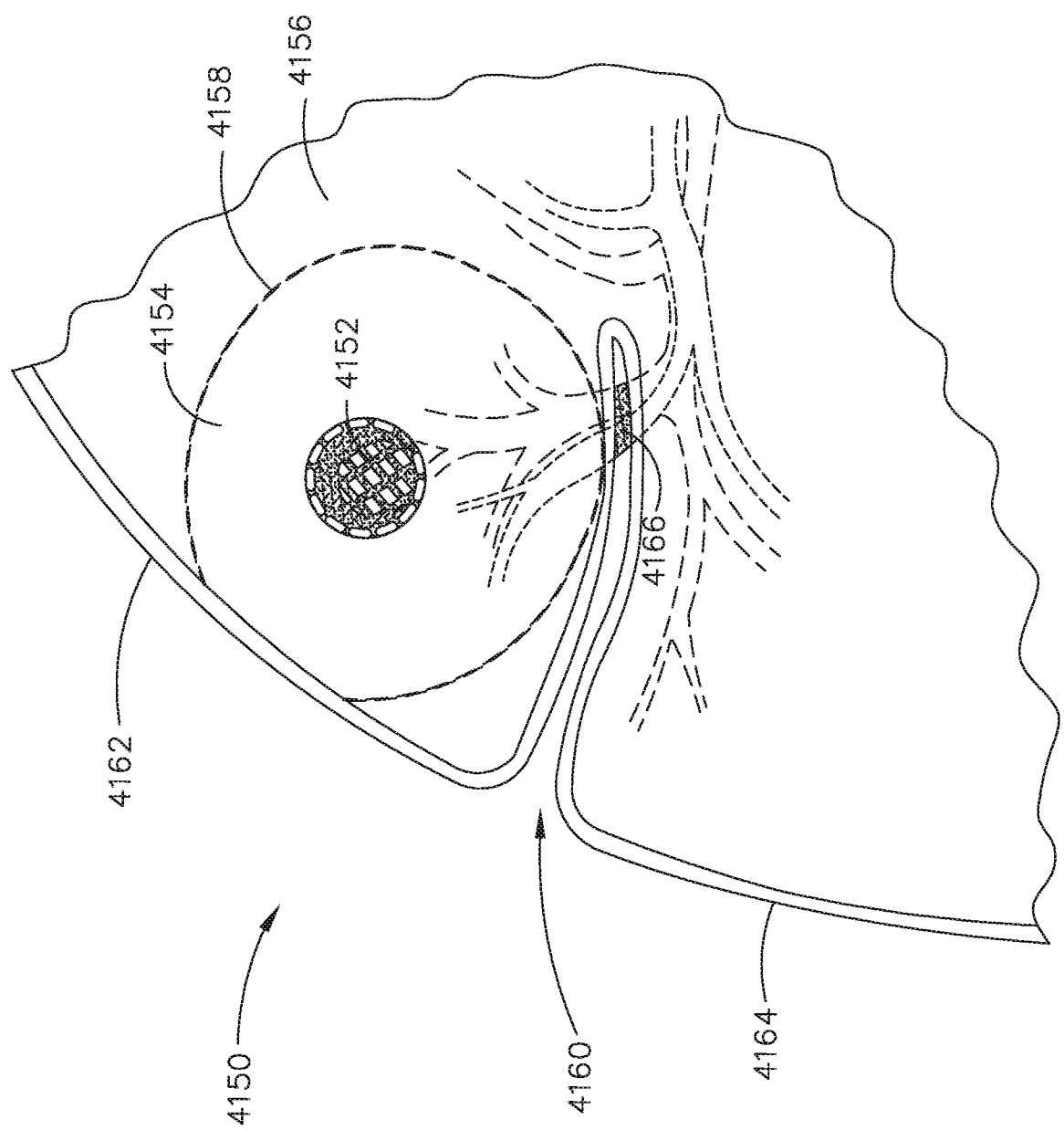
FIG. 72 is a diagram of a tumor embedded in the right superior posterior lobe of the right lung, in accordance with at least one aspect of the present disclosure.
Figure 78:
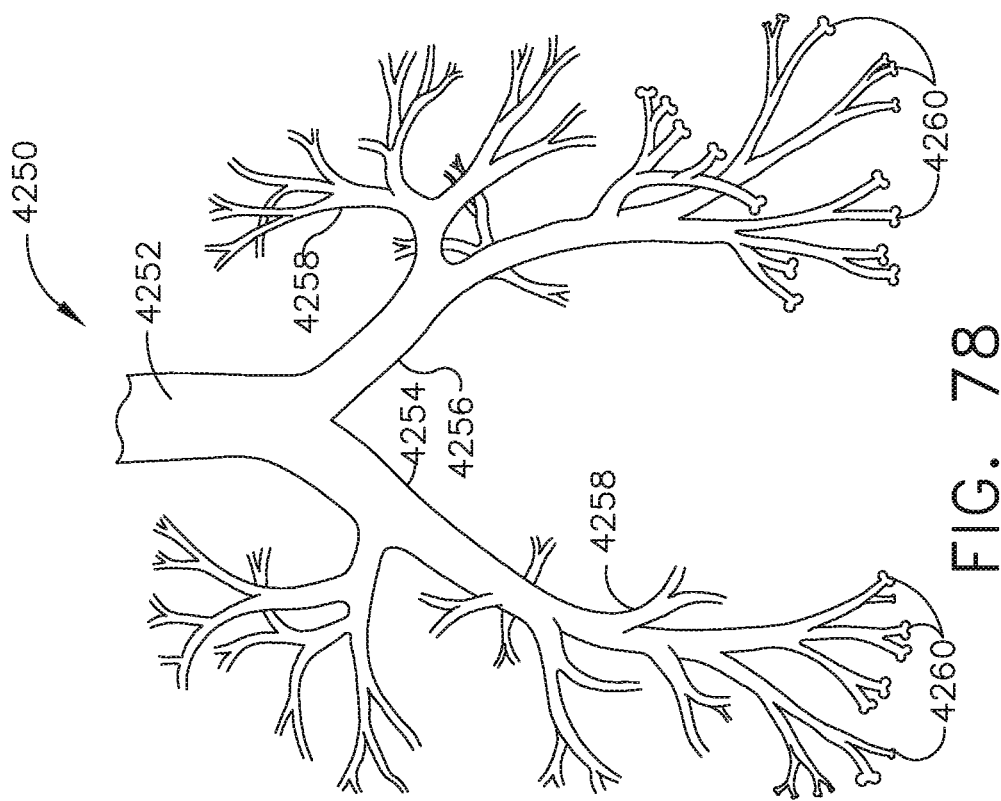
FIG. 78 is a diagram of the bronchial tree including the trachea and bronchi of the lung.
Figure 77:
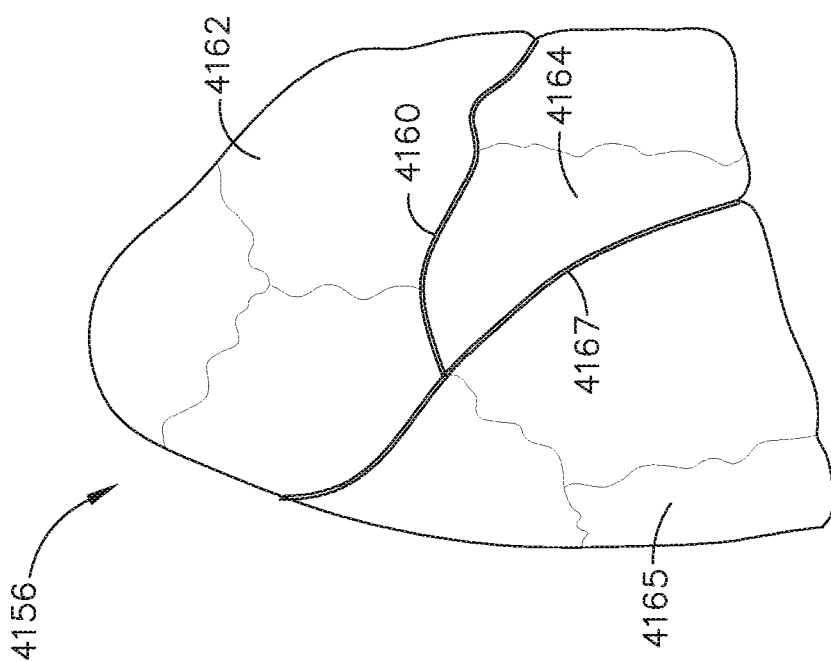
FIG. 77 is a diagram of the right lung.

FIG. 72 is a diagram 4150 of a tumor 4152 embedded in the right superior posterior lobe 4154 of the right lung 4156, according to one aspect of the present disclosure. To remove the tumor 4152, the surgeon cuts around the tumor 4152 along the perimeter generally designated as a margin 4158. A fissure 4160 separates the upper lobe 4162 and the middle lobe 4164 of the right lung 4156. In order to cut out the tumor 4152 about the margin 4158, the surgeon must cut the bronchial vessels 4166 leading to and from the middle lobe 4164 and the upper lobe 4162 of the right lung 4156. The bronchial vessels 4166 must be sealed and cut using a device such as a surgical stapler, electrosurgical instrument, ultrasonic instrument, a combo electrosurgical/ultrasonic instrument, and/or a combo stapler/electrosurgical device generally represented herein as the instrument/device 235 coupled to the surgical hub 206. The device 235 is configured to record data as described above, which is formed as a data packet, encrypted, stored, and/or transmitted to a remote data storage device 105 and processed by the server 113 in the cloud 104. FIGS. 77 and 78 are diagrams that illustrate the right lung 4156 and the bronchial tree 4250 embedded within the parenchyma tissue of the lung.

In one aspect, the data packet may be in the form of the self-describing data 4100 described in connection with FIGS. 69-71. The self-describing data packet 4100 will contain the information recorded by the device 235 during the procedure. Such information may include, for example, a self-describing data header 4102 (e.g., force-to-fire [FTF], force-to-close [FTC], energy amplitude, energy frequency, energy pulse width, speed of firing, and the like) based on the particular variable. The device ID 4104 (e.g., 002) of the instrument/device 235 used in the procedure including components of the instrument/device 235 such as the shaft ID 4106 (e.g., W30) and the cartridge ID 4108 (e.g., ESN736). The self-describing packet 4100 also records a unique time stamp 4110 (e.g., 09:35:15) and procedural variables such as a force-to-fire value 4112 (e.g., 85) when the self-describing data header 4102 includes FTF (force-to-fire), otherwise, this position in the data packet 4100 includes the value of force-to-close (FTC), energy amplitude, energy frequency, energy pulse width, speed of firing, and the like, as shown in TABLE 1, for example. The data packet 4100, further may include tissue thickness value 4114 (e.g., 1.1 mm), which in this example refers to the thickness of the bronchial vessel 4166 exposed in the fissure 4160 that were sealed and cut. Finally, each self-describing packet 4100 includes an identification certificate of data value 4116 (e.g., 01101010001001) that uniquely identifies each data packet 4100 transmitted by the device/instrument 235 to the surgical hub 206, further transmitted from the surgical hub 206 to the cloud 204 and stored on the storage device 205 coupled to the server 213, and/or further transmitted to the robot hub 222 and stored.

The data transmitted by way of a self-describing data packet 4100 is sampled by the instrument device 235 at a predetermined sample rate. Each sample is formed into a self-describing data packet 4100 which is transmitted to the surgical hub 206 and eventually is transmitted from the surgical hub 206 to the cloud 204. The samples may be stored locally in the instrument device 235 prior to packetizing or may be transmitted on the fly. The predetermined sampling rate and transmission rate are dictated by communication traffic in the surgical hub 206 and may be adjusted dynamically to accommodate current bandwidth limitations. Accordingly, in one aspect, the instrument device 235 may record all the samples taken during surgery and at the end of the procedure packetize each sample into a self-describing packet 4100 and transmit the self-describing packet 4100 to the surgical hub 206. In another aspect, the sampled data may be packetized as it is recorded and transmitted to the surgical hub 206 on the fly.

Figure 73:
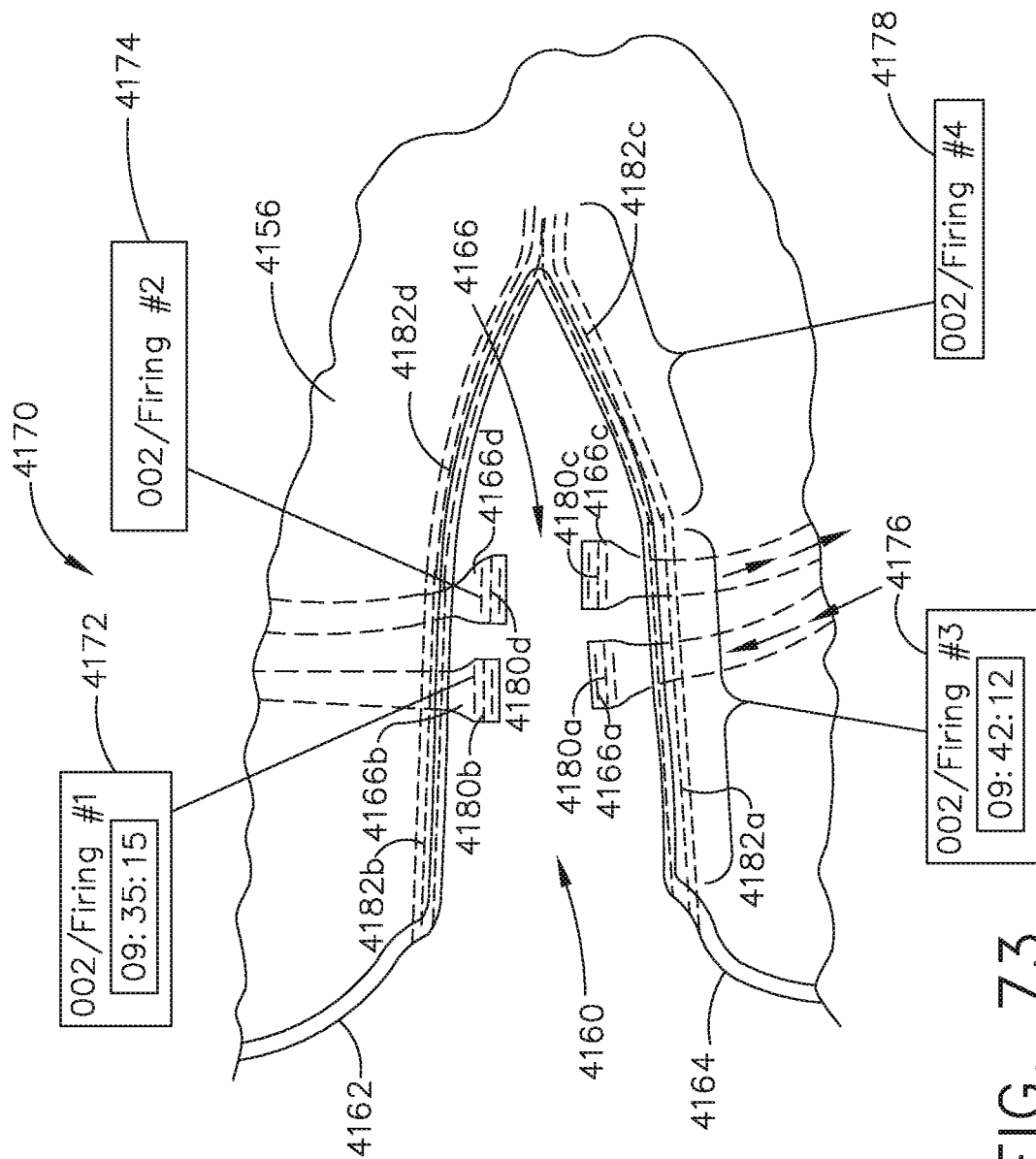
FIG. 73 is a diagram of a lung tumor resection surgical procedure including four separate firings of a surgical stapler to seal and cut bronchial vessels exposed in the fissure leading to and from the upper and lower lobes of the right lung shown in FIG. 72, in accordance with at least one aspect of the present disclosure.

FIG. 73 is a diagram 4170 of a lung tumor resection surgical procedure including four separate firings of a surgical stapler device 235 to seal and cut bronchial vessels 4166 exposed in the fissure 4160 leading to and from the upper and lower lobes 4162, 4164 of the right lung 4156 shown in FIG. 72, according to one aspect of the present disclosure. The surgical stapler device 235 is identified by a Device ID "002". The data from each firing of the surgical stapler device 235 is recorded and formed into a data packet 4100 comprising self-describing data as shown in FIG. 70. The self-describing data packet 4100 shown in FIG. 70 is representative of the first firing of device "002" having a staple cartridge serial number of ESN736, for example. In the following description, reference also is made to FIGS. 12-19 for descriptions of various architectures of instruments/devices 235 that include a processor or a control circuit coupled to a memory for recording (e.g., saving or storing) data collected during a surgical procedure.

Figure 74:
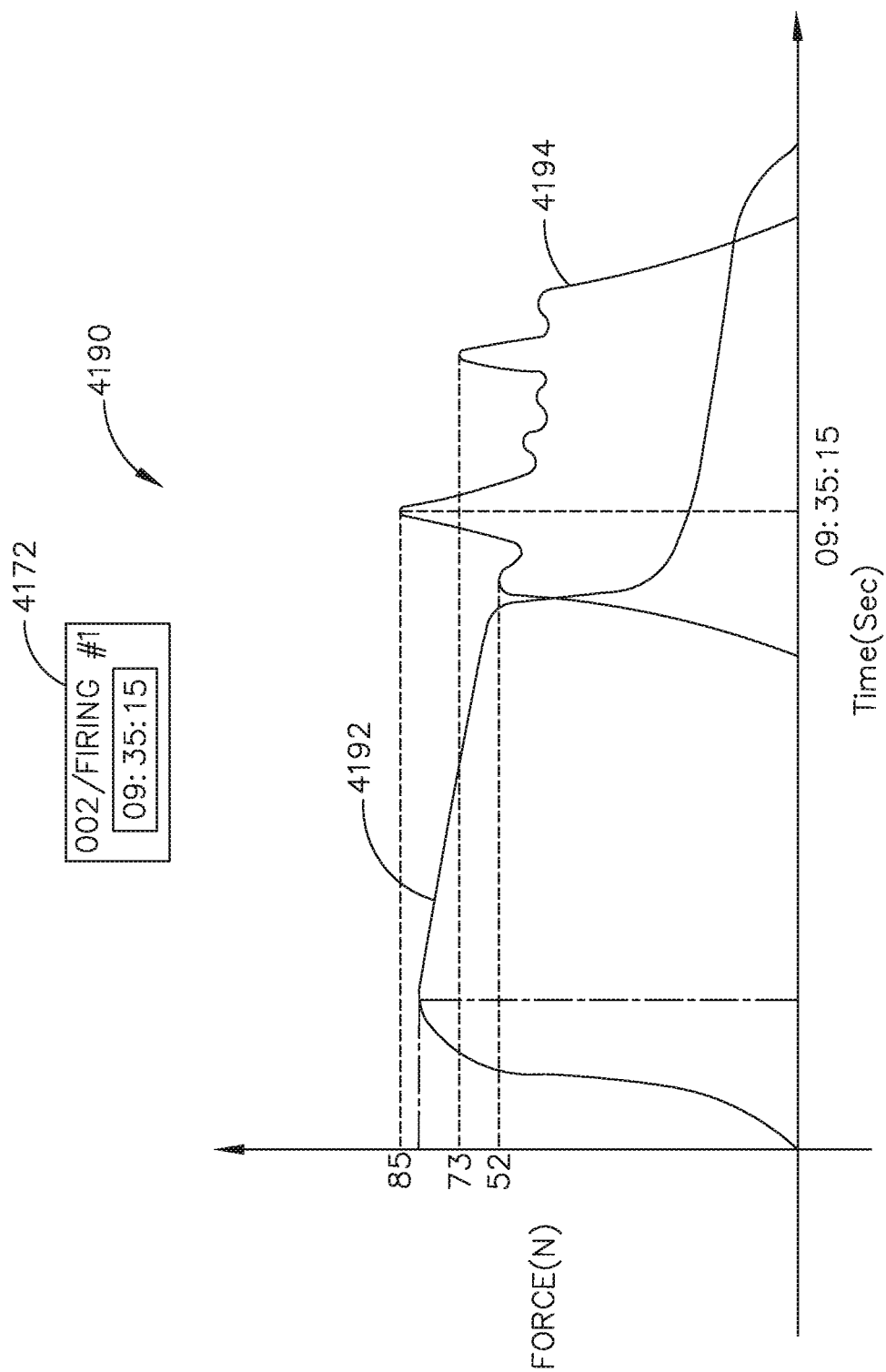
FIG. 74 is a graphical illustration of a force-to-close (FTC) versus time curve and a force-to-fire (FTF) versus time curve characterizing the first firing of device 002 as shown in FIG. 72, in accordance with at least one aspect of the present disclosure.

The first firing 4172 is recorded at anonymous time 09:35:15. The first firing 4172 seals and severs a first bronchial vessel 4166 leading to and from the middle lobe 4164 and the upper lobe 4162 of the right lung 4156 into a first portion 4166a and a second portion 4166b, where each portion 4166a, 4166b is sealed by respective first and second staple lines 4180a, 4180b. Information associated with the first firing 4172, for example the information described in connection with FIG. 70, is recorded in the surgical stapler device 235 memory and is used to build a first self-describing data packet 4100 described in connection with FIGS. 69-71. The first self-describing packet 4100 may be transmitted upon completion of the first firing 4172 or may be kept stored in the surgical stapler device 235 memory until the surgical procedure is completed. Once transmitted by the surgical stapler device 235, the first self-describing data packet 4100 is received by the surgical hub 206. The first self-describing data packet 4100 is anonymized by stripping and time stamping 4038 the data, as discussed, for example, in connection with FIG. 63. After the lung resection surgical is completed, the integrity of the seals of the first and second staple lines 4182a, 4182b will be evaluated as shown in FIG. 74, for example, and the results of the evaluation will be paired with information associated with the first firing 4172.

The second firing 4174 seals and severs a second bronchial vessel of the bronchial vessels 4166 leading to and from the middle lobe 4164 and the upper lobe 4162 of the right lung 4156 into a first portion 4166c and a second portion 4166d, where each portion 4166c, 4166d is sealed by first and second staple lines 4180c, 4180d. Information associated with the second firing 4174, for example the information described in connection with FIGS. 69-71, is recorded in the surgical stapler device 235 memory and is used to build a second self-describing data packet 4100 described in connection with FIGS. 69-71. The second self-describing data packet 4100 may be transmitted upon completion of the second firing 4174 or may be kept stored in the surgical stapler device 235 memory until the surgical procedure is completed. Once transmitted by the surgical stapler device 235, the second self-describing data packet 4100 is received by the surgical hub 206. The second self-describing data packet 4100 is anonymized by stripping and time stamping 4038 the data as discussed, for example, in connection with FIG. 63. After the lung resection surgical is completed, the integrity of the seals of the first and second staple lines 4182c, 4182d will be evaluated as shown in FIG. 74, for example, and the results of the evaluation will be paired with information associated with the second firing 4174.

The third firing 4176 is recorded at anonymous time 09:42:12. The third firing 4176 seals and severs an outer portion of the upper and middle lobes 4162, 4164 of the right lung 4156. First and second staple lines 4182a, 4182b are used to seal the outer portion of the upper and middle lobes 4162, 4162. Information associated with the third firing 4176, for example the information described in connection with FIGS. 69-71, is recorded in the surgical stapler device 235 memory and is used to build a third self-describing data packet 4100 described in connection with FIGS. 69-71. The third self-describing packet 4100 may be transmitted upon completion of the third firing 4176 or may be kept stored in the surgical stapler device 235 memory until the surgical procedure is completed. Once transmitted by the surgical stapler device 235, the third self-describing data packet 4100 is received by the surgical hub 206. The third self-describing data packet 4100 is anonymized by stripping and time stamping 4038 the data, as discussed, for example, in connection with FIG. 63. After the lung resection surgical is completed, the integrity of the seals of the first and second staple lines 4180a, 4180b will be evaluated as shown in FIG. 74, for example, and the results of the evaluation will be paired with information associated with the third firing 4172.

The fourth firing 4178 seals and severs an inner portion of the upper and middle lobes 4162, 4162 of the right lung 4156. First and second staple lines 4182c, 4182d are used to seal the inner portions of the upper and middle lobes 4162, 4164. Information associated with the fourth firing 4178, for example the information described in connection with FIG. 70, is recorded in the surgical stapler device 235 memory and is used to build a fourth self-describing data packet 4100 described in connection with FIGS. 69-71. The fourth self-describing packet 4100 may be transmitted upon completion of the fourth firing 4178 or may be kept stored in the surgical stapler device 235 memory until the surgical procedure is completed. Once transmitted by the surgical stapler device 235, the fourth self-describing data packet 4100 is received by the surgical hub 206. The fourth self-describing data packet 4100 is anonymized by stripping and time stamping 4038 the data, as discussed, for example, in connection with FIG. 63. After the lung resection surgical is completed, the integrity of the seals of the first and second staple lines 4182a, 4182b will be evaluated as shown in FIG. 74, for example, and the results of the evaluation will be paired with information associated with the fourth firing 4172.

FIG. 74 is a graphical illustration 4190 of a force-to-close (FTC) versus time curve 4192 and a force-to-fire (FTF) versus time curve 4194 characterizing the first firing 4172 of device 002 shown in FIG. 73, according to one aspect of the present disclosure. The surgical stapler device 235 is identified as 002 with a 30 mm staple cartridge S/N ESN736 with a PVS shaft S/N M3615N (Shaft ID W30). The surgical stapler device 235 was used for the first firing 4172 to complete the lung resection surgical procedure shown in FIG. 73. As shown in FIG. 74, the peak force-to-fire force of 85 N. is recorded at anonymous time 09:35:15. Algorithms in the surgical stapler device 235 determine a tissue thickness of about 1.1 mm. As described hereinbelow, the FTC versus time curve 4192 and the FTF versus time curve 4194 characterizing the first firing 4172 of the surgical device 235 identified by ID 002 will be paired with the outcome of the lung resection surgical procedure, transmitted to the surgical hub 206, anonymized, and either stored in the surgical hub 206 or transmitted to the cloud 204 for aggregation, further processing, analysis, etc.

Figure 75:
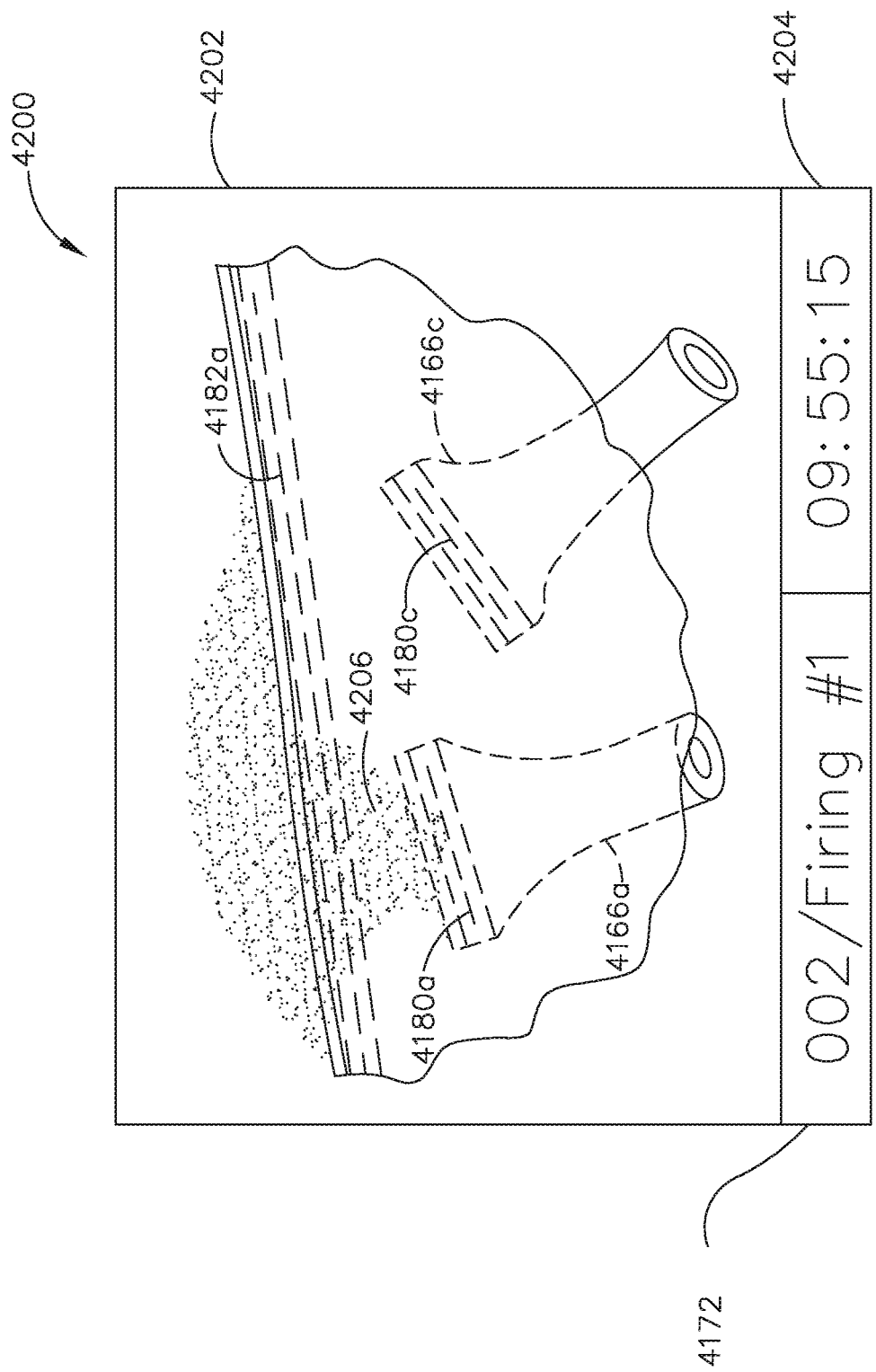
FIG. 75 is a diagram of a staple line visualization laser Doppler to evaluate the integrity of staple line seals by monitoring bleeding of a vessel after a firing of a surgical stapler, in accordance with at least one aspect of the present disclosure.

FIG. 75 is a diagram 4200 illustrating a staple line visualization laser Doppler to evaluate the integrity of staple line seals by monitoring bleeding of a vessel after a firing of a surgical stapler, according to one aspect of the present disclosure. A laser Doppler technique is described in above under the heading "Advanced Imaging Acquisition Module," in U.S. Provisional Patent Application Ser. No. 62/611,341, filed Dec. 28, 2017, and titled INTERACTIVE SURGICAL PLATFORM, which is hereby incorporated by reference herein in its entirety. The laser Doppler provides an image 4202 suitable for inspecting seals along the staple lines 4180a, 4180b, 4182a and for visualizing bleeding 4206 of any defective seals. Laser Doppler inspection of the first firing 4172 of device 002 shows a defective seal at the first staple line 4180a of the first portion 4166a of the bronchial vessel sealed during the first firing 4172. The staple line 4180a seal is bleeding 4206 out at a volume of 0.5 cc. The image 4202 is recorded at anonymous time 09:55:15 4204 and is paired with the force-to-close curve 4192 and force-to-fire curve 4194 shown in FIG. 74. The data pair set is grouped by surgery and is stored locally in the surgical hub 206 storage 248 and/or remotely to the cloud 204 storage 205 for aggregation, processing, and analysis, for example. For example, the cloud 204 analytics engine associates the information contained in the first self-describing packet 4100 associated with the first firing 4172 and indicate that a defective seal was produced at the staple line 4166a. Over time, this information can be aggregated, analyzed, and used to improve outcomes of the surgical procedure, such as, resection of a lung tumor, for example.

Figure 76:
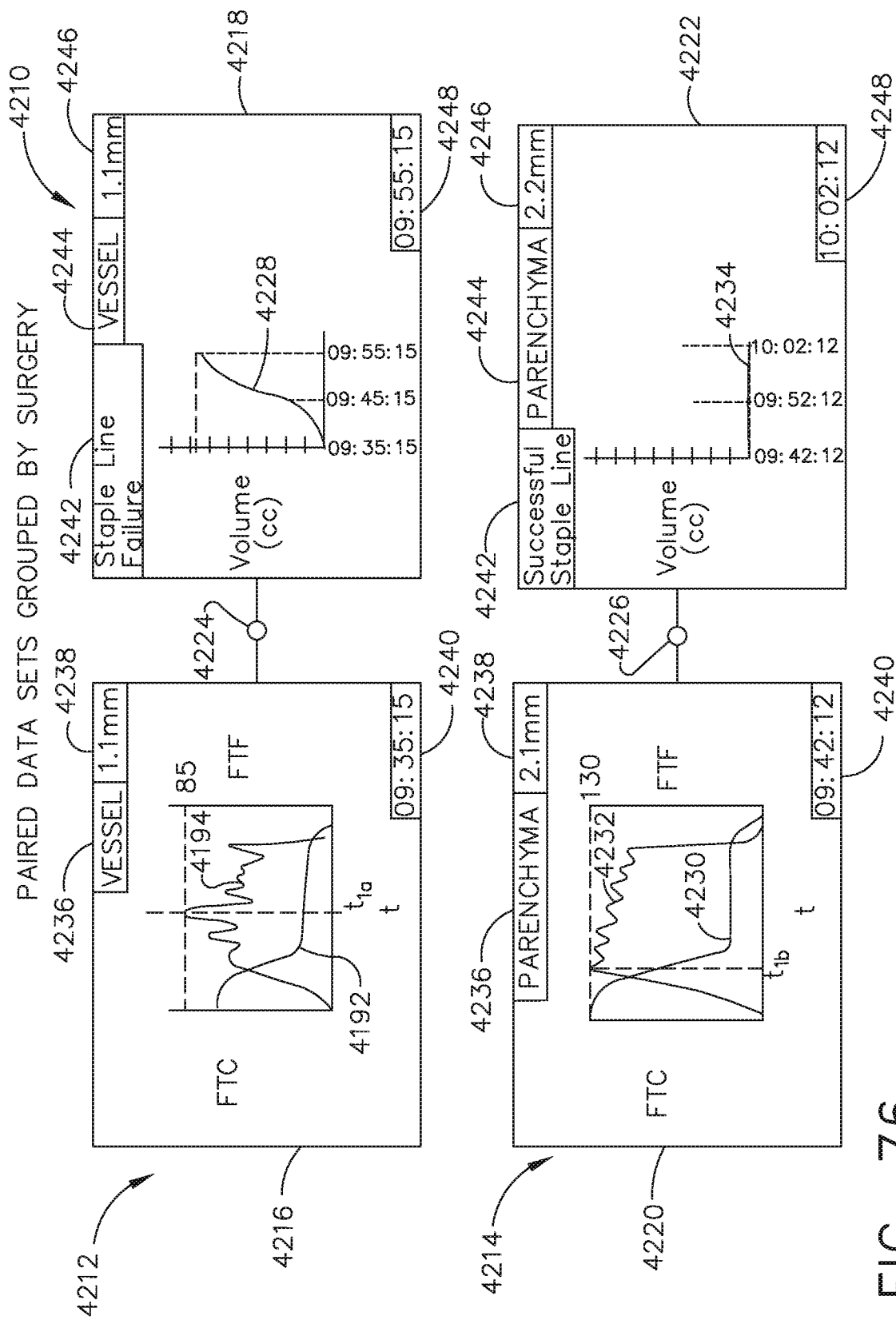
FIG. 76 illustrates a paired data set grouped by surgery, in accordance with at least one aspect of the present disclosure.

FIG. 76 illustrates two paired data sets 4210 grouped by surgery, according to one aspect of the present disclosure. The upper paired data set 4212 is grouped by one surgery and a lower paired data set 4214 grouped by another surgery. The upper paired data set 4212, for example, is grouped by the lung tumor resection surgery discussed in connection with FIGS. 73-76. Accordingly, the rest of the description of FIG. 76 will reference information described in FIGS. 32-35 as well as FIGS. 1-21 to show interaction with an interactive surgical system 100 environment including a surgical hub 106, 206. The lower paired data set 4214 is grouped by a liver tumor resection surgical procedure where the surgeon treated parenchyma tissue. The upper paired data set is associated with a failed staple line seal and the bottom paired data set is associated with a successful staple line seal. The upper and lower paired data sets 4212, 4214 are sampled by the instrument device 235 and each sample formed into a self-describing data packet 4100 which is transmitted to the surgical hub 206 and eventually is transmitted from the surgical hub 206 to the cloud 204. The samples may be stored locally in the instrument device 235 prior to packetizing or may be transmitted on the fly. Sampling rate and transmission rate are dictated by communication traffic in the surgical hub 206 and may be adjusted dynamically to accommodate current bandwidth limitations.

The upper paired data set 4212 includes a left data set 4216 recorded by the instrument/device 235 during the first firing 4172 linked 4224 to a right data set 4218 recorded at the time the staple line seal 4180a of the first bronchial vessel 4166a was evaluated. The left data set 4216 indicates a "Vessel" tissue type 4236 having a thickness 4238 of 1.1 mm. Also included in the left data set 4216 is the force-to-close curve 4192 and force-to-fire curve 4194 versus time (anonymous real time) recorded during the first firing 4172 of the lung tumor resection surgical procedure. The left data set 4216 shows that the force-to-fire peaked at 85 Lbs. and recorded at anonymous real time 4240 $t_{1a}$ (09:35:15). The right data set 4218 depicts the staple line visualization curve 4228 depicting leakage versus time. The right data set 4218 indicates that a "Vessel" tissue type 4244 having a thickness 4246 of 1.1 mm experienced a staple line 4180a seal failure 4242. The staple line visualization curve 4228 depicts leakage volume (cc) versus time of the staple line 4180a seal. The staple line visualization curve 4228 shows that the leakage volume reached 0.5 cc, indicating a failed staple line 4180a seal of the bronchial vessel 4166a, recorded at anonymous time 4248 (09:55:15).

The lower paired data set 4214 includes a left data set 4220 recorded by the instrument/device 235 during a firing linked 4226 to a right data set 4222 recorded at the time the staple line seal of the parenchyma tissue was evaluated. The left data set 4220 indicates a "Parenchyma" tissue type 4236 having a thickness 4238 of 2.1 mm. Also included in the left data set 4220 is the force-to-close curve 4230 and force-to-fire curve 4232 versus time (anonymous real time) recorded during the first firing of the liver tumor resection surgical procedure. The left data set 4220 shows that the force-to-fire peaked at 100 Lbs. and recorded at anonymous real time 4240 $t_{1b}$ (09:42:12). The right data set 4222 depicts the staple line visualization curve 4228 depicting leakage versus time. The right data set 4234 indicates that a "Parenchyma" tissue type 4244 having a thickness 4246 of 2.2 mm experienced a successful staple line seal. The staple line visualization curve 4234 depicts leakage volume (cc) versus time of the staple line seal. The staple line visualization curve 4234 shows that the leakage volume was 0.0 cc, indicating a successful staple line seal of the parenchyma tissue, recorded at anonymous time 4248 (10:02:12).

The paired date sets 4212, 4214 grouped by surgery are collected for many procedures and the data contained in the paired date sets 4212, 4214 is recorded and stored in the cloud 204 storage 205 anonymously to protect patient privacy, as described in connection with FIGS. 62-69. In one aspect, the paired date sets 4212, 4214 data are transmitted from the instrument/device 235, or other modules coupled to the surgical hub 206, to the surgical hub 206 and to the cloud 204 in the form of the self-describing packet 4100 as described in connection with FIGS. 71 and 72 and surgical procedure examples described in connection with FIGS. 72-76. The paired date sets 4212, 4214 data stored in the cloud 204 storage 205 is analyzed in the cloud 204 to provide feedback to the instrument/device 235, or other modules coupled to the surgical hub 206, notifying a surgical robot coupled to the robot hub 222, or the surgeon, that the conditions identified by the left data set ultimately lead to either a successful or failed seal. As described in connection with FIG. 76, the upper left data set 4216 led to a failed seal and the bottom left data set 4220 led to a successful seal. This is advantageous because the information provided in a paired data set grouped by surgery can be used to improve resection, transection, and creation of anastomosis in a variety of tissue types. The information can be used to avoid pitfalls that may lead to a failed seal.

FIG. 77 is a diagram of the right lung 4156 and FIG. 78 is a diagram of the bronchial tree 4250 including the trachea 4252 and the bronchi 4254, 4256 of the lungs. As shown in FIG. 77, the right lung 4156 is composed of three lobes divided into the upper lobe 4162, the middle lobe 4160, and the lower lobe 4165 separated by the oblique fissure 4167 and horizontal fissure 4160. The left lung is composed of only two smaller lobes due to the position of heart. As shown in FIG. 78, inside each lung, the right bronchus 4254 and the left bronchus 4256 divide into many smaller airways called bronchioles 4258, greatly increasing surface area. Each bronchiole 4258 terminates with a cluster of air sacs called alveoli 4260, where gas exchange with the bloodstream occurs.

Figure 79:
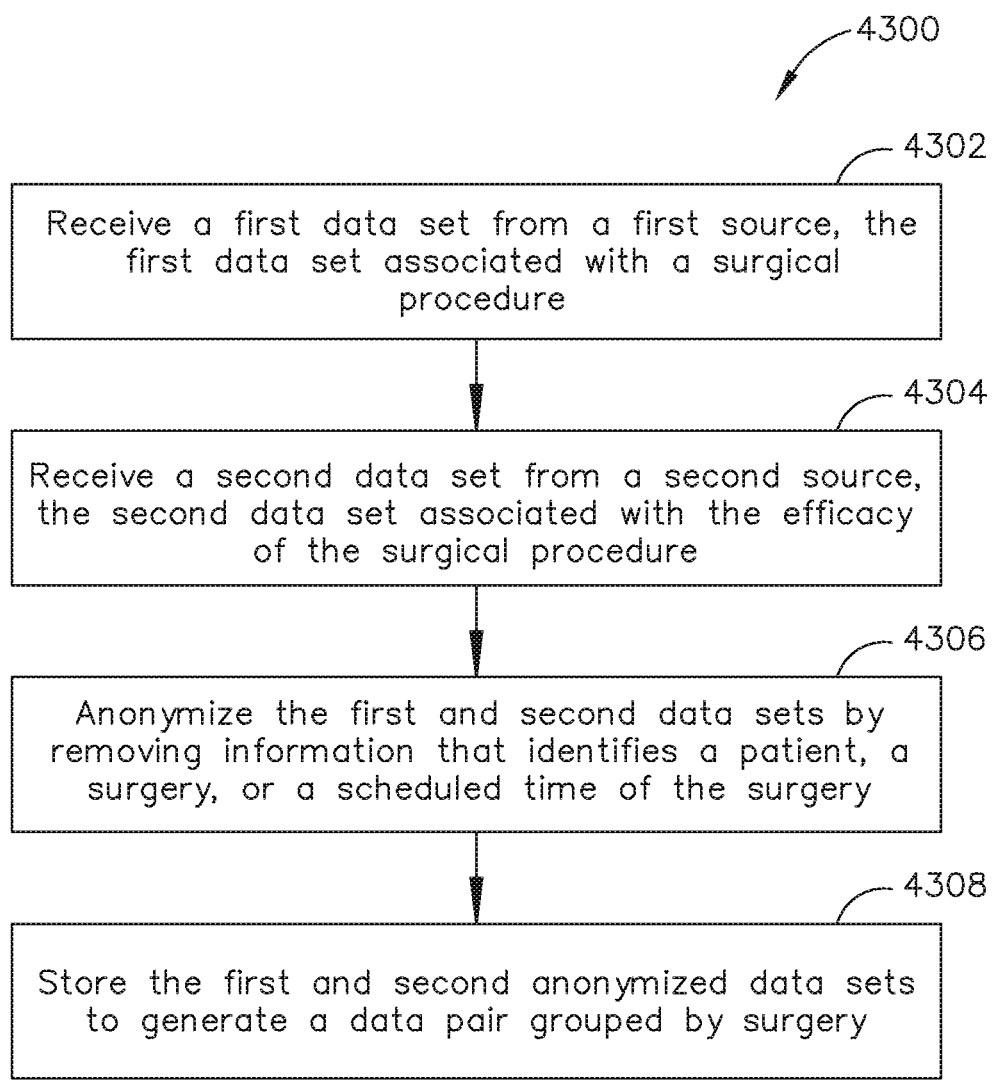
FIG. 79 is a logic flow diagram of a process depicting a control program or a logic configuration for storing paired anonymous data sets grouped by surgery, in accordance with at least one aspect of the present disclosure.

FIG. 79 is a logic flow diagram 4300 of a process depicting a control program or a logic configuration for storing paired anonymous data sets grouped by surgery, according to one aspect of the present disclosure. With reference to FIGS. 1-79, in one aspect, the present disclosure provides a surgical hub 206 configured to communicate with a surgical instrument 235. The surgical hub 206 comprises a processor 244 and a memory 249 coupled to the processor 244. The memory 249 storing instructions executable by the processor 244 to receive 4302 a first data set from a first source, the first data set associated with a surgical procedure, receive 4304 a second data set from a second source, the second data set associated with the efficacy of the surgical procedure, anonymize 4306 the first and second data sets by removing information that identifies a patient, a surgery, or a scheduled time of the surgery, and store 4308 the first and second anonymized data sets to generate a data pair grouped by surgery. The first data set is generated at a first time, the second data set is generated at a second time, and the second time is separate and distinct from the first time.

In another aspect, the memory 249 stores instructions executable by the processor 244 to reconstruct a series of chronological events based on the data pair. In another aspect, the memory 249 stores instructions executable by the processor 244 to reconstruct a series of coupled but unconstrained data sets based on the data pair. In another aspect, the memory 249 stores instructions executable by the processor 244 to encrypt the data pair, define a backup format for the data pair, and mirror the data pair to a cloud 204 storage device 205.

Determination of Data to Transmit to Cloud Based Medical Analytics

In one aspect, the present disclosure provides a communication hub and storage device for storing parameters and status of a surgical device what has the ability to determine when, how often, transmission rate, and type of data to be shared with a cloud based analytics system. The disclosure further provides techniques to determine where the analytics system communicates new operational parameters for the hub and surgical devices.

In a surgical hub environment, large amounts of data can be generated rather quickly and may cause storage and communication bottlenecks in the surgical hub network. One solution may include local determination of when and what data is transmitted for to the cloud-based medical analytics system for further processing and manipulation of surgical hub data. The timing and rate at which the surgical hub data is exported can be determined based on available local data storage capacity. User defined inclusion or exclusion of specific users, patients, or procedures enable data sets to be included for analysis or automatically deleted. The time of uploads or communications to the cloud-based medical analytics system may be determined based on detected surgical hub network down time or available capacity.

With reference to FIGS. 1-79, in one aspect, the present disclosure provides a surgical hub 206 comprising a storage device 248, a processor 244 coupled to the storage device 248, and a memory 249 coupled to the processor 244. The memory 249 stores instructions executable by the processor 244 to receive data from a surgical instrument 235, determine a rate at which to transfer the data to a remote cloud-based medical analytics network 204 based on available storage capacity of the storage device 248, determine a frequency at which to transfer the data to the remote cloud-based medical analytics network 204 based on the available storage capacity of the storage device 248 or detected surgical hub network 206 down time, and determine a type of data to transfer the data to a remote cloud-based medical analytics network 204 based on inclusion or exclusion of data associated with a users, patient, or surgical procedure.

In another aspect, the memory 249 stores instructions executable by the processor 244 to receive new operational parameters for the surgical hub 206 or the surgical instrument 235.

In various aspects, the present disclosure provides a control circuit to determine, rate, frequency and type of data to transfer the data to the remote cloud-based medical analytics network as described above. In various aspects, the present disclosure provides a non-transitory computer-readable medium storing computer readable instructions which, when executed, causes a machine to determine, rate, frequency and type of data to transfer to the remote cloud-based medical analytics network.

In one aspect, the surgical hub 206 is configured to determine what data to transmit to the cloud based analytics system 204. For example, a surgical hub 206 modular device 235 that includes local processing capabilities may determine the rate, frequency, and type of data to be transmitted to the cloud based analytics system 204 for analysis and processing.

In one aspect, the surgical hub 206 comprises a modular communication hub 203 and storage device 248 for storing parameters and status of a device 235 that has the ability to determine when and how often data can be shared with a cloud based analytics system 204, the transmission rate and the type of data that can be shared with the cloud based analytics system 204. In another aspect, the cloud analytics system 204 communicates new operational parameters for the surgical hub 206 and surgical devices 235 coupled to the surgical hub 206. A cloud based analytics system 204 is described in commonly-owned U.S. Provisional Patent Application Ser. No. 62/611,340, filed Dec. 28, 2017, and titled CLOUD-BASED MEDICAL ANALYTICS, which is incorporated herein by reference in its entirety.

In one aspect, a device 235 coupled to a local surgical hub 206 determines when and what data is transmitted to the cloud analytics system 204 for company analytic improvements. In one example, the available local data storage capacity remaining in the storage device 248 controls the timing and rate at which the data is exported. In another example, user defined inclusion or exclusion of specific users, patients, or procedures allows data sets to be included for analysis or automatically deleted. In yet another example, detected network down time or available capacity determines the time of uploads or communications.

In another aspect, transmission of data for diagnosis of failure modes is keyed by specific incidents. For example, user defined failure of a device, instrument, or tool within a procedure initiates archiving and transmission of data recorded with respect to that instrument for failure modes analysis. Further, when a failure event is identified, all the data surrounding the event is archived and packaged for sending back for predictive informatics (PI) analytics. Data that is part of a PI failure is flagged for storage and maintenance until either the hospital or the cloud based analytics system releases the hold on the data.

Catastrophic failures of instruments may initiate an automatic archive and submission of data for implications analysis. Detection of a counterfeit component or adapter on an original equipment manufacturer (OEM) device initiates documentation of the component and recording of the results and outcome of its use.

Figure 80:
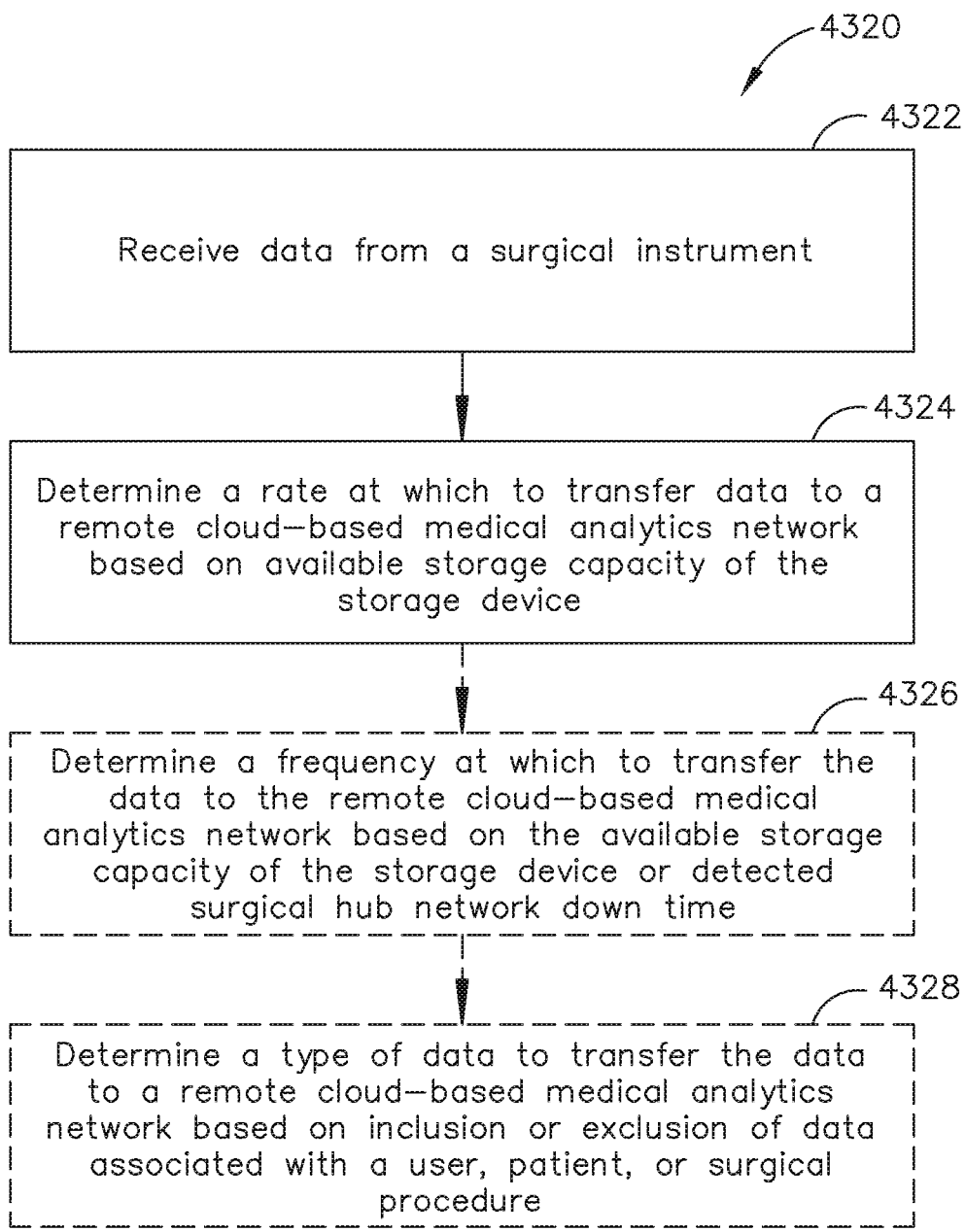
FIG. 80 is a logic flow diagram of a process depicting a control program or a logic configuration for determining rate, frequency, and type of data to transfer to a remote cloud-based analytics network, in accordance with at least one aspect of the present disclosure.

FIG. 80 is a logic flow diagram 4320 of a process depicting a control program or a logic configuration for determining rate, frequency, and type of data to transfer to a remote cloud-based analytics network, according to one aspect of the present disclosure. With reference to FIGS. 1-80, in one aspect, the present disclosure provides a surgical hub 206 comprising a storage device 248, a processor 244 coupled to the storage device 248, and a memory 249 coupled to the processor 244. The memory 249 stores instructions executable by the processor 244 to receive 4322 data from a surgical instrument 235, determine 4324 a rate at which to transfer the data to a remote cloud-based medical analytics network 204 based on available storage capacity of the storage device 248. Optionally, the memory 249 stores instructions executable by the processor 244 to determine 4326 a frequency at which to transfer the data to the remote cloud-based medical analytics network 204 based on the available storage capacity of the storage device 248. Optionally, the memory 249 stores instructions executable by the processor 244 to detect surgical hub network downtime and to determine 4326 a frequency at which to transfer the data to the remote cloud-based medical analytics network 204 based on the detected surgical hub network 206 down time. Optionally, the memory 249 stores instructions executable by the processor 244 to determine 4328 a type of data to transfer the data to a remote cloud-based medical analytics network 204 based on inclusion or exclusion of data associated with a users, patient, or surgical procedure.

In another aspect, the memory 249 stores instructions executable by the processor 244 to receive new operational parameters for the surgical hub 206 or the surgical instrument 235.

In one aspect, the present disclosure provides a surgical hub, comprising: a processor; and a memory coupled to the processor, the memory storing instructions executable by the processor to: interrogate a surgical instrument, wherein the surgical instrument is a first source of patient data; retrieve a first data set from the surgical instrument, wherein the first data set is associated with a patient and a surgical procedure; interrogate a medical imaging device, wherein the medical imaging device is a second source of patient data; retrieve a second data set from the medical imaging device, wherein the second data set is associated with the patient and an outcome of the surgical procedure; associate the first and second data sets by a key; and transmit the associated first and second data sets to remote network outside of the surgical hub. The present disclosure further provides, a surgical hub wherein the memory stores instructions executable by the processor to: retrieve the first data set using the key; anonymize the first data set by removing its association with the patient; retrieve the second data set using the key; anonymize the second data set by removing its association with the patient; pair the anonymized first and second data sets; and determine success rates of surgical procedures grouped by the surgical procedure based on the anonymized paired first and second data sets. The present disclosure further provides a surgical hub, wherein the memory stores instructions executable by the processor to: retrieve the anonymized first data set; retrieve the anonymized second data set; and reintegrate the anonymized first and second data sets using the key. The present disclosure further provides a surgical hub, wherein the first and second data sets define first and second data payloads in respective first and second data packets. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub, comprising: a processor; and a memory coupled to the processor, the memory storing instructions executable by the processor to: receive a first data packet from a first source, the first data packet comprising a first preamble, a first data payload, a source of the first data payload, and a first encryption certificate, wherein the first preamble defines the first data payload and the first encryption certificate verifies the authenticity of the first data packet; receive a second data packet from a second source, the second data packet comprising a second preamble, a second data payload, a source of the second data payload, and a second encryption certificate, wherein the second preamble defines the second data payload and the second encryption certificate verifies the authenticity of the second data packet; associate the first and second data packets; and generate a third data packet comprising the first and second data payloads. The present disclosure further provides a surgical hub, wherein the memory stores instructions executable by the processor to: determine that a data payload is from a new source; verify the new source of the data payload; and alter a data collection process at the surgical hub to receive subsequent data packets from the new source. The present disclosure further provides a surgical, wherein the memory stores instructions executable by the processor to associate the first and second data packets based on a key. The present disclosure further provides a surgical hub, wherein the memory stores instructions executable by the processor to anonymize the data payload of the third data packet. The present disclosure further provides a surgical hub, wherein the memory stores instructions executable by the processor to receive an anonymized third data packet and reintegrate the anonymized third data packet into the first and second data packets using the key. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub configured to communicate with a surgical instrument, the surgical hub comprising: a processor; and a memory coupled to the processor, the memory storing instructions executable by the processor to: receive a first data set associated with a surgical procedure, wherein the first data set is generated at a first time; receive a second data set associated with the efficacy of the surgical procedure, wherein the second data set is generated at a second time, wherein the second time is separate and distinct from the first time; anonymize the first and second data sets by removing information that identifies a patient, a surgery, or a scheduled time of the surgery; and store the first and second anonymized data sets to generate a data pair grouped by surgery. The present disclosure further provides a surgical hub, wherein the memory stores instructions executable by the processor to reconstruct a series of chronological events based on the data pair. The present disclosure further provides a surgical hub, wherein the memory stores instructions executable by the processor to reconstruct a series of coupled but unconstrained data sets based on the data pair. The present disclosure further provides a surgical hub, wherein the memory stores instructions executable by the processor to: encrypt the data pair; define a backup format for the data pair; and mirror the data pair to a cloud storage device. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub comprising: a storage device; a processor coupled to the storage device; and a memory coupled to the processor, the memory storing instructions executable by the processor to: receive data from a surgical instrument; determine a rate at which to transfer the data to a remote cloud-based medical analytics network based on available storage capacity of the storage device; determine a frequency at which to transfer the data to the remote cloud-based medical analytics network based on the available storage capacity of the storage device or detected surgical hub network down time; and determine a type of data to transfer the data to a remote cloud-based medical analytics network based on inclusion or exclusion of data associated with a users, patient, or surgical procedure. The present disclosure further provides a surgical hub, wherein the memory stores instructions executable by the processor to receive new operational parameters for the surgical hub or the surgical instrument. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub comprising: a control configured to: receive data from a surgical instrument; determine a rate at which to transfer the data to a remote cloud-based medical analytics network based on available storage capacity of the storage device; determine a frequency at which to transfer the data to the remote cloud-based medical analytics network based on the available storage capacity of the storage device or detected surgical hub network down time; and determine a type of data to transfer the data to a remote cloud-based medical analytics network based on inclusion or exclusion of data associated with a users, patient, or surgical procedure.

Surgical Hub Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 81:
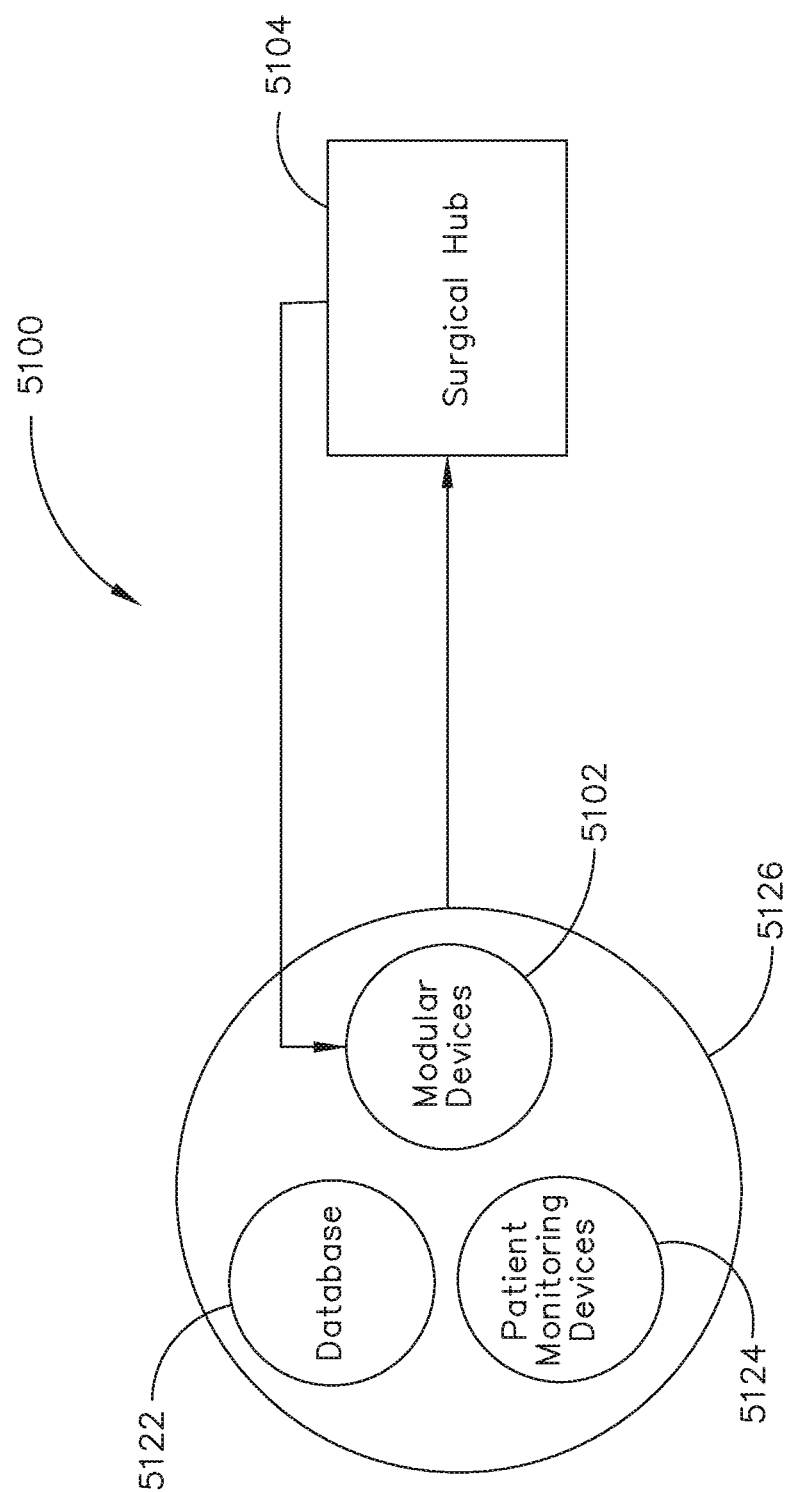
FIG. 81 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 81 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by the scanner 5132 depicted in FIG. 85B, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Figure 82A:
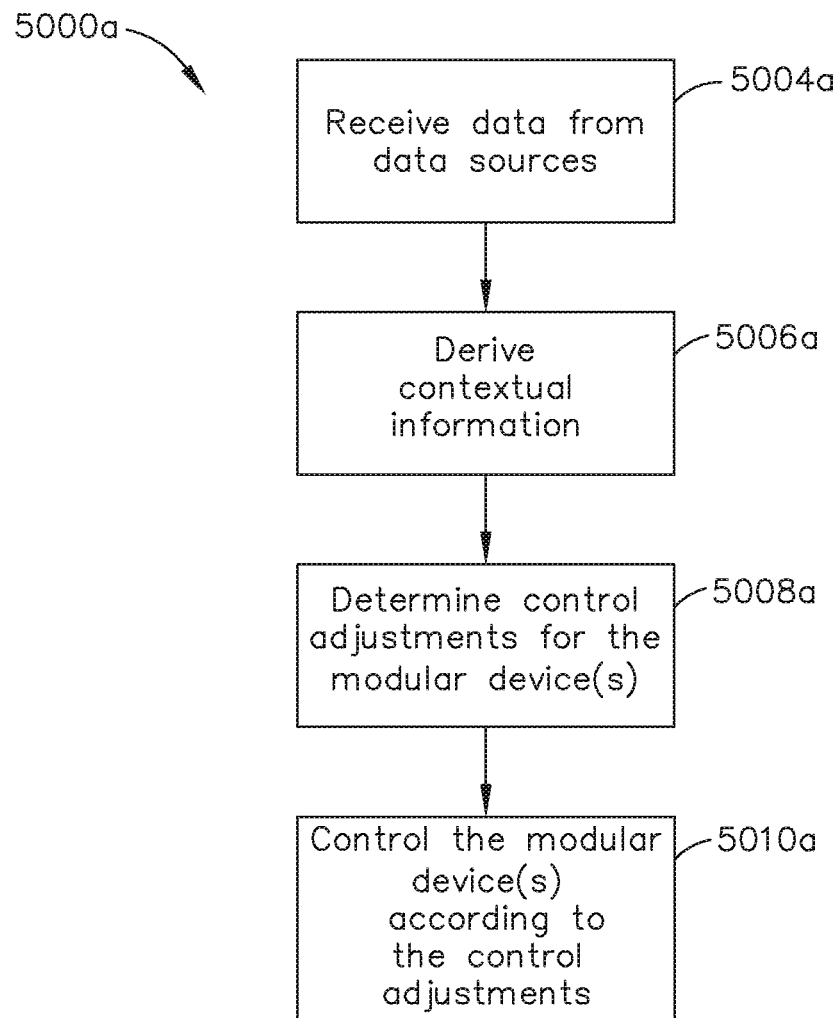
FIG. 82A illustrates a logic flow diagram of a process for controlling a modular device according to contextual information derived from received data, in accordance with at least one aspect of the present disclosure.

FIG. 82A illustrates a logic flow diagram of a process 5000a for controlling a modular device 5102 according to contextual information derived from received data, in accordance with at least one aspect of the present disclosure. In other words, a situationally aware surgical hub 5104 can execute the process 5000a to determine appropriate control adjustments for modular devices 5102 paired with the surgical hub 5104 before, during, or after a surgical procedure as dictated by the context of the surgical procedure. In the following description of the process 5000a, reference should also be made to FIG. 81. In one exemplification, the process 5000a can be executed by a control circuit of a surgical hub 5104, as depicted in FIG. 10 (processor 244). In another exemplification, the process 5000a can be executed by a cloud computing system 104, as depicted in FIG. 1. In yet another exemplification, the process 5000a can be executed by a distributed computing system including at least one of the aforementioned cloud computing system 104 and/or a control circuit of a surgical hub 5104 in combination with a control circuit of a modular device, such as the microcontroller 461 of the surgical instrument depicted in FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5000a will be described as being executed by the control circuit of a surgical hub 5104; however, it should be understood that the description of the process 5000a encompasses all of the aforementioned exemplifications.

Figure 85A:
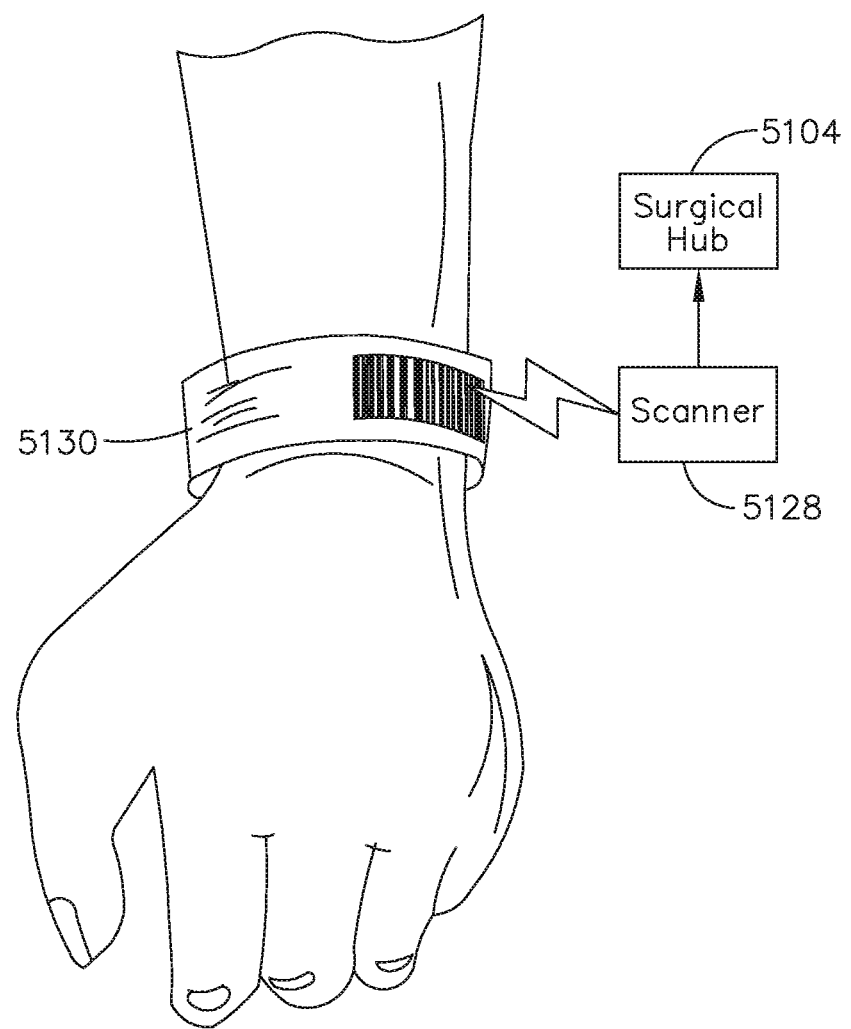
FIG. 85A illustrates a scanner coupled to a surgical hub for scanning a patient wristband, in accordance with at least one aspect of the present disclosure.

The control circuit of the surgical hub 5104 executing the process 5000a receives 5004a data from one or more data sources 5126 to which the surgical hub 5104 is communicably connected. The data sources 5126 include, for example, databases 5122, patient monitoring devices 5124, and modular devices 5102. In one exemplification, the databases 5122 can include a patient EMR database associated with the medical facility at which the surgical procedure is being performed. The data received 5004a from the data sources 5126 can include perioperative data, which includes preoperative data, intraoperative data, and/or postoperative data associated with the given surgical procedure. The data received 5004a from the databases 5122 can include the type of surgical procedure being performed or the patient's medical history (e.g., medical conditions that may or may not be the subject of the present surgical procedure). In one exemplification depicted in FIG. 83A, the control circuit can receive 5004a the patient or surgical procedure data by querying the patient EMR database with a unique identifier associated with the patient. The surgical hub 5104 can receive the unique identifier from, for example, a scanner 5128 for scanning the patient's wristband 5130 encoding the unique identifier associated with the patient when the patient enters the operating theater, as depicted in FIG. 85A. In one exemplification, the patient monitoring devices 5124 include BP monitors, EKG monitors, and other such devices that are configured to monitor one or more parameters associated with a patient. As with the modular devices 5102, the patient monitoring devices 5124 can be paired with the surgical hub 5104 such that the surgical hub 5104 receives 5004a data therefrom. In one exemplification, the data received 5004a from the modular devices 5102 that are paired with (i.e., communicably coupled to) the surgical hub 5104 includes, for example, activation data (i.e., whether the device is powered on or in use), data of the internal state of the modular device 5102 (e.g., force to fire or force to close for a surgical cutting and stapling device, pressure differential for an insufflator or smoke evacuator, or energy level for an RF or ultrasonic surgical instrument), or patient data (e.g., tissue type, tissue thickness, tissue mechanical properties, respiration rate, or airway volume).

As the process 5000a continues, the control circuit of the surgical hub 5104 can derive 5006a contextual information from the data received 5004a from the data sources 5126. The contextual information can include, for example, the type of procedure being performed, the particular step being performed in the surgical procedure, the patient's state (e.g., whether the patient is under anesthesia or whether the patient is in the operating room), or the type of tissue being operated on. The control circuit can derive 5006a contextual information according to data from ether an individual data source 5126 or combinations of data sources 5126. Further, the control circuit can derive 5006a contextual information according to, for example, the type(s) of data that it receives, the order in which the data is received, or particular measurements or values associated with the data. For example, if the control circuit receives data from an RF generator indicating that the RF generator has been activated, the control circuit could thus infer that the RF electrosurgical instrument is now in use and that the surgeon is or will be performing a step of the surgical procedure utilizing the particular instrument. As another example, if the control circuit receives data indicating that a laparoscope imaging device has been activated and an ultrasonic generator is subsequently activated, the control circuit can infer that the surgeon is on a laparoscopic dissection step of the surgical procedure due to the order in which the events occurred. As yet another example, if the control circuit receives data from a ventilator indicating that the patient's respiration is below a particular rate, then the control circuit can determine that the patient is under anesthesia.

The control circuit can then determine 5008a what control adjustments are necessary (if any) for one or more modular devices 5102 according to the derived 5006a contextual information. After determining 5008a the control adjustments, the control circuit of the surgical hub 5104 can then control 5010*a* the modular devices according to the control adjustments (if the control circuit determined 5008*a* that any were necessary). For example, if the control circuit determines that an arthroscopic procedure is being performed and that the next step in the procedure utilizes an RF or ultrasonic surgical instrument in a liquid environment, the control circuit can determine 5008*a* that a control adjustment for the generator of the RF or ultrasonic surgical instrument is necessary to preemptively increase the energy output of the instrument (because such instruments require increased energy in liquid environments to maintain their effectiveness). The control circuit can then control 5010*a* the generator and/or the RF or ultrasonic surgical instrument accordingly by causing the generator to increase its output and/or causing the RF or ultrasonic surgical instrument to increase the energy drawn from the generator. The control circuit can control 5010*a* the modular devices 5102 according to the determined 5008*a* control adjustment by, for example, transmitting the control adjustments to the particular modular device to update the modular device's 5102 programming. In another exemplification wherein the modular device(s) 5102 and the surgical hub 5104 are executing a distributed computing architecture, the control circuit can control 5010*a* the modular device 5102 according to the determined 5008*a* control adjustments by updating the distributed program.

Figure 82B:
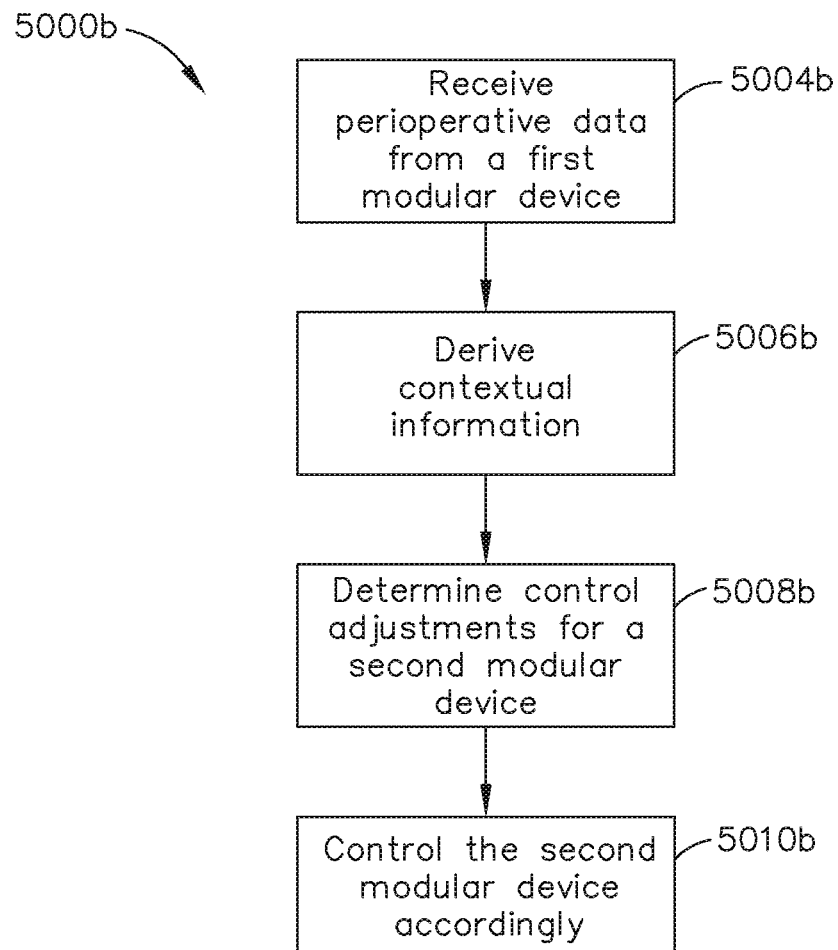
FIG. 82B illustrates a logic flow diagram of a process for controlling a second modular device according to contextual information derived from perioperative data received from a first modular device, in accordance with at least one aspect of the present disclosure.
Figure 82C:
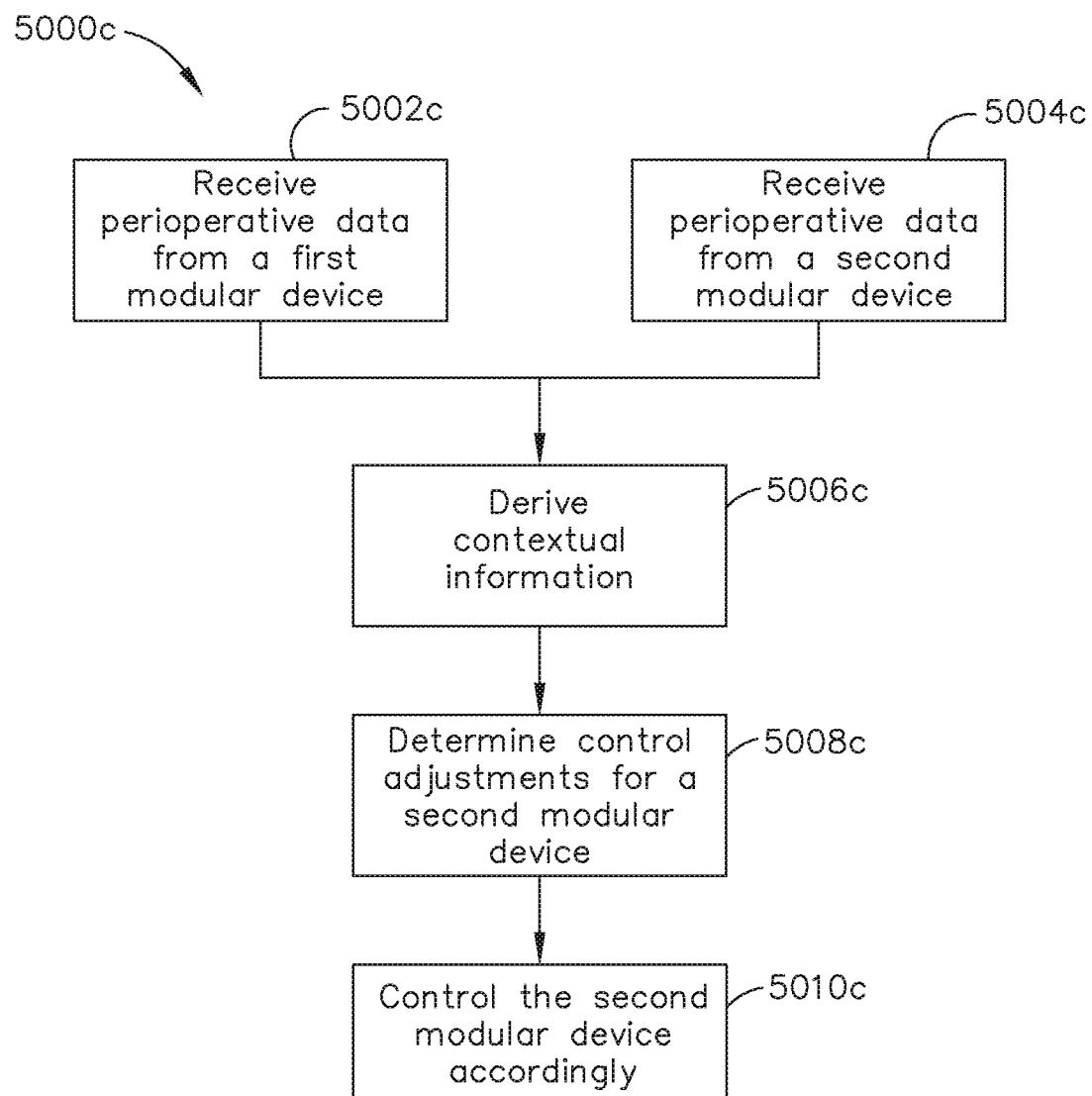
FIG. 82C illustrates a logic flow diagram of a process for controlling a second modular device according to contextual information derived from perioperative data received from a first modular device and the second modular device, in accordance with at least one aspect of the present disclosure.
Figure 82D:
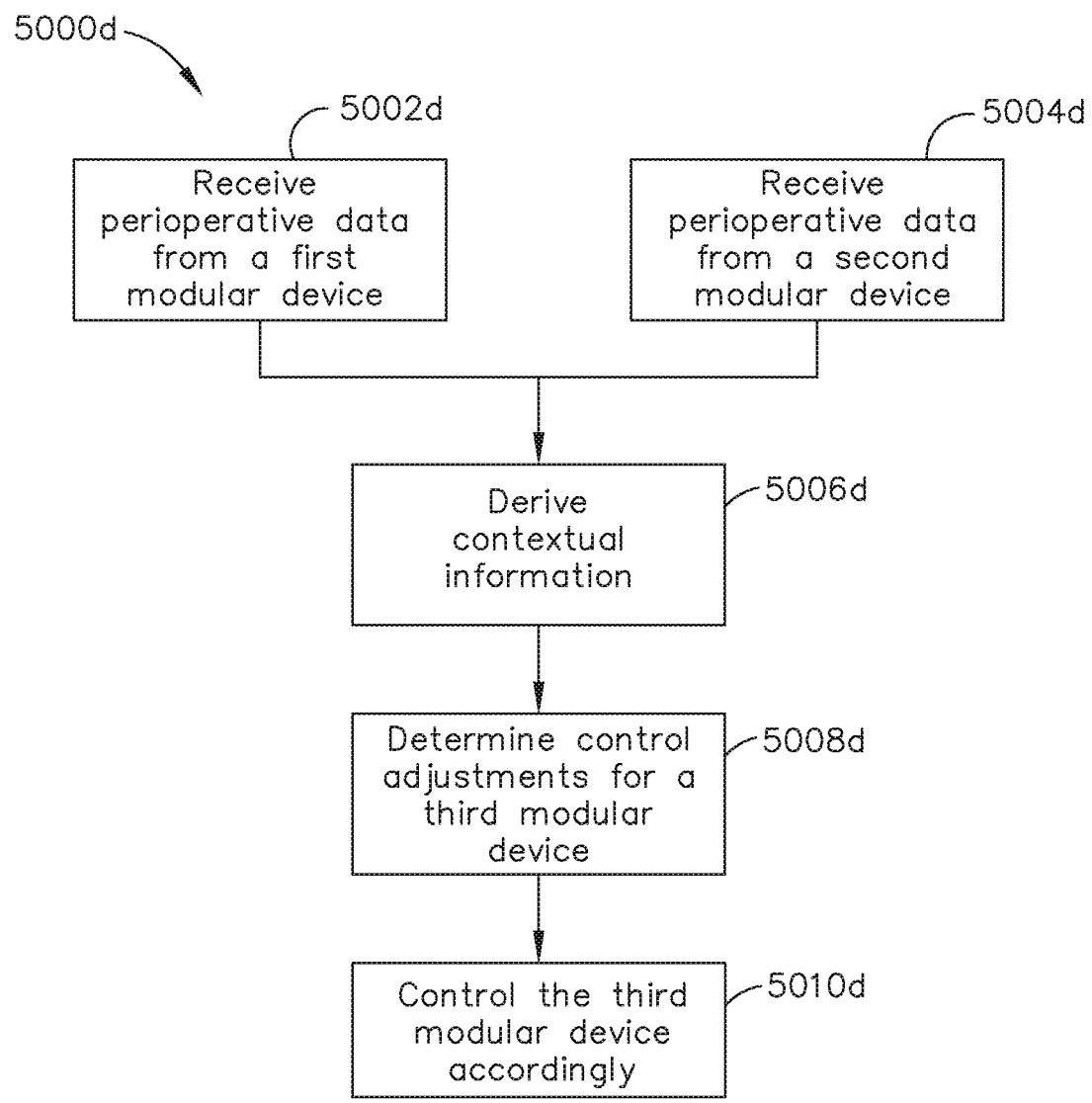
FIG. 82D illustrates a logic flow diagram of a process for controlling a third modular device according to contextual information derived from perioperative data received from a first modular device and a second modular device, in accordance with at least one aspect of the present disclosure.

FIGS. 82B-D illustrate representative implementations of the process 5000*a* depicted in FIG. 82A. As with the process 5000*a* depicted in FIG. 82A, the processes illustrated in FIGS. 82B-D can, in one exemplification, be executed by a control circuit of the surgical hub 5104. FIG. 82B illustrates a logic flow diagram of a process 5000*b* for controlling a second modular device according to contextual information derived from perioperative data received from a first modular device, in accordance with at least one aspect of the present disclosure. In the illustrated exemplification, the control circuit of the surgical hub 5104 receives 5004*b* perioperative data from a first modular device. The perioperative data can include, for example, data regarding the modular device 5102 itself (e.g., pressure differential, motor current, internal forces, or motor torque) or data regarding the patient with which the modular device 5102 is being utilized (e.g., tissue properties, respiration rate, airway volume, or laparoscopic image data). After receiving 5004*b* the perioperative data, the control circuit of the surgical hub 5104 derives 5006*b* contextual information from the perioperative data. The contextual information can include, for example, the procedure type, the step of the procedure being performed, or the status of the patient. The control circuit of the surgical hub 5104 then determines 5008*b* control adjustments for a second modular device based upon the derived 5006*b* contextual information and then controls 5010*b* the second modular device accordingly. For example, the surgical hub 5104 can receive 5004*b* perioperative data from a ventilator indicating that the patient's lung has been deflated, derive 5006*b* the contextual information therefrom that the subsequent step in the particular procedure type utilizes a medical imaging device (e.g., a scope), determine 5008*b* that the medical imaging device should be activated and set to a particular magnification, and then control 5010*b* the medical imaging device accordingly.

FIG. 82C illustrates a logic flow diagram of a process 5000*c* for controlling a second modular device according to contextual information derived from perioperative data received from a first modular device and the second modular device. In the illustrated exemplification, the control circuit of the surgical hub 5104 receives 5002*c* perioperative data from a first modular device and receives 5004*c* perioperative data from a second modular device. After receiving 5002*c*, 5004*c* the perioperative data, the control circuit of the surgical hub 5104 derives 5006*c* contextual information from the perioperative data. The control circuit of the surgical hub 5104 then determines 5008*c* control adjustments for the second modular device based upon the derived 5006*c* contextual information and then controls 5010*c* the second modular device accordingly. For example, the surgical hub 5104 can receive 5002*c* perioperative data from a RF electrosurgical instrument indicating that the instrument has been fired, receive 5004*c* perioperative data from a surgical stapling instrument indicating that the instrument has been fired, derive 5006*c* the contextual information therefrom that the subsequent step in the particular procedure type requires that the surgical stapling instrument be fired with a particular force (because the optimal force to fire can vary according to the tissue type being operated on), determine 5008*c* the particular force thresholds that should be applied to the surgical stapling instrument, and then control 5010*c* the surgical stapling instrument accordingly.

FIG. 82D illustrates a logic flow diagram of a process 5000*d* for controlling a third modular device according to contextual information derived from perioperative data received from a first modular device and a second modular device. In the illustrated exemplification, the control circuit of the surgical hub 5104 receives 5002*d* perioperative data from a first modular device and receives 5004*d* perioperative data from a second modular device. After receiving 5002*d*, 5004*d* the perioperative data, the control circuit of the surgical hub 5104 derives 5006*d* contextual information from the perioperative data. The control circuit of the surgical hub 5104 then determines 5008*d* control adjustments for a third modular device based upon the derived 5006*d* contextual information and then controls 5010*d* the third modular device accordingly. For example, the surgical hub 5104 can receive 5002*d*, 5004*d* perioperative data from an insufflator and a medical imaging device indicating that both devices have been activated and paired to the surgical hub 5104, derive 5006*d* the contextual information therefrom that a video-assisted thoracoscopic surgery (VATS) procedure is being performed, determine 5008*d* that the displays connected to the surgical hub 5104 should be set to display particular views or information associated with the procedure type, and then control 5010*d* the displays accordingly.

Figure 83A:
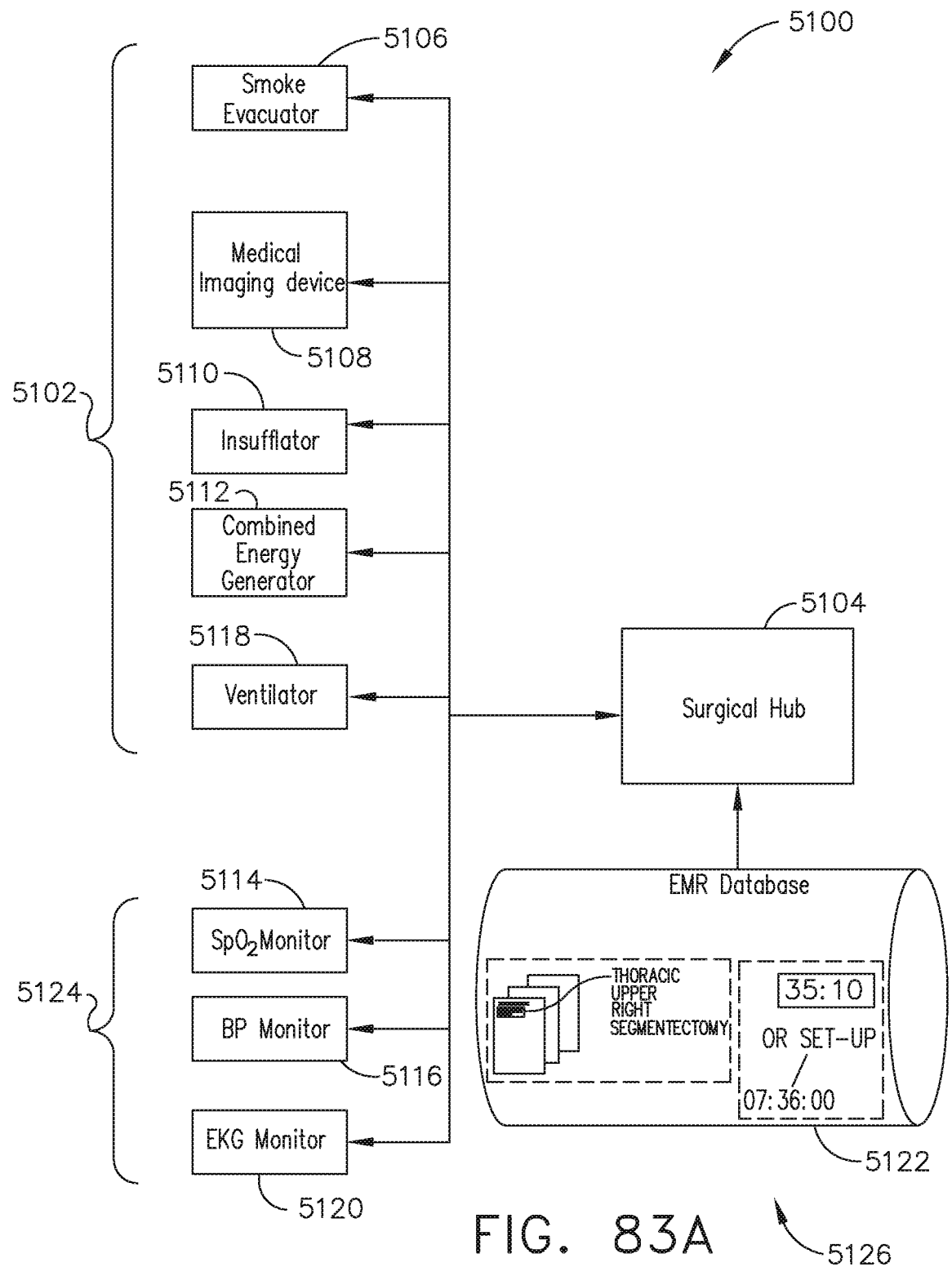
FIG. 83A illustrates a diagram of a surgical hub communicably coupled to a particular set of modular devices and an Electronic Medical Record (EMR) database, in accordance with at least one aspect of the present disclosure.

FIG. 83A illustrates a diagram of a surgical system 5100 including a surgical hub 5104 communicably coupled to a particular set of data sources 5126. A surgical hub 5104 including a situational awareness system can utilize the data received from the data sources 5126 to derive contextual information regarding the surgical procedure that the surgical hub 5104, the modular devices 5102 paired to the surgical hub 5104, and the patient monitoring devices 5124 paired to the surgical hub 5104 are being utilized in connection with. The inferences (i.e., contextual information) that one exemplification of the situational awareness system can derive from the particular set of data sources 5126 are depicted in dashed boxes extending from the data source(s) 5126 from which they are derived. The contextual information derived from the data sources 5126 can include, for example, what step of the surgical procedure is being performed, whether and how a particular modular device 5102 is being used, and the patient's condition.

In the example illustrated in FIG. 83A, the data sources 5126 include a database 5122, a variety of modular devices 5102, and a variety of patient monitoring devices 5124. The surgical hub 5104 can be connected to various databases 5122 to retrieve therefrom data regarding the surgical procedure that is being performed or is to be performed. In one exemplification of the surgical system 5100, the databases 5122 include an EMR database of a hospital. The data that can be received by the situational awareness system of the surgical hub 5104 from the databases 5122 can include, for example, start (or setup) time or operational information regarding the procedure (e.g., a segmentectomy in the upper right portion of the thoracic cavity). The surgical hub 5104 can derive contextual information regarding the surgical procedure from this data alone or from the combination of this data and data from other data sources 5126.

The surgical hub 5104 can also be connected to (i.e., paired with) a variety of patient monitoring devices 5124. In one exemplification of the surgical system 5100, the patient monitoring devices 5124 that can be paired with the surgical hub 5104 can include a pulse oximeter (SpO$_2$ monitor) 5114, a BP monitor 5116, and an EKG monitor 5120. The perioperative data that can be received by the situational awareness system of the surgical hub 5104 from the patient monitoring devices 5124 can include, for example, the patient's oxygen saturation, blood pressure, heart rate, and other physiological parameters. The contextual information that can be derived by the surgical hub 5104 from the perioperative data transmitted by the patient monitoring devices 5124 can include, for example, whether the patient is located in the operating theater or under anesthesia. The surgical hub 5104 can derive these inferences from data from the patient monitoring devices 5124 alone or in combination with data from other data sources 5126 (e.g., the ventilator 5118).

The surgical hub 5104 can also be connected to (i.e., paired with) a variety of modular devices 5102. In one exemplification of the surgical system 5100, the modular devices 5102 that can be paired with the surgical hub 5104 can include a smoke evacuator 5106, a medical imaging device 5108, an insufflator 5110, a combined energy generator 5112 (for powering an ultrasonic surgical instrument and/or an RF electrosurgical instrument), and a ventilator 5118.

The medical imaging device 5108 includes an optical component and an image sensor that generates image data. The optical component includes a lens or a light source, for example. The image sensor includes a charge-coupled device (CCD) or a complementary metal-oxide-semiconductor (CMOS), for example. In various exemplifications, the medical imaging device 5108 includes an endoscope, a laparoscope, a thoracoscope, and other such imaging devices. Various additional components of the medical imaging device 5108 are described above. The perioperative data that can be received by the surgical hub 5104 from the medical imaging device 5108 can include, for example, whether the medical imaging device 5108 is activated and a video or image feed. The contextual information that can be derived by the surgical hub 5104 from the perioperative data transmitted by the medical imaging device 5108 can include, for example, whether the procedure is a VATS procedure (based on whether the medical imaging device 5108 is activated or paired to the surgical hub 5104 at the beginning or during the course of the procedure). Furthermore, the image or video data from the medical imaging device 5108 (or the data stream representing the video for a digital medical imaging device 5108) can processed by a pattern recognition system or a machine learning system to recognize features (e.g., organs or tissue types) in the field of view (FOV) of the medical imaging device 5108, for example. The contextual information that can be derived by the surgical hub 5104 from the recognized features can include, for example, what type of surgical procedure (or step thereof) is being performed, what organ is being operated on, or what body cavity is being operated in.

Figure 83B:
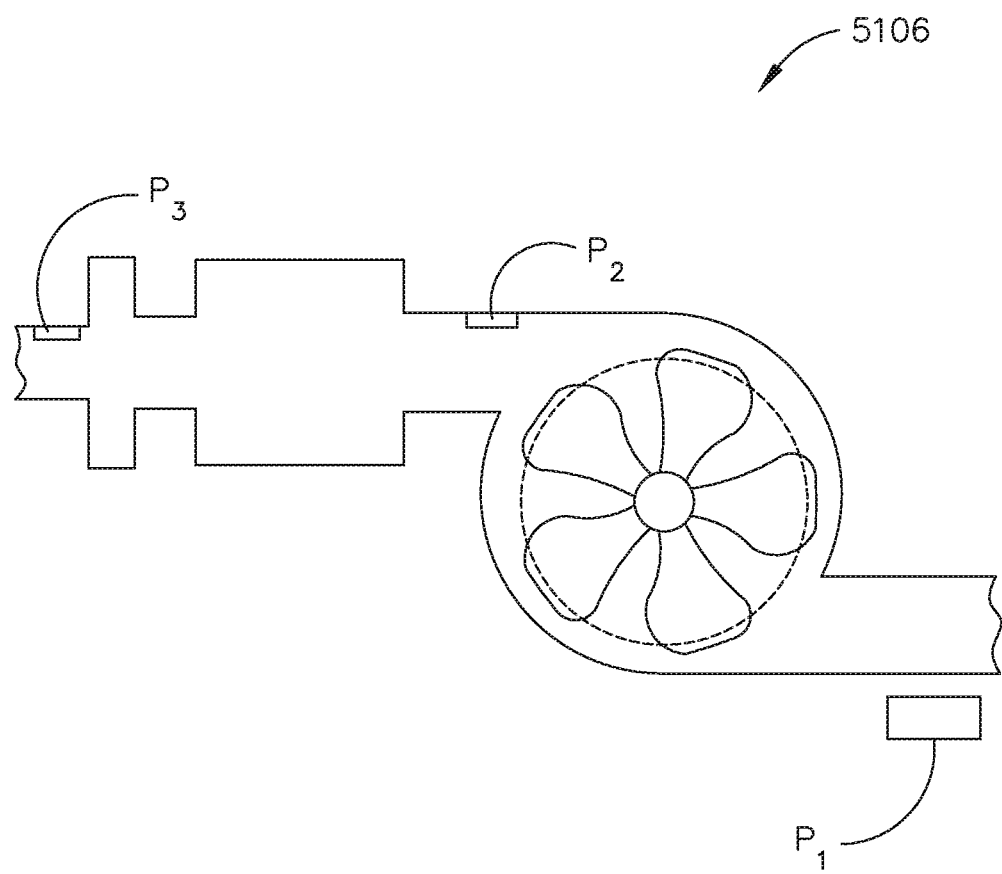
FIG. 83B illustrates a diagram of a smoke evacuator including pressure sensors, in accordance with at least one aspect of the present disclosure.

In one exemplification depicted in FIG. 83B, the smoke evacuator 5106 includes a first pressure sensor $P_1$ configured to detect the ambient pressure in the operating theater, a second pressure sensor $P_2$ configured to detect the internal downstream pressure (i.e., the pressure downstream from the inlet), and a third pressure sensor $P_3$ configured to detect the internal upstream pressure. In one exemplification, the first pressure sensor $P_1$ can be a separate component from the smoke evacuator 5106 or otherwise located externally to the smoke evacuator 5106. The perioperative data that can be received by the surgical hub 5104 from the smoke evacuator 5106 can include, for example, whether the smoke evacuator 5106 is activated, pressure readings from each of the sensors $P_1$, $P_2$, $P_3$, and pressure differentials between pairs of the sensors $P_1$, $P_2$, $P_3$. The perioperative data can also include, for example, the type of tissue being operated on (based upon the chemical composition of the smoke being evacuated) and the amount of tissue being cut. The contextual information that can be derived by the surgical hub 5104 from the perioperative data transmitted by the smoke evacuator 5106 can include, for example, whether the procedure being performed is utilizing insufflation. The smoke evacuator 5106 perioperative data can indicate whether the procedure is utilizing insufflation according to the pressure differential between $P_3$ and $P_1$. If the pressure sensed by $P_3$ is greater than the pressure sensed by $P_1$ (i.e., $P_3-P_1>0$), then the body cavity to which the smoke evacuator 5106 is connected is insufflated. If the pressure sensed by $P_3$ is equal to the pressure sensed by $P_1$ (i.e., $P_3-P_1=0$), then the body cavity is not insufflated. When the body cavity is not insufflated, the procedure may be an open type of procedure.

The insufflator 5110 can include, for example, pressure sensors and current sensors configured to detect internal parameters of the insufflator 5110. The perioperative data that can be received by the surgical hub 5104 from the insufflator can include, for example, whether the insufflator 5110 is activated and the electrical current drawn by the insufflator's 5110 pump. The surgical hub 5104 can determine whether the insufflator 5110 is activated by, for example, directly detecting whether the device is powered on, detecting whether there is a pressure differential between an ambient pressure sensor and a pressure sensor internal to the surgical site, or detecting whether the pressure valves of the insufflator 5110 are pressurized (activated) or non-pressurized (deactivated). The contextual information that can be derived by the surgical hub 5104 from the perioperative data transmitted by the insufflator 5110 can include, for example, the type of procedure being performed (e.g., insufflation is utilized in laparoscopic procedures, but not arthroscopic procedures) and what body cavity is being operated in (e.g., insufflation is utilized in the abdominal cavity, but not in the thoracic cavity). In some exemplifications, the inferences derived from the perioperative data received from different modular devices 5102 can be utilized to confirm and/or increase the confidence of prior inferences. For example, if the surgical hub 5104 determines that the procedure is utilizing insufflation because the insufflator 5110 is activated, the surgical hub 5104 can then confirm that inference by detecting whether the perioperative data from the smoke evacuator 5106 likewise indicates that the body cavity is insufflated.

The combined energy generator 5112 supplies energy to one or more ultrasonic surgical instruments or RF electrosurgical instruments connected thereto. The perioperative data that can be received by the surgical hub 5104 from the combined energy generator 5112 can include, for example, the mode that the combined energy generator 5112 is set to (e.g., a vessel sealing mode or a cutting/coagulation mode). The contextual information that can be derived by the surgical hub 5104 from the perioperative data transmitted by the combined energy generator 5112 can include, for example, the surgical procedural type (based on the number and types of surgical instruments that are connected to the energy generator 5112) and the procedural step that is being performed (because the particular surgical instrument being utilized or the particular order in which the surgical instruments are utilized corresponds to different steps of the surgical procedure). Further, the inferences derived by the surgical hub 5104 can depend upon inferences and/or perioperative data previously received by the surgical hub 5104. Once the surgical hub 5104 has determined the general category or specific type of surgical procedure being performed, the surgical hub 5104 can determine or retrieve an expected sequence of steps for the surgical procedure and then track the surgeon's progression through the surgical procedure by comparing the detected sequence in which the surgical instruments are utilized relative to the expected sequence.

The perioperative data that can be received by the surgical hub 5104 from the ventilator 5118 can include, for example, the respiration rate and airway volume of the patient. The contextual information that can be derived by the surgical hub 5104 from the perioperative data transmitted by the ventilator 5118 can include, for example, whether the patient is under anesthesia and whether the patient's lung is deflated. In some exemplifications, certain contextual information can be inferred by the surgical hub 5104 based on combinations of perioperative data from multiple data sources 5126. For example, the situational awareness system of the surgical hub 5104 can be configured to infer that the patient is under anesthesia when the respiration rate detected by the ventilator 5118, the blood pressure detected by the BP monitor 5116, and the heart rate detected by the EKG monitor 5120 fall below particular thresholds. For certain contextual information, the surgical hub 5104 can be configured to only derive a particular inference when the perioperative data from a certain number or all of the relevant data sources 5126 satisfy the conditions for the inference.

As can be seen from the particular exemplified surgical system 5100, the situational awareness system of a surgical hub 5104 can derive a variety of contextual information regarding the surgical procedure being performed from the data sources 5126. The surgical hub 5104 can utilize the derived contextual information to control the modular devices 5102 and make further inferences about the surgical procedure in combination with data from other data sources 5126. It should be noted that the inferences depicted in FIG. 83A and described in connection with the depicted surgical system 5100 are merely exemplary and should not be interpreted as limiting in any way. Furthermore, the surgical hub 5104 can be configured to derive a variety of other inferences from the same (or different) modular devices 5102 and/or patient monitoring devices 5124. In other exemplifications, a variety of other modular devices 5102 and/or patient monitoring devices 5124 can be paired to the surgical hub 5104 in the operating theater and data received from those additional modular devices 5102 and/or patient monitoring devices 5124 can be utilized by the surgical hub 5104 to derive the same or different contextual information about the particular surgical procedure being performed.

Figure 84A:
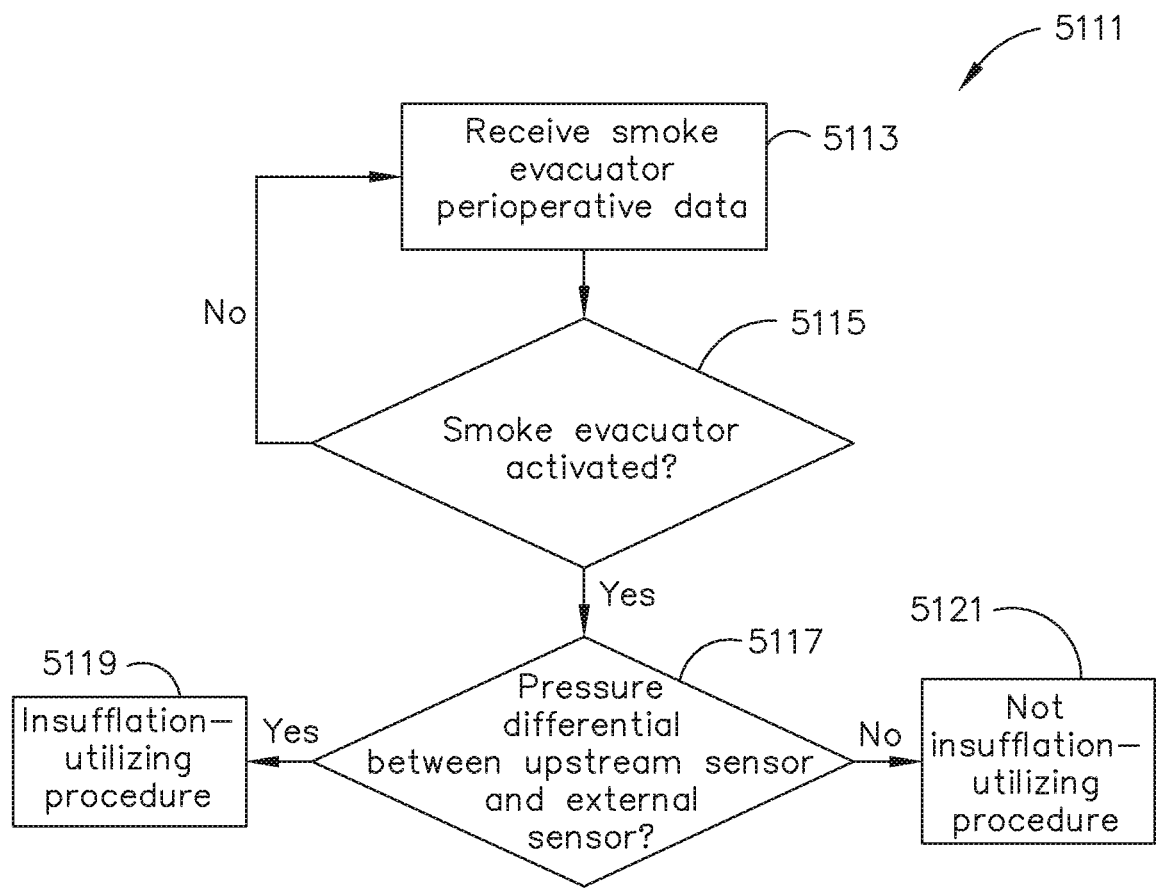
FIG. 84A illustrates a logic flow diagram of a process for determining a procedure type according to smoke evacuator perioperative data, in accordance with at least one aspect of the present disclosure.
Figure 84B:
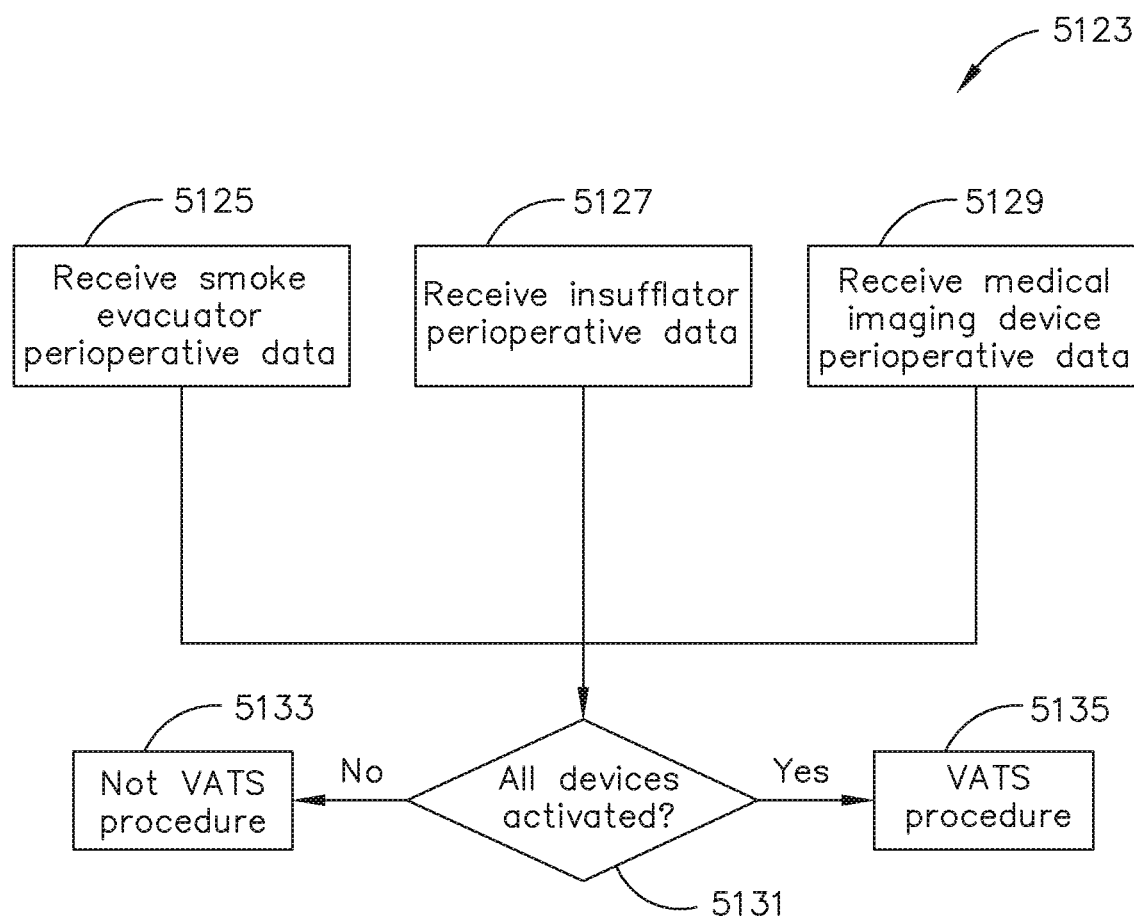
FIG. 84B illustrates a logic flow diagram of a process for determining a procedure type according to smoke evacuator, insufflator, and medical imaging device perioperative data, in accordance with at least one aspect of the present disclosure.
Figure 84C:
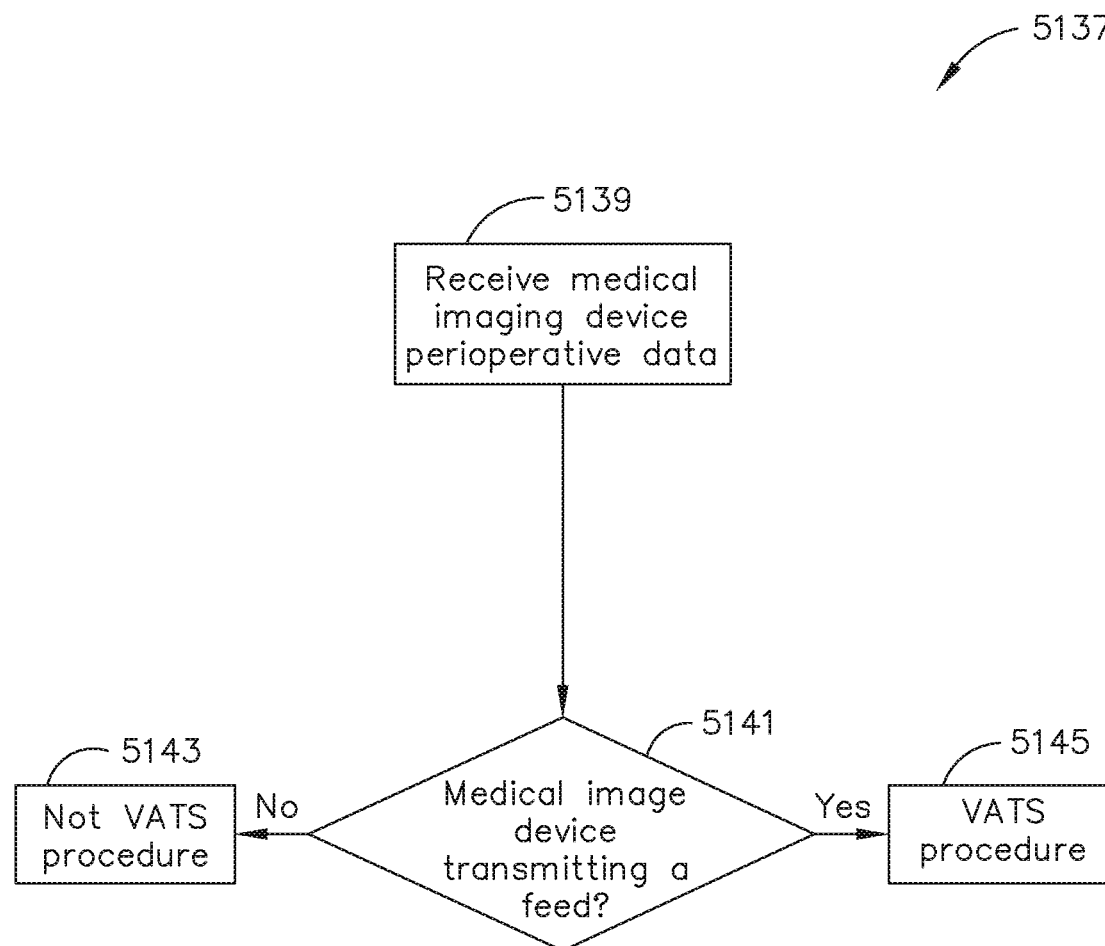
FIG. 84C illustrates a logic flow diagram of a process for determining a procedure type according to medical imaging device perioperative data, in accordance with at least one aspect of the present disclosure.
Figure 84D:
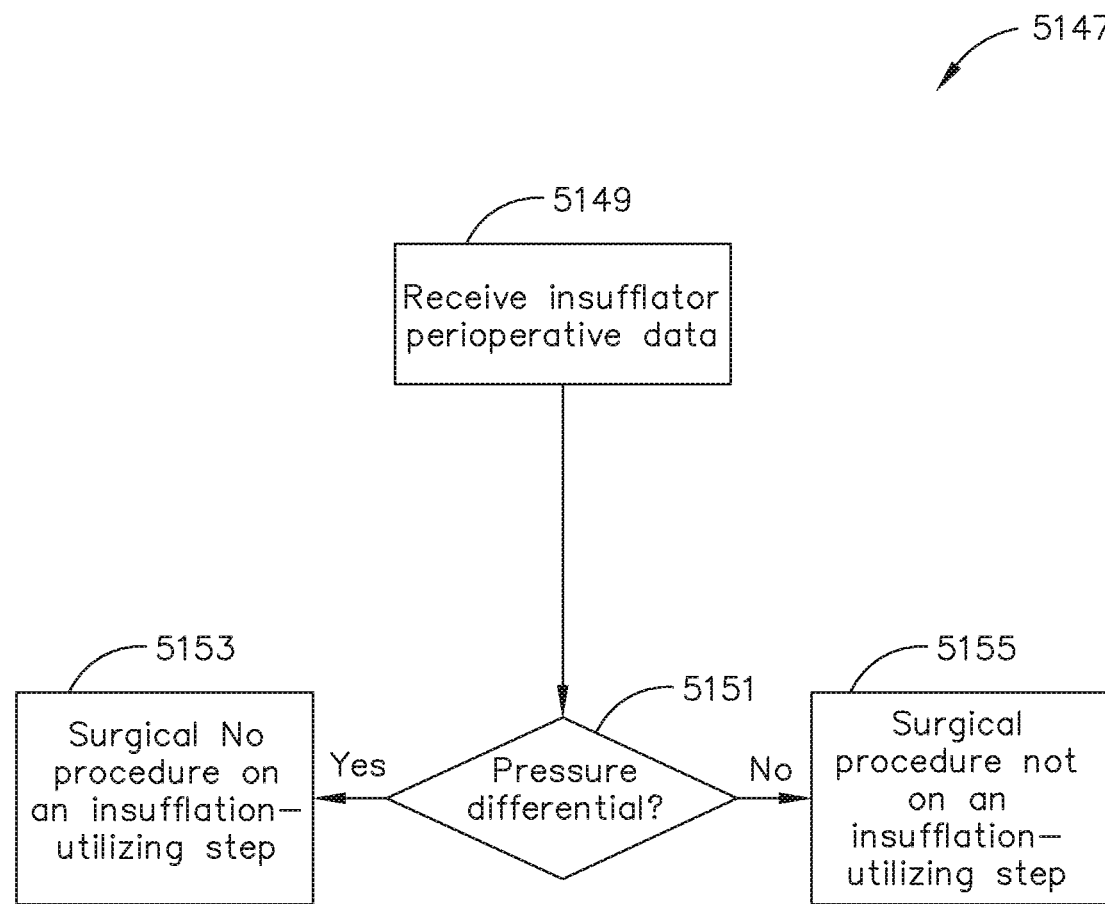
FIG. 84D illustrates a logic flow diagram of a process for determining a procedural step according to insufflator perioperative data, in accordance with at least one aspect of the present disclosure.
Figure 84E:
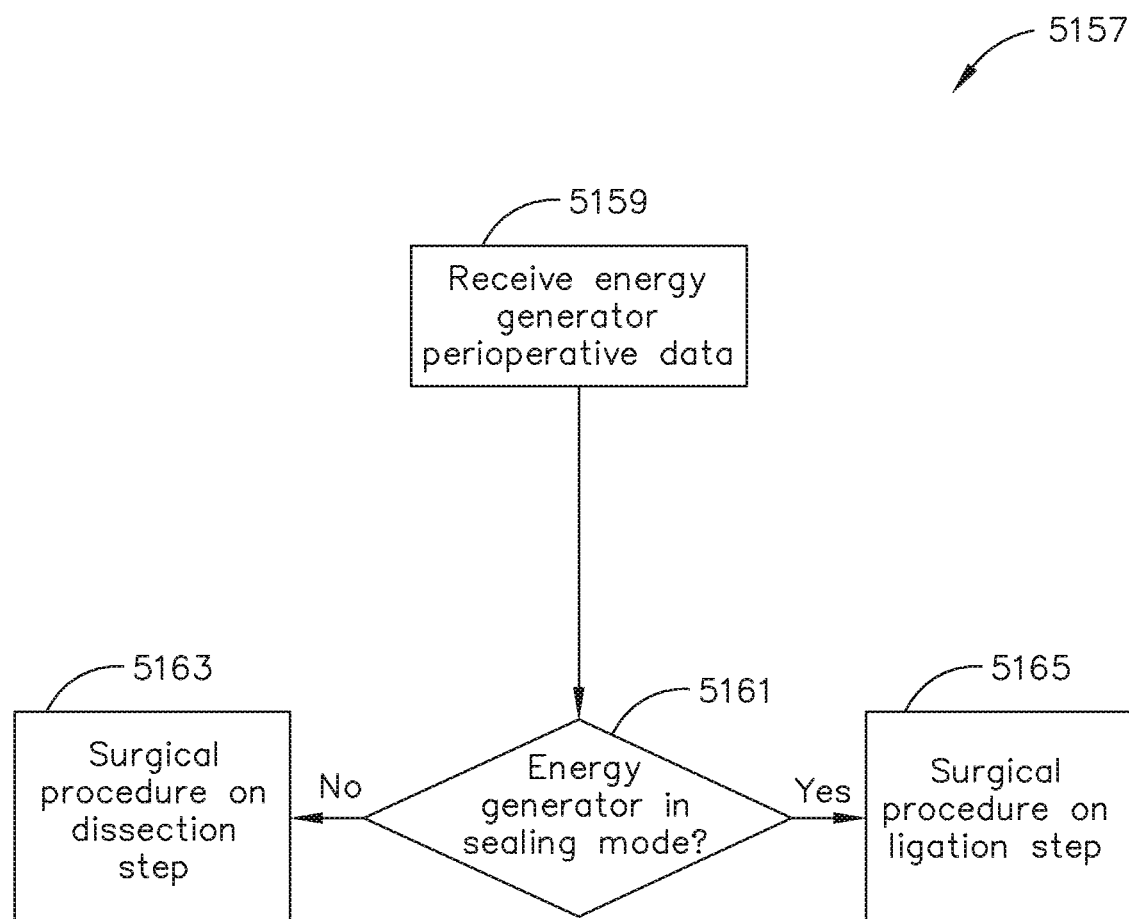
FIG. 84E illustrates a logic flow diagram of a process for determining a procedural step according to energy generator perioperative data, in accordance with at least one aspect of the present disclosure.
Figure 84F:
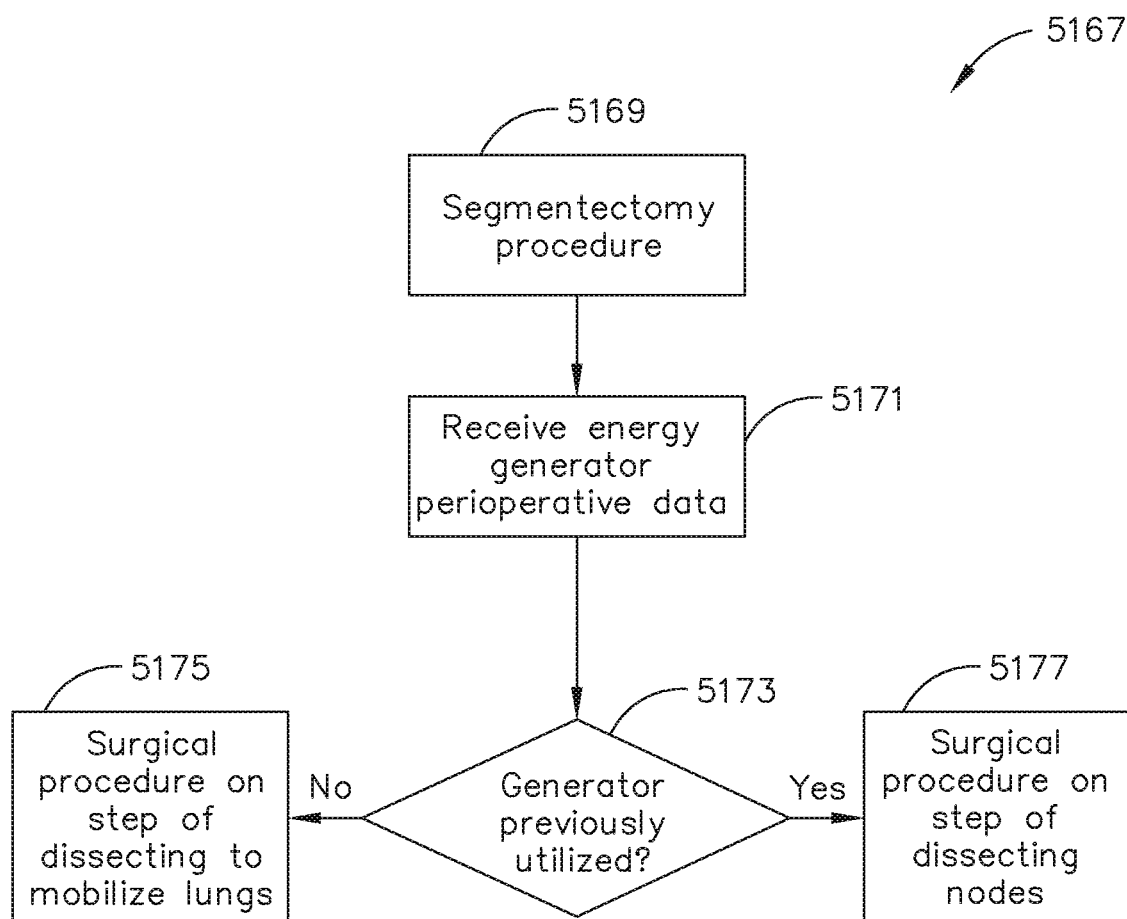
FIG. 84F illustrates a logic flow diagram of a process for determining a procedural step according to energy generator perioperative data, in accordance with at least one aspect of the present disclosure.
Figure 84G:
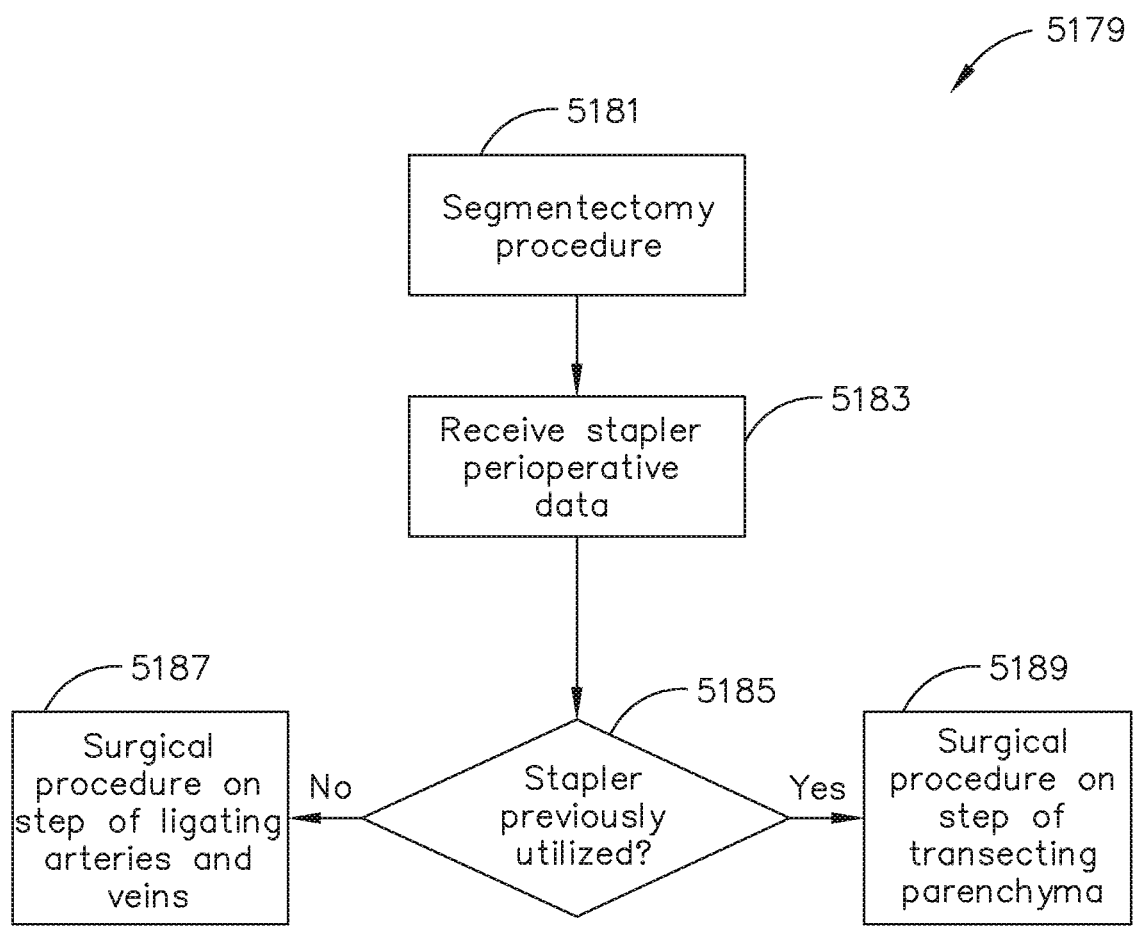
FIG. 84G illustrates a logic flow diagram of a process for determining a procedural step according to stapler perioperative data, in accordance with at least one aspect of the present disclosure.
Figure 84H:
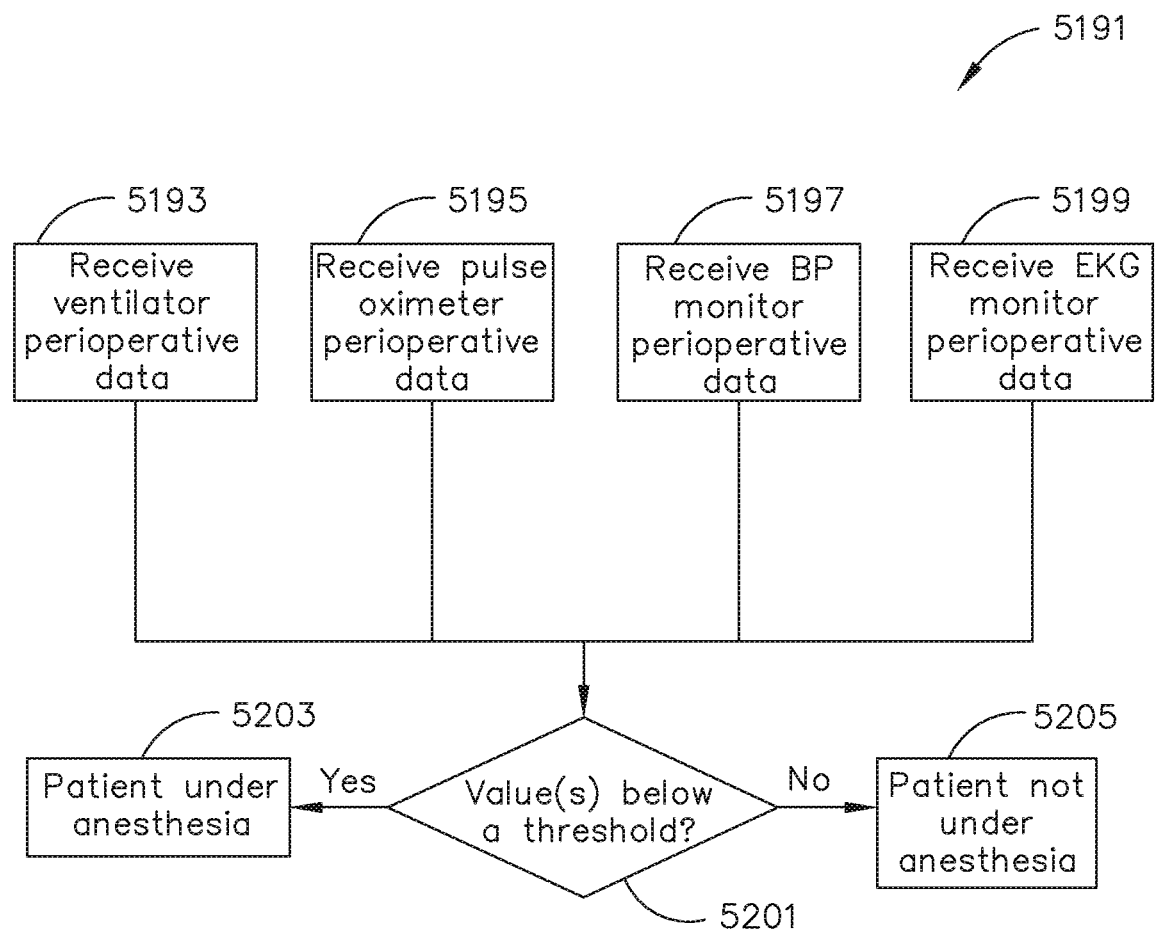
FIG. 84H illustrates a logic flow diagram of a process for determining a patient status according to ventilator, pulse oximeter, blood pressure monitor, and/or EKG monitor perioperative data, in accordance with at least one aspect of the present disclosure.
Figure 841:
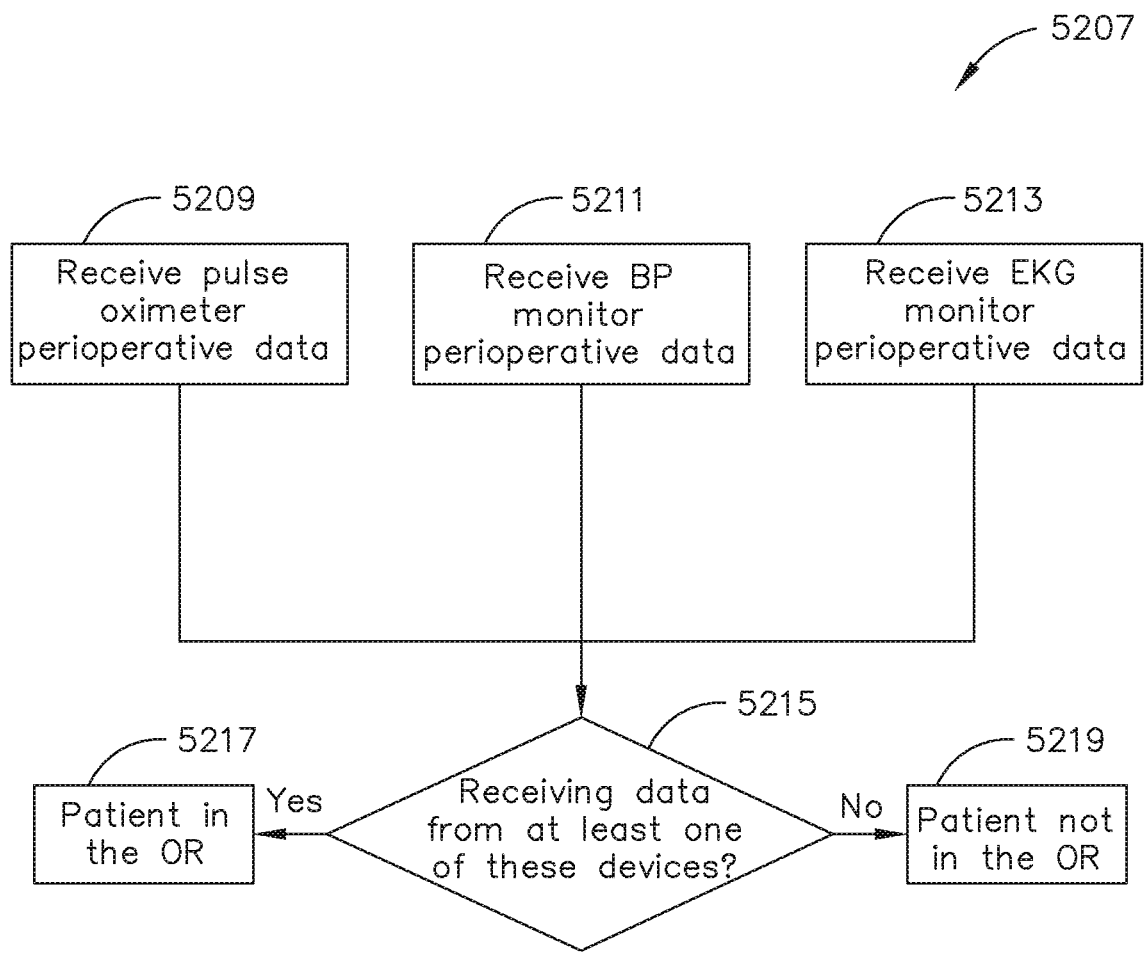
Figure 84J:
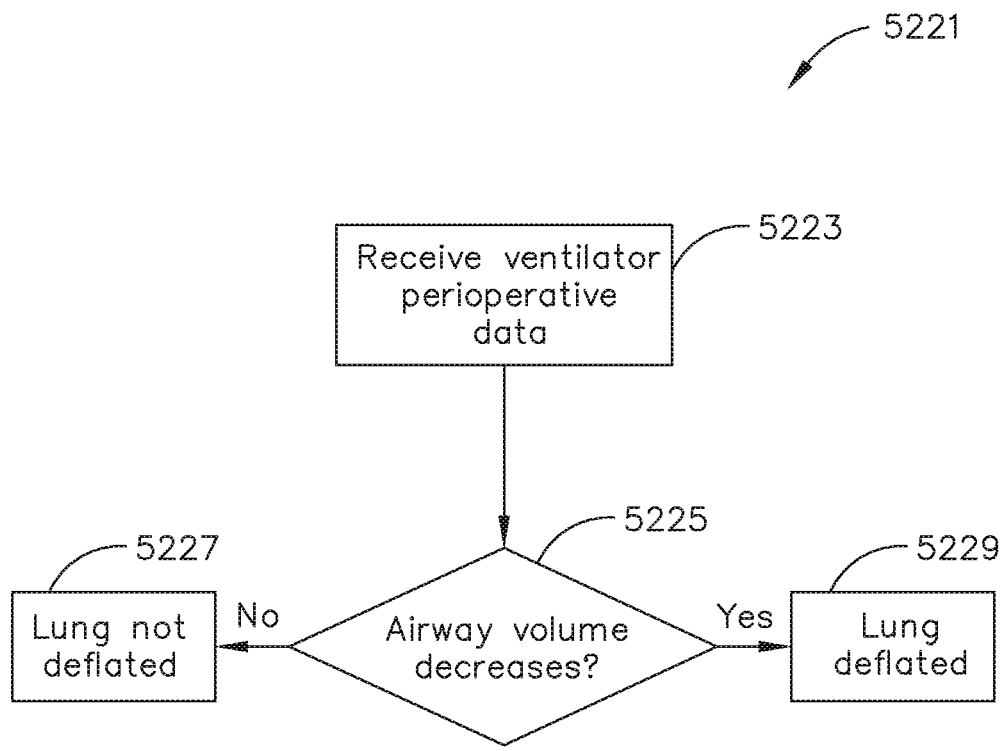
FIG. 84J illustrates a logic flow diagram of a process for determining a patient status according to ventilator perioperative data, in accordance with at least one aspect of the present disclosure.

FIGS. 84A-J depict logic flow diagrams for processes for deriving 5008*a*, 5008*b*, 5008*c*, 5008*d* contextual information from various modular devices, as discussed above with respect to the processes 5000*a*, 5000*b*, 5000*c*, 5000*d* depicted in FIGS. 82A-D. The derived contextual information in FIGS. 84A-C is the procedure type. The procedure type can correspond to techniques utilized during the surgical procedure (e.g., a segmentectomy), the category of the surgical procedure (e.g., a laparoscopic procedure), the organ, tissue, or other structure being operated on, and other characteristics to identify the particular surgical procedure (e.g., the procedure utilizes insufflation). The derived contextual information in FIGS. 84D-G is the particular step of the surgical procedure that is being performed. The derived contextual information in FIGS. 84H-J is the patient's status. It can be noted that the patient's status can also correspond to the particular step of the surgical procedure that is being performed (e.g., determining that the patient's status has changed from not being under anesthesia to being under anesthesia can indicate that the step of the surgical procedure of placing the patient under anesthesia was carried out by the surgical staff). As with the process 5000*a* depicted in FIG. 82A, the processes illustrated in FIGS. 84A-J can, in one exemplification, be executed by a control circuit of the surgical hub 5104. In the following descriptions of the processes illustrated in FIGS. 84A-J, reference should also be made to FIG. 83A.

FIG. 84A illustrates a logic flow diagram of a process 5111 for determining a procedure type according to smoke evacuator 5106 perioperative data. In this exemplification, the control circuit of the surgical hub 5104 executing the process 5111 receives 5113 perioperative data from the smoke evacuator 5106 and then determines 5115 whether the smoke evacuator 5106 is activated based thereon. If the smoke evacuator 5106 is not activated, then the process 5111 continues along the NO branch and the control circuit of the surgical hub 5104 continues monitoring for the receipt of smoke evacuator 5106 perioperative data. If the smoke evacuator 5106 is activated, then the process 5111 continues along the YES branch and the control circuit of the surgical hub 5104 determines 5117 whether there is a pressure differential between an internal upstream pressure sensor $P_3$ (FIG. 83B) and an external or ambient pressure sensor $P_1$ (FIG. 83B). If there is a pressure differential (i.e., the internal upstream pressure of the smoke evacuator 5106 is greater then the ambient pressure of the operating theater), then the process 5111 continues along the YES branch and the control circuit determines 5119 that the surgical procedure is an insufflation-utilizing procedure. If there is not a pressure differential, then the process 5111 continues along the NO branch and the control circuit determines 5121 that the surgical procedure is not an insufflation-utilizing procedure.

FIG. 84B illustrates a logic flow diagram of a process 5123 for determining a procedure type according to smoke evacuator 5106, insufflator 5110, and medical imaging device 5108 perioperative data. In this exemplification, the control circuit of the surgical hub 5104 executing the process 5123 receives 5125, 5127, 5129 perioperative data from the smoke evacuator 5106, insufflator 5110, and medical imaging device 5108 and then determines 5131 whether all of the devices are activated or paired with the surgical hub 5104. If all of these devices are not activated or paired with the surgical hub 5104, then the process 5123 continues along the NO branch and the control circuit determines 5133 that the surgical procedure is not a VATS procedure. If all of the aforementioned devices are activated or paired with the surgical hub 5104, then the process 5123 continues along the YES branch and the control circuit determines 5135 that the surgical procedure is a VATS procedure. The control circuit can make this determination based upon the fact that al of these devices are required for a VATS procedure; therefore, if not all of these devices are being utilized in the surgical procedure, it cannot be a VATS procedure.

FIG. 84C illustrates a logic flow diagram of a process 5137 for determining a procedure type according to medical imaging device 5108 perioperative data. In this exemplification, the control circuit of the surgical hub 5104 executing the process 5137 receives 5139 perioperative data from the medical imaging device 5108 and then determines 5141 whether the medical imaging device 5108 is transmitting an image or video feed. If the medical imaging device 5108 is not transmitting an image or video feed, then the process 5137 continues along the NO branch and the control circuit determines 5143 that the surgical procedure is not a VATS procedure. If the medical imaging device 5108 is not transmitting an image or video feed, then the process 5137 continues along the YES branch and the control circuit determines 5145 that the surgical procedure is a VATS procedure. In one exemplification, the control circuit of the surgical hub 5104 can execute the process 5137 depicted in FIG. 84C in combination with the process 5123 depicted in FIG. 84B in order to confirm or increase the confidence in the contextual information derived by both processes 5123, 5137. If there is a discontinuity between the determinations of the processes 5123, 5137 (e.g., the medical imaging device 5108 is transmitting a feed, but not all of the requisite devices are paired with the surgical hub 5104), then the surgical hub 5104 can execute additional processes to come to a final determination that resolves the discontinuities between the processes 5123, 5137 or display an alert or feedback to the surgical staff as to the discontinuity.

FIG. 84D illustrates a logic flow diagram of a process 5147 for determining a procedural step according to insufflator 5110 perioperative data. In this exemplification, the control circuit of the surgical hub 5104 executing the process 5147 receives 5149 perioperative data from the insufflator 5110 and then determines 5151 whether there is a pressure differential between the surgical site and the ambient environment of the operating theater. In one exemplification, the insufflator 5110 perioperative data can include a surgical site pressure (e.g., the intra-abdominal pressure) sensed by a first pressure sensor associated with the insufflator 5110, which can be compared against a pressure sensed by a second pressure sensor configured to detect the ambient pressure. The first pressure sensor can be configured to detect an intra-abdominal pressure between 0-10 mmHg, for example. If there is a pressure differential, then the process 5147 continues along the YES branch and the control circuit determines 5153 that an insufflation-utilizing step of the surgical procedure is being performed. If there is not a pressure differential, then the process 5147 continues along the NO branch and the control circuit determines 5155 that an insufflation-utilizing step of the surgical procedure is not being performed.

FIG. 84E illustrates a logic flow diagram of a process 5157 for determining a procedural step according to energy generator 5112 perioperative data. In this exemplification, the control circuit of the surgical hub 5104 executing the process 5157 receives 5159 perioperative data from the energy generator 5112 and then determines 5161 whether the energy generator 5112 is in the sealing mode. In various exemplifications, the energy generator 5112 can include two modes: a sealing mode corresponding to a first energy level and a cut/coagulation mode corresponding to a second energy level. If the energy generator 5112 is not in the sealing mode, then the process 5157 proceeds along the NO branch and the control circuit determines 5163 that a dissection step of the surgical procedure is being performed. The control circuit can make this determination 5163 because if the energy generator 5112 is not on the sealing mode, then it must thus be on the cut/coagulation mode for energy generators 5112 having two modes of operation. The cut/coagulation mode of the energy generator 5112 corresponds to a dissection procedural step because it provides an appropriate degree of energy to the ultrasonic surgical instrument or RF electrosurgical instrument to dissect tissue. If the energy generator 5112 is in the sealing mode, then the process 5157 proceeds along the YES branch and the control circuit determines 5165 that a ligation step of the surgical procedure is being performed. The sealing mode of the energy generator 5112 corresponds to a ligation procedural step because it provides an appropriate degree of energy to the ultrasonic surgical instrument or RF electrosurgical instrument to ligate vessels.

FIG. 84F illustrates a logic flow diagram of a process 5167 for determining a procedural step according to energy generator 5112 perioperative data. In various aspects, previously received perioperative data and/or previously derived contextual information can also be considered by processes in deriving subsequent contextual information. This allows the situational awareness system of the surgical hub 5104 to derive additional and/or increasingly detailed contextual information about the surgical procedure as the procedure is performed. In this exemplification, the process 5167 determines 5169 that a segmentectomy procedure is being performed. This contextual information can be derived by this process 5167 or other processes based upon other received perioperative data and/or retrieved from a memory. Subsequently, the control circuit receives 5171 perioperative data from the energy generator 5112 indicating that a surgical instrument is being fired and then determines 5173 whether the energy generator 5112 was utilized in a previous step of the procedure to fire the surgical instrument. The control circuit can determine 5173 whether the energy generator 5112 was previously utilized in a prior step of the procedure by retrieving a list of the steps that have been performed in the current surgical procedure from a memory, for example. In such exemplifications, when the surgical hub 5104 determines that a step of the surgical procedure has been performed or completed by the surgical staff, the surgical hub 5104 can update a list of the procedural steps that have been performed, which can then be subsequently retrieved by the control circuit of the surgical hub 5104. In one exemplification, the surgical hub 5104 can distinguish between sequences of firings of the surgical instrument as corresponding to separate steps of the surgical procedure according to the time delay between the sequences of firings, whether any intervening actions were taken or modular devices 5102 were utilized by the surgical staff, or other factors that the situational awareness system can detect. If the energy generator 5112 has not been previously utilized during the course of the segmentectomy procedure, the process 5167 proceeds along the NO branch and the control circuit determines 5175 that the step of dissecting tissue to mobilize the patient's lungs is being performed by the surgical staff. If the energy generator 5112 has been previously utilized during the course of the segmentectomy procedure, the process 5167 proceeds along the YES branch and the control circuit determines 5177 that the step of dissecting nodes is being performed by the surgical staff. An ultrasonic surgical instrument or RF electrosurgical instrument is utilized twice during the course of an example of a segmentectomy procedure (e.g., FIG. 86); therefore, the situational awareness system of the surgical hub 5104 executing the process 5167 can distinguish between which step the utilization of the energy generator 5112 indicates is currently being performed based upon whether the energy generator 5112 was previously utilized.

FIG. 84G illustrates a logic flow diagram of a process 5179 for determining a procedural step according to stapler perioperative data. As described above with respect to the process 5167 illustrated in FIG. 84F, the process 5179 utilizes previously received perioperative data and/or previously derived contextual information in deriving subsequent contextual information. In this exemplification, the process 5179 determines 5181 that a segmentectomy procedure is being performed. This contextual information can be derived by this process 5179 or other processes based upon other received perioperative data and/or retrieved from a memory. Subsequently, the control circuit receives 5183 perioperative data from the surgical stapling instrument (i.e., stapler) indicating that the surgical stapling instrument is being fired and then determines 5185 whether the surgical stapling instrument was utilized in a previous step of the surgical procedure. As described above, the control circuit can determine 5185 whether the surgical stapling instrument was previously utilized in a prior step of the procedure by retrieving a list of the steps that have been performed in the current surgical procedure from a memory, for example. If the surgical stapling instrument has not been utilized previously, then the process 5179 proceeds along the NO branch and the control circuit determines 5187 that the step of ligating arteries and veins is being performed by the surgical staff. If the surgical stapling instrument has been previously utilized during the course of the segmentectomy procedure, the process 5179 proceeds along the YES branch and the control circuit determines 5189 that the step of transecting parenchyma is being performed by the surgical staff. A surgical stapling instrument is utilized twice during the course of an example of a segmentectomy procedure (e.g., FIG. 86); therefore, the situational awareness system of the surgical hub 5104 executing the process 5179 can distinguish between which step the utilization of the surgical stapling instrument indicates is currently being performed based upon whether the surgical stapling instrument was previously utilized.

FIG. 84H illustrates a logic flow diagram of a process 5191 for determining a patient status according to ventilator 5110, pulse oximeter 5114, BP monitor 5116, and/or EKG monitor 5120 perioperative data. In this exemplification, the control circuit of the surgical hub 5104 executing the process 5191 receives 5193, 5195, 5197, 5199 perioperative data from each of the ventilator 5110, pulse oximeter 5114, BP monitor 5116, and/or EKG monitor 5120 and then determines whether one or more values of the physiological parameters sensed by each of the devices fall below a threshold for each of the physiological parameters. The threshold for each physiological parameter can correspond to a value that corresponds to a patient being under anesthesia. In other words, the control circuit determines 5201 whether the patient's respiration rate, oxygen saturation, blood pressure, and/or heart rate indicate that the patient is under anesthesia according data sensed by the respective modular device 5102 and/or patient monitoring devices 5124. In one exemplification, if the all of the values from the perioperative data are below their respective thresholds, then the process 5191 proceeds along the YES branch and the control circuit determines 5203 that the patient is under anesthesia. In another exemplification, the control circuit can determine 5203 that the patient is under anesthesia if a particular number or ratio of the monitored physiological parameters indicate that the patient is under anesthesia. Otherwise, the process 5191 proceeds along the NO branch and the control circuit determines 5205 that the patient is not under anesthesia.

FIG. 84I illustrates a logic flow diagram of a process 5207 for determining a patient status according to pulse oximeter 5114, BP monitor 5116, and/or EKG monitor 5120 perioperative data. In this exemplification, the control circuit of the surgical hub 5104 executing the process 5207 receives 5209, 5211, 5213 (or attempts to receive) perioperative data the pulse oximeter 5114, BP monitor 5116, and/or EKG monitor 5120 and then determines 5215 whether at least one of the devices is paired with the surgical hub 5104 or the surgical hub 5104 is otherwise receiving data therefrom. If the control circuit is receiving data from at least one of these patient monitoring devices 5124, the process 5207 proceeds along the YES branch and the control circuit determines 5217 that the patient is in the operating theater. The control circuit can make this determination because the patient monitoring devices 5214 connected to the surgical hub 5104 must be in the operating theater and thus the patient must likewise be in the operating theater. If the control circuit is not receiving data from at least one of these patient monitoring devices 5124, the process 5207 proceeds along the NO branch and the control circuit determines 5219 that the patient is not in the operating theater.

FIG. 84J illustrates a logic flow diagram of a process 5221 for determining a patient status according to ventilator 5110 perioperative data. In this exemplification, the control circuit of the surgical hub 5104 executing the process 5221 receives 5223 perioperative data from the ventilator 5110 and then determines 5225 whether the patient's airway volume has decreased or is decreasing. In one exemplification, the control circuit determines 5225 whether the patient's airway volume falls below a particular threshold value indicative of a lung having collapsed or been deflated. In another exemplification, the control circuit determines 5225 whether the patient's airway volume falls below an average or baseline level by a threshold amount. If the patient's airway volume has not decreased sufficiently, the process 5221 proceeds along the NO branch and the control circuit determines 5227 that the patient's lung is not deflated. If the patient's airway volume has decreased sufficiently, the process 5221 proceeds along the YES branch and the control circuit determines 5229 that the patient's lung is not deflated.

Figure 85B:
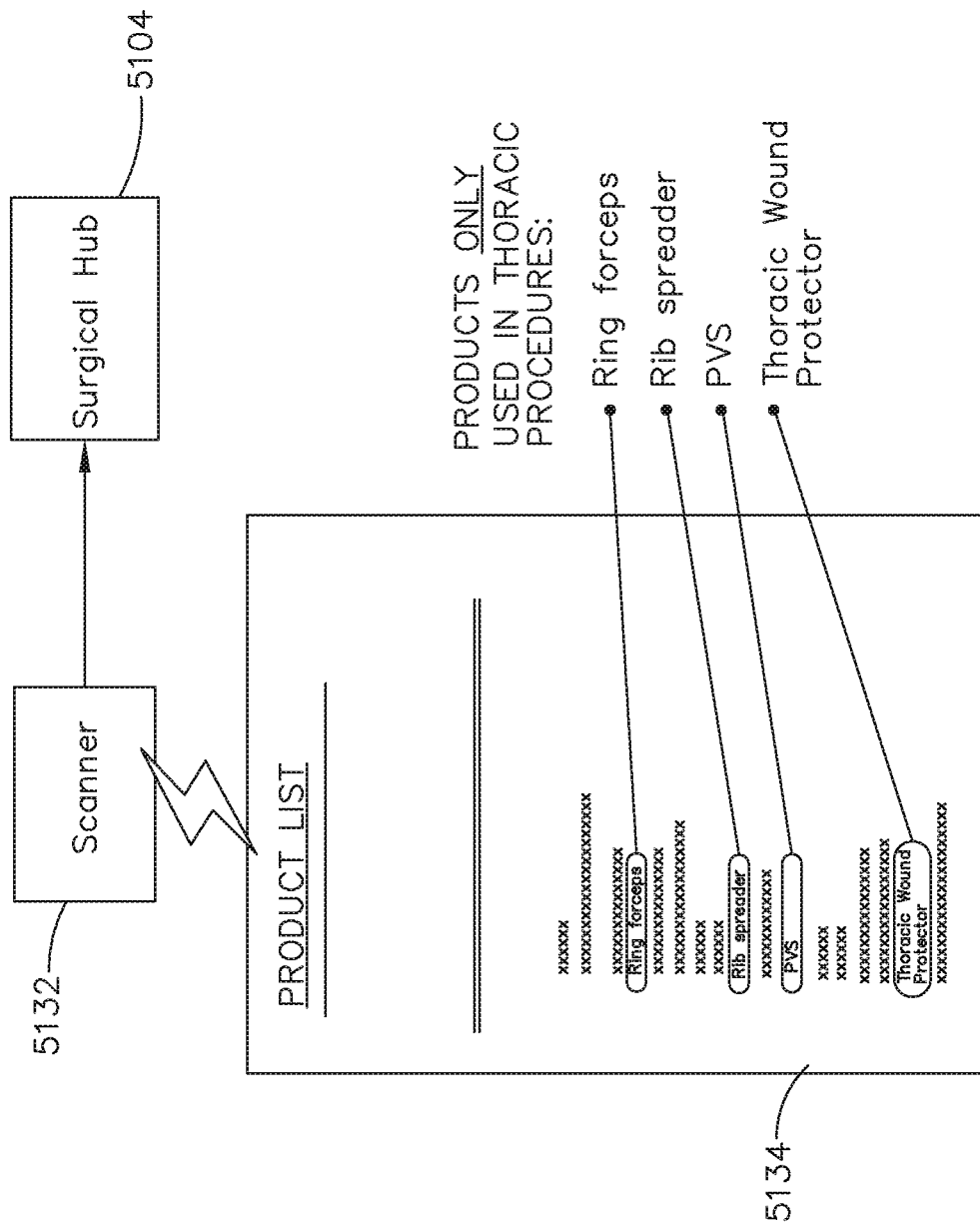
FIG. 85B illustrates a scanner coupled to a surgical hub for scanning a list of surgical items, in accordance with at least one aspect of the present disclosure.

In one exemplification, the surgical system 5100 can further include various scanners that can be paired with the surgical hub 5104 to detect and record objects and individuals that enter and exit the operating theater. FIG. 85A illustrates a scanner 5128 paired with a surgical hub 5104 that is configured to scan a patient wristband 5130. In one aspect, the scanner 5128 includes, for example, a barcode reader or a radio-frequency identification (RFID) reader that is able to read patient information from the patient wristband 5130 and then transmit that information to the surgical hub 5104. The patient information can include the surgical procedure to be performed or identifying information that can be cross-referenced with the hospital's EMR database 5122 by the surgical hub 5104, for example. FIG. 85B illustrates a scanner 5132 paired with a surgical hub 5104 that is configured to scan a product list 5134 for a surgical procedure. The surgical hub 5104 can utilize data from the scanner 5132 regarding the number, type, and mix of items to be used in the surgical procedure to identify the type of surgical procedure being performed. In one exemplification, the scanner 5132 includes a product scanner (e.g., a barcode reader or an RFID reader) that is able to read the product information (e.g., name and quantity) from the product itself or the product packaging as the products are brought into the operating theater and then transmit that information to the surgical hub 5104. In another exemplification, the scanner 5132 includes a camera (or other visualization device) and associated optical character recognition software that is able to read the product information from a product list 5134. The surgical hub 5104 can be configured to cross-reference the list of items indicated by the received data with a lookup table or database of items utilized for various types of surgical procedures in order to infer the particular surgical procedure that is to be (or was) performed. As shown in FIG. 85B, the illustrative product list 5134 includes ring forceps, rib spreaders, a powered vascular stapler (PVS), and a thoracic wound protector. In this example, the surgical hub 5104 can infer that the surgical procedure is a thoracic procedure from this data since these products are only utilized in thoracic procedures. In sum, the scanner(s) 5128, 5132 can provide serial numbers, product lists, and patient information to the surgical hub 5104. Based on this data regarding what devices and instruments are being utilized and the patient's medical information, the surgical hub 5104 can determine additional contextual information regarding the surgical procedure.

In order to assist in the understanding of the process 5000a illustrated in FIG. 82A and the other concepts discussed above, FIG. 86 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 86, reference should also be made to FIG. 81. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports (e.g., see FIGS. 90-101), verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 5104 determines that the procedure to be performed is a thoracic procedure. Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure (e.g., as depicted in FIG. 85B). Further, the surgical hub 5104 is also able to determine that the procedure is not a wedge procedure (because the incoming supplies either lack certain supplies that are necessary for a thoracic wedge procedure or do not otherwise correspond to a thoracic wedge procedure). Third 5206, the medical personnel scan the patient band (e.g., as depicted in FIG. 85A) via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater, as described in the process 5207 depicted in FIG. 84I, for example. Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof, as described in the process 5191 depicted in FIG. 84H, for example. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed, as described in the process 5221 depicted in FIG. 84J, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure. Eighth 5216, the medical imaging device 5108 (e.g., a scope) is inserted and video from the medical imaging device is initiated. The surgical hub 5104 receives the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process. Eleventh 5222, the segmentectomy portion of the procedure is performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example. Lastly, the fourteenth step 5228 is that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

Figure 86:
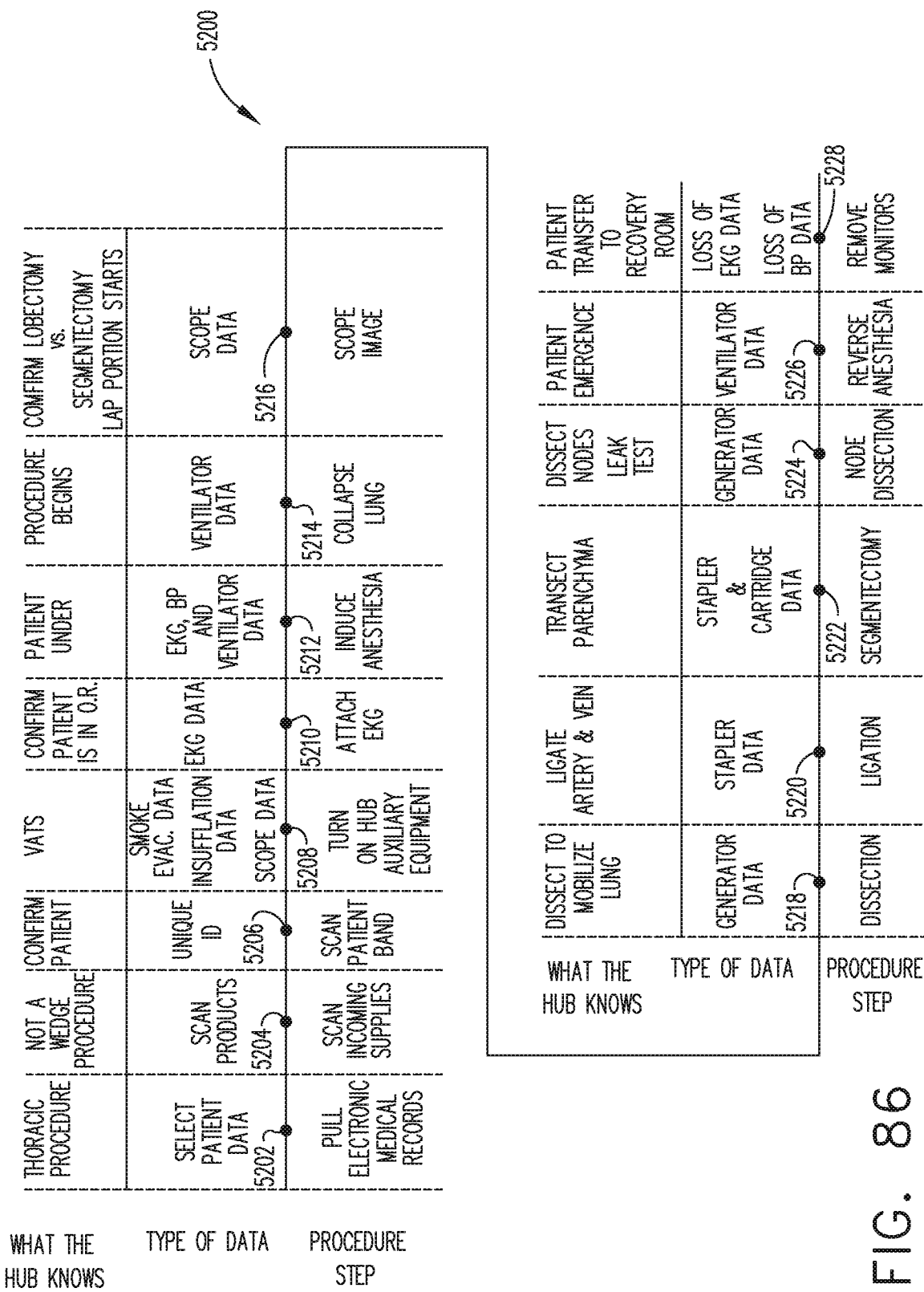
FIG. 86 illustrates a timeline of an illustrative surgical procedure and the inferences that the surgical hub can make from the data detected at each step in the surgical procedure, in accordance with at least one aspect of the present disclosure.
Figure 87A:
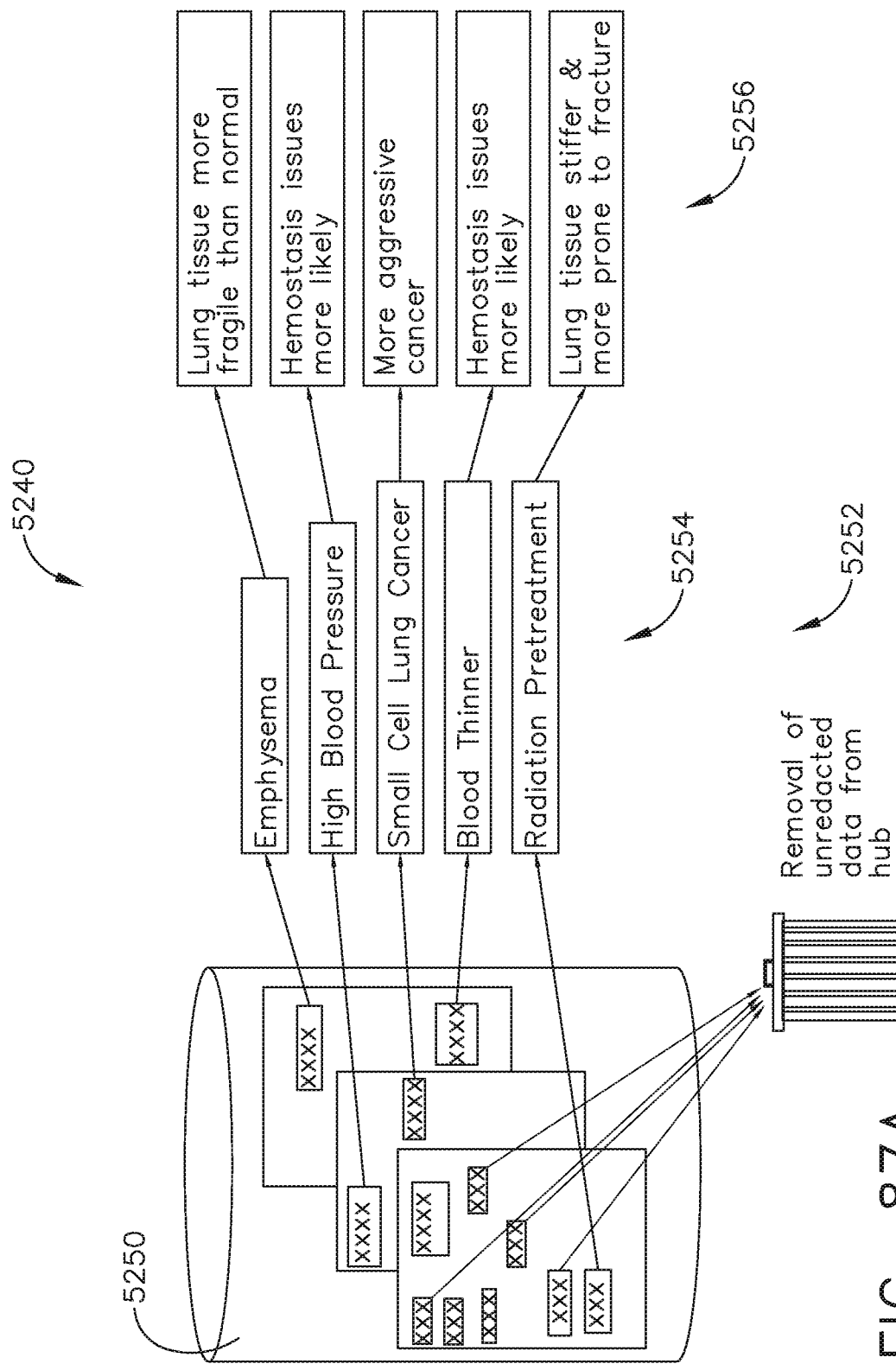
FIG. 87A illustrates a flow diagram depicting the process of importing patient data stored in an EMR database and deriving inferences therefrom, in accordance with at least one aspect of the present disclosure.
Figure 87B:
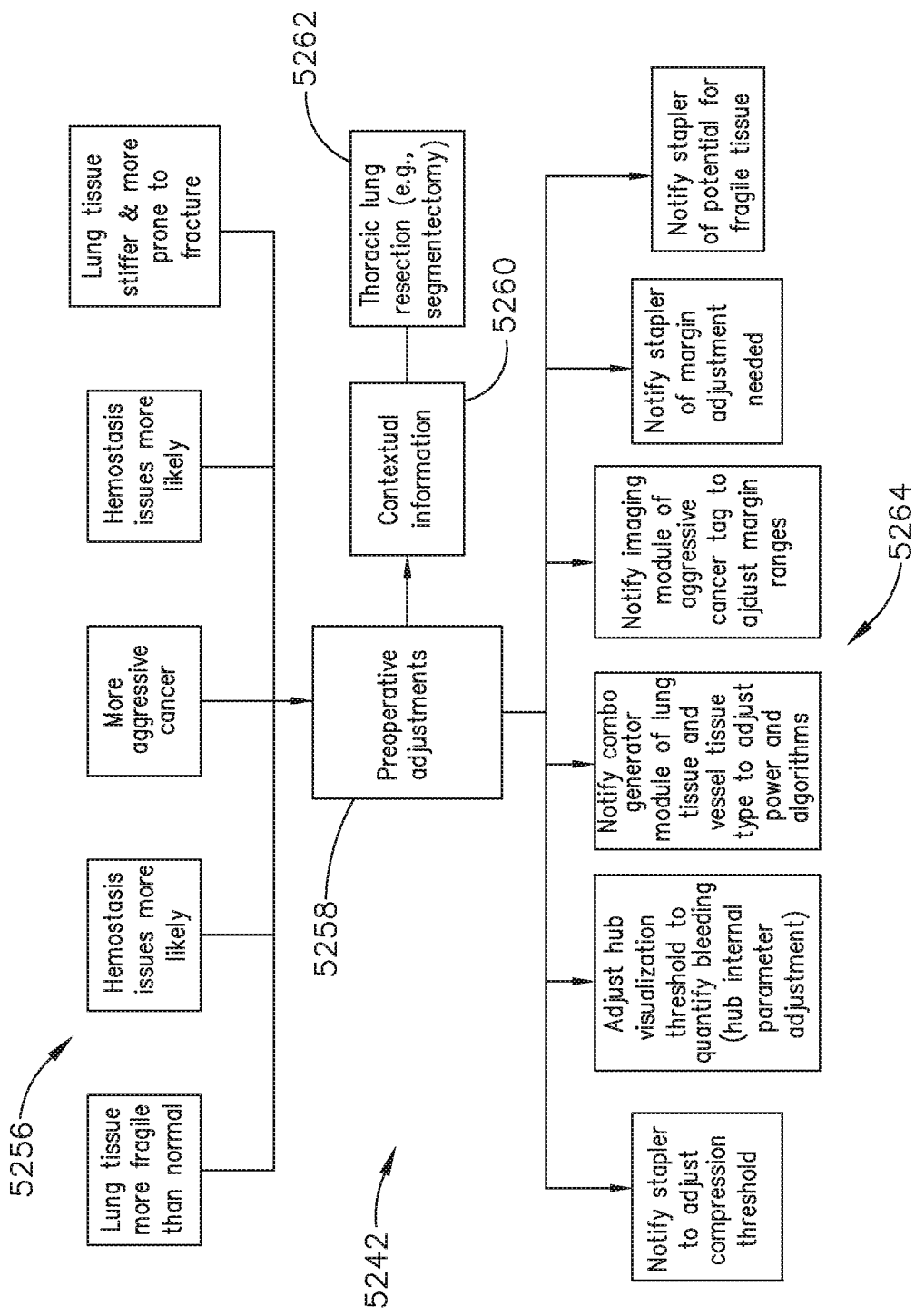
FIG. 87B illustrates a flow diagram depicting the process of determining control adjustments corresponding to the derived inferences from FIG. 87A, in accordance with at least one aspect of the present disclosure.

In addition to utilizing the patient data from EMR database(s) to infer the type of surgical procedure that is to be performed, as illustrated in the first step 5202 of the timeline 5200 depicted in FIG. 86, the patient data can also be utilized by a situationally aware surgical hub 5104 to generate control adjustments for the paired modular devices 5102. FIG. 87A illustrates a flow diagram depicting the process 5240 of importing patient data stored in an EMR database 5250 and deriving inferences 5256 therefrom, in accordance with at least one aspect of the present disclosure. Further, FIG. 87B illustrates a flow diagram depicting the process 5242 of determining control adjustments 5264 corresponding to the derived inferences 5256 from FIG. 87A, in accordance with at least one aspect of the present disclosure. In the following description of the processes 5240, 5242, reference should also be made to FIG. 81.

As shown in FIG. 87A, the surgical hub 5104 retrieves the patient information (e.g., EMR) stored in a database 5250 to which the surgical hub 5104 is communicably connected. The unredacted portion of the patient data is removed 5252 from the surgical hub 5104, leaving anonymized, stripped patient data 5254 related to the patient's condition and/or the surgical procedure to be performed. The unredacted patient data is removed 5252 in order to maintain patient anonymity for the processing of the data (including if the data is uploaded to the cloud for processing and/or data tracking for reports). The stripped patient data 5254 can include any medical conditions that the patient is suffering from, the patient's medical history (including previous treatments or procedures), medication that the patient is taking, and other such medically relevant details. The control circuit of the surgical hub 5104 can then derive various inferences 5256 from the stripped patient data 5254, which can in turn be utilized by the surgical hub 5104 to derive various control adjustments for the paired modular devices 5102. The derived inferences 5256 can be based upon individual pieces of data or combinations of pieces of data. Further, the derived inferences 5256 may, in some cases, be redundant with each other as some data may lead to the same inference. By integrating each patient's stripped patient data 5254 into the situational awareness system, the surgical hub 5104 is thus able to generate pre-procedure adjustments to optimally control each of the modular devices 5102 based on the unique circumstances associated with each individual patient. In the illustrated example, the stripped patient data 5254 includes that (i) the patient is suffering from emphysema, (ii) has high blood pressure, (iii) is suffering from a small cell lung cancer, (iv) is taking warfarin (or another blood thinner), and/or (v) has received radiation pretreatment. In the illustrated example, the inferences 5256 derived from the stripped patient data 5254 include that (i) the lung tissue will be more fragile than normal lung tissue, (ii) hemostasis issues are more likely, (iii) the patient is suffering from a relatively aggressive cancer, (iv) hemostasis issues are more likely, and (v) the lung tissue will be stiffer and more prone to fracture, respectively.

After the control circuit of the surgical hub 5104 receives or identifies the implications 5256 that are derived from anonymized patient data, the control circuit of the surgical hub 5104 is configured to execute a process 5242 to control the modular devices 5102 in a manner consistent with the derived implications 5256. In the example shown in FIG. 87B, the control circuit of the surgical hub 5104 interprets how the derived implications 5256 impacts the modular devices 5102 and then communicates corresponding control adjustments to each of the modular devices 5102. In the example shown in FIG. 87B, the control adjustments include (i) adjusting the compression rate threshold parameter of the surgical stapling and cutting instrument, (ii) adjusting the visualization threshold value of the surgical hub 5104 to quantify bleeding via the visualization system 108 (FIG. 2) (this adjustment can apply to the visualization system 108 itself or as an internal parameter of the surgical hub 5104), (iii) adjusts the power and control algorithms of the combo generator module 140 (FIG. 3) for the lung tissue and vessel tissue types, (iv) adjusts the margin ranges of the medical imaging device 124 (FIG. 2) to account for the aggressive cancer type, (v) notifies the surgical stapling and cutting instrument of the margin parameter adjustment needed (the margin parameter corresponds to the distance or amount of tissue around the cancer that will be excised), and (vi) notifies the surgical stapling and cutting instrument that the tissue is potentially fragile, which causes the control algorithm of the surgical stapling and cutting instrument to adjust accordingly. Furthermore, the data regarding the implications 5256 derived from the anonymized patient data 5254 is considered by the situational awareness system to infer contextual information 5260 regarding the surgical procedure being performed. In the example shown in FIG. 87B, the situational awareness system further infers that the procedure is a thoracic lung resection 5262, e.g., segmentectomy.

Determining where inefficiencies or ineffectiveness may reside in a medical facility's practice can be challenging because medical personnel's efficiency in completing a surgical procedure, correlating positive patient outcomes with particular surgical teams or particular techniques in performing a type of surgical procedure, and other performance measures are not easily quantified using legacy systems. As one solution, the surgical hubs can be employed to track and store data pertaining to the surgical procedures that the surgical hubs are being utilized in connection with and generate reports or recommendations related to the tracked data. The tracked data can include, for example, the length of time spent during a particular procedure, the length of time spent on a particular step of a particular procedure, the length of downtime between procedures, modular device(s) (e.g., surgical instruments) utilized during the course of a procedure, and the number and type of surgical items consumed during a procedure (or step thereof). Further, the tracked data can include, for example, the operating theater in which the surgical hub is located, the medical personnel associated with the particular event (e.g., the surgeon or surgical team performing the surgical procedure), the day and time at which the particular event(s) occurred, and patient outcomes. This data can be utilized to create performance metrics, which can be utilized to detect and then ultimately address inefficiencies or ineffectiveness within a medical facility's practice. In one exemplification, the surgical hub includes a situational awareness system, as described above, that is configured to infer or determine information regarding a particular event (e.g., when a particular step of a surgical procedure is being performed and/or how long the step took to complete) based on data received from data sources connected to the surgical hub (e.g., paired modular devices). The surgical hub can then store this tracked data to provide reports or recommendations to users.

Aggregation and Reporting of Surgical Hub Data

FIG. 88 illustrates a block diagram of a computer-implemented interactive surgical system 5700, in accordance with at least one aspect of the present disclosure. The system 5700 includes a number of surgical hubs 5706 that, as described above, are able to detect and track data related to surgical procedures that the surgical hubs 5706 (and the modular devices paired to the surgical hubs 5706) are utilized in connection with. In one exemplification, the surgical hubs 5706 are connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704a are communicably connected to a first local database 5708a and the surgical hubs 5706 of a second medical facility 5704b are communicably connected to a second local database 5708b. The network of surgical hubs 5706 associated with the first medical facility 5704a can be distinct from the network of surgical hubs 5706 associated with the second medical facility 5704b, such that the aggregated data from each network of surgical hubs 5706 corresponds to each medical facility 5704a, 5704b individually. A surgical hub 5706 or another computer terminal communicably connected to the database 5708a, 5708b can be configured to provide reports or recommendations based on the aggregated data associated with the respective medical facility 5704a, 5704b. In this exemplification, the data tracked by the surgical hubs 5706 can be utilized to, for example, report whether a particular incidence of a surgical procedure deviated from the average in-network time to complete the particular procedure type.

In another exemplification, each surgical hub 5706 is configured to upload the tracked data to the cloud 5702, which then processes and aggregates the tracked data across multiple surgical hubs 5706, networks of surgical hubs 5706, and/or medical facilities 5704a, 5704b that are connected to the cloud 5702. Each surgical hub 5706 can then be utilized to provide reports or recommendations based on the aggregated data. In this exemplification, the data tracked by the surgical hubs 5706 can be utilized to, for example, report whether a particular incidence of a surgical procedure deviated from the average global time to complete the particular procedure type.

In another exemplification, each surgical hub 5706 can further be configured to access the cloud 5702 to compare locally tracked data to global data aggregated from all of the surgical hubs 5706 that are communicably connected to the cloud 5702. Each surgical hub 5706 can be configured to provide reports or recommendations based on the comparison between the tracked local data relative to local (i.e., in-network) or global norms. In this exemplification, the data tracked by the surgical hubs 5706 can be utilized to, for example, report whether a particular incidence of a surgical procedure deviated from either the average in-network time or the average global time to complete the particular procedure type.

In one exemplification, each surgical hub 5706 or another computer system local to the surgical hub 5706 is configured to locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 can be configured to compare the tracked data with the bulk medical facility data. The bulk medical facility data can include EMR data and aggregated data from the local network of surgical hubs 5706. In another exemplification, the cloud 5702 is configured to aggregate the data tracked by the surgical hubs 5706, store the tracked data, and generate reports and/or recommendations according to the tracked data in response to queries.

Each surgical hub 5706 can provide reports regarding trends in the data and/or provide recommendations on improving the efficiency or effectiveness of the surgical procedures being performed. In various exemplifications, the data trends and recommendations can be based on data tracked by the surgical hub 5706 itself, data tracked across a local medical facility network containing multiple surgical hubs 5706, or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

Figure 90:
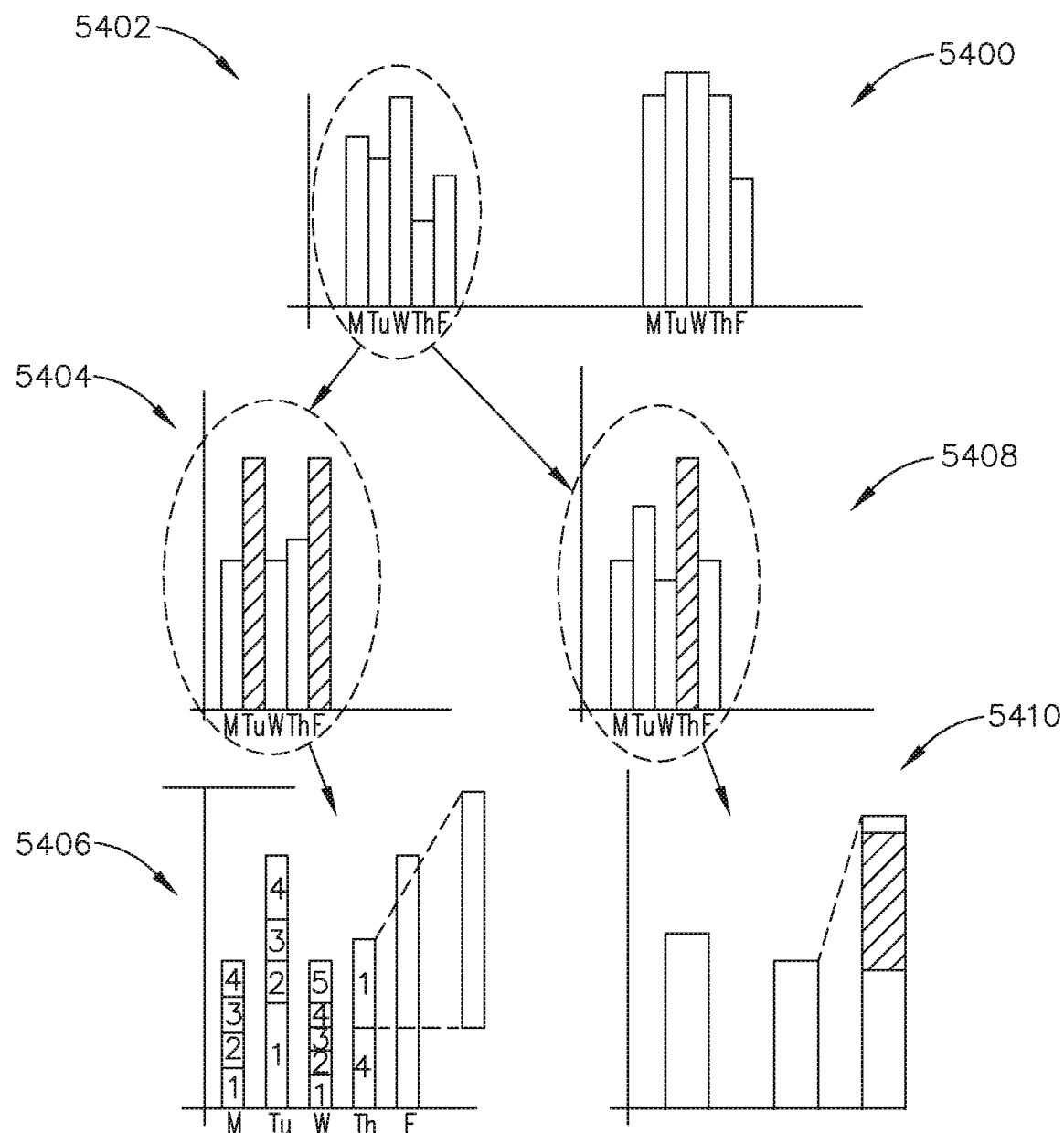
FIG. 90 illustrates a diagram depicting how the data tracked by the surgical hub can be parsed to provide increasingly detailed metrics, in accordance with at least one aspect of the present disclosure.

In one exemplification, each surgical hub 5706 is configured to determine when operating theater events occur (e.g., via a situational awareness system) and then track the length of time spent on each event. An operating theater event is an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets. FIG. 90 illustrates an example of a diagram 5400 depicting the data tracked by the surgical hubs 5706 being parsed to provide increasingly detailed metrics related to surgical procedures or the use of the surgical hub 5706 (as depicted further in FIGS. 91-95) for an illustrative data set. In one exemplification, the surgical hub 5706 is configured to determine whether a surgical procedure is being performed and then track both the length of time spent between procedures (i.e., downtime) and the time spent on the procedures themselves. The surgical hub 5706 can further be configured to determine and track the time spent on each of the individual steps taken by the medical personnel (e.g., surgeons, nurses, orderlies) either between or during the surgical procedures. The surgical hub can determine when surgical procedures or different steps of surgical procedures are being performed via a situational awareness system, which is described in further detail above.

Figure 89:
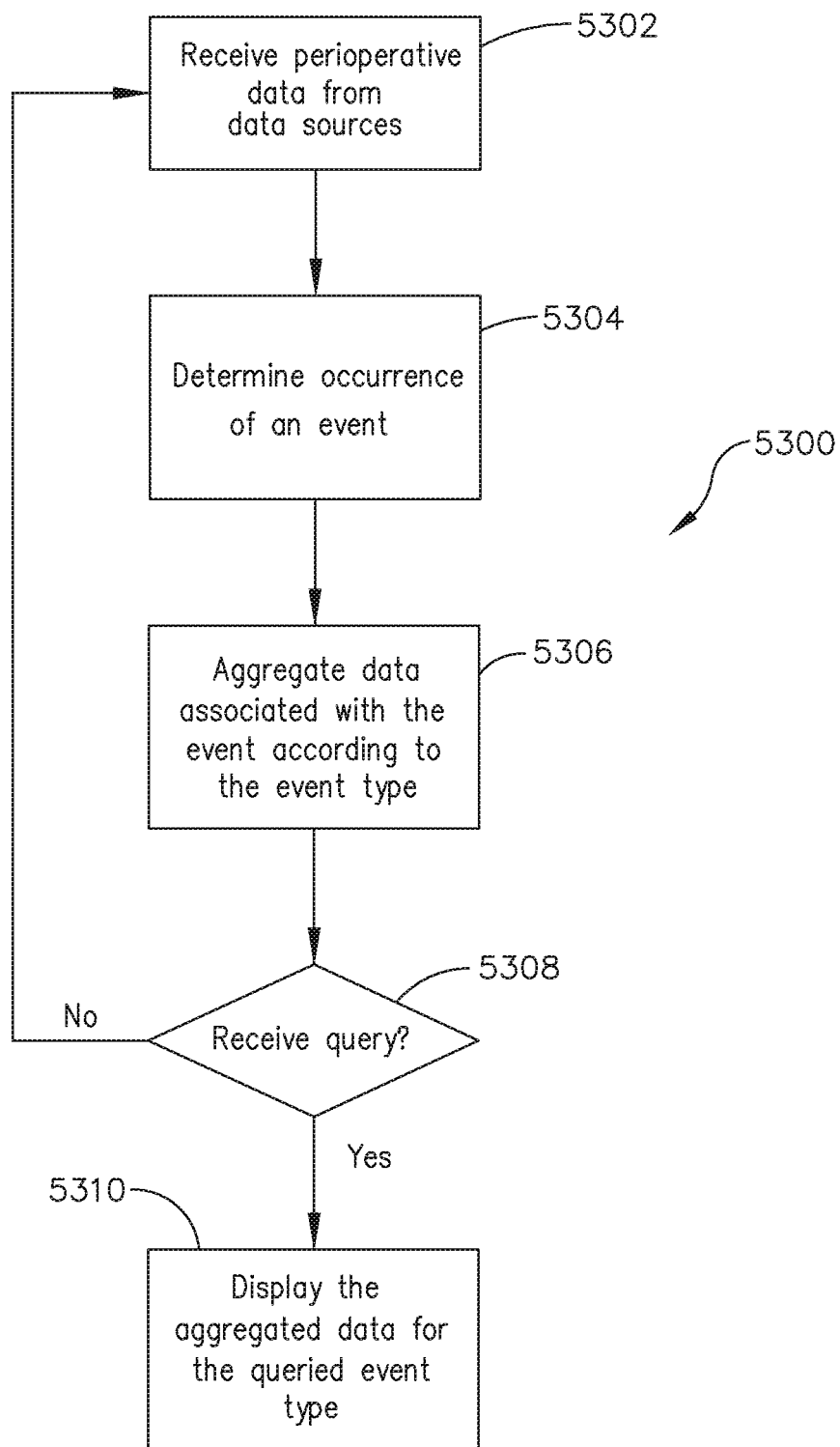
FIG. 89 illustrates a logic flow diagram of tracking data associated with an operating theater event, in accordance with at least one aspect of the present disclosure.

FIG. 89 illustrates a logic flow diagram of a process 5300 for tracking data associated with an operating theater event. In the following description, description of the process 5300, reference should also be made to FIG. 88. In one exemplification, the process 5300 can be executed by a control circuit of a surgical hub 206, as depicted in FIG. 10 (processor 244). In yet another exemplification, the process 5300 can be executed by a distributed computing system including a control circuit of a surgical hub 206 in combination with a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5300 will be described as being executed by the control circuit of a surgical hub 5706; however, it should be understood that the description of the process 5300 encompasses all of the aforementioned exemplifications.

The control circuit of the surgical hub 5706 executing the process 5300 receives 5302 perioperative data from the modular devices and other data sources (e.g., databases and patient monitoring devices) that are communicably coupled to the surgical hub 5706. The control circuit then determines 5304 whether an event has occurred via, for example, a situational awareness system that derives contextual information from the received 5302 data. The event can be associated with an operating theater in which the surgical hub 5706 in being used. The event can include, for example, a surgical procedure, a step or portion of a surgical procedure, or downtime between surgical procedures or steps of a surgical procedure. Furthermore, the control circuit tracks data associated with the particular event, such as the length of time of the event, the surgical instruments and/or other medical products utilized during the course of the event, and the medical personnel associated with the event. The surgical hub 5706 can further determine this information regarding the event via, for example, the situational awareness system.

For example, the control circuit of a situationally aware surgical hub 5706 could determine that anesthesia is being induced in a patient through data received from one or more modular devices 5102 (FIG. 81) and/or patient monitoring devices 5124 (FIG. 81). The control circuit could then determine that the operative portion of the surgical procedure has begun upon detecting that an ultrasonic surgical instrument or RF electrosurgical instrument has been activated. The control circuit could thus determine the length of time for the anesthesia inducement step according to the difference in time between the beginning of that particular step and the beginning of the first step in the operative portion of the surgical procedure. Likewise, the control circuit could determine how long the particular operative step in the surgical procedure took according to when the control circuit detects the subsequent step in the procedure begins. Further, the control circuit could determine how long the overall operative portion of the surgical procedure took according to when the control circuit detects that the final operative step in the procedure ends. The control circuit can also determine what surgical instruments (and other modular devices 5102) are being utilized during the course of each step in the surgical procedure by tracking the activation and/or use of the instruments during each of the steps. The control circuit can also detect the completion of the surgical procedure by, for example, detecting when the patient monitoring devices 5124 have been removed from the patient (as in step fourteen 5228 of FIG. 86). The control circuit can then track the downtime between procedures according to when the control circuit infers that the subsequent surgical procedure has begun.

The control circuit executing the process 5300 then aggregates 5306 the data associated with the event according to the event type. In one exemplification, the aggregated 5306 data can be stored in a memory 249 (FIG. 10) of the surgical hub 5706. In another exemplification, the control circuit is configured to upload the data associated with the event to the cloud 5702, whereupon the data is aggregated 5306 according to the event type for all of the data uploaded by each of the surgical hubs 5706 connected to the cloud 5702. In yet another exemplification, the control circuit is configured to upload the data associated with the event to a database associated with a local network of the surgical hubs 5706, whereupon the data is aggregated 5306 according to the event type for all of the data uploaded across the local network of surgical hubs 5706.

In one exemplification, the control circuit is further configured to compare the data associated with the event type to baseline data associated with the event type. The baseline data can correspond to, for example, average values associated with the particular event type for a particular hospital, network of hospitals, or across the entirety of the cloud 5702. The baseline data can be stored on the surgical hub 5706 or retrieved by the surgical 5706 as the perioperative data is received 5302 thereby.

Aggregating 5306 the data from each of the events according to the event type allows individual incidents of the event type to thereafter be compared against the historical or aggregated data to determine when deviations from the norm for an event type occur. The control circuit further determines 5308 whether it has received a query. If the control circuit does not receive a query, then the process 5300 continues along the NO branch and loops back to continue receiving 5302 data from the data sources. If the control circuit does receive a query for a particular event type, the process 5300 continues along the YES branch and the control circuit then retrieves the aggregated data for the particular event type and displays 5310 the appropriate aggregated data corresponding to the query. In various exemplifications, the control circuit can retrieve the appropriate aggregated data from the memory of the surgical hub 5706, the cloud 5702, or a local database 5708a, 5708b.

In one example, the surgical hub 5706 is configured to determine a length of time for a particular procedure via the aforementioned situational awareness system according to data received from one or more modular devices utilized in the performance of the surgical procedure (and other data sources). Each time a surgical procedure is completed, the surgical hub 5706 uploads or stores the length of time required to complete the particular type of surgical procedure, which is then aggregated with the data from every other instance of the type of procedure. In some aspects, the surgical hub 5706, cloud 5702, and/or local database 5708a, 5708b can then determine an average or expected procedure length for the particular type of procedure from the aggregated data. When the surgical hub 5706 receives a query as to the particular type of procedure thereafter, the surgical hub 5706 can then provide feedback as to the average (or expected) procedure length or compare an individual incidence of the procedure type to the average procedure length to determine whether the particular incidence deviates therefrom.

In some aspects, the surgical hub 5706 can be configured to automatically compare each incidence of an event type to average or expected norms for the event type and then provide feedback (e.g., display a report) when a particular incidence of the event type deviates from the norm. For example, the surgical hub 5706 can be configured to provide feedback whenever a surgical procedure (or a step of the surgical procedure) deviates from the expected length of time to complete the surgical procedure (or the step of the surgical procedure) by more than a set amount.

Referring back to FIG. 90, the surgical hub 5706 could be configured to track, store, and display data regarding the number of patients operated on (or procedures completed) per day per operating theater (bar graph 5402 depicted further in FIG. 91), for example. The surgical hub 5706 could be configured to further parse the number of patients operated on (or procedures completed) per day per operating theater and can be further parsed according to the downtime between the procedures on a given day (bar graph 5404 depicted further in FIG. 92) or the average procedure length on a given day (bar graph 5408 depicted further in FIG. 94). The surgical hub 5706 can be further configured to provide a detailed breakdown of the downtime between procedures according to, for example, the number and length of the downtime time periods and the subcategories of the actions or steps during each time period (bar graph 5406 depicted further in FIG. 93). The surgical hub 5706 can be further configured to provide a detailed breakdown of the average procedure length on a given day according to each individual procedure and the subcategory of actions or steps during each procedure (bar graph 5410 depicted further in FIG. 95). The various graphs shown in FIGS. 90-95 can represent data tracked by the surgical hub 5706 and can further be generated automatically or displayed by the surgical hub 5706 in response to queries submitted by users.

Figure 91:
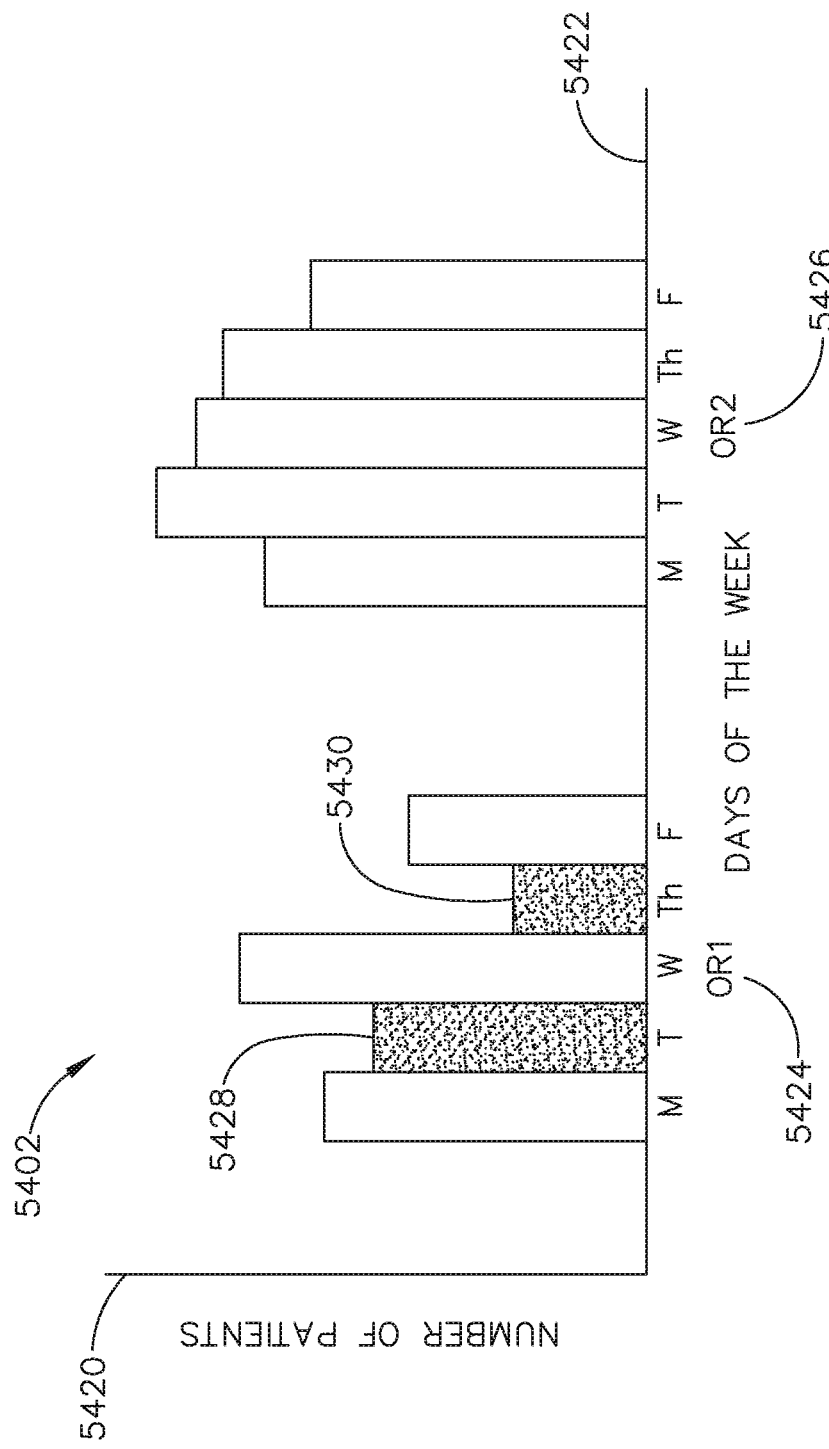
FIG. 91 illustrates a bar graph depicting the number of patients operated on relative to the days of a week for different operating rooms, in accordance with at least one aspect of the present disclosure.

FIG. 91 illustrates an example bar graph 5402 depicting the number of patients 5420 operated on relative to the days of the week 5422 for different operating rooms 5424, 5426. The surgical hub 5706 can be configured to provide (e.g., via a display) the number of patients 5420 operated on or procedures that are completed in connection with each surgical hub 5706, which can be tracked through a situational awareness system or accessing the hospital's EMR database, for example. In one exemplification, the surgical hub 5706 can further be configured to collate this data from different surgical hubs 5706 within the medical facility that are communicably connected together, which allows each individual surgical hub to present the aggregated data of the medical facility on a hub-by-hub or operating theater-by-theater basis. In one exemplification, the surgical hub 5706 can be configured to compare one or more tracked metrics to a threshold value (which may be unique to each tracked metric). When at least one of the tracked metrics exceeds the threshold value (i.e., either increases above or drops below the threshold value, as appropriate for the particular tracked metric), then the surgical hub 5706 provides a visual, audible, or tactile alert to notify a user of such. For example, the surgical hub 5706 can be configured to indicate when the number of patients or procedures deviates from an expected, average, or threshold value. For example, FIG. 91 depicts the number of patients on Tuesday 5428 and Thursday 5430 for a first operating theater 5424 as being highlighted for being below expectation. Conversely, no days are highlighted for a second operating theater 5426 for this particular week, which means in this context that the number of patients for each day falls within expectations.

Figure 92:
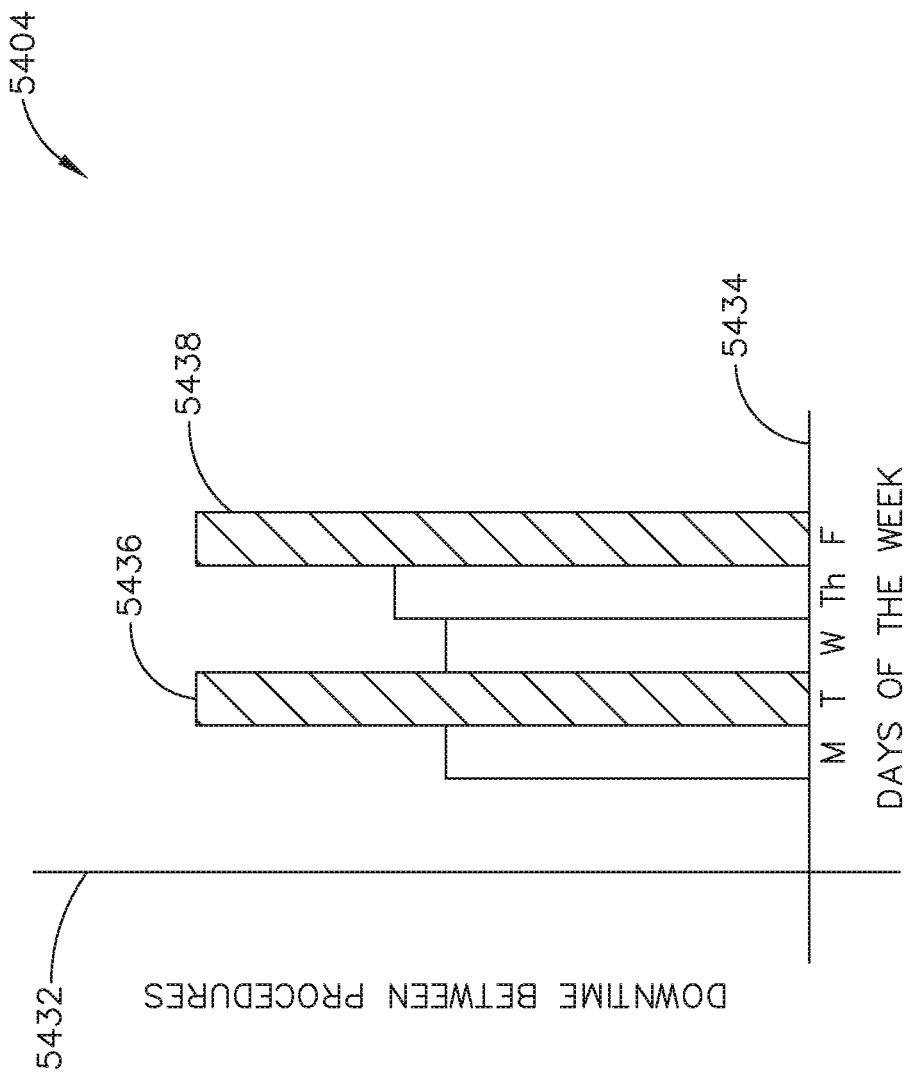
FIG. 92 illustrates a bar graph depicting the total downtime between procedures relative to the days of a week for a particular operating room, in accordance with at least one aspect of the present disclosure.

FIG. 92 illustrates a bar graph 5404 depicting the total downtime between procedures 5432 relative to the days of a week 5434 for a particular operating room. The surgical hub 5706 can be configured to track the length of downtime between surgical procedures through a situational awareness system, for example. The situational awareness system can detect or infer when each particular downtime instance is occurring and then track the length of time for each instance of downtime. The surgical hub 5706 can thereby determine the total downtime 5432 for each day of the week 5434 by summing the downtime instances for each particular day. In one exemplification, the surgical hub 5706 can be configured to provide an alert when the total length of downtime on a given day (or another unit of time) deviates from an expected, average, or threshold value. For example, FIG. 92 depicts the total downtime 5432 on Tuesday 5436 and Friday 5438 as being highlighted for deviating from an expected length of time.

Figure 93:
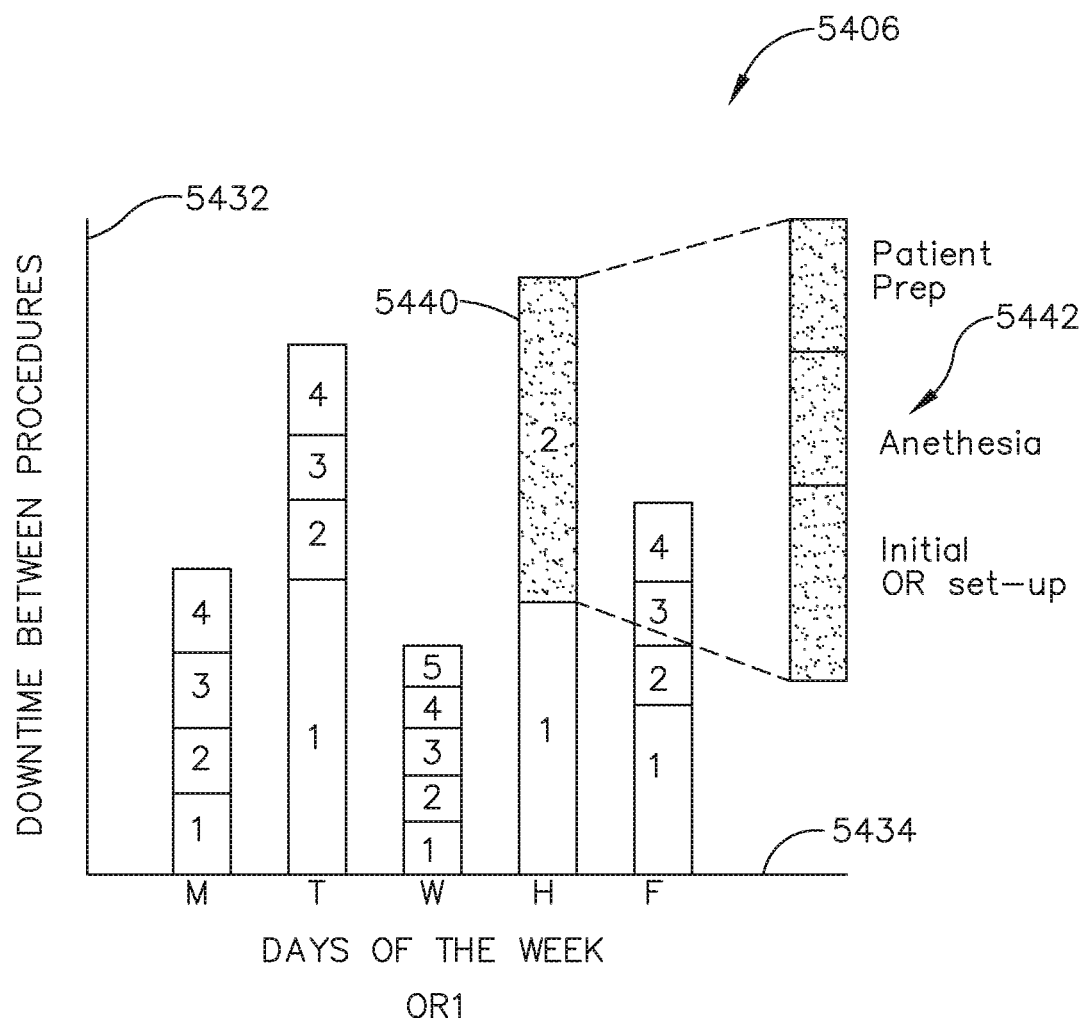
FIG. 93 illustrates a bar graph depicting the total downtime per day of the week depicted in FIG. 92 broken down according to each individual downtime instance, in accordance with at least one aspect of the present disclosure.

FIG. 93 illustrates a bar graph 5406 depicting the total downtime 5432 per day of the week 5434 as depicted in FIG. 92 broken down according to each individual downtime instance. The number of downtime instances and the length of time for each downtime instance can be represented within each day's total downtime. For example, on Tuesday in the first operating theater (OR1) there were four instances of downtime between procedures and the magnitude of the first downtime instance indicates that it was longer than the other three instances. In one exemplification, the surgical hub 5706 is configured to further indicate the particular actions or steps taken during a selected downtime instance. For example, in FIG. 93, Thursday's second downtime instance 5440 has been selected, which then causes a callout 5442 to be displayed indicating that this particular downtime instance consisted of performing the initial set-up of the operating theater, administering anesthesia, and prepping the patient. As with the downtime instances themselves, the relative size or length of the actions or steps within the callout 5442 can correspond to the length of time for each particular action or step. The detail views for the downtime instances can be displayed when a user selects the particular instance, for example.

Figure 94:
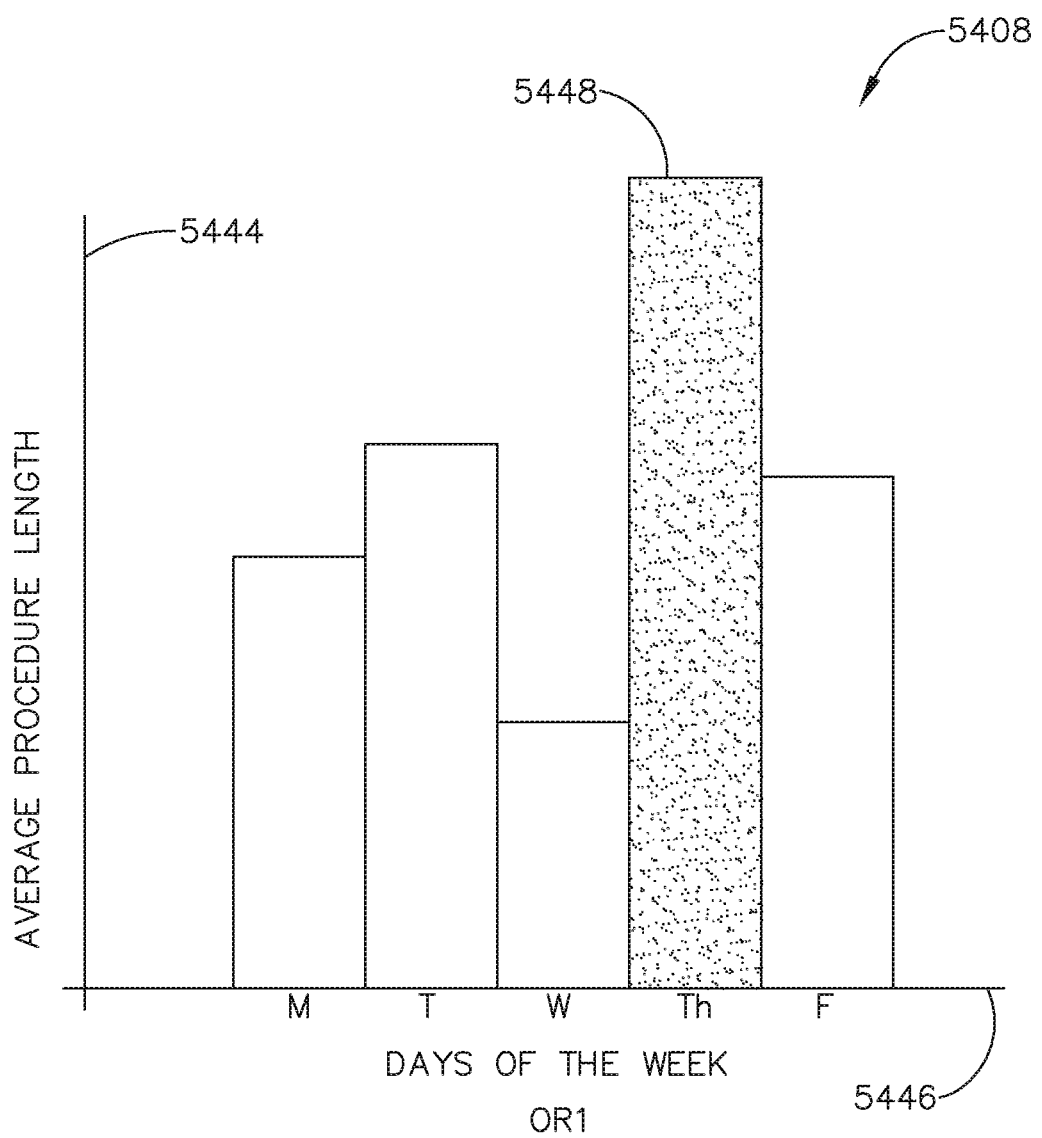
FIG. 94 illustrates a bar graph depicting the average procedure length relative to the days of a week for a particular operating room, in accordance with at least one aspect of the present disclosure.

FIG. 94 illustrates a bar graph 5408 depicting the average procedure length 5444 relative to the days of a week 5446 for a particular operating theater. The surgical hub 5706 can be configured to track the average procedure length through a situational awareness system, for example. The situational awareness system can detect or infer when each particular step of a surgical procedure is occurring (see FIG. 86, for example) and then track the length of time for each of the steps. The surgical hub 5706 can thereby determine the total downtime 5432 for each day of the week 5434 by summing the lengths of the downtime instances for the particular day. In one exemplification, the surgical hub 5706 can be configured to indicate when the average procedure length deviates from an expected value. For example, FIG. 94 depicts Thursday's average procedure length 5448 for the first operating room (OR1) as being highlighted for deviating from an expected length of time.

Figure 95:
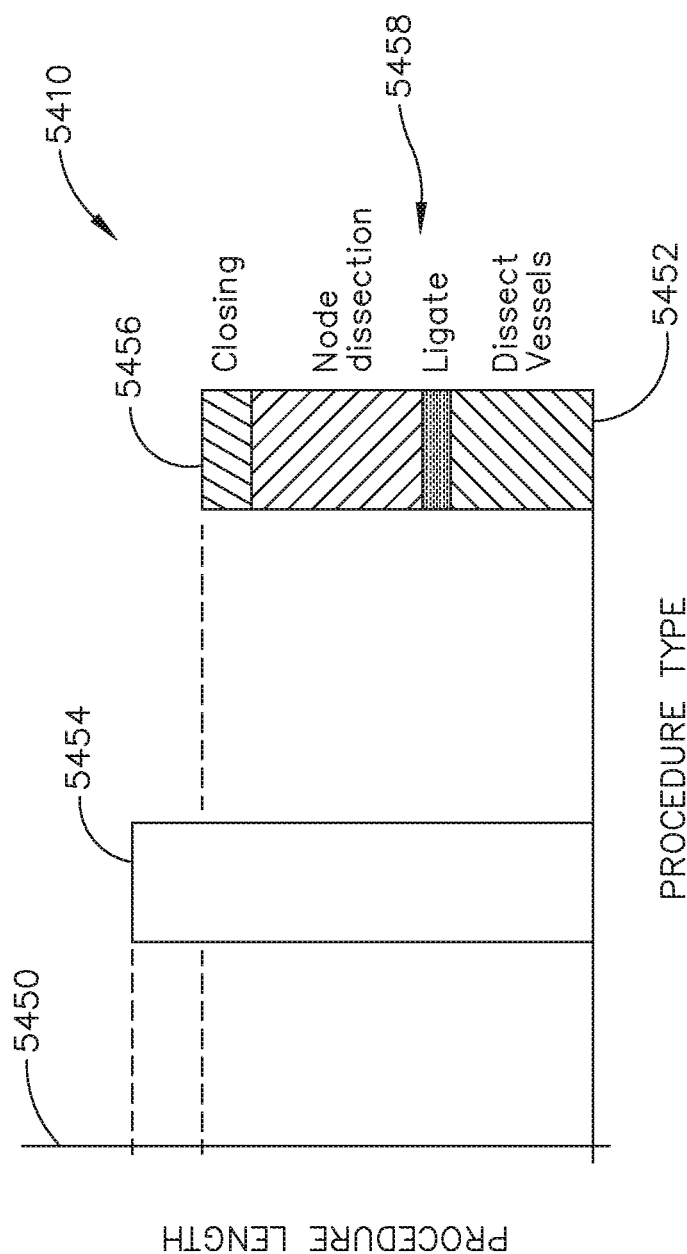
FIG. 95 illustrates a bar graph depicting procedure length relative to procedure type, in accordance with at least one aspect of the present disclosure.

FIG. 95 illustrates a bar graph 5410 depicting the procedure lengths 5450 relative to procedure types 5452. The depicted procedure lengths 5450 can either represent the average procedure lengths for particular types of procedures or the procedure lengths for each individual procedure performed on a given day in a given operating theater. The procedure lengths 5450 for different procedure types 5452 can then be compared. Further, the average lengths for the steps in a procedure type 5452 or the length for each particular step in a particular procedure can be displayed when a procedure is selected. Further, the procedure types 5452 can be tagged with various identifiers for parsing and comparing different data sets. For example, in FIG. 95 the first procedure 5454 corresponds to a colorectal procedure (specifically, a low anterior resection) where there was a preoperative identification of abdominal adhesions. The second procedure 5456 corresponds to a thoracic procedure (specifically, a segmentectomy). It should be noted again that the procedures depicted in FIG. 95 can represent the lengths of time for individual procedures or the average lengths of time for all of the procedures for the given procedure types. Each of the procedures can further be broken down according to the length of time for each step in the procedure. For example, FIG. 95 depicts the second procedure 5456 (a thoracic segmentectomy) as including an icon or graphical representation 5458 of the length of time spent on the dissect vessels, ligate (the vessels), nodal dissection, and closing steps of the surgical procedure. As with the procedure lengths themselves, the relative size or length of the steps within the graphical representation 5442 can correspond to the length of time for each particular step of the surgical procedure. The detail views for the steps of the surgical procedures can be displayed when a user selects the particular procedure, for example. In one exemplification, the surgical hub 5706 can be configured to identify when a length of time to complete a given step in the procedure deviates from an expected length of time. For example, FIG. 95 depicts the nodal dissection step as being highlighted for deviating from an expected length of time.

In one exemplification, an analytics package of the surgical hub 5706 can be configured to provide the user with usage data and results correlations related to the surgical procedures (or downtime between procedures). For example, the surgical hub 5706 can be configured to display methods or suggestions to improve the efficiency or effectiveness of a surgical procedure. As another example, the surgical hub 5706 can be configured to display methods to improve cost allocation. FIGS. 96-101 depict examples of various metrics that can be tracked by the surgical hub 5706, which can then be utilized to provide medical facility personnel suggestions for inventory utilization or technique outcomes. For example, a surgical hub 5706 could provide a surgeon with a suggestion pertaining to a particular technique outcome prior to or at the beginning of a surgical procedure based on the metrics tracked by the surgical hub 5706.

Figure 96:
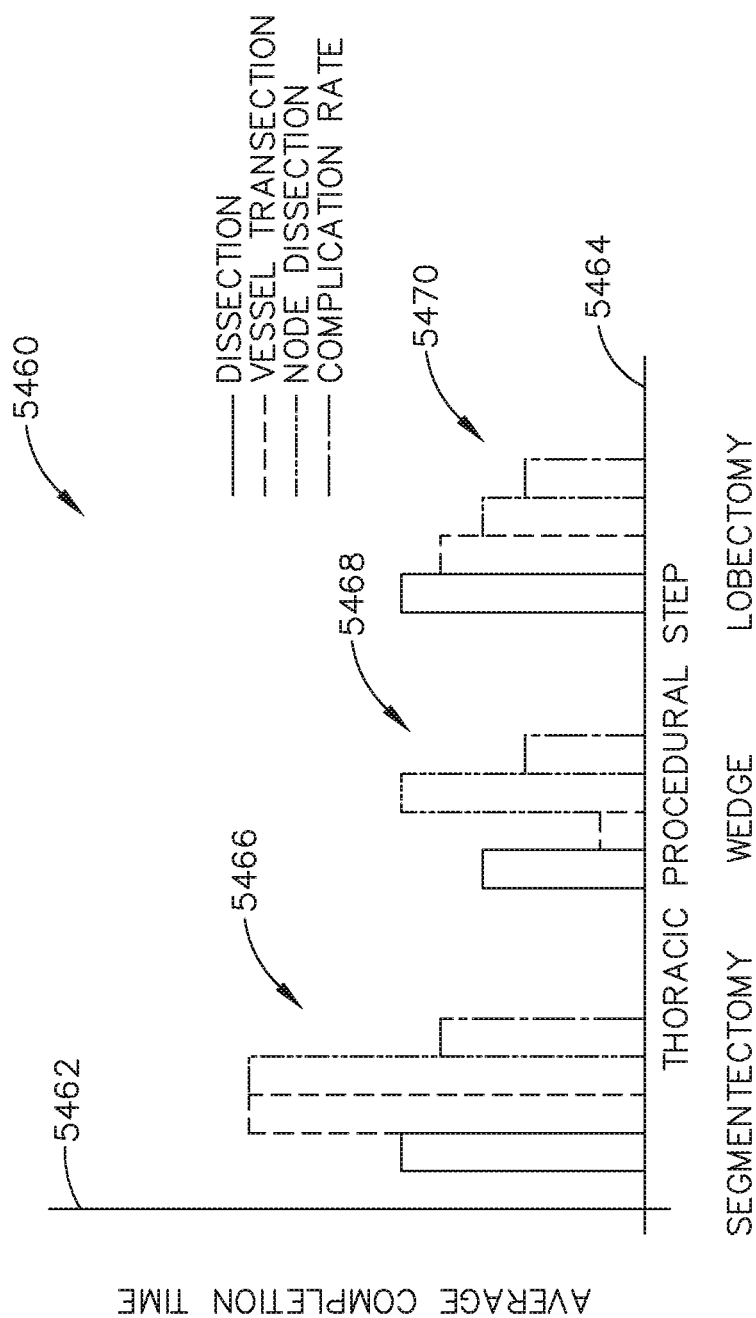
FIG. 96 illustrates a bar graph depicting the average completion time for particular procedural steps for different types of thoracic procedures, in accordance with at least one aspect of the present disclosure.

FIG. 96 illustrates a bar graph 5460 depicting the average completion time 5462 for particular procedural steps 5464 for different types of thoracic procedures. The surgical hub 5706 can be configured to track and store historical data for different types of procedures and calculate the average time to complete the procedure (or an individual step thereof). For example, FIG. 96 depicts the average completion time 5462 for thoracic segmentectomy 5466, wedge 5468, and lobectomy 5470 procedures. For each type of procedure, the surgical hub 5706 can track the average time to complete each step thereof. In this particular example, the dissection, vessel transection, and node dissection steps are indicated for each type of procedure. In addition to tracking and providing the average time for the steps of the procedure types, the surgical hub 5706 can additionally track other metrics or historical data, such as the complication rate for each procedure type (i.e., the rate of procedures having at least one complication as defined by the surgical hub 5706 or the surgeon). Additional tracked metrics for each procedure type, such as the complication rate, can also be depicted for comparison between the different procedure types.

Figure 97:
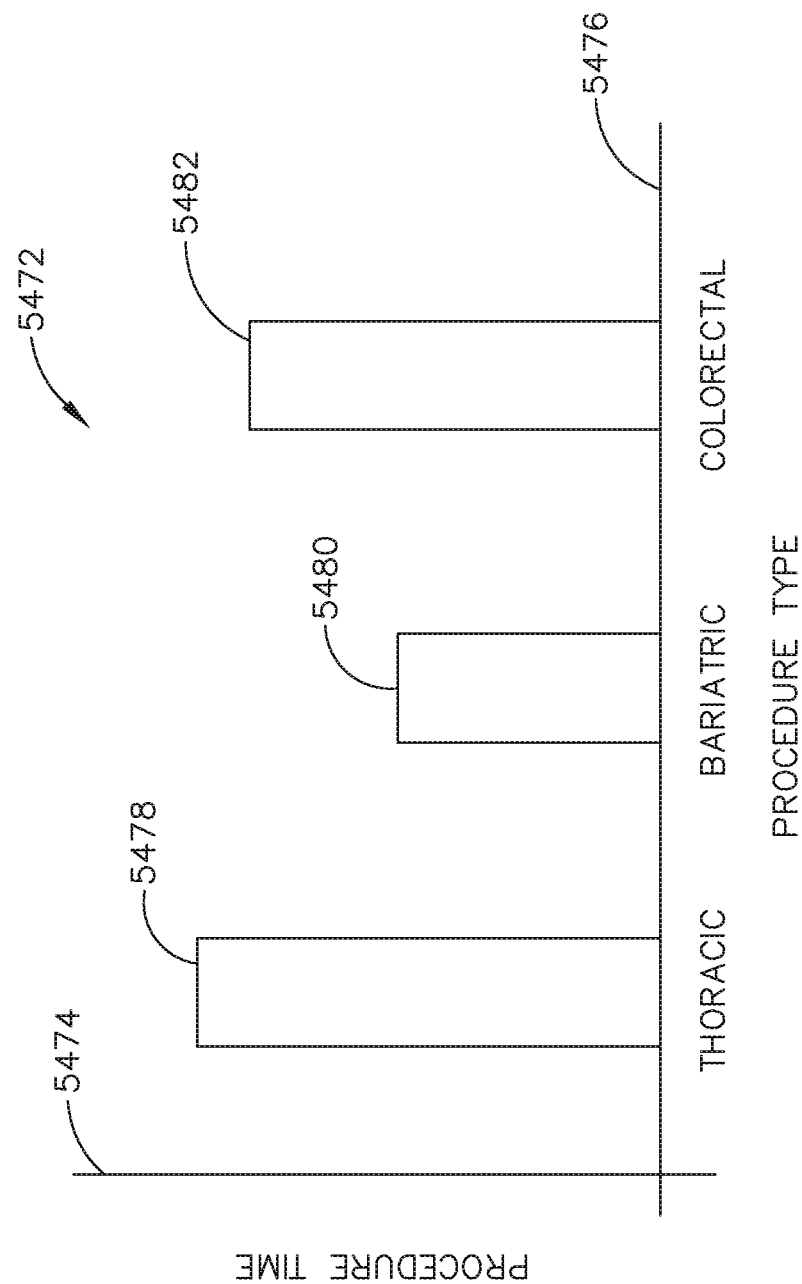
FIG. 97 illustrates a bar graph depicting procedure time relative to procedure types, in accordance with at least one aspect of the present disclosure.

FIG. 97 illustrates a bar graph 5472 depicting the procedure time 5474 relative to procedure types 5476. The surgical hub 5706 can be configured to track and store historical data or metrics for different procedure types 5476 or classes, which can encompass multiple subtypes of procedures. For example, FIG. 97 depicts the procedure time 5474 for surgical procedures classified as a thoracic 5478, bariatric 5480, or colorectal 5482 procedure. In various exemplifications, the surgical hub 5706 can output the procedure time 5474 for the procedure classifications expressed in terms of either the total length of time or the average time spent on the given procedure types 5476. The analytics package of the surgical hub 5706 can, for example, provide this data to the surgeons, hospital officials, or medical personnel to track the efficiency of the queried procedures. For example, FIG. 97 depicts bariatric procedures 5480 as taking a lower average time (i.e., being more time efficient) than either thoracic procedures 5478 or colorectal procedures 5482.

Figure 98:
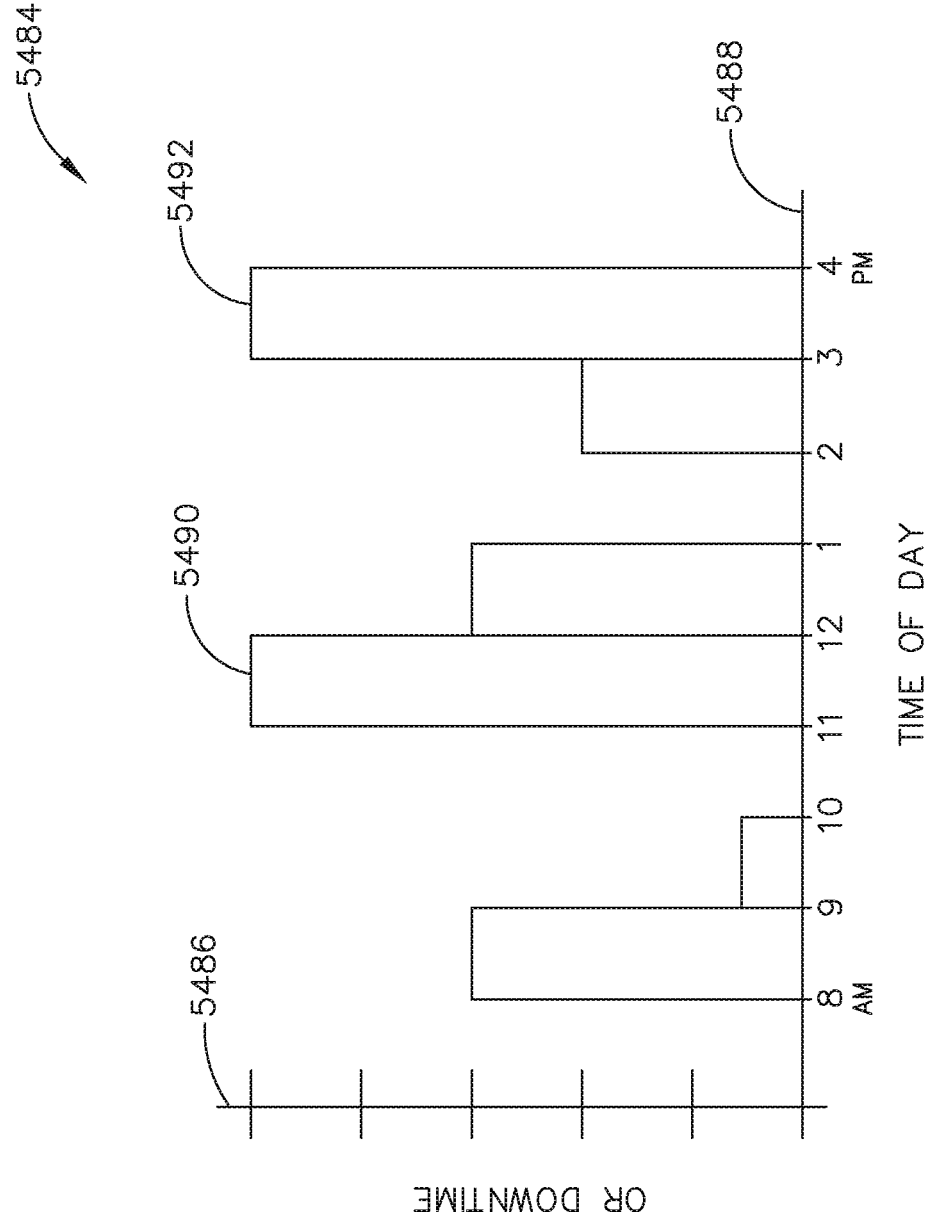
FIG. 98 illustrates a bar graph depicting operating room downtime relative to the time of day, in accordance with at least one aspect of the present disclosure.
Figure 99:
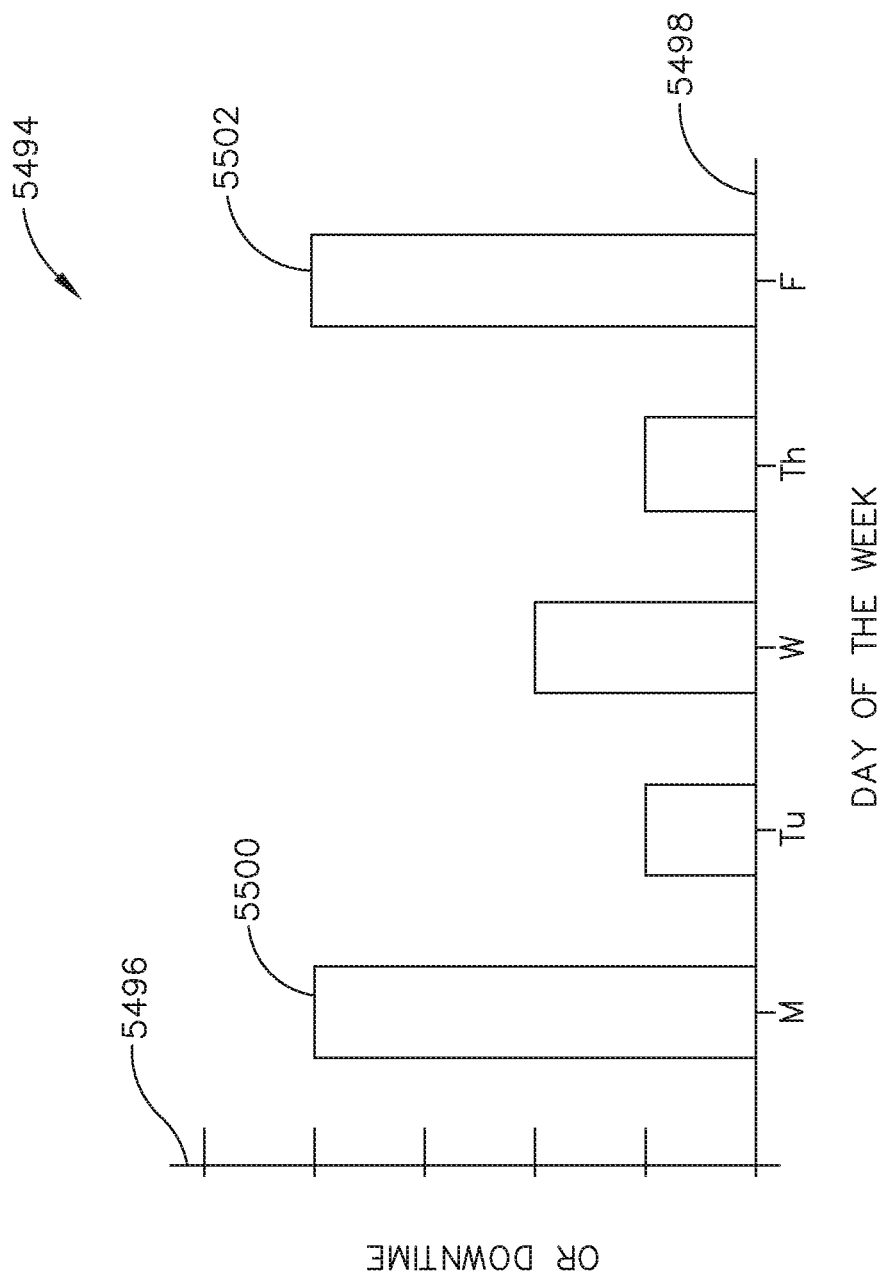
FIG. 99 illustrates a bar graph depicting operating room downtime relative to the day of the week, in accordance with at least one aspect of the present disclosure.

FIG. 98 illustrates a bar graph 5484 depicting operating room downtime 5486 relative to the time of day 5488. Relatedly, FIG. 99 illustrates a bar graph 5494 depicting operating room downtime 5496 relative to the day of the week 5498. Operating room downtime 5486, 5496 can be expressed in, for example, a length of a unit of time or relative utilization (i.e., percentage of time that the operating room is in use). The operating room downtime data can encompass an individual operating room or an aggregation of multiple operating rooms at a medical facility. As discussed above, a surgical hub 5706 can be configured to track whether a surgical procedure is being performed in the operating theater associated with the surgical hub 5706 (including the length of time that a surgical procedure is or is not being performed) utilizing a situational awareness system, for example. As shown in FIGS. 98 and 99, the surgical hub 5706 can provide an output (e.g., bar graphs 5484, 5494 or other graphical representations of data) depicting the tracked data pertaining to when the operating room is being utilized (i.e., when a surgical procedure is being performed) and/or when there is downtime between procedures. Such data can be utilized to identify ineffectiveness or inefficiencies in performing surgical procedures, cleaning or preparing operating theaters for surgery, scheduling, and other metrics associated with operating theater use. For example, FIG. 98 depicts a comparative increase in operating room downtime 5486 at a first instance 5490 from 11:00 a.m.-12:00 p.m. and a second instance 5492 from 3:00-4:00 p.m. As another example, FIG. 99 depicts a comparative increase in operating room downtime 5496 on Mondays 5500 and Fridays 5502. In various exemplifications, the surgical hub 5706 can provide operating theater downtime data for a particular instance (i.e., a specific time, day, week, etc.) or an average operating theater downtime data for a category of instances (i.e., aggregated data for a day, time, week, etc.). Hospital officials or other medical personnel thus could use this data to identify specific instances where an inefficiency may have occurred or identify trends in particular days and/or times of day where there may be inefficiencies. From such data, the hospital officials or other medical personnel could then investigate to identify the specific reasons for these increased downtimes and take corrective action to address the identified reason.

Figure 100:
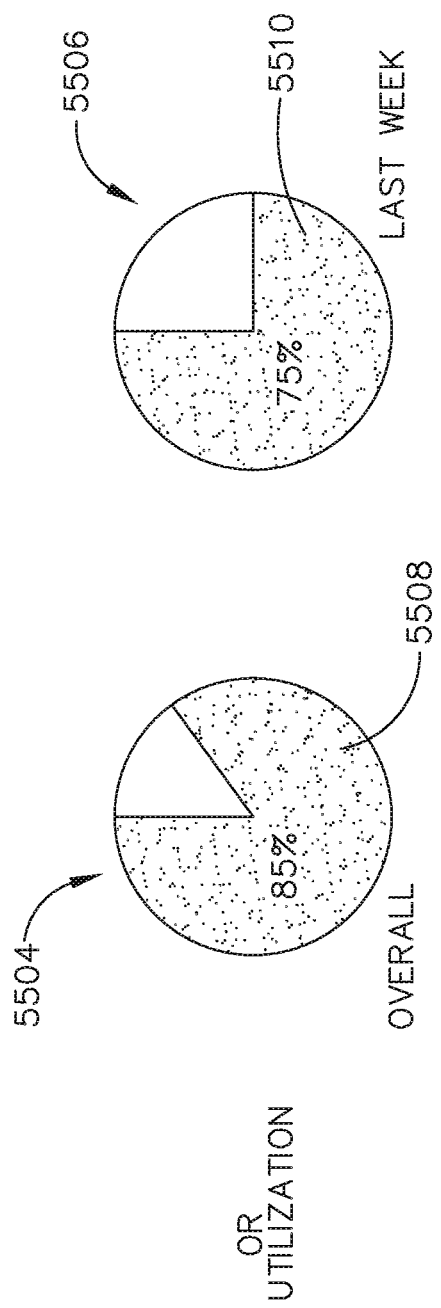
FIG. 100 illustrates a pair of pie charts depicting the percentage of time that the operating theater is utilized, in accordance with at least one aspect of the present disclosure.

In various exemplifications, the surgical hub 5706 can be configured to display data in response to queries in a variety of different formats (e.g., bar graphs, pie graphs, infographics). FIG. 100 illustrates a pair of pie charts depicting the percentage of time that the operating theater is utilized. The operating theater utilization percentage can encompass an individual operating theater or an aggregation of multiple operating theaters (e.g., the operating rooms at a medical facility or every operating room for all medical facilities having surgical hubs 5706 connected to the cloud 5702). As discussed above, a surgical hub 5706 can be configured to determine when a surgical procedure is or is not being performed (i.e., whether the operating theater associated with the surgical hub 5706 is being utilized) using a situational awareness system, for example. In addition to expressing operating theater utilization in terms of an average or absolute amount for different time periods (as depicted in FIGS. 98-99), the surgical hub 5706 can additionally express operating theater utilization in terms of a percentage or relative amount compared to a maximum possible utilization. As above, the operating theater utilization can be parsed for particular time periods, including the overall utilization (i.e., the total historical percentage of time in use) for the particular operating theater (or groups of operating theaters) or the utilization over the span of a particular time period. As shown in FIG. 100, a first pie chart 5504 depicts the overall operating theater utilization 5508 (85%) and a second pie chart 5506 depicts the operating theater utilization for the prior week 5510 (75%). Hospital officials and other medical personnel could use this data to identify that there may have been some inefficiency that occurred in the prior week that caused the particular operating theater (or group of operating theaters) to be utilized less efficiently compared to the historical average so that further investigations can be carried out to identify the specific reasons for this decreased utilization.

Figure 101:
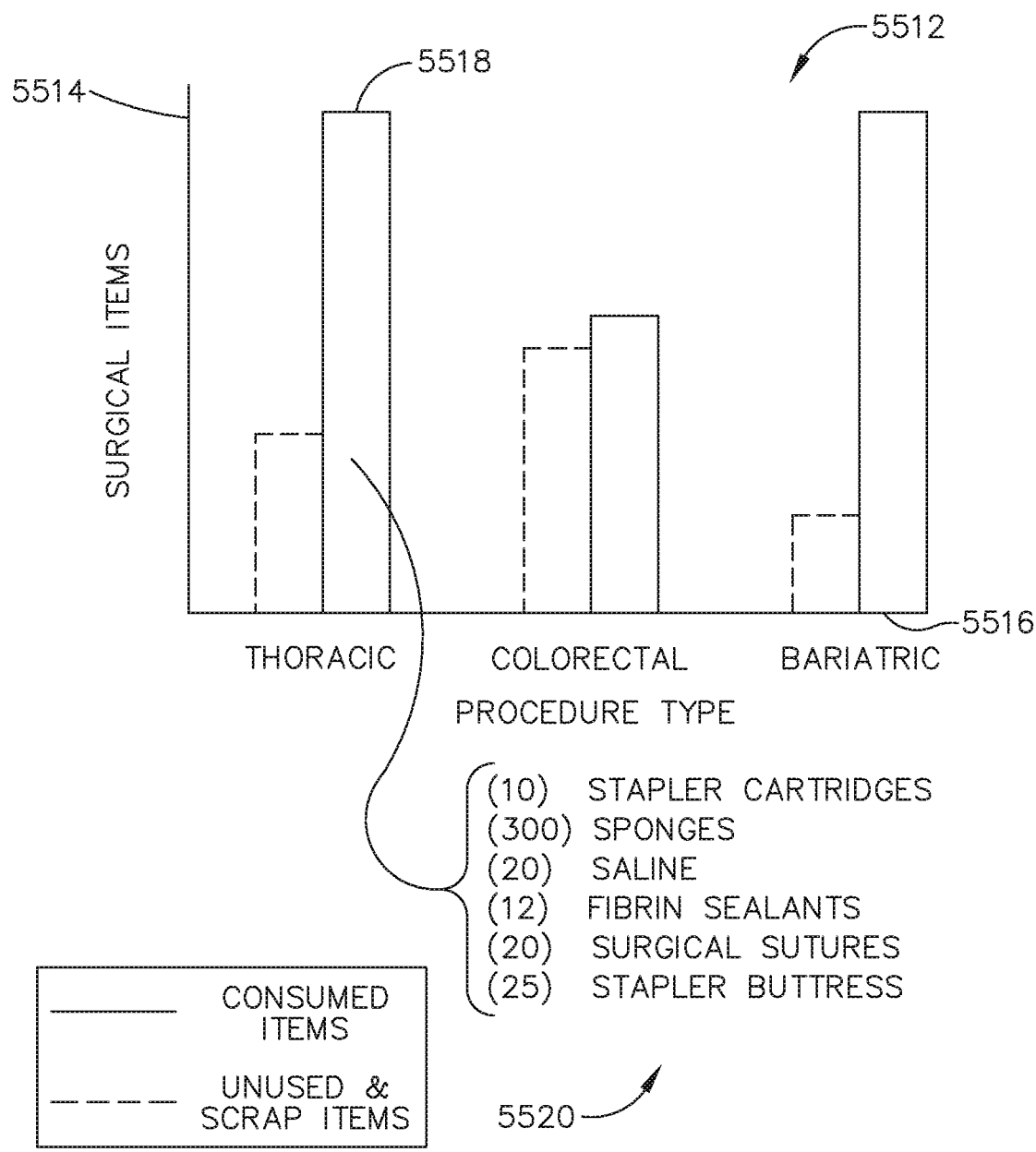
FIG. 101 illustrates a bar graph depicting consumed and unused surgical items relative to procedure type, in accordance with at least one aspect of the present disclosure.

In some exemplifications, the surgical hub 5706 is configured to track detect and track the number of surgical items that are utilized during the course of a surgical procedure. This data can then be aggregated and displayed (either automatically or in response to a query) according to, for example, a particular time period (e.g., per day or per week) or for a particular surgical procedure type (e.g., thoracic procedures or abdominal procedures). FIG. 101 illustrates a bar graph 5512 depicting consumed and unused surgical items 5514 relative to procedure type 5516. The surgical hub 5706 can be configured to determine or infer what surgical items are being consumed during the course of each surgical procedure via a situational awareness system. The situational awareness system can determine or receive the list of surgical items to be used in a procedure (e.g., see FIG. 85B), determine or infer when each procedure (and steps thereof) begins and ends, and determine when a particular surgical item is being utilized according to the procedural step being performed. The inventory of surgical items that are consumed or unused during the course of a surgical procedure can be represented in terms of the total number of surgical items or the average number of surgical items per procedure type 5516, for example. The consumed surgical items can include non-reusable items that are utilized during the course of a surgical procedure. The unused surgical items can include additional items that are not utilized during the procedure(s) or scrap items. The procedure type can correspond to broad classifications of procedures or a specific procedure type or technique for performing a procedure type. For example, in FIG. 101 the procedure types 5516 being compared are thoracic, colorectal, and bariatric procedures. For each of these procedure types 5516, the average number of consumed and unused surgical items 5514 are both provided. In one aspect, the surgical hub 5706 can be configured to further parse the consumed and/or unused surgical items 5514 by the specific item type. In one exemplification, the surgical hub 5706 can provide a detailed breakdown of the surgical items 5514 making up each item category for each surgical procedure type 5516 and graphically represent the different categories of surgical items 5514. For example, in FIG. 101, the unused surgical items are depicted in dashed lines and the consumed surgical items are depicted in solid lines. In one exemplification, the surgical hub 5706 is configured to further indicate the specific within a category for a particular procedure type 5516. For example, in FIG. 93, the consumed items category for the thoracic procedure type has been selected, which then causes a callout 5520 to be displayed listing the particular surgical items in the category: stapler cartridges, sponges, saline, fibrin sealants, surgical sutures, and stapler buttress material. Furthermore, the callout 5520 can be configured to provide the quantities of the listed items in the category, which may be the average or absolute quantities of the items (either consumed or unused) for the particular procedure type.

In one exemplification, the surgical hub 5706 can be configured to aggregate tracked data in a redacted format (i.e., with any patient-identifying information stripped out). Such bulk data can be utilized for academic or business analysis purposes. Further, the surgical hub 5706 can be configured to upload the redacted or anonymized data to a local database of the medical facility in which the surgical hub 5706 is located, an external database system, or the cloud 5702, whereupon the anonymized data can be accessed by user/client applications on demand. The anonymized data can be utilized to compare outcomes and efficiencies within a hospital or between geographic regions, for example.

The process 5300 depicted in FIG. 89 improves scheduling efficiency by allowing the surgical hubs 5706 to automatically store and provide granular detail on correlations between lengths of time required for various procedures according to particular days, particular types of procedures, particular hospital staff members, and other such metrics. This process 5300 also reduces surgical item waste by allowing the surgical hubs 5706 to provide alerts when the amount of surgical items being consumed, either on a per-procedure basis or as a category, are deviating from the expected amounts. Such alerts can be provided either automatically or in response to receiving a query.

Figure 102:
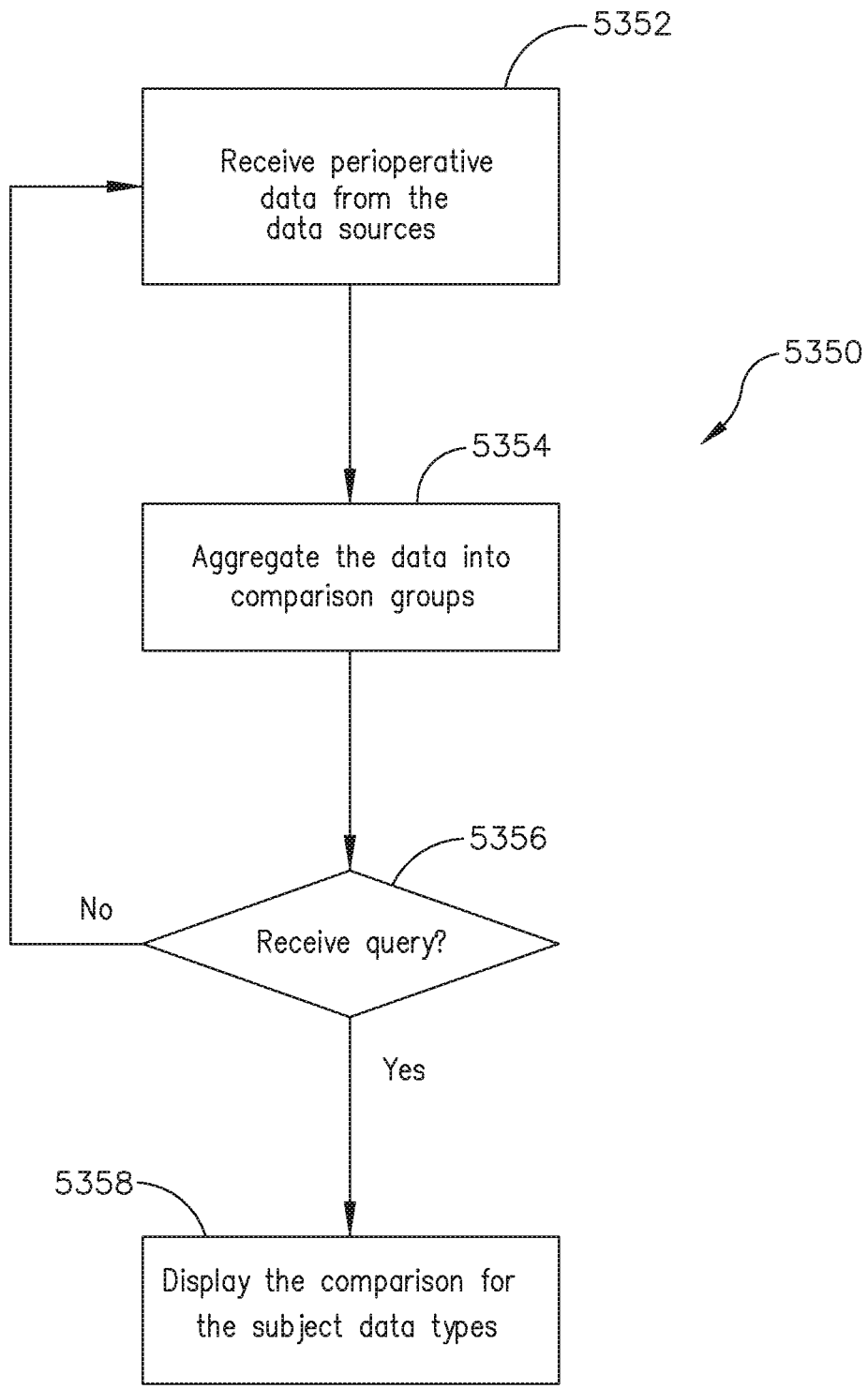
FIG. 102 illustrates a logic flow diagram of a process for storing data from the modular devices and patient information database for comparison, in accordance with at least one aspect of the present disclosure.

FIG. 102 illustrates a logic flow diagram of a process 5350 for storing data from the modular devices and patient information database for comparison. In the following description, description of the process 5350, reference should also be made to FIG. 88. In one exemplification, the process 5350 can be executed by a control circuit of a surgical hub 206, as depicted in FIG. 10 (processor 244). In yet another exemplification, the process 5350 can be executed by a distributed computing system including a control circuit of a surgical hub 206 in combination with a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5350 will be described as being executed by the control circuit of a surgical hub 5706; however, it should be understood that the description of the process 5350 encompasses all of the aforementioned exemplifications.

The control circuit executing the process 5350 receives data from the data sources, such as the modular device(s) and the patient information database(s) (e.g., EMR databases) that are communicably coupled to the surgical hub 5706. The data from the modular devices can include, for example, usage data (e.g., data pertaining to how often the modular device has been utilized, what procedures the modular device has been utilized in connection with, and who utilized the modular devices) and performance data (e.g., data pertaining to the internal state of the modular device and the tissue being operated on). The data from the patient information databases can include, for example, patient data (e.g., data pertaining to the patient's age, sex, and medical history) and patient outcome data (e.g., data pertaining to the outcomes from the surgical procedure). In some exemplifications, the control circuit can continuously receive 5352 data from the data sources before, during, or after a surgical procedure.

As the data is received 5352, the control circuit aggregates 5354 the data in comparison groups of types of data. In other words, the control circuit causes a first type of data to be stored in association with a second type of data. However, more than two different types of data can be aggregated 5354 together into a comparison group. For example, the control circuit could store a particular type of performance data for a particular type of modular device (e.g., the force to fire for a surgical cutting and stapling instrument or the characterization of the energy expended by an RF or ultrasonic surgical instrument) in association with patient data, such as sex, age (or age range), a condition (e.g., emphysema) associated with the patient. In one exemplification, when the data is aggregated 5354 into comparison groups, the data is anonymized such that all patient-identifying information is removed from the data. This allows the data aggregated 5354 into comparison groups to be utilized for studies, without compromising confidential patient information. The various types of data can be aggregated 5354 and stored in association with each other in lookup tables, arrays, and other such formats. In one exemplification, the received 5352 data is automatically aggregated 5354 into comparison groups. Automatically aggregating 5354 and storing the data allows the surgical hub 5706 to quickly return results for queries and the groups of data to be exported for analysis according to specifically desired data types.

When the control circuit receives 5356 a query for a comparison between two or more of the tracked data types, the process 5350 proceeds along the YES branch. The control circuit then retrieves the particular combination of the data types stored in association with each other and then displays 5358 a comparison (e.g., a graph or other graphical representation of the data) between the subject data types. If the control circuit does not receive 5356 a query, the process 5350 continues along the NO branch and the control circuit continues receiving 5352 data from the data sources.

In one exemplification, the control circuit can be configured to automatically quantify a correlation between the received 5352 data types. In such aspects, the control circuit can calculate a correlation coefficient (e.g., the Pearson's coefficient) between pairs of data types. In one aspect, the control circuit can be configured to automatically display a report providing suggestions or other feedback if the quantified correlation exceeds a particular threshold value. In one aspect, the control circuit of the surgical hub 5706 can be configured to display a report on quantified correlations exceeding a particular threshold value upon receiving a query or request from a user.

In one exemplification, a surgical hub 5706 can compile information on procedures that the surgical hub 5706 was utilized in the performance of, communicate with other surgical hubs 5706 within its network (e.g., a local network of a medical facility or a number of surgical hubs 5706 connected by the cloud 5702), and compare results between type of surgical procedures or particular operating theaters, doctors, or departments. Each surgical hub 5706 can calculate and analyze utilization, efficiency, and comparative results (relative to all surgical hubs 5706 across a hospital network, a region, etc.). For example, the surgical hub 5706 can display efficiency and comparative data, including operating theater downtime, operating theater clean-up and recycle time, step-by-step completion timing for procedures (including highlighting which procedural steps take the longest, for example), average times for surgeons to complete procedures (including parsing the completion times on a procedure-by-procedure basis), historical completion times (e.g., for completing classes of procedures, specific procedures, or specific steps within a procedure), and/or operating theater utilization efficiency (i.e., the time efficiency from a procedure to a subsequent procedure). The data that is accessed and shared across networks by the surgical hubs 5706 can include the anonymized data aggregated into comparison groups, as discussed above.

For example, the surgical hub 5706 can be utilized to perform studies of performance by instrument type or cartridge type for various procedures. As another example, the surgical hub 5706 can be utilized to perform studies on the performance of individual surgeons. As yet another example, the surgical hub 5706 can be utilized to perform studies on the effectiveness of different surgical procedures according to patients' characteristics or disease states.

In another exemplification, a surgical hub 5706 can provide suggestions on streamlining processes based on tracked data. For example, the surgical hub 5706 can suggest different product mixes according to the length of certain procedures or steps within a procedure (e.g., suggest a particular item that is more appropriate for long procedure steps), suggest more cost effective product mixes based on the utilization of items, and/or suggest kitting or pre-grouping certain items to lower set-up time. In another exemplification, a surgical hub 5706 can compare operating theater utilization across different surgical groups in order to better balance high volume surgical groups with surgical groups that have more flexible bandwidth. In yet another aspect, the surgical hub 5706 could be put in a forecasting mode that would allow the surgical hub 5706 to monitor upcoming procedure preparation and scheduling, then notify the administration or department of upcoming bottlenecks or allow them to plan for scalable staffing. The forecasting mode can be based on, for example, the anticipated future steps of the current surgical procedure that is being performed using the surgical hub 5706, which can be determined by a situational awareness system.

In another exemplification, a surgical hub 5706 can be utilized as a training tool to allow users to compare their procedure timing to other types of individuals or specific individuals within their department (e.g., a resident could compare his or her timing to a particular specialist or the average time for a specialist within the hospital) or the department average times. For example, users could identify what steps of a surgical procedure they are spending an inordinate amount of time on and, thus, what steps of the surgical procedure that they need to improve upon.

In one exemplification, all processing of stored data is performed locally on each surgical hub 5706. In another exemplification, each surgical hub 5706 is part of a distributed computing network, wherein each individual surgical hub 5706 compiles and analyzes its stored data and then communicates the data to the requesting surgical hub 5706. A distributed computing network could permit fast parallel processing. In another exemplification, each surgical hub 5706 is communicably connected to a cloud 5702, which can be configured to receive the data from each surgical hub 5706 and then perform the necessary processing (data aggregation, calculations, and so on) on the data.

The process 5350 depicted in FIG. 102 improves the ability to determine when procedures are being performed inefficiently by allowing the surgical hubs 5706 to provide alerts when particular procedures, either on a per-procedure basis or as category, are deviating from the expected times to complete the procedures. Such alerts can be provided either automatically or in response to receiving a query. This process 5350 also improves the ability to perform studies on what surgical instruments and surgical procedure techniques provide the best patient outcomes by automatically tracking and indexing such data in easily-retrievable and reportable formats.

Some systems described herein offload the data processing that controls the modular devices (e.g., surgical instruments) from the modular devices themselves to an external computing system (e.g., a surgical hub) and/or a cloud. However in some exemplifications, some modular devices can sample data (e.g., from the sensors of the surgical instruments) at a faster rate that the rate at which the data can be transmitted to and processed by a surgical hub. As one solution, the surgical hub and the surgical instruments (or other modular devices) can utilize a distributed computing system where at least a portion of the data processing is performed locally on the surgical instrument. This can avoid data or communication bottlenecks between the instrument and the surgical hub by allowing the onboard processor of the surgical instrument to handle at least some of the data processing when the data sampling rate is exceeding the rate at which the data can be transmitted to the surgical hub. In some exemplifications, the distributed computing system can cease distributing the processing between the surgical hub and the surgical instrument and instead have the processing be executed solely onboard the surgical instrument. The processing can be executed solely by the surgical instrument in situations where, for example, the surgical hub needs to allocate its processing capabilities to other tasks or the surgical instrument is sampling data at a very high rate and it has the capabilities to execute all of the data processing itself.

Similarly, the data processing for controlling the modular devices, such as surgical instruments, can be taxing for an individual surgical hub to perform. If the surgical hub's processing of the control algorithms for the modular devices cannot keep pace with the use of the modular devices, then the modular devices will not perform adequately because their control algorithms will either not be updated as needed or the updates to the control algorithms will lag behind the actual use of the instrument. As one solution, the surgical hubs can be configured to utilize a distributed computing system where at least a portion of the processing is performed across multiple separate surgical hubs. This can avoid data or communication bottlenecks between the modular devices and the surgical hub by allowing each surgical hub to utilize the networked processing power of multiple surgical hubs, which can increase the rate at which the data is processed and thus the rate at which the control algorithm adjustments can be transmitted by the surgical hub to the paired modular devices. In addition to distributing the computing associated with controlling the various modular devices connected to the surgical hubs, a distributed computing system can also dynamically shift computing resources between multiple surgical hubs in order to analyze tracked data in response to queries from users and perform other such functions. The distributed computing system for the surgical hubs can further be configured to dynamically shift data processing resources between the surgical hubs when any particular surgical hub becomes overtaxed.

The modular devices that are communicably connectable to the surgical hub can include sensors, memories, and processors that are coupled to the memories and configured to receive and analyze data sensed by the sensors. The surgical hub can further include a processor coupled to a memory that is configured to receive (through the connection between the modular device and the surgical hub) and analyze the data sensed by the sensors of the modular device. In one exemplification, the data sensed by the modular device is processed externally to the modular device (e.g., external to a handle assembly of a surgical instrument) by a computer that is communicably coupled to the modular device. For example, the advanced energy algorithms for controlling the operation of a surgical instrument can be processed by an external computing system, rather than on a controller embedded in the surgical instrument (such as instrument using an Advanced RISC Machine (ARM) processor). The external computer system processing the data sensed by the modular devices can include the surgical hub to which the modular devices are paired and/or a cloud computing system. In one exemplification, data sampled at a particular rate (e.g., 20 Ms/sec) and a particular resolution (e.g., 12 bits resolution) by a surgical instrument is decimated and then transmitted over a link to the surgical hub to which the surgical instrument is paired. Based on this received data, the control circuit of the surgical hub then determines the appropriate control adjustments for the surgical instrument, such as controlling power for an ultrasonic surgical instrument or RF electrosurgical instrument, setting motor termination points for a motor-driven surgical instrument, and so on. The control adjustments are then transmitted to the surgical instrument for application thereon.

Distributed Processing

Figure 103:
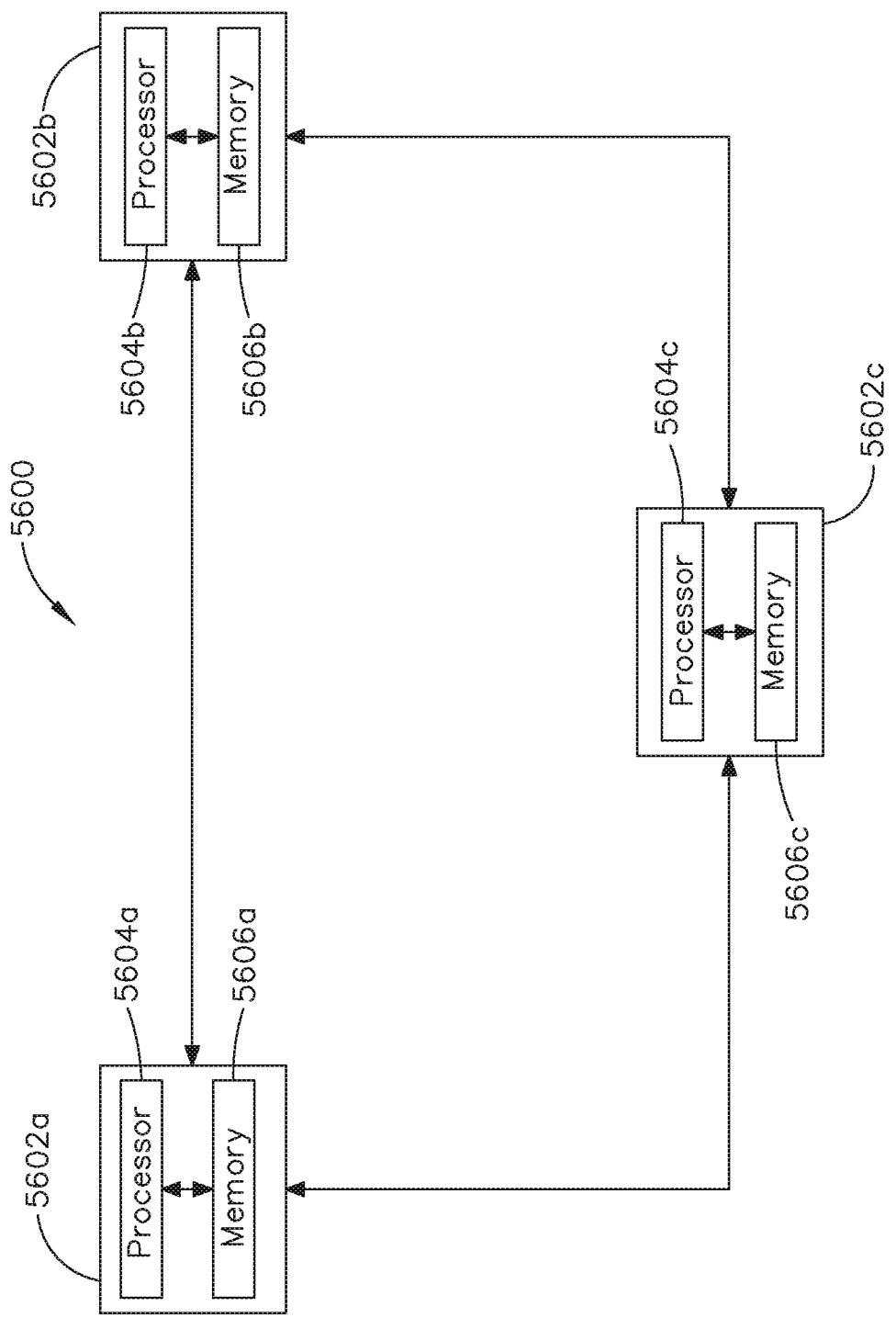
FIG. 103 illustrates a diagram of a distributed computing system, in accordance with at least one aspect of the present disclosure.

FIG. 103 illustrates a diagram of a distributed computing system 5600. The distributed computing system 5600 includes a set of nodes 5602*a*, 5602*b*, 5602*c* that are communicably coupled by a distributed multi-party communication protocol such that they execute a shared or distributed computer program by passing messages therebetween. Although three nodes 5602*a*, 5602*b*, 5602*c* are depicted, the distributed computing system 5600 can include any number of nodes 5602*a*, 5602*b*, 5602*c* that are communicably connected together. Each of the nodes 5602*a*, 5602*b*, 5602*c* comprises a respective memory 5606*a*, 5606*b*, 5606*c* and processor 5604*a*, 5604*b*, 5604*c* coupled thereto. The processors 5604*a*, 5604*b*, 5604*c* execute the distributed multi-party communication protocol, which is stored at least partially in the memories 5606*a*, 5606*b*, 5606*c*. Each node 5602*a*, 5602*b*, 5602*c* can represent either a modular device or a surgical hub. Therefore, the depicted diagram represents aspects wherein various combinations of surgical hubs and/or modular devices are communicably coupled. In various exemplifications, the distributed computing system 5600 can be configured to distribute the computing associated with controlling the modular device(s) (e.g., advanced energy algorithms) over the modular device(s) and/or the surgical hub(s) to which the modular device(s) are connected. In other words, the distributed computing system 5600 embodies a distributed control system for controlling the modular device(s) and/or surgical hub(s).

In some exemplifications, the modular device(s) and surgical hub(s) utilize data compression for their communication protocols. Wireless data transmission over sensor networks can consume a significant amount of energy and/or processing resources compared to data computation on the device itself. Thus data compression can be utilized to reduce the data size at the cost of extra processing time on the device. In one exemplification, the distributed computing system 5600 utilizes temporal correlation for sensing data, data transformation from one dimension to two dimension, and data separation (e.g., upper 8 bit and lower 8 bit data). In another exemplification, the distributed computing system 5600 utilizes a collection tree protocol for data collection from different nodes 5602*a*, 5602*b*, 5602*c* having sensors (e.g., modular devices) to a root node. In yet another aspect, the distributed computing system 5600 utilizes first-order prediction coding to compress the data collected by the nodes 5602*a*, 5602*b*, 5602*c* having sensors (e.g., modular devices), which can minimize the amount of redundant information and greatly reduce the amount of data transmission between the nodes 5602*a*, 5602*b*, 5602*c* of the network. In yet another exemplification, the distributed computing system 5600 is configured to transmit only the electroencephalogram (EEG) features. In still yet another exemplification, the distributed computing system 5600 can be configured to transmit only the complex data features that are pertinent to the surgical instrument detection, which can save significant power in wireless transmission. Various other exemplifications can utilize combinations of the aforementioned data compression techniques and/or additional techniques of data compression.

Figure 104:
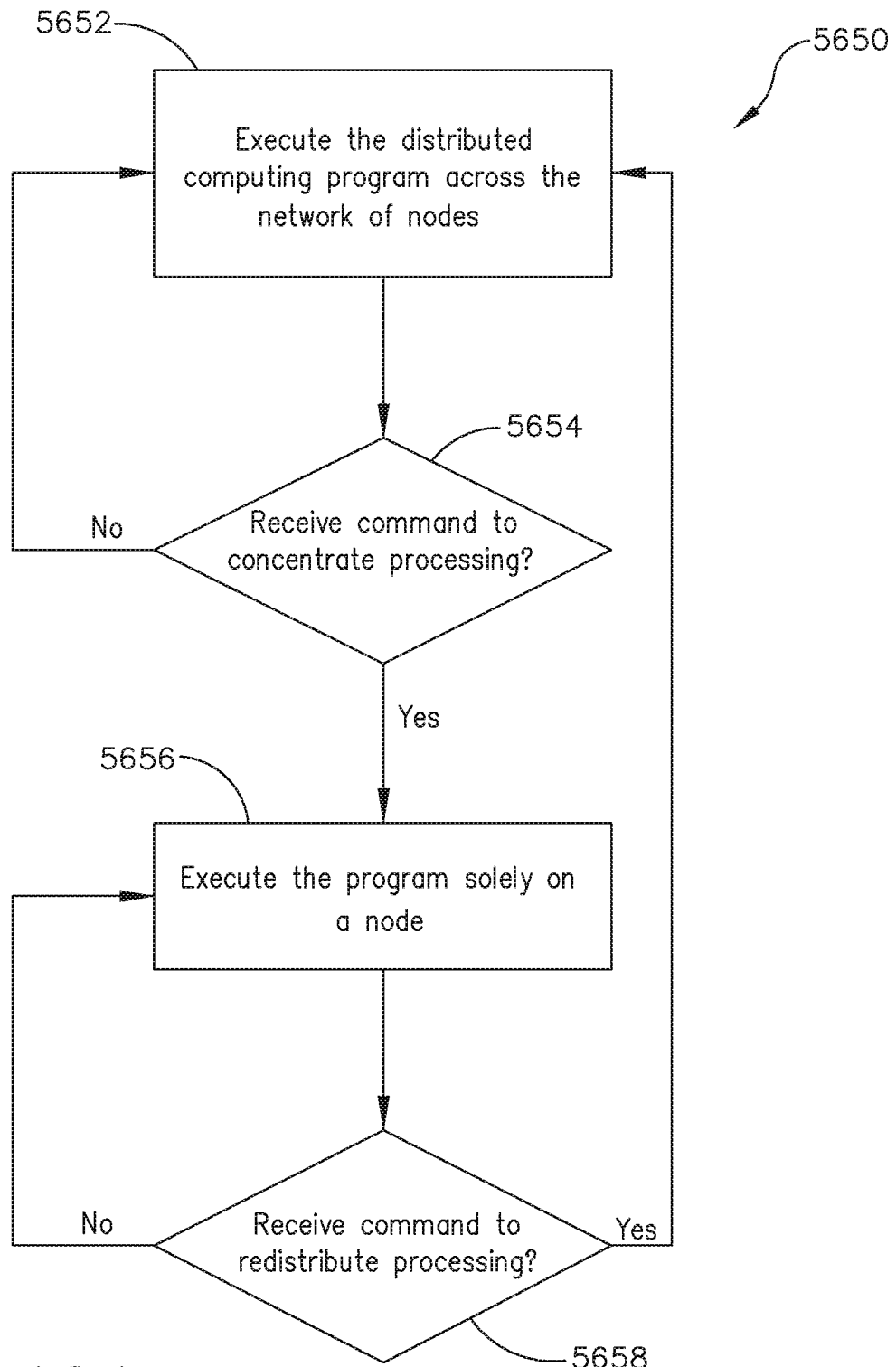

FIG. 104 illustrates a logic flow diagram of a process 5650 for shifting distributed computing resources. In the following description of the 5650, reference should also be made to FIG. 103. In one exemplification, the process 5650 can be executed by a distributed computing system including a control circuit of a surgical hub 206, as depicted in FIG. 10 (processor 244), in combination with a control circuit of a second surgical hub 206 and/or a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5650 will be described as being executed by the control circuits of one or more nodes; however, it should be understood that the description of the process 5650 encompasses all of the aforementioned exemplifications.

The control circuits of each node execute 5652 a distributed control program in synchrony. As the distributed control program is being executed across the network of nodes, at least one of the control circuits monitors for a command instructing the distributed computing system to shift from a first mode, wherein the distributed computing program is executed across the network of nodes, to a second mode, wherein the control program is executed by a single node. In one exemplification, the command can be transmitted by a surgical hub in response to the surgical hub's resources being needed for an alternative computing task. In another exemplification, the command can be transmitted by a modular device in response to the rate at which the data is sampled by the modular device outpacing the rate at which the sampled data can be communicated to the other nodes in the network. If a control circuit determines that an appropriate command has been received 5654, the process 5650 continues along the YES branch and the distributed computing system 5600 shifts to a single node executing 5656 the program. For example, the distributed computing system 5600 shifts the distributed computing program from being executed by both a modular device and a surgical hub to being executed solely by the modular device. As another example, the distributed computing system 5600 shifts the distributed computing program from being executed by both a first surgical hub and a second surgical hub to being executed solely by the first surgical hub. If no control circuit determines that an appropriate command has been received 5654, the process continues along the NO branch and the control circuits of the network of nodes continues executing 5652 the distributed computing program across the network of nodes.

In the event that the program has been shifted to being executed 5656 by a single node, the control circuit of the particular node solely executing the distributed program and/or a control circuit of another node within the network (which previously was executing the distributed program) monitors for a command instructing the node to re-distribute the processing of the program across the distributed computing system. In other words, the node monitors for a command to re-initiate the distributed computing system. In one exemplification, the command to re-distribute the processing across the network can be generated when the sampling rate of the sensor is less than the data communication rate between the modular device and the surgical hub. If a control circuit receives 5658 an appropriate command to re-distribute the processing, then the process 5650 proceeds along the YES branch and the program is once again executed 5652 across the node network. If a control circuit has not received 5658 an appropriate command, then the node continues singularly executing 5656 the program.

The process 5650 depicted in FIG. 104 eliminates data or communication bottlenecks in controlling modular devices by utilizing a distributed computing architecture that can shift computing resources either between the modular devices and surgical hubs or between the surgical hubs as needed. This process 5650 also improves the modular devices' data processing speed by allowing the processing of the modular devices' control adjustments to be executed at least in part by the modular devices themselves. This process 5650 also improves the surgical hubs' data processing speed by allowing the surgical hubs to shift computing resources between themselves as necessary.

It can be difficult during video-assisted surgical procedures, such as laparoscopic procedures, to accurately measure sizes or dimensions of features being viewed through a medical imaging device due to distortive effects caused by the device's lens. Being able to accurately measure sizes and dimensions during video-assisted procedures could assist a situational awareness system for a surgical hub by allowing the surgical hub to accurately identify organs and other structures during video-assisted surgical procedures. As one solution, a surgical hub could be configured to automatically calculate sizes or dimensions of structures (or distances between structures) during a surgical procedure by comparing the structures to markings affixed to devices that are intended to be placed within the FOV of the medical imaging device during a surgical procedure. The markings can represent a known scale, which can then be utilized to make measurements by comparing the unknown measured length to the known scale.

In one exemplification, the surgical hub is configured to receive image or video data from a medical imaging device paired with the surgical hub. When a surgical instrument bearing a calibration scale is within the FOV of the medical imaging device, the surgical hub is able to measure organs and other structures that are likewise within the medical imaging device's FOV by comparing the structures to the calibration scale. The calibration scale can be positioned on, for example, the distal end of a surgical instrument.

Figure 105:
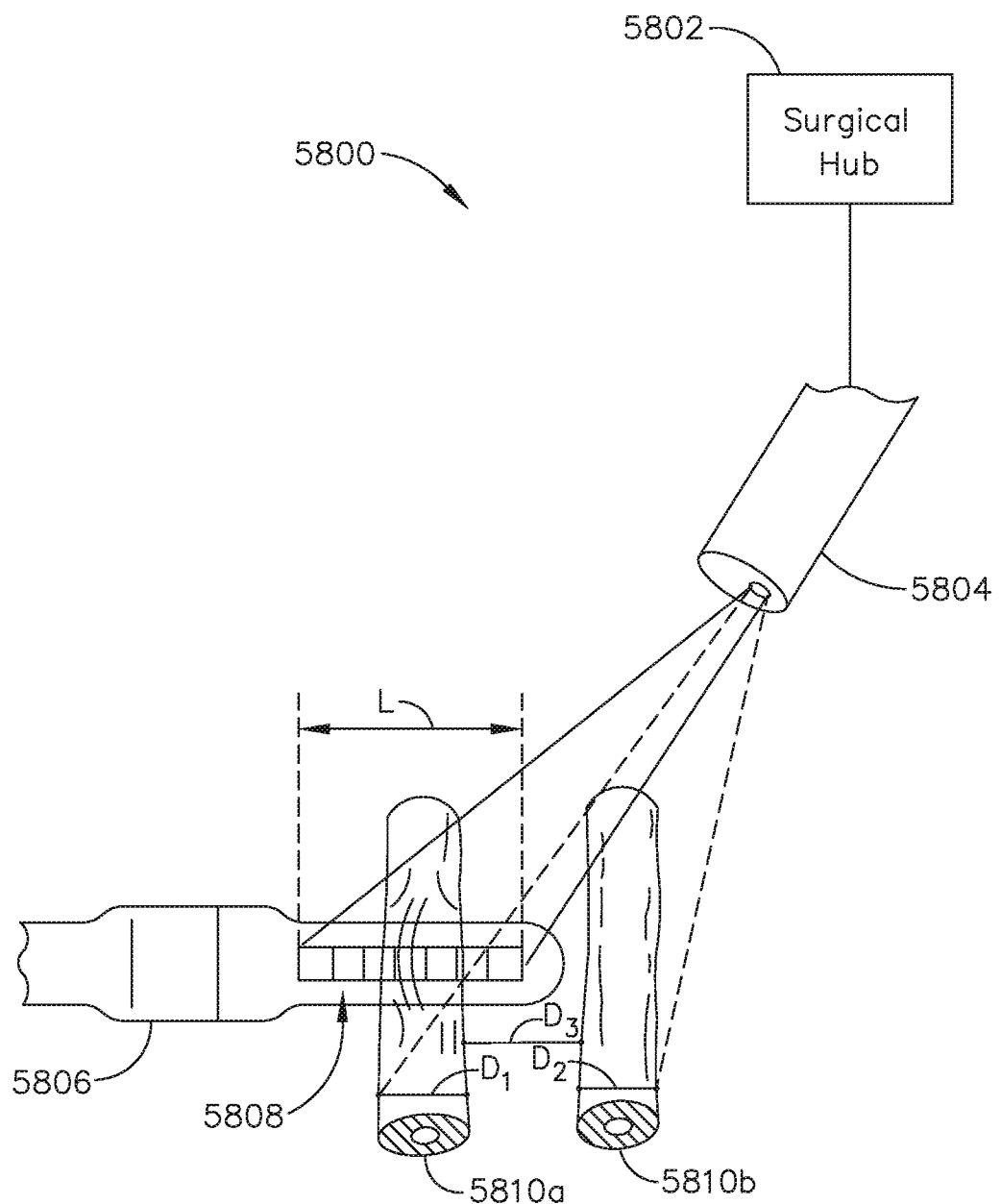

FIG. 105 illustrates a diagram of an imaging system 5800 and a surgical instrument 5806 bearing a calibration scale 5808. The imaging system 5800 includes a medical imaging device 5804 that is paired with a surgical hub 5802. The surgical hub 5802 can include a pattern recognition system or a machine learning system configured to recognize features in the FOV from image or video data received from the medical imaging device 5804. In one exemplification, a surgical instrument 5806 (e.g., a surgical cutting and stapling instrument) that is intended to enter the FOV of the medical imaging device 5804 during a surgical procedure includes a calibration scale 5808 affixed thereon. The calibration scale 5808 can be positioned on the exterior surface of the surgical instrument 5806, for example. In aspects wherein the surgical instrument 5806 is a surgical cutting and stapling instrument, the calibration scale 5808 can be positioned along the exterior surface of the anvil. The calibration scale 5808 can include a series of graphical markings separated at fixed and/or known intervals. The distance between the end or terminal markings of the calibration scale 5808 can likewise be a set distance L (e.g., 35 mm). In one exemplification, the end markings (e.g., the most proximal marking and the most distal marking) of the calibration scale 5808 are differentiated from the intermediate markings in size, shape, color, or another such fashion. This allows the image recognition system of the surgical hub 5802 to identify the end markings separately from the intermediate markings. The distance(s) between the markings can be stored in a memory or otherwise retrieved by the surgical hub 5802. The surgical hub 5802 can thus measure lengths or sizes of structures relative to the provided calibration scale 5808. In FIG. 105, for example, the surgical hub 5802 can calculate that the artery 5810a has a diameter or width of D1 (e.g., 17.0 mm), the vein 5810b has a diameter or width of D2 (e.g., 17.5 mm), and the distance between the vessels is D3 (e.g., 20 mm) by comparing the visualizations of these distances D1, D2, D3 to the known length L of the calibration scale 5808 positioned on the surgical instrument 5806 within the FOV of the medical imaging device 5804. The surgical hub 5802 can recognize the presence of the vessels 5810a, 5810b via an image recognition system. In some exemplifications, the surgical hub 5802 can be configured to automatically measure and display the size or dimension of detected features within the FOV of the medical imaging device 5804. In some exemplifications, the surgical hub 5802 can be configured to calculate the distance between various points selected by a user on an interactive display that is paired with the surgical hub 5802.

The imaging system 5800 configured to detect and measure sizes according to a calibration scale 5808 affixed to surgical instruments 5806 provides the ability to accurately measure sizes and distances during video-assisted procedures. This can make it easier for surgeons to precisely perform video-assisted procedures by compensating for the optically distortive effects inherent in such procedures.

User Feedback Methods

The present disclosure provides user feedback techniques. In one aspect, the present disclosure provides a display of images through a medical imaging device (e.g., laparoscope, endoscope, thoracoscope, and the like). A medical imaging device comprises an optical component and an image sensor. The optical component may comprise a lens and a light source, for example. The image sensor may be implemented as a charge coupled device (CCD) or complementary oxide semiconductor (CMOS). The image sensor provides image data to electronic components in the surgical hub. The data representing the images may be transmitted by wired or wireless communication to display instrument status, feedback data, imaging data, and highlight tissue irregularities and underlining structures. In another aspect, the present disclosure provides wired or wireless communication techniques for communicating user feedback from a device (e.g., instrument, robot, or tool) to the surgical hub. In another aspect, the present disclosure provides identification and usage recording and enabling. Finally, in another aspect, the surgical hub may have a direct interface control between the device and the surgical hub.

Through Laparoscope Monitor Display of Data

In various aspects, the present disclosure provides through laparoscope monitor display of data. The through laparoscope monitor display of data may comprise displaying a current instrument alignment to adjacent previous operations, cooperation between local instrument displays and paired laparoscope display, and display of instrument specific data needed for efficient use of an end-effector portion of a surgical instrument. Each of these techniques is described hereinbelow.

Display of Current Instrument Alignment to Adjacent Previous Operations

In one aspect, the present disclosure provides alignment guidance display elements that—provide the user information about the location of a previous firing or actuation and allow them to align the next instrument use to the proper position without the need for seeing the instrument directly. In another aspect, the first device and second device and are separate; the first device is within the sterile field and the second is used from outside the sterile field.

During a colorectal transection using a double-stapling technique it is difficult to align the location of an anvil trocar of a circular stapler with the center of an overlapping staple line. During the procedure, the anvil trocar of the circular stapler is inserted in the rectum below the staple line and a laparoscope is inserted in the peritoneal cavity above the staple line. Because the staple line seals off the colon, there is no light of sight to align the anvil trocar using the laparoscope to optically align the anvil trocar insertion location relative to the center of the staple line overlap.

One solution provides a non-contact sensor located on the anvil trocar of the circular stapler and a target located at the distal end of the laparoscope. Another solution provides a non-contact sensor located at the distal end of the laparoscope and a target located on the anvil trocar of the circular stapler.

A surgical hub computer processor receives signals from the non-contact sensor and displays a centering tool on a screen indicating the alignment of the anvil trocar of the circular stapler and the overlap portion at the center of staple line. The screen displays a first image of the target staple line with a radius around the staple line overlap portion and a second image of the projected anvil trocar location. The anvil trocar and the overlap portion at the center of staple line are aligned when the first and second images overlap.

In one aspect, the present disclosure provides a surgical hub for aligning a surgical instrument. The surgical hub comprises a processor and a memory coupled to the processor. The memory stores instructions executable by the processor to receive image data from an image sensor, generate a first image based on the image data, display the first image on a monitor coupled to the processor, receive a signal from a non-contact sensor, generate a second image based on the position of the surgical device, and display the second image on the monitor. The first image data represents a center of a staple line seal. The first image represents a target corresponding to the center of the staple line. The signal is indicative of a position of a surgical device relative to the center of the staple line. The second image represents the position of the surgical device along a projected path of the surgical device toward the center of the staple line.

In one aspect, the center of the staple line is a double-staple overlap portion zone. In another aspect, the image sensor receives an image from a laparoscope. In another aspect, the surgical device is a circular stapler comprising an anvil trocar and the non-contact sensor is configured to detect the location of the anvil trocar relative to the center of the staple line seal. In another aspect, the non-contact sensor is an inductive sensor. In another aspect, the non-contact sensor is a capacitive sensor.

In various aspects, the present disclosure provides a control circuit to align the surgical instrument as described above. In various aspects, the present disclosure provides a non-transitory computer readable medium storing computer readable instructions which, when executed, causes a machine to align the surgical instrument as described above.

This technique provides better alignment of a surgical instrument such as a circular stapler about the overlap portion of the staple line to produce a better seal and cut after the circular stapler is fired.

In one aspect, the present disclosure provides a system for displaying the current instrument alignment relative to prior adjacent operations. The instrument alignment information may be displayed on a monitor or any suitable electronic device suitable for the visual presentation of data whether located locally on the instrument or remotely from the instrument through the modular communication hub. The system may display the current alignment of a circular staple cartridge to an overlapping staple line, display the current alignment of a circular staple cartridge relative to a prior linear staple line, and/or show the existing staple line of the linear transection and an alignment circle indicating an appropriately centered circular staple cartridge. Each of these techniques is described hereinbelow.

In one aspect, the present disclosure provides alignment guidance display elements that provide the user information about the location of a previous firing or actuation of a surgical instrument (e.g., surgical stapler) and allows the user to align the next instrument use (e.g., firing or actuation of the surgical stapler) to the proper position without the need for seeing the instrument directly. In another aspect, the present disclosure provides a first device and a second device that is separate from the first device. The first device is located within a sterile field and the second is located outside the sterile field. The techniques described herein may be applied to surgical staplers, ultrasonic instruments, electrosurgical instruments, combination ultrasonic/electrosurgical instruments, and/or combination surgical stapler/electrosurgical instruments.

Figure 106:
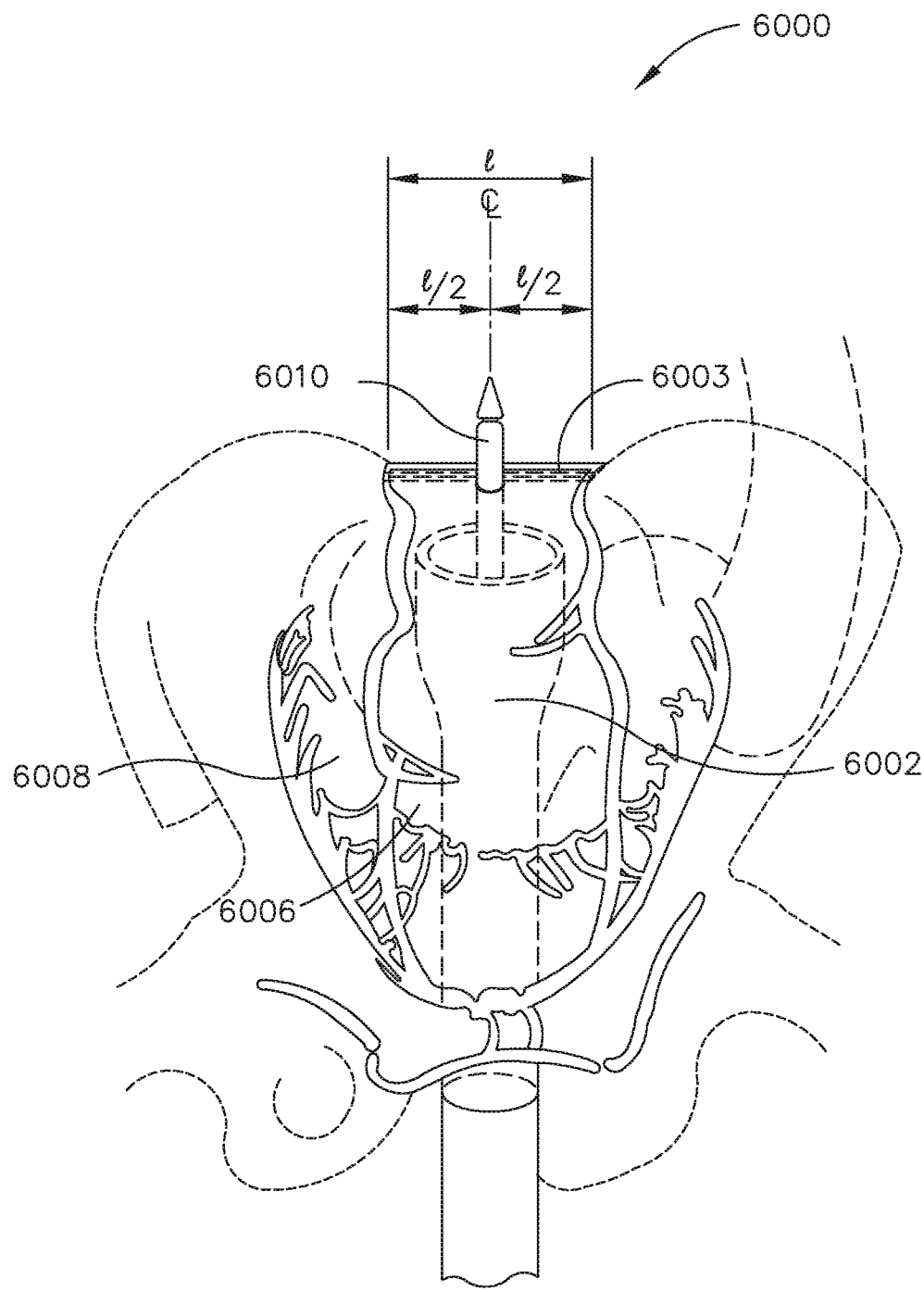

FIG. 106 illustrates a diagram 6000 of a surgical instrument 6002 centered on a staple line 6003 using the benefit of centering tools and techniques described in connection with FIGS. 23-33, according to one aspect of the present disclosure. As used in the following description of FIGS. 107-117 a staple line may include multiple rows of staggered staples and typically includes two or three rows of staggered staples, without limitation. The staple line may be a double staple line 6004 formed using a double-stapling technique as described in connection with FIGS. 107-111 or may be a linear staple line 6052 formed using a linear transection technique as described in connection with FIGS. 112-117. The centering tools and techniques described herein can be used to align the instrument 6002 located in one part of the anatomy with either the staple line 6003 or with another instrument located in another part of the anatomy without the benefit of a line of sight. The centering tools and techniques include displaying the current alignment of the instrument 6002 adjacent to previous operations. The centering tool is useful, for example, during laparoscopic-assisted rectal surgery that employ a double-stapling technique, also referred to as an overlapping stapling technique. In the illustrated example, during a laparoscopic-assisted rectal surgical procedure, a circular stapler 6002 is positioned in the rectum 6006 of a patient within the pelvic cavity 6008 and a laparoscope is positioned in the peritoneal cavity.

During the laparoscopic-assisted rectal surgery, the colon is transected and sealed by the staple line 6003 having a length "1." The double-stapling technique uses the circular stapler 6002 to create an end-to-end anastomosis and is currently used widely in laparoscopic-assisted rectal surgery. For a successful formation of an anastomosis using a circular stapler 6002, the anvil trocar 6010 of the circular stapler 6002 should be aligned with the center "½" of the Staple line 6003 transection before puncturing through the center "½" of the staple line 6003 and/or fully clamping on the tissue before firing the circular stapler 6002 to cut out the staple overlap portion 6012 and forming the anastomosis. Misalignment of the anvil trocar 6010 to the center of the staple line 6003 transection may result in a high rate of anastomotic failures. This technique may be applied to ultrasonic instruments, electrosurgical instruments, combination ultrasonic/electrosurgical instruments, and/or combination surgical stapler/electrosurgical instruments. Several techniques are now described for aligning the anvil trocar 6010 of the circular stapler 6002 to the center "½" of the staple line 6003.

In one aspect, as described in FIGS. 107-109 and with reference also to FIGS. 1-11 to show interaction with an interactive surgical system 100 environment including a surgical hub 106, 206, the present disclosure provides an apparatus and method for detecting the overlapping portion of the double staple line 6004 in a laparoscopic-assisted rectal surgery colorectal transection using a double stapling technique. The overlapping portion of the double staple line 6004 is detected and the current location of the anvil trocar 6010 of the circular stapler 6002 is displayed on a surgical hub display 215 coupled to the surgical hub 206. The surgical hub display 215 displays the alignment of a circular stapler 6002 cartridge relative to the overlapping portion of the double staple line 6004, which is located at the center of the double staple line 6004. The surgical hub display 215 displays a circular image centered around the overlapping double staple line 6004 region to ensure that the overlapping portion of the double staple line 6004 is contained within the knife of the circular stapler 6002 and therefore removed following the circular firing. Using the display, the surgeon aligns the anvil trocar 6010 with the center of the double staple line 6004 before puncturing through the center of the double staple line 6004 and/or fully clamping on the tissue before firing the circular stapler 6002 to cut out the staple overlap portion 6012 and form the anastomosis.

FIGS. 107-109 illustrate a process of aligning an anvil trocar 6010 of a circular stapler 6022 to a staple overlap portion 6012 of a double staple line 6004 created by a double-stapling technique, according to one aspect of the present disclosure. The staple overlap portion 6012 is centered on the double staple line 6004 formed by a double-stapling technique. The circular stapler 6002 is inserted into the colon 6020 below the double staple line 6004 and a laparoscope 6014 is inserted through the abdomen above the double staple line 6004. A laparoscope 6014 and a non-contact sensor 6022 are used to determine an anvil trocar 6010 location relative to the staple overlap portion 6012 of the double staple line 6004. The laparoscope 6014 includes an image sensor to generate an image of the double staple line 6004. The image sensor image is transmitted to the surgical hub 206 via the imaging module 238. The sensor 6022 generates a signal 6024 that detects the metal staples using inductive or capacitive metal sensing technology. The signal 6024 varies based on the position of the anvil trocar 6010 relative to the staple overlap portion 6004. A centering tool 6030 presents an image 6038 of the double staple line 6004 and a target alignment ring 6032 circumscribing the image 6038 of the double staple line 6004 centered about an image 6040 of the staple overlap portion 6012 on the surgical hub display 215. The centering tool 6030 also presents a projected cut path 6034 of an anvil knife of the circular stapler 6002. The alignment process includes displaying an image 6038 of the double staple line 6004 and a target alignment ring 6032 circumscribing the image 6038 of the double staple line 6004 centered on the image 6040 of the staple overlap portion 6012 to be cut out by the circular knife of the circular stapler 6002. Also displayed is an image of a crosshair 6036 (X) relative to the image 6040 of the staple overlap portion 6012.

FIG. 107 illustrates an anvil trocar 6010 of a circular stapler 6002 that is not aligned with a staple overlap portion 6012 of a double staple line 6004 created by a double-stapling technique. The double staple line 6004 has a length "1" and the staple overlap portion 6012 is located midway along the double staple line 6004 at "½." as Shown in FIG. 107, the Circular stapler 6002 is inserted into a section of the colon 6020 and is positioned just below the double staple line 6004 transection. A laparoscope 6014 is positioned above the double staple line 6004 transection and feeds an image of the double staple line 6004 and staple overlap portion 6012 within the field of view 6016 of the laparoscope 6014 to the surgical hub display 215. The position of the anvil trocar 6010 relative to the staple overlap portion 6012 is detected by a sensor 6022 located on the circular stapler 6002. The sensor 6022 also provides the position of the anvil trocar 6010 relative to the staple overlap portion 6012 to the surgical hub display 215.

As shown in In FIG. 107, the projected path 6018 of the anvil trocar 6010 is shown along a broken line to a position marked by an X. As shown in FIG. 107, the projected path 6018 of the anvil trocar 6010 is not aligned with the staple overlap portion 6012. Puncturing the anvil trocar 6010 through the double staple line 6004 at a point off the staple overlap portion 6012 could lead to an anastomotic failure. Using the anvil trocar 6010 centering tool 6030 described in FIG. 109, the surgeon can align the anvil trocar 6010 with the staple overlap portion 6012 using the images displayed by the centering tool 6030. For example, in one implementation, the sensor 6022 is an inductive sensor. Since the staple overlap portion 6012 contains more metal than the rest of the lateral portions of the double staple line 6004, the signal 6024 is maximum when the sensor 6022 is aligned with and proximate to the staple overlap portion 6012. The sensor 6022 provides a signal to the surgical hub 206 that indicates the location of the anvil trocar 6010 relative to the staple overlap portion 6012. The output signal is converted to a visualization of the location of the anvil trocar 6010 relative to the staple overlap portion 6012 that is displayed on the surgical hub display 215.

As shown in FIG. 108, the anvil trocar 6010 is aligned with the staple overlap portion 6012 at the center of the double staple line 6004 created by a double-stapling technique. The surgeon can now puncture the anvil trocar 6010 through the staple overlap portion 6012 of the double staple line 6004 and/or fully clamp on the tissue before firing the circular stapler 6002 to cut out the staple overlap portion 6012 and form an anastomosis.

FIG. 109 illustrates a centering tool 6030 displayed on a surgical hub display 215, the centering tool providing a display of a staple overlap portion 6012 of a double staple line 6004 created by a double-staling technique, where the anvil trocar 6010 is not aligned with the staple overlap portion 6012 of the double staple line 6004 as shown in FIG. 107. The centering tool 6030 presents an image 6038 on the surgical hub display 215 of the double staple line 6004 and an image 6040 of the staple overlap portion 6012 received from the laparoscope 6014. A target alignment ring 6032 centered about the image 6040 of the staple overlap portion 6012 circumscribes the image 6038 of the double staple line 6004 to ensure that the staple overlap portion 6012 is located within the circumference of the projected cut path 6034 of the circular stapler 6002 knife when the projected cut path 6034 is aligned to the target alignment ring 6032. The crosshair 6036 (X) represents the location of the anvil trocar 6010 relative to the staple overlap portion 6012. The crosshair 6036 (X) indicates the point through the double staple line 6004 where the anvil trocar 6010 would puncture if it were advanced from its current location.

As shown in FIG. 109, the anvil trocar 6010 is not aligned with the desired puncture through location designated by the image 6040 of the staple overlap portion 6012. To align the anvil trocar 6010 with the staple overlap portion 6012 the surgeon manipulates the circular stapler 6002 until the projected cut path 6034 overlaps the target alignment ring 6032 and the crosshair 6036 (X) is centered on the image 6040 of the staple overlap portion 6012. Once alignment is complete, the surgeon punctures the anvil trocar 6010 through the staple overlap portion 6012 of the double staple line 6004 and/or fully clamps on the tissue before firing the circular stapler 6002 to cut out the staple overlap portion 6012 and form the anastomosis.

As discussed above, the sensor 6022 is configured to detect the position of the anvil trocar 6010 relative to the staple overlap portion 6012. Accordingly, the location of the crosshair 6036 (X) presented on the surgical hub display 215 is determined by the surgical stapler sensor 6022. In another aspect, the sensor 6022 may be located on the laparoscope 6014, where the sensor 6022 is configured to detect the tip of the anvil trocar 6010. In other aspects, the sensor 6022 may be located either on the circular stapler 6022 or the laparoscope 6014, or both, to determine the location of the anvil trocar 6010 relative to the staple overlap portion 6012 and provide the information to the surgical hub display 215 via the surgical hub 206.

FIGS. 110 and 111 illustrate a before image 6042 and an after image 6043 of a centering tool 6030, according to one aspect of the present disclosure. FIG. 110 illustrates an image of a projected cut path 6034 of an anvil trocar 6010 and circular knife before alignment with the target alignment ring 6032 circumscribing the image 6038 of the double staple line 6004 over the image 6040 of the staple overlap portion 6040 presented on a surgical hub display 215. FIG. 111 illustrates an image of a projected cut path 6034 of an anvil trocar 6010 and circular knife after alignment with the target alignment ring 6032 circumscribing the image 6038 of the double staple line 6004 over the image 6040 of the staple overlap portion 6040 presented on a surgical hub display 215. The current location of the anvil trocar 6010 is marked by the crosshair 6036 (X), which as shown in FIG. 110, is positioned below and to the left of center of the image 6040 of the staple overlap portion 6040. As shown in FIG. 111, as the surgeon moves the anvil trocar 6010 of the along the projected path 6046, the projected cut path 6034 aligns with the target alignment ring 6032. The target alignment ring 6032 may be displayed as a greyed out alignment circle overlaid over the current position of the anvil trocar 6010 relative to the center of the double staple line 6004, for example. The image may include indication marks to assist the alignment process by indication which direction to move the anvil trocar 6010. The target alignment ring 6032 may be shown in bold, change color or may be highlighted when it is located within a predetermined distance of center within acceptable limits.

In another aspect, the sensor 6022 may be configured to detect the beginning and end of a linear staple line in a colorectal transection and to provide the position of the current location of the anvil trocar 6010 of the circular stapler 6002. In another aspect, the present disclosure provides a surgical hub display 215 to present the circular stapler 6002 centered on the linear staple line, which would create even dog ears, and to provide the current position of the anvil trocar 6010 to allow the surgeon to center or align the anvil trocar 6010 as desired before puncturing and/or fully clamping on tissue prior to firing the circular stapler 6002.

In another aspect, as described in FIGS. 112-114 and with reference also to FIGS. 1-11 to show interaction with an interactive surgical system 100 environment including a surgical hub 106, 206, in a laparoscopic-assisted rectal surgery colorectal transection using a linear stapling technique, the beginning and end of the linear staple line 6052 is detected and the current location of the anvil trocar 6010 of the circular stapler 6002 is displayed on a surgical hub display 215 coupled to the surgical hub 206. The surgical hub display 215 displays a circular image centered on the double staple line 6004, which would create even dog ears and the current position of the anvil trocar 6002 is displayed to allow the surgeon to center or align the anvil trocar 6010 before puncturing through the linear staple line 6052 and/or fully clamping on the tissue before firing the circular stapler 6002 to cut out the center 6050 of the linear staple line 6052 to form an anastomosis.

FIGS. 112-114 illustrate a process of aligning an anvil trocar 6010 of a circular stapler 6022 to a center 6050 of a linear staple line 6052 created by a linear stapling technique, according to one aspect of the present disclosure. FIGS. 112 and 113 illustrate a laparoscope 6014 and a sensor 6022 located on the circular stapler 6022 to determine the location of the anvil trocar 6010 relative to the center 6050 of the linear staple line 6052. The anvil trocar 6010 and the sensor 6022 is inserted into the colon 6020 below the linear staple line 6052 and the laparoscope 6014 is inserted through the abdomen above the linear staple line 6052.

FIG. 112 illustrates the anvil trocar 6010 out of alignment with the center 6050 of the linear staple line 6052 and FIG. 113 illustrates the anvil trocar 6010 in alignment with the center 6050 of the linear staple line 6052. The sensor 6022 is used to detect the center 6050 of the linear staple line 6052 to align the anvil trocar 6010 with the center of the staple line 6052. In one aspect, the center 6050 of the linear staple line 6052 may be located by moving the circular stapler 6002 until one end of the linear staple line 6052 is detected. An end may be detected when there are no more staples in the path of the sensor 6022. Once one of the ends is reached, the circular stapler 6002 is moved along the linear staple line 6053 until the opposite end is detected and the length "1" of the linear staple line 6052 is determined by measurement or by counting individual staples by the sensor 6022. Once the length of the linear staple line 6052 is determined, the center 6050 of the linear staple line 6052 can be determined by dividing the length by two "½."

FIG. 114 illustrates a centering tool 6054 displayed on a surgical hub display 215, the centering tool providing a display of a linear staple line 6052, where the anvil trocar 6010 is not aligned with the staple overlap portion 6012 of the double staple line 6004 as shown in FIG. 112. The surgical hub display 215 presents a standard reticle field of view 6056 of the laparoscopic field of view 6016 of the linear staple line 6052 and a portion of the colon 6020. The surgical hub display 215 also presents a target ring 6062 circumscribing the image center of the linear staple line and a projected cut path 6064 of the anvil trocar and circular knife. The crosshair 6066 (X) represents the location of the anvil trocar 6010 relative to the center 6050 of the linear staple line 6052. The crosshair 6036 (X) indicates the point through the linear staple line 6052 where the anvil trocar 6010 would puncture if it were advanced from its current location.

As shown in FIG. 114, the anvil trocar 6010 is not aligned with the desired puncture through location designated by the offset between the target ring 6062 and the projected cut path 6064. To align the anvil trocar 6010 with the center 6050 of the linear staple line 6052 the surgeon manipulates the circular stapler 6002 until the projected cut path 6064 overlaps the target alignment ring 6062 and the crosshair 6066 (X) is centered on the image 6040 of the staple overlap portion 6012. Once alignment is complete, the surgeon punctures the anvil trocar 6010 through the center 6050 of the linear staple line 6052 and/or fully clamps on the tissue before firing the circular stapler 6002 to cut out the staple overlap portion 6012 and forming the anastomosis.

In one aspect, the present disclosure provides an apparatus and method for displaying an image of an linear staple line 6052 using a linear transection technique and an alignment ring or bullseye positioned as if the anvil trocar 6010 of the circular stapler 6022 were centered appropriately along the linear staple line 6052. The apparatus displays a greyed out alignment ring overlaid over the current position of the anvil trocar 6010 relative to the center 6050 of the linear staple line 6052. The image may include indication marks to assist the alignment process by indication which direction to move the anvil trocar 6010. The alignment ring may be bold, change color or highlight when it is located within a predetermined distance of centered.

With reference now to FIGS. 112-115, FIG. 115 is an image 6080 of a standard reticle field view 6080 of a linear staple line 6052 transection of a surgical as viewed through a laparoscope 6014 displayed on the surgical hub display 215, according to one aspect of the present disclosure. In a standard reticle view 6080, it is difficult to see the linear staple line 6052 in the standard reticle field of view 6056. Further, there are no alignment aids to assist with alignment and introduction of the anvil trocar 6010 to the center 6050 of the linear staple line. This view does not show an alignment circle or alignment mark to indicate if the circular stapler is centered appropriately and does not show the projected trocar path. In this view it also difficult to see the staples because there is no contrast with the background image.

With reference now to FIGS. 112-116, FIG. 116 is an image 6082 of a laser-assisted reticle field of view 6072 of the surgical site shown in FIG. 115 before the anvil trocar 6010 and circular knife of the circular stapler 6002 are aligned to the center 6050 of the linear staple line 6052, according to one aspect of the present disclosure. The laser-assisted reticle field of view 6072 provides an alignment mark or crosshair 6066 (X), currently positioned below and to the left of center of the linear staple line 6052 showing the projected path of the anvil trocar 6010 to assist positioning of the anvil trocar 6010. In addition to the projected path marked by the crosshair 6066 (X) of the anvil trocar 6010, the image 6082 displays the staples of the linear staple line 6052 in a contrast color to make them more visible against the background. The linear staple line 6052 is highlighted and a bullseye target 6070 is displayed over the center 6050 of the linear staple line 6052. Outside of the laser-assisted reticle field of view 6072, the image 6082 displays a status warning box 6068, a suggestion box 6074, a target ring 6062, and the current alignment position of the anvil trocar 6010 marked by the crosshair 6066 (X) relative to the center 6050 of the linear staple line 6052. As shown in FIG. 116, the status warning box 6068 indicates that the trocar is "MISALIGNED" and the suggestion box 6074 states "Adjust trocar to center staple line."

With reference now to FIGS. 112-117, FIG. 117 is an image 6084 of a laser-assisted reticle field of view 6072 of the surgical site shown in FIG. 116 after the anvil trocar 6010 and circular knife of the circular stapler 6002 are aligned to the center 6050 of the linear staple line 6052, according to one aspect of the present disclosure. The laser-assisted reticle field of view 6072 provides an alignment mark or crosshair 6066 (X), currently positioned below and to the left of center of the linear staple line 6052 showing the projected path of the anvil trocar 6010 to assist positioning of the anvil trocar 6010. In addition to the projected path marked by the crosshair 6066 (X) of the anvil trocar 6010, the image 6082 displays the staples of the linear staple line 6052 in a contrast color to make them more visible against the background. The linear staple line 6052 is highlighted and a bullseye target 6070 is displayed over the center 6050 of the linear staple line 6052. Outside of the laser-assisted reticle field of view 6072, the image 6082 displays a status warning box 6068, a suggestion box 6074, a target ring 6062, and the current alignment position of the anvil trocar 6010 marked by the crosshair 6066 (X) relative to the center 6050 of the linear staple line 6052. As shown in FIG. 116, the status warning box 6068 indicates that the trocar is "MISALIGNED" and the suggestion box 6074 states "Adjust trocar to center staple line."

FIG. 117 is a laser assisted view of the surgical site shown in FIG. 116 after the anvil trocar 6010 and circular knife are aligned to the center of the staple line 6052. In this view, inside the field of view 6072 of the laser-assisted reticle, the alignment mark crosshair 6066 (X) is positioned over the center of the staple line 6052 and the highlighted bullseye target to indicate alignment of the trocar to the center of the staple line. Outside the field of view 6072 of the laser-assisted reticle, the status warning box indicates that the trocar is "ALIGNED" and the suggestion is "Proceed trocar introduction."

FIG. 118 illustrates a non-contact inductive sensor 6090 implementation of the non-contact sensor 6022 to determine an anvil trocar 6010 location relative to the center of a staple line transection (the staple overlap portion 6012 of the double staple line 6004 shown in FIGS. 107-108 or the center 6050 of the linear staple line 6052 shown in FIGS. 112-113, for example), according to one aspect of the present disclosure. The non-contact inductive sensor 6090 includes an oscillator 6092 that drives an inductive coil 6094 to generate an electromagnetic field 6096. As a metal target 6098, such as a metal staple, is introduced into the electromagnetic field 6096, eddy currents 6100 induced in the target 6098 oppose the electromagnetic field 6096 and the reluctance shifts and the amplitude of the oscillator voltage 6102 drops. An amplifier 6104 amplifies the oscillator voltage 6102 amplitude as it changes.

With reference now to FIGS. 1-11 to show interaction with an interactive surgical system 100 environment including a surgical hub 106, 206 and also to FIGS. 106-117, the inductive sensor 6090 is a non-contact electronic sensor. It can be used for positioning and detecting metal objects such as the metal staples in the staple lines 6003, 6004, 6052 described above. The sensing range of the inductive sensor 6090 is dependent on the type of metal being detected.

Because the inductive sensor 6090 is a non-contact sensor, it can detect metal objects across a stapled tissue barrier. The inductive sensor 6090 can be located either on the circular stapler 6002 to detect staples in the staple lines 6003, 6004, 6052, detect the location of the distal end of the laparoscope 6014, or it may be located on the laparoscope 6014 to detect the location of the anvil trocar 6010. A processor or control circuit located either in the circular stapler 6002, laparoscope 6014, or coupled to the surgical hub 206 receives signals from the inductive sensors 6090 and can be employed to display the centering tool on the surgical hub display 215 to determine the location of the anvil trocar 6010 relative to either staple overlap portion 6012 of a double staple line 6004 or the center 6050 of a linear staple line 6052.

In one aspect, the distal end of the laparoscope 6014 may be detected by the inductive sensor 6090 located on the circular stapler 6002. The inductive sensor 6090 may detect a metal target 6098 positioned on the distal end of the laparoscope 6014. Once the laparoscope 6014 is aligned with the center 6050 of the linear staple line 6052 or the staple overlap portion 6012 of the double staple line 6004, a signal from the inductive sensor 6090 is transmitted to circuits that convert the signals from the inductive sensor 6090 to present an image of the relative alignment of the laparoscope 6014 with the anvil trocar 6010 of the circular stapler 6002.

FIGS. 119A and 119B illustrate one aspect of a non-contact capacitive sensor 6110 implementation of the non-contact sensor 6022 to determine an anvil trocar 6010 location relative to the center of a staple line transection (the staple overlap portion 6012 of the double staple line 6004 shown in FIGS. 107-108 or the center 6050 of the linear staple line 6052 shown in FIGS. 112-113, for example), according to one aspect of the present disclosure. FIG. 119A shows the non-contact capacitive sensor 6110 without a nearby metal target and FIG. 119B shows the non-contact capacitive sensor 6110 near a metal target 6112. The non-contact capacitive sensor 6110 includes capacitor plates 6114, 6116 housed in a sensing head and establishes field lines 6118 when energized by an oscillator waveform to define a sensing zone. FIG. 119A shows the field lines 6118 when no target is present proximal to the capacitor plates 6114, 6116. FIG. 119B shows a ferrous or nonferrous metal target 6120 in the sensing zone. As the metal target 6120 enters the sensing zone, the capacitance increases causing the natural frequency to shift towards the oscillation frequency causing amplitude gain. Because the capacitive sensor 6110 is a non-contact sensor, it can detect metal objects across a stapled tissue barrier. The capacitive sensor 6110 can be located either on the circular stapler 6002 to detect the staple lines 6004, 6052 or the location of the distal end of the laparoscope 6014 or the capacitive sensor 6110 may be located on the laparoscope 6014 to detect the location of the anvil trocar 6010. A processor or control circuit located either in the circular stapler 6002, the laparoscope 6014, or coupled to the surgical hub 206 receives signals from the capacitive sensor 6110 to present an image of the relative alignment of the laparoscope 6014 with the anvil trocar 6010 of the circular stapler 6002.

FIG. 120 is a logic flow diagram 6130 of a process depicting a control program or a logic configuration for aligning a surgical instrument, according to one aspect of the present disclosure. With reference to FIGS. 1-11 to show interaction with an interactive surgical system 100 environment including a surgical hub 106, 206 and also to FIGS. 106-119, the surgical hub 206 comprises a processor 244 and a memory 249 coupled to the processor 244. The memory 249 stores instructions executable by the processor 244 to receive 6132 image data from a laparoscope image sensor, generate 6134 a first image based on the image data, display 6136 the first image on a surgical hub display 215 coupled to the processor 244, receive 6138 a signal from a non-contact sensor 6022, the signal indicative of a position of a surgical device, generate a second image based on the signal indicative of the position of the surgical device, e.g., the anvil trocar 6010 and display 6140 the second image on the surgical hub display 215. The first image data represents a center 6044, 6050 of a staple line 6004, 6052 seal. The first image represents a target corresponding to the center 6044, 6050 of the staple line 6004, 6052 seal. The signal is indicative of a position of a surgical device, e.g., an anvil trocar 6010, relative to the center 6044, 6050 of the staple line 6004, 6052 seal. The second image represents the position of the surgical device, e.g., an anvil trocar 6010, along a projected path 6018 of the surgical device, e.g., an anvil trocar 6010, toward the center 6044, 6050 of the staple line 6004, 6052 seal.

In one aspect, the center 6044 of the double staple line 6004 seal defines a staple overlap portion 6012. In another aspect, an image sensor receives an image from a medical imaging device. In another aspect, the surgical device is a circular stapler 6002 comprising an anvil trocar 6010 and the non-contact sensor 6022 is configured to detect the location of the anvil trocar 6010 relative to the center 6044 of the double staple line 6004 seal. In another aspect, the non-contact sensor 6022 is an inductive sensor 6090. In another aspect, the non-contact sensor 6022 is a capacitive sensor 6110. In one aspect, the staple line may be a linear staple line 6052 formed using a linear transection technique.

Cooperation Between Local Instrument Displays and Paired Imaging Device Display In one aspect, the present disclosure provides an instrument including a local display, a hub having an operating room (OR), or operating theater, display separate from the instrument display. When the instrument is linked to the surgical hub, the secondary display on the device reconfigures to display different information than when it is independent of the surgical hub connection. In another aspect, some portion of the information on the secondary display of the instrument is then displayed on the primary display of the surgical hub. In another aspect, image fusion allowing the overlay of the status of a device, the integration landmarks being used to interlock several images and at least one guidance feature are provided on the surgical hub and/or instrument display. Techniques for overlaying or augmenting images and/or text from multiple image/text sources to present composite images on a single display are described hereinbelow in connection with FIGS. 129-137 and FIGS. 147-151.

In another aspect, the present disclosure provides cooperation between local instrument displays and a paired laparoscope display. In one aspect, the behavior of a local display of an instrument changes when it senses the connectable presence of a global display coupled to the surgical hub. In another aspect, the present disclosure provides 360° composite top visual field of view of a surgical site to avoid collateral structures. Each of these techniques is described hereinbelow.

During a surgical procedure, the surgical site is displayed on a remote "primary" surgical hub display. During a surgical procedure, surgical devices track and record surgical data and variables (e.g., surgical parameters) that are stored in the instrument (see FIGS. 12-19 for instrument architectures comprising processors, memory, control circuits, storage, etc.). The surgical parameters include force-to-fire (FTF), force-to-close (FTC), firing progress, tissue gap, power level, impedance, tissue compression stability (creep), and the like. Using conventional techniques during the procedure the surgeon needs to watch two separate displays. Providing image/text overlay is thus advantageous because during the procedure the surgeon can watch a single display presenting the overlaid image/text information.

One solution detects when the surgical device (e.g., instrument) is connected to the surgical hub and then display a composite image on the primary display that includes a field of view of the surgical site received from a first instrument (e.g., medical imaging device such as, e.g., laparoscope, endoscope, thoracoscope, and the like) augmented by surgical data and variables received from a second instrument (e.g., a surgical stapler) to provide pertinent images and data on the primary display.

During a surgical procedure the surgical site is displayed as a narrow field of view of a medical imaging device on the primary surgical hub display. Items outside the current field of view, collateral structures, cannot be viewed without moving the medical imaging device.

One solution provides a narrow field of view of the surgical site in a first window of the display augmented by a wide field of view of the surgical site in a separate window of the display. This provides a composite over head field of view mapped using two or more imaging arrays to provide an augmented image of multiple perspective views of the surgical site.

In one aspect, the present disclosure provides a surgical hub, comprising a processor and a memory coupled to the processor. The memory stores instructions executable by the processor to detect a surgical device connection to the surgical hub, transmit a control signal to the detected surgical device to transmit to the surgical hub surgical parameter data associated with the detected device, receive the surgical parameter data, receive image data from an image sensor, and display, on a display coupled to the surgical hub, an image received from the image sensor in conjunction with the surgical parameter data received from the surgical device.

In another aspect, the present disclosure provides a surgical hub, comprising a processor and a memory coupled to the processor. The memory stores instructions executable by the processor to receive first image data from a first image sensor, receive second image data from a second image sensor, and display, on a display coupled to the surgical hub, a first image corresponding to the first field of view and a second image corresponding to the second field of view. The first image data represents a first field of view and the second image data represents a second field of view.

In one aspect, the first field of view is a narrow angle field of view and the second field of view is a wide angle field of view. In another aspect, the memory stores instructions executable by the processor to augment the first image with the second image on the display. In another aspect, the memory stores instructions executable by the processor to fuse the first image and the second image into a third image and display a fused image on the display. In another aspect, the fused image data comprises status information associated with a surgical device, an image data integration landmark to interlock a plurality of images, and at least one guidance parameter. In another aspect, the first image sensor is the same as the same image sensor and wherein the first image data is captured as a first time and the second image data is captured at a second time.

In another aspect, the memory stores instructions executable by the processor to receive third image data from a third image sensor, wherein the third image data represents a third field of view, generate composite image data comprising the second and third image data, display the first image in a first window of the display, wherein the first image corresponds to the first image data, and display a third image in a second window of the display, wherein the third image corresponds to the composite image data.

In another aspect, the memory stores instructions executable by the processor to receive third image data from a third image sensor, wherein the third image data represents a third field of view, fuse the second and third image data to generate fused image data, display the first image in a first window of the display, wherein the first image corresponds to the first image data, and display a third image in a second window of the display, wherein the third image corresponds to the fused image data.

In various aspects, the present disclosure provides a control circuit to perform the functions described above. In various aspects, the present disclosure provides a non-transitory computer readable medium storing computer readable instructions, which when executed, causes a machine to perform the functions described above.

By displaying endoscope images augmented with surgical device images on one primary surgical hub display, enables the surgeon to focus on one display to obtain a field of view of the surgical site augmented with surgical device data associated with the surgical procedure such as force-to-fire, force-to-close, firing progress, tissue gap, power level, impedance, tissue compression stability (creep), and the like.

Displaying a narrow field of view image in a first window of a display and a composite image of several other perspectives such as wider fields of view enables the surgeon to view a magnified image of the surgical site simultaneously with wider fields of view of the surgical site without moving the scope.

In one aspect, the present disclosure provides both global and local display of a device, e.g., a surgical instrument, coupled to the surgical hub. The device displays all of its relevant menus and displays on a local display until it senses a connection to the surgical hub at which point a sub-set of the information is displayed only on the monitor through the surgical hub and that information is either mirrored on the device display or is no longer accessible on the device detonated screen. This technique frees up the device display to show different information or display larger font information on the surgical hub display.

In one aspect, the present disclosure provides an instrument having a local display, a surgical hub having an operating theater (e.g., operating room or OR) display that is separate from the instrument display. When the instrument is linked to the surgical hub, the instrument local display becomes a secondary display and the instrument reconfigures to display different information than when it is operating independent of the surgical hub connection. In another aspect, some portion of the information on the secondary display is then displayed on the primary display in the operating theater through the surgical hub.

FIG. 121 illustrates a primary display 6200 of the surgical hub 206 comprising a global display 6202 and a local instrument display 6204, according to one aspect of the present disclosure. With continued reference to FIGS. 1-11 to show interaction with an interactive surgical system 100 environment including a surgical hub 106, 206 and FIGS. 12-21 for surgical hub connected instruments together with FIG. 121, the local instrument display 6204 behavior is displayed when the instrument 235 senses the connectable presence of a global display 6202 through the surgical hub 206. The global display 6202 shows a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 is shown in the field of view 6206 of the surgical site 6208 in the global display 6202. The images shown on the display 237 located on an instrument 235 coupled to the surgical hub 206 is shown, or mirrored, on the local instrument display 6204 located in the lower right corner of the monitor 6200 as shown in FIG. 121, for example. During operation, all relevant instrument and information and menus are displayed on the display 237 located on the instrument 235 until the instrument 235 senses a connection of the instrument 235 to the surgical hub 206 at which point all or some sub-set of the information presented on the instrument display 237 is displayed only on the local instrument display 6204 portion of the surgical hub display 6200 through the surgical hub 206. The information displayed on the local instrument display 6204 may be mirrored on the display 237 located on the instrument 235 or may be no longer accessible on the instrument display 237 detonated screen. This technique frees up the instrument 235 to show different information or to show larger font information on the surgical hub display 6200. Several techniques for overlaying or augmenting images and/or text from multiple image/text sources to present composite images on a single display are described hereinbelow in connection with FIGS. 129-137 and FIGS. 147-151.

The surgical hub display 6200 provides perioperative visualization of the surgical site 6208. Advanced imaging identifies and visually highlights 6222 critical structures such as the ureter 6220 (or nerves, etc.) and also tracks instrument proximity displays 6210 and shown on the left side of the display 6200. In the illustrated example, the instrument proximity displays 6210 show instrument specific settings. For example the top instrument proximity display 6212 shows settings for a monopolar instrument, the middle instrument proximity display 6214 shows settings for a bipolar instrument, and the bottom instrument proximity display 6212 shows settings for an ultrasonic instrument.

In another aspect, independent secondary displays or dedicated local displays can be linked to the surgical hub 206 to provide both an interaction portal via a touchscreen display and/or a secondary screen that can display any number of surgical hub 206 tracked data feeds to provide a clear non-confusing status. The secondary screen may display force to fire (FTF), tissue gap, power level, impedance, tissue compression stability (creep), etc., while the primary screen may display only key variables to keep the feed free of clutter. The interactive display may be used to move the display of specific information to the primary display to a desired location, size, color, etc. In the illustrated example, the secondary screen displays the instrument proximity displays 6210 on the left side of the display 6200 and the local instrument display 6204 on the bottom right side of the display 6200. The local instrument display 6204 presented on the surgical hub display 6200 displays an icon of the end effector 6218, such as the icon of a staple cartridge 6224 currently in use, the size 6226 of the staple cartridge 6224 (e.g., 60 mm), and an icon of the current position of the knife 6228 of the end effector.

In another aspect, the display 237 located on the instrument 235 displays the wireless or wired attachment of the instrument 235 to the surgical hub 206 and the instrument's communication/recording on the surgical hub 206. A setting may be provided on the instrument 235 to enable the user to select mirroring or extending the display to both monitoring devices. The instrument controls may be used to interact with the surgical hub display of the information being sourced on the instrument. As previously discussed, the instrument 235 may comprise wireless communication circuits to communicate wirelessly with the surgical hub 206.

In another aspect, a first instrument coupled to the surgical hub 206 can pair to a screen of a second instrument coupled to the surgical hub 206 allowing both instruments to display some hybrid combination of information from the two devices of both becoming mirrors of portions of the primary display. In yet another aspect, the primary display 6200 of the surgical hub 206 provides a 360° composite top visual view of the surgical site 6208 to avoid collateral structures. For example, a secondary display of the end-effector surgical stapler may be provided within the primary display 6200 of the surgical hub 206 or on another display in order to provide better perspective around the areas within a current the field of view 6206. These aspects are described hereinbelow in connection with FIGS. 122-124.

FIGS. 122-124 illustrate a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques for overlaying or augmenting images and/or text from multiple image/text sources to present composite images on a single display are described hereinbelow in connection with FIGS. 129-137 and FIGS. 147-151.

FIG. 122 illustrates a primary display 6200 of the surgical hub 206, according to one aspect of the present disclosure. A primary window 6230 is located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 displays knitted images to produce a composite image that enables visualization of structures adjacent to the surgical field of view 6232. A second window 6240 is shown in the lower left corner of the primary display 6200. The second window 6240 displays a knitted image in a wide angle view at standard focus of the image shown in the primary window 6230 in an overhead view. The overhead view provided in the second window 6240 enables the viewer to easily see items that are out of the narrow field surgical field of view 6232 without moving the laparoscope, or other imaging device 239 coupled to the imaging module 238 of the surgical hub 206. A third window 6242 is shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 6248 traversed by the knife along the length of the staple cartridge. Below the third window 6242 is displayed an icon 6258 of a frame of the current state of a clamp stabilization sequence 6250 (FIG. 123) that indicates clamp stabilization.

FIG. 123 illustrates a clamp stabilization sequence 6250 over a five second period, according to one aspect of the present disclosure. The clamp stabilization sequence 6250 is shown over a five second period with intermittent displays 6252, 6254, 6256, 6258, 6260 spaced apart at one second intervals 6268 in addition to providing the real time 6266 (e.g., 09:35:10), which may be a pseudo real time to preserve anonymity of the patient. The intermittent displays 6252, 6254, 6256, 6258, 6260 show elapsed by filling in the circle until the clamp stabilization period is complete. At that point, the last display 6260 is shown in solid color. Clamp stabilization after the end effector 6234 clamps the vessel 6236 enables the formation of a better seal.

FIG. 124 illustrates a diagram 6270 of four separate wide angle view images 6272, 6274, 6276, 6278 of a surgical site at four separate times during the procedure, according to one aspect of the present disclosure. The sequence of images shows the creation of an overhead composite image in wide and narrow focus over time. A first image 6272 is a wide angle view of the end-effector 6234 clamping the vessel 6236 taken at an earlier time $t_0$ (e.g., 09:35:09). A second image 6274 is another wide angle view of the end-effector 6234 clamping the vessel 6236 taken at the present time $t_1$ (e.g., 09:35:13). A third image 6276 is a composite image of an overhead view of the end-effector 6234 clamping the vessel 6236 taken at present time $t_1$. The third image 6276 is displayed in the second window 6240 of the primary display 6200 of the surgical hub 206 as shown in FIG. 122. A fourth image 6278 is a narrow angle view of the end-effector 6234 clamping the vessel 6236 at present time $t_1$ (e.g., 09:35:13). The fourth image 6278 is the narrow angle view of the surgical site shown in the primary window 6230 of the primary display 6200 of the surgical hub 206 as shown in FIG. 122.

Display of Instrument Specific Data Needed for Efficient Use of the End-Effector In one aspect, the present disclosure provides a surgical hub display of instrument specific data needed for efficient use of a surgical instrument, such as a surgical stapler. The techniques described herein may be applied to ultrasonic instruments, electrosurgical instruments, combination ultrasonic/electrosurgical instruments, and/or combination surgical stapler/electrosurgical instruments. In one aspect, a clamp time indicator based on tissue properties is shown on the display. In another aspect, a 360° composite top visual view is shown on the display to avoid collateral structures as shown and described in connection with FIGS. 121-124 is incorporated herein by reference and, for conciseness and clarity of disclosure, the description of FIGS. 121-124 will not be repeated here.

In one aspect, the present disclosure provides a display of tissue creep to provide the user with in-tissue compression/tissue stability data and to guide the user making an appropriate choice of when to conduct the next instrument action. In one aspect, an algorithm calculates a constant advancement of a progressive time based feedback system related to the viscoelastic response of tissue. These and other aspects are described hereinbelow.

FIG. 125 is a graph 6280 of tissue creep clamp stabilization curves 6282, 6284 for two tissue types, according to one aspect of the present disclosure. The clamp stabilization curves 6284, 6284 are plotted as force-to-close (FTC) as a function of time, where FTC (N) is displayed along the vertical axis and Time, t, (Sec) is displayed along the horizontal axis. The FTC is the amount of force exerted to close the clamp arm on the tissue. The first clamp stabilization curve 6282 represents stomach tissue and the second clamp stabilization curve 6284 represents lung tissue. In one aspect, the FTC along the vertical axis is scaled from 0-180 N. and the horizontal axis is scaled from 0-5 Sec. As shown, the FTC as a different profile over a five second clamp stabilization period (e.g., as shown in FIG. 123).

With reference to the first clamp stabilization curve 6282, as the stomach tissue is clamped by the end-effector 6234, the force-to-close (FTC) applied by the end-effector 6234 increases from 0 N to a peak force-to-close of ~180 N after ~1 Sec. While the end-effector 6234 remains clamped on the stomach tissue, the force-to-close decays and stabilizes to ~150 N over time due to tissue creep.

Similarly, with reference to the second clamp stabilization curve 6284, as the lung tissue is clamped by the end-effector 6234, the force-to-close applied by the end-effector 6234 increases from 0 N to a peak force-to-close of ~90 N after just less than ~1 Sec. While the end-effector 6234 remains clamped on the lung tissue, the force-to-close decays and stabilizes to ~60 N over time due to tissue creep.

The end-effector 6234 clamp stabilization is monitored as described above in connection with FIGS. 122-124 and is displayed every second corresponding the sampling times $t_1$, $t_2$, $t_3$, $t_4$, $t_5$ of the force-to-close to provide user feedback regarding the state of the clamped tissue. FIG. 125 shows an example of monitoring tissue stabilization for the lung tissue by sampling the force-to-close every second over a 5 seconds period. At each sample time $t_1$, $t_2$, $t_3$, $t_4$, $t_5$, the instrument 235 or the surgical hub 206 calculates a corresponding vector tangent 6288, 6292, 6294, 6298, 6302 to the second clamp stabilization curve 6284. The vector tangent 6288, 6292, 6294, 6298, 6302 is monitored until its slope drops below a threshold to indicate that the tissue creep is complete and the tissue is ready to sealed and cut. As shown in FIG. 125, the lung tissue is ready to be sealed and cut after ~5 Sec. clamp stabilization period, where a solid gray circle is shown at sample time 6300. As shown, the vector tangent 6302 is less than a predetermined threshold.

The equation of a vector tangent 6288, 6292, 6294, 6298, 6302 to the clamp stabilization curve 6284 may be calculated using differential calculus techniques, for example. In one aspect, at a given point on the clamp stabilization curve 6284, the gradient of the curve 6284 is equal to the gradient of the tangent to the curve 6284. The derivative (or gradient function) describes the gradient of the curve 6284 at any point on the curve 6284. Similarly, it also describes the gradient of a tangent to the curve 6284 at any point on the curve 6284. The normal to the curve 6284 is a line perpendicular to the tangent to the curve 6284 at any given point. To determine the equation of a tangent to a curve find the derivative using the rules of differentiation. Substitute the x coordinate (independent variable) of the given point into the derivative to calculate the gradient of the tangent. Substitute the gradient of the tangent and the coordinates of the given point into an appropriate form of the straight line equation. Make the y coordinate (dependent variable) the subject of the formula.

FIG. 126 is a graph 6310 of time dependent proportionate fill of a clamp force stabilization curve, according to one aspect of the present disclosure. The graph 6310 includes clamp stabilization curves 6312, 6314, 6316 for standard thick stomach tissue, thin stomach tissue, and standard lung tissue. The vertical axis represents FTC (N) scaled from 0-240 N and the horizontal axis represents Time, t, (Sec) scaled from 0-15 Sec. As shown, the standard thick stomach tissue curve 6316 is the default force decay stability curve. All three clamp stabilization curves 6312, 6314, 6316 FTC profiles reach a maximum force shortly after clamping on the tissue and then the FTC decreases over time until it eventually stabilizes due to the viscoelastic response of the tissue. As shown the standard lung tissue clamp stabilization curve 6312 stabilizes after a period of ~5 Sec., the thin stomach tissue clamp stabilization curve 6314 stabilizes after a period of ~10 Sec., and the thick stomach tissue clamp stabilization curve 6316 stabilizes after a period of ~15 Sec.

FIG. 127 is a graph 6320 of the role of tissue creep in the clamp force stabilization curve 6322, according to one aspect of the present disclosure. The vertical axis represents force-to-close FTC (N) and the horizontal axis represents Time, t, (Sec) in seconds. Vector tangent angles $d\theta_1$, $d\theta_2$ . . . $d\theta_n$ are measured at each force-to-close sampling ($t_0$, $t_1$, $t_2$, $t_3$, $t_4$, etc.) times. The vector tangent angle $d\theta_n$ is used to determine when the tissue has reached the creep termination threshold, which indicates that the tissue has reached creep stability.

FIGS. 128A and 128B illustrate two graphs 6330, 6340 for determining when the clamped tissue has reached creep stability, according to one aspect of the present disclosure. The graph 6330 in FIG. 128A illustrates a curve 6332 that represents a vector tangent angle $d\theta$ as a function of time. The vector tangent angle $d\theta$ is calculated as discussed in FIG. 127. The horizontal line 6334 is the tissue creep termination threshold. The tissue creep is deemed to be stable at the intersection 6336 of the vector tangent angle $d\theta$ curve 6332 and the tissue creep termination threshold 6334. The graph 6340 in FIG. 128B illustrates a AFTC curve 6342 that represents AFTC as a function of time. The AFTC curve 6342 illustrates the threshold 6344 to 100% complete tissue creep stability meter. The tissue creep is deemed to be stable at the intersection 6346 of the AFTC curve 6342 and the threshold 6344.

Communication Techniques

With reference to FIGS. 1-11 to show interaction with an interactive surgical system 100 environment including a surgical hub 106, 206, and in particular, FIGS. 9-10, in various aspects, the present disclosure provides communications techniques for exchanging information between an instrument 235, or other modules, and the surgical hub 206. In one aspect, the communications techniques include image fusion to place instrument status and analysis over a laparoscope image, such as a screen overlay of data, within and around the perimeter of an image presented on a surgical hub display 215, 217. In another aspect, the communication techniques include combining an intermediate short range wireless, e.g., Bluetooth, signal with the image, and in another aspect, the communication techniques include applying security and identification of requested pairing. In yet another aspect, the communication techniques include an independent interactive headset worn by a surgeon that links to the hub with audio and visual information that avoids the need for overlays, but allows customization of displayed information around periphery of view. Each of these communication techniques is discussed hereinbelow.

Screen Overlay of Data within and Around the Perimeter of the Displayed Image

In one aspect, the present disclosure provides image fusion allowing the overlay of the status of a device, the integration landmarks being used to interlock several images, and at least one guidance feature. In another aspect, the present disclosure provides a technique for screen overlay of data within and around the perimeter of displayed image. Radiographic integration may be employed for live internal sensing and pre-procedure overlay. Image fusion of one source may be superimposed over another. Image fusion may be employed to place instrument status and analysis on a medical imaging device (e.g., laparoscope, endoscope, thoracoscope, etc.) image. Image fusion allows the overlay of the status of a device or instrument, integration landmarks to interlock several images, and at least one guidance feature.

FIG. 129 illustrates an example of an augmented video image 6350 comprising a pre-operative video image 6352 augmented with data 6354, 6356, 6358 identifying displayed elements. An augmented reality vision system may be employed in surgical procedures to implement a method for augmenting data onto a pre-operative image 6352. The method includes generating a pre-operative image 6352 of an anatomical section of a patient and generating an augmented video image of a surgical site within the patient. The augmented video image 6350 includes an image of at least a portion of a surgical tool 6354 operated by a user 6456. The method further includes processing the pre-operative image 6352 to generate data about the anatomical section of the patient. The data includes a label 6358 for the anatomical section and a peripheral margin of at least a portion of the anatomical section. The peripheral margin is configured to guide a surgeon to a cutting location relative to the anatomical section, embedding the data and an identity of the user 6356 within the pre-operative image 6350 to display an augmented video image 6350 to the user about the anatomical section of the patient. The method further includes sensing a loading condition on the surgical tool 6354, generating a feedback signal based on the sensed loading condition, and updating, in real time, the data and a location of the identity of the user operating the surgical tool 6354 embedded within the augmented video image 6350 in response to a change in a location of the surgical tool 6354 within the augmented video image 6350. Further examples are disclosed in U.S. Pat. No. 9,123,155, titled APPARATUS AND METHOD FOR USING AUGMENTED REALITY VISION SYSTEM IN SURGICAL PROCEDURES, which issued on Sep. 1, 2015, which is herein incorporated by reference in its entirety.

In another aspect, radiographic integration techniques may be employed to overlay the pre-operative image 6352 with data obtained through live internal sensing or pre-procedure techniques. Radiographic integration may include marker and landmark identification using surgical landmarks, radiographic markers placed in or outside the patient, identification of radio-opaque staples, clips or other tissue-fixated items. Digital radiography techniques may be employed to generate digital images for overlaying with a pre-operative image 6352. Digital radiography is a form of X-ray imaging that employs a digital image capture device with digital X-ray sensors instead of traditional photographic film. Digital radiography techniques provide immediate image preview and availability for overlaying with the pre-operative image 6352. In addition, special image processing techniques can be applied to the digital X-ray mages to enhance the overall display quality of the image.

Digital radiography techniques employ image detectors that include flat panel detectors (FPDs), which are classified in two main categories indirect FPDs and direct FPDs. Indirect FPDs include amorphous silicon (a-Si) combined with a scintillator in the detector's outer layer, which is made from cesium iodide (CsI) or gadolinium oxy-sulfide (Gd2O2S), converts X-rays to light. The light is channeled through the a-Si photodiode layer where it is converted to a digital output signal. The digital signal is then read out by thin film transistors (TFTs) or fiber-coupled charge coupled devices (CCDs). Direct FPDs include amorphous selenium (a-Se) FPDs that convert X-ray photons directly into charge. The outer layer of a flat panel in this design is typically a high-voltage bias electrode. X-ray photons create electron-hole pairs in a-Se, and the transit of these electrons and holes depends on the potential of the bias voltage charge. As the holes are replaced with electrons, the resultant charge pattern in the selenium layer is read out by a TFT array, active matrix array, electrometer probes or micro plasma line addressing. Other direct digital detectors are based on CMOS and CCD technology. Phosphor detectors also may be employed to record the X-ray energy during exposure and is scanned by a laser diode to excite the stored energy which is released and read out by a digital image capture array of a CCD.

FIG. 130 is a logic flow diagram 6360 of a process depicting a control program or a logic configuration to display images, according to one aspect of the present disclosure. With reference also to FIGS. 1-11 to show interaction with an interactive surgical system 100 environment including a surgical hub 106, 206, the present disclosure provides, in one aspect, a surgical hub 206, comprising a processor 244 and a memory 249 coupled to the processor 244. The memory 249 stores instructions executable by the processor 244 to receive 6362 first image data from a first image sensor, receive 6364 second image data from a second image sensor, and display 6366, on a display 217 coupled to the surgical hub 206, a first image corresponding to the first field of view and a second image corresponding to the second field of view. The first image data represents a first field of view and the second image data represents a second field of view.

In one aspect, the first field of view is a narrow angle field of view and the second field of view is a wide angle field of view. In another aspect, the memory 249 stores instructions executable by the processor 244 to augment the first image with the second image on the display. In another aspect, the memory 249 stores instructions executable by the processor 244 to fuse the first image and the second image into a third image and display a fused image on the display 217. In another aspect, the fused image data comprises status information associated with a surgical device 235, an image data integration landmark to interlock a plurality of images, and at least one guidance parameter. In another aspect, the first image sensor is the same as the same image sensor and wherein the first image data is captured as a first time and the second image data is captured at a second time.

In another aspect, the memory 249 stores instructions executable by the processor 244 to receive third image data from a third image sensor, wherein the third image data represents a third field of view, generate composite image data comprising the second and third image data, display the first image in a first window of the display, wherein the first image corresponds to the first image data, and display a third image in a second window of the display 215, wherein the third image corresponds to the composite image data.

In another aspect, the memory 249 stores instructions executable by the processor 244 to receive third image data from a third image sensor, wherein the third image data represents a third field of view, fuse the second and third image data to generate fused image data, display the first image in a first window of the display 217, wherein the first image corresponds to the first image data, and display a third image in a second window of the display 217, wherein the third image corresponds to the fused image data.

Intermediate Short Range Wireless (e.g., Bluetooth) Signal Combiner

An intermediate short range wireless, e.g., Bluetooth, signal combiner may comprise a wireless heads-up display adapter placed into the communication path of the monitor to a laparoscope console allowing the surgical hub to overlay data onto the screen. Security and identification of requested pairing may augment the communication techniques.

FIG. 131 illustrates a communication system 6370 comprising an intermediate signal combiner 6372 positioned in the communication path between an imaging module 238 and a surgical hub display 217, according to one aspect of the present disclosure. The signal combiner 6372 receives image data from an imaging module 238 in the form of short range wireless or wired signals. The signal combiner 6372 also receives audio and image data form a headset 6374 and combines the image data from the imaging module 238 with the audio and image data from the headset 6374. The surgical hub 206 receives the combined data from the combiner 6372 and overlays the data provided to the display 217, where the overlaid data is displayed. The signal combiner 6372 may communicate with the surgical hub 206 via wired or wireless signals. The headset 6374 receives image data from an imaging device 6376 coupled to the headset 6374 and receives audio data from an audio device 6378 coupled to the headset 6374. The imaging device 6376 may be a digital video camera and the audio device 6378 may be a microphone. In one aspect, the signal combiner 6372 may be an intermediate short range wireless, e.g., Bluetooth, signal combiner. The signal combiner 6374 may comprise a wireless heads-up display adapter to couple to the headset 6374 placed into the communication path of the display 217 to a console allowing the surgical hub 206 to overlay data onto the screen of the display 217. Security and identification of requested pairing may augment the communication techniques. The imaging module 238 may be coupled to a variety if imaging devices such as an endoscope 239, laparoscope, etc., for example.

Independent Interactive Headset

FIG. 132 illustrates an independent interactive headset 6380 worn by a surgeon 6382 to communicate data to the surgical hub, according to one aspect of the present disclosure. Peripheral information of the independent interactive headset 6380 does not include active video. Rather, the peripheral information includes only device settings, or signals that do not have same demands of refresh rates. Interaction may augment the surgeon's 6382 information based on linkage with preoperative computerized tomography (CT) or other data linked in the surgical hub 206. The independent interactive headset 6380 can identify structure—ask whether instrument is touching a nerve, vessel, or adhesion, for example. The independent interactive headset 6380 may include pre-operative scan data, an optical view, tissue interrogation properties acquired throughout procedure, and/or processing in the surgical hub 206 used to provide an answer. The surgeon 6382 can dictate notes to the independent interactive headset 6380 to be saved with patient data in the hub storage 248 for later use in report or in follow up.

In one aspect, the independent interactive headset 6380 worn by the surgeon 6382 links to the surgical hub 206 with audio and visual information to avoid the need for overlays, and allows customization of displayed information around periphery of view. The independent interactive headset 6380 provides signals from devices (e.g., instruments), answers queries about device settings, or positional information linked with video to identify quadrant or position. The independent interactive headset 6380 has audio control and audio feedback from the headset 6380. The independent interactive headset 6380 is still able to interact with all other systems in the operating theater (e.g., operating room), and have feedback and interaction available wherever the surgeon 6382 is viewing.

Identification And Usage Recording

In one aspect, the present disclosure provides a display of the authenticity of reloads, modular components, or loading units. FIG. 133 illustrates a method 6390 for controlling the usage of a device 6392. A device 6392 is connected to an energy source 6394. The device 6392 includes a memory device 6396 that includes storage 6398 and communication 6400 devices. The storage 6398 includes data 6402 that may be locked data 6404 or unlocked data 6406. Additionally, the storage 6398 includes an error-detecting code 6408 such as a cyclic redundancy check (CRC) value and a sterilization indicator 6410. The energy source 6394 includes a reader 6412, display 6414, a processor 6416, and a data port 6418 that couples the energy source 6394 to a network 6420. The network 6420 is coupled to a central server 6422, which is coupled to a central database 6424. The network 6420 also is coupled to a reprocessing facility 6426. The reprocessing facility 6426 includes a reprocessing data reader/writer 6428 and a sterilizing device 6430.

The method comprises connecting the device to an energy source 6394. Data is read from a memory device 6396 incorporated in the device 6392. The data including one or more of a unique identifier (UID), a usage value, an activation value, a reprocessing value, or a sterilization indicator. The usage value is incremented when the device 6392 is connected to the energy source 6394. The activation value is incremented when the device 6392 is activated permitting energy to flow from the energy source 6394 to an energy consuming component of the device 6392. Usage of the device 6392 may be prevented if: the UID is on a list of prohibited UIDs, the usage value is not lower than a usage limitation value, the reprocessing value is equal to a reprocessing limitation value, the activation value is equal to an activation limitation value, and/or the sterilization indicator does not indicate that the device has been sterilized since its previous usage. Further examples are disclosed in U.S. Patent Application Publication No. 2015/0317899, titled SYSTEM AND METHOD FOR USING RFID TAGS TO DETERMINE STERILIZATION OF DEVICES, which published on Nov. 5, 2015, which is herein incorporated by reference in its entirety.

FIG. 134 provides a surgical system 6500 in accordance with the present disclosure and includes a surgical instrument 6502 that is in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 includes a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 includes an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 are configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more that one time prior to being replaced. The second jaw 6534 may include an anvil that deforms or otherwise secures the fasteners about tissue as the fasteners are ejected from the multi-fire fastener cartridge.

The handle 6504 includes a motor that is coupled to the drive shaft to affect rotation of the drive shaft. The handle 6504 includes a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 is in communication with a controller 6528 of the handle 6504 to selectively activate the motor to affect rotation of the drive shafts. The controller 6528 is disposed within the handle 6504 and is configured to receive input from the control interface and adapter data from the adapter 6508 or loading unit data from the loading unit 6514. The controller 6528 analyzes the input from the control interface and the data received from the adapter 6508 and/or loading unit 6514 to selectively activate the motor. The handle 6504 may also include a display that is viewable by a clinician during use of the handle 6504. The display is configured to display portions of the adapter or loading unit data before, during, or after firing of the instrument 6502.

The adapter 6508 includes an adapter identification device 6510 disposed therein and the loading unit 6514 includes a loading unit identification device 6516 disposed therein. The adapter identification device 6510 is in communication with the controller 6528, and the loading unit identification device 6516 is in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 provides an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 are configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 includes a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Multi-Functional Surgical Control System and Switching Interface for Verbal Control of Imaging Device FIG. 135 illustrates a verbal AESOP camera positioning system. Further examples are disclosed in U.S. Pat. No. 7,097,640, titled MULTI-FUNCTIONAL SURGICAL CONTROL SYSTEM AND SWITCHING INTERFACE, which issued on Aug. 29, 2006, which is herein incorporated by reference in its entirety. FIG. 135 shows a surgical system 6550 that may be coupled to surgical hub 206, described in connection with FIGS. 1-11. The system 6550 allows a surgeon to operate a number of different surgical devices 6552, 6554, 6556, and 6558 from a single input device 6560. Providing a single input device reduces the complexity of operating the various devices and improves the efficiency of a surgical procedure performed by a surgeon. The system 6550 may be adapted and configured to operate a positioning system for an imaging device such as a camera or endoscope using verbal commands.

The surgical device 6552 may be a robotic arm which can hold and move a surgical instrument. The arm 6552 may be a device such as that sold by Computer Motion, Inc. of Goleta, Calif. under the trademark AESOP, which is an acronym for Automated Endoscopic System for Optimal Positioning. The arm 6552 is commonly used to hold and move an endoscope within a patient. The system 6550 allows the surgeon to control the operation of the robotic arm 6552 through the input device 6560.

The surgical device 6554 may be an electrocautery device. Electrocautery devices typically have a bi-polar tip which carries a current that heats and denatures tissue. The device is typically coupled to an on-off switch to actuate the device and heat the tissue. The electrocautery device may also receive control signals to vary its power output. The system 6550 allows the surgeon to control the operation of the electrocautery device through the input device 6560.

The surgical device 6556 may be a laser. The laser 6556 may be actuated through an on-off switch. Additionally, the power of the laser 6556 may be controlled by control signals. The system 6550 allows the surgeon to control the operation of the laser 6556 through the input device 6560.

The device 6558 may be an operating table. The operating table 6558 may contain motors and mechanisms which adjust the position of the table. The present invention allows the surgeon to control the position of the table 6558 through the input device 6560. Although four surgical devices 6552, 6554, 6556, and 6558 are described, it is to be understood that other functions within the operating room may be controlled through the input device 6560. By way of example, the system 6560 may allow the surgeon to control the lighting and temperature of the operating room through the input device 6560.

The input device 6560 may be a foot pedal which has a plurality of buttons 6562, 6564, 6565, 6566, and 6568 that can be depressed by the surgeon. Each button is typically associated with a specific control command of a surgical device. For example, when the input device 6560 is controlling the robotic arm 6552, depressing the button 6562 may move the arm in one direction and depressing the button 6566 may move the arm in an opposite direction. Likewise, when the electrocautery device 6554 or the laser 6556 is coupled to the input device 6560, depressing the button 6568 may energize the devices, and so forth and so on. Although a foot pedal is shown and described, it is to be understood that the input device 6560 may be a hand controller, a speech interface which accepts voice commands from the surgeon, a cantilever pedal or other input devices which may be well known in the art of surgical device control. Using the speech interface, the surgeon is able to position a camera or endoscope connected to the robotic arm 6552 using verbal commands. The imaging device, such as a camera or endoscope, may be coupled to the robotic arm 6552 positioning system that be controlled through the system 6550 using verbal commands.

The system 6550 has a switching interface 6570 which couples the input device 6560 to the surgical devices 6552, 6554, 6556, and 6558. The interface 6570 has an input channel 6572 which is connected to the input device 6560 by a bus 6574. The interface 6570 also has a plurality of output channels 6576, 6578, 6580, and 6582 that are coupled to the surgical devices by busses 6584, 6586, 6588, 6590, 6624, 6626, 6628 and which may have adapters or controllers disposed in electrical communication therewith and therebetween. Such adapters and controllers will be discussed in more detail hereinbelow.

Because each device 6552, 6554, 6556, 6558 may require specifically configured control signals for proper operation, adapters 6620, 6622 or a controller 6618 may be placed intermediate and in electrical communication with a specific output channel and a specific surgical device. In the case of the robotic arm system 6552, no adapter is necessary and as such, the robotic arm system 6552 may be in direct connection with a specific output channel. The interface 6570 couples the input channel 6572 to one of the output channels 6576, 6578, 6580, and 6582.

The interface 6570 has a select channel 6592 which can switch the input channel 6572 to a different output channel 6576, 6578, 6580, or 6582 so that the input device 6560 can control any of the surgical devices. The interface 6570 may be a multiplexor circuit constructed as an integrated circuit and placed on an ASIC. Alternatively, the interface 6570 may be a plurality of solenoid actuated relays coupled to the select channel by a logic circuit. The interface 6570 switches to a specific output channel in response to an input signal or switching signal applied on the select channel 6592.

As depicted in FIG. 135, there may be several inputs to the select channel 6592. Such inputs originate from the foot pedal 6560, the speech interface 6600 and the CPU 6662. The interface 6570 may have a multiplexing unit such that only one switching signal may be received at the select channel 6592 at any one time, thus ensuring no substantial hardware conflicts. The prioritization of the input devices may be configured so the foot pedal has highest priority followed by the voice interface and the CPU. This is intended for example as the prioritization scheme may be employed to ensure the most efficient system. As such other prioritization schemes may be employed. The select channel 6592 may sequentially connect the input channel to one of the output channels each time a switching signal is provided to the select channel 6592. Alternatively, the select channel 6592 may be addressable so that the interface 6570 connects the input channel to a specific output channel when an address is provided to the select channel 6592. Such addressing is known in the art of electrical switches.

The select channel 6592 may be connected by line 6594 to a dedicated button 6596 on the foot pedal 6560. The surgeon can switch surgical devices by depressing the button 6596. Alternatively, the select channel 6592 may be coupled by line 6598 to a speech interface 6600 which allows the surgeon to switch surgical devices with voice commands.

The system 6550 may have a central processing unit (CPU) 6602 which receives input signals from the input device 6560 through the interface 6570 and a bus 6585. The CPU 6602 receives the input signals, and can ensure that no improper commands are being input at the controller. If this occurs, the CPU 6602 may respond accordingly, either by sending a different switching signal to select channel 6592, or by alerting the surgeon via a video monitor or speaker.

The CPU 6602 can also provide output commands for the select channel 6592 on the bus 6608 and receives input commands from the speech interface 6600 on the same bi-directional bus 6608. The CPU 6602 may be coupled to a monitor 6610 and/or a speaker 6612 by buses 6614 and 6616, respectively. The monitor 6610 may provide a visual indication of which surgical device is coupled to the input device 6560. The monitor may also provide a menu of commands which can be selected by the surgeon either through the speech interface 6600 or button 6596. Alternatively, the surgeon could switch to a surgical device by selecting a command through a graphic user interface. The monitor 6610 may also provide information regarding improper control signals sent to a specific surgical device 6552, 6554, 6556, 6558 and recognized by the CPU 6602. Each device 6552, 6554, 6556, 6558 has a specific appropriate operating range, which is well known to the skilled artisan. As such, the CPU 6602 may be programmed to recognize when the requested operation from the input device 6560 is inappropriate and will then alert the surgeon either visually via the monitor 6610 or audibly via the speaker 6612. The speaker 6612 may also provide an audio indication of which surgical device is coupled to the input device 6560.

The system 6550 may include a controller 6618 which receives the input signals from the input device 6560 and provides corresponding output signals to control the operating table 6558. Likewise, the system may have adapters 6620, 6622 which provide an interface between the input device 6560 and the specific surgical instruments connected to the system.

In operation, the interface 6570 initially couples the input device 6560 to one of the surgical devices. The surgeon can control a different surgical device by generating an input command that is provided to the select channel 6592. The input command switches the interface 6570 so that the input device 6560 is coupled to a different output channel and corresponding surgical device or adapter. What is thus provided is an interface 6570 that allows a surgeon to select, operate and control a plurality of different surgical devices through a common input device 6560.

FIG. 136 illustrates a multi-functional surgical control system 6650 and switching interface for virtual operating room integration. A virtual control system for controlling surgical equipment in an operating room while a surgeon performs a surgical procedure on a patient, comprising: a virtual control device including an image of a control device located on a surface and a sensor for interrogating contact interaction of an object with the image on the surface, the virtual control device delivering an interaction signal indicative of the contact interaction of the object with the image; and a system controller connected to receive the interaction signal from the virtual control device and to deliver a control signal to the surgical equipment in response to the interaction signal to control the surgical equipment in response to the contact interaction of the object with the image. Further examples are disclosed in U.S. Pat. No. 7,317,955, titled VIRTUAL OPERATING ROOM INTEGRATION, which issued on Jan. 8, 2008, which is herein incorporated by reference in its entirety.

As shown in FIG. 136, communication links 6674 are established between the system controller 6676 and the various components and functions of the virtual control system 6650. The communication links 6674 are preferably optical paths, but the communication links may also be formed by radio frequency transmission and reception paths, hardwired electrical connections, or combinations of optical, radio frequency and hardwired connection paths as may be appropriate for the type of components and functions obtained by those components. The arrows at the ends of the links 6674 represent the direction of primary information flow.

The communication links 6674 with the surgical equipment 6652, a virtual control panel 6556, a virtual foot switch 6654 and patient monitoring equipment 6660 are bidirectional, meaning that the information flows in both directions through the links 6674 connecting those components and functions. For example, the system controller 6676 supplies signals which are used to create a control panel image from the virtual control panel 6656 and a foot switch image from the virtual foot switch 6654. The virtual control panel 6656 and the virtual foot switch 6654 supply information to the system controller 6676 describing the physical interaction of the surgeon's finger and foot relative to a projected control panel image and the projected foot switch image. The system controller 6676 responds to the information describing the physical interaction with the projected image, and supplies control signals to the surgical equipment 6652 and patient monitoring equipment 6660 to control functionality of those components in response to the physical interaction information. The control, status and functionality information describing the surgical equipment 6652 and patient monitoring equipment 6660 flows to the system controller 6676, and after that information is interpreted by the system controller 6676, it is delivered to a system display 6670, a monitor 6666, and/or a heads up display 6668 for presentation.

The communication links 6674 between the system controller 6676 and the system display 6670, the heads up display 6668, the monitor 6666, a tag printer 6658 and output devices 6664 are all uni-directional, meaning that the information flows from the system controller 6676 to those components and functions. In a similar manner, the communication links 6674 between the system controller 6676 and a scanner 6672 and the input devices 6662 are also unidirectional, but the information flows from the components 6662, 6672 to the system controller 6676. In certain circumstances, certain control and status information may flow between the system controller 6676 and the components 6658, 6660, 6662, 6664, 6666, 6668, 6670, 6672 in order to control the functionality of the those components.

Each communication link 6674 preferably has a unique identity so that the system controller 6676 can individually communicate with each of the components of the virtual control system 6650. The unique identity of each communication link is preferable when some or all of the communication links 6674 are through the same medium, as would be the case of optical and radio frequency communications. The unique identity of each communication link 6674 assures that the system controller 6676 has the ability to exercise individual control over each of the components and functions on a very rapid and almost simultaneous manner. The unique identity of each communication link 6674 can be achieved by using different frequencies for each communication link 6674 or by using unique address and identification codes associated with the communications transferred over each communication link 6674.

In one aspect, the present disclosure provides illustrates a surgical communication and control headset that interfaces with the surgical hub 206 described in connection with FIGS. 1-11. Further examples are disclosed in U.S. Patent Application Publication No. 2009/0046146, titled SURGICAL COMMUNICATION AND CONTROL SYSTEM, which published on Feb. 19, 2009, which is herein incorporated by reference in its entirety. FIG. 137 illustrates a diagram 6680 of a beam source and combined beam detector system utilized as a device control mechanism in an operating theater. The system 6680 is configured and wired to allow for device control with the overlay generated on the primary procedural display. The footswitch shows a method to allow the user to click on command icons that would appear on the screen while the beam source is used to aim at the particular desired command icon to be clicked. The control system graphic user interface (GUI) and device control processor communicate and parameters are changed using the system. The system 6680 includes a display 6684 coupled to a beam detecting sensor 6682 and a head mounted source 6686. The beam detecting sensor 6682 is in communication with a control system GUI overlay processor and beam source processor 6688. The surgeon operates a footswitch 6692 or other adjunctive switch, which provides a signal to a device control interface unit 6694.

The system 6680 will provide a means for a sterile clinician to control procedural devices in an easy and quick, yet hands free and centralized fashion. The ability to maximize the efficiency of the operation and minimize the time a patient is under anesthesia is important to the best patient outcomes. It is common for surgeons, cardiologists or radiologists to verbally request adjustments be made to certain medical devices and electronic equipment used in the procedure outside the sterile field. It is typical that he or she must rely on another staff member to make the adjustments he or she needs to settings on devices such as cameras, bovies, surgical beds, shavers, insufflators, injectors, to name a few. In many circumstances, having to command a staff member to make a change to a setting can slow down a procedure because the non-sterile staff member is busy with another task. The sterile physician cannot adjust non-sterile equipment without compromising sterility, so he or she must often wait for the non-sterile staff member to make the requested adjustment to a certain device before resuming the procedure.

The system 6680 allows a user to use a beam source and beam detector to regenerate a pointer overlay coupled with a GUI and a concurrent switching method (i.e., a foot switch, etc.) to allow the clinician to click through commands on the primary display. In one aspect, a GUI could appear on the procedural video display when activated, such as when the user tilts his or her head twice to awaken it or steps on a foot switch provided with the system. Or it is possible that a right head tilt wakes up the system, and a left head tilt simply activates the beam source. When the overlay (called device control GUI overlay) appears on the screen it shows button icons representing various surgical devices and the user can use the beam source, in this case a laser beam, to aim at the button icons. Once the laser is over the proper button icon, a foot switch, or other simultaneous switch method can be activated, effectively acting like a mouse click on a computer. For example a user can "wake up" the system, causing a the device control GUI overlay to pop up that lists button icons on the screen, each one labeled as a corresponding procedural medical device. The user can point the laser at the correct box or device and click a foot pedal (or some other concurrent control—like voice control, waistband button, etc.) to make a selection, much like clicking a mouse on a computer. The sterile physician can then select "insufflator, for example" The subsequent screen shows arrow icons that can be clicked for various settings for the device that need to be adjusted (pressure, rate, etc.). In one iteration, the user can then can point the laser at the up arrow and click the foot pedal repeatedly until the desired setting is attained.

In one aspect, components of the system 6680 could be coupled with existing robotic endoscope holders to "steer" a rigid surgical endoscopic camera by sending movement commands to the robotic endoscope holding arm (provided separately, i.e., AESOP by Computer Motion). The endoscope is normally held by an assistant nurse or resident physician. There are robotic and mechanical scope holders currently on the market and some have even had been introduced with voice control. However, voice control systems have often proven cumbersome, slow and inaccurate. This aspect would employ a series of software and hardware components to allow the overlay to appear as a crosshair on the primary procedural video screen. The user could point the beam source at any part of the quadrant and click a simultaneous switch, such as a foot pedal, to send movement commands to the existing robotic arm, which, when coupled with the secondary trigger (i.e., a foot switch, waist band switch, etc.) would send a command to adjust the arm in minute increments in the direction of the beam source. It could be directed by holding down the secondary trigger until the desired camera angle and position is achieved and then released. This same concept could be employed for surgical bed adjustments by having the overlay resemble the controls of a surgical bed. The surgical bed is commonly adjusted during surgery to allow better access to the anatomy. Using the combination of the beam source, in this case a laser, a beam detecting sensor such as a camera, a control system GUI overlay processing unit and beam source processor, and a device control interface unit, virtually any medical device could be controlled through this system. Control codes would be programmed into the device control interface unit, and most devices can be connected using an RS-232 interface, which is a standard for serial binary data signals connecting between a DTE (Data Terminal Equipment) and a DCE (Data Circuit-terminating Equipment). The present invention while described with reference to application in the medical field can be expanded/modified for use in other fields. Another use of this invention could be in helping those who are without use of their hands due to injury or handicap or for professions where the hands are occupied and hands free interface is desired.

Surgical Hub with Direct Interface Control with Secondary Surgeon Display Units Designed to be within the Sterile Field and Accessible for Input and Display by the Surgeon In one aspect, the surgical hub 206 provides a secondary user interface that enables display and control of surgical hub 206 functions from with the sterile field. The secondary display could be used to change display locations, what information is displayed where, pass off control of specific functions or devices.

During a surgical procedure, the surgeon may not have a user interface device accessible for interactive input by the surgeon and display within the sterile field. Thus, the surgeon cannot interface with the user interface device and the surgical hub from within the sterile field and cannot control other surgical devices through the surgical hub from within the sterile field.

One solution provides a display unit designed to be used within the sterile field and accessible for input and display by the surgeon to allow the surgeon to have interactive input control from the sterile field to control other surgical devices coupled to the surgical hub. The display unit is sterile and located within the sterile field to allow the surgeons to interface with the display unit and the surgical hub to directly interface and configure instruments as necessary without leaving the sterile field. The display unit is a master device and may be used for display, control, interchanges of tool control, allowing feeds from other surgical hubs without the surgeon leaving the sterile field.

In one aspect, the present disclosure provides a control unit, comprising an interactive touchscreen display, an interface configured to couple the interactive touchscreen display to a surgical hub, a processor, and a memory coupled to the processor. The memory stores instructions executable by the processor to receive input commands from the interactive touchscreen display located inside a sterile field and transmits the input commands to a surgical hub to control devices coupled to the surgical hub located outside the sterile field.

In another aspect, the present disclosure provides a control unit, comprising an interactive touchscreen display, an interface configured to couple the interactive touchscreen display to a surgical hub, and a control circuit configured to receive input commands from the interactive touchscreen display located inside a sterile field and transmit the input commands to a surgical hub to control devices coupled to the surgical hub located outside the sterile field.

In another aspect, the present disclosure provides a non-transitory computer readable medium storing computer readable instructions which, when executed, causes a machine to receive input commands from an interactive touchscreen display located inside a sterile field and transmit the input commands to a surgical hub through an interface configured to couple the interactive touchscreen display to the surgical hub to control devices coupled to the surgical hub located outside the sterile field.

Providing a display unit designed to be used within the sterile field and accessible for input and display by the surgeon provides the surgeon interactive input control from the sterile field to control other surgical devices coupled to the surgical hub.

This display unit within the sterile field is sterile and allows the surgeons to interface with it and the surgical hub. This gives the surgeon control of the instruments coupled to the surgical hub and allows the surgeon to directly interface and configure the instruments as necessary without leaving the sterile field. The display unit is a master device and may be used for display, control, interchanges of tool control, allowing feeds from other surgical hubs without the surgeon leaving the sterile field.

In various aspects, the present disclosure provides a secondary user interface to enable display and control of surgical hub functions from within a sterile field. This control could be a display device like an I-pad, e.g., a portable interactive touchscreen display device configured to be introduced into the operating theater in a sterile manner. It could be paired like any other device or it could be location sensitive. The display device would be allowed to function in this manner whenever the display device is placed over a specific location of the draped abdomen of the patient during a surgical procedure. In other aspects, the present disclosure provides a smart retractor and a smart sticker. These and other aspects are described hereinbelow.

In one aspect, the present disclosure provides a secondary user interface to enable display and control of surgical hub functions from within the sterile field. In another aspect, the secondary display could be used to change display locations, determine what information and where the information is displayed, and pass off control of specific functions or devices.

There are four types of secondary surgeon displays in two categories. One type of secondary surgeon display units is designed to be used within the sterile field and accessible for input and display by the surgeon within the sterile field interactive control displays. Sterile field interactive control displays may be shared or common sterile field input control displays.

A sterile field display may be mounted on the operating table, on a stand, or merely laying on the abdomen or chest of the patient. The sterile field display is sterile and allows the surgeons to interface with the sterile field display and the surgical hub. This gives the surgeon control of the system and allows them to directly interface and configure the sterile field display as necessary. The sterile field display may be configured as a master device and may be used for display, control, interchanges of tool control, allowing feeds from other surgical hubs, etc.

In one aspect, the sterile field display may be employed to re-configure the wireless activation devices within the operating theater (OR) and their paired energy device if a surgeon hands the device to another. FIGS. 138A-138E illustrate various types of sterile field control and data input consoles 6700, 6702, 6708, 6712, 6714 according to various aspects of the present disclosure. Each of the disclosed sterile field control and data input consoles 6700, 6702, 6708, 6712, 6714 comprise at least one touchscreen 6701, 6704/6706, 6709, 6713, 6716 input/output device layered on the top of an electronic visual display of an information processing system. The sterile field control and data input consoles 6700, 6702, 6708, 6712, 6714 may include batteries as a power source. Some include a cable 6710 to connect to a separate power source or to recharge the batteries. A user can give input or control the information processing system through simple or multi-touch gestures by touching the touchscreen 6701, 6704/6706, 6709, 6713, 6716 with a stylus, one or more fingers, or a surgical tool. The sterile field control and data input consoles 6700, 6702, 6708, 6712, 6714 may be used to re-configure wireless activation devices within the operating theater and a paired energy device if a surgeon hands the device to another surgeon. The sterile field control and data input consoles 6700, 6702, 6708, 6712, 6714 may be used to accept consult feeds from another operating theater where it would then configure a portion of the operating theater screens or all of them to mirror the other operating theater so the surgeon is able to see what is needed to help. The sterile field control and data input consoles 6700, 6702, 6708, 6712, 6714 are configured to communicate with the surgical hub 206. Accordingly, the description of the surgical hub 206 discussed in connection with FIGS. 1-11 is incorporated in this section by reference.

FIG. 138A illustrates a single zone sterile field control and data input console 6700, according to one aspect of the present disclosure. The single zone console 6700 is configured for use in a single zone within a sterile field. Once deployed in a sterile field, the single zone console 6700 can receive touchscreen inputs from a user in the sterile field. The touchscreen 6701 enables the user to interact directly with what is displayed, rather than using a mouse, touchpad, or other such devices (other than a stylus or surgical tool). The single zone console 6700 includes wireless communication circuits to communicate wirelessly to the surgical hub 206.

FIG. 138B illustrates a multi zone sterile field control and data input console 6702, according to one aspect of the present disclosure. The multi zone console 6702 comprises a first touchscreen 6704 to receive an input from a first zone of a sterile field and a second touchscreen 6706 to receive an input from a second zone of a sterile field. The multi zone console 6702 is configured to receive inputs from multiple users in a sterile field. The multi zone console 6702 includes wireless communication circuits to communicate wirelessly to the surgical hub 206. Accordingly, the multi zone sterile field control and data input console 6702 comprises an interactive touchscreen display with multiple input and output zones.

FIG. 138C illustrates a tethered sterile field control and data input console 6708, according to one aspect of the present disclosure. The tethered console 6708 includes a cable 6710 to connect the tethered console 6708 to the surgical hub 206 via a wired connection. The cable 6710 enables the tethered console 6708 to communicate over a wired link in addition to a wireless link. The cable 6710 also enables the tethered console 6708 to connect to a power source for powering the console 6708 and/or recharging the batteries in the console 6708.

FIG. 138D illustrates a battery operated sterile field control and data input console 6712, according to one aspect of the present disclosure. The sterile field console 6712 is battery operated and includes wireless communication circuits to communicate wirelessly with the surgical hub 206. In particular, in one aspect, the sterile field console 6712 is configured to communicate with any of the modules coupled to the hub 206 such as the generator module 240. Through the sterile field console 6712, the surgeon can adjust the power output level of a generator using the touchscreen 6713 interface. One example is described below in connection with FIG. 138E.

FIG. 138E illustrates a battery operated sterile field control and data input console 6714, according to one aspect of the present disclosure. The sterile field console 6714 includes a user interface displayed on the touchscreen of a generator. The surgeon can thus control the output of the generator by touching the up/down arrow icons 6718A, 6718B that increase/decrease the power output of the generator module 240. Additional icons 6719 enable access to the generator module settings 6174, volume 6178 using the +/− icons, among other features directly from the sterile field console 6714. The sterile field console 6714 may be employed to adjust the settings or reconfigure other wireless activations devices or modules coupled to the hub 206 within the operating theater and their paired energy device when the surgeon hands the sterile field console 6714 to another.

FIGS. 139A-139B illustrate a sterile field console 6700 in use in a sterile field during a surgical procedure, according to one aspect of the present disclosure. FIG. 139A shows the sterile field console 6714 positioned in the sterile field near two surgeons engaged in an operation. In FIG. 139B, one of the surgeons is shown tapping the touchscreen 6701 of the sterile field console with a surgical tool 6722 to adjust the output of a modular device coupled to the surgical hub 206, reconfigure the modular device, or an energy device paired with the modular device coupled to the surgical hub 206.

In another aspect, the sterile field display may be employed to accept consult feeds from another operating room (OR), such as another operating theater or surgical hub 206, where it would then configure a portion of the OR screens or all of them to mirror the other ORs so the surgeon could see what is needed to help. FIG. 140 illustrates a process 6750 for accepting consult feeds from another operating room, according to one aspect of the present disclosure. The sterile field control and data input consoles 6700, 6702, 6708, 6712, 6714 shown in FIGS. 138A-138E, 139A-139B may be used as an interact-able scalable secondary display allowing the surgeon to overlay other feeds or images from laser Doppler image scanning arrays or other image sources. The sterile field control and data input consoles 6700, 6702, 6708, 6712, 6714 may be used to call up a pre-operative scan or image to review. Laser Doppler techniques are described in U.S. Provisional Patent Application No. 62/611,341, filed Dec. 28, 2017, and titled INTERACTIVE SURGICAL PLATFORM, which is incorporated herein by reference in its entirety.

It is recognized that the tissue penetration depth of light is dependent on the wavelength of the light used. Thus, the wavelength of the laser source light may be chosen to detect particle motion (such a blood cells) at a specific range of tissue depth. A laser Doppler employs means for detecting moving particles such as blood cells based at a variety of tissue depths based on the laser light wavelength. A laser source may be directed to a surface of a surgical site. A blood vessel (such as a vein or artery) may be disposed within the tissue at some depth δ from the tissue surface. Red laser light (having a wavelength in the range of about 635 nm to about 660 nm) may penetrate the tissue to a depth of about 1 mm. Green laser light (having a wavelength in the range of about 520 nm to about 532 nm) may penetrate the tissue to a depth of about 2-3 mm. Blue laser light (having a wavelength in the range of about 405 nm to about 445 nm) may penetrate the tissue to a depth of about 4 mm or greater. A blood vessel may be located at a depth of about 2-3 mm below the tissue surface. Red laser light will not penetrate to this depth and thus will not detect blood cells flowing within this vessel. However, both green and blue laser light can penetrate this depth. Therefore, scattered green and blue laser light from the blood cells will result in an observed Doppler shift in both the green and blue.

In some aspects, a tissue may be probed by red, green, and blue laser illumination in a sequential manner and the effect of such illumination may be detected by a CMOS imaging sensor over time. It may be recognized that sequential illumination of the tissue by laser illumination at differing wavelengths may permit a Doppler analysis at varying tissue depths over time. Although red, green, and blue laser sources may be used to illuminate the surgical site, it may be recognized that other wavelengths outside of visible light (such as in the infrared or ultraviolet regions) may be used to illuminate the surgical site for Doppler analysis. The imaging sensor information may be provided to the sterile field control and data input consoles 6700, 6702, 6708, 6712, 6714.

The sterile field control and data input consoles 6700, 6702, 6708, 6712, 6714 provide access to past recorded data. In one operating theater designated as OR1, the sterile field control and data input consoles 6700, 6702, 6708, 6712, 6714 may be configured as "consultants" and to erase all data when the consultation is complete. In another operating theater designated as OR3 (operating room 3), the sterile field control and data input consoles 6700, 6702, 6708, 6712, 6714 may be configured as a "consultees" and are configured to record all data received from operating theater OR1 (operating room 1) sterile field control and data input consoles 6700, 6702, 6708, 6712, 6714. These configurations are summarized in TABLE 2 below:

TABLE 2

| Sterile Field Control And Data Input Console In OR1 | Sterile Field Control And Data Input Console In OR3 |
| --- | --- |
| Access to past recorded data OR1 Consultant Erase data when done | OR 3 Consultee Record all data |

In one implementation of the process 6750, operating theater OR1 receives 6752 a consult request from OR3. Data is transferred to the OR1 sterile field control and data input console 6700, for example. The data is temporarily stored 6754. The data is backed up in time and the OR1 view 6756 of the temporary data begins on the OR1 sterile field control and data input console 6700 touchscreen 6701. When the view is complete, the data is erased 6758 and control returns 6760 to OR1. The data is then erased 6762 from the OR1 sterile field control and data input console 6700 memory.

In yet another aspect, the sterile field display may be employed as an interactable scalable secondary display allowing the surgeon to overlay other feeds or images like laser Doppler scanning arrays. In yet another aspect, the sterile field display may be employed to call up a pre-operative scan or image to review. Once vessel path and depth and device trajectory are estimated, the surgeon employs a sterile field interactable scalable secondary display allowing the surgeon to overlay other feeds or images.

FIG. 141 is a diagram 6770 that illustrates a technique for estimating vessel path, depth, and device trajectory. Prior to dissecting a vessel 6772, 6774 located below the surface of the tissue 6775 using a standard approach, the surgeon estimates the path and depth of the vessel 6772, 6774 and a trajectory 6776 of a surgical device 6778 will take to reach the vessel 6772, 6774. It is often difficult to estimate the path and depth 6776 of a vessel 6772, 6774 located below the surface of the tissue 6775 because the surgeon cannot accurately visualize the location of the vessel 6772, 6774 path and depth 6776.

FIGS. 142A-142D illustrate multiple real time views of images of a virtual anatomical detail for dissection including perspective views (FIGS. 142A, 142C) and side views (FIGS. 142B, 142D). The images are displayed on a sterile field display of tablet computer or sterile field control and data input console employed as an interactable scalable secondary display allowing the surgeon to overlay other feeds or images, according to one aspect of the present disclosure. The images of the virtual anatomy enable the surgeon to more accurately predict the path and depth of a vessel 6772, 6774 located below the surface of the tissue 6775 as shown in FIG. 141 and the best trajectory 6776 of the surgical device 6778.

FIG. 142A is a perspective view of a virtual anatomy 6780 displayed on a tablet computer or sterile field control and data input console. FIG. 142B is a side view of the virtual anatomy 6780 shown in FIG. 142A, according to one aspect of the present disclosure. With reference to FIGS. 142A-142B, in one aspect, the surgeon uses a smart surgical device 6778 and a tablet computer to visualize the virtual anatomy 6780 in real time and in multiple views. The three dimensional perspective view includes a portion of tissue 6775 in which the vessels 6772, 6774 are located below surface. The portion of tissue is overlaid with a grid 6786 to enable the surgeon to visualize a scale and gauge the path and depth of the vessels 6772, 6774 at target locations 6782, 6784 each marked by an X. The grid 6786 also assists the surgeon determine the best trajectory 6776 of the surgical device 6778. As illustrated, the vessels 6772, 6774 have an unusual vessel path.

FIG. 142C illustrates a perspective view of the virtual anatomy 6780 for dissection, according to one aspect of the present disclosure. FIG. 142D is a side view of the virtual anatomy 6780 for dissection, according to one aspect of the present disclosure. With reference to FIGS. 142C-142D, using the tablet computer, the surgeon can zoom and pan 360° to obtain an optimal view of the virtual anatomy 6780 for dissection. The surgeon then determines the best path or trajectory 6776 to insert the surgical device 6778 (e.g., a dissector in this example). The surgeon may view the anatomy in a three-dimensional perspective view or any one of six views. See for example the side view of the virtual anatomy in FIG. 142D and the insertion of the surgical device 6778 (e.g., the dissector).

In another aspect, a sterile field control and data input console may allow live chatting between different departments, such as, for example, with the oncology or pathology department, to discuss margins or other particulars associated with imaging. The sterile field control and data input console may allow the pathology department to tell the surgeon about relationships of the margins within a specimen and show them to the surgeon in real time using the sterile field console.

In another aspect, a sterile field control and data input console may be used to change the focus and field of view of its own image or control that of any of the other monitors coupled to the surgical hub.

In another aspect, a sterile field control and data input console may be used to display the status of any of the equipment or modules coupled to the surgical hub 206. Knowledge of which device coupled to the surgical hub 206 is being used may be obtained via information such as the device is not on the instrument pad or on-device sensors. Based on this information, the sterile field control and data input console may change display, configurations, switch power to drive one device, and not another, one cord from capital to instrument pad and multiple cords from there. Device diagnostics may obtain knowledge that the device is inactive or not being used. Device diagnostics may be based on information such as the device is not on the instrument pad or based on-device sensors.

In another aspect, a sterile field control and data input console may be used as a learning tool. The console may display checklists, procedure steps, and/or sequence of steps. A timer/clock may be displayed to measure time to complete steps and/or procedures. The console may display room sound pressure level as indicator for activity, stress, etc.

FIGS. 143A-143B illustrate a touchscreen display 6890 that may be used within the sterile field, according to one aspect of the present disclosure. Using the touchscreen display 6890, a surgeon can manipulate images 6892 displayed on the touchscreen display 6890 using a variety of gestures such as, for example, drag and drop, scroll, zoom, rotate, tap, double tap, flick, drag, swipe, pinch open, pinch close, touch and hold, two-finger scroll, among others.

FIG. 143A illustrates an image 6892 of a surgical site displayed on a touchscreen display 6890 in portrait mode. FIG. 143B shows the touchscreen display 6890 rotated 6894 to landscape mode and the surgeon uses his index finger 6896 to scroll the image 6892 in the direction of the arrows. FIG. 143C shows the surgeon using his index finger 6896 and thumb 6898 to pinch open the image 6892 in the direction of the arrows 6899 to zoom in. FIG. 143D shows the surgeon using his index finger 6896 and thumb 6898 to pinch close the image 6892 in the direction of the arrows 6897 to zoom out. FIG. 143E shows the touchscreen display 6890 rotated in two directions indicated by arrows 6894, 6896 to enable the surgeon to view the image 6892 in different orientations.

Outside the sterile field, control and static displays are used that are different from the control and static displays used inside the sterile field. The control and static displays located outside the sterile field provide interactive and static displays for operating theater (OR) and device control. The control and static displays located outside the sterile field may include secondary static displays and secondary touchscreens for input and output.

Secondary static non-sterile displays 107, 109, 119 (FIG. 2) for used outside the sterile field include monitors placed on the wall of the operating theater, on a rolling stand, or on capital equipment. A static display is presented with a feed from the control device to which they are attached and merely displays what is presented to it.

Secondary touch input screens located outside the sterile field may be part of the visualization system 108 (FIG. 2), part of the surgical hub 108 (FIG. 2), or may be fixed placement touch monitors on the walls or rolling stands. One difference between secondary touch input screens and static displays is that a user can interact with a secondary touch input screen by changing what is displayed on that specific monitor or others. For capital equipment applications, it could be the interface to control the setting of the connected capital equipment. The secondary touch input screens and the static displays outside the sterile field can be used to preload the surgeon's preferences (instrumentation settings and modes, lighting, procedure and preferred steps and sequence, music, etc.)

Secondary surgeon displays may include personal input displays with a personal input device that functions similarly to the common sterile field input display device but it is controlled by a specific surgeon. Personal secondary displays may be implemented in many form factors such as, for example, a watch, a small display pad, interface glasses, etc. A personal secondary display may include control capabilities of a common display device and since it is located on or controlled by a specific surgeon, the personal secondary display would be keyed to him/her specifically and would indicate that to others and itself. Generally speaking, a personal secondary display would normally not be useful to exchanging paired devices because they are not accessible to more than one surgeon. Nevertheless, a personal secondary display could be used to grant permission for release of a device.

A personal secondary display may be used to provide dedicated data to one of several surgical personnel that wants to monitor something that the others typically would not want to monitor. In addition, a personal secondary display may be used as the command module. Further, a personal secondary display may be held by the chief surgeon in the operating theater and would give the surgeon the control to override any of the other inputs from anyone else. A personal secondary display may be coupled to a short range wireless, e.g., Bluetooth, microphone and earpiece allowing the surgeon to have discrete conversations or calls or the personal secondary display may be used to broadcast to all the others in the operating theater or other department.

FIG. 144 illustrates a surgical site 6900 employing a smart surgical retractor 6902 comprising a direct interface control to a surgical hub 206 (FIGS. 1-11), according to one aspect of the present disclosure. The smart surgical retractor 6902 helps the surgeon and operating room professionals hold an incision or wound open during surgical procedures. The smart surgical retractor 6902 aids in holding back underlying organs or tissues, allowing doctors/nurses better visibility and access to the exposed area. With reference also to FIGS. 1-11, the smart surgical retractor 6902 may comprise an input display 6904 operated by the smart surgical retractor 6902. The smart surgical retractor 6902 may comprise a wireless communication device to communicate with a device connected to a generator module 240 coupled to the surgical hub 206. Using the input display 6904 of the smart surgical retractor 6902, the surgeon can adjust power level or mode of the generator module 240 to cut and/or coagulate tissue. If using automatic on/off for energy delivery on closure of an end effector on the tissue, the status of automatic on/off may be indicated by a light, screen, or other device located on the smart retractor 6902 housing. Power being used may be changed and displayed.

In one aspect, the smart surgical retractor 6902 can sense or know what device/instrument 235 the surgeon is using, either through the surgical hub 206 or RFID or other device placed on the device/instrument 235 or the smart surgical retractor 6902, and provide an appropriate display. Alarm and alerts may be activated when conditions require. Other features include displaying the temperature of the ultrasonic blade, nerve monitoring, light source 6906 or fluorescence.

The light source 6906 may be employed to illuminate the surgical field of view 6908 and to charge photocells 6918 on single use sticker display that stick onto the smart retractor 6902 (see FIG. 145, for example). In another aspect, the smart surgical retractor 6902 may include an augmented reality projected on the patient's anatomy (e.g., like a vein viewer).

FIG. 145 illustrates a surgical site 6910 with a smart flexible sticker display 6912 attached to the body/skin 6914 of a patient, according to one aspect of the present disclosure. As shown, the smart flexible sticker display 6912 is applied to the body/skin 6914 of a patient between the area exposed by the surgical retractors 6916. In one aspect, the smart flexible sticker display 6912 may be powered by light, an on board battery, or a ground pad. The flexible sticker display 6912 may communicate via short range wireless (e.g., Bluetooth) to a device, may provide readouts, lock power, or change power. The smart flexible sticker display 6912 also comprises photocells 6918 to power the smart flexible sticker display 6912 using ambient light energy. The flexible sticker display 6912 includes a display of a control panel 6920 user interface to enable the surgeon to control devices 235 or other modules coupled to the surgical hub 206 (FIGS. 1-11).

FIG. 146 is a logic flow diagram 6920 of a process depicting a control program or a logic configuration to communicate from inside a sterile field to a device located outside the sterile field, according to one aspect of the present disclosure. In one aspect, a control unit comprises an interactive touchscreen display, an interface configured to couple the interactive touchscreen display to a surgical hub, a processor, and a memory coupled to the processor. The memory stores instructions executable by the processor to receive 6922 input commands from the interactive touchscreen display located inside a sterile field and transmits 6924 the input commands to a surgical hub to control devices coupled to the surgical hub located outside the sterile field.

FIG. 147 illustrates a system for performing surgery. The system comprises a control box which includes internal circuitry; a surgical instrument including a distal element and techniques for sensing a position or condition of said distal element; techniques associated with said surgical instrument for transmitting said sensed position or condition to said internal circuitry of said control box; and for transmitting said sensed position or condition from said internal circuitry of said control box to a video monitor for display thereon, wherein said sensed position or condition is displayed on said video monitor as an icon or symbol, further comprising a voltage source for generating a voltage contained entirely within said surgical instrument. Further examples are disclosed in U.S. Pat. No. 5,503,320, titled SURGICAL APPARATUS WITH INDICATOR, which issued on Apr. 2, 1996, which is herein incorporated by reference in its entirety.

FIG. 147 shows schematically a system whereby data is transmitted to a video monitor for display, such data relating to the position and/or condition of one or more surgical instruments. As shown in FIG. 147, a laparoscopic surgical procedure is being performed wherein a plurality of trocar sleeves 6930 are inserted through a body wall 6931 to provide access to a body cavity 6932. A laparoscope 6933 is inserted through one of the trocar sleeves 6930 to provide illumination (light cable 6934 is shown leading toward a light source, not pictured) to the surgical site and to obtain an image thereof. A camera adapter 6935 is attached at the proximal end of laparoscope 6933 and image cable 6936 extends therefrom to a control box 6937 discussed in more detail below. Image cable inputs to image receiving port 416 on control box 6937.

Additional surgical instruments 6939, 6940 are inserted through additional trocar sleeves 6900 which extend through body wall 6931. In FIG. 147, instrument 6939 schematically illustrates an endoscopic stapling device, e.g., an Endo GIA* instrument manufactured by the assignee of this application, and instrument 6940 schematically illustrates a hand instrument, e.g., an Endo Grasp* device also manufactured by the present assignee. Additional and/or alternative instruments may also be utilized according to the present invention; the illustrated instruments are merely exemplary of surgical instruments which may be utilized according to the present invention.

Instruments 6939, 6940 include adapters 6941, 6942 associated with their respective handle portions. The adapters electronically communicate with conductive mechanisms (not pictured). These mechanisms, which include electrically conductive contact members electrically connected by wires, cables and the like, are associated with the distal elements of the respective instruments, e.g., the anvil 6943 and cartridge 6944 of the Endo GIA* instrument, the jaws 6945, 6946 of the Endo Grasp* device, and the like. The mechanisms are adapted to interrupt an electronic circuit when the distal elements are in a first position or condition and to complete the electronic circuit when the distal elements are in a second position or condition. A voltage source for the electronic circuit may be provided in the surgical instrument, e.g., in the form of a battery, or supplied from control box 6937 through cables 6947, 6948.

Control box 6937 includes a plurality of jacks 6949 which are adapted to receive cables 6947, 6948 and the like. Control box 6937 further includes an outgoing adapter 6950 which is adapted to cooperate with a cable 6951 for transmitting the laparoscopic image obtained by the laparoscope 6933 together with data concerning surgical instruments 6939, 6940 to video monitor 6952. Circuitry within control box 6937 is provided for converting the presence of an interrupted circuit, e.g., for the electronics within cable 6947 and the mechanism associated with the distal elements of instrument 6939, to an icon or symbol for display on video monitor 6952. Similarly, the circuitry within control box 6937 is adapted to provide a second icon or symbol to video monitor 6952 when a completed circuit exists for cable 6947 and the associated mechanism.

Illustrative icons/symbols 6953, 6954 are shown on video monitor 6952. Icon 6953 shows a surgical staple and could be used to communicate to the surgeon that the cartridge 6944 and anvil 6943 of instrument 6939 are properly positioned to form staples in tissue 6955. Icon 6953 could take another form when the cartridge 6944 and anvil 6943 are not properly positioned for forming staples, thereby interrupting the circuit. Icon 6954 shows a hand instrument with jaws spread apart, thereby communicating to the surgeon that the jaws 6945, 6946 of instrument 6940 are open. Icon 6954 could take another form when jaws 6945, 6946 are closed, thereby completing the circuit.

FIG. 148 illustrates a second layer of information overlaying a first layer of information. The second layer of information includes a symbolic representation of the knife overlapping the detected position of the knife in the DLU depicted in the first layer of information. Further examples are disclosed in U.S. Pat. No. 9,283,054, titled SURGICAL APPARATUS WITH INDICATOR, which issued on Mar. 15, 2016, which is herein incorporated by reference in its entirety.

Referring to FIG. 148, the second layer of information 6963 can overlay at least a portion of the first layer of information 6962 on the display 6960. Furthermore, the touch screen 6961 can allow a user to manipulate the second layer of information 6963 relative to the video feedback in the underlying first layer of information 6962 on the display 6960. For example, a user can operate the touch screen 6961 to select, manipulate, reformat, resize, and/or otherwise modify the information displayed in the second layer of information 6963. In certain aspects, the user can use the touch screen 6961 to manipulate the second layer of information 6963 relative to the surgical instrument 6964 depicted in the first layer of information 6962 on the display 6960. A user can select a menu, category and/or classification of the control panel 6967 thereof, for example, and the second layer of information 6963 and/or the control panel 6967 can be adjusted to reflect the user's selection. In various aspects, a user may select a category from the instrument feedback category 6969 that corresponds to a specific feature or features of the surgical instrument 6964 depicted in the first layer of information 6962. Feedback corresponding to the user-selected category can move, locate itself, and/or "snap" to a position on the display 6960 relative to the specific feature or features of the surgical instrument 6964. For example, the selected feedback can move to a position near and/or overlapping the specific feature or features of the surgical instrument 6964 depicted in the first layer of information 6962.

The instrument feedback menu 6969 can include a plurality of feedback categories, and can relate to the feedback data measured and/or detected by the surgical instrument 6964 during a surgical procedure. As described herein, the surgical instrument 6964 can detect and/or measure the position 6970 of a moveable jaw between an open orientation and a closed orientation, the thickness 6973 of clamped tissue, the clamping force 6976 on the clamped tissue, the articulation 6974 of the DLU 6965, and/or the position 6971, velocity 6972, and/or force 6975 of the firing element, for example. Furthermore, the feedback controller in signal communication with the surgical instrument 6964 can provide the sensed feedback to the display 6960, which can display the feedback in the second layer of information 6963. As described herein, the selection, placement, and/or form of the feedback data displayed in the second layer of information 6963 can be modified based on the user's input to the touch screen 6961, for example.

When the knife of the DLU 6965 is blocked from view by the end effector jaws 6966 and/or tissue T, for example, the operator can track and/or approximate the position of the knife in the DLU 6964 based on the changing value of the feedback data and/or the shifting position of the feedback data relative to the DLU 6965 depicted in the underlying first layer of information 6962.

In various aspects, the display menu 6977 of the control panel 6967 can relate to a plurality of categories, such as unit systems 6978 and/or data modes 6979, for example. In certain aspects, a user can select the unit systems category 6978 to switch between unit systems, such as between metric and U.S. customary units, for example. Additionally, a user can select the data mode category 6979 to switch between types of numerical representations of the feedback data and/or types of graphical representations of the feedback data, for example. The numerical representations of the feedback data can be displayed as numerical values and/or percentages, for example. Furthermore, the graphical representations of the feedback data can be displayed as a function of time and/or distance, for example. As described herein, a user can select the instrument controller menu 6980 from the control panel 6967 to input directives for the surgical instrument 6964, which can be implemented via the instrument controller and/or the microcontroller, for example. A user can minimize or collapse the control panel 6967 by selecting the minimize/maximize icon 6968, and can maximize or un-collapse the control panel 6967 by re-selecting the minimize/maximize icon 6968.

FIG. 149 depicts a perspective view of a surgeon using a surgical instrument that includes a handle assembly housing and a wireless circuit board during a surgical procedure, with the surgeon wearing a set of safety glasses. The wireless circuit board transmits a signal to a set of safety glasses worn by a surgeon using the surgical instrument during a procedure. The signal is received by a wireless port on the safety glasses. One or more lighting devices on a front lens of the safety glasses change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 149 shows a version of safety glasses 6991 that may be worn by a surgeon 6992 during a surgical procedure while using a medical device. In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991. Additionally or alternatively, wireless communications board 6995 transmits a wireless signal to surgical monitor 6997 such that surgical monitor 6997 may display received indicated status information to surgeon 6992, as described above.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

LEDs may be located at edges or sides of a front lens of the safety glasses 6991 so not to distract from a user's center of vision while still being positioned within the user's field of view such that the user does not need to look away from the surgical site to see the lighting device. Displayed lights may pulse and/or change color to communicate to the wearer of the safety glasses 6991 various aspects of information retrieved from instrument 6993, such as system status information or tissue sensing information (i.e., whether the end effector has sufficiently severed and sealed tissue). Feedback from housed wireless communications board 6995 may cause a lighting device to activate, blink, or change color to indicate information about the use of instrument 6993 to a user. For example, a device may incorporate a feedback mechanism based on one or more sensed tissue parameters. In this case, a change in the device output(s) based on this feedback in synch with a tone change may submit a signal through wireless communications board 6995 to the safety glasses 6991 to trigger activation of the lighting device. Such described means of activation of the lighting device should not be considered limiting as other means of indicating status information of instrument 6993 to the user via the safety glasses 6991 are contemplated. Further, the safety glasses 6991 may be single-use or reusable eyewear. Button-cell power supplies such as button-cell batteries may be used to power wireless receivers and LEDs of versions of safety glasses 6991, which may also include a housed wireless board and tri-color LEDs. Such button-cell power supplies may provide a low-cost means of providing sensory feedback of information about instrument 6993 when in use to surgeon 6992 wearing safety glasses 6991.

FIG. 150 is a schematic diagram of a feedback control system for controlling a surgical instrument. The surgical instrument includes a housing and an elongated shaft that extends distally from the housing and defines a first longitudinal axis. The surgical instrument also includes a firing rod disposed in the elongated shaft and a drive mechanism disposed at least partially within the housing. The drive mechanism mechanically cooperates with the firing rod to move the firing rod. A motion sensor senses a change in the electric field (e.g., capacitance, impedance, or admittance) between the firing rod and the elongated shaft. The measurement unit determines a parameter of the motion of the firing rod, such as the position, speed, and direction of the firing rod, based on the sensed change in the electric field. A controller uses the measured parameter of the motion of the firing rod to control the drive mechanism. Further examples are disclosed in U.S. Pat. No. 8,960,520, titled METHOD AND APPARATUS FOR DETERMINING PARAMETERS OF LINEAR MOTION IN A SURGICAL INSTRUMENT, which issued on Feb. 24, 2015, which is herein incorporated by reference in its entirety.

With reference to FIG. 150, aspects of the present disclosure may include a feedback control system 6150. The system 6150 includes a feedback controller 6152. The surgical instrument 6154 is connected to the feedback controller 6152 via a data port, which may be either wired (e.g., FireWire®, USB, Serial RS232, Serial RS485, USART, Ethernet, etc.) or wireless (e.g., Bluetooth®, ANT3®, KNX®, Z-Wave X10®, Wireless USB®, Wi-Fi®, IrDA®, nanoNET®, TinyOS®, ZigBee®, 802.11 IEEE, and other radio, infrared, UHF, VHF communications and the like). The feedback controller 6152 is configured to store the data transmitted to it by the surgical instrument 6154 as well as process and analyze the data. The feedback controller 6152 is also connected to other devices, such as a video display 6154, a video processor 6156 and a computing device 6158 (e.g., a personal computer, a PDA, a smartphone, a storage device, etc.). The video processor 6156 is used for processing output data generated by the feedback controller 6152 for output on the video display 6154. The computing device 6158 is used for additional processing of the feedback data. In one aspect, the results of the sensor feedback analysis performed by a microcontroller may be stored internally for later retrieval by the computing device 6158.

FIG. 151 illustrates a feedback controller 6152 including an on-screen display (OSD) module and a heads-up-display (HUD) module. The modules process the output of a microcontroller for display on various displays. More specifically, the OSD module overlays text and/or graphical information from the feedback controller 6152 over other video images received from the surgical site via cameras disposed therein. The modified video signal having overlaid text is transmitted to the video display allowing the user to visualize useful feedback information from the surgical instrument 6154 and/or feedback controller 6152 while still observing the surgical site. The feedback controller 6152 includes a data port 6160 coupled to a microcontroller which allows the feedback controller 6152 to be connected to the computing device 6158 (FIG. 150). The data port 6160 may provide for wired and/or wireless communication with the computing device 6158 providing for an interface between the computing device 6158 and the feedback controller 6152 for retrieval of stored feedback data, configuration of operating parameters of the feedback controller 6152 and upgrade of firmware and/or other software of the feedback controller 6152.

The feedback controller 6152 includes a housing 6162 and a plurality of input and output ports, such as a video input 6164, a video output 6166, and a HUD display output 6168. The feedback controller 6152 also includes a screen for displaying status information concerning the feedback controller 6152. Further examples are disclosed in U.S. Pat. No. 8,960,520, titled METHOD AND APPARATUS FOR DETERMINING PARAMETERS OF LINEAR MOTION IN A SURGICAL INSTRUMENT, which issued on Feb. 24, 2015, which is herein incorporated by reference in its entirety.

Visualization System

During a surgical procedure, a surgeon may be required to manipulate tissues to effect a desired medical outcome. The actions of the surgeon are limited by what is visually observable in the surgical site. Thus, the surgeon may not be aware, for example, of the disposition of vascular structures that underlie the tissues being manipulated during the procedure. Since the surgeon is unable to visualize the vasculature beneath a surgical site, the surgeon may accidentally sever one or more critical blood vessels during the procedure. The solution is a surgical visualization system that can acquire imaging data of the surgical site for presentation to a surgeon, in which the presentation can include information related to the presence and depth of vascular structures located beneath the surface of a surgical site.

In one aspect, the surgical hub 106 incorporates a visualization system 108 to acquire imaging data during a surgical procedure. The visualization system 108 may include one or more illumination sources and one or more light sensors. The one or more illumination sources and one or more light sensors may be incorporated together into a single device or may comprise one or more separate devices. The one or more illumination sources may be directed to illuminate portions of the surgical field. The one or more light sensors may receive light reflected or refracted from the surgical field including light reflected or refracted from tissue and/or surgical instruments. The following description includes all of the hardware and software processing techniques disclosed above and in those applications incorporated herein by reference as presented above.

In some aspects, the visualization system 108 may be integrated into a surgical system 100 as disclosed above and depicted in FIGS. 1 and 2. In addition to the visualization system 108, the surgical system 100 may include one or more hand-held intelligent instruments 112, a multi-functional robotic system 110, one or more visualization systems 108, and a centralized surgical hub system 106, among other components. The centralized surgical hub system 106 may control several functions a disclosed above and also depicted in FIG. 3. In one non-limiting example, such functions may include supplying and controlling power to any number of powered surgical devices. In another non-limiting example, such functions may include controlling fluid supplied to and evacuated from the surgical site. The centralized surgical hub system 106 may also be configured to manage and analyze data received from any of the surgical system components as well as communicate data and other information among and between the components of the surgical system. The centralized surgical hub system 106 may also be in data communication with a cloud computing system 104 as disclosed above and depicted, for example, in FIG. 1.

In some non-limiting examples, imaging data generated by the visualization system 108 may be analyzed by on-board computational components of the visualization system 108, and analysis results may be communicated to the centralized surgical hub 106. In alternative non-limiting examples, the imaging data generated by the visualization system 108 may be communicated directly to the centralized surgical hub 106 where the data may be analyzed by computational components in the hub system 106. The centralized surgical hub 106 may communicate the image analysis results to any one or more of the other components of the surgical system. In some other non-limiting examples, the centralized surgical hub may communicate the image data and/or the image analysis results to the cloud computing system 104.

FIGS. 152A-D and FIGS. 153A-F depict various aspects of one example of a visualization system 2108 that may be incorporated into a surgical system. The visualization system 2108 may include an imaging control unit 2002 and a hand unit 2020. The imaging control unit 2002 may include one or more illumination sources, a power supply for the one or more illumination sources, one or more types of data communication interfaces (including USB, Ethernet, or wireless interfaces 2004), and one or more a video outputs 2006. The imaging control unit 2002 may further include an interface, such as a USB interface 2010, configured to transmit integrated video and image capture data to a USB enabled device. The imaging control unit 2002 may also include one or more computational components including, without limitation, a processor unit, a transitory memory unit, a non-transitory memory unit, an image processing unit, a bus structure to form data links among the computational components, and any interface (e.g. input and/or output) devices necessary to receive information from and transmit information to components not included in the imaging control unit. The non-transitory memory may further contain instructions that when executed by the processor unit, may perform any number of manipulations of data that may be received from the hand unit 2020 and/or computational devices not included in the imaging control unit.

The illumination sources may include a white light source 2012 and one or more laser light sources. The imaging control unit 2002 may include one or more optical and/or electrical interfaces for optical and/or electrical communication with the hand unit 2020. The one or more laser light sources may include, as non-limiting examples, any one or more of a red laser light source, a green laser light source, a blue laser light source, an infrared laser light source, and an ultraviolet laser light source. In some non-limiting examples, the red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some non-limiting examples, the green laser light source may source illumination having a peak wavelength that may range between 520 nm and 532 nm, inclusive. Non-limiting examples of a green laser peak wavelength may include about 520 nm, about 522 nm, about 524 nm, about 526 nm, about 528 nm, about 530 nm, about 532 nm, or any value or range of values therebetween. In some non-limiting examples, the blue laser light source may source illumination having a peak wavelength that may range between 405 nm and 445 nm, inclusive. Non-limiting examples of a blue laser peak wavelength may include about 405 nm, about 410 nm, about 415 nm, about 420 nm, about 425 nm, about 430 nm, about 435 nm, about 440 nm, about 445 nm, or any value or range of values therebetween. In some non-limiting examples, the infrared laser light source may source illumination having a peak wavelength that may range between 750 nm and 3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. In some non-limiting examples, the ultraviolet laser light source may source illumination having a peak wavelength that may range between 200 nm and 360 nm, inclusive. Non-limiting examples of an ultraviolet laser peak wavelength may include about 200 nm, about 220 nm, about 240 nm, about 260 nm, about 280 nm, about 300 nm, about 320 nm, about 340 nm, about 360 nm, or any value or range of values therebetween.

In one non-limiting aspect, the hand unit 2020 may include a body 2021, a camera scope cable 2015 attached to the body 2021, and an elongated camera probe 2024. The body 2021 of the hand unit 2020 may include hand unit control buttons 2022 or other controls to permit a health professional using the hand unit 2020 to control the operations of the hand unit 2020 or other components of the imaging control unit 2002, including, for example, the light sources. The camera scope cable 2015 may include one or more electrical conductors and one or more optical fibers. The camera scope cable 2015 may terminate with a camera head connector 2008 at a proximal end in which the camera head connector 2008 is configured to mate with the one or more optical and/or electrical interfaces of the imaging control unit 2002. The electrical conductors may supply power to the hand unit 2020, including the body 2021 and the elongated camera probe 2024, and/or to any electrical components internal to the hand unit 2020 including the body 2021 and/or elongated camera probe 2024. The electrical conductors may also serve to provide bi-directional data communication between any one or more components the hand unit 2020 and the imaging control unit 2002. The one or more optical fibers may conduct illumination from the one or more illumination sources in the imaging control unit 2002 through the hand unit body 2021 and to a distal end of the elongated camera probe 2024. In some non-limiting aspects, the one or more optical fibers may also conduct light reflected or refracted from the surgical site to one or more optical sensors disposed in the elongated camera probe 2024, the hand unit body 2021, and/or the imaging control unit 2002.

FIG. 152B (a top plan view) depicts in more detail some aspects of a hand unit 2020 of the visualization system 2108. The hand unit body 2021 may be constructed of a plastic material. The hand unit control buttons 2022 or other controls may have a rubber overmolding to protect the controls while permitting them to be manipulated by the surgeon. The camera scope cable 2015 may have optical fibers integrated with electrical conductors, and the camera scope cable 2015 may have a protective and flexible overcoating such as PVC. In some non-limiting examples, the camera scope cable 2015 may be about 10 ft. long to permit ease of use during a surgical procedure. The length of the camera scope cable 2015 may range from about 5 ft. to about 15 ft. Non-limiting examples of a length of the camera scope cable 2015 may be about 5 ft., about 6 ft., about 7 ft., about 8 ft., about 9 ft., about 10 ft., about 11 ft., about 12 ft., about 13 ft., about 14 ft., about 15 ft., or any length or range of lengths therebetween. The elongated camera probe 2024 may be fabricated from a rigid material such as stainless steel. In some aspects, the elongated camera probe 2024 may be joined with the hand unit body 2021 via a rotatable collar 2026. The rotatable collar 2026 may permit the elongated camera probe 2024 to be rotated with respect to the hand unit body 2021. In some aspects, the elongated camera probe 2024 may terminate at a distal end with a plastic window 2028 sealed with epoxy.

The side plan view of the hand unit, depicted in FIG. 152C illustrates that a light or image sensor 2030 maybe disposed at a distal end 2032*a* of the elongated camera probe or within the hand unit body 2032*b*. In some alternative aspects, the light or image sensor 2030 may be dispose with additional optical elements in the imaging control unit 2002. FIG. 152C further depicts an example of a light sensor 2030 comprising a CMOS image sensor 2034 disposed within a mount 2036 having a radius of about 4 mm. FIG. 152D illustrates aspects of the CMOS image sensor 2034, depicting the active area 2038 of the image sensor. Although the CMOS image sensor in FIG. 152C is depicted to be disposed within a mount 2036 having a radius of about 4 mm, it may be recognized that such a sensor and mount combination may be of any useful size to be disposed within the elongated camera probe 2024, the hand unit body 2021, or in the image control unit 2002. Some non-limiting examples of such alternative mounts may include a 5.5 mm mount 2136*a*, a 4 mm mount 2136*b*, a 2.7 mm mount 2136*c*, and a 2 mm mount 2136*d*. It may be recognized that the image sensor may also comprise a CCD image sensor. The CMOS or CCD sensor may comprise an array of individual light sensing elements (pixels).

FIGS. 153A-153F depict various aspects of some examples of illumination sources and their control that may be incorporated into the visualization system 2108.

FIG. 153A illustrates an aspect of a laser illumination system having a plurality of laser bundles emitting a plurality of wavelengths of electromagnetic energy. As can be seen in the figure, the illumination system 2700 may comprise a red laser bundle 2720, a green laser bundle 2730, and a blue laser bundle 2740 that are all optically coupled together though fiber optics 2755. As can be seen in the figure, each of the laser bundles may have a corresponding light sensing element or electromagnetic sensor 2725, 2735, 2745 respectively, for sensing the output of the specific laser bundle or wavelength.

Additional disclosures regarding the laser illumination system depicted in FIG. 153A for use in a surgical visualization system 2108 may be found in U.S. Patent Application Publication No. 2014/0268860, titled CONTROLLING THE INTEGRAL LIGHT ENERGY OF A LASER PULSE filed on Mar. 15, 2014, which issued on Oct. 3, 2017 as U.S. Pat. No. 9,777,913, the contents thereof being incorporated by reference herein in its entirety and for all purposes.

FIG. 153B illustrates the operational cycles of a sensor used in rolling readout mode. It will be appreciated that the x direction corresponds to time and the diagonal lines 2202 indicate the activity of an internal pointer that reads out each frame of data, one line at a time. The same pointer is responsible for resetting each row of pixels for the next exposure period. The net integration time for each row 2219a-c is equivalent, but they are staggered in time with respect to one another due to the rolling reset and read process. Therefore, for any scenario in which adjacent frames are required to represent different constitutions of light, the only option for having each row be consistent is to pulse the light between the readout cycles 2230a-c. More specifically, the maximum available period corresponds to the sum of the blanking time plus any time during which optical black or optically blind (OB) rows (2218, 2220) are serviced at the start or end of the frame.

FIG. 153B illustrates the operational cycles of a sensor used in rolling readout mode or during the sensor readout 2200. The frame readout may start at and may be represented by vertical line 2210. The read out period is represented by the diagonal or slanted line 2202. The sensor may be read out on a row by row basis, the top of the downwards slanted edge being the sensor top row 2212 and the bottom of the downwards slanted edge being the sensor bottom row 2214. The time between the last row readout and the next readout cycle may be called the blanking time 2216a-d. It may be understood that the blanking time 2216a-d may be the same between success readout cycles or it may differ between success readout cycles. It should be noted that some of the sensor pixel rows might be covered with a light shield (e.g., a metal coating or any other substantially black layer of another material type). These covered pixel rows may be referred to as optical black rows 2218 and 2220. Optical black rows 2218 and 2220 may be used as input for correction algorithms.

As shown in FIG. 153B, these optical black rows 2218 and 2220 may be located on the top of the pixel array or at the bottom of the pixel array or at the top and the bottom of the pixel array. In some aspects, it may be desirable to control the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. In some aspects, an electronic shutter or rolling shutter may be used to start the integration time (2219a-c) by resetting the pixel. The light will then integrate until the next readout phase. In some aspects, the position of the electronic shutter can be moved between two readout cycles 2202 in order to control the pixel saturation for a given amount of light. In some alternative aspects lacking an electronic shutter, the integration time 2219a-c of the incoming light may start during a first readout cycle 2202 and may end at the next readout cycle 2202, which also defines the start of the next integration. In some alternative aspects, the amount of light accumulated by each pixel may be controlled by a time during which light is pulsed 2230a-d during the blanking times 2216a-d. This ensures that all rows see the same light issued from the same light pulse 2230a-c. In other words, each row will start its integration in a first dark environment 2231, which may be at the optical black back row 2220 of read out frame (m) for a maximum light pulse width, and will then receive a light strobe and will end its integration in a second dark environment 2232, which may be at the optical black front row 2218 of the next succeeding read out frame (m+1) for a maximum light pulse width. Thus, the image generated from the light pulse 2230a-c will be solely available during frame (m+1) readout without any interference with frames (m) and (m+2).

It should be noted that the condition to have a light pulse 2230a-c to be read out only in one frame and not interfere with neighboring frames is to have the given light pulse 2230a-c firing during the blanking time 2216. Because the optical black rows 2218, 2220 are insensitive to light, the optical black back rows 2220 time of frame (m) and the optical black front rows 2218 time of frame (m+1) can be added to the blanking time 2216 to determine the maximum range of the firing time of the light pulse 2230.

In some aspects, FIG. 153B depicts an example of a timing diagram for sequential frame captures by a conventional CMOS sensor. Such a CMOS sensor may incorporate a Bayer pattern of color filters, as depicted in FIG. 153C. It is recognized that the Bayer pattern provides for greater luminance detail than chrominance. It may further be recognized that the sensor has a reduced spatial resolution since a total of 4 adjacent pixels are required to produce the color information for the aggregate spatial portion of the image. In an alternative approach, the color image may be constructed by rapidly strobing the visualized area at high speed with a variety of optical sources (either laser or light-emitting diodes) having different central optical wavelengths.

The optical strobing system may be under the control of the camera system, and may include a specially designed CMOS sensor with high speed readout. The principal benefit is that the sensor can accomplish the same spatial resolution with significantly fewer pixels compared with conventional Bayer or 3-sensor cameras. Therefore, the physical space occupied by the pixel array may be reduced. The actual pulse periods (2230a-c) may differ within the repeating pattern, as illustrated in FIG. 153B. This is useful for, e.g., apportioning greater time to the components that require the greater light energy or those having the weaker sources. As long as the average captured frame rate is an integer multiple of the requisite final system frame rate, the data may simply be buffered in the signal processing chain as appropriate.

The facility to reduce the CMOS sensor chip-area to the extent allowed by combining all of these methods is particularly attractive for small diameter (~3-10 mm) endoscopy. In particular, it allows for endoscope designs in which the sensor is located in the space-constrained distal end, thereby greatly reducing the complexity and cost of the optical section, while providing high definition video. A consequence of this approach is that to reconstruct each final, full color image, requires that data be fused from three separate snapshots in time. Any motion within the scene, relative to the optical frame of reference of the endoscope, will generally degrade the perceived resolution, since the edges of objects appear at slightly different locations within each captured component. In this disclosure, a means of diminishing this issue is described which exploits the fact that spatial resolution is much more important for luminance information, than for chrominance.

The basis of the approach is that, instead of firing monochromatic light during each frame, combinations of the three wavelengths are used to provide all of the luminance information within a single image. The chrominance information is derived from separate frames with, e.g., a repeating pattern such as Y-Cb-Y-Cr (FIG. 153D). While it is possible to provide pure luminance data by a shrewd choice of pulse ratios, the same is not true of chrominance.

In one aspect, as illustrated in FIG. 153D, an endoscopic system 2300a may comprise a pixel array 2302a having uniform pixels and the system 2300a may be operated to receive Y (luminance pulse) 2304a, Cb (ChromaBlue) 2306a and Cr (ChromaRed) 2308a pulses.

To complete a full color image requires that the two components of chrominance also be provided. However, the same algorithm that was applied for luminance cannot be directly applied for chrominance images since it is signed, as reflected in the fact that some of the RGB coefficients are negative. The solution to this is to add a degree of luminance of sufficient magnitude that all of the final pulse energies become positive. As long as the color fusion process in the ISP is aware of the composition of the chrominance frames, they can be decoded by subtracting the appropriate amount of luminance from a neighboring frame. The pulse energy proportions are given by:

$$Y = 0.183 \cdot R + 0.614 \cdot G + 0.062 \cdot B$$

$$Cb = \lambda \cdot Y - 0.101 \cdot R - 0.339 \cdot G + 0.439 \cdot B$$

$$Cr = \delta \cdot Y + 0.439 \cdot R - 0.399 \cdot G - 0.040 \cdot B$$

where $$\lambda \geq 0.399/0.614 = 0.552$$

$$\delta \geq 0.399/0.614 = 0.650$$

It turns out that if the $\lambda$, factor is equal to 0.552; both the red and the green components are exactly cancelled, in which case the Cb information can be provided with pure blue light. Similarly, setting $\delta = 0.650$ cancels out the blue and green components for Cr which becomes pure red. This particular example is illustrated in FIG. 153E, which also depicts $\lambda$, and $\delta$ as integer multiples of $½^8$. This is a convenient approximation for the digital frame reconstruction.

In the case of the Y-Cb-Y-Cr pulsing scheme, the image data is already in the YCbCr space following the color fusion. Therefore, in this case it makes sense to perform luminance and chrominance based operations up front, before converting back to linear RGB to perform the color correction etc.

The color fusion process is more straightforward than de-mosaic, which is necessitated by the Bayer pattern (see FIG. 153C), since there is no spatial interpolation. It does require buffering of frames though in order to have all of the necessary information available for each pixel. In one general aspect, data for the Y-Cb-Y-Cr pattern may be pipelined to yield one full color image per two raw captured images. This is accomplished by using each chrominance sample twice. In FIG. 153F the specific example of a 120 Hz frame capture rate providing 60 Hz final video is depicted.

Additional disclosures regarding the control of the laser components of an illumination system as depicted in FIGS. 153B-153F for use in a surgical visualization system 108 may be found in U.S. Patent Application Publication No. 2014/0160318, titled YCBCR PULSED ILLUMINATION SCHEME IN A LIGHT DEFICIENT ENVIRONMENT, filed on Jul. 26, 2013, which issued on Dec. 6, 2016 as U.S. Pat. No. 9,516,239, and U.S. Patent Application Publication No. 2014/0160319, titled CONTINUOUS VIDEO IN A LIGHT DEFICIENT ENVIRONMENT, filed on Jul. 26, 2013, which issued on Aug. 22, 2017 as U.S. Pat. No. 9,743,016, the contents thereof being incorporated by reference herein in their entirety and for all purposes.

Subsurface Vascular Imaging

During a surgical procedure, a surgeon may be required to manipulate tissues to effect a desired medical outcome. The actions of the surgeon are limited by what is visually observable in the surgical site. Thus, the surgeon may not be aware, for example, of the disposition of vascular structures that underlie the tissues being manipulated during the procedure.

Since the surgeon is unable to visualize the vasculature beneath a surgical site, the surgeon may accidentally sever one or more critical blood vessels during the procedure.

Therefore, it is desirable to have a surgical visualization system that can acquire imaging data of the surgical site for presentation to a surgeon in which the presentation can include information related to the presence of vascular structures located beneath the surface of a surgical site.

Some aspects of the present disclosure further provide for a control circuit configured to control the illumination of a surgical site using one or more illumination sources such as laser light sources and to receive imaging data from one or more image sensors. In some aspects, the present disclosure provides for a non-transitory computer readable medium storing computer readable instructions that, when executed, cause a device to detect a blood vessel in a tissue and determine its depth below the surface of the tissue.

In some aspects, a surgical image acquisition system may include a plurality of illumination sources wherein each illumination source is configured to emit light having a specified central wavelength, a light sensor configured to receive a portion of the light reflected from a tissue sample when illuminated by the one or more of the plurality of illumination sources, and a computing system. The computing system may be configured to: receive data from the light sensor when the tissue sample is illuminated by each of the plurality of illumination sources; determine a depth location of a structure within the tissue sample based on the data received by the light sensor when the tissue sample is illuminated by each of the plurality of illumination sources, and calculate visualization data regarding the structure and the depth location of the structure. In some aspects, the visualization data may have a data format that may be used by a display system, and the structure may comprise one or more vascular tissues.

Vascular Imaging Using NIR Spectroscopy

In one aspect, a surgical image acquisition system may include an independent color cascade of illumination sources comprising visible light and light outside of the visible range to image one or more tissues within a surgical site at different times and at different depths. The surgical image acquisition system may further detect or calculate characteristics of the light reflected and/or refracted from the surgical site. The characteristics of the light may be used to provide a composite image of the tissue within the surgical site as well as provide an analysis of underlying tissue not directly visible at the surface of the surgical site. The surgical image acquisition system may determine tissue depth location without the need for separate measurement devices.

In one aspect, the characteristic of the light reflected and/or refracted from the surgical site may be an amount of absorbance of light at one or more wavelengths. Various chemical components of individual tissues may result in specific patterns of light absorption that are wavelength dependent.

In one aspect, the illumination sources may comprise a red laser source and a near infrared laser source, wherein the one or more tissues to be imaged may include vascular tissue such as veins or arteries. In some aspects, red laser sources (in the visible range) may be used to image some aspects of underlying vascular tissue based on spectroscopy in the visible red range. In some non-limiting examples, a red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some other aspects, near infrared laser sources may be used to image underlying vascular tissue based on near infrared spectroscopy. In some non-limiting examples, a near infrared laser source may emit illumination have a wavelength that may range between 750-3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. It may be recognized that underlying vascular tissue may be probed using a combination of red and infrared spectroscopy. In some examples, vascular tissue may be probed using a red laser source having a peak wavelength at about 660 nm and a near IR laser source having a peak wavelength at about 750 nm or at about 850 nm.

Near infrared spectroscopy (NIRS) is a non-invasive technique that allows determination of tissue oxygenation based on spectro-photometric quantitation of oxy- and deoxyhemoglobin within a tissue. In some aspects, NIRS can be used to image vascular tissue directly based on the difference in illumination absorbance between the vascular tissue and non-vascular tissue. Alternatively, vascular tissue can be indirectly visualized based on a difference of illumination absorbance of blood flow in the tissue before and after the application of physiological interventions, such as arterial and venous occlusions methods.

Instrumentation for near-IR (NIR) spectroscopy may be similar to instruments for the UV-visible and mid-IR ranges. Such spectroscopic instruments may include an illumination source, a detector, and a dispersive element to select a specific near-IR wavelength for illuminating the tissue sample. In some aspects, the source may comprise an incandescent light source or a quartz halogen light source. In some aspects, the detector may comprise semiconductor (for example, an InGaAs) photodiode or photo array. In some aspects, the dispersive element may comprise a prism or, more commonly, a diffraction grating. Fourier transform NIR instruments using an interferometer are also common, especially for wavelengths greater than about 1000 nm. Depending on the sample, the spectrum can be measured in either reflection or transmission mode.

FIG. 154 depicts schematically one example of instrumentation 2400 similar to instruments for the UV-visible and mid-IR ranges for NIR spectroscopy. A light source 2402 may emit a broad spectral range of illumination 2404 that may impinge upon a dispersive element 2406 (such as a prism or a diffraction grating). The dispersive element 2406 may operate to select a narrow wavelength portion 2408 of the light emitted by the broad spectrum light source 2402, and the selected portion 2408 of the light may illuminate the tissue 2410. The light reflected from the tissue 2412 may be directed to a detector 2416 (for example, by means of a dichroic mirror 2414) and the intensity of the reflected light 2412 may be recorded. The wavelength of the light illuminating the tissue 2410 may be selected by the dispersive element 2406. In some aspects, the tissue 2410 may be illuminated only by a single narrow wavelength portion 2408 selected by the dispersive element 2406 form the light source 2402. In other aspects, the tissue 2410 may be scanned with a variety of narrow wavelength portions 2408 selected by the dispersive element 2406. In this manner, a spectroscopic analysis of the tissue 2410 may be obtained over a range of NIR wavelengths.

FIG. 155 depicts schematically one example of instrumentation 2430 for determining NIRS based on Fourier transform infrared imaging. In FIG. 155, a laser source emitting 2432 light in the near IR range 2434 illuminates a tissue sample 2440. The light reflected 2436 by the tissue 2440 is reflected 2442 by a mirror, such as a dichroic mirror 2444, to a beam splitter 2446. The beam splitter 2446 directs one portion of the light 2448 reflected 2436 by the tissue 2440 to a stationary mirror 2450 and one portion of the light 2452 reflected 2436 by the tissue 2440 a moving mirror 2454. The moving mirror 2454 may oscillate in position based on an affixed piezoelectric transducer activated by a sinusoidal voltage having a voltage frequency. The position of the moving mirror 2454 in space corresponds to the frequency of the sinusoidal activation voltage of the piezoelectric transducer. The light reflected from the moving mirror and the stationary mirror may be recombined 2458 at the beam splitter 2446 and directed to a detector 2456. Computational components may receive the signal output of the detector 2456 and perform a Fourier transform (in time) of the received signal. Because the wavelength of the light received from the moving mirror 2454 varies in time with respect to the wavelength of the light received from the stationary mirror 2450, the time-based Fourier transform of the recombined light corresponds to a wavelength-based Fourier transform of the recombined light 2458. In this manner, a wavelength-based spectrum of the light reflected from the tissue 2440 may be determined and spectral characteristics of the light reflected 2436 from the tissue 2440 may be obtained. Changes in the absorbance of the illumination in spectral components from the light reflected from the tissue 2440 may thus indicate the presence or absence of tissue having specific light absorbing properties (such as hemoglobin).

An alternative to near infrared light to determine hemoglobin oxygenation would be the use of monochromatic red light to determine the red light absorbance characteristics of hemoglobin. The absorbance characteristics of red light having a central wavelength of about 660 nm by the hemoglobin may indicate if the hemoglobin is oxygenated (arterial blood) or deoxygenated (venous blood).

In some alternative surgical procedures, contrasting agents can be used to improve the data that is collected on oxygenation and tissue oxygen consumption. In one non-limiting example, NIRS techniques may be used in conjunction with a bolus injection of a near-IR contrast agent such as indocyanine green (ICG) which has a peak absorbance at about 800 nm. ICG has been used in some medical procedures to measure cerebral blood flow.

Vascular Imaging Using Laser Doppler Flowmetry

In one aspect, the characteristic of the light reflected and/or refracted from the surgical site may be a Doppler shift of the light wavelength from its illumination source.

Laser Doppler flowmetry may be used to visualize and characterized a flow of particles moving relative to an effectively stationary background. Thus, laser light scattered by moving particles, such as blood cells, may have a different wavelength than that of the original illuminating laser source. In contrast, laser light scattered by the effectively stationary background (for example, the vascular tissue) may have the same wavelength of that of the original illuminating laser source. The change in wavelength of the scattered light from the blood cells may reflect both the direction of the flow of the blood cells relative to the laser source as well as the blood cell velocity. FIGS. 156A-C illustrate the change in wavelength of light scattered from blood cells that may be moving away from (FIG. 156A) or towards (FIG. 156C) the laser light source.

In each of FIGS. 156A-C, the original illuminating light 2502 is depicted having a relative central wavelength of 0. It may be observed from FIG. 156A that light scattered from blood cells moving away from the laser source 2504 has a wavelength shifted by some amount 2506 to a greater wavelength relative to that of the laser source (and is thus red shifted). It may also be observed from FIG. 156C that light scattered from blood cells moving towards from the laser source 2508 has a wavelength shifted by some amount 2510 to a shorter wavelength relative to that of the laser source (and is thus blue shifted). The amount of wavelength shift (for example 2506 or 2510) may be dependent on the velocity of the motion of the blood cells. In some aspects, an amount of a red shift (2506) of some blood cells may be about the same as the amount of blue shift (2510) of some other blood cells. Alternatively, an amount of a red shift (2506) of some blood cells may differ from the amount of blue shift (2510) of some other blood cells Thus, the velocity of the blood cells flowing away from the laser source as depicted in FIG. 156A may be less than the velocity of the blood cells flowing towards the laser source as depicted in FIG. 156C based on the relative magnitude of the wavelength shifts (2506 and 2510). In contrast, and as depicted in FIG. 156B, light scattered from tissue not moving relative to the laser light source (for example blood vessels 2512 or non-vascular tissue 2514) may not demonstrate any change in wavelength.

FIG. 157 depicts an aspect of instrumentation 2530 that may be used to detect a Doppler shift in laser light scattered from portions of a tissue 2540. Light 2534 originating from a laser 2532 may pass through a beam splitter 2544. Some portion of the laser light 2536 may be transmitted by the beam splitter 2544 and may illuminate tissue 2540. Another portion of the laser light may be reflected 2546 by the beam splitter 2544 to impinge on a detector 2550. The light back-scattered 2542 by the tissue 2540 may be directed by the beam splitter 2544 and also impinge on the detector 2550. The combination of the light 2534 originating from the laser 2532 with the light back-scattered 2542 by the tissue 2540 may result in an interference pattern detected by the detector 2550. The interference pattern received by the detector 2550 may include interference fringes resulting from the combination of the light 2534 originating from the laser 2532 and the Doppler shifted (and thus wavelength shifted) light back-scattered 2452 from the tissue 2540.

It may be recognized that back-scattered light 2542 from the tissue 2540 may also include back scattered light from boundary layers within the tissue 2540 and/or wavelength-specific light absorption by material within the tissue 2540. As a result, the interference pattern observed at the detector 2550 may incorporate interference fringe features from these additional optical effects and may therefore confound the calculation of the Doppler shift unless properly analyzed.

FIG. 158 depicts some of these additional optical effects. It is well known that light traveling through a first optical medium having a first refractive index, n1, may be reflected at an interface with a second optical medium having a second refractive index, n2. The light transmitted through the second optical medium will have a transmission angle relative to the interface that differs from the angle of the incident light based on a difference between the refractive indices n1 and n2 (Snell's Law). FIG. 158 illustrates the effect of Snell's Law on light impinging on the surface of a multi-component tissue 2150, as may be presented in a surgical field. The multi-component tissue 2150 may be composed of an outer tissue layer 2152 having a refractive index n1 and a buried tissue, such as a blood vessel having a vessel wall 2156. The blood vessel wall 2156 may be characterized by a refractive index n2. Blood may flow within the lumen of the blood vessel 2160. In some aspects, it may be important during a surgical procedure to determine the position of the blood vessel 2160 below the surface 2154 of the outer tissue layer 2152 and to characterize the blood flow using Doppler shift techniques.

An incident laser light 2170a may be used to probe for the blood vessel 2160 and may be directed on the top surface 2154 of the outer tissue layer 2152. A portion 2172 of the incident laser light 2170a may be reflected at the top surface 2154. Another portion 2170b of the incident laser light 2170a may penetrate the outer tissue layer 2152. The reflected portion 2172 at the top surface 2154 of the outer tissue layer 2152 has the same path length of the incident light 2170a, and therefore has the same wavelength and phase of the incident light 2170a. However, the portion 2170b of light transmitted into the outer tissue layer 2152 will have a transmission angle that differs from the incidence angle of the light impinging on the tissue surface because the outer tissue layer 2152 has an index of refraction n1 that differs from the index of refraction of air.

If the portion of light transmitted through the outer tissue layer 2152 impinges on a second tissue surface 2158, for example of the blood vessel wall 2156, some portion 2174a,b of light will be reflected back towards the source of the incident light 2170a. The light thus reflected 2174a at the interface between the outer tissue layer 2152 and the blood vessel wall 2156 will have the same wavelength as the incident light 2170a, but will be phase shifted due to the change in the light path length. Projecting the light reflected 2174a,b from the interface between the outer tissue layer 2152 and the blood vessel wall 2156 along with the incident light on the sensor, will produce an interference pattern based on the phase difference between the two light sources.

Further, a portion of the incident light 2170a may be transmitted through the blood vessel wall 2156 and penetrate into the blood vessel lumen 2160. This portion of the incident light 2170c may interact with the moving blood cells in the blood vessel lumen 2160 and may be reflected back 2176a-c towards the source of the impinging light having a wavelength Doppler shifted according to the velocity of the blood cells, as disclosed above. The Doppler shifted light reflected 2176a-c from the moving blood cells may be projected along with the incident light on the sensor, resulting in an interference pattern having a fringe pattern based on the wavelength difference between the two light sources.

In FIG. 158, a light path 2178 is presented of light impinging on the red blood cells in the blood vessel lumen 2160 if there are no changes in refractive index between the emitted light and the light reflected by the moving blood cells. In this example, only a Doppler shift in the reflected light wavelength can be detected. However, the light reflected by the blood cells (2176a-c) may incorporate phase changes due to the variation in the tissue refractive indices in addition to the wavelength changes due to the Doppler Effect.

Thus, it may be understood that if the light sensor receives the incident light, the light reflected from one or more tissue interfaces (2172, and 2174a,b) and the Doppler shifted light from the blood cells (2176a-c), the interference pattern thus produced on the light sensor may include the effects due to the Doppler shift (change in wavelength) as well as the effects due to the change in refractive index within the tissue (change in phase). As a result, a Doppler analysis of the light reflected by the tissue sample may produce erroneous results if the effects due to changes in the refractive index within the sample are not compensated for.

FIG. 159 illustrates an example of the effects on a Doppler analysis of light that impinge 2250 on a tissue sample to determine the depth and location of an underlying blood vessel. If there is no intervening tissue between the blood vessel and the tissue surface, the interference pattern detected at the sensor may be due primarily to the change in wavelength reflected from the moving blood cells. As a result, a spectrum 2252 derived from the interference pattern may generally reflect only the Doppler shift of the blood cells. However, if there is intervening tissue between the blood vessel and the tissue surface, the interference pattern detected at the sensor may be due to a combination of the change in wavelength reflected from the moving blood cells and the phase shift due to the refractive index of the intervening tissue. A spectrum 2254 derived from such an interference pattern, may result in the calculation of the Doppler shift that is confounded due to the additional phase change in the reflected light. In some aspects, if information regarding the characteristics (thickness and refractive index) of the intervening tissue is known, the resulting spectrum 2256 may be corrected to provide a more accurate calculation of the change in wavelength.

It is recognized that the tissue penetration depth of light is dependent on the wavelength of the light used. Thus, the wavelength of the laser source light may be chosen to detect particle motion (such a blood cells) at a specific range of tissue depth. FIGS. 160A-C depict schematically a means for detect moving particles such as blood cells at a variety of tissue depths based on the laser light wavelength. As illustrated in FIG. 160A, a laser source 2340 may direct an incident beam of laser light 2342 onto a surface 2344 of a surgical site. A blood vessel 2346 (such as a vein or artery) may be disposed within the tissue 2348 at some depth δ from the tissue surface. The penetration depth 2350 of a laser into a tissue 2348 may be dependent at least in part on the laser wavelength. Thus, laser light having a wavelength in the red range of about 635 nm to about 660 nm, may penetrate the tissue 2351a to a depth of about 1 mm. Laser light having a wavelength in the green range of about 520 nm to about 532 nm may penetrate the tissue 2351b to a depth of about 2-3 mm. Laser light having a wavelength in the blue range of about 405 nm to about 445 nm may penetrate the tissue 2351c to a depth of about 4 mm or greater. In the example depicted in FIGS. 160A-C, a blood vessel 2346 may be located at a depth δ of about 2-3 mm below the tissue surface. Red laser light will not penetrate to this depth and thus will not detect blood cells flowing within this vessel. However, both green and blue laser light can penetrate this depth. Therefore, scattered green and blue laser light from the blood cells within the blood vessel 2346 may demonstrate a Doppler shift in wavelength.

FIG. 160B illustrates how a Doppler shift 2355 in the wavelength of reflected laser light may appear. The emitted light (or laser source light 2342) impinging on a tissue surface 2344 may have a central wavelength 2352. For example, light from a green laser may have a central wavelength 2352 within a range of about 520 nm to about 532 nm. The reflected green light may have a central wavelength 2354 shifted to a longer wavelength (red shifted) if the light was reflected from a particle such as a red blood cell that is moving away from the detector. The difference between the central wavelength 2352 of the emitted laser light and the central wavelength 2354 of the emitted laser light comprises the Doppler shift 2355.

As disclosed above with respect to FIGS. 158 and 159, laser light reflected from structures within a tissue 2348 may also show a phase shift in the reflected light due to changes in the index of refraction arising from changes in tissue structure or composition. The emitted light (or laser source light 2342) impinging on a tissue surface 2344 may have a first phase characteristic 2356. The reflected laser light may have a second phase characteristic 2358. It may be recognized that blue laser light that can penetrate tissue to a depth of about 4 mm or greater 2351c may encounter a greater variety of tissue structures than red laser light (about 1 mm 2351a) or green laser light (about 2-3 mm 2351b). Consequently, as illustrated in FIG. 160C, the phase shift 2358 of reflected blue laser light may be significant at least due to the depth of penetration.

FIG. 160D illustrates aspects of illuminating tissue by red 2360a, green 2360b and blue 2360c laser light in a sequential manner. In some aspects, a tissue may be probed by red 2360a, green 2360b and blue 2360c laser illumination in a sequential manner. In some alternative examples, one or more combinations of red 2360a, green 2360b, and blue 2360c laser light, as depicted in FIGS. 153D-153F and disclosed above, may be used to illuminate the tissue according to a defined illumination sequence. 30D illustrates the effect of such illumination on a CMOS imaging sensor 2362a-d over time. Thus, at a first time $t_1$, the CMOS sensor 2362a may be illuminated by the red 2360a laser. At a second time $t_2$ the CMOS sensor 2362b may be illuminated by the green 2360b laser. At a third time $t_3$, the CMOS sensor 2362c may be illuminated by the blue 2360c laser. The illumination cycle may then be repeated starting at a fourth time $t_4$ in which the CMOS sensor 2362d may be illuminated by the red 2360a lase again. It may be recognized that sequential illumination of the tissue by laser illumination at differing wavelengths may permit a Doppler analysis at varying tissue depths over time. Although red 2360a, green 2360b and blue 2360c laser sources may be used to illuminate the surgical site, it may be recognized that other wavelengths outside of visible light (such as in the infrared or ultraviolet regions) may be used to illuminate the surgical site for Doppler analysis.

FIG. 161 illustrates an example of a use of Doppler imaging to detect the present of blood vessels not otherwise viewable at a surgical site 2600. In FIG. 161, a surgeon may wish to excise a tumor 2602 found in the right superior posterior lobe 2604 of a lung. Because the lungs are highly vascular, care must be taken to identify only those blood vessels associate with the tumor and to seal only those vessels without compromising the blood flow to the non-affected portions of the lung. In FIG. 161, the surgeon has identified the margin 2606 of the tumor 2604. The surgeon may then cut an initial dissected area 2608 in the margin region 2606, and exposed blood vessels 2610 may be observed for cutting and sealing. The Doppler imaging detector 2620 may be used to locate and identify blood vessels not observable 2612 in the dissected area. An imaging system may receive data from the Doppler imaging detector 2620 for analysis and display of the data obtained from the surgical site 2600. In some aspects, the imaging system may include a display to illustrate the surgical site 2600 including a visible image of the surgical site 2600 along with an image overlay of the hidden blood vessels 2612 on the image of the surgical site 2600.

In the scenario disclosed above regarding FIG. 161, a surgeon wishes to sever blood vessels that supply oxygen and nutrients to a tumor while sparing blood vessels associated with non-cancerous tissue. Additionally, the blood vessels may be disposed at different depths in or around the surgical site 2600. The surgeon must therefore identify the position (depth) of the blood vessels as well as determine if they are appropriate for resection. FIG. 162 illustrates one method for identifying deep blood vessels based on a Doppler shift of light from blood cells flowing therethrough. As disclosed above, red laser light has a penetration depth of about 1 mm and green laser light has a penetration depth of about 2-3 mm. However, a blood vessel having a below-surface depth of 4 mm or more will be outside the penetration depths at these wavelengths. Blue laser light, however, can detect such blood vessels based on their blood flow.

FIG. 162 depicts the Doppler shift of laser light reflected from a blood vessel at a specific depth below a surgical site. The site may be illuminated by red laser light, green laser light, and blue laser light. The central wavelength 2630 of the illuminating light may be normalized to a relative central 3631. If the blood vessel lies at a depth of 4 or more mm below the surface of the surgical site, neither the red laser light nor the green laser light will be reflected by the blood vessel. Consequently, the central wavelength 2632 of the reflected red light and the central wavelength 2634 of the reflected green light will not differ much from the central wavelength 2630 of the illuminating red light or green light, respectively. However, if the site is illuminated by blue laser light, the central wavelength 2638 of the reflected blue light 2636 will differ from the central wavelength 2630 of the illuminating blue light. In some instances, the amplitude of the reflected blue light 2636 may also be significantly reduced from the amplitude of the illuminating blue light. A surgeon may thus determine the presence of a deep lying blood vessel along with its approximate depth, and thereby avoiding the deep blood vessel during surface tissue dissection.

FIGS. 163 and 164 illustrates schematically the use of laser sources having differing central wavelengths (colors) for determining the approximate depth of a blood vessel beneath the surface of a surgical site. FIG. 163 depicts a first surgical site 2650 having a surface 2654 and a blood vessel 2656 disposed below the surface 2654. In one method, the blood vessel 2656 may be identified based on a Doppler shift of light impinging on the flow 2658 of blood cells within the blood vessel 2656. The surgical site 2650 may be illuminated by light from a number of lasers 2670, 2676, 2682, each laser being characterized by emitting light at one of several different central wavelengths. As noted above, illumination by a red laser 2670 can only penetrate tissue by about 1 mm. Thus, if the blood vessel 2656 was located at a depth of less than 1 mm 2672 below the surface 2654, the red laser illumination would be reflected 2674 and a Doppler shift of the reflected red illumination 2674 may be determined. Further, as noted above, illumination by a green laser 2676 can only penetrate tissue by about 2-3 mm. If the blood vessel 2656 was located at a depth of about 2-3 mm 2678 below the surface 2654, the green laser illumination would be reflected 2680 while the red laser illumination 2670 would not, and a Doppler shift of the reflected green illumination 2680 may be determined. However, as depicted in FIG. 163, the blood vessel 2656 is located at a depth of about 4 mm 2684 below the surface 2654. Therefore, neither the red laser illumination 2670 nor the green laser illumination 2676 would be reflected. Instead, only the blue laser illumination would be reflected 2686 and a Doppler shift of the reflected blue illumination 2686 may be determined.

In contrast to the blood vessel 2656 depicted in FIG. 163, the blood vessel 2656' depicted in FIG. 164 is located closer to the surface of the tissue at the surgical site. Blood vessel 2656' may also be distinguished from blood vessel 2656 in that blood vessel 2656' is illustrated to have a much thicker wall 2657. Thus, blood vessel 2656' may be an example of an artery while blood vessel 2656 may be an example of a vein because arterial walls are known to be thicker than venous walls. In some examples, arterial walls may have a thickness of about 1.3 mm. As disclosed above, red laser illumination 2670' can penetrate tissue to a depth of about 1 mm 2672'. Thus, even if a blood vessel 2656' is exposed at a surgical site (see 2610 at FIG. 161), red laser light that is reflected 2674' from the surface of the blood vessel 2656', may not be able to visualize blood flow 2658' within the blood vessel 2656' under a Doppler analysis due to the thickness of the blood vessel wall 2657. However, as disclosed above, green laser light impinging 2676' on the surface of a tissue may penetrate to a depth of about 2-3 mm 2678'. Further, blue laser light impinging 2682' on the surface of a tissue may penetrate to a depth of about 4 mm 2684'. Consequently, green laser light may be reflected 2680' from the blood cells flowing 2658' within the blood vessel 2656' and blue laser light may be reflected 2686' from the blood cells flowing 2658' within the blood vessel 2656'. As a result, a Doppler analysis of the reflected green light 2680' and reflected blue light 2686' may provide information regarding blood flow in near-surface blood vessel, especially the approximate depth of the blood vessel.

As disclosed above, the depth of blood vessels below the surgical site may be probed based on wavelength-dependent Doppler imaging. The amount of blood flow through such a blood vessel may also be determined by speckle contrast (interference) analysis. Doppler shift may indicate a moving particle with respect to a stationary light source. As disclosed above, the Doppler wavelength shift may be an indication of the velocity of the particle motion. Individual particles such as blood cells may not be separately observable. However, the velocity of each blood cell will produce a proportional Doppler shift. An interference pattern may be generated by the combination of the light back-scattered from multiple blood cells due to the differences in the Doppler shift of the back-scattered light from each of the blood cells. The interference pattern may be an indication of the number density of blood cells within a visualization frame. The interference pattern may be termed speckle contrast. Speckle contrast analysis may be calculated using a full frame $300x300$ CMOS imaging array, and the speckle contrast may be directly related to the amount of moving particles (for example blood cells) interacting with the laser light over a given exposure period.

A CMOS image sensor may be coupled to a digital signal processor (DSP). Each pixel of the sensor may be multiplexed and digitized. The Doppler shift in the light may be analyzed by looking at the source laser light in comparison to the Doppler shifted light. A greater Doppler shift and speckle may be related to a greater number of blood cells and their velocity in the blood vessel.

FIG. 165 depicts an aspect of a composite visual display 2800 that may be presented a surgeon during a surgical procedure. The composite visual display 2800 may be constructed by overlaying a white light image 2830 of the surgical site with a Doppler analysis image 2850.

In some aspects, the white light image 2830 may portray the surgical site 2832, one or more surgical incisions 2834, and the tissue 2836 readily visible within the surgical incision 2834. The white light image 2830 may be generated by illuminating 2840 the surgical site 2832 with a white light source 2838 and receiving the reflected white light 2842 by an optical detector. Although a white light source 2838 may be used to illuminate the surface of the surgical site, in one aspect, the surface of the surgical site may be visualized using appropriate combinations of red 2854, green 2856, and blue 2858 laser light as disclosed above with respect to FIGS. 153C-153F.

In some aspects, the Doppler analysis image 2850 may include blood vessel depth information along with blood flow information 2852 (from speckle analysis). As disclosed above, blood vessel depth and blood flow velocity may be obtained by illuminating the surgical site with laser light of multiple wavelengths, and determining the blood vessel depth and blood flow based on the known penetration depth of the light of a particular wavelength. In general, the surgical site 2832 may be illuminated by light emitted by one or more lasers such as a red leaser 2854, a green laser 2856, and a blue laser 2858. A CMOS detector 2872 may receive the light reflected back (2862, 2866, 2870) from the surgical site 2832 and its surrounding tissue. The Doppler analysis image 2850 may be constructed 2874 based on an analysis of the multiple pixel data from the CMOS detector 2872.

In one aspect, a red laser 2854 may emit red laser illumination 2860 on the surgical site 2832 and the reflected light 2862 may reveal surface or minimally subsurface structures. In one aspect, a green laser 2856 may emit green laser illumination 2864 on the surgical site 2832 and the reflected light 2866 may reveal deeper subsurface characteristics. In another aspect, a blue laser 2858 may emit blue laser illumination 2868 on the surgical site 2832 and the reflected light 2870 may reveal, for example, blood flow within deeper vascular structures. In addition, the speckle contrast analysis my present the surgeon with information regarding the amount and velocity of blood flow through the deeper vascular structures.

Although not depicted in FIG. 165, it may be understood that the imaging system may also illuminate the surgical site with light outside of the visible range. Such light may include infrared light and ultraviolet light. In some aspects, sources of the infrared light or ultraviolet light may include broad-band wavelength sources (such as a tungsten source, a tungsten-halogen source, or a deuterium source). In some other aspects, the sources of the infrared or ultraviolet light may include narrow-band wavelength sources (IR diode lasers, UV gas lasers or dye lasers).

FIG. 166 is a flow chart 2900 of a method for determining a depth of a surface feature in a piece of tissue. An image acquisition system may illuminate 2910 a tissue with a first light beam having a first central frequency and receive 2912 a first reflected light from the tissue illuminated by the first light beam. The image acquisition system may then calculate 2914 a first Doppler shift based on the first light beam and the first reflected light. The image acquisition system may then illuminate 2916 the tissue with a second light beam having a second central frequency and receive 2918 a second reflected light from the tissue illuminated by the second light beam. The image acquisition system may then calculate 2920 a second Doppler shift based on the second light beam and the second reflected light. The image acquisition system may then calculate 2922 a depth of a tissue feature based at least in part on the first central wavelength, the first Doppler shift, the second central wavelength, and the second Doppler shift. In some aspects, the tissue features may include the presence of moving particles, such as blood cells moving within a blood vessel, and a direction and velocity of flow of the moving particles. It may be understood that the method may be extended to include illumination of the tissue by any one or more additional light beams. Further, the system may calculate an image comprising a combination of an image of the tissue surface and an image of the structure disposed within the tissue.

In some aspects, multiple visual displays may be used. For example, a 3D display may provide a composite image displaying the combined white light (or an appropriate combination of red, green, and blue laser light) and laser Doppler image. Additional displays may provide only the white light display or a displaying showing a composite white light display and an NIRS display to visualize only the blood oxygenation response of the tissue. However, the NIRS display may not be required every cycle allowing for response of tissue.

Subsurface Tissue Characterization Using Multispectral OCT

During a surgical procedure, the surgeon may employ "smart" surgical devices for the manipulation of tissue. Such devices may be considered "smart" in that they include automated features to direct, control, and/or vary the actions of the devices based parameters relevant to their uses. The parameters may include the type and/or composition of the tissue being manipulated. If the type and/or composition of the tissue being manipulated is unknown, the actions of the smart devices may be inappropriate for the tissue being manipulated. As a result, tissues may be damaged or the manipulation of the tissue may be ineffective due to inappropriate settings of the smart device.

The surgeon may manually attempt to vary the parameters of the smart device in a trial-and-error manner, resulting in an inefficient and lengthy surgical procedure.

Therefore, it is desirable to have a surgical visualization system that can probe tissue structures underlying a surgical site to determine their structural and compositional characteristics, and to provide such data to smart surgical instruments being used in a surgical procedure.

Some aspects of the present disclosure further provide for a control circuit configured to control the illumination of a surgical site using one or more illumination sources such as laser light sources and to receive imaging data from one or more image sensors. In some aspects, the present disclosure provides for a non-transitory computer readable medium storing computer readable instructions that, when executed, cause a device to characterize structures below the surface at a surgical site and determine the depth of the structures below the surface of the tissue.

In some aspects, a surgical image acquisition system may comprise a plurality of illumination sources wherein each illumination source is configured to emit light having a specified central wavelength, a light sensor configured to receive a portion of the light reflected from a tissue sample when illuminated by the one or more of the plurality of illumination sources, and a computing system. The computing system may be configured to receive data from the light sensor when the tissue sample is illuminated by each of the plurality of illumination sources, calculate structural data related to a characteristic of a structure within the tissue sample based on the data received by the light sensor when the tissue sample is illuminated by each of the illumination sources, and transmit the structural data related to the characteristic of the structure to be received by a smart surgical device. In some aspects, the characteristic of the structure is a surface characteristic or a structure composition.

In one aspect, a surgical system may include multiple laser light sources and may receive laser light reflected from a tissue. The light reflected from the tissue may be used by the system to calculate surface characteristics of components disposed within the tissue. The characteristics of the components disposed within the tissue may include a composition of the components and/or a metric related to surface irregularities of the components.

In one aspect, the surgical system may transmit data related to the composition of the components and/or metrics related to surface irregularities of the components to a second instrument to be used on the tissue to modify the control parameters of the second instrument.

In some aspects, the second device may be an advanced energy device and the modifications of the control parameters may include a clamp pressure, an operational power level, an operational frequency, and a transducer signal amplitude.

As disclosed above, blood vessels may be detected under the surface of a surgical site base on the Doppler shift in light reflected by the blood cells moving within the blood vessels.

Laser Doppler flowmetry may be used to visualize and characterized a flow of particles moving relative to an effectively stationary background. Thus, laser light scattered by moving particles, such as blood cells, may have a different wavelength than that of the original illuminating laser source. In contrast, laser light scattered by the effectively stationary background (for example, the vascular tissue) may have the same wavelength of that of the original illuminating laser source. The change in wavelength of the scattered light from the blood cells may reflect both the direction of the flow of the blood cells relative to the laser source as well as the blood cell velocity. As previously disclosed, FIGS. 156A-C illustrate the change in wavelength of light scattered from blood cells that may be moving away from (FIG. 156A) or towards (FIG. 156C) the laser light source.

In each of FIGS. 156A-C, the original illuminating light 2502 is depicted having a relative central wavelength of 0. It may be observed from FIG. 156A that light scattered from blood cells moving away from the laser source 2504 has a wavelength shifted by some amount 2506 to a greater wavelength relative to that of the laser source (and is thus red shifted). It may also be observed from FIG. 154C that light scattered from blood cells moving towards from the laser source 2508 has a wavelength shifted by some amount 2510 to a shorter wavelength relative to that of the laser source (and is thus blue shifted). The amount of wavelength shift (for example 2506 or 2510) may be dependent on the velocity of the motion of the blood cells. In some aspects, an amount of a red shift (2506) of some blood cells may be about the same as the amount of blue shift (2510) of some other blood cells. Alternatively, an amount of a red shift (2506) of some blood cells may differ from the amount of blue shift (2510) of some other blood cells Thus, the velocity of the blood cells flowing away from the laser source as depicted in FIG. 154A may be less than the velocity of the blood cells flowing towards the laser source as depicted in FIG. 156C based on the relative magnitude of the wavelength shifts (2506 and 2510). In contrast, and as depicted in FIG. 156B, light scattered from tissue not moving relative to the laser light source (for example blood vessels 2512 or non-vascular tissue 2514) may not demonstrate any change in wavelength.

As previously disclosed, FIG. 157 depicts an aspect of instrumentation 2530 that may be used to detect a Doppler shift in laser light scattered from portions of a tissue 2540. Light 2534 originating from a laser 2532 may pass through a beam splitter 2544. Some portion of the laser light 2536 may be transmitted by the beam splitter 2544 and may illuminate tissue 2540. Another portion of the laser light may be reflected 2546 by the beam splitter 2544 to impinge on a detector 2550. The light back-scattered 2542 by the tissue 2540 may be directed by the beam splitter 2544 and also impinge on the detector 2550. The combination of the light 2534 originating from the laser 2532 with the light back-scattered 2542 by the tissue 2540 may result in an interference pattern detected by the detector 2550. The interference pattern received by the detector 2550 may include interference fringes resulting from the combination of the light 2534 originating from the laser 2532 and the Doppler shifted (and thus wavelength shifted) light back-scattered 2452 from the tissue 2540.

It may be recognized that back-scattered light 2542 from the tissue 2540 may also include back scattered light from boundary layers within the tissue 2540 and/or wavelength-specific light absorption by material within the tissue 2540. As a result, the interference pattern observed at the detector 2550 may incorporate interference fringe features from these additional optical effects and may therefore confound the calculation of the Doppler shift unless properly analyzed.

It may be recognized that light reflected from the tissue may also include back scattered light from boundary layers within the tissue and/or wavelength-specific light absorption by material within the tissue. As a result, the interference pattern observed at the detector may incorporate fringe features that may confound the calculation of the Doppler shift unless properly analyzed.

As previously disclosed, FIG. 158 depicts some of these additional optical effects. It is well known that light traveling through a first optical medium having a first refractive index, n1, may be reflected at an interface with a second optical medium having a second refractive index, n2. The light transmitted through the second optical medium will have a transmission angle relative to the interface that differs from the angle of the incident light based on a difference between the refractive indices n1 and n2 (Snell's Law). FIG. 156 illustrates the effect of Snell's Law on light impinging on the surface of a multi-component tissue 2150, as may be presented in a surgical field. The multi-component tissue 2150 may be composed of an outer tissue layer 2152 having a refractive index n1 and a buried tissue, such as a blood vessel having a vessel wall 2156. The blood vessel wall 2156 may be characterized by a refractive index n2. Blood may flow within the lumen of the blood vessel 2160. In some aspects, it may be important during a surgical procedure to determine the position of the blood vessel 2160 below the surface 2154 of the outer tissue layer 2152 and to characterize the blood flow using Doppler shift techniques.

An incident laser light 2170*a* may be used to probe for the blood vessel 2160 and may be directed on the top surface 2154 of the outer tissue layer 2152. A portion 2172 of the incident laser light 2170*a* may be reflected at the top surface 2154. Another portion 2170*b* of the incident laser light 2170a may penetrate the outer tissue layer 2152. The reflected portion 2172 at the top surface 2154 of the outer tissue layer 2152 has the same path length of the incident light 2170a, and therefore has the same wavelength and phase of the incident light 2170a. However, the portion 2170b of light transmitted into the outer tissue layer 2152 will have a transmission angle that differs from the incidence angle of the light impinging on the tissue surface because the outer tissue layer 2152 has an index of refraction n1 that differs from the index of refraction of air.

If the portion of light transmitted through the outer tissue layer 2152 impinges on a second tissue surface 2158, for example of the blood vessel wall 2156, some portion 2174a,b of light will be reflected back towards the source of the incident light 2170a. The light thus reflected 2174a at the interface between the outer tissue layer 2152 and the blood vessel wall 2156 will have the same wavelength as the incident light 2170a, but will be phase shifted due to the change in the light path length. Projecting the light reflected 2174a,b from the interface between the outer tissue layer 2152 and the blood vessel wall 2156 along with the incident light on the sensor, will produce an interference pattern based on the phase difference between the two light sources.

Further, a portion of the incident light 2170c may be transmitted through the blood vessel wall 2156 and penetrate into the blood vessel lumen 2160. This portion of the incident light 2170c may interact with the moving blood cells in the blood vessel lumen 2160 and may be reflected back 2176a-c towards the source of the impinging light having a wavelength Doppler shifted according to the velocity of the blood cells, as disclosed above. The Doppler shifted light reflected 2176a-c from the moving blood cells may be projected along with the incident light on the sensor, resulting in an interference pattern having a fringe pattern based on the wavelength difference between the two light sources.

In FIG. 158, a light path 2178 is presented of light impinging on the red blood cells in the blood vessel lumen 2160 if there are no changes in refractive index between the emitted light and the light reflected by the moving blood cells. In this example, only a Doppler shift in the reflected light wavelength can be detected. However, the light reflected by the blood cells (2176a-c) may incorporate phase changes due to the variation in the tissue refractive indices in addition to the wavelength changes due to the Doppler Effect.

Thus, it may be understood that if the light sensor receives the incident light, the light reflected from one or more tissue interfaces (2172, and 2174a,b) and the Doppler shifted light from the blood cells (2176a-c), the interference pattern thus produced on the light sensor may include the effects due to the Doppler shift (change in wavelength) as well as the effects due to the change in refractive index within the tissue (change in phase). As a result, a Doppler analysis of the light reflected by the tissue sample may produce erroneous results if the effects due to changes in the refractive index within the sample are not compensated for.

As previously disclosed, FIG. 159 illustrates an example of the effects on a Doppler analysis of light that impinge 2250 on a tissue sample to determine the depth and location of an underlying blood vessel. If there is no intervening tissue between the blood vessel and the tissue surface, the interference pattern detected at the sensor may be due primarily to the change in wavelength reflected from the moving blood cells. As a result, a spectrum 2252 derived from the interference pattern may generally reflect only the Doppler shift of the blood cells. However, if there is intervening tissue between the blood vessel and the tissue surface, the interference pattern detected at the sensor may be due to a combination of the change in wavelength reflected from the moving blood cells and the phase shift due to the refractive index of the intervening tissue. A spectrum 2254 derived from such an interference pattern, may result in the calculation of the Doppler shift that is confounded due to the additional phase change in the reflected light. In some aspects, if information regarding the characteristics (thickness and refractive index) of the intervening tissue is known, the resulting spectrum 2256 may be corrected to provide a more accurate calculation of the change in wavelength.

It may be recognized that the phase shift in the reflected light from a tissue may provide additional information regarding underlying tissue structures, regardless of Doppler effects.

FIG. 167 illustrates that the location and characteristics of non-vascular structures may be determined based on the phase difference between the incident light 2372 and the light reflected from the deep tissue structures (2374, 2376, 2378). As noted above, the penetration depth of light impinging on a tissue is dependent on the wavelength of the impinging illumination. Red laser light (having a wavelength in the range of about 635 nm to about 660 nm) may penetrate the tissue to a depth of about 1 mm. Green laser light (having a wavelength in the range of about 520 nm to about 532 nm) may penetrate the tissue to a depth of about 2-3 mm. Blue laser light (having a wavelength in the range of about 405 nm to about 445 nm) may penetrate the tissue to a depth of about 4 mm or greater. In one aspect, an interface 2381a between two tissues differing in refractive index that is located less than or about 1 mm below a tissue surface 2380 may reflect 2374 red, green, or blue laser light. The phase of the reflected light 2374 may be compared to the incident light 2372 and thus the difference in the refractive index of the tissues at the interface 2381a may be determined. In another aspect, an interface 2381b between two tissues differing in refractive index that is located between 2 and 3 mm 2381b below a tissue surface 2380 may reflect 2376 green or blue laser light, but not red light. The phase of the reflected light 2376 may be compared to the incident light 2372 and thus the difference in the refractive index of the tissues at the interface 2381b may be determined. In yet another aspect, an interface 2381c between two tissues differing in refractive index that is located between 3 and 4 mm 2381c below a tissue surface 2380 may reflect 2378 only blue laser light, but not red or green light. The phase of the reflected light 2378 may be compared to the incident light 2372 and thus the difference in the refractive index of the tissues at the interface 2381c may be determined.

A phase interference measure of a tissue illuminated by light having different wavelengths may therefore provide information regarding the relative indices of refraction of the reflecting tissue as well as the depth of the tissue. The indices of refraction of the tissue may be assessed using the multiple laser sources and their intensity, and thereby relative indices of refraction may be calculated for the tissue. It is recognized that different tissues may have different refractive indices. For example, the refractive index may be related to the relative composition of collagen and elastin in a tissue or the amount of hydration of the tissue. Therefore, a technique to measure relative tissue index of refraction may result in the identification of a composition of the tissue.

In some aspects, smart surgical instruments include algorithms to determine parameters associated with the function of the instruments. One non-limiting example of such parameters may be the pressure of an anvil against a tissue for a smart stapling device. The amount of pressure of an anvil against a tissue may depend on the type and composition of the tissue. For example, less pressure may be required to staple a highly compressive tissue, while a greater amount of pressure may be required to stable a more non-compressive tissue. Another non-limiting example of a parameter associated with a smart surgical device may include a rate of firing of an i-beam knife to cut the tissue. For example, a stiff tissue may require more force and a slower cutting rate than a less stiff tissue. Another non-limiting example of such parameters may be the amount of current provided to an electrode in a smart cauterizing or RF sealing device. Tissue composition, such as percent tissue hydration, may determine an amount of current necessary to heat seal the tissue. Yet another non-limiting example of such parameters may be the amount of power provided to an ultrasonic transducer of a smart ultrasound cutting device or the driving frequency of the cutting device. A stiff tissue may require more power for cutting, and contact of the ultrasonic cutting tool with a stiff tissue may shift the resonance frequency of the cutter.

It may be recognized that a tissue visualization system that can identify tissue type and depth may provide such data to one or more smart surgical devices. The identification and location data may then be used by the smart surgical devices to adjust one or more of their operating parameters thereby allowing them to optimize their manipulation of the tissue. It may be understood that an optical method to characterize a type of tissue may permit automation of the operating parameters of the smart surgical devices. Such automation of the operation of smart surgical instruments may be preferable to relying on human estimation to determine the operational parameters of the instruments.

In one aspect, Optical Coherence Tomography (OCT) is a technique that can visual subsurface tissue structures based on the phase difference between an illuminating light source, and light reflected from structures located within the tissue. FIG. 168 depicts schematically one example of instrumentation 2470 for Optical Coherence Tomography. In FIG. 168, a laser source 2472 may emit light 2482 according to any optical wavelength of interest (red, green, blue, infrared, or ultraviolet). The light 2482 may be directed to a beam splitter 2486. The beam splitter 2486 directs one portion of the light 2488 to a tissue sample 2480. The beam splitter 2486 may also direct a portion of the light 2492 to a stationary reference mirror 2494. The light reflected from the tissue sample 2480 and from the stationary mirror 2494 may be recombined 2498 at the beam splitter 2486 and directed to a detector 2496. The phase difference between the light from the reference mirror 2494 and from the tissue sample 2480 may be detected at the detector 2496 as an interference pattern. Appropriate computing devices may then calculate phase information from the interference pattern. Additional computation may then provide information regarding structures below the surface of the tissue sample. Additional depth information may also be obtained by comparing the interference patterns generated from the sample when illuminated at different wavelengths of laser light.

As disclosed above, depth information regarding subsurface tissue structures may be ascertained from a combination of laser light wavelength and the phase of light reflected from a deep tissue structure. Additionally, local tissue surface inhomogeneity may be ascertained by comparing the phase as well as amplitude difference of light reflected from different portions of the same sub-surface tissues. Measurements of a difference in the tissue surface properties at a defined location compared to those at a neighboring location may be indicative of adhesions, disorganization of the tissue layers, infection, or a neoplasm in the tissue being probed.

FIG. 169 illustrates this effect. The surface characteristics of a tissue determine the angle of reflection of light impinging on the surface. A smooth surface 2551a reflects the light essentially with the same spread 2544 as the light impinging on the surface 2542 (specular reflection). Consequently, the amount of light received by a light detector having a known fixed aperture may effectively receive the entire amount of light reflected 2544 from the smooth surface 2551a. However, increased surface roughness at a tissue surface may result in an increase spread in the reflected light with respect to the incident light (diffuse reflection).

Some amount of the reflected light 2546 from a tissue surface having some amount of surface irregularities 2551b will fall outside the fixed aperture of the light detector due to the increased spread of the reflected light 2546. As a result, the light detector will detect less light (shown in FIG. 169 as a decrease in the amplitude of the reflected light signal 2546). It may be understood that the amount of reflected light spread will increase as the surface roughness of a tissue increases. Thus, as depicted in FIG. 169, the amplitude of light reflected 2548 from a surface 2551c having significant surface roughness may have a smaller amplitude than the light reflected 2544 from a smooth surface 2551a, or light reflected 2546 form a surface having only a moderate amount of surface roughness 2551b. Therefore, in some aspects, a single laser source may be used to investigate the quality of a tissue surface or subsurface by comparing the optical properties of reflected light from the tissue with the optical properties of reflected light from adjacent surfaces.

In other aspects, light from multiple laser sources (for example, lasers emitting light having different central wavelengths) may be used sequentially to probe tissue surface characteristics at a variety of depths below the surface 2550. As disclosed above (with reference to FIG. 167), the absorbance profile of a laser light in a tissue is dependent on the central wavelength of the laser light. Laser light having a shorter (more blue) central wavelength can penetrate tissue deeper than laser light having a longer (more red) central wavelength. Therefore, measurements related to light diffuse reflection made at different light wavelengths can indicate both an amount of surface roughness as well as the depth of the surface being measured.

FIG. 170 illustrates one method of displaying image processing data related to a combination of tissue visualization modalities. Data used in the display may be derived from image phase data related to tissue layer composition, image intensity (amplitude) data related to tissue surface features, and image wavelength data related to tissue mobility (such as blood cell transport) as well as tissue depth. As one example, light emitted by a laser in the blue optical region 2562 may impinge on blood flowing at a depth of about 4 mm below the surface of the tissue. The reflected light 2564 may be red shifted due to the Doppler effect of the blood flow. As a result, information may be obtained regarding the existence of a blood vessel and its depth below the surface.

In another example, a layer of tissue may lie at a depth of about 2-3 mm below the surface of the surgical site. This tissue may include surface irregularities indicative of scarring or other pathologies. Emitted red light 2572 may not penetrate to the 2-3 mm depth, so consequently, the reflected red light 2580 may have about the same amplitude of the emitted red light 2572 because it is unable to probe structures more than 1 mm below the top surface of the surgical site. However, green light reflected from the tissue 2578 may reveal the existence of the surface irregularities at that depth in that the amplitude of the reflected green light 2578 may be less than the amplitude of the emitted green light 2570. Similarly, blue light reflected from the tissue 2574 may reveal the existence of the surface irregularities at that depth in that the amplitude of the reflected blue light 2574 may be less than the amplitude of the emitted blue light 2562. In one example of an image processing step, the image 2582 may be smoothed using a moving window filter 2584 to reduce inter-pixel noise as well as reduce small local tissue anomalies 2586 that may hide more important features 2588.

FIGS. 171A-C illustrate several aspects of displays that may be provided to a surgeon for a visual identification of surface and sub-surface structures of a tissue in a surgical site. FIG. 171A may represent a surface map of the surgical site with color coding to indicate structures located at varying depths below the surface of the surgical site. FIG. 171B depicts an example of one of several horizontal slices through the tissue at varying depths, which may be color coded to indicate depth and further include data associated with differences in tissue surface anomalies (for example, as displayed in a 3D bar graph). FIG. 171C depicts yet another visual display in which surface irregularities as well as Doppler shift flowmetry data may indicate sub-surface vascular structures as well as tissue surface characteristics.

FIG. 172 is a flow chart 2950 of a method for providing information related to a characteristic of a tissue to a smart surgical instrument. An image acquisition system may illuminate 2960 a tissue with a first light beam having a first central frequency and receive 2962 a first reflected light from the tissue illuminated by the first light beam. The image acquisition system may then calculate 2964 a first tissue surface characteristic at a first depth based on the first emitted light beam and the first reflected light from the tissue. The image acquisition system may then illuminate 2966 the tissue with a second light beam having a second central frequency and receive 2968 a second reflected light from the tissue illuminated by the second light beam. The image acquisition system may then calculate 2970 a second tissue surface characteristic at a second depth based on the second emitted light beam and the second reflected light from the tissue. Tissue features that may include a tissue type, a tissue composition, and a tissue surface roughness metric may be determined from the first central light frequency, the second central light frequency, the first reflected light from the tissue, and the second reflected light from the tissue. The tissue characteristic may be used to calculate 2972 one or more parameters related to the function of a smart surgical instrument such as jaw pressure, power to effect tissue cauterization, or current amplitude and/or frequency to drive a piezoelectric actuator to cut a tissue. In some additional examples, the parameter may be transmitted 2974 either directly or indirectly to the smart surgical instrument which may modify its operating characteristics in response to the tissue being manipulated.

Multifocal Minimally Invasive Camera

In a minimally invasive procedure, e.g., laparoscopic, a surgeon may visualize the surgical site using imaging instruments including a light source and a camera. The imaging instruments may allow the surgeon to visualize the end effector of a surgical device during the procedure. However, the surgeon may need to visualize tissue away from the end effector to prevent unintended damage during the surgery. Such distant tissue may lie outside the field of view of the camera system when focused on the end effector. The imaging instrument may be moved in order to change the field of view of the camera, but it may be difficult to return the camera system back to its original position after being moved.

The surgeon may attempt to move the imaging system within the surgical site to visualize different portions of the site during the procedure. Repositioning of the imaging system is time consuming and the surgeon is not guaranteed to visualize the same field of view of the surgical site when the imaging system is returned to its original location.

It is therefore desirable to have a medical imaging visualization system that can provide multiple fields of view of the surgical site without the need to reposition the visualization system. Medical imaging devices include, without limitation, laparoscopes, endoscopes, thoracoscopes, and the like, as described herein. In some aspects, a single display system may display each of the multiple fields of view of the surgical site at about the same time. The display of each of the multiple fields of view may be independently updated depending on a display control system composed of one or more hardware modules, one or more software modules, one or more firmware modules, or any combination or combinations thereof.

Some aspects of the present disclosure further provide for a control circuit configured to control the illumination of a surgical site using one or more illumination sources such as laser light sources and to receive imaging data from one or more image sensors. In some aspects, the control circuit may be configured to control the operation of one or more light sensor modules to adjust a field of view. In some aspects, the present disclosure provides for a non-transitory computer readable medium storing computer readable instructions that, when executed, cause a device to adjust one or more components of the one or more light sensor modules and to process an image from each of the one or more light sensor modules.

An aspect of a minimally invasive image acquisition system may comprise a plurality of illumination sources wherein each illumination source is configured to emit light having a specified central wavelength, a first light sensing element having a first field of view and configured to receive illumination reflected from a first portion of the surgical site when the first portion of the surgical site is illuminated by at least one of the plurality of illumination sources, a second light sensing element having a second field of view and configured to receive illumination reflected from a second portion of the surgical site when the second portion of the surgical site is illuminated by at least one of the plurality of illumination sources, wherein the second field of view overlaps at least a portion of the first field of view; and a computing system.

The computing system may be configured to receive data from the first light sensing element, receive data from the second light sensing element, compute imaging data based on the data received from the first light sensing element and the data received from the second light sensing element, and transmit the imaging data for receipt by a display system.

A variety of surgical visualization systems have been disclosed above. Such systems provide for visualizing tissue and sub-tissue structures that may be encountered during one or more surgical procedures. Non-limiting examples of such systems may include: systems to determine the location and depth of subsurface vascular tissue such as veins and arteries; systems to determine an amount of blood flowing through the subsurface vascular tissue; systems to determine the depth of non-vascular tissue structures; systems to characterize the composition of such non-vascular tissue structures; and systems to characterize one or more surface characteristics of such tissue structures.

It may be recognized that a single surgical visualization system may incorporate components of any one or more of these visualization modalities. FIGS. 152A-D depict some examples of such a surgical visualization system 2108.

As disclosed above, in one non-limiting aspect, a surgical visualization system 2108 may include an imaging control unit 2002 and a hand unit 2020. The hand unit 2020 may include a body 2021, a camera scope cable 2015 attached to the body 2021, and an elongated camera probe 2024. The elongated camera probe 2024 may also terminate at its distal end with at least one window. In some non-limiting examples, a light sensor 2030 may be incorporated in the hand unit 2020, for example either in the body of the hand unit 2032b, or at a distal end 2032a of the elongated camera probe, as depicted in FIG. 152C. The light sensor 2030 may be fabricated using a CMOS sensor array or a CCD sensor array. As illustrated in FIG. 153C, a typical CMOS or CCD sensor array may generate an RGB (red-green-blue) image from light impinging on a mosaic of sensor elements, each sensor element having one of a red, green, or blue optical filter.

Alternatively, the illumination of the surgical site may be cycled among visible illumination sources as depicted in FIG. 160D. In some example, the illumination sources may include any one or more of a red laser 2360a, a green laser 2360b, or a blue laser 2360c. In some non-limiting examples, a red laser 2360a light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some non-limiting examples, a green laser 2360b light source may source illumination having a peak wavelength that may range between 520 nm and 532 nm, inclusive. Non-limiting examples of a red laser peak wavelength may include about 520 nm, about 522 nm, about 524 nm, about 526 nm, about 528 nm, about 530 nm, about 532 nm, or any value or range of values therebetween. In some non-limiting examples, the blue laser 2360c light source may source illumination having a peak wavelength that may range between 405 nm and 445 nm, inclusive. Non-limiting examples of a blue laser peak wavelength may include about 405 nm, about 410 nm, about 415 nm, about 420 nm, about 425 nm, about 430 nm, about 435 nm, about 440 nm, about 445 nm, or any value or range of values therebetween.

Additionally, illumination of the surgical site may be cycled to include non-visible illumination sources that may supply infrared or ultraviolet illumination. In some non-limiting examples, an infrared laser light source may source illumination having a peak wavelength that may range between 750 nm and 3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. In some non-limiting examples, an ultraviolet laser light source may source illumination having a peak wavelength that may range between 200 nm and 360 nm, inclusive. Non-limiting examples of an ultraviolet laser peak wavelength may include about 200 nm, about 220 nm, about 240 nm, about 260 nm, about 280 nm, about 300 nm, about 320 nm, about 340 nm, about 360 nm, or any value or range of values therebetween.

The outputs of the sensor array under the different illumination wavelengths may be combined to form the RGB image, for example, if the illumination cycle time is sufficiently fast and the laser light is in the visible range. FIGS. 173A and 173B illustrate a multi-pixel light sensor receiving by light reflected by a tissue illuminated, for example, by sequential exposure to red, green, blue, infrared, (FIG. 173A) or red, green, blue, and ultraviolet laser light sources (FIG. 173B).

FIG. 174A depicts the distal end of a flexible elongated camera probe 2120 having a flexible camera probe shaft 2122 and a single light sensor module 2124 disposed at the distal end 2123 of the flexible camera probe shaft 2122. In some non-limiting examples, the flexible camera probe shaft 2122 may have an outer diameter of about 5 mm. The outer diameter of the flexible camera probe shaft 2122 may depend on geometric factors that may include, without limitation, the amount of allowable bend in the shaft at the distal end 2123. As depicted in FIG. 174A, the distal end 2123 of the flexible camera probe shaft 2122 may bend about 90° with respect to a longitudinal axis of an un-bent portion of the flexible camera probe shaft 2122 located at a proximal end of the elongated camera probe 2120. It may be recognized that the distal end 2123 of the flexible camera probe shaft 2122 may bend any appropriate amount as may be required for its function. Thus, as non-limiting examples, the distal end 2123 of the flexible camera probe shaft 2122 may bend any amount between about 0° and about 90°. Non-limiting examples of the bend angle of the distal end 2123 of the flexible camera probe shaft 2122 may include about 0°, about 10°, about 20°, about 30°, about 40°, about 50°, about 60°, about 70°, about 80°, about 90°, or any value or range of values therebetween. In some examples, the bend angle of the distal end 2123 of the flexible camera probe shaft 2122 may be set by a surgeon or other health care professional prior to or during a surgical procedure. In some other example, the bend angle of the distal end 2123 of the flexible camera probe shaft 2122 may be a fixed angle set at a manufacturing site.

The single light sensor module 2124 may receive light reflected from the tissue when illuminated by light emitted by one or more illumination sources 2126 disposed at the distal end of the elongated camera probe. In some examples, the light sensor module 2124 may be a 4 mm sensor module such as 4 mm mount 2136b, as depicted in FIG. 152D. It may be recognized that the light sensor module 2124 may have any appropriate size for its intended function. Thus, the light sensor module 2124 may include a 5.5 mm mount 2136a, a 2.7 mm mount 2136c, or a 2 mm mount 2136d as depicted in FIG. 152D.

It may be recognized that the one or more illumination sources 2126 may include any number of illumination sources 2126 including, without limitation, one illumination source, two illumination sources, three illumination sources, four illumination sources, or more than four illumination sources. It may be further understood that each illumination source may source illumination having any central wavelength including a central red illumination wavelength, a central green illumination wavelength, a central blue illumination wavelength, a central infrared illumination wavelength, a central ultraviolet illumination wavelength, or any other wavelength. In some examples, the one or more illumination sources 2126 may include a white light source, which may illuminate tissue with light having wavelengths that may span the range of optical white light from about 390 nm to about 700 nm.

FIG. 174B depicts the distal end 2133 of an alternative elongated camera probe 2130 having multiple light sensor modules, for example the two light sensor modules 2134a,b, each disposed at the distal end 2133 of the elongated camera probe 2130. In some non-limiting examples, the alternative elongated camera probe 2130 may have an outer diameter of about 7 mm. In some examples, the light sensor modules 2134a,b may each comprise a 4 mm sensor module, similar to light sensor module 2124 in FIG. 174A. Alternatively, each of the light sensor modules 2134a,b may comprise a 5.5 mm light sensor module, a 2.7 mm light sensor module, or a 2 mm light sensor module as depicted in FIG. 152D. In some examples, both light sensor modules 2134a,b may have the same size. In some examples, the light sensor modules 2134a,b may have different sizes. As one non-limiting example, an alternative elongated camera probe 2130 may have a first 4 mm light sensor and two additional 2 mm light sensors. In some aspects, a visualization system may combine the optical outputs from the multiple light sensor modules 2134a,b to form a 3D or quasi-3D image of the surgical site. In some other aspects, the outputs of the multiple light sensor modules 2134a,b may be combined in such a manner as to enhance the optical resolution of the surgical site, which may not be otherwise practical with only a single light sensor module.

Each of the multiple light sensor modules 2134a,b may receive light reflected from the tissue when illuminated by light emitted by one or more illumination sources 2136a,b disposed at the distal end 2133 of the alternative elongated camera probe 2130. In some non-limiting examples, the light emitted by all of the illumination sources 2136a,b may be derived from the same light source (such as a laser). In other non-limiting examples, the illumination sources 2136a surrounding a first light sensor module 2134a may emit light at a first wavelength and the illumination sources 2136b surrounding a second light sensor module 2134b may emit light at a second wavelength. It may be further understood that each illumination source 2136a,b may source illumination having any central wavelength including a central red illumination wavelength, a central green illumination wavelength, a central blue illumination wavelength, a central infrared illumination wavelength, a central ultraviolet illumination wavelength, or any other wavelength. In some examples, the one or more illumination sources 2136a,b may include a white light source, which may illuminate tissue with light having wavelengths that may span the range of optical white light from about 390 nm to about 700 nm.

In some additional aspects, the distal end 2133 of the alternative elongated camera probe 2130 may include one or more working channels 2138. Such working channels 2138 may be in fluid communication with an aspiration port of a device to aspirate material from the surgical site, thereby permitting the removal of material that may potentially obscure the field of view of the light sensor modules 2134a,b. Alternatively, such working channels 2138 may be in fluid communication with an fluid source port of a device to provide a fluid to the surgical site, to flush debris or material away from the surgical site. Such fluids may be used to clear material from the field of view of the light sensor modules 2134a,b.

FIG. 174C depicts a perspective view of an aspect of a monolithic sensor 2160 having a plurality of pixel arrays for producing a three dimensional image in accordance with the teachings and principles of the disclosure. Such an implementation may be desirable for three dimensional image capture, wherein the two pixel arrays 2162 and 2164 may be offset during use. In another implementation, a first pixel array 2162 and a second pixel array 2164 may be dedicated to receiving a predetermined range of wave lengths of electromagnetic radiation, wherein the first pixel array 2162 is dedicated to a different range of wave length electromagnetic radiation than the second pixel array 2164.

Additional disclosures regarding a dual sensor array may be found in U.S. Patent Application Publication No. 2014/0267655, titled SUPER RESOLUTION AND COLOR MOTION ARTIFACT CORRECTION IN A PULSED COLOR IMAGING SYSTEM, filed on Mar. 14, 2014, which issued on May 2, 2017 as U.S. Pat. No. 9,641,815, the contents thereof being incorporated by reference herein in its entirety and for all purposes.

In some aspects, a light sensor module may comprise a multi-pixel light sensor such as a CMOS array in addition to one or more additional optical elements such as a lens, a reticle, and a filter.

In some alternative aspects, the one or more light sensors may be located within the body 2021 of the hand unit 2020. Light reflected from the tissue may be acquired at a light receiving surface of one or more optical fibers at the distal end of the elongated camera probe 2024. The one or more optical fibers may conduct the light from the distal end of the elongated camera probe 2024 to the one or more light sensors, or to additional optical elements housed in the body of the hand unit 2020 or in the imaging control unit 2002. The additional optical elements may include, without limitation, one or more dichroic mirrors, one or more reference mirrors, one or more moving mirrors, and one or more beam splitters and/or combiners, and one or more optical shutters. In such alternative aspects, the light sensor module may include any one or more of a lens, a reticle and a filter, disposed at the distal end of the elongated camera probe 2024.

Images obtained from each of the multiple light sensors for example 2134a,b may be combined or processed in several different manners, either in combination or separately, and then displayed in a manner to allow a surgeon to visualize different aspects of the surgical site.

In one non-limiting example, each light sensor may have an independent field of view. In some additional examples, the field of view of a first light sensor may partially or completely overlap the field of view of a second light sensor.

As disclosed above, an imaging system may include a hand unit 2020 having an elongated camera probe 2024 with one or more light sensor modules 2124, 2134a,b disposed at its distal end 2123, 2133. As an example, the elongated camera probe 2024 may have two light sensor modules 2134a,b, although it may be recognized that there may be three, four, five, or more light sensor modules at the distal end of the elongated camera probe 2024. Although FIGS. 175 and 176A-D depict examples of the distal end of an elongated camera probe having two light sensor modules, it may be recognized that the description of the operation of the light sensor modules is not limited to solely two light sensor modules. As depicted in FIGS. 175, and 46A-D, the light sensor modules may include an image sensor, such as a CCD or CMOS sensor that may be composed of an array of light sensing elements (pixels). The light sensor modules may also include additional optical elements, such as lenses. Each lens may be adapted to provide a field of view for the light sensor of the respective light sensor module.

FIG. 175 depicts a generalized view of a distal end 2143 of an elongated camera probe having multiple light sensor modules 2144a,b. Each light sensor module 2144a,b may be composed of a CCD or CMOS sensor and one or more optical elements such as filters, lenses, shutters, and similar. In some aspects, the components of the light sensor modules 2144a,b may be fixed within the elongated camera probe. In some other aspects, one or more of the components of the light sensor modules 2144a,b may be adjustable. For example, the CCD or CMOS sensor of a light sensor module 2144a,b may be mounted on a movable mount to permit automated adjustment of the center 2145a,b of a field of view 2147a,b of the CCD or CMOS sensor. In some other aspects, the CCD or CMOS sensor may be fixed, but a lens in each light sensor modules 2144a,b may be adjustable to change the focus. In some aspects, the light sensor modules 2144a,b may include adjustable irises to permit changes in the visual aperture of the sensor modules 2144a,b.

As depicted in FIG. 175, each of the sensor modules 2144a,b may have a field of view 2147a,b having an acceptance angle. As depicted in FIG. 175, the acceptance angle for each sensor modules 2144a,b may have an acceptance angle of greater than 90°. In some examples, the acceptance angle may be about 100°. In some examples, the acceptance angle may be about 120°. In some examples, if the sensor modules 2144a,b have an acceptance angle of greater than 90° (for example, 100°), the fields of view 2147a and 2147b may form an overlap region 2150a,b. In some aspects, an optical field of view having an acceptance angle of 100° or greater may be called a "fish-eyed" field of view. A visualization system control system associated with such an elongated camera probe may include computer readable instructions that may permit the display of the overlap region 2150a,b in such a manner so that the extreme curvature of the overlapping fish-eyed fields of view is corrected, and a sharpened and flattened image may be displayed. In FIG. 175, the overlap region 2150a may represent a region wherein the overlapping fields of view 2147a,b of the sensor modules 2144a,b have their respective centers 2145a,b directed in a forward direction. However, if any one or more components of the sensor modules 2144a,b is adjustable, it may be recognized that the overlap region 2150b may be directed to any attainable angle within the fields of view 2147a,b of the sensor modules 2144a,b.

FIGS. 176A-D depict a variety of examples of an elongated light probe having two light sensor modules 2144a,b with a variety of fields of view. The elongated light probe may be directed to visualize a surface 2152 of a surgical site.

In FIG. 176A, the first light sensor module 2144a has a first sensor field of view 2147a of a tissue surface 2154a, and the second light sensor module 2144b has a second sensor field of view 2147b of a tissue surface 2154b. As depicted in FIG. 176A, the first field of view 2147a and the second field of view 2147b have approximately the same angle of view. Additionally, the first sensor field of view 2147a is adjacent to but does not overlap the second sensor field of view 2147b. The image received by the first light sensor module 2144a may be displayed separately from the image received by the second light sensor module 2144b, or the images may be combined to form a single image. In some non-limiting examples, the angle of view of a lens associated with the first light sensor module 2144a and the angle of view of a lens associated with the second light sensor module 2144b may be somewhat narrow, and image distortion may not be great at the periphery of their respective images. Therefore, the images may be easily combined edge to edge.

As depicted in FIG. 176B, the first field of view 2147a and the second field of view 2147b have approximately the same angular field of view, and the first sensor field of view 2147a overlaps completely the second sensor field of view 2147b. This may result in a first sensor field of view 2147a of a tissue surface 2154a being identical to the view of a tissue surface 2154b as obtained by the second light sensor module 2144b from the second sensor field 2147b of view. This configuration may be useful for applications in which the image from the first light sensor module 2144a may be processed differently than the image from the second light sensor module 2144b. The information in the first image may complement the information in the second image and refer to the same portion of tissue.

As depicted in FIG. 176C, the first field of view 2147a and the second field of view 2147b have approximately the same angular field of view, and the first sensor field of view 2147a partially overlaps the second sensor field of view 2147b. In some non-limiting examples, a lens associated with the first light sensor module 2144a and a lens associated with the second light sensor module 2144b may be wide angle lenses. These lenses may permit the visualization of a wider field of view than that depicted in FIG. 176A. Wide angle lenses are known to have significant optical distortion at their periphery. Appropriate image processing of the images obtained by the first light sensor module 2144a and the second light sensor module 2144b may permit the formation of a combined image in which the central portion of the combined image is corrected for any distortion induced by either the first lens or the second lens. It may be understood that a portion of the first sensor field of view 2147a of a tissue surface 2154a may thus have some distortion due to the wide angle nature of a lens associated with the first light sensor module 2144a and a portion of the second sensor field of view 2147b of a tissue surface 2154b may thus have some distortion due to the wide angle nature of a lens associated with the second light sensor module 2144b. However, a portion of the tissue viewed in the overlap region 2150' of the two light sensor modules 2144a,b may be corrected for any distortion induced by either of the light sensor modules 2144a,b. The configuration depicted in FIG. 176C may be useful for applications in which it is desired to have a wide field of view of the tissue around a portion of a surgical instrument during a surgical procedure. In some examples, lenses associated with each light sensor module 2144a,b may be independently controllable, thereby controlling the location of the overlap region 2150' of view within the combined image.

As depicted in FIG. 176D, the first light sensor module 2144a may have a first angular field of view 2147a that is wider than the second angular field of view 2147b of the second light sensor module 2144b. In some non-limiting examples, the second sensor field of view 2147b may be totally disposed within the first sensor field of view 2147a. In alternative examples, the second sensor field of view may lie outside of or tangent to the wide angle field of view 2147a of the first sensor 2144a. A display system that may use the configuration depicted in FIG. 176D may display a wide angle portion of tissue 2154a imaged by the first sensor module 2144a along with a magnified second portion of tissue 2154b imaged by the second sensor module 2144b and located in an overlap region 2150" of the first field of view 2147a and the second field of view 2147b. This configuration may be useful to present a surgeon with a close-up image of tissue proximate to a surgical instrument (for example, imbedded in the second portion of tissue 2154b) and a wide-field image of the tissue surrounding the immediate vicinity of the medical instrument (for example, the proximal first portion of tissue 2154a). In some non-limiting examples, the image presented by the narrower second field of view 2147b of the second light sensor module 2144b may be a surface image of the surgical site. In some additional examples, the image presented in the first wide field view 2147a of the first light sensor module 2144a may include a display based on a hyperspectral analysis of the tissue visualized in the wide field view.

FIGS. 177A-C illustrate an example of the use of an imaging system incorporating the features disclosed in FIG. 176D. FIG. 177A illustrates schematically a proximal view 2170 at the distal end of the elongated camera probe depicting the light sensor arrays 2172a,b of the two light sensor modules 2174a,b. A first light sensor module 2174a may include a wide angle lens, and the second light sensor module 2174b may include a narrow angle lens. In some aspects, the second light sensor module 2174b may have a narrow aperture lens. In other aspects, the second light sensor module 2174b may have a magnifying lens. The tissue may be illuminated by the illumination sources disposed at the distal end of the elongated camera probe. The light sensor arrays 2172' (either light sensor array 2172a or 2172b, or both 2172a and 2172b) may receive the light reflected from the tissue upon illumination. The tissue may be illuminated by light from a red laser source, a green laser source, a blue laser source, an infrared laser source, and/or an ultraviolet laser source. In some aspects, the light sensor arrays 2172' may sequentially receive the red laser light 2175a, green laser light 2175b, blue laser light 2175c, infrared laser light 2175d, and the ultra-violet laser light 2175e. The tissue may be illuminated by any combination of such laser sources simultaneously, as depicted in FIGS. 153E and 153F. Alternatively, the illuminating light may be cycled among any combination of such laser sources, as depicted for example in FIG. 153D, and FIGS. 173A and 173B.

FIG. 177B schematically depicts a portion of lung tissue 2180 which may contain a tumor 2182. The tumor 2182 may be in communication with blood vessels including one or more veins 2184 and/or arteries 2186. In some surgical procedures, the blood vessels (veins 2184 and arteries 2186) associated with the tumor 2182 may require resection and/or cauterization prior to the removal of the tumor.

FIG. 177C illustrates the use of a dual imaging system as disclosed above with respect to FIG. 177A. The first light sensor module 2174a may acquire a wide angle image of the tissue surrounding a blood vessel 2187 to be severed with a surgical knife 2190. The wide angle image may permit the surgeon to verify the blood vessel to be severed 2187. In addition, the second light sensor module 2174b may acquire a narrow angle image of the specific blood vessel 2187 to be manipulated. The narrow angle image may show the surgeon the progress of the manipulation of the blood vessel 2187. In this manner, the surgeon is presented with the image of the vascular tissue to be manipulated as well as its environs to assure that the correct blood vessel is being manipulated.

FIGS. 178A and 178B depict another example of the use of a dual imaging system.

FIG. 178A depicts a primary surgical display providing an image of a section of a surgical site. The primary surgical display may depict a wide view image 2800 of a section of intestine 2802 along with its vasculature 2804. The wide view image 2800 may include a portion of the surgical field 2809 that may be separately displayed as a magnified view 2810 in a secondary surgical display (FIG. 178B). As disclosed above with respect to surgery to remove a tumor from a lung (FIGS. 177A-C), it may be necessary to dissect blood vessels supplying a tumor 2806 before removing the cancerous tissue. The vasculature 2804 supplying the intestines 2802 is complex and highly ramified. It may necessary to determine which blood vessels supply the tumor 2806 and to identify blood vessels supplying blood to healthy intestinal tissue. The wide view image 2800 permits a surgeon to determine which blood vessel may supply the tumor 2806. The surgeon may then test a blood vessel using a clamping device 2812 to determine if the blood vessel supplies the tumor 2806 or not.

FIG. 178B depicts a secondary surgical display that may only display a narrow magnified view image 2810 of one portion of the surgical field 2809. The narrow magnified view image 2810 may present a close-up view of the vascular tree 2814 so that the surgeon can focus on dissecting only the blood vessel of interest 2815. For resecting the blood vessel of interest 2815, a surgeon may use a smart RF cautery device 2816. It may be understood that any image obtained by the visualization system may include not only images of the tissue in the surgical site but also images of the surgical instruments inserted therein. In some aspects, such a surgical display (either the primary display in FIG. 178A or the secondary display in FIG. 178B) may also include indicia 2817 related to functions or settings of any surgical device used during the surgical procedure. For example, the indicia 2817 may include a power setting of the smart RF cautery device 2816. In some aspects, such smart medical devices may transmit data related to their operating parameters to the visualization system to incorporate in display data to be transmitted to one or more display devices.

FIGS. 179A-C illustrate examples of a sequence of surgical steps for the removal of an intestinal/colon tumor and which may benefit from the use of multi-image analysis at the surgical site. FIG. 179A depicts a portion of the surgical site, including the intestines 2932 and the ramified vasculature 2934 supplying blood and nutrients to the intestines 2932. The intestines 2932 may have a tumor 2936 surrounded by a tumor margin 2937. A first light sensor module of a visualization system may have a wide field of view 2930, and it may provide imaging data of the wide field of view 2930 to a display system. A second light sensor module of the visualization system may have a narrow or standard field of view 2940, and it may provide imaging data of the narrow field of view 2940 to the display system. In some aspects, the wide field image and the narrow field image may be displayed by the same display device. In another aspect, the wide field image and the narrow field image may be displayed by separate display devices.

During the surgical procedure, it my be important to remove not just the tumor 2936 but the margin 2937 surrounding it to assure complete removal of the tumor. A wide angle field of view 2930 may be used to image both the vasculature 2934 as well as the section of the intestines 2932 surrounding the tumor 2936 and the margin 2637. As noted above, the vasculature feeding the tumor 2936 and the margin 2637 should be removed, but the vasculature feeding the surrounding intestinal tissue must be preserved to provide oxygen and nutrients to the surrounding tissue. Transection of the vasculature feeding the surrounding colon tissue will remove oxygen and nutrients from the tissue, leading to necrosis. In some examples, laser Doppler imaging of the tissue visualized in the wide angle field 2630 may be analyzed to provide a speckle contrast analysis 2933, indicating the blood flow within the intestinal tissue.

FIG. 179B illustrates a step during the surgical procedure. The surgeon may be uncertain which part of the vascular tree supplies blood to the tumor 2936. The surgeon may test a blood vessel 2944 to determine if it feeds the tumor 2936 or the healthy tissue. The surgeon may clamp a blood vessel 2944 with a clamping device 2812 and determine the section of the intestinal tissue 2943 that is no longer perfused by means of the speckle contrast analysis. The narrow field of view 2940 displayed on an imaging device may assist the surgeon in the close-up and detailed work required to visualize the single blood vessel 2944 to be tested. When the suspected blood vessel 2944 is clamped, a portion of the intestinal tissue 2943 is determined to lack perfusion based on the Doppler imaging speckle contras analysis. As depicted in FIG. 159B, the suspected blood vessel 2944 does not supply blood to the tumor 2935 or the tumor margin 2937, and therefore is recognized as a blood vessel to be spared during the surgical procedure.

FIG. 179C depicts a following stage of the surgical procedure. In stage, a supply blood vessel 2984 has been identified to supply blood to the margin 2937 of the tumor. When this supply blood vessel 2984 has been severed, blood is no longer supplied to a section of the intestine 2987 that may include at least a portion of the margin 2937 of the tumor 2936. In some aspects, the lack of perfusion to the section 2987 of the intestines may be determined by means of a speckle contrast analysis based on a Doppler analysis of blood flow into the intestines. The non-perfused section 2987 of the intestines may then be isolated by a seal 2985 applied to the intestine. In this manner, only those blood vessels perfusing the tissue indicated for surgical removal may be identified and sealed, thereby sparing healthy tissue from unintended surgical consequences.

In some additional aspects, a surgical visualization system may permit imaging analysis of the surgical site.

In some aspects, the surgical site may be inspected for the effectiveness of surgical manipulation of a tissue. Non-limiting examples of such inspection may include the inspection of surgical staples or welds used to seal tissue at a surgical site. Cone beam coherent tomography using one or more illumination sources may be used for such methods.

In some additional aspects, an image of a surgical site may have landmarks denoted in the image. In some examples, the landmarks may be determined through image analysis techniques. In some alternative examples, the landmarks may be denoted through a manual intervention of the image by the surgeon.

In some additional aspects, non-smart ready visualizations methods may be imported for used in Hub image fusion techniques.

In additional aspects, instruments that are not integrated in the Hub system may be identified and tracked during their use within the surgical site. In this aspect, computational and/or storage components of the Hub or in any of its components (including, for example, in the cloud system) may include a database of images related to EES and competitive surgical instruments that are identifiable from one or more images acquired through any image acquisition system or through visual analytics of such alternative instruments. The imaging analysis of such devices may further permit identification of when an instrument is replaced with a different instrument to do the same or a similar job. The identification of the replacement of an instrument during a surgical procedure may provide information related to when an instrument is not doing the job or a failure of the device.

Cloud System Hardware and Functional Modules

Aspects of the present disclosure include a cloud-based medical analytics system that communicatively couples to multiple Hub systems, as described above, and multiple robotic surgical devices, described more below. The cloud-based medical analytics system is configured to receive data pertaining to a patient and/or medical procedure and provide various integrated processes that span multiple Hub systems and multiple robotic surgical devices. The cloud-based medical analytics system generally aggregates data and forms insights based on the aggregated data that may not otherwise be concluded without gathering the various disparate data sources that span the multiple Hub systems and robotic devices. Described below are various examples of different types of functions and structures present in the cloud-based medical analytics system that provide more detail toward these ends.

FIG. 180 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG. 180, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 180, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 180, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 180, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 are configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 181.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

FIG. 181 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 181, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical databases 7012 for the operations of the applications 7014. The caches 7018 also store data (e.g., temporarily) and are coupled to the APIs 7016 for more efficient retrieval of data used by the applications 7014. The data analytics modules 7034 in FIG. 181 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 180 and 181 as one example of hardware and software implementation.

Usage, Resource, and Efficiency Modeling for Medical Facility

Aspects of the present disclosure are presented for a cloud-based analytics system, communicatively coupled to a plurality of hubs and smart medical instruments, and configured to provide customized recommendations to localized medical care facilities regarding usage of medical supplies and other resources to improve efficiency and optimize resource allocation. A medical care facility, such as a hospital or medical clinic, may develop a set of practices for procuring, using, and disposing of various medical supplies that are often derived from routines and traditions maintained over time. The behaviors of a medical facility typically are risk-averse, and generally would be hesitant to adopt new and better practices unless and until convincingly shown of a better practice. Similarly, even if a better usage or efficiency model has been developed in a nearby facility, it is difficult for a local facility to adopt the improved practice because 1) each facility may be more natively resistant to change from the outside and 2) there are many unknowns for how or why the improved practice works in the nearby facility in relation to what the local facility does instead. Furthermore, even if a medical facility desired to improve its practices, it may be unable to do so optimally because it lacks enough knowledge from other similarly situated facilities, either in its region, according to a similar size, and/or according to similar practices or patients, and the like.

To help facilitate the dissemination of improved practices across multiple medical facilities, it would be desirable if a common source could have knowledge of the contexts from multiple medical facilities and be able to determine what changes should be made for any particular medical facility, based on the knowledge of the practices of any or all of the multiple facilities.

In some aspects, a cloud-based system communicatively coupled to knowledge centers in a medical facility, such as one or more medical hubs, may be configured to aggregate medical resource usage data from multiple medical facilities. The cloud-based system may then correlate the medical resource usage data with outcomes from those facilities, and may be able to derive various patterns within the data. For example, in some aspects, the cloud-based system may find which hospitals generate the least amount of waste per unit cost, based on an aggregation of all waste and procurement data obtained from medical facilities in a wide geographic region (e.g., all surgery centers in Japan). The cloud-based system may be configured to identify which medical facility produced the least amount of waste per unit cost, and then may analyze what practices differentiate that medical facility. If a trend is found, the cloud-based system may disseminate this information to all of the similarly situated medical facilities to improve their practices. This analysis may help improve inventory management, throughput efficiency, or overall efficiency of a medical facility. The improved inventory management may help surgical devices and other medical resources be utilized at their peak performance levels for longer periods of time, compared to if resources were badly managed, and therefore medical devices may be continuously used while they are older and more worn down.

In general, the cloud-based system may be configured to aggregate data from multiple medical facilities, something that no single facility alone would be able to accomplish on its own. Furthermore, the cloud-based system may be configured to analyze the large collection of data, controlling for common variables, such as type of practice, type of patient, number of patients, geographic similarity, which facilities use similar types of instruments, etc., that no single facility alone would be able to analyze on its own.

In this way, the cloud-based system of the present disclosure may be able to find more accurate causalities that lead to best practices at a particular facility, which can then be disseminated to all of the other facilities. Furthermore, the cloud-based system may be able to provide the data from all of the disparate sources that no single facility may be able to do on its own.

Referring to FIG. 182, shown is an example illustration of a tabulation of various resources correlated to particular types of surgical categories. There are two bars for each category, with the dashed line bars 7102, 7106, and 7110 representing unused and/or scrap resources, and the solid line bars 7104, 7108, and 7112 showing a totality of resourced in use for that category. In this example, bars 7104, 7108, and 7112 show a total amount of endocutter cartridges, sponges, saline, fibrin sealants, sutures, and stapler buttresses, for thoracic, colorectal, and bariatric procedures, respectively, compared to the lower amounts 7102, 7106, and 7110 representing an amount of unused resources for the thoracic, colorectal, and bariatric procedures, respectively.

The cloud system may be configured to identify wasted product that was gathered and not used or gathered and used in a manner that was not beneficial to the patient or the surgery. To do this, the cloud system may record in memory all records of inventory intake and disposal. During each intake, the inventory may be scanned and entered, and the bar codes of each inventory item may identify what type of product it is, as an example. In some aspects, smart disposal bins may be utilized to automatically tabulate when a product is being disposed of. These may be connected to the cloud system ultimately, either through one or more surgical hubs or through a separate inventory management system throughout the entire facility. Each facility may be tracked by its location, for example through a set GPS coordinate, inputted address or the like. This data may be organized in memory using one or more databases with various meta data associated with it, such as date and time of use, location of origin, type of procedure used for if applicable, cost per item, expiration date if applicable, and so on.

In addition, the cloud system may be configured to identify misfired or misused product and tracking of where the product was used, and may archive these results. For example, each surgical instrument communicatively coupled to a surgical hub may transmit a record of when the instrument was fired, such as to fire a staple or apply ultrasonic energy. Each record may be transmitted through the instrument and recorded at the cloud system ultimately. The action by the instrument may be tied with an outcome, either at that instant or with an overall outcome stating whether the procedure was successful or not. The action may be associated with a precise timestamp that places the action at an exact point during a surgery, where all of the actions of the surgery are also automatically recorded to the cloud, including start and end times of the surgery. This enables all of the human medical care workers to focus on their respective duties during surgery, rather than worry about an exact instance an action of a medical instrument occurred. The recordings of the medical instruments can be used to identify what products may be wasted during surgery, and the cloud system may be configured to also identify usage trends in this way.

In some aspects, the cloud system may be configured to perform trending analysis of the product tied to the overall length or amount of the product to identify short fires, or discarded product. For example, the cloud system may place the use of a product within a known period of when a surgical procedure is occurring, with a time stamp. The cloud system may then record an amount of resources utilized during that procedure, and may compare the materials used in that procedure with similarly situated procedures performed elsewhere. Out of this, several conclusions may be reached by the cloud system. For example, the cloud system may provide recommendations of a mix that provides smaller portions or an alternative usage that results in less wasted product. As another example, the cloud system may provide a suggestion or specified protocol change of specialized kits that would assemble the product in a manner more aligned to the detected institution usage. As yet another example, the cloud system may provide a suggestion or a change in protocol for alternative product mixes that would be more aligned to the detected usage and therefore should result in less wasted product. As yet another example, the cloud system may provide a recommendation on how to adjust a medical procedure during surgery based on timings of actions occurring before or after an event that typically results in wasteful resources, such as misfirings or multiple firings, based on identifying a correlation or pattern that actions during surgery occurring within a certain time interval relative to a prior action tend to result in wasteful actions. These analyses may be derived in part using algorithms that attempt to optimize the available resources with the rates of their disposals, taking into account various factors such as misfirings, native practices of the surgeons or the facility at large, and so forth.

Still referring to FIG. 182, based on the tabulation of the used and unused product, the cloud system can also generate several other conclusions. For example, the cloud system may be configured to generate a correlation of unused product to cost overhead. The cloud system may also generate a calculation of expired product and how that impacts rates of change with inventory. It may also generate an indication of where in the supply chain the product is being unused and how it is being accounted for. It may also generate ways to reduce costs or inventory space by finding substitutes of some resources over others for the same procedure. This may be based on comparing similar practices at different medical facilities that use different resources to perform the same procedures.

In some aspects, the cloud system may be configured to analyze the inventory usage of any and all medical products and conduct procurement management for when to acquire new product. The cloud system may optimize the utilization of inventory space to determine how best to utilize what space is available, in light of rates of usage for certain products compared to others. It may often be the case that inventory is not closely monitored in terms of how long a product remains in storage. If certain products are utilized at slower rates, but there is a large amount of it, it may be determined that the storage space is allocated poorly. Therefore, the cloud system may better apportion the storage space to reflect actual resource usage.

To improve in this area, in some aspects, the cloud system may for example, identify missing or insufficient product within an operating room (OR) for a specified procedure. The cloud system may then provide an alert or notification or transmit data to display that deficiency at the surgical hub in the OR. As another example, when a product is used in the OR, it may communicate its usage information to the cloud, such as activate a sensor or activation identification. The product may be registered with a scan or a power on switch. Analysis of this information for a given hospital coupled with its ordering information, may eventually inform the supply status and can enable ordering recommendations. This may occur automatically, once the cloud system registers that products are being used in the OR, or through other means.

In some aspects, device utilization within a procedure is monitored by the cloud system and compared for a given segment (e.g., individual surgeon, individual hospital, network of hospitals, region, etc.) against device utilization for similar procedures in other segments. Recommendations are presented to optimize utilization based on unit resource used or expenditure spent to supply such resource. In general, the cloud system may focus on a comparison of product utilization between different institutions that it is connected with.

FIG. 183 provides an example illustration of how the data is analyzed by the cloud system to provide a comparison between multiple facilities to compare use of resources. In general, the cloud system 7200 may obtain usage data from all facilities, such as any of the types of data described with respect to FIG. 182, and may associate each datum with various other meta data, such as time, procedure, outcome of the procedure, cost, date of acquisition, and so forth. FIG. 183 shows an example set of data 7202 being uploaded to the cloud 7200, each circle in the set 7202 representing an outcome and one or more resources and contextual metadata that may be relevant to leading to the outcome. In addition, high performing outcomes 7204 and their associated resources and contextual metadata are also uploaded to the cloud 7200, though at the time of upload, it may not be known which data has very good outcomes or simply average (or below average) outcomes. The cloud system may identify which use of resources is associated with better results compared to an average or expected outcome. This may be based on determining which resources last longer, are not wasted as often, ultimately cost less per unit time or unit resource, as some examples. The cloud system may analyze the data to determine best outcomes based on any and all of these variables, or even one or more combinations of them. The trends identified may then be used to find a correlation or may prompt request of additional data associated with these data points. If a pattern is found, these recommendations may be alerted to a user to examine as possible ways to improve resource usage and efficiency.

The example graph 7206 provides a visual depiction of an example trend or pattern that the cloud may derive from examining the resource and outcome data, according to some aspects. In this example, the cloud system may have analyzed resource and outcome data of number of stapler firings and their relation to performance in surgery. The cloud system may have gathered the data from multiple medical facilities, and multiple surgeons within each facility, based on automatically recorded firing data during each surgery that is generated directly from the operation of the surgical staplers themselves. The performance outcomes may be based on post-op examinations and evaluations, and/or immediate outcomes during surgery, such as whether there is a bleeding event or a successful wound closure. Based on all of the data, trends may be determined, and here, it may be discovered that there is a small window of the number of firings that results in the best performance outcomes, at interval "a" as shown. The magnitude of this performance compared to the most common number of firings is shown as interval "b." Because the number of firings that results in the best outcomes may not be what is commonly practiced, it may not be readily easily to have discovered these outcomes without the aggregation and analytical abilities of the cloud system.

As another example: cartridge type, color, and adjunct usage that are monitored for sleeve gastrectomy procedures for individual surgeons within the same hospital may be obtained. The data may reveal an average procedure cost for one surgeon is higher for this surgeon when compared to others within the same hospital, yet short term patient outcomes remain the same. The hospital is then informed and is encouraged to look into differences in device utilization, techniques, etc. in search of optimizing costs potentially through the elimination of adjuncts.

In some aspects, the cloud system may also identify specialty cases. For example, specific cost information provided within the hospital, including OR time, device utilization, and staff, may be identified. These aspects may be unique to a particular OR, or facility. The cloud system may be configured to suggest efficiencies in OR time usage (scheduling), device inventory, etc. across specialties (orthopedics, thoracic, colorectal, bariatric, etc.) for these specialty cases.

In some aspects, the cloud system may also be configured to compare cost-benefit of robotic surgery vs traditional methods, such as laparoscopic procedures for given procedure type. The cloud system may compare device costs, OR time, patient discharge times, efficacy of the procedure done by the robot vs performed by surgeons exclusively, and the like.

Linking of Local Usage Trends with the Resource Acquisition Behaviors of the Larger Data Set (Individualized Change)

According to some aspects of the cloud system, whereas the above disclosure focuses on a determination of efficiency (i.e., value) and optimizing based on that, here, this section centers around on identifying which local practices may be best disseminated to other similarly situated medical facilities.

A medical care facility, such as a hospital or medical clinic, may develop a set of practices for how to utilize medical devices for aiding medical procedures that are often derived from routines and traditions maintained over time. The behaviors of a medical facility typically are risk-averse, and generally would be hesitant to adopt new and better practices unless and until convincingly shown of a better practice. Similarly, even if a better practice for utilizing a device or for adjusting a procedure has been developed in a nearby facility, it is difficult for a local facility to adopt the improved practice because 1) each facility may be more natively resistant to change from the outside and 2) there are many unknowns for how or why the improved practice works in the nearby facility in relation to what the local facility does instead. Furthermore, even if a medical facility desired to improve its practices, it may be unable to do so optimally because it lacks enough knowledge from other similarly situated facilities, either in its region, according to a similar size, and/or according to similar practices or patients, and the like.

To help facilitate the dissemination of improved practices across multiple medical facilities, it would be desirable if a common source could have knowledge of the contexts from multiple medical facilities and be able to determine what changes should be made for any particular medical facility, based on the knowledge of the practices of any or all of the multiple facilities.

In some aspects, a cloud-based system communicatively coupled to knowledge centers in a medical facility, such as one or more medical hubs, may be configured to aggregate resource utilization data and patient outcomes from multiple medical facilities. The cloud-based system may then correlate the resource utilization data with the outcomes from those facilities, and may be able to derive various patterns within the data. For example, in some aspects, the cloud-based system may find which hospitals produce better outcomes for a particular type of procedure, based on an aggregation of all the patient outcome data for that particular procedure collected in a wide geographic region (e.g., all surgery centers in Germany). The cloud-based system may be configured to identify which medical facility produced a better procedural outcome compared to the average across the geographic region, and then may analyze what differences in that procedure occur in that medical facility. If a trend is found and one or more differences are identified, the cloud-based system may disseminate this information to all of the similarly situated medical facilities to improve their practices.

In general, the cloud-based system may be configured to aggregate data from multiple medical facilities, something that no single facility alone would be able to accomplish on its own. Furthermore, the cloud-based system may be configured to analyze the large collection of data, controlling for common variables, such as type of practice, type of patient, number of patients, geographic similarity, which facilities use similar types of instruments, etc., that no single facility alone would be able to analyze on its own.

In this way, the cloud-based system of the present disclosure may be able to find more accurate causalities that give rise to best practices at a particular facility, which can then be disseminated to all of the other facilities. Furthermore, the cloud-based system may be able to provide the data from all of the disparate sources that no single facility may be able to do on its own.

The cloud system may be configured to generate conclusions about the efficacy of any local facility in a number of ways. For example, the cloud system may determine if a local treatment facility is using a product mixture or usage that differs from the larger community and their outcomes are superior. The cloud system may then correlate the differences and highlight them for use in other facilities, other surgical hub, or in clinical sales as some examples. In general, this information may be disseminated widely in a way that no single facility may have had access or knowledge of, including the facility that practiced this improve procedure.

As another example, the cloud system may determine if the local facility has equal to or inferior outcomes to the larger community. The cloud system may then correlate suggestions and provide that information back to the local facility as recommendations. The system may display data showing their performance in relation to others, and may also display suggestions on what that facility is doing compared to what everybody else is doing. Again, the local facility may not even know they have an inefficiency in that respect, nor may everybody else realize they are utilizing their resources more efficiently, and thus nobody would ever know to examine these issues without the cloud system having a bigger picture of all of the data.

These suggestions can come in various forms. For example, the cloud system may provide recommendations at the purchasing level that suggest improvements in cost for similar outcomes. As another example, the cloud system may provide recommendations at the OR level when the procedure is being planned and outfitted as the less desirable products are being pulled suggest other techniques and product mixes that would be in line with the broader community which is achieving higher outcomes. As yet another example, the cloud system may display outcomes comparison needs to account for surgeon experience, possibly through a count of similar cases performed by that surgeon from cloud data. In some aspects, the learning curve of an individual may be reported against an aggregated larger dataset, as expectation of improved outcomes, or of surgeon performance relative to peers in obtaining a steady state outcome level.

FIG. 184 illustrates one example of how the cloud system 7300 may determine efficacy trends from an aggregated set of data 7302 across whole regions, according to some aspects. Here, for each circle of the set of data 7302, device utilization, cost, and procedure outcomes for a procedure is monitored and compared for a given segment (e.g., individual surgeon, individual hospital, network of hospitals, region, etc.) against device utilization, cost, and procedure outcomes for similar procedures in other segments. These data may possess metadata that associates it to a particular facility. In general, an outcome of a procedure may be linked to multiple types of data associated with it, such as what resources were used, what procedure was performed, who performed the procedure, where the procedure was performed, and so on. The data linked to the outcome may then be presented as a data pair. The data may be subdivided in various ways, such as between good and inferior outcomes, filtered by particular facilities, particular demographics, and so forth. A regional filter 7304 is visually depicted as an example. The data set 7302 contains both good outcomes and inferior outcomes, with the inferior outcomes being darkened for contrast.

FIG. 184 also shows examples of charts that have these distinctions made and may be derived from the aggregated data set 7302, using one or more data pairs. Chart 7306 shows a global analysis in one example, while a regionally segmented analysis is provided in the other chart 7308. Statistical analysis may be performed to determine whether the outcomes are statistically significant. In chart 7306, the cloud system may determine that no statistical difference was found between good outcomes and inferior outcomes based on rates of occurrence. In contrast, in chart 7308, the cloud system may determine that there is a statistically higher occurrence of inferior outcomes for a given region, when filtering for a particular region. Recommendations are presented to share outcomes vs. cost vs. device utilization and all combinations therein to help inform optimization of outcomes against procedure costs with device utilization potentially being a key contributor of differences, according to some aspects.

As another example, a cartridge type and color are monitored for lobectomy procedures for individual surgeons within the same hospital. The data reveals average cost for one surgeon is higher on average for this surgeon, yet average length of stay is less. The hospital is informed by the cloud system and is encouraged to look into differences in device utilization, techniques, etc. in search of improving patient outcomes.

In some aspects, the cloud system may also be configured to provide predictive modeling of changes to procedures, product mixes, and timing for a given localized population or for the general population as a whole. The predictive modeling may be used to assess impact on resource utilization, resource efficiency, and resource performance, as some examples.

FIG. 185 provides an example illustration of some types of analysis the cloud system may be configured to perform to provide the predicting modeling, according to some aspects. The cloud system may combine its knowledge of the required steps and instruments for performing a procedure, and may compare the different avenues via various metrics, such as resources utilized, time, procedural cost, and the like. In this example of chart 7400, a thoracic lobectomy procedure is analyzed using two different types of methods to perform the same procedure. Option A describes a disposable ultrasonic instrument as the method for performing the procedure, while Option B shows a combination of different methods that in the aggregate perform the same procedure. The graphical illustration may help a surgeon or administrator see how the resources are utilized and their cost. Option B is broken down into multiple sections, including sterilization cost, reusable dissectors and additional time in the OR for performing the procedure. The cloud system may be configured to convert these somewhat abstract notions into a quantitative cost value based on combining its knowledge of time spent in the OR, staff salaries and resource costs per unit time in the OR, and resources utilized for sterilization and reusable dissectors and their associated costs. The cloud system may be configured to associate the various amounts of resources and costs with its knowledge of the required steps to perform the thoracic lobectomy procedure using the prescribed method in Option B.

As another example, chart 7404 in FIG. 185 shows a comparison between using an ultrasonic long dissector and a monopolar reusable dissector to perform various portions of a procedure. Chart 7404 shows a comparison in terms of time needed to perform each portion of the procedure for each instrument. The surgeon may then be able to select which instrument may be desired for a particular procedure. The breakout times may be automatically recorded empirically during live procedures, with the times for each portion of the overall procedure broken out due to the cloud system's knowledge of the expected sequence to perform the procedure. Demarcations between each portion may be set by a surgeon providing an input to manually denote when each change occurs. In other cases, the cloud system may utilize situational awareness to determine when a portion of the procedure has ended based on the way the devices are used and not used. The cloud system may aggregate a number of these procedures, performed across multiple surgeons and multiple facilities, and then compute an average time for each section, as an example.

As another example, chart 7402 in FIG. 185 shows an example graphical interface for comparing relative cost when utilizing the ultrasonic long dissector or a monopolar reusable dissector, according to some aspect. The value of each instrument per unit time is displayed for a particular procedure. The data used to generate these values may be similar to those obtained for charts 7400 and 7404, as some examples. The graphical display may allow for a succinct description of the key points of efficiency that would be most useful to make a determination. This analysis may help a surgeon see how valuable each instrument is for a given procedure.

In general, to perform the predictive modeling, the cloud system may combine its knowledge of the exact steps to perform a procedure, what instruments may be used to perform each step, and its aggregated data for how each instrument performs each particular step. A surgeon may not have the combination of such knowledge in order to provide such an assessment alone. The predictive modeling therefore may be the result of continued monitoring and acquisition of data across multiple facilities, the likes of which would not be possible without the cloud system.

In some aspects, the cloud system may also derive the distilled information from multiple sources (e.g., HUB data collection sources, literature, etc.) to identify the optimal procedure technique. Various other examples for how predictive modeling may be utilized include:
(1) sigmoidectomy: multi-quadrant surgery; which is the best order of operations, etc.;
(2) RYGB: what is the ideal limb length, etc. based on the circumstances for this patient;
(3) Lobectomy: how many and which lymph nodes should be removed; and
(4) VSG: Bougie size and distance from pylorus.

In some aspects, when a suggestion is made to a surgeon, the surgeon is given the option to decline future suggestions like this, or to continue. In addition, through interface with the hub, the surgeon may inquire to the cloud system additional information to inform his or her decision. For example, the surgeon may want to isolate the times to a more localized set of data, such as the particular facility or a certain demographic that better caters to the patient undergoing the surgery. The data may change, for example, if the patient is a child or the patient is a woman.

Device Setup Modifications Based on Surgeon, Regional, Hospital, or Patient Parameters (Preoperatively)

Similar to the above section, the cloud-based system may also be configured to monitor smart instrument configurations and, more generally, configurations that utilize multiple smart instruments, such as an operating room preparing for surgery. For similar reasons as described above, such as to improve medical efficacy and efficiency, it may be useful to compare a procedural setup at any particular medical facility to aggregate data pertaining to the procedural setups at multiple other medical facilities.

The cloud-based system of the present disclosure may be configured to aggregate data pertaining to smart medical instrument configurations and operating room (OR) setups that utilize multiple smart medical instruments. The smart medical instruments may include: manual devices that are communicatively coupled to a medical data tower and are configured to generate sensor data; and robotic instruments that perform procedures in a more automated fashion. The cloud-based system may be configured to detect irregularities in an OR setup, either pertaining to what devices are present in the room and/or what materials are used to create a product mix for a medical procedure. The irregularities may be based on comparing the materials and equipment present in the OR with other setups from other medical facilities for a similar situation. The cloud system may then generate a change in firmware, software, or other settings and transmit those changes to the surgical devices like a device update.

In this way, the cloud-based system of the present disclosure may be able to identify errors and find more accurate causalities that give rise to best practices at a particular facility, which can then be disseminated to all of the other facilities. Furthermore, the cloud-based system may be able to provide the data from all of the disparate sources that no single facility may be able to do on its own. This can lead to safe and more efficient operating room procedures and medical practices in general.

In some aspects, the cloud system may be configured to provide recommendations of instrument configurations, and even generate the appropriate device settings changes, to customize performance to that of a pre-specified user.

For example, the cloud system may focus on a surgical device user or surgeon based on a comparison of current usage of a device with the historic trends of a larger data set. As some examples, the cloud system may provide recommendations of what type of cartridge to use based on what the user has previously used for the particular procedure or just what the particular surgeon desires in general. The cloud system may access data based on the particular surgeon, the type of procedure, and the type of instruments used in order to make this determination.

As another example, the cloud system may provide a recommendation based on an identified anatomy indicated in a display of the cartridge. As another example, the cloud system may provide a recommendation by referring to a baseline surgical device clamping and firing speed, based on local previous usage data that it has stored in its memory.

As yet another example, the cloud system may conduct a comparison of current device tissue interaction against a historical average for the same surgeon, or for the same step in the same procedure for a segment of surgeons in the database. The cloud system again may have access to all steps used to perform a procedure, and may access a catalog of all data when performing a particular step in a procedure across all surgeons who have ever performed that procedure in its network. The recommendation may also come from an analysis of how the current surgical device has been observed to interact with tissue historically. This type of analysis may be useful because it is often not the case that large amounts of live patient data can be collected for how a surgical device interacts precisely with the tissue. Furthermore, a surgeon typically knows only his or her experience, and does not have outside knowledge of what other surgeons experience for the same procedure. The cloud, on the other hand, is capable of collecting all of this data and providing new insights that any individual surgeon would not know alone.

As another example: In stapling, more than one of the following are known: cartridge color, stapler type, procedure, procedure step, patient information, clamp force over time, prior firing information, end effector deformations, etc. This information is compared against a historical average for a similar dataset. The current situation is compared against this average, informing the user about the nature of the current firing.

FIG. 186 provides a graphical illustration of a type of example analysis the cloud system may perform to provide these recommendations, according to some aspects. In this example, chart 7500 shows data for parenchyma staple firing analysis. In the bar graphs 7502 are various types of staples used, where each color of staple reflects a different amount of force applied to the surgical site. The y axis (on the left) associated with the bar graphs 7502 reflects a percent level of usage of that type of staple color, and each color shows bar graphs for three different categories: regional average usage (in Japan in this case), global average usage with best outcomes, and the local facility average usage. Based on this data, the cloud system may be configured to develop a recommendation for what staples to change to for a given situation. A series of suggested actions is shown in chart 7506 as a result. The chart 7500 also shows a set of line graphs 7504 that reflect a percentage of prolonged air leaks (the y axis on the right) for each color used, and for each type of category (regional, global average, facility average). If staples are too thick and do not match the level of tissue thickness, there could be holes in the staples that lead to undesirable air leaks. Here, the cloud system may provide a recommendation based on all of the data shown as well as data not shown, according to some aspects. The cloud system may simply provide a recommendation in the form of a letter as the label, and the surgeon may verify whether the data supports such a finding and decide to accept the cloud system's recommendation.

As another example, the cloud system may be configured to provide a recommendation of ultrasonic blade lengths or capacities based on likely to encounter vascular structures in a procedure. Similar to what is described above in reference to FIG. 186, the cloud system may collect the relevant data for blade lengths, and their outcomes that have been obtained from multiple surgical hubs, and illustrate the various outcomes for using different blade lengths on a particular procedure. A recommendation may be provided in a graphical display where the surgeon can verify the recommendation using the graphical presentation created by the cloud system.

In some aspects, the cloud system is also configured to provide recommendations to the staff about which devices to pull for an upcoming procedure. These recommendations may be based on a combination of surgeon preference (pick list) against historical device utilization rates for the same procedures performed by some segment of the larger database, as well as average recommendations or utilizations across different facilities that produce the best results. The data may be obtained by pairing good outcomes with the metadata, such as what devices were used to achieve those good outcomes. Recommendations can be influenced by other factors, including patient information, demographic data, etc.

Relatedly, in some aspects, the cloud system may also provide identification of pulled instruments that might not be the preferred device for a given procedure. The blacklisting of sorts can more clearly eliminate any obviously flaw uses of devices to help surgeons make the best decisions. This data may be obtained from manufacturer input, analysis of poor outcomes, specific input provided to the cloud system, and so on.

In addition, based on interrogating tissue for properties (elasticity, impedance, perfusion rate), a specific device with a given parameter set (clamp preload) could be suggested to be used from current stock in inventory by the cloud system. Some of the metadata associated with the outcomes of past procedures may include a description of the type of tissue being operated on, and an associated description of the physical characteristics of that tissue. The cloud system may then draw trends or patterns based on different types of procedures, but having in common all procedures that deal with similar types of tissue. This kind of analysis may be used as a secondary recommendation, when a new or unknown procedure must take place and new suggestions are welcome. If the recommendation is accepted, the cloud system may be configured to generate the change in parameters and transmit them to the interconnected medical device, through the surgical hub, to make the medical device readily available for use in the adjusted procedure.

In some aspects, the device setup recommendations can include suggestions of adjuncts for devices based on the pre-surgery imaging or locally collected data during the beginning of a procedure. That is, this suggestion of adjuncts may be for use on or with devices based on the local correlation of use to efficacy of the device. As an example, based on a given procedure, surgeon, and patient information, bleeding in a case must be tightly controlled, and therefore the cloud system may conclude that a buttress is recommended on all staple firings.

In some aspects, the cloud system may also be configured to provide awareness of any newly-launched products that are available and suitable for operation as well as instructions for use (IFU). The data may be gathered from one or more surgical hubs, or from direct factory input for the newly-launched products. The cloud system can download the information and make the information displayable to multiple medical hubs across multiple facilities.

In some aspects, regarding any of the above examples for recommendations being provided by the cloud system, the cloud system may also conversely provide alerts or other signals when a device or suggested setup is not followed or is disregarded. The cloud system may be configured to access procedural data from a surgical hub during a surgical procedure, for example. The surgical hub may collect data for what type of devices are in use during a procedure. The cloud system may monitor the progress of the procedure by verifying if an accepted method or device is used in the correct or prescribed order for the procedure. If there is a deviation, in that a particular device is not expected or a step is missed, the cloud system may send an alert to the surgical hub that a particular device is not being used properly, as an example. This would occur in real time, as the timing of the procedure is important for the patient's safety.

Medical Facility Segmented Individualization of Instrument Function

In some aspects, the cloud-based system may also be configured to provide recommendations or automatically adjust surgical instrument settings to account for specific differences at a medical facility. While there are a number of similarities that can be normalized across multiple facilities, there may also be particular differences that should be accounted for. For example, patient demographic differences, patient physiological differences more native to a local population, procedural differences—for example preferences by each individual surgeon—and region specific instrument availability or other differences may inspire certain adjustments to be made at any particular medical facility.

The cloud-based system of the present disclosure may be configured to aggregate not only data pertaining to smart medical instrument configurations and operating room (OR) setups that utilize multiple smart medical instruments, but also data that highlight specific differences that may be unique to that region or that particular medical facility. The cloud-based system may then factor in adjustments to device settings or recommendations to changes in procedures based on these differences. For example, the cloud-based system may first provide a baseline recommendation for how a smart instrument should be used, based on best practices discovered in the aggregate data. Then, the cloud-based system may augment the recommendation to account for one or more unique differences specific to a medical facility. Examples of these differences are described above. The cloud-based system may be made aware of what demographics and patient data gave rise to the optimal baseline procedure, and then compare the local facility demographics and patient data against that. The cloud-based system may develop or extrapolate a correlation from that baseline setting in order to develop an adjustment or offset that accounts for the differences in demographics and patient data.

In this way, the cloud-based system of the present disclosure may be able to make optimal adjustments specific to each medical facility or even specific to each operating room, or surgeon. The adjustments may offer improved performance that take into account the observed best practices as well as any unique differences.

In some aspects, the cloud system may be configured to provide changes to instrument variation of usage to improve outcomes. For example, the cloud system may determine a localized undesirable effect that is due to a specific manner of utilizing a surgical device. FIG. 187 provides an illustration of how the cloud system may conduct analysis to identify a statistical correlation to a local issue that is tied to how a device is used in the localized setting. The cloud 7600 may aggregate usage data of all types of devices and record their outcomes. The data set may be filtered down to only those outcomes that utilized the particular device in question. The cloud system may then perform statistical analysis to determine if there is a trend in how the procedures are performed at a particular facility when utilizing that device. A pattern may emerge that suggests there is a consistent flaw in how the device is used at that facility, represented as the data points 7602 that demonstrate the statistical correlation. Additional data may then be examined, to see if a second pattern may arise in comparison to how others are using the device in the aggregate. A suggestion may be provided once a pattern is identified and addressed to the local outlier 7604. In other cases, the cloud system may provide a facility-specific update to the device to offset the local practice of how that device is used.

In some aspects, the cloud system may be configured to communicate the deviation to the specific user and the recommendation of a differing technique or usage to improve outcomes from the specific device. The cloud system may transmit the data for display at the surgical hub to illustrate what changes ought to be made.

As an example: A stapler configured with a means to sense the force required to clamp the device transmits data indicating that the clamp force is still rapidly changing (viscoelastic creep) when the surgeon initiates firing of the staple, and it is observed that the staple line bleeds more often than expected. The cloud system and/or device is able to communicate a need to wait longer (e.g., 15 seconds) before firing the device to improve outcomes. This may be based on performing the statistical analysis described in FIG. 187 using data points from similar procedures aggregated from multiple surgeons and multiple facilities. In the moment of the surgery, it would be infeasible or impractical for anybody on the surgery team to come to these conclusions without the help of the cloud system aggregating such knowledge and arriving at such conclusions.

In some aspects, the cloud system may also be configured for intentional deployment of control algorithms to devices with an in-use criteria meeting specific criteria. For regional differences, the cloud system may adjust the control algorithms of various surgical devices. A different amount of force may be applied to a device for patients in a different demographic, for example. As another example, surgeons may have different uses for a type of surgical device, and control algorithms can be adjusted to account for this. The cloud system may be configured to send out a wide area update to a device, and may target the regional and specific instrument IDs which allow for targeted updates to their control programs.

In some aspects, the cloud system may provide for coding of the serial numbers of sales units and/or individual devices, which enables updated control programs to be pushed to a specific device or specific groups of devices based on meeting a specific criteria or threshold.

In addition, according to some aspects, the cloud system may be configured to perform analysis of peri-operative data against outcomes data seeking correlations that identify exceptional results (positive and negative). The analysis may be performed at multiple levels (e.g., individual, hospital, and geographic (e.g., city, county, state, country, etc.) filters). Furthermore, regional corroboration of improved outcomes may be target for only a limited geographic area, as it is known that the changes occur only within a limited area. The ability to tune devices to regional preferences, techniques, and surgical preferences may allow for nuanced improvements for regionally specific areas.

In addition to directly changing instrument settings, the cloud system may also be configured to provide recommendations on different instruments or equivalent device suggestions due to regional availability. That is, an equivalent suggestion to a device to perform a particular function may be recommended by the cloud system, in the event a device is lacking and a particular region has an excess or general availability of the different device that may be used to serve an equivalent purpose.

For example, the cloud system may determine that PPH hemorrhoid stapling devices or curved cutter 30 devices are only available in Italy due to a unique procedure configuration or teaching hospital procedure design. As another example, the cloud system may determine that there is an Asia-specific TX and open vascular stapler use due to cost sensitivity, lack of laparoscopic adoption, and teaching hospital preferred techniques and patient thoracic cavity size. As another example, the cloud system may provide awareness messages to OR staff of sub-standard knock-off products available in a certain region. This data may be derived from an ingestion of information from multiple sources, such as inputs provided by experts and doctors, and employing machine learning and natural language processing to interpret trends and news related to a local area. FIG. 188 provides a graphical illustration of an example of how some devices may satisfy an equivalent use compared to an intended device. Here, a circular stapling device 7702 is compared to a compression ring 7704 for use in a PPH stapler 7700 for hemorrhoidopexy procedures. The type of analysis performed to reach the recommendations by the cloud system may be similar to those described in FIG. 187. The cloud system may provide a display of this suggestion, as well as an analysis of its efficiency and resource utilization, in example display 7706 that may be shown at a display in a surgical hub. In this case, the instrument cost is compared, as well as time and efficacy for each type of instrument. The cloud system may derive these recommendations by obtaining usage examples from different facilities, observing how other facilities and doctors treat the same procedure.

In some aspects, the cloud system may also be configured to provide a surgical hub decision tree and local suggestions of post-operative care, based on data processed during the procedure and Cloud Analytics trending of results or performance of the devices aggregated from larger population sets.

In some aspects, the cloud system may provide updateable decision trees for post-operative care suggestions, based on device measured situational usage. The post-operative care decisions may initially be derived from traditionally known responses that doctors would normally recommend. Once additional data becomes available, say from aggregating types of post-operative care from other facilities, or from analyzing new types of care from literature or from research on new surgical devices, the decision can be updated by the cloud system. The decision tree may be displayable at a surgical hub and in a graphical form.

In using this decision tree, feedback can be provided for each node to state how effective the current solutions are. The data may be inputted based on whatever feedback patients may provide. A doctor or data admin need not perform any analysis at the time, but the cloud system can aggregate all of the data and observe what trends may arise. Feedback can then be provided to update the decision tree.

In some aspects, the cloud system may incorporate operative data & device performance to propose post-operative monitoring & activities. For example, various patient measures may change what decisions in post-operative care should be taken. These measurements can include but are not limited to: (a) blood pressure; (b) low hematocrit; (c) PTT (partial thromboplastin time); (d) INR (international normalized ratio); (e) Oxygen saturation; (f) Ventilation changes; and (g) X-Ray data.

As another example, anesthesia protocol can dictate what post-operative decisions should be taken. This may account for: (a) any fluids administered; (b) Anesthesia time; and (3) Medications, as some non-limiting examples.

As another example, the types of medications may also play a role. The application of Warfarin is one notable example. A patient post-operatively has abnormal PTT and INR, for example. Because the patient is on Warfarin, potential treatments could include vitamin K, factor 7, or the delivery of plasma (fpp). Plavix can be another example. A patient post-operatively has abnormal PTT and INR. Because patient is on Plavix, potential treatments for Warfarin would be ineffective. Deliver platelets instead may be the suggestion in the decision tree.

As a fourth example, post-operative instructions may be provided that are dependent on the type of procedure. Some non-limiting examples include colorectal time to solid food (motility); and (b) time to physical activity & PT. These varying decisions can be reflected in the decision tree, and all of the types of branching decisions may be stored in the cloud system and updated when additional data is gained from any connected facility.

FIG. 189 provides various examples of how some data may be used as variables in deciding how the post-operative decision tree may branch out. As shown, some factors 7802 may include the parameters used in surgical devices, such as the force to fire (FTF) used in an operation, or the force to close (FTC) used in a surgical device. Graph 7800 shows a visual depiction of how the FTC and FTF curves may interrelate with one another. Other factors include compression rate, wait time, and staple adaptability. Based on some of these variables, a type of post-operative care should be adjusted. In this case, a multi-factored analysis is applied, which may be too complex to calculate or modify without the aid of the processing power of a system like the cloud system. This example suggests that a decision tree 7804 provided by the cloud system can be more than a simple two dimensional decision tree. To account for multiple variables to make a single decision, the decision tree generated by the cloud may be visually available for perhaps just a portion, and the ultimate conclusion may have to be displayed without a full display of all of the other branches that were not considered. The chart 7806 may be an example of providing additional information of how to respond within the decision tree.

Adaptive Control Program Updates for Surgical Devices

Modular devices include the modules (as described in connection with FIGS. 3 and 9, for example) that are receivable within a surgical hub and the surgical devices or instruments that can be connected to the various modules. The modular devices include, for example, intelligent surgical instruments, medical imaging devices, suction/irrigation devices, smoke evacuators, energy generators, ventilators, and insufflators. Various operations of the modular devices described herein can be controlled by one or more control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Although an "intelligent" device including control algorithms that respond to sensed data can be an improvement over a "dumb" device that operates without accounting for sensed data, if the device's control program does not adapt or update over time in response to collected data, then the devices may continue to repeat errors or otherwise perform suboptimally. One solution includes transmitting operational data collected by the modular devices in combination with the outcomes of each procedure (or step thereof) to an analytics system. In one exemplification, the procedural outcomes can be inferred by a situational awareness system of a surgical hub to which the modular devices are paired, as described in U.S. patent application Ser. No. 15/940,654, titled SURGICAL HUB SITUATIONAL AWARENESS, which is herein incorporated by reference in its entirety. The analytics system can analyze the data aggregated from a set of modular devices or a particular type of modular device to determine under what conditions the control programs of the analyzed modular devices are controlling the modular devices suboptimally (i.e., if there are repeated faults or errors in the control program or if an alternative algorithm performs in a superior manner) or under what conditions medical personnel are utilizing the modular devices suboptimally. The analytics system can then generate an update to fix or improve the modular devices' control programs. Different types of modular devices can be controlled by different control programs; therefore, the control program updates can be specific to the type of modular device that the analytics system determines is performing suboptimally. The analytics system can then push the update to the appropriate modular devices connected to the analytics system through the surgical hubs.

FIG. 190 illustrates a block diagram of a computer-implemented adaptive surgical system 9060 that is configured to adaptively generate control program updates for modular devices 9050, in accordance with at least one aspect of the present disclosure. In one exemplification, the surgical system includes a surgical hub 9000, multiple modular devices 9050 communicably coupled to the surgical hub 9000, and an analytics system 9100 communicably coupled to the surgical hub 9000. Although a single surgical hub 9000 is depicted, it should be noted that the surgical system 9060 can include any number of surgical hubs 9000, which can be connected to form a network of surgical hubs 9000 that are communicably coupled to the analytics system 9010. In one exemplification, the surgical hub 9000 includes a processor 9010 coupled to a memory 9020 for executing instructions stored thereon and a data relay interface 9030 through which data is transmitted to the analytics system 9100. In one exemplification, the surgical hub 9000 further includes a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further includes an interface 9040 for communicably coupling the modular devices 9050 to the surgical hub 9000. In one aspect, the interface 9040 includes a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In one exemplification, the surgical hub 9000 can further be communicably coupled to one or more patient monitoring devices 9052, such as EKG monitors or BP monitors. In another exemplification, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data indicates how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In one exemplification, the analytics system 9100 includes a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 are connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 9-10.

FIG. 191 illustrates a logic flow diagram of a process 9200 for updating the control program of a modular device 9050, in accordance with at least one aspect of the present disclosure. In the following description of the process 9200, reference should also be made to FIG. 190. The process 9200 can be executed by, for example, one or more processors of the analytics servers 9070 of the analytics system 9100. In one exemplification, the analytics system 9100 can be a cloud computing system. For economy, the following description of the process 9200 will be described as being executed by the analytics system 9100; however, it should be understood that the analytics system 9100 includes processor(s) and/or control circuit(s) that are executing the describe steps of the process 9200.

The analytics system 9100 receives 9202 modular device 9050 perioperative data and surgical procedural outcome data from one or more of the surgical hubs 9000 that are communicably connected to the analytics system 9100. The perioperative data includes preoperative data, intraoperative data, and/or postoperative data detected by a modular device 9050 in association with a given surgical procedure. For modular devices 9050 or particular functions of modular devices 9050 that are manually controlled, the perioperative data indicates the manner in which a surgical staff member operated the modular devices 9050. For modular devices 9050 or particular functions of modular devices 9050 that are controlled by the modular devices' control programs, the perioperative data indicates the manner in which the control programs operated the modular devices 9050. The manner in which the modular devices 9050 function under particular sets of conditions (either due to manual control or control by the modular devices' 9050 control programs) can be referred to as the "operational behavior" exhibited by the modular device 9050. The modular device 9050 perioperative data includes data regarding the state of the modular device 9050 (e.g., the force to fire or force to close for a surgical stapling and cutting instrument or the power output for an electrosurgical or ultrasonic instrument), tissue data measured by the modular device 9050 (e.g., impedance, thickness, or stiffness), and other data that can be detected by a modular device 9050. The perioperative data indicates the manner in which the modular devices 9050 were programmed to operate or were manually controlled during the course of a surgical procedure because it indicates how the modular devices 9050 functioned in response to various detected conditions.

The surgical procedural outcome data includes data pertaining to an overall outcome of a surgical procedure (e.g., whether there was a complication during the surgical procedure) or data pertaining to an outcome of a specific step within a surgical procedure (e.g., whether a particular staple line bled or leaked). The procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. patent application Ser. No. 15/940,654, or retrieved from a database 9054 (e.g., an EMR database) by the surgical hub 9000 or the analytics system 9100. The procedural outcome data can include whether each outcome represented by the data was a positive or negative result. Whether each outcome was positive or negative can be determined by the modular devices 9050 themselves and included in the perioperative data transmitted to the surgical hubs 9000 or determined or inferred by the surgical hubs 9000 from the received perioperative data. For example, the procedural outcome data for a staple line that bled could include that the bleeding represented a negative outcome. Similarly, the procedural outcome data for a staple line that did not bleed could include that the lack of bleeding represented a positive outcome. In another exemplification, the analytics system 9100 can be configured to determine whether a procedural outcome is a positive or negative outcome based upon the received procedural outcome data. In some exemplifications, correlating the modular device 9050 data to positive or negative procedural outcomes allows the analytics system 9100 to determine whether a control program update should be generated 9208.

Upon the analytics system 9100 receiving 9202 the data, the analytics system 9100 analyzes the modular device 9050 and procedural outcome data to determine 9204 whether the modular devices 9050 are being utilized suboptimally in connection with the particular procedure or the particular step of the procedure. A modular device 9050 can be controlled suboptimally if the particular manner in which the modular device 9050 is being controlled is repeatedly causing an error or if an alternative manner of controlling the modular device 9050 is superior under the same conditions. The analytics system 9100 can thus determine whether a modular device 9050 is being controlled suboptimally (either manually or by its control program) by comparing the rate of positive and/or negative outcomes produced by the modular device 9050 relative to set thresholds or the performance of other modular devices 9050 of the same type.

For example, the analytics system 9100 can determine whether a type of modular device 9050 is being operated suboptimally if the rate of negative procedural outcomes produced by the modular device 9050 under a particular set of conditions in association with a particular operational behavior exceeds an average or threshold level. As a specific example, the analytics system 9100 can analyze 9204 whether a control program for a surgical stapling instrument that dictates a particular force to fire (or ranges of forces to fire) is suboptimal for a particular tissue thickness and tissue type. If the analytics system 9100 determines that the instrument generates an abnormally high rate of leaky staple lines when fired at the particular force (e.g., causing the staples to be malformed, not fully penetrate the tissue, or tear the tissue) relative to an average or threshold staple line leakage rate, then the analytics system 9100 can determine that the control program for the surgical stapling instrument is performing suboptimally given the tissue conditions.

As another example, the analytics system 9100 can determine whether a type of modular device 9050 is being operated suboptimally if the rate of positive outcomes produced by an alternative manner of control under a particular set of conditions in association with a particular operational behavior exceeds the rate of positive outcomes generated by the analyzed manner of control under the same conditions. In other words, if one subpopulation of the type of modular device 9050 exhibits a first operational behavior under a certain set of conditions and a second subpopulation of the same type of modular device 9050 exhibits a second operational behavior under the same set of conditions, then the analytics system 9100 can determine whether to update the control programs of the modular devices 9050 according to whether the first or second operational behavior is more highly correlated to a positive procedural outcome. As a specific example, the analytics system 9100 can analyze 9204 whether a control program for an RF electrosurgical or ultrasonic instrument that dictates a particular energy level is suboptimal for a particular tissue type and environmental conditions. If the analytics system 9100 determines that a first energy level given a set of tissue conditions and environmental conditions (e.g., the instrument being located in a liquid-filled environment, as in an arthroscopic procedure) produces a lower rate of hemostasis than a second energy level, then the analytics system 9100 can determine that the control program for the electrosurgical or ultrasonic instrument dictating the first energy level is performing suboptimally for the given tissue and environmental conditions.

After analyzing 9204 the data, the analytics system 9100 determines 9206 whether to update the control program. If the analytics system 9100 determines that the modular device 9050 is not being controlled suboptimally, then the process 9200 continues along the NO branch and the analytics system 9100 continues analyzing 9204 received 9202 data, as described above. If the analytics system 9100 determines that the modular device 9050 is being controlling suboptimally, then the process 9200 continues along the YES branch and the analytics system 9100 generates 9208 a control program update. The generated 9208 control program update includes, for example, a new version of the control program for the particular type of modular device 9050 to overwrite the prior version or a patch that partially overwrites or supplements the prior version.

The type of control program update that is generated 9208 by the analytics system 9100 depends upon the particular suboptimal behavior exhibited by the modular device 9050 that is identified by the analytics system 9100. For example, if the analytics system 9100 determines that a particular force to fire a surgical stapling instrument results in an increased rate of leaking staple lines, then the analytics system 9100 can generate 9208 a control program update that adjusts the force to fire from a first value to a second value that corresponds to a higher rate of non-leaking staple lines or a lower rate of leaking staple lines. As another example, if the analytics system 9100 determines that a particular energy level for an electrosurgical or ultrasonic instrument produces a low rate of hemostasis when the instrument is used in a liquid-filled environment (e.g., due to the energy dissipating effects of the liquid), then the analytics system 9100 can generated 9208 a control program update that adjusts the energy level of the instrument when it is utilized in surgical procedures where the instrument will be immersed in liquid.

The type of control program update that is generated 9208 by the analytics system 9100 also depends upon whether the suboptimal behavior exhibited by the modular device 9050 is caused by manual control or control by the control program of the modular device 9050. If the suboptimal behavior is caused by manual control, the control program update can be configured to provide warnings, recommendations, or feedback to the users based upon the manner in which they are operating the modular devices 9050. Alternatively, the control program update can change the manually controlled operation of the modular device 9050 to an operation that is controlled by the control program of the modular device 9050. The control program update may or may not permit the user to override the control program's control of the particular function. In one exemplification, if the analytics system 9100 determines 9204 that surgeons are manually setting an RF electrosurgical instrument to a suboptimal energy level for a particular tissue type or procedure type, then the analytics system 9100 can generate 9208 a control program update that provides an alert (e.g., on the surgical hub 9000 or the RF electrosurgical instrument itself) recommending that the energy level be changed. In another exemplification, the generated 9208 control program update can automatically set the energy level to a default or recommended level given the particular detected circumstances, which could then be changed as desired by the medical facility staff. In yet another exemplification, the generated 9208 control program update can automatically set the energy level to a set level determined by the analytics system 9100 and not permit the medical facility staff to change the energy level. If the suboptimal behavior is caused by the control program of the modular device 9050, then the control program update can alter how the control program functions under the particular set of circumstances that the control program is performing suboptimally under.

Once the control program update has been generated 9208 by the analytics system 9100, the analytics system 9100 then transmits 9210 or pushes the control program update to all of the modular devices 9050 of the relevant type that are connected to the analytics system 9100. The modular devices 9050 can be connected to the analytics system 9100 through the surgical hubs 900, for example. In one exemplification, the surgical hubs 9000 are configured to download the control program updates for the various types of modular devices 9050 from the analytics system 9100 each time an update is generated 9208 thereby. When the modular devices 9050 subsequently connect to or pair with a surgical hub 9000, the modular devices 9050 then automatically download any control program updates therefrom. In one exemplification, the analytics system 9100 can thereafter continue receiving 9202 and analyzing 9204 data from the modular devices 9050, as described above.

In one exemplification, instead of the modular devices 9050 transmitting recorded data to a surgical hub 9000 to which the modular devices 9050 are connected, the modular devices 9050 are configured to record the perioperative data and the procedural outcome data on a memory of the modular device 9050. The data can be stored for indefinitely or until the data is downloaded from the modular devices 9050. This allows the data to be retrieved at a later time. For example, the modular devices 9050 could be returned to the manufacturer after they are utilized in a surgical procedure. The manufacturer could then download the data from the modular devices 9050 and then analyze the data as described above to determine whether a control program update should be generated for the modular devices 9050. In one exemplification, the data could be uploaded to an analytics system 9100 for analysis, as described above. The analytics system 9100 could then generate update control programs according to the recorded data and then either incorporate that update in future manufactured product or push the update to modular devices 9050 currently in the field.

In order to assist in the understanding of the process 9200 illustrated in FIG. 191 and the other concepts discussed above, FIG. 192 illustrates a diagram of an illustrative analytics system 9100 updating a surgical instrument control program, in accordance with at least one aspect of the present disclosure. In one exemplification, a surgical hub 9000 or network of surgical hubs 9000 is communicably coupled to an analytics system 9100, as illustrated above in FIG. 190. The analytics system 9100 is configured to filter and analyze modular device 9050 data associated with surgical procedural outcome data to determine whether adjustments need to be made to the control programs of the modular devices 9050. The analytics system 9100 can then push updates to the modular devices 9050 through the surgical hubs 9000, as necessary. In the depicted exemplification, the analytics system 9100 comprises a cloud computing architecture. The modular device 9050 perioperative data received by the surgical 9000 hubs from their paired modular devices 9050 can include, for example, force to fire (i.e., the force required to advance a cutting member of a surgical stapling instrument through a tissue), force to close (i.e., the force required to clamp the jaws of a surgical stapling instrument on a tissue), the power algorithm (i.e., change in power over time of electrosurgical or ultrasonic instruments in response to the internal states of the instrument and/or tissue conditions), tissue properties (e.g., impedance, thickness, stiffness, etc.), tissue gap (i.e., the thickness of the tissue), and closure rate (i.e., the rate at which the jaws of the instrument clamped shut). It should be noted that the modular device 9050 data that is transmitted to the analytics system 9100 is not limited to a single type of data and can include multiple different data types paired with procedural outcome data. The procedural outcome data for a surgical procedure (or step thereof) can include, for example, whether there was bleeding at the surgical site, whether there was air or fluid leakage at the surgical site, and whether the staples of a particular staple line were formed properly. The procedural outcome data can further include or be associated with a positive or negative outcome, as determined by the surgical hub 9000 or the analytics system 9100, for example. The modular device 9050 data and the procedural outcome data corresponding to the modular device 9050 perioperative data can be paired together or otherwise associated with each other when they are uploaded to the analytics system 9100 so that the analytics system 9100 is able to recognize trends in procedural outcomes based on the underlying data of the modular devices 9050 that produced each particular outcome. In other words, the analytics system 9100 can aggregate the modular device 9050 data and the procedural outcome data to search for trends or patterns in the underlying device modular data 9050 that can indicate adjustments that can be made to the modular devices' 9050 control programs.

In the depicted exemplification, the analytics system 9100 executing the process 9200 described in connection with FIG. 190 is receiving 9202 modular device 9050 data and procedural outcome data. When transmitted to the analytics system 9100, the procedural outcome data can be associated or paired with the modular device 9050 data corresponding to the operation of the modular device 9050 that caused the particular procedural outcome. The modular device 9050 perioperative data and corresponding procedural outcome data can be referred to as a data pair. The data is depicted as including a first group 9212 of data associated with successful procedural outcomes and a second group 9214 of data associated with negative procedural outcomes. For this particular exemplification, a subset of the data 9212, 9214 received 9202 by the analytics system 9100 is highlighted to further elucidate the concepts discussed herein.

For a first data pair 9212*a*, the modular device 9050 data includes the force to close (FTC) over time, the force to fire (FTF) over time, the tissue type (parenchyma), the tissue conditions (the tissue is from a patient suffering from emphysema and had been subject to radiation), what number firing this was for the instrument (third), an anonymized time stamp (to protect patient confidentiality while still allowing the analytics system to calculate elapsed time between firings and other such metrics), and an anonymized patient identifier (002). The procedural outcome data includes data indicating that there was no bleeding, which corresponds to a successful outcome (i.e., a successful firing of the surgical stapling instrument). For a second data pair 9212*b*, the modular device 9050 data includes the wait time prior the instrument being fired (which corresponds to the first firing of the instrument), the FTC over time, the FTF over time (which indicates that there was a force spike near the end of the firing stroke), the tissue type (1.1 mm vessel), the tissue conditions (the tissue had been subject to radiation), what number firing this was for the instrument (first), an anonymized time stamp, and an anonymized patient identifier (002). The procedural outcome data includes data indicating that there was a leak, which corresponds to a negative outcome (i.e., a failed firing of the surgical stapling instrument). For a third data pair 9212*c*, the modular device 9050 data includes the wait time prior the instrument being fired (which corresponds to the first firing of the instrument), the FTC over time, the FTF over time, the tissue type (1.8 mm vessel), the tissue conditions (no notable conditions), what number firing this was for the instrument (first), an anonymized time stamp, and an anonymized patient identifier (012). The procedural outcome data includes data indicating that there was a leak, which corresponds to a negative outcome (i.e., a failed firing of the surgical stapling instrument). It should be noted again that this data is intended solely for illustrative purposes to assist in the understanding of the concepts discussed herein and should not be interpreted to limit the data that is received and/or analyzed by the analytics system 9100 to generate control program updates.

When the analytics system 9100 receives 9202 perioperative data from the communicably connected surgical hubs 9000, the analytics system 9100 proceeds to aggregate and/or store the data according to the procedure type (or a step thereof) associated with the data, the type of the modular device 9050 that generated the data, and other such categories. By collating the data accordingly, the analytics system 9100 can analyze the data set to identify correlations between particular ways of controlling each particular type of modular device 9050 and positive or negative procedural outcomes. Based upon whether a particular manner of controlling a modular device 9050 correlates to positive or negative procedural outcomes, the analytics system 9100 can determine 9204 whether the control program for the type of modular device 9050 should be updated.

For this particular exemplification, the analytics system 9100 performs a first analysis 9216*a* of the data set by analyzing the peak FTF 9213 (i.e., the maximum FTF for each particular firing of a surgical stapling instrument) relative to the number of firings 9211 for each peak FTF value. In this exemplary case, the analytics system 9100 can determine that there is no particular correlation between the peak FTF 9213 and the occurrence of positive or negative outcomes for the particular data set. In other words, there are not distinct distributions for the peak FTF 9213 for positive and negative outcomes. As there is no particular correlation between peak FTF 9213 and positive or negative outcomes, the analytics system 9100 would thus determine that a control program update to address this variable is not necessary. Further, the analytics system 9100 performs a second analysis 9216*b* of the data set by analyzing the wait time 9215 prior to the instrument being fired relative to the number of firings 9211. For this particular analysis 9216*b*, the analytics system 9100 can determine that there is a distinct negative outcome distribution 9217 and a positive outcome distribution 9219. In this exemplary case, the negative outcome distribution 9217 has a mean of 4 seconds and the positive outcome distribution has a mean of 11 seconds. Thus, the analytics system 9100 can determine that there is a correlation between the wait time 9215 and the type of outcome for this surgical procedure step. Namely, the negative outcome distribution 9217 indicates that there is a relatively large rate of negative outcomes for wait times of 4 seconds or less. Based on this analysis 9216*b* demonstrating that there is a large divergence between the negative outcome distribution 9217 and the positive outcome distribution 9219, the analytics system 9100 can then determine 9204 that a control program update should be generated 9208.

Once the analytics system 9100 analyzes the data set and determines 9204 that an adjustment to the control program of the particular module device 9050 that is the subject of the data set would improve the performance of the modular device 9050, the analytics system 9100 then generates 9208 a control program update accordingly. In this exemplary case, the analytics system 9100 can determine based on the analysis 9216b of the data set that a control program update 9218 recommending a wait time of more than 5 seconds would prevent 90% of the distribution of the negative outcomes with a 95% confidence interval. Alternatively, the analytics system 9100 can determine based on the analysis 9216b of the data set that a control program update 9218 recommending a wait time of more than 5 seconds would result in the rate of positive outcomes being greater than the rate of negative outcomes. The analytics system 9100 could thus determine that the particular type of surgical instrument should wait more than 5 seconds before being fired under the particular tissue conditions so that negative outcomes are less common than positive outcomes. Based on either or both of these constraints for generating 9208 a control program update that the analytics system 9100 determines are satisfied by the analysis 9216b, the analytics system 9100 can generate 9208 a control program update 9218 for the surgical instrument that causes the surgical instrument, under the given circumstances, to either impose a 5 second or longer wait time before the particular surgical instrument can be fired or causes the surgical instrument to display a warning or recommendation to the user that indicates to the user that the user should wait at least 5 seconds before firing the instrument. Various other constraints can be utilized by the analytics system 9100 in determining whether to generate 9208 a control program update, such as whether a control program update would reduce the rate of negative outcomes by a certain percentage or whether a control program update maximizes the rate of positive outcomes.

After the control program update 9218 is generated 9208, the analytics system 9100 then transmits 9210 the control program update 9218 for the appropriate type of modular devices 9050 to the surgical hubs 9000. In one exemplification, when a modular device 9050 that corresponds to the control program update 9218 is next connected to a surgical hub 9000 that has downloaded the control program update 9218, the modular device 9050 then automatically downloads the update 9218. In another exemplification, the surgical hub 9000 controls the modular device 9050 according to the control program update 9218, rather than the control program update 9218 being transmitted directly to the modular device 9050 itself.

In one aspect, the surgical system 9060 is configured to push down verification of software parameters and updates if modular devices 9050 are detected to be out of date in the surgical hub 9000 data stream. FIG. 193 illustrates a diagram of an analytics system 9100 pushing an update to a modular device 9050 through a surgical hub 9000, in accordance with at least one aspect of the present disclosure. In one exemplification, the analytics system 9000 is configured to transmit a generated control program update for a particular type of modular device 9050 to a surgical hub 9000. In one aspect, each time a modular device 9050 connects to a surgical hub 9000, the modular device 9050 determines whether there is an updated version of its control program on or otherwise accessible via the surgical hub 9000. If the surgical hub 9000 does have an updated control program (or the updated control program is otherwise available from the analytics system 9100) for the particular type of modular device 9050, then the modular device 9050 downloads the control program update therefrom.

In one exemplification, any data set being transmitted to the analytics systems 9100 includes a unique ID for the surgical hub 9000 and the current version of its control program or operating system. In one exemplification, any data set being sent to the analytics systems 9100 includes a unique ID for the modular device 9050 and the current version of its control program or operating system. The unique ID of the surgical hub 9000 and/or modular device 9050 being associated with the uploaded data allows the analytics system 9100 to determine whether the data corresponds to the most recent version of the control program. The analytics system 9100 could, for example, elect to discount (or ignore) data generated by a modular device 9050 or surgical hub 9000 being controlled by an out of date control program and/or cause the updated version of the control program to be pushed to the modular device 9050 or surgical hub 9000.

In one exemplification, the operating versions of all modular devices 9050 the surgical hub 9000 has updated control software for could also be included in a surgical hub 9000 status data block that is transmitted to the analytics system 9100 on a periodic basis. If the analytics system 9100 identifies that the operating versions of the control programs of the surgical hub 9100 and/or any of the connectable modular devices 9050 are out of date, the analytics system 9100 could push the most recent revision of the relevant control program to the surgical hub 9000.

In one exemplification, the surgical hub 9000 and/or modular devices 9050 can be configured to automatically download any software updates. In another exemplification, the surgical hub 9000 and/or modular devices 9050 can be configured to provide a prompt for the user to ask at the next setup step (e.g., between surgical procedures) if the user wants to update the out of date control program(s). In another exemplification, the surgical hub 9000 could be programmable by the user to never allow updates or only allow updates of the modular devices 9050 and not the surgical hub 9000 itself.

Adaptive Control Program Updates for Surgical Hubs

As with the modular devices 9050 described above, the surgical hubs 9000 can likewise include control programs that control the various operations of the surgical hub 9000 during the course of a surgical procedure. If the surgical hubs' 9000 control programs do not adapt over time in response to collected data, then the surgical hubs 9000 may continue to repeat errors, not provide warnings or recommendations to the surgical staff based on learned information, and not adjust to the surgical staff's preferences. One solution includes transmitting operational data from the surgical hubs 9000 that indicates how the surgical hubs 9000 are being utilized or controlled during the course of a surgical procedure to an analytics system 9100. The analytics system 9100 can then analyze the data aggregated from the network of surgical hubs 9000 connected to the analytics system 9100 to determine if a particular manner of operating the surgical hubs 9000 corresponds to improved patient outcomes or is otherwise preferred across the population of the surgical hubs 9000. In one exemplification, if a particular manner in which the surgical hubs 9000 are operated satisfies a defined condition or set of conditions, then the analytics system 9100 can determine that this particular manner should be implemented across the network of surgical hubs 9000. The analytics system 9100 can generate an update to the surgical hubs' 9000 control program to fix or improve the control program and then push the update to the surgical hubs 9000 so that the improvement is shared across every surgical hub 9000 that is connected to the analytics system 9100. For example, if a threshold number of the surgical hubs 9000 are controlled in a particular manner and/or if a particular manner of controlling the surgical hubs 9000 correlates to an improvement in the surgical procedure outcomes that exceeds a threshold level, then the analytics system 9100 can generate a control program update that controls the surgical hubs 9000 in a manner corresponding to the preferred or improved manner of control. The control program update can then be pushed to the surgical hubs 9000.

In one exemplification, an analytics system 9100 is configured to generate and push control program updates to surgical hubs 9000 in the field based on perioperative data relating to the manner in which the surgical hubs 9000 are controlled or utilized. In other words, the surgical hubs 9000 can be updated with improved decision-making abilities according to data generated from the hub network. In one aspect, external and perioperative data is collected by an analytics system. The data is then analyzed to generate a control update to improve the performance of the surgical hubs 9000. The analytics system 9100 can analyze the data aggregated from the surgical hubs 9000 to determine the preferred manner for the surgical hubs 9000 to operate, under what conditions the surgical hubs' 9000 control programs are controlling the surgical hubs 9000 suboptimally (i.e., if there are repeated faults or errors in the control program or if an alternative algorithm performs in a superior manner), or under what conditions medical personnel are utilizing the surgical hubs 9000 suboptimally. The analytics system 9100 can then push the update to the surgical hubs 9000 connected thereto.

FIG. 194 illustrates a diagram of a computer-implemented adaptive surgical system 9060 that is configured to adaptively generate control program updates for surgical hubs 9000, in accordance with at least one aspect of the present disclosure. The surgical system 9060 includes several surgical hubs 9000 that are communicably coupled to the analytics system 9100. Subpopulations of surgical hubs 9000 (each of which can include individual surgical hubs 9000 or groups of surgical hubs 9000) within the overall population connected to the analytics system 9100 can exhibit different operational behaviors during the course of a surgical procedure. The differences in operational behavior between groups of surgical hubs 9000 within the population can result from the surgical hubs 9000 running different versions of their control program, by the surgical hubs' 9000 control programs being customized or programmed differently by local surgical staff, or by the local surgical staff manually controlling the surgical hubs 9000 differently. In the depicted example, the population of surgical hubs 9000 includes a first subpopulation 9312 that is exhibiting a first operational behavior and a second subpopulation 9314 that is exhibiting a second operational behavior for a particular task. Although the surgical hubs 9000 are divided into a pair of subpopulations 9312, 9314 in this particular example, there is no practical limit to the number of different behaviors exhibited within the population of surgical hubs 9000. The tasks that the surgical hubs 9000 can be executing include, for example, controlling a surgical instrument or analyzing a dataset in a particular manner.

The surgical hubs 9000 can be configured to transmit perioperative data pertaining to the operational behavior of the surgical hubs 9000 to the analytics system 9100. The perioperative data can include preoperative data, intraoperative data, and postoperative data. The preoperative data can include, for example, patient-specific information, such as demographics, health history, preexisting conditions, preoperative workup, medication history (i.e., medications currently and previously taken), genetic data (e.g., SNPs or gene expression data), EMR data, advanced imaging data (e.g., MRI, CT, or PET), metabolomics, and microbiome. Various additional types of patient-specific information that can be utilized by the analytics system 9100 are described by U.S. Pat. No. 9,250,172, U.S. patent application Ser. No. 13/631,095, U.S. patent application Ser. No. 13/828,809, and U.S. Pat. No. 8,476,227, each of which is incorporated by reference herein to the extent that they describe patient-specific information. The preoperative data can also include, for example, operating theater-specific information, such as geographic information, hospital location, operating theater location, operative staff performing the surgical procedure, the responsible surgeon, the number and type of modular devices 9050 and/or other surgical equipment that could potentially be used in the particular surgical procedure, the number and type of modular devices 9050 and/or other surgical equipment that are anticipated to be used in the particular surgical procedure, patient identification information, and the type of procedure being performed.

The intraoperative data can include, for example, modular device 9050 utilization (e.g., the number of firings by a surgical stapling instrument, the number of firings by an RF electrosurgical instrument or an ultrasonic instrument, or the number and types of stapler cartridges utilized), operating parameter data of the modular devices 9050 (e.g., the FTF curve for a surgical stapling instrument, a FTC curve for a surgical stapling instrument, the energy output of a generator, the internal pressure or pressure differential of a smoke evacuator), unexpected modular device 9050 utilization (i.e., the detection of the utilization of a modular device that is nonstandard for the procedure type), adjunctive therapies administered to the patient, and utilization of equipment other than the modular devices 9050 (e.g., sealants to address leaks). The intraoperative data can also include, for example, detectable misuse of a modular device 9050 and detectable off-label use of a modular device 9050.

The postoperative data can include, for example, a flag if the patient does not leave the operating theater and/or is sent for nonstandard postoperative care (e.g., a patient undergoing a routine bariatric procedure is sent to the ICU after the procedure), a postoperative patient evaluation relating to the surgical procedure (e.g., data relating to a spirometric performance after a thoracic surgery or data relating to a staple line leakage after bowel or bariatric procedures), data related to postoperative complications (e.g., transfusions or air leaks), or the patient's length of stay in the medical facility after the procedure. Because hospitals are increasingly being graded on readmission rates, complication rates, average length of stay, and other such surgical quality metrics, the postoperative data sources can be monitored by the analytics system 9100 either alone or in combination with surgical procedural outcome data (discussed below) to assess and institute updates to the controls programs of the surgical hubs 9000 and/or modular devices 9050.

In some exemplifications, the intraoperative and/or postoperative data can further include data pertaining to the outcome of each surgical procedure or a step of the surgical procedure. The surgical procedural outcome data can include whether a particular procedure or a particular step of a procedure had a positive or negative outcome. In some exemplifications, the surgical procedural outcome data can include procedure step and/or time stamped images of modular device 9050 performance, a flag indicating whether a modular device 9050 functioned properly, notes from the medical facility staff, or a flag for poor, suboptimal, or unacceptable modular device 9050 performance. The surgical procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. patent application Ser. No. 15/940,654, or retrieved from a database 9054 (e.g., an EMR database) by the surgical hub 9000 or the analytics system 9100. In some exemplifications, perioperative data including a flag indicating that a modular device 9050 failed or otherwise performed poorly during the course of a surgical procedure can be prioritized for communication to and/or analysis by the analytics system 9100.

In one exemplification, the perioperative data can be assembled on a procedure-by-procedure basis and uploaded by the surgical hubs 9000 to the analytics system 9100 for analysis thereby. The perioperative data indicates the manner in which the surgical hubs 9000 were programmed to operate or were manually controlled in association with a surgical procedure (i.e., the operational behavior of the surgical hubs 9000) because it indicates what actions the surgical hub 9000 took in response to various detected conditions, how the surgical hubs 9000 controlled the modular devices 9050, and what inferences the situationally aware surgical hubs 9000 derived from the received data. The analytics system 9100 can be configured to analyze the various types and combinations of preoperative, intraoperative, and post-operative data to determine whether a control program update should be generated and then push the update to the overall population or one or more subpopulations of surgical hubs 9000, as necessary.

FIG. 195 illustrates a logic flow diagram of a process 9300 for updating the control program of a surgical hub 9000, in accordance with at least one aspect of the present disclosure. During the following description of the process 9300, reference should also be made to FIGS. 190 and 194. The process 9200 can be executed by, for example, one or more processors of the analytics servers 9070 of the analytics system 9100. In one exemplification, the analytics system 9100 can be a cloud computing system. For economy, the following description of the process 9300 will be described as being executed by the analytics system 9100; however, it should be understood that the analytics system 9100 includes processor(s) and/or control circuit(s) that are executing the describe steps of the process 9300.

The analytics system 9100 executing the process 9300 receives 9302 perioperative data from the surgical hubs 9000 that are communicably connected to the analytics system 9100. The perioperative data indicates the manner in which the surgical hubs 9000 are programmed to operate by their control programs or are controlled by the surgical staff during a surgical procedure. In some aspects, the perioperative data can include or being transmitted to the analytics system 9100 in association with surgical procedural outcome data. The surgical procedural outcome data can include data pertaining to an overall outcome of a surgical procedure (e.g., whether there was a complication during the surgical procedure) or data pertaining to a specific step within a surgical procedure (e.g., whether a particular staple line bled or leaked).

After an analytics system 9100 executing the process 9300 has received 9302 the perioperative data, the analytics system 9100 then analyzes 9304 the data to determine whether an update condition has been satisfied. In one exemplification, the update condition includes whether a threshold number or percentage of surgical hubs 9000 within the population exhibit a particular operational behavior. For example, the analytics system 9100 can determine that a control program update should be generated to automatically active an energy generator at a particular step in a type of surgical procedure when a majority of the surgical hubs 9000 are utilized to active the energy generator at that procedural step. In another exemplification, the update condition includes whether the rate of positive procedural outcomes (or lack of negative procedural outcomes) correlated to a particular operational behavior exceeds a threshold value (e.g., an average rate of positive procedural outcomes for a procedure step). For example, the analytics system 9100 can determine that a control program update should be generated to recommend that the energy generator be set at a particular energy level when the associated rate of hemostasis (i.e., lack of bleeding) at that energy level for the particular tissue type exceeds a threshold rate. In another exemplification, the update condition includes whether the rate of positive procedural outcomes (or lack of negative procedural outcomes) for a particular operational behavior is higher than the rate of positive procedural outcomes (or a lack of negative procedural outcomes) for related operational behaviors. In other words, if one subpopulation of surgical hubs 9000 exhibits a first operational behavior under a certain set of conditions and a second subpopulation of surgical hubs 9000 exhibits a second operational behavior under the same set of conditions, then the analytics system 9100 can determine whether to update the control programs of the surgical hubs 9000 according to whether the first or second operational behavior is more highly correlated to a positive procedural outcome. In another exemplification, the analytics system 9100 analyzes 9304 the data to determine whether multiple update conditions have been satisfied.

If an update condition has not been satisfied, the process 9300 continues along the NO branch and the analytics system 9100 continues receiving 9302 and analyzing 9304 perioperative data from the surgical hubs 9000 to monitor for the occurrence of an update condition. If an update condition has been satisfied, the process 9300 continues along the YES branch and the analytics system 9100 proceeds to generate 9308 a control program update. The nature of the generated 9308 control program update corresponds to the particular operational behavior of the surgical hub 9000 that is identified by the analytics system 9100 as triggering the update condition. In other words, the control program update adds, removes, or otherwise alters functions performed by the surgical hub 9000 so that the surgical hub 9000 operates differently under the conditions that gave rise to the identified operational behavior. Furthermore, the type of control program update also depends upon whether the identified operational behavior results from manual control or control by the control program of the surgical hub 9000. If the identified operational behavior results from manual control, the control program update can be configured to provide warnings, recommendations, or feedback to the users based upon the manner in which they are operating the surgical hub 9000. For example, if the analytics system 9100 determines that taking a particular action or utilizing a particular instrument for a step in a surgical procedure improves outcomes, then the analytics system 9100 can generate 9308 a control program update that provides a prompt or warning to the surgical staff when the surgical hub 9000 determines that the designated step of the surgical procedure is occurring or will subsequently occur. Alternatively, the control program update can change one or more functions of the surgical hub 9000 from being manually controllable to being controlled by the control program of the surgical hub 9000. For example, if the analytics system 9100 determines that a display of the visualization system 108 (FIG. 2) is set to a particular view by the surgical staff in a predominant number of surgical procedures at a particular step, the analytics system 9100 can generate a control program update that causes the surgical hub 9000 to automatically change the display to that view under those conditions. If the identified operational behavior results from the control program of the surgical hub 9000, then the control program update can alter how the control program functions under the set of circumstances that cause the identified operational behavior. For example, if the analytics system 9100 determines that a particular energy level for an RF electrosurgical or ultrasonic instrument correlates to poor or negative outcomes under a certain set of conditions, then the analytics system 9100 can generate 9308 a control program update that causes the surgical hub 9000 to adjust the energy level of the connected instrument to a different value when the set of conditions is detected (e.g., when the surgical hub 9000 determines that an arthroscopic procedure is being performed).

The analytics system 9100 then transmits 9310 the control program update to the overall population of surgical hubs 9000 or the subpopulation(s) of surgical hubs 9000 that are performing the operational behavior that is identified by the analytics system 9100 as triggering the update condition. In one exemplification, the surgical hubs 9000 are configured to download the control program updates from the analytics system 9100 each time an update is generated 9308 thereby. In one exemplification, the analytics system 9100 can thereafter continue the process 9300 of analyzing 9304 the data received 9302 from the surgical hubs 9000, as described above.

FIG. 196 illustrates a representative implementation of the process 9300 depicted in FIG. 195. FIG. 196 illustrates a logic flow diagram of a process 9400 for updating the data analysis algorithm of a control program of a surgical hub 9000, in accordance with at least one aspect of the present disclosure. As with the process 9300 depicted in FIG. 195, the process 9400 illustrated in FIG. 196 can, in one exemplification, be executed by the analytics system 9100. In the following description of the process 9400, reference should also be made to FIG. 194. In one exemplification of the adaptive surgical system 9060 depicted in FIG. 194, the first surgical hub subpopulation 9312 is utilizing a first data analysis algorithm and the second surgical hub subpopulation 9314 is utilizing a second data analysis algorithm. For example, the first surgical hub subpopulation 9312 can be utilizing a normal continuous probability distribution to analyze a particular dataset, whereas the second surgical hub subpopulation 9314 can be utilizing a bimodal distribution for analyzing the particular dataset. In this exemplification, the analytics system 9100 receives 9402, 9404 the perioperative data from the first and second surgical hub subpopulations 9312, 9314 corresponding to the respective data analysis algorithms. The analytics system 9100 then analyzes 9406 the perioperative datasets to determine whether one of the perioperative datasets satisfies one or more update conditions. The update conditions can include, for example, a particular analysis method being utilized by a threshold percentage (e.g., 75%) of the surgical hubs 9000 in the overall population and a particular analysis method being correlated to positive surgical procedural outcomes in a threshold percentage (e.g., 50%) of cases.

In this exemplification, the analytics system 9100 determines 9408 whether one of the data analysis algorithms utilized by the first and second surgical hub subpopulations 9312, 9314 satisfies both of the update conditions. If the update conditions are not satisfied, then the process 9400 proceeds along the NO branch and the analytics system 9100 continues receiving 9402, 9404 and analyzing 9406 perioperative data from the first and second surgical hub subpopulations 9312, 9314. If the update conditions are satisfied, the process 9400 proceeds along the YES branch and the analytics system 9100 generates 9412 a control program update according to which of the data analysis algorithms the analysis 9406 determined satisfied the update conditions. In this exemplification, the control program update would include causing the surgical hub 9000 to utilize the data analysis algorithm that satisfied the update conditions when performing the corresponding analysis type. The analytics system 9100 then transmits 9414 the generated 9412 control program update to the population of surgical hubs 9000. In one exemplification, the control program update is transmitted 9414 to the entire population of surgical hubs 9000. In another exemplification, the control program update is transmitted 9414 to the subpopulation of surgical hubs 9000 that did not utilize the data analysis algorithm that satisfied the update conditions. In other words, if the analytics system 9100 analyzes 9406 the perioperative data and determines 9408 that the second (bimodal) data analysis method satisfies the update conditions, then the generated 9412 control program update is transmitted 9414 to the first subpopulation of surgical hubs 9000 in this exemplification. Furthermore, the control program update can either force the updated surgical hubs 9000 to utilize the second (bimodal) data analysis algorithm when analyzing the particular dataset or cause the updated surgical hubs 9000 to provide a warning or recommend to the user that the second (bimodal) data analysis algorithm be used under the given conditions (allowing the user to choose whether to follow the recommendation).

This technique improves the performance of the surgical hubs 9000 by updating their control programs generated from data aggregated across the entire network of surgical hubs 9000. In effect, each surgical hub 9000 can be adjusted according to shared or learned knowledge across the surgical hub 9000 network. This technique also allows the analytics system 9100 to determine when unexpected devices (e.g., modular devices 9050) are utilized during the course of a surgical procedure by providing the analytics system 9100 with knowledge of the devices being utilized in each type of surgical procedure across the entire surgical hub 9000 network.

Security and Authentication Trends and Reactive Measures

In a cloud-based medical system communicatively coupled to multiple communication and data gathering centers located in different geographical areas, security risks are ever present. The cloud-based medical system may aggregate data from the multiple communication and data gathering centers, where the data collected by any data gathering center may originate from one or more medical devices communicatively coupled to the data gathering center. It may be possible to connect an unauthorized medical device to the data gathering center, such as a pirated device, a knock-off or counterfeit device, or a stolen device. These devices may contain viruses, may possess faulty calibration, lack the latest updated settings, or otherwise fail to pass safety inspections that can be harmful to a patient if used during surgery. Furthermore, the multiple data gathering centers may contain multiple points of entry, such as multiple USB or other input ports, or opportunities to enter user passwords, that if improperly accessed could represent security breaches that can reach the cloud-based medical system, other data gathering centers, and connected medical devices. The risk of devices being tampered with, or data being stolen or manipulated, can lead to severe consequences, particularly because the entire system is purposed for improving medical care.

A security system that reaches all facets of the cloud-based medical system may not be effective unless there is a centralized component that is configured to be made aware of all communication and data gathering centers, and all devices connected therein. If the security systems were merely localized to each data gathering center or at each point of entry, information from one point of entry may not be properly disseminated to other security points. Thus, if a breach occurs at one point, or if improper devices are used at one point, that information may not be properly disseminated to the other centers or devices. Therefore, a centralized security system, or at least a system configured to communicate with all medical hubs that control access points, would be preferable to be made aware of all of the different issues that may occur and to communicate those issues to other ports as needed.

In some aspects, the cloud-based medical system includes a security and authentication system that is configured to monitor all communication and data gathering centers, such as a medical hub or tower located in an operating room, as well as any smart medical instruments communicatively coupled to those centers. The cloud-based security and authentication system, as part of the cloud-based medical system, may be configured to detect unauthorized or irregular access to any hub system or other protected data sets contained within the cloud. Because of the centralized nature of the cloud-based security system—in the sense that the cloud system is configured to communicate with every hub in the system—if there is any identified irregularity found at one hub, the security system is operable to improve security at all other hubs by communicating this information to the other hubs. For example, if surgical instruments with unauthorized serial numbers are used at a hub in one hospital, the cloud-based security system may learn of this at the local hub located in that hospital, and then communicate that information to all other hubs in the same hospital, as well as all hospitals in the surrounding region.

In some aspects, the cloud-based medical system may be configured to monitor surgical devices and approve or deny access for each surgical device for use with a surgical hub. Each surgical device may be registered with a hub, by performing an authentication protocol exchange with the hub. The cloud-based medical system may possess knowledge of all surgical devices and a status indicating whether the surgical device is acceptable, such as whether the device has been pirated, lacks a proper serial number, was faulty, possesses a virus, as so on. The cloud-based medical system may then be configured to prevent interaction with the surgical device, even if the surgical device is connected to the hub.

In this way, the cloud-based security system can provide the most comprehensive security for any particular hub or medical facility due to its ability to see problems located elsewhere.

FIG. 197 provides an illustration of example functionality by a cloud medical analytics system 10000 for providing improved security and authentication to multiple medical facilities that are interconnected, according to some aspects. Starting at block A reference 10002, suspicious activity may be registered from one facility or region as a starting point. The suspicious activity may come in various forms. For example, a surgical device may be recorded at a hub as having a duplicate serial number, or a number that is not known to be within an acceptable range, or that the serial number may already be registered at a different location. In some aspects, surgical devices may possess additional authentication mechanisms, such as a type of electronic or digital handshake exchange between the surgical device and the surgical hub when they are connected. Each device may be programmed with a digital signature and/or knowledge of how to perform an authentication process. The firmware of the surgical device may need to be properly programmed to know how to perform during this exchange. The authentication handshake may periodically change, and may be specified by the cloud on a periodic basis. Any of these may fail during interconnection of the device with a medical hub, triggering an alert with the medical hub and the cloud system 10000.

In some aspects, the cloud system 10000 may review the information supplied by the medical device that triggered the suspicious activity, and if the information is unequivocally fraudulent or faulty, an alert and a rejection of the device can occur, such that the medical device will be prevented from operating with the medical hub and/or other medical hubs in the same facility. While the cloud system 10000 may be configured to prevent singularities, the cloud system 10000 may also be capable of utilizing its vast array of knowledge to develop additional security measures that a single hub as an entry port would be unable to perform on its own. An example is described further below.

At block B reference 10004, the activity at the local medical hub may be transmitted to the cloud for authentication by at least comparing the surgical device to all known devices within the cloud network. In this scenario, the surgical device may register as being suspicious or having some suspicious activity or property. The cloud may be configured to then undergo a feedback loop of exchange with the local hub or facility from which the suspicious device originated. The cloud may determine to request additional data from that facility. In addition, the medical facility, via one or more surgical hubs, may request authentication or interrogation data about one or more surgical devices from the cloud. In this example, a medical hub in a facility in Texas requests a communication exchange with the cloud system 10000 for more data to determine if the suspicious activity at one of its local hubs is truly problematic.

At block C reference 10006, the cloud authentication and security system may then be configured to perform additional data analysis to determine the veracity of any threat and larger context of the nature of this suspicious activity. In this example, the cloud-based security system has performed analysis and brings to light at least two pieces of evidence of a security threat, which is expressed visually in the chart of block C. First, upon comparing the number of data requests and medical interrogations across multiple medical facilities, it is determined that the current requesting facility in Texas has an inordinate number of data requests or medical interrogations compared to all other facilities. The cloud may be configured to flag this as one security issue that needs to be addressed. Second, in comparison to the number of data requests, the number of suspicious data points or findings is also inordinately high at the Texas facility. One or both of these realizations may prompt the cloud security system to enact different security changes at the Texas facility in particular.

Thus, at block D reference 10008, in response to the identified anomalous behavior of the facilities in Texas as a whole, the cloud security system may request additional data related to Texas to better understand the nature of the practices and potential threats. For example, additional data regarding purchasing practices, vendors, the type of surgical instruments being used, the type of surgical procedures performed in comparison to other facilities, and so forth, may be obtained from one or more surgical hubs at the Texas facility, or may be accessed in data already stored in the cloud system 10000. The cloud security system may be configured to look for additional anomalies and patterns that may help determine how to change security procedures specific to the Texas facility, or the facilities in the Texas region generally.

At block E reference 10010, once the additional information has been gathered and analyzed, the cloud security system may initiate a changed security protocol for the Texas facility in particular that triggered this analysis from block A, as well as any new security procedures for any surgical devices that indicate a unique or above average threat. For example, it may be determined that a particular type of surgical devices, such as devices originating from a particular manufacturing facility or having a particular set of unique identification numbers, may be faulty, pirated, or have some other kind of security risk. The cloud system 10000 may have analyzed the suspicious data points originating from the Texas region, determined if there were any commonalities or patterns, and issued a change in security protocol based on these identified patterns. These devices may then be locked out from use at all surgical hubs, even if they are not connected to any surgical hub at the present time. Other example changes regarding security include modifying the types of data gathered to learn more about the types of threats or how widespread the threats are. For example, the suspicious activity in Texas may exhibit a certain pattern or authentication signature of attempting to login in with the system, and so this pattern may be placed on an alert to other facilities in Texas and/or to other facilities to pay special attention to. In some cases, the pattern of suspicious activity may be correlated with another indicator, such as a brand or manufacturer, or a series of serial numbers. The cloud system may send out alerts to those facilities known to associate with these correlated indicators, such as all facilities that utilize medical devices with the same manufacturer.

In addition, an augmented authentication procedure may be enacted at the localized Texas region. The cloud-security system may opt to perform additional authentication protocols for all devices originating out of the Texas facility, for example. These additional protocols may not be present or required at other facilities, since there is considered a lower level of security risk based on the lack of suspicious activity.

In some aspects, as alluded to previously, the cloud-based security system may also be configured to protect against unwanted intrusions, either to any hub or to the cloud system itself. This means that the suspect medical device may be unable to access any data from any medical hub, and may also be prevented from operating if it is connected to a medical hub. In a medical system utilizing the cloud system and multiple medical hubs, the common protocol may require that only medical devices connected to a medical hub are authorized to operate on a patient, and therefore the medical hub will have the capability of preventing a device from activating. The limitation of any faulty or fraudulent surgical device may be designed to protect a patient during a surgical procedure, and it can also be used to protect any surgical hub and the cloud itself. The same lockout procedure may be designed to stop both scenarios from occurring.

In some aspects, the surgical hub may be configured to transmit data to the cloud security system that better characterizes the nature of the security flaws or intrusions. For example, the cloud security system may be configured to store in memory the number of intrusion attempts, the source of the intrusion attempt (e.g., from which surgical hub or even what port or connection via the surgical hub), and what method for attempted intrusion there is, if any (e.g., virus attack, authentication spoofing, etc.).

In some aspects, the cloud security system may also determine what types of behaviors by a surgical device or other functions by a surgical hub are irregular, compared to a global average or just by each institution. The cloud security system may better identify what practices seem irregular in this way. The data logs of any surgical hub, or across an entire facility, may be recorded and securely stored in the cloud system. The cloud security system may then analyze the attempted access requests and actions to determine trends, similarities and differences across regions or institutions. The cloud security system may then report any irregularities to the institution and flag any identified irregularities for internal investigation into updates to protect against future breaches. Of note, a local hub or local facility with multiple hubs may not realize if any of their authentication behaviors are irregular, unless they are compared to a broader average or comparison of other facilities. The cloud system may be configured to identify these patterns, because it has access to authentication data and procedures from these multiple facilities.

In some aspects, the cloud security system may be configured to analyze any current hub control program versions and when it was updated. The cloud security system may verify all updates are correct, and determine where their origins are. This may be an additional check to ensure that the software and firmware systems of the surgical devices are proper and have not been tampered with.

In some aspects, the cloud security system may also determine larger threats by analyzing multiple facilities at once. The system may determine, after aggregating data from multiple locations, any trends or patterns of suspicious activity across a wider region. The security system may then change security parameters across multiple facilities immediately or in near real time. This may be useful to quickly react to simultaneous attacks, and may make it even easier to solve simultaneous attacks by gathering data from the multiple attacks at once to better increase the chances and speed of finding a pattern to the attacks. Having the cloud system helps confirm whether attacks or suspicious activity occurs in isolation or is part of a grander scheme.

Data Handling and Prioritization

Aspects of the present disclosure are presented for a cloud computing system (computer-implemented interactive surgical system as described above) for providing data handling, sorting, and prioritization, which may be applied to critical data generated during various medical operations. The cloud computing system constitutes a cloud-based analytics system, communicatively coupled to a plurality of surgical hubs 7006 and smart medical instruments such as surgical instruments 7012. Typically, a healthcare facility, such as a hospital or medical clinic, does not necessarily immediately recognize the criticality of data as it is generated. For example, if a medical instrument used during a perioperative period experiences a failure, the response of medical care facility personnel such as nurses and doctors may be directed towards diagnosis of any medical complications, emergency medical assistance, and patient safety generally. In this situation, the criticality of the data might not be analyzed in a time sensitive manner, or at all. Accordingly, the healthcare facility does not necessarily timely respond to or even recognize critical data as such data is generated. Additionally, a particular healthcare facility can lack knowledge of the management of critical data from other similarly situated facilities, either in its region, according to a similar size, and/or according to similar practices or patients, and the like. The cloud-based analytics system may be specifically designed to address this issue of critical data and particularly the timing of data handling that is performed based on the criticality of data within the context of healthcare facility operations. The cloud-based analytics system may quickly and efficiently identify critical data based on specific criteria. In some situations, aggregate data is determined to be critical after the individual non-critical data comprising the aggregated data are aggregated. As used herein, handling critical data (which could be aggregated) may refer to data sorting, prioritizing, and other data handling based on specific criteria or thresholds.

To help facilitate timely and improved data sorting, handling, and prioritization, it would be desirable if a common source connected to multiple healthcare facilities could sort, handle, and prioritize critical data from these medical facilities in a holistic manner. In this way, insights could be generated by the common source based on using this aggregated data from the multiple healthcare facilities. In various aspects, the cloud-based analytics system comprises the cloud 7004 that is communicatively coupled to knowledge centers in a medical facility, such as one or more surgical hubs 7006, and is configured to sort, handle, and prioritize medical data from multiple healthcare facilities. In particular, the cloud-based system can identify critical data and respond to such critical data based on the extent of the associated criticality. For example, the cloud-based system could prioritize a response as requiring urgent action based on the critical data indicating a serious perioperative surgical instrument 7012 failure, such as one that requires intensive care unit (ICU) postoperative treatment. The data handling, sorting, and prioritization described herein may be performed by the processors 7008 of the central servers 7013 of the cloud 7004 by, for example, executing one or more data analytics modules 7034.

Critical data can be determined to be critical based on factors such as severity, unexpectedness, suspiciousness, or security. Other criticality criteria can also be specifically selected such as by a healthcare facility. Criticality can also be indicated by flagging a surgical instrument 7012, which in turn can be based on predetermined screening criteria, which could be the same or different as the factors described above. For example, a surgical instrument 7012 can be flagged based on its usage being correlated with severe post surgical operation complications. Flagging could also be used to trigger the prioritized data handling of the cloud-based analytics system. In connection with a determination of criticality or flagging a surgical instrument 7012, the cloud 7004 can transmit a push message or request to one or more surgical hubs 7006 for additional data associated with the use of the surgical instrument 7012. The additional data could be used for aggregating data associated with the surgical instrument 7012. For example, after receiving the additional data, the cloud 7004 may determine there is a flaw in the surgical instrument 7012 (e.g., malfunctioning generator in an energy surgical instrument) that is common to other corresponding surgical instruments 7012 in a particular healthcare facility. Accordingly, the cloud 7004 could determine that all such flawed surgical instruments 7012 should be recalled. These flawed surgical instruments 7012 might share a common identification number or quality or a common aspect of a unique identifier, such as a serial number family identifier.

In general, the cloud-based analytics system may be capable of aggregating, sorting, handling, and prioritizing data in a timely and systematic manner that a single healthcare facility would not be able to accomplish on its own. The cloud-based analytics system further can enable timely response to the aggregated, sorted, and prioritized data by obviating the need for multiple facilities to coordinate analysis of the particular medical data generated during medical operations at each particular facility. In this way, the cloud-based system can aggregate data to determine critical data or flagging for enabling appropriate responses across the entire network of surgical hubs 7006 and instruments 7012. Specifically, appropriate responses include sorting, handling, and prioritization by the cloud 7004 according to a priority status of the critical data, which can enable timely and consistent responses to aggregated critical data (or critical aggregated data) across the entire network. Criticality of the data may be defined universally and consistently across all surgical hub 7006 and instruments 7012. Furthermore, the cloud-based analytics system may be able to verify the authenticity of data from the plurality of medical facilities before such data is assigned a priority status or stored in the aggregated medical data databases. As with the categorization of critical data, data verification can also be implemented in a universal and consistent manner across the system which a single facility may not be able to achieve individually.

FIG. 198 is a flow diagram of the computer-implemented interactive surgical system programmed to use screening criteria to determine critical data and to push requests to a surgical hub to obtain additional data, according to one aspect of the present disclosure. In one aspect, once a surgical hub 7006 receives device data 11002 from a surgical instrument 7012 data may be flagged and/or determined to be critical based on predetermined screening criteria. As shown in FIG. 198, the hub 7006 applies 11004 the screening criteria to flag devices and to identify critical data. The screening criteria include severity, unexpectedness, suspiciousness, and security. Severity can refer to the severity of any adverse medical consequences resulting from an operation performed using the surgical instrument 7012. Severity could be assessed using a severity threshold for surgical instrument 7012 failures. For example, the severity threshold could be a temporal or loss rate threshold of bleeding such as over 1.0 milliliters per minute (mL/min). Other suitable severity thresholds could be used. Unexpectedness can refer to a medical parameter of a deviation that exceeds a threshold such as an amount of standard deviation from the mean medical parameter value such as a determined tissue compression parameter significantly exceeding the expected mean value at a time during an operation.

Suspiciousness can refer to data that appears to have been improperly manipulated or tampered with. For example, the total therapeutic energy applied to tissue value indicated by the data may be impossible given a total amount energy applied via the generator of the surgical instrument 7012. In this situation, the impossibility of the data suggests improper manipulation or tampering. Similarly, security can refer to improperly secured data, such as data including a force to close parameter that was inadvertently deleted. The screening criteria also may be specified by a particular surgical hub 7006 or by the cloud 7004. The screening criteria can also incorporate specific thresholds, which can be used for prioritization, for example. In one example, multiple severity thresholds can be implemented such that the extent of perioperative surgical instrument 7012 failures can be sorted into multiple categories according to the multiple severity thresholds. In particular, the multiple severity thresholds could be based on the number of misaligned staples from a stapling surgical instrument 7012 to reflect an extent of the severity of misalignment. By using the cloud-based analytic system, the cloud may systemically identify critical data and flag surgical instruments 7012 for providing a timely and appropriate response which an individual healthcare facility could not achieve on its own. This timely response by the cloud 7004 can be especially advantageous for severe post surgical operation complications.

Determining critical data and flagging the surgical instrument 7012 by the hub 7006 may include determining a location to store data. Data may be routed or stored based on whether the data is critical and whether the corresponding surgical instrument 7012 is flagged. For example, binary criteria can be used to sort data into two storage locations, namely, a memory of a surgical hub 7006 or the memory 7010 of the cloud 7004. Surgical instruments 7012 generate this medical data and transmit such data, which is denoted as device data 11002 in FIG. 198, to their corresponding surgical hub devices 7006. FIG. 198 illustrates an example of this binary sorting process. Specifically, in one aspect, the data routing can be determined based on severity screening criteria as shown at the severity decision steps 11006, 11008. At step 11006, the hub 7006 determines 11006 whether the surgical instrument 7012 that provided the device data 11002 has experienced a failure or malfunction during operation at the perioperative stage and whether this failure is considered severe. The severity thresholds discussed above or other suitable means could be used to determine whether the failure is severe. For example, severe failure may be determined based on whether undesirable patient bleeding occurred during use or firing of the surgical instrument. If the determination at step 11006 is yes, the corresponding data (i.e., critical data) of the surgical instrument 7012 is transmitted 11012 by the hub 7006 to the cloud 7004. Conversely, if the determination at step 11006 is no, the flow diagram may proceed to step 11008.

If the determination at step 11006 is no, then the flow diagram proceeds to step 11008 in FIG. 198, where the surgical hub 7006 determines whether the patient transitioned to non-standard post-operation care (i.e. the ICU) after the operation was performed with the specific surgical instrument 7012. However, even if the determination at step 11006 is no, the inquiry at step 11008 may still be performed. If the determination at step 11008 is yes, then the critical device data 11002 is transmitted to the cloud 7004. For example, the determination at step 11008 is yes if a patient transitioned into the ICU from the operating room subsequent to a routine bariatric surgical procedure. Upon transfer of a patient into the ICU, the surgical hub 7006 may receive a timely signal from the surgical instrument 7012 used to perform the bariatric procedure indicating that the patient has experienced complications necessitating entry into the ICU. Since this signal indicates the step 11008 determination is yes, corresponding device data 11002 is sent 11012 to the cloud 7004. Additionally, the specific surgical instrument 7012 may be flagged by the cloud 7004 for a prompt specific response by the cloud 7004, such as designating the surgical instrument 7012 with a prioritization of requiring urgent action. If the determination at step 11008 is no, a signal can be transmitted from the surgical instrument 7012 to the surgical hub 7006 indicating that the procedure was successful. In this scenario, the device data 11002 can be stored 11010 locally in a memory device of the surgical hub 7006.

Additionally or alternatively, the specific surgical instrument 7012 may also be flagged by the hub 7006 or the cloud 7004 to trigger data handling by the cloud 7004, which can comprise an internal response of the cloud 7004. When the surgical instrument 7012 is flagged or the device data 11002 is determined to be critical, the triggered response may be the cloud 7004 transmitting a signal comprising a request for additional data regarding the surgical instrument 7012. Additional data may pertain to the critical device data 11002. The cloud 7004 can also request additional data even if the specific surgical instrument 7012 is not flagged, such as if the device data 11002 is determined to be critical without the surgical instrument 7012 being flagged. Flagging could also indicate an alarm or alert associated with the surgical instrument 7012. In general, the hub 7006 is configured to execute determination logic for determining whether the device data 11002 should be sent to the cloud 7004. The determination logic can be considered screening criteria for determining criticality or flagging surgical instruments 7012. Besides the severity thresholds used at steps decision steps 11006, 11008, the data routing can be based on frequency thresholds (e.g., the use of a surgical instrument 7012 exceeds a usage quantity threshold such as a number of times an energy generator is used), data size thresholds, or other suitable thresholds such as the other screening criteria discussed above. Flagging may also result in storing a unique identifier of the specific surgical instrument in a database of the cloud-based system.

A triggered request 11014 for additional data by the cloud 7004 to the hub 7006 may be made based on a set of inquiries as shown in FIG. 198. This triggered request 11014 may be a push request sent by the central servers 7013 of the cloud 7004. In particular, the processors 7008 can execute the data collection and aggregation data analytic module 7022 to implement this trigger condition functionality. This push request may comprise an update request sent by the cloud 7004 to the hub 7006 to indefinitely collect new data associated with the device data 11002. That is, the hub 7006 may collect additional data until the cloud 7004 transmits another message rescinding the update request. The push request could also be a conditional update request. Specifically, the push request could comprise initiating a prompt for the hub 7006 to send additional information only if certain conditions or events occur. For example, one condition might be if the sealing temperature used by the surgical instrument 7012 to treat tissue exceeds a predetermined threshold. The push request could also have a time bounding component. In other words, the push request could cause the surgical hub 7006 to obtain additional data for a specific predetermined time period, such as three months. The time period could be based on an estimated remaining useful life of the surgical instrument 7012, for example. As discussed above, the request 11014 for additional data may occur after the specific surgical instrument 7012 is flagged, which may be due to an affirmative determination at steps 11006, 11008 described above.

As shown in FIG. 198, the triggered request 11014 for additional data may include four inquiries that can be considered trigger conditions for additional information. At the first inquiry, the hub 7006 determines 11016 whether the device data 11002 represents an outlier with no known cause. For example, application of therapeutic energy to tissue during a surgical procedure by the surgical instrument 7012 may cause patient bleeding even though surgical parameters appear to be within a normal range (e.g., temperature and pressure values are within expected range). In this situation, the critical device data 11002 indicates an irregularity without a known reason. The outlier determination 11016 can be made based on comparison of the device data 11002 to an expected value or based on a suitable statistical process control methodology. For example, an actual value of the device data 11002 may be determined to be an outlier based on a comparison of the actual value to a mean expected (i.e., average) value. Calculating that the comparison is beyond a certain threshold can also indicate an outlier. For example, a statistical process control chart could be used to monitor and indicate that the difference between the actual and expected value is a number of standard deviations beyond a threshold (e.g., 3 standard deviations). If the device data 11002 is determined to be an outlier without a known reason, the request 11014 is triggered by the cloud 7004 to the hub 7006. In response, the hub 7006 timely transmits 11024 additional information to the cloud 7004, which may provide different, supporting, or additional information to diagnose the reason for the outlier. Other insights into the outlier may also be derived in this way. For example, the cloud 7004 may receive additional surgical procedure parameter information such as the typical clamping force used by other surgical instruments 7012 at the same point in the surgical procedure when the patient bleeding occurred. The expected value may be determined based on aggregated data stored in the aggregated medical data database 7012, such as by averaging the outcomes or performance of groups of similarly situated surgical instruments 7012. If at step 11016, the data is not determined to be an outlier, the flow diagram proceeds to step 11018.

The second inquiry is another example of a trigger condition. At step 11018, the hub 7006 determines 11018 whether device data 11002 involves data that can be classified as suspicious, which can be implemented by the authorization and security module 7024. For example, suspicious data may include situations in which an unauthorized manipulation is detected. These include situations where the data appears significantly different than expected so as to suggest unauthorized tampering, data or serial numbers appear to be modified, security of surgical instruments 7012 or corresponding hub 7006 appears to be comprised. Significantly different data can refer to, for example, an unexpected overall surgical outcome such as a successful surgical procedure occurring despite a surgical instrument 7012 time of usage being significantly lower than expected or a particular unexpected surgical parameter such as a power level applied to the tissue significantly exceeding what would be expected for the tissue (e.g., calculated based on a tissue impedance property). Significant data discrepancies could indicate data or serial number modification. In one example, a stapling surgical instrument 7012 may generate a separate unique staple pattern in a surgical operation which may be used to track or verify whether the serial number of that stapling surgical instrument 7012 is subsequently modified. Furthermore, data or serial number modification such as tampering may be detected via other associated information of a surgical instrument 7012 that can be independently verified with the aggregated medical data databases 7011 or some other suitable data modification detection technique.

Moreover, compromised security, such as unauthorized or irregular access to any surgical hub 7006 or other protected data sets stored within the cloud 7004 can be detected by a cloud-based security and authentication system incorporating the authorization and security module 7024. The security and authentication system can be a suitable cloud based intrusion detection system (IDS) for detecting compromised security or integrity. The cloud IDS system can analyze the traffic (i.e. network packets) of the cloud computing network 7001 or collect information (e.g., system logs or audit trails) at various surgical hub 7006 for detecting security breaches. Compromised security detection techniques include comparison of collected information against a predefined set of rules corresponding to a known attack which is stored in the cloud 7004 and anomaly based detection. The cloud 7004 can monitor data from a series of surgical operations to determine whether outliers or data variations significantly reduce without an apparent reason, such as a reduction without a corresponding change in parameters of used surgical instruments 7012 or a change in surgical technique. Additionally, suspiciousness can be measured by a predetermined suspiciousness or unexpectedness threshold, unauthorized modification of device data 11002, unsecure communication of data, or placement of the surgical instrument 7012 on a watch list (as described in further detail below). The suspiciousness or unexpectedness threshold can refer to a deviation (e.g., measured in standard deviations) that exceeds surgical instrument 7012 design specifications. Unauthorized data communication or modification can be determined by the authorization and security module 7024 when the data encryption of the cloud 7004 is violated or bypassed. In sum, if the hub 7006 determines 11018 the data is suspicious for any of the reasons described above, the request 11014 for additional data may be triggered. In response, the hub 7006 timely transmits 11024 additional information to the cloud 7004, which may provide different, supporting, or additional information to better characterize the suspiciousness. If at step 11018, the answer to the second inquiry is no, the flow diagram proceeds to step 11020.

The third and fourth inquiries depict additional trigger conditions. At step 11020, the hub 7006 may determine that device data 11002 indicates a unique identifier of the surgical instrument 7012 that matches an identifier maintained on a watchlist (e.g., "black list" of prohibited devices). As described above, the "black list" is a watch list that can be maintained as a set of database records comprising identifiers corresponding to prohibited surgical hubs 7006, surgical instruments 7012, and other medical devices. The black list can be implemented by the authorization and security module 7024. Moreover, surgical instruments 7012 on the black list may be prevented from fully functioning or restricted from access with surgical hubs 7006. For example, an energy surgical instrument 7012 may be prevented from functioning (i.e. an operational lockout) via the cloud 7004 or surgical hub 7006 transmitting a signal to the hub 7006 or surgical instrument 7012 to prevent the generator from applying power to the energy surgical instrument 7012. This operational lockout can generally be implemented in response to an irregularity indicated by the critical device data 11002. Surgical instruments can be included on the black list for a variety of reasons such as the authorization and security module 7012 determining the presence of counterfeit surgical instruments 7012 using internal authentication codes, unauthorized reselling of surgical instruments 7012 or related products from one region to another, deviation in performance of surgical instruments 7012 that is nonetheless within design specifications, and reuse of surgical instruments 7012 or related products that are designed for single patient use. For example, internal authentication codes may be unique identifiers maintained by the cloud 7004 in the memory devices 7010. Other unauthorized usage could also result in placement on the black list.

The use of counterfeit authentication codes may be a security breach that is detectable by the cloud IDS system. Reselling of surgical instruments 7012 into other regions could be detected via region specific indicators of resold surgical instrument 7012 or surgical hubs 7006, for example. The region specific indicator could be encrypted using a suitable encryption technique. In this way, the cloud 7004 may detect when the region specific indicators of a resold surgical instrument 7012 do not match the corresponding region of intended use. Reuse of a single use surgical instrument 7012 can be monitored by detecting tampering with a lockout mechanism (e.g., a stapler cartridge lockout mechanism of a stapling surgical instrument), programming a microprocessor of the single use surgical instrument 7012 to transmit a warning signal to the corresponding surgical hub 7006 when more than one use occurs, or another suitable detection technique. Performance deviation could be monitored using statistical process control methods as described above. The design specifications of particular surgical instruments 7012 may be considered the control limits of a statistical process control methodology. In one example, when detected by the cloud 7004, a significant trend toward one of the lower or upper control limits constitutes a sufficient deviation that results in the cloud 7004 adding the corresponding surgical instrument to the black list. As discussed above, a deviation that exceeds design specifications may result determining 11018 the device data 11002 is suspicious. Surgical instruments 7012 may be added to or removed from the black list by the cloud 7004 based on analysis of the requested additional data. In sum, if the hub 7006 determines 11020 the surgical instrument 7012 corresponding to the device data 11002 is on the watchlist, the request 11014 for additional data may be triggered. In response, the hub 7006 timely transmits 11024 additional information to the cloud 7004, which may provide different, supporting, or additional information. If at step 11020, the answer to the second inquiry is no, the flow diagram proceeds to step 11022.

The trigger condition at step 11022 comprises the hub 70006 determining whether the device data 11002 indicates the surgical instrument 7012 has malfunctioned. In one aspect, a surgical instrument 7012 malfunction results in an automated product inquiry through the corresponding surgical hub 7006. The hub 7006 sending 11024 additional data to the cloud 7004 may comprise all pertinent data of the surgical instrument 7012 being immediately transmitted to the cloud through the surgical hub 7006, which may result in central server 7013 processors 7008 of the cloud 7004 executing an automated product inquiry algorithm. However, such an algorithm may not be immediately executed or at all if the malfunction is not significant. The cloud 7004 may be configured to record this set of pertinent data for all surgical instruments 7012 for contingent use when such automated product inquiries are instituted. The automated product inquiry algorithm comprises the cloud 7004 searching for previous incidents that are related to the malfunction. The cloud 7004 may populate a group of records in the aggregated medical data databases 7011 with any incidents or activity related to the malfunction. Subsequently, a corrective and preventive action (CAPA) portion of the algorithm may be instituted for reducing or eliminating such malfunctions or non-conformities. CAPA and the automated product inquiry algorithm are one example of a possible internal response 11102 of the cloud 7004 of the cloud-based analytics system.

CAPA involves investigating, recording and analyzing the cause of a malfunction or non-conformity. To implement CAPA, the cloud 7004 may analyze the populated related records in the aggregated medical data databases 7011, which may include aggregated data fields such as surgical instrument 7012 manufacture dates, times of use, initial parameters, final state/parameters, and surgical instrument 7012 numbers of uses. Thus, both individual and aggregated data maybe used. In other words, the cloud 7004 may analyze both individual data corresponding to the malfunctioning surgical instrument 7012 as well as aggregated data, collected from all related surgical instruments 7012 to the malfunctioning surgical instrument 7012, for example. Initial and final parameters may be, for example, an initial and final frequency of an applied RF signal of the surgical instrument. CAPA can also involve analysis of the previous time period from when the malfunction occurred or was detected. Such a time period can be, for example, one to two minutes. Based on this CAPA analysis, the cloud 7004 may diagnose the root cause of the malfunction and recommend or execute any suitable corrective action (e.g., readjusting miscalibrated parameters). The automated product inquiry algorithm can also involve a longer follow up of patient outcomes for patients treated with the specific surgical instrument 7012.

For example, the cloud 7004 may determine a priority status of watch list for the surgical instrument 7012 so that the surgical instrument 7012 may be monitored for a period of time after the malfunction is detected and addressed. Moreover, the malfunction may cause the cloud 7004 to expand a list of medical items to be tracked (e.g., the integrity of tissue seals made during surgery). This list of items to be tracked may be performed in conjunction with the patient outcome monitoring by the patient outcome analysis module 7028. The cloud 7004 may also respond to an irregularity indicated by the malfunction by monitoring patient outcomes corresponding to the irregularity. For example, the cloud 7004 can monitor whether the irregularity corresponds to unsuccessful surgical operations for a predetermined amount of time such as 30 days. Any corrective action also can be assessed by the cloud 7004. Other data fields can also be monitored in addition to the fields discussed above. In this way, the cloud may timely diagnose and respond to surgical instrument 7012 malfunctions using individual and aggregate data in a manner that an individual healthcare facility could not achieve.

In one aspect, if the answer to any of steps 11016, 11018, 11020, 11022 (i.e. trigger conditions) is affirmative (i.e. the trigger condition is activated), then additional data associated or pertinent to the device data 11002 is sent to the cloud 7004, as can be seen in FIG. 198. This additional data may be handled by the data sorting and prioritization module 7032 while the patient outcome analysis module 7028 may analyze the data, for example. In contrast, if the answer to all of steps 11016, 11018, 11020, 11022 is negative, then the respective data is stored 11026 within the corresponding surgical hub 7006. Thus, when the answer at step 11022 is no, the device data 11002 may be stored locally within the hub 7006 and no additional data is requested of the hub 7006. Alternatively, the device data may be sent to the cloud 7006 for storage within the memory devices 7010, for example, without any triggered requests 11014 by the cloud 7004 for additional data. Steps 11016, 11018, 11020, 11022 could also be used for identifying critical data or flagging the surgical instrument (if the specific surgical device has not already been flagged based on steps 11006, 11008) as part of the screening criteria applied at step 11004. Other trigger conditions aside from steps 11016, 11018, 11020, 11022 are also possible for triggering the request 11014 for additional data. The request can be sent to all surgical hubs 7006 or a subset thereof. The subset can be geographically specific such that, for example, if surgical hub 7006 used in healthcare facilities located in Illinois and Iowa have malfunctioned in a similar manner, only surgical hub 7006 corresponding to healthcare facilities in the Midwestern United States are requested 11014 for additional information. The requested additional data can be different or supporting data concerning the particular use of surgical instruments 7012 so that the cloud 7004 may gain additional insight into the source of the irregularity, as represented by steps 11016, 11018, 11020, 11022. For example, if malfunctioning surgical instruments 7012 are causing undesirable patient bleeding, the cloud 7004 may request timing information regarding this bleeding for help in potentially diagnosing why the malfunction is causing the bleeding.

The criticality of data can be identified based on the screening criteria as described above, or by any other suitable data analysis technique. In one aspect, as shown in FIG. 199, when the critical data is determined, an internal analytic response 11102 of the cloud 7004 may commence. The internal analytic response 11102 can advantageously be made in a timely manner such as in real time or near real time. As discussed above, the criticality of data can be identified based on the severity of an event, the unexpected nature of the data, the suspiciousness of the data, or some other screening criteria (e.g., an internal business flag). The determination of critical data can involve a request generated by a surgical hub 7006 based on the surgical hub 7006 detecting an irregularity or failure of a corresponding surgical instrument 7012 or of a component of the surgical hub 7006 itself. The request by the surgical hub 7006 may comprise a request for a particular prioritization or special treatment of critical data by the cloud 7004. In various aspects, the cloud internal analytic response 11102 could be to escalate an alarm or response based on the frequency of the event associated with the critical device data 11002, route the device data 11002 to different locations within the cloud computing system, or exclude the device data 11002 from the aggregated medical data databases 7011. In addition, the cloud 7004 could also automatically alter a parameter of a malfunctioning surgical instrument 7012 so that modifications for addressing the malfunction can be implemented in real time or near real time. In this manner, even malfunctions that are not readily detected by a clinician in a healthcare facility, for example, may still be advantageously addressed in a timely manner by the cloud 7004.

FIG. 199 is a flow diagram of an aspect of responding to critical data by the computer-implemented interactive surgical system, according to one aspect of the present disclosure. In particular, the internal analytic response 11102 by the cloud 7004 can include handling critical data which includes determining a priority status to determine a time component or prioritization of the response. The response 11102 itself may be based on an operational characteristic indicated by the critical data, such as the characteristics described above in connection with the screening criteria or the trigger conditions of FIG. 198. The internal response 11102 may be implemented by the data sorting and prioritization module 7032 as well as the data collection and aggregation module 7022. As shown in FIG. 199, in the prioritization branch of the flow diagram (labeled as Q1 in FIG. 199) the cloud may incorporate the binary decision of whether to exclude the critical data from the aggregated medical data databases 7011 with a priority escalation decision framework. At step 11104 of FIG. 199, the cloud 7004 determines whether the critical data should be excluded from the aggregated medical data databases 7011. The exclusion determination may be considered a threshold determination.

It can be desirable to exclude critical data from the aggregated medical data databases 7011 for verification purposes. For example, critical data that is flagged or designated for special routing may be placed on a hold list maintained by the cloud 7004. The hold list is maintained at a separate storage location in the memory 7010 relative to the aggregated medical data databases 7011 within the cloud 7004, such as the caches 7018. The excluded critical data could also be stored in a more permanent storage location in the memory 7010. Accordingly, if the answer to step 11104 is yes, the cloud 7004 stores 11118 the critical data in the hold list. The cloud 7004 may then validate or verify that the critical device data 11002 is accurate. For example, the cloud 7004 may analyze whether the device data 11002 is logical in light of a corresponding patient outcome or analyze additional associated data of the device data 11002. Upon proper verification, the device data 11002 may also be stored within the aggregated medical data databases 7011. But if the device data 11002 is not verified, the cloud 7004 may not include the unverified device data 11002 in the priority escalation decision framework. That is, before verification, the device data 11002 may not be assigned a priority status according to the priority status classification 11106 for the internal cloud response 11102.

However, if the device data 11002 is verified, the flow diagram may proceed to the priority status classification 11106. Accordingly, if the answer to the exclusion determination at step 11104 is no, the device data 11002 is prioritized according to the priority escalation decision framework, which can define a predetermined escalation method for handling critical data. As shown in FIG. 199, a predetermined escalation prioritization system 11106 (i.e., priority escalation decision framework) can comprise four categories, including watch list, automated response, notification, and urgent action required. This predetermined escalation prioritization system 11106 can be considered a form of triage based on classifying critical data according a priority status and escalating between statuses based on particular thresholds. For example, priority can be escalated based on a frequency of event threshold such as the number of misaligned staples fired by a stapling surgical instrument 7012 over a predetermined number of surgical operations. Multiple staggered frequency or other thresholds could also be used. The lowest priority level of the priority status classification 11106 is the watch list level designated at level A. As discussed above, the watch list may be a black list maintained in the memory 7010 as a set of database records of identifiers corresponding to prohibited surgical hubs 7006. Surgical hubs 7006 can be prohibited to different extents depending on the nature of the critical device data 11002 or additional data. For example, surgical hubs 7006 may be partially locked out such that only the device components experiencing problems are prevent from functioning. Alternatively, surgical hub 7006 on the watch list may not be restricted from functioning in any way. Instead, the surgical hubs 7006 may be monitored by the cloud 7004 for any additional irregularities that occur. Accordingly, the watch list is designated at level A, the least urgent priority status. As shown in the priority status classification 11106, the automated response at level B is the next most urgent priority status. An automated response could be, for example, an automated initial analysis of the device data 11002 by the patient outcome analysis module 7028 of the cloud 7004 via a set of predefined diagnostic tests.

The third most urgent priority status is notification, which is designated at level C of the priority status classification 11106. In this situation, the cloud 7004 transmits a wireless signal to a healthcare facility employee, clinician, healthcare facility department, or other responsible party depending on the nature of the device data 11002. The notification signal can be received at a receiver device located at a suitable location within the healthcare facility, for example. Receiving the notification signal can be indicated by a vibration or sound to notify the responsible party at the healthcare facility. The holder of the receiver device (e.g., a healthcare facility clinician) may then conduct further analysis of the critical device data 11002 or additional data or other analysis for resolving an indicated irregularity. If a solution to the irregularity is known, the solution may be timely implemented. The most urgent priority status as depicted in the priority status classification 11106 is urgent action required, which is designed at level D. Urgent action required indicates that a responsible party, device or instrument should immediately analyze and diagnose the problem implicated by the critical data. Upon proper diagnosis, an appropriate response should immediately be performed. In this way, the cloud 7004 may implement a comprehensive approach to critical data prioritization and triaging that no individual medical facility could achieve on its own. Critical data may be handled in a timely manner according to suitable priority levels which can address solving time sensitive problems that arise in the healthcare field. Moreover, the cloud 7004 can prioritize aggregated critical data from all healthcare facilities categorized within a particular region. Accordingly, the time sensitive prioritized approach to handling critical data can be applied system wide, such as to a group of healthcare facilities. Furthermore, the cloud 7004 can generate an alert for a responsible party to respond to critical data (and associated issues implicated by such critical data) in a timely way such as in real time or in near real time according to a corresponding priority status. This alert can be received by a suitable receiver of the responsible party. The priority status of the device data 11002 could also be determined based on the severity of the surgical issue implicated by the device data 11002. As discussed above, the cloud 7004 may receive additional data from surgical hubs 7006 or surgical instruments 7012 (via the hubs 7006) which causes the cloud 7004 to elevate the priority status of the device data 11002.

In one aspect, based on a priority status, the device data 11002 may be subject to the flagging screening at a specific time depending on priority. For example, the device data 11002 may be indicated as critical data but not yet flagged. Additionally, the device data 11002 may first receive an automated response level of priority according to the priority status classification 11106. In this situation, the severity determination at step 11108 may be relatively quickly in accordance with the level B of priority. Specifically, step 11108 may be reached without first placing the surgical instrument 7012 on a watch list. The severity threshold used at step 11108 can be the same or different from the severity threshold used in 11006. Aside from the severity determination at step 11108, other determinations pertinent to the irregularity indicated by the critical device data 11002 or additional data may be made. These determinations may be used to diagnose the occurrence of a critical event. Accordingly, if the answer at step 11108 is yes, the frequency of the event may be assessed at step 11110. Conversely, if the answer at step 11108 is no, the device data 11002 or additional data can be stored 11118 in the hold list. Additionally or alternatively, the device data 11002 or additional data can be routed to different storage locations within the cloud 7004 according to the routing branch of the flow diagram (labeled as Q2 in FIG. 199). The cloud 7004 may wait for a request from the hub 7006 for alternative routing 11120 of the device data 11002 or additional data. At step 11110, the cloud 7004 determines the frequency that the critical event is occurring. Based on this frequency, the priority status assigned according to the priority status classification 11106 can be escalated (see step 11116). For example, the critical event may be the generator of the surgical instrument 7012 is applying an insufficient sealing temperature to therapeutically treat tissue. In other words, the inquiry of step 11110 inquires whether the medical event implicated by the critical data is occurring at an increasing frequency after the problem was initially identified.

An increase in the number of times this insufficient sealing temperature occurs can be monitored to escalate priority status at step 11116, based on frequency thresholds (see step 11112), for example. If at step 11110, the event is not increasing in frequency, the data can be stored 11118 in the hold list. If the answer at step 11110 is yes (i.e., the event is increasing in frequency), the flow diagram proceeds to step 11112. At step 11112, another data verification inquiry is made. In particular, specific thresholds such as the frequency thresholds described above may be applied to determine whether the combination of device data 11002 or additional data is sufficiently correct to ensure that the critical data should be added to the aggregated medical data databases 7011. Furthermore, the data verification inquiry at step 11112 may comprise a decision regarding whether the sample size of the critical data is sufficiently large (i.e., reached critical mass). Additionally or alternatively, the sample size is analyzed for whether there is sufficient information to determine an appropriate internal response 11102 of the cloud 7004. The data verification inquiry can also comprise verifying the accuracy of the data by comparison to predetermined standards or verification tests. If the answer to the inquiry at step 11112 is negative, then the critical data is stored within the separate storage location (e.g., hold list) in the cloud 7004. If the answer to the inquiry at step 11110 is affirmative, the device data 11002 or additional data is added to the aggregated medical data databases 7011. At step 11116, the priority status of the device data 11002 or additional data is increased according to the priority status classification 11106. However, besides the event frequency determination, the addition to the aggregated medical data databases 7011 may itself be an action that results in an elevation of the priority status of the critical data at step 7. In any case, the priority status of the device data 11002 or additional data may be escalated or deescalated as appropriate based on additional analysis or data, for example. An internal response 11102 of the cloud 7004 may be made according to the current priority status (i.e., one of levels A-D) of the critical data.

In addition to prioritizing critical data, the internal response 11102 of the cloud 7004 can also involve advantageously routing, grouping, or sorting critical data the aggregated critical data in a timely manner. In particular, the data may be routed to different storage locations within the cloud 7004, such as in the memory devices 7010. This routing is illustrated by routing branch of the flow diagram labeled as Q2 in FIG. 199 at step 11120. As such, the memory devices 7010 of the central servers 7013 of the cloud 7004 can be organized into various locations that correspond to a characteristic of the critical data or a response corresponding to the critical data. For example, the total memory capability of the memory devices 7010 may be divided into portions that only store data according to individual data routing categories, such as those used at steps 11122, 11124, 11126. As shown at step 11120 of FIG. 199, the critical data may be routed to different various cloud storage locations. Step 11120 can occur in conjunction with or separately from the prioritization branch of the flow diagram. Step 11120 may be triggered by a request generated by a hub 7006. The hub 7006 may transmit such a request because of detecting a failure or irregularity associated with a surgical instrument 7012, for example. The associated critical data may then receive alternative routing 11120 by the cloud 7004 to different cloud storage locations. At step 11122, the alternative routing 11120 can comprise geographical location based routing. That is, the different cloud storage locations may correspond to location based categorization of the cloud memory devices 7010. Various subsets of the cloud memory devices 7010 can correspond to various geographical regions. For example, surgical instruments produced from a manufacturing plant in Texas could be grouped together in storage within the cloud memory devices 7010. In another example, surgical instruments produced from a specific manufacturing company can be categorized together in the cloud memory devices 7010. Therefore, location based categorization can comprise the cloud 7004 routing critical data based on associations with different manufacturing sites or operating companies.

At step 11124, the alternative routing 11120 can comprise routing for device data 11002 or additional data that requires a rapid internal response 11102 of the cloud 7004. This alternative routing 11120 at step 11124 could be integrated with the priority status classification 11106. For example, escalated or urgent priority critical data, such as those at priority level C and D, may be routed by the cloud 7004 to rapid response portions of the memory devices 7010 to enable a rapid response. For example, such critical data may be routed to rapid response caches 7018 which signifies that a rapid response is necessary. At step 11126, device data 11002 or additional data that implicates a failure of a type that requires special processing are routed to a special processing portion of the memory devices 7010. For example, a surgical instrument 7012 may be determined to have experienced a failure or malfunction during operation based on a control program deficiency common to a whole group of surgical instruments 7012. In this situation, special processing may be required to transmit a collective control program update to the group of surgical instruments 7012. Accordingly, the cloud may route the critical data to the special processing portion of the memory devices 7010 to trigger this special processing. Subsequently, the special processing could also include the patient outcome analysis data analytics module 7028 analyzing and monitoring the effect of the control program update on patient outcomes. The patient outcome analysis module 7028 may also execute an automated product inquiry algorithm as discussed above if necessary.

FIG. 200 is a flow diagram of an aspect of data sorting and prioritization by the computer-implemented interactive surgical system, according to one aspect of the present disclosure. This sorting and prioritization may be implemented by the data sorting and prioritization module 7032, the data collection and aggregation module 7022, and patient outcome analysis module 7028. As discussed above, critical device data 11002 or additional data can implicate or correspond to various medical events, such as events 1 through 3 as depicted in FIG. 200. An event may be for example, a shift from a phase of tissue treatment to another phase such as a shift from a phase corresponding to cutting with the specific surgical instrument to a phase corresponding to coagulation. In FIG. 200, critical data associated with a first medical event 11202 is detected by the surgical hub 7006 and transmitted to the cloud 7004. Upon receiving the critical data, the cloud 7004 analyzes the critical data at step 11208 to determine that it is comparable to an expected value of the critical data, as described above for example at step 11016. When the critical data is determined as comparable (i.e., the value of the critical data is expected), the critical data may be aggregated within a large data set in the aggregated medical data databases 7011, for example. That is, at step 11216, the critical data is stored within the aggregated databases of the cloud. As shown in FIG. 200, the critical data is also subject to a binary classification at steps 11218, 11220. For example, the critical data can be distinguished by good properties and bad properties. The data sorting and prioritization modules can classify the critical data as associated with a bleeding or a non-bleeding event, for example. In this way, the patient outcome analysis module 7028 may classify critical data as corresponding to a positive patient outcome at step 11218 or a negative patient outcome at step 11210.

FIG. 200 also shows the critical data associated with a second medical event 11204 is detected by the surgical hub 7006 and transmitted to the cloud 7004. The critical data associated with the second medical event 11204 is determined by the cloud to be suspicious or unusual data at step 11210, which is a trigger condition as described above with reference to step 11118. Accordingly, the cloud 7004 is triggered to request 11114 additional data from the surgical hub 7006 at step 11212 by transmitting a push message to the surgical hub 7006. As discussed above, the additional data may enable the patient outcome analysis module 7028 of the cloud 7004 to gain additional insight into the source of the irregularity implicated by the critical data. If the patient outcome analysis module 7028 sufficiently diagnoses the cause of the second medical event 11214, the critical data or associated additional data is aggregated into the aggregated medical data databases 7011 at step 11216 (see also step 11114). Subsequently, the critical data or additional data is classified according to the good/bad binary classification at steps 11218, 11220. If the cloud 7004 cannot sufficiently diagnose the cause of the second medical event 11204, the process may proceed to step 11224, in which the critical data is evaluated by a suitable person or department of the corresponding medical facility. Step 11224 can include the threshold data exclusion determination at step 11104. That is, because a good reason cannot be readily determined for the suspicious or unusual data, the data may be stored in a hold list in accordance with step 11118. Additionally, the device data 11002 or additional data may be designated at priority status level C, which triggers the evaluation at step 11224 (i.e., healthcare facility employee, clinician, healthcare facility department, or other responsible party evaluates the data).

As illustrated in FIG. 200, the critical data associated with a third medical event 11206 is detected by the surgical hub 7006 and transmitted to the cloud 7004. The critical data associated with the third medical event 11206 is determined by the cloud 7004 to indicate that the corresponding surgical instrument 7012 is experiencing a failure or malfunction at step 11220. As discussed above, severity thresholds can be used to determine whether the failure is severe. The failure or malfunction may refer back to the trigger condition at step 11022 in FIG. 198 such that the surgical instrument malfunction results in an automated product inquiry through the surgical hub 7006. As discussed above, the automated product inquiry algorithm may comprise the patient outcome analysis module 7028 searching for data of related incidents stored within the cloud 7004 (e.g., the memory devices 7010). The data of related incidents can include video, manufacturer, temporal, and other suitable types of data. Depending on the results of the automated product inquiry, the third medical event 11206 critical data can be prioritized according to priority status classification 11106. Thus, for example, the inquiry may result in a suspicious or unusual result without a sufficient reason, so the critical data is designated at priority level C. In this connection, a suitable person or department of the corresponding medical facility evaluates the critical data and the results of the automated product inquiry at step 11224. The results of the evaluation could be, for example, that the results constitute an error to be disregarded at step 11226 or that the results require additional special processing via the patient outcome analysis module 7028 at step 11228 (see also step 11126). Such special processing at step 11228 can be the CAPA portion of the automated product inquiry algorithm, as described above. Thus, the cloud-based analytics system may generate timely alerts for triggering a response by the suitable person or department in real time or near real time.

In general, the cloud-based analytics system described herein may determine critical data and perform timely data handling, sorting, and prioritizing based on priority status and specific thresholds as described above. Accordingly, the cloud-based analytics system advantageously handles critical data in a timely, systematic, and holistic manner over multiple health care facilities. The critical data handling comprises internal responses by the cloud 7004 based on assigned priority levels. Moreover, based on requests by surgical hubs 7006, special routing of data within the memory device 7010 of the cloud 7004 may be achieved. The rerouting, prioritizing, confirming, or requesting supporting as described above may be used to improve analysis of the data by the cloud 7004.

Cloud Interface for Client Care Institutions

All client care institutions require some level of control in a treatment environment. For example, an institution may wish to control inventory that is present within an operating room. Inventory items within an operating room may include not only medical devices to be used during surgery (e.g., scalpels, clamps, surgical tools, etc.) but also medical supplies to be used during surgery in conjunction with such medical devices (e.g., gauze, sutures, staples, etc.). Heretofore, inventory control for many institutions comprises a simple manual count of inventory items on a periodic basis (e.g., daily, weekly, monthly, etc.). Similarly, other institutions utilize a barcode scanner to count and/or document inventory items on a periodic basis.

Aspects of the present disclosure are presented for a cloud interface accessible by participating client care institutions via a cloud-based analytics system. In order to monitor and/or control inventory items to be utilized or being utilized by an institution, each institution adopts its own practice of documenting inventory item usage. For example, an institution may manually count and/or scan inventory items on a periodic basis. Additional example details are disclosed in U.S. Patent Application Publication No. 2016/0249917, titled SURGICAL APPARATUS CONFIGURED TO TRACK AN END-OF-LIFE PARAMETER, which published on Sep. 1, 2016, U.S. Patent Application Publication No. 2014/0110453, titled SURGICAL INSTRUMENT WITH RAPID POST EVENT DETECTION, which issued on Feb. 23, 2016 as U.S. Pat. No. 9,265,585, U.S. Patent Application Publication No. 2016/0310134, titled HANDHELD ELECTROMECHANICAL SURGICAL SYSTEM, which published on Oct. 27, 2017, and U.S. Patent Application Publication No. 2015/0317899, titled SYSTEM AND METHOD FOR USING RFID TAGS TO DETERMINE STERILIZATION OF DEVICES, which published on Nov. 5, 2015, the entire disclosures of which are hereby incorporated by reference herein. Information regarding counted and/or scanned inventory items may then be stored in a local computer system to track inventory item usage. Such a manual process is not only labor intensive and inefficient, but also prone to human error. As a result, an institution may be unable to perform a surgical procedure(s) and/or the surgical procedure(s) may be unnecessarily delayed because one or more inventory items, required for the surgical procedure(s), are not available for use for various reasons (e.g., out of stock, in stock but expired, in stock but no longer considered sterile, in stock but defective, etc.). Knowing this, some institutions are forced to carry and/or hold an overstock of inventory items. This, of course, may result in increase expense (e.g., more inventories) and ultimately unnecessary waste (e.g., expired inventory items).

To help institutions control inventory items, it would be desirable for institutions to have access, via a cloud interface, to a cloud-based analytics system configured to automate inventory control by automatically receiving data associated with inventory items of the institutions, deriving information based on the received data, and conveying, via the cloud interface, real-time knowledge back to the institutions regarding inventory items. Referring to FIG. 201, according to one aspect of the present disclosure, a client care institution system 8000 may transmit (e.g., periodically, in real-time, in batches, etc.) inventory data to a cloud-based analytics system 8002 and the cloud-based analytics system 8002 may derive/extract information from that inventory data. In such an aspect, a cloud-interface 8004 may be accessed/queried by the client care institution system 8000 and the cloud-based analytics system 8002 may transmit its derived/extracted information to the cloud-interface 8004. Further, in such an aspect, the cloud-interface 8004 may convey/package/structure the derived/extracted information to the client care institution system 8000 to reveal knowledge about the client care institution's inventory. In one aspect, the client care institution system may comprise a surgical system 102 (e.g., FIG. 1), the cloud-based analytics system may comprise the cloud-based system 105 (e.g., FIG. 1) and the cloud-interface may comprise at least one of a visualization system 108/208 (e.g., FIGS. 1-2) or a display 135/177 associated with the surgical hub 106 (e.g., FIGS. 1-3, 7, etc.).

Referring to FIG. 1, in some aspects of the present disclosure, a cloud-based system 105 is communicatively coupled to one or more than one surgical hub of an institution (e.g., one or more than one surgical hub 106 of a surgical system 102). Here, each surgical hub is in communication (e.g., wirelessly) with one or more than one inventory item (e.g., intelligent instrument 112). The cloud-based system 105 may be configured to aggregate data associated with each inventory item of each institution, analyze that data with respect to system-defined constraints, and generate or facilitate a cloud interface for each institution to monitor and control inventory items. In one example, the cloud-based system 105 may be configured to compute a current availability of each inventory item (e.g., an indication of real-time usage and/or scheduled usage for each inventory item in a surgical system 102), a current usage associated with each inventory item (e.g., based on data received from one or more than one surgical hub 106 that has read usage data from a chip/memory associated with each inventory item), irregularities, if any, associated with each inventory item (e.g., defects, etc.), current possible medical device combinations that utilize each inventory item (e.g., various shafts, staple cartridges, end effectors, etc. combinable to form numerous medical device combinations), and available alternatives to each inventory item (e.g., available shaft B and/or shaft C may be substituted for unavailable shaft A for a desired/input surgical procedure(s)). Referring to FIGS. 202-203, in such an exemplification, after input of a desired surgical procedure(s) (e.g., "cholecystectomy") by an institution in its cloud interface 8104, the cloud-based system 105 may provide up-to-date, real-time and/or near real-time knowledge regarding the availability and/or usability of inventory items (e.g., associated with and/or needed to perform the input surgical procedure(s)) based on the system-defined constraints. Referring to FIG. 203, in one example, the institution's cloud interface 8104 may display an inventory item 8106 (e.g., Handles A, B, and C) in association with its current 8108 and/or remaining usage 8110. If the remaining usage is not adequate (e.g., based on anticipated usage necessary for the desired surgical procedure, etc.), the cloud interface may further display a warning or alert regarding the inadequacy (e.g., 8112, highlighting, blacked out, etc.). Such a warning or alert may indicate that the surgical procedure(s) input at the cloud interface cannot be performed based on current inventory items. In one aspect, a same or similar warning or alert may be communicated to the inventory item itself for display on a user interface of the inventory item itself (e.g., a user interface of Handle C). In another aspect, the cloud interface may further display available alternatives to the inventory item (e.g., Handle B). Here, anticipated usage and/or available alternatives may be determined at the surgical hub 106 (e.g., based on local data) and/or the cloud-based analytics system 105 (e.g., based on local data of the surgical hub 106 and/or global data from multiple surgical hubs 106 of multiple institutions). In one example, the surgical hub 106 may infer anticipated usage and/or available alternatives from local data associated with the same or similar surgical procedure (e.g., average number of uses to perform the same or similar surgical procedure, alternative inventory items used to perform the same or similar surgical procedure, etc.). In another example, the cloud-based analytics system 105 may similarly infer anticipated usage and/or available alternatives from local data of the surgical hub 106 and/or global data from multiple surgical hubs 106 of multiple institutions (e.g., average number of uses to perform the same or similar surgical procedure, alternative inventory items used to perform the same or similar surgical procedure, etc.).

In other aspects of the present disclosure, a cloud-based system 105 is communicatively coupled to one or more than one surgical hub 106 of an institution, each surgical hub 106 in communication (e.g., wirelessly) with one or more than one inventory item (e.g., intelligent instrument 112). The cloud-based system 105 may be configured to create a list of inventory items not authorized to perform surgical procedures due to one or more system-defined constraints. In one exemplification, after input of a desired surgical procedure(s) by an institution into its cloud interface (e.g., FIG. 202), the cloud-based system 105 may determine that one or more inventory items of the institution (e.g., detected by and associated with and/or needed to perform the input surgical procedure(s)) are not authorized to perform the input surgical procedure(s) based on system-defined constraints. In such an exemplification, it may be determined that an identifier (e.g., serial number, unique ID, etc.) associated with an inventory item is not authorized to perform the input surgical procedure(s) (e.g., inventory item exceeds usable life, inventory item is counterfeit, inventory item is defective, etc.). In one example, the institution's cloud interface may display an inventory item in association with its unauthorized status 8114. In such an aspect, the cloud interface may further display a warning or alert regarding the unauthorized status (e.g., highlighting, blacked out, etc.). Such a warning or alert may indicate that the surgical procedure(s) input at the cloud interface cannot be performed based on current inventory items. In one aspect, a same or similar warning or alert may be communicated to the inventory item itself for display on a user interface of the inventory item itself (e.g., a user interface of Handle D). Similar to above, the cloud interface 8104 may display available alternatives to the unauthorized inventory item (e.g., Handle B).

In yet other aspects of the present disclosure, a cloud-based system 105 is communicatively coupled to one or more than one surgical hub 106 of an institution, each surgical hub 106 in communication (e.g., wirelessly) with one or more than one inventory item (e.g., intelligent instrument 112). The cloud-based system 105 may be configured to create a list of inventory items no longer authorized to perform surgical procedures due to one or more system-defined constraints. In one exemplification, after input of a desired surgical procedure(s) by an institution in its cloud interface (e.g., FIG. 202), the cloud-based system may determine that one or more inventory items are no longer authorized to perform the input surgical procedure(s) based on system-defined constraints. In such an exemplification, it may be determined that an identifier (e.g., serial number, unique ID, etc.) associated with an inventory item is unusable (e.g., expired, no longer sterile, defective, etc.). In one example, the institution's cloud interface may display an inventory item in association with its unusable status 8116. In such an aspect, the cloud interface may further display a warning or alert regarding the unusable status (e.g., highlighting, blacked out, etc.). Such a warning or alert may indicate that the surgical procedure(s) input at the cloud interface cannot be performed based on current inventory items. In one aspect, a same or similar warning or alert may be communicated to the inventory item itself for display on a user interface of the inventory item itself (e.g., a user interface of Handle E). Similar to above, the cloud interface may display available alternatives to the unusable inventory item (e.g., Handle B).

In this way, the cloud-based system 105 of the present disclosure may provide up-to-date, real-time, and/or near real-time knowledge regarding the availability of inventory items pertinent to the surgical procedure(s) input to the cloud interface of the participating institutions. Such a system goes well-beyond conventional processes of manually counting and/or scanning inventory items.

FIG. 204 illustrates an example multi-component surgical tool (e.g., a wireless surgical device/instrument 235) comprising a plurality of modular components 8204, 8206, 8208, 8210, wherein each modular component is associated with an identifier 8214, 8216, 8218, 8220 respectively (e.g., a serial number). In particular, the surgical tool 235 of FIG. 204 includes a handle 8204, a modular adapter 8206, and end effector 8208 (e.g., a disposable loading unit and/or a reloadable disposable loading unit in various aspects), and a staple cartridge 8210. In this example, the handle 8204 is associated with serial number "SN135b", the modular adapter 8206 is associated with serial number "SN33b", the end effector 8208 is associated with serial number "SN1a" and the staple cartridge 8210 is associated with serial number SN121b. In such an aspect, each modular component (e.g., 8204, 8206, 8208, 8210, etc.) is configured to request a communication link to a surgical hub 106 of an institution. In other aspects, the surgical hub 106 may be configured to request a communication link with each modular component. Nonetheless, the surgical hub 106 is positioned within a communicative distance from each modular component (e.g., in an operating room). In one aspect of the present disclosure, a requested communication link is established via BLUETOOTH pairing. In other aspects of the present disclosure, other forms of wireless communication (e.g., WiFi, RFID, etc.) or wired communication are contemplated. Referring again to FIG. 204, each modular component (e.g., handle 8204, modular adapter 8206, end effector 8208, staple cartridge 8210, etc.) may comprise a processor and a memory unit (not shown) that stores its respective serial number. Here, according to one aspect, once a communication link is established between the surgical hub 106 and each modular component, the identifier (e.g., serial number) associated with each modular component is transmitted by each modular component to the surgical hub 106 (e.g., via the same form or different forms of wired/wireless communication). In one alternative aspect, in light of FIG. 204, a modular component (e.g., modular adapter 8206, end effector 8208, and/or staple cartridge 8210, etc.) may transmit its respective identifier (e.g., serial number) to another modular component (e.g., handle 8204) that transmits/relays all identifier(s) to the surgical hub 106. Here, similar to above, the same form or different forms of wired/wireless communication may be used. For example, each of the modular adapter 8206, the end effector 8208 and the staple cartridge 8210 may transmit its respective identifier (e.g., 8216, 8218, 8220) to the handle 8204 via RFID and the handle 8204 may relay such identifiers (e.g., 8216, 8218, 8220) along with its own identifier 8214, via BLUETOOTH, to the surgical hub 106. In one aspect, once the surgical hub 106 has received all identifiers for all modular components, the surgical hub 106 may transmit the identifiers to the cloud-based analytics system (e.g., comprising cloud-based system 105).

In various aspects of the present disclosure, the memory unit of each modular component may be configured to store more than its identifier. In one aspect of the present disclosure, each modular component (e.g., 8204, 8206, 8208, 8210, etc.) may further comprise a counter (not shown) configured to track a usage parameter of the modular component and its memory unit may be configured to store that usage parameter. In another aspect, the memory unit of each respective modular component may be further configured to store a usable life metric. Such a usable life metric may be stored during manufacture of the modular component. For example, in view of FIG. 204, the memory unit of the handle 8204 may store both the usage parameter (e.g., 235) and the usable life metric (e.g., 400). In such an aspect, the handle 8204 has been used 235 times out of its usable life of 400 uses. Similarly, in view of FIG. 204, the modular adapter has been used 103 times out of its usable life of 100 uses, and the end effector has been used 5 times out of its usable life of 12 uses. Here, similar to above, once a communication link is established with the surgical hub 106, the identifier, usage parameter and/or usable life metric stored in the memory unit of each modular component may be transmitted directly from each modular component to the surgical hub 106 or indirectly via another modular component. In addition, similar to above, the same form or different forms of wired/wireless communication may be used. In one aspect, once the surgical hub 106 has received all identifiers for all modular components, the surgical hub 106 may transmit the identifiers to the cloud-based analytics system (e.g., comprising cloud-based system 105).

In an alternative aspect of the present disclosure, the memory unit of each modular component may not store its usage parameter and/or the usable life metric. In such an aspect, the usage parameter and/or the usable life metric may be stored in a database or other memory (see FIG. 10, e.g., 248/249) at the surgical hub 106/206. In such an aspect, the surgical hub 106 may comprise a counter configured to track a usage parameter of each modular component in inventory. Furthermore, the surgical hub 106 may be configured to download usable life metrics (e.g., from a manufacturer server) based on the identifier (e.g., serial number) received from each modular component. In various aspects, storage at the surgical hub 106 may be preferred to minimize memory unit requirements in each modular component and/or to avoid any concerns regarding the tampering with and/or the alteration of usage parameters and/or usable life metrics stored at the modular component level (e.g., altering a memory unit of a modular component to reset a usage parameter and/or increase a usable life metric, etc.).

In one example, in aspects where the memory unit of each modular component stores its usage parameter and/or usable life metric, the surgical hub 106 may also store/track the usage parameter and/or usable life metric associated with each modular component in its inventory. In such an example, if a usage parameter and/or a usable life metric transmitted from a modular component differs from a usage parameter and/or a usable life metric stored/tracked at the surgical hub 106, the surgical hub 106 may flag the discrepancy and modify the status of that modular component (e.g., to unavailable, to unauthorized, to unusable, etc.).

In another alternative aspect, the memory unit of each modular component may not store its usage parameter and/or the usable life metric. In such an aspect, the usage parameter and/or the usable life metric may be stored in a database (e.g., aggregated medical data database 7012 in FIG. 180) at a cloud-based analytics system. In such an aspect, the cloud-based analytics system may comprise a counter configured to track a usage parameter of each modular component in inventory at each surgical hub. Furthermore, the cloud-based analytics system may be configured to download usable life metrics (e.g., from a manufacturer server) based on the identifier (e.g., a serial number) received from each modular component (e.g., via a surgical hub). Alternatively, the cloud-based analytics system may download a file comprising all identifiers for all modular components (e.g., from a plurality of manufacturers) wherein each identifier is associated with a usable life metric. Here, the cloud-based analytics system may be configured to look-up a received identifier to determine each respective usable life metric. In various aspects, storage at the cloud-based analytics system may be preferred to minimize memory requirements in each modular component and/or to avoid any concerns regarding the tampering with and/or the alteration of usage parameters and/or usable life metrics at the modular component level and/or at the surgical hub level (e.g., altering memory unit of a modular component to reset a usage parameter and/or increase a usable life metric, modifying the database/memory of the surgical hub to reset a usage parameter and/or increase a usable life metric). Such as aspect gives the cloud-based analytics system of the present disclosure more control over modular component use in the interactive surgical system.

Looking again to FIG. 204, the illustrated multi-component surgical tool 235 comprises four modular components (e.g., handle 8204, modular adapter 8206, end effector 8208, and staple cartridge 8210). Such modular devices may comprise reusable and/or reprocessed components. In various aspects, each modular component must satisfy system-defined constraints for the combined multi-component surgical tool 235 to be available/usable/authorized for use by the cloud-based analytics system. Notably, system-defined constraints may include restrictions other than and/or in addition to the usable life metric discussed above. Such system-defined constraints may be established at the manufacturer level, at the surgical hub level, and/or at the cloud-based analytics system level. One aspect of the present disclosure comprises a user interface at the surgical hub and/or cloud-based analytics system to create system-defined constraints.

In one aspect, the surgical hub 106 may be configured to enforce system-defined constraints (e.g., lockout at the hub level). In such an aspect, this may be preferred so that the surgical hub 106 is a local gateway to accessing the cloud-based analytics system. In another aspect, the cloud-based analytics system (e.g., comprising cloud-based system 105) may be configured to enforce system-defined constraints (e.g., lockout at the cloud-based analytics system level). In such an aspect, this may be preferred to maintain control over all surgical hubs communicatively coupled to the cloud-based analytics system (e.g., at one institution or at multiple institutions). System-defined constraints, similar to the usable life metric, may be associated with the identifier of each modular component. For example, a system-defined constraint associated with a modular component may include an expiration date, a requirement that an identifier (e.g., serial number) is a system-recognizable identifier (e.g., not counterfeit), and/or flexible system-defined constraints (e.g., constraints deemed non-critical until a threshold is met and the constraint is deemed critical). In one aspect of the present disclosure, if one system-defined constraint is not met, a modular component (e.g., 8204, 8206, 8208, 8210, etc.) may be deemed unavailable/unusable/unauthorized despite being available/usable/authorized based on other system-defined constraint(s) (e.g., having remaining usable life). In various aspects, one or more predetermined system-defined constraints are non-critical system-defined constraints. Such non-critical system-defined constraints may be waived (see FIG. 204, e.g., 8274, manual override) to render the modular component available/usable/authorized and/or may produce in a warning indicator/message (see FIG. 204, e.g., 8244). Critical system-defined constraints cannot be waived.

In view of FIG. 204, an example non-critical system-defined constraint is applied (e.g., by the surgical hub 106 and/or the cloud-based analytics system) to the handle 8204. Here, although the handle 8204 has 165 remaining uses (usable life metric less determined usage parameter, e.g., 400-235) an expiration date associated with its identifier 8214 (e.g., SN135b) indicates that the handle's control program is out-of-date. In such an aspect, an interface 8200 may be displayed to show a current status of the handle 8204 (see FIG. 204, e.g., "Count 235/400" and/or "Out-of-Date"). More specifically, the interface 8200 may comprise a grid including fields defined by columns and rows. In one example, the modular components of a proposed multi-component surgical tool 235 may be presented (e.g., in an exploded, unassembled view) across the columns of the grid in a first row 8201 and a current/updated status associated with each modular component may be presented across corresponding columns of the grid in a second row 8202. As such, in accordance with the example, status field 8224 of the interface 8200 corresponds to the handle 8204 and indicates its current status as "COUNT: 235/400" and "OUT-OF-DATE". According to other aspects, the status field 8224 of the interface 8200 may further show the usage remaining, remaining capabilities, and/or compatibility with other connected modular components, etc.

According to one aspect, the interface 8200 may comprise a cloud-based interface (see FIG. 203, e.g., 8104) accessible on a cloud-access terminal of the surgical hub (via at least one of a visualization system 108/208 (e.g., FIGS. 1-2) or a display 135/177 associated with the surgical hub 106 (e.g., FIGS. 1-3, 7, etc.)). According to another aspect, the interface 8200 may comprise only a portion(s) of the grid (e.g., status field 8224, modular component field 8234, etc.) accessible on the physical handle 8204 itself via a user interface positioned on the handle 8204. Further, in the context of a non-critical system-defined constraint, the interface 8200 may visually indicate a warning associated with a modular component (e.g., warning indicator 8244, e.g., box associated with identifier 8214 highlighted and/or encircled and/or comprises a link 8254 (e.g., "A") in association with modular component field 8234 of the interface 8200). In one aspect, the link 8254 (e.g., "A") may key to a corresponding "Description of Problem" section of the interface 8200 (e.g., "A" "Handle Serial Number Indicates OUT OF DATE Control Program"). In another aspect, the link 8254 (e.g., "A") may be a hyperlink to present the corresponding description (e.g., "A" "Handle Serial Number Indicates OUT OF DATE Control Program") in the interface 8200. According to such aspects, a portion of the descriptive text (e.g., "OUT OF DATE"), keyed/hyperlinked via link 8254, may be a hyperlink/button 8264. Upon/After selection of the hyperlink/button 8264 a bypass interface 8274 may be presented in the interface 8200. According to another aspect, a portion of descriptive text (e.g., OUT-OF-DATE) in status field 8224 may be a hyperlink/button 8284 to, upon/after selection, directly present the bypass interface 8274 in the interface 8200. Such an aspect may be beneficial/more efficient if the interface 8200 is being presented via a (e.g., smaller) user interface of a modular component (e.g., handle 8204). Further, according to such aspects, the interface 8200 may be configured to receive user input to waive (e.g., manually bypass) a predetermined, non-critical system-defined constraint (e.g., the expiration date constraint). In the context of a non-critical system-defined constraint, the bypass interface 8274 may instruct "USER INPUT NEEDED" and present a first user-interface element (e.g., "Y" button) selectable to bypass the non-critical system-defined constraint (e.g., to permit use of the handle 8204) and a second user-interface element (e.g., "N" button) selectable to not bypass the non-critical system-defined constraint (e.g., to inhibit use of the handle 8204). Here, a selection in the bypass interface 8274 may be transmitted to update the surgical hub 206 and/or the cloud-based system 205.

Next, in view of FIG. 204, an example flexible system-defined constraint is applied (e.g., by the surgical hub 106 and/or the cloud-based analytics system) to the modular adapter 8206. Here, the modular adapter 8206 associated with identifier 8216 (e.g., SN33b) has a usage parameter of 103 (e.g., already 3 times over its suggested usable life metric of 100 uses). In this example, the exceeding use is deemed non-critical until a 10% overage threshold is met (e.g., 110% of the suggested 100 uses, or 110 uses) and the exceeding use is deemed critical. In such an aspect an interface 8200 may be displayed to show a current status of the modular adapter 8206 (see FIG. 204, e.g., "COUNT: 103/100" "EXCEEDS"). More specifically, in accordance with the example described above, status field 8226 corresponds to the modular adapter 8206 and indicates its current status as "COUNT: 103/100" and "EXCEEDS". According to other aspects the status field 8226 of the interface 8200 may further show overage remaining, remaining capabilities, and/or compatibility with other connected modular components.

Again, according to one aspect the interface 8200 may comprise a cloud-based interface (see FIG. 203, e.g., 8104) accessible on a cloud-access terminal of the surgical hub (via at least one of a visualization system 108/208 (e.g., FIGS. 1-2) or a display 135/177 associated with the surgical hub 106 (e.g., FIGS. 1-3, 7, etc.)). According to another aspect, the interface 8200 may comprise only a portion(s) of the grid (e.g., the status field 8226, modular component field 8236, etc.) accessible directly on the physical modular adapter 8206 itself via a user interface positioned on the modular adapter 8206 and/or indirectly on the physical handle 8204 itself via a user interface positioned on the handle 8204. Further, in the context of a flexible system-defined constraint, the interface 8200 may visually indicate a warning associated with a modular component (e.g., warning indicator 8246, e.g., description of current status encircled and/or comprises a link 8256 (e.g., "B") in association with status field 8226 of the interface 8200). In one aspect, the link 8256 (e.g., "B") may key to a corresponding "Description of Problem" section of the interface 8200 (e.g., "B" "Modular Adapter EXCEEDS Suggested Life Limit"). In another aspect, the link 8256 (e.g., "B") may be a hyperlink to present the corresponding description (e.g., "B" "Modular Adapter EXCEEDS Suggested Life Limit") in the interface 8200. According to such aspects, a portion of the descriptive text (e.g., "EXCEEDS"), keyed/hyperlinked via link 8256, may be a hyperlink/button 8266. Upon/After selection of the hyperlink/button 8266 a warning interface 8276 may be presented in the interface 8200. According to another aspect, a portion of descriptive text (e.g., EXCEEDS) in status field 8226 may be a hyperlink/button 8286 to, upon/after selection, directly present the warning interface 8276 in the interface 8200. Such an aspect may be beneficial/more efficient if the interface 8200 is being presented via a (e.g., smaller) user interface of a modular component (e.g., modular adapter 8206 and/or handle 8204). Further, according to such aspects, the interface 8200 may be configured to present a warning that the modular adapter 8206 is approaching its overage threshold. In one aspect, the warning interface 8276 may instruct "NO INPUT NEEDED" and present a warning indicating that the overage threshold is being approached (e.g., "Approaching 10% Limit Warning"). In other aspects, the warning may indicate how many uses remain until the overage threshold is met (e.g., "7 Uses Until 10% Overage Limit Is Met").

Next, in view of FIG. 204, an example system-defined constraint is applied (e.g., by the surgical hub 106 and/or the cloud-based analytics system) to the end effector 8208. Here, the end effector 8208 associated with identifier 8218 (e.g., SN1a) has a usage parameter of 5 (e.g., 7 uses under its suggested usable life metric of 12 uses remain). As such, in accordance with this example, the system-defined constraint is deemed satisfied and the end effector 8208 is rendered available/usable/authorized. In such an aspect, an interface 8200 may be displayed to show a current status of the end effector 8208 (see FIG. 204, e.g., "COUNT: 5/12"). More specifically, in accordance with the example described above, status field 8228 corresponds to the modular adapter 8208 and indicates its current status as "COUNT: 5/12". According to other aspects the status field 8228 of the interface 8200 may further show usage remaining, remaining capabilities, and/or compatibility with other connected modular components.

Yet again, according to one aspect, the interface 8200 may comprise a cloud-based interface (see FIG. 203, e.g., 8104) accessible on a cloud-access terminal of the surgical hub (via at least one of a visualization system 108/208 (e.g., FIGS. 1-2) or a display 135/177 associated with the surgical hub 106 (e.g., FIGS. 1-3, 7, etc.)). According to another aspect, the interface 8200 may comprise only a portion(s) of the grid (e.g., the status field 8228, modular component field 8238, etc.) accessible directly on the physical end effector 8208 itself via a user interface positioned on the end effector 8208 and/or indirectly on the physical handle 8204 itself via a user interface positioned on the handle 8204. Here, since the system-defined constraint is satisfied, no warning interface and/or bypass interface is displayed.

Lastly, still in view of FIG. 204, an example critical system-defined constraint is applied (e.g., by the surgical hub 106 and/or the cloud-based analytics system) to the staple cartridge 8210. Here, identifier 8220 (e.g., SN121b), associated with the staple cartridge 8210, is not a system-recognizable identifier. According to one aspect, this may occur when the surgical hub 206 and/or the cloud-based analytics system (e.g., comprising cloud-based system 205) is unable to match an identifier (e.g., serial number) received from a modular component with identifiers (e.g., serial numbers) downloaded from the manufacturer(s) of the modular component(s). As such, continuing the example, the system-defined constraint is critical, the system-defined constraint is deemed not satisfied, and the staple cartridge 8210 is rendered unavailable/unusable/unauthorized. Further, as a result, since the critical system-defined constraint cannot be waived, any combined multi-component surgical tool comprising the staple cartridge 8210 may be similarly rendered unavailable/unusable/unauthorized. In such as aspect, an interface 8200 may be displayed to show a current status of the staple cartridge 8210 (see FIG. 204, e.g., "LOADED" "COUNTERFEIT"). More specifically, in accordance with the example described above, status field 8230 corresponds to the staple cartridge 8210 and indicates its current status as "LOADED" and "COUNTERFEIT".

Yet again, according to one aspect, the interface 8200 may comprise a cloud-based interface (see FIG. 203, e.g., 8104) accessible on a cloud-access terminal of the surgical hub (via at least one of a visualization system 108/208 (e.g., FIGS. 1-2) or a display 135/177 associated with the surgical hub 106 (e.g., FIGS. 1-3, 7, etc.)). According to another aspect, the interface 8200 may comprise only a portion(s) of the grid (e.g., the status field 8230, modular component field 8240, etc.) accessible directly on the physical staple cartridge 8210 itself via a user interface positioned on the staple cartridge 8210 and/or indirectly on the physical handle 8204 itself via a user interface positioned on the handle 8204. Further, in the context of a critical system-defined constraint, the interface 8200 may visually indicate a warning associated with a modular component (e.g., warning indicator 8250, e.g., box associated with identifier 8220 highlighted and/or encircled and/or comprises a link 8260 (e.g., "C") in association with modular component field 8240 of the interface 8200). In one aspect, the link 8260 (e.g., "C") may key to a corresponding "Description of Problem" section of the interface 8200 (e.g., "C" "Serial Number of Cartridge Indicates COUNTERFEIT Cartridge"). In another aspect, the link 8260 (e.g., "C") may be a hyperlink to present the corresponding description (e.g., "C" "Serial Number of Cartridge Indicates COUNTERFEIT Cartridge") in the interface 8200. According to such aspects, a portion of the descriptive text (e.g., "COUNTERFEIT"), keyed/hyperlinked via link 8260, may be a hyperlink/button 8270. Upon/After selection of the hyperlink/button 8270 an action interface 8280 may be presented in the interface 8200. According to another aspect, a portion of descriptive text (e.g., COUNTERFEIT) in status field 8230 may be a hyperlink/button 8290 to, upon/after selection, directly present the action interface 8280 in the interface 8200. Such an aspect may be beneficial/more efficient if the interface 8200 is being presented via a (e.g., smaller) user interface of a modular component (e.g., staple cartridge 8210 and/or handle 8204). Further, according to such aspects, the interface 8200 may be configured to instruct a user to perform an action (e.g., to remove the staple cartridge 8210 associated with the identifier 8220 (e.g., SN121b) and reload with a staple cartridge associated with a system-recognizable identifier. In one aspect, the action interface 8280 may instruct "ACTION REQUIRED" and present a directive "Remove & Reload". Here, since the system-defined constraint is critical, no warning interface and/or bypass interface is displayed. In one further aspect, a list of available and/or alternative modular components (e.g., staple cartridges) may be displayed.

In a similar manner, a list (e.g., black-listed devices) of surgical tools (e.g., wireless surgical devices/instruments 235) and/or modular components (e.g., handles, modular adapters, end effectors, staple cartridges, etc.) may be declared unavailable/unusable/unauthorized to communicate with and/or access the surgical hub 206 and/or cloud-based analytics system (e.g., comprising cloud-based system 205). In one aspect of the present disclosure, such black-listed devices may comprise inventory items that are known and/or established to be counterfeit, defective, damaged, beyond their usable life, expired, unsterile, etc. In such an aspect, black-listed devices may be used as critical system-defined constraints (e.g., if the device is on the "black-list," it cannot communicate with and/or access the surgical hub and/or cloud-based analytics system). In line with above, critical system-defined constraints cannot be waived/bypassed. Creating and/or maintaining such a "black-list" of devices at the surgical hub level and/or the cloud-based analytics level, may improve safety and reliability in the operating room. In one aspect, a database (e.g., aggregated medical data database 7012 in FIG. 180) at the cloud-based analytics system may be updated each time a counterfeit device is detected via a surgical hub 206 (e.g., similar to the staple cartridge in FIG. 204). Since a plurality of surgical hubs associated with a plurality institutions may communicate with the cloud-based analytics system, such a database, and associated "black-list", builds rather quickly. Such a database at the cloud-based analytics system would prevent a black-listed device from being used at a different surgical hub (e.g., a surgical hub other than the surgical hub at which the counterfeit was initially detected) communicatively coupled to the cloud-based analytics system.

In another aspect of the present disclosure, black-listed devices may include surgical tools (e.g., wireless surgical devices/instruments 235) and/or modular components (e.g., handles, modular adapters, end effectors, staple cartridges, etc.) developed by third-parties wishing to take advantage of benefits provided by the surgical hub and/or cloud-based analytics system (e.g., various inventory control aspects discussed herein). In such an aspect of the present disclosure, black-listed devices may be used as non-critical system-defined constraints and/or flexible system-defined constraints (e.g., if the device is on the "black-list," it cannot communicate with and/or access the surgical hub and/or cloud-based analytics system). However, contrary to the previously disclosed aspect, such non-critical system-defined constraints and/or flexible system-defined constraints may be waived/bypassed. In one aspect of the present disclosure, such a black-listed device (e.g., a third-party device) may be granted access to the surgical hub and/or cloud-based analytics system for a fee. In one example a competitor product may be initially declared counterfeit. However, once an agreed upon fee is paid, that competitor product may be granted access to the surgical hub and/or cloud-based analytics system. In another aspect, such a black-listed device may be granted partial access to the surgical hub and/or cloud-based analytics system but may be subject to established secondary system-defined constraints. In another aspect, such a black-listed device may be granted access to the surgical hub and/or cloud-based analytics system but may not be able to fully function (e.g., limited functionality) when paired with the surgical hub. Similar to above, a database (e.g., aggregated medical data database 7012 in FIG. 180) at the cloud-based analytics system may be updated each time a previously black-listed device is granted access, partial access with secondary system-defined constraints and/or access with limited functionality. Since a plurality of surgical hubs associated with a plurality institutions may communicate with the cloud-based analytics system, such a database, and its associated access levels, can be implemented across all communicatively coupled surgical hubs. In all such aspects, the surgical hub and/or cloud-based analytics system maintains complete control over devices seeking access.

In yet another aspect of the present disclosure a database of the surgical hub (see FIG. 10, e.g., 248/249) and/or a database (e.g., aggregated medical data database 7012 in FIG. 180) of the cloud-based analytics system may record each modular component and/or surgical tool identifier (e.g., serial number) in a "used identifier list" when first used in the system. As such, each time a new modular component and/or a new surgical tool is plugged in and/or requests communication with the surgical hub and/or cloud-based analytics system, an identifier of the new modular component and/or surgical tool is cross-checked with the "used identifier list." In such an aspect, if the identifier of the new modular component and/or the new surgical tool matches an identifier already in the "used identifier list," that identifier may be automatically placed on a "black-list" (e.g., critical system-defined constraint). Here, identifiers (e.g., serial numbers) should be unique. If an already used identifier is presented at first use multiple times, this may evidence fraud and/or counterfeit activity.

As discussed herein, various aspects of the present disclosure are directed to the application of system-defined constraints. For example, as discussed with reference to FIG. 204 above, each modular component of a surgical tool may be associated with an identifier and each identifier may be associated with one or more than one parameter (e.g., usage parameter, expiration date, flexible parameter, etc.). In another aspect of the present disclosure, a surgical tool may be associated with an identifier wherein that identifier is associated with one or more than one parameter. In such an aspect, either the surgical tool does not comprise modular components or the surgical tool comprises modular components associated with the same identifier (e.g., serial number, activation code). Here, system-defined constraints, as discussed herein, may be applied to such a surgical tool in a similar manner.

Further, as discussed herein, various aspects of the present disclosure pertain to the identification of reusable/reprocessed devices (e.g., modular components, surgical tools, etc.) and the display of each reusable device's availability/readiness for a next/proposed surgical procedure and its operational status on a screen other than the screen of the reusable device (e.g., a screen of a cloud-access terminal of the surgical hub). In one aspect of the present disclosure the status of each reusable device (e.g., status of each modular component, status of a surgical tool, and/or overall status of combined modular components and/or subassemblies) is queried and/or determined when the reusable device connects to the system or as the reusable device connects to the system (e.g., to the surgical hub and/or the cloud-based analytics system). In another aspect of the present disclosure, once/after the reusable device is used, the surgical hub and/or cloud-based analytics system time-stamps the use and updates the usage of each modular component and/or surgical tool in its respective database.

In further various aspects of the present disclosure, a modular component and/or a surgical tool may be flagged by the surgical hub and/or cloud based analytics system based on predetermined criteria. For example, if a modular component is incompatible with other modular components, its identifier (e.g., serial number) is known to be fake, and/or it is subject to a recall, a database of the surgical hub and/or the cloud-based analytics system may be updated to not allow use of the modular component and/or surgical tool in the system (e.g., creation of critical system-defined constraints). Such created system-defined constraints may be applied as discussed herein.

In yet further aspects of the present disclosure, a modular component and/or a surgical tool may be flagged by the surgical hub and/or cloud based analytics system based on a previous use. For example, the surgical hub and/or the cloud based analytics system may track performance of the modular component and/or the surgical tool. Here, performance results may be analyzed by the cloud-based analytics system to inform future uses of the modular component and/or surgical tool. For example, if the end effector did not clamp properly or jammed in a previous use, the end effector may be flagged in a database of the surgical hub and/or the cloud-based analytics system (e.g., black-listed) so that the end effector cannot be used again in the system.

Various aspects of the present disclosure are also directed to a cloud-based analytics system that generates a cloud interface for a client care institution. More specifically, aspects of the present disclosure pertain to a cloud-based system including a client care institution surgical hub coupleable with a plurality of inventory items (e.g., handles, modular adapters, end effectors, staple cartridges, etc.) and a cloud-based analytics system. The surgical hub may include a processor programmed to communicate with the plurality of inventory items and the cloud-based analytics system. The cloud-based analytics system may include a processor programmed to i) receive, via the surgical hub, data associated with the plurality of inventory items, wherein the received data comprises a unique identifier for each inventory item, ii) determine whether each inventory item is available for use based on its respective unique identifier and system-defined constraints, wherein the system-defined constraints comprise at least one use restriction, iii) generate a cloud interface for the institution, wherein the institution's cloud interface comprises a plurality of user-interface elements, wherein at least one user-interface element enables the institution to select one or more than one surgical procedure to be performed, and wherein after selection of a surgical procedure, via the at least one user-interface element, the availability of each inventory item associated with the selected surgical procedure is dynamically generated on the institution's cloud interface, and iv) display an alert for each inventory item determined as not available based on the system-defined constraints, wherein the alert is displayable on at least one of the institution's cloud interface or the inventory item. Here, in line with the disclosure herein, alternative inventory items for unavailable items may also be displayed. Such a cloud interface enables an institution to evaluate whether a desired/proposed surgical procedure can proceed based on current inventories. Here, data at the surgical hub level (e.g., historical local usage) and/or the cloud-based analytics system level (e.g., historical local and/or global usage) may be used to determine combinations of modular components and/or surgical tools usable for the surgical procedure selected via the user-interface element. Furthermore, alternative and/or preferred modular components and/or surgical tools may be recommended for the surgical procedure selected via the user-interface element. Such a recommendation (e.g., best practices) may be based on a statistical analysis of data at the surgical hub level and/or the cloud-based analytics system level. Such a recommendation may or may not be based on current inventory of the institution.

In yet another aspect of the present disclosure, a modular component and/or surgical tool may be a single-use device rather than a reusable and/or reprocessed device. In such an aspect, packaging associated with the single-use device may include a one-time use activation code. In such an aspect, the one-time use activation code may be entered into an activation input field on a cloud interface via the cloud-access terminal of the surgical hub and transmitted to the cloud-based analytics system. Here, upon receipt, the cloud-based analytics system may cross-check the one-time use activation code with a database of one-time use activation codes (e.g., downloaded from a manufacturer) to authorize use with the system. If the one-time use activation code matches an unused activation code, the modular component and/or surgical tool is authorized. However, if the one-time use activation code does not match an activation code in the database or the one-time use activation code matches an already used activation code, that one-time use activation code may be placed on a black-list such that the single-use modular component and/or surgical tool is not authorized (e.g., critical system-defined constraint).

Robotic Systems

Aspects of the present disclosure also include detailed description of various robotic surgical devices and systems that are configured to interface with a Hub system, which may ultimately be interconnected to the cloud-based medical analytics system. The combination of multiple Hub systems, each communicatively coupled to a robotic surgical system, with the Hub systems communicatively coupled to the cloud-based medical analytics system, forms a comprehensive digital medical system that is capable of servicing a great number of patients while providing improved care and insights through the aggregation and analysis of data provided by each of the multiple Hub systems and respectively coupled robotic surgical systems. Described below are examples of structures and functions of various robotic surgical devices and systems configured to integrate with this comprehensive digital medical system.

Robotic surgical systems can be used in minimally invasive medical procedures. During such medical procedures, a patient can be placed on a platform adjacent to a robotic surgical system, and a surgeon can be positioned at a console that is remote from the platform and/or from the robot. For example, the surgeon can be positioned outside the sterile field that surrounds the surgical site. The surgeon provides input to a user interface via an input device at the console to manipulate a surgical tool coupled to an arm of the robotic system. The input device can be a mechanical input devices such as control handles or joysticks, for example, or contactless input devices such as optical gesture sensors, for example.

The robotic surgical system can include a robot tower supporting one or more robotic arms. At least one surgical tool (e.g. an end effector and/or endoscope) can be mounted to the robotic arm. The surgical tool(s) can be configured to articulate relative to the respective robotic arm via an articulating wrist assembly and/or to translate relative to the robotic arm via a linear slide mechanism, for example. During the surgical procedure, the surgical tool can be inserted into a small incision in a patient via a cannula or trocar, for example, or into a natural orifice of the patient to position the distal end of the surgical tool at the surgical site within the body of the patient. Additionally or alternatively, the robotic surgical system can be employed in an open surgical procedure in certain instances.

A schematic of a robotic surgical system 15000 is depicted in FIG. 205. The robotic surgical system 15000 includes a central control unit 15002, a surgeon's console 15012, a robot 15022 including one or more robotic arms 15024, and a primary display 15040 operably coupled to the control unit 15002. The surgeon's console 15012 includes a display 15014 and at least one manual input device 15016 (e.g., switches, buttons, touch screens, joysticks, gimbals, etc.) that allow the surgeon to telemanipulate the robotic arms 15024 of the robot 15022. The reader will appreciate that additional and alternative input devices can be employed.

The central control unit 15002 includes a processor 15004 operably coupled to a memory 15006. The processor 15004 includes a plurality of inputs and outputs for interfacing with the components of the robotic surgical system 15000. The processor 15004 can be configured to receive input signals and/or generate output signals to control one or more of the various components (e.g., one or more motors, sensors, and/or displays) of the robotic surgical system 15000. The output signals can include, and/or can be based upon, algorithmic instructions which may be pre-programmed and/or input by the surgeon or another clinician. The processor 15004 can be configured to accept a plurality of inputs from a user, such as the surgeon at the console 15012, and/or may interface with a remote system. The memory 15006 can be directly and/or indirectly coupled to the processor 15004 to store instructions and/or databases.

The robot 15022 includes one or more robotic arms 15024. Each robotic arm 15024 includes one or more motors 15026 and each motor 15026 is coupled to one or more motor drivers 15028. For example, the motors 15026, which can be assigned to different drivers and/or mechanisms, can be housed in a carriage assembly or housing. In certain instances, a transmission intermediate a motor 15026 and one or more drivers 15028 can permit coupling and decoupling of the motor 15026 to one or more drivers 15028. The drivers 15028 can be configured to implement one or more surgical functions. For example, one or more drivers 15028 can be tasked with moving a robotic arm 15024 by rotating the robotic arm 15024 and/or a linkage and/or joint thereof. Additionally, one or more drivers 15028 can be coupled to a surgical tool 15030 and can implement articulating, rotating, clamping, sealing, stapling, energizing, firing, cutting, and/or opening, for example. In certain instances, the surgical tools 15030 can be interchangeable and/or replaceable. Examples of robotic surgical systems and surgical tools are further described herein.

The reader will readily appreciate that the computer-implemented interactive surgical system 100 (FIG. 1) and the computer-implemented interactive surgical system 200 (FIG. 9) can incorporate the robotic surgical system 15000. Additionally or alternatively, the robotic surgical system 15000 can include various features and/or components of the computer-implemented interactive surgical systems 100 and 200.

In one exemplification, the robotic surgical system 15000 can encompass the robotic system 110 (FIG. 2), which includes the surgeon's console 118, the surgical robot 120, and the robotic hub 122. Additionally or alternatively, the robotic surgical system 15000 can communicate with another hub, such as the surgical hub 106, for example. In one instance, the robotic surgical system 15000 can be incorporated into a surgical system, such as the computer-implemented interactive surgical system 100 (FIG. 1) or the computer-implemented interactive surgical system 200 (FIG. 9), for example. In such instances, the robotic surgical system 15000 may interact with the cloud 104 or the cloud 204, respectively, and the surgical hub 106 or the surgical hub 206, respectively. In certain instances, a robotic hub or a surgical hub can include the central control unit 15002 and/or the central control unit 15002 can communicate with a cloud. In other instances, a surgical hub can embody a discrete unit that is separate from the central control unit 15002 and which can communicate with the central control unit 15002.

Another surgical robotic system is the da Vinci® surgical robotic system by Intuitive Surgical, Inc. of Sunnyvale, Calif. An example of a system is depicted in FIGS. 206-212. FIG. 206 depicts a minimally invasive robotic surgical (MIRS) system 12010 typically used for performing a minimally invasive diagnostic or surgical procedure on a patient 12012 who is lying down on an operating table 12014. The system 12010 includes a surgeon's console 12016 for use by a surgeon 12018 during the procedure. One or more assistants 12020 may also participate in the procedure. The MIRS system 12010 can further include a patient side cart 12022, i.e. a surgical robot, and an electronics cart 12024. The surgical robot 12022 can manipulate at least one removably coupled tool assembly 12026 (hereinafter referred to as a "tool") through a minimally invasive incision in the body of the patient 12012 while the surgeon 12018 views the surgical site through the console 12016. An image of the surgical site can be obtained by an imaging device such as a stereoscopic endoscope 12028, which can be manipulated by the surgical robot 12022 to orient the endoscope 12028. Various alterative imaging devices are further described herein.

The electronics cart 12024 can be used to process the images of the surgical site for subsequent display to the surgeon 12018 through the surgeon's console 12016. The number of robotic tools 12026 used at one time will generally depend on the diagnostic or surgical procedure and the space constraints within the operating room among other factors. If it is necessary to change one or more of the robotic tools 12026 being used during a procedure, an assistant 12020 may remove the robotic tool 12026 from the surgical robot 12022, and replace it with another tool 12026 from a tray 12030 in the operating room.

Referring primarily to FIG. 207, the surgeon's console 12016 includes a left eye display 12032 and a right eye display 12034 for presenting the surgeon 12018 with a coordinated stereo view of the surgical site that enables depth perception. The console 12016 further includes one or more input control devices 12036, which in turn cause the surgical robot 12022 (FIG. 206) to manipulate one or more tools 12026 (FIG. 206). The input control devices 12036 can provide the same degrees of freedom as their associated tools 12026 (FIG. 206) to provide the surgeon with telepresence, or the perception that the input control devices 12036 are integral with the robotic tools 12026 so that the surgeon has a strong sense of directly controlling the robotic tools 12026. To this end, position, force, and tactile feedback sensors may be employed to transmit position, force, and tactile sensations from the robotic tools 12026 back to the surgeon's hands through the input control devices 12036. The surgeon's console 12016 is usually located in the same room as the patient 12012 so that the surgeon 12018 may directly monitor the procedure, be physically present if necessary, and speak to an assistant 12020 directly rather than over the telephone or other communication medium. However, the surgeon 12018 can be located in a different room, a completely different building, or other remote location from the patient 12012 allowing for remote surgical procedures. A sterile field can be defined around the surgical site. In various instances, the surgeon 12018 can be positioned outside the sterile field. A sterile adapter can define a portion of the boundary of the sterile field. An example of a sterile adapter for a robotic arm is described in U.S. Patent Application Publication No. 2015/0257842, filed Mar. 17, 2015, titled BACKUP LATCH RELEASE FOR SURGICAL INSTRUMENT, which issued on Dec. 12, 2017 as U.S. Pat. No. 9,839,487, which is herein incorporated by reference in its entirety.

Referring primarily now to FIG. 208, the electronics cart 12024 can be coupled with the endoscope 12028 and can include a processor to process captured images for subsequent display, such as to a surgeon on the surgeon's console, or on another suitable display located locally and/or remotely. For example, where the stereoscopic endoscope 12028 is used, the electronics cart 12024 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations, for example.

FIG. 209 diagrammatically illustrates a robotic surgery system 12050, such as the MIRS system 12010 of FIG. 206. As discussed herein, a surgeon's console 12052, such as the surgeon's console 12016 in FIG. 206, can be used by a surgeon to control a surgical robot 12054, such as the surgical robot 12022 in FIG. 206, during a minimally invasive procedure. The surgical robot 12054 can use an imaging device, such as a stereoscopic endoscope, to capture images of the procedure site and output the captured images to an electronics cart 12056, such as the electronics cart 12024 in FIG. 206. As discussed herein, the electronics cart 12056 can process the captured images in a variety of ways prior to any subsequent display. For example, the electronics cart 12056 can overlay the captured images with a virtual control interface prior to displaying the combined images to the surgeon via the surgeon's console 12052. The surgical robot 12054 can output the captured images for processing outside the electronics cart 12056. For example, the surgical robot 12054 can output the captured images to a processor 12058, which can be used to process the captured images. The images can also be processed by a combination of the electronics cart 12056 and the processor 12058, which can be coupled together to process the captured images jointly, sequentially, and/or combinations thereof. One or more separate displays 12060 can also be coupled with the processor 12058 and/or the electronics cart 12056 for local and/or remote display of images, such as images of the procedure site, or other related images.

FIGS. 210 and 211 show the surgical robot 12022 and a robotic tool 12062, respectively. The robotic tool 12062 is an example of the robotic tools 12026 (FIG. 206). The reader will appreciate that alternative robotic tools can be employed with the surgical robot 12022 and exemplary robotic tools are described herein. The surgical robot 12022 shown provides for the manipulation of three robotic tools 12026 and the imaging device 12028, such as a stereoscopic endoscope used for the capture of images of the site of the procedure. Manipulation is provided by robotic mechanisms having a number of robotic joints. The imaging device 12028 and the robotic tools 12026 can be positioned and manipulated through incisions in the patient so that a kinematic remote center or virtual pivot is maintained at the incision to minimize the size of the incision. Images of the surgical site can include images of the distal ends of the robotic tools 12026 when they are positioned within the field-of-view (FOV) of the imaging device 12028. Each tool 12026 is detachable from and carried by a respective surgical manipulator 12031, which is located at the distal end of one or more of the robotic joints. The surgical manipulator 12031 provides a moveable platform for moving the entirety of a tool 12026 with respect to the surgical robot 12022, via movement of the robotic joints. The surgical manipulator 12031 also provides power to operate the robotic tool 12026 using one or more mechanical and/or electrical interfaces.

FIG. 212 is a schematic of a telesurgically-controlled surgical system 12100. The surgical system 12100 includes a surgeon console 12102, which for example can be the surgeon's console 12052 (FIG. 209). The surgeon console 12102 drives a surgical robot 12104, which for example can be the surgical robot 12022 (FIG. 206). The surgical robot 12104 includes a surgical manipulator 12106, which for example can be the surgical manipulator 12031 (FIG. 210). The surgical manipulator 12106 includes a motor unit 12108 and a robotic tool 12110. The motor unit 12108 is a carriage assembly that holds five motors, which can be assigned to different mechanisms. In some exemplifications only five motors are used, while in other exemplifications more or less than five motors can be used. The motor unit 12108 includes a power motor 12112, a camshaft motor 12140, a pitch motor 12116, a yaw motor 12118, and low-force grip motor 12120, although these motors can be used for different purposes depending on the attached instrument. Generally, each motor is an electric motor that mechanically and electrically couples with corresponding inputs of the robotic tool 12110. In some exemplifications, the motor unit 12108 may be located at a proximal end of the robotic tool 12110 in a shared chassis with the robotic tool, as generally depicted by the proximal housing shown in FIG. 211. A motor housing is further described in U.S. Patent Application Publication No. 2012/0150192, filed Nov. 15, 2011, titled METHOD FOR PASSIVELY DECOUPLING TORQUE APPLIED BY A REMOTE ACTUATOR INTO AN INDEPENDENTLY ROTATING MEMBER, which issued on Aug. 4, 2015 as U.S. Pat. No. 9,095,362, which is herein incorporated by reference in its entirety.

The robotic tool 12110 for example, can be the robotic tool 12026 (FIG. 206) described herein. The robotic tool 12110 includes an elongated effector unit 12122 that includes three discrete inputs that each mechanically couple with the pitch motor 12116, the yaw motor 12118, and the low-force grip motor 12120, respectively, by way of the surgical manipulator 12106. The robotic tool 12110 also includes a transmission 12124, which mechanically couples with the power motor 12112 and the camshaft motor 12140. Examples of tools are further described in International Patent Application Publication No. WO 2015/153642, filed Mar. 31, 2015, titled SURGICAL INSTRUMENT WITH SHIFTABLE TRANSMISSION, and in International Patent Application Publication No. WO 2015/153636, filed Mar. 31, 2015, titled CONTROL INPUT ACCURACY FOR TELEOPERATED SURGICAL INSTRUMENT, each of which is herein incorporated by reference in its entirety.

A surgical end effector 12126 is located at the distal end of the effector unit 12122. The surgical end effector 12126 and effector unit 12122 are connected by way of a moveable wrist. An example of such a wrist is shown at U.S. Patent Application Publication No. 2011/0118708, filed Nov. 12, 2010, titled DOUBLE UNIVERSAL JOINT, and in U.S. Pat. No. 9,216,062, filed Feb. 15, 2012, titled SEALS AND SEALING METHODS FOR A SURGICAL INSTRUMENT HAVING AN ARTICULATED END EFFECTOR ACTUATED BY A DRIVE SHAFT, each of which is herein incorporated by reference in its entirety. In simplistic terms, the surgical end effector can be characterized by a plurality of discrete but interrelated mechanisms, with each mechanism providing a degree of freedom (DOF) for the surgical end effector 12126. As used herein with respect to surgical system 12100, a DOF is one or more interrelated mechanisms for affecting a corresponding movement. The DOFs endow the surgical end effector 12126 with different modes of operation that can operate concurrently or discretely. For example, the wrist enables the surgical end effector 12126 to pitch and yaw with respect to the surgical manipulator 12106, and accordingly includes a pitch DOF 12128 and a yaw DOF 12130. The surgical end effector 12126 also includes a roll DOF 12132 rotating surgical end effector 12126 about an elongated axis. Different robotic tool can have different DOFs, as further described herein.

The surgical end effector 12126 may include a clamping and cutting mechanism, such as a surgical stapler. An example of such an instrument, including a staple cartridge therefor, is further described in U.S. Patent Application Publication No. 2013/0105552, filed Oct. 26, 2012, titled CARTRIDGE STATUS AND PRESENCE DETECTION, and U.S. Patent Application Publication No. 2013/0105545, filed Oct. 26, 2012, titled SURGICAL INSTRUMENT WITH INTEGRAL KNIFE BLADE, both of which are incorporated by reference herein in their respective entireties. A clamping mechanism can grip according to two modes, and accordingly include two DOFs. A low-force DOF 12134 (e.g., a cable actuated mechanism) operates to toggle the clamp with low force to gently manipulate tissue. The low-force DOF 12134 is useful for staging the surgical end effector for a cutting or stapling operation. A high-force DOF 12136 (e.g., a lead screw actuated mechanism) operates to further open the clamp or close the clamp onto tissue with relatively high force, for example, to tourniquet tissue in preparation for a cutting or stapling operation. Once clamped, the surgical end effector 12126 employs a tool actuation DOF 12138 to further affect the tissue, for example, to affect tissue by a stapling, cutting, and/or cauterizing device. Clamping systems for a surgical end effector are further described in U.S. Pat. No. 9,393,017, filed May 15, 2012, titled METHODS AND SYSTEMS FOR DETECTING STAPLE CARTRIDGE MISFIRE OR FAILURE, which issued on Jul. 19, 2016, U.S. Pat. No. 8,989,903, filed Jan. 13, 2012, titled METHODS AND SYSTEMS FOR INDICATING A CLAMPING PREDICTION, which issued on Mar. 2, 2015, and U.S. Pat. No. 9,662,177, filed Mar. 2, 2015, titled METHODS AND SYSTEMS FOR INDICATING A CLAMPING PREDICTION, which issued on May 30, 2017, all of which are incorporated by reference herein in their respective entireties.

As shown in FIG. 212, the pitch motor 12116, the yaw motor 12118, and the low-force grip motor 12120 drive the pitch DOF 12128, the yaw DOF 12130, and the low-force grip DOF 12134, respectively. Accordingly, each of the pitch DOF 12128, the yaw DOF 12130, and the low force grip DOF 12134 is discretely paired with a motor, and can operate independently and concurrently with respect to other DOFs. However, the high force grip DOF 12136, the roll DOF 12132, and the tool actuation DOF 12138 share a single input with the power motor 12112, via the transmission 12124. Accordingly, only one of the high-force grip DOF 12136, the roll DOF 12132, and the tool actuation DOF 12138 can operate at one time, since coupling with the power motor 12112 occurs discretely. The camshaft motor 12140 is actuated to shift output of the power motor 12112 between the high force grip DOF 12136, the roll DOF 12132, and the tool actuation DOF 12138. Accordingly, the transmission 12124 advantageously allows a greater amount of DOFs than an arrangement where each motor is dedicated to a single DOF.

Additional features and operations of a surgical robotic system, such as the robotic surgical system of FIGS. 206-212, are further described in the following references, which are herein incorporated by reference in their respective entireties:

U.S. Patent Application Publication No. 2011/0118708, filed Nov. 12, 2010, titled DOUBLE UNIVERSAL JOINT;

U.S. Pat. No. 9,095,362, filed Nov. 15, 2011, titled METHOD FOR PASSIVELY DECOUPLING TORQUE APPLIED BY A REMOTE ACTUATOR INTO AN INDEPENDENTLY ROTATING MEMBER, which issued on Aug. 4, 2015;

U.S. Pat. No. 8,989,903, filed Jan. 13, 2012, titled METHODS AND SYSTEMS FOR INDICATING A CLAMPING PREDICTION, which issued on Mar. 24, 2015;

U.S. Pat. No. 9,216,062, filed Feb. 15, 2012, titled SEALS AND SEALING METHODS FOR A SURGICAL INSTRUMENT HAVING AN ARTICULATED END EFFECTOR ACTUATED BY A DRIVE SHAFT, which issued on Dec. 22, 2015;

U.S. Pat. No. 9,393,017, filed May 15, 2012, titled METHODS AND SYSTEMS FOR DETECTING STAPLE CARTRIDGE MISFIRE OR FAILURE, which issued on Jul. 19, 2016;

U.S. Patent Application Publication No. 2013/0105552, filed Oct. 26, 2012, titled CARTRIDGE STATUS AND PRESENCE DETECTION;

U.S. Patent Application Publication No. 2013/0105545, filed Oct. 26, 2012, titled SURGICAL INSTRUMENT WITH INTEGRAL KNIFE BLADE;

International Patent Application Publication No. WO 2015/142814, filed Mar. 17, 2015, titled SURGICAL CANNULA MOUNTS AND RELATED SYSTEMS AND METHODS;

U.S. Patent Application Publication No. 2015/0257842, filed Mar. 17, 2015, titled BACKUP LATCH RELEASE FOR SURGICAL INSTRUMENT, which issued on Dec. 12, 2017 as U.S. Pat. No. 9,839,487;

U.S. Patent Application Publication No. 2015/0257841, filed Mar. 17, 2015, titled LATCH RELEASE FOR SURGICAL INSTRUMENT;

International Patent Application Publication No. WO 2015/153642, filed Mar. 31, 2015, titled SURGICAL INSTRUMENT WITH SHIFTABLE TRANSMISSION;

International Patent Application Publication No. WO 2015/153636, filed Mar. 31, 2015, titled CONTROL INPUT ACCURACY FOR TELEOPERATED SURGICAL INSTRUMENT; and U.S. Pat. No. 9,662,177, filed Mar. 2, 2015, titled METHODS AND SYSTEMS FOR INDICATING A CLAMPING PREDICTION, which issued on May 30, 2017.

The robotic surgical systems and features disclosed herein can be employed with the da Vinci® surgical robotic system referenced herein and/or the system of FIGS. 206-212. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, the robotic hub 222, and/or the robotic surgical system 15000, for example.

In various instances, a robotic surgical system can include a robotic control tower, which can house the control unit of the system. For example, the processor 12058 (FIG. 209) can be housed within a robotic control tower. The robotic control tower can comprise a robot hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, a suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices based on the synthesized data. In various instances, a sensor system encompassing a plurality of sensors distributed throughout the robotic system can provide data, images, and/or other information to the situational awareness module. Such a situational awareness module can be accessible to the processor 12058, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and in U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

Surgical systems including a robot, a visualization system (such as the visualization system 108 or the visualization system 208), and one or more hubs (such as the hub 106, the robotic hub 122, the hub 206, and/or the robotic hub 222) can benefit from robust communication systems for data collection and dissemination. For example, various parameters regarding the surgical site, the surgical instrument(s), and/or the surgical procedure can be important information to the robot, the visualization system, and the hub(s). Moreover, the robot can include one or more subassemblies, such as a control console, which may require information regarding the surgical site, the surgical instrument(s), and/or the surgical procedure, for example. It can be helpful to collect and disseminate the information to the appropriate assemblies and/or subassemblies in real-time or near real-time to inform the machine learning and/or decision-making process, for example. In certain instances, data collection and dissemination can inform the situational awareness of a surgical system that includes one or more robotic systems.

In one aspect, a robotic surgical system can include additional communication paths. For example, a robotic surgical system can include a primary wired communication path and a secondary wireless communication path. In certain instances, the two communication paths can be independent such that a secondary path is redundant and/or parallel to a primary path. In various instances, a first type and/or amount of data can be transferred along the primary path and a second type and/or amount of data can be transferred along the secondary path. The multiple communication paths can improve connectivity of the robot and/or the robotic surgical tools to one or more displays within the surgical theater, a control console, and/or control unit. The communication paths can connect a surgical robot to a central control unit (e.g. a hub) and/or a visualization system (e.g. a display), for example. In various instances, the additional communication paths can provide additional data to the robot and/or to a generator module and/or a processor in communication with the generator module.

Referring primarily to FIG. 213, a robotic surgical system 12200 including a console 12216 and a robot 12222 is depicted. The console 12216 can be similar in many respects to the console 12016 (FIGS. 206 and 207), and the robot 12222 can be similar in many respects to the robot 12022 (FIGS. 206 and 210). A robotic tool 12226, which can be similar in many respects to the robotic tool 12026 (FIG. 206), for example, is positioned at the distal end of one of the arms of the robot 12222. The robotic tool 12226 is an energy device. For example, energy can be supplied to the robotic tool 12226 by a generator that is coupled to the robotic tool 12226.

The robotic surgical system 12200 also includes a hub 12224, which can be similar in many respects to the robotic hub 122 (FIG. 2) and/or the robotic hub 222 (FIG. 9). The hub 12224 includes a generator module 12230, which is similar in many respects to the generator module 140 (FIG. 3), and a wireless communication module 12238, which is similar in many respects to the communication module 130

(FIG. 3). The generator module 12230 is configured to supply energy to the robotic tool 12226 via a first wired connection 12244.

In one instance, the first wired connection 12244 can be a two-way communication path between the robotic tool 12226 and the surgical hub 12224. The first wired connection 12244 can convey advanced energy parameters or other electrical data between the robotic tool 12226 and the surgical hub 12224. For example, the surgical hub 12224 can provide information to the robotic tool 12226 regarding the power level (e.g. current for an RF device and amplitude and/or frequency for an ultrasonic device) supplied thereto. Additionally, the robotic tool 12226 can provide information to the robot 12222 regarding the detected conductivity and/or impendence at the tissue interface, corresponding to a property of the tissue and/or the effectiveness of the energy device.

Additionally, a second wired connection 12240 between the console 12216 and the robotic tool 12226 mounted to the robot 12222 provides a communication path for control signals from the robot console 12216 to the robotic tool 12226. In one instance, the second wired connection 12240 can be a one-way communication path from the robot 12222 to the console 12216 with respect to control parameters or other mechanical data collected by the robot 12222 and/or the robotic tool 12226. For example, the robot 12222 can provide information to the console 12216 about a surgical actuation of the robotic tool, such as a closing motion and/or a firing motion. More specifically, the robot can communicate force-to-clamp parameters (e.g. clamping pressure by the robotic tool 12226 on tissue) and/or force-to-fire parameters from the robotic tool 12226 to the console 12216, for example.

Referring still to FIG. 213, absent the wireless communication paths 12242 and 12246, the robotic hub 12224 may be unable to communicate with the console 12216 and vice versa. Additionally, the robotic tool 12226 may be unable to communicate with the hub 12224. In instances in which communication paths between the hub 12224 and the robot 12222 and/or the robotic tool 12226 are lacking, the mechanical control parameters (e.g. clamping force) from the robotic tool 12226 may not be communicated to the robotic hub 12224 and the generator module 12230 thereof. Additionally, electrical advanced energy parameters may not be communicated from the robot 12222 to the robotic hub 12224 and/or to the console 12216. In such instances, the system 12200 would comprise open-loop controls.

Different energy parameters and different clamping pressures may be better suited for certain types of tissue and/or certain applications. For example, an ultrasonic weld is generally a function of transducer amplitude and clamping pressure over time. Similarly, an RF weld is generally a function of current and clamping pressure over time. However, without the wireless communication paths 12242 and 12246 mentioned above, the generator module 12230 can be unaware of the clamping pressure. Similarly, the console 12216 can be unaware of the energy parameters.

To optimize the control of the robotic tool 12226, the robotic tool 12226 can convey one or more mechanical control parameters to the robotic hub 12224. Additionally, the hub 12224 can convey one or more advanced energy parameters to the console 12216. The data transfer can provide closed-loop controls for the system 12200. In one instance, the mechanical control parameters and advanced energy parameters can be balanced for different types of tissue and/or particular applications. For example, the clamping pressure can be decreased and the power to the robotic tool 12226 can be increased, or vice versa.

Referring still to FIG. 213, the robotic tool 12226 includes a wireless communication module 12228, as further described herein. The wireless communication module 12228 is in signal communication with the wireless communication module 12238 of the robotic hub 12224 via the wireless communication path 12242. For example, the wireless communication module 12238 can include a first receiver 12232 configured to receive wireless signals from the robotic tool 12226. The wireless communication module 12238 also includes a second receiver 12234, which can receive signals from the console 12216 via the second wireless communication path 12246. In such instances, the first and second wireless communication paths 12242 and 12246, respectively, can complete a communication circuit back to the console 12216 from the robotic tool 12226 via the surgical hub 12224, for example.

In other instances, the wireless communication module 12228 can be on the robot 12222. For example, the wireless communication module 12228 can be positioned on an arm of the robot and/or a tool mounting portion of the robot 12222.

Additionally or alternatively, a wireless communication path can be provided between the robotic tool 12226 and the console 12216.

The wireless paths described herein can provide data transfer without encumbering the mobility of the robotic tool 12226 and/or creating additional opportunities for entanglement or cords and/or wires. In other instances, one or more of the wireless communication paths described herein can be replaced with wired connection(s).

In one aspect, the robotic tool 12226 and/or the hub 12224 can share information regarding sensed tissue parameters (e.g. conductivity or inductance corresponding to a property of the tissue) and/or control algorithms for energizing the tissue (e.g. power levels), which can be based on the sensed tissue parameters. The robotic tool 12226 can provide information regarding the status, the activation state, identification information, and/or smart data to the hub 12224, for example. Data provided to the hub 12224 can be stored, analyzed, and/or further disseminated by the hub 12224 such as to a display screen 12236 thereof. In such instances, the hub 12224 is a conduit or relay post for transmitting the data to additional locations via the wired or wireless connections.

In certain instances, the hub 12224 includes a situational awareness module, as further described herein. The situational awareness module can be configured to determine and/or confirm a step in a surgical procedure and/or suggest a particular surgical action based on information received from various sources, including the robot 12222 and the console 12216. The wireless communication paths 12242 and 12246 linking the hub 12224 to the robot 12222 and the console 12216, respectively, can be configured to inform the situational awareness module. For example, mechanical control parameters regarding clamping and/or firing can be communicated to the hub 12224 and the situational awareness module thereof via the second wireless communication path 12246. Additionally or alternatively, energy parameters regarding activation of the energy tool and/or sensed tissue parameters can be communicated to the hub 12224 and the situational awareness module thereof via the first wireless communication path 12242.

In certain instances, the data wirelessly transmitted to the hub 12224 can inform the situational awareness module thereof. For example, based on sensed tissue parameters detected by the robotic tool 12226 and transmitted along the first wireless communication path 12242, the situational awareness module can determine and/or confirm the type of tissue involved in the surgical procedure and, in certain instances, can suggest a therapeutic response based on the type of tissue encountered.

Referring still to FIG. 213, the second wired connection 12240 from the robot 12222 to the console 12216 provides a first communication path. Moreover, the wired or wireless connection between the robot 12222 and the hub 12224 in combination with the wireless communication path 12246 between the hub 12224 and the console 12216 forms a second, parallel communication path from the robot 12222 to the console 12212. Because the second communication path communicates via the hub 12224 and the wireless communication module 12238 thereof, the second communication path is different than the first communication path. However, such a path provides a parallel and alternative path to the second wired connection 12240 between the robot 12222 and the console 12216. Similarly, parallel and/or redundant paths are also provided via the wireless path 12242 and the wired path 12244 between the robot 12222 and the hub 12224. The alternative parallel communication path(s) can bolster the integrity of the communications systems and enables robot communication between the various components of the surgical system.

Additionally or alternatively, information may be communicated directly to a device or system having wireless capabilities such as a visualization system or display like the visualization system 108 or the visualization system 208, for example. A surgical system 12300 depicted in FIG. 238 includes the console 12216 for a surgeon S, the robot 12222 including the robotic tool 12226 mounted thereto, and the surgical hub 12224. The surgical system 12300 also includes a monitor 12350, which is positioned within the surgical theater. Additional clinicians can be within the surgical theater including a nurse N, a medical assistant MA, and an anesthesiologist A. Certain clinicians can be positioned within the sterile field. For example, the nurse N, who is stationed at a table 12352 supporting a plurality of medical instruments and robotic tools, can be sterile. The medical assistant MA holding the handheld surgical instrument and the anesthesiologist A may be positioned outside the sterile field. The monitor 12350 is viewable by clinicians within the sterile field and outside the sterile field. An additional display 12354 can be positioned within the sterile field. The additional display 12354 can be a mobile computer with wireless, cellular and/or Bluetooth capabilities, for example. In one instance, the additional display 12354 can be a tablet, such as an iPad® tablet, that is positionable on the patient P or patient table 12358. In such instances, the display 12354 is positioned within the sterile field.

The wireless communication module 12228 (FIG. 213) on the robotic tool 12226 can be in signal communication with the monitor 12350 and/or the display 12354. In such instances, data and/or information obtained at the surgical site and/or by the robotic tool 12226 can be directly communicated to a screen within the surgical theater and immediately viewable to various clinicians with the surgical theater, including clinicians within the sterile field or outside the sterile field. In such instances, data can be provided in real time, or near real time, to inform the clinicians' decisions during the surgical procedure. Additionally, certain information can be communicated to the hub 12224 for further storage, analysis and/or dissemination, as further described herein.

Owing to wireless communication paths, the monitor 12350 and/or the display 12354 can also display information from the hub, including energy parameters, in certain instances. For example, the hub 12224 can obtain data indicative of an activation state or activation level of the generator module 12230 (FIG. 213) and/or can receive data indicative of sensed tissue parameters from the robotic tool 12226, as further described herein. In such instances, the activation information and/or tissue information can be displayed on the monitor 12350 and/or the display 12354 such that the information is readily available to operators both within the sterile filed and outside the sterile field.

In one aspect, the hub 12224 can ultimately communicate with a cloud, such as the cloud 104 or the cloud 204, for example, to further inform the machine-learning and decision-making processes related to the advanced energy parameters and/or mechanical control parameters of the robotic tool 12226. For example, a cloud can determine an appropriate surgical action and/or therapeutic response for a particular tissue parameter, surgical procedure, and/or patient demographic based on aggregated data stored therein. To protect patient confidentiality, the hub 12224 can communicate redacted and/or a confidential version of the data, for example.

As described herein with respect to FIG. 213, the robotic tool 12226 includes the wireless communication module 12228. The wireless communication module 12228 is also shown in FIG. 214. Specifically, a proximal portion of the robotic tool 12226 including the wireless communication module 12228 is depicted in FIG. 214, as well as a tool mounting portion, or attachment portion, 12250 of the robot 12222 for releasably attaching the proximal housing of the robotic tool 12226. A detailed view of a mechanical and electrical interface between the robotic tool 12226 and the tool mounting portion 12250 is depicted in FIG. 215.

The robotic tool 12226 includes a first drive interface 12252 that drivingly couples with a second drive interface 12254 on the tool mounting portion 12250. The tool mounting portion 12250 includes a carriage or motor housing that houses a plurality of motors, which can be similar in many respects to the motors 12112, 12116, 12118, 12120, and 12140 (FIG. 212), for example. The motors are driving coupled to rotary outputs 12256 at the second drive interface 12254 that engage rotary inputs 12258 on the robotic tool 12226. For example, the rotary inputs 12258 are positioned and structured to mechanically mate with the rotary outputs 12256 on the tool mounting portion 12250.

A plug 12260 for supplying power to the motors is shown in FIG. 214. The plug 12260 is also coupled to the wireless communication module 12228. In such instances, the wireless communication module 12228 can be powered via a current supplied by the plug 12260. The plug 12260 can ultimately be wired to the generator module 12230 in the hub 12224 to complete the wired connection 12244 between the robotic tool 12226 and the hub 12224 (see FIG. 213).

Referring primarily now to FIG. 214, the tool mounting portion 12250 also includes electrical contacts 12262, and the robotic tool 12226 includes electrical contacts 12264 positioned and structured to mate with the electrical contacts 12262 on the tool mounting portion 12250. Electrical signals can be communicated between the robotic tool 12226 and the robot 12222 (FIG. 213) via the mating electrical contacts 12262, 12264. In certain instances, mechanical control parameters from the robotic tool 12262 can be communicated to the robot 12222 via the electrical contacts 12262, 12264, as further described herein. Additionally or alternatively, advanced energy parameters can be communicated to the robot 12222 and/or to the robotic tool 12226 via the mating electrical contacts 12262, 12264, or vice versa, as further described herein.

As depicted in FIG. 215, when the robotic tool 12226 is mounted to the tool mounting portion 12250, a flex circuit 12270 is positioned intermediate the mating electrical contacts 12264 of the robotic tool 12226 and the electrical contacts 12262 of the tool mounting portion 12250 to facilitate data transmission. The flex circuit 12270 is positioned to intercept communication signals between the robotic tool 12262 and the tool mounting portion 12250. In such instances, the flex circuit 12270 is configured to capture signals passing between those contacts 12262, 12264. In certain instances, the flex circuit 12270 can provide intelligence features to the robotic tool 12226.

In various instances, the flex circuit 12270 can include a feedback pigtail connector. The pigtail connector can intercept the connection between the robotic tool 12226 and the tool mounting portion 12250.

In various instances, the flex circuit 12270 of FIG. 214 can also include a wireless transmitter that is configured to communicate with the hub 12224 (FIG. 213) via the wireless communication path 12242. In other instances, the flex circuit 12270 can be coupled to a wireless communication module like the module 12228 in FIGS. 213 and 214, which can include a wireless transmitter and/or a wireless receiver.

The flex circuit 12270 occupies a small footprint between the tool mounting portion 12250 and the robotic tool 12226. In one aspect, existing robotic systems can be retrofit with such flex circuits. In other words, existing robotic tools and tool mounting portion can utilize the robust communication systems described herein without modifying the current robotic tools and/or tool mounting portions.

In various instances, the flex circuit 12270, or another intermediate pigtail connector, can be configured to acquire one or more signals between an external controller (e.g., an energy generator of a generator module 140 in a hub 106 (FIG. 3)) and the robotic tool 12226. Moreover, such a circuit or connector can be used to deliver signals to the robotic tool 12226 via the intercepting connections.

In one aspect, the robotic hub includes a processor and a memory communicatively coupled to the processor, as described herein. The memory stores instructions executable by the processor to relay a wireless signal between a robot and a control console, as described herein. In certain instances, the memory stores instructions executable by the processor to adjust a control parameter of the generator (e.g. power level) based on signals intercepted by a flex circuit and/or transmitted along a wireless communication path. Additionally or alternatively, the memory stores instructions executable by the processor to adjust a control parameter of the energy tool (e.g. clamping pressure) based on signals indicative of a tissue property intercepted by the flex circuit and/or transmitted along the wireless communication path.

In various aspects, the present disclosure provides a control circuit to relay a wireless signal between a robot and a control console, adjust a control parameter of the generator, and/or adjust a control parameter of an energy tool, as described herein. In various aspects, the present disclosure provides a non-transitory computer readable medium storing computer readable instructions which, when executed, cause a machine to relay a wireless signal between a robot and a control console, adjust a control parameter of the generator, and/or adjust a control parameter of an energy tool, as described herein.

In one aspect, one or more features and/or effects of a robotically-controlled surgical tool and end effector thereof can be controlled by a control algorithm. For example, the intensity of an end effector effect can be controlled by a control algorithm stored in the memory of the robot and executable by a processor. In one instance, an end effector effect can be smoke evacuation, insufflation, and/or cooling. In another instance, an end effector effect can be articulation and/or retraction. As an example, a robot can implement a load control holding algorithm for articulation of a robotic tool that results in a predefined lateral load on tissue and is limited by a displacement limit, as further described herein.

In certain instances, it can be desirable to incorporate a pump into a robotically-controlled surgical tool, such as an energy tool including an RF electrode and/or an ultrasonic blade, for example. A pump can provide insufflation gases or air to a surgical site. In certain instances, a pump can provide coolant to a surgical site and/or can extract smoke and/or steam from the surgical site.

Robotically-controlled surgical tools include a drive system for releasably engaging with a robot and transferring drive motions from the robot to the robotic tool. For example, a robotically-controlled surgical tool can include an interface including rotary driver(s) configured to receive rotary inputs from motor(s) in a motor housing or tool mounting portion. Exemplary drive systems and interfaces therefor are further described herein.

The rotary drivers in the robotic tools are configured to actuate various surgical functions such as rotation of a shaft, closure of end effector jaws, and articulation of the end effector, for example. Examples of interface configurations are further described herein and in International Patent Application Publication No. WO 2015/153642, filed Mar. 31, 2015, titled SURGICAL INSTRUMENT WITH SHIFTABLE TRANSMISSION, in International Patent Application Publication No. WO 2015/153636, filed Mar. 31, 2015, titled CONTROL INPUT ACCURACY FOR TELEOPERATED SURGICAL INSTRUMENT, and in U.S. Pat. No. 9,095,362, filed Nov. 15, 2011, titled METHOD FOR PASSIVELY DECOUPLING TORQUE APPLIED BY A REMOTE ACTUATOR INTO AN INDEPENDENTLY ROTATING MEMBER, each of which is herein incorporated by reference in its entirety.

In certain instances, the number of motors, the number of rotary drivers, and/or the arrangements of motors and/or rotary drivers can be limited or constrained by the footprint of the drive system and/or coupling between the robotic tool and the tool mounting portion. In one aspect, it can be desirable for new and/or improved robotically-controlled surgical tools to be compatible with existing robotic platforms. For example, without enlarging the motor housing or tool mounting portion, it can be desirable to change the functionality and/or add functionality to robotic tools for use with an existing motor housing and tool mounting portion. In such instances, it can be challenging to incorporate certain features, like a pump for example, into a robotic tool compatible with an existing surgical robot. Moreover, it can be desirable to include controls and/or control algorithms for such a pump within the existing architecture of the surgical robot.

In one aspect, a pump for a robotic tool can be powered by a rotary drive of the robotic tool interface. The rotary drive and, thus, the pump can be driven at a variable rate, which can depend on the needs of the robotic tool and/or the surgical procedure. For example, the speed of the rotary drive coupled to the pump can be related to the volume of smoke being evacuated from the surgical site and/or the application of energy to tissue by the robotic tool. In one instance, the robotic tool can be an intelligent tool that includes a processor configured to determine the appropriate rate for the pump based on sensors on the robotic tool and/or other inputs thereto. In other instances, a processor in the control unit of the robot can be configured to determine the appropriate rate for the pump based on sensors on the robot and/or modules thereof, such as a smoke evacuation module in a robotic hub, for example.

Energy devices utilize energy to affect tissue. In an energy device, the energy is supplied by a generator. Energy devices include devices with tissue-contacting electrodes, such as an electrosurgical device having one or more radio frequency (RF) electrodes, and devices with vibrating surfaces, such as an ultrasonic device having an ultrasonic blade. For an electrosurgical device, a generator is configured to generate oscillating electric currents to energize the electrodes. For an ultrasonic device, a generator is configured to generate ultrasonic vibrations to energize the ultrasonic blade.

As provided herein, energy devices deliver mechanical or electrical energy to a target tissue in order to treat the tissue (e.g. to cut the tissue and/or cauterize blood vessels within and/or near the target tissue). The cutting and/or cauterization of tissue can result in fluids and/or particulates being released into the air. Such fluids and/or particulates emitted during a surgical procedure can constitute smoke, for example, which can include carbon and/or other particles suspended in air.

In various instances, an energy tool for use with a robotic system can include a suction port coupled to a pump that is powered by a motor on the tool driver. For example, an energy tool for the da Vinci® surgical robotic system can include a suction port coupled to a pump that is powered by a motor on the tool driver. The pump can be configured to extract smoke from a surgical site via the suction port. In such instances, the energy tool can include a smoke evacuation system. In one aspect, the robotic tool can include a pump. Alternatively, the robotic tool can be coupled to a pump.

The reader will appreciate that such an evacuation system can be referred to as a "smoke evacuation system" though such an evacuation system can be configured to evacuate more than just smoke from a surgical site. Throughout the present disclosure, the "smoke" evacuated by an evacuation system is not limited to just smoke. Rather, the evacuation systems disclosed herein can be used to evacuate a variety of fluids, including liquids, gases, vapors, smoke, steam, or combinations thereon. The fluids can be biologic in origin and/or can be introduced to the surgical site from an external source during a procedure. The fluids can include water, saline, lymph, blood, exudate, and/or pyogenic discharge, for example. Moreover, the fluids can include particulates or other matter (e.g. cellular matter or debris) that is evacuated by the evacuation system. For example, such particulates can be suspended in the fluid.

Referring primarily to FIGS. 216-218, a robotic tool 12426 for use with a robotic surgical system is depicted. The robotic tool 12426 can be employed with the robotic surgical system 12010 (FIG. 206), for example. The robotic tool 12426 is a bipolar radio-frequency (RF) robotic tool. For example, the tool can be similar in many respects to the tool disclosed in U.S. Pat. No. 8,771,270, filed on Jul. 16, 2008, titled BIPOLAR CAUTERY INSTRUMENT, which is herein incorporated by reference in its entirety.

In other instances, the robotic tool 12426 can be a monopolar RF tool, an ultrasonic tool, or a combination ultrasonic-RF tool. For example, the robotic tool 12426 can be similar in many similar to the tool disclosed in U.S. Pat. No. 9,314,308, filed Mar. 13, 2013, titled ROBOTIC ULTRASONIC SURGICAL DEVICE WITH ARTICULATING END EFFECTOR, which is herein incorporated by reference in its entirety.

The robotic tool 12426 includes a proximal housing 12437, a shaft 12438 extending from the proximal housing 12437, and an end effector 12428 extending from a distal end of the shaft 12438. Referring primarily to FIG. 217, the end effector 12428 includes opposing jaws 12430*a*, 12430*b*. Each jaw 12430*a*, 12430*b* includes a tissue-contacting surface including an electrode. For example, the jaw 12430*a* can include a supply electrode, and the jaw 12430*b* can include a return electrode, or vice versa. The end effector 12428 is shown in a clamped configuration and generating an RF weld in FIG. 217. In such instances, smoke S from the RF weld may accumulate around the end effector 12428. For example, the smoke S can accumulate in the abdomen of a patient in certain instances.

The robotic tool 12426 also includes an evacuation system 12436. For example, to improve visibility and efficiency of the robotic tool 12426, the smoke S at the surgical site can be evacuated along an evacuation channel, or suction conduit, 12440 extending proximally from the end effector 12428. The evacuation channel 12440 can extend through the shaft 12438 of the robotic tool 12426 to the proximal housing 12437. The evacuation conduit 12440 terminates at a suction port 12442 adjacent to the end effector 12428. During operating of the evacuation system 12436, smoke S at the surgical site is drawn into the suction port 12442 and through the evacuation conduit 12440.

In various instances, the robotic tool 12426 can include insufflation, cooling, and/or irrigation capabilities, as well. For example, the evacuation system 12436 can be configured to selectively pump a fluid, such as saline or $CO_2$ for example, toward the end effector 12428 and into the surgical site.

In various instances, the evacuation channel 12440 can be coupled to a pump for drawing the smoke S along the evacuation channel 12440 within the shaft 12438 of the robotic tool 12426. Referring primarily to FIG. 218, the evacuation system 12436 includes a pump 12446. The pump 12446 is housed in the proximal housing 12437 of the robotic tool 12426. The pump 12446 is a lobe pump, which has been incorporated into a drive interface 12448 of the robotic tool 12426. The drive interface 12448 includes rotary drivers 12450, which are driven by rotary outputs from motors in the tool mounting portion of the robot, as described herein (see rotary outputs 12256 (FIG. 214) and rotary outputs 12824*a*-12824*e* (FIG. 222), for example).

Lobe pumps can be low volume and quiet or noiseless and, thus, desirable in certain instances. For example, a lobe pump can ensure the noise generated by the evacuation system 12436 is not distracting to the clinicians and/or allows communication between clinicians in the surgical theater. The reader will readily appreciate that different pumps can be utilized by the evacuation system 12436 in other instances.

A channel 12452 terminating in a fitting 12454 extends from the pump 12446 in FIGS. 216 and 218. The fitting 12454 is a luer fitting, however, the reader will readily appreciate that alternative fittings are envisioned. The luer fitting can be selectively coupled to a reservoir that is configured to receive the smoke S from the surgical site, for example. Additionally or alternatively, the luer fitting can supply discharge from the pump 12446 to a filter.

Referring still to FIG. 218, internal components of the drive interface 12448 are depicted, however, certain components are excluded for clarity. The evacuation channel 12440 extends through the shaft 12438 to the lobe pump 12446 in the proximal housing 12437. The pump 12446 is driven by a rotary driver 12450 of the interface 12448. In various instances, the interface 12448 can include four rotary drivers 12450. In one example, a first rotary driver 12450 is configured to power an articulation motion, a second rotary driver 12450 is configured to power a jaw closure motion, a third rotary driver 12450 is configured to power a shaft rotation, and a fourth rotary driver 12450 is configured to power the pump 12446. The reader will appreciate that alternative interface arrangements can include more than or less than four rotary drivers 12450. Additionally, the drive motions generated by the rotary drivers 12450 can vary depending on the desired functionality of the robotic tool 12426. Moreover, in certain instances, the drive interface 12448 can include a transmission or shifter such that the rotary drivers 12450 can shift between multiple surgical functions, as further described herein (see transmission 12124 in FIG. 212 and transmission assembly 12840 in FIGS. 223-228, for example). In one instance, the rotary driver 12450 coupled to the pump 12446 can also actuate a clamping motion of the end effector 12428, for example.

In one aspect, activation of the pump 12446 of the robotic tool 12426 can be coordinated with the application of energy by the robotic tool 12426. In various instances, a control algorithm for the rotary driver 12450 for the pump 12446 can be related to the rate at which smoke S is extracted from the surgical site. In such instances, the robot (e.g. the robot 12022 in FIGS. 206 and 210) can have direct control over the volume of evacuation and/or extraction from the surgical site.

In one instance, the on/off control for the pump 12446 is controlled based on inputs from a camera, such as the camera of the imaging device 124 (FIG. 2) like an endoscope, for example. The imaging device 124 can be configured to detect the presence of smoke S in a visual field at the surgical site. In another aspect, the on/off control for the pump 12446 is controlled based on inputs from a smoke sensor 12453 (FIG. 217) in-line with the fluid being pumped out of the patient. For example, the pump 12446 can remain on as long as a threshold amount of smoke S is detected by the smoke sensor 12453 and can be turned off or paused when the detected volume of smoke S falls below the threshold amount. In still another aspect, the pump 12446 is turned on when energy is activated and, in certain instances, can remain on for a period of time after the energy has been stopped. The duration of time for which the pump 12446 can remain on after the energy has stopped may be fixed or may be proportional to the length of time the energy was activated, for example.

Referring primarily to FIG. 220, a flow chart depicting logic steps for operating a pump, such as the pump 12446, is depicted. A processor for the robot (e.g. robot 12022) and/or a processor of a hub (e.g. hub 106, hub 206, robotic hub 122, and robotic hub 222) that is in signal communication with the robot can determine or estimate the rate of smoke evacuation from the surgical site. The rate of smoke evacuation can be determined at step 12510 by one or more factors or inputs including the activation of energy by the robotic tool (a first input 12502), a smoke sensor in-line with the smoke evacuation channel (a second input 12504), and/or an imaging device configured to view the surgical site (a third input 12506). The first input 12502 can correspond to the duration of energy application and/or the power level, for example. Based on the one or more factors, the pump can be adjusted at step 12512. For example, the rate at which the rotary driver drives the pump can be adjusted. In other instances, the rotary driver can stop or pause the operation of the pump while the detected rate of smoke evacuation is below a threshold volume. The flow chart of FIG. 220 can continue throughout the operation of a robotic tool. In certain instances, the steps 12510 and 12512 can be repeated at predefined intervals during a surgical procedure and/or when requested by a clinician and/or recommend by a hub.

Referring now to FIG. 219, a robotic tool 12526 for use with a robotic surgical system is depicted. The robotic tool 12526 can be employed with the robotic surgical system 12010 (FIG. 206), for example. The robotic tool 12526 is an ultrasonic robotic tool having cooling and insufflation capabilities. For example, the robotic tool 12526 can be similar in many respects to the robotic tool disclosed in U.S. Pat. No. 9,314,308, filed Mar. 13, 2013, titled ROBOTIC ULTRASONIC SURGICAL DEVICE WITH ARTICULATING END EFFECTOR, which is herein incorporated by reference in its entirety.

The robotic tool 12526 includes a proximal housing 12537, a shaft 12538 extending from the proximal housing 12537, and an end effector 12528 extending from a distal end of the shaft 12538. The end effector 12528 includes an ultrasonic blade 12530$a$ and an opposing clamp arm 12530$b$. The robotic tool 12526 also includes an irrigation system 12536, which is configured to provide a coolant, such as saline or cool $CO_2$ for example, to the surgical site. Irrigation can be configured to cool the tissue and/or the ultrasonic blade 12530$a$, for example. The irrigation system 12536 includes an irrigation channel 12540, which extends through the shaft 12538 to the proximal housing 12537. The irrigation channel 12540 terminates at an irrigation port adjacent to the end effector 12528.

In various instances, the irrigation channel 12540 can be coupled to a blower configured to direct fluid along the irrigation channel 12540 within the shaft 12538 of the robotic tool 12526. The irrigation system 12536 includes a blower 12546. The blower 12546 is housed in the proximal housing 12537 of the robotic tool 12526. The blower 12546 is a regenerative blower, which has been incorporated into a drive interface 12548 of the robotic tool 12526. The drive interface 12548 includes rotary drivers 12550, which are driven by rotary outputs from motors in the tool mounting portion of the robot, as described herein (see rotary outputs 12256 (FIG. 214) and rotary outputs 12824$a$-12824$e$ (FIG. 222), for example).

A channel 12552 terminating in a fitting 12554 extends from the blower 12546. The fitting 12554 is a luer fitting, however, the reader will readily appreciate that alternative fittings are envisioned. The luer fitting can be selectively coupled to a reservoir that is configured to provide the irrigation fluid to the blower 12546. In operation, coolant can enter the insufflation line through the fitting 12554 and the blower 12546 can draw the coolant toward the blower 12546 at the drive interface 12548 and then blow the coolant distally along the shaft 12538 of the robotic tool 12526 toward the end effector 12528. The coolant can be expelled at or adjacent to the end effector 12528, which can cool the ultrasonic blade and/or maintain insufflation of the surgical site, such as insufflation of an abdomen, for example.

In FIG. 219, internal components of the drive interface 12548 are depicted, however, certain components are excluded for clarity. The irrigation channel 12540 extends through the shaft 12538 to the blower 12546 in the proximal housing 12537. The blower 12546 is driven by a rotary driver 12550 of the drive interface 12548. Similar to the interface 12448 (FIG. 218), the interface 12548 includes four rotary drivers 12550. In one example, a first rotary driver 12550 is configured to power an articulation motion, a second rotary driver 12550 is configured to power a jaw closure motion, a third rotary driver 12550 is configured to power a shaft rotation, and a fourth rotary driver 12550 is configured to power the irrigation system 12536. The reader will appreciate that alternative interface arrangements can include more than or less than four rotary drivers 12550. Additionally, the drive motions generated by the rotary drivers 12550 can vary depending on the desired functionality of the robotic tool. Moreover, in certain instances, the drive interface 12548 can include a transmission or shifter such that the rotary drivers 12550 can shift between multiple surgical functions, as further described herein (see transmission 12124 in FIG. 212 and transmission assembly 12840 in FIGS. 223-228, for example). In one instance, the rotary driver 12550 coupled to the blower 12546 can also actuate a clamping motion of the end effector 12528, for example.

As described herein with respect to the pump 12446 in FIG. 218, operation of the blower 12546 in FIG. 219 can be coordinated with the application of energy by the robotic tool 12526. For example, the blower 12546 can be turned on when energy is activated, and, in certain instances, the blower 12546 can remain on for a period of time after the energy has been stopped. The duration of time for which the blower 12546 can remain on after the energy has stopped may be fixed or may be proportional to the length of time the energy was activated, for example. Additionally or alternatively, the power level of the blower 12546 can be proportional or otherwise related to the activation level of the robotic tool 12526. For example, a high power level can correspond to a first rate and a lower power level can correspond to a second rate. In one example, the second rate can be less than the first rate.

In one aspect, the robotic tool 12526 can also include an insufflation pump that is upstream of the regenerative blower 12546. The insufflation pump can direct a first volume of fluid into a trocar and a second volume of fluid into the regenerative blower 12546. The fluid provided to the trocar can be configured to insufflate the surgical site, for example, the abdomen of a patient. The fluid provided by the regenerative blower 12546 can be configured to cool the ultrasonic blade, for example.

The robotic surgical tools 12426 and 12526 can be used in connection with a hub, such as the robotic hub 122 or the robotic hub 222, for example. In one aspect, the robotic hubs can include a situational awareness module, as described herein. The situational awareness module can be configured to determine and/or confirm a step in a surgical procedure and/or suggest a particular surgical action based on information received from various sources, including one or more robotic surgical tool(s) and/or a generator module. In one instance, the actuation of a pump on a robotic surgical tool can inform the situational awareness module that evacuation and/or irrigation have been employed, which can lead to a conclusion regarding a particular surgical procedure or group of surgical procedures. Similarly, data from the situational awareness module can be supplied to a processor. In certain instances, the processor can be communicatively coupled to a memory that stores instructions executable by the processor to adjust a pumping rate of the pump based on data from the situational awareness module which can indicate, for example, the type of surgical procedure and/or the step in the surgical procedure. For example, situational awareness can indicate that insufflation is necessary for at least a portion of a particular surgical procedure. In such instances, a pump, such as the blower 12546 (FIG. 219) can be activated and/or maintained at a level to maintain a sufficient insufflation.

In one aspect, the robotic surgical system includes a processor and a memory communicatively coupled to the processor, as described herein. The memory stores instructions executable by the processor to rotate a driver in a robotic tool at a variable rate to provide an adjustable power level to a pump in the robotic tool, as described herein.

In various aspects, the present disclosure provides a control circuit to rotate a rotary driver in a robotic tool at a variable rate, as described herein. In various aspects, the present disclosure provides a non-transitory computer readable medium storing computer readable instructions which, when executed, cause a machine to rotate a rotary driver in a robotic tool at a variable rate to provide an adjustable power level to a pump in the robotic tool, as described herein.

Referring now to FIGS. 234 and 235, a surgical procedure utilizing two robotic tools is depicted. In FIG. 234, the robotic tools are engaged with tissue at a surgical site. The first tool in this example is a flexible robotic retractor 12902, which is applying a retracting force to a portion of a patient's liver L. In FIG. 235, the flexible robotic retractor 12902 can be moved along a longitudinal axis of the tool shaft in a direction A and/or can be moved laterally (e.g. pivoted at a joint between two rigid linkages in the robotic retractor) in a direction B.

The second tool in this example is an articulating bipolar tool 12904, which is being clamped on tissue. For example, the articulating bipolar tool 12904 can be configured to mobilize liver attachments A to the liver utilizing bipolar RF currents. The articulating bipolar tool 12904 can be articulated laterally (e.g. pivoted at an articulation joint proximal to the bipolar jaws of the robotic tool 12904) in the direction C. The directions A, B, and C are indicated with arrows in FIG. 235.

In the depicted example, the flexible robotic retractor 12902 seeks to hold back an organ, the liver L, as the bipolar jaws of the articulating bipolar tool 12904 seek to cut and/or seal clamped tissue to mobilize the liver attachments A. In one aspect, movement of the liver L by the flexible robotic retractor 12902 can be configured to maintain a constant retraction force as the bipolar tool 12904 mobilizes the liver attachments A to the liver L. A load control algorithm can be configured to maintain the constant retraction force on the tissue. In certain instances, the load control algorithm can be an articulation control algorithm that provides a set, or predetermined, torque at the articulation joint(s) of the articulating bipolar tool 12904 and/or the flexible robotic retractor 12902. The set torque at an articulation joint can be approximated based on current supplied to the articulation motor, for example.

In certain instances, the flexible robotic retractor 12902 can risk or otherwise threaten over-retraction of the liver L. For example, if displacement of the flexible robotic retractor 12902 approaches a set displacement limit, the flexible robot retractor 12902 can risk tearing a portion of the tissue. To prevent such an over-retraction, as the displacement of the flexible robotic retractor 12902 approaches the displacement limit, the force generated by the flexible robotic retractor 12902 can be reduced by the load control algorithm. For example, the force can be reduced below a constant, or substantially constant, retraction force when a displacement limit has been met.

Referring now to a graphical display 12910 in FIG. 236, the retraction force F exerted on an organ and the displacement 6 of the robotic tool, and by extension the organ, is plotted over time. The reader will appreciate that the robotic tools 12902 and 12904, as depicted in the surgical procedure of FIGS. 234 and 235, can be utilized to generate the graphical display 12910. Alternative surgical tool(s) and surgical procedures are also contemplated. In one aspect, an operator can set a retraction force threshold Y and a displacement limit X as depicted in FIG. 236. In other instances, the retraction force threshold Y and/or the displacement limit X can be determined and/or computed based on information from a surgical hub and/or cloud. In certain instances, a particular retraction force threshold Y and/or displacement limit X can be recommended to a clinician based on data stored in the memory of the robot, the surgical hub, and/or the cloud. The retraction force threshold Y and/or the displacement limit X can depend on patient information, for example.

During the surgical procedure, if the retraction force F drops below the constant retraction force threshold Y, or drops by a predefined percentage or amount relative to the constant retraction force threshold Y, as at times $t_1$, $t_2$, and $t_3$, the flexible robotic retractor 12902 can be further displaced, to displace the organ, and increase the retraction force F toward the threshold Y. Similarly, if the displacement 6 approaches the displacement limit X, as at time $t_4$, the retraction force can be reduced to limit further displacement beyond the displacement limit X. For example, referring again to FIG. 234, the liver L is depicted in a second position indicated as L'. The position of the liver L' can correspond to the displacement limit X of the flexible robotic retractor 12902.

Referring now to FIG. 237, a flow chart depicting logic steps for operating a robotic tool, such as the tool 12902 (FIGS. 234 and 235) for example, is depicted. A processor for the robot (e.g. the robot 12022) and/or of a processor of a hub (e.g. the hub 106, the hub 206, the robotic hub 122, and the robotic hub 222) that is in signal communication with the robot can set a displacement limit at step 12920. Additionally, the processor can set a force limit at step 12922. The displacement limit and the force limit can be selected based on input from one or more sources including a clinician input 12930, a robot input 12932, a hub input 12934, and/or a cloud input 12936, as further described herein. In certain instances, the hub can suggest a particular limit based on data collected by a robot, provided to the hub, and/or stored in the cloud. For example, a situational awareness module can suggest a particular limit based on the surgical procedure or step thereof ascertained by the situational awareness module. Additionally or alternatively, the clinician can provide an input and/or select the limit from the hub's suggestions. In other instances, the clinician can override the hub's suggestions. The limits can correspond to a range of values, such as the limit ±one percent, ±five percent, or ±ten percent, for example.

The robotic tool can initially operate in a constant force mode. At step 12924 in the constant force mode, the force exerted by the robotic tool can be maintained at the force limit. The processor can monitor the force to ensure the force stays below the force limit Y. If the force exceeds the force limit Y, the displacement value can be increased at step 12926 until the force reaches or sufficiently approaches the force limit Y. A force can sufficiently approach the force limit when the force is within a range of values corresponding to the force limit. The processor can monitor the displacement to ensure the displacement stays below the displacement limit X.

If the displacement approaches the displacement limit X (or enters the range of values corresponding to the displacement limit), the robotic tool can switch to a displacement limit mode. In the displacement limit mode, the force value can be decreased at step 12928 to ensure the robotic tool stays within the displacement limit. A new force limit can be set at step 12922 to ensure the displacement stays within the displacement limit. In such instances, the robotic tool can switch back to the constant force mode (with the new, reduced force limit) and steps 12924, 12926, and 12928 can be repeated.

In certain instances, the stiffness of the shaft of one or more of the robotic tools can be factored into the load control algorithm in order to achieve the desired amount of lateral force on an organ, like the liver L. For example, the flexible robotic retractor 12902 can define a stiffness that affects the lateral load exerted on a tissue by the end effector thereof.

In certain instances, a drive housing for a robotic tool can include a plurality of rotary drivers, which can be operably driven by one or more motors. The motors can be positioned in a motor carriage, which can be located at the distal end of a robotic arm. In other instances, the motors can be incorporated into the robotic tool. In certain instances, a motor can operably drive multiple rotary drivers and a transmission can be configured to switch between the multiple rotary drivers. In such instances, the robotic tool cannot simultaneously actuate two or more rotary drivers that are associated with the single drive motor. For example, as described herein with respect to FIG. 212, the motor 12112 can selectively power one of the roll DOF 12132, the high force grip DOF 12136, or the tool actuation DOF 12138. The transmission 12124 can selectively couple the motor 12112 to the appropriate DOF.

In certain instances, it can be desirable to increase the torque delivered to an output of the robotic tool. For example, clamping and/or firing of a surgical stapler may benefit from additional torque in certain instances, such as when the tissue to be cut and/or stapled is particularly thick or tough. Especially for longer end effectors and/or longer firing strokes, additional torque can be required to complete the firing stroke. In certain instances, an I-beam firing structure can be utilized, especially for longer end effectors and/or longer firing strokes. The I-beam can limit deflection at the distal tip of the firing stroke for example. However, an I-beam can require increased torque.

Additionally, certain robotic tools may require additional flexibility regarding the simultaneous operation of multiple DOFs or surgical end effector functions. To increase the power, torque, and flexibility of a robotic system, additional motors and/or larger motors can be incorporated into the motor carriage. However, the addition of motors and/or utilization of larger motors can increase the size of the motor carriage and the drive housing.

In certain instances, a robotic surgical tool can include a compact drive housing. A compact drive housing can improve the access envelope of the robotic arm. Moreover, a compact drive housing can minimize the risk of arm collisions and entanglements. Though the drive housing is compact, it can still provide sufficient power, torque, and flexibility to the robotic tool.

In certain instances, shifting between end effector functions can be achieved with one of the drive shafts. Shifting and locking of the rotary drives may only occur when a robotic surgical system is in a rest mode, for example. In one aspect, it can be practical to have three rotary drives operate as many end effector functions as needed based on the cam structure of the shifting drive. In one aspect, by using three rotary drives in cooperation, a robotic surgical tool can shift between four different possible functions instead of three different functions. For example, three rotary drives can affect shaft rotation, independent head rotation, firing, closing, and a secondary closing means. In still other instances, a rotary drive can selectively power a pump, such as in the surgical tools 12426 and 12526 in FIGS. 218 and 219, respectively, for example.

Additionally or alternatively, multiple rotary drives can cooperatively drive a single output shaft in certain instances. For example, to increase the torque delivered to a surgical tool, multiple motors can be configured to deliver torque to the same output shaft at a given time. For example, in certain instances, two drive motors can drive a single output. A shifter drive can be configured to independently engage and disengage the two drive motors from the single output. In such instances, increased torque can be delivered to the output by a compact drive housing that is associated with multiple rotary drivers and end effector functions. As a result, load capabilities of the surgical tool can be increased. Moreover, the drive housing can accommodate surgical tools that require different surgical functions, including the operation of multiple DOFs or surgical functions.

Referring now to FIGS. 221-228, a drive system 12800 for a robotic surgical tool 12830 is depicted. The drive system 12800 includes a housing 12832 and a motor carriage 12828. A shaft 12834 of the surgical tool 12830 extends from the housing 12832. The motor carriage 12828 houses five motors 12826 similar to the motor carriage 12108 (FIG. 212). In other instances, the motor carriage 12828 can house less than five motors or more than five motors. In other instances, the motors 12826 can be housed in the robotic surgical tool 12830.

Each motor 12826 is coupled to a rotary output 12824 and each rotary output 12824 is coupled to a rotary input 12836 in the housing 12832 at a drive interface 12822. The rotary motions from the motors 12826 and corresponding rotary outputs 12824 are transferred to a respective rotary input 12836. The rotary inputs 12836 correspond to rotary drivers, or rotary drive shafts, in the housing 12832. In one example, a first motor 12826a can be a left/right articulation (or yaw) motor, a second motor 12826b can be an up/down articulation (or pitch) motor, a third motor 12826c can be a shifter motor, a fourth motor 12826d can be a first cooperative motor, and a fifth motor 12826e can be a second cooperative motor. Similarly, a first rotary output 12824a can be a left/right articulation (or yaw) output, a second rotary output 12824b can be an up/down articulation (or pitch) output, a third rotary output 12824c can be a shifter output, a fourth rotary output 12824d can be a first cooperative output, and a fifth rotary output 12824e can be a second cooperative output. Furthermore, a first rotary input 12836a can be a left/right articulation (or yaw) drive shaft, a second rotary input 12836b can be an up/down articulation (or pitch) drive shaft, a third rotary input 12836c can be a shifter drive shaft, a fourth rotary input 12836d can be a first cooperative drive shaft, and a fifth rotary input 12836e can be a second cooperative drive shaft. In other instances, the drive shafts 12836a-12836e can be operably positionable in different orientations to effectuate different gear trains configurations to transmit a desired rotary output.

The surgical tool 12830 is depicted in a plurality of different configurations in FIGS. 230-233. For example, the surgical tool 12830 is in an unactuated configuration in FIG. 230. The shaft 12834 has been articulated about the yaw and pitch axes (in the directions of the arrows A and B) in FIG. 231. Rotation of the first and second rotary inputs 12836a and 12836b is configured to articulate the shaft 12834 about the yaw and pitch axes, respectively. In FIG. 232, the shaft 12834 has been rotated in the direction of the arrow C about the longitudinal axis of the shaft 12834 and a jaw of the end effector 12835 has been closed with a low-force actuation in the direction of arrow D. Rotation of the fourth rotary output 12836d is configured to selectively affect the rotation of the shaft 12834, and rotation of the fifth rotary output 12836e is configured to selectively affect the low-force closure of the end effector 12835. In FIG. 233, the jaw of the end effector 12835 has been clamped with a high-force actuation in the direction of arrow E, and the firing member has been advanced in the direction of arrow F. Rotation of the fourth rotary output 12836d and the fifth rotary output 12836e is configured to selectively and cooperatively affect the high-force closure of the end effector 12835 and the firing of the firing member therein, respectively.

Referring primarily now to FIGS. 223-228, the housing 12832 includes multiple layers of gear train assemblies. Specifically, the housing 12832 includes a first gear train assembly 12838a layered under a second gear train assembly 12838b, which is layered under a third gear train assembly 12838c, which is layered under a fourth gear train assembly 12838d. The first gear train assembly 12838a corresponds to a first DOF, such as rotation of the shaft 12834, for example. The second gear train assembly 12838b corresponds to a second DOF, such as closure (i.e. fast closure) of the end effector 12835 with a low closure force, for example. The third gear train assembly 12838c corresponds to a third DOF, such as clamping (i.e. slow closure) of the end effector 12835 with a high closure force, for example. The fourth gear train assembly 12838d corresponds to a fourth DOF, such as firing of a firing element in the end effector 12835, for example. The five rotary inputs 12836a-12836e extend through the four layers of gear train assemblies 12838a-12838d.

The first motor 12826a is drivingly coupled to the first rotary input 12836a. In such instances, the first motor 12826a is singularly configured to drive the first rotary input 12836a, which affects the first DOF. For example, referring primarily to FIG. 224, articulation wires 12842 can extend from the first rotary input 12836a through the shaft 12834 of the robotic tool 12830 toward the end effector 12835. Rotation of the first rotary input 12836a is configured to actuate the articulation wires 12842 to affect left/right articulation of the end effector 12835. Similarly, the second motor 12826b is drivingly coupled to the second rotary input 12836b. In such instances, the second motor 12826b is singularly configured to drive the second rotary input 12836b, which affects the second DOF. Referring still to FIG. 224, articulation wires 12844 can extend from the second rotary input 12836b through the shaft 12834 of the robotic tool 12830 toward the end effector 12835. Rotation of the second rotary input 12836b is configured to actuate the articulation wires 12844 to affect up/down articulation of the end effector 12835. In other instances, at least one of the first rotary input 12836a and the second rotary input 12836b can correspond to a different DOF or different surgical function.

The housing 12832 also includes a transmission assembly 12840. For example, the third rotary input 12836c is a shifter drive shaft of the transmission assembly 12840. As depicted in FIGS. 223-228, the third rotary input 12836c can be a camshaft, including a plurality of camming lobes. An arrangement of cam lobes 12839 can correspond with each gear train assembly 12838a-12838d layered in the housing 12832. Moreover, each gear train assembly 12838a-12838d includes a respective shuttle 12846a-12846d operably engaged by the third rotary input 12836c. For example, the third rotary input 12836c can extend through an opening in each shuttle 12846a-12846d and selectively engage at least one protrusion 12848 on the shuttle 12846a-12846d to affect shifting of the respective shuttle 12846a-12846d relative to the third rotary input 12836c. In other words, rotation of the third rotary input 12836c is configured to affect shifting of the shuttles 12846a-12846d. As the shuttles 12846a-12846d shift within each gear train assembly 12838a-12838d, respectively, the cooperative drive shafts 12836d and 12836e are selectively drivingly coupled to one or more output shafts of the robotic tool 12830, as further described herein.

In other instances, a drive system for a robotic tool can include a vertically shifting gear selector, which can be configured to shift the shuttles 12846a-12846d or otherwise engage an output drive from a motor to one or more input drives on the robotic tool 12830.

Referring still to FIGS. 221-228, the fourth and fifth output drives, or the first and second cooperative drive shafts, 12836d and 12836e, respectively, can operate independently or in a coordinated, synchronized manner. For example, in certain instances, each cooperative drive shaft 12836d and 12836e can be paired with a single output gear or output shaft. In other instances, both cooperative drives 12836d and 12836e can be paired with a single output gear or output shaft.

Referring primarily to FIG. 225, in a first configuration of the transmission arrangement 12840, the first cooperative drive shaft 12836d is drivingly engaged with a first output gear 12852 of the first gear train assembly 12838a. For example, the first gear train assembly 12838a includes one or more first idler gears 12850a. In FIG. 225, the first gear train assembly 12838a includes two first idler gears 12850a. The first idler gears 12850a are positioned on the first shuttle 12846a in the first gear train assembly 12838a. In the first configuration (FIG. 225), the first shuttle 12846a has been shifted toward the first output gear 12852 by the camshaft 12836c such that one of the first idler gears 12850a on the first shuttle 12846a is moved into meshing engagement with the first output gear 12852 and one of the first idler gears 12850a is moved into meshing engagement with the first cooperative drive shaft 12836d. In other words, the first cooperative drive shaft 12836d is drivingly engaged with the first output gear 12852.

Rotation of the first output gear 12852 corresponds to a particular DOF. For example, rotation of the first output gear 12852 is configured to rotate the shaft 12834 of the robotic tool 12830. In other words, in the first configuration of the transmission arrangement 12840 (FIG. 225), a rotation of the fourth motor 12826d and the fourth rotary output 12824d is configured to rotate the first cooperative drive shaft 12836d, which is coupled to the first output gear 12852 via the first idlers gears 12850a and rotates (or rolls) the shaft 12834.

The first gear train assembly 12838a also includes a first locking arm 12860a. The first locking arm 12860a extends from the first shuttle 12846a. Movement of the first shuttle 12846a is configured to move the first locking arm 12860a. For example, in the first configuration of FIG. 225, the first locking arm 12860a is disengaged from the first gear train assembly 12838a such that the first output gear 12852 can rotate. Movement of the first shuttle 12846a can move the first locking arm 12860a into engagement with the first output gear 12852. For example, when the first idler gears 12850a are moved out of engagement with the first output gear 12852, the first locking arm 12860a can engage the first output gear 12852 or another gear in the first gear train assembly 12838a to prevent the rotation of the first output gear 12852.

Referring still to FIG. 225, in the first configuration of the transmission arrangement 12840, the second cooperative drive shaft 12836e is drivingly engaged with a second output gear 12854 of the second gear train assembly 12838b. For example, the second gear train assembly 12838b includes one or more second idler gears 12850b and a planetary gear 12853 that is meshingly engaged with the second output gear 12854. In FIG. 225, the second gear train assembly 12838b includes two second idler gears 12850b. The second idler gears 12850b are positioned on the second shuttle 12846b in the second gear train assembly 12838b. In the first configuration, the second shuttle 12846b has been shifted toward the second output gear 12854 by the camshaft 12836c such that one of the second idler gears 12850b on the second shuttle 12846b is moved into meshing engagement with the planetary gear 12853, and one of the second idler gears 12850b is moved into meshing engagement with the second cooperative drive shaft 12836e. In other words, the second cooperative drive shaft 12836e is drivingly engaged with the second output gear 12854 via the second idler gears 12850b and the planetary gear 12853. The second output gear 12854 is configured to drive a second output shaft 12864 (FIGS. 226-228), which transfers a drive motion to the end effector 12835.

Rotation of the second output gear 12854 corresponds to a particular DOF. For example, a rotation of the second output gear 12854 is configured to close the end effector 12835 of the robotic tool 12830 with a low closure force. In other words, in the first configuration of the transmission arrangement 12840, a rotation of the fifth motor 12826e and the fifth rotary output 12824e is configured to rotate the second cooperative drive shaft 12836e, which is coupled to the second output gear 12854, via the second idlers gears 12850b and the planetary gear 12853, and closes the end effector 12835 of the robotic tool 12830 with a low closure force.

The second gear train assembly 12838b also includes a second locking arm 12860b. The second locking arm 12860b extends from the second shuttle 12846b. Movement of the second shuttle 12846b is configured to move the second locking arm 12860b. For example, in the first configuration of FIG. 225, the second locking arm 12860b is disengaged from the planetary gear 12853. Movement of the second shuttle 12846b can move the second locking arm 12860b into engagement with the second planetary gear 12853. For example, when the second idler gears 12850b are moved out of engagement with the second gear train assembly 12838b or planetary gear 12853 thereof, the second locking arm 12860b can engage a portion of the second gear train assembly 12838b, such as planetary gear 12853, for example, to prevent rotation of the planetary gear 12853 and the second output gear 12854.

In the first configuration, rotary drive motions can be concurrently applied to the first and second cooperative drive shafts 12836d and 12836e, respectively, to concurrently affect multiple degrees of freedom. For example, the transmission arrangement 12840 can permit the simultaneous rotation of the shaft 12834 and closing of the end effector jaws. In other instances, one of the output gears 12852, 12854 can be locked by the respective locking arm when the other output gear 12852, 12854 is drivingly coupled to the respective cooperative drive shaft 12836d, 12836e.

Referring still to FIG. 225, in the first configuration of the transmission arrangement 12840, a third output gear 12856 in the third gear train assembly 12838c and a fourth output gear 12858 in the fourth gear train assembly 12838d are locked via the locking arms 12860c and 12860d, respectively. As a result, rotation of the third output gear 12856, which corresponds to clamping or high-force closing of the end effector jaws, is prevented by the first configuration. Additionally, rotation of the fourth output gear 12858, which corresponds to firing the firing member in the end effector 12835, is also prevented. In other words, when the transmission arrangement 12840 is configured to deliver rotary motions to affect a low-force closure DOF or shaft rotation DOF, high-force clamping and firing is prevented. In such instances, the high-force clamping function and firing function can be selectively locked out by the transmission arrangement 12840.

Referring now to FIG. 226, a second configuration of the transmission arrangement 12840 is depicted. In the second configuration, the first and second cooperative drive shafts 12836d and 12836e are drivingly engaged with a third output gear 12856 of the third gear train assembly 12838c. The third output gear 12856 is configured to drive a third output shaft 12866 (FIGS. 226-228), which transfers a drive motion to the end effector 12835. For example, the third gear train assembly 12838c includes one or more third idler gears 12850c and a planetary gear 12855 that is meshingly engaged with the third output gear 12856. In FIG. 226, the third gear train assembly 12838c includes three third idler gears 12850c. The third idler gears 12850c are positioned on the third shuttle 12846c in the third gear train assembly 12838c. In the second configuration, the third shuttle 12846c has been shifted toward the third output gear 12856 by the camshaft 12836c such that one of the third idler gears 12850c is moved into meshing engagement with the planetary gear 12855, one of the third idler gears 12850c is moved into meshing engagement with the first cooperative drive shaft 12836d, and one of the third idler gears 12850c is moved into meshing engagement with the second cooperative drive shaft 12836e. In other words, both cooperative drive shafts 12836d and 12836e are drivingly engaged with the third output gear 12856 via the third idler gears 12850c and the planetary gear 12855.

Rotation of the third output gear 12856 corresponds to a particular DOF. For example, a rotation of the third output gear 12856 is configured to clamp the end effector 12835 of the robotic tool 12830 with a high closure force. In other words, in the second configuration of the transmission arrangement 12840, a rotation of the fourth motor 12826d and the fifth motor 12826e and the corresponding rotation of the fourth rotary output 12824d and the fifth rotary output 12824e are configured to rotate the cooperative drive shafts 12836d and 12836e, respectively. In such instances, a torque supplied by both cooperative drive shafts 12836d and 12836e is coupled to the third output gear 12856 via the third idlers gears 12850c to clamp the end effector 12835 of the robotic tool 12830 with a high closure force.

Referring still to FIG. 226, in the second configuration of the transmission arrangement 12840, the third output gear 12856 is unlocked. More specifically, the third locking arm 12860c is disengaged from the third gear train assembly 12838c such that the third output gear 12856 can rotate. Additionally, the camshaft 12836c has moved the first locking arm 12860a into engagement with the first gear train assembly 12838a, the second locking arm 12860b into engagement with the second gear train assembly 12838b, and the fourth locking arm 12860d into engagement with the fourth gear train assembly 12838d to prevent rotation of the first output gear 12852, the second output gear 12854, and the fourth output gear 12858, respectively. As a result, rotation of the shaft 12834, low-force closing of the end effector jaws, and firing of the end effector 12835, is prevented by the transmission arrangement 12840 in the second configuration. In such instances, the shaft rotation function, the low-force closing function, and the firing function can be selectively locked out by the transmission arrangement 12840.

Referring now to FIG. 227, a third configuration of the transmission arrangement 12840 is depicted. In the third configuration, the first and second cooperative drive shafts 12836d and 12836e are drivingly engaged with a fourth output gear 12858 of the fourth gear train assembly 12838d. For example, the fourth gear train assembly 12838d includes one or more fourth idler gears 12850d and a planetary gear 12857 that is meshingly engaged with the fourth output gear 12858. In FIG. 227, the fourth gear train assembly 12838d includes three fourth idler gears 12850d. The fourth idler gears 12850d are positioned on the fourth shuttle 12846d in the fourth gear train assembly 12838d. In the third configuration, the fourth shuttle 12846d has been shifted toward the fourth output gear 12858 by the camshaft 12836c such that one of the fourth idler gears 12850d is moved into meshing engagement with the planetary gear 12857, one of the fourth idler gears 12850d is moved into meshing engagement with the first cooperative drive shaft 12836d, and one of the fourth idler gears 12850d is moved into meshing engagement with the second cooperative drive shaft 12836e. In other words, both cooperative drive shafts 12836e and 12836e are drivingly engaged with the fourth output gear 12858 via the fourth idler gears 12850d and the planetary gear 12857. The fourth output gear 12858 is configured to drive a third output shaft 12868 (FIGS. 226-228), which transfers a drive motion to the end effector 12835.

Rotation of the fourth output gear 12858 corresponds to a particular DOF. For example, a rotation of the fourth output gear 12858 is configured to firing a firing member in the end effector 12835 of the robotic tool 12830. In other words, in the third configuration of the transmission arrangement 12840, a rotation of the fourth motor 12826d and the fifth motor 12826e and the corresponding rotation of the fourth rotary output 12824d and the fifth rotary output 12824e are configured to rotate the cooperative drive shafts 12836d and 12836e, respectively. In such instances, a torque supplied by both cooperative drive shafts 12836d and 12836e is coupled to the fourth output gear 12858 via the fourth idlers gears 12850d and planetary gear 12857 to fire the end effector 12835 of the robotic tool 12830.

Referring still to FIG. 227, in the third configuration of the transmission arrangement 12840, the fourth output gear 12858 is unlocked. More specifically, the fourth locking arm 12860d is disengaged from the fourth gear train assembly 12838d such that the fourth output gear 12858 can rotate. Additionally, the camshaft 12836c has moved the first locking arm 12860a into engagement with the first gear train assembly 12838a, the second locking arm 12860b into engagement with the second gear train assembly 12838b, and the third locking arm 12860c into engagement with the third gear train assembly 12838c to prevent rotation of the first output gear 12852, the second output gear 12854, and the third output gear 12856, respectively. As a result, rotation of the shaft 12852, low-force closing of the end effector jaws, and high-force clamping of the end effector jaws is prevented by the transmission arrangement 12840 in the third configuration. In such instances, the shaft rotation function, the low-force closing function, and the high-force clamping function can be selectively locked out by the transmission arrangement 12840.

In one aspect, the dual drive motors 12826*d* and 12826*e* can coordinate with the shifting motor 12826*c* to provide a compact drive housing 12832 that enables multiple end effector functions. Moreover, a greater torque can be supplied for one or more end effector functions via the cooperative drive shafts 12836*d* and 12836*e*.

In one aspect, when the cooperative drive shafts 12836*d* and 12836*e* are operated together, the two drives shafts 12836*d* and 12836*e* are synchronized. For example, the drive shafts 12836*d* and 12836*e* can both drive a common output shaft such as the output shafts 12866 and/or 12868. Torque can be provided to the common output shafts 12866 and/or 12868 via both drive shafts 12836*d* and 12836*e*.

Referring now to FIG. 229, a graphical display 12890 of output torque for different surgical functions of a robotic tool, such as the robotic tool 12830 (FIGS. 221-228), for example, is depicted. The output torque for rotating the tool shaft (e.g. shaft 12834) via a first cooperative drive shaft and for low-force closing of end effector jaws via a second cooperative drive shaft are less than t1, the maximum output torque from a single shaft. The lower output torques for shaft rotation and low-force jaw closure can be within the range of loads obtainable from a cable on a spindle, for example. In certain instances, other lower load functionalities of the surgical tool can be affected with the output from a single shaft.

To affect high-force clamping, the torque approaches t2, the maximum output torque from the cooperative drive shafts (e.g. cooperative drive shafts 12836*d* and 12836*e*). For example, t2 can be twice the value of t1. The values "a" and "b" in FIG. 229 show relative forces for the robotic tool. The value "a" is the load difference between a low-force closure and high-force clamping, such as closure with a closure tube system and clamping via an I-beam, example. In certain instances, a closure tube system and an I-beam system can cooperate, or overlap temporally as shown in FIG. 229, to complete the clamping of the end effector. The value "b" can be equal to or less than the value "a". For example, the torque required to fire the end effector can be the same, or substantially the same, as the difference in torque between low-force closing and high-force clamping. The values "a" and "b" are more than the maximum output torque from a single shaft, but less than the maximum output torque from cooperative drive shafts.

In one instance, the synchronization of multiple drive shafts (e.g. cooperative drive shafts 12836*d* and 12836*e*) can be the slaving of one drive shaft to the following of the other drive shaft. For example, a different maximum torque threshold can be set on the slaved drive shaft such that it can push up to the first drive shaft's limit but not over it. In one aspect, the speed of the output shaft can be monitored for increases and/or decreases in rotational speed. For example, a sensor can be positioned to detect the rotational speed of the output shaft. Further, the cooperative drive shafts can be coordinated to balance the torque when one of the cooperative drive shafts begins to slow down or brake the output shaft instead of both cooperative drive shafts accelerating it.

The motors described herein are housed in a tool mount on a robotic arm. In other instances, one or more of the motors can be housed in the robotic tool.

In one aspect, input drivers at an interface of the robotic tool are configured to mechanically and electrically couple with output drivers in a tool mount. As described herein, motors in the tool mount can be configured to deliver rotary drive motions to the drivers in the robotic tool. In other instances, the drivers in the robotic tool can be configured to receive linear drive motions from output drivers in the tool mount. For example, one or more linear drive motions can be transferred across the interface between the tool mount and the robotic tool.

When a single motor is drivingly coupled to an output shaft, the transmission assembly is in a low-torque operating state in comparison to a high-torque operating state in which more than one motor is drivingly coupled to the output shaft. The maximum torque deliverable to the output shaft in the high-torque operating state is greater than the maximum torque deliverable to the output shaft in the low-torque operating state. In one instance, the maximum torque in the high-torque operating state can be double the maximum torque in the low-torque operating state. The maximum torques deliverable to the output shaft can be based on the size and torque capabilities of the motors.

In one aspect, the robotic surgical system includes a processor and a memory communicatively coupled to the processor, as described herein. The memory stores instructions executable by the processor to selectively operably couple a first rotary driver and a second rotary driver to output shafts of a tool housing, wherein one of the first rotary driver and the second rotary driver is configured to supply torque to an output shaft in a low-torque operating state, and wherein the first rotary driver and the second rotary driver are configured to concurrently supply torque to an output shaft in the high-torque operating state, as described herein.

In various aspects, the present disclosure provides a control circuit to selectively operably couple a first rotary driver and/or a second rotary driver to an output shaft as described herein. In various aspects, the present disclosure provides a non-transitory computer readable medium storing computer readable instructions which, when executed, cause a machine to selectively operably couple a first rotary driver and/or a second rotary driver to an output shaft, as described herein.

Another robotic surgical system is depicted in FIGS. 239 and 240. With reference to FIG. 239, the robotic surgical system 13000 includes robotic arms 13002, 13003, a control device 13004, and a console 13005 coupled to the control device 13004. As illustrated in FIG. 239, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Controls for a surgeon's console, such as the console 13005, are further described in International Patent Publication No. WO 2017/075121, filed Oct. 27, 2016, titled HAPTIC FEEDBACK FOR A ROBOTIC SURGICAL SYSTEM INTERFACE, which is herein incorporated by reference in its entirety.

Each of the robotic arms 13002, 13003 is made up of a plurality of members connected through joints and includes a surgical assembly 13010 connected to a distal end of a corresponding robotic arm 13002, 13003. Support of multiple arms is further described in U.S. Patent Application Publication No. 2017/0071693, filed Nov. 11, 2016, titled SURGICAL ROBOTIC ARM SUPPORT SYSTEMS AND METHODS OF USE, which is herein incorporated by reference in its entirety. Various robotic arm configurations are further described in International Patent Publication No. WO 2017/044406, filed Sep. 6, 2016, titled ROBOTIC SURGICAL CONTROL SCHEME FOR MANIPULATING ROBOTIC END EFFECTORS, which is herein incorporated by reference in its entirety. In an exemplification, the surgical assembly 13010 includes a surgical instrument 13020 supporting an end effector 13023. Although two robotic arms 13002, 13003, are depicted, the surgical system 13000 may include a single robotic arm or more than two robotic arms 13002, 13003. Additional robotic arms are likewise connected to the control device 13004 and are telemanipulatable via the console 13005. Accordingly, one or more additional surgical assemblies 13010 and/or surgical instruments 13020 may also be attached to the additional robotic arm(s).

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor 1 . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023. For example, articulation of an end effector by a robotic assembly such as the surgical assembly 13010 is further described in U.S. Patent Application Publication No. 2016/0303743, filed Jun. 6, 2016, titled WRIST AND JAW ASSEMBLIES FOR ROBOTIC SURGICAL SYSTEMS and in International Patent Publication No. WO 2016/144937, filed Mar. 8, 2016, titled MEASURING HEALTH OF A CONNECTOR MEMBER OF A ROBOTIC SURGICAL SYSTEM, each of which is herein incorporated by reference in its entirety. In an exemplification, each motor is configured to actuate a drive rod or a lever arm to affect operation and/or movement of end effectors 13023 in addition to, or instead of, one or more cables.

Driver configurations for surgical instruments, such as drive arrangements for a surgical end effector, are further described in International Patent Publication No. WO 2016/183054, filed May 10, 2016, titled COUPLING INSTRUMENT DRIVE UNIT AND ROBOTIC SURGICAL INSTRUMENT, International Patent Publication No. WO 2016/205266, filed Jun. 15, 2016, titled ROBOTIC SURGICAL SYSTEM TORQUE TRANSDUCTION SENSING, International Patent Publication No. WO 2016/205452, filed Jun. 16, 2016, titled CONTROLLING ROBOTIC SURGICAL INSTRUMENTS WITH BIDIRECTIONAL COUPLING, and International Patent Publication No. WO 2017/053507, filed Sep. 22, 2016, titled ELASTIC SURGICAL INTERFACE FOR ROBOTIC SURGICAL SYSTEMS, each of which is herein incorporated by reference in its entirety. The modular attachment of surgical instruments to a driver is further described in International Patent Publication No. WO 2016/209769, filed Jun. 20, 2016, titled ROBOTIC SURGICAL ASSEMBLIES, which is herein incorporated by reference in its entirety. Housing configurations for a surgical instrument driver and interface are further described in International Patent Publication No. WO 2016/144998, filed Mar. 9, 2016, titled ROBOTIC SURGICAL SYSTEMS, INSTRUMENT DRIVE UNITS, AND DRIVE ASSEMBLIES, which is herein incorporated by reference in its entirety. Various endocutter instrument configurations for use with the robotic arms 13002, 13003 are further described in International Patent Publication No. WO 2017/053358, filed Sep. 21, 2016, titled SURGICAL ROBOTIC ASSEMBLIES AND INSTRUMENT ADAPTERS THEREOF and International Patent Publication No. WO 2017/053363, filed Sep. 21, 2016, titled ROBOTIC SURGICAL ASSEMBLIES AND INSTRUMENT DRIVE CONNECTORS THEREOF, each of which is herein incorporated by reference in its entirety. Bipolar instrument configurations for use with the robotic arms 13002, 13003 are further described in International Patent Publication No. WO 2017/053698, filed Sep. 23, 2016, titled ROBOTIC SURGICAL ASSEMBLIES AND ELECTROMECHANICAL INSTRUMENTS THEREOF, which is herein incorporated by reference in its entirety. Reposable shaft arrangements for use with the robotic arms 13002, 13003 are further described in International Patent Publication No. WO 2017/116793, filed Dec. 19, 2016, titled ROBOTIC SURGICAL SYSTEMS AND INSTRUMENT DRIVE ASSEMBLIES, which is herein incorporated by reference in its entirety.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The remote system "RS" can include any suitable electronic service, database, platform, cloud "C" (see FIG. 239), or the like. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

In accordance with an exemplification, the distal end of each robotic arm 13002, 13003 is configured to releasably secure the end effector 13023 (or other surgical tool) therein and may be configured to receive any number of surgical tools or instruments, such as a trocar or retractor, for example.

A simplified functional block diagram of a system architecture 13400 of the robotic surgical system 13010 is depicted in FIG. 240. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. For example, the core module 13420 maps control devices to the arms 13002, 13003, determines current status, performs all kinematics and frame transformations, and relays resulting movement commands. In this regard, the core module 13420 receives and analyzes data from each of the other modules 13430, 13440, 13450 in order to provide instructions or commands to the other modules 13430, 13440, 13450 for execution within the robotic surgical system 13000. Although depicted as separate modules, one or more of the modules 13420, 13430, 13440, and 13450 are a single component in other exemplifications.

The core module 13420 includes models 13422, observers 13424, a collision manager 13426, controllers 13428, and a skeleton 13429. The models 13422 include units that provide abstracted representations (base classes) for controlled components, such as the motors (for example, Motor 1 . . . n) and/or the arms 13002, 13003. The observers 13424 create state estimates based on input and output signals received from the other modules 13430, 13440, 13450. The collision manager 13426 prevents collisions between components that have been registered within the system 13010. The skeleton 13429 tracks the system 13010 from a kinematic and dynamics point of view. For example, the kinematics item may be implemented either as forward or inverse kinematics, in an exemplification. The dynamics item may be implemented as algorithms used to model dynamics of the system's components.

The surgeon master module 13430 communicates with surgeon control devices at the console 13005 and relays inputs received from the console 13005 to the core module 13420. In accordance with an exemplification, the surgeon master module 13430 communicates button status and control device positions to the core module 13420 and includes a node controller 13432 that includes a state/mode manager 13434, a fail-over controller 13436, and a N-degree of freedom ("DOF") actuator 13438.

The robotic arm module 13440 coordinates operation of a robotic arm subsystem, an arm cart subsystem, a set up arm, and an instrument subsystem in order to control movement of a corresponding arm 13002, 13003. Although a single robotic arm module 13440 is included, it will be appreciated that the robotic arm module 13440 corresponds to and controls a single arm. As such, additional robotic arm modules 13440 are included in configurations in which the system 13010 includes multiple arms 13002, 13003. The robotic arm module 13440 includes a node controller 13442, a state/mode manager 13444, a fail-over controller 13446, and a N-degree of freedom ("DOF") actuator 13348.

The instrument module 13450 controls movement of an instrument and/or tool component attached to the arm 13002, 13003. The instrument module 13450 is configured to correspond to and control a single instrument. Thus, in configurations in which multiple instruments are included, additional instrument modules 13450 are likewise included. In an exemplification, the instrument module 13450 obtains and communicates data related to the position of the end effector or jaw assembly (which may include the pitch and yaw angle of the jaws), the width of or the angle between the jaws, and the position of an access port. The instrument module 13450 has a node controller 13452, a state/mode manager 13454, a fail-over controller 13456, and a N-degree of freedom ("DOF") actuator 13458.

The position data collected by the instrument module 13450 is used by the core module 13420 to determine when the instrument is within the surgical site, within a cannula, adjacent to an access port, or above an access port in free space. The core module 13420 can determine whether to provide instructions to open or close the jaws of the instrument based on the positioning thereof. For example, when the position of the instrument indicates that the instrument is within a cannula, instructions are provided to maintain a jaw assembly in a closed position. When the position of the instrument indicates that the instrument is outside of an access port, instructions are provided to open the jaw assembly.

Additional features and operations of a robotic surgical system, such as the surgical robot system depicted in FIGS. 239 and 240, are further described in the following references, each of which is herein incorporated by reference in its entirety:

U.S. Patent Application Publication No. 2016/0303743, filed Jun. 6, 2016, titled WRIST AND JAW ASSEMBLIES FOR ROBOTIC SURGICAL SYSTEMS;

U.S. Patent Application Publication No. 2017/0071693, filed Nov. 11, 2016, titled SURGICAL ROBOTIC ARM SUPPORT SYSTEMS AND METHODS OF USE;

International Patent Publication No. WO 2016/144937, filed Mar. 8, 2016, titled MEASURING HEALTH OF A CONNECTOR MEMBER OF A ROBOTIC SURGICAL SYSTEM;

International Patent Publication No. WO 2016/144998, filed Mar. 9, 2016, titled ROBOTIC SURGICAL SYSTEMS, INSTRUMENT DRIVE UNITS, AND DRIVE ASSEMBLIES;

International Patent Publication No. WO 2016/183054, filed May 10, 2016, titled COUPLING INSTRUMENT DRIVE UNIT AND ROBOTIC SURGICAL INSTRUMENT;

International Patent Publication No. WO 2016/205266, filed Jun. 15, 2016, titled ROBOTIC SURGICAL SYSTEM TORQUE TRANSDUCTION SENSING;

International Patent Publication No. WO 2016/205452, filed Jun. 16, 2016, titled CONTROLLING ROBOTIC SURGICAL INSTRUMENTS WITH BIDIRECTIONAL COUPLING;

International Patent Publication No. WO 2016/209769, filed Jun. 20, 2016, titled ROBOTIC SURGICAL ASSEMBLIES;

International Patent Publication No. WO 2017/044406, filed Sep. 6, 2016, titled ROBOTIC SURGICAL CONTROL SCHEME FOR MANIPULATING ROBOTIC END EFFECTORS;

International Patent Publication No. WO 2017/053358, filed Sep. 21, 2016, titled SURGICAL ROBOTIC ASSEMBLIES AND INSTRUMENT ADAPTERS THEREOF;

International Patent Publication No. WO 2017/053363, filed Sep. 21, 2016, titled ROBOTIC SURGICAL ASSEMBLIES AND INSTRUMENT DRIVE CONNECTORS THEREOF;

International Patent Publication No. WO 2017/053507, filed Sep. 22, 2016, titled ELASTIC SURGICAL INTERFACE FOR ROBOTIC SURGICAL SYSTEMS;

International Patent Publication No. WO 2017/053698, filed Sep. 23, 2016, titled ROBOTIC SURGICAL ASSEMBLIES AND ELECTROMECHANICAL INSTRUMENTS THEREOF;

International Patent Publication No. WO 2017/075121, filed Oct. 27, 2016, titled HAPTIC FEEDBACK CONTROLS FOR A ROBOTIC SURGICAL SYSTEM INTERFACE;

International Patent Publication No. WO 2017/116793, filed Dec. 19, 2016, titled ROBOTIC SURGICAL SYSTEMS AND INSTRUMENT DRIVE ASSEMBLIES.

The robotic surgical systems and features disclosed herein can be employed with the robotic surgical system of FIGS. 239 and 240. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, the robotic hub 222, and/or the robotic surgical system 15000, for example.

In various instances, a robotic surgical system can include a robotic control tower, which can house the control unit of the system. For example, the control unit 13004 of the robotic surgical system 13000 (FIG. 239) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 13004, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

In certain instances, the activation of a surgical tool at certain times during a surgical procedure and/or for certain durations may cause tissue trauma and/or may prolong a surgical procedure. For example, a robotic surgical system can utilize an electrosurgical tool having an energy delivery surface that should only be energized when a threshold condition is met. In one example, the energy delivery surface should only be activated when the energy delivery surface is in contact with the appropriate, or targeted, tissue. As another example, a robotic surgical system can utilize a suction element that should only be activated when a threshold condition is met, such as when an appropriate volume of fluid is present. Due to visibility restrictions, evolving situations, and the multitude of moving parts during a robotic surgical procedure, it can be difficult for a clinician to determine and/or monitor certain conditions at the surgical site. For example, it can be difficult to determine if an energy delivery surface of an electrosurgical tool is in contact with tissue. It can also be difficult to determine if a particular suctioning pressure is sufficient for the volume of fluid in the proximity of the suctioning port.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. One or more of the surgical devices can include a sensor. For example, multiple sensors can be positioned around the surgical site and/or the operating room. A sensor system including the one or more sensors can be configured to detect one or more conditions at the surgical site. For example, data from the sensor system can determine if a surgical tool mounted to the surgical robot is being used and/or if a feature of the surgical tool should be activated. More specifically, a sensor system can detect if an electrosurgical device is positioned in abutting contact with tissue, for example. As another example, a sensor system can detect if a suctioning element of a surgical tool is applying a sufficient suctioning force to fluid at the surgical site.

When in an automatic activation mode, the robotic surgical system can automatically activate one or more features of one or more surgical tools based on data, images, and/or other information received from the sensor system. For example, an energy delivery surface of an electrosurgical tool can be activated upon detecting that the electrosurgical tool is in use (e.g. positioned in abutting contact with tissue). As another example, a suctioning element on a surgical tool can be activated when the suction port is moved into contact with a fluid. In certain instances, the surgical tool can be adjusted based on the sensed conditions.

A robotic surgical system incorporating an automatic activation mode can automatically provide a scenario-specific result based on detected condition(s) at the surgical site. The scenario-specific result can be outcome-based, for example, and can streamline the decision-making process of the clinician. In certain instances, such an automatic activation mode can improve the efficiency and/or effectiveness of the clinician. For example, the robotic surgical system can aggregate data to compile a more complete view of the surgical site and/or the surgical procedure in order to determine the best possible course of action. Additionally or alternatively, in instances in which the clinician makes fewer decisions, the clinician can be better focused on other tasks and/or can process other information more effectively.

In one instance, a robotic surgical system can automatically adjust a surgical tool based on the proximity of the tool to a visually-detectable need and/or the situational awareness of the system. Referring to FIGS. 241A and 241B, an ultrasonic surgical tool for a robotic system 13050 is depicted in two different positions. In a first position, as depicted in FIG. 241A, the blade 13052 of an ultrasonic surgical tool 13050 is positioned out of contact with tissue 13060. In such a position, a sensor on the ultrasonic surgical tool 13050 can detect a high resistance. When the resistance detected is above a threshold value, the ultrasonic blade 13052 can be de-energized. Referring now to FIG. 241B, the ultrasonic blade 13052 is depicted in a second position in which the distal end of the blade 13052 is positioned in abutting contact with tissue 13060. In such instances, a sensor on the ultrasonic surgical tool 13050 can detect a low resistance. When the detected resistance is below a threshold value, the ultrasonic blade 13052 can be activated such that therapeutic energy is delivered to the tissue 13060. Alternative sensor configurations are also envisioned and various sensors are further described herein.

Referring to FIGS. 242A and 242B, another surgical tool, a monopolar cautery pencil 13055, is depicted in two different positions. In a first position, as depicted in FIG. 242A, the monopolar cautery pencil 13055 is positioned out of contact with tissue. In such a position, a sensor on the monopolar cautery pencil 13055 can detect a high resistance. When the resistance detected is above a threshold value, the monopolar cautery pencil 13055 can be de-energized. Referring now to FIG. 242B, the monopolar cautery pencil 13055 is depicted in a second position in which the distal end of the monopolar cautery pencil 13055 is positioned in abutting contact with tissue. In such instances, a sensor on the monopolar cautery pencil 13055 can detect a low resistance. When the detected resistance is below a threshold value, the monopolar cautery pencil 13055 can be activated such that therapeutic energy is delivered to the tissue. Alternative sensor configurations are also envisioned and various sensors are further described herein.

FIG. 243 shows a graphical display 13070 of continuity C and current I over time t for the ultrasonic surgical tool 13050 of FIGS. 241A and 241B. Similarly, the monopolar cautery pencil 13055 can generate a graphical display similar in many respects to the graphical display 13070, in certain instances. In the graphical display 13070, continuity C is represented by a dotted line, and current I is represented by a solid line. When the resistance is high and above a threshold value, the continuity C can also be high. The threshold value can be between 40 and 400 ohms, for example. At time A', the continuity C can decrease below the threshold value, which can indicate a degree of tissue contact. As a result, the robotic surgical system can automatically activate advanced energy treatment of the tissue. The ultrasonic transducer current depicted in FIG. 243 increases from time A' to B' when the continuity parameters indicate the degree of tissue contact. In various instances, the current I can be capped at a maximum value indicated at B', which can correspond to an open jaw transducer limit, such as in instances in which the jaw is not clamped, as shown in FIGS. 241A and 241B. In various instances, the situational awareness module of the robotic surgical system may indicate that the jaw is unclamped. Referring again to the graphical display 13070 in FIG. 243, energy is applied until time C', at which time a loss of tissue contact is indicated by the increase in continuity C above the threshold value. As a result, the ultrasonic transducer current I can decrease to zero as the ultrasonic blade is de-energized.

In various instances, a sensor system can be configured to detect at least one condition at the surgical site. For example, a sensor of the sensor system can detect tissue contact by measuring continuity along the energy delivery surface of the ultrasonic blade. Additionally or alternatively, the sensor system can include one or more additional sensors positioned around the surgical site. For example, one or more surgical tools and/or instruments being used in the surgical procedure can be configured to detect a condition at the surgical site. The sensor system can be in signal communication with a processor of the robotic surgical system. For example, the robotic surgical system can include a central control tower including a control unit housing a processor and memory, as further described herein. The processor can issue commands to the surgical tool based on inputs from the sensor system. In various instances, situational awareness can also dictate and/or influence the commands issued by the processor.

Turning now to FIG. 244, an end effector 196400 includes RF data sensors 196406, 196408a, 196408b located on jaw member 196402. The end effector 196400 includes jaw member 196402 and an ultrasonic blade 196404. The jaw member 196402 is shown clamping tissue 196410 located between the jaw member 196402 and the ultrasonic blade 196404. A first sensor 196406 is located in a center portion of the jaw member 196402. Second and third sensors 196408a, 196408b, respectively, are located on lateral portions of the jaw member 196402. The sensors 196406, 196408a, 196408b are mounted or formed integrally with a flexible circuit 196412 (shown more particularly in FIG. 245) configured to be fixedly mounted to the jaw member 196402.

The end effector 196400 is an example end effector for various surgical devices described herein. The sensors 196406, 196408a, 196408b are electrically connected to a control circuit via interface circuits. The sensors 196406, 196408a, 196408b are battery powered and the signals generated by the sensors 196406, 196408a, 196408b are provided to analog and/or digital processing circuits of the control circuit.

In one aspect, the first sensor 196406 is a force sensor to measure a normal force $F_3$ applied to the tissue 196410 by the jaw member 196402. The second and third sensors 196408a, 196408b include one or more elements to apply RF energy to the tissue 196410, measure tissue impedance, down force $F_1$, transverse forces $F_2$, and temperature, among other parameters. Electrodes 196409a, 196409b are electrically coupled to an energy source such as an electrical circuit and apply RF energy to the tissue 196410. In one aspect, the first sensor 196406 and the second and third sensors 196408a, 196408b are strain gauges to measure force or force per unit area. It will be appreciated that the measurements of the down force $F_1$, the lateral forces $F_2$, and the normal force $F_3$ may be readily converted to pressure by determining the surface area upon which the force sensors 196406, 196408a, 196408b are acting upon. Additionally, as described with particularity herein, the flexible circuit 196412 may include temperature sensors embedded in one or more layers of the flexible circuit 196412. The one or more temperature sensors may be arranged symmetrically or asymmetrically and provide tissue 196410 temperature feedback to control circuits of an ultrasonic drive circuit and an RF drive circuit.

One or more sensors such as a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure tissue compression and/or impedance.

FIG. 245 illustrates one aspect of the flexible circuit 196412 shown in FIG. 244 in which the sensors 196406, 196408a, 196408b may be mounted to or formed integrally therewith. The flexible circuit 196412 is configured to fixedly attach to the jaw member 196402. As shown particularly in FIG. 245, asymmetric temperature sensors 196414a, 196414b are mounted to the flexible circuit 196412 to enable measuring the temperature of the tissue 196410 (FIG. 244).

The reader will appreciate that alternative surgical tools can be utilized in the automatic activation mode described above with respect to FIGS. 241A-245.

FIG. 246 is a flow chart 13150 depicting an automatic activation mode 13151 of a surgical tool. In various instances, the robotic surgical system and processor thereof is configured to implement the processes indicated in FIG. 246. Initially, a sensor system is configured to detect a condition at step 13152. The detected condition is communicated to a processor, which compares the detected condition to a threshold parameter at step 13154. The threshold parameter can be a maximum value, minimum value, or range of values. If the sensed condition is an out-of-bounds condition, the processor can adjust the surgical function at step 13156 and the processor can repeat the comparison process of steps 13152 and 13154. If the sensed condition is not an out-of-bounds condition, no adjustment is necessary (13158) and the comparison process of steps 13152 and 13154 can be repeated again.

In various instances, the robotic surgical system can permit a manual override mode 13153. For example, upon activation of the manual override input 13160, such as by a clinician, the surgical system can exit the automatic activation mode 13151 at step 13162 depicted in FIG. 246. In such instances, even when a sensed condition is an out-of-bounds condition, the surgical function would not be automatically adjusted by the processor. However, in such instances, the processor can issue a warning or recommendation to the clinician recommending a particular course of action based on the sensed condition(s).

In various instances, an automatic activation mode can be utilized with a robotic surgical system including a suctioning feature. In one instance, a robotic surgical system can communicate with a suction and/or irrigation tool. For example, a suction and/or irrigation device (see module 128 in FIG. 3) can communicate with a robotic surgical system via the surgical hub 106 (FIG. 1) and/or the surgical hub 206 (FIG. 9) and a suction and/or irrigation tool can be mounted to a robotic arm. The suction/irrigation device can include a distal suction port and a sensor. In another instance, a robotic surgical tool, such as an electrosurgical tool, can include a suctioning feature and a suction port on the end effector of the tool.

Referring to FIG. 247, when a suction port on an end effector 13210 is moved into contact with a fluid, a processor of the robotic surgical system can automatically activate the suction feature. For example, a fluid detection sensor 13230 on the tool 13200 can detect fluid 13220 in the proximity of the tool 13200 and/or contacting the tool 13200. The fluid detection sensor 13230 can be a continuity sensor, for example. The fluid detection sensor 13230 can be in signal communication with the processor such that the processor is configured to receive input and/or feedback from the fluid detection sensor 13230. In certain instances, the suctioning feature can be automatically activated when the suction port is moved into proximity with a fluid 13220. For example, when the suction port moves within a predefined spatial range of a fluid 13220, the suction feature can be activated by the processor. The fluid 13220 can be saline, for example, which can be provided to the surgical site to enhance conductivity and/or irrigate the tissue.

In various instances, the tool can be a smoke evacuation tool and/or can include a smoke evacuation system, for example. A detail view of an end effector 13210 of a bipolar radio-frequency surgical tool 13200 is shown in FIG. 247. The end effector 13210 is shown in a clamped configuration. Moreover, smoke and steam 13220 from an RF weld accumulate around the end effector 13210. In various instances, to improve visibility and efficiency of the tool 13200, the smoke and steam 13220 at the surgical site can be evacuated along a smoke evacuation channel 13240 extending proximally from the end effector. The evacuation channel 13240 can extend through the shaft 13205 of the surgical tool 13200 to the interface of the surgical tool 13200 and the robot. The evacuation channel 13240 can be coupled to a pump for drawing the smoke and/or steam 13220 along the smoke evacuation channel 13240 within the shaft 13205 of the surgical tool 13200. In various instances, the surgical tool 13200 can include insufflation, cooling, and/or irrigation capabilities, as well.

In one instance, the intensity of the suction pressure can be automatically adjusted based on a measured parameter from one or more surgical devices. In such instances, the suction pressure can vary depending on the sensed parameters. Suction tubing can include a sensor for detecting the volume of fluid being extracted from the surgical site. When increased volumes of fluid are being extracted, the power to the suction feature can be increased such that the suctioning pressure is increased. Similarly, when decreased volumes of fluid are being extracted, the power to the suction feature can be decreased such that the suctioning pressure is decreased.

In various instances, the sensing system for a suction tool can include a pressure sensor. The pressure sensor can detect when an occlusion is obstructing, or partially obstructing, the fluid flow. The pressure sensor can also detect when the suction port is moved into abutting contact with tissue. In such instances, the processor can reduce and/or pause the suctioning force to release the tissue and/or clear the obstruction. In various instances, the processor can compare the detected pressure to a threshold maximum pressure. Exceeding the maximum threshold pressure may lead to unintentional tissue trauma from the suctioning tool. Thus, to avoid such trauma, the processor can reduce and/or pause the suctioning force to protect the integrity of tissue in the vicinity thereof.

A user can manually override the automatic adjustments implemented in the automatic activation mode(s) described herein. The manual override can be a one-time adjustment to the surgical tool. In other instances, the manual override can be a setting that turns off the automatic activation mode for a specific surgical action, a specific duration, and/or a global override for the entire procedure.

In one aspect, the robotic surgical system includes a processor and a memory communicatively coupled to the processor, as described herein. The processor is communicatively coupled to a sensor system, and the memory stores instructions executable by the processor to determine a use of a robotic tool based on input from the sensor system and to automatically energize an energy delivery surface of the robotic tool when the use is determined, as described herein.

In various aspects, the present disclosure provides a control circuit to automatically energize an energy delivery surface, as described herein. In various aspects, the present disclosure provides a non-transitory computer readable medium storing computer readable instructions which, when executed, cause a machine to automatically energize an energy delivery surface of a robotic tool, as described herein.

In one aspect, the robotic surgical system includes a processor and a memory communicatively coupled to the processor, as described herein. The processor is communicatively coupled to a fluid detection sensor, and the memory stores instructions executable by the processor to receive input from the fluid detection sensor and to automatically activate a suctioning mode when fluid is detected, as described herein.

In various aspects, the present disclosure provides a control circuit to automatically activate a suctioning mode, as described herein. In various aspects, the present disclosure provides a non-transitory computer readable medium storing computer readable instructions which, when executed, cause a machine to automatically activate a suctioning mode, as described herein.

Multiple surgical devices, including a robotic surgical system and various handheld instruments, can be used by a clinician during a particular surgical procedure. When manipulating one or more robotic tools of the robotic surgical system, a clinician is often positioned at a surgeon's command console or module, which is also referred to as a remote control console. In various instances, the remote control console is positioned outside of a sterile field and, thus, can be remote to the sterile field and, in some instances, remote to the patient and even to the operating room. If the clinician desires to use a handheld instrument, the clinician may be required to step away from the remote control console. At this point, the clinician may be unable to control the robotic tools. For example, the clinician may be unable to adjust the position or utilize the functionality of the robotic tools. Upon stepping away from the remote control console, the clinician may also lose sight of one or more displays on the robotic surgical system. The separation between the control points for the handheld instruments and the robotic surgical system may inhibit the effectiveness with which the clinician can utilize the surgical devices, both robotic tools and surgical instruments, together.

In various instances, an interactive secondary display is configured to be in signal communication with the robotic surgical system. The interactive secondary display includes a control module in various instances. Moreover, the interactive secondary display is configured to be wireless and movable around an operating room. In various instances, the interactive secondary display is positioned within a sterile field. In one instance, the interactive secondary display allows the clinician to manipulate and control the one or more robotic tools of the robotic surgical system without having to be physically present at the remote control console. In one instance, the ability for the clinician to operate the robotic surgical system away from the remote control console allows multiple devices to be used in a synchronized manner. As a safety measure, in certain instances, the remote control console includes an override function configured to prohibit control of the robotic tools by the interactive secondary display.

FIG. 248 depicts a surgical system 13100 for use during a surgical procedure that utilizes a surgical instrument 13140 and a robotic surgical system 13110. The surgical instrument 13140 is a powered handheld instrument. The surgical instrument 13140 can be a radio frequency (RF) instrument, an ultrasonic instrument, a surgical stapler, and/or a combination thereof, for example. The surgical instrument 13140 includes a display 13142 and a processor 13144. In certain instances, the handheld surgical instrument 13140 can be a smart or intelligent surgical instrument having a plurality of sensors and a wireless communication module.

The robotic surgical system 13110 includes a robot 13112 including at least one robotic tool 13117 configured to perform a particular surgical function. The robotic surgical system 13110 is similar in many respects to robotic surgical system 13000 discussed herein. The robotic tool 13117 is movable in a space defined by a control envelope of the robotic surgical system 13110. In various instances, the robotic tool 13117 is controlled by various clinician inputs at a remote control console 13116. In other words, when a clinician applies an input at the remote control console 13116, the clinician is away from the patient's body and outside of a sterile field 13138. Clinician input to the remote control console 13116 is communicated to a robotic control unit 13114 that includes a robot display 13113 and a processor 13115. The processor 13115 directs the robotic tool(s) 13117 to perform the desired function(s).

In various instances, the surgical system 13100 includes a surgical hub 13120, which is similar in many respects to the hub 106, the hub 206, the robotic hub 122, or the robotic hub 222, for example. The surgical hub 13120 is configured to enhance cooperative and/or coordinated usage of the robotic surgical system 13110 and the surgical instrument(s) 13140. The surgical hub 13120 is in signal communication with the control unit 13114 of the robotic surgical system 13110 and the processor 13144 of the surgical instrument(s) 13140. In various instances, a signal is transmitted through a wireless connection, although any suitable connection can be used to facilitate the communication. The control unit 13114 of the robotic surgical system 13110 is configured to send information to the surgical hub 13120 regarding the robotic tool(s) 13117. Such information includes, for example, a position of the robotic tool(s) 13117 within the surgical site, an operating status of the robotic tool(s) 13117, a detected force by the robotic tool(s), and/or the type of robotic tool(s) 13117 attached to the robotic surgical system 13110, although any relevant information and/or operating parameters can be communicated. Examples of surgical hubs are further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

In other instances, the robotic surgical system 13110 can encompass the surgical hub 13120 and/or the control unit 13114 can be incorporated into the surgical hub 13120. For example, the robotic surgical system 13110 can include a robotic hub including a modular control tower that includes a computer system and a modular communication hub. One or more modules can be installed in the modular control tower of the robotic hub. Examples of robotic hubs are further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

The processor 13144 of the surgical instrument(s) 13140 is configured to send information to the surgical hub 13120 regarding the surgical instrument 13140. Such information includes, for example, a position of the surgical instrument(s) 13140 within the surgical site, an operating status of the surgical instrument(s) 13140, a detected force by the surgical instrument(s) 13140, and/or identification information regarding the surgical instrument(s) 13140, although any relevant information and/or operating parameters can be sent to the surgical hub.

In various instances, a hub display 13125 is in signal communication with the surgical hub 13120 and may be incorporated into the modular control tower, for example. The hub display 13125 is configured to display information received from the robotic surgical system 13110 and the surgical instrument(s) 13140. The hub display 13125 can be similar in many respects to the visualization system 108 (FIG. 1), for example. In one aspect, the hub display 13125 can include an array of displays such as video monitors and/or heads-up displays around the operating room, for example.

In various instances, the surgical hub 13120 is configured to recognize when the surgical instrument 13140 is activated by a clinician via wireless communication signal(s). Upon activation, the surgical instrument 13140 is configured to send identification information to the surgical hub 13120. Such identification information may include, for example, a model number of the surgical instrument, an operating status of the surgical instrument, and/or a location of the surgical instrument, although other suitable device parameters can be communicated. In various instances, the surgical hub 13120 is configured to utilize the communicated information to assess the compatibility of the surgical instrument 13140 with the capabilities of the surgical hub 13120. Examples of capabilities of the surgical hub with compatible surgical instruments are further discussed herein.

In various instances, the control unit 13114 of the robotic surgical system 13110 is configured to communicate a video feed to the surgical hub 13120, and the surgical hub 13120 is configured to communicate the information, or a portion thereof, to the surgical instrument 13140, which can replicate a portion of the robot display 13113, or other information from the robotic surgical system 13110, on a display 13142 of the surgical instrument 13140. In other instances, the robotic surgical system 13110 (e.g. the control unit 13114 or surgical tool 13117) can communicate directly with the surgical instrument 13140, such as when the robotic surgical system 13110 includes a robotic hub and/or the surgical tool 13117 includes a wireless communication module, for example. The reproduction of a portion of the robot display 13113 on the surgical instrument 13140 allows the clinician to cooperatively use both surgical devices by providing, for example, alignment data to achieve integrated positioning of the surgical instrument 13140 relative to the robotic tool(s) 13117. In various instances, the clinician is able to remove any unwanted information displayed on the display 13142 of the surgical instrument 13140.

Referring still to FIG. 248, in various instances, the surgical system 13100 further includes an interactive secondary display 13130 within the sterile field 13138. The interactive secondary display 13130 is also a local control module within the sterile field 13138. The remote control console 13116, or the primary control, can be positioned outside the sterile field 13138. For example, the interactive secondary display 13130 can be a handheld mobile electronic device, such as an iPad® tablet, which can be placed on a patient or the patient's table during a surgical procedure. For example, the interactive secondary display 13130 can be placed on the abdomen or leg of the patient during the surgical procedure. In other instances, the interactive secondary display 13130 can be incorporated into the surgical instrument 13140 within the sterile field 13138. In various instances, the interactive secondary display 13130 is configured to be in signal communication with the robotic surgical system 13110 and/or the surgical instrument 13140. In such instances, the interactive secondary display 13130 is configured to display information received from the robotic tool(s) 13117 (for example, robotic tool 1, robotic tool 2, . . . robotic tool n) and the surgical instruments 13140 (for example, surgical instrument 1, surgical instrument 2, . . . surgical instrument n). The interactive secondary display 13130 depicts tool information 13133 and instrument information 13135 thereon. In various instances, the user is able to interact with the interactive secondary display 13130 to customize the size and/or location of the information displayed.

Referring still to FIG. 248, in various instances, the surgical hub 13120 is configured to transmit robot status information of the surgical robot system 13100 to the surgical instrument 13140, and the surgical instrument 13140 is configured to display the robot status information on the display 13142 of the surgical instrument 13140.

In various instances, the display 13142 of the surgical instrument 13140 is configured to communicate commands through the surgical hub 13120 to the control unit 13114 of the robotic surgical system 13110. After viewing and interpreting the robot status information displayed on the display 13142 of the surgical instrument 13140 as described herein, a clinician may want to utilize one or more functions of the robotic surgical system 13110. Using the buttons and/or a touch-sensitive display 13142 on the surgical instrument 13140, the clinician is able to input a desired utilization of and/or adjustment to the robotic surgical system 13110. The clinician input is communicated from the surgical instrument 13140 to the surgical hub 13120. The surgical hub 13120 is then configured to communicate the clinician input to the control unit 13114 of the robotic surgical system 13110 for implementation of the desired function. In other instances, the handheld surgical instrument 13140 can communicate directly with the control unit 13114 of the robotic surgical system 13110, such as when the robotic surgical system 13110 includes a robotic hub, for example.

In various instances, the surgical hub 13120 is in signal communication with both the robotic surgical system 13110 and the surgical instrument 13140, allowing the surgical system 13100 to adjust multiple surgical devices in a synchronized, coordinated, and/or cooperative manner. The information communicated between the surgical hub 13120 and the various surgical devices includes, for example, surgical instrument identification information and/or the operating status of the various surgical devices. In various instances, the surgical hub 13120 is configured to detect when the surgical instrument 13140 is activated. In one instance, the surgical instrument 13140 is an ultrasonic dissector. Upon activation of the ultrasonic dissector, the surgical hub 13120 is configured to communicate the received activation information to the control unit 13114 of the robotic surgical system 13110.

In various instances, the surgical hub 13120 automatically communicates the information to the control unit 13114 of the robotic surgical system 13110. The reader will appreciate that the information can be communicated at any suitable time, rate, interval and/or schedule. Based on the information received from the surgical hub 13120, the control unit 13114 of the robotic surgical system 13110 is configured to decide whether to activate at least one robotic tool 13117 and/or activate a particular operating mode, such as a smoke evacuation mode, for example. For example, upon activation of a surgical tool that is known to generate, or possibly generate, smoke and/or contaminants at the surgical site, such as an ultrasonic dissector, the robotic surgical system 13110 can automatically activate the smoke evacuation mode or can cue the surgeon to activate the smoke evacuation mode. In various instances, the surgical hub 13120 is configured to continuously communicate additional information to the control unit 13114 of the robotic surgical system 13110, such as various sensed tissue conditions, in order to adjust, continue, and/or suspend further movement of the robotic tool 13117 and/or the entered operating mode.

In various instances, the surgical hub 13120 may calculate parameters, such as smoke generation intensity, for example, based on the additional information communicated from the surgical instrument 13140. Upon communicating the calculated parameter to the control unit 13114 of the robotic surgical system 13110, the control unit 13114 is configured to move at least one robotic tool and/or adjust the operating mode to account for the calculated parameter. For example, when the robotic surgical system 13110 enters the smoke evacuation mode, the control unit 13114 is configured to adjust a smoke evacuation motor speed to be proportionate to the calculated smoke generation intensity.

In certain instances, an ultrasonic tool mounted to the robot 13112 can include a smoke evacuation feature that can be activated by the control unit 13114 to operate in a smoke evacuation mode. In other instances, a separate smoke evacuation device can be utilized. For example, a smoke evacuation tool can be mounted to another robotic arm and utilized during the surgical procedure. In still other instances, a smoke evacuation instrument that is separate from the robotic surgical system 13110 can be utilized. The surgical hub 13120 can coordinate communication between the robotically-controlled ultrasonic tool and the smoke evacuation instrument, for example.

In FIGS. 249-252, various surgical devices and components thereof are described with reference to a colon resection procedure. The reader will appreciate that the surgical devices, systems, and procedures described with respect to those figures are an exemplary application of the system of FIG. 248. Referring now to FIG. 249, a handle portion 13202 of a handheld surgical instrument 13300 is depicted. In certain aspects, the handheld surgical instrument 13300 corresponds to the surgical instrument 13140 of the surgical system 13100 in FIG. 248. In one instance, the handheld surgical instrument 13300 is a powered circular stapler and includes a display 13310 on the handle portion 13302 thereof.

Before pairing the handheld surgical instrument 13300 to a robotic surgical system (e.g. the robotic surgical system 13110 in FIG. 248) via the surgical hub 13320 (FIG. 250), as described herein, the display 13310 on the handle 13302 of the handheld surgical instrument 13300 can include information regarding the status of the instrument 13300, such as the clamping load 13212, the anvil status 13214, and/or the instrument or cartridge status 13216, for example. In various instances, the display 13310 of the handheld surgical instrument 13300 includes an alert 13318 to the user that communicates the status of the firing system. In various instances, the display 13310 is configured to display the information in a manner that communicates the most important information to the user. For example, in various instances, the display 13310 is configured to display warning information in a larger size, in a flashing manner, and/or in a different color. When the handheld surgical instrument 13300 is not paired with a surgical hub, the display 13310 can depict information gathered only from the handheld surgical instrument 13300 itself.

Referring now to FIG. 250, after pairing the handheld surgical instrument 13300 with the surgical hub 13320, as described herein with respect to FIG. 248, for example, the information detected and displayed by the handheld surgical instrument 13300 can be communicated to the surgical hub 13320 and displayed on a hub display (e.g. the hub display 13125 of FIG. 248). Additionally or alternatively, the information can be displayed on the display of the robotic surgical system. Additionally or alternatively, the information can be displayed on the display 13310 on the handle portion 13302 of the handheld surgical instrument 13300. In various instances, a clinician can decide what information is displayed at the one or multiple locations. As mentioned above, in various instances, the clinician is able to remove any unwanted information displayed on the display 13310 of the handheld surgical instrument 13300, the display of the robotic surgical system, and/or the display on the hub display.

Referring still to FIG. 250, after pairing the handheld surgical instrument 13300 with the robotic surgical system, the display 13310 on the handle portion 13302 of the handheld surgical instrument 13300 can be different than the display 13310 on the handheld surgical instrument 13300 before pairing with the robotic surgical system. For example, procedural information from the surgical hub 13320 and/or robotic surgical system can be displayed on the powered circular stapler. For example, as seen in FIG. 250, robot status information including alignment information 13312 from the surgical hub 13320 and one or more retraction tensions 13316, 13317 exerted by a robotic tool on particular tissue(s), is displayed on the display 13310 of the handheld surgical instrument 13300 for the convenience of the clinician. In various instances, the display 13310 of the handheld surgical instrument 13300 includes an alert 13318 to the user that communicates a parameter monitored by the surgical hub 13320 during a surgical procedure. In various instances, the display 13310 is configured to display the information in a manner that communicates the most important information to the user. For example, in various instances, the display 13310 is configured to display warning information in a larger size, in a flashing manner, and/or in a different color.

Referring still to FIG. 250, the display 13310 of the handheld surgical instrument 13300 is configured to display information regarding one or more retraction tensions 13316, 13317 exerted by one or more devices during a surgical procedure involving one or more robotic tools. For example, the handheld surgical instrument 13300, the powered circular stapler, is involved a the colon resection procedure of FIG. 251. In this procedure, one device (e.g. a robotic tool) is configured to grasp colonic tissue and another device (e.g. the handheld circular stapler) is configured to grasp rectal tissue. As the devices move apart from one another, the force of retracting the colonic tissue $F_{RC}$ and the force of retracting the rectal tissue $F_{RR}$ are monitored. In the illustrated example, an alert notification 13318 is issued to the user as the force of retracting the colonic tissue has exceeded a predetermined threshold. Predetermined thresholds for both retracting forces $F_{RC}$, $F_{RR}$ are indicated by horizontal dotted lines on the display 13310. The user is notified when one or both thresholds are surpassed and/or reached in an effort to minimize damage and/or trauma to the surrounding tissue.

In FIG. 252, graphical displays 13330, 13340 of retracting forces $F_{RC}$, $F_{RR}$ are illustrated. In the circumstances illustrated in the graphical displays 13330, 13340, the user is notified when pre-determined thresholds are exceeded, depicted by the shaded region 13332 of the graphical display 13330, indicating that the retracting force of the colonic tissue $F_{RC}$ has exceeded a predetermined threshold of 0.5 lbs.

In certain instances, it can be difficult to align the end effector of a circular stapler with targeted tissue during a colorectal procedure because of visibility limitations. For example, referring again to FIG. 251, during a colon resection, the surgical instrument 13300, a circular stapler, can be positioned adjacent to a transected rectum 13356. Moreover, the anvil 13301 of the surgical instrument 13300 can be engaged with a transected colon 13355. A robotic tool 133175 is configured to engage the anvil 13301 and apply the retracting force $F_{RC}$. It can be difficult to confirm the relative position of the surgical instrument 13300 with the targeted tissue, for example, with the staple line through the transected colon 13355. In certain instances, information from the surgical hub 13320 and robotic surgical system can facilitate the alignment. For example, as shown in FIG. 250, the center of the surgical instrument 13300 can be shown relative to the center of the targeted tissue 13318 on the display screen 13310 of the surgical instrument 13300. In certain instances, and as shown in FIG. 251, sensors and a wireless transmitter on the surgical instrument 13300 can be configured to convey positioning information to the surgical hub 13320, for example.

A colorectal procedure, visibility limitations thereof, and an alignment tool for a surgical hub are further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

As mentioned above, the display 13310 on the handheld instrument 13300 can also be configured to alert the clinician in certain scenarios. For example, the display 13310 in FIG. 250 includes an alert 13318 because the one or more of the forces exceed the predefined force thresholds. Referring again to FIGS. 251 and 252, during the colon resection, the robotic arm can exert a first force $F_{RC}$ on the anvil, and the handheld instrument 13300 can exert a second force $F_{RR}$ on the rectum 13356. The tension on the rectum 13356 by the circular stapler can be capped at a first limit (for example 0.5 lb in FIG. 252), and the tension on the colon 13355 from the robotic arm can be capped at a second limit (for example 0.5 lb in FIG. 252). An intervention may be suggested to the clinician when the tension on the rectum 13356 or colon 13355 exceeds a threshold value.

The tension on the colon $F_{RC}$ in FIGS. 251 and 252 can be ascertained by resistance to the robotic arm, and thus, can be determined by a control unit (e.g. the control unit 13114 of the robotic surgical system 13110). Such information can be communicated to the handheld surgical instrument 13300 and displayed on the display 13310 thereof in the sterile field such that the information is readily available to the appropriate clinician in real-time, or near real-time, or any suitable interval, rate, and/or schedule, for example.

In various instances, a surgical system, such as a surgical system 13360 of FIGS. 253 and 254, includes interactive secondary displays 13362, 13364 within the sterile field. The interactive secondary displays 13362, 13364 are also mobile control modules in certain instances and can be similar to the interactive secondary displays 13130 in FIG. 248, for example. A surgeon's command console, or remote control module, 13370, is the primary control module and can be positioned outside the sterile field. In one instance, the interactive secondary display 13362 can be a mobile device, a watch, and/or a small tablet, which can be worn on the wrist and/or forearm of the user, and the interactive secondary display 13364 can be a handheld mobile electronic device, such as an iPad® tablet, which can be placed on a patient 13361 or the patient's table during a surgical procedure. For example, the interactive secondary displays 13362, 13364 can be placed on the abdomen or leg of the patient 13361 during the surgical procedure. In other instances, the interactive secondary displays 13362, 13364 can be incorporated into a handheld surgical instrument 13366 within the sterile field.

In one instance, the surgical system 13360 is shown during a surgical procedure. For example, the surgical procedure can be the colon resection procedure described herein with respect to FIGS. 249-252. In such instances, the surgical system 13360 includes a robot 13372 and a robotic tool 13374 extending into the surgical site. The robotic tool can be an ultrasonic device comprising an ultrasonic blade and a clamp arm, for example. The surgical system 13360 also includes the remote command console 13370 that encompasses a robotic hub 13380. The control unit for the robot 13372 is housed in the robotic hub 13380. A surgeon 13371 is initially positioned at the remote command console 13370. An assistant 13367 holds the handheld surgical instrument 13366, a circular stapler that extends into the surgical site. The assistant 13367 also holds a secondary display 13364 that communicates with the robotic hub 13380. The secondary display 13364 is a mobile digital electronic device, which can be secured to the assistant's forearm, for example. The handheld surgical instrument 13366 includes a wireless communication module. A second surgical hub 13382 is also stationed in the operating room. The surgical hub 13382 includes a generator module and can include additional modules as further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

Referring primarily to FIG. 253, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the display 13130). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system, such as the robotic surgical systems 13000 (FIG. 239), 13400 (FIG. 240), 13150 (FIG. 246), 13100 (FIG. 248), and/or the surgical hub 13380, 13382, for example, is programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instances, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In one aspect, the robotic surgical system includes a processor and a memory communicatively coupled to the processor, as described herein. The memory stores instructions executable by the processor to receive a first user input from a console and to receive a second user input from a mobile wireless control module for controlling a function of a robotic surgical tool, as described herein.

In various aspects, the present disclosure provides a control circuit to receive a first user input from a console and to receive a second user input from a mobile wireless control module for controlling a function of a robotic surgical tool, as described herein. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

A robotic surgical system may include multiple robotic arms that are configured to assist the clinician during a surgical procedure. Each robotic arm may be operable independently of the others. A lack of communication may exist between each of the robotic arms as they are independently operated, which may increase the risk of tissue trauma. For example, in a scenario where one robotic arm is configured to apply a force that is stronger and in a different direction than a force configured to be applied by a second robotic arm, tissue trauma can result. For example, tissue trauma and/or tearing may occur when a first robotic arm applies a strong retracting force to the tissue while a second robotic arm is configured to rigidly hold the tissue in place.

In various instances, one or more sensors are attached to each robotic arm of a robotic surgical system. The one or more sensors are configured to sense a force applied to the surrounding tissue during the operation of the robotic arm. Such forces can include, for example, a holding force, a retracting force, and/or a dragging force. The sensor from each robotic arm is configured to communicate the magnitude and direction of the detected force to a control unit of the robotic surgical system. The control unit is configured to analyze the communicated forces and set limits for maximum loads to avoid causing trauma to the tissue in a surgical site. For example, the control unit may minimize the holding force applied by a first robotic arm if the retracting or dragging force applied by a second robotic arm increases.

FIG. 255 depicts a robotic surgical system 13800 including a control unit 13820 and a robot 13810. The robotic surgical system 13800 is similar in many respects to the robotic surgical system 13000 including the robot 13002 (FIG. 239), for example. The control unit 13820 includes a processor 13822 and a display 13824. The robot 13810 includes two robotic arms, 13830, 13840 configured to carry out various surgical functions. Each of the robotic arms 13830, 13840 are independently operable and are free to move in a space defining a control envelope of the robotic surgical system 13800. The one or more robotic arms, 13830, 13840, are configured to receive a tool, such as a stapler, a radio frequency (RF) tool, an ultrasonic blade, graspers, and/or a cutting instrument, for example. Other suitable surgical tool can be used. In various instances, the robotic arms 13830, 13840 each include a different tool configured to perform different functions. In other instances, all of the robotic arms 13830, 13840 include the same tool, although any suitable arrangement can be used.

The first robotic arm 13830 includes a first driver 13834 and a first motor 13836. When activated by the processor 13822, the first motor 13836 drives the first driver 13834 actuating the corresponding component of the first robotic arm 13830. The second robotic arm 13840 includes a second driver, 13844 and a second motor 13846. When activated by the processor 13822, the second motor 13846 drives the second driver 13844 actuating the corresponding component of the second robotic arm 13840.

Each of the robotic arms 13830, 13840, includes a sensor 13832, 13842 in signal communication with the processor 13822 of the control unit 13820. The sensors 13832, 13842 can be positioned on the drivers 13834, 13844, respectively, and/or on the motors 13836, 13846, respectively. In various instances, the sensors 13832, 13842 are configured to detect the location of each individual robotic arm 13830, 13840 within the control envelope of the robotic surgical system 13800. The sensors 13832, 13842 are configured to communicate the detected locations to the processor 13822 of the robotic surgical system 13800. In various instances, the positions of the robotic arms 13830, 13840 are displayed on the display 13824 of the control unit 13820. As described in more detail below, in various instances, the processor 13822 is configured to run an algorithm to implement position limits specific to each robotic arm 13830, 13840 in an effort to avoid tissue trauma and damage to the robotic surgical system 13800, for example. Such position limits may increase the clinician's ability to cooperatively operate numerous robotic arms 13830, 13840 of the robotic surgical system 13800 at the same time.

In various instances, the sensors 13832, 13842 are configured to detect the force exerted by each robotic arm 13830, 13840. The sensors 13832, 13842 can be torque sensors. As stated above, each robotic arm 13830, 13840 of the robotic surgical system 13800 is independently operable. During a particular surgical procedure, a clinician may want to perform different surgical functions with each robotic arm 13830, 13840. Upon detecting the exerted forces of each robotic arm 13830, 13840, each sensor 13832, 13842 is configured to communicate the detected forces to the processor 13822. The processor 13822 is then configured to analyze the communicated information and set maximum and/or minimum force limits for each robotic arm 13830, 13840 to reduce the risk of causing tissue trauma, for example. In addition, the processor 13822 is configured to continuously monitor the exerted forces by each robotic arm 13830, 13840 and, based on the direction and magnitude of the exerted forces, proportionally control each robotic arm 13830, 13840 with respect to one another. For example, the opposing force between two robotic arms 13830, 13840 can be measured and maintained below a maximum force limit. To maintain the opposing force below a maximum force limit, at least one of the forces can be reduced, which can result in displacement of the robotic arm 13830, 13840.

By way of example, FIG. 256 depicts a surgical site and a portion of the surgical system 13800, which includes three robotic arms, including a robotic arm 13850 (a third robotic arm) in addition to the robotic arms 13830 and 13840, which are also schematically depicted in FIG. 255. The first robotic arm 13830 is configured to hold a portion of stomach connective tissue. In order to hold the portion of stomach connective tissue, the first robotic arm 13830 exerts an upward force $F_{IR}$. The second robotic arm 13840 applies a dragging and/or cutting force $F_{D2}$ to the tissue. Simultaneously, the third robotic arm 13850 retracts a portion of liver tissue away from the current surgical cut location, further exposing the next surgical cut location. In order to move the portion of liver tissue out of the way of the advancing second robotic arm 13840, the third robotic arm 13850 applies a retracting force $F_{R3}$ away from the second robotic arm 13840. In various exemplifications, as the second robotic arm 13840 advances further into the surgical site, the control unit of the robotic surgical system directs the third robotic arm 13850 to increase the exerted retracting force $F_{R3}$ to continue exposing the next surgical cut location. While FIG. 256 depicts a particular surgical procedure and specific robotic arms, any suitable surgical procedure can be performed, and any suitable combination of robotic arms can utilize the control algorithms disclosed herein.

FIG. 257 depicts graphical representations 13852, 13854 of the forces exerted by the robotic arms 13830, 13840, and 13850 of FIG. 256 and the relative locations of the robotic arm 13830, 13840, and 13850, respectively, from the particular surgical procedure detailed above. The graphical display 13852 in FIG. 257 represents the exerted forces of each robotic arm 13830, 13840, and 13850 over a period of time, while the graphical display 13854 represents the relative positions of each robotic arm 13830, 13840, and 13850 over the same period of time. As discussed above, the first robotic arm 13830 is configured to exert a holding force $F_{IR}$ on a portion of stomach connective tissue. The holding force $F_{H1}$ is represented by a solid line on the graphs 13852, 13854. The second robotic arm 13840 is configured to exert a dragging and/or cutting force $F_{D2}$ on the stomach connective tissue. The dragging force $F_{D2}$ is represented by a dash-dot line on the graphs 13852, 13854. The third robotic arm 13850 is configured to exert a retracting force $F_{R3}$ on a portion of liver tissue. The retracting force $F_{R3}$ is represented by a dotted line on the graphs 13852, 13854.

In various instances, the control unit of the robotic surgical system imposes at least one force threshold, such as a maximum force threshold, as depicted in the graphical display 13852. Thus, the third robotic arm 13850 is prevented from exerting a retraction force $F_{R3}$ greater than the maximum retraction force threshold. Such maximum force limits are imposed in order to avoid tissue trauma and/or avoid damage to the various robotic arms 13830, 13840, and 13850, for example.

Additionally or alternatively, the control unit 13820 of the robotic surgical system 13800 can impose least one force threshold, such as a minimum force threshold, as depicted in the graphical display 13852. In the depicted instance, the first robotic arm 13830 is prevented from exerting a holding force $F_{H1}$ less than the minimum holding force threshold. Such minimum force limits are imposed in order to avoid maintain appropriate tissue tension and/or visibility of the surgical site, for example.

In various instances, the control unit 13820 of the robotic surgical system 13800 imposes maximum force differentials detected between various robotic arms during a load control mode. In order to set maximum force differentials, the control unit 13820 of the robotic surgical system is configured to continuously monitor the difference in magnitude and direction of opposing forces by the robotic arms. As stated above, the first robotic arm 13830 is configured to hold a portion of the stomach connective tissue by exerting a holding force $F_{H1}$. The second robotic arm 13840 is configured to apply a dragging force $F_{D2}$, which opposes the holding force $F_{H1}$ exerted by the first robotic arm 13830. In various instances, maximum force differentials prevent inadvertent overloading and/or damaging an object caught between the robotic arms 13830, 13840, and 13850. Such objects include, for example, surrounding tissue and/or surgical components like clasps, gastric bands, and/or sphincter reinforcing devices. $F_{max\ opposing}$ represents the maximum force differential set by the control unit 13820 in this particular exemplification.

As can be seen in the graphical display 13852, the holding force $F_{IR}$ and the dragging force $F_{D2}$ both increase in magnitude at the beginning of the surgical procedure. Such an increase in magnitudes can indicate a pulling of the tissue. The holding force $F_{H1}$ and the dragging force $F_{D2}$ increase in opposite directions to a point where the difference between the opposing forces is equal to $F_{max\ opposing}$. In the graphic display 13852, the slanted lines highlight the point in time when $F_{max\ opposing}$ is reached. Upon reaching $F_{max\ opposing}$, the processor 13822 instructs the first robotic arm 13830 to reduce the holding force $F_{H1}$ and continues to allow the second robotic arm 13840 to exert the dragging force $F_{D2}$ at the same value, and may allow a clinician to increase the dragging force. In various instances, the value of $F_{max\ opposing}$ is set by the processor 13822 based on various variables, such as the type of surgery and/or relevant patient demographics. In various instances, $F_{max\ opposing}$ is a default value stored in a memory of the processor 13822.

The relative positions of the robotic arms 13830, 13840, and 13850 within the surgical site are depicted in the graph display 13854 of FIG. 257. As the first robotic arm 13830 exerts a holding force $F_{H1}$ on the stomach connective tissue and the third robotic arm 13850 exerts a retracting force $F_{R3}$ on the liver tissue, the surgical site becomes clear and allows the second robotic arm 13840 to exert a dragging and/or cutting force $F_{D2}$ on the desired tissue. The second robotic arm 13840 and the third robotic arm 13850 become farther away from the first robotic arm 13830 as the procedure progresses. When the force differential $F_{max\ opposing}$ is reached between the holding force $F_{H1}$ and the dragging force $F_{D2}$, the first robotic arm 13830 is moved closer towards the second robotic arm 13840, lessening the exerted holding force $F_{H1}$ by the first robotic arm 13830. In one aspect, the processor 13822 can transition the first robotic arm 13830 from the load control mode into a position control mode such that the position of the first robotic arm 13830 is held constant. As depicted in the graphical representations of FIG. 257, when the first robotic arm 13830 is held in a constant position, the force control for the second robotic arm 13840 can continue to displace the second robotic arm 13840.

In various instances, the control unit 13820 of the robotic surgical system directs the first robotic arm 13830 to hold a specific position until a pre-determined force threshold between the first robotic arm 13830 and a second robotic arm 13840 is reached. When the pre-determined force threshold is reached, the first robotic arm 13830 is configured to automatically move along with the second robotic arm 13840 in order to maintain the pre-determined force threshold. The first robotic arm 13830 stops moving (or may move at a different rate) when the detected force of the second robotic arm 13840 no longer maintains the pre-determined force threshold.

In various instances, the control unit 13820 of the robotic surgical system is configured to alternate between the position control mode and the load control mode in response to detected conditions by the robotic arms 13830, 13840, and 13850. For example, when the first robotic arm 13830 and the second robotic arm 13840 of the robotic surgical system 13800 are freely moving throughout a surgical site, the control unit 13820 may impose a maximum force that each arm 13830, 13840 can exert. In various instances, the first and second arms 13830, 13840 each include a sensor configured to detect resistance. In other instances, the sensors can be positioned on a surgical tool, such as an intelligent surgical stapler or jawed tool. A resistance can be encountered upon contact with tissue and/or other surgical instruments. When such resistance is detected, the control unit 13820 may activate the load control mode and lower the exerted forces by one and/or more than one of the robotic arms 13830, 13840 to, for example, reduce damage to the tissue. In various instances, the control unit 13820 may activate the position control mode and move the one and/or more than one of the robotic arms 13830, 13840 to a position where such resistance is no longer detected.

In one aspect, the processor 13822 of the control unit 13820 is configured to switch from the load control mode to the position control mode upon movement of a surgical tool mounted to one of the robotic arms 13830, 13840 outside a defined surgical space. For example, if one of the robotic arms 13830, 13840 moves out of a defined boundary around the surgical site, or into abutting contact with an organ or other tissue, or too close to another surgical device, the processor 13822 can switch to a position control mode and prevent further movement of the robotic arm 13830, 13840 and/or move the robotic arm 13830, 13840 back within the defined surgical space.

Turning now to the flow chart shown in FIG. 258, an algorithm 13500 is initiated at step 13501 when the clinician and/or the robotic surgical system activates one or more of the robotic arms at step 13505. The algorithm 13500 can be employed by the robotic surgical system 13800 in FIG. 255, for example. Each robotic arm is in signal communication with the processor 13822 of the robotic surgical system. Following activation, each robotic arm is configured to send information to the processor. In various instances, the information may include, for example, identification of the tool attachment and/or the initial position of the activated robotic arm. In various instances, such information is communicated automatically upon attachment of the tool to the robotic arm, upon activation of the robotic arm by the robotic surgical system, and/or after interrogation of the robotic arm by the processor, although the information may be sent at any suitable time. Furthermore, the information may be sent automatically and/or in response to an interrogation signal.

Based on the information gathered from each of the activated robotic arms at step 13510, the processor is configured to set a position limit for each specific robotic arm within a work envelope of the robotic surgical system at step 13515. The position limit can set three-dimensional boundaries for where each robotic arm can travel. The setting of position limits allows for efficient and cooperative usage of each activated robotic arm while, for example, preventing trauma to surrounding tissue and/or collisions between activated robotic arms. In various instances, the processor includes a memory including a set of stored data to assist in defining each position limit. The stored data can be specific to the particular surgical procedure, the robotic tool attachment, and/or relevant patient demographics, for example. In various instances, the clinician can assist in the definition of the position limit for each activated robotic arm. The processor is configured to determine if the robotic arms are still activated at step 13520. If the processor determines that the robotic arms are no longer activated, the processor is configured to end position monitoring at step 13522. Once the processor determines that the robotic arms are still activated, the processor is configured to monitor the position of each activated robotic arm at step 13525.

The processor is then configured to evaluate whether the detected position is within the predefined position limit(s) at step 13530. In instances where information is unable to be gathered from the robotic arm and clinician input is absent, a default position limit is assigned at step 13533. Such a default position limit assigns a conservative three-dimensional boundary to minimize, for example, tissue trauma and/or collisions between robotic arms. If the detected limit is within the position limit, the processor is configured to allow the robotic arm(s) to remain in position and/or freely move within the surgical site at step 13535, and the monitoring process continues as long as the robotic arm is still activated. If the detected limit is outside of the position limit, the processor is configured to move the robotic arm back into the position limit at step 13532, and the monitoring process continues as long as the robotic arm is still activated.

The processor is configured to continuously monitor the position of each robotic arm at step 13525. In various instances, the processor is configured to repeatedly send interrogation signals in pre-determined time intervals. As discussed above, if the detected position exceeds the position limit set for the specific robotic arm, in certain instances, the processor is configured to automatically move the robotic arm back within the three-dimensional boundary at step 13532. In certain instances, the processor is configured to re-adjust the position limits of the other robotic arms in response to one robotic arm exceeding its original position limit. In certain instances, prior to moving the robotic arm back within its position limit and/or adjusting the position limits of the other robotic arms, the processor is configured to alert the clinician. If the detected position is within the position limit set for the robotic arm, the processor permits the robotic arm to remain in the same position and/or freely travel until the detected position exceeds the position limit at step 13535. If the processor is unable to detect the position of the robotic arm, the processor is configured to alert the clinician and/or assign the robotic arm with the default position limit at step 13533. The processor is configured to monitor the position of each robotic arm until the surgery is completed and/or the robotic arm is deactivated.

Similar to the algorithm of FIG. 258, the flow chart of FIG. 259 depicts an algorithm 13600 that is initiated at step 13601 when a clinician and/or a robotic surgical system activates one or more of the robotic arms at step 13605. The algorithm 13600 can be employed by the robotic surgical system 13800 in FIG. 255, for example. Each robotic arm is in signal communication with the processor. Following activation, each robotic arm is configured to send information to the processor at step 13610. In various instances, the information may include, for example, identification of the tool attachment, exerted forces detected by one or more force sensors on the robotic arm, and/or the initial position of the activated robotic arm. In various instances, such information is communicated automatically upon attachment of the tool to the robotic arm, upon activation of the robotic arm by the robotic surgical system, and/or after interrogation of the robotic arm by the processor, although the information may be sent at any suitable time. Furthermore, the information may be sent automatically and/or in response to an interrogation signal.

Based on the information gathered from each of the activated robotic arms, the processor is configured to set a force limit for each specific robotic arm at step 13615. The force limit sets maximum and minimum force thresholds for forces exerted by each robotic arm. Additionally or alternatively, a force limit can be the maximum force differential between two or more arms. The setting of force limits allows for efficient and cooperative usage of all of the activated robotic arms while, for example, preventing trauma to surrounding tissue and/or damage to the robotic arms. In various instances, the processor includes a memory including a set of stored data to assist in defining each force limit. The stored data can be specific to the particular surgical procedure, the robotic tool attachment, and/or relevant patient demographics, for example. In various instances, the clinician can assist in the definition of the force limit for each activated robotic arm. In instances where information is unable to be gathered from the robotic arm and clinician input is absent, a default force limit is assigned. Such a default force limit assigns conservative maximum and minimum force thresholds to minimize, for example, tissue trauma and/or damage to the robotic arms.

The processor is configured to determine if the robotic arm is active at step at step 13620. If the processor determines that the robotic arm has been deactivated, the processor is configured to end force monitoring at step 13622. Once it has been determined that the robotic arm is still activated at step 13620, the processor is configured to continuously monitor the force exerted by each robotic arm at step 13625. In various instances, the processor is configured to repeatedly send interrogation signals in pre-determined time intervals. If the detected force exceeds the maximum force threshold set for the specific robotic arm, in certain instances, the processor is configured to automatically decrease the force exerted by the robotic arm and/or decrease an opposing force exerted by another robotic arm at step 13632. In certain instances, the processor is configured to re-adjust the force limits assigned to the other robotic arms in response to one robotic arm exceeding its original force limits. In certain instances, prior to adjusting the force exerted by the robotic arm, adjusting the opposing force exerted by another robotic arm, and/or adjusting the force limits of the other robotic arms, the processor is configured to alert the clinician. If the detected force is within the force limit set for the robotic arm, the robotic arm is permitted to maintain the exertion of the force and/or the clinician can increase or decrease the exerted force until the force is out of the set force limit at step 13635. If the processor is unable to detect the exerted force of the robotic arm, the processor is configured to alert the clinician and/or assign the robotic arm with a default force limit at step 13633. The processor is configured to monitor the exerted force of each robotic arm until the surgery is completed and/or the robotic arm is deactivated at step 13620.

Similar to the algorithms of FIGS. 258 and 259, the flow chart of FIG. 260 depicts an algorithm 13700 that is initiated 13701 when a clinician and/or a robotic surgical system activates one or more of the robotic arms 13705. The algorithm 13700 can be employed by the robotic surgical system 13800 in FIG. 255, for example. Each robotic arm is in signal communication with the processor. Following activation, each robotic arm is configured to send information to the processor at step 13710. In various instances, the information may include, for example, identification of the tool attachment, forces detected by one or more force sensors on the robotic arm, and/or the initial position of the activated robotic arm. In various instances, such information is communicated automatically upon attachment of the tool to the robotic arm, upon activation of the robotic arm by the robotic surgical system, and/or after interrogation of the robotic arm by the processor, although the information may be sent at any suitable time. In various instances, the information is sent automatically and/or in response to an interrogation signal.

Based on the information gathered from all of the activated robotic arms, the processor is configured to set both a position limit within a work envelope of the robotic surgical system and a force limit for each specific robotic arm at step 13715. The position limit sets three-dimensional boundaries for where each robotic arm can travel. The setting of position limits allows for efficient and cooperative usage of all of the activated robotic arms while, for example, preventing trauma to surrounding tissue and/or collisions between activated robotic arms. The force limit sets maximum and/or minimum force thresholds for forces exerted by each robotic arm. Additionally or alternatively, a force limit can be the maximum force differential between two or more arms. The setting of force limits allows for efficient and cooperative usage of the activated robotic arms while, for example, preventing trauma to surrounding tissue and/or damage to the robotic arms.

In various instances, the processor includes a memory including a set of stored data to assist in defining each position limit and force limit. The stored data can be specific to the particular surgical procedure, the robotic tool attachment, and/or relevant patient demographics, for example. In various instances, the clinician can assist in the definition of the position limit and force limit for each activated robotic arm. In instances where information is unable to be gathered from the robotic arm and clinician input is absent, a default position limit and/or default force limit is assigned to the robotic arm. Such a default position limit assigns a conservative three-dimensional boundary to minimize, for example, tissue trauma and/or collisions between robotic arms, while the default force limit assigns conservative maximum and/or minimum force thresholds to minimize, for example, tissue trauma and/or damage to the robotic arms. In various instances, the processor is configured to adjust the position limit of one robotic arm based on the force limit of another robotic arm, adjust the force limit of one robotic arm based on the position limit of another robotic arm, and vice versa.

The processor is configured to determine whether the robotic arm is active at step 13720. Once the processor has determined that the robotic arm is activated at step 13720, the processor is configured to continuously monitor the position of each arm 13737 and the force exerted by each robotic arm at step 13725. If the robotic arm is no longer activated, the processor is configured to end position monitoring at step 13727 and end force monitoring at step 13722. In various instances, the processor is configured to repeatedly send interrogation signals in pre-determined time intervals. If the detected position exceeds the position limit set for the specific robotic arm, in certain instances, the processor is configured to automatically move the robotic arm back within the three-dimensional boundary at step 13742. In certain instances, prior to moving the robotic arm back within its position limit, the processor is configured to alert the clinician. If the detected position is within the position limit set for the robotic arm, the robotic arm is permitted to remain in the same position and/or freely travel until the detected position exceeds the position limit at step 13745. If the processor is unable to detect the position of the robotic arm, the processor is configured to alert the clinician and/or rewrite the original position limit of the robotic arm with the default position limit at step 13743. The processor is configured to monitor the position of each robotic arm until the surgery is completed and/or the robotic arm is deactivated.

In certain instances, the robotic surgical system includes a manual override configured to control the position of each robotic arm. If the detected force exceeds the maximum force threshold set for the specific robotic arm, in certain instances, the processor is configured to automatically decrease the force exerted by the robotic arm and/or decrease an opposing force exerted by another robotic arm at step 13732. In certain instances, prior to decreasing the force exerted by the robotic arm and/or decrease the opposing force exerted by another robotic arm, the processor is configured to alert the clinician. If the detected force is within the force limit set for the robotic arm, the robotic arm is permitted to maintain the exertion of the force and/or increase or decrease the exerted force until the force is out of the set force limit at step 13735. If the processor is unable to detect the exerted force of the robotic arm, the processor is configured to alert the clinician and/or rewrite the original force limit of the robotic arm with the default force limit at step 13733. The processor is configured to monitor the exerted force of each robotic arm until the surgery is completed and/or the robotic arm is deactivated.

In various instances, the position monitoring system and the force monitoring system are interconnected. In certain instances, the force monitoring system can override the resultant decision 13742, 14743, 14745 of the position detection step 13740. In certain instances, the position monitoring system can override the resultant decision 13732, 13733, 13735 of the force detection step 13730. In other instances, the position monitoring system and the force monitoring system are independent of one another.

A clinician can manually override the automatic adjustments implemented in the automatic load and/or position control mode(s) described herein. The manual override can be a one-time adjustment to the surgical robot. In other instances, the manual override can be a setting that turns off the automatic load and/or position mode for a specific surgical action, a specific duration, and/or a global override for the entire procedure.

In one aspect, the robotic surgical system includes a processor and a memory communicatively coupled to the processor, as described herein. The processor is communicatively coupled to a first force sensor and a second force sensor, and the memory stores instructions executable by the processor to affect cooperative movement of a first robotic arm and a second robotic arm based on a first input from the first force sensor and from a second input from the second force sensor in a load control mode, as described herein.

In various aspects, the present disclosure provides a control circuit to affect cooperative movement of a first robotic arm and a second robotic arm, as described herein. In various aspects, the present disclosure provides a non-transitory computer readable medium storing computer readable instructions which, when executed, cause a machine to affect cooperative movement of a first robotic arm and a second robotic arm, as described herein.

During a particular surgical procedure, clinicians may rely on one or more powered handheld surgical instruments in addition to a robotic surgical system. In various instances, the instruments are controlled and monitored through different platforms, which may inhibit communication between the instruments and the robotic surgical system. For example, the instruments can be produced by different manufacturers and even by competitors. Such instruments may have different communication packages and/or communication and/or linking protocols. The lack of communication between a powered instrument and the robotic surgical system may hinder cooperative and/or coordinated usage and may complicate the surgical procedure for the clinician. For example, each surgical instrument may include an individual display to communicate various information and operating parameters. In such a scenario, a clinician may have to look at numerous instrument-specific displays to monitor the operating status of and analyze data gathered by each device.

In various instances, a robotic surgical system is configured to detect the presence of other powered surgical instruments that are controlled by platforms other than the robotic surgical system. The robotic surgical system can incorporate a hub, i.e., a robotic hub like the robotic hubs 122 (FIG. 2) and 222 (FIG. 9), which can detect other powered surgical instruments, for example. In other instances, a stand-alone surgical hub like the hub 106 (FIGS. 1-3) or the hub 206 (FIG. 9) in communication with the robotic surgical system can facilitate detection of the non-robotic surgical instruments and cooperative and/or coordinated usage of the detected surgical instruments with the robotic surgical system. The hub, which can be a robotic hub or a surgical hub, is configured to display the position and orientation of the powered surgical instruments with respect to the work envelope of the robotic surgical system. In certain instances, the work envelope can be an operating room, for example. A surgical hub having spatial awareness capabilities is further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety. In one aspect, the hub can first ascertain the boundaries of the work envelope and then detect the presence of other powered surgical instruments within the work envelope.

FIG. 261 depicts a surgical system 13860 including a robotic surgical system 13865, a surgical instrument 13890, and a surgical hub 13870. The surgical instrument 13890 is a powered handheld instrument, and can be a motorized surgical stapler, such as the motorized linear stapler depicted in FIG. 262, for example. The surgical system 13865 can be similar in many respects to the robotic surgical system 13000 (FIG. 239), for example. As described herein, the surgical hub 13870 can be incorporated into the robotic surgical system 13865, for example. The surgical hub 13870 is configured to be in signal communication with the robotic surgical system 13865 and the surgical instrument 13890. In other instances, the surgical system 13860 can include additional handheld surgical instruments. The robotic surgical system 13865 includes a robot 13861, which can be similar to the robot 13002, for example. The robotic surgical system 13865 also includes a control unit 13862 and a surgeon's command console, or remote control module, 13864. The surgeon's command console 13864 is configured to receive a clinician input. The control unit 13862 includes a robot display 13868 and a processor 13866. The surgical instrument 13890 includes a display 13894 and a processor 13892.

In various instances, the surgical hub 13870 includes a surgical hub display 13880, which can be similar to the displays of the visualization system 108 (FIG. 1). The surgical hub display 13880 can include, for example, a heads up display. The surgical hub 13880 is configured to detect the presence of the surgical instrument 13890 within a certain distance of the surgical hub 13870. For example, the surgical hub 13870 is configured to detect the presence of all activated surgical instruments 13890 within one operating room, although any suitable distance can be monitored. In various instances, the surgical hub 13870 is configured to display the presence of all activated surgical instruments 13890 on the surgical hub display 13880.

A particular handheld surgical instrument communicates via a first communication process through a first language. A particular robotic surgical system communicates via a second communication process through a second language. In various instances, the first communication process is the same as the second communication process. When the first communication process is the same as the second communication process, the surgical instrument 13890 is configured to directly communicate information to the surgical hub 13870 and/or to the robotic surgical system 13865. Such information includes, for example, a model number and/or type of the surgical instrument, a position of the surgical instrument, an operating status of the surgical instrument, and/or any other relevant parameter of the surgical instrument.

In various instances, the first communication process is different from the second communication process. For example, a surgical system (e.g. a robot) developed by a first manufacturer may utilize a first proprietary language or communication scheme and a surgical system (e.g. a handheld surgical tool) developed by a second manufacturer may utilize a second, different proprietary language or communication scheme. Despite the language difference/barrier, the surgical hub 13870 and/or surgical robot 13865 is configured to sense surgical instruments 13890 that operate on different communication processes. When the surgical hub 13870 does not recognize the communication process utilized by a particular powered handheld surgical instrument, the surgical hub 13870 is configured to detect various signals, such as Wi-Fi and Bluetooth transmissions emitted by activated powered handheld surgical instruments. Based on the detected signal transmissions, the surgical hub 13870 is configured to alert the clinician of all powered handheld surgical instruments that do not use the same communication process as the robotic surgical system 13865. All data received from newly-detected powered handheld surgical instruments can be stored within the surgical hub 13870 so that the newly-detected powered handheld surgical instruments are recognized by the surgical hub 13870 in the future.

In various instances, the surgical hub 13870 is configured to detect the presence of powered handheld surgical instruments by sensing a magnetic presence of a battery, power usage, and/or electro-magnetic field emitted from activated powered handheld surgical instruments, regardless of whether the activated powered handheld surgical instruments made any attempt to communicate with another surgical instrument, such as the robotic surgical system.

The robot 13861 and the surgical instrument 13890 are exemplified in an example surgical procedure in FIG. 262. In this exemplification, the surgical instrument 13890 is an articulating linear stapler. As depicted in FIG. 262, the surgical instrument 13890 includes a motor 13895 in the handle 13892 thereof. In other instances, the surgical instrument 13890 can include a plurality of motors positioned throughout the surgical instrument. The motor 13895 is configured to emit an electromagnetic field 13896, which can be detected by the robotic surgical system 13865 or the surgical hub 13870. For example, the main robot tower or the modular control tower of the surgical hub 13870 can include a receiver for detecting the electromagnetic fields within the operating room.

In one aspect, a processor of the robotic surgical system (e.g. a processor of the control unit 13862) is configured to calculate a boundary around the surgical instrument 13890. For example, based on the electromagnetic field 13896 and corresponding type of surgical instrument, the processor can determine the dimensions of the surgical instrument 13890 and possible range of positions thereof. For example, when the surgical instrument 13890 includes one or more articulation joints 13891, the range of positions can encompass the articulated positions of the surgical instrument 13890.

In one instance, the robotic surgical system can calculate a first wider boundary $B_2$ around the surgical instrument. When a robotic surgical tool approaches the wider boundary $B_2$, the robotic surgical tool 13861 can issue a notification or warning to the surgeon that the robotic surgical tool attached to the robot 13861 is approaching another surgical instrument 13890. In certain instances, if the surgeon continues to advance the robotic surgical tool toward the surgical instrument 13890 and to a second narrower boundary $B_1$, the robotic surgical system 13865 can stop advancing the robotic surgical tool. For example, if the robotic surgical tool crosses the narrower boundary $B_1$, advancement of the robotic surgical tool can be stopped. In such instances, if the surgeon still desires to continue advancing the robotic surgical tool within the narrower boundary $B_1$, the surgeon can override the hard stop feature of the robotic surgical system 13865.

Referring again to FIG. 261, the surgical system 13860 includes multiple display monitors. Each handheld surgical instrument 13890 and the robotic surgical system 13865 is configured to communicate a video and/or image feed representative of the display on each device to the surgical hub 13870 and/or the hub display 13880. Such video and/or image feeds can include operating parameters of and/or detected conditions by each handheld surgical instrument 13890 and/or the robotic surgical system 13865. The hub 13870 is configured to control the displayed video and/or image feeds on each of the one or more display monitors throughout the system 13800. In various instances, each of the display monitors displays an individual video and/or image feed from a particular surgical device or system. In various instances, the individual video and/or image feed can be overlaid with additional information and/or video and/or image feeds from other devices or systems. Such information can include operating parameters and/or detected conditions. The surgical hub 13870 is configured to request which display monitor displays which video and/or image feed. In other words, the communication link between the surgical hub 13870 and the hub display 13880 allows the surgical hub 13870 to dictate which video and/or image feed is assigned to which display monitor, while direct control of the one or more display monitors remains with the video hub. In various instances, the hub display 13880 is configured to separate one or more of the display monitors from the surgical hub 13870 and allow a different surgical hub or surgical device to display relevant information on the separated display monitors.

In various instances, the surgical hub is configured to communicate stored data with other data systems within an institution data barrier allowing for cooperative utilization of data. Such established data systems may include, for example, an electronic medical records (EMR) database. The surgical hub is configured to utilize the communication between the surgical hub and the EMR database to link overall surgical trends for the hospital with local data sets recorded during use of the surgical hub.

In various instances, the surgical hub is located in a particular operating room at a hospital and/or surgery center. As shown in FIG. 263, the hospital and/or surgery center includes operating rooms, $OR_1$, $OR_2$, $OR_3$, and $OR_4$. Three of the operating rooms $OR_2$, $OR_3$, and $OR_4$ shown in FIG. 263 includes a surgical hub 13910, 13920, 13930, respectively, however any suitable number of surgical hubs can be used. Each surgical hub 13910, 13920, 13930 is configured to be in signal communication with one another, represented by signal arrows A. Each surgical hub 13910, 13920, 13930 is also configured to be in signal communication with a primary server 13940, represented by signal arrows B in FIG. 263.

In various exemplifications, as data is communicated between the surgical hub(s) 13910, 13920, 13930 and the various surgical instruments during a surgical procedure, the surgical hub(s) 13910, 13920, 13930 are configured to temporarily store the communicated data. At the end of the surgical procedure and/or at the end of a pre-determined time period, each surgical hub 13910, 13920, 13930 is configured to communicate the stored information to the primary server 13940. Once the stored information is communicated to the primary server 13940, the information can be deleted from the memory of the individual surgical hub 13910, 13920, 13930. The stored information is communicated to the primary server 13940 to alleviate the competition amongst the surgical hubs 13910, 13920, 13930 for bandwidth to transmit the stored data to cloud analytics "C", for example. Instead, the primary server 13940 is configured to compile and store and communicated data. The primary server 13940 is configured to be the single clearinghouse for communication of information back to the individual surgical hubs 13910, 13920, 13930 and/or for external downloading. In addition, as all of the data is stored in one location in the primary server 13940, the data is better protected from data destructive events, such as power surges and/or data intrusion, for example. In various instances, the primary server 13940 includes additional server-level equipment that allows for better data integrity. Examples of cloud systems are further described herein and in U.S. Provisional Patent Application Ser. No. 62/611,340, titled CLOUD-BASED MEDICAL ANALYTICS, filed Dec. 28, 2017, the disclosure of which is herein incorporated by reference in its entirety.

Referring to FIGS. 263 and 264, as data begins to be communicated from each control hub 13910, 13920, 13930 to the primary server 13940, a queue 13990 is created to prioritize the order in which data is communicated. In various instances, the queue 13990 prioritizes data as first in, first out, although any suitable prioritization protocol can be used. In various instances, the queue 13990 is configured to re-prioritize the order in which received data is communicated when priority events and/or abnormal data are detected. As illustrated in FIG. 264, a first surgical hub communicates a first set of data at a time t=1 at block 13960. As the first set of data is the only data in the queue for external output at block 13992, the first set of data is the first to be communicated. Thus, the queue 13990 prioritizes the first set of data for external output at block 13965. A second surgical hub communicates a second set of data at a time t=2 at block 13970. At the time t=2, the first set of data has not been externally communicated at block 13994. However, because no priority events and/or abnormal data are present in the second set of data, the second set of data is the second in line to be externally communicated at block 13975. A third surgical hub communicates a third set of data flagged as urgent at a time t=3 at block 13980. At the time t=3, the first set of data and the second set of data have not been externally communicated, however a priority event has been detected in the third set of data at block 13985. The queue is configured to re-prioritize the sets of data to allow the prioritized third set of data to be in the first position for external output at block 13996 above the first set of data and the second set of data collected at time t=1 and t=2, respectively.

In one aspect, the surgical hub includes a processor and a memory communicatively coupled to the processor, as described herein. The memory stores instructions executable by the processor to detect the presence of a powered surgical instrument and represent the powered surgical instrument on a hub display, as described herein.

In various aspects, the present disclosure provides a control circuit to detect the presence of a powered surgical instrument and represent the powered surgical instrument on a hub display, as described herein. In various aspects, the present disclosure provides a non-transitory computer readable medium storing computer readable instructions which, when executed, cause a machine to detect the presence of a powered surgical instrument and represent the powered surgical instrument on a hub display, as described herein.

Another robotic surgical system is the VERSIUS® robotic surgical system by Cambridge Medical Robots Ltd. of Cambridge, England. An example of such a system is depicted in FIG. 265. Referring to FIG. 265, the surgical robot includes an arm 14400 which extends from a base 14401. The arm 14400 includes a number of rigid limbs 14402 that are coupled together by revolute joints 14403. The most proximal limb 14402a is coupled to the base 14401 by a joint 14403a. The most proximal limb 14402a and the other limbs (e.g. limbs 14402b and 14402c) are coupled in series to further limbs at the joints 14403. A wrist 14404 can be made up of four individual revolute joints. The wrist 14404 couples one limb (e.g. limb 14402b) to the most distal limb (e.g. the limb 14402c in FIG. 265) of the arm 14400. The most distal limb 14402c carries an attachment 14405 for a surgical tool 14406. Each joint 14403 of the arm 14400 has one or more motors 14407, which can be operated to cause rotational motion at the respective joint, and one or more position and/or torque sensors 14408, which provide information regarding the current configuration and/or load at that joint 14403. The motors 14407 can be arranged proximally of the joints 14403 whose motion they drive, so as to improve weight distribution, for example. For clarity, only some of the motors and sensors are shown in FIG. 265. The arm 14400 may be generally as described in Patent Application PCT/GB2014/053523 and International Patent Application Publication No. WO 2015/025140, titled DISTRIBUTOR APPARATUS WITH A PAIR OF INTERMESHING SCREW ROTORS, filed Aug. 18, 2014, which published on Feb. 26, 2015, and which is herein incorporated by reference in its entirety. Torque sensing is further described in U.S. Patent Application Publication No. 2016/0331482, titled TORQUE SENSING IN A SURGICAL ROBOTIC WRIST, filed May 13, 2016, which published on Nov. 17, 2016, which is herein incorporated by reference in its entirety.

The arm 14400 terminates in the attachment 14405 for interfacing with the surgical tool 14406. The attachment 14405 includes a drive assembly for driving articulation of the surgical tool 14406. Movable interface elements of a drive assembly interface mechanically to engage corresponding movable interface elements of the tool interface in order to transfer drive motions from the robot arm 14400 to the surgical tool 14406. One surgical tool may be exchanged for another surgical tool one or more times during a typical operation. The surgical tool 14406 can be attachable and detachable from the robot arm 14400 during the operation. Features of the drive assembly interface and the tool interface can aid in their alignment when brought into engagement with each other, so as to reduce the accuracy with which they need to be aligned by the user. A bar for guiding engagement of a robotic arm and surgical tool is further described in U.S. Patent Application Publication No. 2017/0165012, titled GUIDING ENGAGEMENT OF A ROBOT ARM AND SURGICAL INSTRUMENT, filed Dec. 9, 2016, which published on Jun. 15, 2017, which is herein incorporated by reference in its entirety.

The surgical tool 14406 further includes an end effector for performing an operation. The end effector may take any suitable form. For example, the end effector may include smooth jaws, serrated jaws, a gripper, a pair of shears, a needle for suturing, a camera, a laser, a knife, a stapler, one or more electrodes, an ultrasonic blade, a cauterizer, and/or a suctioner. Alternative end effectors are further described herein. The surgical tool 14406 can include an articulation junction between the shaft and the end effector, which can permit the end effector to move relative to the shaft of the tool. The joints in the articulation junction can be actuated by driving elements, such as pulley cables. Pulley arrangements for articulating the surgical tool 14406 are described in U.S. Patent Application Publication No. 2017/0172553, titled PULLEY ARRANGEMENT FOR ARTICULATING A SURGICAL INSTRUMENT, filed Dec. 9, 2016, which published on Jun. 22, 2017, which is herein incorporated by reference in its entirety. The driving elements for articulating the surgical tool 14406 are secured to the interface elements of the tool interface. Thus, the robot arm 14400 can transfer drive motions to the end effector as follows: movement of a drive assembly interface element moves a tool interface element, which moves a driving element in the tool 14406, which moves a joint of the articulation junction, which moves the end effector. Control of a robotic arm and tool, such as the arm 14400 and the tool 14406, are further described in U.S. Patent Application Publication No. 2016/0331482, titled TORQUE SENSING IN A SURGICAL ROBOTIC WRIST, filed May 13, 2016 and which was published on Nov. 17, 2016, and in International Patent Application Publication No. WO 2016/116753, titled ROBOT TOOL RETRACTION, filed Jan. 21, 2016 and which was published on Jul. 28, 2016, each of which is herein incorporated by reference in its entirety.

Controllers for the motors 14407 and the sensors 14408 (e.g. torque sensors and encoders) are distributed within the robot arm 14400. The controllers are connected via a communication bus to a control unit 14409. Examples of communication paths in a robotic arm, such as the arm 14400, are further described in U.S. Patent Application Publication No. 2017/0021507, titled DRIVE MECHANISMS FOR ROBOT ARMS and in U.S. Patent Application Publication No. 2017/0021508, titled GEAR PACKAGING FOR ROBOTIC ARMS, each of which was filed Jul. 22, 2016 and published on Jan. 26, 2017, and each of which is herein incorporated by reference in its entirety. The control unit 14409 includes a processor 14410 and a memory 14411. The memory 14411 can store software in a non-transient way that is executable by the processor 14410 to control the operation of the motors 14407 to cause the arm 14400 to operate in the manner described herein. In particular, the software can control the processor 14410 to cause the motors 14407 (for example via distributed controllers) to drive in dependence on inputs from the sensors 14408 and from a surgeon command interface 14412.

The control unit 14409 is coupled to the motors 14407 for driving them in accordance with outputs generated by execution of the software. The control unit 14409 is coupled to the sensors 14408 for receiving sensed input from the sensors 14408, and to the command interface 14412 for receiving input from it. The respective couplings may, for example, each be electrical or optical cables, and/or may be provided by a wireless connection. The command interface 14412 includes one or more input devices whereby a user can request motion of the end effector in a desired way. The input devices could, for example, be manually operable mechanical input devices such as control handles or joysticks, or contactless input devices such as optical gesture sensors. The software stored in the memory 14411 is configured to respond to those inputs and cause the joints of the arm 14400 and the tool 14406 to move accordingly, in compliance with a pre-determined control strategy. The control strategy may include safety features which moderate the motion of the arm 144400 and the tool 14406 in response to command inputs. In summary, a surgeon at the command interface 14412 can control the surgical tool 14406 to move in such a way as to perform a desired surgical procedure. The control unit 14409 and/or the command interface 14412 may be remote from the arm 14400.

Additional features and operations of a surgical robot system, such as the robotic surgical system depicted in FIG. 265, are further described in the following references, each of which is herein incorporated by reference in its entirety:

International Patent Application Publication No. WO 2016/116753, titled ROBOT TOOL RETRACTION, filed Jan. 21, 2016, which published on Jul. 28, 2016;

U.S. Patent Application Publication No. 2016/0331482, titled TORQUE SENSING IN A SURGICAL ROBOTIC WRIST, filed May 13, 2016, which published on Nov. 17, 2016;

U.S. Patent Application Publication No. 2017/0021507, titled DRIVE MECHANISMS FOR ROBOT ARMS, filed Jul. 22, 2016, which published on Jan. 27, 2017;

U.S. Patent Application Publication No. 2017/0021508, titled GEAR PACKAGING FOR ROBOTIC ARMS, filed Jul. 22, 2016, which published on Jan. 27, 2017;

U.S. Patent Application Publication No. 2017/0165012, titled GUIDING ENGAGEMENT OF A ROBOT ARM AND SURGICAL INSTRUMENT, filed Dec. 9, 2016, which published on Jun. 15, 2017; and U.S. Patent Application Publication No. 2017/0172553, titled PULLEY ARRANGEMENT FOR ARTICULATING A SURGICAL INSTRUMENT, filed Dec. 9, 2016, which published on Jun. 22, 2017.

In one instance, the robotic surgical systems and features disclosed herein can be employed with the VERSIUS® robotic surgical system and/or the robotic surgical system of FIG. 265. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, the robotic hub 222, and/or the robotic surgical system 15000, for example.

In various instances, a robotic surgical system can include a robotic control tower, which can house the control unit of the system. For example, the control unit 14409 of the robotic surgical system depicted in FIG. 265 can be housed within a robotic control tower. The robotic control tower can include a robot hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, a suction module, an irrigation module, a smoke evacuation module, and/or a communication module, for example.

The reader will readily appreciate that the computer-implemented interactive surgical system 100 (FIG. 1) and the computer-implemented interactive surgical system 200 (FIG. 9) disclosed herein can incorporate the robotic arm 14400. Additionally or alternatively, the robotic surgical system depicted in FIG. 265 can include various features and/or components of the computer-implemented interactive surgical systems 100 and 200.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 14409, for example. In various instances, the situational awareness module can obtain data and/or information from a non-robotic surgical hub and/or a cloud, such as the surgical hub 106, the surgical hub 206, the cloud 104, and/or the cloud 204, for example. Situational awareness of a surgical system is further disclosed herein and in U.S. Provisional Patent Application Ser. No. 62/611,341, titled INTERACTIVE SURGICAL PLATFORM, filed Dec. 28, 2017, and in U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

Referring again to FIG. 265, the robotic arm 14400 does not include a linear slide mechanism for moving the attached surgical tool 14406 along a longitudinal axis of the tool 14406. Rather, the limbs 14402 of the arm 14400 are configured to rotate about the various joints 14403 of the arm 14400 to move the surgical tool 14406. In other words, even movement of the surgical tool 14406 along the longitudinal axis $A_T$ thereof requires the articulation of various limbs 14402. For example, to move the surgical tool 14406 along the longitudinal axis $A_T$, the robotic arm 14400 would move at multiple revolute joints 14403 thereof. In effect, linear displacement of the tool 14406 for extending the end effector through a trocar, retracting the end effector from the trocar, and/or for localized displacements of the surgical tool 14406 along the longitudinal axis $A_T$, such as during a suturing process, for example, would require the actuation of multiple revolute joints 14403 and the corresponding movement of multiple rigid limb portions 14402 of the arm 14400.

In instances in which a robotic surgical system lacks a linear slide mechanism, as described herein, intelligent sensing systems, additional communication paths, and/or interactive displays can enable more precise control of the robotic arm including the implementation of control motions that involve a linear displacement of the surgical tool along an axis thereof. For example, to ensure the accurate positioning of the tool 14406 and to avoid inadvertent collisions within an operating room, it may be desirable to include additional systems in the robotic system for determining the position of a surgical tool 14406 and/or portions of the robotic arm 14400, for repositioning of the robotic arm 14400 from within the sterile field, for communicating the position of the surgical tool 14406 relative to the surgical site, for visualizing the surgical tool 14406 at the surgical site, and/or for manipulating the surgical tool 14406 around the surgical site, for example.

In one aspect, a robotic surgical system can include a primary control mechanism for positioning the tool and a secondary means for directly and/or independently measuring the position of the tool. In one aspect, a redundant or secondary sensing system can be configured to determine and/or verify a position of a robotic arm and/or a surgical tool attached to the robotic arm. The secondary sensing system can be independent of a primary sensing system.

In one instance, the primary control mechanism can rely on closed-loop feedback to calculate the position of the tool. For example, a control unit of a robotic surgical system can issue control motions for the robotic arm, including the various motors and/or drivers thereof to move portions of the robotic arm in a three-dimensional space, as further described herein. Such a control unit can determine the position and/or orientation of the portions of the robotic arm based on torque sensors on the motors and/or displacement sensors on the drivers, for example. In such instances, the position of the surgical tool, the end effector, and/or components thereof can be determined by proximally-located sensors. The proximally-located sensors can be located in a proximal housing or mounting portion of the tool and/or the robotic arm. In one instance, such proximally-located sensors can be positioned outside the sterile field, for example. The position of a surgical tool mounted to a robotic arm can be determined by measuring the angle(s) of each joint of the arm, for example. The control unit and sensors in communication therewith, which determine the position of the arm based on the control motions delivered thereto, can be considered a primary or first sensing system of the robotic surgical system.

In addition to a primary sensing system, as described herein, a redundant or secondary sensing system can be employed by the robotic surgical system. The secondary sensing system can include one or more distally-located sensors. The distally-located sensors can be positioned within the sterile field and/or on the end effector, for example. The distally-located sensors are distal to the proximally-located sensors of the primary sensing system, for example. In one instance, the distally-located sensors can be "local" sensors because they are local to the sterile field and/or the surgical site, and the proximally-located sensors can be "remote" sensors because they are remote from the sterile field and/or the surgical site.

Referring now to FIG. 273, portions of a robotic surgical system 14300 are schematically depicted. The robotic surgical system 14300 is similar in many respects to the robotic surgical system of FIG. 265. For example, the robotic surgical system 14300 includes a plurality of movable components 14302. In one aspect, the movable components 14302 are rigid limbs that are mechanically coupled in series at revolute joints. Such moveable components 14302 can form a robotic arm, similar to the robotic arm 14440 (FIG. 265), for example. The distal-most component 14302 includes an attachment for releasably attaching interchangeable surgical tools, such as the surgical tool 14306, for example. Each component 14302 of the robotic arm has one or more motors 14307 and motor drivers 14314, which can be operated to affect rotational motion at the respective joint.

Each component 14302 includes one or more sensors 14308, which can be position sensors and/or torque sensors, for example. The sensors 14308 can provide information regarding the current configuration and/or load at the respective joint between the components 14402. The motors 14307 can be controlled by a control unit 14309, which is configured to receive inputs from the sensors 14308 and/or from a surgical command interface, such as surgical command interface 14412 (FIG. 265), for example.

A primary sensing system 14310 is incorporated into the control unit 14309. In one aspect, the primary sensing system 14310 can be configured to detect the position of one or more components 14302. For example, the primary sensing system 14310 can include the sensors 14308 for the motors 14307 and/or the drivers 14314. Such sensors 14308 are remote from the patient P and located outside of the sterile field. Though located outside of the sterile field, the primary sensing system 14310 can be configured to detect the position(s) of the component(s) 14302 and/or the tool 14306 within the sterile field, such as at the position of the distal end of the robotic arm and/or the attachment portion thereof. Based on the position of the robotic arm and components 14302 thereof, the control unit 14309 can extrapolate the position of the surgical tool 14306, for example.

The robotic surgical system 14300 of FIG. 273 also includes a secondary sensing system 14312 for directly tracking the position and/or orientation or various parts of the robotic surgical system 14300 and/or parts of an associated, non-robotic system such as handheld surgical instruments 14350. Referring still to FIG. 273, the secondary sensing system 14312 includes a magnetic field emitter 14320 that is configured to emit a magnetic field in the vicinity of one or more magnetic sensors to detect the positions thereof. Components 14302 of the robotic arm include magnetic sensors 14322, which can be utilized to determine and/or verify the position of the respective components 14302. The magnetic sensors 14322 are remote to the motors 14307 and the drivers 14308, for example. In any event, the torque through the motor and/or the displacement of a driver may not affect the output from the magnetic sensors. Consequently, the sensing systems are independent.

In certain instances, the magnetic sensors 14322 can be positioned within the sterile field. For example, the surgical tool 14306 can include the magnetic sensor 14324, which can be utilized to determine and/or verify the position of the surgical tool 14306 attached to the robotic arm and/or to determine and/or verify the position of a component of the surgical tool 14306, such as a firing element, for example. Additionally or alternatively, one or more patient sensors 14326 can be positioned within the patient P to measure the patient's location and/or anatomic orientation. Additionally or alternatively, one or more trocar sensors 14328 can be positioned on a trocar 14330 to measure the trocar's location and/or orientation, for example.

Referring again to the robotic arm 14400 depicted in FIG. 265, the surgical tool 14406 is attached to the attachment portion 14405 at the distal end of the robotic arm 14400. When the surgical tool 14406 is positioned within a trocar, the robotic surgical system can establish a virtual pivot which can be fixed by the robotic surgical system, such that the arm 14400 and/or the surgical tool 14406 can be manipulated thereabout to avoid and/or minimize the application of lateral forces to the trocar. In certain instances, applying force(s) to the trocar may damage the surrounding tissue, for example. Thus, to avoid inadvertent damage to tissue, the robotic arm 14400 and/or the surgical tool 14406 can be configured to move about the virtual pivot of the trocar without upsetting the position thereof and, thus, without upsetting the corresponding position of the trocar. Even when applying a linear displacement of the surgical tool 14406 to enter or exit the trocar, the virtual pivot can remain undisturbed.

In one aspect, the trocar sensor(s) 14328 in FIG. 273A can be positioned at a virtual pivot 14332 on the trocar 14330. In other instances, the trocar sensors 14328 can be adjacent to the virtual pivot 14332. Placement of the trocar sensors 14328 at and/or adjacent to the virtual pivot 14332 thereof can track the position of the trocar 14330 and virtual pivot 14332 and help to ensure that the trocar 14330 does not move during displacement of the surgical tool 14306, for example. In such instances, without physically engaging or holding the trocar 14330, the robotic surgical system 14300 can confirm and/or maintain the location of the trocar 14330. For example, the secondary sensing system 14312 can confirm the location of the virtual pivot 14332 of the trocar 14330 and the surgical tool 14306 relative thereto.

Additionally or alternatively, one or more sensors 14352 can be positioned on one or more handheld surgical instruments 14350, which can be employed during a surgical procedure in combination with the surgical tools 14306 utilized by the robotic surgical system 14300. The secondary sensing system 14312 is configured to detect the position and/or orientation of one or more handheld surgical instruments 14350 within the surgical field, for example, within the operating room and/or sterile field. Such handheld surgical instruments 14350 can include autonomous control units, which may not be robotically controlled, for example. As depicted in FIG. 273, the handheld surgical instruments 14350 can include sensors 14352, which can be detected by the magnetic field emitter 14320, for example, such that the position and/or location of the handheld surgical instruments 14350 can be ascertained by the robotic surgical system 14300. In other instances, components of the handheld surgical instruments 14350 can provide a detectable output. For example, a motor and/or battery pack can be detectable by a sensor in the operating room.

In one aspect, the magnetic field emitter 14320 can be incorporated into a main robot tower. The sensors 14322, 14324, 14326, 14328, and/or 14352 within the sterile field can reflect the magnetic field back to the main robot tower to identity the positions thereof. In various instances, data from the magnetic field emitter 14320 can be communicated to a display 14340, such that the position of the various components of the surgical robot, surgical tool 14302, trocar 14330, patient P, and/or handheld surgical instruments 14350 can be overlaid onto a real-time view of the surgical site, such as views obtained by an endoscope at the surgical site. For example, the display 14340 can be in signal communication with the control unit of the robotic surgical system and/or with a robotic hub, such as the hub 106, robotic hub 122, the hub 206, and/or the robot hub 222 (FIG. 9), for example.

In other instances, the magnetic field emitter 14320 can be external to the robot control tower. For example, the magnetic field emitter 14320 can be incorporated into a hub.

Similar to the secondary sensing system 14312, which includes the magnetic field emitter 14320, in certain instances, time-of-flight sensors can be positioned on one or more of the robot component(s) 14302, the surgical tool(s) 14306, the patient P, the trocar(s) 14328, and/or the handheld surgical instrument(s) 14350 to provide an array of distances between the emitter and the reflector points. Such time-of-flight sensors can provide primary or secondary (e.g. redundant) sensing of the position of the robot component(s) 14302, the surgical tool(s) 14306, the patient P, the trocar(s) 14328, and/or the handheld surgical instrument(s) 14350, for example. In one instance, the time-of-flight sensor(s) can employ an infrared light pulse to provide distance mapping and/or facilitate 3D imaging within the sterile field.

In one instance, the secondary sensing system 14312 can include a redundant sensing system that is configured to confirm the position of the robotic components and/or tools. Additionally or alternatively, the secondary sensing system 14312 can be used to calibrate the primary sensing system 14310. Additionally or alternatively, the secondary sensing system 14312 can be configured to prevent inadvertent entanglement and/or collisions between robotic arms and/or components of a robotic surgical system.

Referring again to FIG. 273, in one instance, the components 14302 of the robotic surgical system 14300 can correspond to discrete robotic arms, such as the robotic arms 15024 in the robotic surgical system 15000 (FIG. 22) and/or the robotic arms depicted in FIG. 2, for example. The secondary sensing system 14312 can be configured to detect the position of the robotic arms and/or portions thereof as the multiple arms are manipulated around the surgical theater. In certain instances, as one or more arms are commanded to move towards a potential collision, the secondary sensing system 14312 can alert the surgeon via an alarm and/or an indication at the surgeon's console in order to prevent an inadvertent collision of the arms.

Referring now to FIG. 274, a flow chart for a robotic surgical system is depicted. The flow chart can be utilized by the robotic surgical system 14300 (FIG. 273), for example. In various instances, two independent sensing systems can be configured to detect the location and/or orientation of a surgical component, such as a portion of a robotic arm and/or a surgical tool. The first sensing system, or primary sensing system, can rely on the torque and/or load sensors on the motors and/or motor drivers of the robotic arm. The second sensing system, or secondary sensing system, can rely on magnetic and/or time-of-flight sensors on the robotic arm and/or surgical tool. The first and second sensing systems are configured to operate independently and in parallel. For example, at step 14502, the first sensing system determines the location and orientation of a robotic component and, at step 14504, communicates the detected location and orientation to a control unit. Concurrently, at step 14506, the second sensing system determines the location and orientation of the robotic component and, at step 14508, communicates the detected location and orientation to the control unit.

The independently-ascertained locations and orientations of the robotic component are communicated to a central control unit at step 14510, such as to the robotic control unit 14309 and/or a surgical hub. Upon comparing the locations and/or orientations, the control motions for the robotic component can be optimized at step 14512. For example, discrepancies between the independently-determined positions can be used to improve the accuracy and precision of control motions. In certain instances, the control unit can calibrate the control motions based on the feedback from the secondary sensing system. The data from the primary and secondary sensing systems can be aggregated by a hub, such as the hub 106 or the hub 206, for example, and/or data stored in a cloud, such as the cloud 104 or the cloud 204, for example, to further optimize the control motions of the robotic surgical system.

In certain instances, the robotic system 14300 can be in signal communication with a hub, such as the hub 106 of the hub 206, for example. The hubs 106, 206 can include a situational awareness module, as further described herein. In one aspect, at least one of the first sensor system 14310 and the second sensor system 14312 are data sources for the situational awareness module. For example, the sensor systems 14310 and 14312 can provide position data to the situational awareness module. Further, the hub 106, 206 can be configured to optimize and/or calibrate the control motions of the robotic arm 14300 and/or the surgical tool 14306 based on the data from the sensor systems in combination with the situational awareness, for example. In one aspect, a sensing system, such as the secondary sensing system 14312 can inform the hub 106, 206 and situational awareness module thereof when a handheld surgical instrument 14350 has entered the operating room or surgical theater and/or when an end effector has been fired, for example. Based on such information, the hub 106, 206 can determine and/or confirm the particular surgical procedure and/or step thereof.

The reader will appreciate that various independent and redundant sensing systems disclosed herein can be utilized by a robotic surgical system to improve the accuracy of the control motions, especially when moving the surgical tool along a longitudinal axis without relying on a linear slide mechanism, for example.

In one aspect, the surgical hub includes a processor and a memory communicatively coupled to the processor, as described herein. The memory stores instructions executable by the processor to detect a position of a robotically-controlled component independent of a primary sensing system, as described above.

In various aspects, the present disclosure provides a control circuit configured to detect a position of a robotically-controlled component independent of a primary sensing system, as described above. In various aspects, the present disclosure provides a non-transitory computer readable medium storing computer readable instructions which, when executed, cause a machine to detect a position of a robotically-controlled component independent of a primary sensing system, as described above.

In one aspect, a robotic surgical system can be configured to wirelessly communicate with one or more intelligent surgical tools mounted to a robotic arm thereof. The control unit of the robotic system can communicate with the one or more intelligent surgical tools via a wireless connection, for example. Additionally or alternatively, the robotic surgical system can include a robotic hub, which can wirelessly communicate with the intelligent surgical tool(s) mounted to the robotic arm(s). In still other instances, a non-robotic surgical hub can wirelessly communicate with the intelligent surgical tool(s) mounted to a robotic arm. In certain instances, information and/or commands can be provided to the intelligent surgical tool(s) from the control unit via the wireless connection. For example, certain functions of a surgical tool can be controlled via data received through a wireless communication link on the surgical tool. Similarly, in one aspect, closed-loop feedback can be provided to the robotic surgical system via data received via the wireless communication link to the surgical tool.

Referring primarily to FIGS. 270-272, a surgical tool 14206 is mounted to a robotic arm 14000 of a surgical robot. The robotic arm 14000 is similar in many respects to the robotic arm 14400 in FIG. 265. For example, the arm 14000 includes a plurality of movable components 14002. In one aspect, the movable components 14002 are rigid limbs that are mechanically coupled in series at revolute joints 14003. Such moveable components 14002 form the robotic arm 14400, similar to the arm 14400 (FIG. 265), for example. A distal-most component 14002c of the robotic arm 14400 includes an attachment 14005 for releasably attaching interchangeable surgical tools, such as the surgical tool 14206. Each component 14002 of the arm 14000 has one or more motors and motor drivers, which can be operated to affect rotational motion at the respective joint 14003.

Each component 14002 includes one or more sensors, which can be position sensors and/or torque sensors, for example, and can provide information regarding the current configuration and/or load at the respective joint between the components 14002. The motors can be controlled by a control unit, such as the control unit 14409 (FIG. 265), which is configured to receive inputs from the sensors 14008 and/or from a command interface, such as the surgeon's command console 14412 (FIG. 265), for example.

The surgical tool 14206 is a linear stapler including a wireless communication module 14208 (FIG. 271). The linear stapler can be an intelligent linear stapler and can include an intelligent fastener cartridge, an intelligent end effector, and/or an intelligent shaft, for example. Intelligent surgical components can be configured to determine various tissue properties, for example. In one instance, one or more advanced end effector functions may be implemented based on the detected tissue properties. A surgical end effector can include one or more sensors for determining tissue thickness, compression, and/or impedance, for example. Moreover, certain sensed parameters can indicate tissue variations, such as the location of a tumor, for example. Intelligent surgical devices for sensing various tissue properties are further disclosed the following references:

U.S. Pat. No. 9,757,128, filed Sep. 5, 2014, titled MULTIPLE SENSORS WITH ONE SENSOR AFFECTING A SECOND SENSOR'S OUTPUT OR INTERPRETATION, which issued on Sep. 12, 2017;

U.S. patent application Ser. No. 14/640,935, titled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071, which published on Sep. 8, 2016;

U.S. patent application Ser. No. 15/382,238, titled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591, which published on Jul. 20, 2017; and U.S. patent application Ser. No. 15/237,753, titled CONTROL OF ADVANCEMENT RATE AND APPLICATION FORCE BASED ON MEASURED FORCES, filed Aug. 16, 2016, now U.S. Patent Application Publication No. 2018/0049822, which published on Feb. 22, 2018;

each of which is herein incorporated by reference in its entirety.

As depicted in FIG. 270, a wireless communication link 14210 is provided between the surgical tool 14206 and a hub 14212. The hub 14212 is a surgical hub, like the hub 106 or the hub 206, for example. In other instances, the hub 14212 can be a robotic hub, like the robotic hub 122 or the robotic hub 222, for example. In FIG. 270, the wireless communication module 14208 includes a wireless signal transmitter that is located near the distal end of the end effector of the surgical tool 14206. In other instances, the wireless transmitter can be positioned on a proximal portion of the end effector or on the shaft of the surgical tool 14206.

The wireless communication link 14212 between the surgical tool 14206 and the surgical hub 14212 provides real-time data transfer through a sterile barrier 14230. Additionally or alternatively, the wireless communication module 14208 can be configured to communicate with a robot control tower and/or the control unit, which issues the control motions to the robotic arm 14000 and actuations to the surgical tool 14206 based on inputs at the surgeon's command console. In certain instances, the control unit for the robotic arm 14000 can be incorporated into the surgical hub 14212 and/or a robotic hub, such as the robotic hub 122 (FIG. 2) or the robotic hub 222 (FIG. 9), for example.

In certain instances, it can be difficult to confirm the position of the surgical tool 14206 within the surgical theater, around the surgical site, and/or relative to the targeted tissue. For example, lateral displacement of the surgical tool 14206 can be constrained by a physical boundary, such as a longitudinally-extending trocar, for example. In such instances, lateral displacement of the surgical tool 14206 can be determined by a resistance force from and/or on the trocar. Conversely, linear displacement of the surgical tool 14206 can be unconstrained by physical boundaries of the surgical system. In such instances, when the control unit directs linear displacement of the surgical tool 14206 or a portion thereof, and the various movable links 14002 and joints 14003 articulate to affect the linear displacement, it can be difficult to determine and/or confirm the position of the surgical tool 14206 and respective portions thereof.

When the surgical tool 14206 is moved along the longitudinal axis of the tool $A_T$ (FIG. 271), which is collinear with the shaft of the surgical tool 14206, it can be difficult to determine and/or confirm the exact position of the surgical tool 14206. In certain instances, as provided herein, the robotic surgical system can include a secondary sensing system, which is configured to detect the position of the surgical tool 14206. For example, the wireless communication module 14208 can be in signal communication with a secondary sensing system, such as the secondary sensing system 14312 (FIG. 273) and/or a sensor thereof. Moreover, the wireless communication module 14208 can communicate the position of the surgical tool 14206, as detected by the secondary sensing system 14312, to the surgical hub 14212 via the wireless communication link 14210. Additionally or alternatively, the wireless communication module 14208 can communicate information from the various sensors and/or systems of the intelligent surgical tool 14206 to the surgical hub 14212. The surgical hub 14212 can disseminate the information to displays within the operating room or external displays, to a cloud, and/or to one or more hubs and/or control units used in connection with the surgical procedure.

Referring primarily to FIG. 271, in one instance, the surgical tool 14206 can be employed to remove a cancerous tumor 14242 from patient tissue T. To ensure complete removal of the tumor 14242 while minimizing the removal of healthy tissue, a predefined margin zone 14240 can be defined around the tumor 14242. The margin zone can be determined by the surgeon based on patient data, aggregated data from a hub and/or a cloud, and/or data sensed by one or more intelligent components of the surgical system, for example. During the operation, the surgical tool 14206 can transect the tissue T along the margin zone 14240 such that the margin zone 14240 is removed along with the tumor 14242. The primary and secondary sensing systems 14310 and 14312 (FIG. 273) can determine the position of the surgical tool 14206 relative to the margin zone, for example. Moreover, the wireless communication module 14208 can communicate the detected position(s) to the control unit.

In certain instances, the robotic system of FIGS. 271 and 272 can be configured to actuate (e.g. fire) the surgical tool 14206 when the surgical tool 14206 moves within the margin zone 14240. For example, referring primarily to FIG. 272, a graphical display 14250 of distance and force-to-close over time for the linear stapler 14206 during the surgical procedure of FIG. 270 is depicted. As the surgical tool 14206 approaches the margin zone 14240 at time $t_1$, the force-to-close (FTC) increases indicating that the surgical tool 14206 is being clamped on tissue T around the tumor 14242 between time $t_1$ and time $t_2$. More specifically, the surgical tool 14206 is clamped when moved into position a distance between distances $D_1$ and $D_2$. The distance $D_1$ can refer to the outer boundary of the margin zone 14240 around the tumor 14242, for example, and the distance $D_2$ can refer to the inner boundary of the margin zone 14240, which can be assumed boundary of the tumor 14242, for example.

In various instances, the control unit and the processor thereof can automatically affect the clamping motion when the surgical tool 14206 is positioned at the appropriate distance based on input from a primary sensing system and/or a secondary sensing system. In other instances, the control unit and the processor thereof can automatically alert the surgeon that the surgical tool 14206 is positioned at the appropriate distance. Similarly, in certain instances, the processor can automatically fire the surgical tool 14206 and/or suggest to the surgeon that the surgical tool 14206 be fired based on the detected position(s) of the surgical tool 14206. The reader will readily appreciate that other actuation motions are envisioned, such as energizing an energy tool and/or articulating and articulatable end effector, for example.

In certain instances, the hub 14212 can include a situational awareness system, as further described herein. In one aspect, the position of the tumor 14242 and/or the margin zone 14240 therearound can be determined by the situational awareness system or module of the hub 14212. In certain instances, the wireless communication module 14208 can be in signal communication with the situational awareness module of the hub 14212. For example, referring again to FIG. 86, the stapler data and/or the cartridge data provided at steps S220 and S222 can be provided via the wireless communication module 14208 of the stapling tool 14206, for example.

In one aspect, sensors positioned on the surgical tool 14206 can be utilized to determine and/or confirm the position of the surgical tool 14206 (i.e. a secondary sensing system). Moreover, the detected position of the linear stapler can be communicated to the surgical hub 14212 across the wireless communication link 14210, as further described herein. In such instances, the surgical hub 14212 can obtain real-time, or near real-time, information regarding the position of the surgical tool 14206 relative to the tumor 14242 and the margin zone 14240 based on the data communicated via the wireless communication link 14230. In various instances, the robotic surgical system can also determine the position of the surgical tool 14206 based on the motor control algorithms utilized to position the robotic arm 14000 around the surgical theater (i.e. a primary sensing system).

In one aspect, a robotic surgical system can integrate with an imaging system. Real-time feeds from the surgical site, which are obtained by the imaging system, can be communicated to the robotic surgical system. For example, referring again to FIGS. 2 and 3, real-time feeds from the imaging module 138 in the hub 106 can be communicated to the robotic surgical system 110. For example, the real-time feeds can be communicated to the robotic hub 122. In various instances, the real-time feed can be overlaid onto one or more active robot displays, such as the feeds at the surgeon's command console 118. Overlaid images can be provided to one or more displays within the surgical theater, such as the displays 107, 109, and 119, for example.

In certain instances, the overlay of real-time feeds onto a robot display can enable the surgical tools to be precisely controlled within an axes system that is defined by the surgical tool and/or the end effector(s) thereof as visualized by the real-time imaging system. In various instances, cooperating between the robotic surgical system 110 and the imaging system 138 can provide triangulation and instrument mapping of the surgical tools within the visualization field, which can enable precise control of the tool angles and/or advancements thereof. Moreover, shifting control from a standard multi-axes, fixed Cartesian coordinate system to the axis defined by the currently-mounted tool and/or to the end effector thereof can enable the surgeon to issue commands along clear planes and/or axes. For example, a processor of the robotic surgical system can direct a displacement of a surgical tool along the axis of the elongate shaft of the surgical tool or a rotation of the surgical tool at a specific angle from the current position based on a selected point to rotate about. In one exemplification, the overlaid feed of a surgical tool can incorporate a secondary or redundant sensing system, as further described herein, to determine the location and/or orientation of the surgical tool.

In certain instances, a robotic arm, such as the robotic arm 14400 (FIG. 265) can be significantly heavy. For example, the weight of a robotic arm can be such that manually lifting or repositioning the robotic arm is difficult for most able-bodied clinicians. Moreover, the motors and drive mechanisms of the robotic arm may only be controlled by a primary control system located at the control unit based on inputs from the surgeon's command console. Stated differently, a robotic surgical system, such as the system depicted in FIG. 265, for example, may not include a secondary control system for the robotic arm 14400 that is local to the robotic arm 14400 and within the sterile field.

A robotic arm in a robotic surgical system may be prone to inadvertent collisions with equipment and/or people within the sterile field. For example, during a surgical procedure, surgeon(s), nurse(s), and/or medical assistant(s) positioned within the sterile field may move around the sterile field and/or around the robotic arms. In certain instances, the surgeon(s), nurse(s), and/or medical assistant(s), for example, may reposition equipment within the sterile field, such as tables and/or carts, for example. When a surgeon positioned outside of the sterile field is controlling the robotic arm, another surgeon, nurse, and/or medical assistant positioned within the sterile field may also want to manually move and/or adjust the position of one of more robotic arms in order to avoid a potential collision with the arm(s), entanglement of the arm with other equipment and/or other arms, and/or to replace, reload, and/or reconfigure a surgical tool mounted to the arm. However, to reposition the robotic arm, the surgeon may need to power down the robotic surgical system to enable the clinician within the sterile field to manually reposition the robotic arm. In such instances, the clinician can be required to carry the significant weight of the unpowered, or powered down, robotic arm.

In one instance, a robotic surgical system can include an interactive display that is local to the sterile field and/or local to the robotic arm(s). Such a local display can facilitate manipulation and/or positioning of the arm(s) by a clinician within the sterile field. Stated differently, an operator other than the surgeon at the command console can control the position of the robotic arm(s).

Referring now to FIG. 266, a clinician is applying a force to the robotic arm 14000 to manually adjust the position of the robotic arm 14000. In certain instances, the robotic surgical system employing the robotic arm 14000 can employ a passive power assist mode, in which the robotic arm 14400 can easily be repositioned by a clinician within the sterile field. For example, though the robotic arm 14000 is powered and is controlled by a remote control unit, the clinician can manually adjust the position of the robotic arm 14000 without requiring the clinician to carry the entire weight of the robotic arm 14000. The clinician can pull and/or push the robotic arm 14000 to adjust the position thereof. In the passive power assist mode, the power to the robotic arm 14000 can be constrained and/or limited to permit the passive repositioning by the clinician.

Referring now to FIG. 267, a graphical display 14050 of force over time of the robotic arm 14000 (FIG. 266) in a passive power assist mode is depicted. In the passive power assist mode, a clinician can apply a manual force to the robotic arm 14000 to initiate the repositioning of the robotic arm 14000. The clinician can be within the sterile field. In certain instances, the passive power assist mode can be activated when the robotic arm 14000 senses a manual manipulation.

As depicted in FIG. 267, the manual force exerted by a clinician can increase to exceed a predefined threshold, such as the 15-lb limit indicated in FIG. 267, for example, to affect repositioning of the robotic arm 14000. In certain instances, the predefined threshold can correspond to the maximum force an able-bodied assist can easily exert on the robotic arm 14000 without undue stress or strain. In other instances, the predefined threshold can correspond to a minimum threshold force on the robotic arm 14000 in order to avoid providing a powered assist to unintentional or inadvertent contacts with the robotic arm 14000.

When the user exerts a force on the robotic arm 14000 above the predefined threshold, one or more motors (e.g. motors 14407 in FIG. 265) of the robotic surgical system can apply an assisting force to the robotic arm 14000 to help reposition the robotic arm 14000 in the direction indicated by the operator's force on the robotic arm 14000. In such instances, the operator can easily manipulate the position of the arm to avoid inadvertent collisions and/or entanglements and, when the operator's force exceeds a comfortable threshold force, the motors can assist or cooperate in the repositioning of the arm. The passive power assist provided by the motors of the robotic surgical system can compensate for the weight of the robotic arm 14000. In other instances, the assisting force can be less than the weight of the robotic arm 14000. In certain instances, the assisting force can be capped at a maximum force, such as the 5-lb limit indicated in FIG. 267, for example. Capping the assisting force may ensure that the robotic arm 14000 does not forcefully collide with a person, surgical equipment, and/or another robotic arm in the surgical theater.

In one aspect, the passive power assist mode can be deactivated or locked out during portions of a surgical procedure. For example, when a surgical tool is positioned at the surgical site or within a predefined radius of the surgical site and/or the target tissue, the passive power assist mode can be locked out. Additionally or alternatively, during certain steps of a surgical procedure the passive power assist mode can be locked out. Situational awareness can be configured to determine whether the passive power assist mode should be locked out. For example, based on information that a hub knows regarding the step of the surgical procedure (see, e.g. FIG. 86), a passive power assist mode may be ill-advised by the situational awareness module. Similarly, the passive power assist mode can be activated during certain portions of the surgical timeline shown in FIG. 86.

In one aspect, the control unit for operating a robotic arm includes a processor and a memory communicatively coupled to the processor, as described herein. The memory stores instructions executable by the processor to operate in a passive power assist mode in which the processor is configured to process a manual force applied to the robotic arm and, if the manual force exceeds a predefined threshold, to direct one or more motors of the robotic arm to provide an assisting force to reposition the robotic arm in the direction indicated by the manual force.

In various aspects, the present disclosure provides a control circuit configured to operate a passive power assist mode, as described above. In various aspects, the present disclosure provides a non-transitory computer readable medium storing computer readable instructions which, when executed, cause a machine to operate a passive power assist mode, as described above.

Referring now to FIGS. 268 and 269, a clinician within the sterile field is utilizing a local control module 14160 within a sterile field to affect repositioning of a robotic arm 14100. The robotic arm 14100 is similar in many respects to the robotic arm 14400 in FIG. 265. For example, the robotic arm 14100 includes a plurality of movable components 14102. The movable components 14102 are rigid limbs that are mechanically coupled in series at revolute joints 14103. The moveable components 14102 form the robotic arm 14100, similar to the robotic arm 14400 (FIG. 265), for example. A distal-most component 14102*c* includes an attachment 14105 for releasably attaching interchangeable surgical tools, such as the surgical tool 14106, for example. Each component 14102 of the robotic arm 14100 has one or more motors and motor drivers, which can be operated to affect rotational motion at the respective joint 14103.

Each component 14102 includes one or more sensors, which can be position sensors and/or torque sensors, for example, and can provide information regarding the current configuration and/or load at the respective joint between the components 14102. The motors can be controlled by a control unit, such as the control unit 14409 (FIG. 265), which is configured to receive inputs from the sensors and/or from a surgical command interface, such as the surgical command interface 14412 (FIG. 265), for example.

The local control module 14160 includes an interactive display 14164 and a touch screen 14166 that is configured to accept inputs, such as inputs from a finger and/or a stylus 14168, for example. The local control module 14160 is a handheld, mobile digital electronic device. For example, the local control module 14160 can be an iPad® tablet or other mobile tablet or smart phone, for example. In use, the clinician provides repositioning instructions to the robotic arm 14100 via the display 14164 and/or the touch screen 14166 of the local control module 14160. The local control module 14160 is a wireless communication module 14162 such that the inputs from the clinician can be communicated to the robotic arm 14140 to affect arm control motions. The local control module 14140 can wirelessly communicate with the robotic arm 14140 and/or a control unit (e.g. the control unit 14409 in FIG. 265) of the robotic system via a Wi-Fi connection, for example.

The robotic arm 14100 includes six degrees of freedom indicated by the six arrows in FIG. 268. The proximal degrees of freedom can be controlled by the local control module 14160 and the distal degrees of freedom can be controlled by the remote control module. In one instance, the three most-proximal degrees of freedom (articulation about the two most-proximal joints 14103 and rotation of the intermediate limb 14102 about the axis thereof) can be controlled by the local control module and the three most-distal degrees of freedom (articulation about the most-distal joint 14103, rotation of the most-distal limb 14102*c* about the axis thereof, and displacement of the surgical tool 14106 along the axis thereof) can be controlled by the remote control module. In such instances, the clinician within the sterile field can affect gross robotic arm control motions, such as control motions of the proximal arms and/or joints. For example, the clinician within the sterile field can quickly and easily move a robotic arm to a general position, such as a pre-operative position, tool exchanging position, and/or reloading position via the local control module 14160. In such instances, the local control module 14160 is a secondary control system for the robotic arm 14100. The surgeon outside the sterile field can affect more localized or finessed robotic arm control motions via inputs at the surgeon's command interface 14412 (FIG. 265). In such instances, the surgeon's command interface 14412 outside the sterile field is the primary control system.

The reader will readily appreciate that fewer or greater than six degrees of freedom are contemplated. Alternative degrees of freedom are also contemplated. Moreover, different degrees of freedom can be assigned to the local control module 14160 and/or the remote control module. In certain instances, one or more degrees of freedom can be assigned to both the local control module 14106 and the remote control module.

Referring primarily now to FIG. 269, a graphical display 14150 of force over time of the robotic arm 14100 is depicted. From time 0 to time $t_1$, locally-actuated, in-field forces are applied to the robotic arm 14100 by a clinician within the sterile field to adjust the general position of the robotic arm 14100. In certain instances, the force attributable to inputs from the local control module 14160 can be capped at a first maximum force (for example the 50-lb limit indicated in FIG. 269). By utilizing the local control module 14160, the clinician within the sterile field can quickly reposition the robotic arm 14100 to exchange and/or reload the surgical tool 14160, for example. Time 0 to time $t_1$ can correspond to a local actuation mode. Active setup or reloading time in a surgical procedure can occur during the local actuation mode. For example, during the local actuation mode, the robotic arm 14100 can be out of contact with patient tissue and/or outside a predefined boundary around the surgical site, for example.

Thereafter, the surgeon at the surgeon's command console can further actuate the robotic arm 14100. For example, from time $t_2$ to time $t_3$, the remotely-actuated forces are attributable to inputs from the surgeon's command console. The remotely-actuated forces can be capped at a second maximum force (for example the 5-lb limit indicated in FIG. 269), which is less than the first maximum force. By limiting the second maximum force, a surgeon is less likely to cause a high-force or high-speed collision within the sterile field while the larger first maximum force allows the robotic arm 14100 to be quickly repositioned in certain instances. Time $t_2$ to time $t_3$ can correspond to a remote actuation mode during a surgical procedure, which can include when the robotic tool 14106 is actively manipulating tissue (grasping, pulling, holding, transecting, sealing, etc.) and/or when the robotic arm 14100 and/or surgical tool 14106 thereof is within the predefined boundary around the surgical site.

In one aspect, the local actuation mode and/or the remote actuation mode can be deactivated or locked out during portions of a surgical procedure. For example, the local actuation mode can be locked out when the surgical tool is engaged with tissue or otherwise positioned at the surgical site. Situational awareness can be configured to determine whether the local actuation mode should be locked out. For example, based on information that a hub knows regarding the step of the surgical procedure (see, e.g. FIG. 86), a local actuation mode may be ill-advised by the situational awareness module. Similarly, the remote actuation mode may be ill-advised during other portions of the surgical procedure.

In one aspect, the control unit for operating a robotic arm includes a processor and a memory communicatively coupled to the processor, as described herein. The memory stores instructions executable by the processor to provide control motions to the robotic arm based on input from a local control module during portion(s) of a surgical procedure and to provide control motions to the robotic arm based on input from a remote control module during portion(s) of the surgical procedure. A first maximum force can limit the control motions from the local control module and a second maximum force can limit the control motions from the remote control module.

In various aspects, the present disclosure provides a control circuit configured to operate a robotic arm via a local control module and a remote control module, as described above. In various aspects, the present disclosure provides a non-transitory computer readable medium storing computer readable instructions which, when executed, cause a machine to operate a robotic arm via a local control module and a remote control module, as described above.

The entire disclosures of:
U.S. Pat. No. 9,072,535, filed May 27, 2011, titled SURGICAL STAPLING INSTRUMENTS WITH ROTATABLE STAPLE DEPLOYMENT ARRANGEMENTS, which issued Jul. 7, 2015;
U.S. Pat. No. 9,072,536, filed Jun. 28, 2012, titled DIFFERENTIAL LOCKING ARRANGEMENTS FOR ROTARY POWERED SURGICAL INSTRUMENTS, which issued Jul. 7, 2015;
U.S. Pat. No. 9,204,879, filed Jun. 28, 2012, titled FLEXIBLE DRIVE MEMBER, which issued on Dec. 8, 2015;
U.S. Pat. No. 9,561,038, filed Jun. 28, 2012, titled INTERCHANGEABLE CLIP APPLIER, which issued on Feb. 7, 2017;
U.S. Pat. No. 9,757,128, filed Sep. 5, 2014, titled MULTIPLE SENSORS WITH ONE SENSOR AFFECTING A SECOND SENSOR'S OUTPUT OR INTERPRETATION, which issued on Sep. 12, 2017;
U.S. patent application Ser. No. 14/640,935, titled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071;
U.S. patent application Ser. No. 15/382,238, titled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591; and
U.S. patent application Ser. No. 15/237,753, titled CONTROL OF ADVANCEMENT RATE AND APPLICATION FORCE BASED ON MEASURED FORCES, filed Aug. 16, 2016, now U.S. Patent Application Publication No. 2018/0049822;

are herein incorporated by reference in their respective entireties.

A surgical instrument, such as a grasper, for example, can comprise a handle, a shaft extending from the handle, and an end effector extending from the shaft. In various instances, the end effector comprises a first jaw and a second jaw, wherein one or both of the jaws are movable relative to the other to grasp the tissue of a patient. That said, an end effector of a surgical instrument can comprise any suitable arrangement and can perform any suitable function. For instance, an end effector can comprise first and second jaws configured to dissect or separate the tissue of a patient. Also, for instance, an end effector can be configured to suture and/or clip the tissue of a patient. In various instances, the end effector and/or shaft of the surgical instrument are configured to be inserted into a patient through a trocar, or cannula, and can have any suitable diameter, such as approximately 5 mm, 8 mm, and/or 12 mm, for example. U.S. patent application Ser. No. 11/013,924, entitled TROCAR SEAL ASSEMBLY, now U.S. Pat. No. 7,371,227, is incorporated by reference in its entirety. The shaft can define a longitudinal axis and at least a portion of the end effector can be rotatable about the longitudinal axis. Moreover, the surgical instrument can further comprise an articulation joint which can permit at least a portion of the end effector to be articulated relative to the shaft. In use, a clinician can rotate and/or articulate the end effector in order to maneuver the end effector within the patient.

A surgical instrument system is depicted in FIG. 275. The surgical instrument system comprises a handle assembly 1000 which is selectively usable with a shaft assembly 2000, a shaft assembly 3000, a shaft assembly 4000, a shaft assembly 5000, and/or any other suitable shaft assembly. The shaft assembly 2000 is attached to the handle assembly 1000 in FIG. 276 and the shaft assembly 4000 is attached to the handle assembly 1000 in FIG. 320. The shaft assembly 2000 comprises a proximal portion 2100, an elongate shaft 2200 extending from the proximal portion 2100, a distal attachment portion 2400, and an articulation joint 2300 rotatably connecting the distal attachment portion 2400 to the elongate shaft 2200. The shaft assembly 2000 further comprises a replaceable end effector assembly 7000 attached to the distal attachment portion 2400. The replaceable end effector assembly 7000 comprises a jaw assembly 7100 configured to be opened and closed to clamp and/or manipulate the tissue of a patient. In use, the end effector assembly 7000 can be articulated about the articulation joint 2300 and/or rotated relative to the distal attachment portion 2400 about a longitudinal axis to better position the jaw assembly 7100 within the patient, as described in greater detail further below.

Referring again to FIG. 275, the handle assembly 1000 comprises, among other things, a drive module 1100. As described in greater detail below, the drive module 1100 comprises a distal mounting interface which permits a clinician to selectively attach one of the shaft assemblies 2000, 3000, 4000, and 5000, for example, to the drive module 1100. Thus, each of the shaft assemblies 2000, 3000, 4000, and 5000 comprises an identical, or an at least similar, proximal mounting interface which is configured to engage the distal mounting interface of the drive module 1100. As also described in greater detail below, the mounting interface of the drive module 1100 mechanically secures and electrically couples the selected shaft assembly to the drive module 1100. The drive module 1100 further comprises at least one electric motor, one or more controls and/or displays, and a controller configured to operate the electric motor—the rotational output of which is transmitted to a drive system of the shaft assembly attached to the drive module 1100. Moreover, the drive module 1100 is usable with one ore more power modules, such as power modules 1200 and 1300, for example, which are operably attachable to the drive module 1100 to supply power thereto.

Further to the above, referring again to FIGS. 275 and 276, the handle drive module 1100 comprises a housing 1110, a first module connector 1120, and a second module connector 1120'. The power module 1200 comprises a housing 1210, a connector 1220, one or more release latches 1250, and one or more batteries 1230. The connector 1220 is configured to be engaged with the first module connector 1120 of the drive module 1100 in order to attach the power module 1200 to the drive module 1100. The connector 1220 comprises one or more latches 1240 which mechanically couple and fixedly secure the housing 1210 of the power module 1200 to the housing 1110 of the drive module 1100. The latches 1240 are movable into disengaged positions when the release latches 1250 are depressed so that the power module 1200 can be detached from the drive module 1100. The connector 1220 also comprises one or more electrical contacts which place the batteries 1230, and/or an electrical circuit including the batteries 1230, in electrical communication with an electrical circuit in the drive module 1100.

Further to the above, referring again to FIGS. 275 and 276, the power module 1300 comprises a housing 1310, a connector 1320, one or more release latches 1350, and one or more batteries 1330 (FIG. 322). The connector 1320 is configured to be engaged with the second module connector 1120' of the drive module 1100 to attach the power module 1300 to the drive module 1100. The connector 1320 comprises one or more latches 1340 which mechanically couple and fixedly secure the housing 1310 of the power module 1300 to the housing 1110 of the drive module 1100. The latches 1340 are movable into disengaged positions when the release latches 1350 are depressed so that the power module 1300 can be detached from the drive module 1100. The connector 1320 also comprises one or more electrical contacts which place the batteries 1330 of the power module 1300, and/or an electrical power circuit including the batteries 1330, in electrical communication with an electrical power circuit in the drive module 1100.

Further to the above, the power module 1200, when attached to the drive module 1100, comprises a pistol grip which can allow a clinician to hold the handle 1000 in a manner which places the drive module 1100 on top of the clinician's hand. The power module 1300, when attached to the drive module 1100, comprises an end grip which allows a clinician to hold the handle 1000 like a wand. The power module 1200 is longer than the power module 1300, although the power modules 1200 and 1300 can comprise any suitable length. The power module 1200 has more battery cells than the power module 1300 and can suitably accommodate these additional battery cells owing to its length. In various instances, the power module 1200 can provide more power to the drive module 1100 than the power module 1300 while, in some instances, the power module 1200 can provide power for a longer period of time. In some instances, the housing 1110 of the drive module 1100 comprises keys, and/or any other suitable features, which prevent the power module 1200 from being connected to the second module connector 1120' and, similarly, prevent the power module 1300 from being connected to the first module connector 1120. Such an arrangement can assure that the longer power module 1200 is used in the pistol grip arrangement and that the shorter power module 1300 is used in the wand grip arrangement. In alternative embodiments, the power module 1200 and the power module 1300 can be selectively coupled to the drive module 1100 at either the first module connector 1120 or the second module connector 1120'. Such embodiments provide a clinician with more options to customize the handle 1000 in a manner suitable to them.

In various instances, further to the above, only one of the power modules 1200 and 1300 is coupled to the drive module 1100 at a time. In certain instances, the power module 1200 can be in the way when the shaft assembly 4000, for example, is attached to the drive module 1100. Alternatively, both of the power modules 1200 and 1300 can be operably coupled to the drive module 1100 at the same time. In such instances, the drive module 1100 can have access to power provided by both of the power modules 1200 and 1300. Moreover, a clinician can switch between a pistol grip and a wand grip when both of the power modules 1200 and 1300 are attached to the drive module 1100. Moreover, such an arrangement allows the power module 1300 to act as a counterbalance to a shaft assembly, such as shaft assemblies 2000, 3000, 4000, or 5000, for example, attached to the drive module 1100.

Referring to FIGS. 281 and 282, the handle drive module 1100 further comprises a frame 1500, a motor assembly 1600, a drive system 1700 operably engaged with the motor assembly 1600, and a control system 1800. The frame 1500 comprises an elongate shaft that extends through the motor assembly 1600. The elongate shaft comprises a distal end 1510 and electrical contacts, or sockets, 1520 defined in the distal end 1510. The electrical contacts 1520 are in electrical communication with the control system 1800 of the drive module 1100 via one or more electrical circuits and are configured to convey signals and/or power between the control system 1800 and the shaft assembly, such as the shaft assembly 2000, 3000, 4000, or 5000, for example, attached to the drive module 1100. The control system 1800 comprises a printed circuit board (PCB) 1810, at least one microprocessor 1820, and at least one memory device 1830.

The board 1810 can be rigid and/or flexible and can comprise any suitable number of layers. The microprocessor 1820 and the memory device 1830 are part of a control circuit defined on the board 1810 which controls the operation of the motor assembly 1600, as described in greater detail below.

Referring to FIGS. 286 and 287, the motor assembly 1600 comprises an electric motor 1610 including a housing 1620, a drive shaft 1630, and a gear reduction system. The electric motor 1610 further comprises a stator including windings 1640 and a rotor including magnetic elements 1650. The stator windings 1640 are supported in the housing 1620 and the rotor magnetic elements 1650 are mounted to the drive shaft 1630. When the stator windings 1640 are energized with an electric current controlled by the control system 1800, the drive shaft 1630 is rotated about a longitudinal axis. The drive shaft 1630 is operably engaged with a first planetary gear system 1660 which includes a central sun gear and several planetary gears operably intermeshed with the sun gear. The sun gear of the first planetary gear system 1660 is fixedly mounted to the drive shaft 1630 such that it rotates with the drive shaft 1630. The planetary gears of the first planetary gear system 1660 are rotatably mounted to the sun gear of a second planetary gear system 1670 and, also, intermeshed with a geared or splined inner surface 1625 of the motor housing 1620. As a result of the above, the rotation of the first sun gear rotates the first planetary gears which rotate the second sun gear. Similar to the above, the second planetary gear system 1670 further comprises planetary gears 1665 (FIG. 287) which drive a third planetary gear system and, ultimately, the drive shaft 1710. The planetary gear systems 1660, 1670, and 1680 co-operate to gear down the speed applied to the drive shaft 1710 by the motor shaft 1620. Various alternative embodiments are envisioned without a speed reduction system. Such embodiments are suitable when it is desirable to drive the end effector functions quickly. Notably, the drive shaft 1630 comprises an aperture, or hollow core, extending therethrough through which wires and/or electrical circuits can extend.

The control system 1800 is in communication with the motor assembly 1600 and the electrical power circuit of the drive module 1100. The control system 1800 is configured to control the power delivered to the motor assembly 1600 from the electrical power circuit. The electrical power circuit is configured to supply a constant, or at least nearly constant, direct current (DC) voltage. In at least one instance, the electrical power circuit supplies 3 VDC to the control system 1800. The control system 1800 comprises a pulse width modulation (PWM) circuit which is configured to deliver voltage pulses to the motor assembly 1600. The duration or width of the voltage pulses, and/or the duration or width between the voltage pulses, supplied by the PWM circuit can be controlled in order to control the power applied to the motor assembly 1600. By controlling the power applied to the motor assembly 1600, the PWM circuit can control the speed of the output shaft of the motor assembly 1600. In addition to or in lieu of a PWM circuit, the control system 1800 can include a frequency modulation (FM) circuit. As discussed in greater detail below, the control system 1800 is operable in more than one operating mode and, depending on the operating mode being used, the control system 1800 can operate the motor assembly 1600 at a speed, or a range of speeds, which is determined to be appropriate for that operating mode.

Further to the above, referring again to FIGS. 281 and 282, the drive system 1700 comprises a rotatable shaft 1710 comprising a splined distal end 1720 and a longitudinal aperture 1730 defined therein. The rotatable shaft 1710 is operably mounted to the output shaft of the motor assembly 1600 such that the rotatable shaft 1710 rotates with the motor output shaft. The handle frame 1510 extends through the longitudinal aperture 1730 and rotatably supports the rotatable shaft 1710. As a result, the handle frame 1510 serves as a bearing for the rotatable shaft 1710. The handle frame 1510 and the rotatable shaft 1710 extend distally from a mounting interface 1130 of the drive module 1110 and are coupled with corresponding components on the shaft assembly 2000 when the shaft assembly 2000 is assembled to the drive module 1100. Referring primarily to FIGS. 277-280, the shaft assembly 2000 further comprises a frame 2500 and a drive system 2700. The frame 2500 comprises a longitudinal shaft 2510 extending through the shaft assembly 2000 and a plurality of electrical contacts, or pins, 2520 extending proximally from the shaft 2510. When the shaft assembly 2000 is attached to the drive module 1100, the electrical contacts 2520 on the shaft frame 2510 engage the electrical contacts 1520 on the handle frame 1510 and create electrical pathways therebetween.

Similar to the above, the drive system 2700 comprises a rotatable drive shaft 2710 which is operably coupled to the rotatable drive shaft 1710 of the handle 1000 when the shaft assembly 2000 is assembled to the drive module 1100 such that the drive shaft 2710 rotates with the drive shaft 1710. To this end, the drive shaft 2710 comprises a splined proximal end 2720 which mates with the splined distal end 1720 of the drive shaft 1710 such that the drive shafts 1710 and 2710 rotate together when the drive shaft 1710 is rotated by the motor assembly 1600. Given the nature of the splined interconnection between the drive shafts 1710 and 2710 and the electrical interconnection between the frames 1510 and 2510, the shaft assembly 2000 is assembled to the handle 1000 along a longitudinal axis; however, the operable interconnection between the drive shafts 1710 and 2710 and the electrical interconnection between the frames 1510 and 2510 can comprise any suitable configuration which can allow a shaft assembly to be assembled to the handle 1000 in any suitable manner.

As discussed above, referring to FIGS. 277-282, the mounting interface 1130 of the drive module 1110 is configured to be coupled to a corresponding mounting interface on the shaft assemblies 2000, 3000, 4000, and 5000, for example. For instance, the shaft assembly 2000 comprises a mounting interface 2130 configured to be coupled to the mounting interface 1130 of the drive module 1100. More specifically, the proximal portion 2100 of the shaft assembly 2000 comprises a housing 2110 which defines the mounting interface 2130. Referring primarily to FIG. 282, the drive module 1100 comprises latches 1140 which are configured to releasably hold the mounting interface 2130 of the shaft assembly 2000 against the mounting interface 1130 of the drive module 1100. When the drive module 1100 and the shaft assembly 2000 are brought together along a longitudinal axis, as described above, the latches 1140 contact the mounting interface 2130 and rotate outwardly into an unlocked position. Referring primarily to FIGS. 282, 284, and 285, each latch 1140 comprises a lock end 1142 and a pivot portion 1144. The pivot portion 1144 of each latch 1140 is rotatably coupled to the housing 1110 of the drive module 1100 and, when the latches 1140 are rotated outwardly, as mentioned above, the latches 1140 rotate about the pivot portions 1144. Notably, each latch 1140 further comprises a biasing spring 1146 configured to bias the latches 1140 inwardly into a locked position. Each biasing spring 1146 is compressed between a latch 1140 and the housing 1110 of the drive module 1100 such that the biasing springs 1146 apply biasing forces to the latches 1140; however, such biasing forces are overcome when the latches 1140 are rotated outwardly into their unlocked positions by the shaft assembly 2000. That said, when the latches 1140 rotate outwardly after contacting the mounting interface 2130, the lock ends 1142 of the latches 1140 can enter into latch windows 2140 defined in the mounting interface 2130. Once the lock ends 1142 pass through the latch windows 2140, the springs 1146 can bias the latches 1140 back into their locked positions. Each lock end 1142 comprises a lock shoulder, or surface, which securely holds the shaft assembly 2000 to the drive module 1100.

Further to the above, the biasing springs 1146 hold the latches 1140 in their locked positions. The distal ends 1142 are sized and configured to prevent, or at least inhibit, relative longitudinal movement, i.e., translation along a longitudinal axis, between the shaft assembly 2000 and the drive module 1100 when the latches 1140 are in their locked positions. Moreover, the latches 1140 and the latch windows 1240 are sized and configured to prevent relative lateral movement, i.e., translation transverse to the longitudinal axis, between the shaft assembly 2000 and the drive module 1100. In addition, the latches 1140 and the latch windows 2140 are sized and configured to prevent the shaft assembly 2000 from rotating relative to the drive module 1100. The drive module 1100 further comprises release actuators 1150 which, when depressed by a clinician, move the latches 1140 from their locked positions into their unlocked positions. The drive module 1100 comprises a first release actuator 1150 slideably mounted in an opening defined in the first side of the handle housing 1110 and a second release actuator 1150 slideably mounted in an opening defined in a second, or opposite, side of the handle housing 1110. Although the release actuators 1150 are actuatable separately, both release actuators 1150 typically need to be depressed to completely unlock the shaft assembly 2000 from the drive module 1100 and allow the shaft assembly 2000 to be detached from the drive module 1100. That said, it is possible that the shaft assembly 2000 could be detached from the drive module 1100 by depressing only one release actuator 1150.

Once the shaft assembly 2000 has been secured to the handle 1000 and the end effector 7000, for example, has been assembled to the shaft 2000, the clinician can maneuver the handle 1000 to insert the end effector 7000 into a patient. In at least one instance, the end effector 7000 is inserted into the patient through a trocar and then manipulated in order to position the jaw assembly 7100 of the end effector assembly 7000 relative to the patient's tissue. Oftentimes, the jaw assembly 7100 must be in its closed, or clamped, configuration in order to fit through the trocar. Once through the trocar, the jaw assembly 7100 can be opened so that the patient tissue fit between the jaws of the jaw assembly 7100. At such point, the jaw assembly 7100 can be returned to its closed configuration to clamp the patient tissue between the jaws. The clamping force applied to the patient tissue by the jaw assembly 7100 is sufficient to move or otherwise manipulate the tissue during a surgical procedure. Thereafter, the jaw assembly 7100 can be re-opened to release the patient tissue from the end effector 7000. This process can be repeated until it is desirable to remove the end effector 7000 from the patient. At such point, the jaw assembly 7100 can be returned to its closed configuration and retracted through the trocar. Other surgical techniques are envisioned in which the end effector 7000 is inserted into a patient through an open incision, or without the use of the trocar. In any event, it is envisioned that the jaw assembly 7100 may have to be opened and closed several times throughout a surgical technique.

Referring again to FIGS. 277-280, the shaft assembly 2000 further comprises a clamping trigger system 2600 and a control system 2800. The clamping trigger system 2600 comprises a clamping trigger 2610 rotatably connected to the proximal housing 2110 of the shaft assembly 2000. As discussed below, the clamping trigger 2610 actuates the motor 1610 to operate the jaw drive of the end effector 7000 when the clamping trigger 2610 is actuated. The clamping trigger 2610 comprises an elongate portion which is graspable by the clinician while holding the handle 1000. The clamping trigger 2610 further comprises a mounting portion 2620 which is pivotably connected to a mounting portion 2120 of the proximal housing 2110 such that the clamping trigger 2610 is rotatable about a fixed, or an at least substantially fixed, axis. The closure trigger 2610 is rotatable between a distal position and a proximal position, wherein the proximal position of the closure trigger 2610 is closer to the pistol grip of the handle 1000 than the distal position. The closure trigger 2610 further comprises a tab 2615 extending therefrom which rotates within the proximal housing 2110. When the closure trigger 2610 is in its distal position, the tab 2615 is positioned above, but not in contact with, a switch 2115 mounted on the proximal housing 2110. The switch 2115 is part of an electrical circuit configured to detect the actuation of the closure trigger 2610 which is in an open condition the closure trigger 2610 is in its open position. When the closure trigger 2610 is moved into its proximal position, the tab 2615 comes into contact with the switch 2115 and closes the electrical circuit. In various instances, the switch 2115 can comprise a toggle switch, for example, which is mechanically switched between open and closed states when contacted by the tab 2615 of the closure trigger 2610. In certain instances, the switch 2115 can comprise a proximity sensor, for example, and/or any suitable type of sensor. In at least one instance, the switch 2115 comprises a Hall Effect sensor which can detect the amount in which the closure trigger 2610 has been rotated and, based on the amount of rotation, control the speed in which the motor 1610 is operated. In such instances, larger rotations of the closure trigger 2610 result in faster speeds of the motor 1610 while smaller rotations result in slower speeds, for example. In any event, the electrical circuit is in communication with the control system 2800 of the shaft assembly 2000, which is discussed in greater detail below.

Further to the above, the control system 2800 of the shaft assembly 2000 comprises a printed circuit board (PCB) 2810, at least one microprocessor 2820, and at least one memory device 2830. The board 2810 can be rigid and/or flexible and can comprise any suitable number of layers. The microprocessor 2820 and the memory device 2830 are part of a control circuit defined on the board 2810 which communicates with the control system 1800 of the handle 1000. The shaft assembly 2000 further comprises a signal communication system 2900 and the handle 1000 further comprises a signal communication system 1900 which are configured to convey data between the shaft control system 2800 and the handle control system 1800. The signal communication system 2900 is configured to transmit data to the signal communication system 1900 utilizing any suitable analog and/or digital components. In various instances, the communication systems 2900 and 1900 can communicate using a plurality of discrete channels which allows the input gates of the microprocessor 1820 to be directly controlled, at least in part, by the output gates of the microprocessor

2820. In some instances, the communication systems 2900 and 1900 can utilize multiplexing. In at least one such instance, the control system 2900 includes a multiplexing device that sends multiple signals on a carrier channel at the same time in the form of a single, complex signal to a multiplexing device of the control system 1900 that recovers the separate signals from the complex signal.

The communication system 2900 comprises an electrical connector 2910 mounted to the circuit board 2810. The electrical connector 2910 comprises a connector body and a plurality of electrically-conductive contacts mounted to the connector body. The electrically-conductive contacts comprise male pins, for example, which are soldered to electrical traces defined in the circuit board 2810. In other instances, the male pins can be in communication with circuit board traces through zero-insertion-force (ZIF) sockets, for example. The communication system 1900 comprises an electrical connector 1910 mounted to the circuit board 1810. The electrical connector 1910 comprises a connector body and a plurality of electrically-conductive contacts mounted to the connector body. The electrically-conductive contacts comprise female pins, for example, which are soldered to electrical traces defined in the circuit board 1810. In other instances, the female pins can be in communication with circuit board traces through zero-insertion-force (ZIF) sockets, for example. When the shaft assembly 2000 is assembled to the drive module 1100, the electrical connector 2910 is operably coupled to the electrical connector 1910 such that the electrical contacts form electrical pathways therebetween. The above being said, the connectors 1910 and 2910 can comprise any suitable electrical contacts. Moreover, the communication systems 1900 and 2900 can communicate with one another in any suitable manner. In various instances, the communication systems 1900 and 2900 communicate wirelessly. In at least one such instance, the communication system 2900 comprises a wireless signal transmitter and the communication system 1900 comprises a wireless signal receiver such that the shaft assembly 2000 can wirelessly communicate data to the handle 1000. Likewise, the communication system 1900 can comprise a wireless signal transmitter and the communication system 2900 can comprise a wireless signal receiver such that the handle 1000 can wirelessly communicate data to the shaft assembly 2000.

As discussed above, the control system 1800 of the handle 1000 is in communication with, and is configured to control, the electrical power circuit of the handle 1000. The handle control system 1800 is also powered by the electrical power circuit of the handle 1000. The handle communication system 1900 is in signal communication with the handle control system 1800 and is also powered by the electrical power circuit of the handle 1000. The handle communication system 1900 is powered by the handle electrical power circuit via the handle control system 1800, but could be directly powered by the electrical power circuit. As also discussed above, the handle communication system 1900 is in signal communication with the shaft communication system 2900. That said, the shaft communication system 2900 is also powered by the handle electrical power circuit via the handle communication system 1900. To this end, the electrical connectors 1910 and 2010 connect both one or more signal circuits and one or more power circuits between the handle 1000 and the shaft assembly 2000. Moreover, the shaft communication system 2900 is in signal communication with the shaft control system 2800, as discussed above, and is also configured to supply power to the shaft control system 2800. Thus, the control systems 1800 and 2800 and the communication systems 1900 and 2900 are all powered by the electrical power circuit of the handle 1000; however, alternative embodiments are envisioned in which the shaft assembly 2000 comprises its own power source, such as one or more batteries, for example, an and electrical power circuit configured to supply power from the batteries to the handle systems 2800 and 2900. In at least one such embodiment, the handle control system 1800 and the handle communication system 1900 are powered by the handle electrical power system and the shaft control system 2800 and the handle communication system 2900 are powered by the shaft electrical power system.

Further to the above, the actuation of the clamping trigger 2610 is detected by the shaft control system 2800 and communicated to the handle control system 1800 via the communication systems 2900 and 1900. Upon receiving a signal that the clamping trigger 2610 has been actuated, the handle control system 1800 supplies power to the electric motor 1610 of the motor assembly 1600 to rotate the drive shaft 1710 of the handle drive system 1700, and the drive shaft 2710 of the shaft drive system 2700, in a direction which closes the jaw assembly 7100 of the end effector 7000. The mechanism for converting the rotation of the drive shaft 2710 to a closure motion of the jaw assembly 7100 is discussed in greater detail below. So long as the clamping trigger 2610 is held in its actuated position, the electric motor 1610 will rotate the drive shaft 1710 until the jaw assembly 7100 reaches its fully-clamped position. When the jaw assembly 7100 reaches its fully-clamped position, the handle control system 1800 cuts the electrical power to the electric motor 1610. The handle control system 1800 can determine when the jaw assembly 7100 has reached its fully-clamped position in any suitable manner. For instance, the handle control system 1800 can comprise an encoder system which monitors the rotation of, and counts the rotations of, the output shaft of the electric motor 1610 and, once the number of rotations reaches a predetermined threshold, the handle control system 1800 can discontinue supplying power to the electric motor 1610. In at least one instance, the end effector assembly 7000 can comprise one or more sensors configured to detect when the jaw assembly 7100 has reached its fully-clamped position. In at least one such instance, the sensors in the end effector 7000 are in signal communication with the handle control system 1800 via electrical circuits extending through the shaft assembly 2000 which can include the electrical contacts 1520 and 2520, for example.

When the clamping trigger 2610 is rotated distally out of its proximal position, the switch 2115 is opened which is detected by the shaft control system 2800 and communicated to the handle control system 1800 via the communication systems 2900 and 1900. Upon receiving a signal that the clamping trigger 2610 has been moved out of its actuated position, the handle control system 1800 reverses the polarity of the voltage differential being applied to the electric motor 1610 of the motor assembly 1600 to rotate the drive shaft 1710 of the handle drive system 1700, and the drive shaft 2710 of the shaft drive system 2700, in an opposite direction which, as a result, opens the jaw assembly 7100 of the end effector 7000. When the jaw assembly 7100 reaches its fully-open position, the handle control system 1800 cuts the electrical power to the electric motor 1610. The handle control system 1800 can determine when the jaw assembly 7100 has reached its fully-open position in any suitable manner. For instance, the handle control system 1800 can utilize the encoder system and/or the one or more sensors described above to determine the configuration of the jaw assembly 7100. In view of the above, the clinician needs to be mindful about holding the clamping trigger 2610 in its actuated position in order to maintain the jaw assembly 7100 in its clamped configuration as, otherwise, the control system 1800 will open jaw assembly 7100. With this in mind, the shaft assembly 2000 further comprises an actuator latch 2630 configured to releasably hold the clamping trigger 2610 in its actuated position to prevent the accidental opening of the jaw assembly 7100. The actuator latch 2630 can be manually released, or otherwise defeated, by the clinician to allow the clamping trigger 2610 to be rotated distally and open the jaw assembly 7100.

The clamping trigger system 2600 further comprises a resilient biasing member, such as a torsion spring, for example, configured to resist the closure of the clamping trigger system 2600. The torsion spring can also assist in reducing and/or mitigating sudden movements and/or jitter of the clamping trigger 2610. Such a torsion spring can also automatically return the clamping trigger 2610 to its unactuated position when the clamping trigger 2610 is released. The actuator latch 2630 discussed above can suitably hold the clamping trigger 2610 in its actuated position against the biasing force of the torsion spring.

As discussed above, the control system 1800 operates the electric motor 1610 to open and close the jaw assembly 7100. The control system 1800 is configured to open and close the jaw assembly 7100 at the same speed. In such instances, the control system 1800 applies the same voltage pulses to the electric motor 1610, albeit with different voltage polarities, when opening and closing the jaw assembly 7100. That said, the control system 1800 can be configured to open and close the jaw assembly 7100 at different speeds. For instance, the jaw assembly 7100 can be closed at a first speed and opened at a second speed which is faster than the first speed. In such instances, the slower closing speed affords the clinician an opportunity to better position the jaw assembly 7100 while clamping the tissue. Alternatively, the control system 1800 can open the jaw assembly 7100 at a slower speed. In such instances, the slower opening speed reduces the possibility of the opening jaws colliding with adjacent tissue. In either event, the control system 1800 can decrease the duration of the voltage pulses and/or increase the duration between the voltage pulses to slow down and/or speed up the movement of the jaw assembly 7100.

As discussed above, the control system 1800 is configured to interpret the position of the clamping trigger 2610 as a command to position the jaw assembly 7100 in a specific configuration. For instance, the control system 1800 is configured to interpret the proximal-most position of the clamping trigger 2610 as a command to close the jaw assembly 7100 and any other position of the clamping trigger as a command to open the jaw assembly 7100. That said, the control system 1800 can be configured to interpret the position of the clamping trigger 2610 in a proximal range of positions, instead of a single position, as a command to close the jaw assembly 7100. Such an arrangement can allow the jaw assembly 7000 to be better responsive to the clinician's input. In such instances, the range of motion of the clamping trigger 2610 is divided into ranges—a proximal range which is interpreted as a command to close the jaw assembly 7100 and a distal range which is interpreted as a command to open the jaw assembly 7100. In at least one instance, the range of motion of the clamping trigger 2610 can have an intermediate range between the proximal range and the distal range. When the clamping trigger 2610 is in the intermediate range, the control system 1800 can interpret the position of the clamping trigger 2610 as a command to neither open nor close the jaw assembly 7100. Such an intermediate range can prevent, or reduce the possibility of, jitter between the opening and closing ranges. In the instances described above, the control system 1800 can be configured to ignore cumulative commands to open or close the jaw assembly 7100. For instance, if the closure trigger 2610 has already been fully retracted into its proximal-most position, the control assembly 1800 can ignore the motion of the clamping trigger 2610 in the proximal, or clamping, range until the clamping trigger 2610 enters into the distal, or opening, range wherein, at such point, the control system 1800 can then actuate the electric motor 1610 to open the jaw assembly 7100.

In certain instances, further to the above, the position of the clamping trigger 2610 within the clamping trigger range, or at least a portion of the clamping trigger range, can allow the clinician to control the speed of the electric motor 1610 and, thus, the speed in which the jaw assembly 7100 is being opened or closed by the control assembly 1800. In at least one instance, the sensor 2115 comprises a Hall Effect sensor, and/or any other suitable sensor, configured to detect the position of the clamping trigger 2610 between its distal, unactuated position and its proximal, fully-actuated position. The Hall Effect sensor is configured to transmit a signal to the handle control system 1800 via the shaft control system 2800 such that the handle control system 1800 can control the speed of the electric motor 1610 in response to the position of the clamping trigger 2610. In at least one instance, the handle control system 1800 controls the speed of the electric motor 1610 proportionately, or in a linear manner, to the position of the clamping trigger 2610. For example, if the clamping trigger 2610 is moved half way through its range, then the handle control system 1800 will operate the electric motor 1610 at half of the speed in which the electric motor 1610 is operated when the clamping trigger 2610 is fully-retracted. Similarly, if the clamping trigger 2610 is moved a quarter way through its range, then the handle control system 1800 will operate the electric motor 1610 at a quarter of the speed in which the electric motor 1610 is operated when the clamping trigger 2610 is fully-retracted. Other embodiments are envisioned in which the handle control system 1800 controls the speed of the electric motor 1610 in a non-linear manner to the position of the clamping trigger 2610. In at least one instance, the control system 1800 operates the electric motor 1610 slowly in the distal portion of the clamping trigger range while quickly accelerating the speed of the electric motor 1610 in the proximal portion of the clamping trigger range.

As described above, the clamping trigger 2610 is movable to operate the electric motor 1610 to open or close the jaw assembly 7100 of the end effector 7000. The electric motor 1610 is also operable to rotate the end effector 7000 about a longitudinal axis and articulate the end effector 7000 relative to the elongate shaft 2200 about the articulation joint 2300 of the shaft assembly 2000. Referring primarily to FIGS. 281 and 282, the drive module 1100 comprises an input system 1400 including a rotation actuator 1420 and an articulation actuator 1430. The input system 1400 further comprises a printed circuit board (PCB) 1410 which is in signal communication with the printed circuit board (PCB) 1810 of the control system 1800. The drive module 1100 comprises an electrical circuit, such as a flexible wiring harness or ribbon, for example, which permits the input system 1400 to communicate with the control system 1800. The rotation actuator 1420 is rotatably supported on the housing 1110 and is in signal communication with the input board 1410 and/or control board 1810, as described in greater detail below. The articulation actuator 1430 is supported by and in signal communication with the input board 1410 and/or control board 1810, as also described in greater detail below.

Referring primarily to FIGS. 282, 284, and 285, further to the above, the handle housing 1110 comprises an annular groove or slot defined therein adjacent the distal mounting interface 1130. The rotation actuator 1420 comprises an annular ring 1422 rotatably supported within the annular groove and, owing to the configuration of the sidewalls of the annular groove, the annular ring 1422 is constrained from translating longitudinally and/or laterally with respect to the handle housing 1110. The annular ring 1422 is rotatable in a first, or clockwise, direction and a second, or counter-clockwise direction, about a longitudinal axis extending through the frame 1500 of the drive module 1100. The rotation actuator 1420 comprises one or more sensors configured to detect the rotation of the annular ring 1422. In at least one instance, the rotation actuator 1420 comprises a first sensor positioned on a first side of the drive module 1100 and a second sensor positioned on a second, or opposite, side of the drive module 1100 and the annular ring 1422 comprises a detectable element which is detectable by the first and second sensors. The first sensor is configured to detect when the annular ring 1422 is rotated in the first direction and the second sensor is configured to detect when the annular ring 1422 is rotated in the second direction. When the first sensor detects that the annular ring 1422 is rotated in the first direction, the handle control system 1800 rotates the handle drive shaft 1710, the drive shaft 2710, and the end effector 7000 in the first direction, as described in greater detail below. Similarly, the handle control system 1800 rotates the handle drive shaft 1710, the drive shaft 2710, and the end effector 7000 in the second direction when the second sensor detects that the annular ring 1422 is rotated in the second direction. In view of the above, the reader should appreciate that the clamping trigger 2610 and the rotation actuator 1420 are both operable to rotate the drive shaft 2710.

In various embodiments, further to the above, the first and second sensors comprise switches which are mechanically closable by the detectable element of the annular ring 1422. When the annular ring 1422 is rotated in the first direction from a center position, the detectable element closes the switch of the first sensor. When the switch of the first sensor is closed, the control system 1800 operates the electric motor 1610 to rotate the end effector 7000 in the first direction. When the annular ring 1422 is rotated in the second direction toward the center position, the detectable element is disengaged from the first switch and the first switch is re-opened. Once the first switch is re-opened, the control system 1800 cuts the power to the electric motor 1610 to stop the rotation of the end effector 7000. Similarly, the detectable element closes the switch of the second sensor when the annular ring 1422 is rotated in the second direction from the center position. When the switch of the second sensor is closed, the control system 1800 operates the electric motor 1610 to rotate the end effector 7000 in the second direction. When the annular ring 1422 is rotated in the first direction toward the center position, the detectable element is disengaged from the second switch and the second switch is re-opened. Once the second switch is re-opened, the control system 1800 cuts the power to the electric motor 1610 to stop the rotation of the end effector 7000.

In various embodiments, further to the above, the first and second sensors of the rotation actuator 1420 comprise proximity sensors, for example. In certain embodiments, the first and second sensors of the rotation actuator 1420 comprise Hall Effect sensors, and/or any suitable sensors, configured to detect the distance between the detectable element of the annular ring 1422 and the first and second sensors. If the first Hall Effect sensor detects that the annular ring 1422 has been rotated in the first direction, then, as discussed above, the control system 1800 will rotate the end effector 7000 in the first direction. In addition, the control system 1800 can rotate the end effector 7000 at a faster speed when the detectable element is closer to the first Hall Effect sensor than when the detectable element is further away from the first Hall Effect sensor. If the second Hall Effect sensor detects that the annular ring 1422 has been rotated in the second direction, then, as discussed above, the control system 1800 will rotate the end effector 7000 in the second direction. In addition, the control system 1800 can rotate the end effector 7000 at a faster speed when the detectable element is closer to the second Hall Effect sensor than when the detectable element is further away from the second Hall Effect sensor. As a result, the speed in which the end effector 7000 is rotated is a function of the amount, or degree, in which the annular ring 1422 is rotated. The control system 1800 is further configured to evaluate the inputs from both the first and second Hall Effect sensors when determining the direction and speed in which to rotate the end effector 7000. In various instances, the control system 1800 can use the closest Hall Effect sensor to the detectable element of the annular ring 1422 as a primary source of data and the Hall Effect sensor furthest away from the detectable element as a confirmational source of data to double-check the data provided by the primary source of data. The control system 1800 can further comprise a data integrity protocol to resolve situations in which the control system 1800 is provided with conflicting data. In any event, the handle control system 1800 can enter into a neutral state in which the handle control system 1800 does not rotate the end effector 7000 when the Hall Effect sensors detect that the detectable element is in its center position, or in a position which is equidistant between the first Hall Effect sensor and the second Hall Effect sensor. In at least one such instance, the control system 1800 can enter into its neutral state when the detectable element is in a central range of positions. Such an arrangement would prevent, or at least reduce the possibility of, rotational jitter when the clinician is not intending to rotate the end effector 7000.

Further to the above, the rotation actuator 1420 can comprise one or more springs configured to center, or at least substantially center, the rotation actuator 1420 when it is released by the clinician. In such instances, the springs can act to shut off the electric motor 1610 and stop the rotation of the end effector 7000. In at least one instance, the rotation actuator 1420 comprises a first torsion spring configured to rotate the rotation actuator 1420 in the first direction and a second torsion spring configured to rotate the rotation actuator 1420 in the second direction. The first and second torsion springs can have the same, or at least substantially the same, spring constant such that the forces and/or torques applied by the first and second torsion springs balance, or at least substantially balance, the rotation actuator 1420 in its center position.

In view of the above, the reader should appreciate that the clamping trigger 2610 and the rotation actuator 1420 are both operable to rotate the drive shaft 2710 and either, respectively, operate the jaw assembly 7100 or rotate the end effector 7000. The system that uses the rotation of the drive shaft 2710 to selectively perform these functions is described in greater detail below.

Referring to FIGS. 281 and 282, the articulation actuator 1430 comprises a first push button 1432 and a second push button 1434. The first push button 1432 is part of a first articulation control circuit and the second push button 1434 is part of a second articulation circuit of the input system 1400. The first push button 1432 comprises a first switch that is closed when the first push button 1432 is depressed. The handle control system 1800 is configured to sense the closure of the first switch and, moreover, the closure of the first articulation control circuit. When the handle control system 1800 detects that the first articulation control circuit has been closed, the handle control system 1800 operates the electric motor 1610 to articulate the end effector 7000 in a first articulation direction about the articulation joint 2300. When the first push button 1432 is released by the clinician, the first articulation control circuit is opened which, once detected by the control system 1800, causes the control system 1800 to cut the power to the electric motor 1610 to stop the articulation of the end effector 7000.

In various instances, further to the above, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the first direction. In addition to or in lieu of the encoder system, the shaft assembly 2000 can comprise a first sensor configured to detect when the end effector 7000 has reached the limit of its articulation in the first direction. In any event, when the control system 1800 determines that the end effector 7000 has reached the limit of articulation in the first direction, the control system 1800 can cut the power to the electric motor 1610 to stop the articulation of the end effector 7000.

Similar to the above, the second push button 1434 comprises a second switch that is closed when the second push button 1434 is depressed. The handle control system 1800 is configured to sense the closure of the second switch and, moreover, the closure of the second articulation control circuit. When the handle control system 1800 detects that the second articulation control circuit has been closed, the handle control system 1800 operates the electric motor 1610 to articulate the end effector 7000 in a second direction about the articulation joint 2300. When the second push button 1434 is released by the clinician, the second articulation control circuit is opened which, once detected by the control system 1800, causes the control system 1800 to cut the power to the electric motor 1610 to stop the articulation of the end effector 7000.

In various instances, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the second direction. In addition to or in lieu of the encoder system, the shaft assembly 2000 can comprise a second sensor configured to detect when the end effector 7000 has reached the limit of its articulation in the second direction. In any event, when the control system 1800 determines that the end effector 7000 has reached the limit of articulation in the second direction, the control system 1800 can cut the power to the electric motor 1610 to stop the articulation of the end effector 7000.

As described above, the end effector 7000 is articulatable in a first direction (FIG. 290) and/or a second direction (FIG. 291) from a center, or unarticulated, position (FIG. 289). Once the end effector 7000 has been articulated, the clinician can attempt to re-center the end effector 7000 by using the first and second articulation push buttons 1432 and 1434. As the reader can appreciate, the clinician may struggle to re-center the end effector 7000 as, for instance, the end effector 7000 may not be entirely visible once it is positioned in the patient. In some instances, the end effector 7000 may not fit back through a trocar if the end effector 7000 is not re-centered, or at least substantially re-centered. With that in mind, the control system 1800 is configured to provide feedback to the clinician when the end effector 7000 is moved into its unarticulated, or centered, position. In at least one instance, the feedback comprises audio feedback and the handle control system 1800 can comprise a speaker which emits a sound, such as a beep, for example, when the end effector 7000 is centered. In certain instances, the feedback comprises visual feedback and the handle control system 1800 can comprise a light emitting diode (LED), for example, positioned on the handle housing 1110 which flashes when the end effector 7000 is centered. In various instances, the feedback comprises haptic feedback and the handle control system 1800 can comprise an electric motor comprising an eccentric element which vibrates the handle 1000 when the end effector 7000 is centered. Manually re-centering the end effector 7000 in this way can be facilitated by the control system 1800 slowing the motor 1610 when the end effector 7000 is approaching its centered position. In at least one instance, the control system 1800 slows the articulation of the end effector 7000 when the end effector 7000 is within approximately 5 degrees of center in either direction, for example.

In addition to or in lieu of the above, the handle control system 1800 can be configured to re-center the end effector 7000. In at least one such instance, the handle control system 1800 can re-center the end effector 7000 when both of the articulation buttons 1432 and 1434 of the articulation actuator 1430 are depressed at the same time. When the handle control system 1800 comprises an encoder system configured to monitor the rotational output of the electric motor 1610, for example, the handle control system 1800 can determine the amount and direction of articulation needed to re-center, or at least substantially re-center, the end effector 7000. In various instances, the input system 1400 can comprise a home button, for example, which, when depressed, automatically centers the end effector 7000.

Referring primarily to FIGS. 279 and 280, the elongate shaft 2200 of the shaft assembly 2000 comprises an outer housing, or tube, 2210 mounted to the proximal housing 2110 of the proximal portion 2100. The outer housing 2210 comprises a longitudinal aperture 2230 extending therethrough and a proximal flange 2220 which secures the outer housing 2210 to the proximal housing 2110. The frame 2500 of the shaft assembly 2000 extends through the longitudinal aperture 2230 of the elongate shaft 2200. More specifically, the shaft 2510 of the shaft frame 2500 necks down into a smaller shaft 2530 which extends through the longitudinal aperture 2230. That said, the shaft frame 2500 can comprise any suitable arrangement. The drive system 2700 of the shaft assembly 2000 also extends through the longitudinal aperture 2230 of the elongate shaft 2200. More specifically, the drive shaft 2710 of the shaft drive system 2700 necks down into a smaller drive shaft 2730 which extends through the longitudinal aperture 2230. That said, the shaft drive system 2700 can comprise any suitable arrangement.

Referring primarily to FIGS. 294, 298, and 299, the outer housing 2210 of the elongate shaft 2200 extends to the articulation joint 2300. The articulation joint 2300 comprises a proximal frame 2310 mounted to the outer housing 2210 such that there is little, if any, relative translation and/or rotation between the proximal frame 2310 and the outer housing 2210. Referring primarily to FIG. 296, the proximal frame 2310 comprises an annular portion 2312 mounted to the sidewall of the outer housing 2210 and tabs 2314 extending distally from the annular portion 2312. The articulation joint 2300 further comprises links 2320 and 2340 which are rotatably mounted to the frame 2310 and mounted to an outer housing 2410 of the distal attachment portion 2400. The link 2320 comprises a distal end 2322 mounted to the outer housing 2410. More specifically, the distal end 2322 of the link 2320 is received and fixedly secured within a mounting slot 2412 defined in the outer housing 2410. Similarly, the link 2340 comprises a distal end 2342 mounted to the outer housing 2410. More specifically, the distal end 2342 of the link 2340 is received and fixedly secured within a mounting slot defined in the outer housing 2410. The link 2320 comprises a proximal end 2324 rotatably coupled to a tab 2314 of the proximal articulation frame 2310. Although not illustrated in FIG. 296, a pin extends through apertures defined in the proximal end 2324 and the tab 2314 to define a pivot axis therebetween. Similarly, the link 2340 comprises a proximal end 2344 rotatably coupled to a tab 2314 of the proximal articulation frame 2310. Although not illustrated in FIG. 296, a pin extends through apertures defined in the proximal end 2344 and the tab 2314 to define a pivot axis therebetween. These pivot axes are collinear, or at least substantially collinear, and define an articulation axis A of the articulation joint 2300.

Referring primarily to FIGS. 294, 298, and 299, the outer housing 2410 of the distal attachment portion 2400 comprises a longitudinal aperture 2430 extending therethrough. The longitudinal aperture 2430 is configured to receive a proximal attachment portion 7400 of the end effector 7000. The end effector 7000 comprises an outer housing 6230 which is closely received within the longitudinal aperture 2430 of the distal attachment portion 2400 such that there is little, if any, relative radial movement between the proximal attachment portion 7400 of the end effector 7000 and the distal attachment portion 2400 of the shaft assembly 2000. The proximal attachment portion 7400 further comprises an annular array of lock notches 7410 defined on the outer housing 6230 which is releasably engaged by an end effector lock 6400 in the distal attachment portion 2400 of the shaft assembly 2000. When the end effector lock 6400 is engaged with the array of lock notches 7410, the end effector lock 6400 prevents, or at least inhibits, relative longitudinal movement between the proximal attachment portion 7400 of the end effector 7000 and the distal attachment portion 2400 of the shaft assembly 2000. As a result of the above, only relative rotation between the proximal attachment portion 7400 of the end effector 7000 and the distal attachment portion 2400 of the shaft assembly 2000 is permitted. To this end, the outer housing 6230 of the end effector 7000 is closely received within the longitudinal aperture 2430 defined in the distal attachment portion 2400 of the shaft assembly 2000.

Further to the above, referring to FIG. 295, the outer housing 6230 further comprises an annular slot, or recess, 6270 defined therein which is configured to receive an O-ring 6275 therein. The O-ring 6275 is compressed between the outer housing 6230 and the sidewall of the longitudinal aperture 2430 when the end effector 7000 is inserted into the distal attachment portion 2400. The O-ring 6275 is configured to resist, but permit, relative rotation between the end effector 7000 and the distal attachment portion 2400 such that the O-ring 6275 can prevent, or reduce the possibility of, unintentional relative rotation between the end effector 7000 and the distal attachment portion 2400. In various instances, the O-ring 6275 can provide a seal between the end effector 7000 and the distal attachment portion 2400 to prevent, or at least reduce the possibility of, fluid ingress into the shaft assembly 2000, for example.

Referring to FIGS. 288-295, the jaw assembly 7100 of the end effector 7000 comprises a first jaw 7110 and a second jaw 7120. Each jaw 7110, 7120 comprises a distal end which is configured to assist a clinician in dissecting tissue with the end effector 7000. Each jaw 7110, 7120 further comprises a plurality of teeth which are configured to assist a clinician in grasping and holding onto tissue with the end effector 7000. Moreover, referring primarily to FIG. 295, each jaw 7110, 7120 comprises a proximal end, i.e., proximal ends 7115, 7125, respectively, which rotatably connect the jaws 7110, 7120 together. Each proximal end 7115, 7125 comprises an aperture extending therethrough which is configured to closely receive a pin 7130 therein. The pin 7130 comprises a central body 7135 closely received within the apertures defined in the proximal ends 7115, 7125 of the jaws 7110, 7120 such that there is little, if any, relative translation between the jaws 7110, 7120 and the pin 7130. The pin 7130 defines a jaw axis J about which the jaws 7110, 7120 can be rotated and, also, rotatably mounts the jaws 7110, 7120 to the outer housing 6230 of the end effector 7000. More specifically, the outer housing 6230 comprises distally-extending tabs 6235 having apertures defined therein which are also configured to closely receive the pin 7130 such that the jaw assembly 7100 does not translate relative to a shaft portion 7200 of the end effector 7000. The pin 7130 further comprises enlarged ends which prevent the jaws 7110, 7120 from becoming detached from the pin 7130 and also prevents the jaw assembly 7100 from becoming detached from the shaft portion 7200. This arrangement defines a rotation joint 7300.

Referring primarily to FIGS. 295 and 298, the jaws 7110 and 7120 are rotatable between their open and closed positions by a jaw assembly drive including drive links 7140, a drive nut 7150, and a drive screw 6130. As described in greater detail below, the drive screw 6130 is selectively rotatable by the drive shaft 2730 of the shaft drive system 2700. The drive screw 6130 comprises an annular flange 6132 which is closely received within a slot, or groove, 6232 (FIG. 300) defined in the outer housing 6230 of the end effector 7000. The sidewalls of the slot 6232 are configured to prevent, or at least inhibit, longitudinal and/or radial translation between the drive screw 6130 and the outer housing 6230, but yet permit relative rotational motion between the drive screw 6130 and the outer housing 6230. The drive screw 6130 further comprises a threaded end 6160 which is threadably engaged with a threaded aperture 7160 defined in the drive nut 7150. The drive nut 7150 is constrained from rotating with the drive screw 6130 and, as a result, the drive nut 7150 is translated when the drive screw 6130 is rotated. In use, the drive screw 6130 is rotated in a first direction to displace the drive nut 7150 proximally and in a second, or opposite, direction to displace the drive nut 7150 distally. The drive nut 7150 further comprises a distal end 7155 comprising an aperture defined therein which is configured to closely receive pins 7145 extending from the drive links 7140. Referring primarily to FIG. 295, a first drive link 7140 is attached to one side of the distal end 7155 and a second drive link 7140 is attached to the opposite side of the distal end 7155. The first drive link 7140 comprises another pin 7145 extending therefrom which is closely received in an aperture defined in the proximal end 7115 of the first jaw 7110 and, similarly, the second drive link 7140 comprises another pin extending therefrom which is closely received in an aperture defined in the proximal end 7125 of the second jaw 7120. As a result of the above, the drive links 7140 operably connect the jaws 7110 and 7120 to the drive nut 7150. When the drive nut 7150 is driven proximally by the drive screw 6130, as described above, the jaws 7110, 7120 are rotated into the closed, or clamped, configuration. Correspondingly, the jaws 7110, 7120 are rotated into their open configuration when the drive nut 7150 is driven distally by the drive screw 6130.

As discussed above, the control system 1800 is configured to actuate the electric motor 1610 to perform three different end effector functions—clamping/opening the jaw assembly 7100 (FIGS. 288 and 289), rotating the end effector 7000 about a longitudinal axis (FIGS. 292 and 293), and articulating the end effector 7000 about an articulation axis (FIGS. 290 and 291). Referring primarily to FIGS. 301 and 302, the control system 1800 is configured to operate a transmission 6000 to selectively perform these three end effector functions. The transmission 6000 comprises a first clutch system 6100 configured to selectively transmit the rotation of the drive shaft 2730 to the drive screw 6130 of the end effector 7000 to open or close the jaw assembly 7100, depending on the direction in which the drive shaft 2730 is rotated. The transmission 6000 further comprises a second clutch system 6200 configured to selectively transmit the rotation of the drive shaft 2730 to the outer housing 6230 of the end effector 7000 to rotate the end effector 7000 about the longitudinal axis L. The transmission 6000 also comprises a third clutch system 6300 configured to selectively transmit the rotation of the drive shaft 2730 to the articulation joint 2300 to articulate the distal attachment portion 2400 and the end effector 7000 about the articulation axis A. The clutch systems 6100, 6200, and 6300 are in electrical communication with the control system 1800 via electrical circuits extending through the shaft 2510, the connector pins 2520, the connector pins 1520, and the shaft 1510, for example. In at least one instance, each of these clutch control circuits comprises two connector pins 2520 and two connector pins 1520, for example.

In various instances, further to the above, the shaft 2510 and/or the shaft 1510 comprise a flexible circuit including electrical traces which form part of the clutch control circuits. The flexible circuit can comprise a ribbon, or substrate, with conductive pathways defined therein and/or thereon. The flexible circuit can also comprise sensors and/or any solid state component, such as signal smoothing capacitors, for example, mounted thereto. In at least one instance, each of the conductive pathways can comprise one or more signal smoothing capacitors which can, among other things, even out fluctuations in signals transmitted through the conductive pathways. In various instances, the flexible circuit can be coated with at least one material, such as an elastomer, for example, which can seal the flexible circuit against fluid ingress.

Referring primarily to FIG. 303, the first clutch system 6100 comprises a first clutch 6110, an expandable first drive ring 6120, and a first electromagnetic actuator 6140. The first clutch 6110 comprises an annular ring and is slideably disposed on the drive shaft 2730. The first clutch 6110 is comprised of a magnetic material and is movable between a disengaged, or unactuated, position (FIG. 303) and an engaged, or actuated, position (FIG. 304) by electromagnetic fields EF generated by the first electromagnetic actuator 6140. In various instances, the first clutch 6110 is at least partially comprised of iron and/or nickel, for example. In at least one instance, the first clutch 6110 comprises a permanent magnet. As illustrated in FIG. 297, the drive shaft 2730 comprises one or more longitudinal key slots 6115 defined therein which are configured to constrain the longitudinal movement of the clutch 6110 relative to the drive shaft 2730. More specifically, the clutch 6110 comprises one or more keys extending into the key slots 6115 such that the distal ends of the key slots 6115 stop the distal movement of the clutch 6110 and the proximal ends of the key slots 6115 stop the proximal movement of the clutch 6110.

When the first clutch 6110 is in its disengaged position (FIG. 303), the first clutch 6110 rotates with the drive shaft 2130 but does not transmit rotational motion to the first drive ring 6120. As can be seen in FIG. 303, the first clutch 6110 is separated from, or not in contact with, the first drive ring 6120. As a result, the rotation of the drive shaft 2730 and the first clutch 6110 is not transmitted to the drive screw 6130 when the first clutch assembly 6100 is in its disengaged state. When the first clutch 6110 is in its engaged position (FIG. 304), the first clutch 6110 is engaged with the first drive ring 6120 such that the first drive ring 6120 is expanded, or stretched, radially outwardly into contact with the drive screw 6130. In at least one instance, the first drive ring 6120 comprises an elastomeric band, for example. As can be seen in FIG. 304, the first drive ring 6120 is compressed against an annular inner sidewall 6135 of the drive screw 6130. As a result, the rotation of the drive shaft 2730 and the first clutch 6110 is transmitted to the drive screw 6130 when the first clutch assembly 6100 is in its engaged state. Depending on the direction in which the drive shaft 2730 is rotated, the first clutch assembly 6100 can move the jaw assembly 7100 into its open and closed configurations when the first clutch assembly 6100 is in its engaged state.

As described above, the first electromagnetic actuator 6140 is configured to generate magnetic fields to move the first clutch 6110 between its disengaged (FIG. 303) and engaged (FIG. 304) positions. For instance, referring to FIG. 303, the first electromagnetic actuator 6140 is configured to emit a magnetic field $EF_L$ which repulses, or drives, the first clutch 6110 away from the first drive ring 6120 when the first clutch assembly 6100 is in its disengaged state. The first electromagnetic actuator 6140 comprises one or more wound coils in a cavity defined in the shaft frame 2530 which generate the magnetic field $EF_L$ when current flows in a first direction through a first electrical clutch circuit including the wound coils. The control system 1800 is configured to apply a first voltage polarity to the first electrical clutch circuit to create the current flowing in the first direction. The control system 1800 can continuously apply the first voltage polarity to the first electric shaft circuit to continuously hold the first clutch 6110 in its disengaged position. While such an arrangement can prevent the first clutch 6110 from unintentionally engaging the first drive ring 6120, such an arrangement can also consume a lot of power. Alternatively, the control system 1800 can apply the first voltage polarity to the first electrical clutch circuit for a sufficient period of time to position the first clutch 6110 in its disengaged position and then discontinue applying the first voltage polarity to the first electric clutch circuit, thereby resulting in a lower consumption of power. That being said, the first clutch assembly 6100 further comprises a first clutch lock 6150 mounted in the drive screw 6130 which is configured to releasably hold the first clutch 6110 in its disengaged position. The first clutch lock 6150 is configured to prevent, or at least reduce the possibility of, the first clutch 6110 from becoming unintentionally engaged with the first drive ring 6120. When the first clutch 6110 is in its disengaged position, as illustrated in FIG. 303, the first clutch lock 6150 interferes with the free movement of the first clutch 6110 and holds the first clutch 6110 in position via a friction force and/or an interference force therebetween. In at least one instance, the first clutch lock 6150 comprises an elastomeric plug, seat, or detent, comprised of rubber, for example. In certain instances, the first clutch lock 6150 comprises a permanent magnet which holds the first clutch 6110 in its disengaged position by an electromagnetic force. In any event, the first electromagnetic actuator 6140 can apply an electromagnetic pulling force to the first clutch 6110 that overcomes these forces, as described in greater detail below.

Further to the above, referring to FIG. 304, the first electromagnetic actuator 6140 is configured to emit a magnetic field $EF_D$ which pulls, or drives, the first clutch 6110 toward the first drive ring 6120 when the first clutch assembly 6100 is in its engaged state. The coils of the first electromagnetic actuator 6140 generate the magnetic field $EF_D$ when current flows in a second, or opposite, direction through the first electrical clutch circuit. The control system 1800 is configured to apply an opposite voltage polarity to the first electrical clutch circuit to create the current flowing in the opposite direction. The control system 1800 can continuously apply the opposite voltage polarity to the first electrical clutch circuit to continuously hold the first clutch 6110 in its engaged position and maintain the operable engagement between the first drive ring 6120 and the drive screw 6130. Alternatively, the first clutch 6110 can be configured to become wedged within the first drive ring 6120 when the first clutch 6110 is in its engaged position and, in such instances, the control system 1800 may not need to continuously apply a voltage polarity to the first electrical clutch circuit to hold the first clutch assembly 6100 in its engaged state. In such instances, the control system 1800 can discontinue applying the voltage polarity once the first clutch 6110 has been sufficiently wedged in the first drive ring 6120.

Notably, further to the above, the first clutch lock 6150 is also configured to lockout the jaw assembly drive when the first clutch 6110 is in its disengaged position. More specifically, referring again to FIG. 303, the first clutch 6110 pushes the first clutch lock 6150 in the drive screw 6130 into engagement with the outer housing 6230 of the end effector 7000 when the first clutch 6110 is in its disengaged position such that the drive screw 6130 does not rotate, or at least substantially rotate, relative to the outer housing 6230. The outer housing 6230 comprises a slot 6235 defined therein which is configured to receive the first clutch lock 6150. When the first clutch 6110 is moved into its engaged position, referring to FIG. 304, the first clutch 6110 is no longer engaged with the first clutch lock 6150 and, as a result, the first clutch lock 6150 is no longer biased into engagement with the outer housing 6230 and the drive screw 6130 can rotate freely with respect to the outer housing 6230. As a result of the above, the first clutch 6110 can do at least two things—operate the jaw drive when the first clutch 6110 is in its engaged position and lock out the jaw drive when the first clutch 6110 is in its disengaged position.

Moreover, further to the above, the threads of the threaded portions 6160 and 7160 can be configured to prevent, or at least resist, backdriving of the jaw drive. In at least one instance, the thread pitch and/or angle of the threaded portions 6160 and 7160, for example, can be selected to prevent the backdriving, or unintentional opening, of the jaw assembly 7100. As a result of the above, the possibility of the jaw assembly 7100 unintentionally opening or closing is prevented, or at least reduced.

Referring primarily to FIG. 305, the second clutch system 6200 comprises a second clutch 6210, an expandable second drive ring 6220, and a second electromagnetic actuator 6240. The second clutch 6210 comprises an annular ring and is slideably disposed on the drive shaft 2730. The second clutch 6210 is comprised of a magnetic material and is movable between a disengaged, or unactuated, position (FIG. 305) and an engaged, or actuated, position (FIG. 306) by electromagnetic fields EF generated by the second electromagnetic actuator 6240. In various instances, the second clutch 6210 is at least partially comprised of iron and/or nickel, for example. In at least one instance, the second clutch 6210 comprises a permanent magnet. As illustrated in FIG. 297, the drive shaft 2730 comprises one or more longitudinal key slots 6215 defined therein which are configured to constrain the longitudinal movement of the second clutch 6210 relative to the drive shaft 2730. More specifically, the second clutch 6210 comprises one or more keys extending into the key slots 6215 such that the distal ends of the key slots 6215 stop the distal movement of the second clutch 6210 and the proximal ends of the key slots 6215 stop the proximal movement of the second clutch 6210.

When the second clutch 6210 is in its disengaged position, referring to FIG. 305, the second clutch 6210 rotates with the drive shaft 2730 but does not transmit rotational motion to the second drive ring 6220. As can be seen in FIG. 305, the second clutch 6210 is separated from, or not in contact with, the second drive ring 6220. As a result, the rotation of the drive shaft 2730 and the second clutch 6210 is not transmitted to the outer housing 6230 of the end effector 7000 when the second clutch assembly 6200 is in its disengaged state. When the second clutch 6210 is in its engaged position (FIG. 306), the second clutch 6210 is engaged with the second drive ring 6220 such that the second drive ring 6220 is expanded, or stretched, radially outwardly into contact with the outer housing 6230. In at least one instance, the second drive ring 6220 comprises an elastomeric band, for example. As can be seen in FIG. 306, the second drive ring 6220 is compressed against an annular inner sidewall 7415 of the outer housing 6230. As a result, the rotation of the drive shaft 2730 and the second clutch 6210 is transmitted to the outer housing 6230 when the second clutch assembly 6200 is in its engaged state. Depending on the direction in which the drive shaft 2730 is rotated, the second clutch assembly 6200 can rotate the end effector 7000 in a first direction or a second direction about the longitudinal axis L when the second clutch assembly 6200 is in its engaged state.

As described above, the second electromagnetic actuator 6240 is configured to generate magnetic fields to move the second clutch 6210 between its disengaged (FIG. 305) and engaged (FIG. 306) positions. For instance, the second electromagnetic actuator 6240 is configured to emit a magnetic field $EF_L$ which repulses, or drives, the second clutch 6210 away from the second drive ring 6220 when the second clutch assembly 6200 is in its disengaged state. The second electromagnetic actuator 6240 comprises one or more wound coils in a cavity defined in the shaft frame 2530 which generate the magnetic field $EF_L$ when current flows in a first direction through a second electrical clutch circuit including the wound coils. The control system 1800 is configured to apply a first voltage polarity to the second electrical clutch circuit to create the current flowing in the first direction. The control system 1800 can continuously apply the first voltage polarity to the second electric clutch circuit to continuously hold the second clutch 6120 in its disengaged position. While such an arrangement can prevent the second clutch 6210 from unintentionally engaging the second drive ring 6220, such an arrangement can also consume a lot of power. Alternatively, the control system 1800 can apply the first voltage polarity to the second electrical clutch circuit for a sufficient period of time to position the second clutch 6210 in its disengaged position and then discontinue applying the first voltage polarity to the second electric clutch circuit, thereby resulting in a lower consumption of power. That being said, the second clutch assembly 6200 further comprises a second clutch lock 6250 mounted in the outer housing 6230 which is configured to releasably hold the second clutch 6210 in its disengaged position. Similar to the above, the second clutch lock 6250 can prevent, or at least reduce the possibility of, the second clutch 6210 from becoming unintentionally engaged with the second drive ring 6220. When the second clutch 6210 is in its disengaged position, as illustrated in FIG. 305, the second clutch lock 6250 interferes with the free movement of the second clutch 6210 and holds the second clutch 6210 in position via a friction and/or interference force therebetween. In at least one instance, the second clutch lock 6250 comprises an elastomeric plug, seat, or detent, comprised of rubber, for example. In certain instances, the second clutch lock 6250 comprises a permanent magnet which holds the second clutch 6210 in its disengaged position by an electromagnetic force. That said, the second electromagnetic actuator 6240 can apply an electromagnetic pulling force to the second clutch 6210 that overcomes these forces, as described in greater detail below.

Further to the above, referring to FIG. 306, the second electromagnetic actuator 6240 is configured to emit a magnetic field $EF_D$ which pulls, or drives, the second clutch 6210 toward the second drive ring 6220 when the second clutch assembly 6200 is in its engaged state. The coils of the second electromagnetic actuator 6240 generate the magnetic field $EF_D$ when current flows in a second, or opposite, direction through the second electrical shaft circuit. The control system 1800 is configured to apply an opposite voltage polarity to the second electrical shaft circuit to create the current flowing in the opposite direction. The control system 1800 can continuously apply the opposite voltage polarity to the second electric shaft circuit to continuously hold the second clutch 6210 in its engaged position and maintain the operable engagement between the second drive ring 6220 and the outer housing 6230. Alternatively, the second clutch 6210 can be configured to become wedged within the second drive ring 6220 when the second clutch 6210 is in its engaged position and, in such instances, the control system 1800 may not need to continuously apply a voltage polarity to the second shaft electrical circuit to hold the second clutch assembly 6200 in its engaged state. In such instances, the control system 1800 can discontinue applying the voltage polarity once the second clutch 6210 has been sufficiently wedged in the second drive ring 6220.

Notably, further to the above, the second clutch lock 6250 is also configured to lockout the rotation of the end effector 7000 when the second clutch 6210 is in its disengaged position. More specifically, referring again to FIG. 305, the second clutch 6210 pushes the second clutch lock 6250 in the outer shaft 6230 into engagement with the articulation link 2340 when the second clutch 6210 is in its disengaged position such that the end effector 7000 does not rotate, or at least substantially rotate, relative to the distal attachment portion 2400 of the shaft assembly 2000. As illustrated in FIG. 302, the second clutch lock 6250 is positioned or wedged within a slot, or channel, 2345 defined in the articulation link 2340 when the second clutch 6210 is in its disengaged position. As a result of the above, the possibility of the end effector 7000 unintentionally rotating is prevented, or at least reduced. Moreover, as a result of the above, the second clutch 6210 can do at least two things— operate the end effector rotation drive when the second clutch 6210 is in its engaged position and lock out the end effector rotation drive when the second clutch 6210 is in its disengaged position.

Referring primarily to FIGS. 296, 299, and 300, the shaft assembly 2000 further comprises an articulation drive system configured to articulate the distal attachment portion 2400 and the end effector 7000 about the articulation joint 2300. The articulation drive system comprises an articulation drive 6330 rotatably supported within the distal attachment portion 2400. That said, the articulation drive 6330 is closely received within the distal attachment portion 2400 such that the articulation drive 6330 does not translate, or at least substantially translate, relative to the distal attachment portion 2400. The articulation drive system of the shaft assembly 2000 further comprises a stationary gear 2330 fixedly mounted to the articulation frame 2310. More specifically, the stationary gear 2330 is fixedly mounted to a pin connecting a tab 2314 of the articulation frame 2310 and the articulation link 2340 such that the stationary gear 2330 does not rotate relative to the articulation frame 2310. The stationary gear 2330 comprises a central body 2335 and an annular array of stationary teeth 2332 extending around the perimeter of the central body 2335. The articulation drive 6330 comprises an annular array of drive teeth 6332 which is meshingly engaged with the stationary teeth 2332. When the articulation drive 6330 is rotated, the articulation drive 6330 pushes against the stationary gear 2330 and articulates the distal attachment portion 2400 of the shaft assembly 2000 and the end effector 7000 about the articulation joint 2300.

Referring primarily to FIG. 307, the third clutch system 6300 comprises a third clutch 6310, an expandable third drive ring 6320, and a third electromagnetic actuator 6340. The third clutch 6310 comprises an annular ring and is slideably disposed on the drive shaft 2730. The third clutch 6310 is comprised of a magnetic material and is movable between a disengaged, or unactuated, position (FIG. 307) and an engaged, or actuated, position (FIG. 308) by electromagnetic fields EF generated by the third electromagnetic actuator 6340. In various instances, the third clutch 6310 is at least partially comprised of iron and/or nickel, for example. In at least one instance, the third clutch 6310 comprises a permanent magnet. As illustrated in FIG. 297, the drive shaft 2730 comprises one or more longitudinal key slots 6315 defined therein which are configured to constrain the longitudinal movement of the third clutch 6310 relative to the drive shaft 2730. More specifically, the third clutch 6310 comprises one or more keys extending into the key slots 6315 such that the distal ends of the key slots 6315 stop the distal movement of the third clutch 6310 and the proximal ends of the key slots 6315 stop the proximal movement of the third clutch 6310.

When the third clutch 6310 is in its disengaged position, referring to FIG. 307, the third clutch 6310 rotates with the drive shaft 2730 but does not transmit rotational motion to the third drive ring 6320. As can be seen in FIG. 307, the third clutch 6310 is separated from, or not in contact with, the third drive ring 6320. As a result, the rotation of the drive shaft 2730 and the third clutch 6310 is not transmitted to the articulation drive 6330 when the third clutch assembly 6300 is in its disengaged state. When the third clutch 6310 is in its engaged position, referring to FIG. 308, the third clutch 6310 is engaged with the third drive ring 6320 such that the third drive ring 6320 is expanded, or stretched, radially outwardly into contact with the articulation drive 6330. In at least one instance, the third drive ring 6320 comprises an elastomeric band, for example. As can be seen in FIG. 308, the third drive ring 6320 is compressed against an annular inner sidewall 6335 of the articulation drive 6330. As a result, the rotation of the drive shaft 2730 and the third clutch 6310 is transmitted to the articulation drive 6330 when the third clutch assembly 6300 is in its engaged state. Depending on the direction in which the drive shaft 2730 is rotated, the third clutch assembly 6300 can articulate the distal attachment portion 2400 of the shaft assembly 2000 and the end effector 7000 in a first or second direction about the articulation joint 2300.

As described above, the third electromagnetic actuator 6340 is configured to generate magnetic fields to move the third clutch 6310 between its disengaged (FIG. 307) and engaged (FIG. 308) positions. For instance, referring to FIG. 307, the third electromagnetic actuator 6340 is configured to emit a magnetic field $EF_L$ which repulses, or drives, the third clutch 6310 away from the third drive ring 6320 when the third clutch assembly 6300 is in its disengaged state. The third electromagnetic actuator 6340 comprises one or more wound coils in a cavity defined in the shaft frame 2530 which generate the magnetic field $EF_L$ when current flows in a first direction through a third electrical clutch circuit including the wound coils. The control system 1800 is configured to apply a first voltage polarity to the third electrical clutch circuit to create the current flowing in the first direction. The control system 1800 can continuously apply the first voltage polarity to the third electric clutch circuit to continuously hold the third clutch 6310 in its disengaged position. While such an arrangement can prevent the third clutch 6310 from unintentionally engaging the third drive ring 6320, such an arrangement can also consume a lot of power. Alternatively, the control system 1800 can apply the first voltage polarity to the third electrical clutch circuit for a sufficient period of time to position the third clutch 6310 in its disengaged position and then discontinue applying the first voltage polarity to the third electric clutch circuit, thereby resulting in a lower consumption of power.

Further to the above, the third electromagnetic actuator 6340 is configured to emit a magnetic field $EF_D$ which pulls, or drives, the third clutch 6310 toward the third drive ring 6320 when the third clutch assembly 6300 is in its engaged state. The coils of the third electromagnetic actuator 6340 generate the magnetic field $EF_D$ when current flows in a second, or opposite, direction through the third electrical clutch circuit. The control system 1800 is configured to apply an opposite voltage polarity to the third electrical shaft circuit to create the current flowing in the opposite direction. The control system 1800 can continuously apply the opposite voltage polarity to the third electric shaft circuit to continuously hold the third clutch 6310 in its engaged position and maintain the operable engagement between the third drive ring 6320 and the articulation drive 6330. Alternatively, the third clutch 6210 can be configured to become wedged within the third drive ring 6320 when the third clutch 6310 is in its engaged position and, in such instances, the control system 1800 may not need to continuously apply a voltage polarity to the third shaft electrical circuit to hold the third clutch assembly 6300 in its engaged state. In such instances, the control system 1800 can discontinue applying the voltage polarity once the third clutch 6310 has been sufficiently wedged in the third drive ring 6320. In any event, the end effector 7000 is articulatable in a first direction or a second direction, depending on the direction in which the drive shaft 2730 is rotated, when the third clutch assembly 6300 is in its engaged state.

Further to the above, referring to FIGS. 296, 307, and 308, the articulation drive system further comprises a lockout 6350 which prevents, or at least inhibits, the articulation of the distal attachment portion 2400 of the shaft assembly 2000 and the end effector 7000 about the articulation joint 2300 when the third clutch 6310 is in its disengaged position (FIG. 307). Referring primarily to FIG. 296, the articulation link 2340 comprises a slot, or groove, 2350 defined therein wherein the lockout 6350 is slideably positioned in the slot 2350 and extends at least partially under the stationary articulation gear 2330. The lockout 6350 comprises at attachment hook 6352 engaged with the third clutch 6310. More specifically, the third clutch 6310 comprises an annular slot, or groove, 6312 defined therein and the attachment hook 6352 is positioned in the annular slot 6312 such that the lockout 6350 translates with the third clutch 6310. Notably, however, the lockout 6350 does not rotate, or at least substantially rotate, with the third clutch 6310. Instead, the annular groove 6312 in the third clutch 6310 permits the third clutch 6310 to rotate relative to the lockout 6350. The lockout 6350 further comprises a lockout hook 6354 slideably positioned in a radially-extending lockout slot 2334 defined in the bottom of the stationary gear 2330. When the third clutch 6310 is in its disengaged position, as illustrated in FIG. 307, the lockout 6350 is in a locked position in which the lockout hook 6354 prevents the end effector 7000 from rotating about the articulation joint 2300. When the third clutch 6310 is in its engaged position, as illustrated in FIG. 308, the lockout 6350 is in an unlocked position in which the lockout hook 6354 is no longer positioned in the lockout slot 2334. Instead, the lockout hook 6354 is positioned in a clearance slot defined in the middle or body 2335 of the stationary gear 2330. In such instances, the lockout hook 6354 can rotate within the clearance slot when the end effector 7000 rotates about the articulation joint 2300.

Further to the above, the radially-extending lockout slot 2334 depicted in FIGS. 307 and 308 extends longitudinally, i.e., along an axis which is parallel to the longitudinal axis of the elongate shaft 2200. Once the end effector 7000 has been articulated, however, the lockout hook 6354 is no longer aligned with the longitudinal lockout slot 2334. With this in mind, the stationary gear 2330 comprises a plurality, or an array, of radially-extending lockout slots 2334 defined in the bottom of the stationary gear 2330 such that, when the third clutch 6310 is deactuated and the lockout 6350 is pulled distally after the end effector 7000 has been articulated, the lockout hook 6354 can enter one of the lockout slots 2334 and lock the end effector 7000 in its articulated position. Thus, as a result, the end effector 7000 can be locked in an unarticulated and an articulated position. In various instances, the lockout slots 2334 can define discrete articulated positions for the end effector 7000. For instance, the lockout slots 2334 can be defined at 10 degree intervals, for example, which can define discrete articulation orientations for the end effector 7000 at 10 degree intervals. In other instances, these orientations can be at 5 degree intervals, for example. In alternative embodiments, the lockout 6350 comprises a brake that engages a circumferential shoulder defined in the stationary gear 2330 when the third clutch 6310 is disengaged from the third drive ring 6320. In such an embodiment, the end effector 7000 can be locked in any suitable orientation. In any event, the lockout 6350 prevents, or at least reduces the possibility of, the end effector 7000 unintentionally articulating. As a result of the above, the third clutch 6310 can do things—operate the articulation drive when it is in its engaged position and lock out the articulation drive when it is in its disengaged position.

Referring primarily to FIGS. 299 and 300, the shaft frame 2530 and the drive shaft 2730 extend through the articulation joint 2300 into the distal attachment portion 2400. When the end effector 7000 is articulated, as illustrated in FIGS. 290 and 291, the shaft frame 2530 and the drive shaft 2730 bend to accommodate the articulation of the end effector 7000. Thus, the shaft frame 2530 and the drive shaft 2730 are comprised of any suitable material which accommodates the articulation of the end effector 7000. Moreover, as discussed above, the shaft frame 2530 houses the first, second, and third electromagnetic actuators 6140, 6240, and 6340. In various instances, the first, second, and third electromagnetic actuators 6140, 6240, and 6340 each comprise wound wire coils, such as copper wire coils, for example, and the shaft frame 2530 is comprised of an insulative material to prevent, or at least reduce the possibility of, short circuits between the first, second, and third electromagnetic actuators 6140, 6240, and 6340. In various instances, the first, second, and third electrical clutch circuits extending through the shaft frame 2530 are comprised of insulated electrical wires, for example. Further to the above, the first, second, and third electrical clutch circuits place the electromagnetic actuators 6140, 6240, and 6340 in communication with the control system 1800 in the drive module 1100.

As described above, the clutches 6110, 6210, and/or 6310 can be held in their disengaged positions so that they do not unintentionally move into their engaged positions. In various arrangements, the clutch system 6000 comprises a first biasing member, such as a spring, for example, configured to bias the first clutch 6110 into its disengaged position, a second biasing member, such as a spring, for example, configured to bias the second clutch 6210 into its disengaged position, and/or a third biasing member, such as a spring, for example, configured to bias the third clutch 6110 into its disengaged position. In such arrangements, the biasing forces of the springs can be selectively overcome by the electromagnetic forces generated by the electromagnetic actuators when energized by an electrical current. Further to the above, the clutches 6110, 6210, and/or 6310 can be retained in their engaged positions by the drive rings 6120, 6220, and/or 6320, respectively. More specifically, in at least one instance, the drive rings 6120, 6220, and/or 6320 are comprised of an elastic material which grips or frictionally holds the clutches 6110, 6210, and/or 6310, respectively, in their engaged positions. In various alternative embodiments, the clutch system 6000 comprises a first biasing member, such as a spring, for example, configured to bias the first clutch 6110 into its engaged position, a second biasing member, such as a spring, for example, configured to bias the second clutch 6210 into its engaged position, and/or a third biasing member, such as a spring, for example, configured to bias the third clutch 6110 into its engaged position. In such arrangements, the biasing forces of the springs can be overcome by the electromagnetic forces applied by the electromagnetic actuators 6140, 6240, and/or 6340, respectively, as needed to selectively hold the clutches 6110, 6210, and 6310 in their disengaged positions. In any one operational mode of the surgical system, the control assembly 1800 can energize one of the electromagnetic actuators to engage one of the clutches while energizing the other two electromagnetic actuators to disengage the other two clutches.

Although the clutch system 6000 comprises three clutches to control three drive systems of the surgical system, a clutch system can comprise any suitable number of clutches to control any suitable number of systems. Moreover, although the clutches of the clutch system 6000 slide proximally and distally between their engaged and disengaged positions, the clutches of a clutch system can move in any suitable manner. In addition, although the clutches of the clutch system 6000 are engaged one at a time to control one drive motion at a time, various instances are envisioned in which more than one clutch can be engaged to control more than one drive motion at a time.

In view of the above, the reader should appreciate that the control system 1800 is configured to, one, operate the motor system 1600 to rotate the drive shaft system 2700 in an appropriate direction and, two, operate the clutch system 6000 to transfer the rotation of the drive shaft system 2700 to the appropriate function of the end effector 7000. Moreover, as discussed above, the control system 1800 is responsive to inputs from the clamping trigger system 2600 of the shaft assembly 2000 and the input system 1400 of the handle 1000. When the clamping trigger system 2600 is actuated, as discussed above, the control system 1800 activates the first clutch assembly 6100 and deactivates the second clutch assembly 6200 and the third clutch assembly 6300. In such instances, the control system 1800 also supplies power to the motor system 1600 to rotate the drive shaft system 2700 in a first direction to clamp the jaw assembly 7100 of the end effector 7000. When the control system 1800 detects that the jaw assembly 7100 is in its clamped configuration, the control system 1800 stops the motor assembly 1600 and deactivates the first clutch assembly 6100. When the control system 1800 detects that the clamping trigger system 2600 has been moved to, or is being moved to, its unactuated position, the control system 1800 activates, or maintains the activation of, the first clutch assembly 6100 and deactivates, or maintains the deactivation of, the second clutch assembly 6200 and the third clutch assembly 6300. In such instances, the control system 1800 also supplies power to the motor system 1600 to rotate the drive shaft system 2700 in a second direction to open the jaw assembly 7100 of the end effector 7000.

When the rotation actuator 1420 is actuated in a first direction, further to the above, the control system 1800 activates the second clutch assembly 6200 and deactivates the first clutch assembly 6100 and the third clutch assembly 6300. In such instances, the control system 1800 also supplies power to the motor system 1600 to rotate the drive shaft system 2700 in a first direction to rotate the end effector 7000 in a first direction. When the control system 1800 detects that the rotation actuator 1420 has been actuated in a second direction, the control system 1800 activates, or maintains the activation of, the second clutch assembly 6200 and deactivates, or maintains the deactivation of, the first clutch assembly 6100 and the third clutch assembly 6300. In such instances, the control system 1800 also supplies power to the motor system 1600 to rotate the drive shaft system 2700 in a second direction to rotate the drive shaft system 2700 in a second direction to rotate the end effector 7000 in a second direction. When the control system 1800 detects that the rotation actuator 1420 is not actuated, the control system 1800 deactivates the second clutch assembly 6200.

When the first articulation actuator 1432 is depressed, further to the above, the control system 1800 activates the third clutch assembly 6300 and deactivates the first clutch assembly 6100 and the second clutch assembly 6200. In such instances, the control system 1800 also supplies power to the motor system 1600 to rotate the drive shaft system 2700 in a first direction to articulate the end effector 7000 in a first direction. When the control system 1800 detects that the second articulation actuator 1434 is depressed, the control system 1800 activates, or maintains the activation of, the third clutch assembly 6200 and deactivates, or maintains the deactivation of, the first clutch assembly 6100 and the second clutch assembly 6200. In such instances, the control system 1800 also supplies power to the motor system 1600 to rotate the drive shaft system 2700 in a second direction to articulate the end effector 7000 in a second direction. When the control system 1800 detects that neither the first articulation actuator 1432 nor the second articulation actuator 1434 are actuated, the control system 1800 deactivates the third clutch assembly 6200.

Further to the above, the control system 1800 is configured to change the operating mode of the stapling system based on the inputs it receives from the clamping trigger system 2600 of the shaft assembly 2000 and the input system 1400 of the handle 1000. The control system 1800 is configured to shift the clutch system 6000 before rotating the shaft drive system 2700 to perform the corresponding end effector function. Moreover, the control system 1800 is configured to stop the rotation of the shaft drive system 2700 before shifting the clutch system 6000. Such an arrangement can prevent the sudden movements in the end effector 7000. Alternatively, the control system 1800 can shift the clutch system 600 while the shaft drive system 2700 is rotating. Such an arrangement can allow the control system 1800 to shift quickly between operating modes.

As discussed above, referring to FIG. 309, the distal attachment portion 2400 of the shaft assembly 2000 comprises an end effector lock 6400 configured to prevent the end effector 7000 from being unintentionally decoupled from the shaft assembly 2000. The end effector lock 6400 comprises a lock end 6410 selectively engageable with the annular array of lock notches 7410 defined on the proximal attachment portion 7400 of the end effector 7000, a proximal end 6420, and a pivot 6430 rotatably connecting the end effector lock 6400 to the articulation link 2320. When the third clutch 6310 of the third clutch assembly 6300 is in its disengaged position, as illustrated in FIG. 309, the third clutch 6310 is contact with the proximal end 6420 of the end effector lock 6400 such that the lock end 6410 of the end effector lock 6400 is engaged with the array of lock notches 7410. In such instances, the end effector 7000 can rotate relative to the end effector lock 6400 but cannot translate relative to the distal attachment portion 2400. When the third clutch 6310 is moved into its engaged position, as illustrated in FIG. 310, the third clutch 6310 is no longer engaged with the proximal end 6420 of the end effector lock 6400. In such instances, the end effector lock 6400 is free to pivot upwardly and permit the end effector 7000 to be detached from the shaft assembly 2000.

The above being said, referring again to FIG. 309, it is possible that the second clutch 6210 of the second clutch assembly 6200 is in its disengaged position when the clinician detaches, or attempts to detach, the end effector 7000 from the shaft assembly 2000. As discussed above, the second clutch 6210 is engaged with the second clutch lock 6250 when the second clutch 6210 is in its disengaged position and, in such instances, the second clutch lock 6250 is pushed into engagement with the articulation link 2340. More specifically, the second clutch lock 6250 is positioned in the channel 2345 defined in the articulation 2340 when the second clutch 6210 is engaged with the second clutch lock 6250 which may prevent, or at least impede, the end effector 7000 from being detached from the shaft assembly 2000. To facilitate the release of the end effector 7000 from the shaft assembly 2000, the control system 1800 can move the second clutch 6210 into its engaged position in addition to moving the third clutch 6310 into its engaged position. In such instances, the end effector 7000 can clear both the end effector lock 6400 and the second clutch lock 6250 when the end effector 7000 is removed.

In at least one instance, further to the above, the drive module 1100 comprises an input switch and/or sensor in communication with the control system 1800 via the input system 1400, and/or the control system 1800 directly, which, when actuated, causes the control system 1800 to unlock the end effector 7000. In various instances, the drive module 1100 comprises an input screen 1440 in communication with the board 1410 of the input system 1400 which is configured to receive an unlock input from the clinician. In response to the unlock input, the control system 1800 can stop the motor system 1600, if it is running, and unlock the end effector 7000 as described above. The input screen 1440 is also configured to receive a lock input from the clinician in which the input system 1800 moves the second clutch assembly 6200 and/or the third clutch assembly 6300 into their unactuated states to lock the end effector 7000 to the shaft assembly 2000.

FIG. 312 depicts a shaft assembly 2000' in accordance with at least one alternative embodiment. The shaft assembly 2000' is similar to the shaft assembly 2000 in many respects, most of which will not be repeated herein for the sake of brevity. Similar to the shaft assembly 2000, the shaft assembly 2000' comprises a shaft frame, i.e., shaft frame 2530'. The shaft frame 2530' comprises a longitudinal passage 2535' and, in addition, a plurality of clutch position sensors, i.e., a first sensor 6180', a second sensor 6280', and a third sensor 6380' positioned in the shaft frame 2530'. The first sensor 6180' is in signal communication with the control system 1800 as part of a first sensing circuit. The first sensing circuit comprises signal wires extending through the longitudinal passage 2535'; however, the first sensing circuit can comprise a wireless signal transmitter and receiver to place the first sensor 6180' in signal communication with the control system 1800. The first sensor 6180' is positioned and arranged to detect the position of the first clutch 6110 of the first clutch assembly 6100. Based on data received from the first sensor 6180', the control system 1800 can determine whether the first clutch 6110 is in its engaged position, its disengaged position, or somewhere in-between. With this information, the control system 1800 can assess whether or not the first clutch 6110 is in the correct position given the operating state of the surgical instrument. For instance, if the surgical instrument is in its jaw clamping/opening operating state, the control system 1800 can verify whether the first clutch 6110 is properly positioned in its engaged position. In such instances, further to the below, the control system 1800 can also verify that the second clutch 6210 is in its disengaged position via the second sensor 6280' and that the third clutch 6310 is in its disengaged position via the third sensor 6380'. Correspondingly, the control system 1800 can verify whether the first clutch 6110 is properly positioned in its disengaged position if the surgical instrument is not in its jaw clamping/opening state. To the extent that the first clutch 6110 is not in its proper position, the control system 1800 can actuate the first electromagnetic actuator 6140 in an attempt to properly position the first clutch 6110. Likewise, the control system 1800 can actuate the electromagnetic actuators 6240 and/or 6340 to properly position the clutches 6210 and/or 6310, if necessary.

The second sensor 6280' is in signal communication with the control system 1800 as part of a second sensing circuit. The second sensing circuit comprises signal wires extending through the longitudinal passage 2535'; however, the second sensing circuit can comprise a wireless signal transmitter and receiver to place the second sensor 6280' in signal communication with the control system 1800. The second sensor 6280' is positioned and arranged to detect the position of the second clutch 6210 of the first clutch assembly 6200. Based on data received from the second sensor 6280', the control system 1800 can determine whether the second clutch 6210 is in its engaged position, its disengaged position, or somewhere in-between. With this information, the control system 1800 can assess whether or not the second clutch 6210 is in the correct position given the operating state of the surgical instrument. For instance, if the surgical instrument is in its end effector rotation operating state, the control system 1800 can verify whether the second clutch 6210 is properly positioned in its engaged position. In such instances, the control system 1800 can also verify that the first clutch 6110 is in its disengaged position via the first sensor 6180' and, further to the below, the control system 1800 can also verify that the third clutch 6310 is in its disengaged position via the third sensor 6380'. Correspondingly, the control system 1800 can verify whether the second clutch 6110 is properly positioned in its disengaged position if the surgical instrument is not in its end effector rotation state. To the extent that the second clutch 6210 is not in its proper position, the control system 1800 can actuate the second electromagnetic actuator 6240 in an attempt to properly position the second clutch 6210. Likewise, the control system 1800 can actuate the electromagnetic actuators 6140 and/or 6340 to properly position the clutches 6110 and/or 6310, if necessary.

The third sensor 6380' is in signal communication with the control system 1800 as part of a third sensing circuit. The third sensing circuit comprises signal wires extending through the longitudinal passage 2535'; however, the third sensing circuit can comprise a wireless signal transmitter and receiver to place the third sensor 6380' in signal communication with the control system 1800. The third sensor 6380' is positioned and arranged to detect the position of the third clutch 6310 of the third clutch assembly 6300. Based on data received from the third sensor 6380', the control system 1800 can determine whether the third clutch 6310 is in its engaged position, its disengaged position, or somewhere in-between. With this information, the control system 1800 can assess whether or not the third clutch 6310 is in the correct position given the operating state of the surgical instrument. For instance, if the surgical instrument is in its end effector articulation operating state, the control system 1800 can verify whether the third clutch 6310 is properly positioned in its engaged position. In such instances, the control system 1800 can also verify that the first clutch 6110 is in its disengaged position via the first sensor 6180' and that the second clutch 6210 is in its disengaged position via the second sensor 6280'. Correspondingly, the control system 1800 can verify whether the third clutch 6310 is properly positioned in its disengaged position if the surgical instrument is not in its end effector articulation state. To the extent that the third clutch 6310 is not in its proper position, the control system 1800 can actuate the third electromagnetic actuator 6340 in an attempt to properly position the third clutch 6310. Likewise, the control system 1800 can actuate the electromagnetic actuators 6140 and/or 6240 to properly position the clutches 6110 and/or 6210, if necessary.

Further to the above, the clutch position sensors, i.e., the first sensor 6180', the second sensor 6280', and the third sensor 6380' can comprise any suitable type of sensor. In various instances, the first sensor 6180', the second sensor 6280', and the third sensor 6380' each comprise a proximity sensor. In such an arrangement, the sensors 6180', 6280', and 6380' are configured to detect whether or not the clutches 6110, 6210, and 6310, respectively, are in their engaged positions. In various instances, the first sensor 6180', the second sensor 6280', and the third sensor 6380' each comprise a Hall Effect sensor, for example. In such an arrangement, the sensors 6180', 6280', and 6380' can not only detect whether or not the clutches 6110, 6210, and 6310, respectively, are in their engaged positions but the sensors 6180', 6280', and 6380' can also detect how close the clutches 6110, 6210, and 6310 are with respect to their engaged or disengaged positions.

FIG. 313 depicts the shaft assembly 2000' and an end effector 7000" in accordance with at least one alternative embodiment. The end effector 7000" is similar to the end effector 7000 in many respects, most of which will not be repeated herein for the sake of brevity. Similar to the end effector 7000, the shaft assembly 7000" comprises a jaw assembly 7100 and a jaw assembly drive configured to move the jaw assembly 7100 between its open and closed configurations. The jaw assembly drive comprises drive links 7140, a drive nut 7150", and a drive screw 6130". The drive nut 7150" comprises a sensor 7190" positioned therein which is configured to detect the position of a magnetic element 6190" positioned in the drive screw 6130". The magnetic element 6190" is positioned in an elongate aperture 6134" defined in the drive screw 6130" and can comprise a permanent magnet and/or can be comprised of iron, nickel, and/or any suitable metal, for example. In various instances, the sensor 7190" comprises a proximity sensor, for example, which is in signal communication with the control system 1800. In certain instances, the sensor 7190" comprises a Hall Effect sensor, for example, in signal communication with the control system 1800. In certain instances, the sensor 7190" comprises an optical sensor, for example, and the detectable element 6190" comprises an optically detectable element, such as a reflective element, for example. In either event, the sensor 7190" is configured to communicate wirelessly with the control system 1800 via a wireless signal transmitter and receiver and/or via a wired connection extending through the shaft frame passage 2532', for example.

The sensor 7190", further to the above, is configured to detect when the magnetic element 6190" is adjacent to the sensor 7190" such that the control system 1800 can use this data to determine that the jaw assembly 7100 has reached the end of its clamping stroke. At such point, the control system 1800 can stop the motor assembly 1600. The sensor 7190" and the control system 1800 are also configured to determine the distance between where the drive screw 6130" is currently positioned and where the drive screw 6130" should be positioned at the end of its closure stroke in order to calculate the amount of closure stroke of the drive screw 6130" that is still needed to close the jaw assembly 7100. Moreover, such information can be used by the control system 1800 to assess the current configuration of the jaw assembly 7100, i.e., whether the jaw assembly 7100 is in its open configuration, its closed configuration, or a partially closed configuration. The sensor system could be used to determine when the jaw assembly 7100 has reached its fully open position and stop the motor assembly 1600 at that point. In various instances, the control system 1800 could use this sensor system to confirm that the first clutch assembly 6100 is in its actuated state by confirming that the jaw assembly 7100 is moving while the motor assembly 1600 is turning. Similarly, the control system 1800 could use this sensor system to confirm that the first clutch assembly 6100 is in its unactuated state by confirming that the jaw assembly 7100 is not moving while the motor assembly 1600 is turning.

FIG. 314 depicts a shaft assembly 2000''' and an end effector 7000' in accordance with at least one alternative embodiment. The shaft assembly 2000''' is similar to the shaft assemblies 2000 and 2000' in many respects, most of which will not be repeated herein for the sake of brevity. The end effector 7000' is similar to the end effectors 7000 and 7000" in many respects, most of which will not be repeated herein for the sake of brevity. Similar to the end effector 7000, the end effector 7000' comprises a jaw assembly 7100 and a jaw assembly drive configured to move the jaw assembly 7100 between its open and closed configurations and, in addition, an end effector rotation drive that rotates the end effector 7000' relative to the distal attachment portion 2400 of the shaft assembly 2000'. The end effector rotation drive comprises an outer housing 6230' that is rotated relative to a shaft frame 2530' of the end effector 7000' by the second clutch assembly 6200. The shaft frame 2530''' comprises a sensor 6290' positioned therein which is configured to detect the position of a magnetic element 6190''' positioned in and/or on the outer housing 6230'''. The magnetic element 6190''' can comprise a permanent magnet and/or can be comprised of iron, nickel, and/or any suitable metal, for example. In various instances, the sensor 6290''' comprises a proximity sensor, for example, in signal communication with the control system 1800. In certain instances, the sensor 6290' comprises a Hall Effect sensor, for example, in signal communication with the control system 1800. In either event, the sensor 6290' is configured to communicate wirelessly with the control system 1800 via a wireless signal transmitter and receiver and/or via a wired connection extending through the shaft frame passage 2532', for example. In various instances, the control system 1800 can use the sensor 6290''' to confirm whether the magnetic element 6190''' is rotating and, thus, confirm that the second clutch assembly 6200 is in its actuated state. Similarly, the control system 1800 can use the sensor 6290''' to confirm whether the magnetic element 6190''' is not rotating and, thus, confirm that the second clutch assembly 6200 is in its unactuated state. The control system 1800 can also use the sensor 6290''' to confirm that the second clutch assembly 6200 is in its unactuated state by confirming that the second clutch 6210 is positioned adjacent the sensor 6290'''.

FIG. 315 depicts a shaft assembly 2000"" in accordance with at least one alternative embodiment. The shaft assembly 2000"" is similar to the shaft assemblies 2000, 2000', and 2000' in many respects, most of which will not be repeated herein for the sake of brevity. Similar to the shaft assembly 2000, the shaft assembly 2000"" comprises, among other things, an elongate shaft 2200, an articulation joint 2300, and a distal attachment portion 2400 configured to receive an end effector, such as end effector 7000', for example. Similar to the shaft assembly 2000, the shaft assembly 2000"" comprises an articulation drive, i.e., articulation drive 6330"" configured to rotate the distal attachment portion 2400 and the end effector 7000' about the articulation joint 2300. Similar to the above, a shaft frame 2530"" comprises a sensor positioned therein configured to detect the position, and/or rotation, of a magnetic element 6390"" positioned in and/or on the articulation drive 6330'. The magnetic element 6390"" can comprise a permanent magnet and/or can be comprised of iron, nickel, and/or any suitable metal, for example. In various instances, the sensor comprises a proximity sensor, for example, in signal communication with the control system 1800. In certain instances, the sensor comprises a Hall Effect sensor, for example, in signal communication with the control system 1800. In either event, the sensor is configured to communicate wirelessly with the control system 1800 via a wireless signal transmitter and receiver and/or via a wired connection extending through the shaft frame passage 2532', for example. In various instances, the control system 1800 can use the sensor to confirm whether the magnetic element 6390' is rotating and, thus, confirm that the third clutch assembly 6300 is in its actuated state. Similarly, the control system 1800 can use the sensor to confirm whether the magnetic element 6390"" is not rotating and, thus, confirm that the third clutch assembly 6300 is in its unactuated state. In certain instances, the control system 1800 can use the sensor to confirm that the third clutch assembly 6300 is in its unactuated state by confirming that the third clutch 6310 is positioned adjacent the sensor.

Referring to FIG. 315 once again, the shaft assembly 2000"" comprises an end effector lock 6400' configured to releasably lock the end effector 7000', for example, to the shaft assembly 2000'. The end effector lock 6400' is similar to the end effector lock 6400 in many respects, most of which will not be discussed herein for the sake of brevity. Notably, though, a proximal end 6420' of the lock 6400' comprises a tooth 6422' configured to engage the annular slot 6312 of the third clutch 6310 and releasably hold the third clutch 6310 in its disengaged position. That said, the actuation of the third electromagnetic assembly 6340 can disengage the third clutch 6310 from the end effector lock 6400'. Moreover, in such instances, the proximal movement of the third clutch 6310 into its engaged position rotates the end effector lock 6400' into a locked position and into engagement with the lock notches 7410 to lock the end effector 7000' to the shaft assembly 2000"". Correspondingly, the distal movement of the third clutch 6310 into its disengaged position unlocks the end effector 7000' and allows the end effector 7000' to be disassembled from the shaft assembly 2000"".

Further to the above, an instrument system including a handle and a shaft assembly attached thereto can be configured to perform a diagnostic check to assess the state of the clutch assemblies 6100, 6200, and 6300. In at least one instance, the control system 1800 sequentially actuates the electromagnetic actuators 6140, 6240, and/or 6340—in any suitable order—to verify the positions of the clutches 6110, 6210, and/or 6310, respectively, and/or verify that the clutches are responsive to the electromagnetic actuators and, thus, not stuck. The control system 1800 can use sensors, including any of the sensors disclosed herein, to verify the movement of the clutches 6110, 6120, and 6130 in response to the electromagnetic fields created by the electromagnetic actuators 6140, 6240, and/or 6340. In addition, the diagnostic check can also include verifying the motions of the drive systems. In at least one instance, the control system 1800 sequentially actuates the electromagnetic actuators 6140, 6240, and/or 6340—in any suitable order—to verify that the jaw drive opens and/or closes the jaw assembly 7100, the rotation drive rotates the end effector 7000, and/or the articulation drive articulates the end effector 7000, for example. The control system 1800 can use sensors to verify the motions of the jaw assembly 7100 and end effector 7000.

The control system 1800 can perform the diagnostic test at any suitable time, such as when a shaft assembly is attached to the handle and/or when the handle is powered on, for example. If the control system 1800 determines that the instrument system passed the diagnostic test, the control system 1800 can permit the ordinary operation of the instrument system. In at least one instance, the handle can comprise an indicator, such as a green LED, for example, which indicates that the diagnostic check has been passed. If the control system 1800 determines that the instrument system failed the diagnostic test, the control system 1800 can prevent and/or modify the operation of the instrument system. In at least one instance, the control system 1800 can limit the functionality of the instrument system to only the functions necessary to remove the instrument system from the patient, such as straightening the end effector 7000 and/or opening and closing the jaw assembly 7100, for example. In at least one respect, the control system 1800 enters into a limp mode. The limp mode of the control system 1800 can reduce a current rotational speed of the motor 1610 by any percentage selected from a range of about 75% to about 25%, for example. In one example, the limp mode reduces a current rotational speed of the motor 1610 by 50%. In one example, the limp mode reduces the current rotational speed of the motor 1610 by 75%. The limp mode may cause a current torque of the motor 1610 to be reduced by any percentage selected from a range of about 75% to about 25%, for example. In one example, the limp mode reduces a current torque of the motor 1610 by 50%. The handle can comprise an indicator, such as a red LED, for example, which indicates that the instrument system failed the diagnostic check and/or that the instrument system has entered into a limp mode. The above being said, any suitable feedback can be used to warn the clinician that the instrument system is not operating properly such as, for example, an audible warning and/or a tactile or vibratory warning, for example.

FIGS. 316-318 depict a clutch system 6000' in accordance with at least one alternative embodiment. The clutch system 6000' is similar to the clutch system 6000 in many respects, most of which will not be repeated herein for the sake of brevity. Similar to the clutch system 6000, the clutch system 6000' comprises a clutch assembly 6100' which is actuatable to selectively couple a rotatable drive input 6030' with a rotatable drive output 6130'. The clutch assembly 6100' comprises clutch plates 6110' and drive rings 6120'. The clutch plates 6110' are comprised of a magnetic material, such as iron and/or nickel, for example, and can comprise a permanent magnet. As described in greater detail below, the clutch plates 6110' are movable between unactuated positions (FIG. 317) and actuated positions (FIG. 318) within the drive output 6130'. The clutch plates 6110' are slideably positioned in apertures defined in the drive output 6130' such that the clutch plates 6110' rotate with the drive output 6130' regardless of whether the clutch plates 6110' are in their unactuated or actuated positions.

When the clutch plates 6110' are in their unactuated positions, as illustrated in FIG. 317, the rotation of the drive input 6030' is not transferred to the drive output 6130'. More specifically, when the drive input 6030' is rotated, in such instances, the drive input 6030' slides past and rotates relative to the drive rings 6120' and, as a result, the drive rings 6120' do not drive the clutch plates 6110' and the drive output 6130'. When the clutch plates 6110' are in their actuated positions, as illustrated in FIG. 318, the clutch plates 6110' resiliently compress the drive rings 6120' against the drive input 6030'. The drive rings 6120' are comprised of any suitable compressible material, such as rubber, for example. In any event, in such instances, the rotation of the drive input 6030' is transferred to the drive output 6130' via the drive rings 6120' and the clutch plates 6110'. The clutch system 6000' comprises a clutch actuator 6140' configured to move the clutch plates 6110' into their actuated positions. The clutch actuator 6140' is comprised of a magnetic material such as iron and/or nickel, for example, and can comprise a permanent magnet. The clutch actuator 6140' is slideably positioned in a longitudinal shaft frame 6050' extending through the drive input 6030' and can be moved between an unactuated position (FIG. 317) and an actuated position (FIG. 318) by a clutch shaft 6060'. In at least one instance, the clutch shaft 6060' comprises a polymer cable, for example. When the clutch actuator 6140' is in its actuated position, as illustrated in FIG. 318, the clutch actuator 6140' pulls the clutch plates 6110' inwardly to compress the drive rings 6120', as discussed above. When the clutch actuator 6140' is moved into its unactuated position, as illustrated in FIG. 317, the drive rings 6120' resiliently expand and push the clutch plates 6110' away from the drive input 6030'. In various alternative embodiments, the clutch actuator 6140' can comprise an electromagnet. In such an arrangement, the clutch actuator 6140' can be actuated by an electrical circuit extending through a longitudinal aperture defined in the clutch shaft 6060', for example. In various instances, the clutch system 6000' further comprises electrical wires 6040', for example, extending through the longitudinal aperture.

FIG. 319 depicts an end effector 7000a including a jaw assembly 7100a, a jaw assembly drive, and a clutch system 6000a in accordance with at least one alternative embodiment. The jaw assembly 7100a comprises a first jaw 7110a and a second jaw 7120a which are selectively rotatable about a pivot 7130a. The jaw assembly drive comprises a translatable actuator rod 7160a and drive links 7140a which are pivotably coupled to the actuator rod 7160a about a pivot 7150a. The drive links 7140a are also pivotably coupled to the jaws 7110a and 7120a such that the jaws 7110a and 7120a are rotated closed when the actuator rod 7160a is pulled proximally and rotated open when the actuator rod 7160a is pushed distally. The clutch system 6000a is similar to the clutch systems 6000 and 6000' in many respects, most of which will not be repeated herein for the sake of brevity. The clutch system 6000a comprises a first clutch assembly 6100a and a second clutch assembly 6200a which are configured to selectively transmit the rotation of a drive input 6030a to rotate the jaw assembly 7100a about a longitudinal axis and articulate the jaw assembly 7100a about an articulation joint 7300a, respectively, as described in greater detail below.

The first clutch assembly 6100a comprises clutch plates 6110a and drive rings 6120a and work in a manner similar to the clutch plates 6110' and drive rings 6120' discussed above. When the clutch pates 6110a are actuated by an electromagnetic actuator 6140a, the rotation of the drive input 6030a is transferred to an outer shaft housing 7200a. More specifically, the outer shaft housing 7200a comprises a proximal outer housing 7210a and a distal outer housing 7220a which is rotatably supported by the proximal outer housing 7210a and is rotated relative to the proximal outer housing 7210a by the drive input 6030a when the clutch plates 6110a are in their actuated position. The rotation of the distal outer housing 7220a rotates the jaw assembly 7100a about the longitudinal axis owing to fact that the pivot 7130a of the jaw assembly 7100a is mounted to the distal outer housing 7220a. As a result, the outer shaft housing 7200a rotates the jaw assembly 7100a in a first direction when the outer shaft housing 7200a is rotated in a first direction by the drive input 6030a. Similarly, the outer shaft housing 7200a rotates the jaw assembly 7100a in a second direction when the outer shaft housing 7200a is rotated in a second direction by the drive input 6030a. When the electromagnetic actuator 6140a is de-energized, the drive rings 6120a expand and the clutch plates 6110a are moved into their unactuated positions, thereby decoupling the end effector rotation drive from the drive input 6030a.

The second clutch assembly 6200a comprises clutch plates 6210a and drive rings 6220a and work in a manner similar to the clutch plates 6110' and drive rings 6120' discussed above. When the clutch pates 6210a are actuated by an electromagnetic actuator 6240a, the rotation of the drive input 6030a is transferred to an articulation drive 6230a. The articulation drive 6230a is rotatably supported within an outer shaft housing 7410a of an end effector attachment portion 7400a and is rotatably supported by a shaft frame 6050a extending through the outer shaft housing 7410a. The articulation drive 6230a comprises a gear face defined thereon which is operably intermeshed with a stationary gear face 7230a defined on the proximal outer housing 7210a of the outer shaft housing 7200a. As a result, the articulation drive 6230a articulates the outer shaft housing 7200a and the jaw assembly 7100a in a first direction when the articulation drive 6230a is rotated in a first direction by the drive input 6030a. Similarly, the articulation drive 6230a articulates the outer shaft housing 7200a and the jaw assembly 7100a in a second direction when the articulation drive 6230a is rotated in a second direction by the drive input 6030a. When the electromagnetic actuator 6240a is de-energized, the drive rings 6220a expand and the clutch plates 6210a are moved into their unactuated positions, thereby decoupling the end effector articulation drive from the drive input 6030a.

Further to the above, the shaft assembly 4000 is illustrated in FIGS. 320-324. The shaft assembly 4000 is similar to the shaft assemblies 2000, 2000', 2000''', and 2000' in many respects, most of which will not be repeated herein for the sake of brevity. The shaft assembly 4000 comprises a proximal portion 4100, an elongate shaft 4200, a distal attachment portion 2400, and an articulate joint 2300 which rotatably connects the distal attachment portion 2040 to the elongate shaft 4200. The proximal portion 4100, similar to the proximal portion 2100, is operably attachable to the drive module 1100 of the handle 1000. The proximal portion 4100 comprises a housing 4110 including an attachment interface 4130 configured to mount the shaft assembly 4000 to the attachment interface 1130 of the handle 1000. The shaft assembly 4000 further comprises a frame 4500 including a shaft 4510 configured to be coupled to the shaft 1510 of the handle frame 1500 when the shaft assembly 4000 is attached to the handle 1000. The shaft assembly 4000 also comprises a drive system 4700 including a rotatable drive shaft 4710 configured to be operably coupled to the drive shaft 1710 of the handle drive system 1700 when the shaft assembly 4000 is attached to the handle 1000. The distal attachment portion 2400 is configured to receive an end effector, such as end effector 8000, for example. The end effector 8000 is similar to the end effector 7000 in many respects, most of which will not be repeated herein for the sake of brevity. That said, the end effector 8000 comprises a jaw assembly 8100 configured to, among other things, grasp tissue.

As discussed above, referring primarily to FIGS. 322-324, the frame 4500 of the shaft assembly 4000 comprises a frame shaft 4510. The frame shaft 4510 comprises a notch, or cut-out, 4530 defined therein. As discussed in greater detail below, the cut-out 4530 is configured to provide clearance for a jaw closure actuation system 4600. The frame 4500 further comprises a distal portion 4550 and a bridge 4540 connecting the distal portion 4550 to the frame shaft 4510. The frame 4500 further comprises a longitudinal portion 4560 extending through the elongate shaft 4200 to the distal attachment portion 2400. Similar to the above, the frame shaft 4510 comprises one or more electrical traces defined thereon and/or therein. The electrical traces extend through the longitudinal portion 4560, the distal portion 4550, the bridge 4540, and/or any suitable portion of the frame shaft 4510 to the electrical contacts 2520. Referring primarily to FIG. 323, the distal portion 4550 and longitudinal portion 4560 comprise a longitudinal aperture defined therein which is configured to receive a rod 4660 of the jaw closure actuation system 4600, as described in greater detail below.

As also discussed above, referring primarily to FIGS. 323 and 324, the drive system 4700 of the shaft assembly 4000 comprises a drive shaft 4710. The drive shaft 4710 is rotatably supported within the proximal shaft housing 4110 by the frame shaft 4510 and is rotatable about a longitudinal axis extending through the frame shaft 4510. The drive system 4700 further comprises a transfer shaft 4750 and an output shaft 4780. The transfer shaft 4750 is also rotatably supported within the proximal shaft housing 4110 and is rotatable about a longitudinal axis extending parallel to, or at least substantially parallel to, the frame shaft 4510 and the longitudinal axis defined therethrough. The transfer shaft 4750 comprises a proximal spur gear 4740 fixedly mounted thereto such that the proximal spur gear 4740 rotates with the transfer shaft 4750. The proximal spur gear 4740 is operably intermeshed with an annular gear face 4730 defined around the outer circumference of the drive shaft 4710 such that the rotation of the drive shaft 4710 is transferred to the transfer shaft 4750. The transfer shaft 4750 further comprises a distal spur gear 4760 fixedly mounted thereto such that the distal spur gear 4760 rotates with the transfer shaft 4750. The distal spur gear 4760 is operably intermeshed with an annular gear 4770 defined around the outer circumference of the output shaft 4780 such that the rotation of the transfer shaft 4750 is transferred to the output shaft 4780. Similar to the above, the output shaft 4780 is rotatably supported within the proximal shaft housing 4110 by the distal portion 4550 of the shaft frame 4500 such that the output shaft 4780 rotates about the longitudinal shaft axis. Notably, the output shaft 4780 is not directly coupled to the input shaft 4710; rather, the output shaft 4780 is operably coupled to the input shaft 4710 by the transfer shaft 4750. Such an arrangement provides room for the manually-actuated jaw closure actuation system 4600 discussed below.

Further to the above, referring primarily to FIGS. 322 and 323, the jaw closure actuation system 4600 comprises an actuation, or scissors, trigger 4610 rotatably coupled to the proximal shaft housing 4110 about a pivot 4620. The actuation trigger 4610 comprises an elongate portion 4612, a proximal end 4614, and a grip ring aperture 4616 defined in the proximal end 4614 which is configured to be gripped by the clinician. The shaft assembly 4000 further comprises a stationary grip 4160 extending from the proximal housing

4110. The stationary grip 4160 comprises an elongate portion 4162, a proximal end 4164, and a grip ring aperture 4166 defined in the proximal end 4164 which is configured to be gripped by the clinician. In use, as described in greater detail below, the actuation trigger 4610 is rotatable between an unactuated position and an actuated position (FIG. 323), i.e., toward the stationary grip 4160, to close the jaw assembly 8100 of the end effector 8000.

Referring primarily to FIG. 323, the jaw closure actuation system 4600 further comprises a drive link 4640 rotatably coupled to the proximal shaft housing 4110 about a pivot 4650 and, in addition, an actuation rod 4660 operably coupled to the drive link 4640. The actuation rod 4660 extends through an aperture defined in the longitudinal frame portion 4560 and is translatable along the longitudinal axis of the shaft frame 4500. The actuation rod 4660 comprises a distal end operably coupled to the jaw assembly 8100 and a proximal end 4665 positioned in a drive slot 4645 defined in the drive link 4640 such that the actuation rod 4660 is translated longitudinally when the drive link 4640 is rotated about the pivot 4650. Notably, the proximal end 4665 is rotatably supported within the drive slot 4645 such that the actuation rod 4660 can rotate with the end effector 8000.

Further to the above, the actuation trigger 4610 further comprises a drive arm 4615 configured to engage and rotate the drive link 4640 proximally, and translate the actuation rod 4660 proximally, when the actuation trigger 4610 is actuated, i.e., moved closer to the proximal shaft housing 4110. In such instances, the proximal rotation of the drive link 4640 resiliently compresses a biasing member, such as a coil spring 4670, for example, positioned intermediate the drive link 4640 and the frame shaft 4510. When the actuation trigger 4610 is released, the compressed coil spring 4670 re-expands and pushes the drive link 4640 and the actuation rod 4660 distally to open the jaw assembly 8100 of the end effector 8000. Moreover, the distal rotation of the drive link 4640 drives, and automatically rotates, the actuation trigger 4610 back into its unactuated position. That being said, the clinician could manually return the actuation trigger 4610 back into its unactuated position. In such instances, the actuation trigger 4610 could be opened slowly. In either event, the shaft assembly 4000 further comprises a lock configured to releasably hold the actuation trigger 4610 in its actuated position such that the clinician can use their hand to perform another task without the jaw assembly 8100 opening unintentionally.

In various alternative embodiments, further to the above, the actuation rod 4660 can be pushed distally to close the jaw assembly 8100. In at least one such instance, the actuation rod 4660 is mounted directly to the actuation trigger 4610 such that, when the actuation trigger 4610 is actuated, the actuation trigger 4610 drives the actuation rod 4660 distally. Similar to the above, the actuation trigger 4610 can compress a spring when the actuation trigger 4610 is closed such that, when the actuation trigger 4610 is released, the actuation rod 4660 is pushed proximally.

Further to the above, the shaft assembly 4000 has three functions—opening/closing the jaw assembly of an end effector, rotating the end effector about a longitudinal axis, and articulating the end effector about an articulation axis. The end effector rotation and articulation functions of the shaft assembly 4000 are driven by the motor assembly 1600 and the control system 1800 of the drive module 1100 while the jaw actuation function is manually-driven by the jaw closure actuation system 4600. The jaw closure actuation system 4600 could be a motor-driven system but, instead, the jaw closure actuation system 4600 has been kept a manually-driven system such that the clinician can have a better feel for the tissue being clamped within the end effector. While motorizing the end effector rotation and actuation systems provides certain advantages for controlling the position of the end effector, motorizing the jaw closure actuation system 4600 may cause the clinician to lose a tactile sense of the force being applied to the tissue and may not be able to assess whether the force is insufficient or excessive. Thus, the jaw closure actuation system 4600 is manually-driven even though the end effector rotation and articulation systems are motor-driven.

FIG. 325 is a logic diagram of the control system 1800 of the surgical system depicted in FIG. 275 in accordance with at least one embodiment. The control system 1800 comprises a control circuit. The control circuit includes a microcontroller 1840 comprising a processor 1820 and a memory 1830. One or more sensors, such as sensors 1880, 1890, 6180', 6280', 6380', 7190'', and/or 6290''', for example, provide real time feedback to the processor 1820. The control system 1800 further comprises a motor driver 1850 configured to control the electric motor 1610 and a tracking system 1860 configured to determine the position of one or more longitudinally movable components in the surgical instrument, such as the clutches 6110, 6120, and 6130 and/or the longitudinally-movable drive nut 7150 of the jaw assembly drive, for example. The tracking system 1860 is also configured to determine the position of one or more rotational components in the surgical instrument, such as the drive shaft 2530, the outer shaft 6230, and/or the articulation drive 6330, for example. The tracking system 1860 provides position information to the processor 1820, which can be programmed or configured to, among other things, determine the position of the clutches 6110, 6120, and 6130 and the drive nut 7150 as well as the orientation of the jaws 7110 and 7120. The motor driver 1850 may be an A3941 available from Allegro Microsystems, Inc., for example; however, other motor drivers may be readily substituted for use in the tracking system 1860. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 1840 may be any single core or multicore processor such as those known under the trade name ARM Cortex by Texas Instruments, for example. In at least one instance, the microcontroller 1840 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EE-PROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 1840 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 1840 is programmed to perform various functions such as precisely controlling the speed and/or position of the drive nut 7150 of the jaw closure assembly, for example. The microcontroller 1840 is also programmed to precisely control the rotational speed and position of the end effector 7000 and the articulation speed and position of the end effector 7000. In various instances, the microcontroller 1840 computes a response in the software of the microcontroller 1840. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 1610 is controlled by the motor driver 1850. In various forms, the motor 1610 is a DC brushed driving motor having a maximum rotational speed of approximately 25,000 RPM, for example. In other arrangements, the motor 1610 includes a brushless motor, a cordless motor, a synchronous motor, a stepper motor, or any other suitable electric motor. The motor driver 1850 may comprise an H-bridge driver comprising field-effect transistors (FETs), for example. The motor driver 1850 may be an A3941 available from Allegro Microsystems, Inc., for example. The A3941 driver 1850 is a full-bridge controller for use with external N-channel power metal oxide semiconductor field effect transistors (MOSFETs) specifically designed for inductive loads, such as brush DC motors. In various instances, the driver 1850 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, over-temperature, and power bridge faults, and can be configured to protect the power MOSFETs under most short circuit conditions. Other motor drivers may be readily substituted.

The tracking system 1860 comprises a controlled motor drive circuit arrangement comprising one or more position sensors, such as sensors 1880, 1890, 6180', 6280', 6380', 7190", and/or 6290''', for example. The position sensors for an absolute positioning system provide a unique position signal corresponding to the location of a displacement member. As used herein, the term displacement member is used generically to refer to any movable member of the surgical system. In various instances, the displacement member may be coupled to any position sensor suitable for measuring linear displacement. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 1880, 1890, 6180', 6280', 6380', 7190", and/or 6290''', for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 1860 comprise a magnetic rotary absolute positioning system. Such position sensors may be implemented as an AS5055EQFT single-chip magnetic rotary position sensor available from Austria Microsystems, AG and can be interfaced with the controller 1840 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 1840. The position sensors can provide 12 or 14 bits of resolution, for example. The position sensors can be an AS5055 chip provided in a small QFN 16-pin 4×4×0.85 mm package, for example.

The tracking system 1860 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 1610 has taken to infer the position of a device actuator, drive bar, knife, and the like.

A sensor 1880 comprising a strain gauge or a micro-strain gauge, for example, is configured to measure one or more parameters of the end effector, such as, for example, the strain experienced by the jaws 7110 and 7120 during a clamping operation. The measured strain is converted to a digital signal and provided to the processor 1820. In addition to or in lieu of the sensor 1880, a sensor 1890 comprising a load sensor, for example, can measure the closure force applied by the closure drive system to the jaws 7110 and 7120. In various instances, a current sensor 1870 can be employed to measure the current drawn by the motor 1610. The force required to clamp the jaw assembly 7100 can correspond to the current drawn by the motor 1610, for example. The measured force is converted to a digital signal and provided to the processor 1820. A magnetic field sensor can be employed to measure the thickness of the captured tissue. The measurement of the magnetic field sensor can also be converted to a digital signal and provided to the processor 1820.

The measurements of the tissue compression, the tissue thickness, and/or the force required to close the end effector on the tissue as measured by the sensors can be used by the controller 1840 to characterize the position and/or speed of the movable member being tracked. In at least one instance, a memory 1830 may store a technique, an equation, and/or a look-up table which can be employed by the controller 1840 in the assessment. In various instances, the controller 1840 can provide the user of the surgical instrument with a choice as to the manner in which the surgical instrument should be operated. To this end, the display 1440 can display a variety of operating conditions of the instrument and can include touch screen functionality for data input. Moreover, information displayed on the display 1440 may be overlaid with images acquired via the imaging modules of one or more endoscopes and/or one or more additional surgical instruments used during the surgical procedure.

As discussed above, the drive module 1100 of the handle 1000 and/or the shaft assemblies 2000, 3000, 4000, and/or 5000, for example, attachable thereto comprise control systems. Each of the control systems can comprise a circuit board having one or more processors and/or memory devices. Among other things, the control systems are configured to store sensor data, for example. They are also configured to store data which identifies the shaft assembly to the handle 1000. Moreover, they are also configured to store data including whether or not the shaft assembly has been previously used and/or how many times the shaft assembly has been used. This information can be obtained by the handle 1000 to assess whether or not the shaft assembly is suitable for use and/or has been used less than a predetermined number of times, for example.

A drive module 1100' in accordance with at least one alternative embodiment is illustrated in FIGS. 326-329. The drive module 1100' is similar to the drive module 1100 in many respects, most of which will not be discussed herein for the sake of brevity. The drive module 1100' comprises an actuator 1420' configured to control the rotation and articulation of the end effector 7000. Similar to the actuator 1420, discussed above, the actuator 1420' is rotatable about a longitudinal axis LA that extends through a shaft assembly attached to the drive module 1100. For instance, the longitudinal axis LA extends through the center, or substantially the center, of the elongate shaft 2200 of the shaft assembly 3000 (FIG. 275) when the shaft assembly 3000 is assembled to the drive module 1100'. The longitudinal axis LA also extends through the center, or substantially the center, of the end effector 7000 when the end effector 7000 is attached to the shaft assembly 3000, for example.

The actuator 1420' is rotatable within a channel 1190' defined in the housing 1110 in a first direction to rotate the end effector 7000 in the first direction and, similarly, in a second, or opposite, direction to rotate the end effector 7000 in the second direction. Similar to the drive module 1100, the drive module 1100' comprises a sensor system in communication with the control system 1800 configured to detect the rotation of the actuator 1420' about the longitudinal axis LA. In at least one instance, the sensor system comprises a first sensor 1422' configured to detect the rotation of the actuator 1420' about the longitudinal axis LA in the first direction (FIG. 327) and a second sensor 1424' configured to detect the rotation of the actuator 1420' about the longitudinal axis LA in the second direction (FIG. 328). The first and second sensors 1422' and 1424' comprise Hall Effect sensors, for example, but could comprise any suitable type of sensor. In at least one such instance, further to the above, the actuator 1420' comprises a center magnetic element 1426' positioned in the top of the actuator 1420' which is detectable by the first and second sensors 1422' and 1424' to determine the rotation of the actuator 1420'. The center magnetic element 1426' can comprise a permanent magnet and/or can be comprised of iron and/or nickel, for example.

Further to the above, the control system 1800 is configured to control the motor assembly 1600 and the clutch system 6000 to rotate the end effector 7000 about the longitudinal axis LA in the first direction when the actuator 1420' is rotated about the longitudinal axis LA in the first direction. Similarly, the control system 1800 is configured to control the motor assembly 1600 and the clutch system 6000 to rotate the end effector 7000 about the longitudinal axis LA in the second direction when the actuator 1420' is rotated about the longitudinal axis LA in the second direction. By associating the rotation of the end effector 7000 about the longitudinal axis LA with the rotation of the actuator 1420' about the longitudinal axis LA, the clinician is provided with a system that is very intuitive to use.

As discussed above, the end effector 7000 is configured to rotate about a longitudinal axis within a socket defined in the distal attachment portion 2400 of the shaft assembly 2000. Depending on the amount of rotation desired, the end effector 7000 can be rotated less than 360 degrees or more than 360 degrees in either direction. In various instances, the end effector 7000 can be rotated through several rotations in either direction. In alternative embodiments, the rotation of the end effector 7000 about the longitudinal axis can be limited. In at least one embodiment, the shaft assembly 2000 comprises one or more stops which limit the rotation of the end effector 7000 to less than one rotation. In certain embodiments, the control system 1800 monitors the rotation of the drive shaft 1710, such as by an encoder and/or an absolute positioning sensor system, for example, and limits the rotation of the end effector 7000 by stopping or pausing the motor 1610 when the end effector 7000 has reached the end of its permitted range. In at least one instance, the control system 1800 can disengage the second clutch 6210 from the drive shaft 2730 to stop or pause the rotation of the end effector 7000 when the end effector 7000 has reached the end of its permitted range.

Further to the above, the drive module 1100' and/or a shaft module attached to the drive module 1100' can provide feedback to the clinician that the end effector 7000 has reached the end of its rotation. The drive module 1100' and/or the shaft module attached thereto can comprise an indicator light 1427', such as a red LED, for example, on a first side of the module housing 1110' which is illuminated by the control system 1800 when the end effector 7000 has reached the end of its permitted rotation in the first direction, as illustrated in FIG. 327. In at least one instance, the drive module 1100' and/or the shaft module attached thereto can comprise an indicator light 1429', such as a red LED, for example, on a second side of the module housing 1110' which is illuminated by the control system 1800 when the end effector 7000 has reached the end of its permitted rotation in the second direction, as illustrated in FIG. 328. In various instances, further to the above, the illumination of either the first light 1427' or the second light 1429' can indicate to the clinician that the motor 1610 has been paused and that the end effector 7000 is no longer rotating. In at least one instance, the first light 1427' and/or the second light 1429' can blink when the motor 1610 is paused.

In addition to or in lieu of the above, the drive module 1100' and/or the shaft assembly attached thereto can comprise an annular series, or array, of indicator lights 1428' extending around the perimeter thereof which is in communication with the control system 1800 and can indicate the rotational orientation of the end effector 7000. In at least one instance, the control system 1800 is configured to illuminate the particular indicator light which corresponds, or at least substantially corresponds, with the position in which the top of the end effector 7000 is oriented. In at least one instance, the center of the first jaw 7110 can be deemed the top of the end effector 7000, for example. In such instances, the illuminated light indicates the top-dead-center position of the end effector 7000. In other instances, the control system 1800 can illuminate the particular indicator light which corresponds, or at least substantially corresponds, with the position in which the bottom, or bottom-dead-center, of the end effector 7000 is oriented. In at least one instance, the center of the second jaw 7210 can be deemed the bottom of the end effector 7000, for example. As a result of the above, the illuminated indicator light can follow the rotation of the end effector 7000 around the array of indicator lights 1428'.

Further to the above, the actuator 1420' is also rotatable, or tiltable, about a transverse axis TA within the housing channel 1190'. The sensor system of the drive module 1100' is further configured to detect the rotation of the actuator 1420' about the transverse axis TA in a first tilt direction and a second tilt direction. In at least one instance, the sensor system comprises a first tilt sensor 1423' configured to detect the rotation of the actuator 1420' about the longitudinal axis TA in the first tilt direction (FIG. 329) and a second tilt sensor 1425' configured to detect the rotation of the actuator 1420' in the second tilt direction (FIG. 330). The first and second tilt sensors 1423' and 1425' comprise Hall Effect sensors, for example, but could comprise any suitable type of sensor. The actuator 1420' further comprises a first lateral magnetic element adjacent the first tilt sensor 1423', the motion of which is detectable by the first tilt sensor 1423'. The actuator 1420' also comprises a second lateral magnetic element adjacent the second tilt sensor 1425', the motion of which is detectable by the second tilt sensor 1425'. The first and second lateral magnetic elements can comprise a permanent magnet and/or can be comprised of iron and/or nickel, for example. As illustrated in FIGS. 329 and 330, the lateral sides of the actuator 1420' are movable proximally and distally about the transverse axis TA and, as a result, the first and second lateral magnetic elements are also movable proximally and distally relative to the first and second tilt sensors. The reader should appreciate that, while the first and second lateral magnetic elements actually travel along arcuate paths about the transverse axis TA, the distances in which the first and second lateral magnetic elements move is small and, as a result, the arcuate motion of the first and second lateral magnetic elements approximates translation in the proximal and distal directions.

In various embodiments, further to the above, the entire actuator 1420' comprises a magnetic ring of material which is detectable by the tilt sensors 1423' and 1425' of the drive module 1100'. In such embodiments, the rotation of the actuator 1420' about the longitudinal axis LA would not create a compound motion relative to the tilt sensors when the actuator 1420' is tilted. The magnetic ring of material can comprise a permanent magnet and/or can be comprised of iron and/or nickel, for example.

In any event, when the sensor system detects that the actuator 1420' has been tilted in the first direction, as illustrated in FIG. 329, the control system 1800 operates the motor assembly 1600 and the clutch system 6000 to articulate the end effector 7000 about the articulation joint 2300 in the first direction. Similarly, the control system 1800 operates the motor assembly 1600 and the clutch system 6000 to articulate the end effector 7000 about the articulation joint 2300 in the second direction when the sensor system detects that the actuator 1420' has been tilted in the second direction, as illustrated in FIG. 330. By associating the rotation of the end effector 7000 about the articulation joint 2300 with the rotation of the actuator 1420' about the transverse axis TA, the clinician is provided with a system that is very intuitive to use.

Further to the above, the actuator 1420' comprises a biasing system configured to center the actuator 1420' in its unrotated and untilted position. In various instances, the biasing system comprises first and second rotation springs configured to center the actuator 1420' in its unrotated position and first and second tilt springs configured to center the actuator 1420' in its untilted position. These springs can comprise torsion springs and/or linear displacement springs, for example.

As discussed above, the end effector 7000 rotates relative to the distal attachment portion 2400 of the shaft assembly 3000. Such an arrangement allows the end effector 7000 to be rotated without having to rotate the shaft assembly 3000, although embodiments are possible in which an end effector and shaft assembly rotate together. That said, by rotating the end effector 7000 relative to the shaft assembly 3000, all of the rotation of the surgical system occurs distally relative to the articulation joint 2300. Such an arrangement prevents a large sweep of the end effector 7000 when the end effector 7000 is articulated and then rotated. Moreover, the articulation joint 2300 does not rotate with the end effector 7000 and, as a result, the articulation axis of the articulation joint 2300 is unaffected by the rotation of the end effector 7000. In order to mimic this arrangement, the transverse axis TA does not rotate with the actuator 1420'; rather, the transverse axis TA remains stationary with respect to the drive module 1100'. That said, in alternative embodiments, the transverse axis TA can rotate, or track the end effector 7000, when the articulation joint rotates with the end effector. Such an arrangement can maintain an intuitive relationship between the motion of the actuator 1420' and the motion of the end effector 7000.

Further to the above, the transverse axis TA is orthogonal, or at least substantially orthogonal, to the longitudinal axis LA. Similarly, the articulation axis of the articulation joint 2300 is orthogonal, or at least substantially orthogonal, to the longitudinal axis LA. As a result, the transverse axis TA is parallel to, or at least substantially parallel to, the articulation axis.

In various alternative embodiments, the tiltable actuator 1420' is only used to control the articulation of the end effector 7000 and is not rotatable about the longitudinal axis LA. Rather, in such embodiments, the actuator 1420' is only rotatable about the transverse axis TA. In at least one instance, the housing of the drive module 1100' comprises two posts 1421' (FIG. 326) about which the actuator 1120' is rotatably mounted which defines the transverse axis TA. The posts 1421' are aligned along a common axis. The above being said, the posts 1421', or any suitable structure, can be used in embodiments in which the actuator 1420' is both rotatable and tiltable to control the rotation and articulation of the end effector 7000. In at least one such instance, the actuator 1420' comprises an annular groove defined therein in which the posts 1421' are positioned.

In various instances, the drive module 1100 and/or the shaft assembly attached thereto can comprise a series, or array, of indicator lights 1438' which is in communication with the control system 1800 and can indicate the articulation orientation of the end effector 7000. In at least one instance, the control system 1800 is configured to illuminate the particular indicator light which corresponds, or at least substantially corresponds, with the position in which the end effector 7000 is articulated. As a result of the above, the illuminated indicator light can follow the articulation of the end effector 7000. Such an array of indicator lights can assist a clinician in straightening the end effector 7000 before attempting to remove the end effector 7000 from a patient through a trocar. In various instances, an unstraightened end effector may not pass through a trocar and prevent the removable of the end effector from the patient.

A drive module 1100" in accordance with at least one alternative embodiment is illustrated in FIGS. 331-334. The drive module 1100" is similar to the drive modules 1100 and 1100' in many respects, most of which will not be discussed herein for the sake of brevity. The drive module 1100" comprises a feedback system configured to inform the clinician using the surgical instrument system that the drive shaft and/or any other rotatable component of the surgical instrument system is rotating. The feedback system can use visual feedback, audio feedback, and/or tactile feedback, for example. Referring primarily to FIG. 332, the drive module 1100" comprises a tactile feedback system which is operably engageable with the drive shaft 1710" of the drive module 1100". The tactile feedback system comprises a slideable clutch 1730", a rotatable drive ring 1750", and an eccentric, or offset, mass 1770" mounted to the drive ring 1750". The clutch 1730" is slideable between an unactuated position (FIG. 333) and an actuated position (FIG. 334) along the drive shaft 1710". The drive shaft 1710" comprises one or more slots 1740" defined therein which are configured to constrain the movement of the slideable clutch 1730" relative to the drive shaft 1710" such that the clutch 1730" translates longitudinally relative to the drive shaft 1710" but also rotates with the drive shaft 1710". The frame shaft 1510" of the handle frame 1500" comprises an electromagnet 1530" embedded therein which is configured to emit a first electromagnetic field to slide the clutch 1730" toward its actuated position, as illustrated in FIG. 334, and a second, or opposite, electromagnetic field to slide the clutch 1730" toward its unactuated position, as illustrated in FIG. 333. The clutch 1730" is comprised of a permanent magnet and/or a magnetic material such as iron and/or nickel, for example. The electromagnet 1530" is controlled by the control system 1800 to apply a first voltage polarity to a circuit including the electromagnet 1530" to create the first electromagnetic field and a second, or opposite, voltage polarity to the circuit to create the second electromagnetic field.

When the clutch 1730" is in its unactuated position, as illustrated in FIG. 333, the clutch 1730" is not operably engaged with the drive ring 1750". In such instances, the clutch 1730" rotates with the drive shaft 1710", but rotates relative to the drive ring 1750". Stated another way, the drive ring 1750" is stationary when the clutch 1730" is in its unactuated position. When the clutch 1730" is in its actuated position, as illustrated in FIG. 334, the clutch 1730" is operably engaged with an angled face 1760" of the drive ring 1750" such that the rotation of the drive shaft 1710" is transmitted to the drive ring 1750" via the clutch 1730" when the drive shaft 1710" is rotated. The eccentric, or offset, mass 1770" is mounted to the drive ring 1750" such that the eccentric mass 1770" rotates with the drive ring 1750". In at least one instance, the eccentric mass 1770" is integrally-formed with the drive ring 1750". When the drive ring 1750" and eccentric mass 1770" rotate with the drive shaft 1710", the eccentric mass 1770" creates a vibration that can be felt by the clinician through the drive module 1100" and/or the power modules assembled thereto. This vibration confirms to the clinician that the drive shaft 1710" is rotating. In at least one instance, the control system 1800 energizes the electromagnet 1530" when one of the clutches of the clutch system 6000 is energized. In such instances, the vibration can confirm to the clinician that the drive shaft 1710" is rotating and that one of the clutches in the clutch system 6000 is engaged with the drive shaft 1710". In at least one instance, the clutch 1730" can be actuated when the jaw assembly 7100, for example, has reached or is reaching its closed position such that the clinician knows that the tissue has been clamped within the jaw assembly 7100 and that the surgical instrument can be used to manipulate the tissue. The above being said, the tactile feedback system, and/or any other feedback system, of the drive module 1100" can be used to provide tactile feedback when appropriate.

Sterilization processes are part of customary surgical preparation procedures. A variety of sterilization processes exist for surgical instruments. Various methods include sterilization by way of autoclave which utilizes high heat and pressure, and sterilization utilizing steam, dry heat, and/or radiation, for example. However, one of the most widely used methods of sterilization is ethylene oxide processing. Ethylene oxide is an alkylating chemical compound which inhibits and disrupts the DNA of microorganisms in order to prevent reproduction of those organisms. Ethylene oxide processing is a highly effective sterilization process, but it does not come without cost. Some of the early steps involved during ethylene oxide processing involve heating the surgical instruments to a sustainable internal temperature and humidifying the surgical instruments. Often times, the surgical instruments undergo the heating and humidifying processes for anywhere from twelve to seventy-two hours during a single sterilization process. In addition to the heat and humidity, the potency of ethylene oxide tends to affect the soft electronic circuitry of powered surgical instruments. In the field of endoscopy, certain components of the powered endoscopy surgical instruments, such as display screens, for example, react poorly to the sterilization process when ethylene oxide is used. Improperly functioning display screens could result in difficulties and/or delays during a surgical procedure. Thus, a need exists for a surgical instrument system which incorporates a variety of cost-efficient disposable and replaceable components in order to avoid the damage caused by the sterilization process.

A surgical instrument system is illustrated in FIG. 335. The surgical instrument system illustrated in FIG. 335 is similar to the surgical instrument system depicted in FIG. 275 in many respects, most of which will not be repeated herein out of the sake of brevity. The surgical instrument system comprises a variety of interchangeable shaft assemblies and power modules, as will be discussed in greater detail below. The surgical instrument system comprises a handle assembly 11000. The handle assembly 11000 is usable with a variety of interchangeable shaft assemblies, such as a shaft assembly 12000, a shaft assembly 13000, a shaft assembly 14000, a shaft assembly 15000, and/or other any other suitable shaft assembly. The interchangeable shaft assemblies 12000, 13000, 14000, and 15000 are similar to the shaft assemblies 2000, 3000, 4000, and 5000 in many respects. Similar to the shaft assembly 2000, the shaft assembly 12000 comprises a proximal end portion 12100 and an elongate shaft 12200 extending from the proximal end portion 12100. The shaft assembly 12000 also comprises an end effector 12400 which is rotatably attached to the elongate shaft 12200 by an articulation joint 12300. The end effector 12400 comprises a first jaw 17000 and a second jaw 17100. Similar to the shaft assembly 12000, the shaft assembly 13000 comprises a proximal end portion 13100, and an elongate shaft 13200 extending from the proximal end portion 13100. The shaft assembly 13000 is also configured for use with the end effector 12400 which is rotatably attached to the elongate shaft 13200 by an articulation joint 12300. Similar to the shaft assembly 12000, the shaft assembly 14000 comprises a proximal end portion 14100, and an elongate shaft 14200 extending from the proximal end portion 14100. The shaft assembly 14000 is also configured for use with an end effector 12400' which is rotatably attached to the elongate shaft 14200 by an articulation joint 12300. The end effector 12400' comprises a first jaw 18000 and a second jaw 18100. The shaft assembly 15000 comprises similar components to those of the shaft assemblies 12000, 13000, and 14000, many of which will not be discussed in detail for the sake of brevity.

Still referring to FIG. 335, the handle assembly 11000 comprises a drive module 11100. The drive module 11100 comprises a distal mounting interface 11130 which allows for the selective and separate engagement of any one of the shaft assemblies 12000, 13000, 14000, and 15000 with the drive module 11100. Each of the shaft assemblies 12000, 13000, 14000, and 15000 comprises the same or a substantially similar proximal mounting interface which is configured to engage the distal mounting interface of the drive module 11100. Still referring to FIG. 335, the shaft assembly 12000 comprises a proximal mounting interface 12130 which is configured for attachment to the distal mounting interface 11130 of the drive module 11100 by at least one latch 11140 of the drive module 11100. Similarly, the shaft assembly 13000 comprises a proximal mounting interface 13130 which is configured for attachment to the distal mounting interface 11130 of the drive module 11100 by at least one latch 11140 of the drive module 11100. Also, similarly, the shaft assembly 14000 comprises a proximal mounting interface 14130 which is configured for attachment to the distal mounting interface 11130 of the drive module 11100 by at least one latch 11140 of the drive module 11100. Likewise, the shaft assembly 15000 comprises a proximal mounting interface 15130 which is configured for attachment to the distal mounting interface 11130 of the drive module 11100. The drive module 11100 is configured to electrically couple to each of the shaft assembles 12000, 13000, 14000, and 15000. The surgical instrument system comprises a motor positioned in the handle assembly 11000, as will be discussed in greater detail below. Each of the shaft assemblies 12000, 13000, 14000, and 15000 comprises a control circuit as will be discussed in greater detail below. The control circuit is configured to interact with the motor in order to control various functions of the surgical instrument system. The surgical instrument system further comprises a motor-control processor which is configured to communicate with the control circuit in order to control the motor. Referring to FIG. 368, the processor is positioned in any suitable portion of the surgical instrument apart from the drive module 11100. For example, the processor is positioned in a shaft assembly of the surgical instrument system. The handle assembly 11000 is configured for use with at least one power module as will be discussed in greater detail below.

Referring to FIGS. 335 and 336, the drive module 11100 comprises a housing 11110 which is capable of use with a variety of power modules such as the power modules 11200 and 11300, for example. In various instances, each power module 11200 and 11300 comprises one or more battery cells, as illustrated in FIG. 336, which are configured to enable pistol, scissor, and/or pencil grip configurations comprising different load requirements. In particular, the housing 11110 comprises a first attachment portion 11120 and a second attachment portion 11120' which are configured to engage either the power module 11200 or the power module 11300 at either the bottom of the handle assembly 11000 or the proximal end of the handle assembly 11000 depending on which shaft assembly is attached to the handle assembly 11000. For example, when the shaft assembly 14000 is attached to the handle assembly 11000, a power module is attached to the proximal end of the handle assembly 11000 in a first configuration as illustrated in FIG. 335. As another example, when the shaft assembly 13000 is attached to the handle assembly 11000, a power module is attached to the bottom of the handle assembly 11000 in a second configuration. As illustrated in FIGS. 335 and 336, the first configuration and the second configuration are different from one another.

Still referring to FIG. 336, the drive module 11100 comprises a rotation actuator 11420 which is similar to the rotation actuator 1420, which is described in greater detail above. The drive module 11100 further comprises release actuators 11150 which, when depressed by a clinician, move the latches 11140 from their locked positions into their unlocked positions. The drive module 11100 comprises a first release actuator 11150 slideably mounted in an opening defined in the first side of the handle housing 11110 and a second release actuator 11150 slideably mounted in an opening defined in a second, or opposite, side of the handle housing 11110.

Referring to FIG. 336 and FIG. 337, the drive module 11100 comprises an articulation actuator 11430. The articulation actuator 11430 comprises a first push button 11432 and a second push button 11434. The first push button 11432 is part of a first articulation control circuit and the second push button 11434 is part of a second articulation circuit of an input system similar to the input system 1400 discussed in greater detail above.

Referring again to FIG. 335, the surgical instrument system comprises a power module 11200. The power module 11200 comprises a housing 11210, a connector portion 11220, and at least one battery (as illustrated in at least FIG. 336). The connector portion 11220 is configured to be engaged with the first connector portion 11120 in order to attach the power module 11200 to the bottom of the handle assembly 11000. The power module 11200 comprises at least one latch 11240 positioned at the top of the power module 11200 which is configured to secure the power module 11200 to the bottom of the drive module 11100. More specifically, the latch 11240 is configured to securely attach the housing 11210 of the power module 11200 to the housing 11110 of the drive module 11100 located within the handle assembly 11000. The connector portion 11220 comprises a plurality of electrical contacts which enable an electrical connection between the power module 11200 and the drive module 11100. The power module 11200 comprises a release latch 11250 which is configured to release the power module 11250 from the drive module 11000.

Referring again to FIG. 335, the surgical instrument system comprises a power module 11300. The power module 11300 comprises a housing 11310, a connector portion 11320, and at least one battery. The connector portion 11320 is configured to be engaged with the second connector portion 11120' in order to attach the power module 11300 to the handle assembly 11000. The power module 11300 comprises at least one latch 11340 positioned at a distal end of the power module 11300 which is configured to secure the power module 11300 to the drive module 11100. More specifically, the latch 11340 is configured to securely attach the housing 11310 of the power module 11300 to the housing 11110 of the drive module 11100 located within the handle assembly 11000. The connector portion 11320 comprises a plurality of electrical contacts which enable an electrical connection between the power module 11300 and the drive module 11100.

Still referring to FIG. 335, the power module 11200 and the power module 11300 each comprise at least one display unit. The power module 11200 comprises a display unit 11440 located on the power module housing 11210. The power module 11300 comprises a display unit 11440'. The display units 11440 and 11440' can comprise any suitable display screen, for example, configured for use with a powered surgical device. In various instances, the display units 11440 and 11440' comprise an electrochromic display. The electrochromic display comprises an array of electrodes created from a metal oxide semi conductor. The electrodes are mounted on a flexible film comprising attachments of electrochromic molecules. As a charge is applied to the semiconducting electrodes, the electrochromic molecules travel to the surface of the film to receive the charge. As the electrochromic molecules are charged, a change in color occurs in the molecules. Suitable versions of this type of display screen are available from Ntera and Seiko, for instance.

In certain instances, the display units 11440 and 11440' comprise an electrophoretic display. The electrophoretic display comprises titanium dioxide particles approximately one micrometer in diameter which are dispersed in a hydrocarbon oil, for example. A dark-colored dye is also added to the oil, along with surfactants and charging agents that cause the particles to take on an electric charge. The mixture of titanium dioxide particles and hydrocarbon oil is placed between two parallel conductive plates separated by a gap of 10 to 100 micrometers, for example. The parallel conductive plates comprise opposite charges from one another. When a voltage is applied across the two plates, the titanium dioxide particles migrate electrophoretically to the plate that bears the opposite charge from the charge of the particles. When the particles are located at the front (viewing) side of the display, it appears white, because light is scattered back to the viewer by the high-index titanium dioxide particles. When the particles are located at the rear side of the display, it appears dark, because the incident light is absorbed by the colored dye. If the rear electrode is divided into a number of small picture elements (pixels), then an image can be formed by applying the appropriate voltage to each region of the display to create a pattern of reflecting and absorbing regions.

Other suitable variations of display screens include various types of liquid-crystal displays including liquid-crystal character display modules, thin film transistor liquid-crystal displays, and/or any other suitable display screens. Liquid crystal character display modules are flat-panel displays which use the light-modulating properties of liquid crystals in order to produce images in color or monochrome by using a backlight or a reflector. Thin film transistor liquid-crystal displays use thin-film transistor technology to provide for improved image qualities including, but not limited to, contrast. Additional types of display screens comprise touch screen capable screens and/or active matrix backplanes comprising an amorphous silicon semiconductor or a polythiophene semiconductor, for example.

Referring primarily to FIG. 336, the power module 11200 is attached to the handle assembly 11000 in a first orientation. When the power module 11200 is positioned in the first orientation, a first maximum level of power is supplied to the surgical instrument system. As seen in FIG. 336, the surgical instrument system comprises a pistol grip when the power module 11200 is attached to the surgical instrument. Still referring to FIG. 336, the power module 11200 comprises at least a first battery 11230 and a second battery 11260. Referring to FIG. 337, the power module 11300 comprises a housing 11310 which is configured to attach the power module 11300 to the handle assembly 11000 in a second orientation. The second orientation of the power module 11300 is configured to supply an appropriate amount of power when the surgical instrument comprises a pencil or wand grip configuration. The power module 11200 is configured to supply more power to the surgical instrument when the power 11200 is in the first orientation, and the power module 11300 is configured to supply less power to the surgical instrument in the second orientation. The use of various power modules ensures that the necessary amount of power for the operation of the surgical instrument system is provided. With respect to FIGS. 337-339, the drive module 11100 comprises the same and/or similar components as the drive module 1100 discussed in detail above with respect to FIGS. 281-283. That is, the drive module 11100 interacts with each of the shaft assemblies 12000, 13000, 14000, and 15000 in the same and/or a similar manner as the drive module 1100 interacts with the shaft assemblies 2000, 3000, 4000, and 5000.

FIGS. 340-342 illustrate the surgical instrument system comprising the power module 11300 in the first orientation for use with the scissor grip configuration of the shaft assembly 14000. The surgical instrument system illustrated in FIGS. 340-342 is similar in some aspects to the surgical instrument system illustrated in FIGS. 320-322, which is discussed in greater detail above and is also configured for use with the power module 11300 which comprises the display unit 11440'. Various surgical instruments described herein are compatible with the power modules 11200 and 11300.

Turning now to FIG. 343, a surgical instrument system can comprise a variety of handle assemblies such as a pencil grip handle, a scissor grip handle, a pistol grip handle, among others, and a shaft assembly, such as the shaft assembly 20000, for example, that can be used with each of the handle assemblies. The surgical instrument system comprises a first handle assembly 21000, which is a pencil grip handle. Referring primarily to FIGS. 344 and 352, the first handle assembly 21000 comprises one electric drive motor, a first drive shaft 21100, and a first set of controls which controls the one electric drive motor. The drive shaft 21100 of the one drive motor is configured to be coupled with a drive system of the shaft assembly 20000 when the shaft assembly 20000 is attached to the handle assembly 21000. The drive motor used in connection with the surgical instrument system of FIG. 343 is similar in many respects to other motors discussed in detail above, such as the motor 1610, for example. The first handle assembly 21000 further comprises a plurality of electrical contacts 21022 for placing the handle assembly 21000 in electrical communication with the shaft assembly 20000 via electrical contacts 20022 defined thereon. Referring to FIGS. 343 and 344, the first handle assembly 21000 further comprises an insertable power module 21020 at the proximal end of the handle assembly 21000.

The surgical instrument system further comprises a second handle assembly 22000, which is a scissors grip handle. Referring primarily to FIG. 345, the second handle assembly 22000 comprises first and second electric drive motors, a drive shaft 22100, a second drive shaft 22200, a first set of controls which controls the first drive motor, and a second set of controls which controls the second drive motor. The first drive shaft 22100 and the second drive shaft 22200 of the first and second drive motors can be coupled with two drive systems of the shaft assembly 20000. The first and second drive motors are similar in many respects to other motors discussed in detail above, such as the motor 1610, for example. The second handle assembly 22000 further comprises a plurality of electrical contacts 22022 for placing the handle assembly 22000 in electrical communication with the shaft assembly 20000 via electrical contacts 20022 defined thereon as seen in FIG. 347. Referring primarily to FIGS. 343 and 345, the second handle assembly 22000 further comprises an insertable power module 22020 at the proximal end of the handle assembly 22000.

Referring to FIGS. 343 and 346, the surgical instrument system further comprises a third handle assembly 23000, which is a pistol grip handle. The third handle assembly 23000 comprises first, second, and third electric drive motors, a first drive shaft 23100, a second drive shaft 23200, a third drive shaft 23300, a first set of controls which controls the first drive motor, a second set of controls which controls the second drive motor, and a third set of controls which controls the third drive motor. The third handle assembly 23000 comprises a third set of controls. The first drive shaft 23100, the second drive shaft 23200, and the third drive shaft 23300 can be coupled with the three drive systems of the shaft assembly 20000. The third handle assembly 23000 further comprises a plurality of electrical contacts 23022 for placing the handle assembly 23000 in electrical communication with the shaft assembly 20000 via electrical contacts 20022 defined thereon as seen in FIGS. 346 and 350. The third handle assembly 23000 further comprises an insertable power module 23020 at the proximal end of the handle assembly 23000.

Further to the above, the shaft assembly 20000 comprises three drive systems which are drivable by a drive motor of a handle assembly—this is, of course, assuming that the handle assembly that the shaft assembly 20000 is attached to has a sufficient number of drive motors to drive all three drive systems of the shaft assembly 20000. Stated another way, the first handle assembly 21000 has only one drive motor to drive one of the drive systems of the shaft assembly 20000 and, similarly, the second handle assembly 22000 has only two drive motors to drive two of the drive systems of the shaft assembly 20000. Thus, two drive systems of the shaft assembly 20000 cannot be driven by the first handle assembly 21000 and one drive system of the shaft assembly 20000 cannot be driven by the second handle assembly 22000. In various instances, the undriven system, or systems, of the shaft assembly 20000 can remain inert while the other drive system, or systems, of the shaft assembly 20000 are being used. In at least one embodiment, the handle assemblies 21000 and 22000 can be configured to lock out the drive systems of the shaft assembly 20000 that aren't being used. In at least one instance, the handle assembly 21000 comprises two stationary posts extending therefrom which engage the second and third drive systems of the shaft assembly 20000 when the shaft assembly 20000 is assembled to the handle assembly 21000. The stationary posts prevent the second and third drive systems of the shaft assembly 20000 from being unintentionally actuated. Similarly, the handle assembly 22000 comprises one stationary post extending therefrom which engages the third drive system of the shaft assembly 20000 to prevent the third drive system from being unintentionally actuated. The third handle assembly 23000 does not comprise stationary posts to lock a drive system of the shaft assembly 20000 as all three drive systems of the shaft assembly 20000 are coupled to a drive motor in the third handle assembly 23000.

In addition to or in lieu of the above, the shaft assembly 20000 can comprise a second lock that is biased into a locked configuration to lock the second drive system in place and a third lock that is biased into a locked configuration to lock the third drive in place. When the shaft assembly 20000 is attached to the first handle assembly 21000, the shaft assembly 20000 does not receive electrical power from the first handle assembly 21000 to unlock the second lock or the third lock. When the shaft assembly 20000 is attached to the second handle assembly 22000, the shaft assembly 20000 receives electrical power from the second handle assembly 22000, via the electrical contacts 22022, and the second lock is unlocked so that the second drive system of the shaft assembly 20000 can be used by the second handle assembly 22000. That said, the second handle assembly 22000 does not receive electrical power from the second handle assembly 22000 to unlock the third lock as the second and third locks are part of separate and distinct circuits. When the shaft assembly 20000 is attached to the third handle assembly 23000, the shaft assembly 20000 receives power from the third handle assembly 23000, via the electrical contacts 23022, to unlock the second and third locks so that the second and third drive systems of the shaft assembly 20000 can be used by the third handle assembly 23000.

As discussed above and referring to FIG. 343, the shaft assembly 20000 is selectively attachable to the first handle assembly 21000, the second handle assembly 22000, and the third handle assembly 23000. That being said, the handle assemblies 21000, 22000, and 23000 are all configured to be held differently by a clinician. The pen configuration of the first handle assembly 21000 is configured to be held, or pinched, between the clinician's thumb and index finger on one hand. The scissors configuration of the second handle assembly 22000 is configured to be gripped by an outstretched hand of the clinician. The pistol configuration of the third handle assembly 23000 is configured to be gripped by a closed, clenched hand of the clinician. As a result, the handle configurations 21000, 22000, and 23000 can be configured such that the shaft assembly 20000 is attached thereto in different orientations to match the grip orientation of the clinician's hand. For instance, the shaft assembly 20000 is attached to the handle assembly 21000 in a first orientation and attached to the shaft assemblies 22000 and 23000 in a second orientation which is rotated 90 degrees from the first orientation. Such an arrangement matches the typical expectations of the clinician regarding the orientation of the shaft assembly 20000 relative to their hand. Similarly, the first set of controls on the first handle assembly 21000 for controlling the first drive motor can be oriented 90 degrees relative to the orientation of the first set of controls on the second handle assembly 22000 and the third handle assembly 23000. Moreover, it can be desirable for a certain function of the shaft assembly 20000 to be always coupled to a motor-driven drive system regardless of the handle assembly that it is attached to. To achieve this, in various instances, the shaft assembly 20000 may have to be attached to the handles 21000, 22000, and 23000 in different orientations to align the articulation drive system, for example, to a motor-driven drive system.

Further information regarding the different configurations of the handle assemblies 21000, 22000, and 23000 are presented in FIG. 356. For example, the pencil handle assembly 21000 comprises a motor-driven output which is configured to enable right and left articulation of the shaft 20400. The end effector can be manually rotated relative to the shaft 20400. The pencil handle assembly 21000 is not configured to perform any actuation motions of the end effector or rotation of the shaft 20400 as it does not comprise a motor driven output for the actuation motions of the end effector or the rotation of the shaft 20400. As another example, the scissor grip handle assembly 22000 comprises a motor-driven output which is configured to enable right and left articulation of the shaft 20400. The scissor grip handle assembly 22000 comprises another motor-driven output which is configured to enable a first actuation motion of the end effector. The scissor grip handle assembly 22000 is not configured to perform a second actuation motion of the end effector or rotation of the shaft 20400 as it does not comprise a motor-driven output for the second actuation motion of the end effector or the rotation of the shaft 20400. As another example, the pistol handle assembly 23000 comprises motor-driven outputs which are configured to enable right and left articulation of the shaft 20400. The pistol handle assembly also comprises motor-driven outputs which are configured to enable the first and second actuation motions of the end effector as well as rotation of the shaft 20400 via a motor and a shiftable transmission.

Referring primarily to FIGS. 347 and 355, a handle assembly 24000, which is similar to the handle assembly 22000 in many respects, comprises at least one spring loaded pin 24024 which is configured to flex to allow the shaft assembly 20000 to be releasably held to the shaft assembly 20000. Such an arrangement can be adapted to the handle assemblies 21000, 22000, and 23000 to releasably hold the shaft assembly 20000 thereto. Similar to the handle assembly 22000, the handle assembly 24000 comprises a set of electrical contacts 24022, a first drive shaft 24100, and a second drive shaft 24200.

As discussed above, the shaft assembly 20000 comprises a first drive shaft 20100, a second drive shaft 20200, and a third drive shaft 20300, each of which enables a particular function of the surgical instrument system by establishing a mechanical connection with a drive shaft in any one of the handle assemblies 21000, 22000, and 23000—so long as the handle assembly has a sufficient number of drives to be coupled to. While the shaft assembly 20000 is attached to the first handle assembly 21000, certain functions of the surgical instrument and/or the end effector are enabled and certain functions of the surgical instrument and/or the end effector are locked out as seen in FIG. 356 and described in greater detail above. For example, the first handle assembly 21000 can drive the articulation system of the shaft 20400 with its one drive motor. All other functions of the shaft assembly 20000 would have to be performed by the manual manipulation of the first handle assembly 21000. Referring primarily to FIG. 343, the pencil grip configuration of the handle assembly 21000 does not afford a motor-driven output for actuating the end effector and/or rotating the shaft 20400.

The second handle assembly 22000 comprises two motors configured to drive two of the drives of the shaft assembly 20000. While the shaft assembly 20000 is attached to the second handle assembly 22000, certain functions of the surgical instrument and/or the end effector are enabled and certain functions of the surgical instrument and/or the end effector are locked out as seen in Table A of FIG. 356 and described in greater detail above. The first motor of the second handle assembly 22000 drives the articulation drive of the shaft assembly 20000 and the second motor of the second handle assembly 22000 drives a jaw assembly of the shaft assembly 20000 to move the jaw assembly between open and closed configurations. The third function of the shaft assembly 20000, i.e., the rotation of the jaw assembly about a longitudinal axis must be performed manually by rotating the second handle assembly 22000 about the longitudinal axis. The third handle assembly 23000 comprises three motors configured to drive all three of the drives of the shaft assembly 20000. While the shaft assembly 20000 is attached to the third handle assembly 23000 in the third orientation, none of the functions of the surgical instrument and/or the end effector are locked out as seen in Table A of FIG. 356 and described in greater detail above.

Referring to FIG. 357, the third handle assembly 23000 comprises a pistol grip configured for use with a smoke evacuation tube 23400. The smoke evacuation tube 23400 is configured to fit inside a groove 23420 within the handle assembly 23000. The shaft assembly 20000 further comprises a smoke evacuation tube 20410 which fits over the shaft 20400. Referring to FIG. 358, the third handle assembly 23000 comprises a first motor 23062 configured to power the right and left articulation of the end effector. The third handle assembly comprises a second motor configured to power the jaw drive of the shaft assembly 20000. The third handle assembly 23000 comprises a third motor configured to power the rotation of the end effector about the longitudinal axis. The handle assembly 23000 further comprises a first gear box 23064 to reduce the speed of the first motor and a second gear box 23068 to reduce the speed of the second motor. Still referring to FIG. 358, the insertable power module 23020 comprises at least two battery cells 23040 and 23050.

Referring to FIG. 359, the second handle assembly 22000 comprises a scissor grip configuration for use with a smoke evacuation tube 22400. The smoke evacuation tube 22400 is configured to fit inside a groove 22420 within the handle assembly 22000. Referring to FIG. 360, the handle assembly 22000 comprises a first motor 22062 and a second motor 22066 which are configured to power certain functions of the surgical instrument system as discussed above. Referring to FIG. 362 for example, the first motor 22062 is configured to power right and left articulation of the end effector, for example. The second motor 22066 is configured to power the jaw drive of the shaft assembly 20000. When the handle assembly 22000 is in use, the rotation of the end effector is performed manually by the clinician. The handle assembly 22000 further comprises a first speed reduction gear box 22064 and a second speed reduction gear box 22068 disposed within the handle assembly 22000. Still referring to FIG. 360, the insertable power module 22020 comprises at least two battery cells 22040 and 22050.

Referring to FIG. 363, the first handle assembly 21000 comprises a pencil grip configured for use with a smoke evacuation tube 21400. The smoke evacuation tube 21400 is configured to fit inside a groove 21420 within the handle assembly 21000. The shaft assembly 20000 further comprises a smoke evacuation tube 20410 which fits over the shaft 20400. Referring to FIG. 364, the handle assembly 21000 comprises a motor 21062 which is configured to power the right and left articulation of the end effector. When the handle assembly 21000 is in use, the rotation of the end effector is performed manually by the clinician, and certain functions such as a first actuation motion and a second actuation motion of the end effector are locked out as seen in FIG. 366. The handle assembly 21000 further comprises a speed reduction gear box 21064 disposed within the handle assembly 21000. Still referring to FIG. 364, the insertable power module 21020 comprises at least two battery cells 21040 and 21050.

Referring to FIG. 369, various surgical instrument systems described herein comprise one or more feedback systems which are configured to alert the clinician as to the state of the surgical instrument system. The surgical instrument system comprises a handle assembly 26000 which includes a first drive 26100, a second drive 26200, and a third drive 26300 which are configured to permit drive systems within the handle assembly 26000 to be operably coupled to the drive systems of a shaft assembly 27000. The shaft assembly 27000 is similar to the shaft assembly 20000 in many respects. The handle assembly 26000 further comprises a plurality of electrical contacts 26022 configured to place the handle assembly 26000 in electrical communication with the shaft assembly 27000. The shaft assembly 27000 comprises an actuation rod 27700 extending within a shaft 27770, wherein the actuation rod 27700 is drivable by a drive system of the handle assembly 26000. The shaft assembly 27000 further comprises an end effector 27200 rotatably attached to the shaft 27770 about an articulation joint 27300. The end effector 27200 comprises a first jaw 27220 and a second jaw 27222 which are movable between open and closed positions in response to the motions of the actuation rod 27700. The handle assembly 26000 further comprises a curved trigger 26400 rotatably connected to the handle assembly 26000 which, as described in greater detail below, is used to control the drive system. The curved trigger 26400 comprises a curved trigger rod 26500 extending therefrom, as also discussed in greater detail below.

Referring to FIG. 374, further to the above, the handle assembly 26000 comprises a motor control system 26010 which is configured to run a motor 26030 configured to drive the drive system of the shaft assembly 27000 as mentioned above. The handle assembly 26000 further comprises a power module 26028 configured to supply power to the motor 26030 at the direction of a motor control system 26010. The handle assembly 26000 comprises a trigger sensor 26800 which is in communication with the motor control system 26010 and is configured to monitor the motion of the trigger 26400. The trigger sensor 26800 is configured to generate a voltage potential which is detectable by the motor control system 26010—the magnitude of which can be used to ascertain the actuation and/or position of the trigger 26400. In response to the signal from the trigger sensor 26800, the motor control system 26010 is configured to run the motor 26030 to drive the drive rod 26050. In various instances, the trigger sensor 26800 comprises a variable resistance sensor, for example, and the speed of the motor 26030 is responsive to the signal provided by the trigger sensor 26800.

As the drive rod 26050 is driven distally by the motor 26030, the drive rod 26050 experiences a force load. There is a wide range of acceptable force loads that the drive rod 26050 may experience during use. That said, such force loads can suggest certain information about the performance of the surgical system. For instance, force loads toward the top of the acceptable range can indicate that thick and/or dense tissue is captured within the end effector 27200 while force loads toward the bottom of the acceptable range can indicate that thin and/or less dense tissue is captured within the end effector 27200, for example. Without more, this information is not conveyed to the clinician as the trigger 26400 is not mechanically coupled to the drive rod 26050; rather, the trigger 26400 is electrically coupled to the motor 26030 via the motor control system 26010. Without this information, a clinician may not fully appreciate what is occurring within the surgical system. To this end, the surgical instrument system comprises means for detecting the force load experienced by the drive rod 26050 and communicating this information to the clinician. In at least one instance, the surgical instrument system comprises one or more load cells and/or strain gauges configured to detect the force load within the drive rod 26050. In addition to or in lieu of these mechanical detection systems, the motor control system 26010 is configured to monitor the current drawn by the electric motor 26030 during use and this information as a proxy for the force load being experienced by the drive rod 26050. Referring to FIG. 374, the handle assembly comprises a current sensor 26012 in communication with the power control system 26020, and/or the motor control system 26010, which is configured to monitor the amount of current drawn by the motor 26030. Discussed below are systems which can restore the clinician's sense for the loads being experienced within the drive system based on the load data supplied to the power control system 26020.

Referring to FIGS. 370 and 371, the handle assembly 26000 further comprises an electroactive polymer (hereinafter "EAP") 26600 positioned within an aperture defined therein. The EAP 26600 is in signal communication with the power control system 26020 and is responsive to a voltage output provided by the power control system 26020. Referring primarily to FIG. 371, the handle assembly 26000 comprises a curved cylinder 26900 which surrounds a portion of the curved trigger rod 26500 of the trigger 26400. More specifically, the curved trigger rod 26500 comprises a trigger bar 26550 extending through the curved cylinder 26900 positioned within the handle assembly 26000. The EAP 26600 is radially constrained by the sidewalls of the curved aperture defined in the handle 26000. The EAP 26600 reacts to the voltage potential applied thereto by the power control system 26020 and expands and contracts proportionately in size to the magnitude of the force being applied to the drive rod 26050. When the voltage applied to the EAP 26600 is increased, the walls of the handle assembly 26000 prevent the EAP 26600 from expanding. As a result, the EAP 26600 expands toward the trigger bar 26550 extending from the curved trigger 26500 and, thus, applies a compressive force to the trigger bar 26550. The compression force applied by the EAP 26600 on the trigger bar 26550 compresses the trigger bar 26550 which, in turn, creates a drag force between the EAP 26600 and the trigger bar 26550 when the trigger bar 26550 is moved by the trigger 26400. This drag force is felt by the clinician pulling the trigger 26400 and directly communicates the forces of the end effector 27200 to the clinician. As the magnitude of the load force experienced by the drive rod 26050 increases, the voltage applied to the EAP 26600 by the power control system 26020 increases, and the drag experienced by the trigger 26400 also increases. As the magnitude of the load force experienced by the drive rod 26050 decreases, the voltage applied to the EAP 26600 by the power control system 26020 decreases, and the drag experienced by the trigger 26400 also decreases. These relationships are linearly proportional; however, any proportional relationship could be used. Moreover, further to the above, the magnitude of the voltage potential applied to the EAP 26600 by the power control system 26020 is proportionately coupled to the motor current drawn by the motor 26030, the voltage supplied by the load cell circuit, and/or the voltage supplied by the strain gauge circuit, for example.

Turning to FIG. 372, the EAP 26600 is shown in a non-energized state before the voltage potential is applied to the EAP 26600. As seen in FIG. 372, there is space defined between the EAP 26600 within the curved cylinder 26900 and the curved trigger 26500. Referring to FIG. 373, as the voltage potential is applied to the EAP 26600, the EAP 26600 constricts the trigger bar 26550 of the curved trigger 26500 which creates the drag force discussed above. The relationship between the forces on the end effector 27200 and/or the shaft 27770 and the compressive force on the curved trigger 26500 is further illustrated in FIGS. 375 and 376.

Referring to FIG. 375, $L_1$ illustrates the torque experienced by the motor drive shaft. $L_2$ illustrates the load force experienced by the drive rod 26050. $L_3$ illustrates the voltage applied to the EAP 26600. The load force on the drive rod 26050 and the torque on the motor drive shaft are proportional to the amount of voltage applied to the EAP 26600. That is, as the load force and torque increase, as illustrated by way of $L_1$ and $L_2$ in FIG. 375, the voltage applied to the EAP 26600 also increases. Further to the above, there is a proportional relationship between the compressive force applied to the trigger 26500 and the voltage applied to the EAP 26600. As the voltage applied to the EAP 26600 increases, the drag force on the trigger 26500 increases, as discussed in greater detail above. The voltage applied to the EAP 26600 increases as a reaction to the amount of current flowing through the motor 26030 which is an indicator of the forces on the drive rod 26050 and the torques on the motor drive shaft. Referring to FIG. 376, $L_4$ illustrates the change in the voltage potential applied to the EAP 26600 over time.

Turning to FIG. 384, additional feedback systems similar to those are configured for use with suturing devices. In particular, various surgical instrument systems are equipped with programs which are capable of measuring bending and axial loads applied to a suturing device shaft such as the shaft 28100 of the suturing device 28000 illustrated in FIG. 384. The suturing device 28000 comprises at least one motor configured to provide power to the suturing device during a surgical procedure. The suturing device 28000 further comprises a distal head 28300 rotatably connected to the shaft 28100 by an articulation joint 28200. The handle of the suturing device 28000 comprises a display which is configured to indicate a predefined proportion of loads to a user. The surgical instrument systems described herein are also configured for use with robotic surgical systems as well as cloud-based technology. Various applications disclosed which are incorporated by reference disclose situational awareness of an interactive HUB system which is configured to define various surgical steps. The devices, systems, and methods disclosed in the Subject Application can also be used with the devices, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated by reference in their entireties herein. Such surgical steps include providing the handle of the suturing device 28000 with and updated ration of the amount of the load being exerted as a portion of the suture stitch or knot tension. The tension is used by the user to create more standardization of the stitch to stitch tightness. Further uses are contemplated which include instructional uses for new users of the surgical instrument systems described herein. FIG. 385 further illustrates the relationship between the forces applied to the shaft 28100 and the distal head 28300 based on the different motors (e.g. the motor supplying power to perform an actuation motion of an end effector and the motor supplying power to perform a distal head rotation motion).

The surgical instrument systems discussed in greater detail above are configured for use with locking and safety mechanisms. The locking mechanisms comprise electrical sensing means configured to detect whether a modular attachment is in a usable or unusable state. The locking mechanisms further comprise electrical sensing means configured to detect whether a loadable mechanism is in a usable or unusable state. FIG. 377 illustrates an exemplary shaft assembly 30000 which is similar to the shaft assembly 20000. The locking mechanisms which will be discussed in greater detail below are configured for use with any of the surgical instrument systems described herein. The shaft assembly 30000 comprises a drive 30100, a second drive 30200, and a third drive 30300. The shaft assembly 30000 comprises a plurality of electrical contacts 30022 configured to place the shaft assembly 30000 in electrical communication with any of the handle assemblies described herein upon being attached thereto. The shaft assembly 30000 further comprises an on-board control circuit 30500. One example of a single use lockout 30400 is illustrated in FIG. 378. The single use lockout comprises a lock solenoid 30410, a lock spring 30420, and a lock pin 30430 as seen in FIGS. 379 and 380. The lock solenoid 30410 is energized upon power being supplied to the shaft assembly 30000.

In such instances, the lock solenoid 30410 is configured to push the lock pin 30430 outwardly into a locked position; however the lock pin 30430 is held in a staged position until the shaft assembly 30000 is detached from the handle. At such point, the lock spring 30420 can push the lock pin 30430 from its staged position into its locked position. In various instances, the shaft assembly 30000 comprises a lock shoulder 30440 configured to hold the lock pin 30430 in its locked position and prevent the lock pin 30430 from being reset. In such instances, the lock pin 30430 protrudes proximally from the housing of the shaft assembly 30000 which prevents the shaft assembly 30000 from being reattached to a handle. While the solenoid 30410 can drive the lock pin 30430 into its locked position in certain instances; in other instances, the solenoid 30410 holds the lock pin 30430 in its unlocked position until energized by the attachment of the shaft assembly 30000 to the handle wherein, at such point, the solenoid 30410 can release the lock pin 30430 such that the lock spring 30420 can move the lock pin 30430 into its staged position where the shaft assembly 30000 is attached to the handle and into its locked position once the shaft assembly 30000 is removed from the handle.

Other lockout mechanisms comprise a locking member which immobilizes a drive shaft of a surgical instrument if a modular shaft is attached to an incompatible handle can be used. For example, when a scissor grip handle is attached to an articulating clip applier shaft with distal head rotation, a lockout prevents distal head rotation drive because the scissor grip handle is used for only one drive system which is often the clip drive. In various instances, the lockout fixes the rotation of the distal head by engaging a lockout member into the drive shaft at the proximal end of the shaft.

An additional locking mechanism for use with the surgical instrument systems described herein comprises a distal locking mechanism which prevents actuation motions of a clip applier or suturing device if a loaded cartridge is not in the jaws. A similar lockout mechanism comprises a distal locking mechanism which prevents actuation motions of a clip applier or suturing device if a spent cartridge is positioned in the jaws. The distal locking mechanism further comprises a means for sensing the engagement state of the distal lockout through a power system of the surgical instrument in order to prevent the activation of the motor or to instruct the motor to provide haptic vibration feedback that the handle assembly is incompatible with the attachment portion. Additional lockout assemblies include a modular lockout which prohibits or changes the operation of the motor if the shaft is detected to be in an unusable state.

Turning now to FIG. 386, an exemplary system for identifying the components of a surgical instrument system is disclosed. Step 32100 comprises attaching a shaft module to a handle assembly. Step 32200 comprises attaching a battery to a handle assembly. Step 32300 comprises energizing a safety circuit or watchdog processor wherein either is compatible with surgical instrument systems discussed in greater detail above. Decision 32400 comprises the verification of the integrity of the electrical circuit within the surgical instrument system. If the integrity of the circuit is bad, then the system is configured to display an error signal and shut down in step 32410. If the integrity of the circuit is good, the system is configured to identify and log a serial number associated with a handle assembly, battery, and/or shaft assembly, as illustrated in step 32420. Decision 32500 is configured to identify the type of handle assembly. For example, if the handle assembly is a simple scissors handle, the system is configured to control a program for a simple mechanism configuration which includes a shaft rotation lockout, as illustrated in step 32500. If the system determines that the handle assembly is not a simple scissors handle, then the system is configured to verify the functionality of all instrument mechanisms as illustrated in step 32510.

With further reference to FIG. 386, once the system identifies the type of handle assembly, the system is configured to determine whether the shaft assembly comprises a loadable portion in decision 32600, and is further configured to determine the status of the loadable portion. If the loadable portion is unloaded, the system is configured to generate an error message in step 32610 which indicates that the system is waiting for the loadable portion to be reloaded before a surgical procedure can continue. If the loadable portion is loaded, the system is configured detect whether a display unit is present during decision 32700. If the surgical instrument does not comprise a display unit, for example, the system is configured use a simple green light to indicate that the surgical instrument is ready for use. If the surgical instrument comprises a display unit, for example, the system configures the display unit for use with whatever shaft assembly is attached to the surgical instrument in step 32720. Additional systems comprise the identification of various compatible shaft assemblies and handle assemblies. Other systems comprise the identification of the status of a power module and the status of the power module. The verification processes described above are configured for use with any of the surgical instrument systems described herein. The surgical instruments, modules, systems, and methods disclosed herein can be used with the various disclosures incorporated by reference. The devices, systems, and methods disclosed in the Subject Application can also be used with the devices, systems, and methods disclosed in U.S. Provisional Patent Application No. 62/659,900, entitled METHOD OF HUB COMMUNICATION, filed on Apr. 19, 2018, U.S.

Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S.

Provisional Patent Application No. 62/611,339, entitled ROBOT ASSISTED SURGICAL PLATFORM, filed on Dec. 28, 2017, which are incorporated by reference in their entireties herein.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skilled in the art in light of this disclosure. In addition, those skilled in the art will appreciate that the mechanisms of the subject matter described herein are capable of being distributed as one or more program products in a variety of forms and that an illustrative form of the subject matter described herein applies regardless of the particular type of signal-bearing medium used to actually carry out the distribution.

Instructions used to program logic to perform various disclosed aspects can be stored within a memory in the system, such as DRAM, cache, flash memory, or other storage. Furthermore, the instructions can be distributed via a network or by way of other computer-readable media. Thus a machine-readable medium may include any mechanism for storing or transmitting information in a form readable by a machine (e.g., a computer), but is not limited to, floppy diskettes, optical disks, CD-ROMs, magneto-optical disks, ROM, RAM, EPROM, EEPROM, magnetic or optical cards, flash memory, or tangible, machine-readable storage used in the transmission of information over the Internet via electrical, optical, acoustical, or other forms of propagated signals (e.g., carrier waves, infrared signals, digital signals). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, DSP, PLD, programmable logic array (PLA), or FPGA), state machine circuitry, firmware that stores instructions executed by programmable circuitry, and any combination thereof. The control circuit may, collectively or individually, be embodied as circuitry that forms part of a larger system, for example, an integrated circuit, an application-specific integrated circuit (ASIC), a system on-chip (SoC), desktop computers, laptop computers, tablet computers, servers, smart phones, etc. Accordingly, as used herein, "control circuit" includes, but is not limited to, electrical circuitry having at least one discrete electrical circuit, electrical circuitry having at least one integrated circuit, electrical circuitry having at least one application-specific integrated circuit, electrical circuitry forming a general-purpose computing device configured by a computer program (e.g., a general-purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware, and/or circuitry configured to perform any of the aforementioned operations. Software may be embodied as a software package, code, instructions, instruction sets, and/or data recorded on non-transitory computer-readable storage medium. Firmware may be embodied as code, instructions, instruction sets, and/or data that are hard-coded (e.g., non-volatile) in memory devices.

As used in any aspect herein, the terms "component," "system," "module," and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet-switched network. The communication devices may be capable of communicating with each other using a selected packet-switched network communications protocol. One example communications protocol may include an Ethernet communications protocol which may be capable permitting communication using a Transmission Control Protocol/IP. The Ethernet protocol may comply or be compatible with the Ethernet standard published by the Institute of Electrical and Electronics Engineers (IEEE) titled "IEEE 802.3 Standard," published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum, titled "ATM-MPLS Network Interworking 2.0," published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components, inactive-state components, and/or standby-state components, unless context requires otherwise.

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures, or characteristics may be combined in any suitable manner in one or more aspects.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for downloading data from a surgical hub to a surgical instrument, comprising:
   assembling a first shaft assembly to a handle;
   downloading a first set of operational data from the surgical hub to the surgical instrument once the first shaft assembly is attached to the handle;
   assembling a second shaft assembly to the handle; and
   downloading a second set of operational data from the surgical hub to the surgical instrument once the second shaft assembly is attached to the handle, wherein the second set of operational data is different than the first set of operational data.

2. The method of claim 1, wherein the handle comprises a first motor, a second motor, and a third motor, wherein the first set of operational data can operate all of the first, second, and third motors, and wherein the second set of operational data can only operate less than all of the first, second, and third motors.

3. The method of claim 2, wherein the handle comprises a controller configured to receive the first set of operational data and the second set of operational data from the surgical hub.

4. The method of claim 3, further comprising transmitting operational signals to the first motor, the second motor, and the third motor via the controller in order to perform functions of the surgical instrument.

5. The method of claim 1, further comprising providing tactile feedback to a clinician via the handle of the surgical instrument.

6. A method for downloading data from a surgical hub to a surgical instrument, comprising:
   assembling a first shaft assembly to a handle;
   downloading a first set of operational data from the surgical hub to the surgical instrument once the first shaft assembly is attached to the handle;

assembling a second shaft assembly to the handle; and downloading a second set of operational data from the surgical hub to the surgical instrument once the second shaft assembly is attached to the handle, wherein the second set of operational data is different than the first set of operational data, wherein the handle comprises an actuation trigger surrounded by an electroactive polymer which is configured to apply force to the actuation trigger in order to provide tactile feedback to a clinician via the handle of the surgical instrument, said method further comprising:

actuating the electroactive polymer to apply a first force to the actuation trigger when the surgical instrument has received the first set of operational data; and actuating the electroactive polymer to apply a second force to the actuation trigger when the surgical instrument has received the second set of operational data, wherein the first force is larger than the second force.

7. A method for downloading data from a surgical hub to a surgical instrument system, comprising:
assembling a first shaft assembly to a handle;
downloading a first set of operational data from the surgical hub to the surgical instrument system after the first shaft assembly is attached to the handle;
assembling a second shaft assembly to the handle;
downloading a second set of operational data from the surgical hub to the surgical instrument system after the second shaft assembly is attached to the handle;
assembling a third shaft assembly to the handle; and
downloading a third set of operational data from the surgical hub to the handle after the third shaft assembly is attached to the handle, wherein the first set of operational data, the second set of operational data, and the third set of operational data relate to different functions of the surgical instrument system.

8. The method of claim 7, wherein the handle comprises a first motor, a second motor, and a third motor, wherein the first set of operational data can operate all of the first, second, and third motors, wherein the second set of operational data can operate less than all of the first, second, and third motors, and wherein the third set of operational data operates none of the first, second, and third motors.

9. The method of claim 8, wherein the handle comprises a controller configured to receive the first set of operational data, the second set of operational data, and the third set of operational data from the surgical hub.

10. The method of claim 9, further comprising transmitting operational signals to the first motor, the second motor, and the third motor via the controller.

11. The method of claim 7, further comprising providing tactile feedback to a clinician via the handle.

12. A method for downloading data from a surgical hub to a surgical instrument system, comprising:
assembling a first shaft assembly to a handle;
downloading a first set of operational data from the surgical hub to the surgical instrument system after the first shaft assembly is attached to the handle;
assembling a second shaft assembly to the handle;
downloading a second set of operational data from the surgical hub to the surgical instrument system after the second shaft assembly is attached to the handle;
assembling a third shaft assembly to the handle; and
downloading a third set of operational data from the surgical hub to the handle after the third shaft assembly is attached to the handle, wherein the first set of operational data, the second set of operational data, and the third set of operational data relate to different functions of the surgical instrument system, wherein the handle comprises an actuation trigger surrounded by an electroactive polymer which is configured to apply force to the actuation trigger in order to provide tactile feedback to a clinician via the handle, said method further comprising:

actuating the electroactive polymer to apply a first force to the actuation trigger when the surgical instrument system has received the first set of operational data;

actuating the electroactive polymer to apply a second force to the actuation trigger when the surgical instrument system has received the second set of operational data, wherein the first force is larger than the second force; and actuating the electroactive polymer to apply a third force to the actuation trigger when the surgical instrument system has received the third set of operational data, wherein the second force is larger than the third force.

13. A method for downloading operating instructions from a surgical hub to a surgical instrument, comprising:
assembling a first shaft assembly to a handle assembly;
downloading a first set of operating instructions from the surgical hub to the surgical instrument after the first shaft assembly is attached to the handle assembly;
assembling a second shaft assembly to the handle assembly; and
downloading a second set of operating instructions from the surgical hub to the surgical instrument after the second shaft assembly is attached to the handle assembly, wherein the second set of operating instructions is different than the first set of operating instructions.

14. The method of claim 13, wherein the handle assembly comprises a first motor, a second motor, and a third motor, wherein the first set of operating instructions can operate all of the first, second, and third motors, and wherein the second set of operating instructions can operate less than all of the first, second, and third motors.

15. The method of claim 14, wherein the handle assembly comprises a controller configured to receive the first set of operating instructions and the second set of operating instructions from the surgical hub.

16. The method of claim 15, further comprising transmitting operational signals to the first motor, the second motor, and the third motor via the controller.

17. The method of claim 13, further comprising providing tactile feedback to a clinician after the first set of operating instructions and the second set of operating instructions are downloaded to the handle assembly.

18. The method of claim 17, wherein the handle assembly comprises an actuation trigger surrounded by an electroactive polymer which applies forces to the actuation trigger in order to provide the tactile feedback to the clinician.

19. The method of claim 13, wherein said downloading steps occur automatically once the respective shaft assembly is assembled to the handle assembly.

20. The method of claim 13, wherein said downloading steps do not occur automatically once the respective shaft assembly is assembled to the handle assembly, said method further comprising:
actuating a control to download the first set of operational instructions; and
actuating the control to download the second set of operational instructions.

21. The method of claim 13, wherein said downloading steps do not occur automatically once the respective shaft assembly is assembled to the handle assembly, said method further comprising:

actuating a first control to download the first set of operational instructions; and actuating a second control to download the second set of operational instructions.

* * * * *